US012590102B2

(12) United States Patent
Kim et al.

(10) Patent No.: US 12,590,102 B2
(45) Date of Patent: Mar. 31, 2026

(54) COMPOUND AND ORGANIC LIGHT EMITTING DEVICE COMPRISING THE SAME

(71) Applicant: LG CHEM, LTD., Seoul (KR)

(72) Inventors: Minjun Kim, Daejeon (KR); Dong Hoon Lee, Daejeon (KR); Sang Duk Suh, Daejeon (KR); Young Seok Kim, Daejeon (KR); Seoyeon Kim, Daejeon (KR); Da Jung Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 905 days.

(21) Appl. No.: 17/798,366

(22) PCT Filed: May 24, 2021

(86) PCT No.: PCT/KR2021/006438
§ 371 (c)(1),
(2) Date: Aug. 9, 2022

(87) PCT Pub. No.: WO2021/235906
PCT Pub. Date: Nov. 25, 2021

(65) Prior Publication Data

US 2023/0157159 A1 May 18, 2023

(30) Foreign Application Priority Data

May 22, 2020 (KR) ........................ 10-2020-0061903
May 24, 2021 (KR) ........................ 10-2021-0066065

(51) Int. Cl.
*C07D 491/048* (2006.01)
*C07D 495/04* (2006.01)
*H10K 50/00* (2023.01)
*H10K 77/00* (2023.01)
*H10K 85/60* (2023.01)
*H10K 50/11* (2023.01)

(52) U.S. Cl.
CPC ....... *C07D 491/048* (2013.01); *C07D 495/04* (2013.01); *H10K 50/00* (2023.02); *H10K 77/00* (2023.02); *H10K 85/633* (2023.02); *H10K 85/636* (2023.02); *H10K 50/11* (2023.02); *H10K 85/615* (2023.02); *H10K 85/622* (2023.02); *H10K 85/624* (2023.02); *H10K 85/657* (2023.02); *H10K 85/6572* (2023.02); *H10K 85/6576* (2023.02)

(58) Field of Classification Search
None
See application file for complete search history.

(56) References Cited

U.S. PATENT DOCUMENTS

2004/0251816 A1 12/2004 Leo et al.
2010/0187984 A1 7/2010 Lin et al.
2014/0027747 A1 1/2014 Mun et al.
2014/0183517 A1 7/2014 Huh et al.
(Continued)

FOREIGN PATENT DOCUMENTS

CN 104230645 12/2014
CN 104557440 4/2015
(Continued)

*Primary Examiner* — Robert S Loewe
(74) *Attorney, Agent, or Firm* — Bryan Cave Leighton Paisner LLP

(57) ABSTRACT

Provided is a compound of Chemical Formula 1:

[Chemical Formula 1]

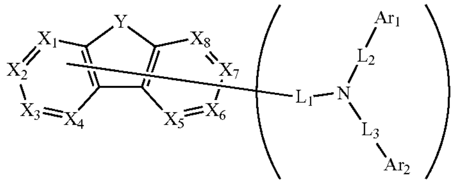

wherein one of $X_1$ to $X_8$ is N, and one of the rest is C bonded to $L_1$, and the rest are each independently CR; R is hydrogen or deuterium; Y is O or S; $L_1$ is a single bond or

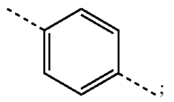

$L_2$ and $L_3$ are each independently a single bond, phenylene, or naphthylene; $Ar_1$ and $Ar_2$ are each independently phenyl, biphenyl, terphenyl, quaterphenyl, naphthyl, binaphthyl, (naphthyl)phenyl, (phenyl)naphthyl, phenanthrenyl, triphenylenyl, chrysenyl, tetracenyl, benz[a]anthracenyl, benzo[c]phenanthrenyl, fluorenyl, 9,9-dimethylfluorenyl, 9,9-diphenylfluorenyl, spirobifluorenyl, fluoranthenyl, dibenzothiophenyl, dibenzofuranyl, carbazolyl or 9-phenylcarbazolyl, with the proviso that $Ar_1$ and $Ar_2$ are not phenyl at the same time, and $Ar_1$ and $Ar_2$ are each independently unsubstituted or substituted with at least one of deuterium, a $C_{1-20}$ alkyl, a $C_{3-20}$ cycloalkyl, or a $C_{6-20}$ aryl, and an organic light emitting device including the same.

7 Claims, 1 Drawing Sheet

(56) References Cited

U.S. PATENT DOCUMENTS

| | | | | |
|---|---|---|---|---|
| 2014/0197402 | A1 | 7/2014 | Huh et al. | |
| 2014/0231774 | A1 | 8/2014 | Huh et al. | |
| 2015/0021555 | A1 | 1/2015 | Kwong et al. | |
| 2016/0118594 | A1* | 4/2016 | Itoi | C07D 495/04 546/89 |
| 2016/0118597 | A1 | 4/2016 | Itoi et al. | |
| 2019/0185412 | A1 | 6/2019 | Xia | |
| 2019/0189927 | A1 | 6/2019 | Lee et al. | |
| 2019/0229271 | A1 | 7/2019 | Lee et al. | |
| 2020/0055822 | A1 | 2/2020 | Wirges et al. | |
| 2022/0093870 | A1 | 3/2022 | Mun et al. | |
| 2023/0172057 | A1* | 6/2023 | Gao | H10K 50/16 257/40 |

FOREIGN PATENT DOCUMENTS

| | | | | |
|---|---|---|---|---|
| CN | 106146538 A | * | 11/2016 | C09K 11/06 |
| CN | 108623479 | | 10/2018 | |
| CN | 109111461 A | | 1/2019 | |
| CN | 111662189 | | 9/2020 | |
| CN | 111662259 | | 9/2020 | |
| CN | 112341470 | | 2/2021 | |
| JP | 2014-527021 | | 10/2014 | |
| JP | 2014-527066 | | 10/2014 | |
| JP | 2019-131575 | | 8/2019 | |
| KR | 10-2000-0051826 | | 8/2000 | |
| KR | 10-2011-0116177 | | 10/2011 | |
| KR | 10-2015-0009461 | | 1/2015 | |
| KR | 10-2015-0132993 | | 11/2015 | |
| KR | 10-2016-0047971 | | 5/2016 | |
| KR | 10-2016-0052136 | | 5/2016 | |
| KR | 10-2016-0053561 | | 5/2016 | |
| KR | 10-2016-0054855 | | 5/2016 | |
| KR | 10-2016-0058742 | | 5/2016 | |
| KR | 10-2016-0059602 | | 5/2016 | |
| KR | 10-2016-0059609 | | 5/2016 | |
| KR | 10-2019-0076375 | | 7/2019 | |
| KR | 10-2019-0125993 | | 11/2019 | |
| KR | 10-2019-0139160 | | 12/2019 | |
| WO | 2003-012890 A2 | | 2/2003 | |
| WO | 2010-083359 A2 | | 7/2010 | |
| WO | 2015-037675 | | 3/2015 | |
| WO | 2016-072690 | | 5/2016 | |
| WO | 2016-072691 | | 5/2016 | |
| WO | 2017-204556 | | 11/2017 | |
| WO | 2018-012780 | | 1/2018 | |
| WO | 2018-021737 | | 2/2018 | |
| WO | 2018-234917 | | 12/2018 | |

* cited by examiner

【FIG. 1】
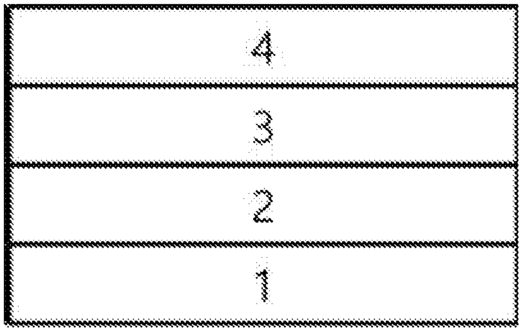
【FIG. 2】
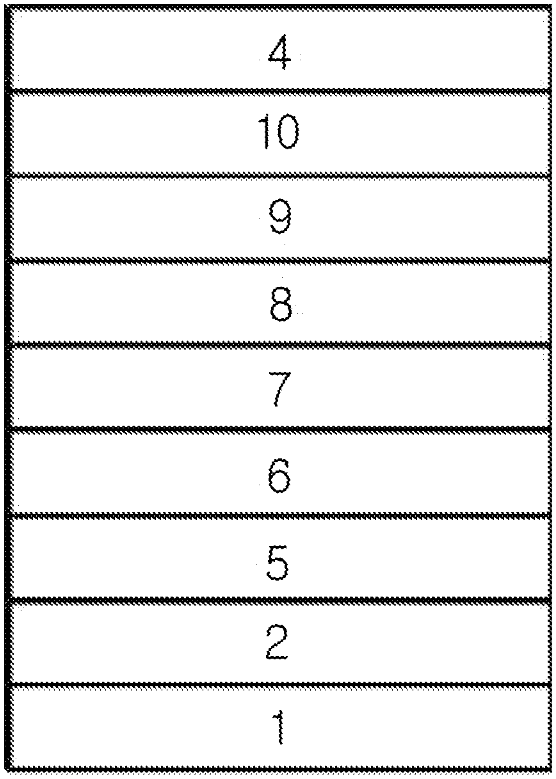

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2021/006438 filed on May 24, 2021, which claims the benefit of Korean Patent Application No. 10-2020-0061903 filed on May 22, 2020 and Korean Patent Application No. 10-2021-0066065 filed on May 24, 2021 in the Korean Intellectual Property Office, the disclosures of which are incorporated herein by reference in their entirety.

TECHNICAL FIELD

The present disclosure relates to a novel compound and an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer, and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuous need to develop a new material for the organic material used in the organic light emitting device as described above.

Prior Art Literature

Patent Literature (Patent Literature 0001) Korean Unexamined Patent Publication No. 10-2000-0051826

BRIEF DESCRIPTION

Technical Problem

It is an object of the present disclosure to provide a novel compound and an organic light emitting device comprising the same.

Technical Solution

According to an aspect of the present disclosure, provided is a compound of Chemical Formula 1:

[Chemical Formula 1]

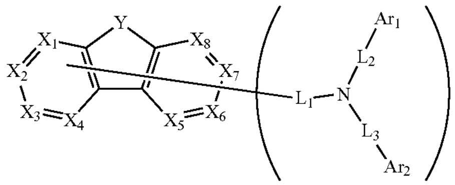

wherein, in Chemical Formula 1:

one of $X_1$ to $X_8$ is N, and one of the rest is C bonded to $L_1$, and the rest are each independently CR;

R is hydrogen or deuterium;

Y is O or S;

$L_1$ is a single bond or

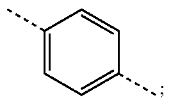

$L_2$ and $L_3$ are each independently a single bond, phenylene, or naphthylene;

$Ar_1$ and $Ar_2$ are each independently phenyl, biphenyl, terphenyl, quaterphenyl, naphthyl, binaphthyl, (naphthyl)phenyl, (phenyl)naphthyl, phenanthrenyl, triphenylenyl, chrysenyl, tetracenyl, benz[a]anthracenyl, benzo[c]phenanthrenyl, fluorenyl, 9,9-dimethylfluorenyl, 9,9-diphenylfluorenyl, spirobifluorenyl, fluoranthenyl, dibenzothiophenyl, dibenzofuranyl, carbazolyl or 9-phenylcarbazolyl, with the proviso that $Ar_1$ and $Ar_2$ are not phenyl at the same time, and $Ar_1$ and $Ar_2$ are each independently unsubstituted or substituted with at least one of deuterium, a $C_{1-20}$ alkyl, a $C_{3-20}$ cycloalkyl, or a $C_{6-20}$ aryl.

According to another aspect of the present disclosure, provided is an organic light emitting device comprising: a first electrode; a second electrode opposite to the first electrode; and one or more organic material layers between the first electrode and the second electrode, wherein one or more layers of the organic material layers comprises the compound of Chemical Formula 1.

Advantageous Effects

The above-mentioned compound of Chemical Formula 1 can be used as a material of an organic material layer in an organic light emitting device, and can improve the efficiency, achieve low driving voltage and/or improve lifetime characteristics in the organic light emitting device. In particular, the compound of the Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, an organic material layer 3, and a cathode 4.

FIG. 2 shows an example of an organic light emitting device comprising a substrate 1, an anode 2, a hole injection layer 5, a hole transport layer 6, an electron blocking layer 7, a light emitting layer 8, a hole blocking layer 9, an electron injection and transport layer 10, and a cathode 4.

DETAILED DESCRIPTION

Hereinafter, embodiments of the present disclosure will be described in more detail to facilitate understanding of the invention.

As used herein, the notation  and  mean a bond linked to another substituent group.

As used herein, the term "substituted or unsubstituted" means being unsubstituted or substituted with one or more substituents selected from the group consisting of deuterium, a halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent to which two or more substituents of the above-exemplified substituents are linked. For example, "a substituent in which two or more substituents are linked" can be a biphenyl group. Namely, a biphenyl group can be an aryl group, or it can also be interpreted as a substituent in which two phenyl groups are linked.

In the present disclosure, the carbon number of a carbonyl group is not particularly limited, but is preferably 1 to 40. Specifically, the carbonyl group can have the following structural formulas, but is not limited thereto:

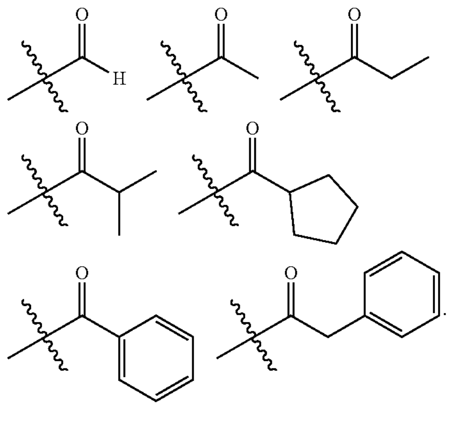

In the present disclosure, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can have the following structural formulas, but is not limited thereto:

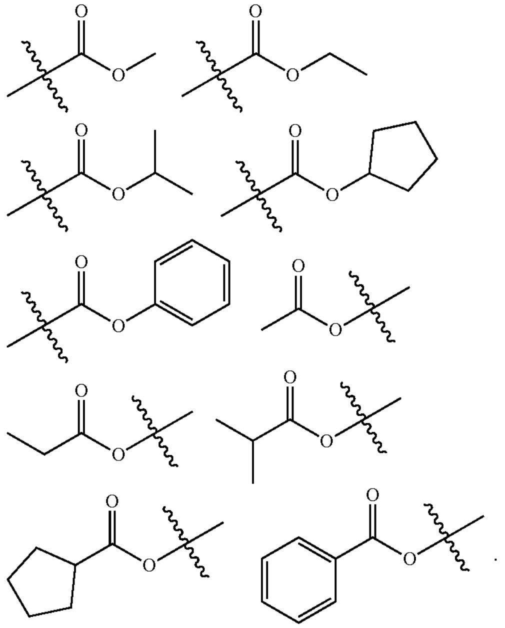

In the present disclosure, the carbon number of an imide group is not particularly limited, but is preferably 1 to 25. Specifically, the imide group can have the following structural formulas, but is not limited thereto:

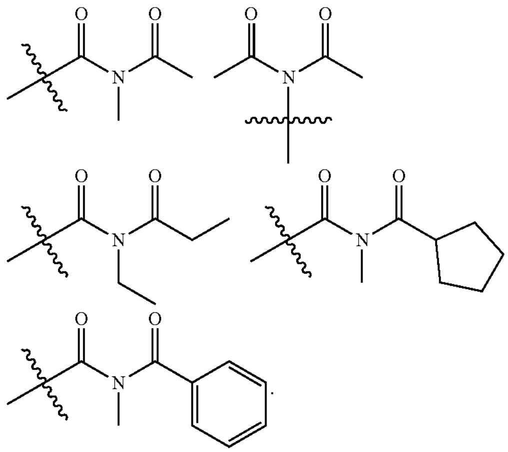

In the present disclosure, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present disclosure, a boron group specifically includes a dimethylboron group, a diethylboron group, a t-butylmethylboron group, a diphenylboron group, and a phenylboron group, but is not limited thereto.

In the present disclosure, examples of a halogen group include fluorine, chlorine, bromine, or iodine.

In the present disclosure, the alkyl group can be straight-chain or branched-chain, and the carbon number thereof is not particularly limited, but is preferably 1 to 40. According to one embodiment, the carbon number of the alkyl group is 1 to 20. According to another embodiment, the carbon number of the alkyl group is 1 to 10. According to another embodiment, the carbon number of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, n-octyl, isooctyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

In the present disclosure, the alkenyl group can be straight-chain or branched-chain, and the carbon number thereof is not particularly limited, but is preferably 2 to 40. According to one embodiment, the carbon number of the alkenyl group is 2 to 20. According to another embodiment, the carbon number of the alkenyl group is 2 to 10. According to still another embodiment, the carbon number of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present disclosure, a cycloalkyl group is not particularly limited, but the carbon number thereof is preferably 3 to 60. According to one embodiment, the carbon number of the cycloalkyl group is 3 to 30. According to another embodiment, the carbon number of the cycloalkyl group is 3 to 20. According to still another embodiment, the carbon number of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present disclosure, an aryl group is not particularly limited, but the carbon number thereof is preferably 6 to 60, and it can be a monocyclic aryl group or a polycyclic aryl group. According to one embodiment, the carbon number of the aryl group is 6 to 30. According to one embodiment, the carbon number of the aryl group is 6 to 20. The aryl group can be a phenyl group, a biphenylyl group, a terphenylyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group, or the like, but is not limited thereto.

In the present disclosure, the fluorenyl group can be substituted, and two substituents can be linked with each other to form a spiro structure. In the case where the fluorenyl group is substituted,

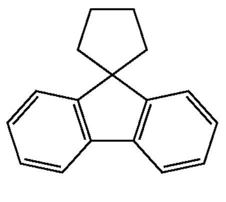

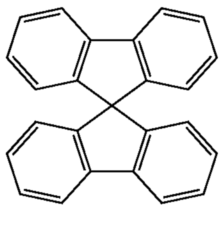

-continued

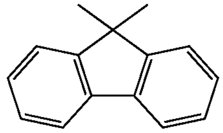

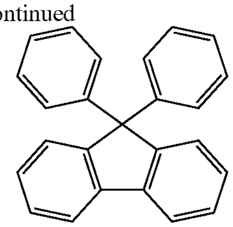

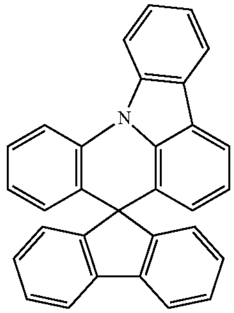

and the like can be formed.

In the present disclosure, a heterocyclic group is a heterocyclic group containing at least one of O, N, Si and S as a heteroatom, and the carbon number thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present disclosure, the aryl group in the aralkyl group, the aralkenyl group, the alkylaryl group and the arylamine group is the same as the above-mentioned examples of the aryl group. In the present disclosure, the alkyl group in the aralkyl group, the alkylaryl group and the alkylamine group is the same as the above-mentioned examples of the alkyl group. In the present disclosure, the heteroaryl in the heteroarylamine can be applied to the above-mentioned description of the heterocyclic group. In the present disclosure, the alkenyl group in the aralkenyl group is the same as the above-mentioned examples of the alkenyl group. In the present disclosure, the above-mentioned description of the aryl group can be applied except that the arylene is a divalent group. In the present disclosure, the above-mentioned description of the heterocyclic group can be applied except that the heteroarylene is a divalent group. In the present disclosure, the above-mentioned description of the aryl group or cycloalkyl group can be applied except that the hydrocarbon ring is not a monovalent group but formed by combining two substituent groups.

The present disclosure provides a compound of Chemical Formula 1.

Specifically, the compound of Chemical Formula 1 can be a compound of the following Chemical Formula 1-1 or 1-2:

[Chemical Formula 1-1]

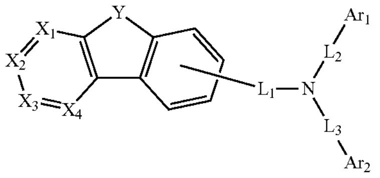

wherein, in Chemical Formula 1-1:

one of $X_1$ to $X_4$ is N, and one of the rest is C bonded to $L_1$, and the rest are each independently CR; and R, Y, $L_1$, $L_2$, $L_3$, $Ar_1$, and $Ar_2$ are as defined above;

[Chemical Formula 1-2]

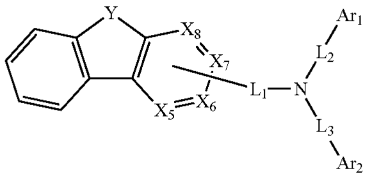

wherein, in Chemical Formula 1-2:

one of $X_5$ to $X_8$ is N, and one of the rest is C bonded to $L_1$, and the rest are each independently CR; and R, Y, $L_1$, $L_2$, $L_3$, $Ar_1$, and $Ar_2$ are as defined above.

More specifically, the compound of Chemical Formula 1 can be a compound of any one of the following Chemical Formulas 1-1-1 to 1-1-8:

[Chemical Formula 1-1-1]

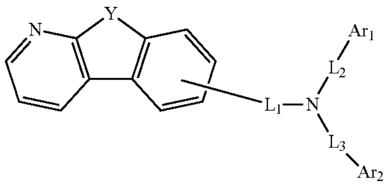

[Chemical Formula 1-1-2]

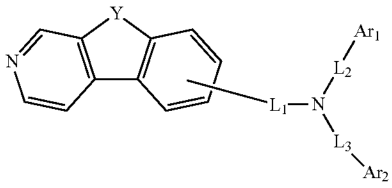

[Chemical Formula 1-1-3]

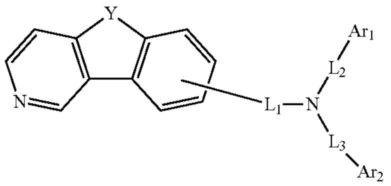

-continued

[Chemical Formula 1-1-4]

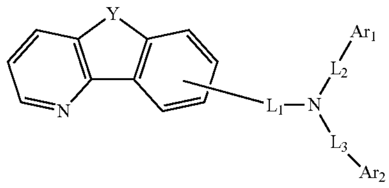

[Chemical Formula 1-1-5]

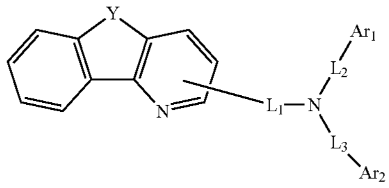

[Chemical Formula 1-1-6]

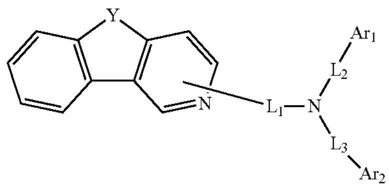

[Chemical Formula 1-1-7]

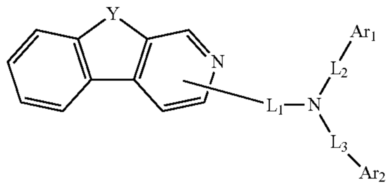

[Chemical Formula 1-1-8]

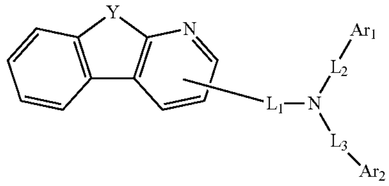

wherein, in Chemical Formulas 1-1-1 to 1-1-8, Y, $L_1$, $L_2$, $L_3$, $Ar_1$, and $Ar_2$ are as defined above.

Further, in Chemical Formula 1, in the case of CR among $X_1$ to $X_8$, R can be preferably hydrogen or deuterium, and more preferably all of R can be hydrogen.

Further, in Chemical Formula 1, $L_1$ can preferably be a single bond.

Further, in Chemical Formula 1, $L_1$ can have preferably

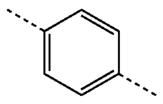

in which an amino group ($-N(L_2Ar_1)(L_3Ar_2)$) is bonded to $L_1$ at a para position.

Further, in Chemical Formula 1, $L_2$ and $L_3$ can be each independently a single bond, phenylene, or naphthylene, and $L_2$ and $L_3$ can be identical to or different from each other.

Further, in Chemical Formula 1, preferably, $Ar_1$ can be phenyl, biphenyl, terphenyl, quaterphenyl, naphthyl, binaphthyl, (naphthyl)phenyl, (phenyl)naphthyl, phenanthrenyl, or triphenylenyl, and $Ar_2$ can be phenyl, biphenyl, terphenyl, quaterphenyl, naphthyl, binaphthyl, (naphthyl)phenyl, (phenyl)naphthyl, phenanthrenyl, triphenylenyl, chrysenyl, tetracenyl, benz[a]anthracenyl, benzo[c]phenanthrenyl, fluorenyl, 9,9-dimethylfluorenyl, 9,9-diphenylfluorenyl, spirobifluorenyl, fluoranthenyl, dibenzothiophenyl, dibenzofuranyl, carbazolyl or 9-phenylcarbazolyl. In this case, $Ar_1$ and $Ar_2$ are not phenyl at the same time.

Further, $Ar_1$ and $Ar_2$ can be each independently unsubstituted or substituted with at least one of deuterium, a $C_{1-20}$ alkyl, a $C_{3-20}$ cycloalkyl, or a $C_{6-20}$ aryl. More specifically, the $Ar_1$ and $Ar_2$ can be each independently unsubstituted or substituted with one or two of deuterium, methyl, adamantyl, or phenyl.

Further, in Chemical Formula 1, $Ar_1$ and $Ar_2$ are different from each other.

Further, in Chemical Formula 1, $Ar_1$ and $Ar_2$ are identical to each other, with the proviso that that $Ar_1$ and $Ar_2$ are not phenyl at the same time.

Further, in Chemical Formula 1, $-L_2-Ar_1$ and $-L_3-Ar_2$ have the same structure as each other, with the proviso that $Ar_1$ and $Ar_2$ are not phenyl at the same time. That is, in Chemical Formula 1, $L_2$ and $L_3$ are identical to each other, and $Ar_1$ and $Ar_2$ are identical to each other, with the proviso that $Ar_1$ and $Ar_2$ are not phenyl at the same time.

Further, in Chemical Formula 1, $-L_2-Ar_1$ and $-L_3-Ar_2$ have different structures from each other, with the proviso that $Ar_1$ and $Ar_2$ are not phenyl at the same time.

Representative examples of the compound of Chemical Formula 1 are as follows:

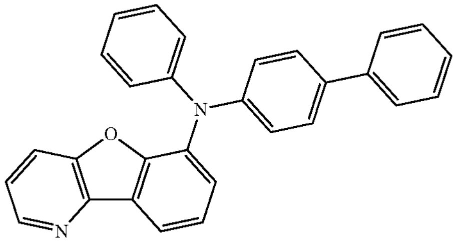

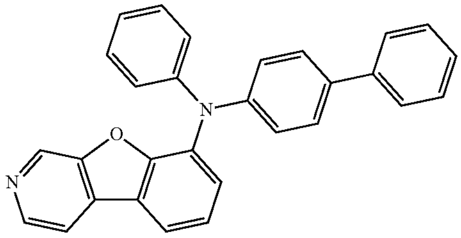

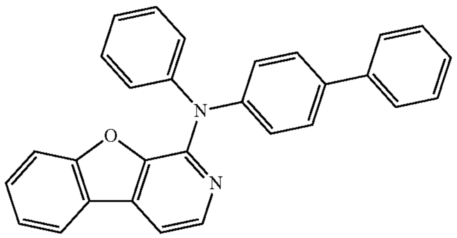

-continued

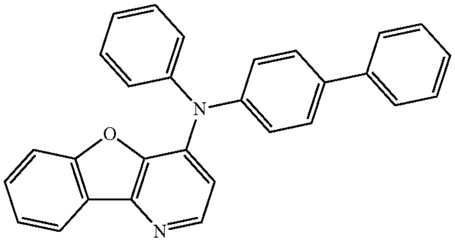

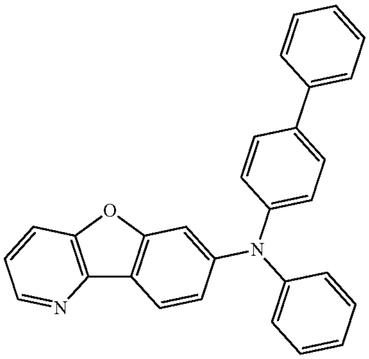

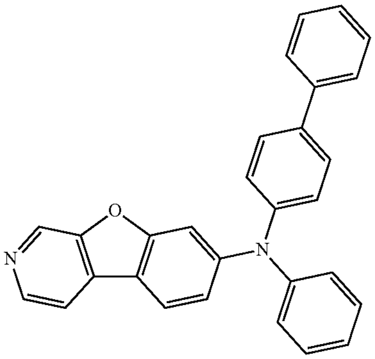

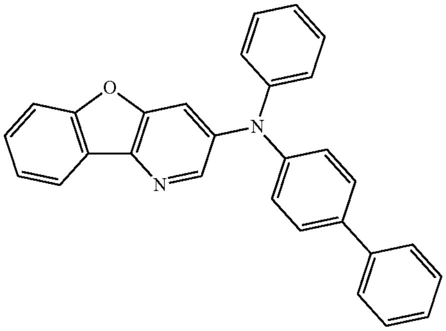

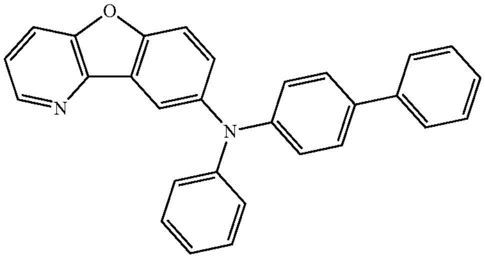

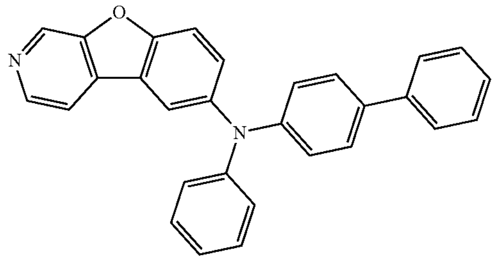
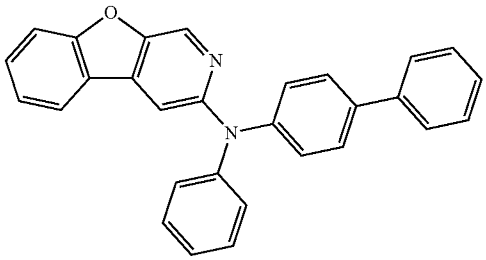
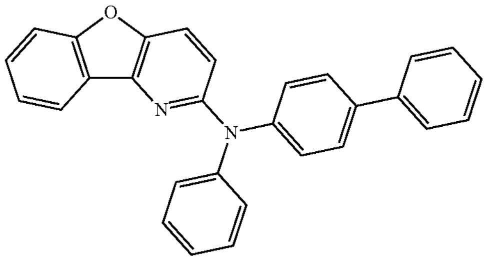
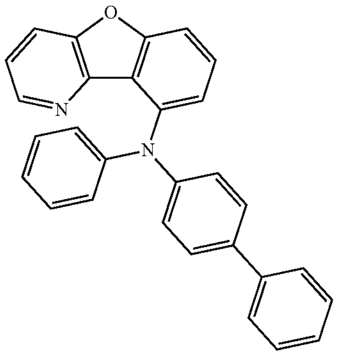
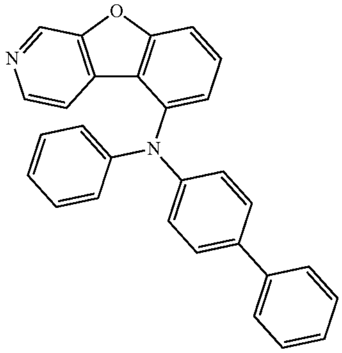
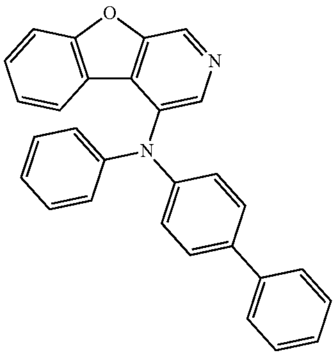
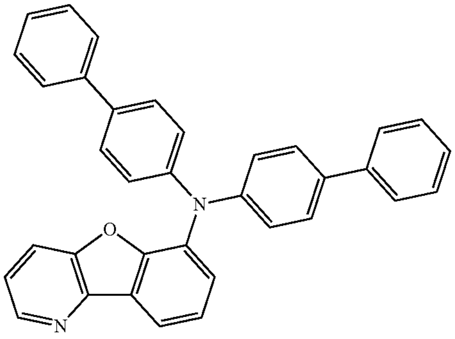
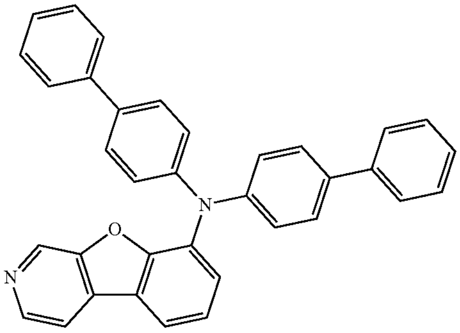
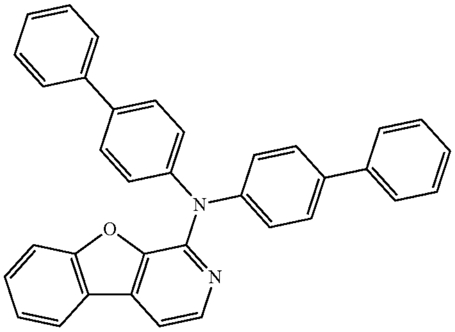
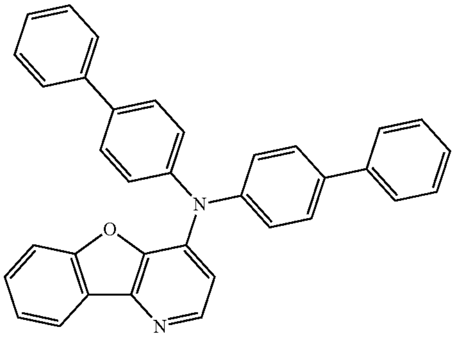

-continued
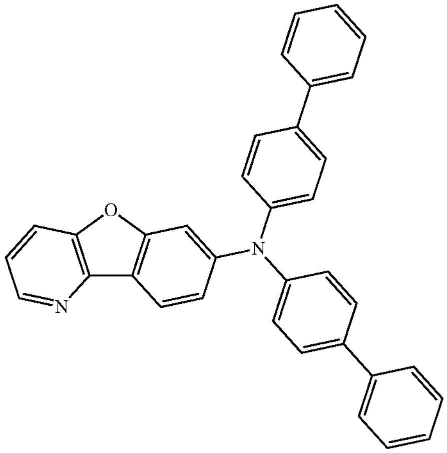
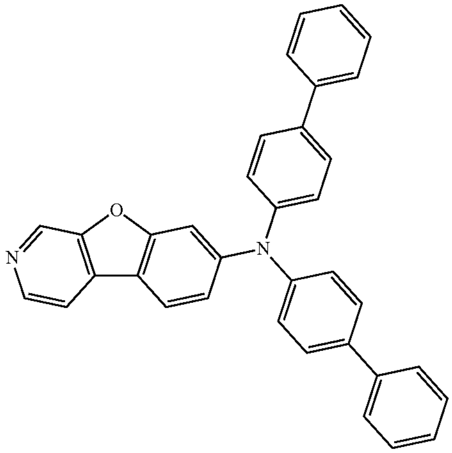
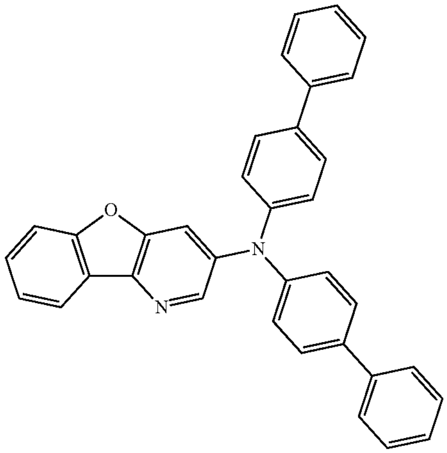
-continued
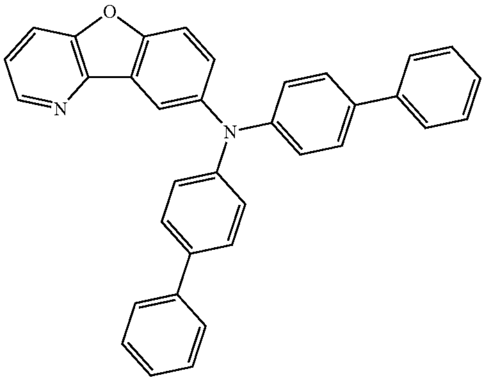
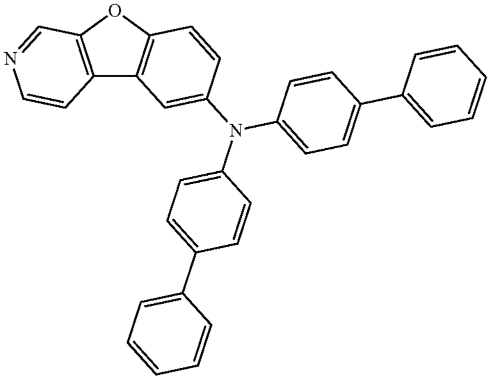
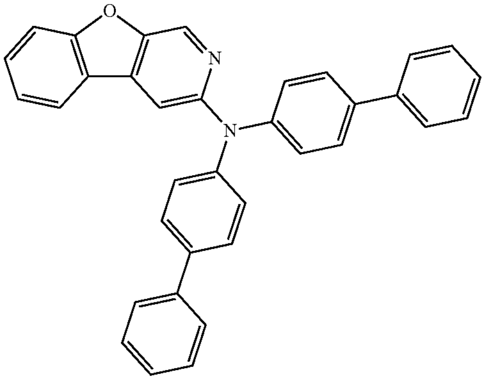
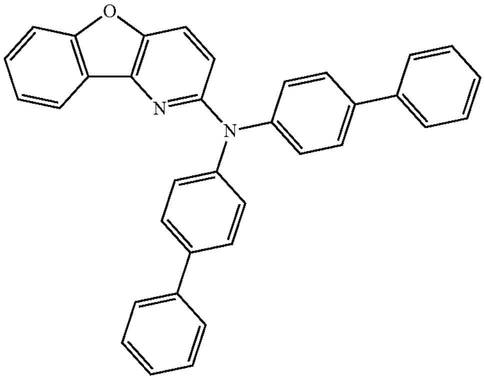

-continued
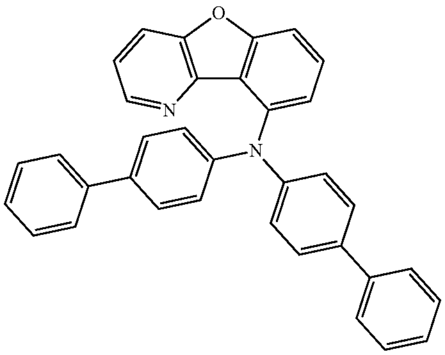
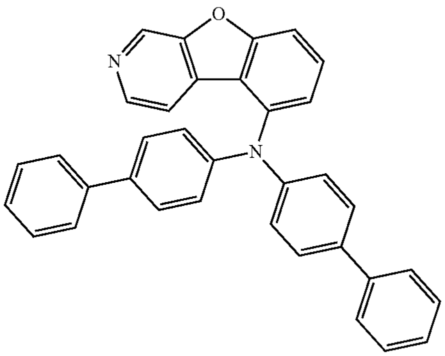
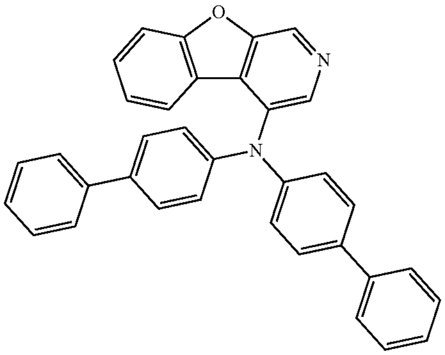
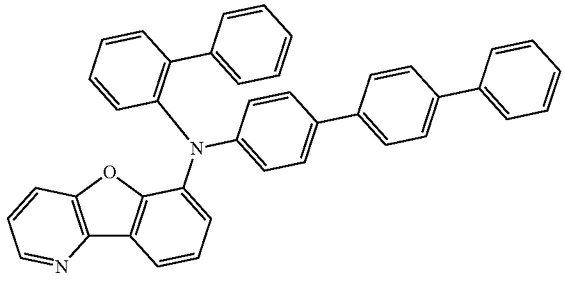
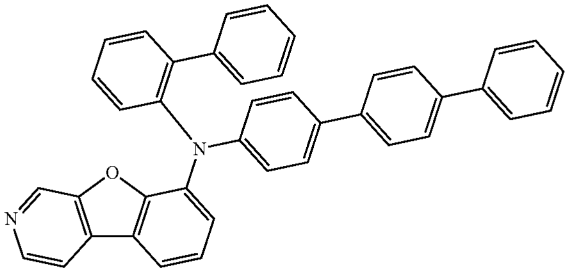
-continued
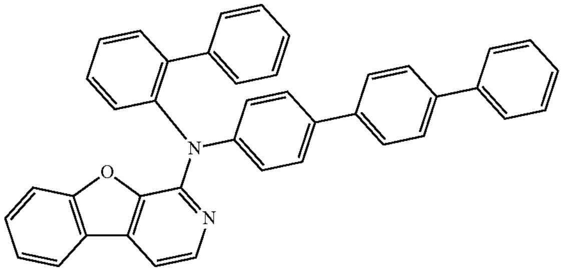
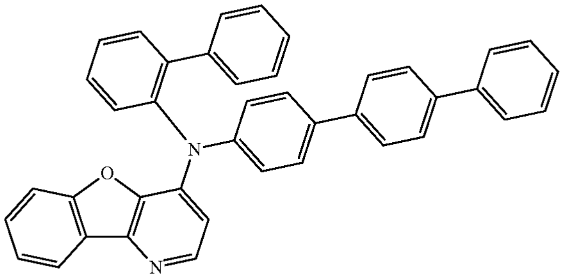
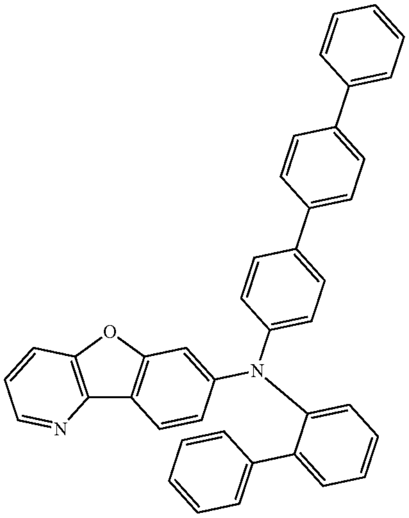
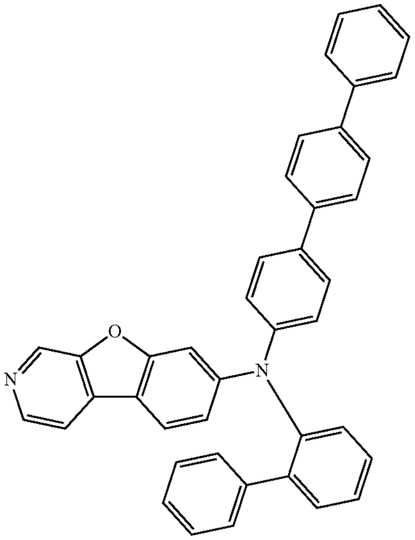

-continued
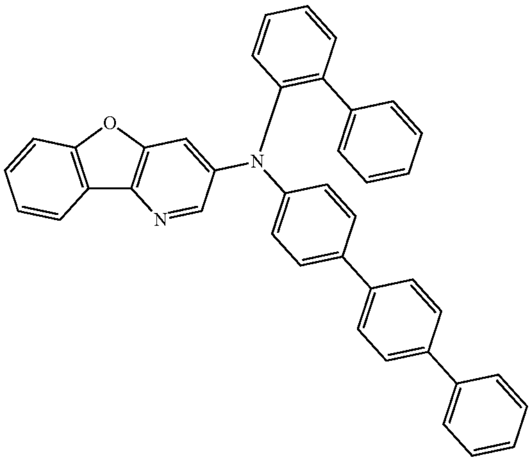
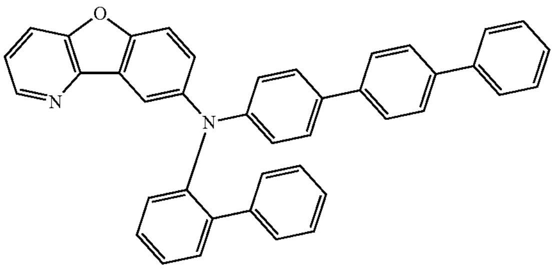
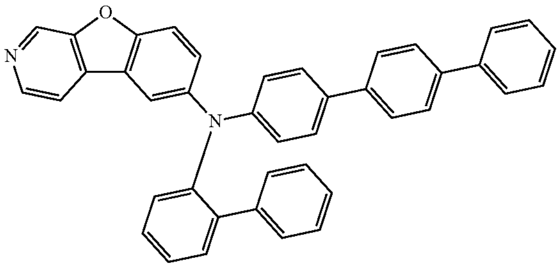
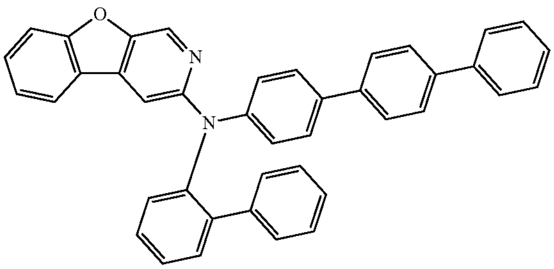
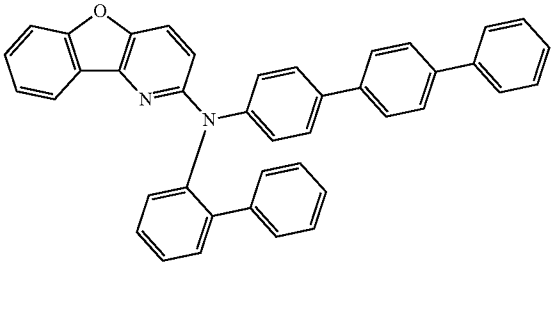
-continued
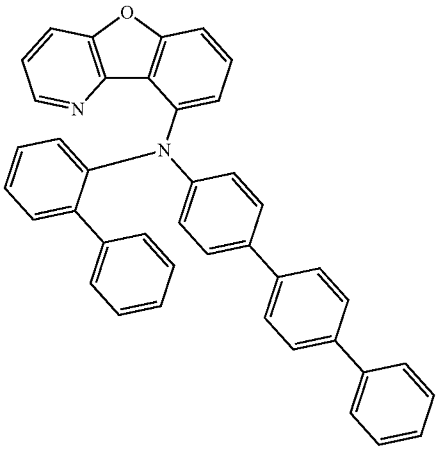
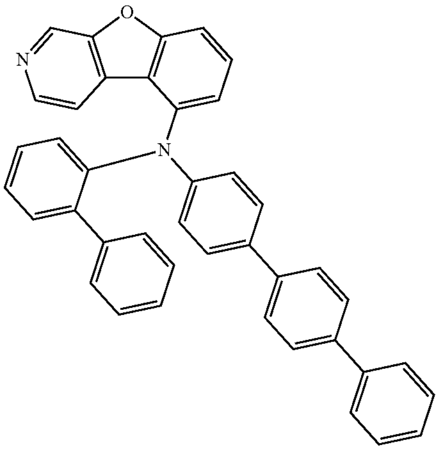
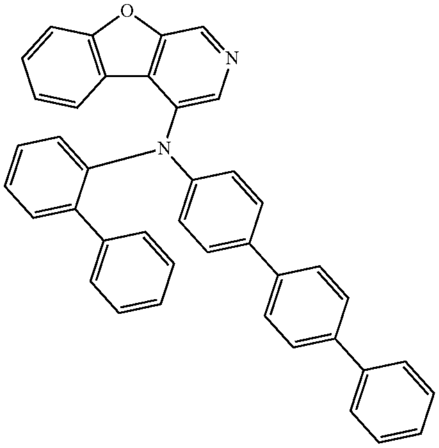
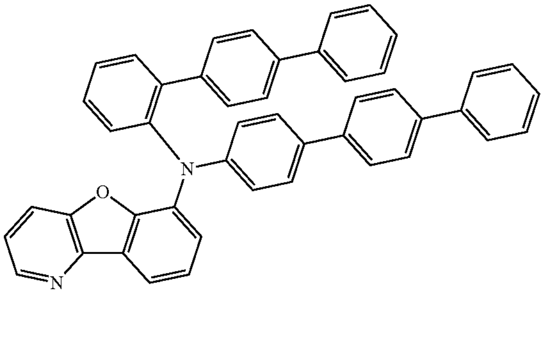

-continued
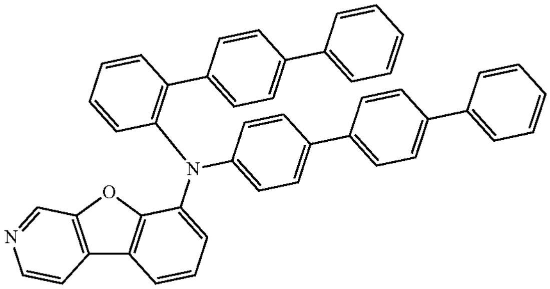
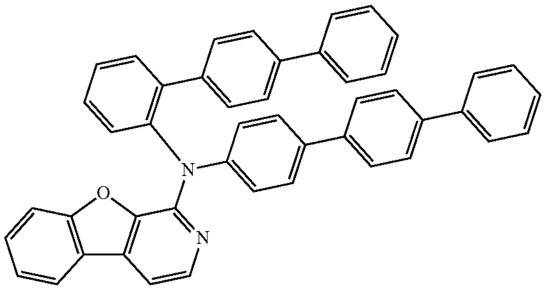
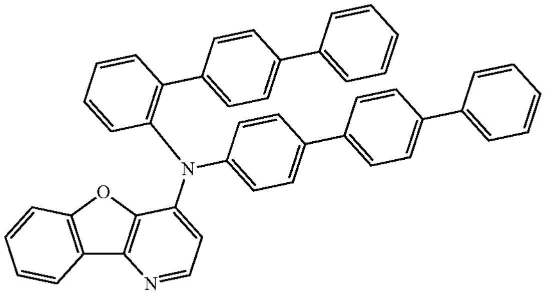
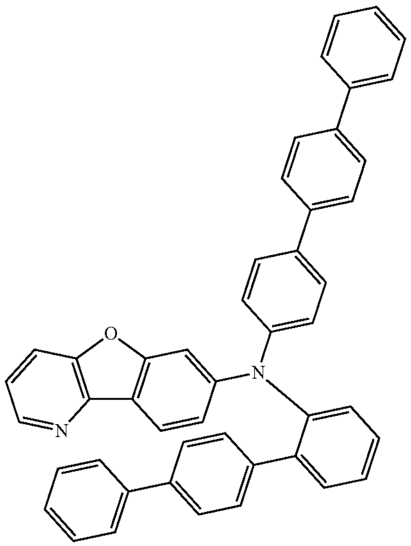
-continued
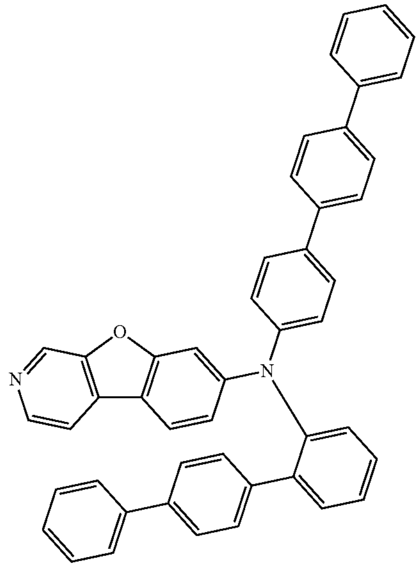
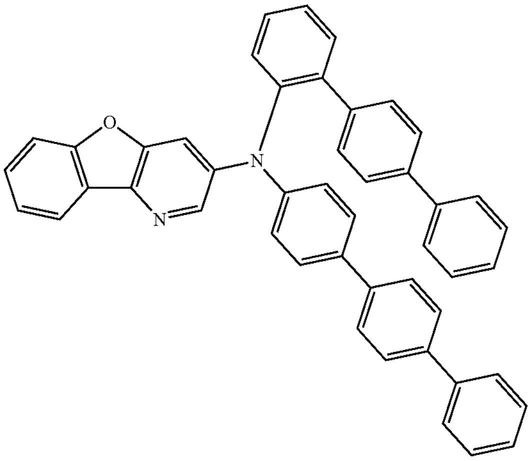
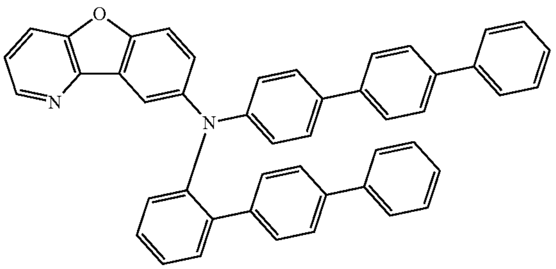
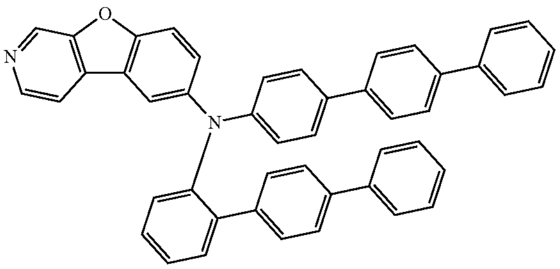

-continued
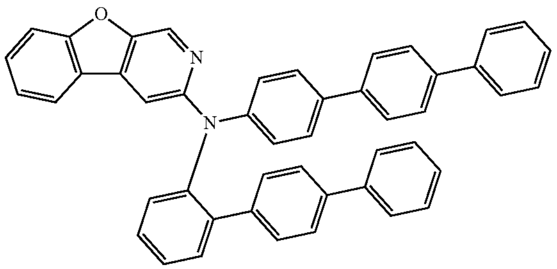
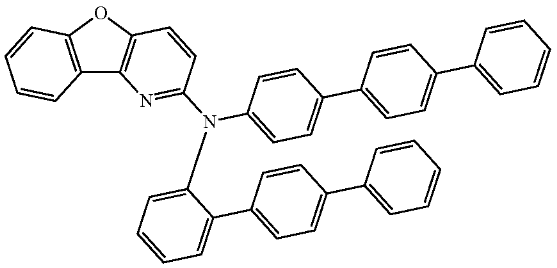
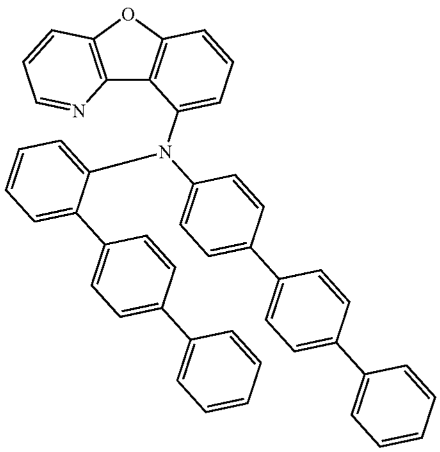
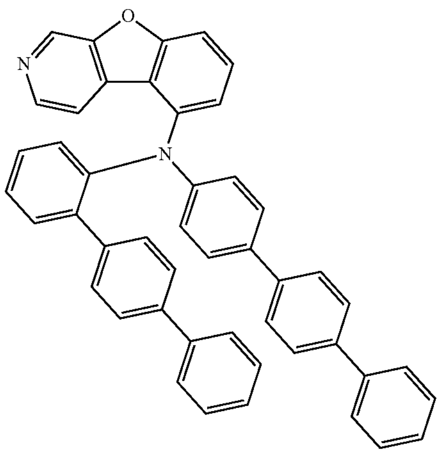
-continued
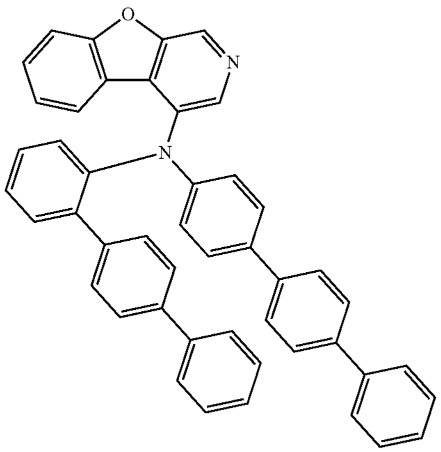
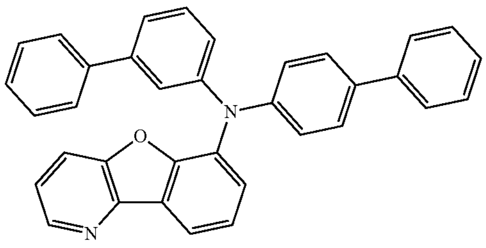
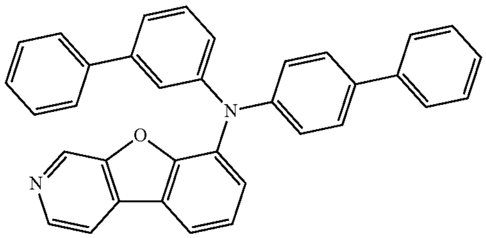
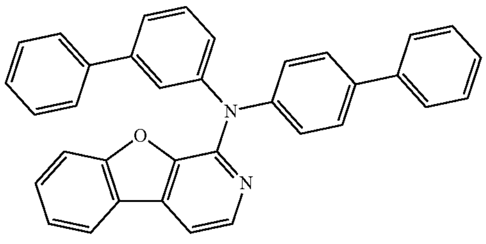
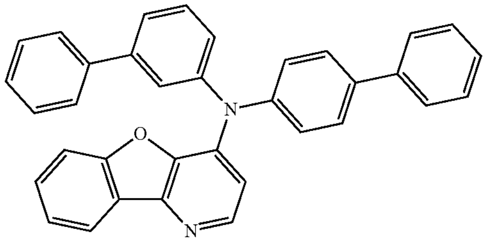

-continued
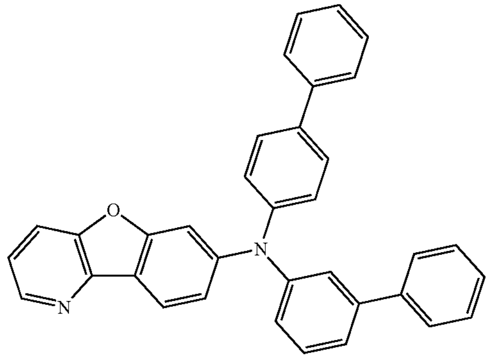
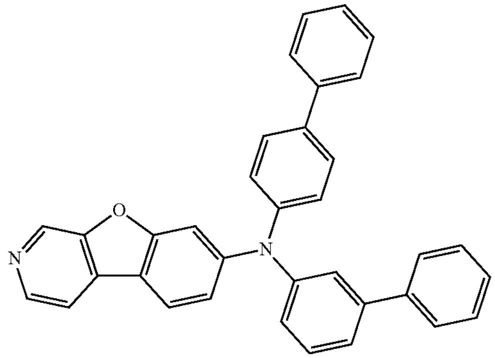
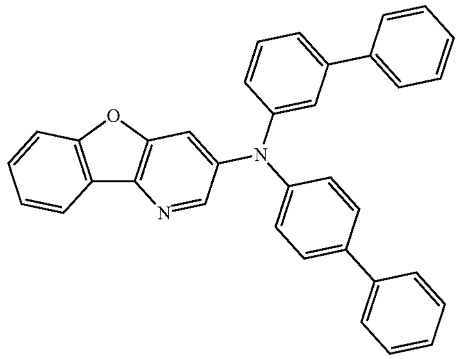
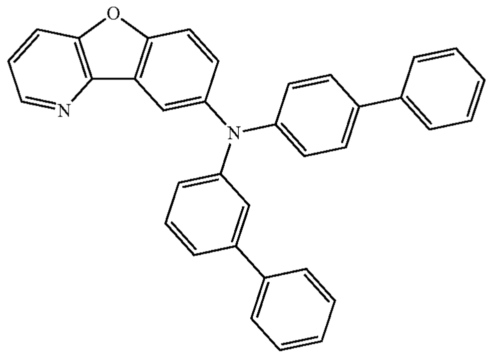
-continued
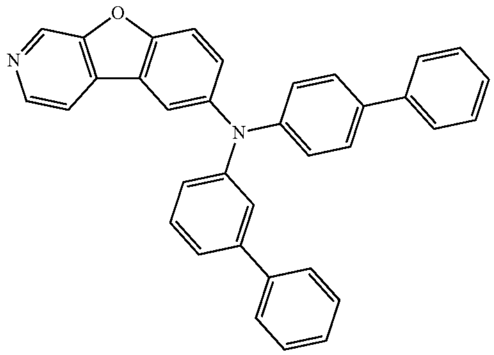
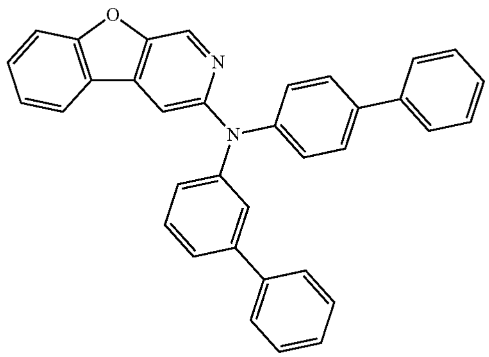
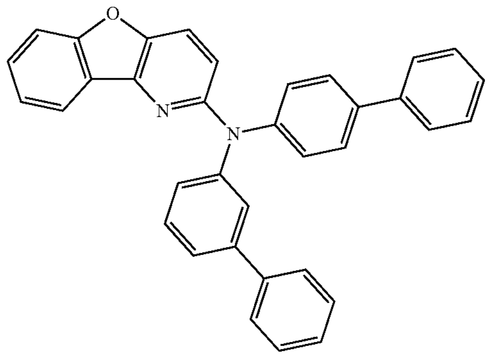
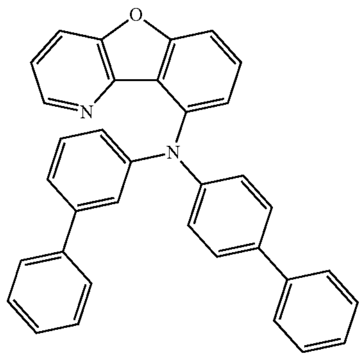

-continued
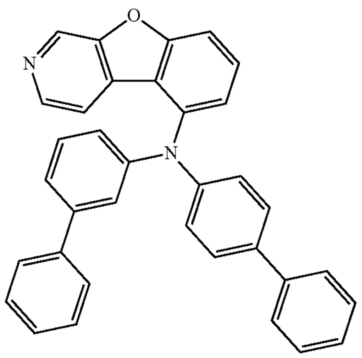
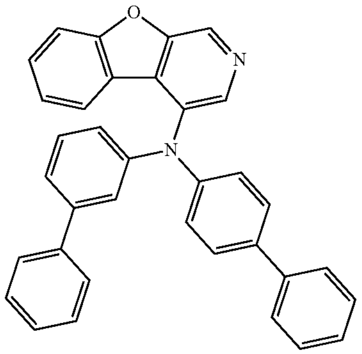
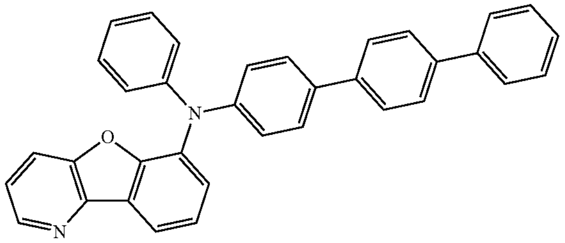
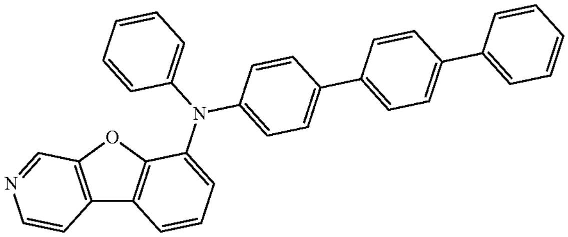
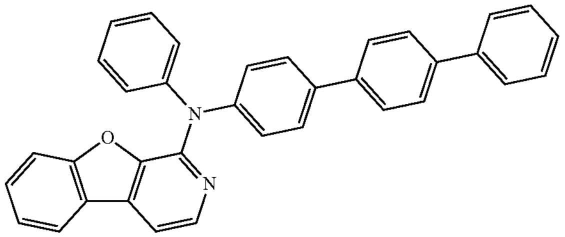
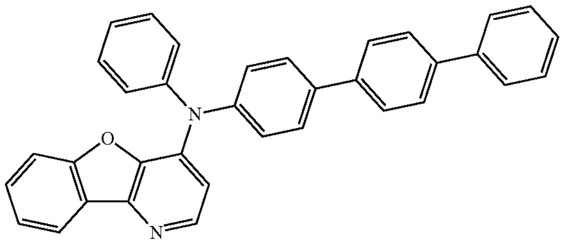
-continued
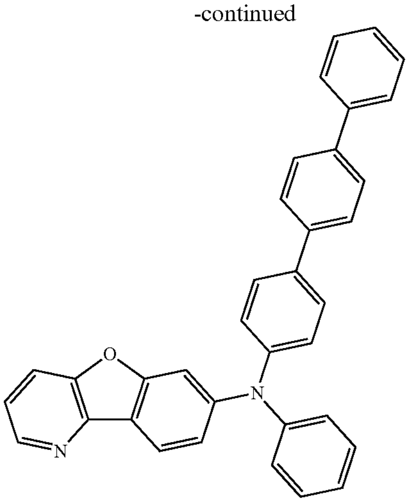
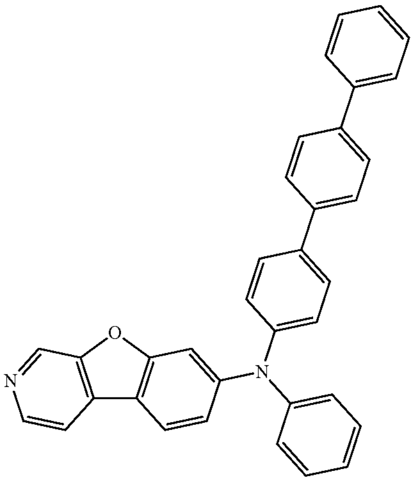
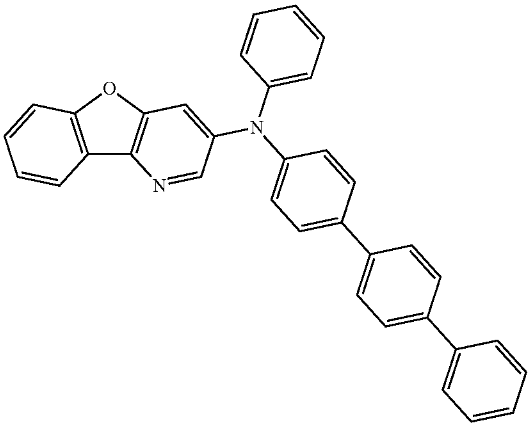
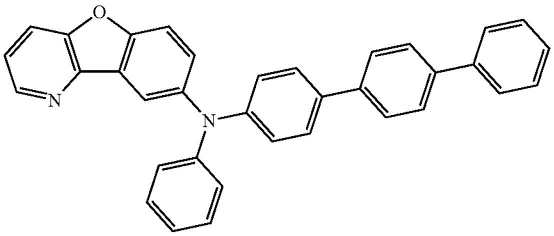

-continued
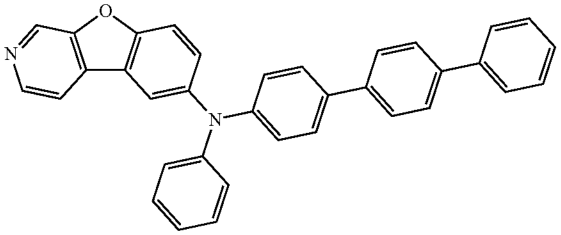
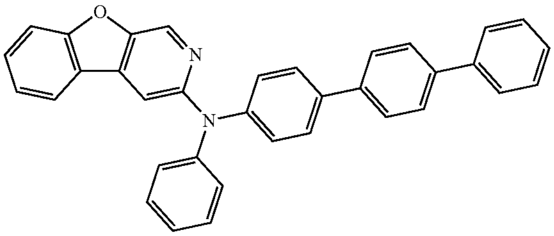
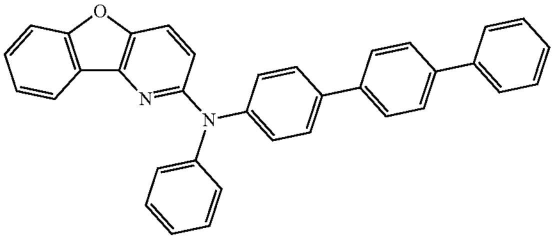
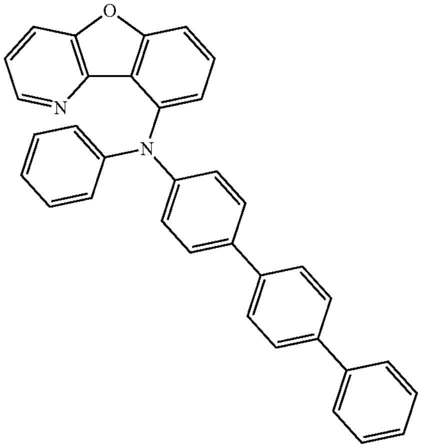
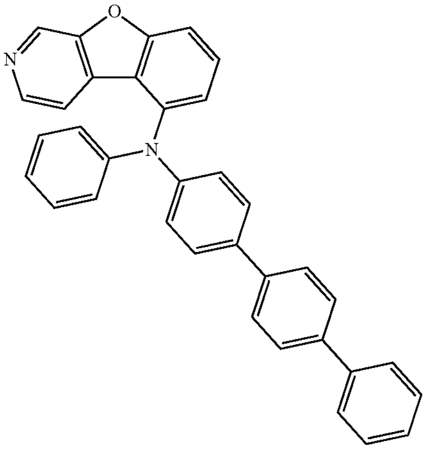
-continued
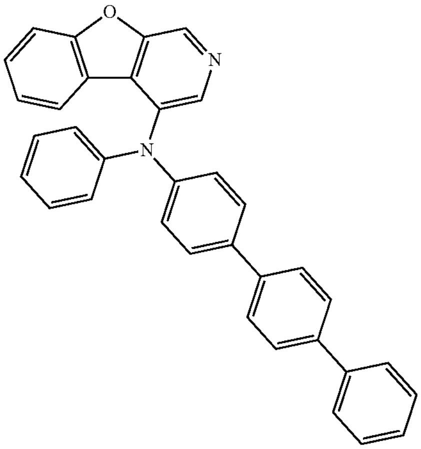
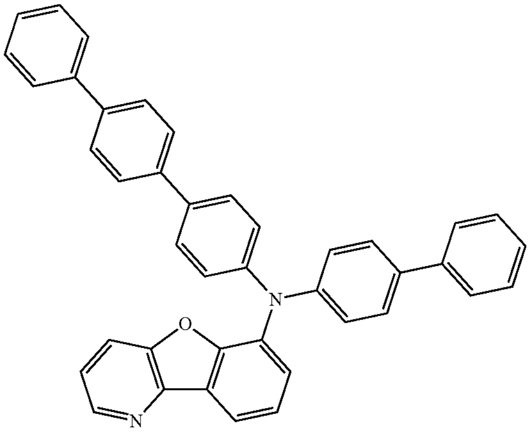
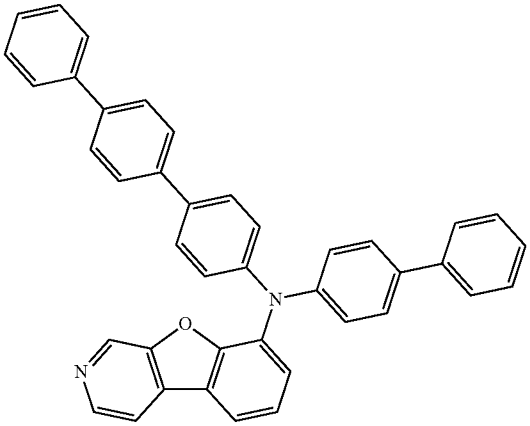

-continued
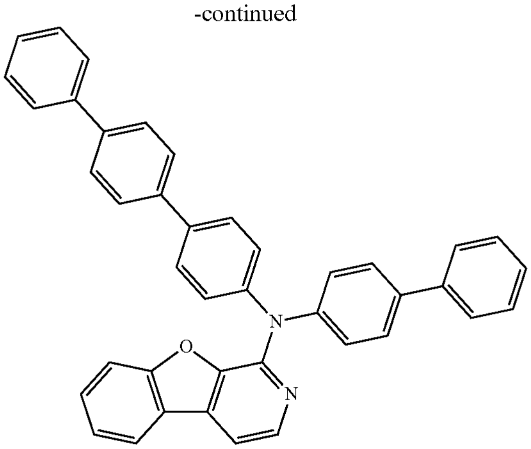
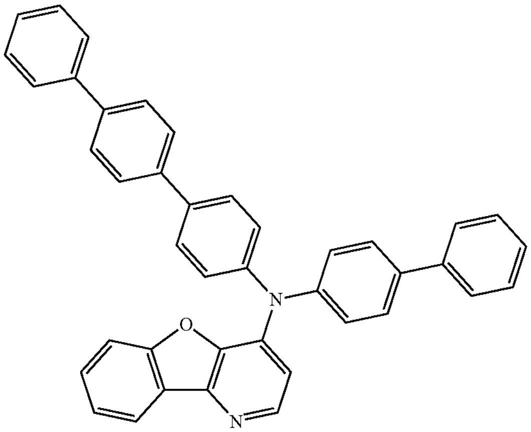
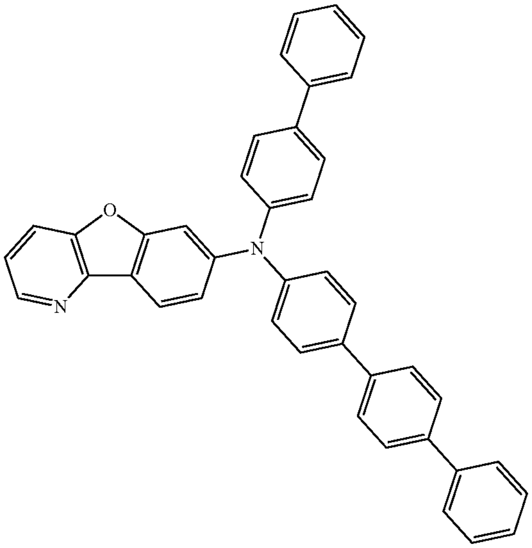
-continued
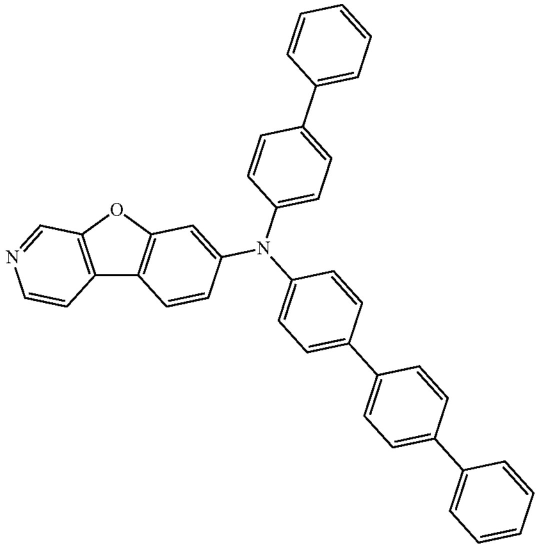
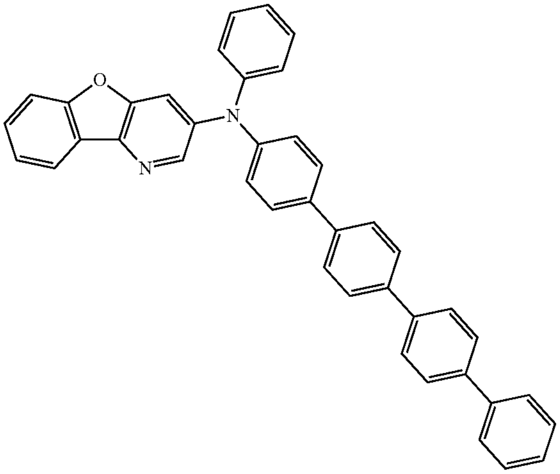
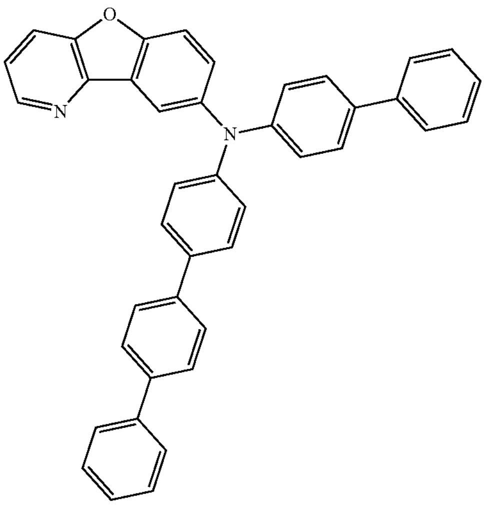

-continued
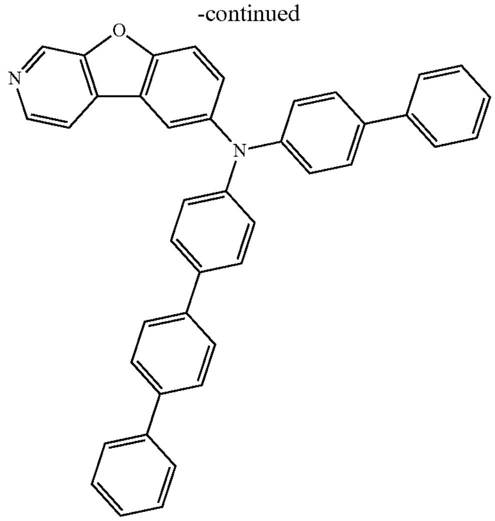
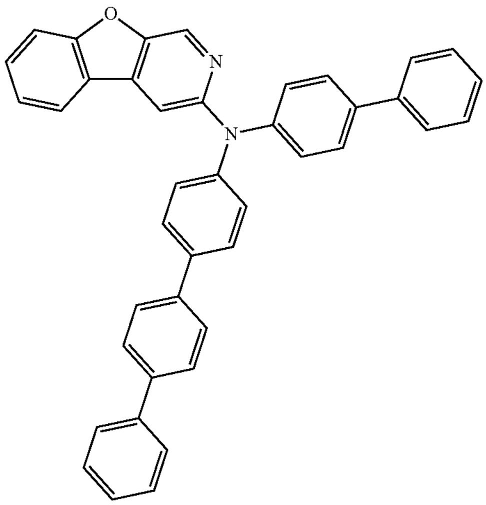
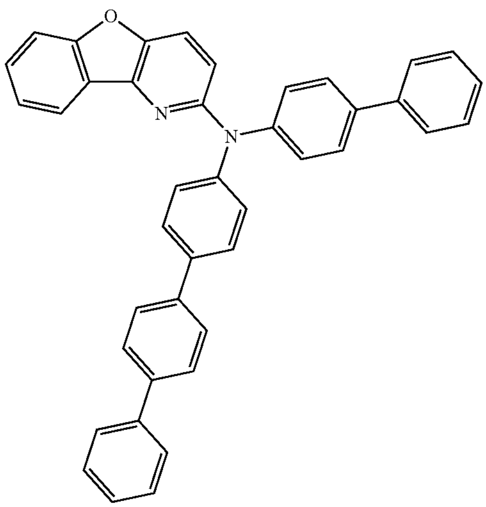
-continued
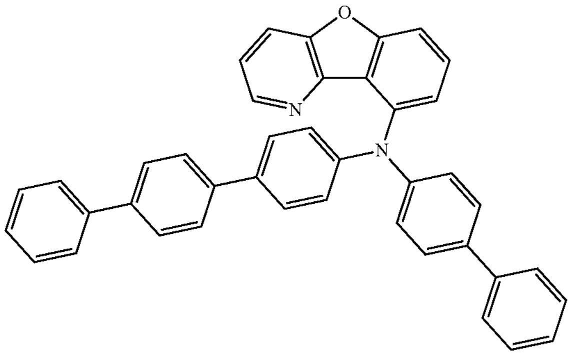
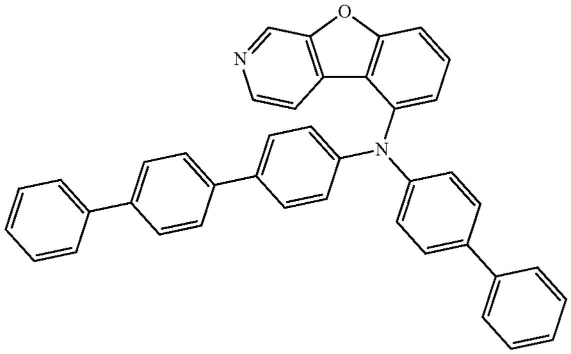
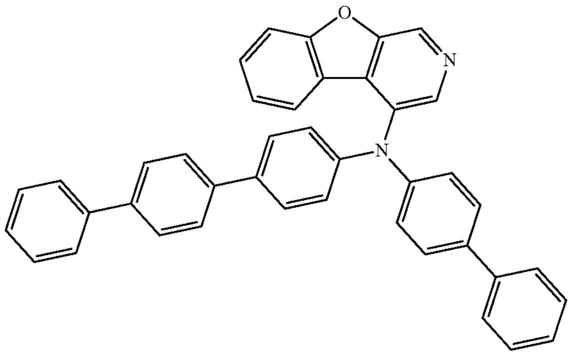
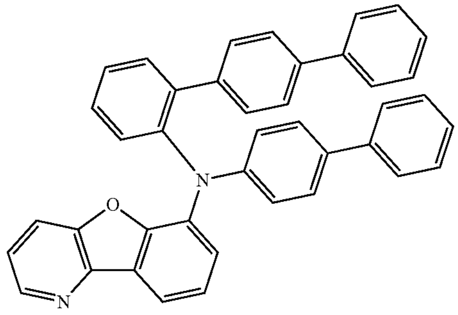
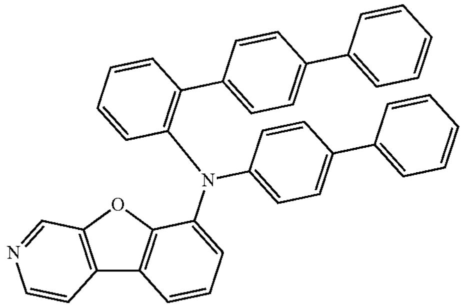

-continued
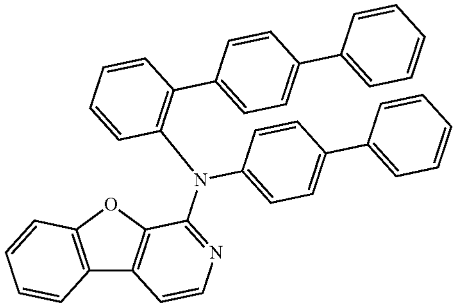
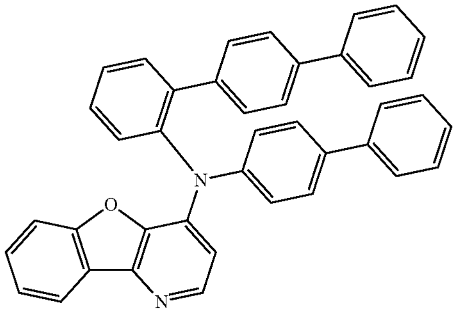
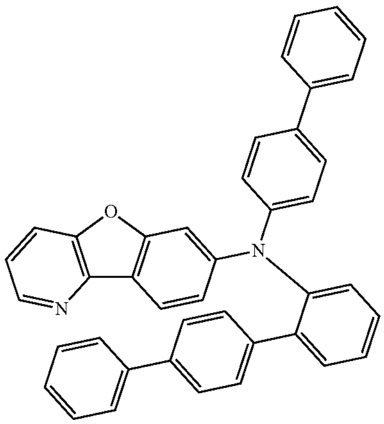
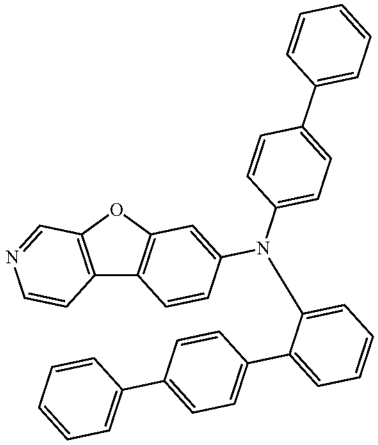
-continued
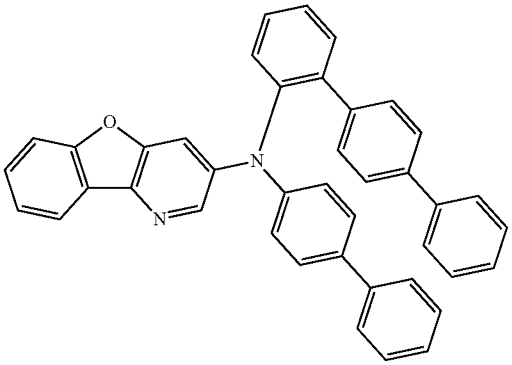
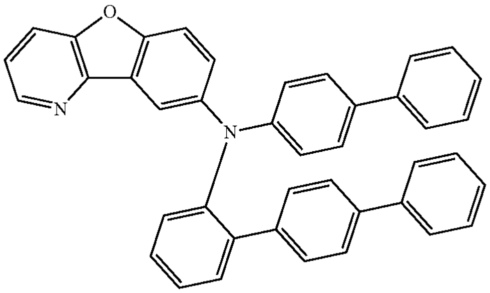
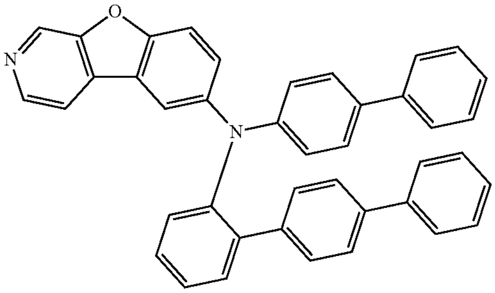
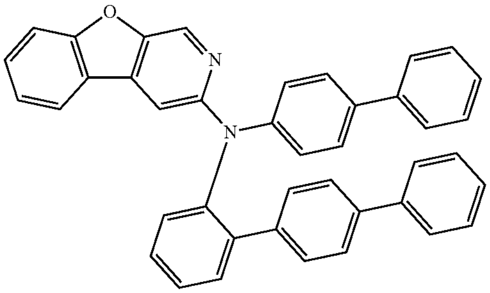
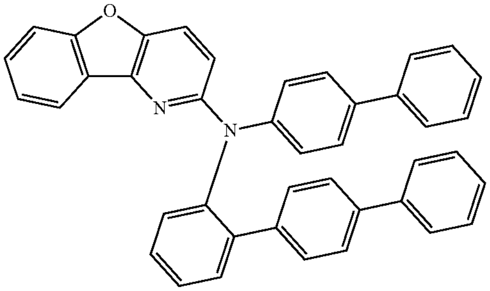

-continued
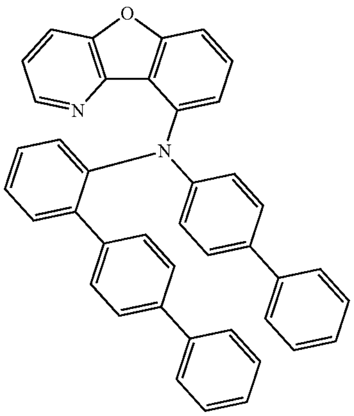
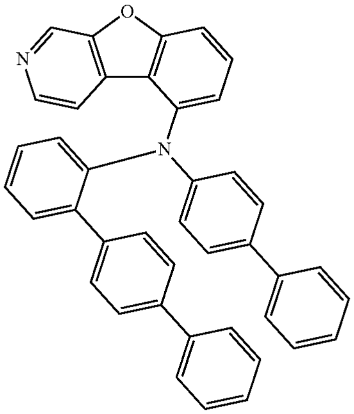
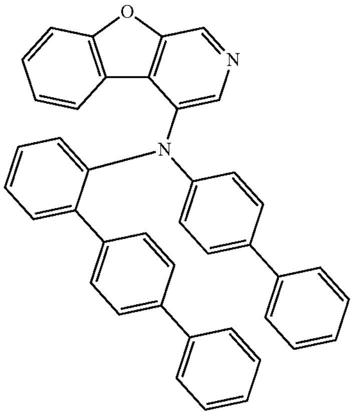
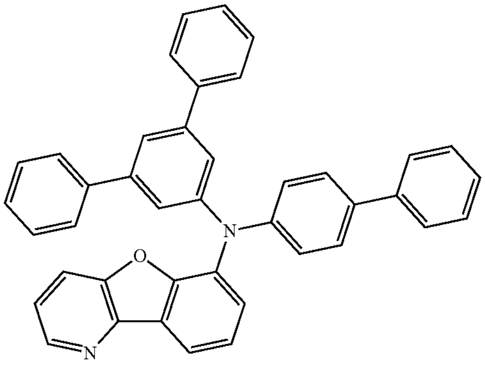
-continued
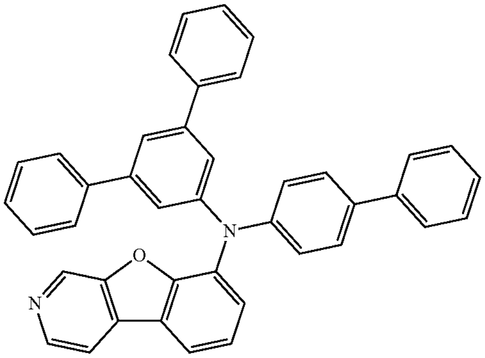
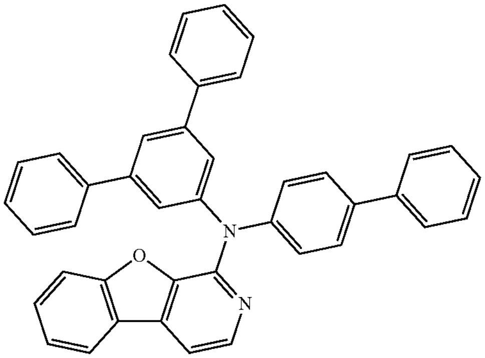
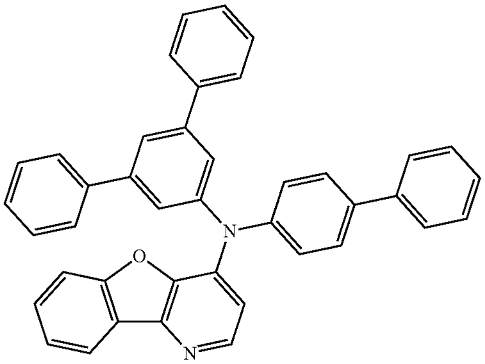
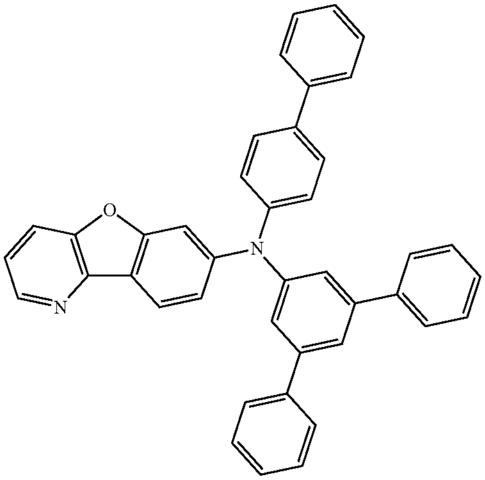

-continued
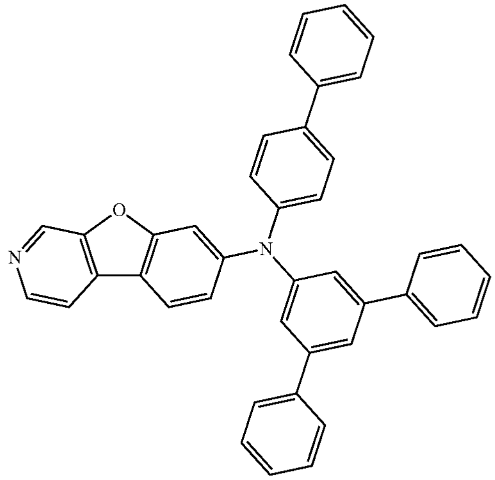
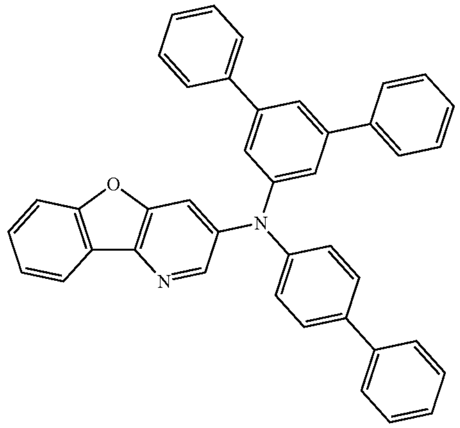
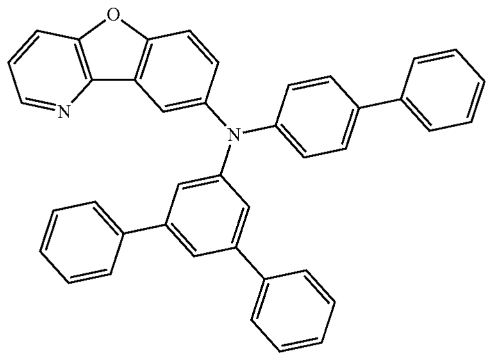
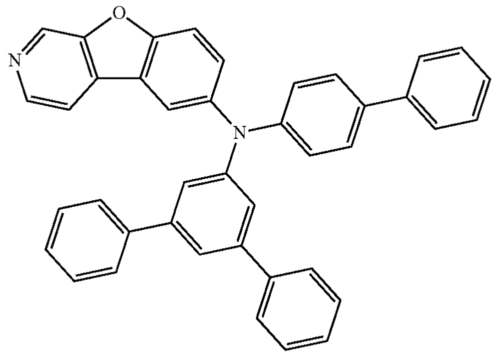
-continued
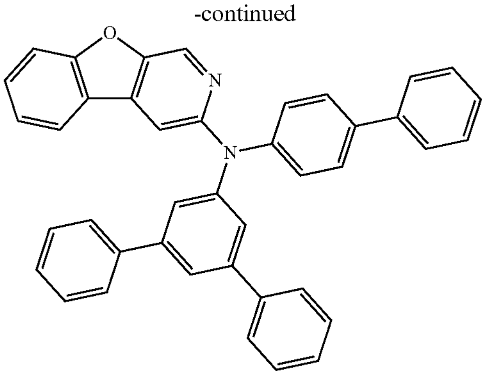
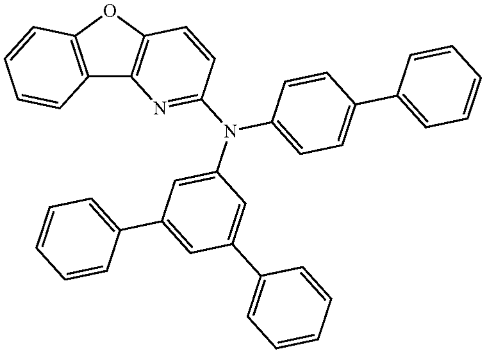
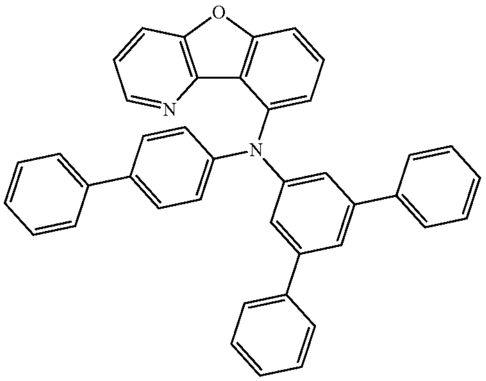
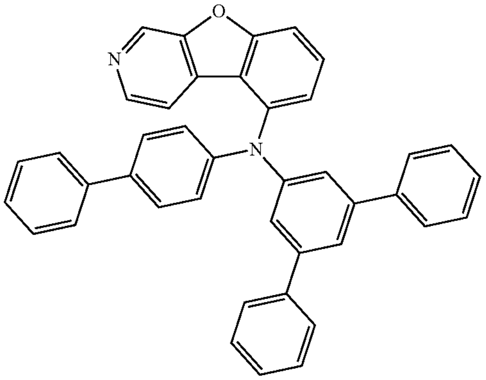

-continued
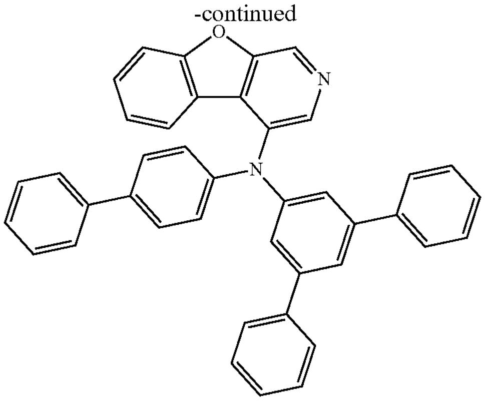
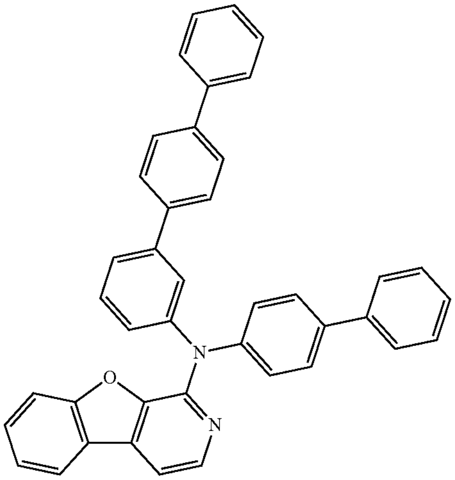
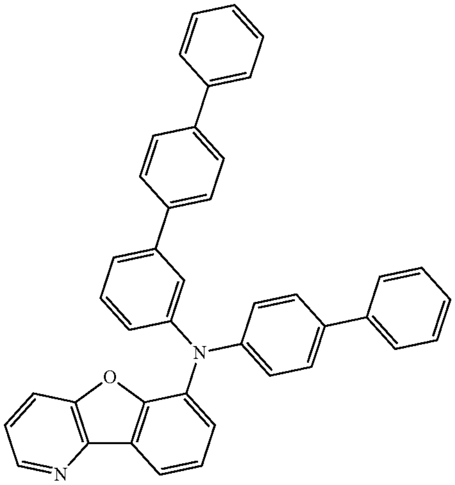
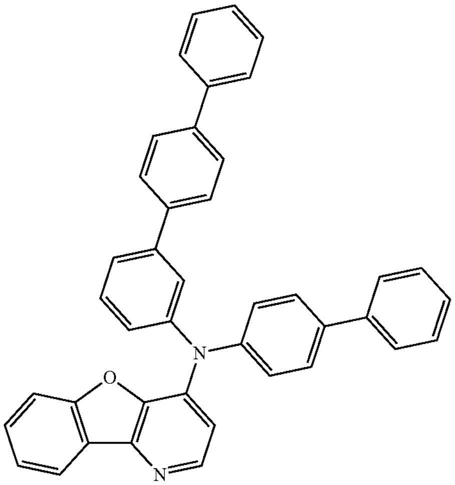
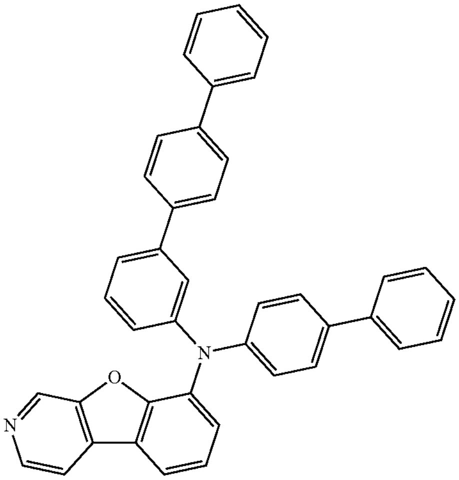
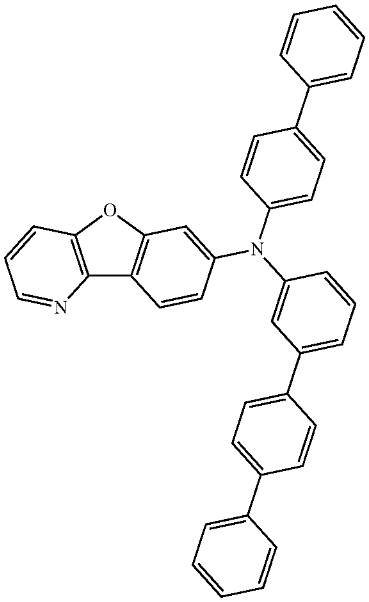

-continued
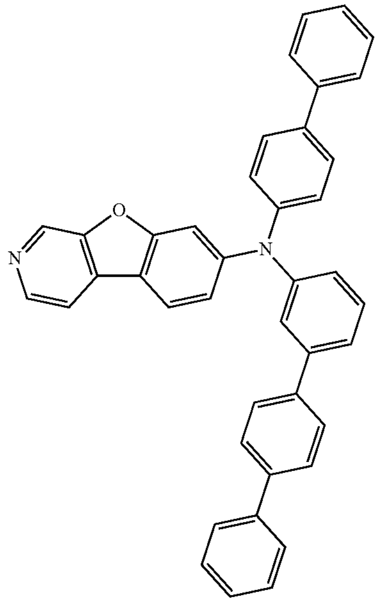
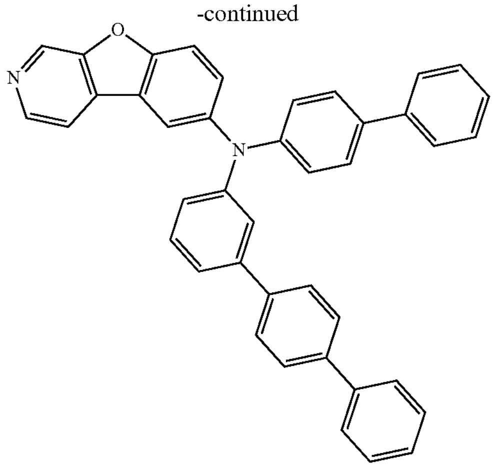
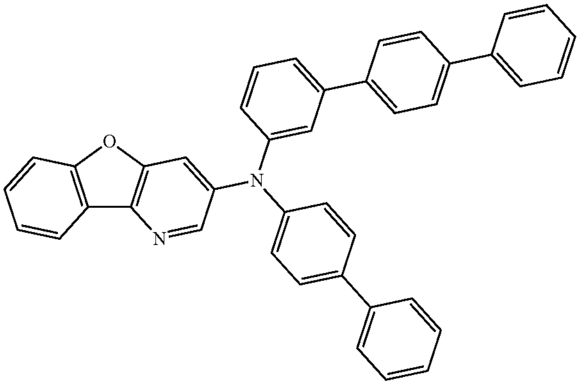
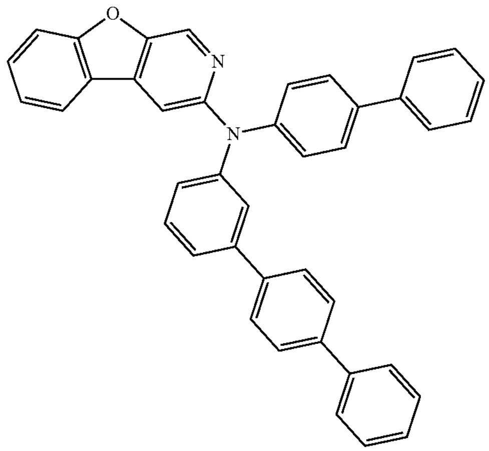
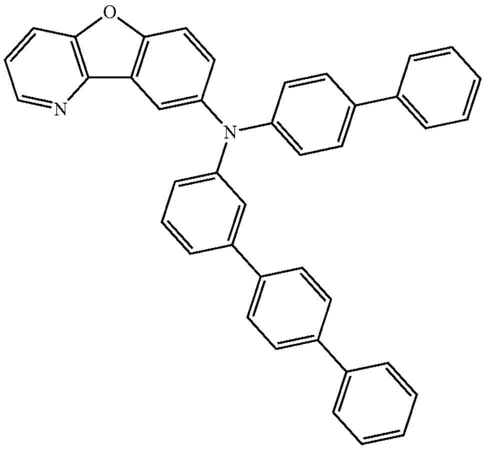
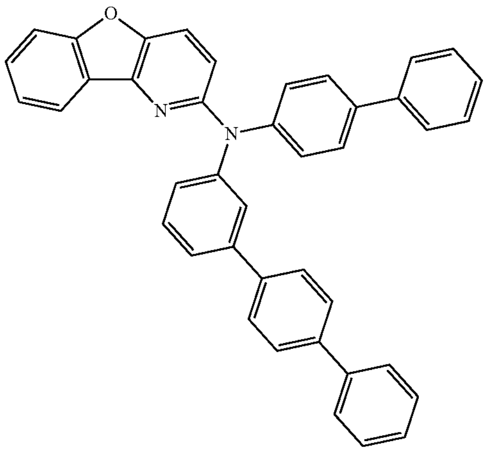

-continued
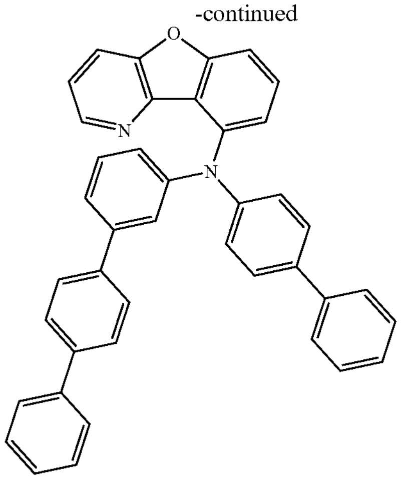
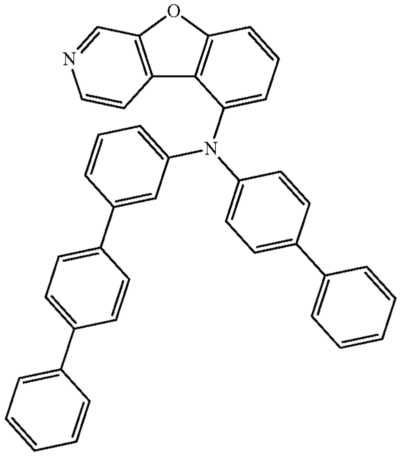
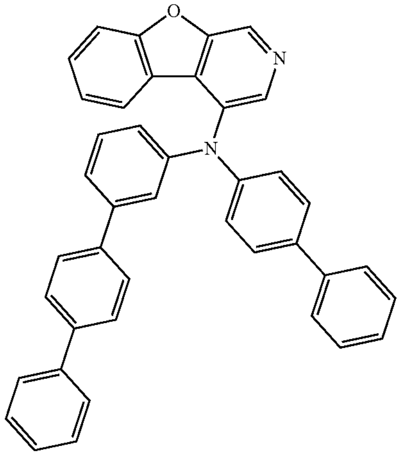
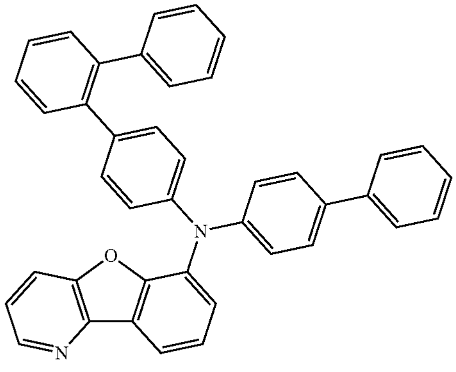
-continued
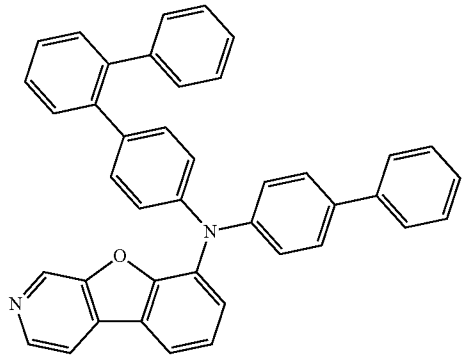
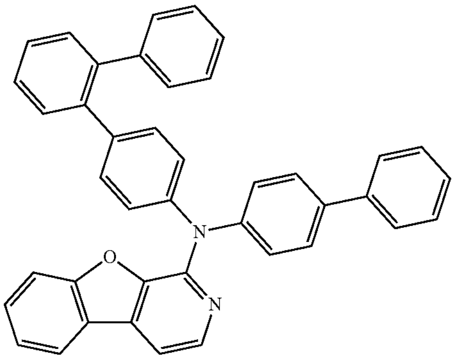
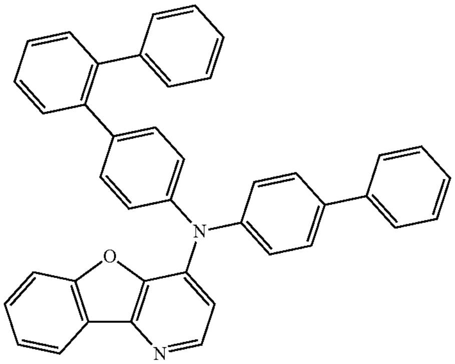
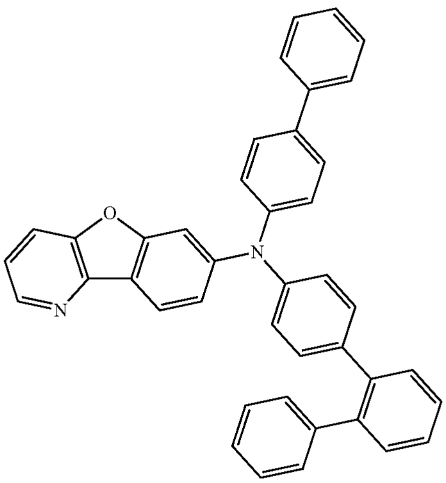

-continued
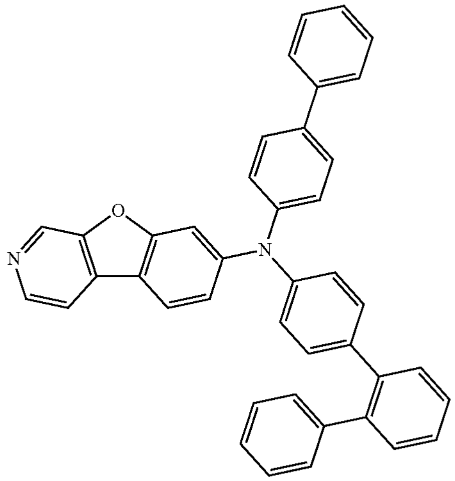
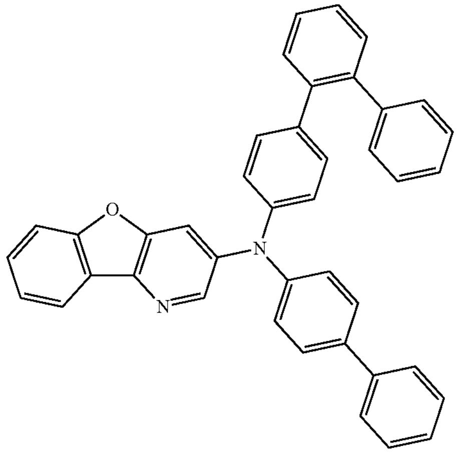
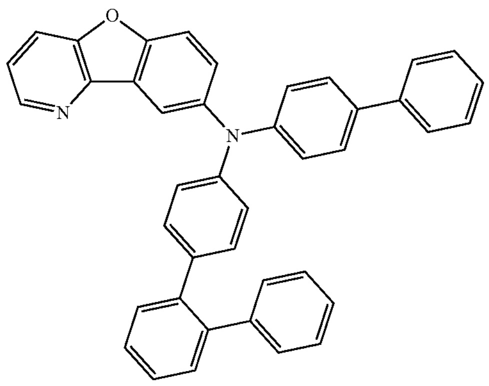
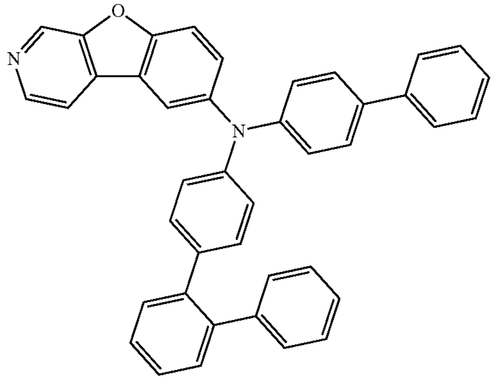
-continued
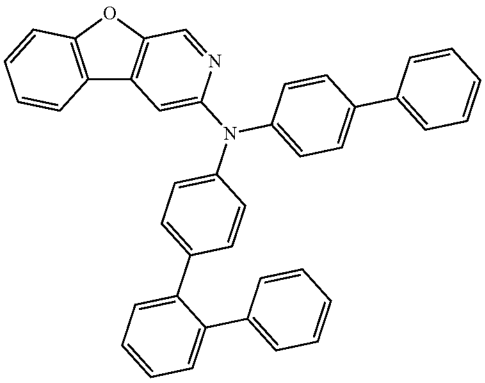
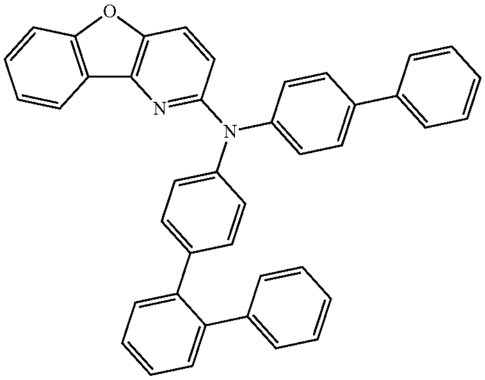
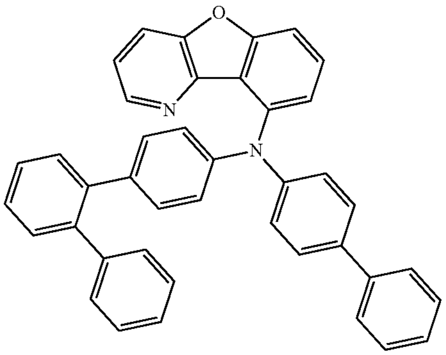
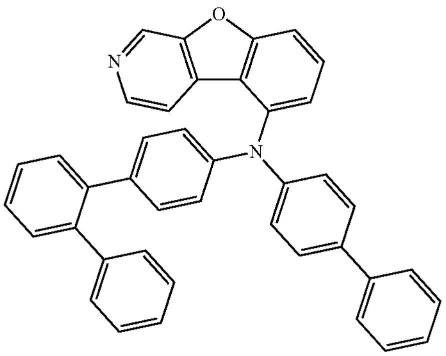

-continued
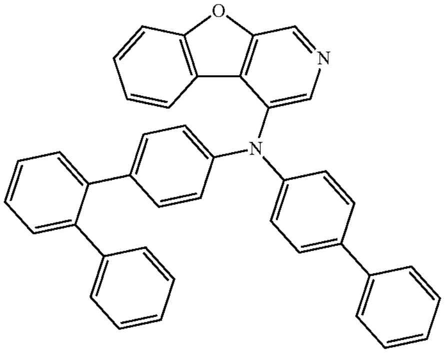
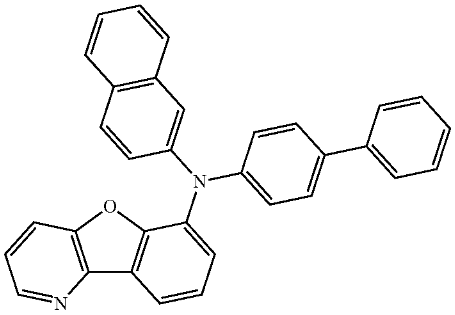
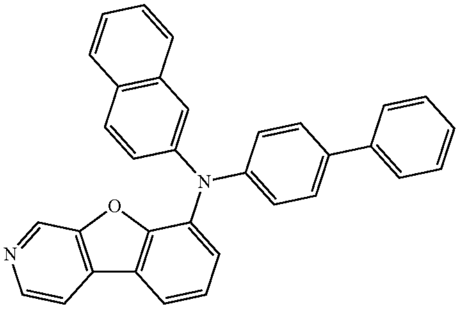
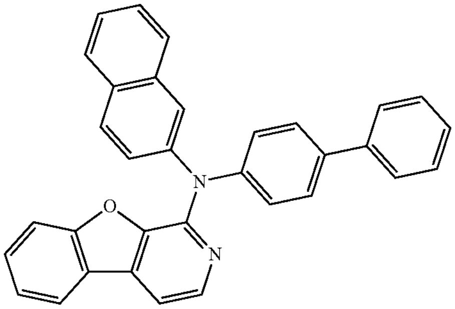
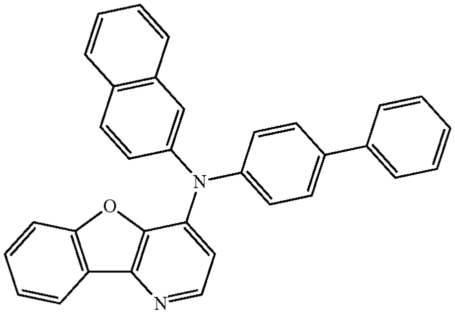
-continued
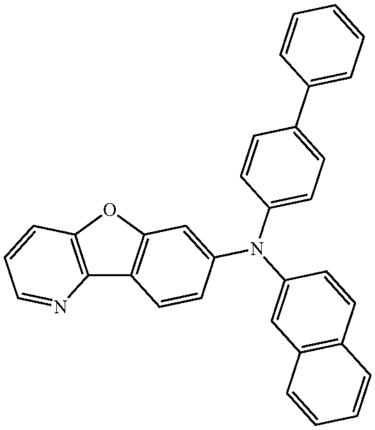
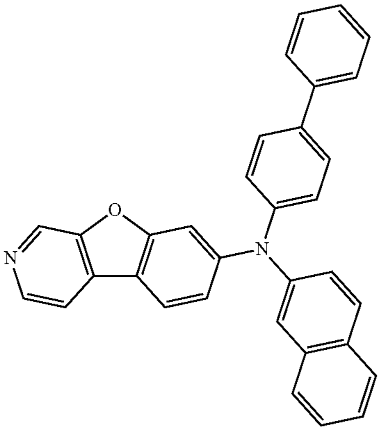
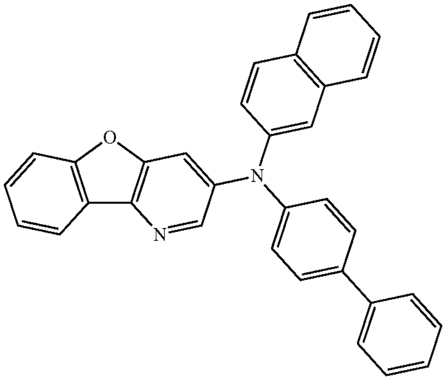
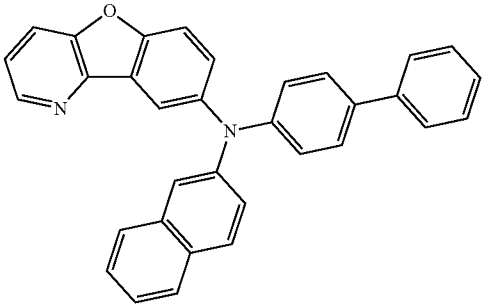

-continued
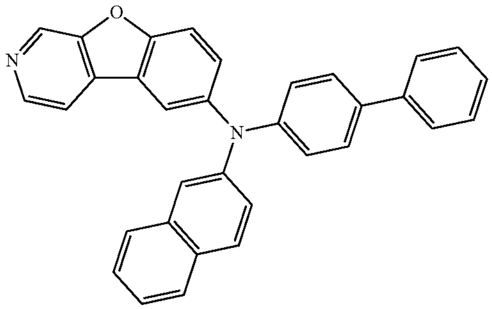
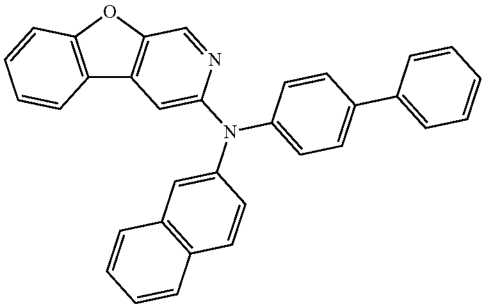
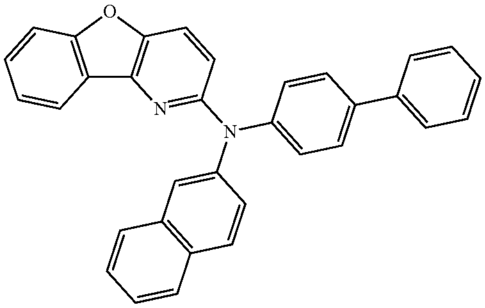
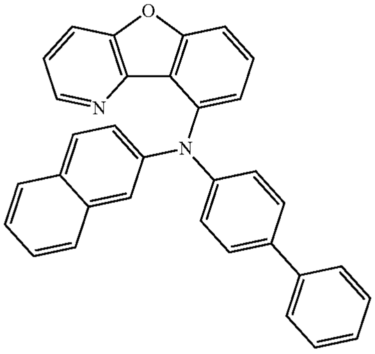
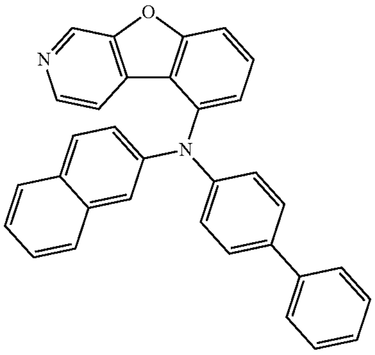
-continued
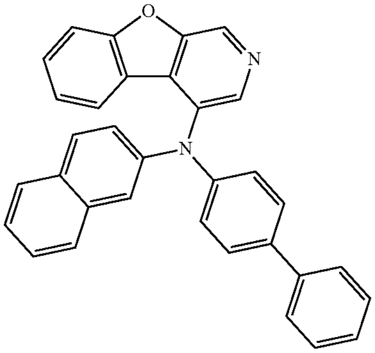
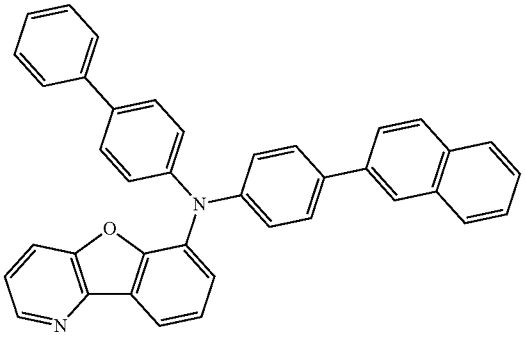
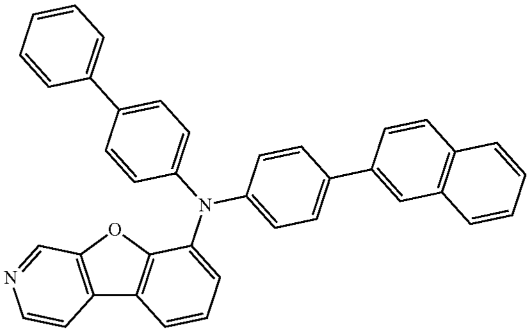
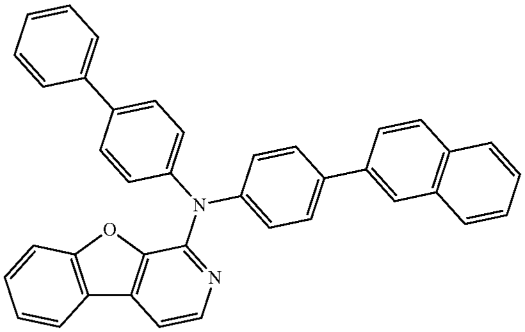
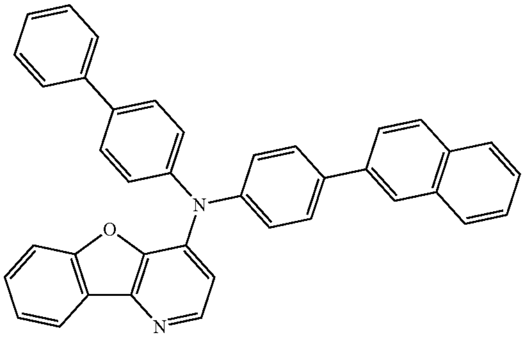

-continued
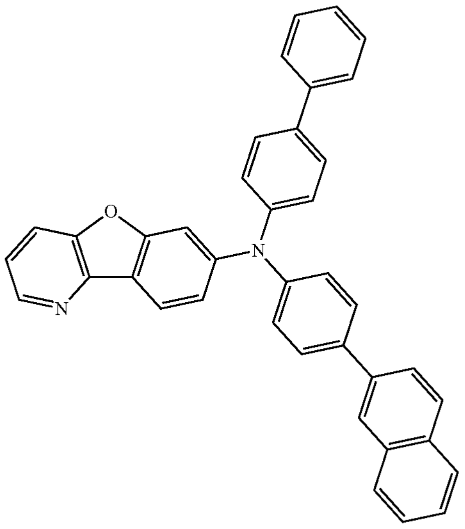
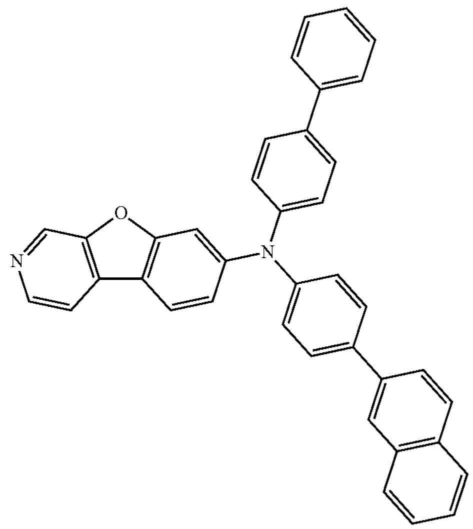
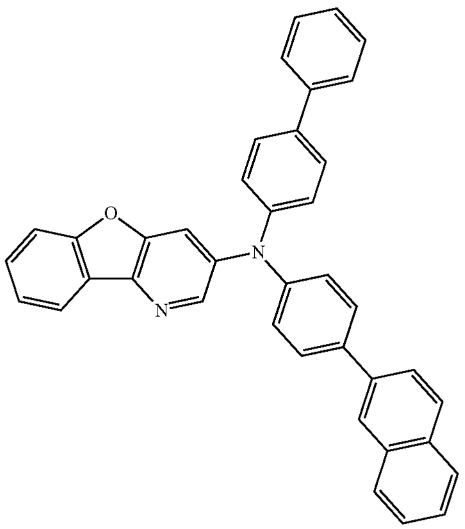
-continued
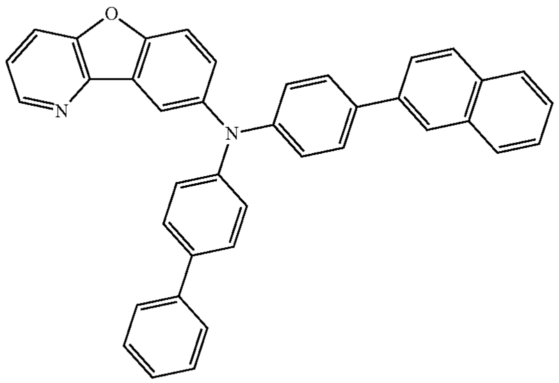
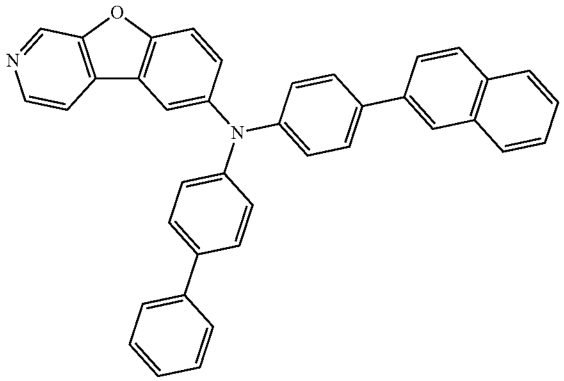
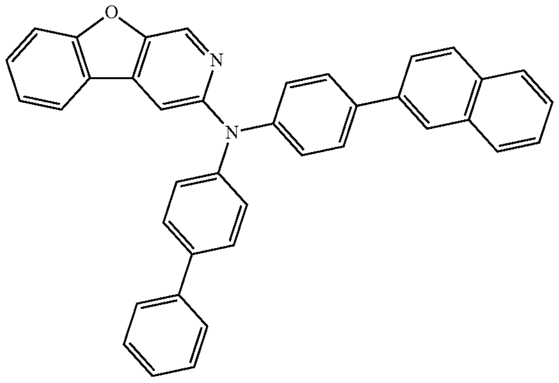
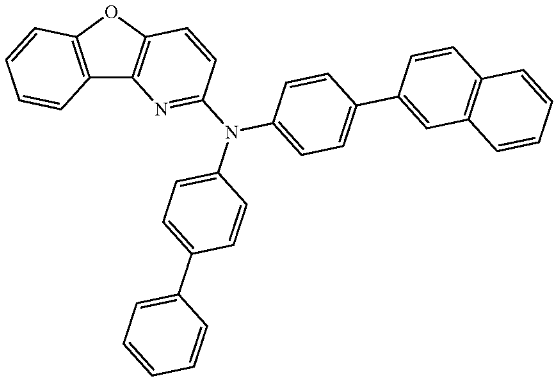

-continued
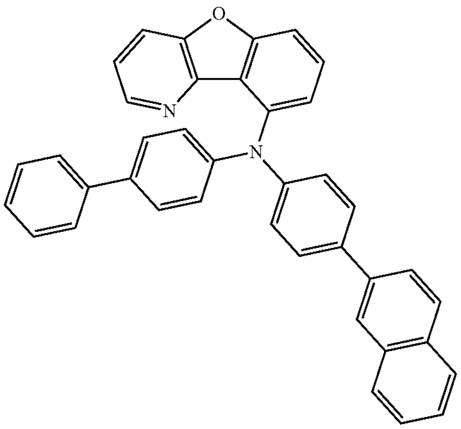
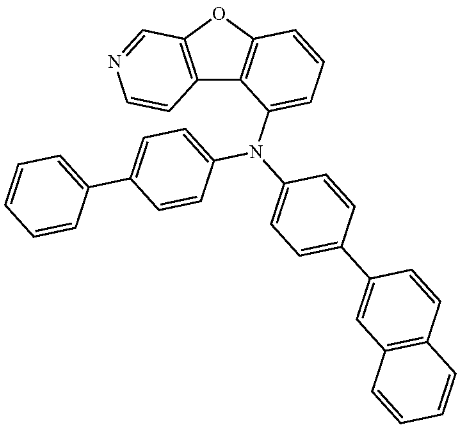
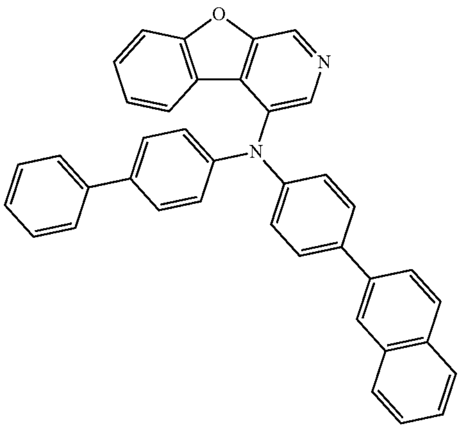
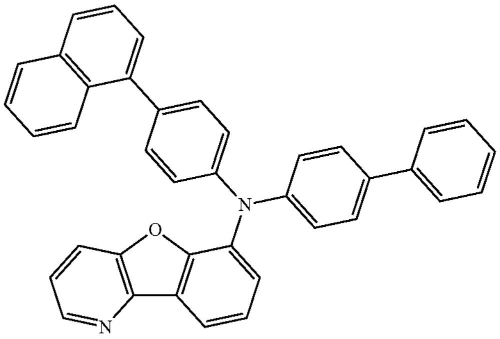
-continued
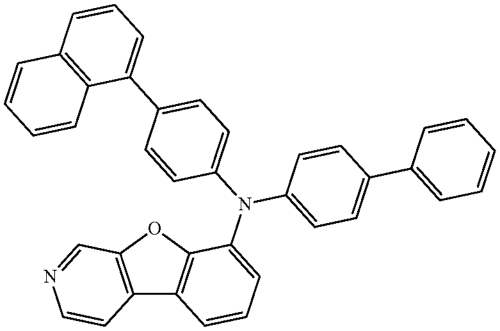
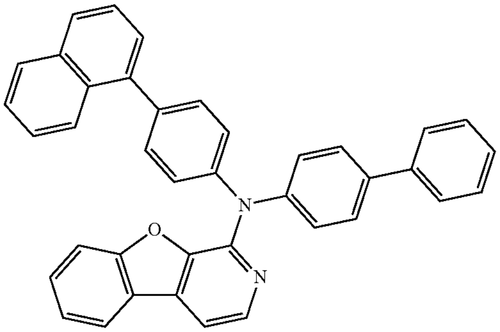
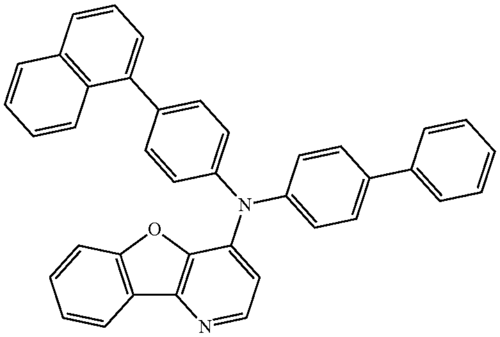
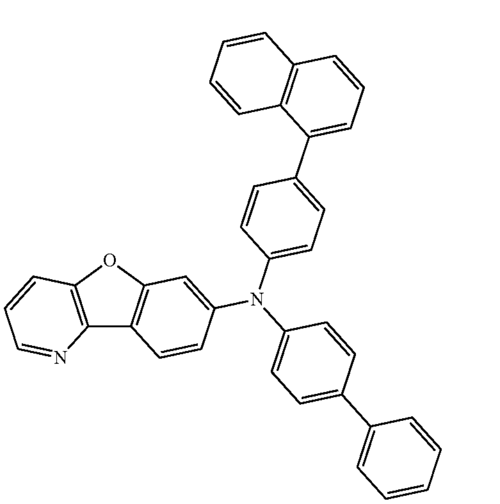

-continued
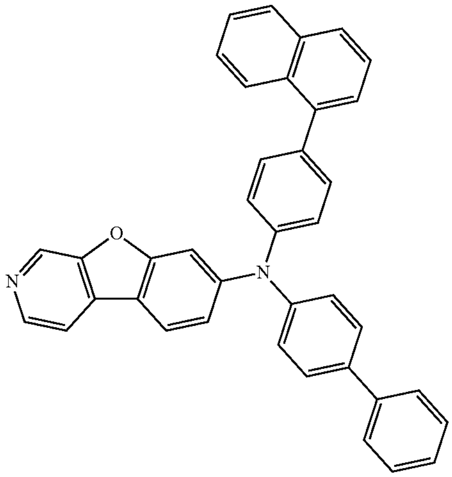
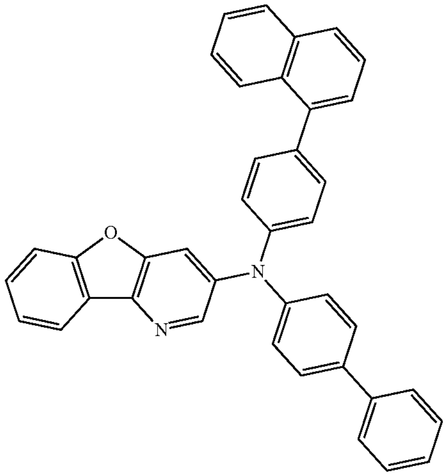
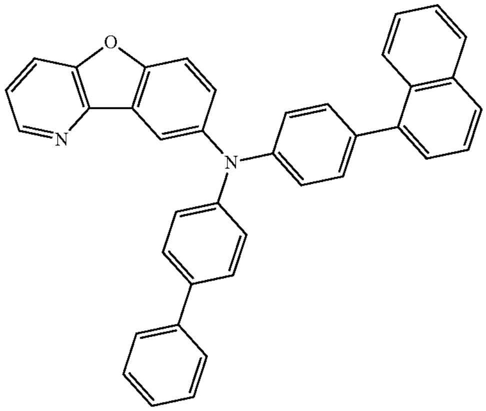
-continued
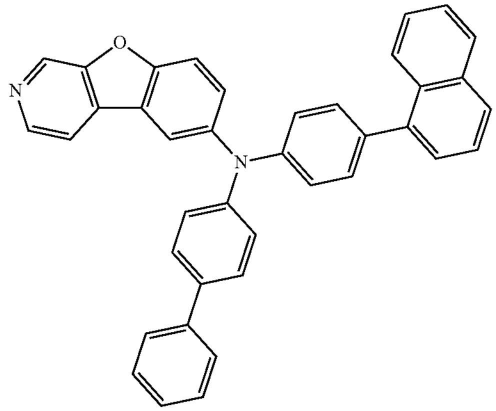
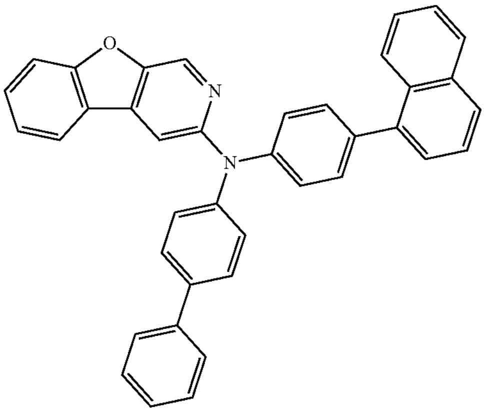
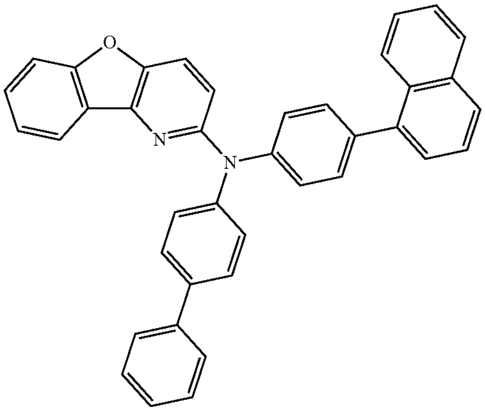
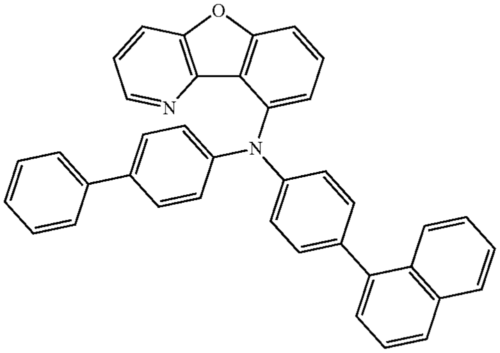

-continued
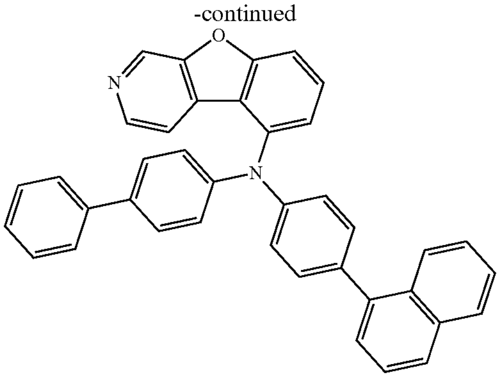
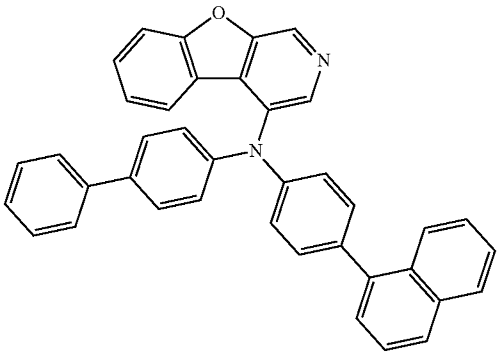
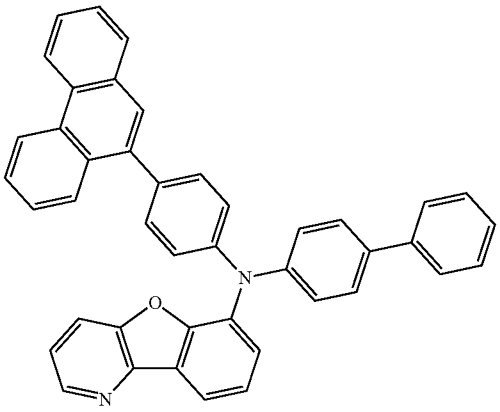
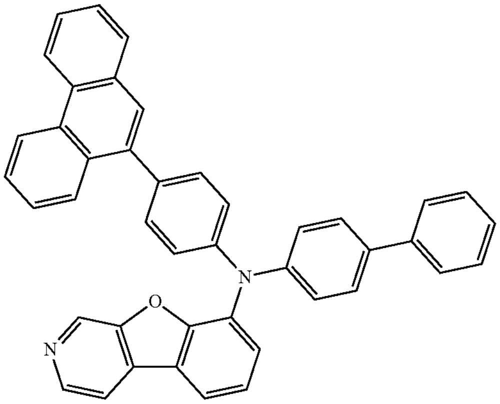
-continued
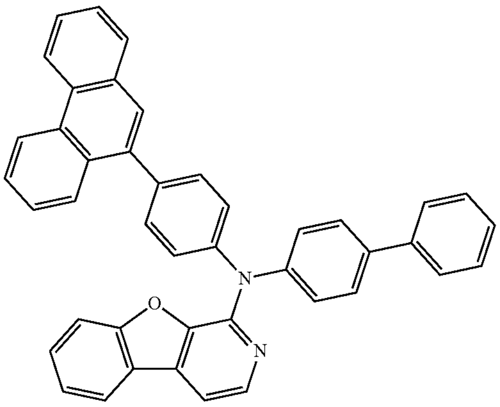
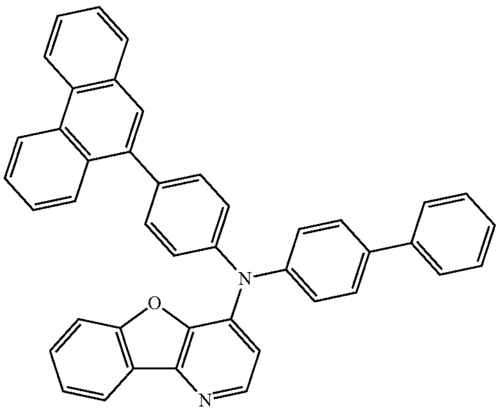
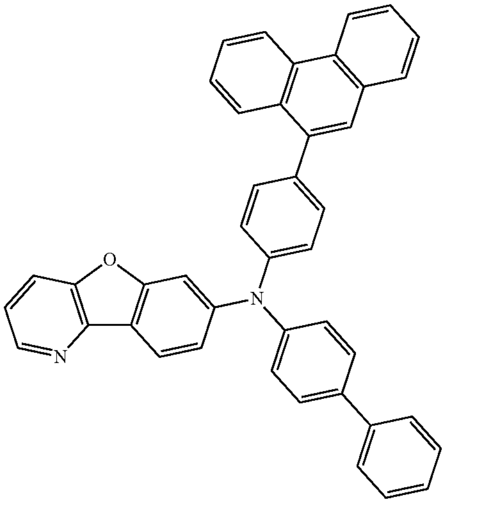

-continued
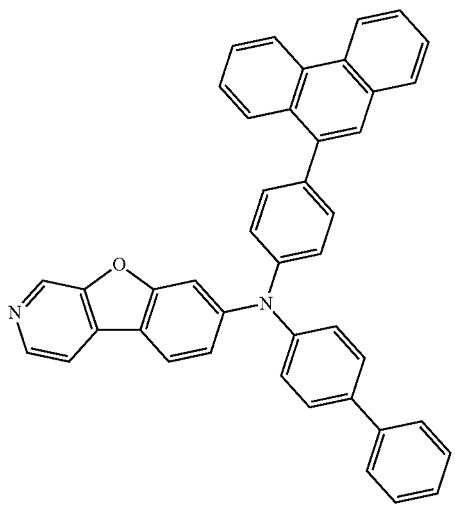
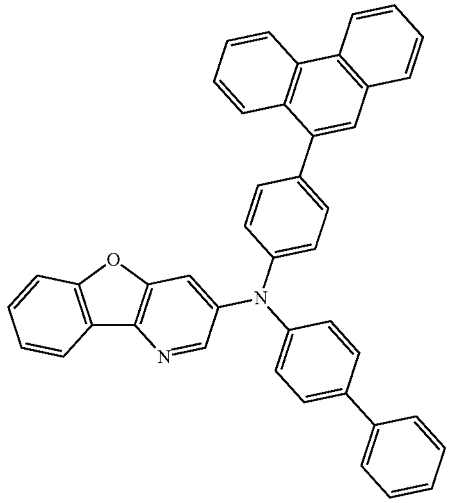
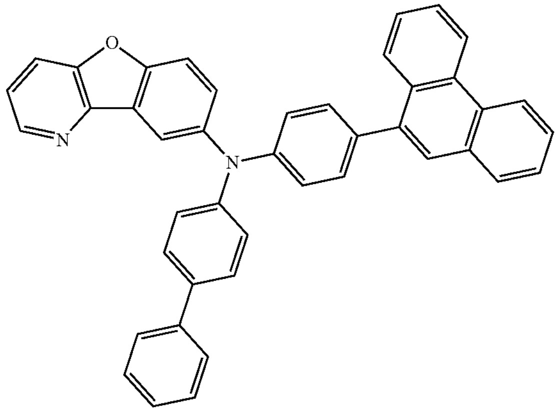
-continued
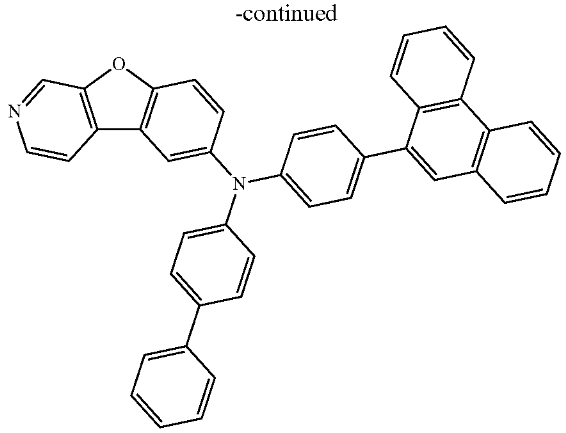
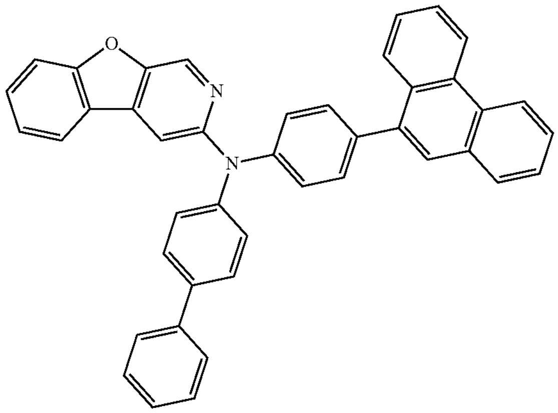
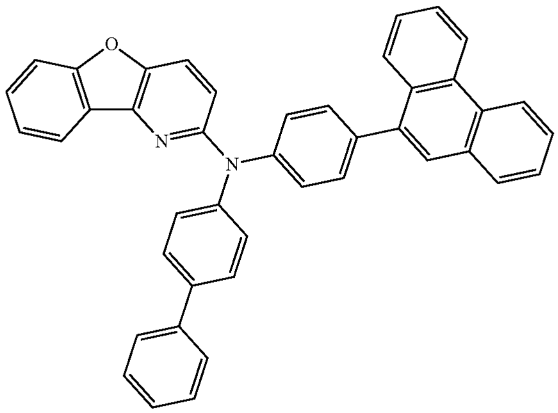
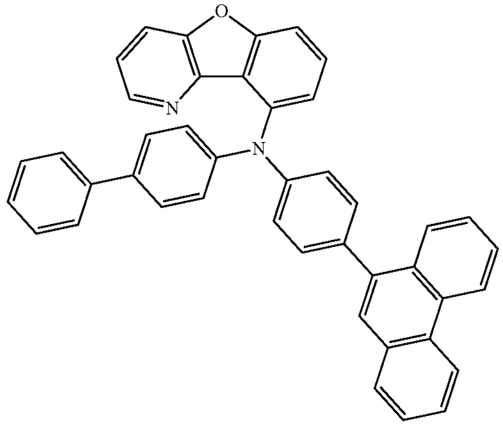

-continued
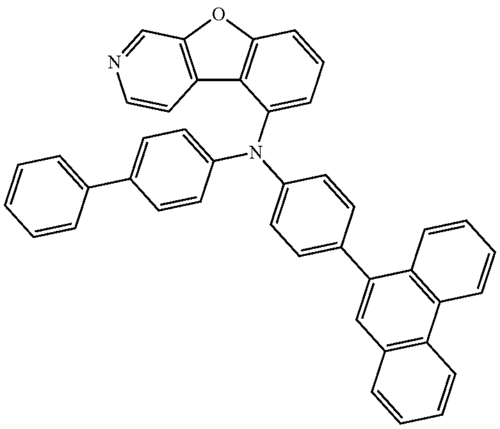
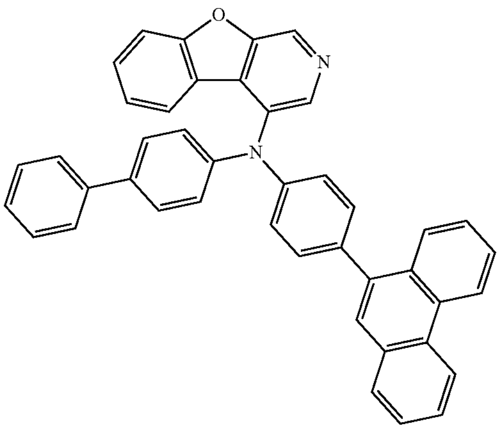
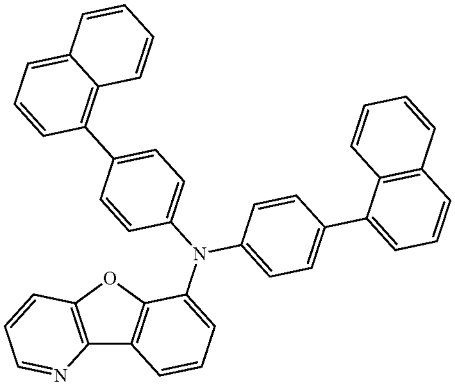
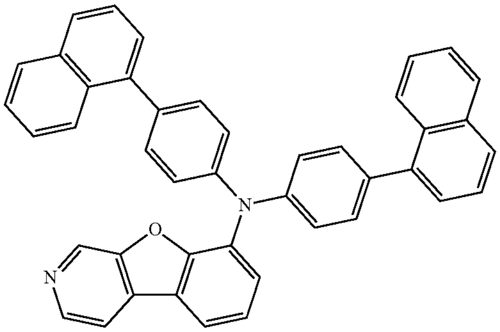
-continued
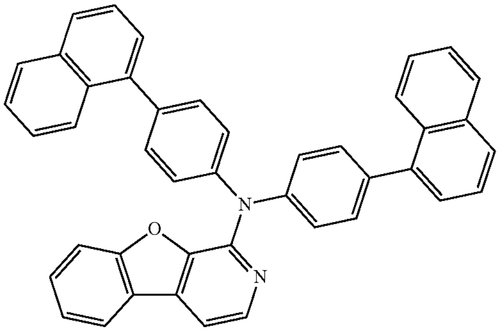
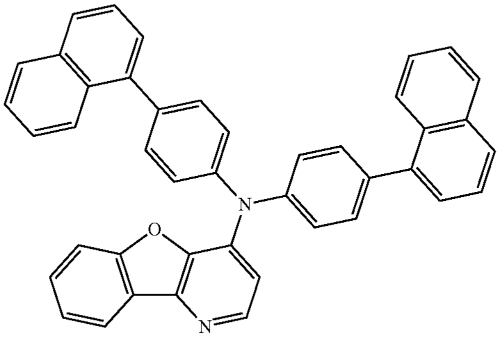
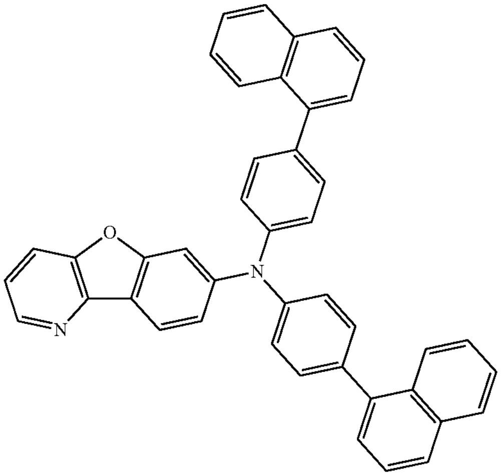
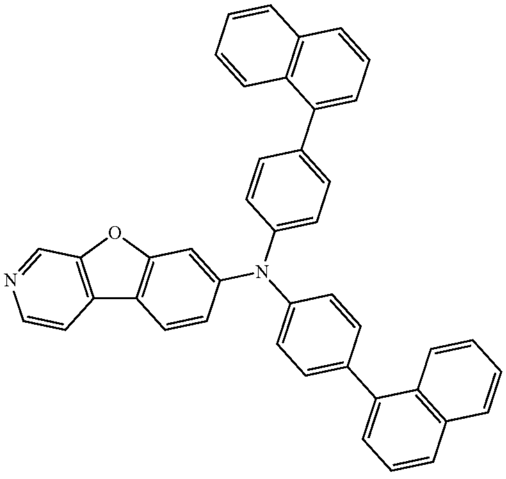

-continued
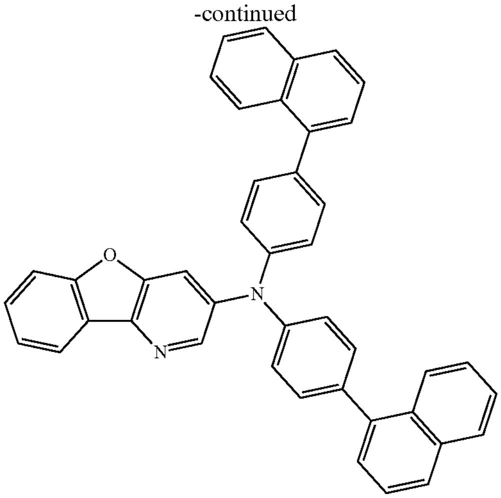
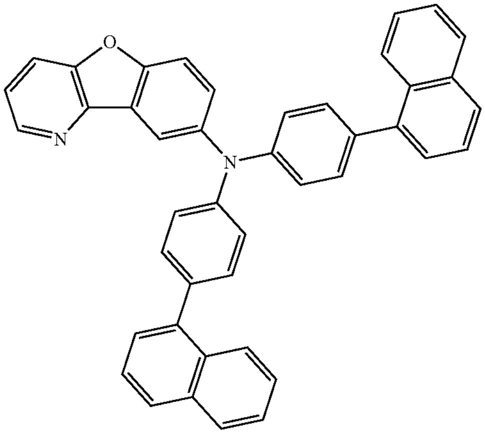
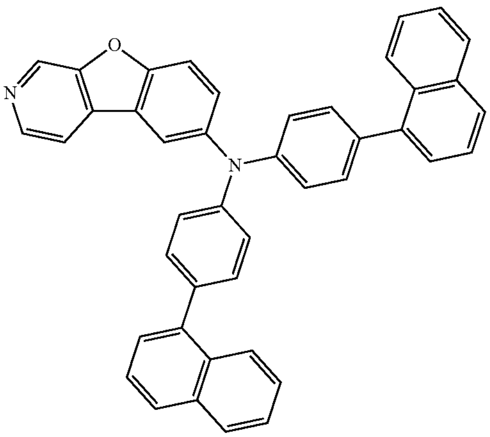
-continued
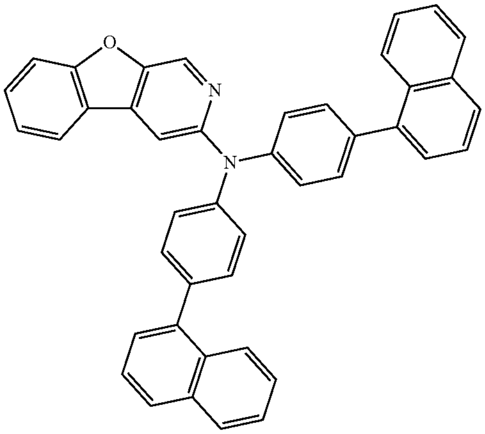
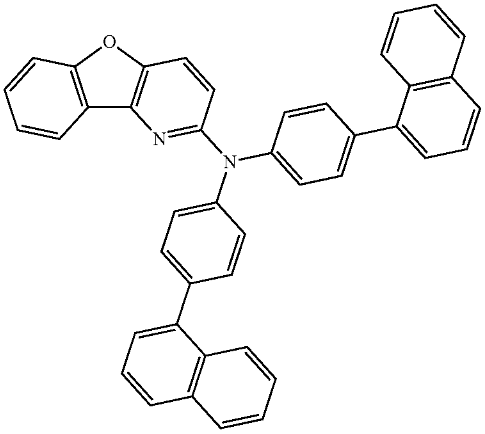
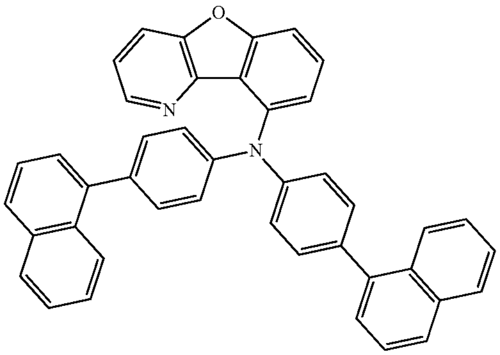
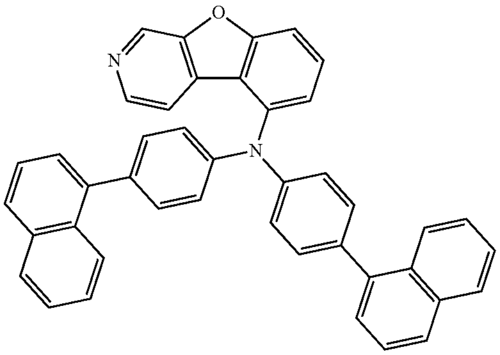

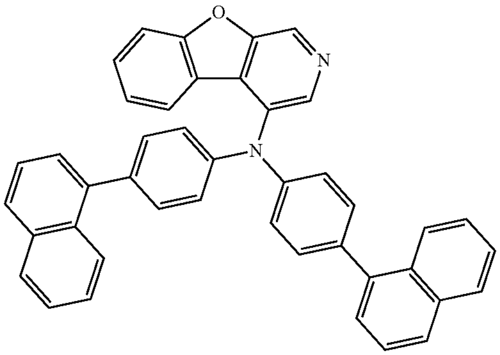
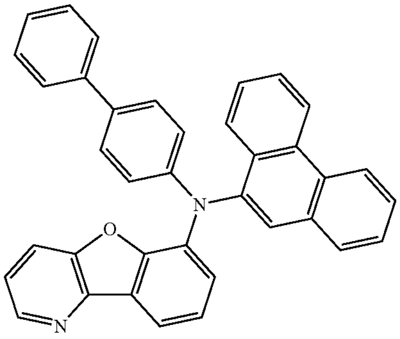
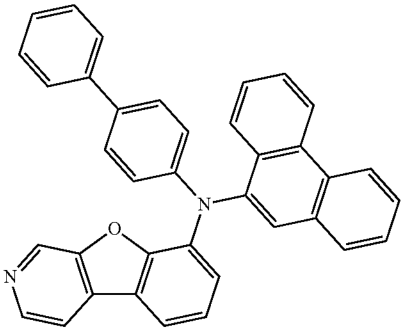
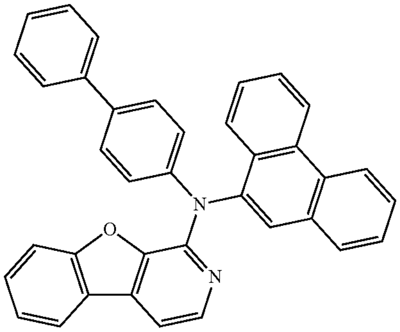
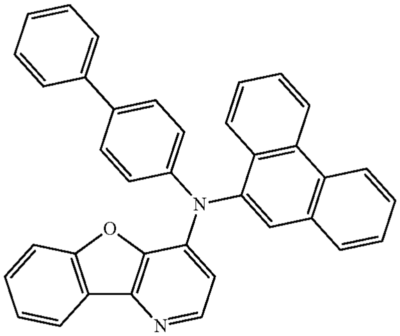
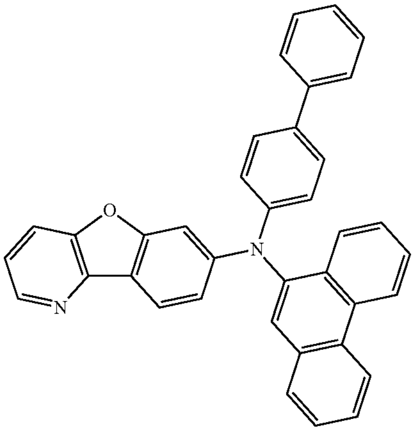
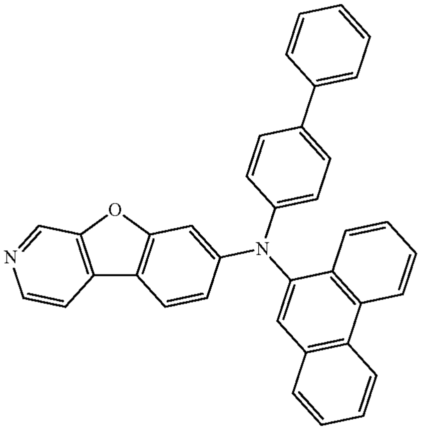
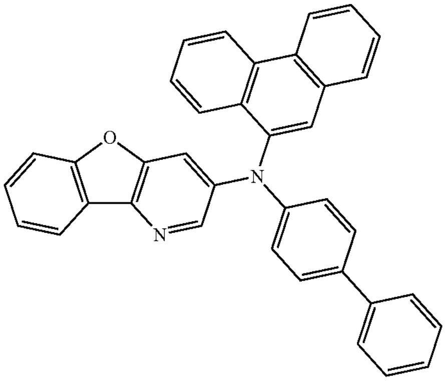
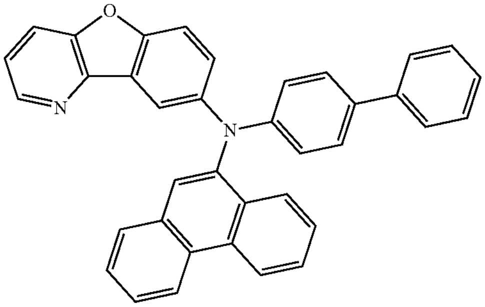

-continued
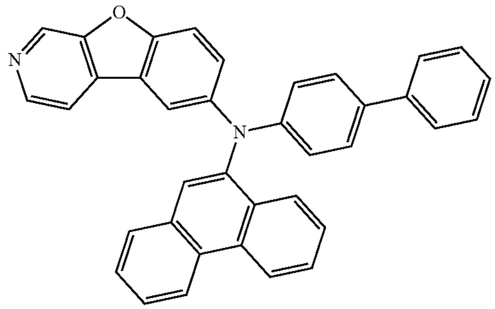
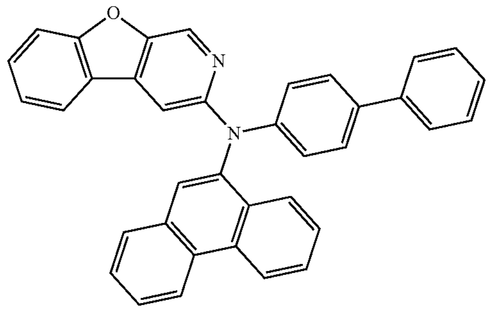
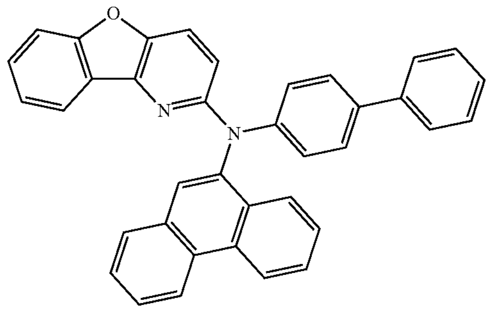
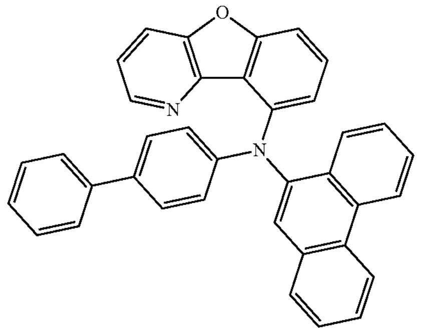
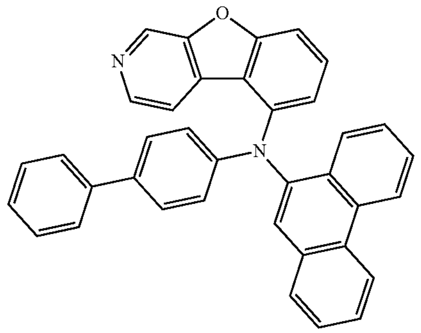
-continued
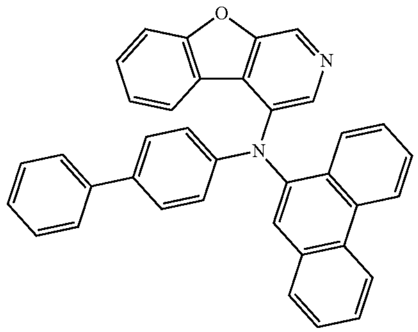
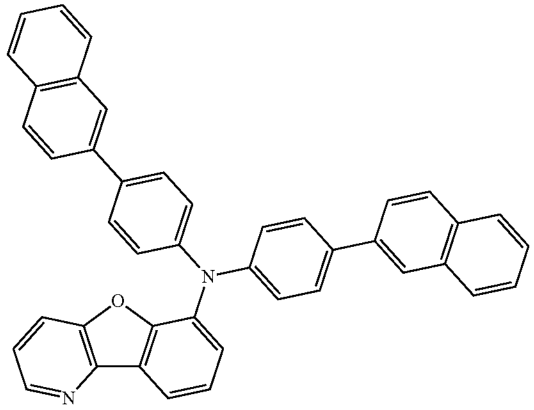
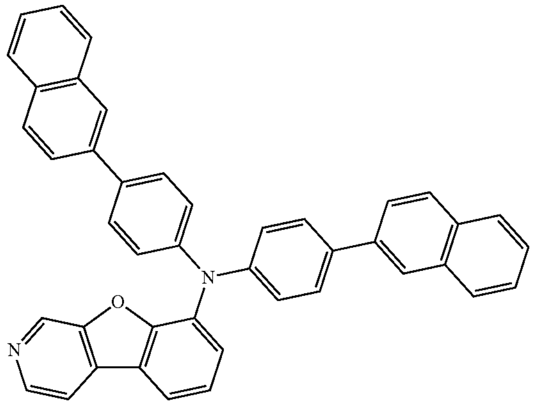
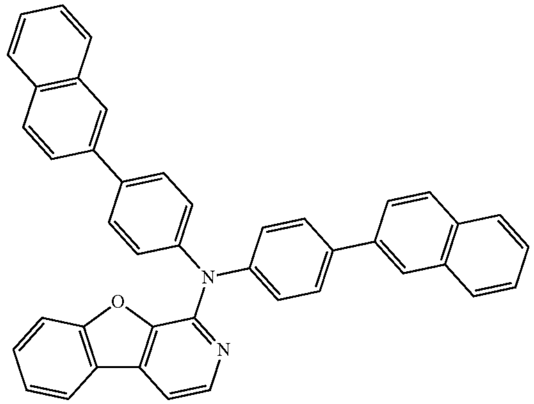

-continued
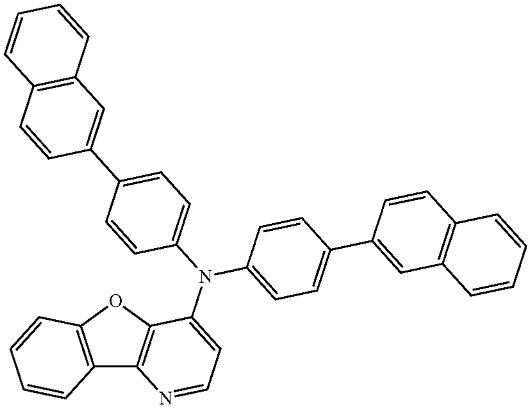
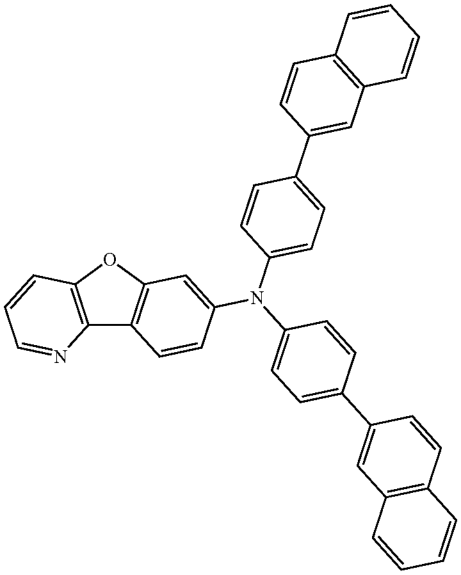
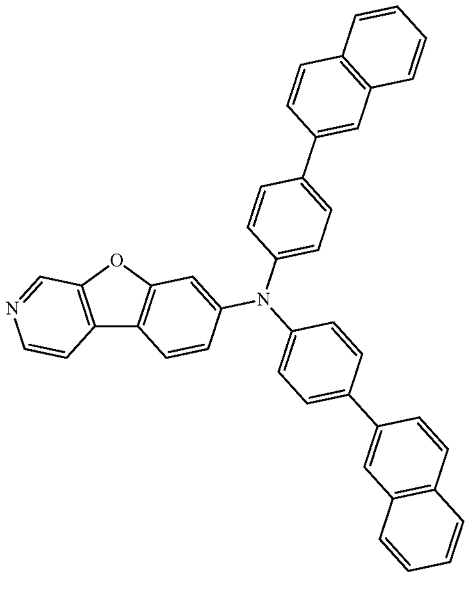
-continued
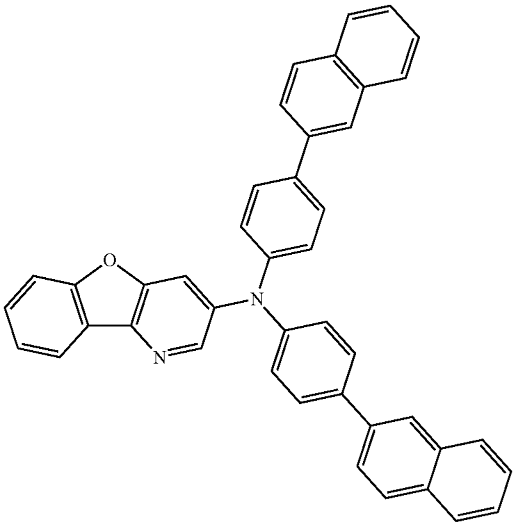
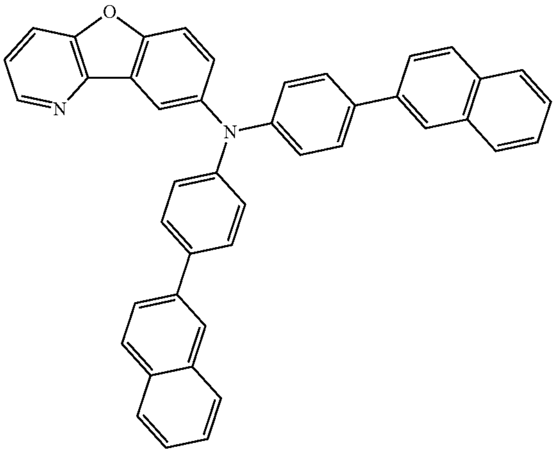
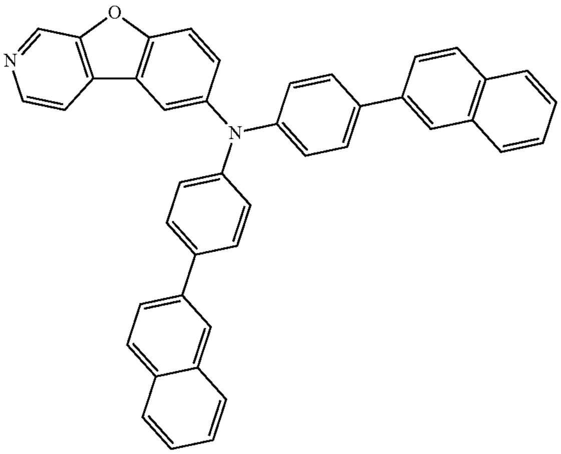

-continued
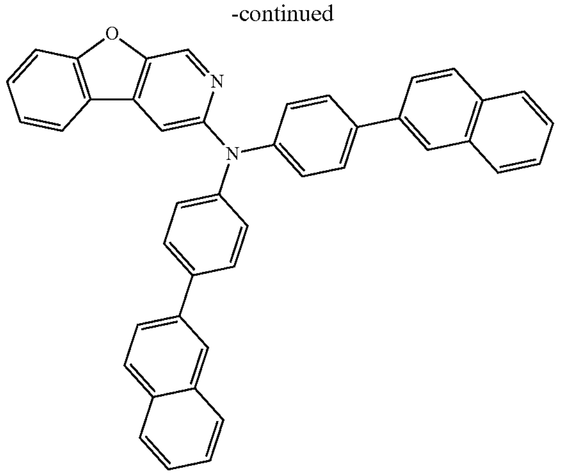
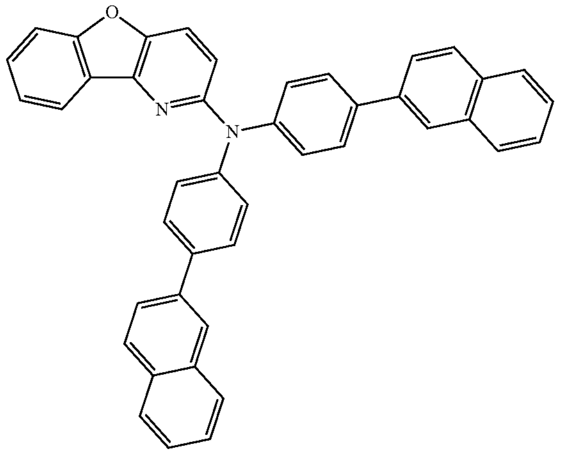
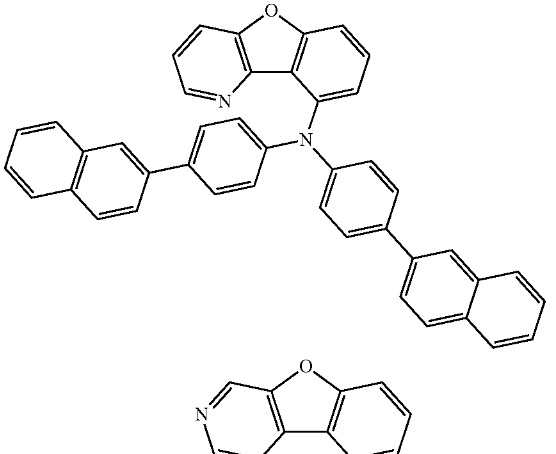
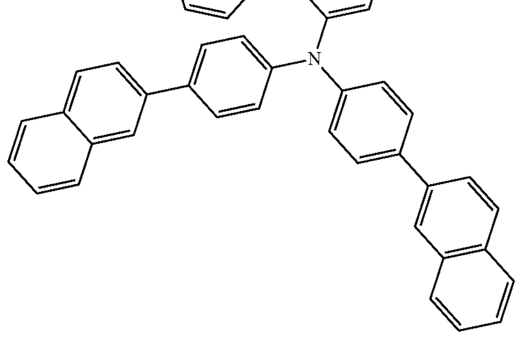
-continued
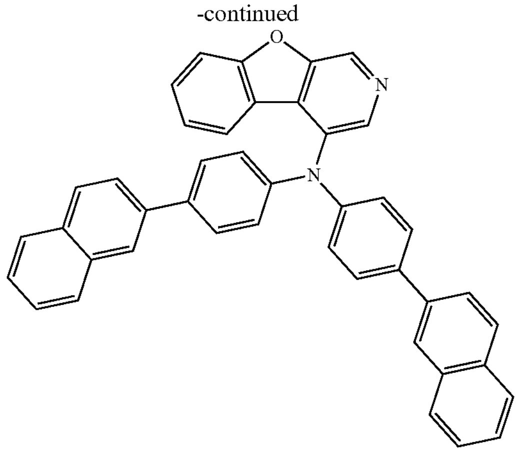
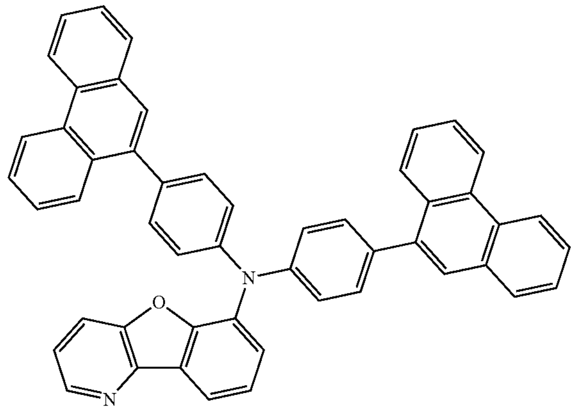
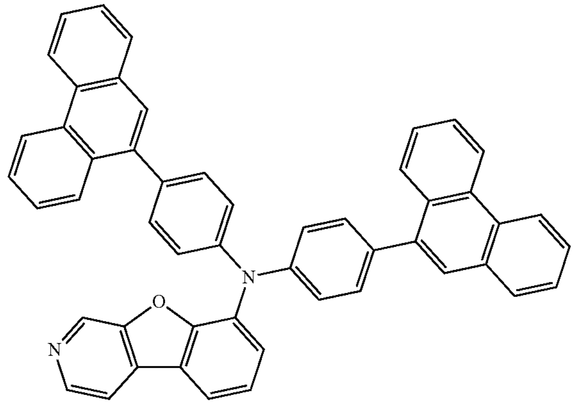
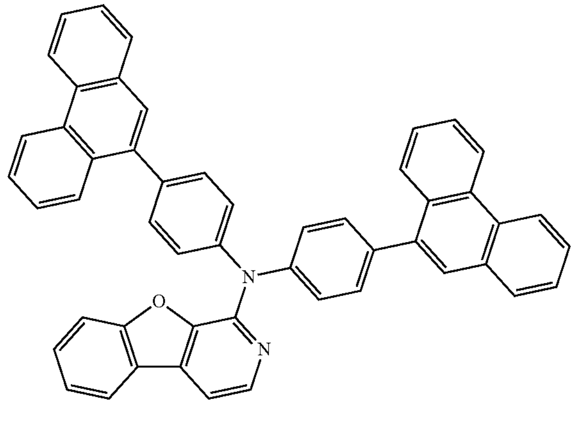

-continued
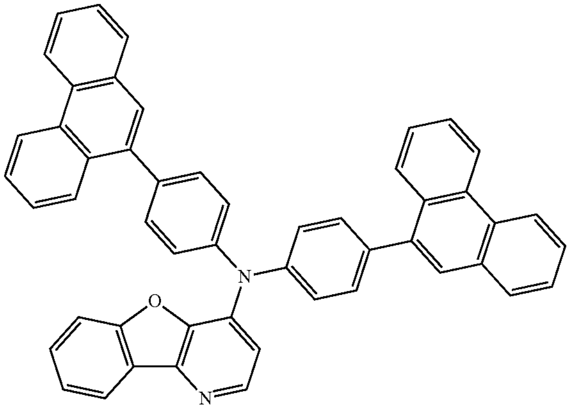
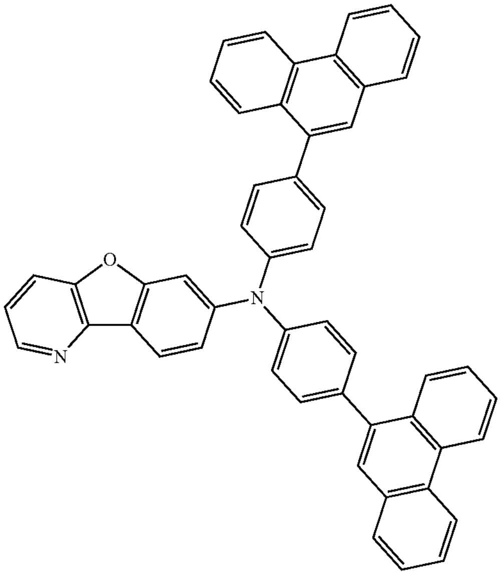
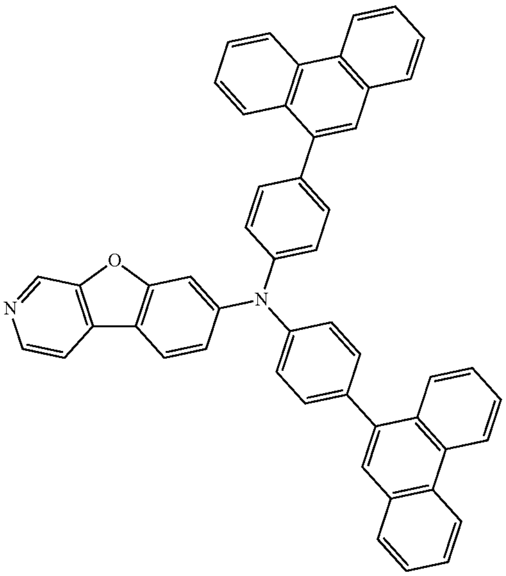
-continued
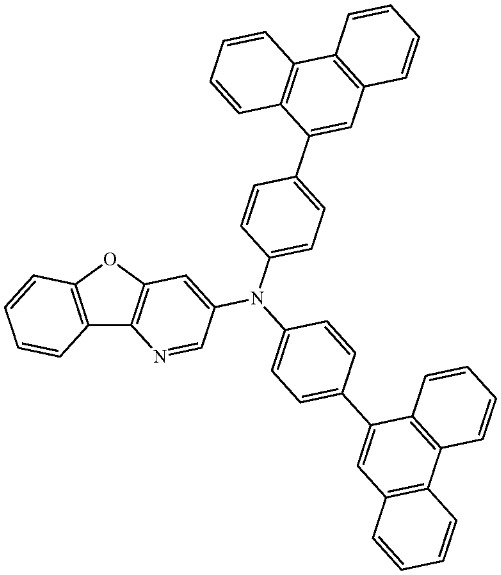
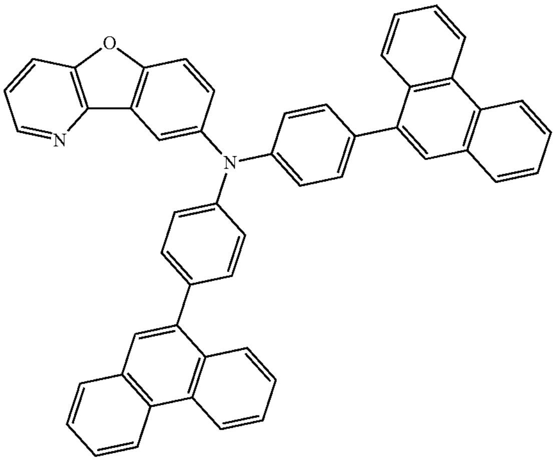
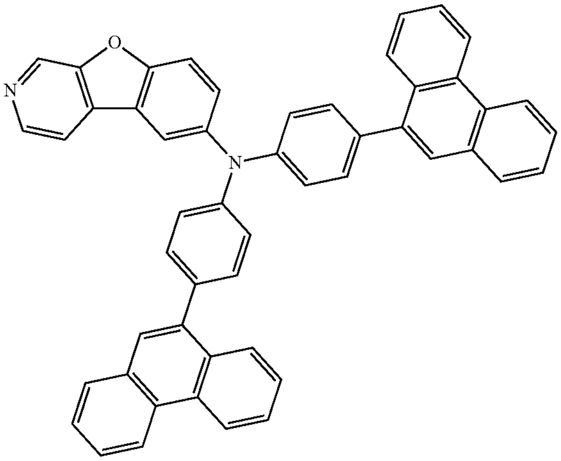

-continued
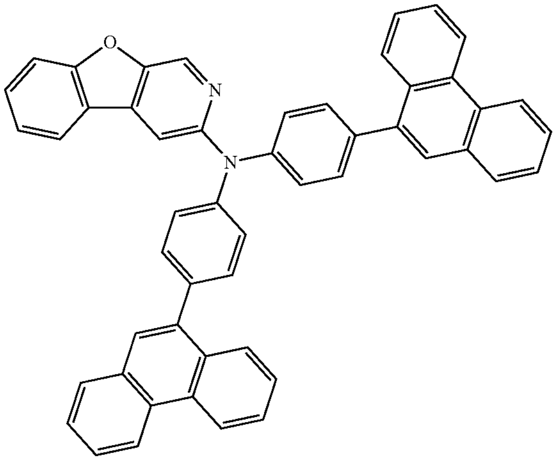
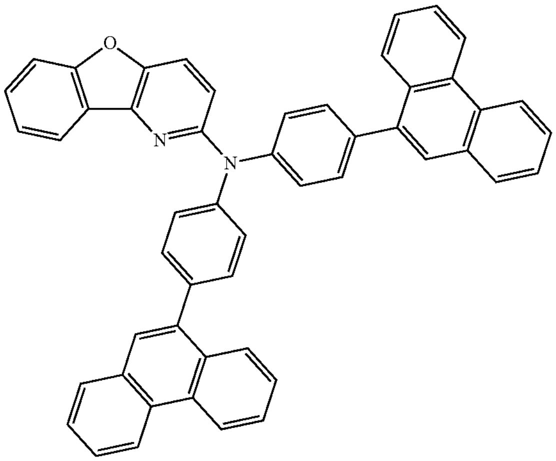
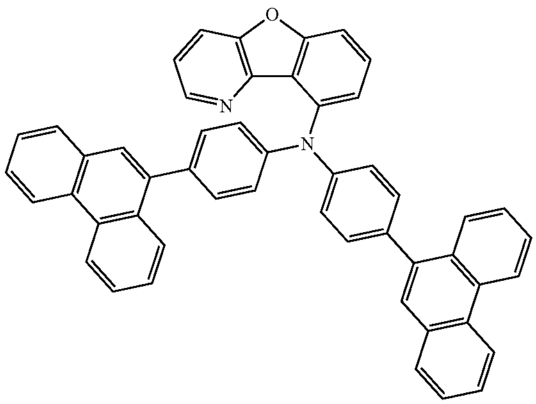
-continued
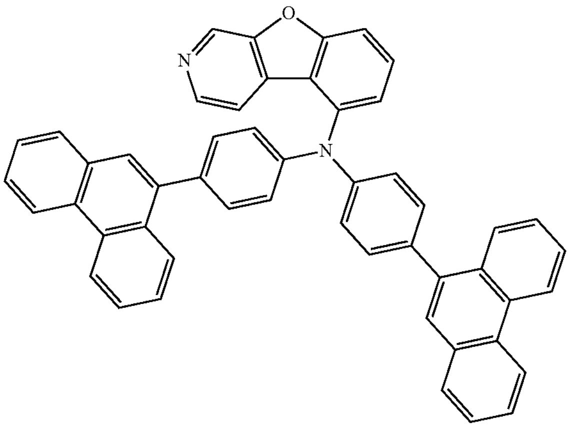
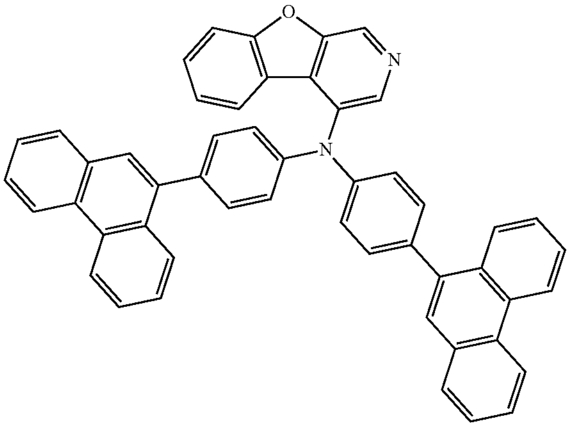
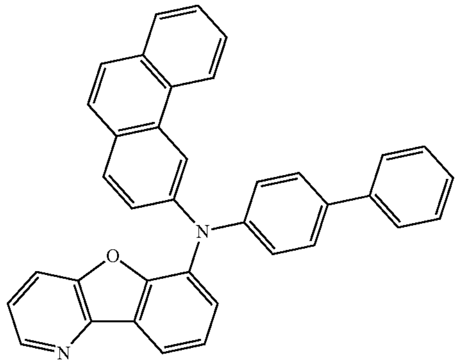
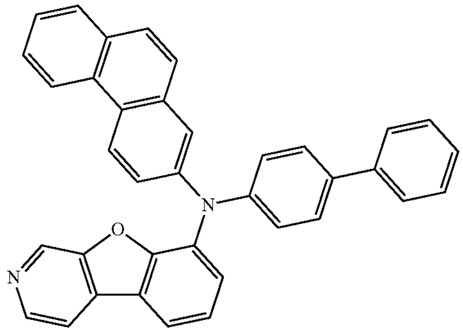

-continued
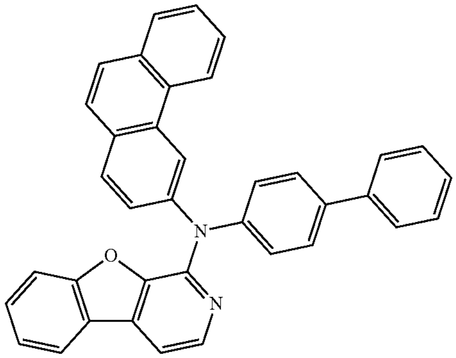
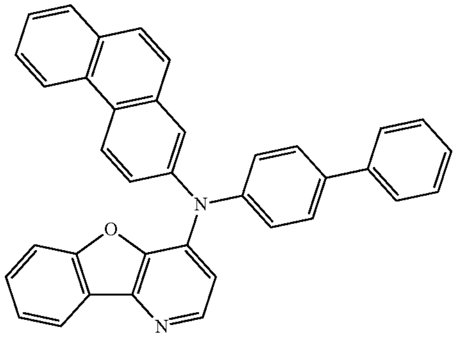
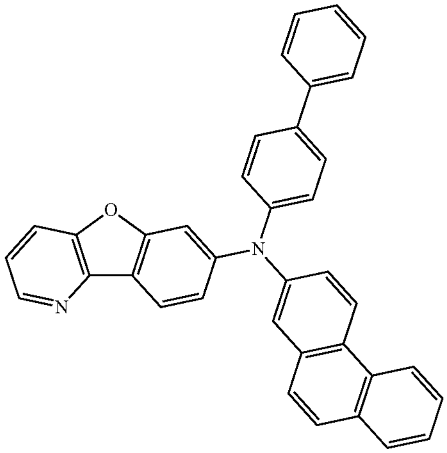
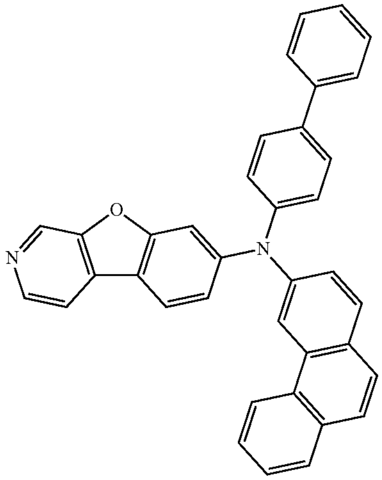
-continued
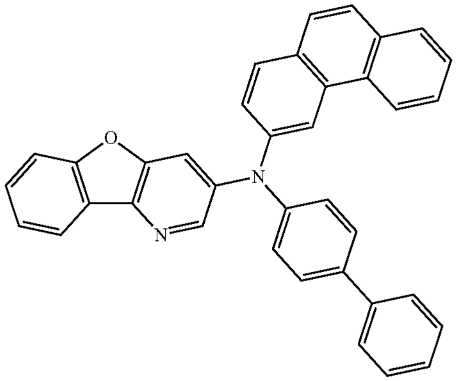
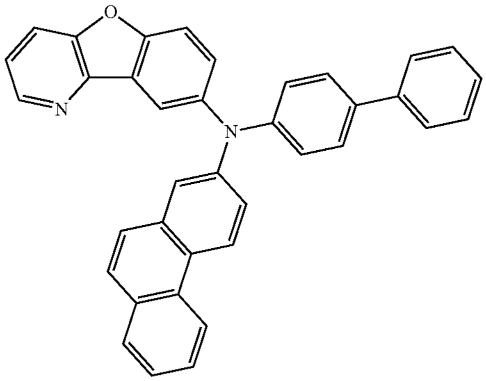
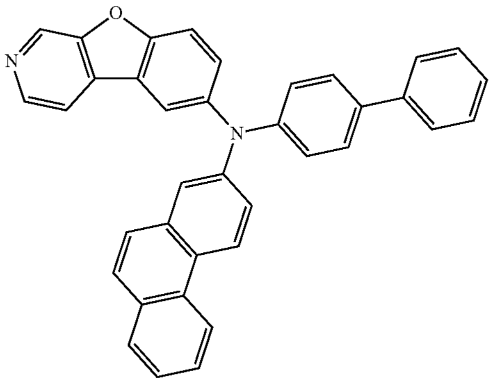
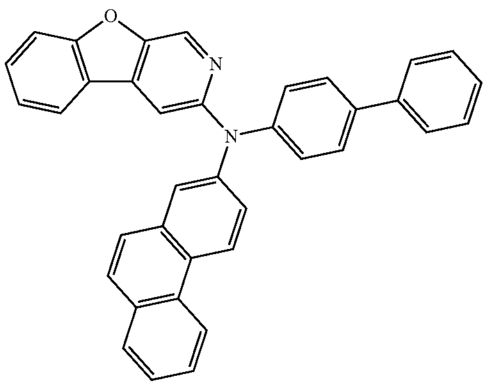

-continued
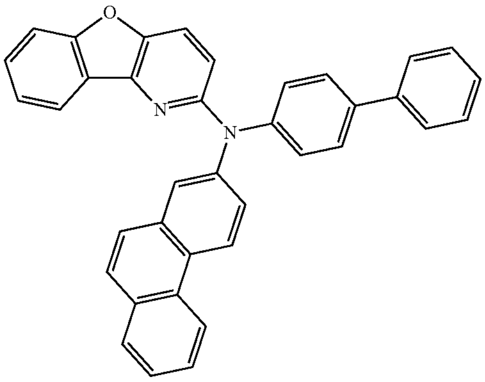
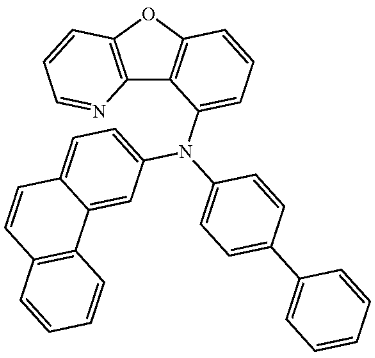
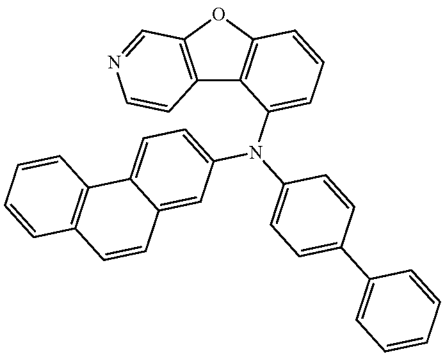
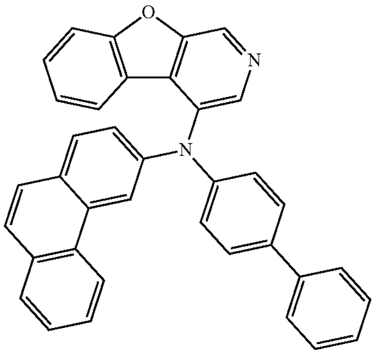
-continued
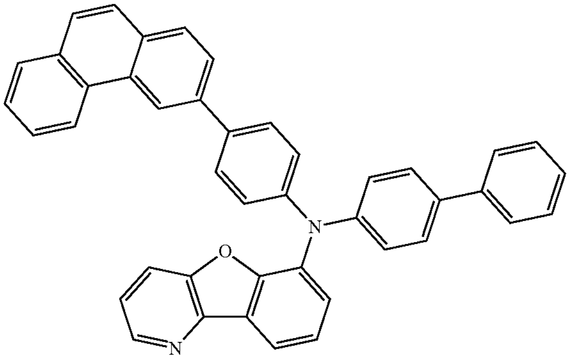
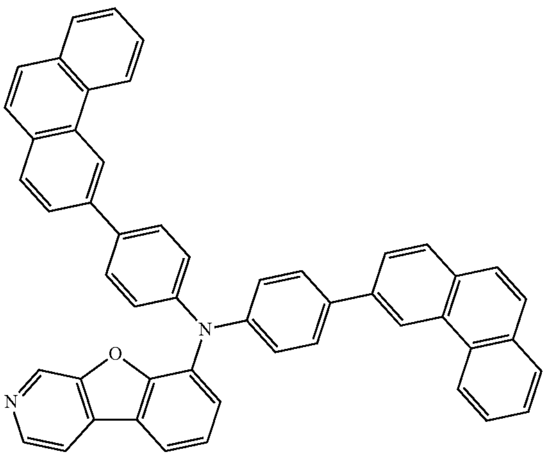
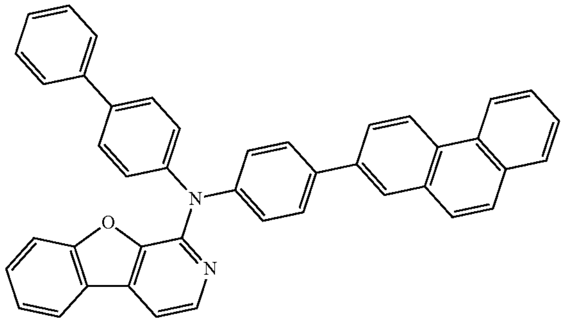
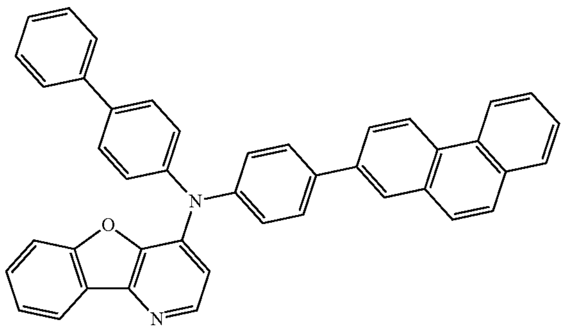

-continued
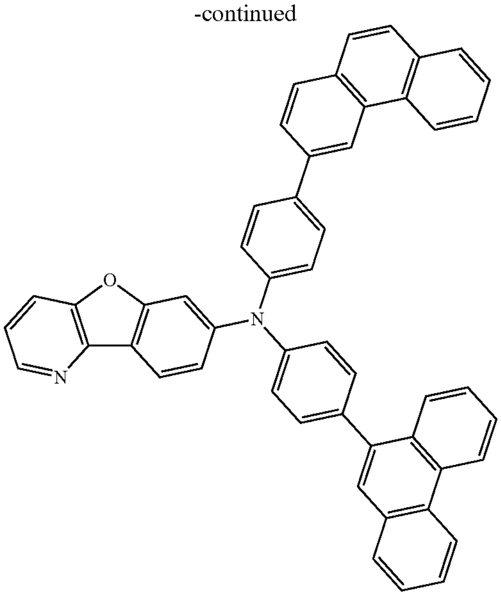
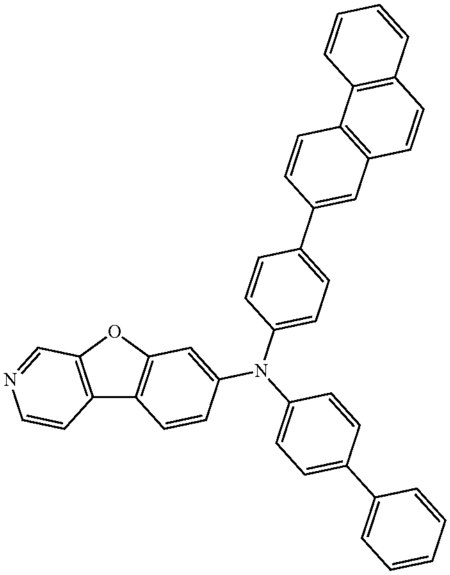
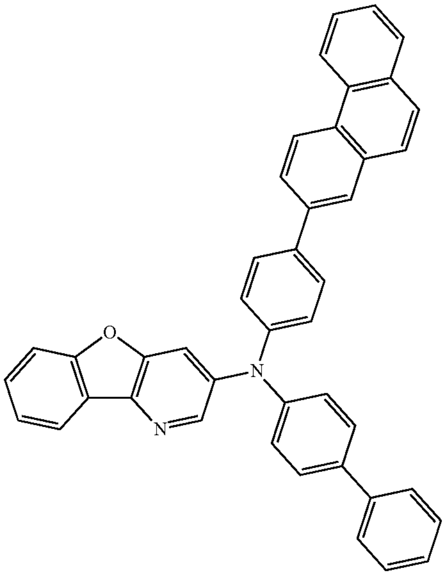
-continued
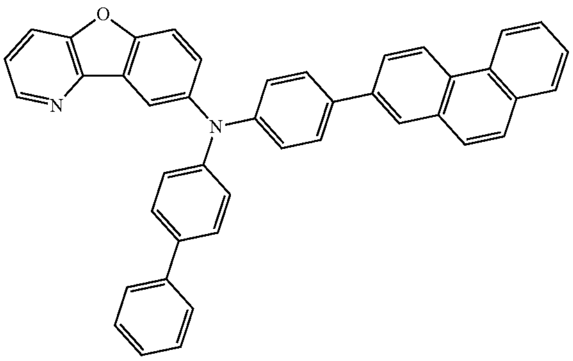
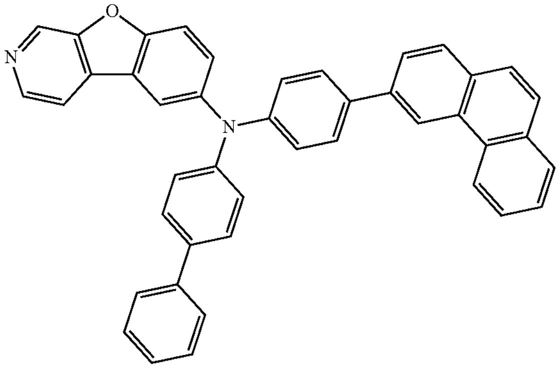
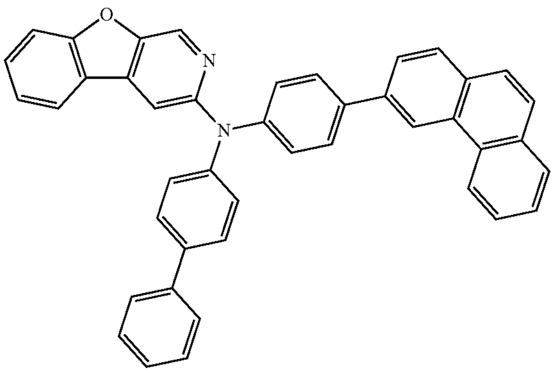
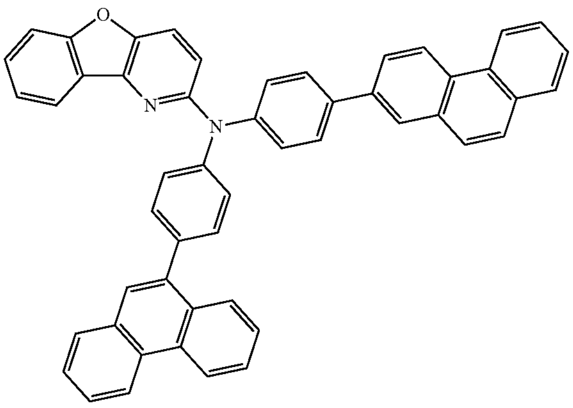

-continued
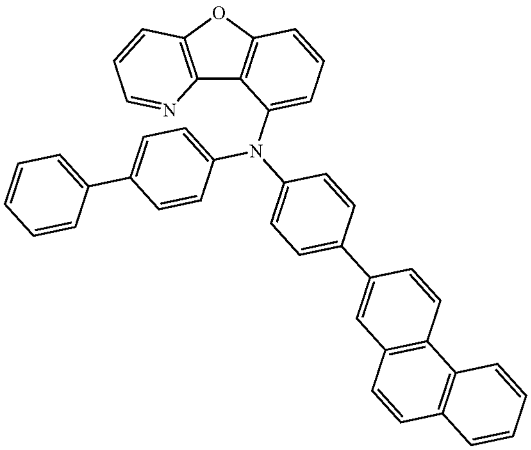
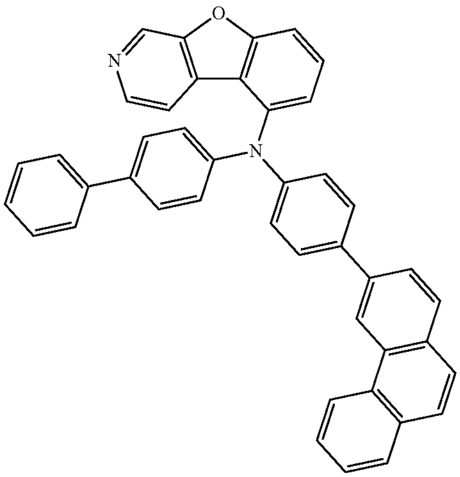
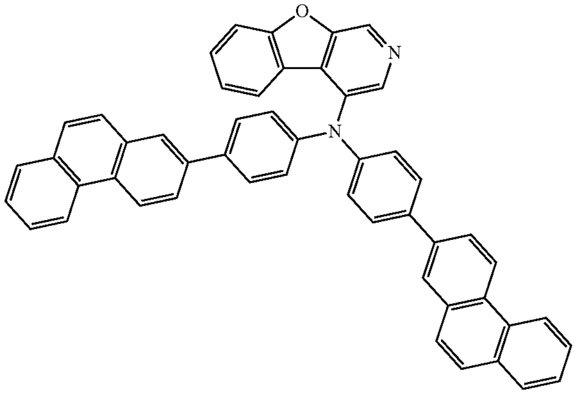
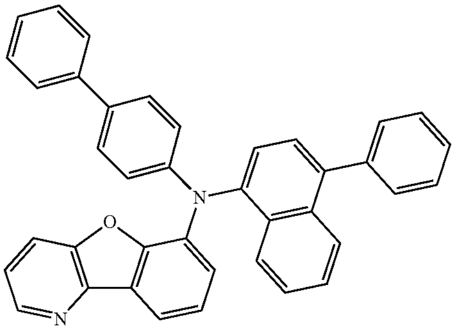
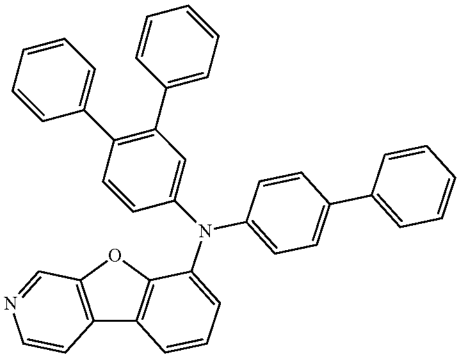
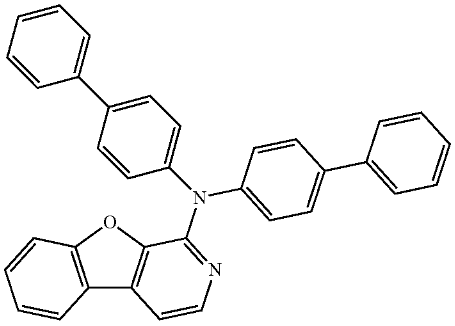
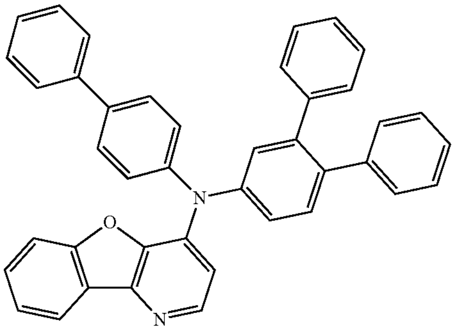

-continued
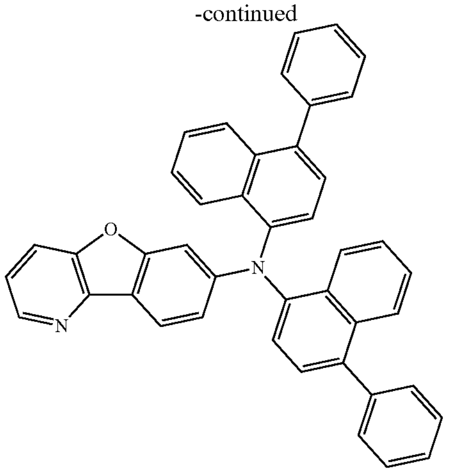
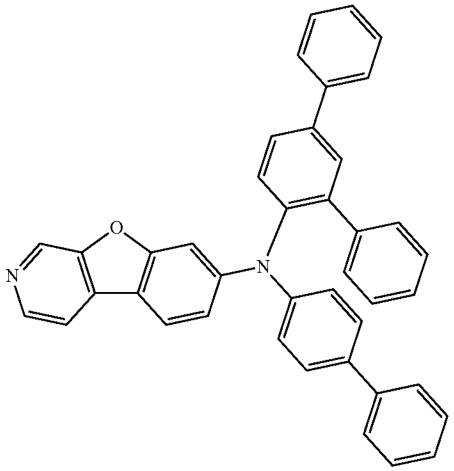
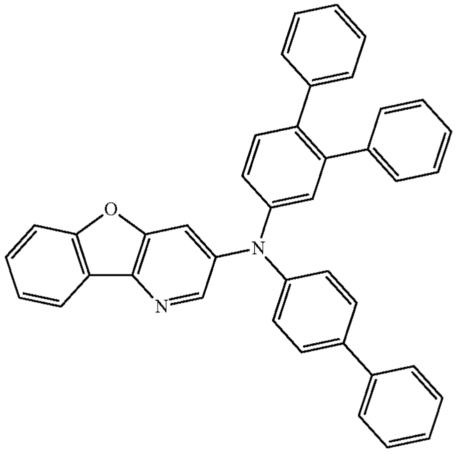
-continued
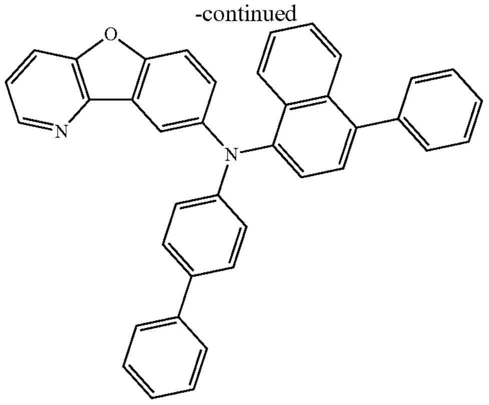
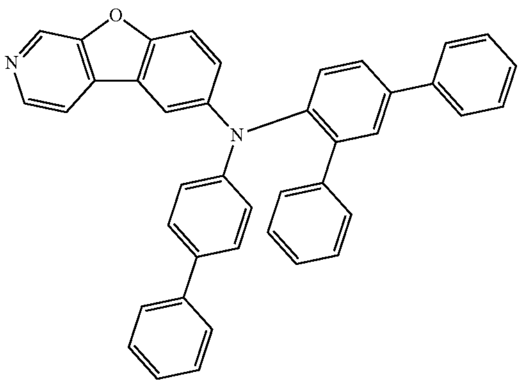
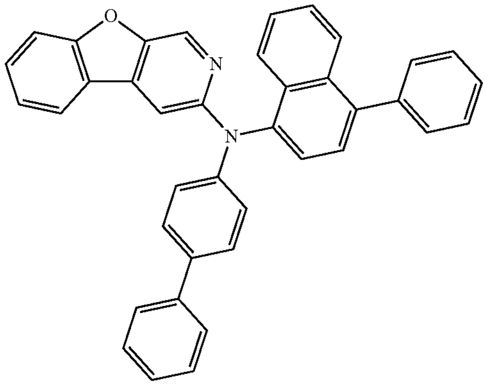
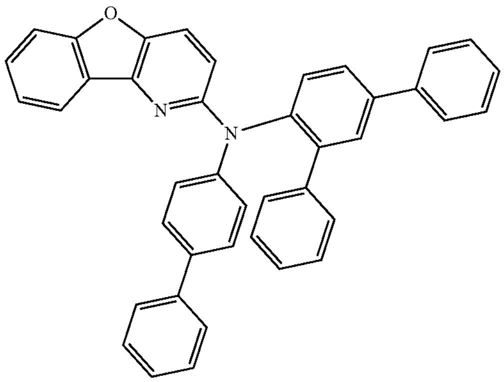

-continued
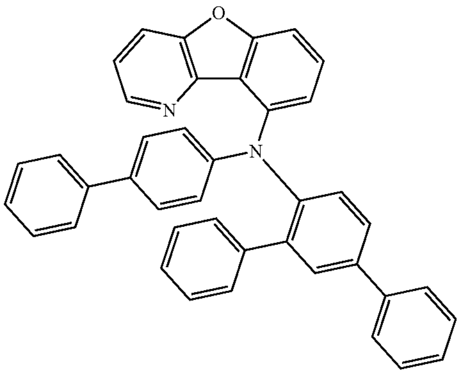
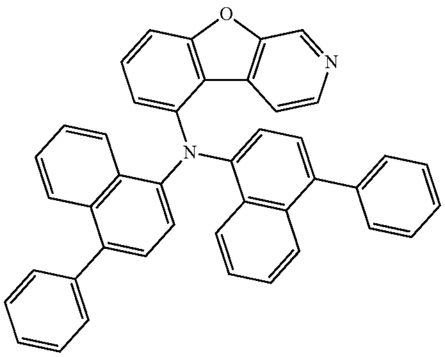
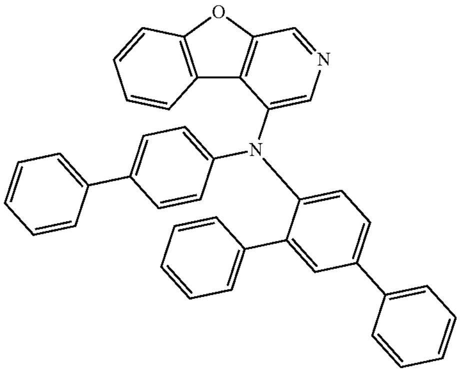
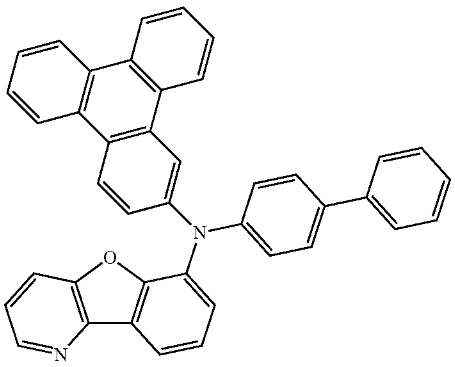
-continued
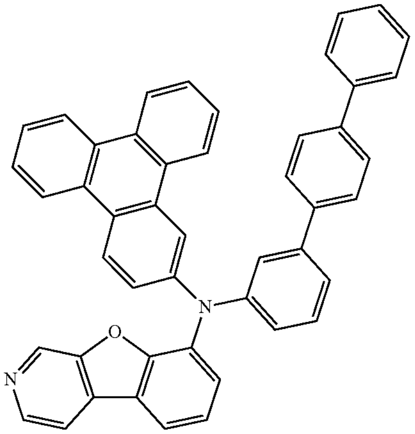
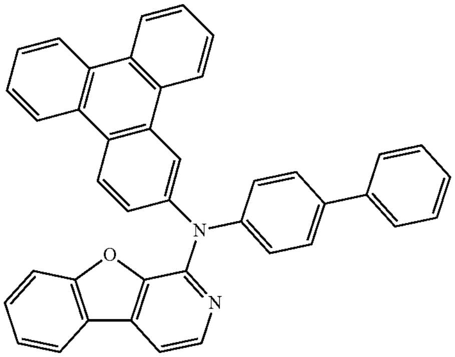
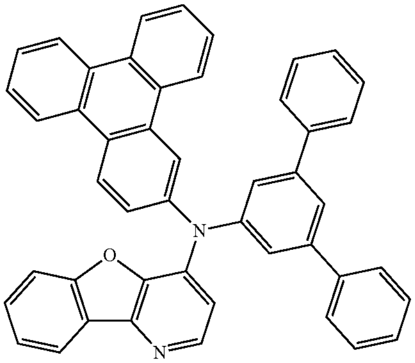
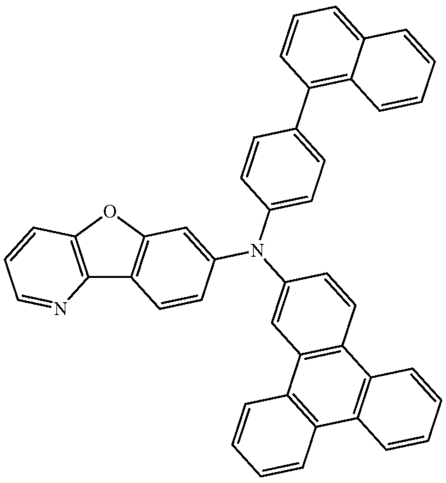

-continued
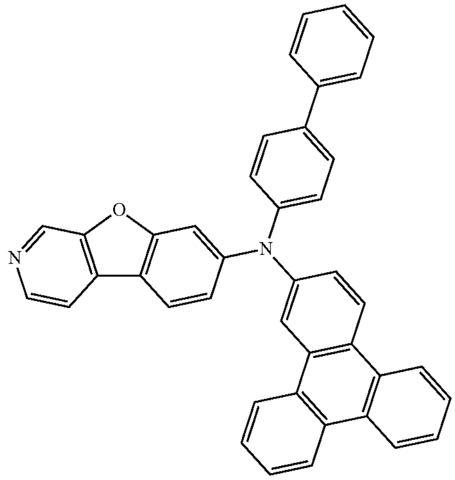
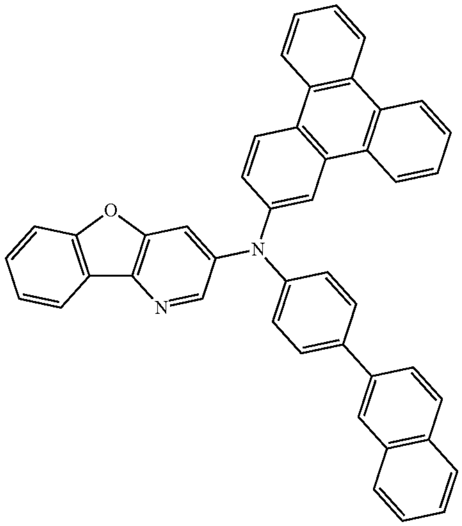
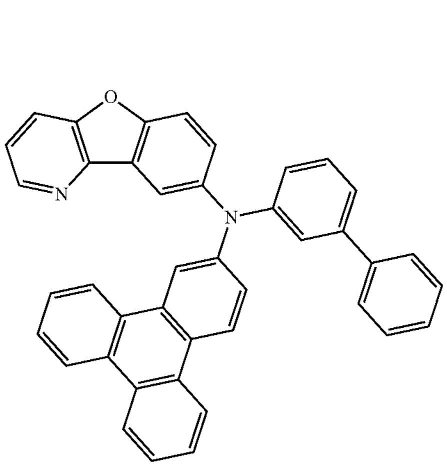
-continued
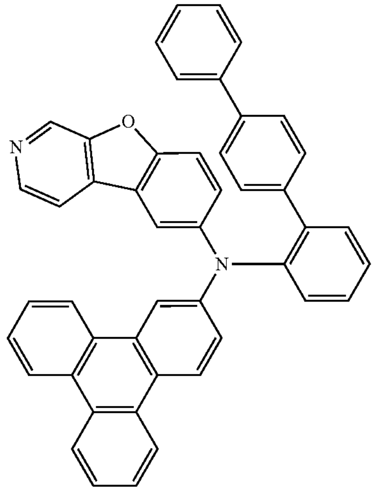
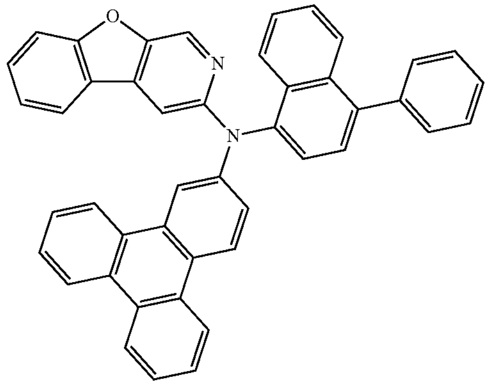
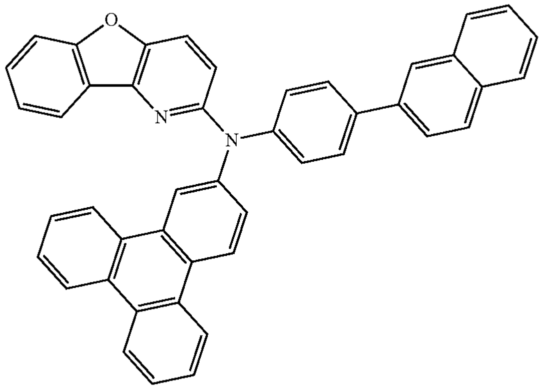
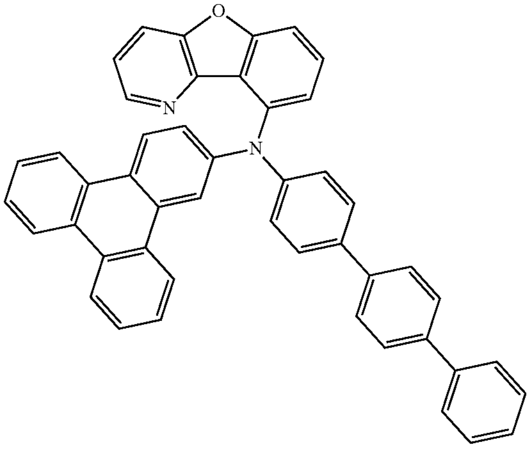

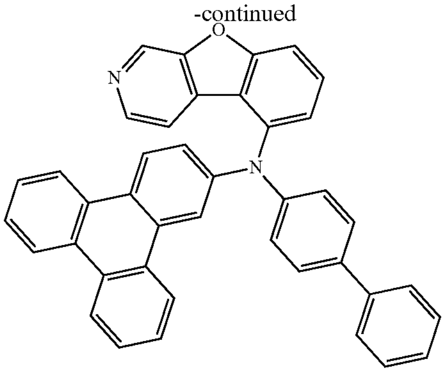
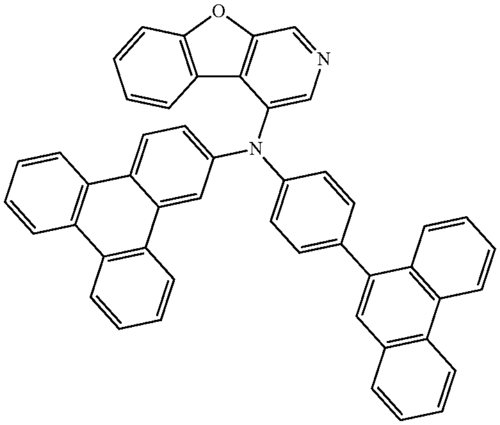
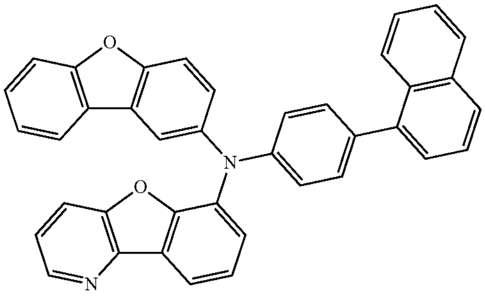
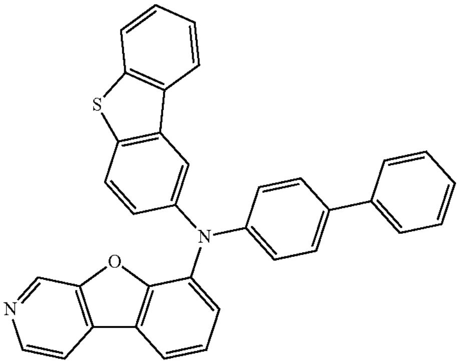
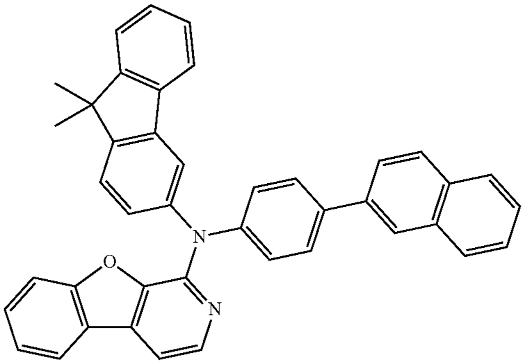
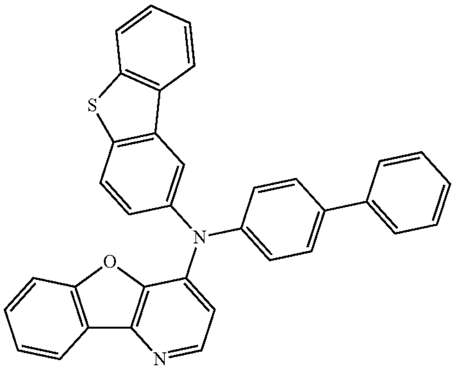
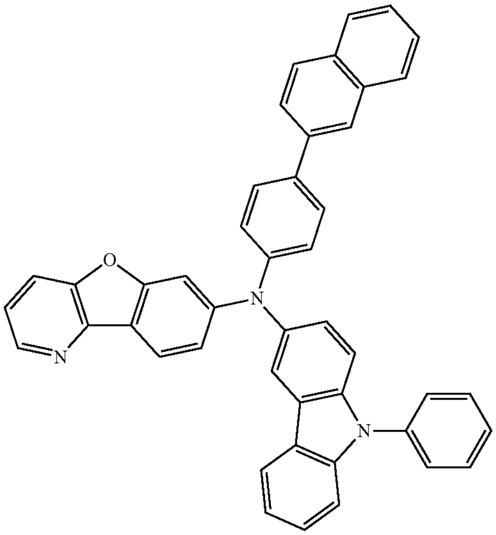

-continued
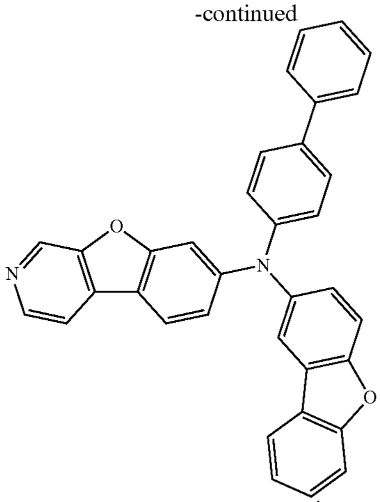
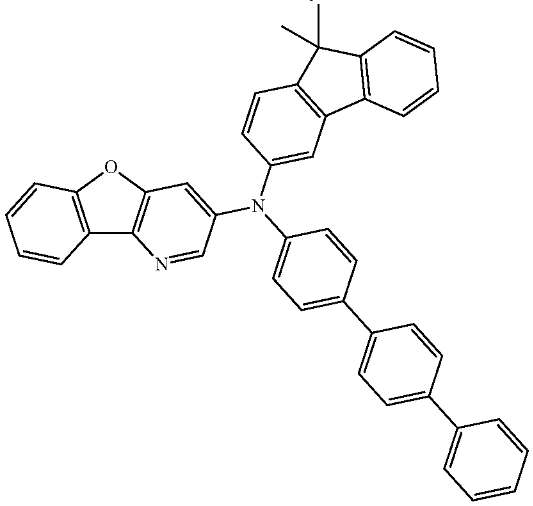
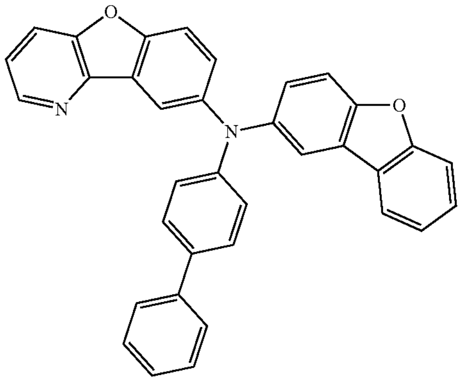
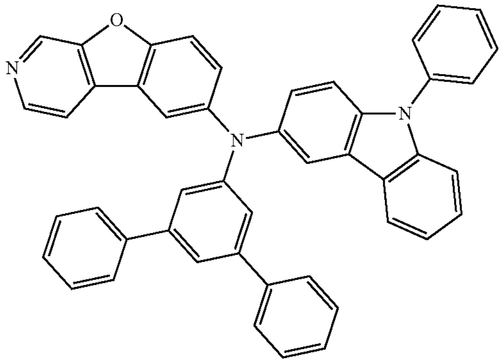
-continued
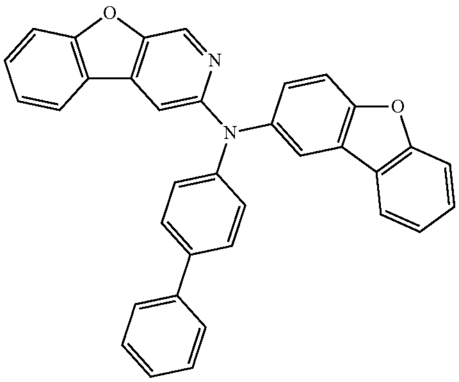
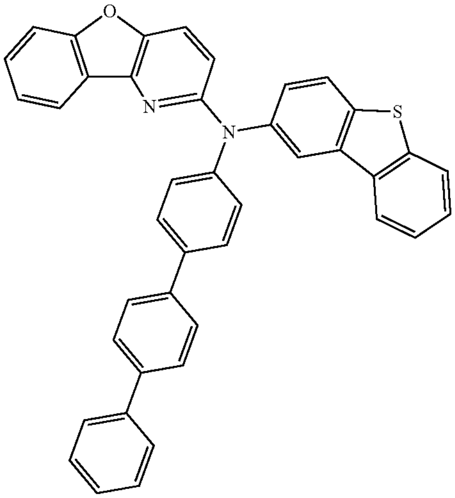
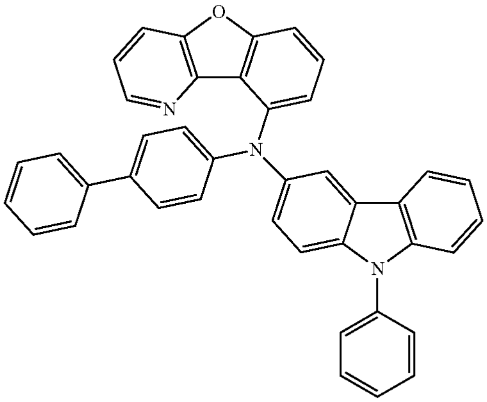
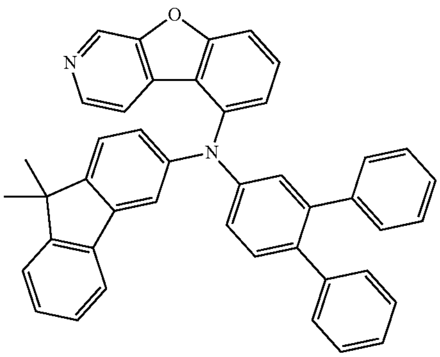

-continued
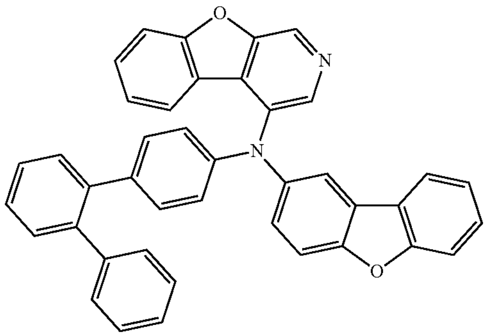
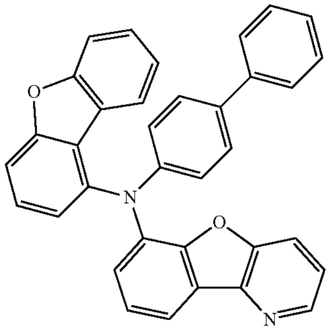
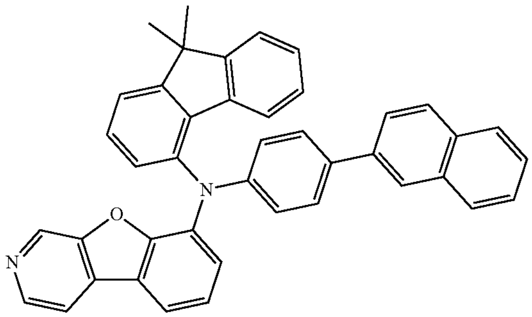
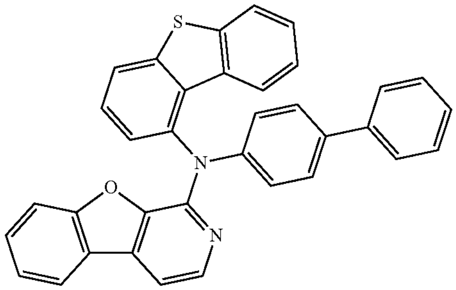
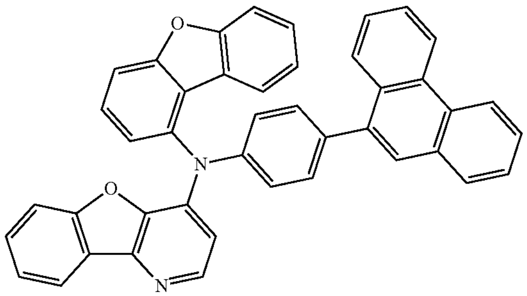
-continued
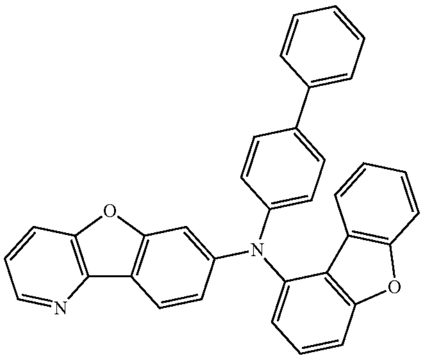
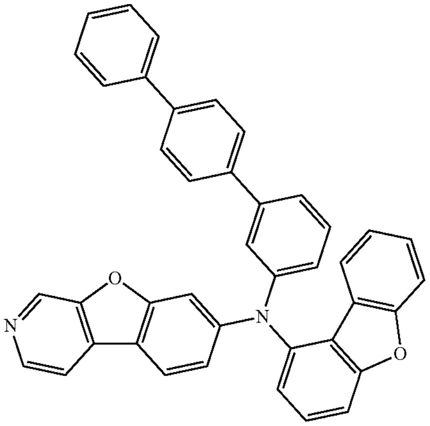
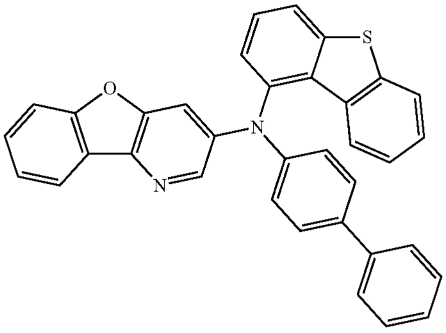
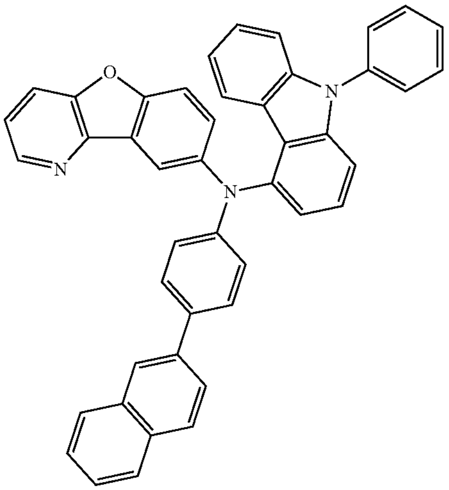

-continued
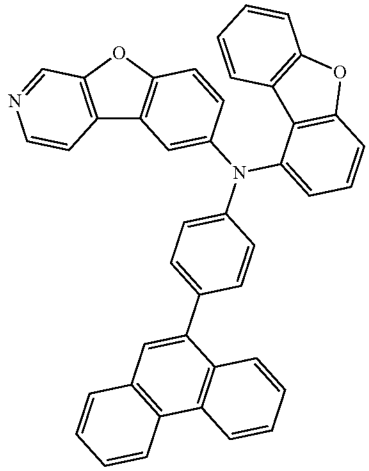
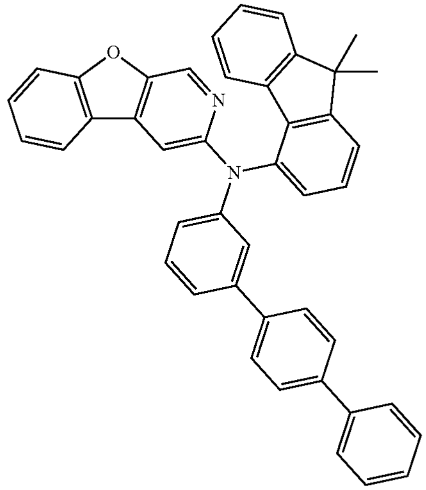
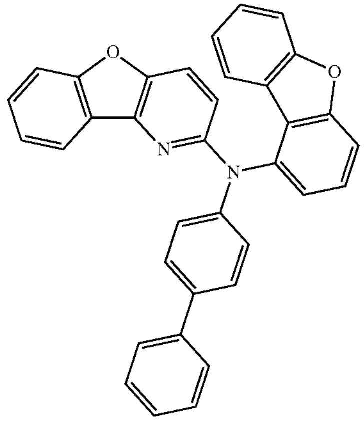
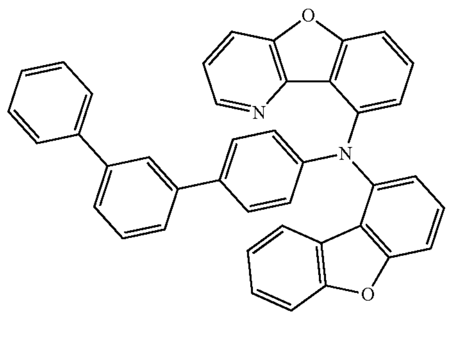
-continued
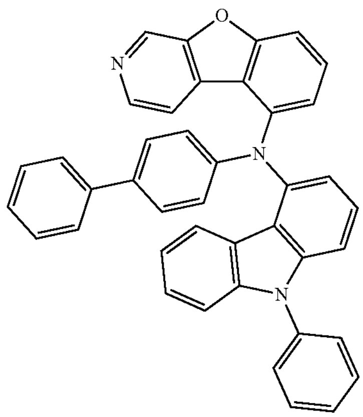
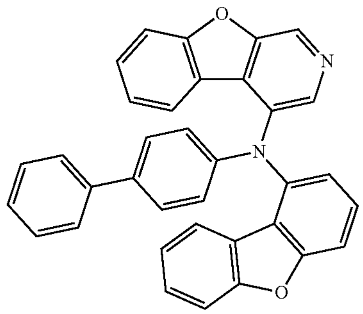
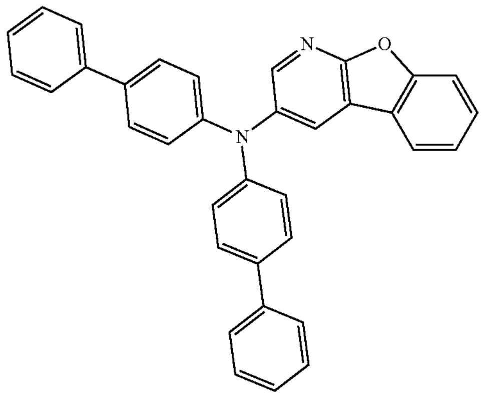
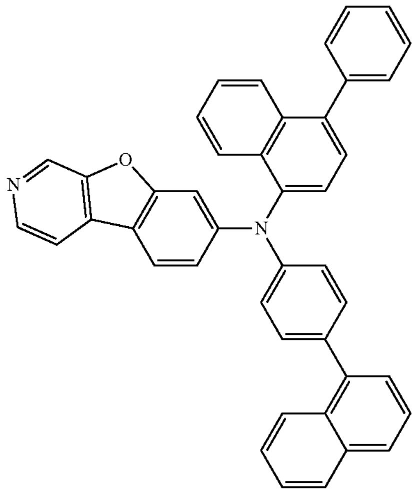

-continued
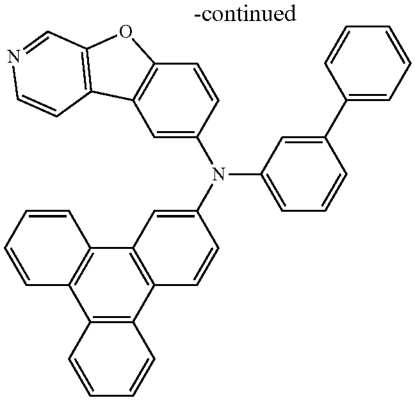
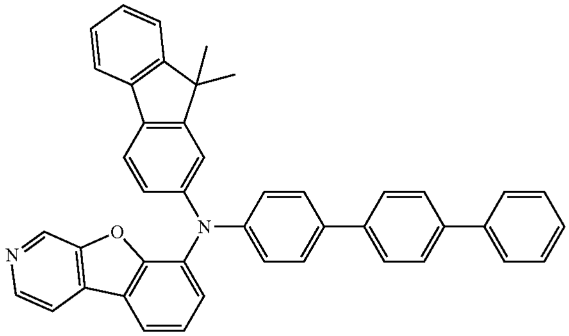
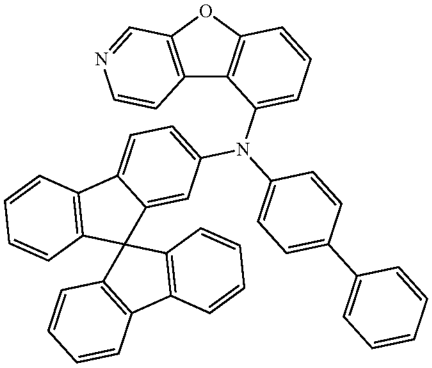
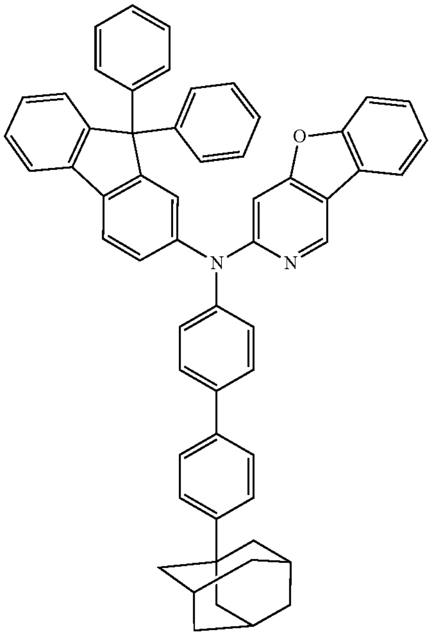
-continued
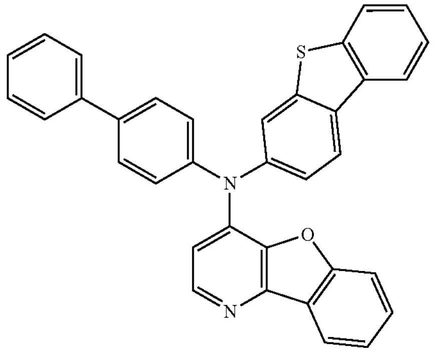
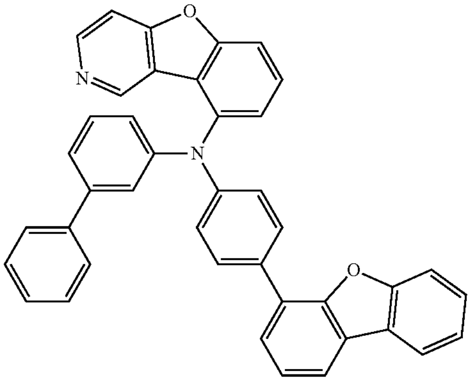
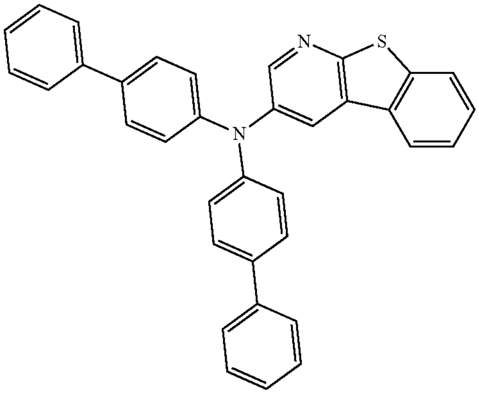
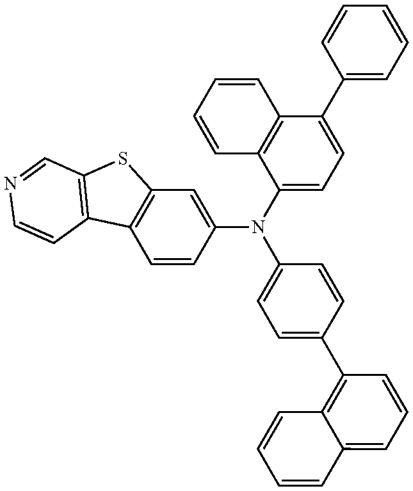

-continued
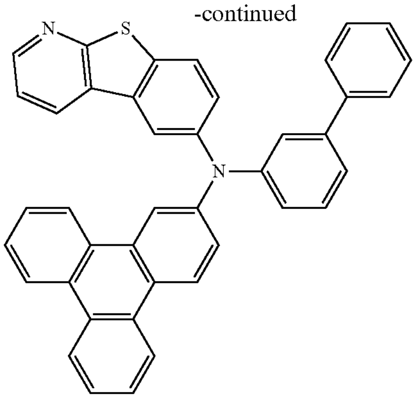
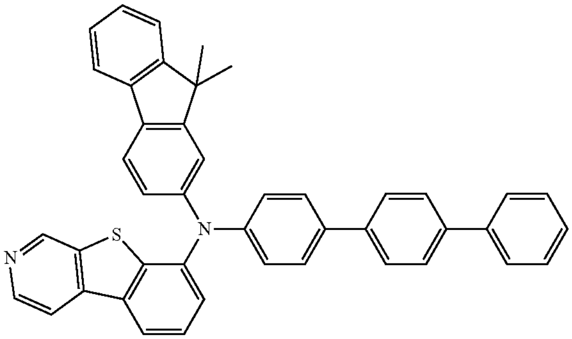
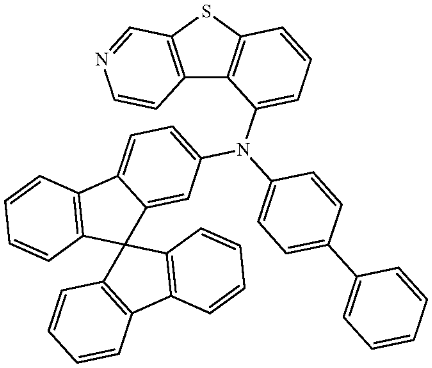
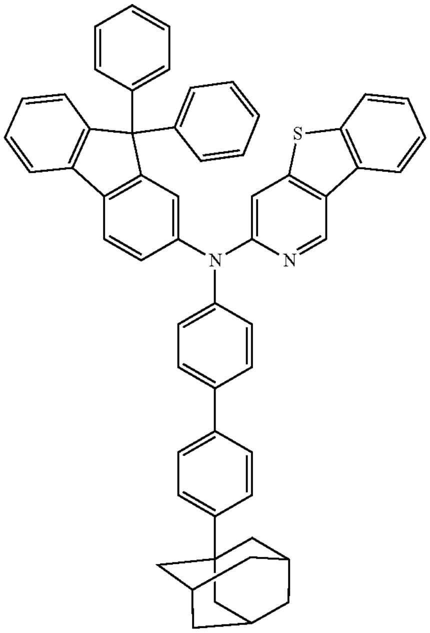
-continued
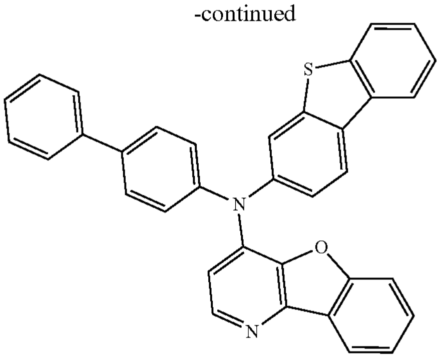
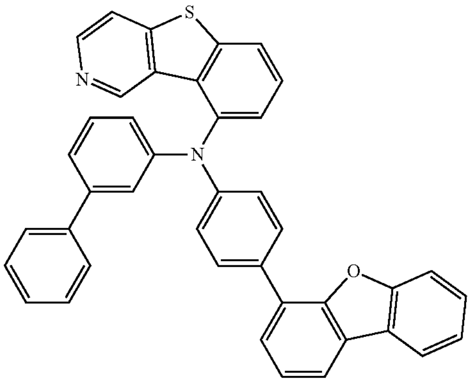
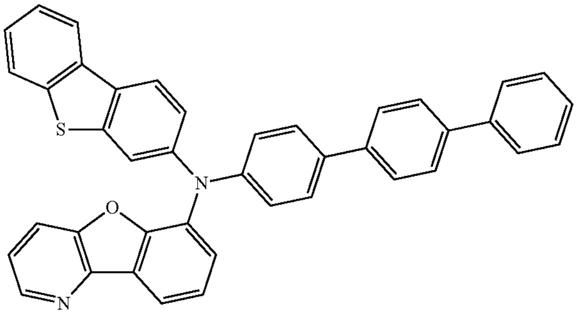
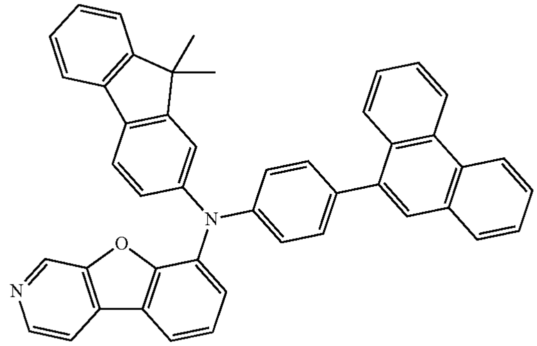
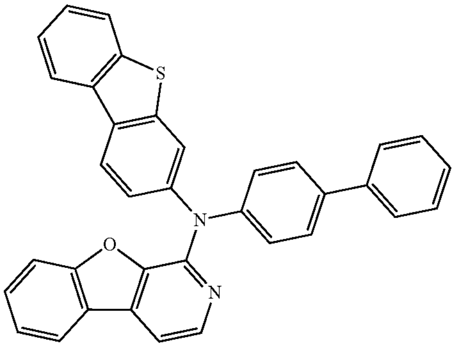

-continued
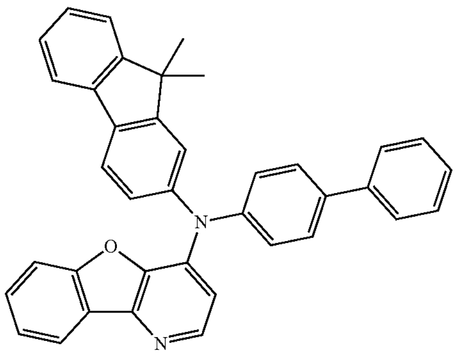
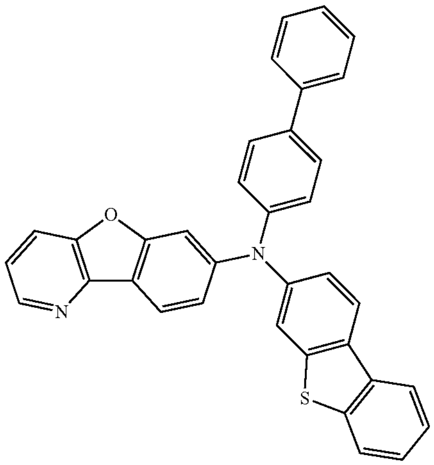
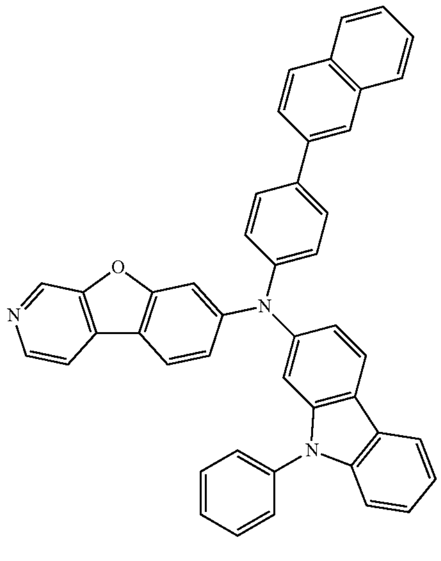
-continued
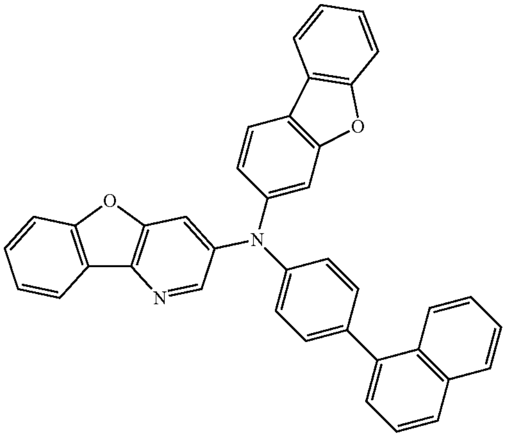
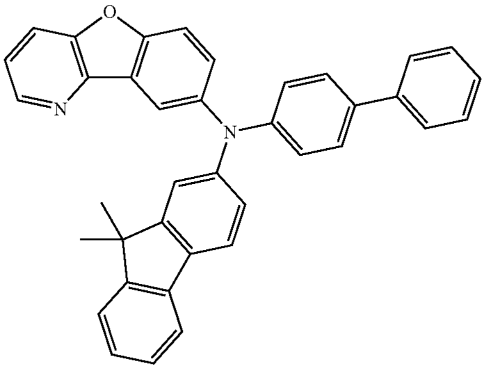
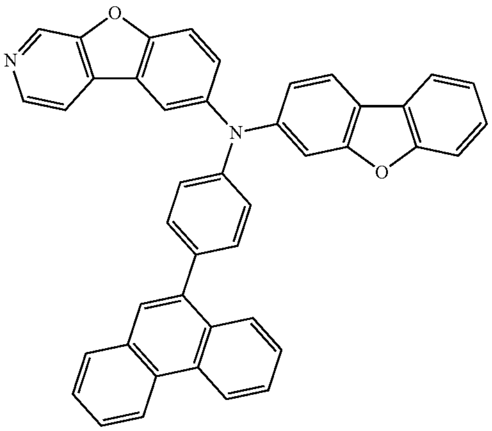
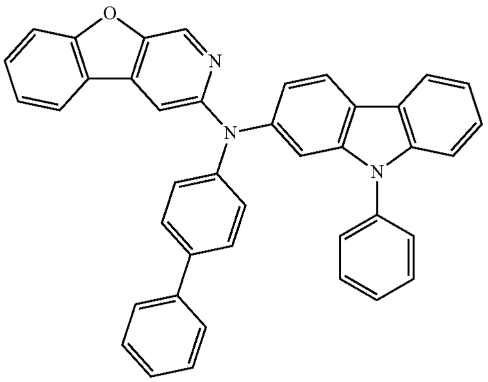

-continued
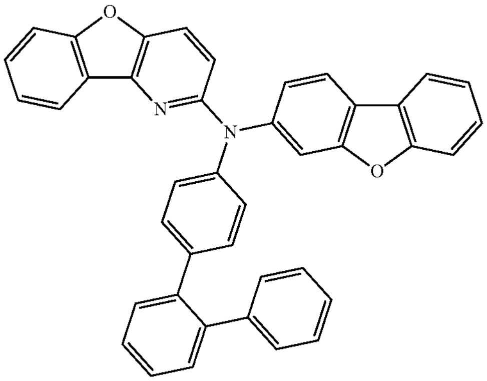
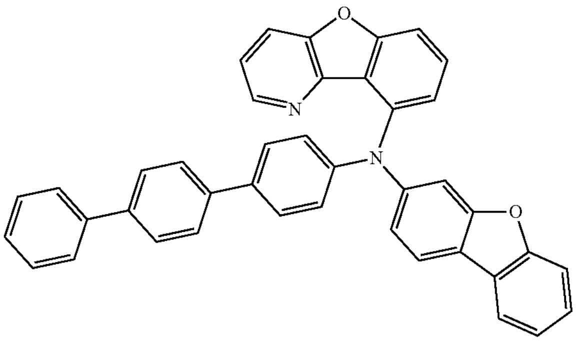
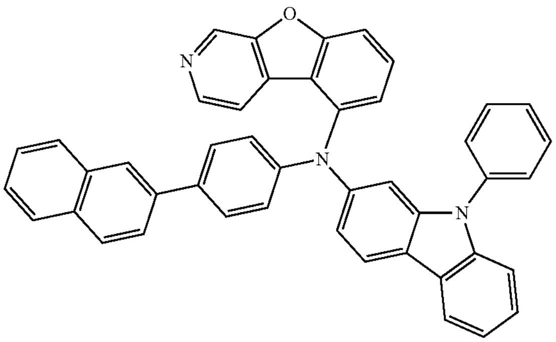
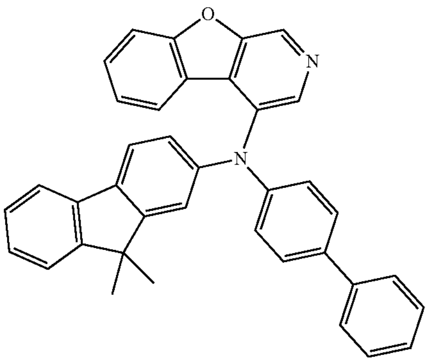
-continued
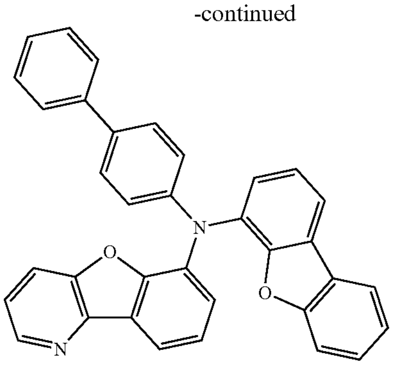
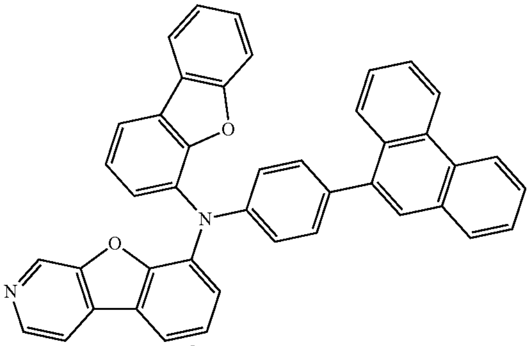
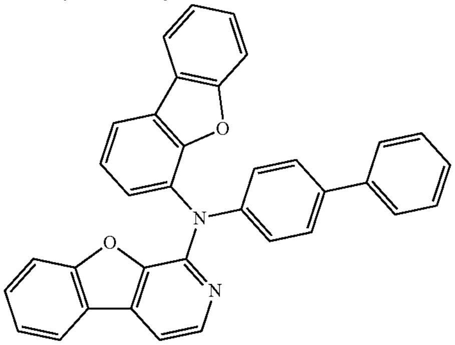
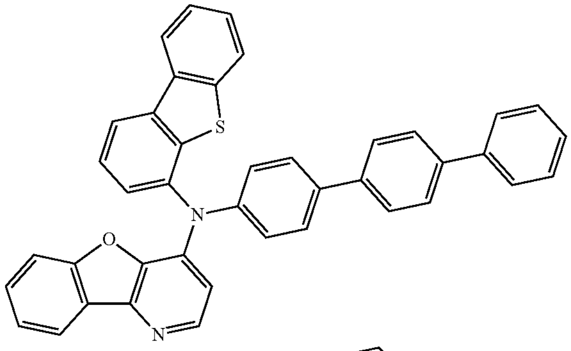
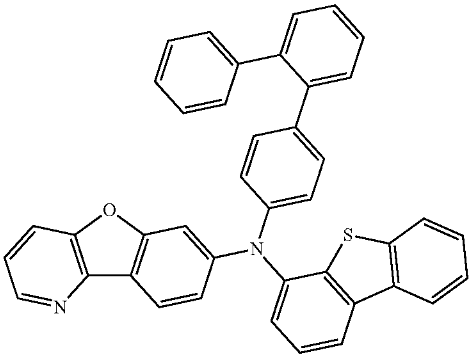

-continued
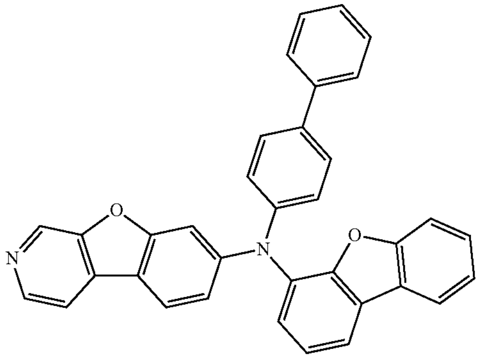
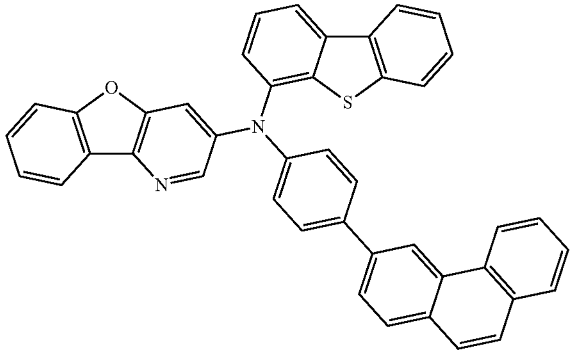
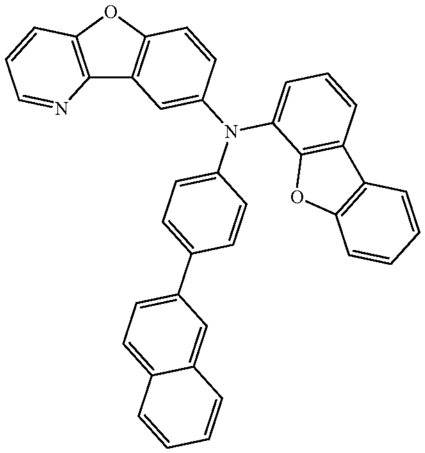
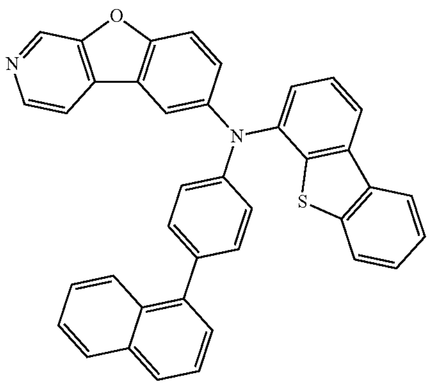
-continued
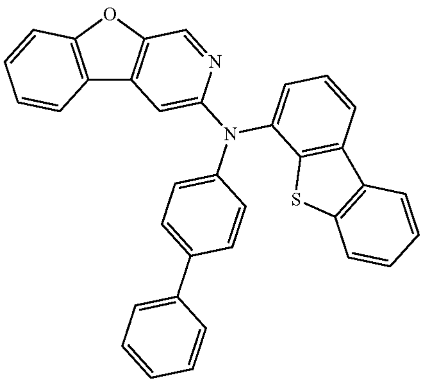
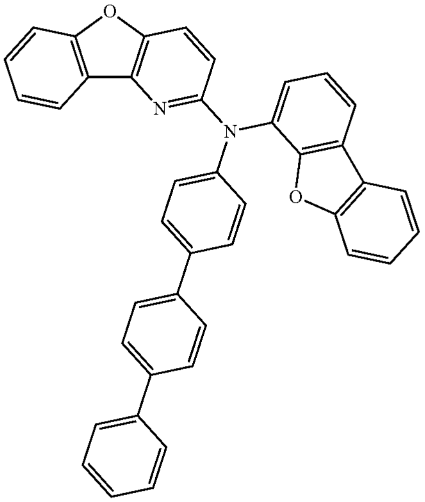
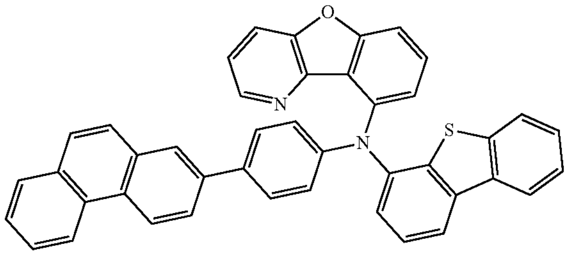
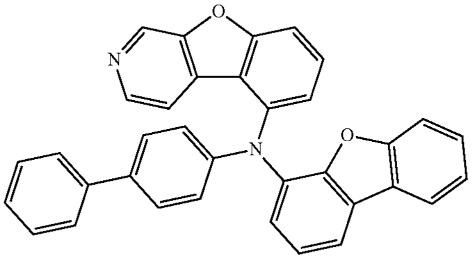
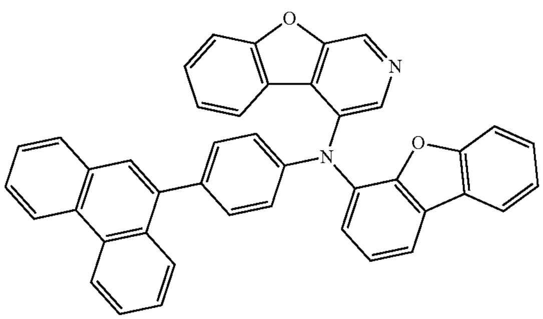

-continued
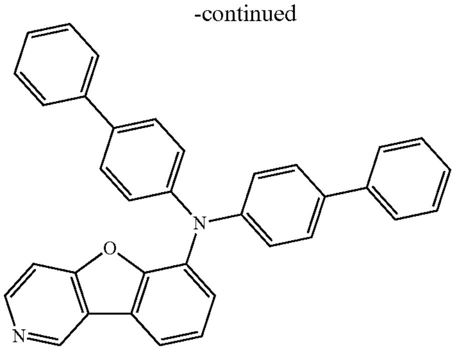
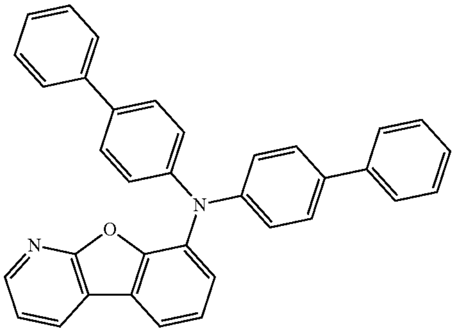
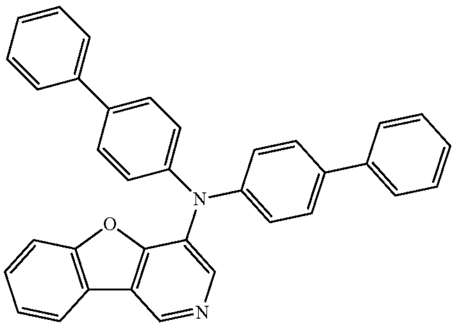
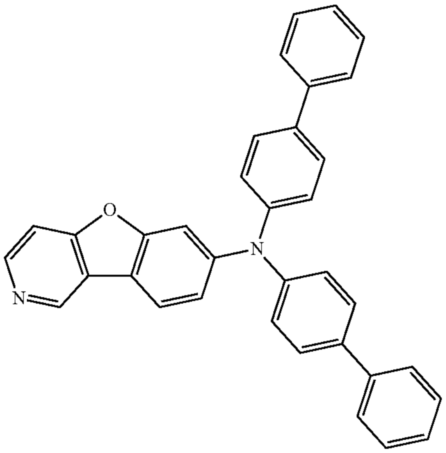
-continued
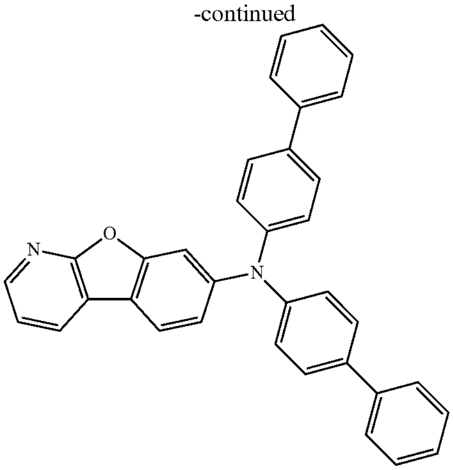
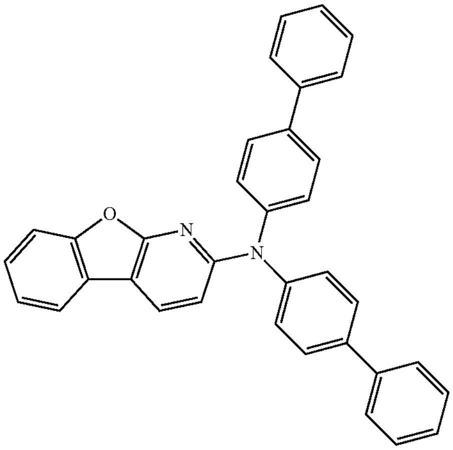
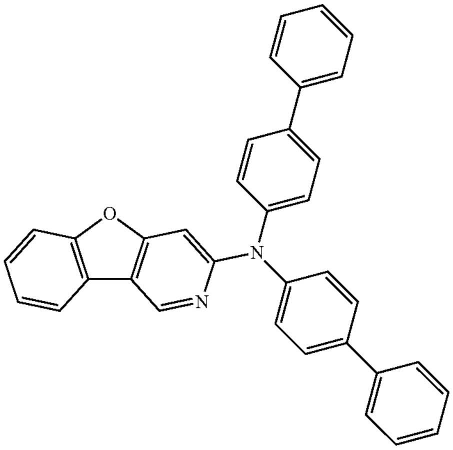
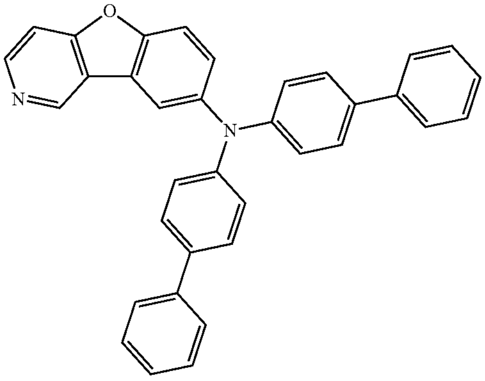

-continued
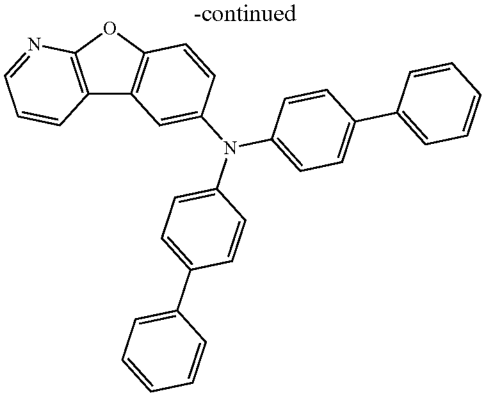
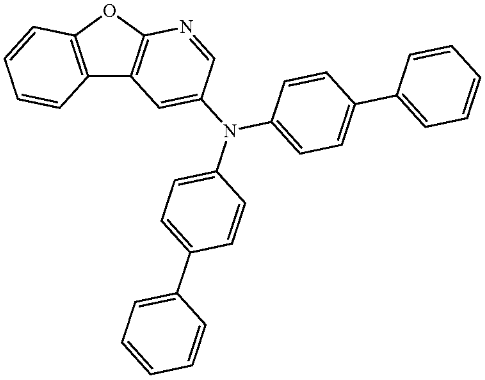
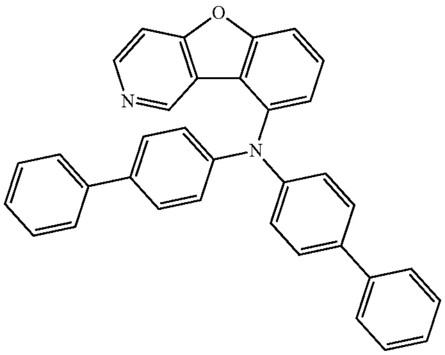
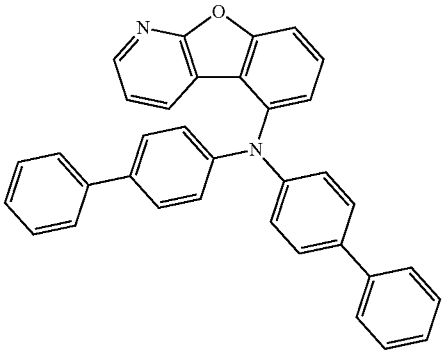
-continued
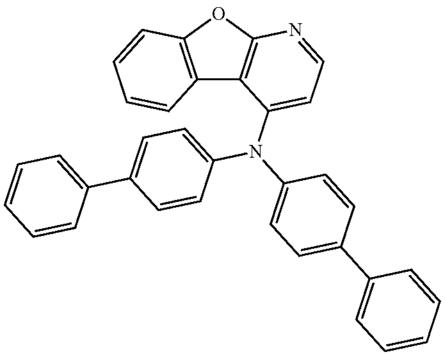
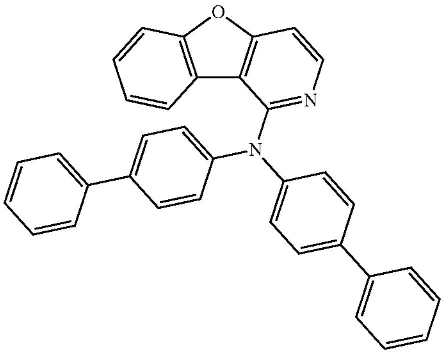
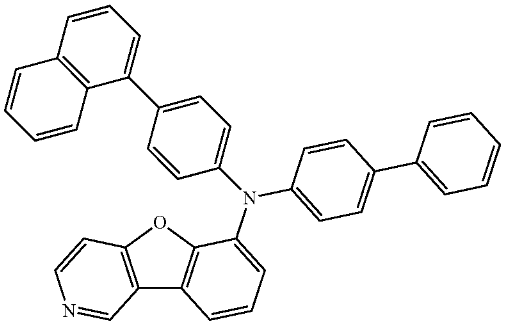
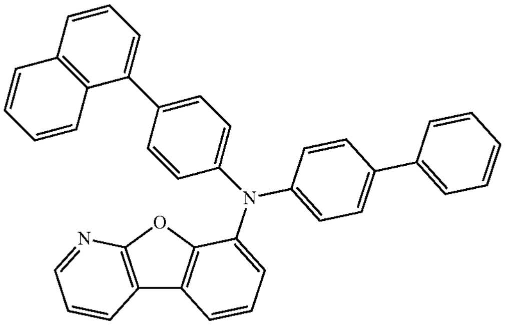
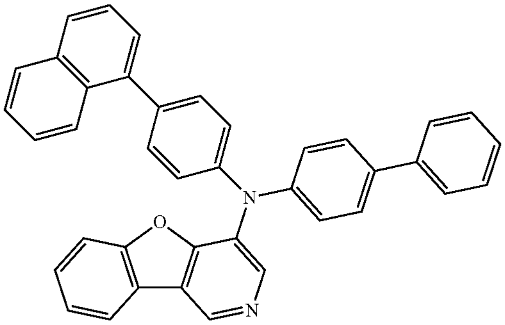

-continued
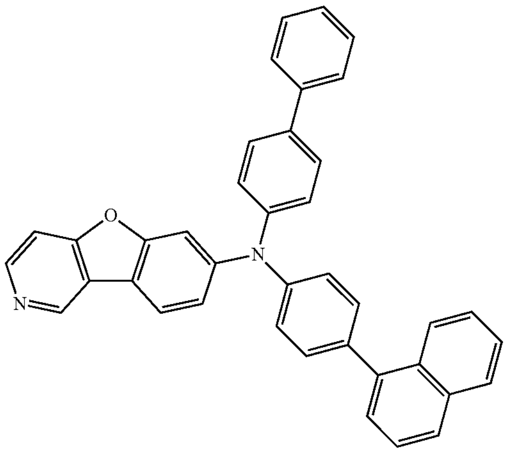
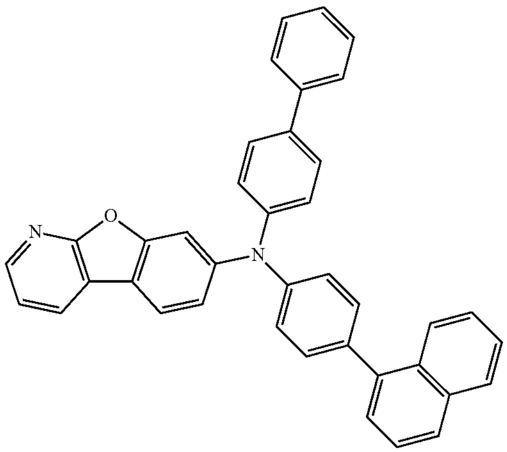
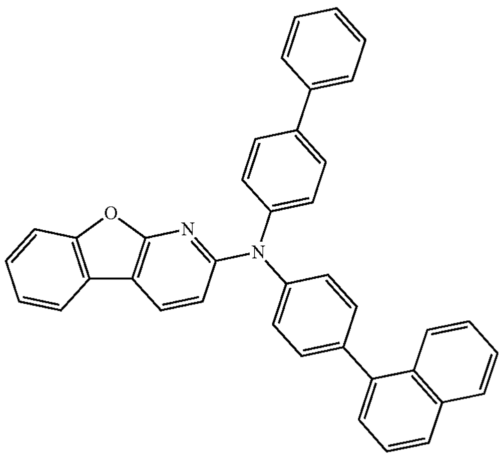
-continued
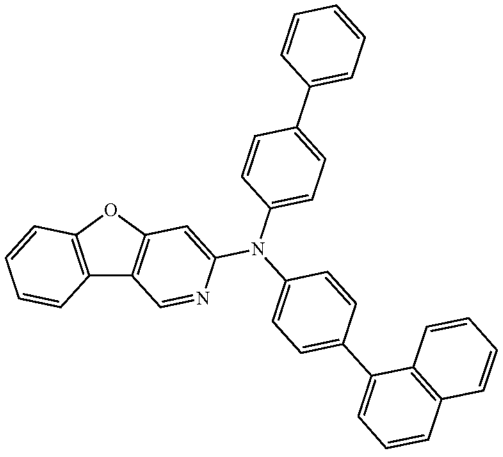
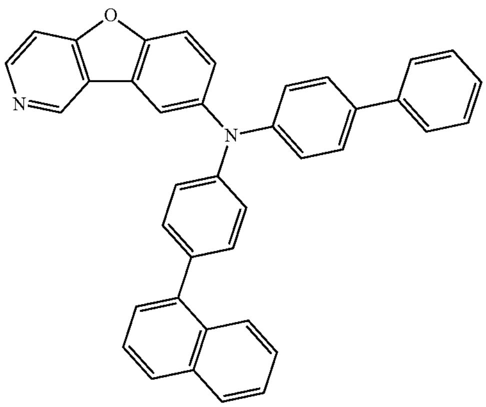
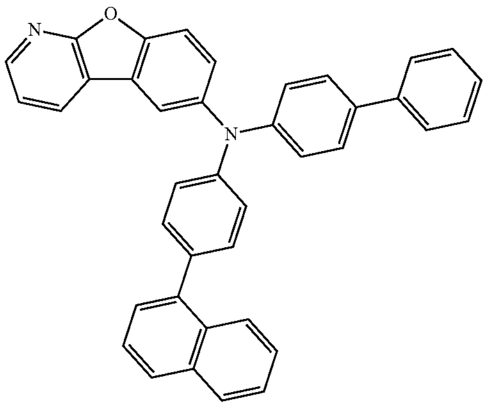
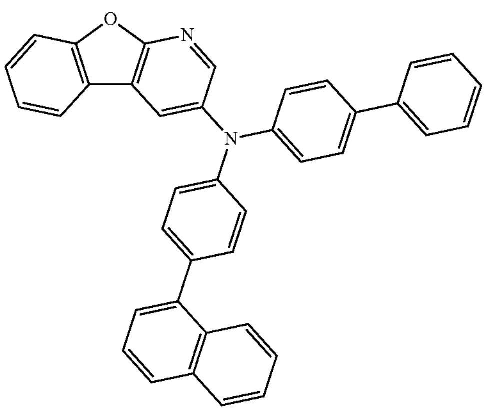

-continued
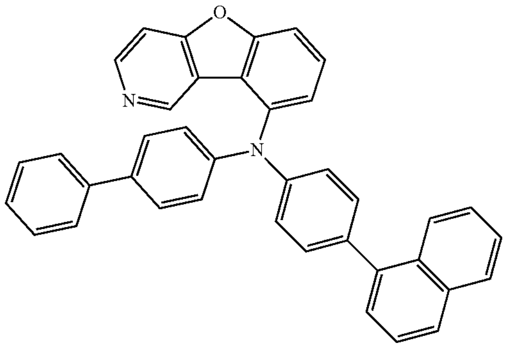
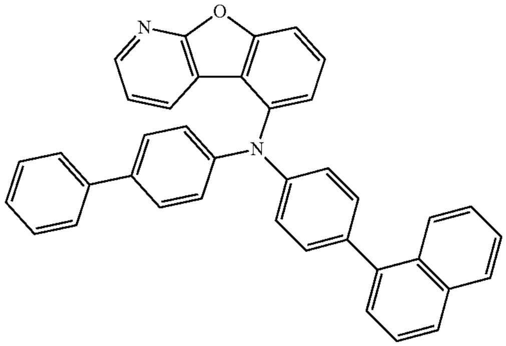
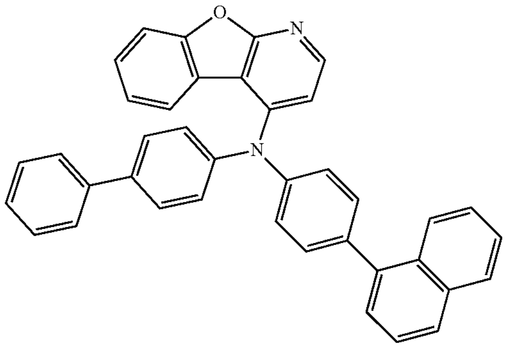
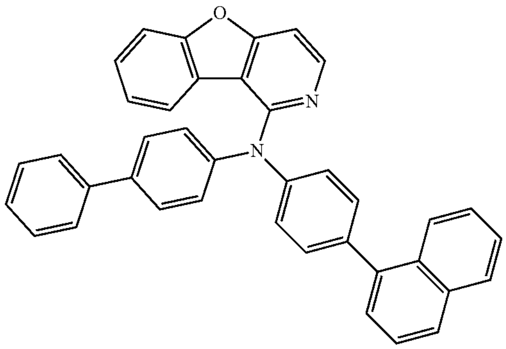
-continued
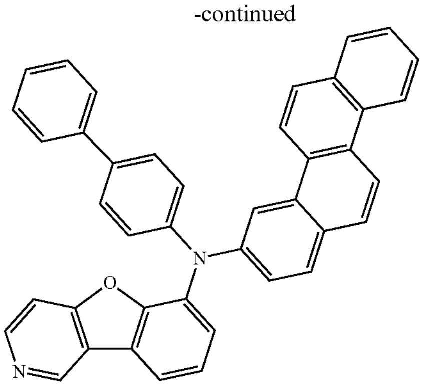
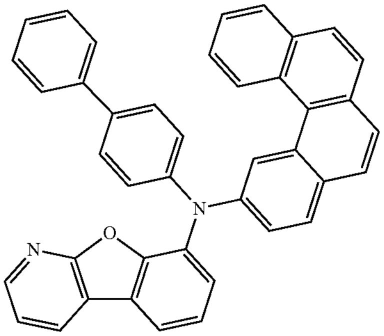
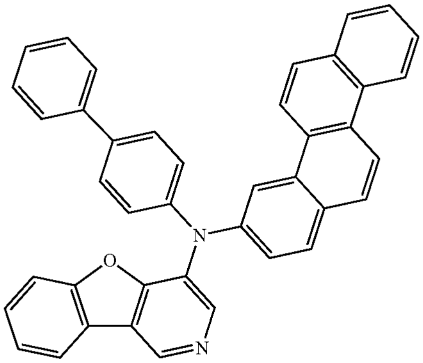
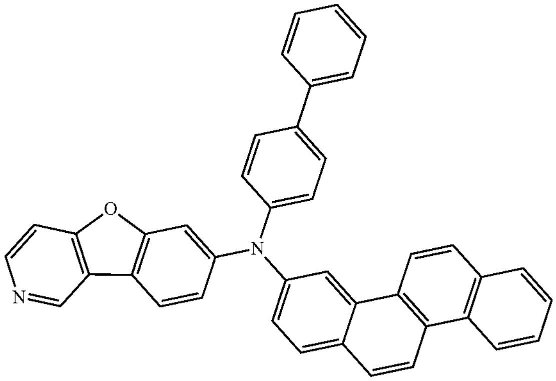

-continued
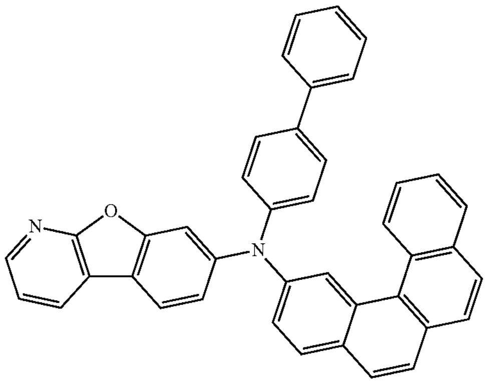
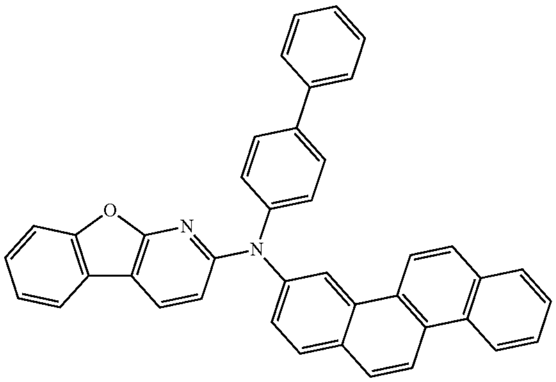
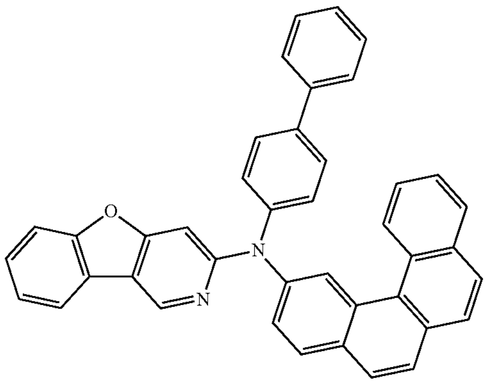
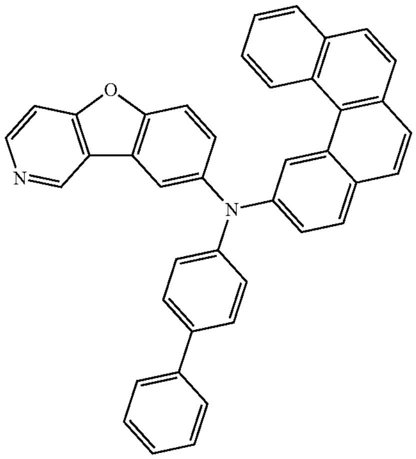
-continued
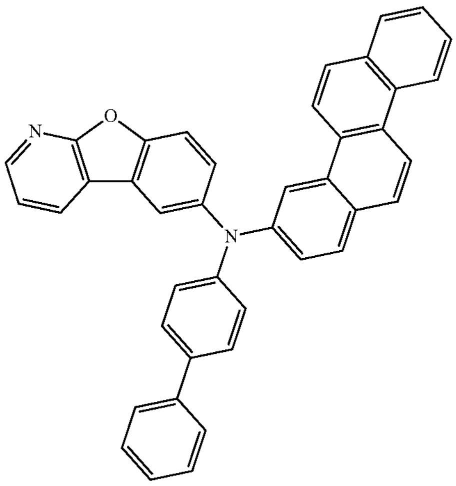
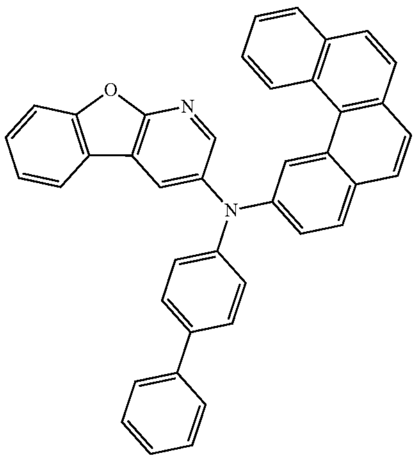
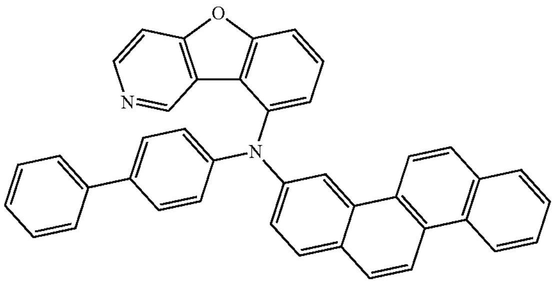
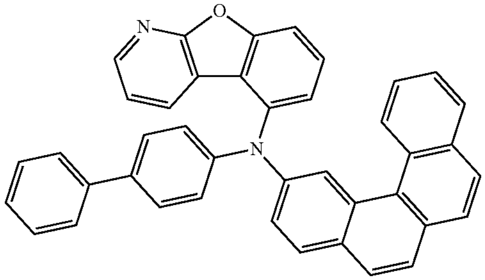

-continued
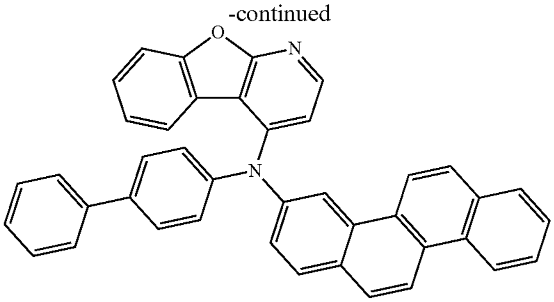
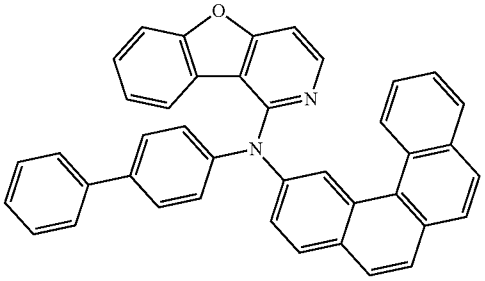
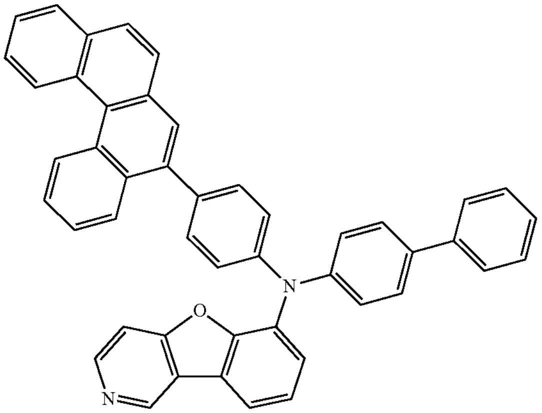
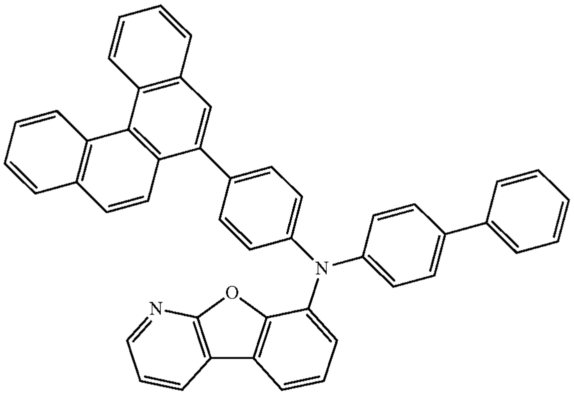
-continued
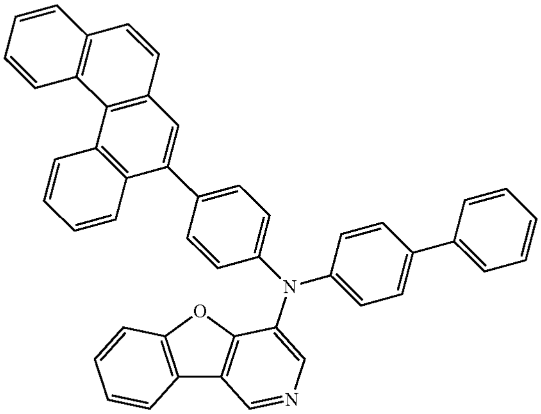
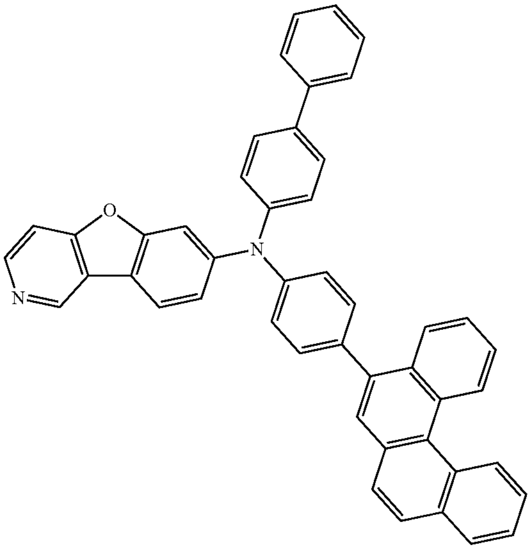
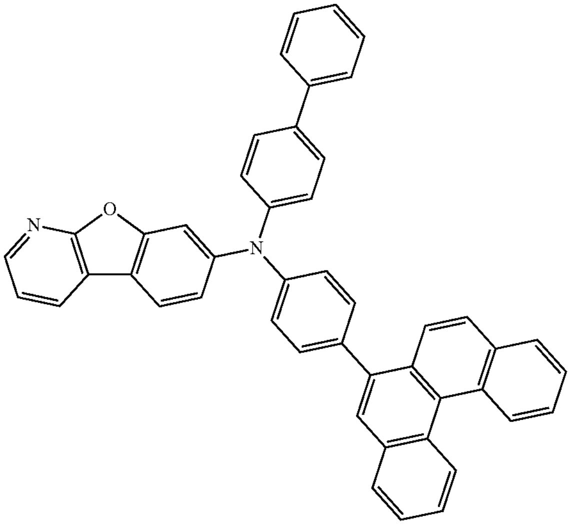

-continued
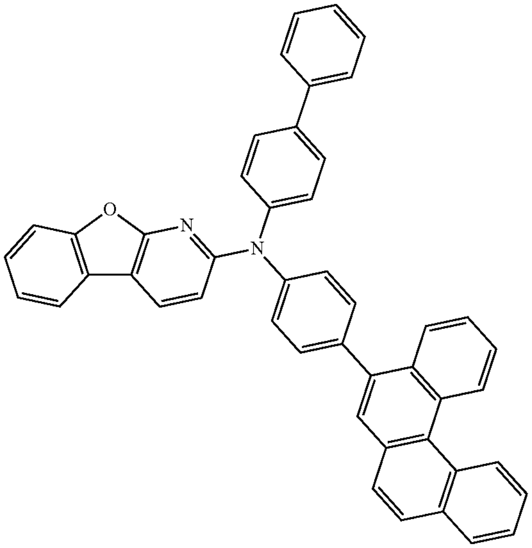
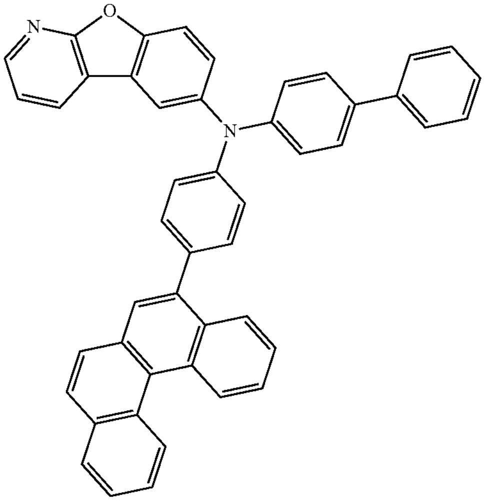
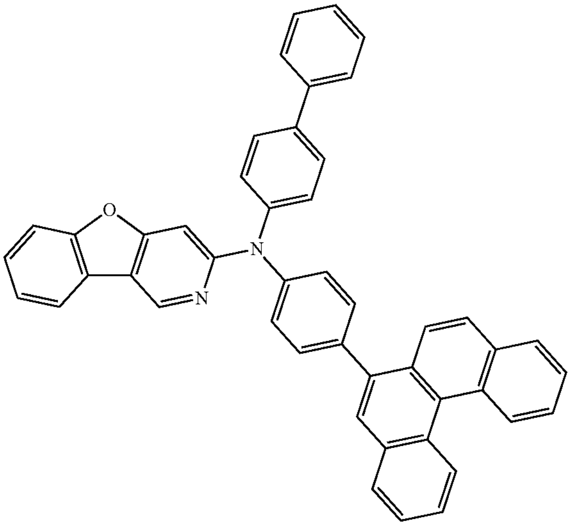
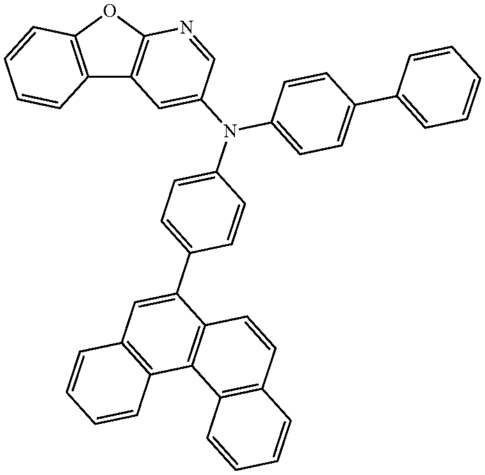
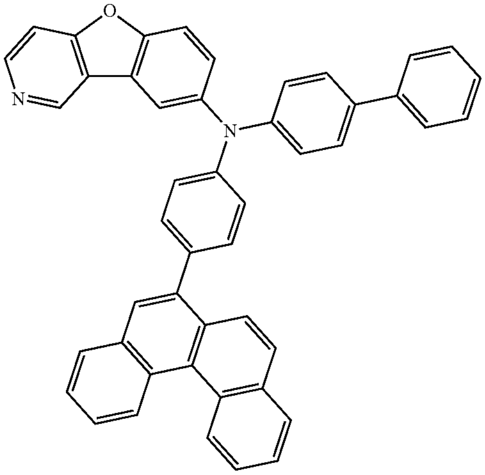
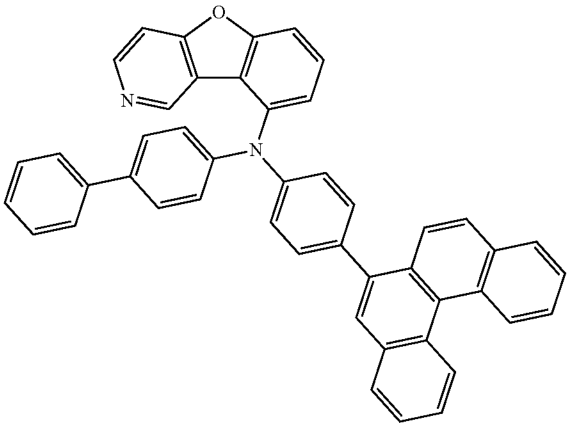
-continued -continued
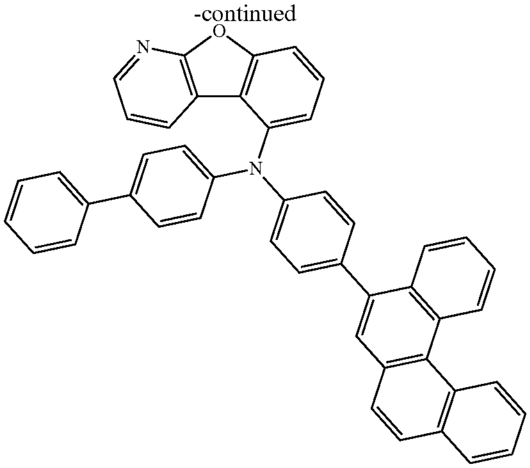
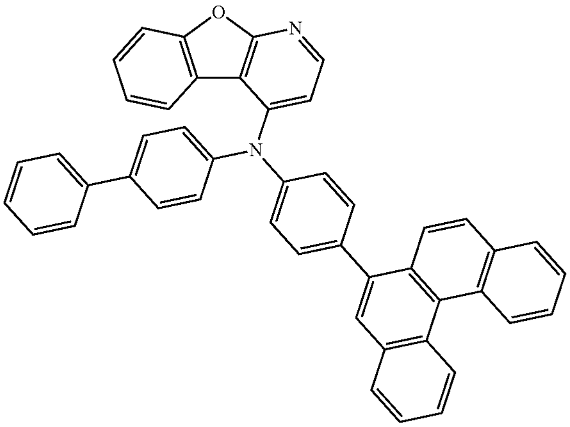
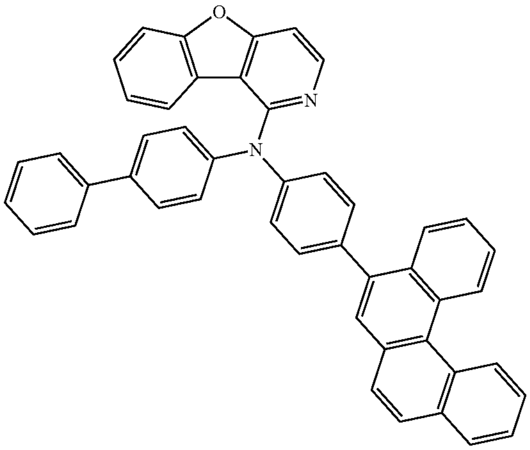
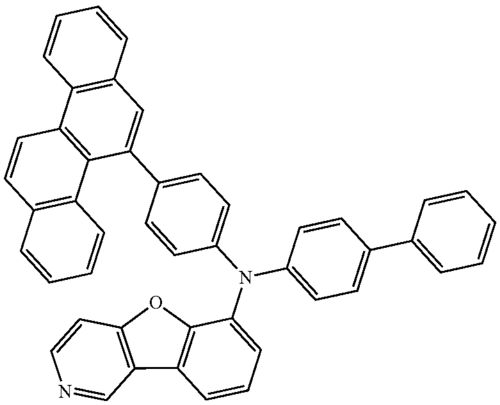
-continued
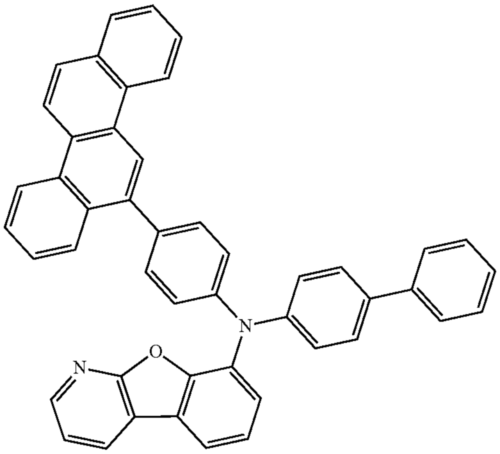
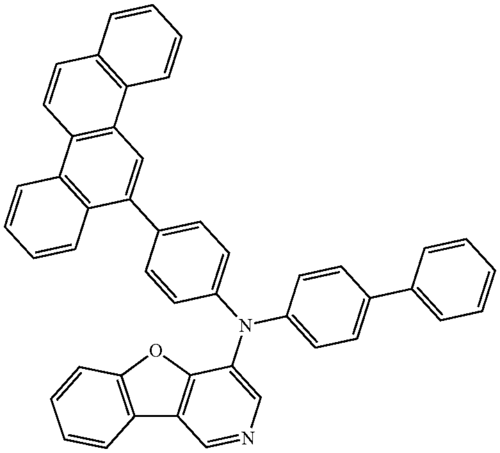
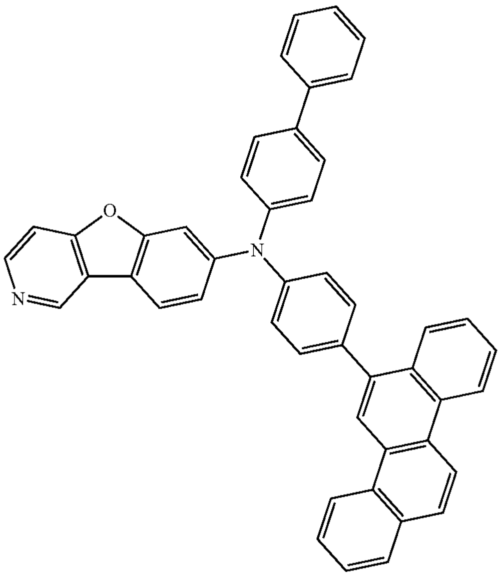

-continued
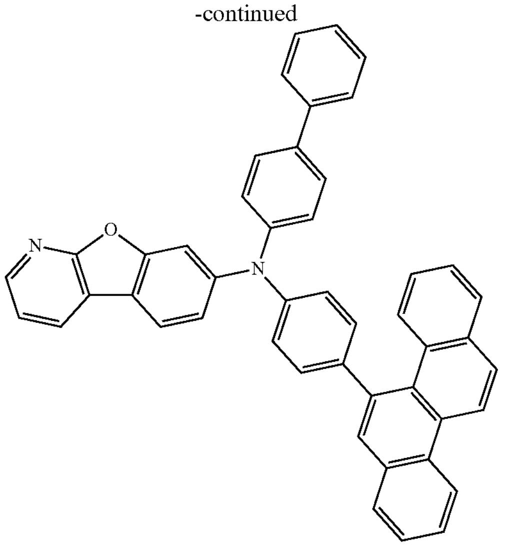
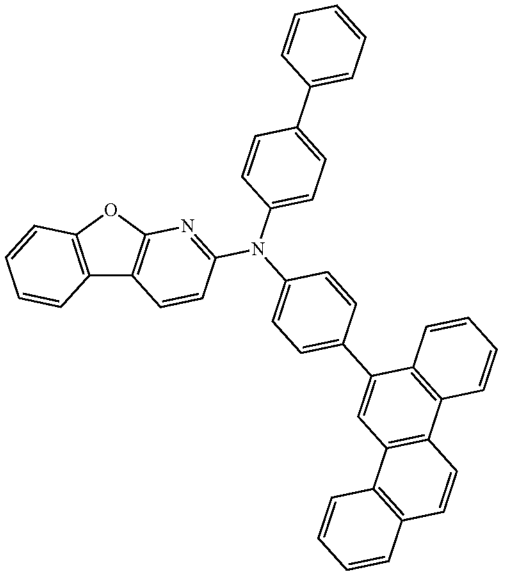
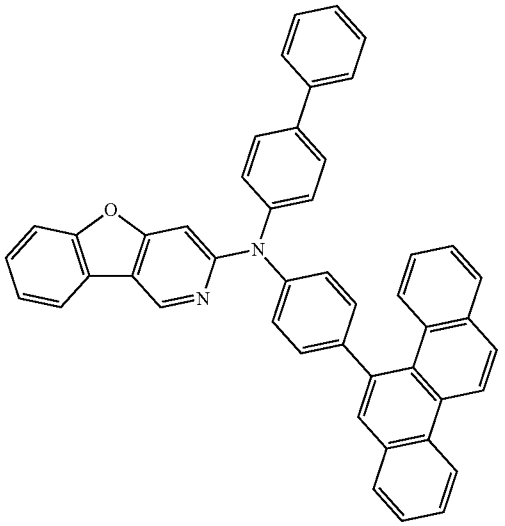
-continued
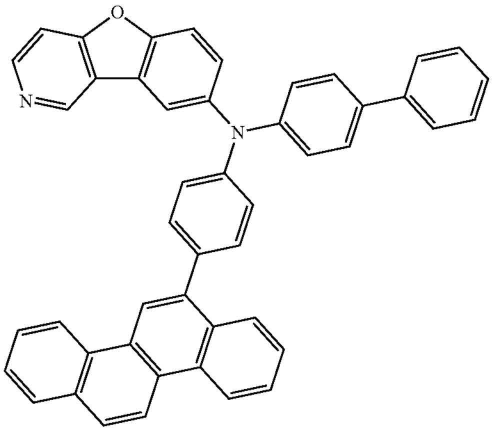
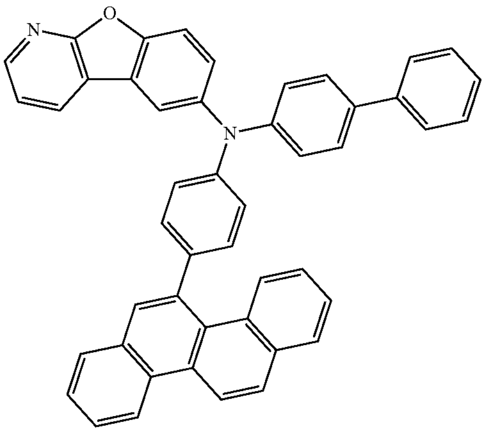
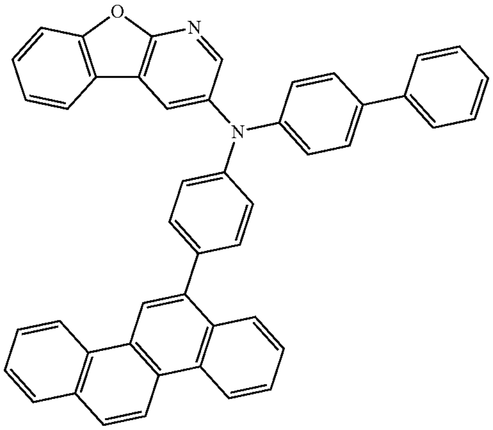
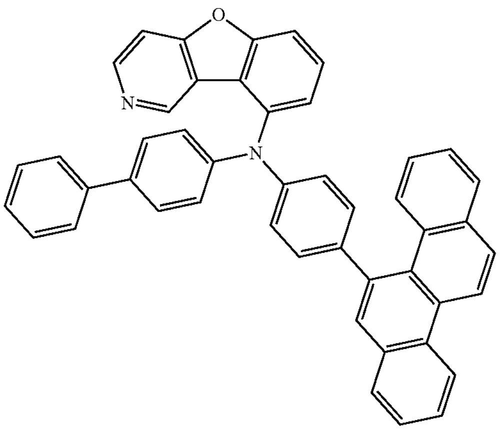

-continued
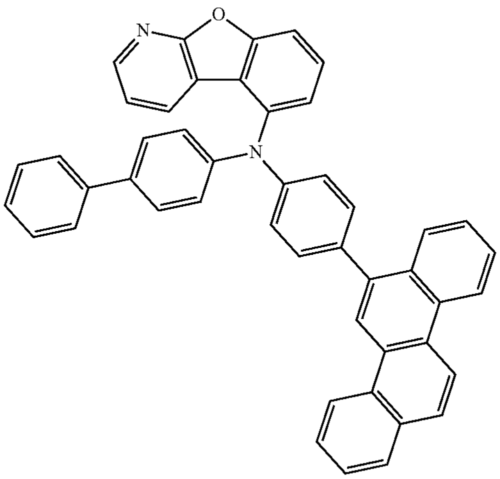
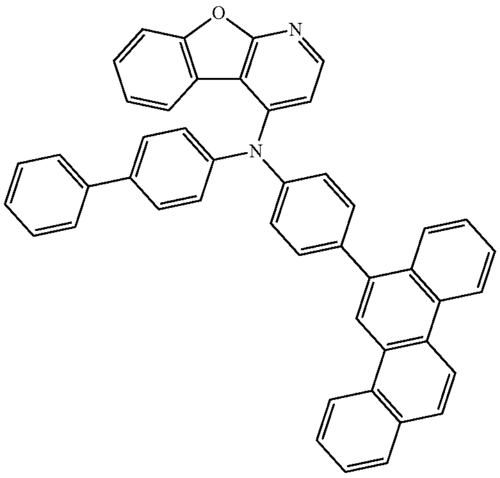
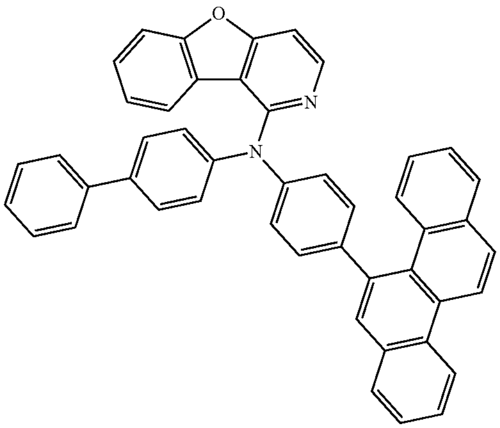
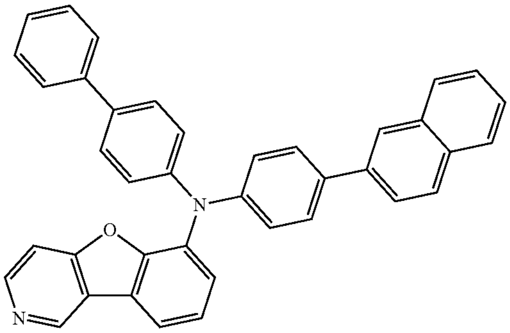
-continued
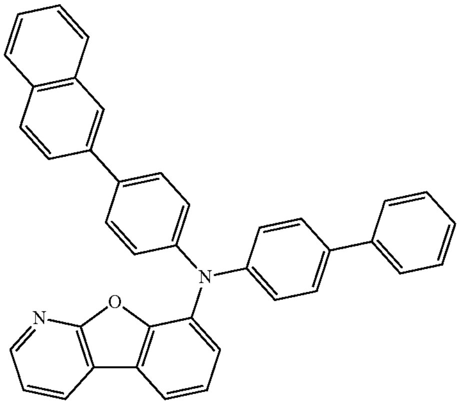
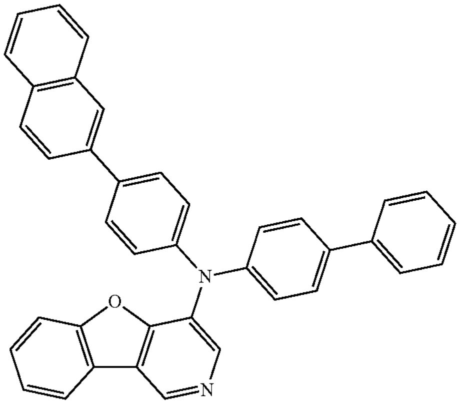
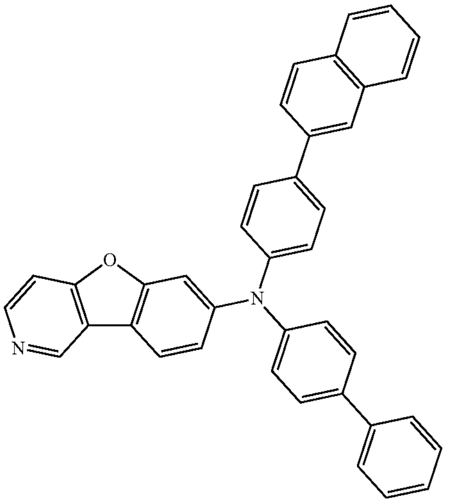

-continued
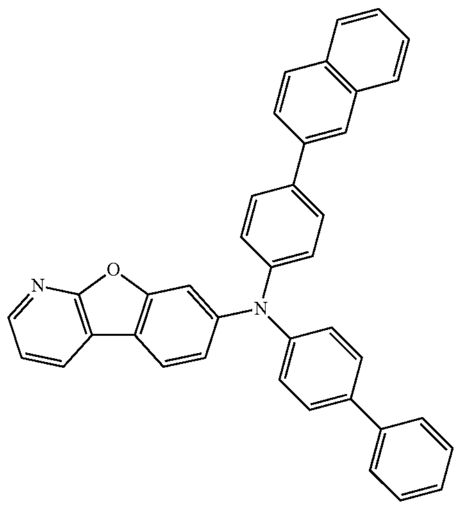
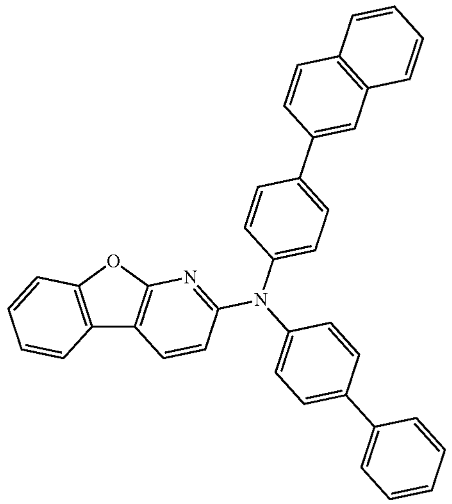
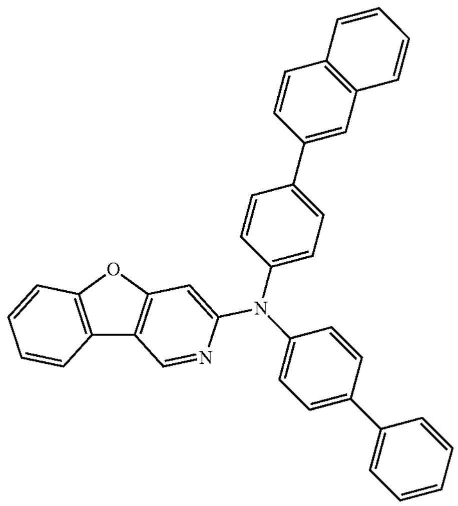
-continued
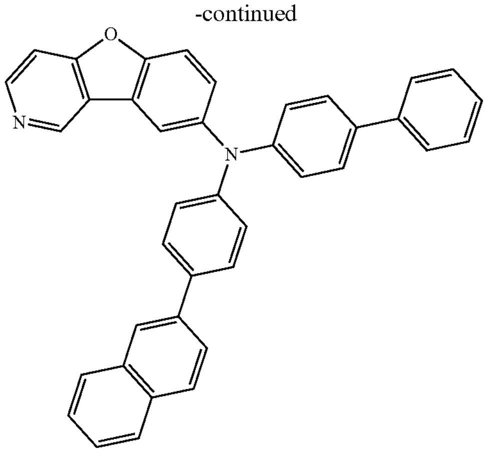
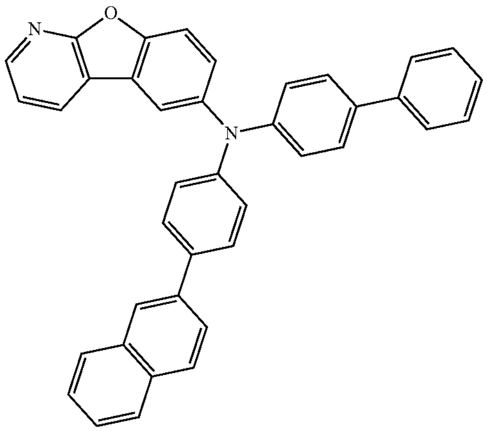
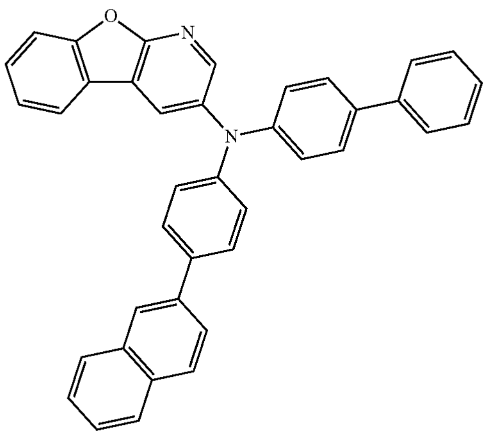
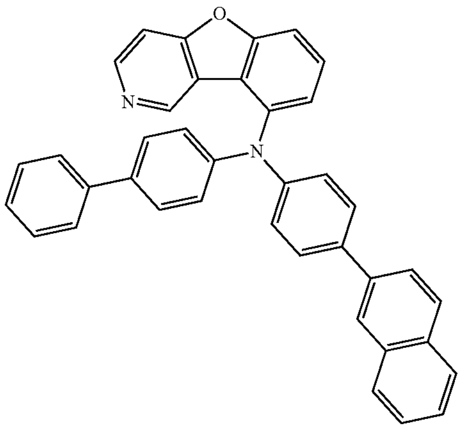

-continued
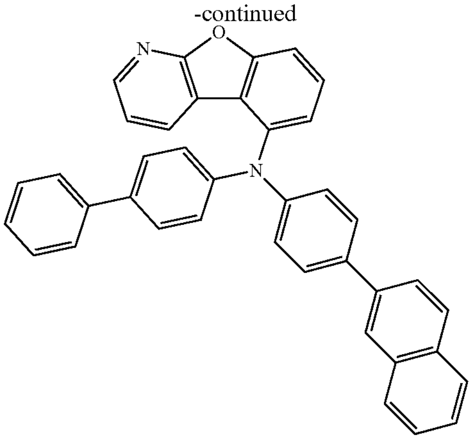
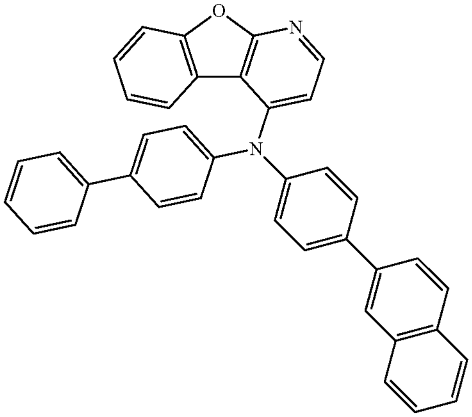
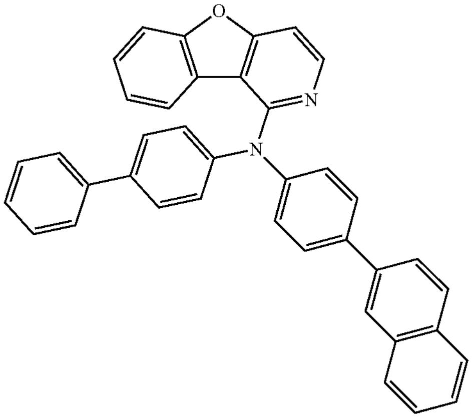
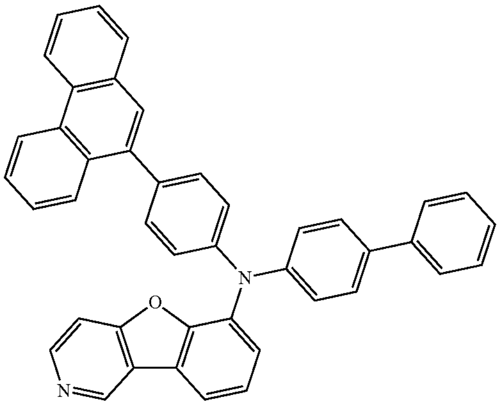
-continued
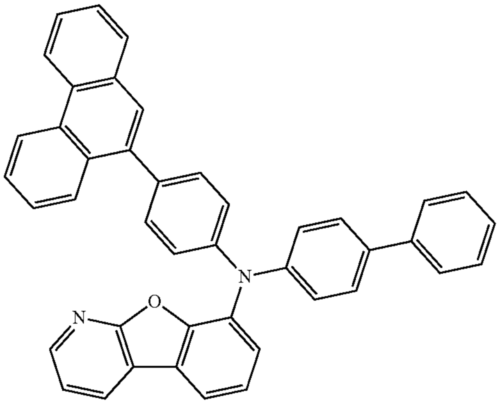
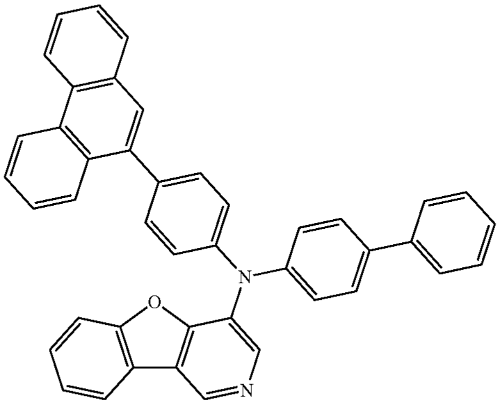
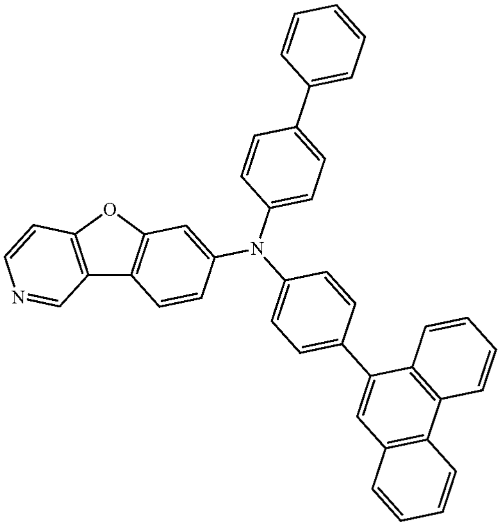

-continued
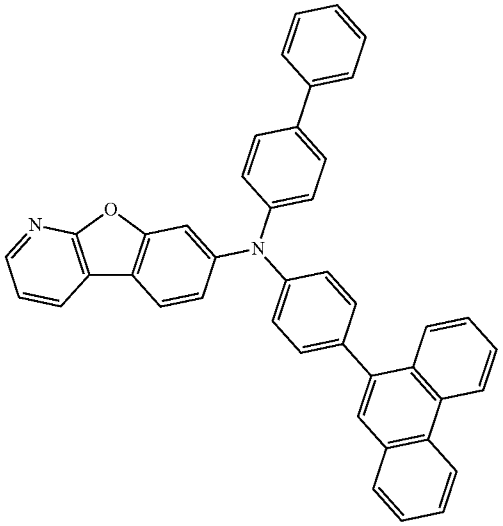
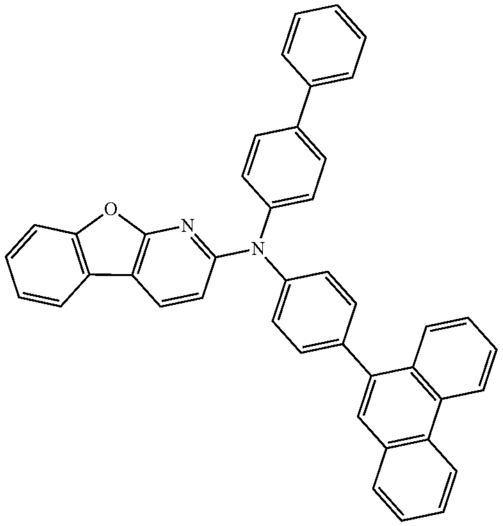
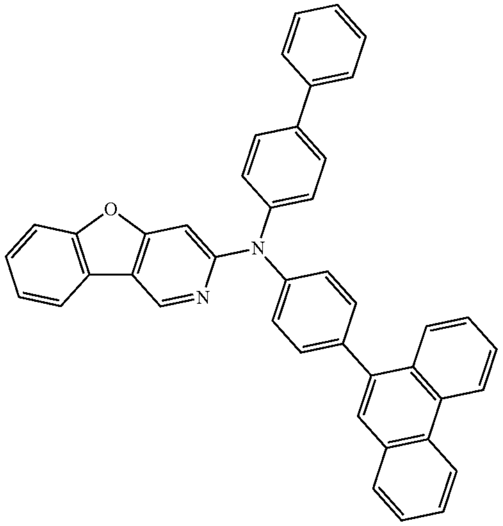
-continued
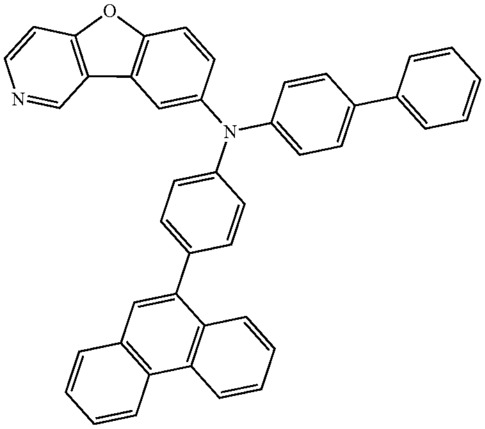
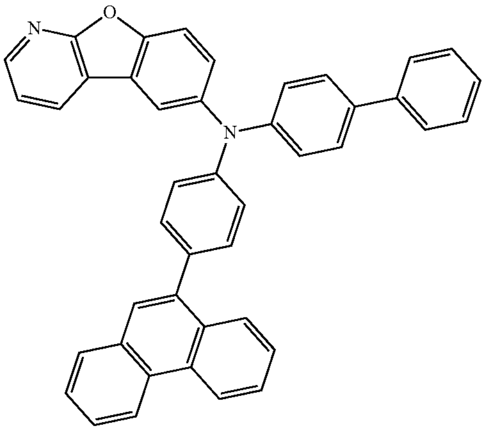
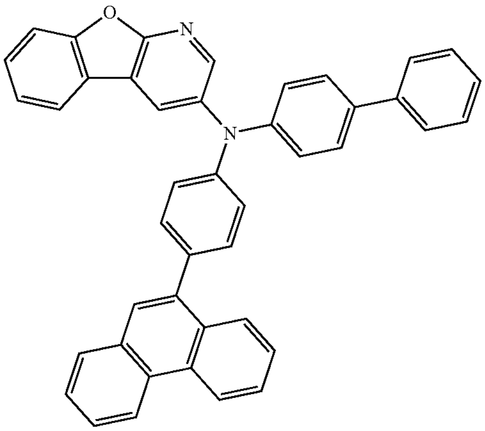
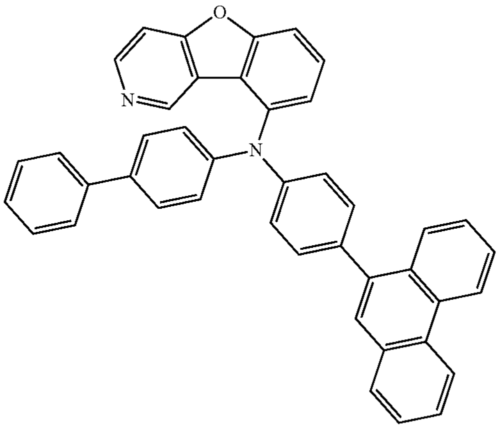

-continued
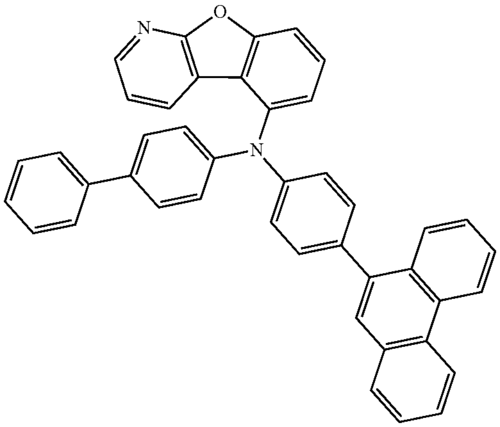
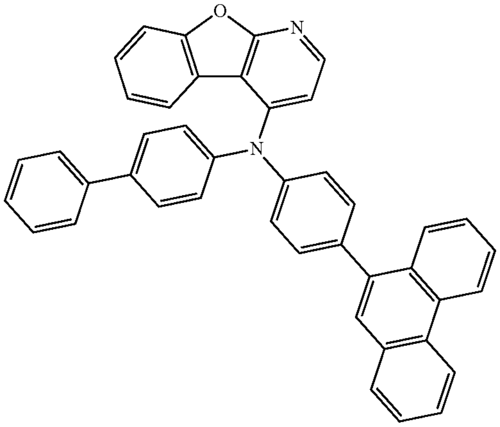
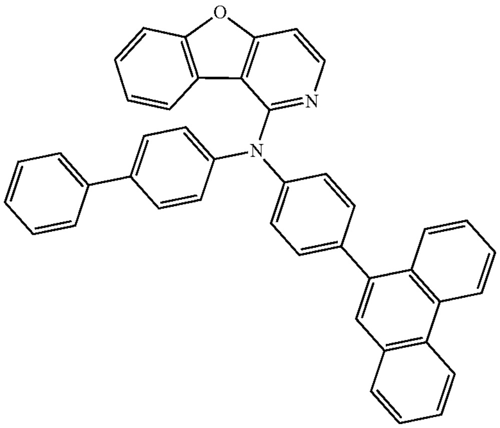
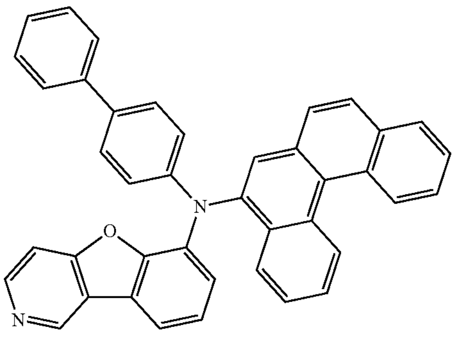
-continued
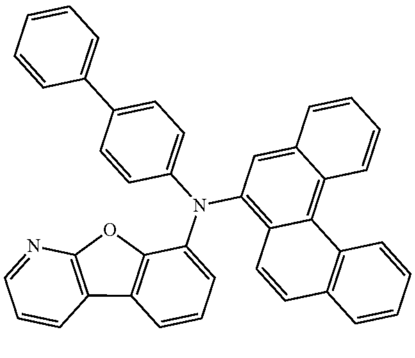
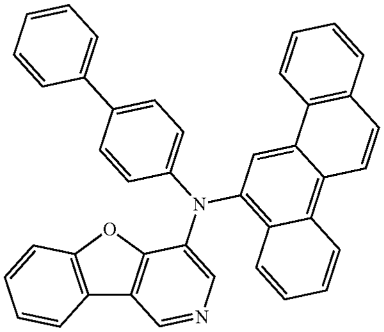
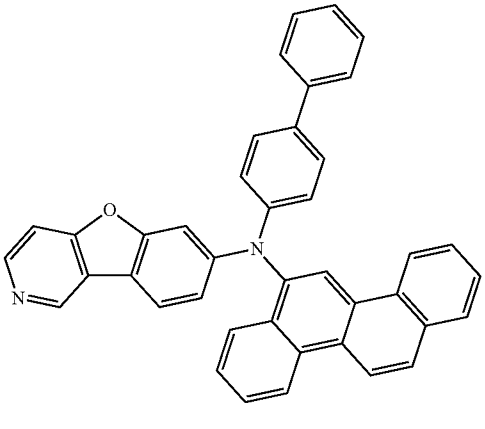
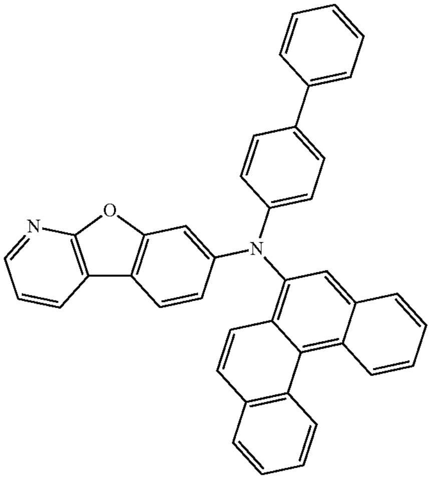

-continued
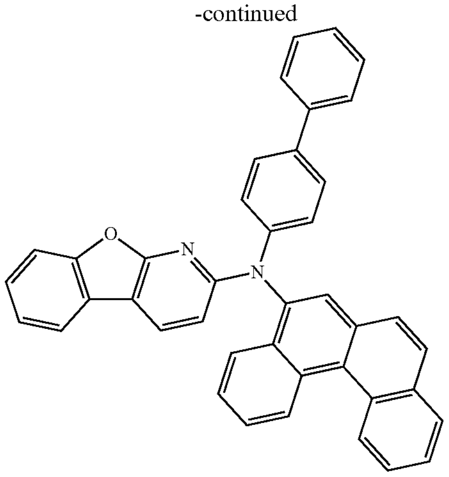
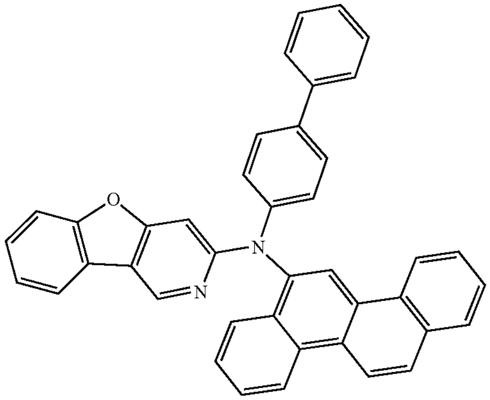
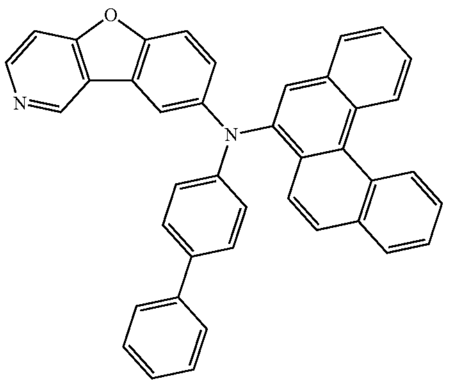
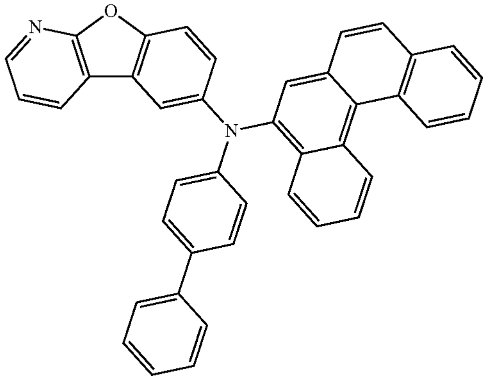
-continued
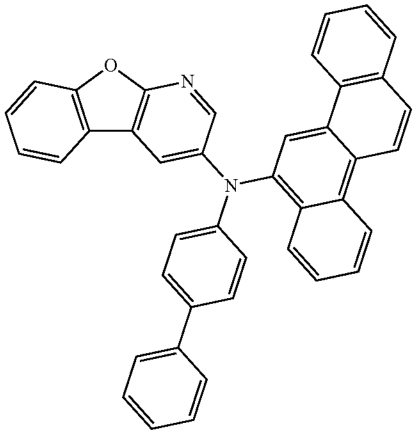
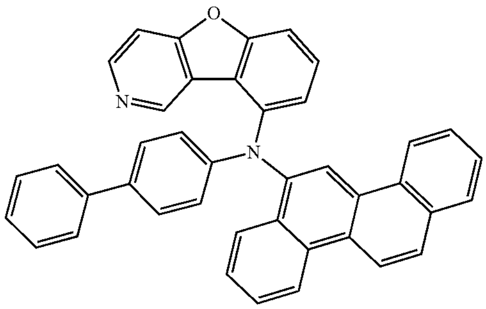
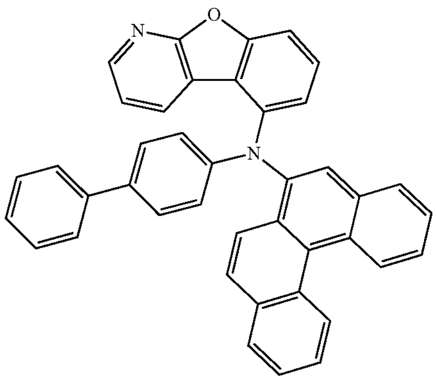
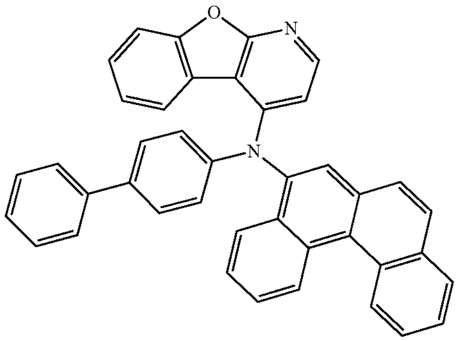

-continued
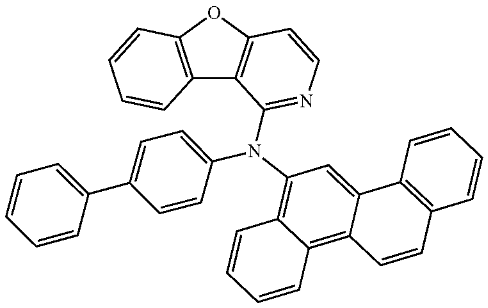
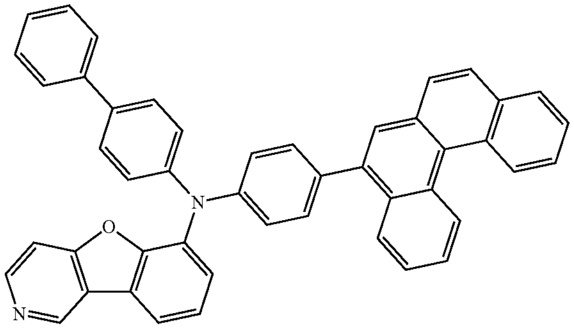
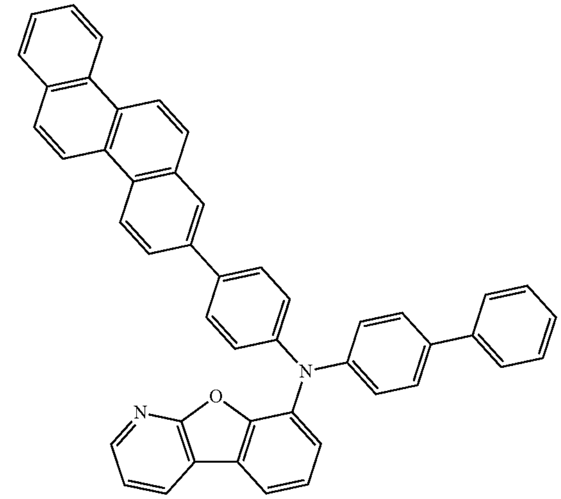
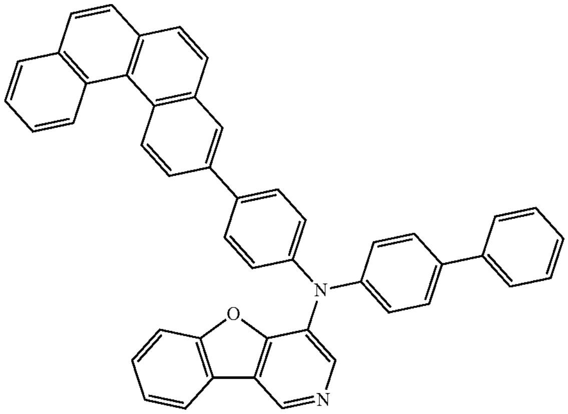
-continued
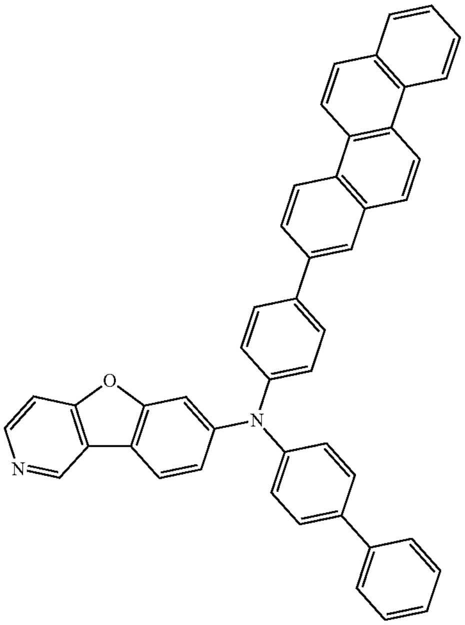
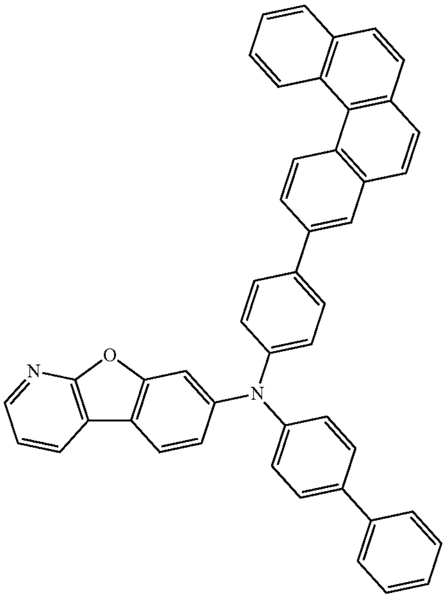

-continued
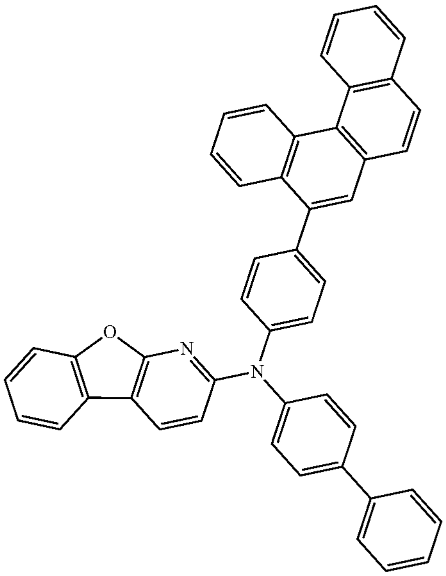
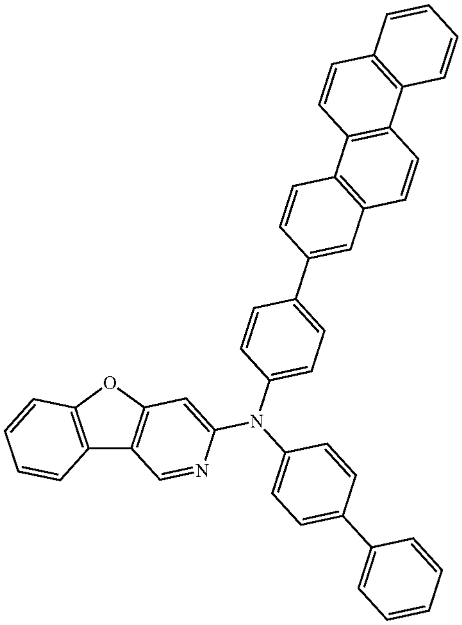
-continued
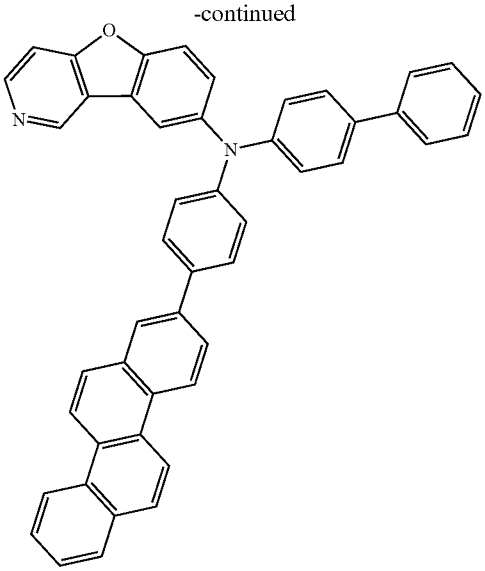
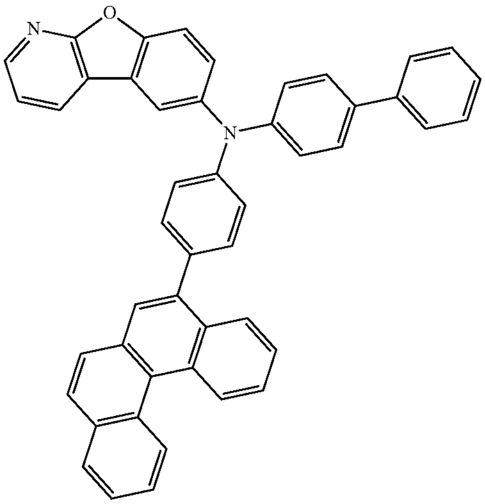
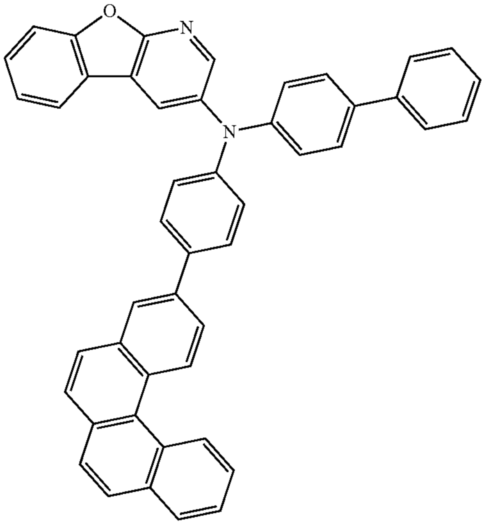

-continued
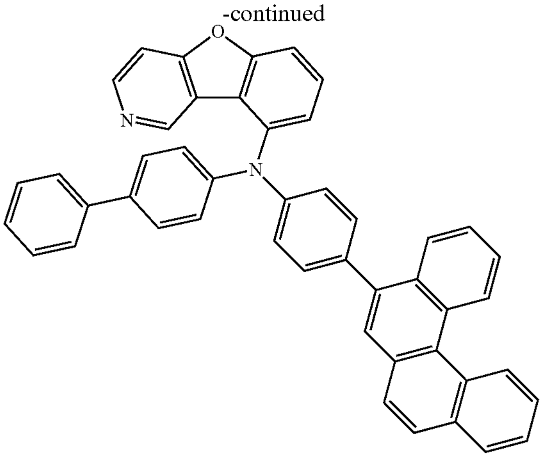
-continued
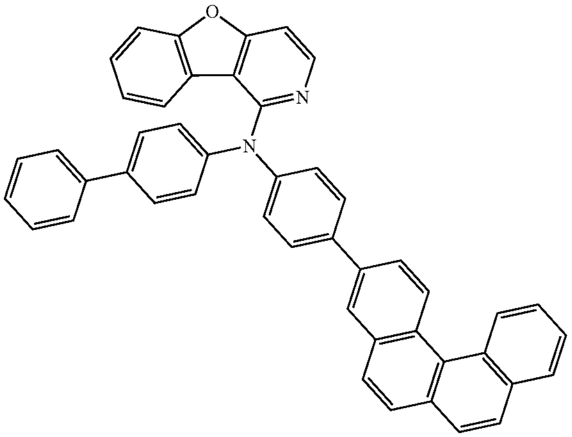
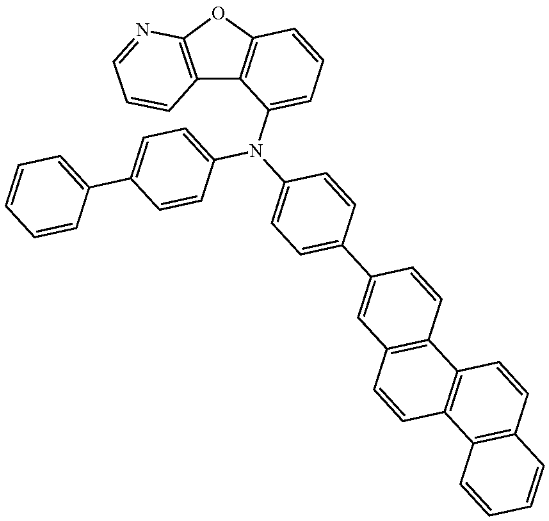
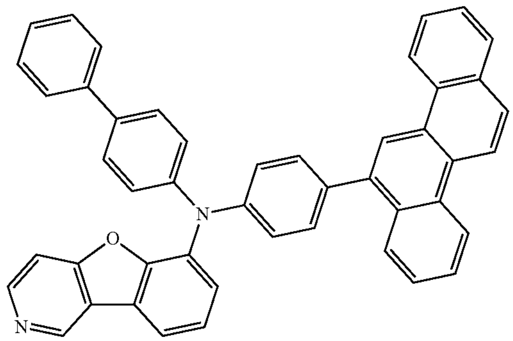
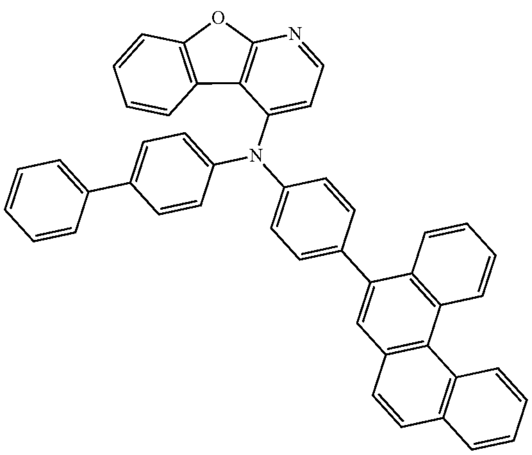
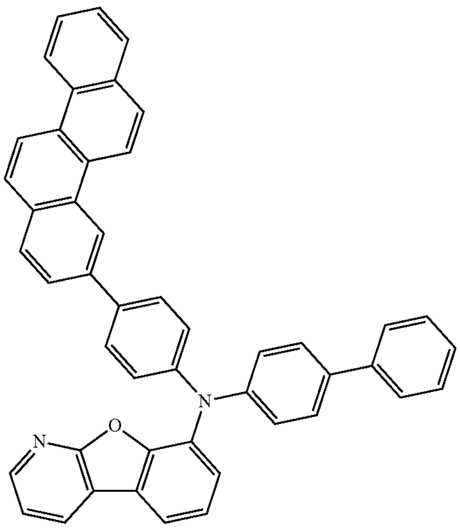

-continued
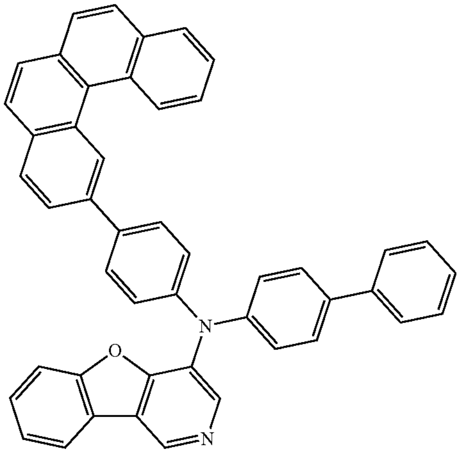
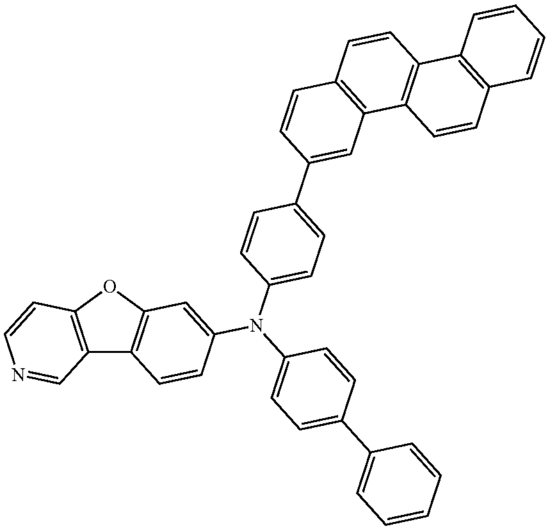
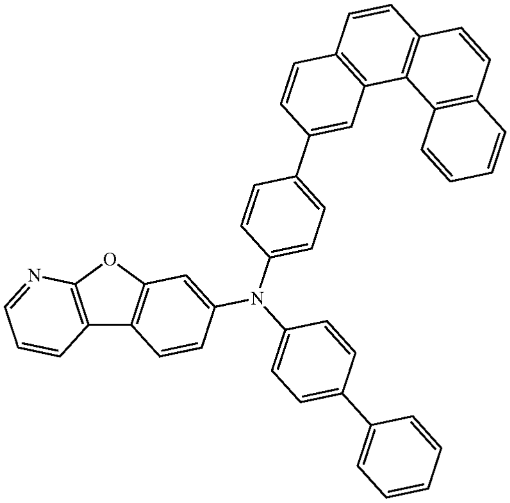
-continued
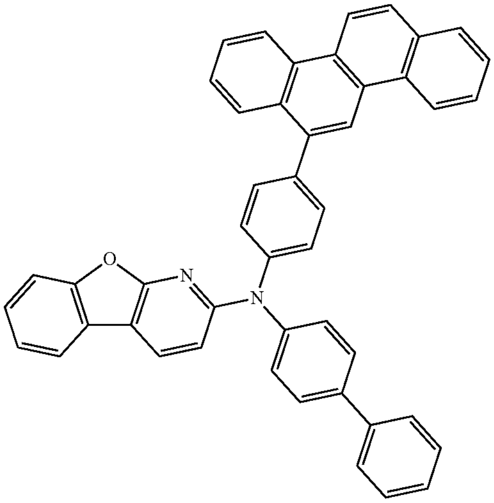 [SMILES: c1ccc(-c2ccc(N(c3ccc(-c4cc5c6ccccc6ccc5c5ccccc45)cc3)c3ccc4c(n3)oc3ccccc34)cc2)cc1]
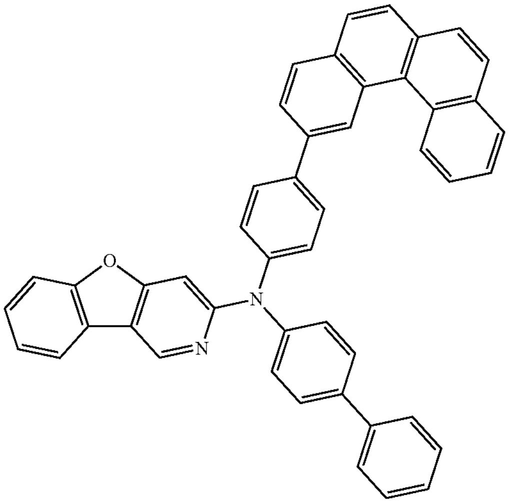
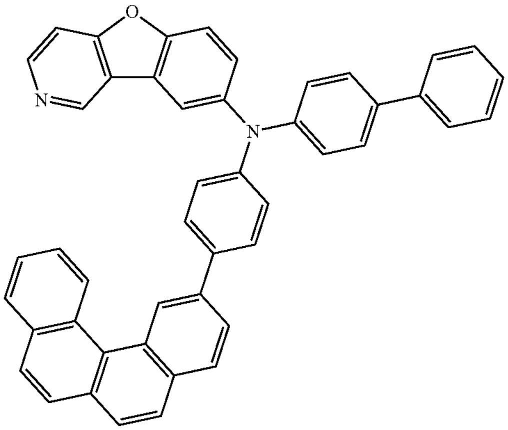

-continued
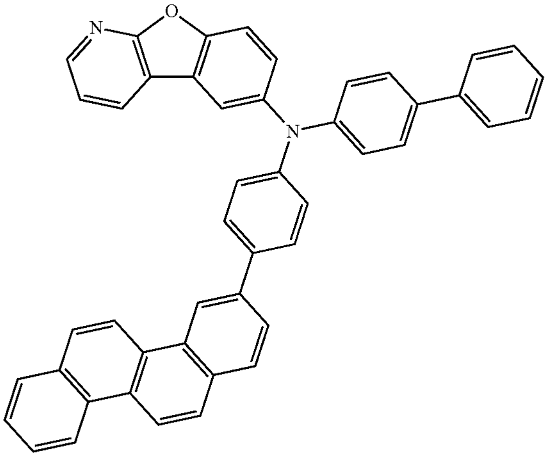
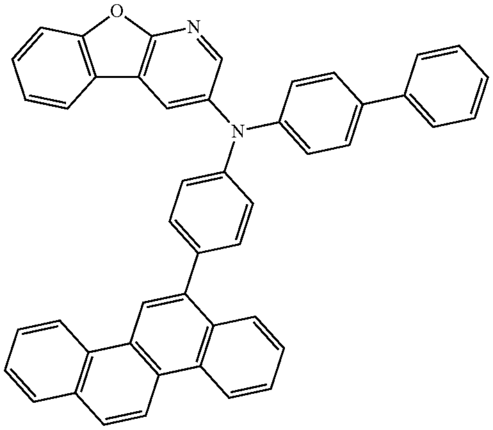
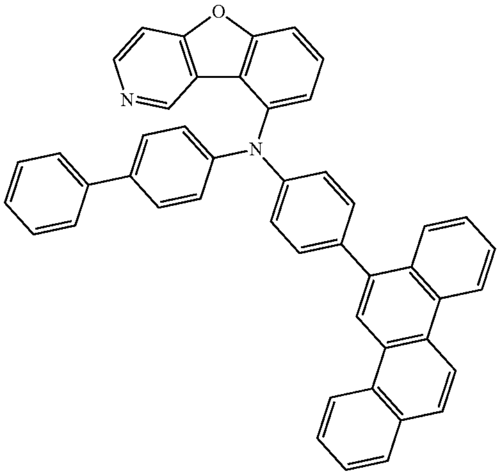
-continued
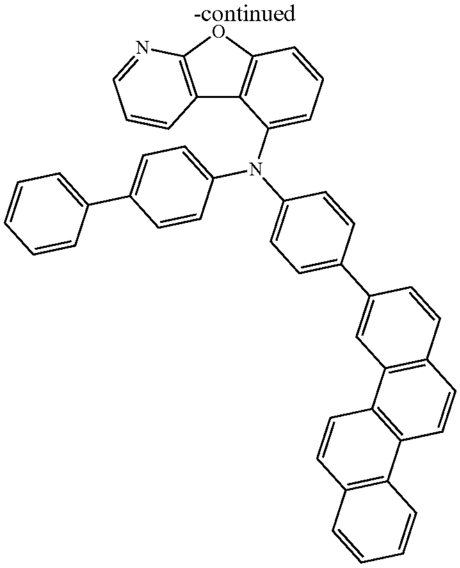
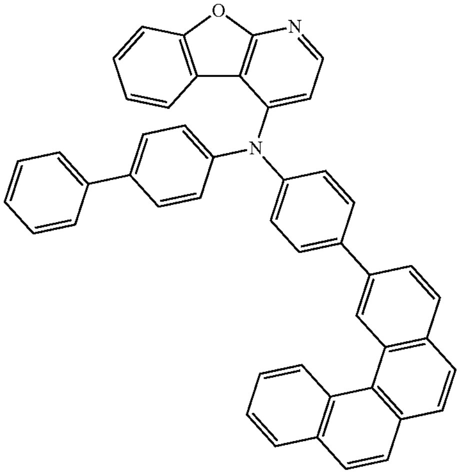
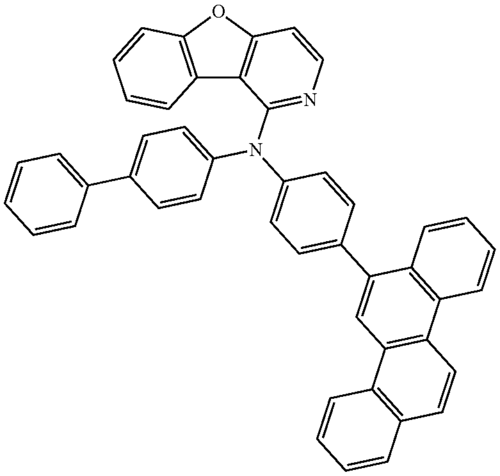

-continued
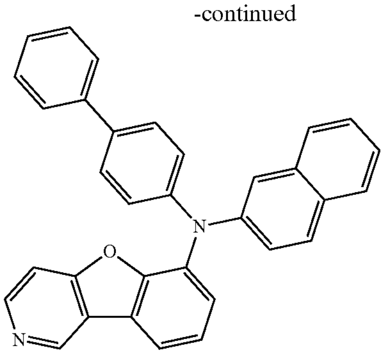
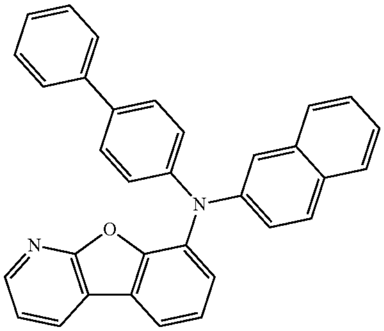
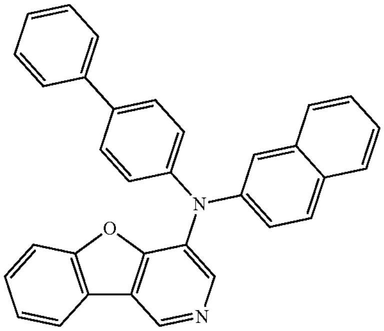
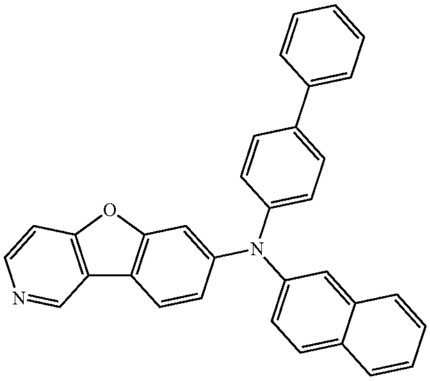
-continued
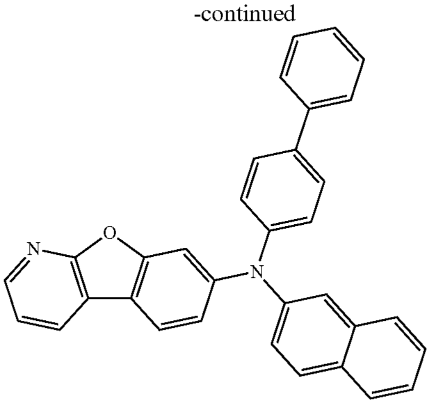
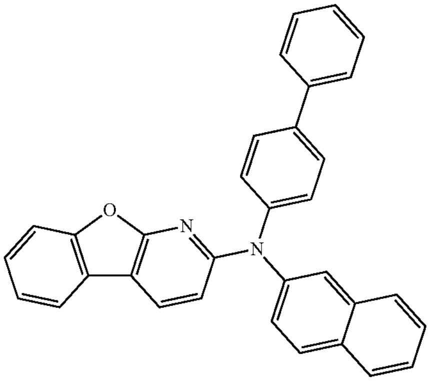
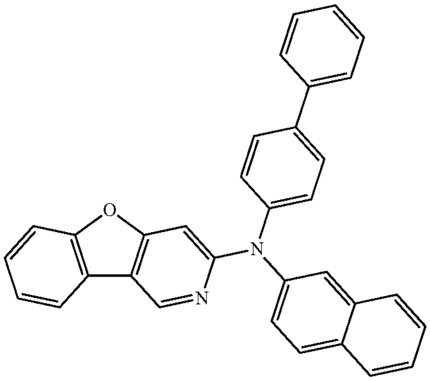
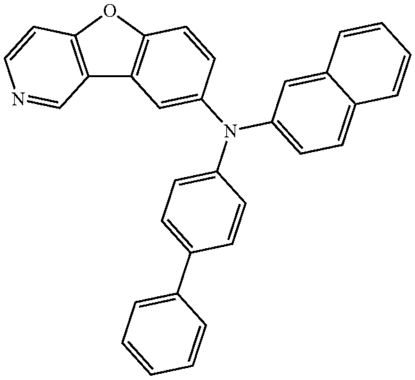

-continued
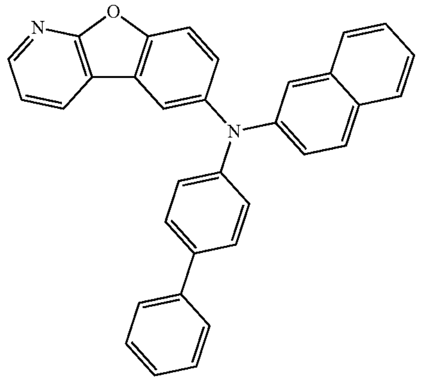
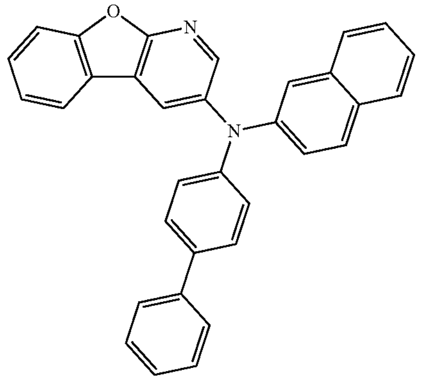
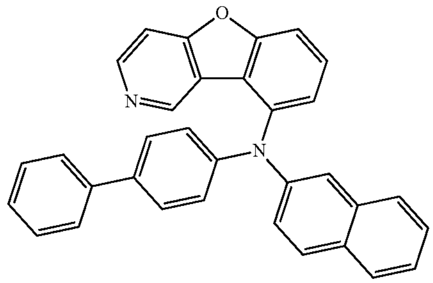
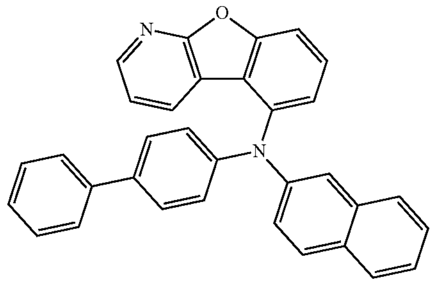
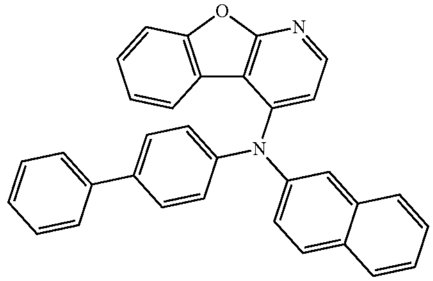
-continued
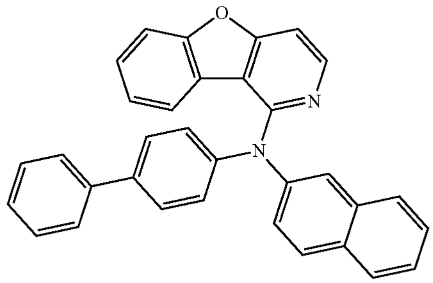
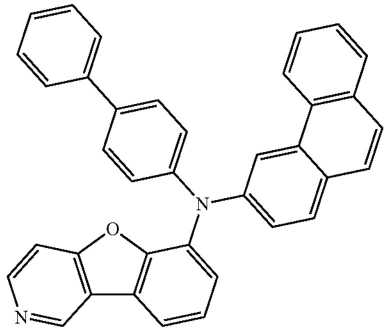
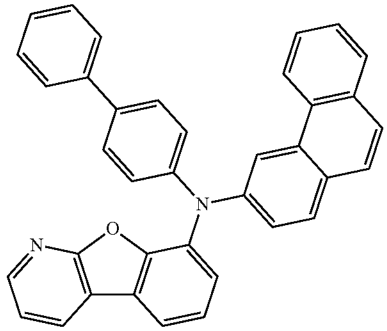
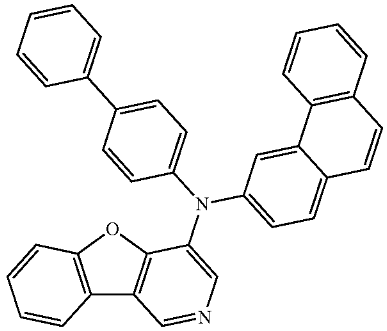
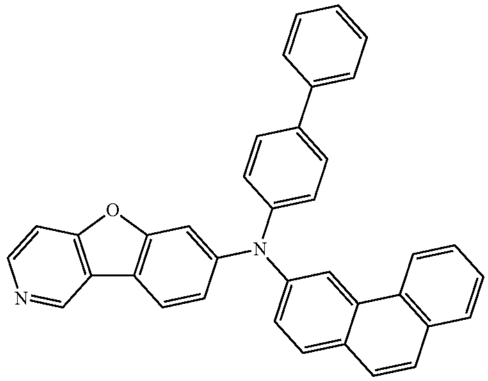

-continued
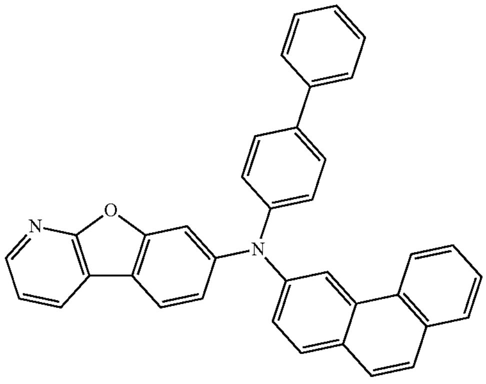
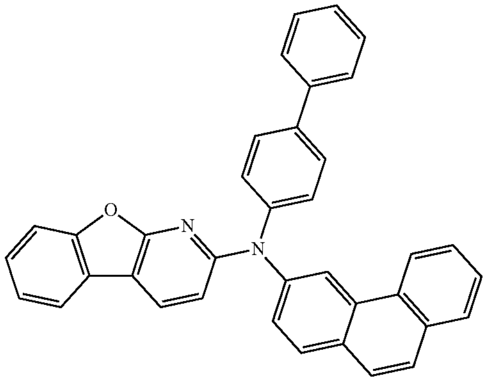
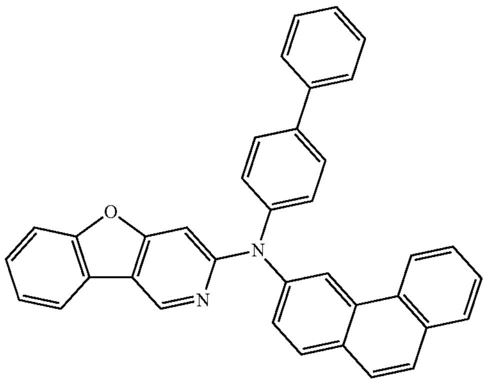
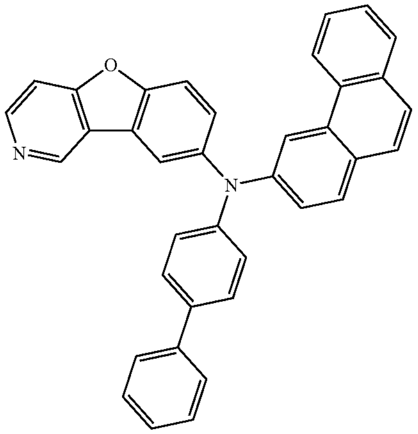
-continued
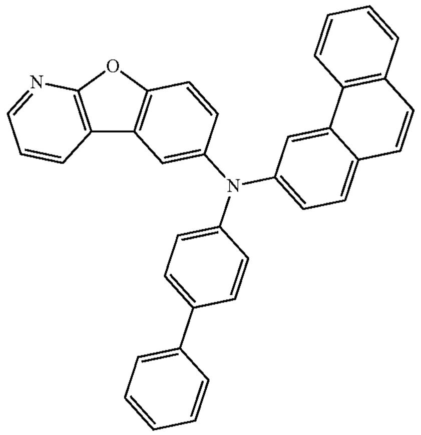
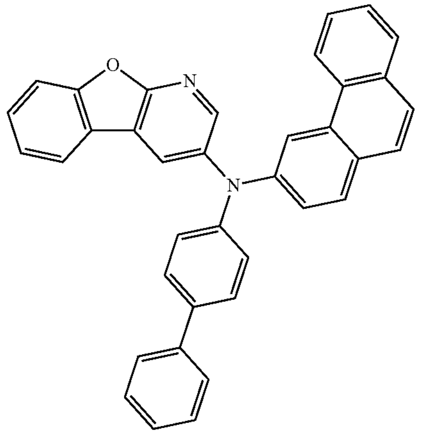
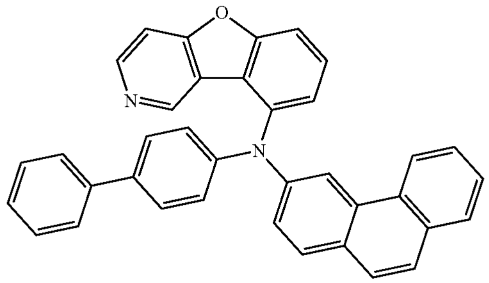
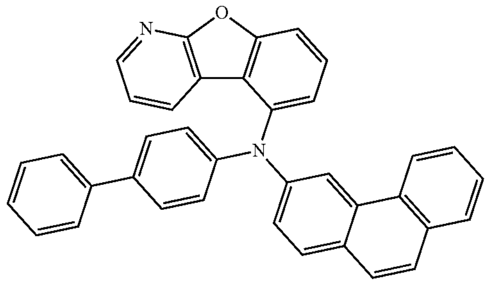
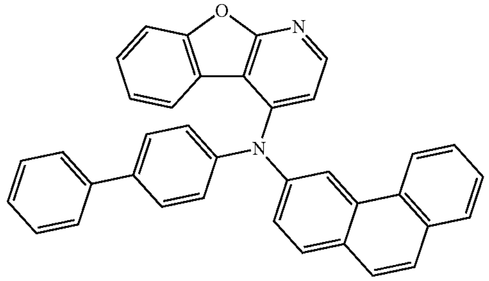

-continued
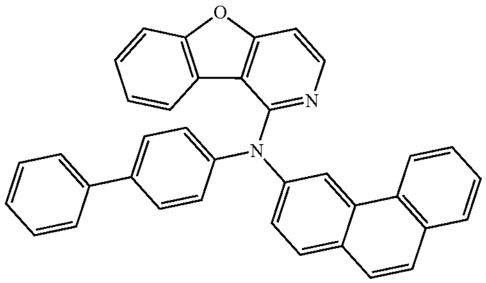
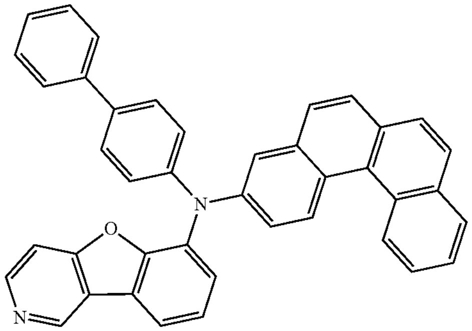
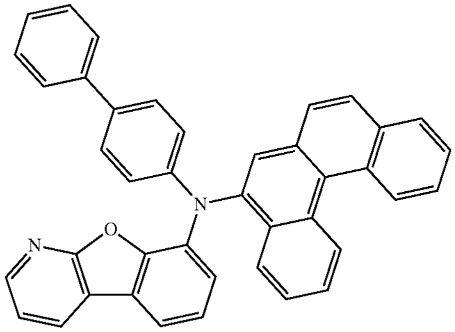
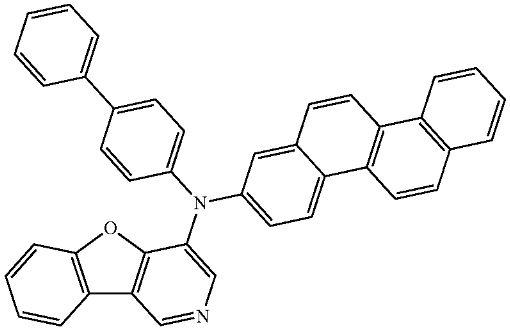
-continued
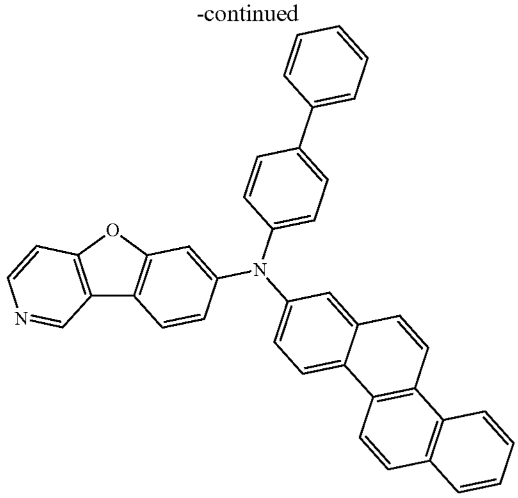
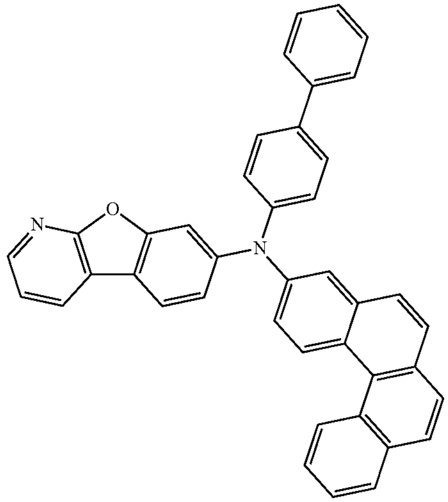
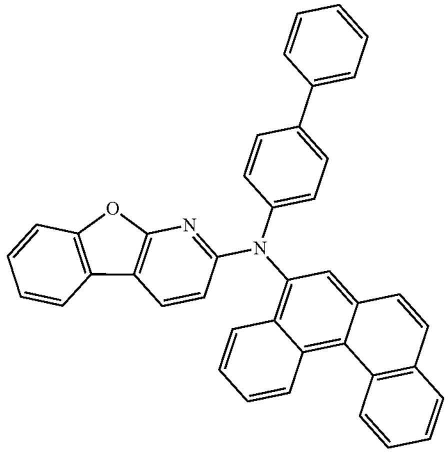

-continued
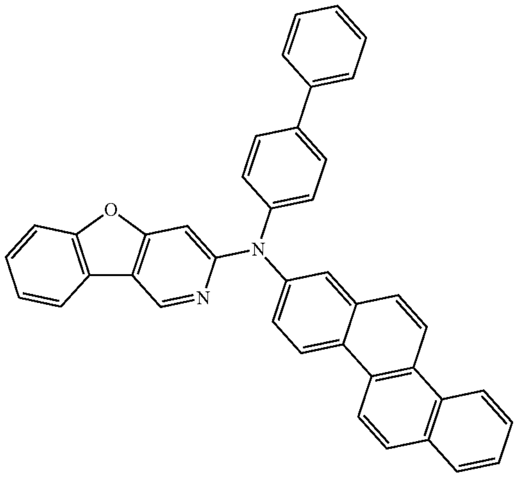
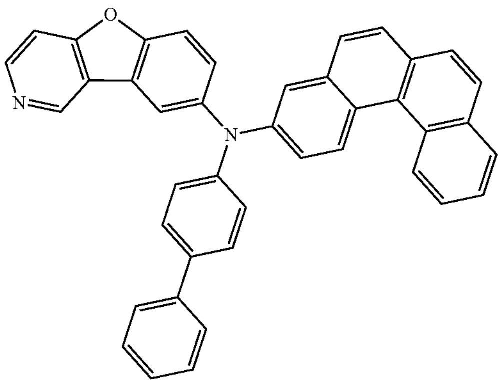
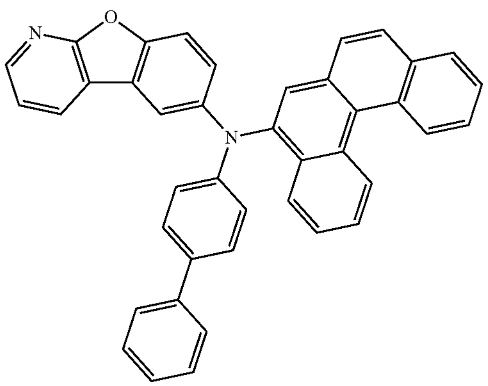
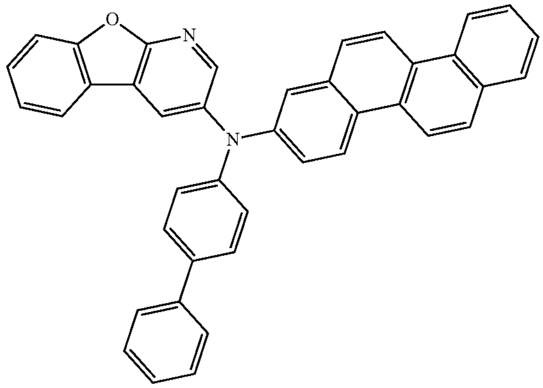
-continued
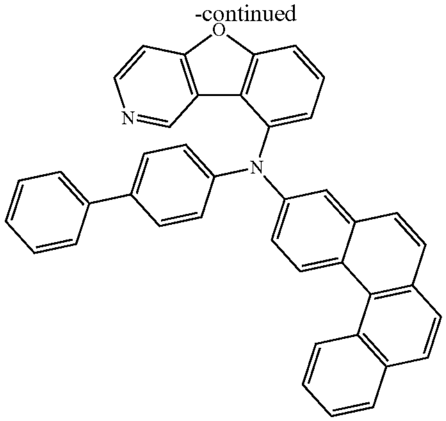
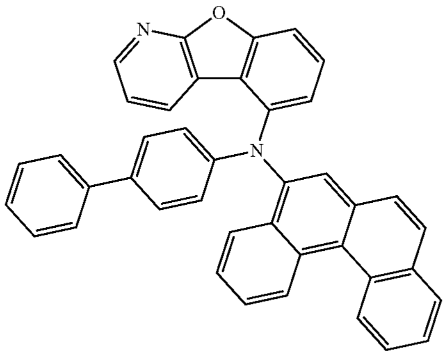
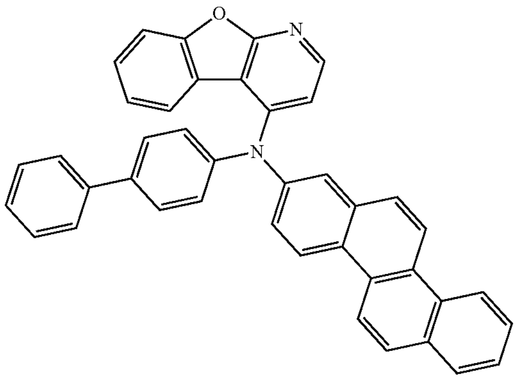
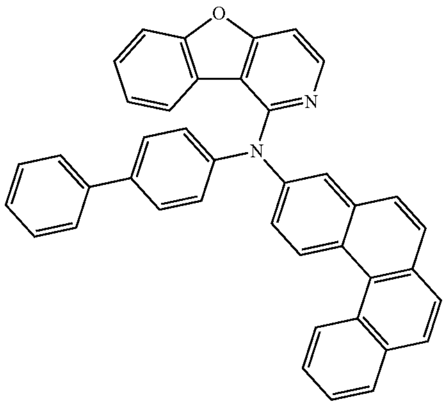

-continued
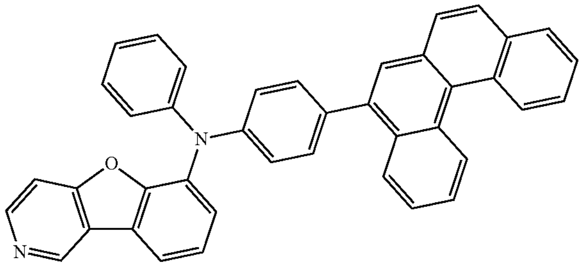
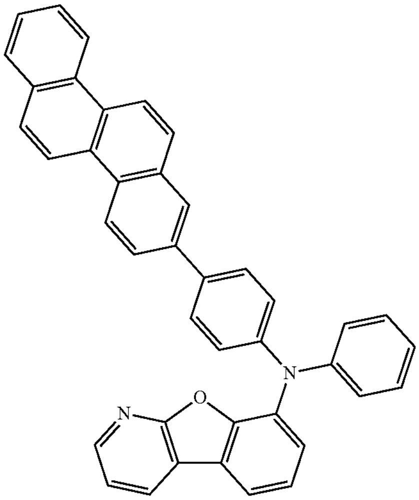
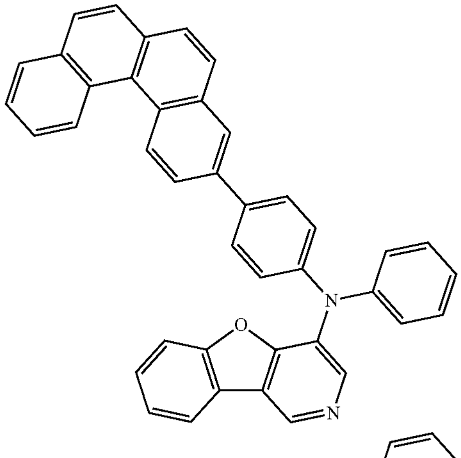
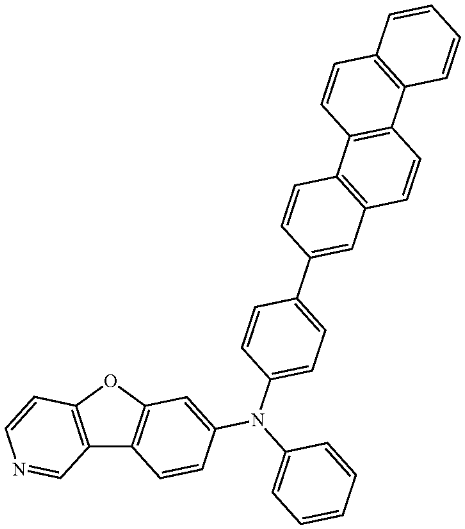
-continued
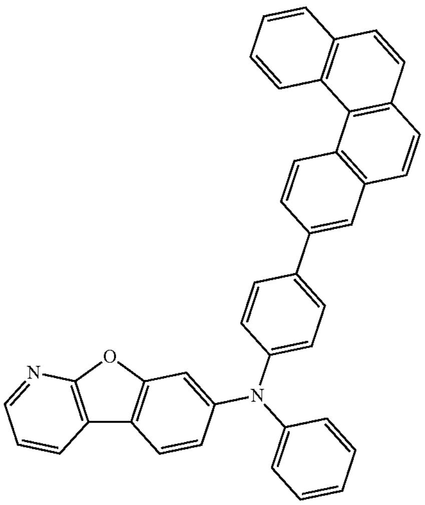
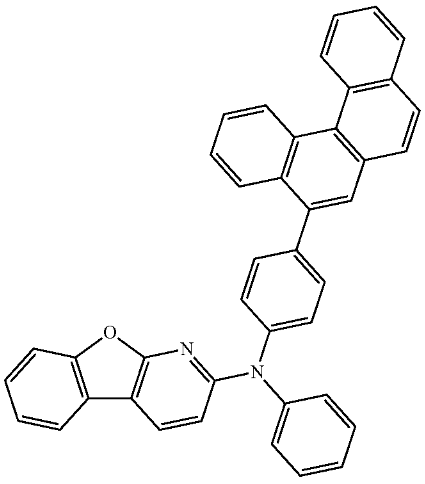
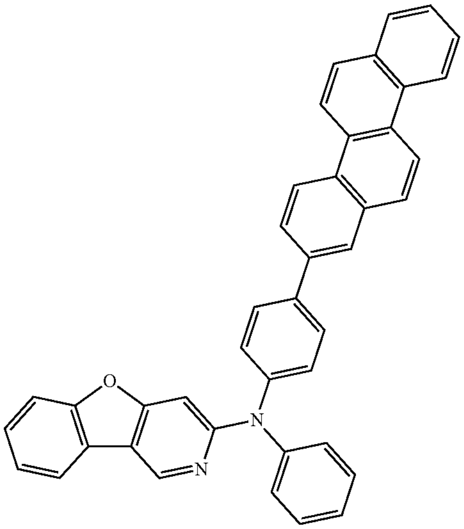

-continued
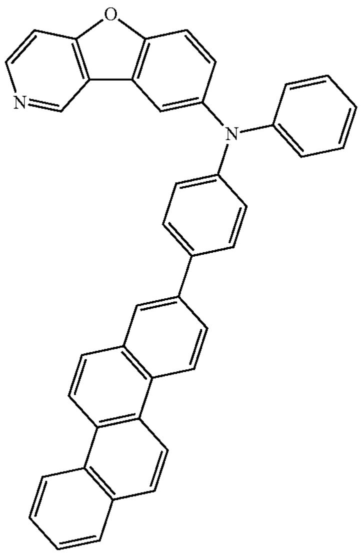
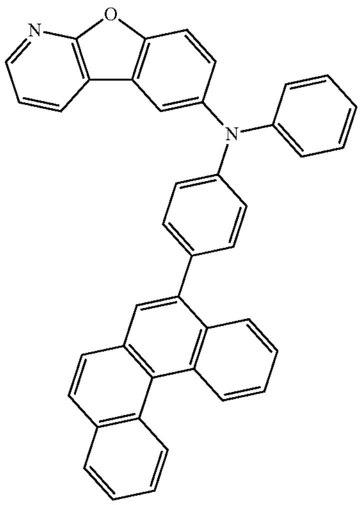
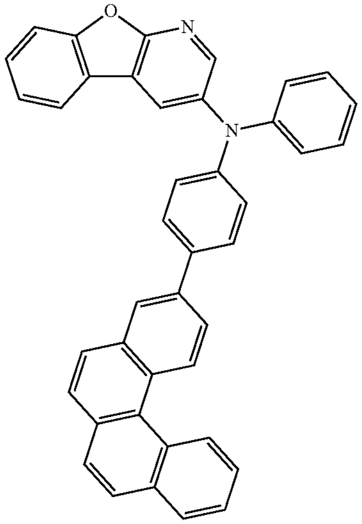
-continued
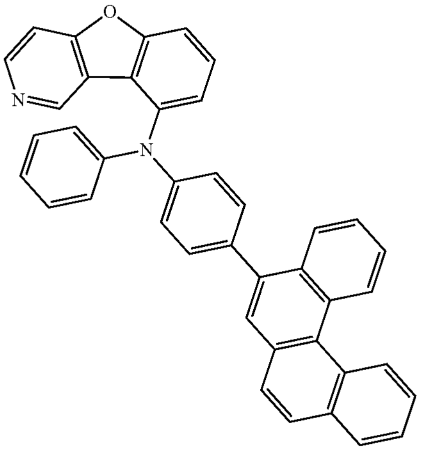
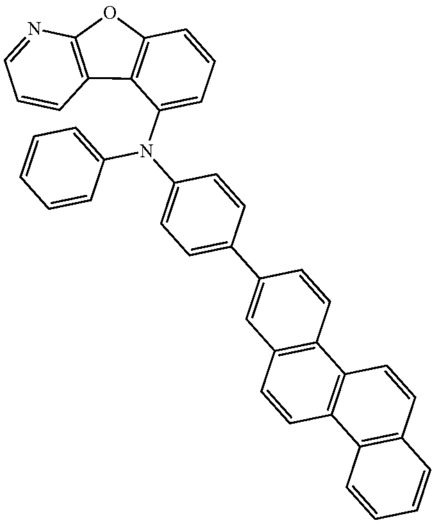
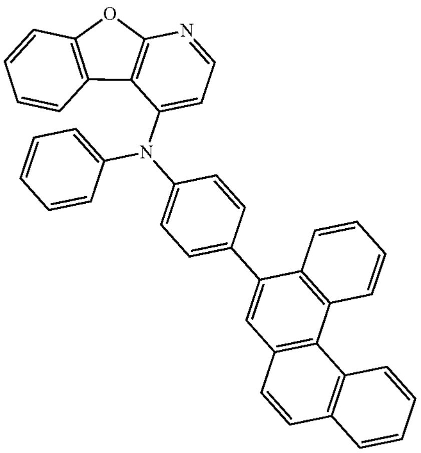

-continued
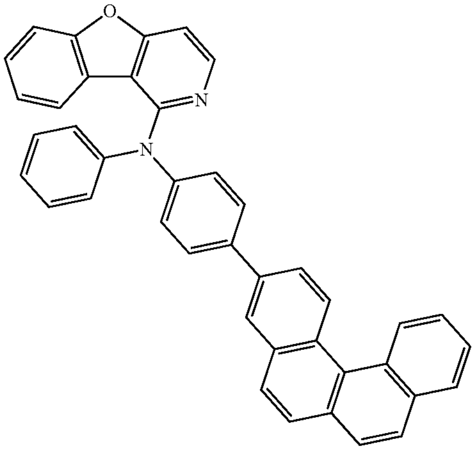
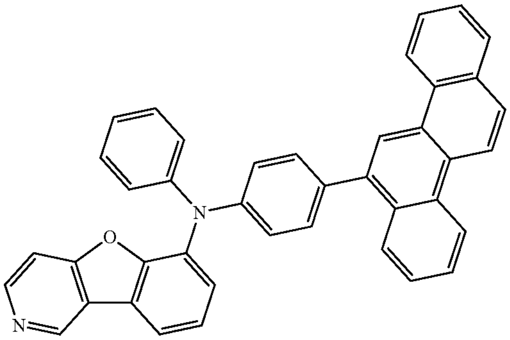
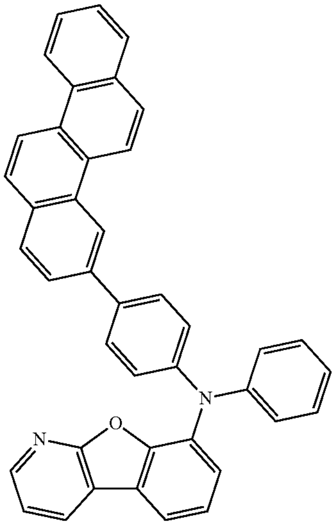
-continued
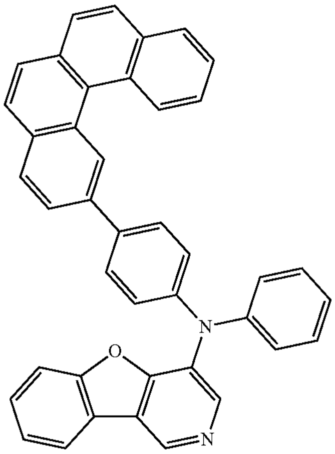
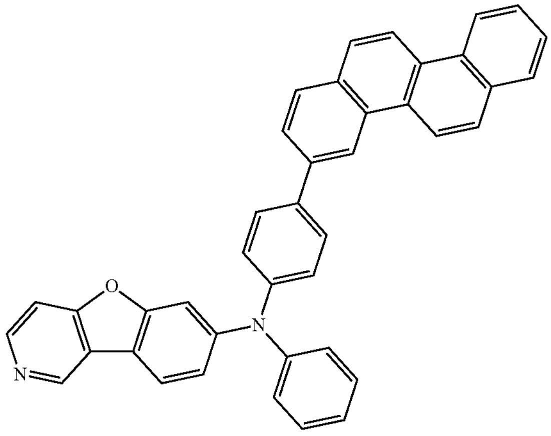
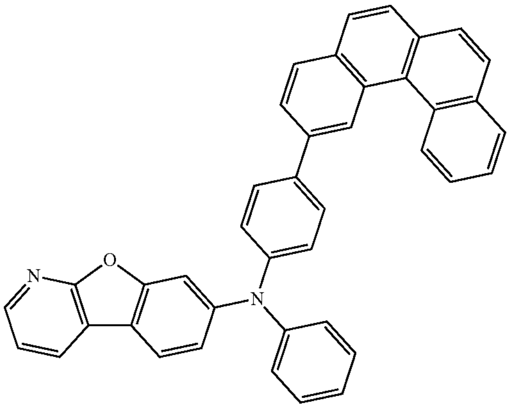
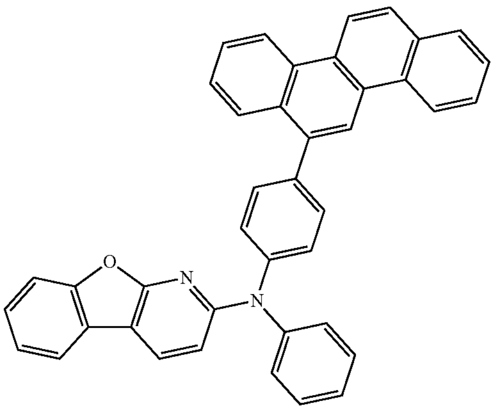

-continued
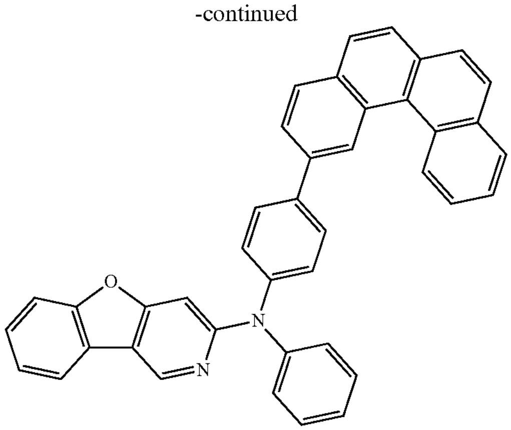
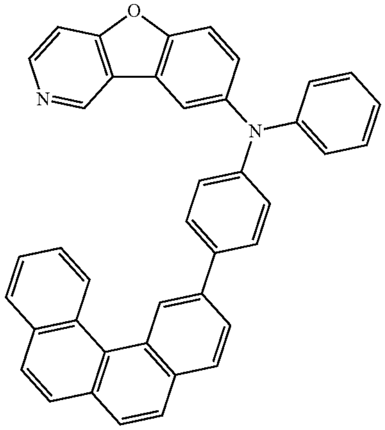
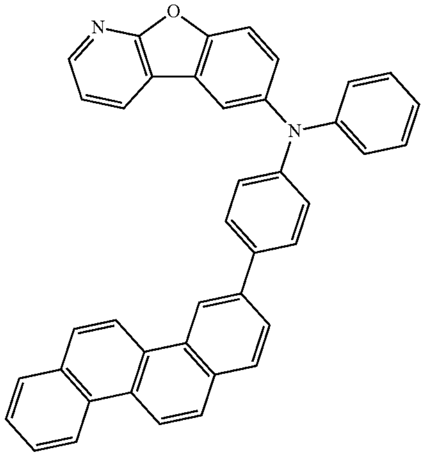
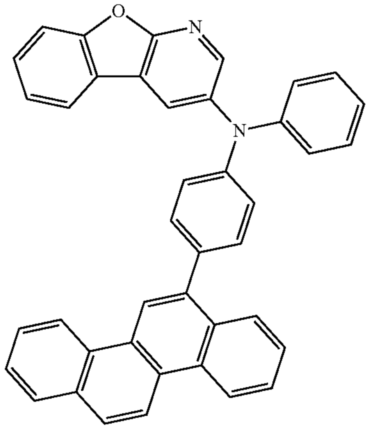
-continued
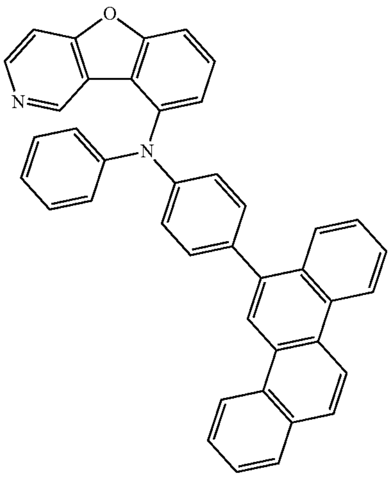
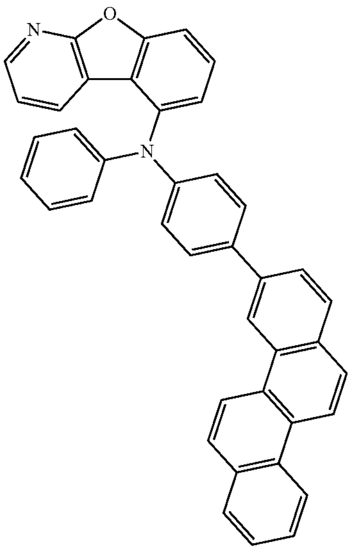
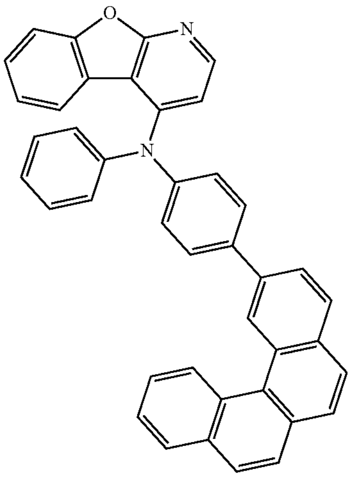

-continued
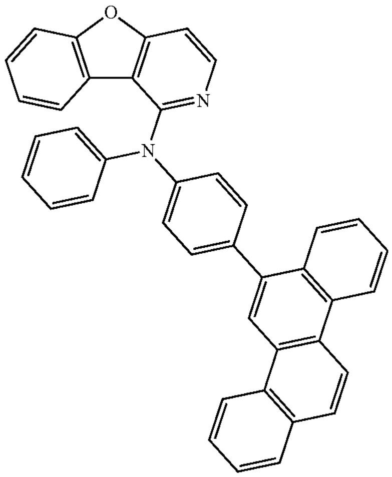
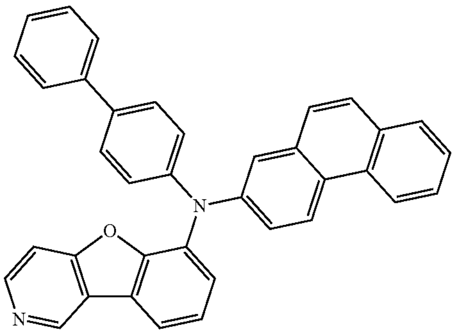
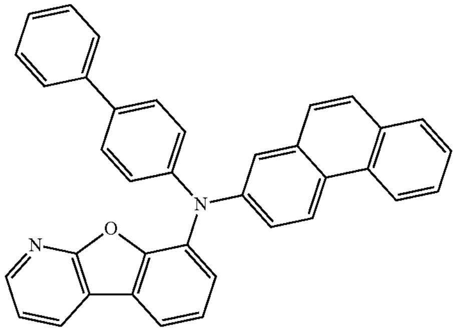
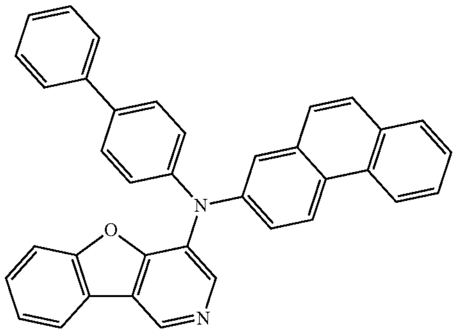
-continued
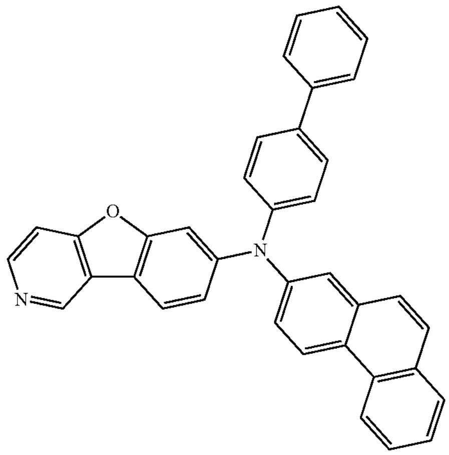
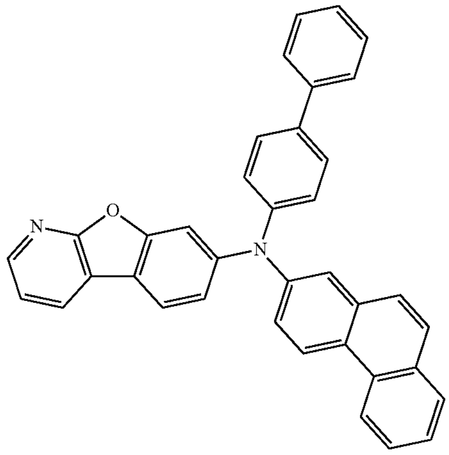
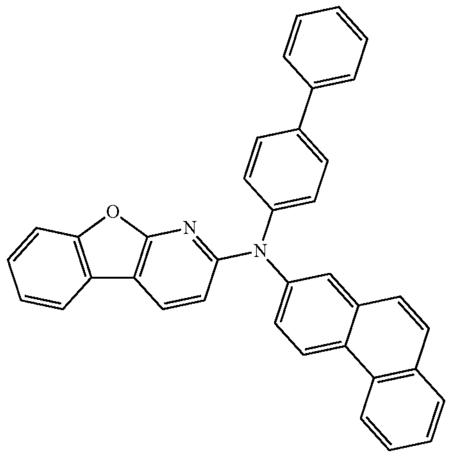

-continued
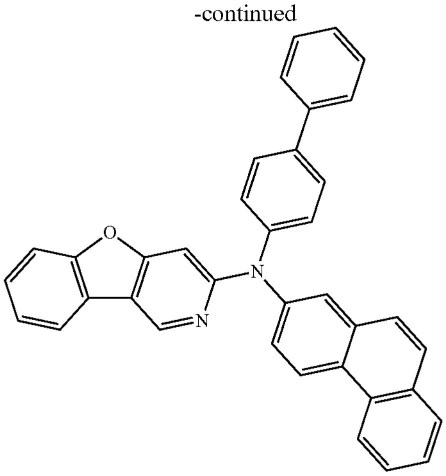
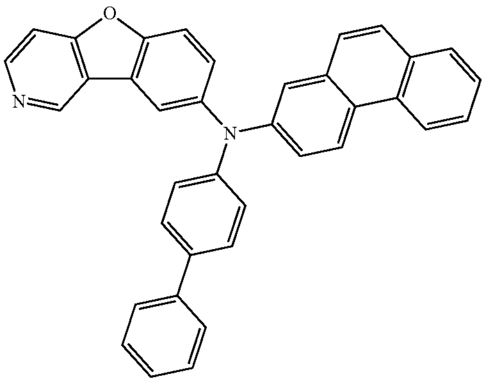
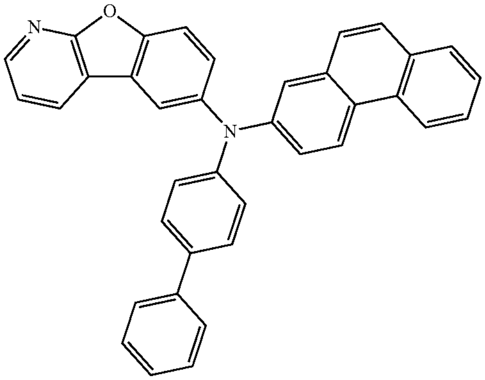
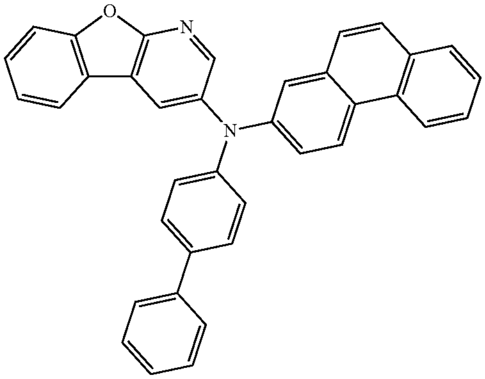
-continued
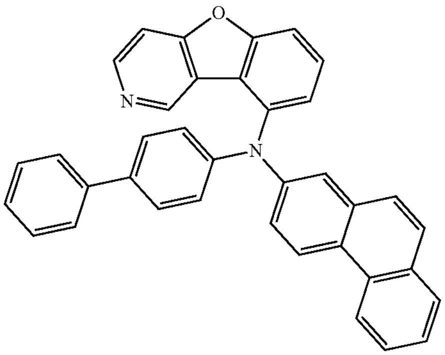
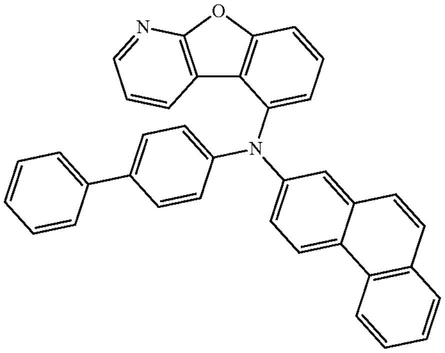
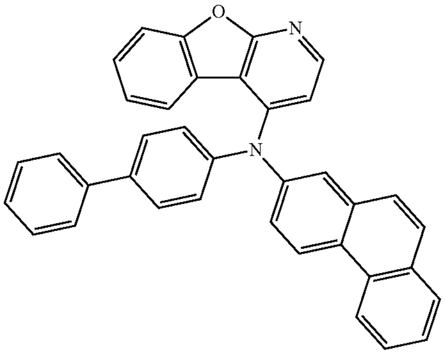
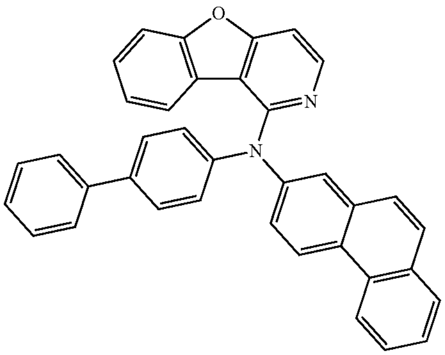

-continued
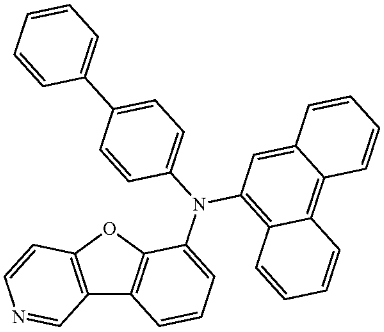
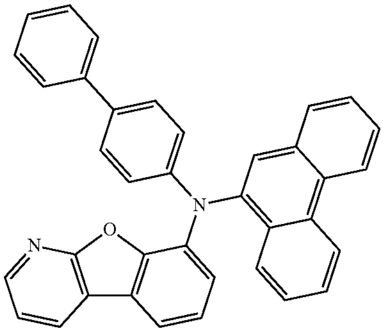
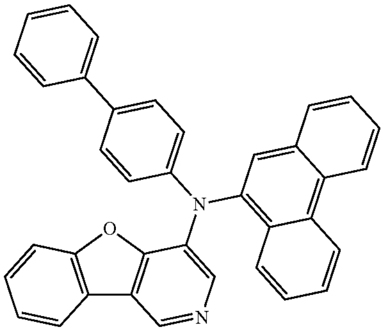
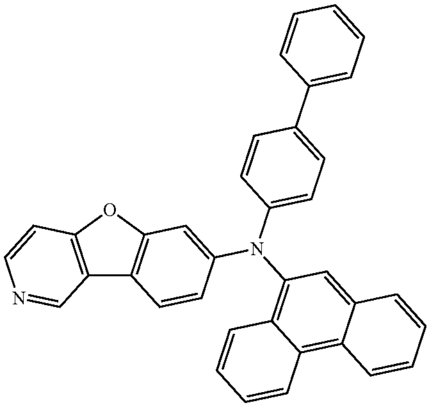
-continued
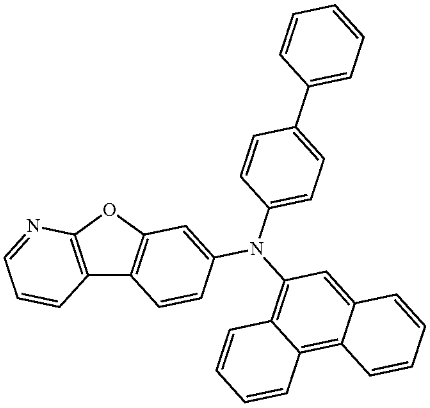
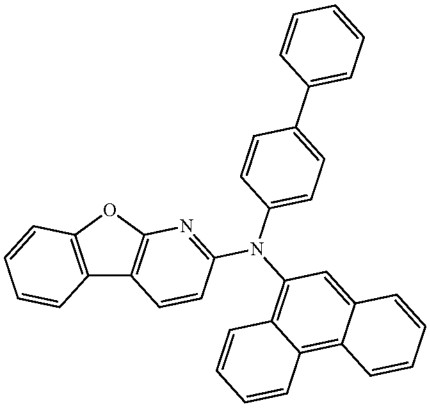
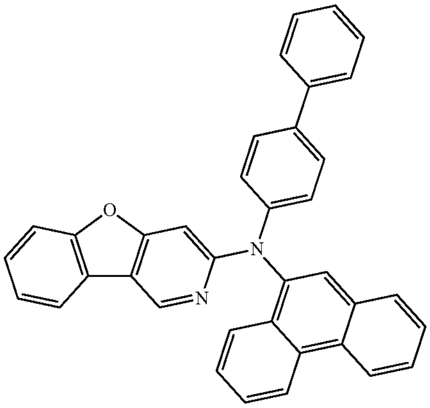
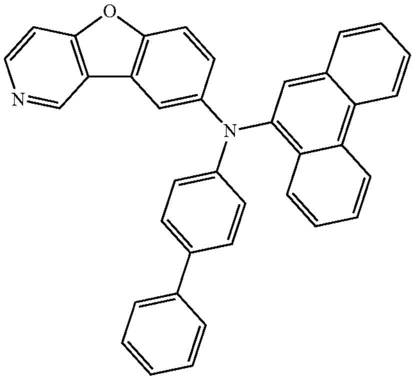

-continued
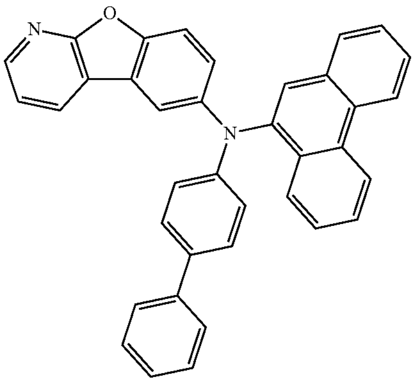
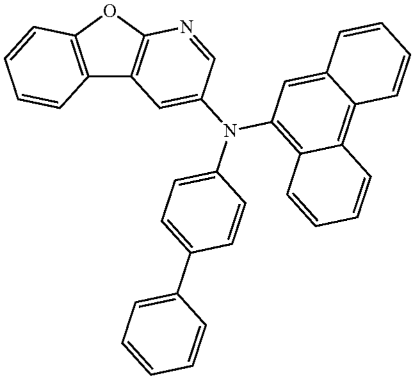
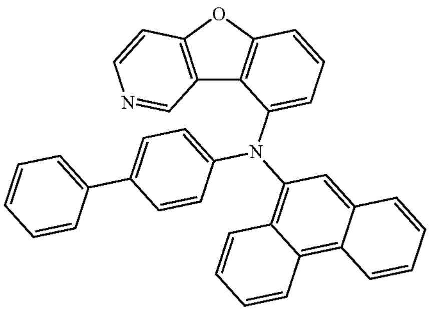
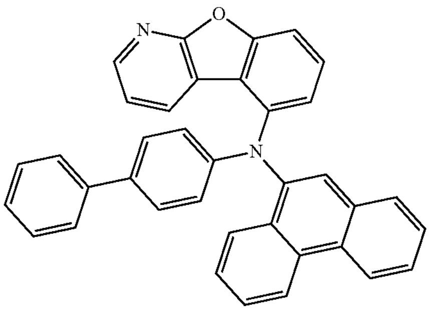
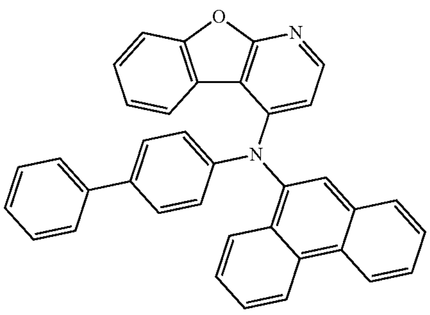
-continued
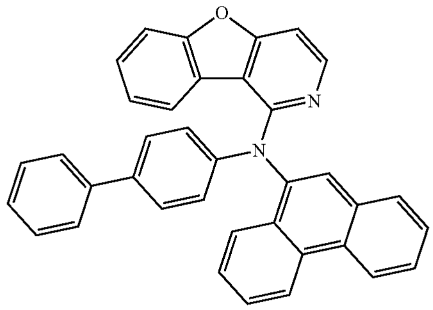
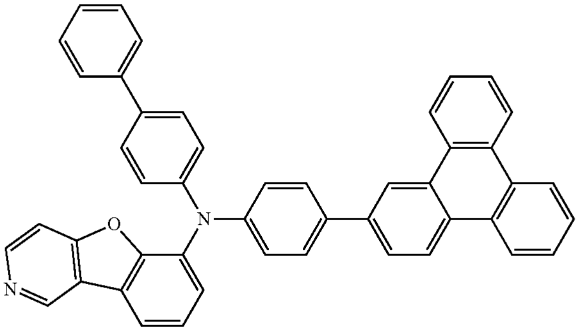
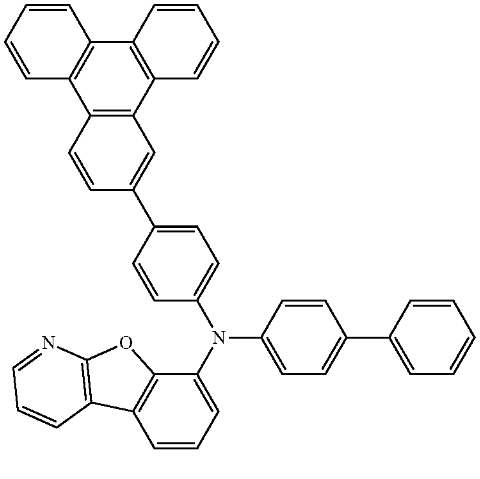
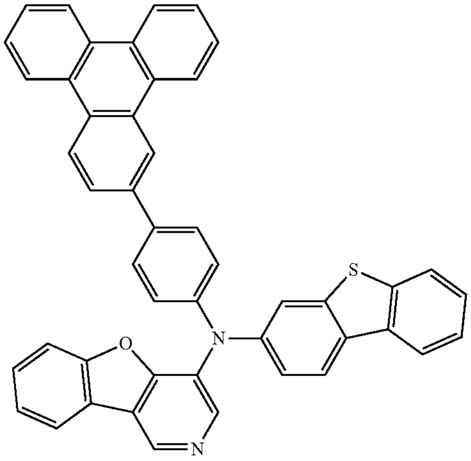

-continued
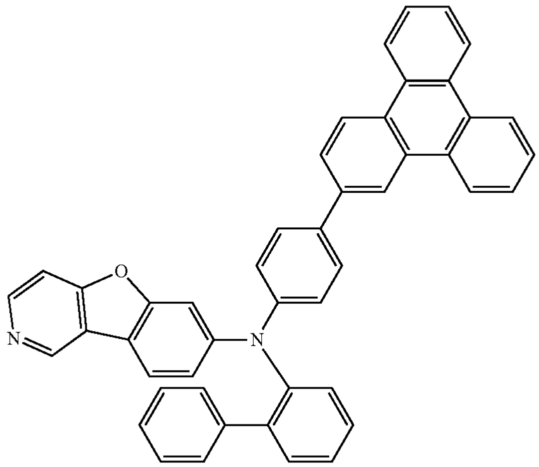
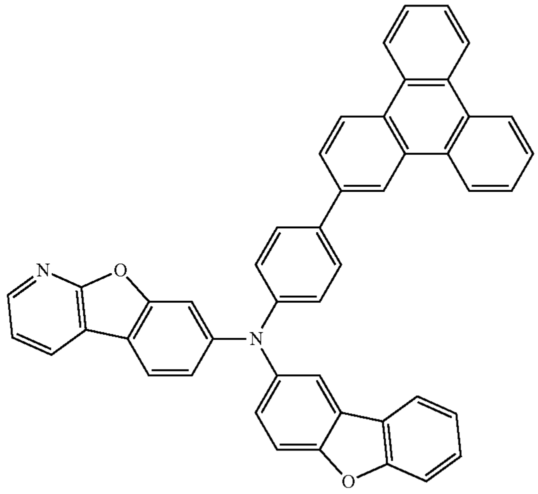
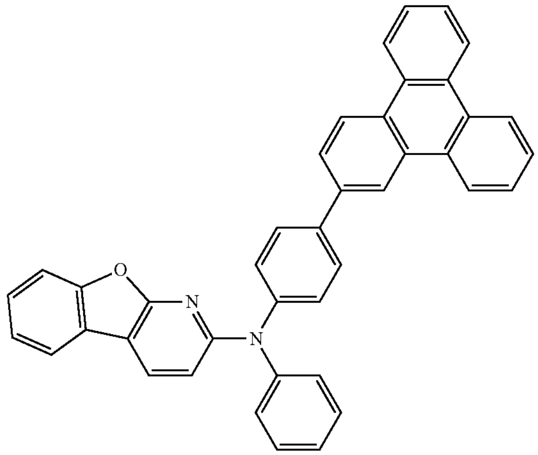
-continued
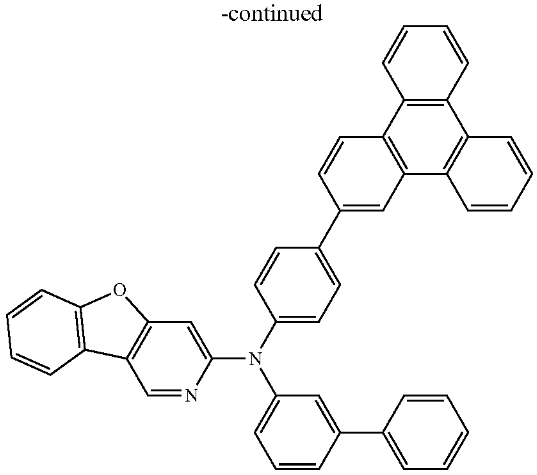
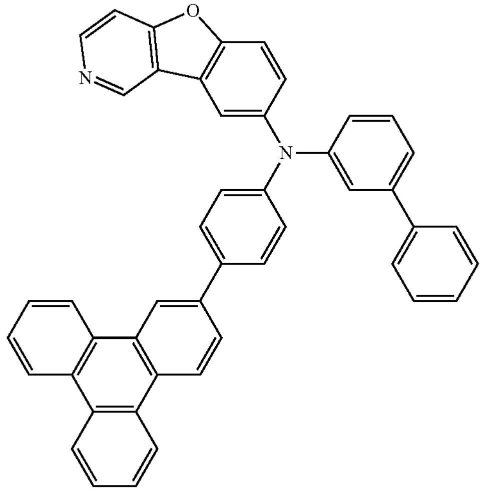
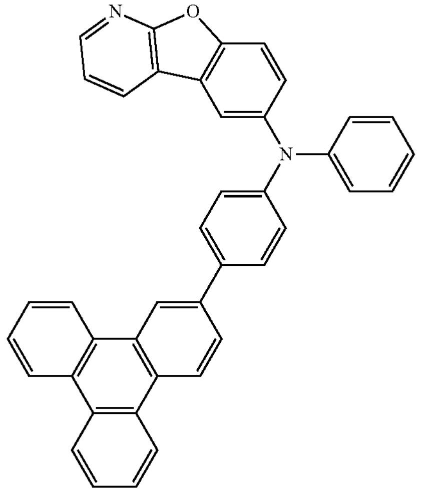

-continued
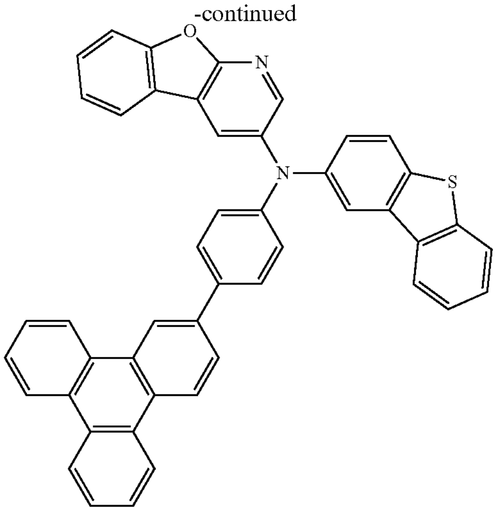
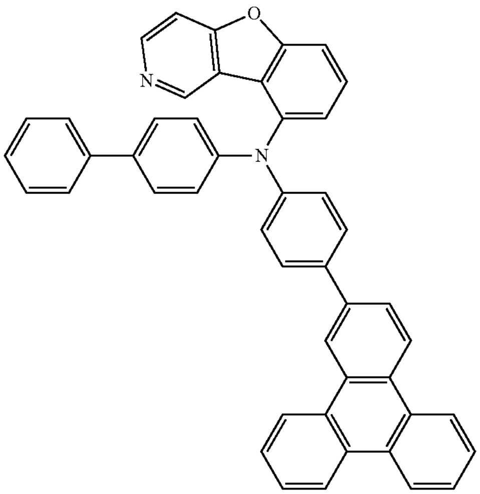
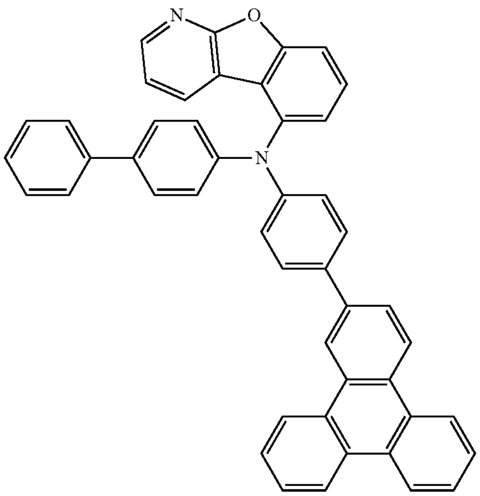
-continued
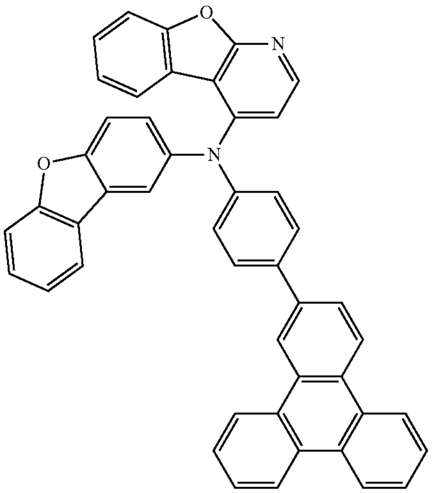
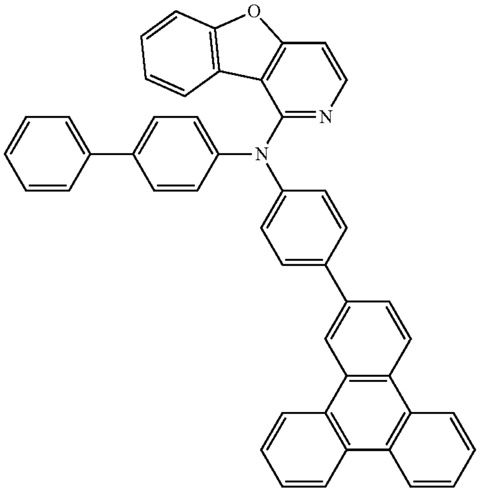
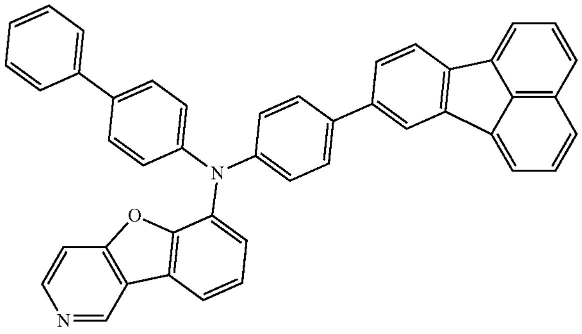
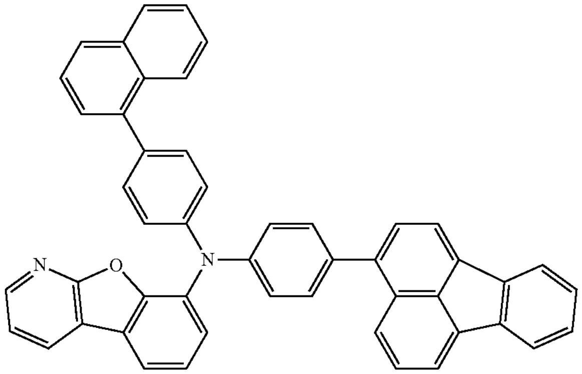

-continued
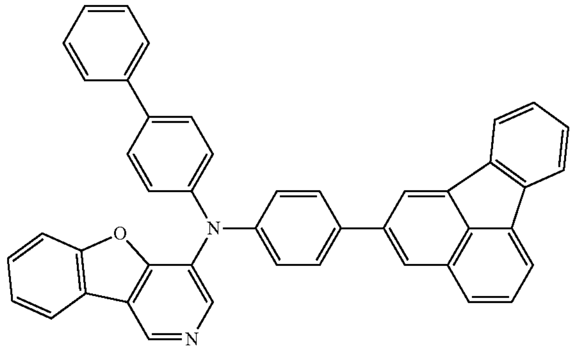
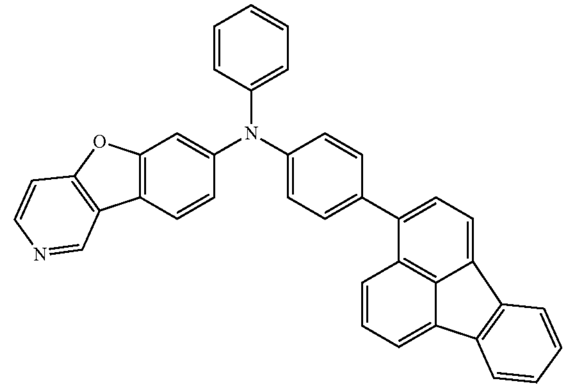
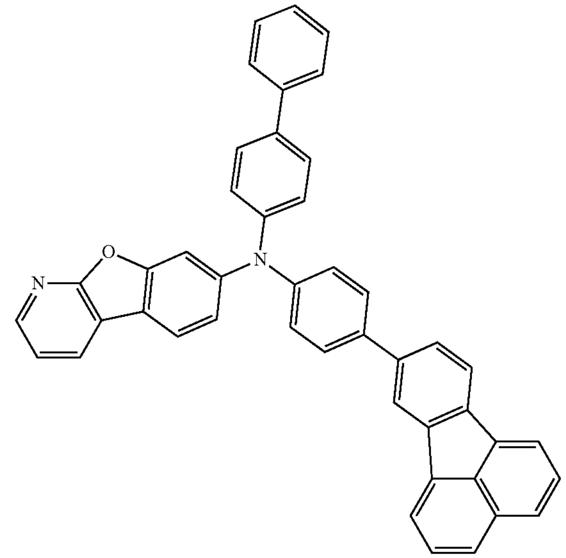
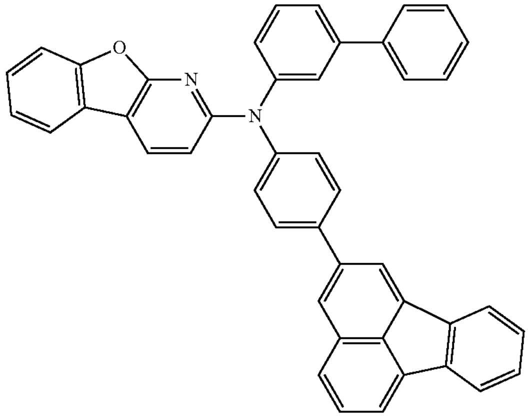
-continued
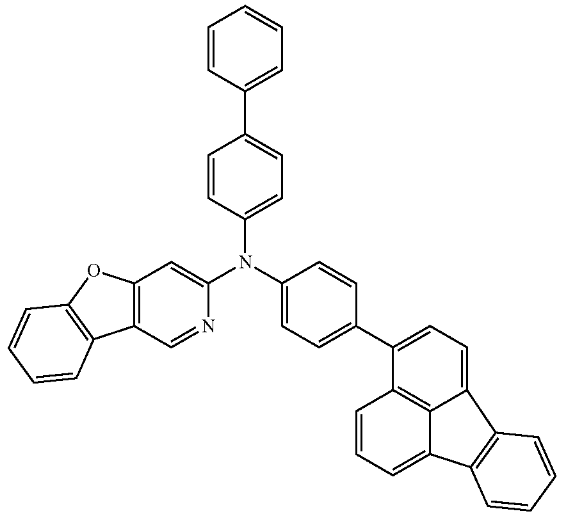
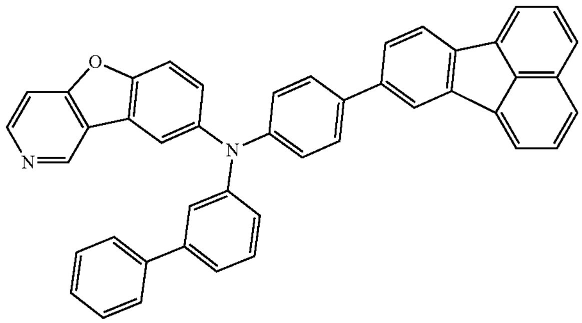
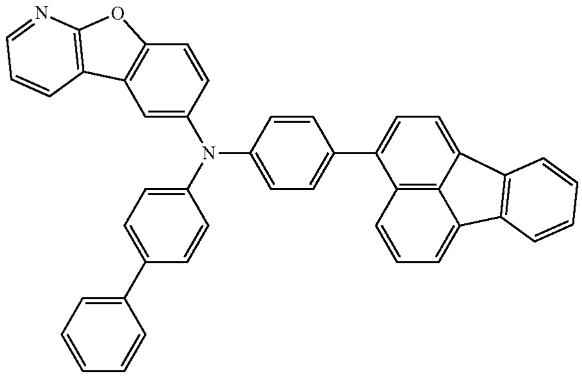
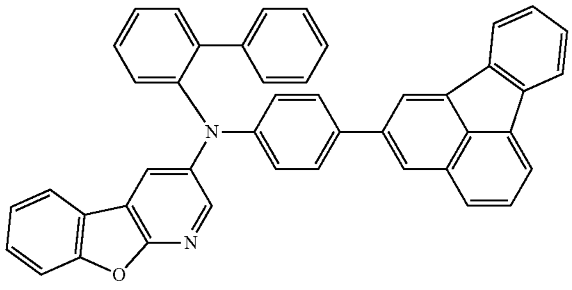

-continued
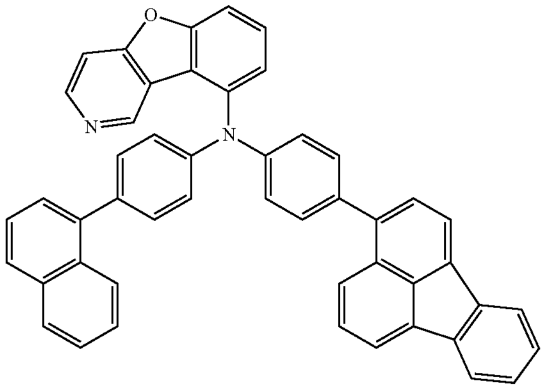
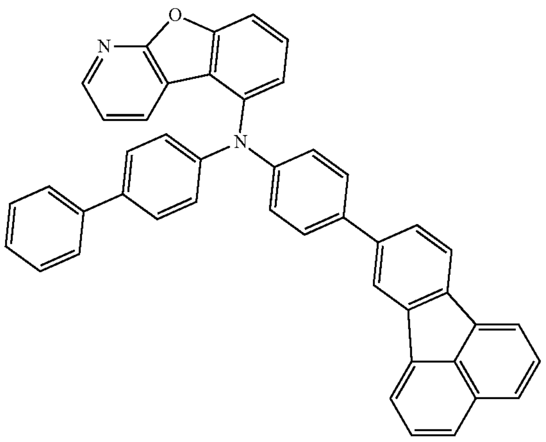
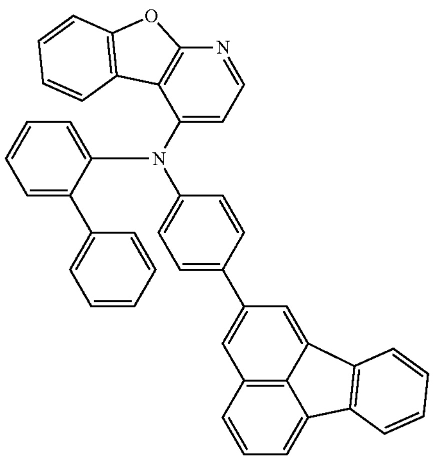
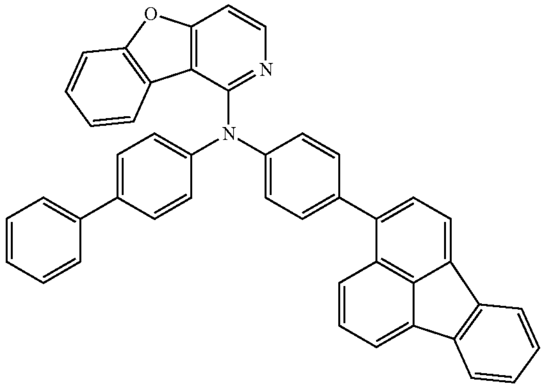
-continued
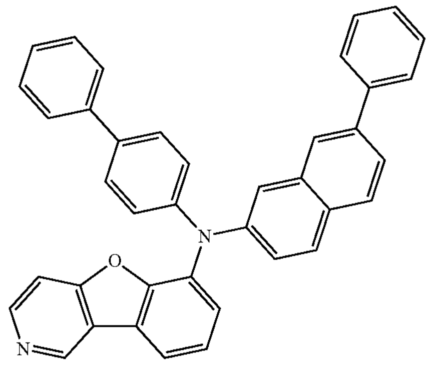
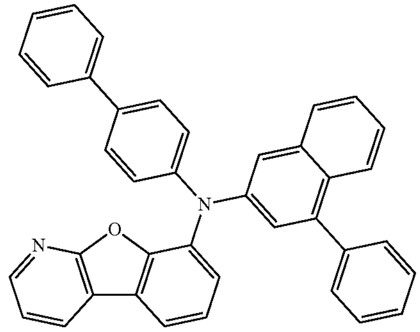
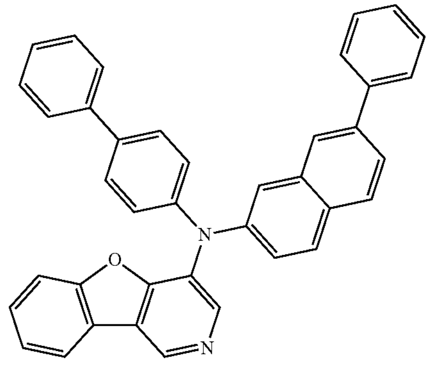
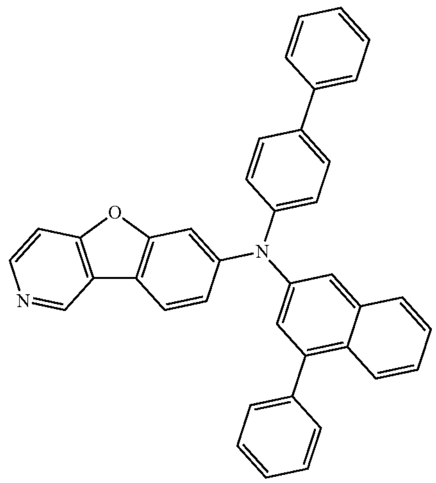

-continued
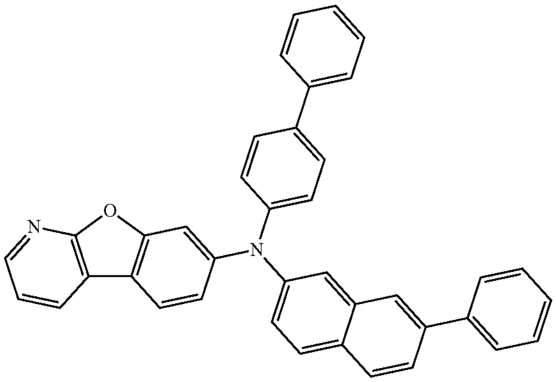
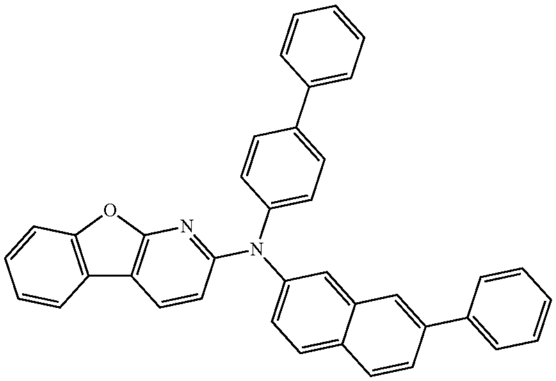
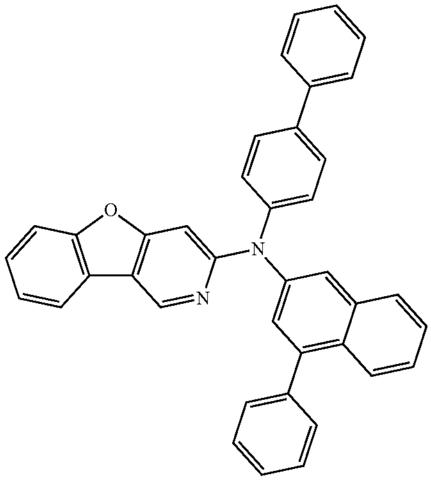
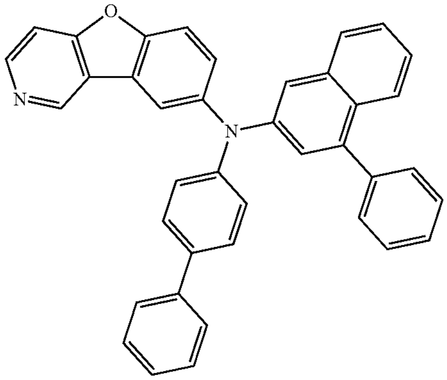
-continued
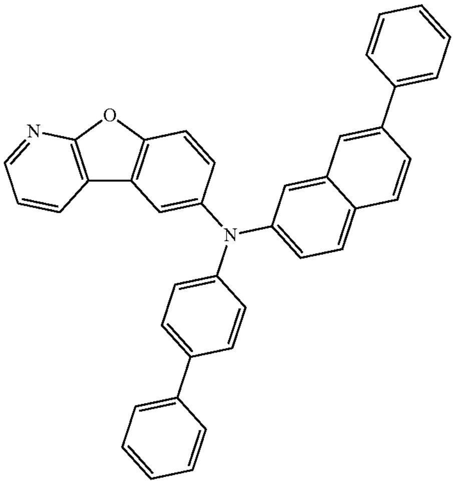
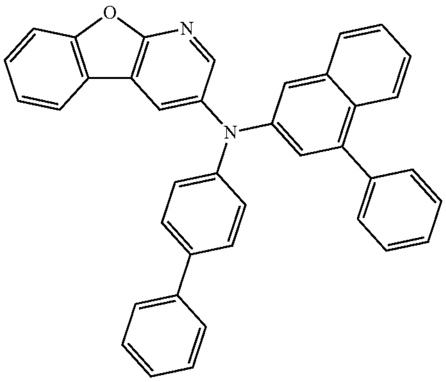
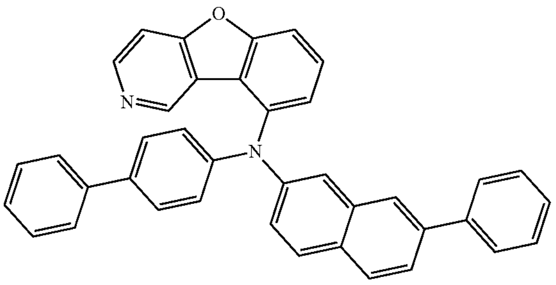
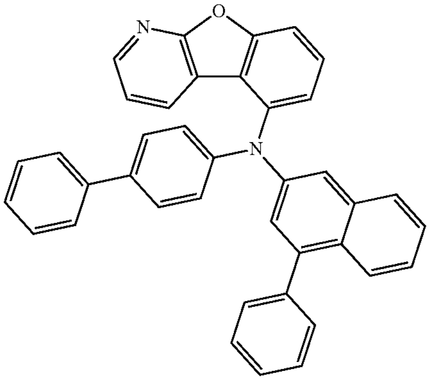

-continued
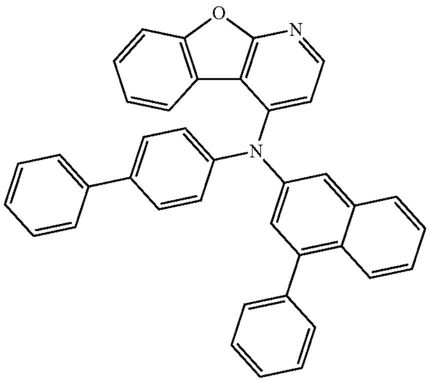
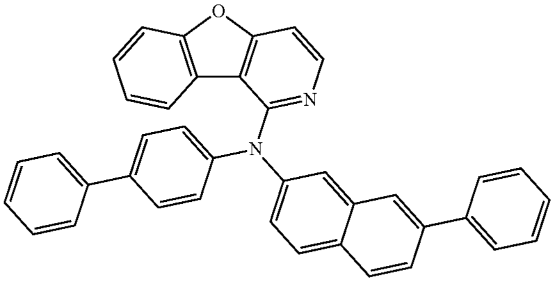
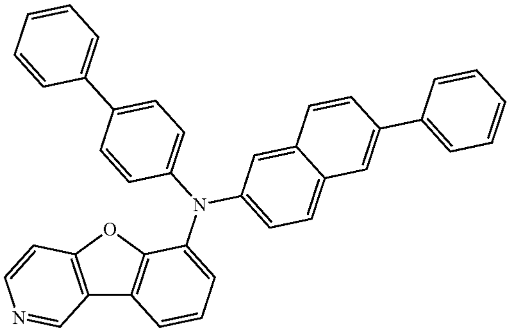
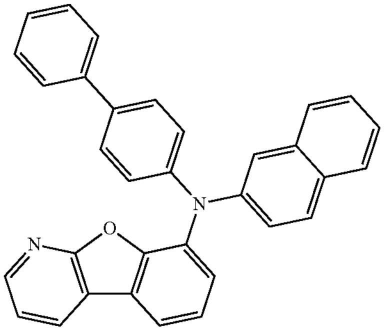
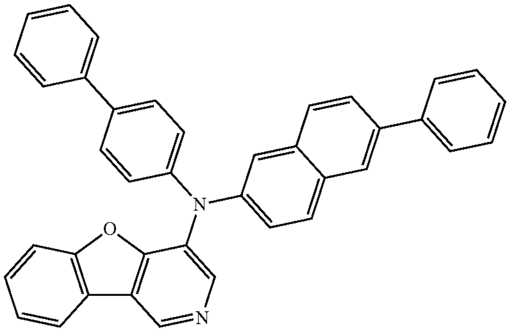
-continued
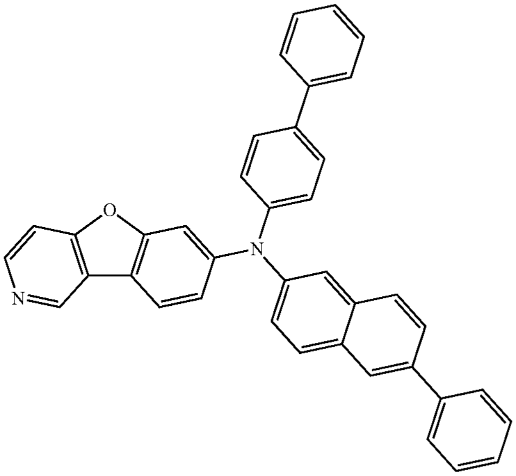
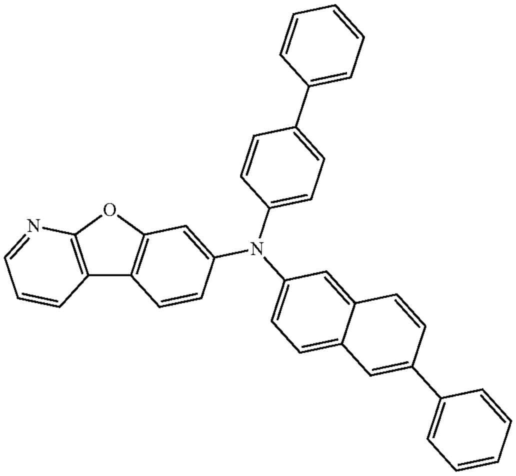
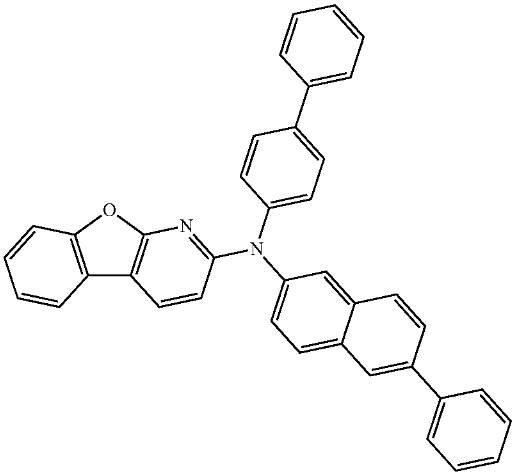

-continued
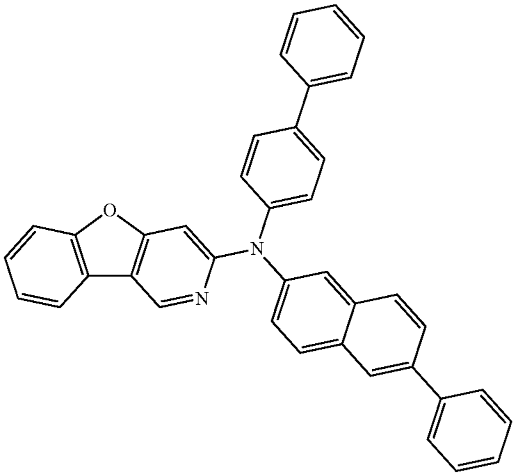
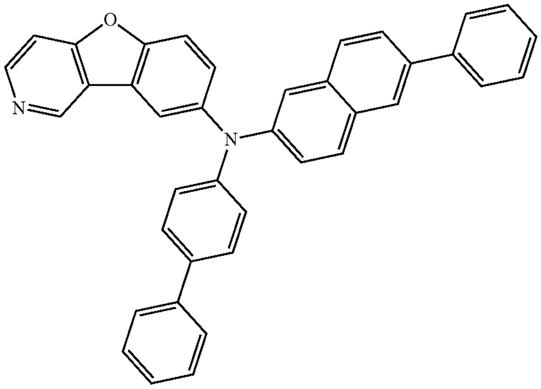
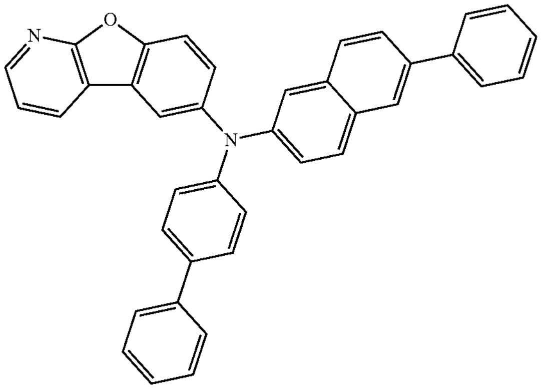
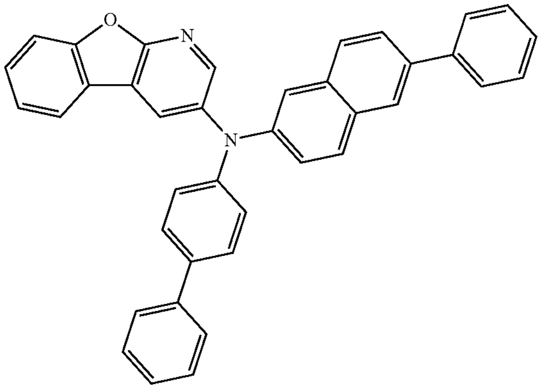
-continued
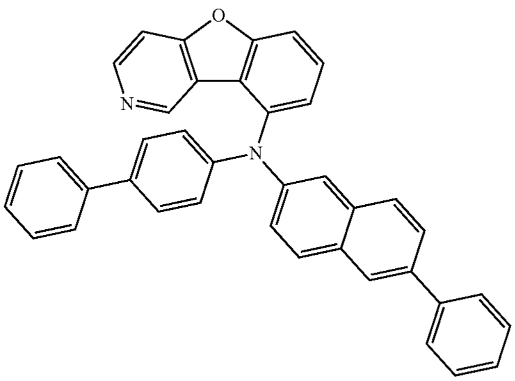
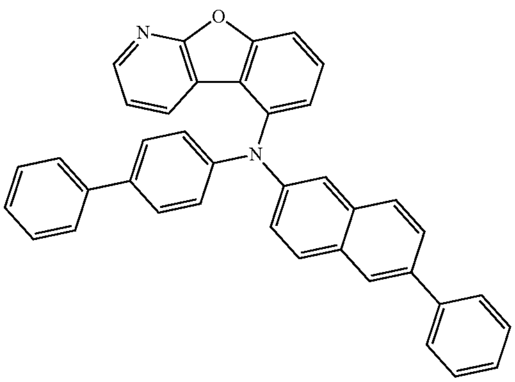
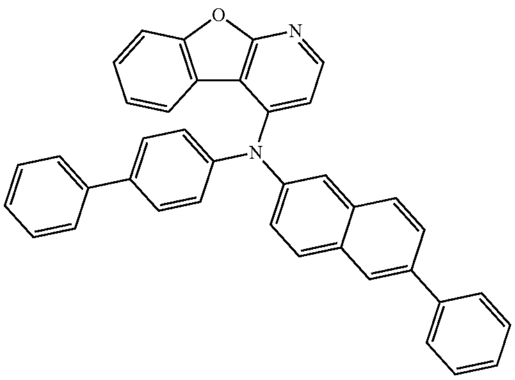
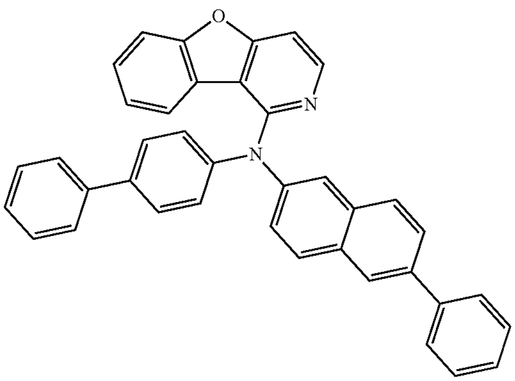

-continued
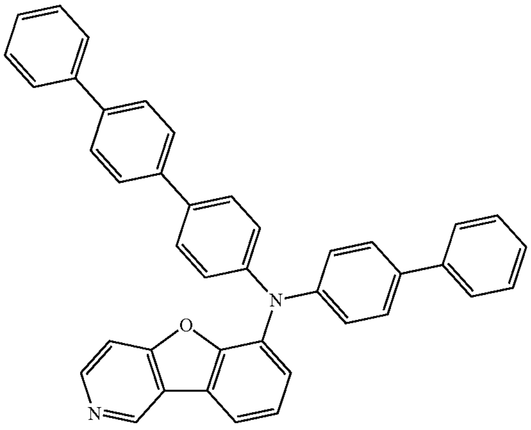
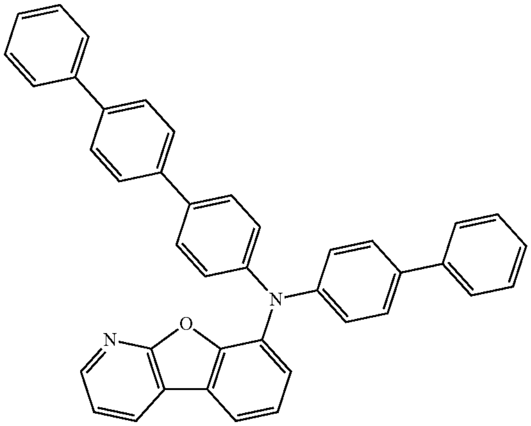
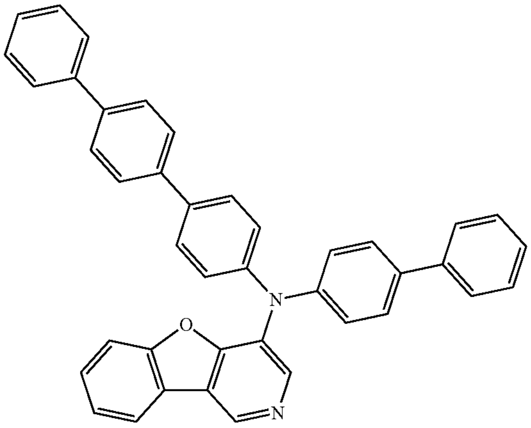
-continued
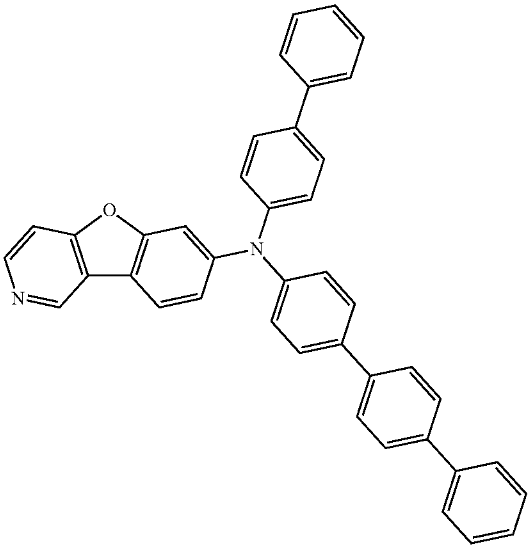
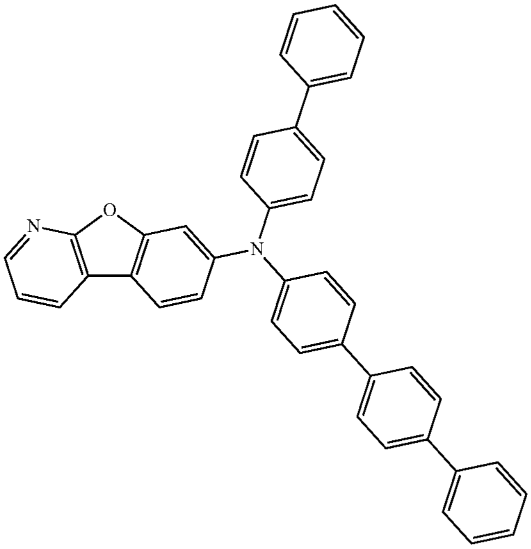
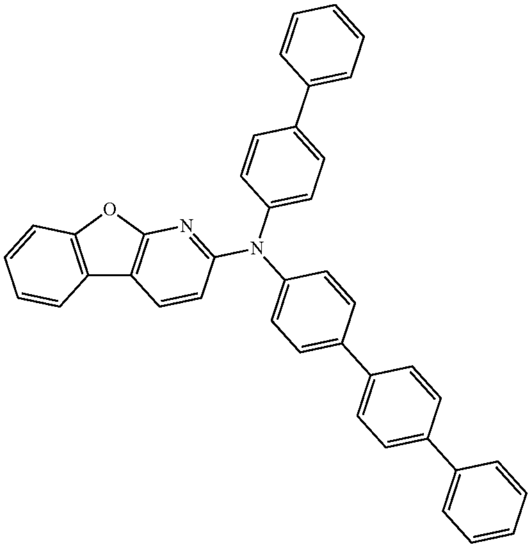

-continued
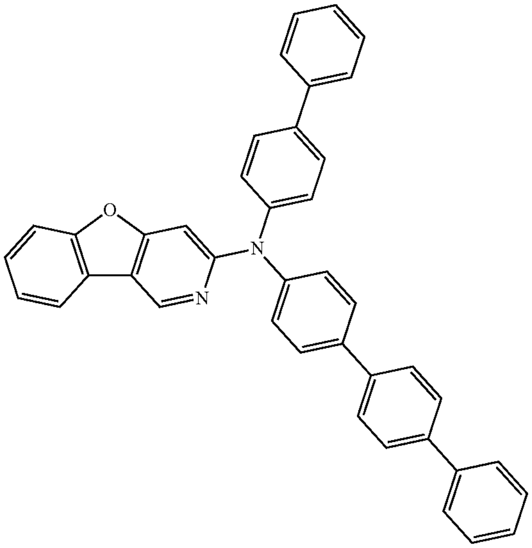
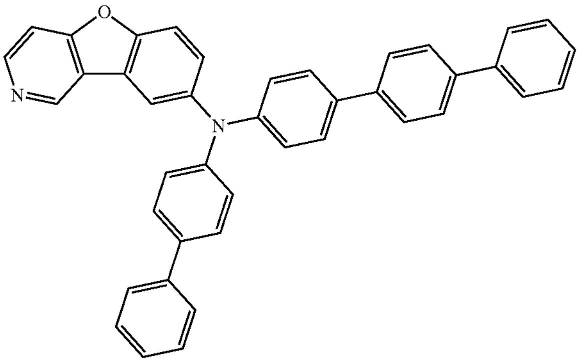
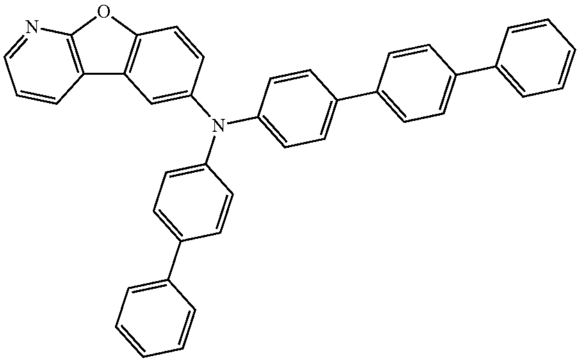
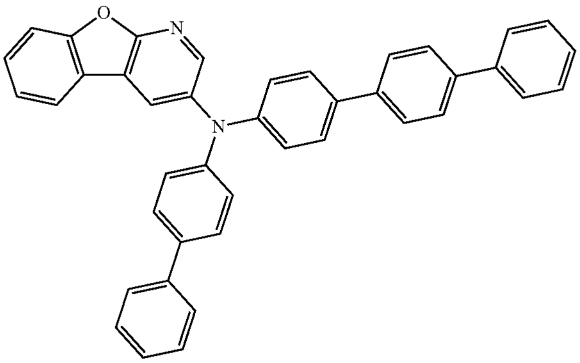
-continued
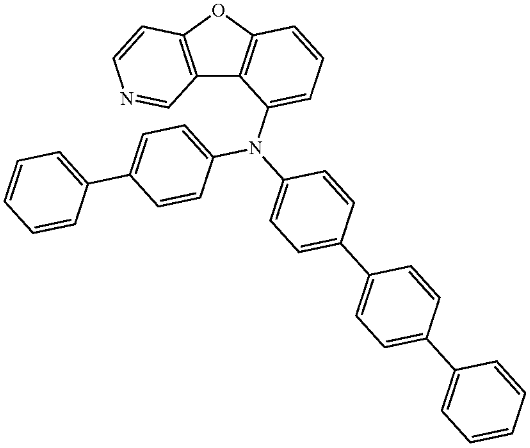
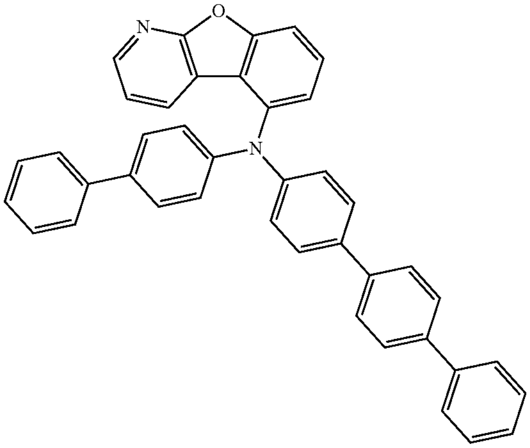
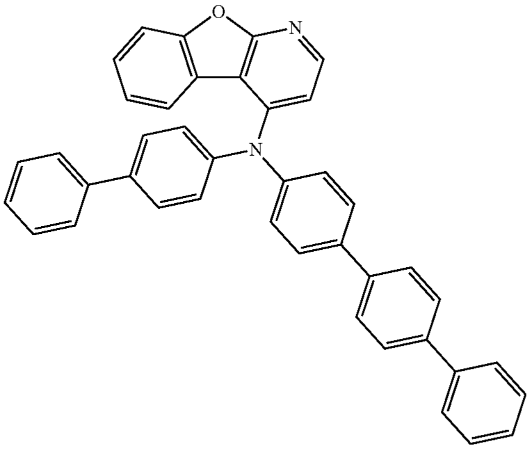

-continued
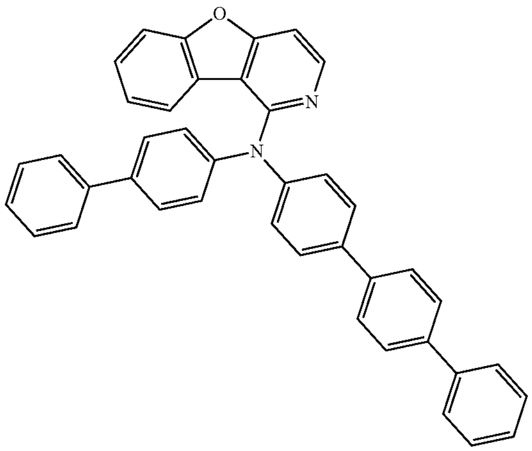
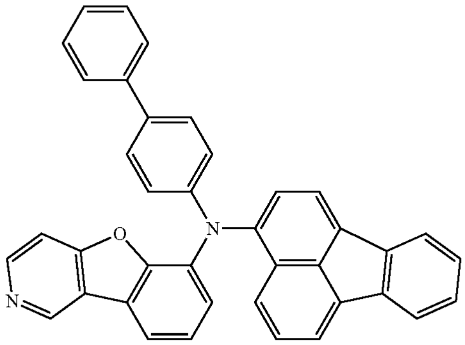
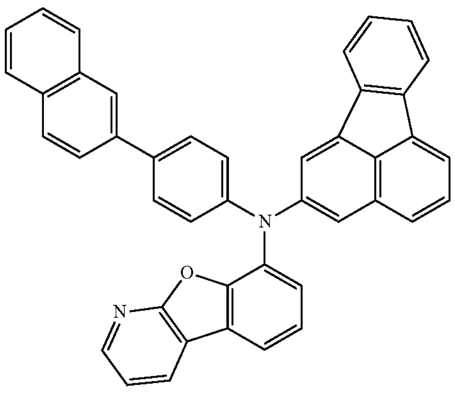
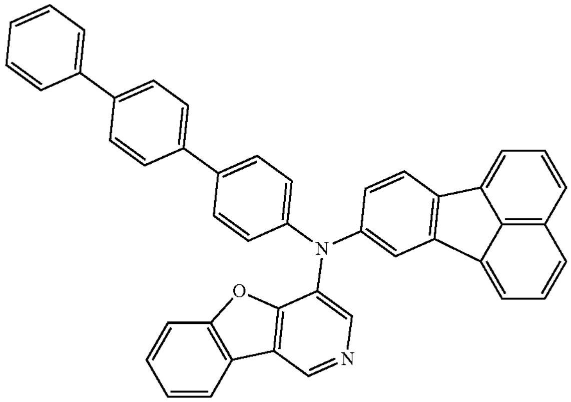
-continued
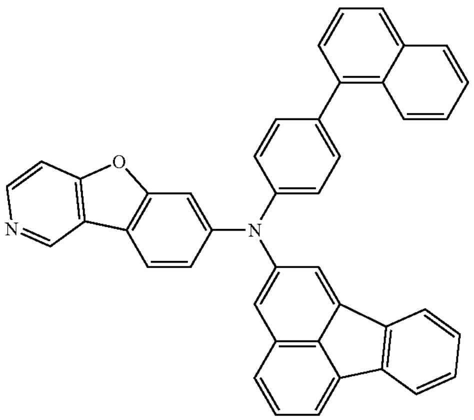
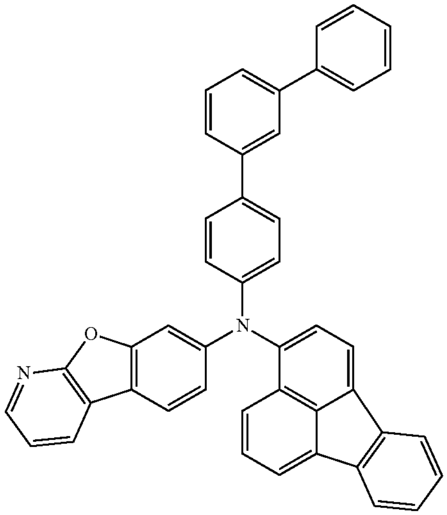
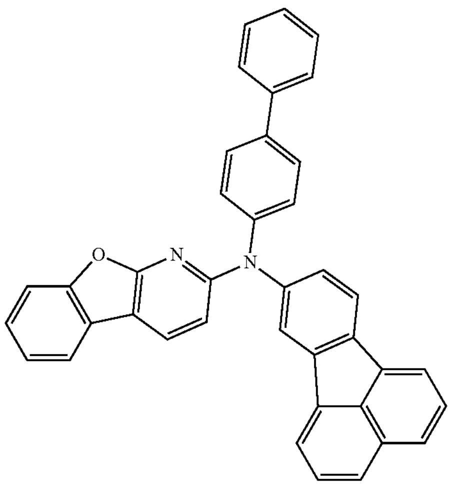

-continued
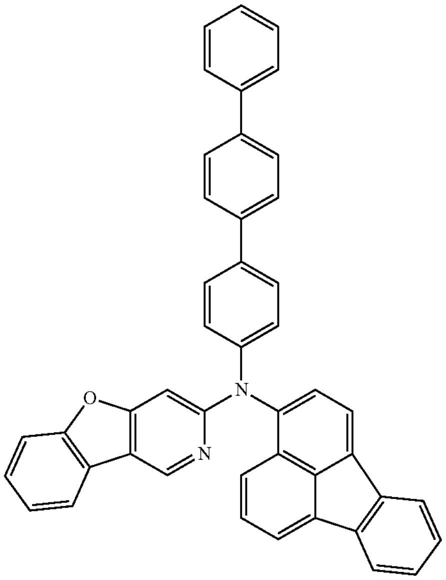
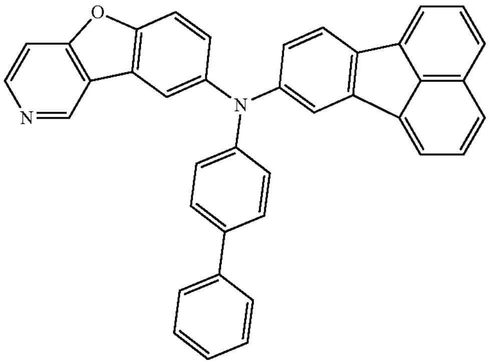
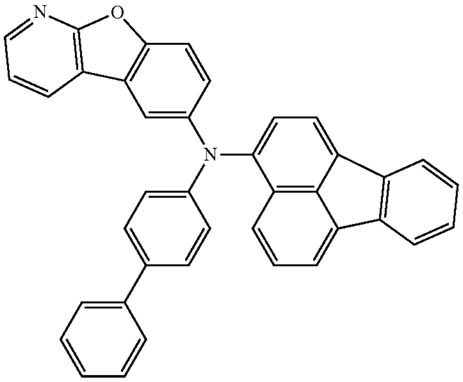
-continued
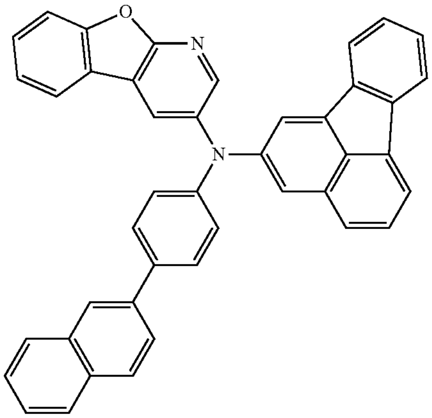
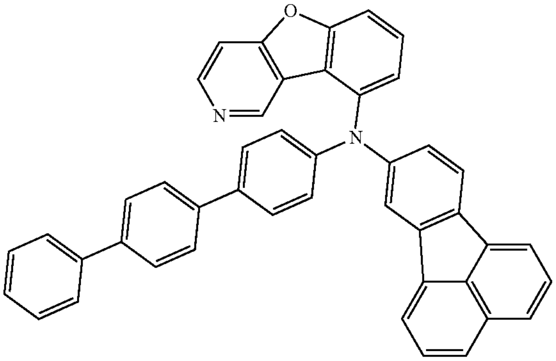
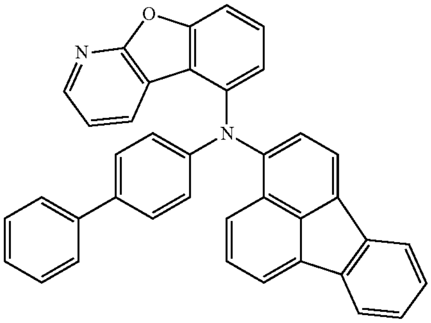
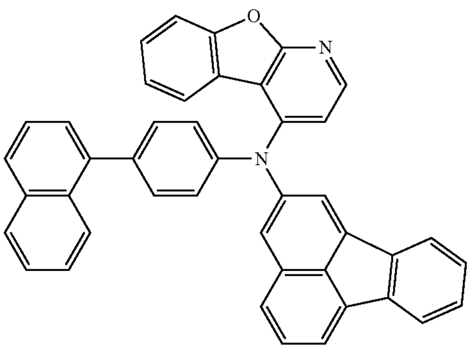

-continued
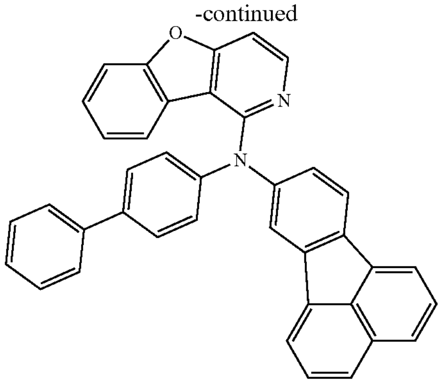
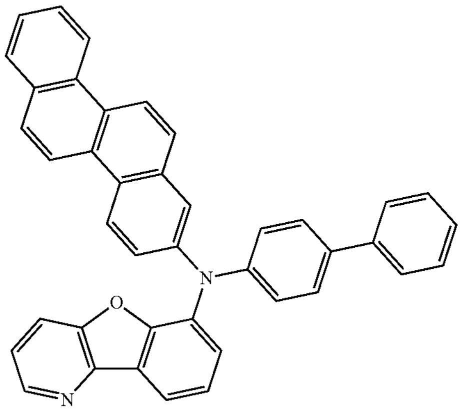
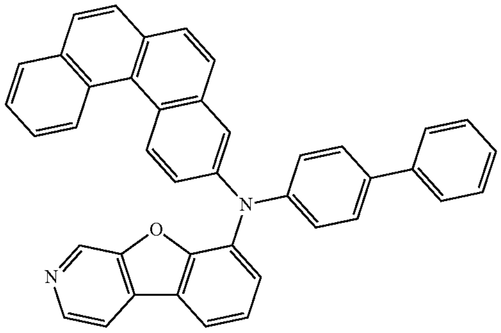
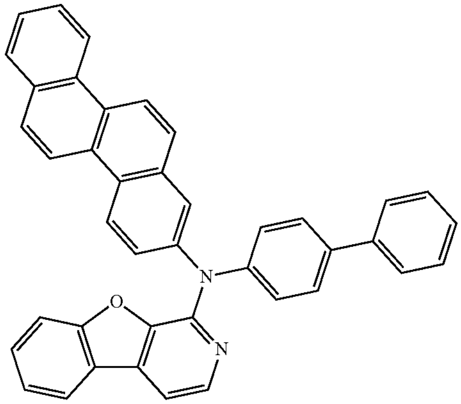
-continued
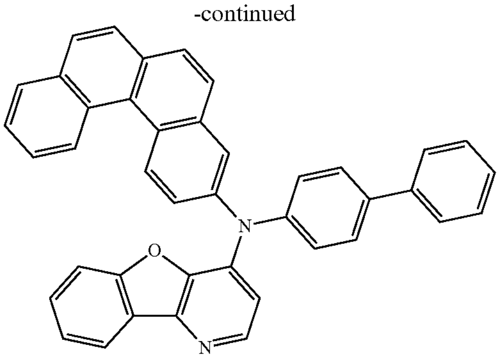
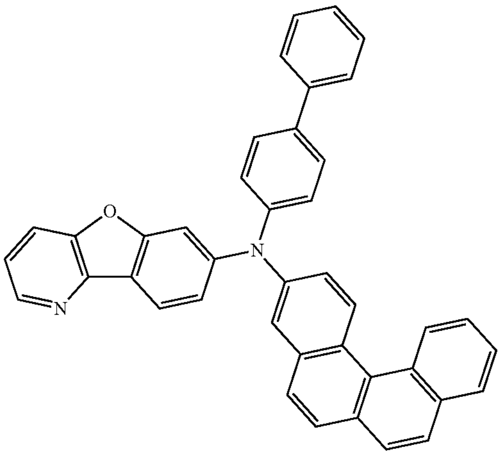
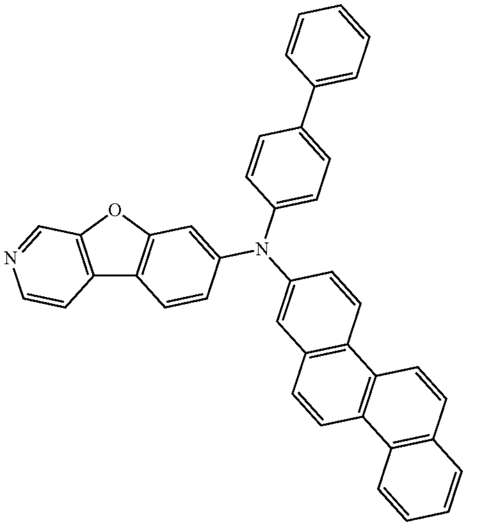

-continued
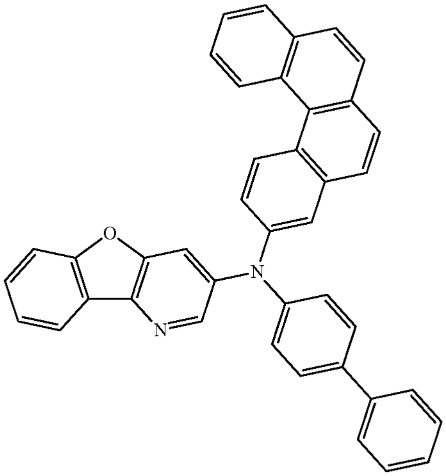
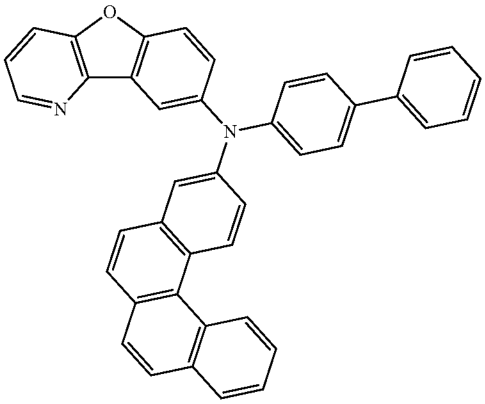
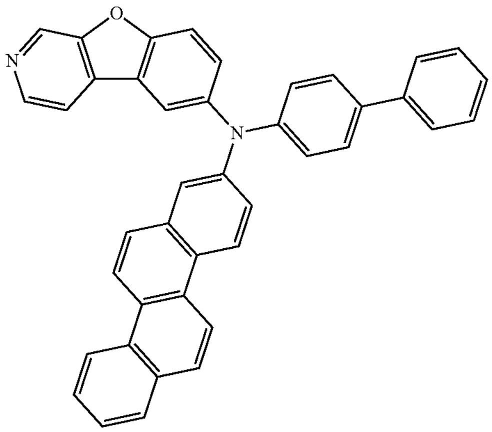
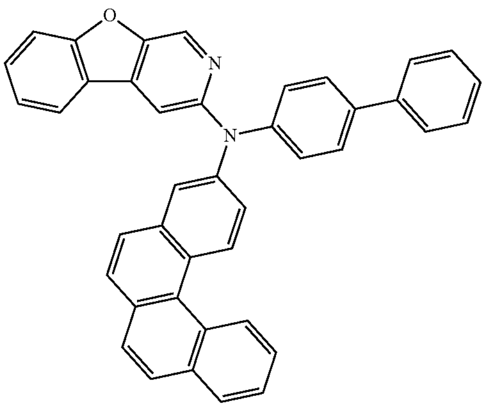
-continued
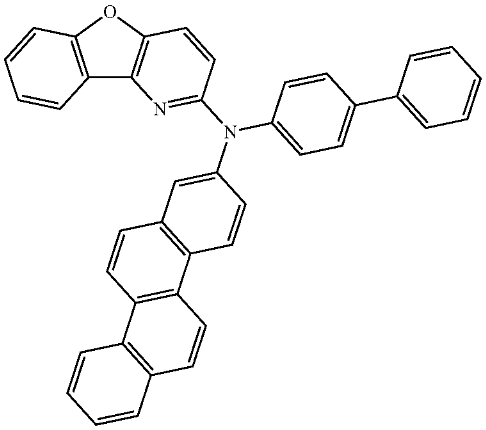
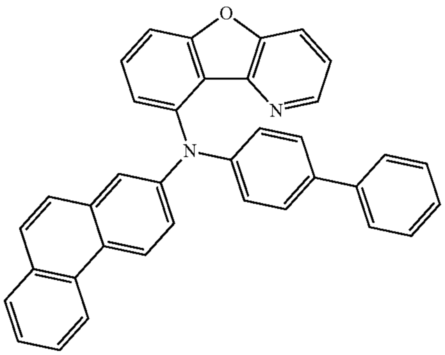
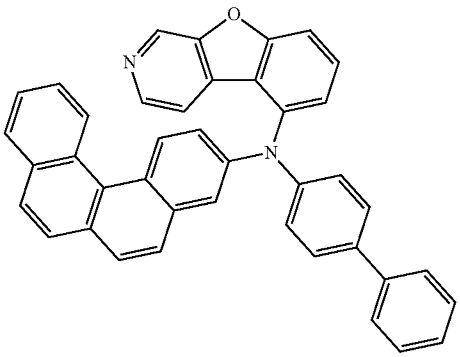
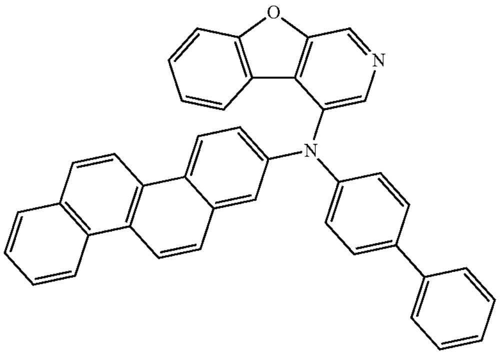

-continued
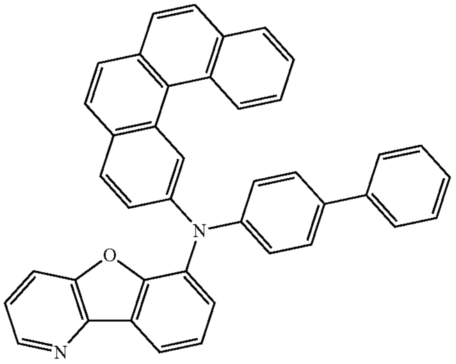
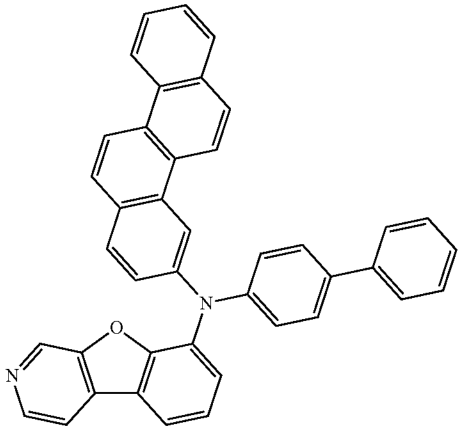
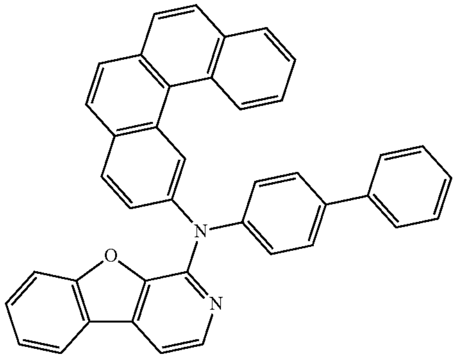
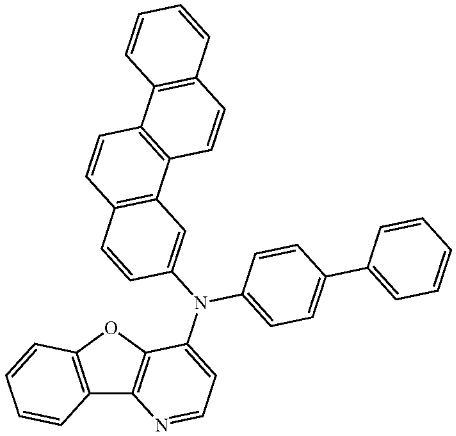
-continued
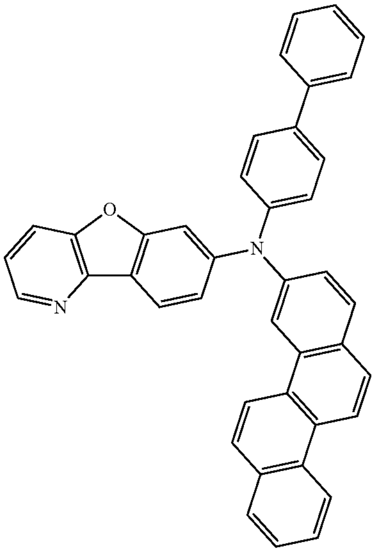
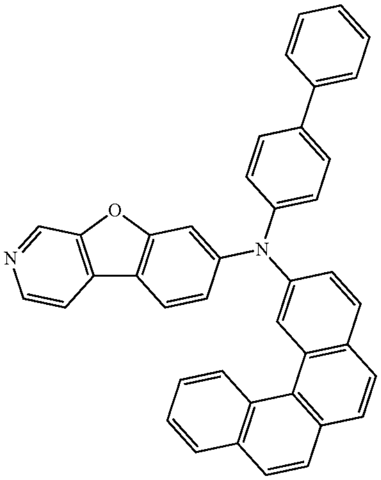
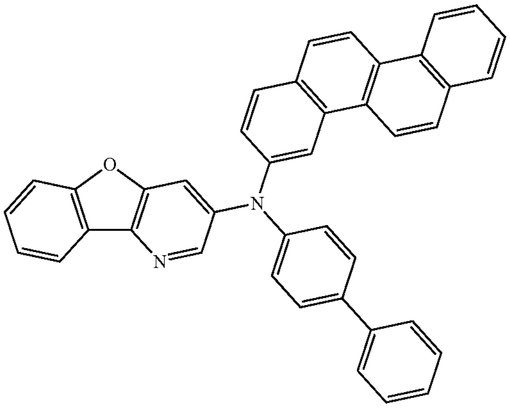

-continued
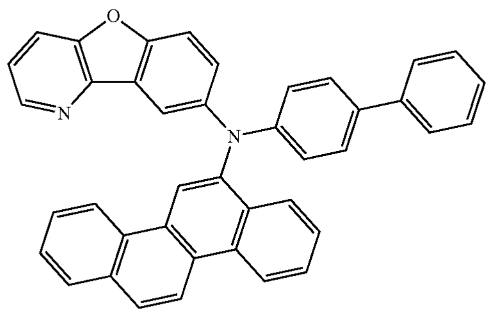
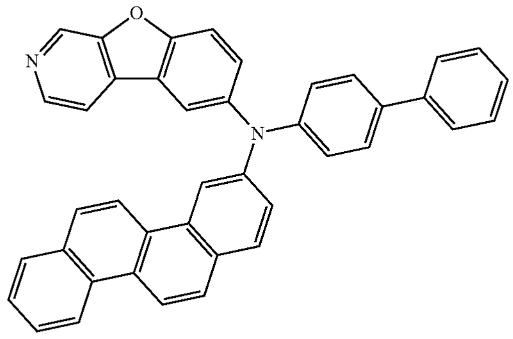
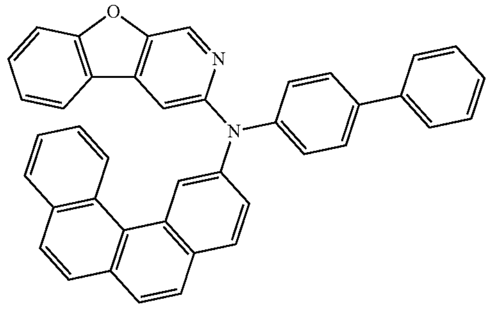
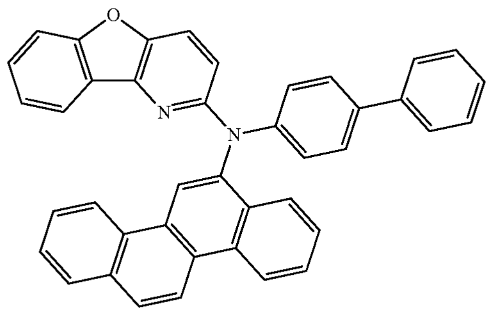
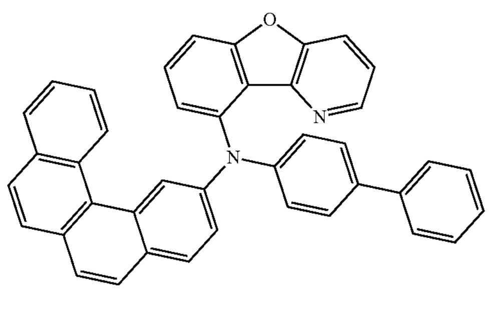
-continued
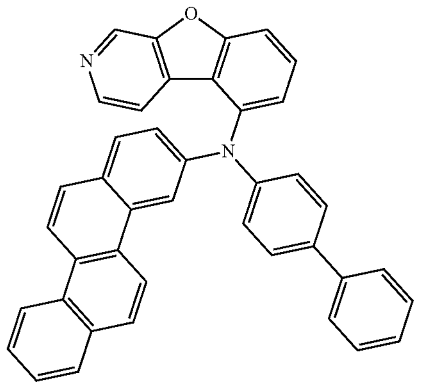
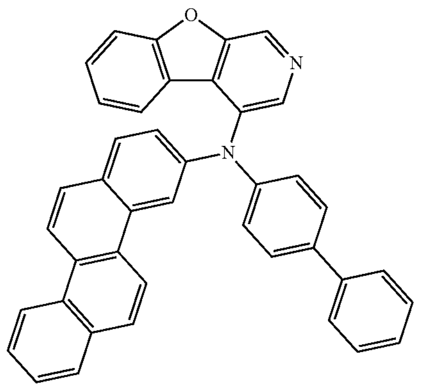
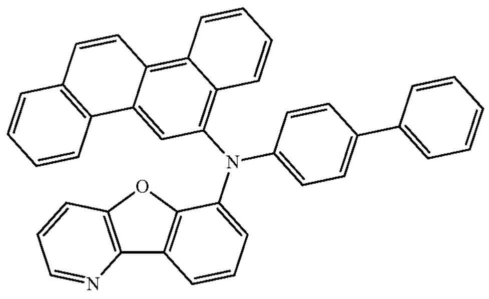
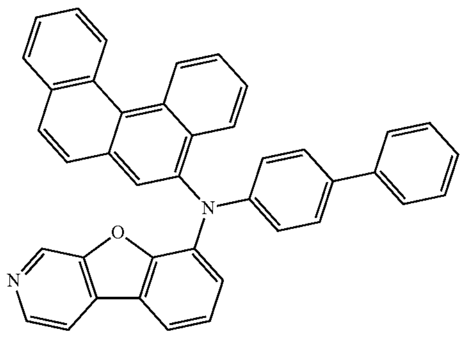

-continued
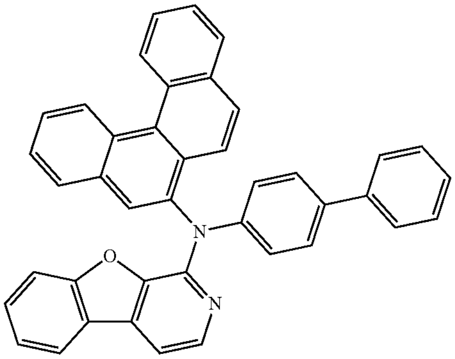
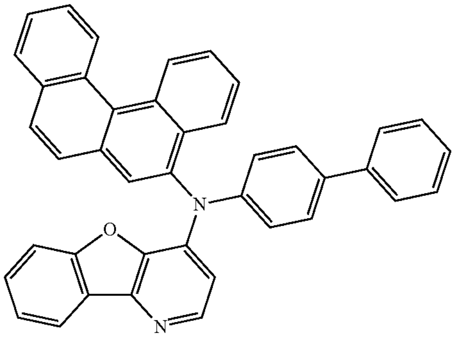
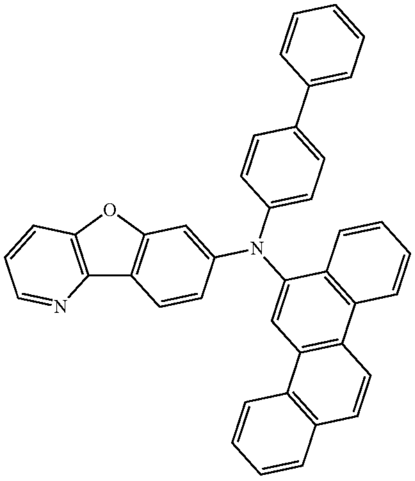
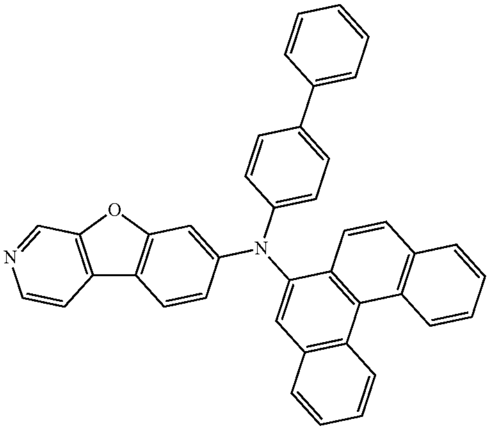
-continued
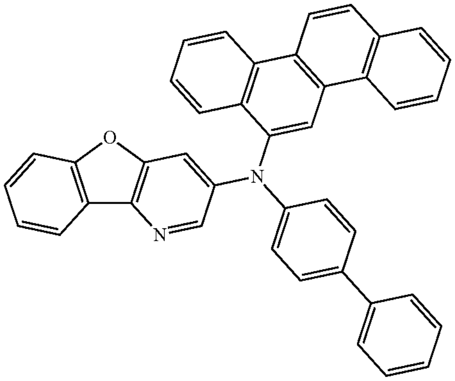
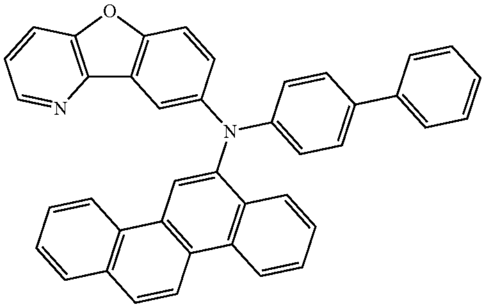
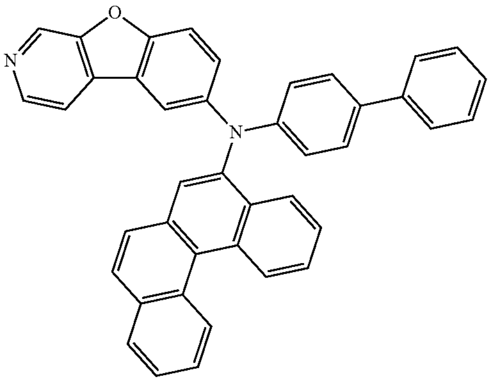
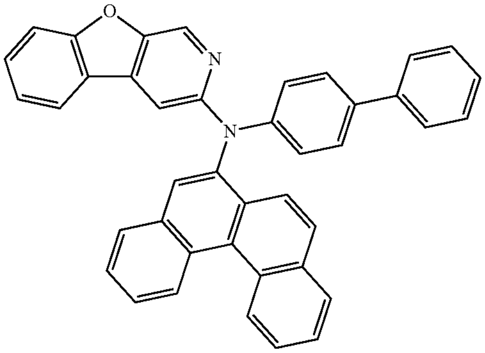
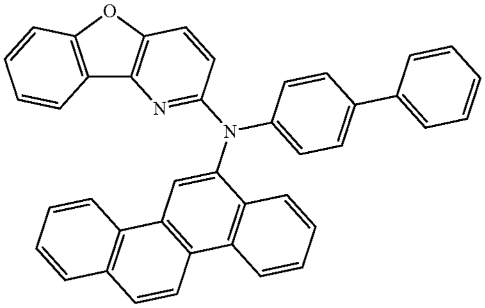

-continued
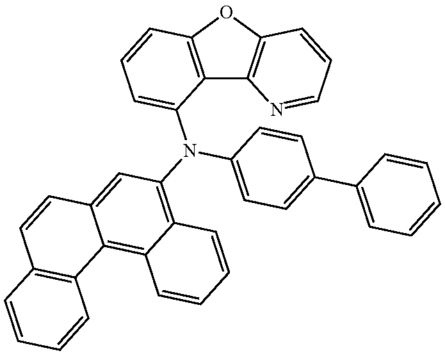
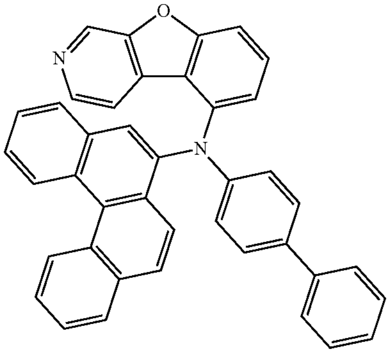
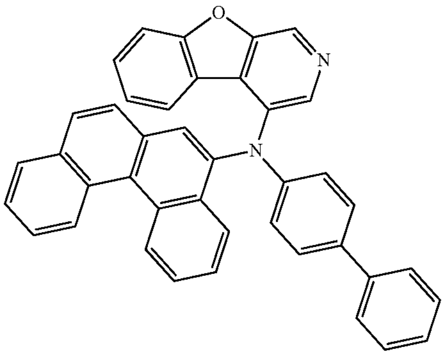
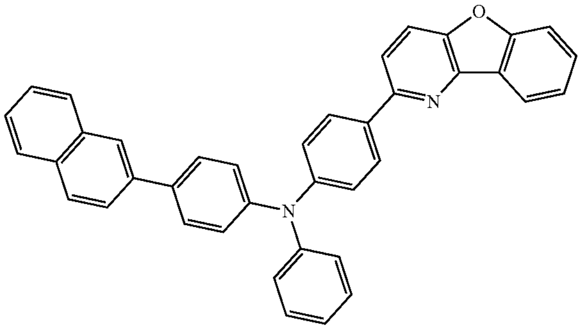
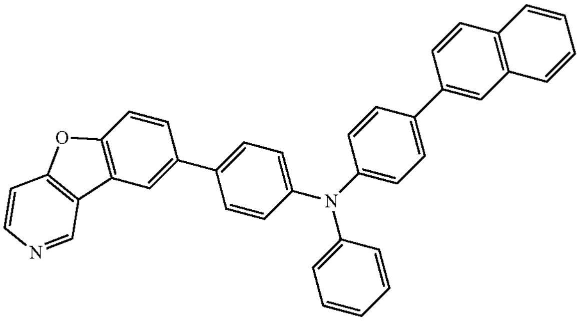
-continued
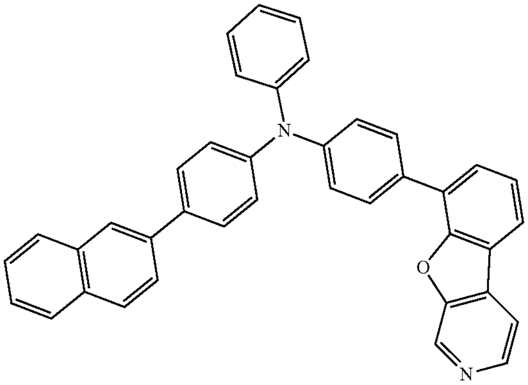
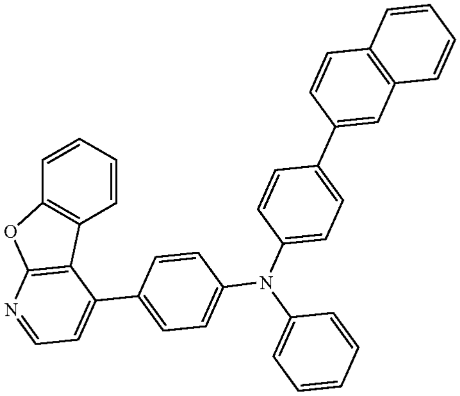
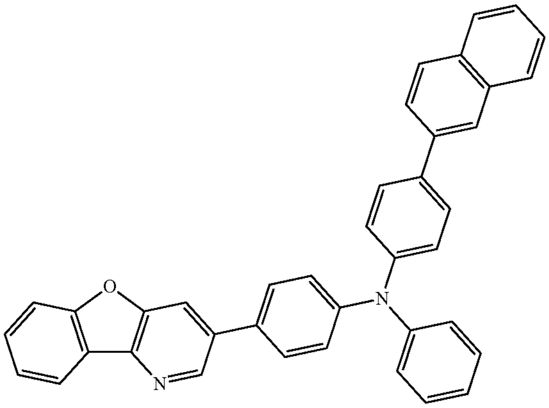
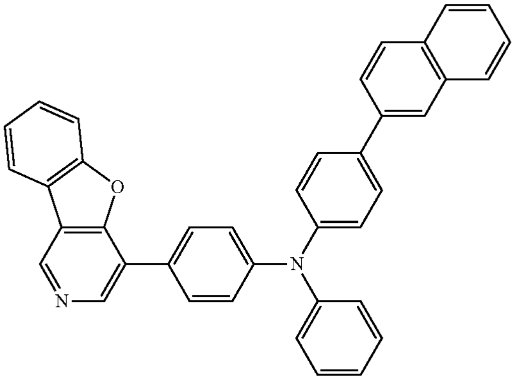

-continued
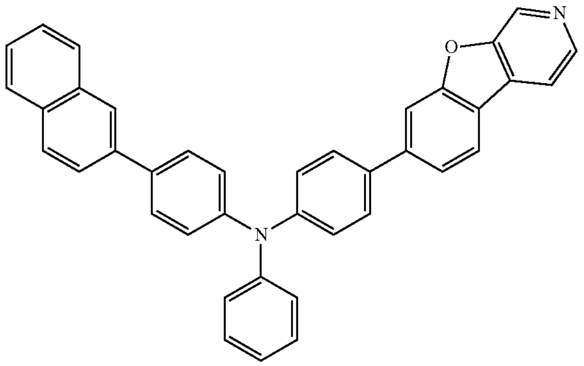
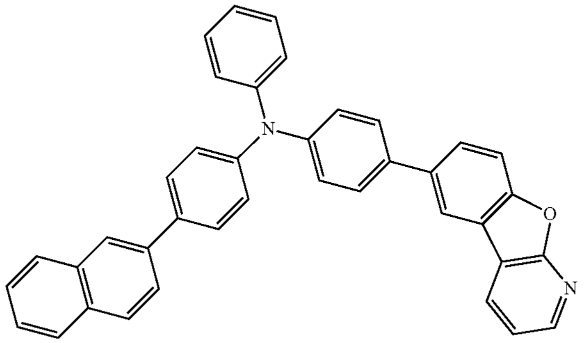
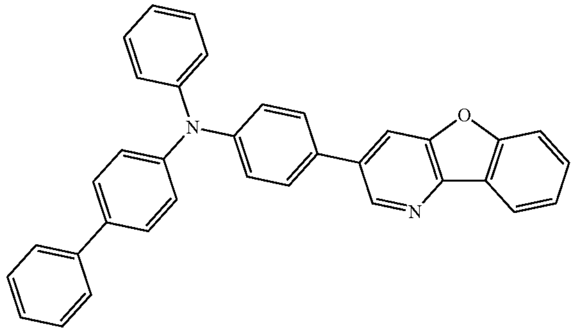
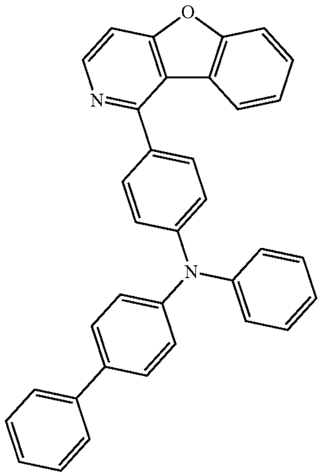
-continued
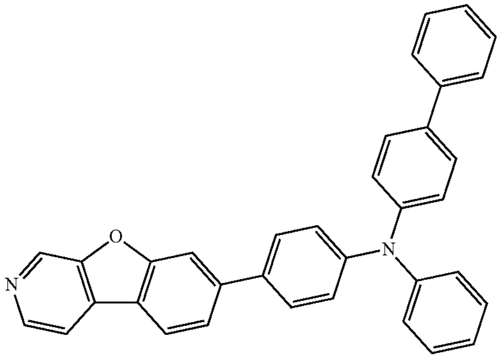
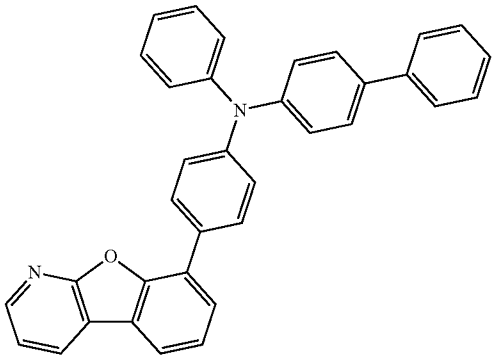
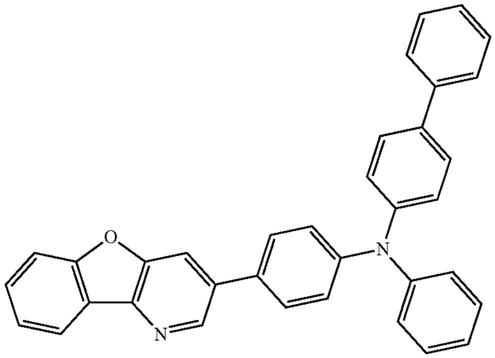
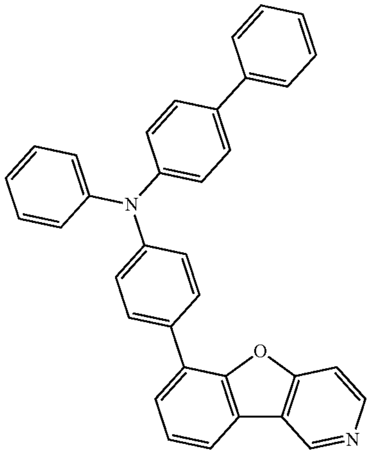

-continued
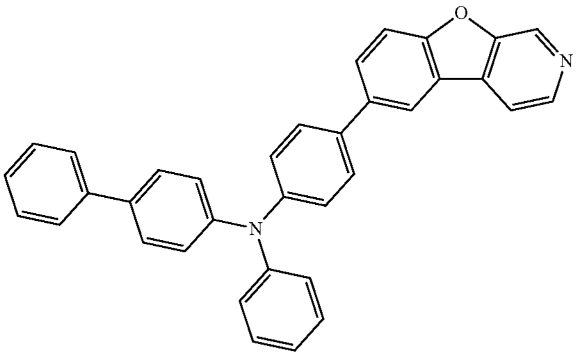
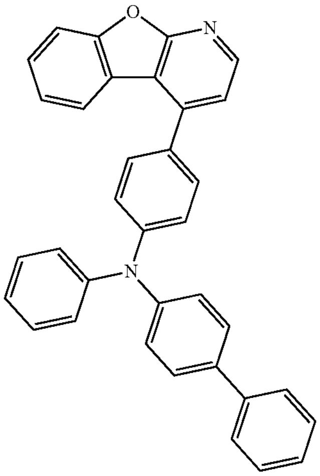
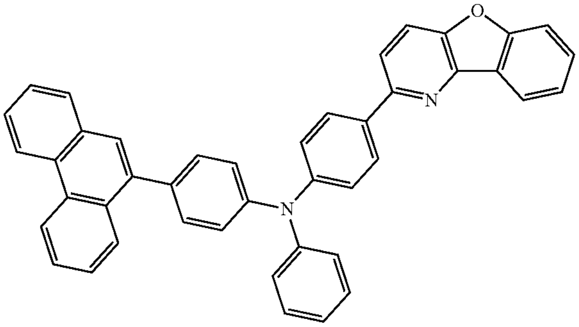
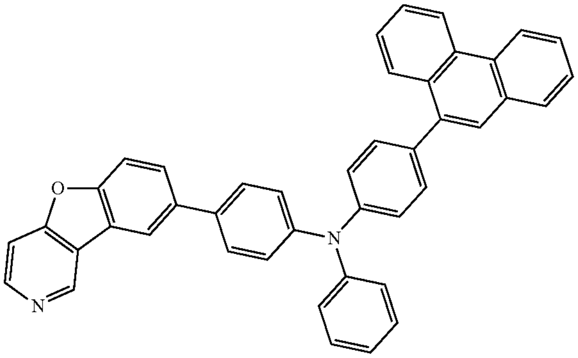
-continued
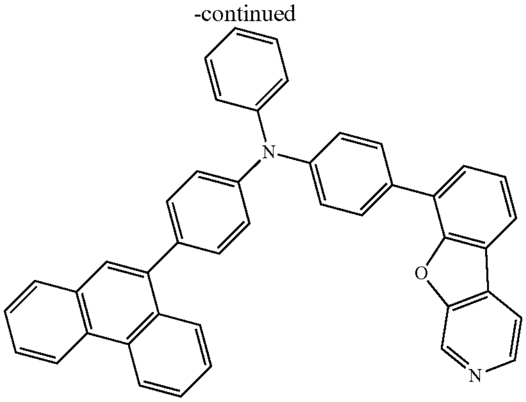
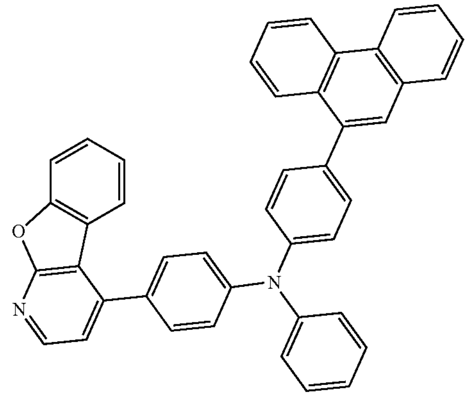
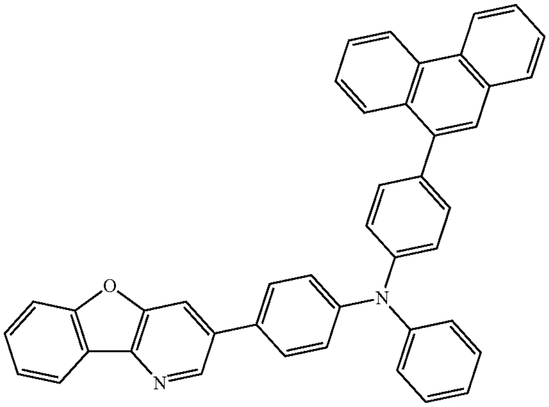
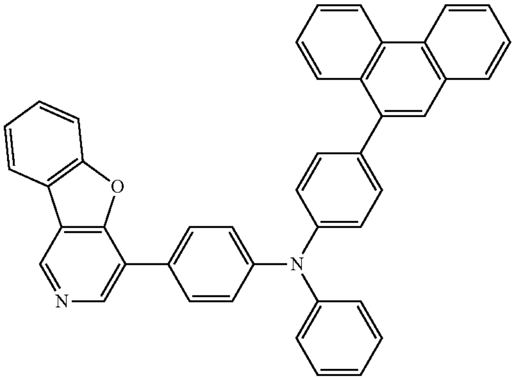

-continued
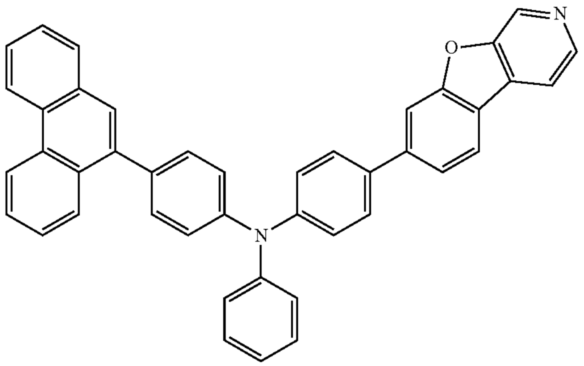
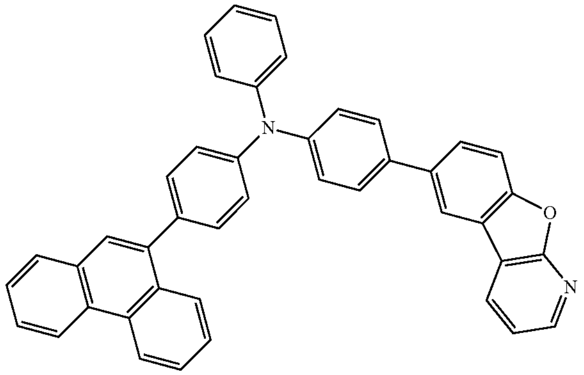
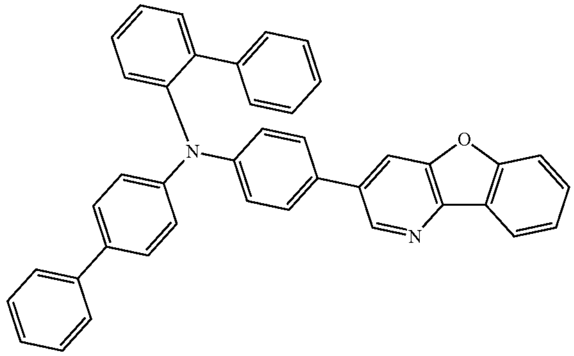
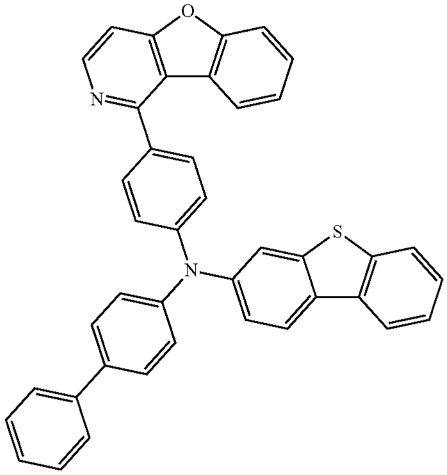
-continued
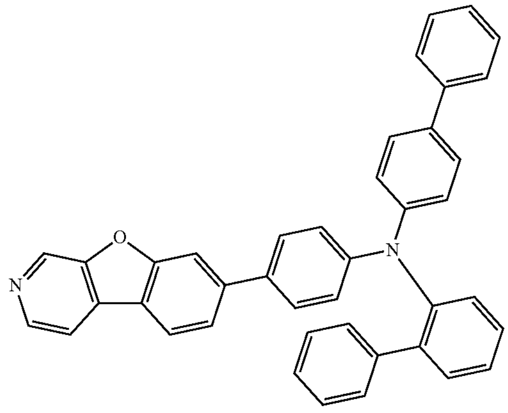
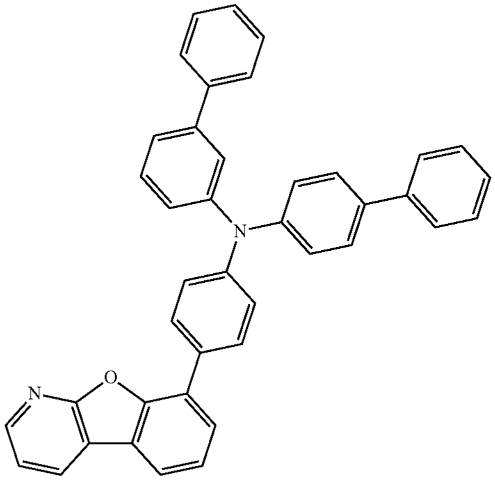
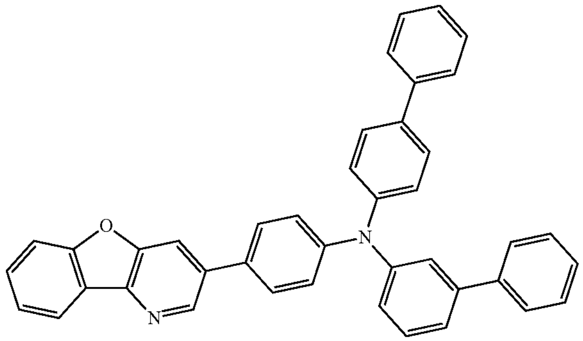

-continued
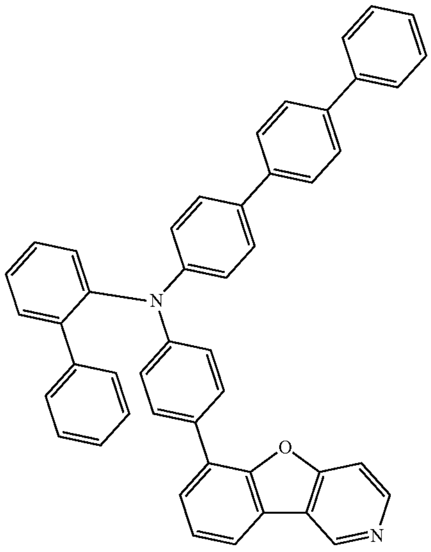
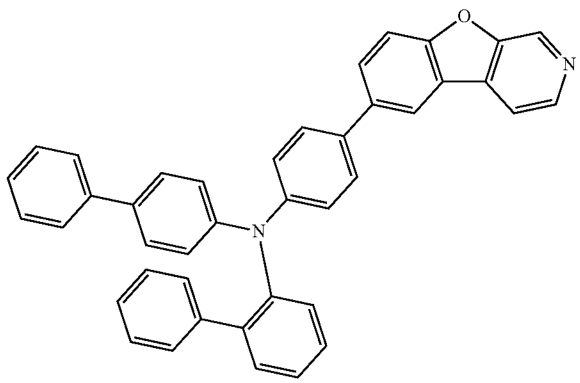
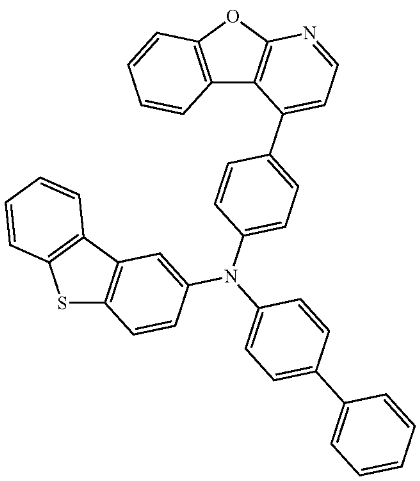
-continued
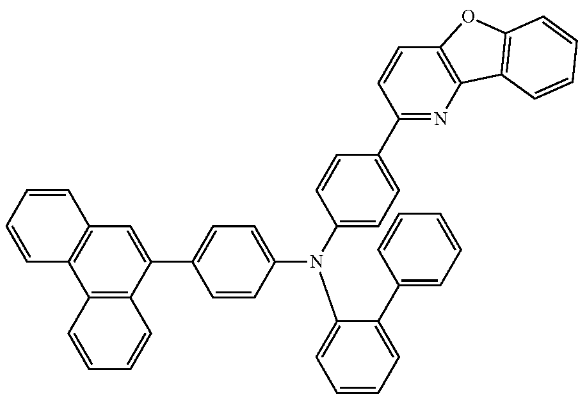
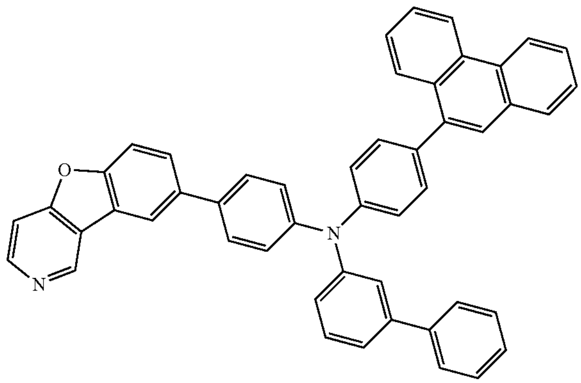
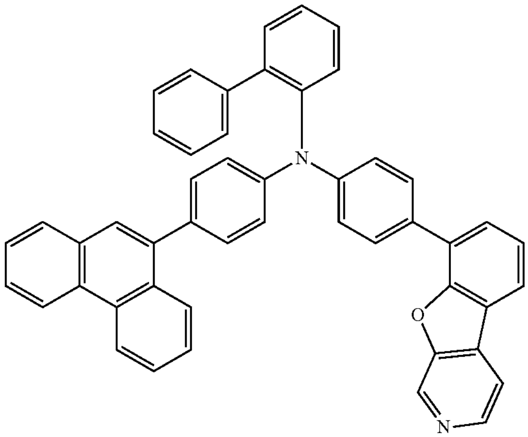
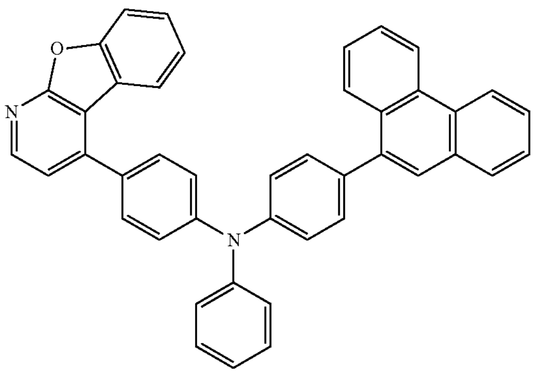

-continued
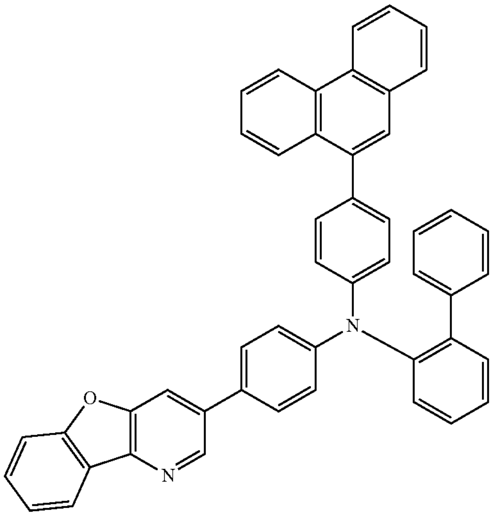
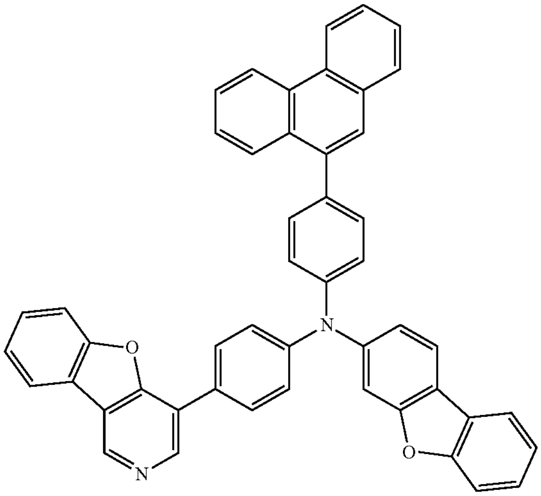
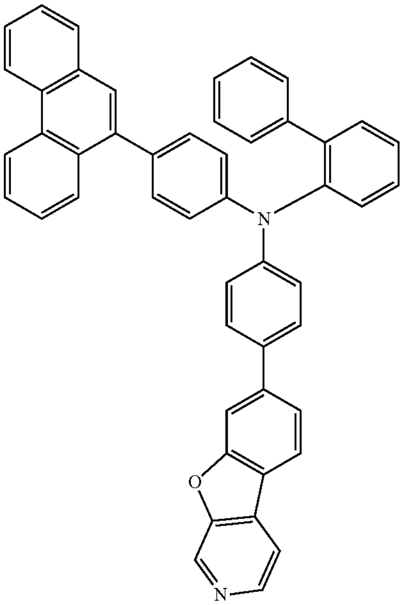
-continued
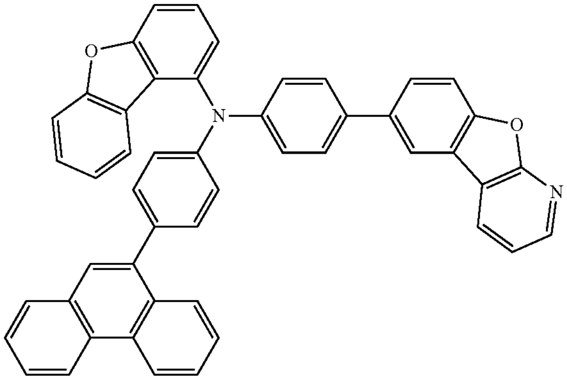
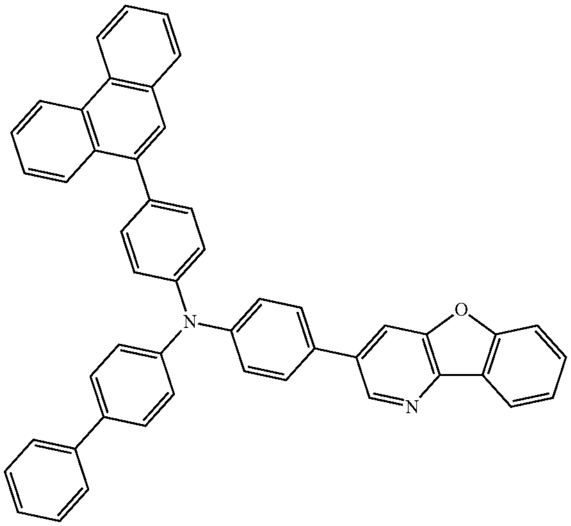
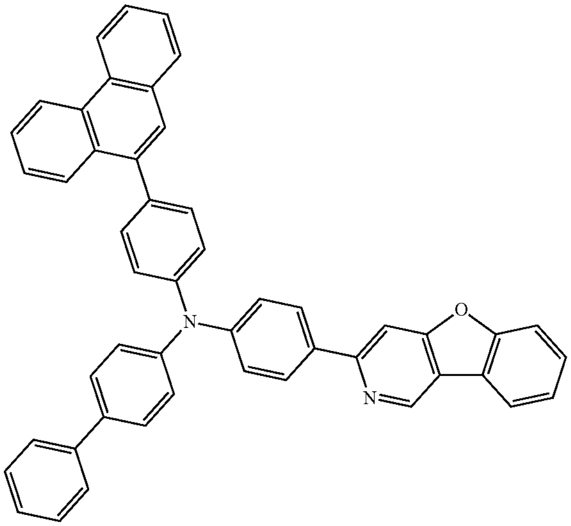

-continued
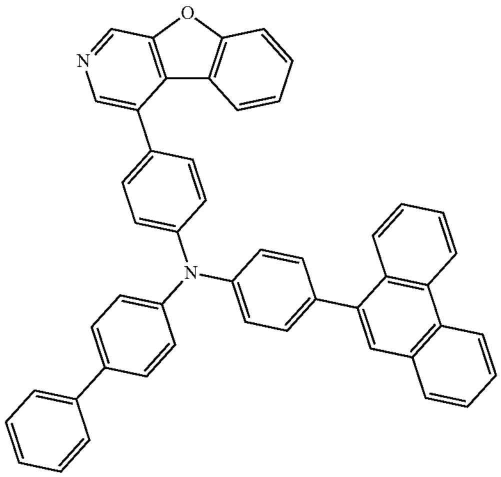
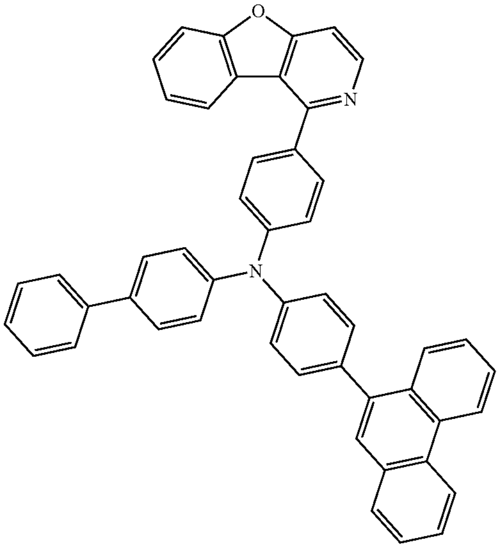
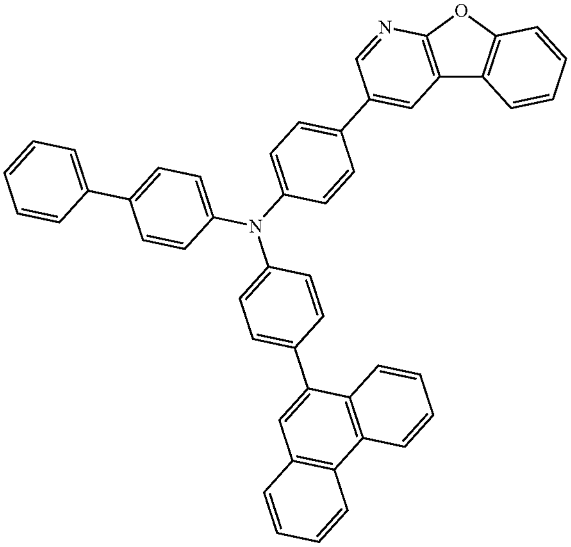
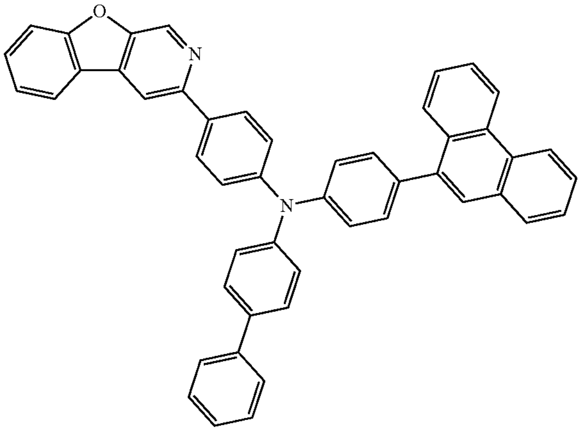
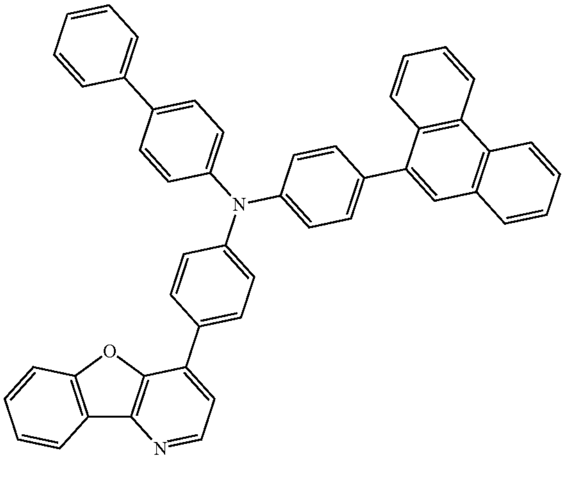
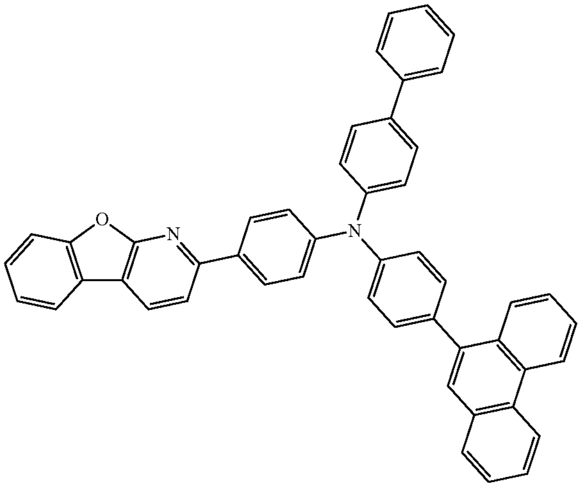

-continued
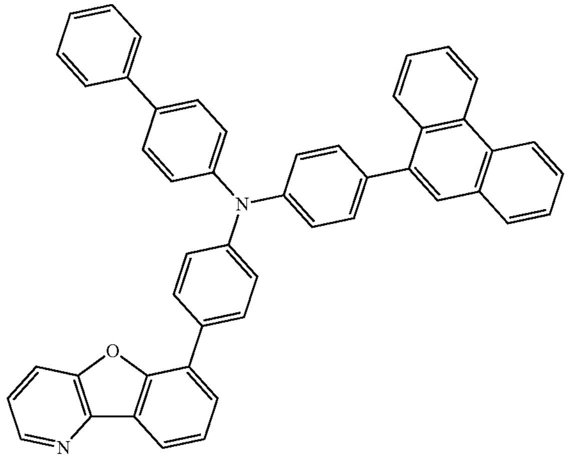
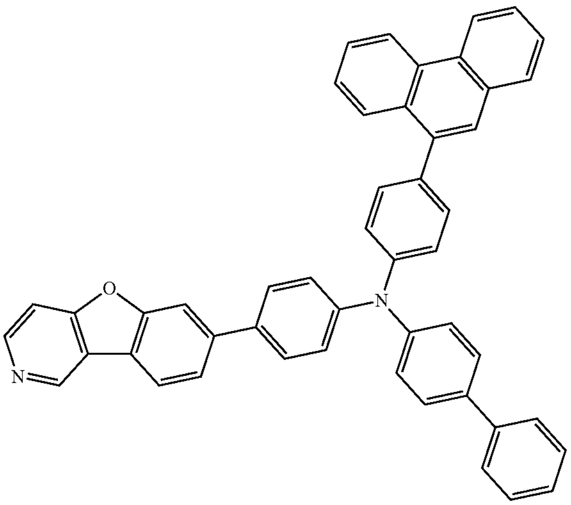
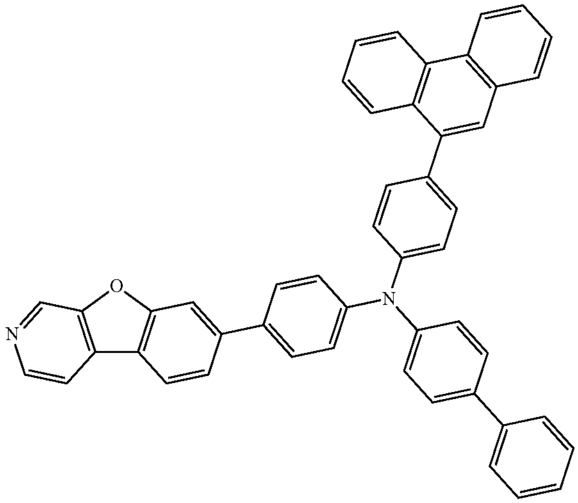
-continued
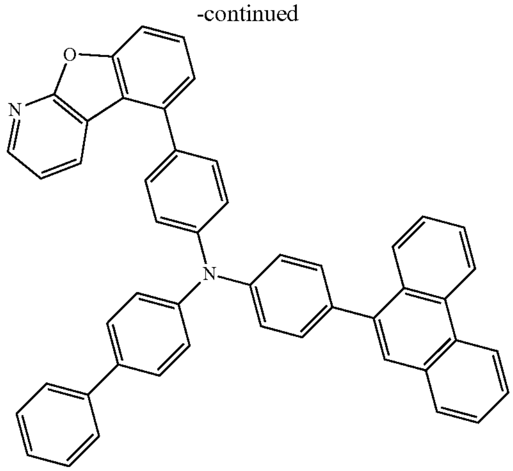
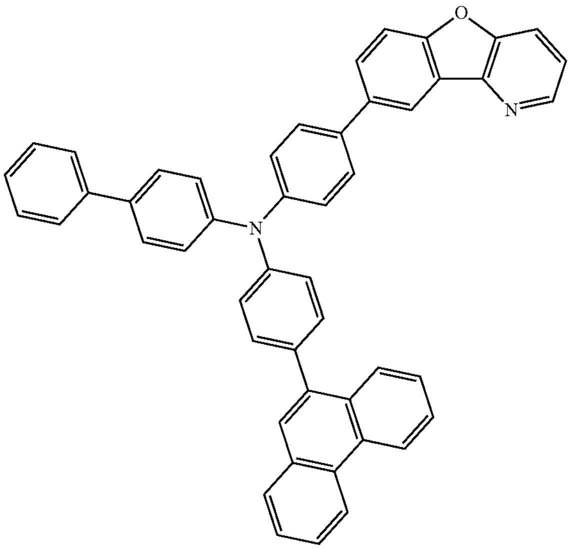
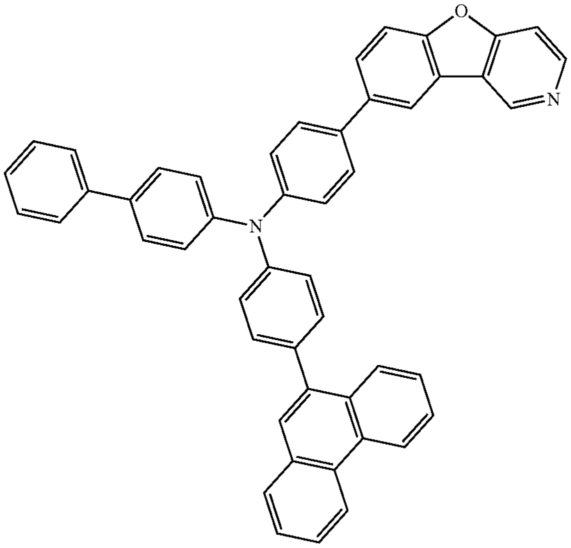

-continued
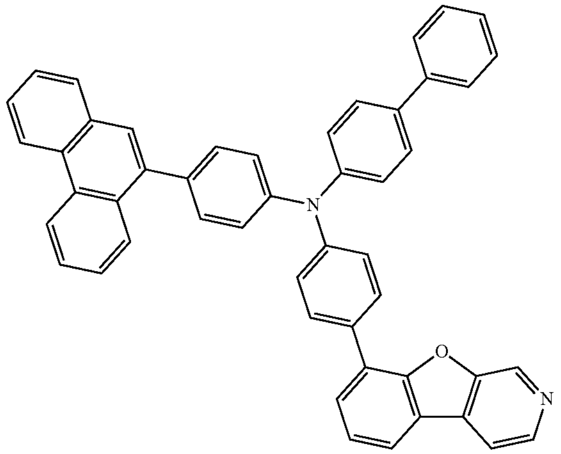
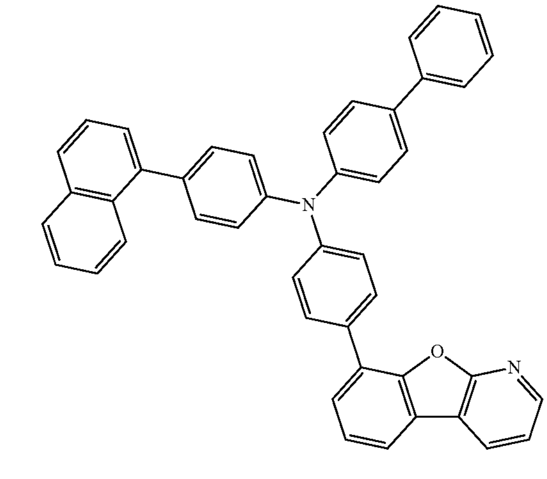
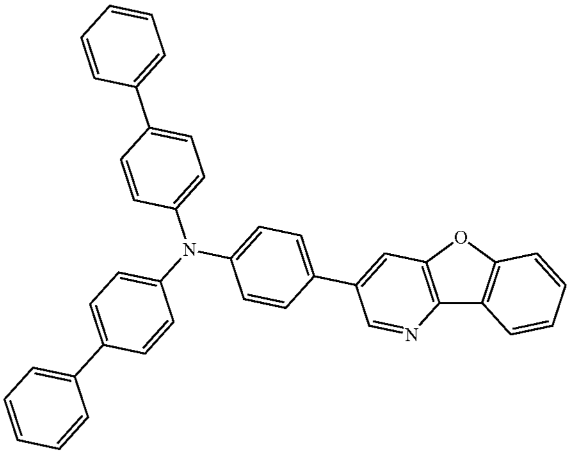
-continued
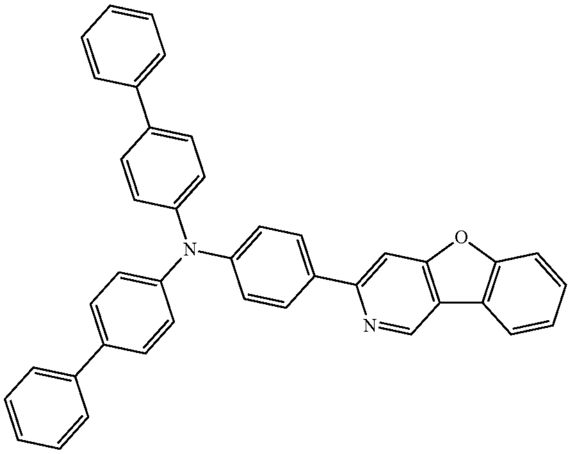
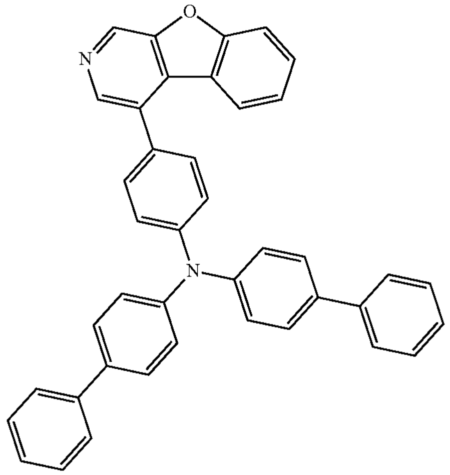
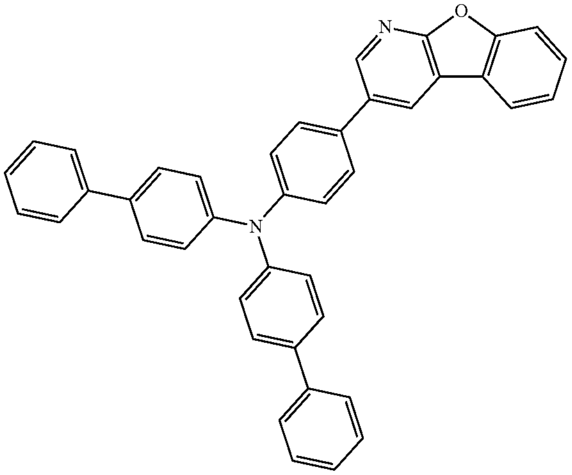

-continued
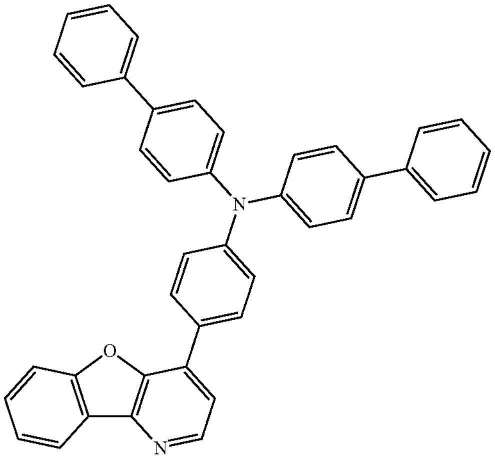
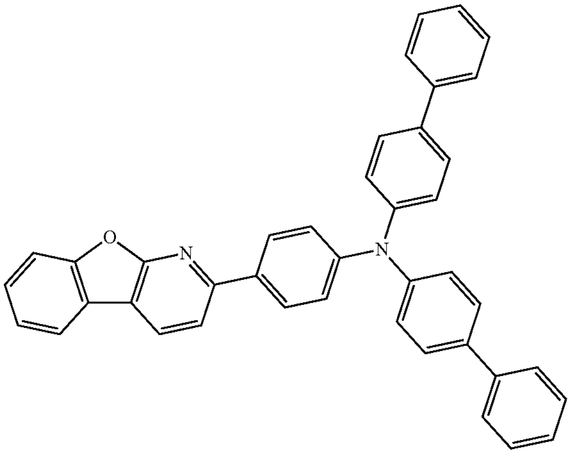
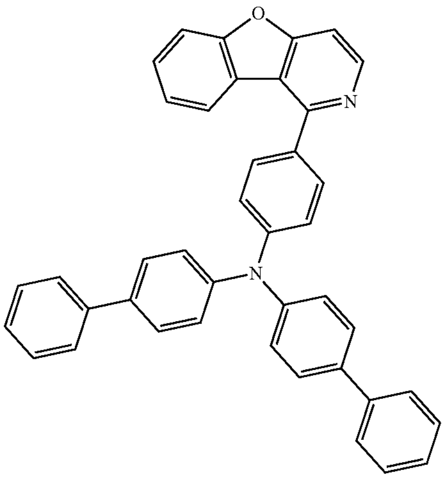
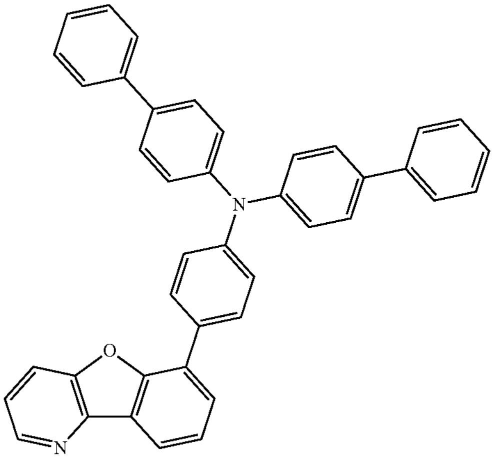
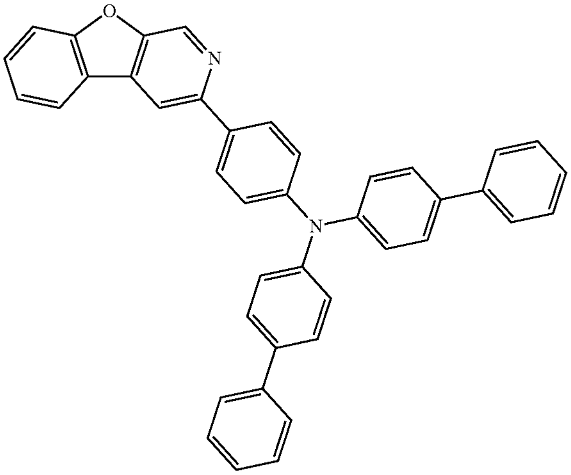
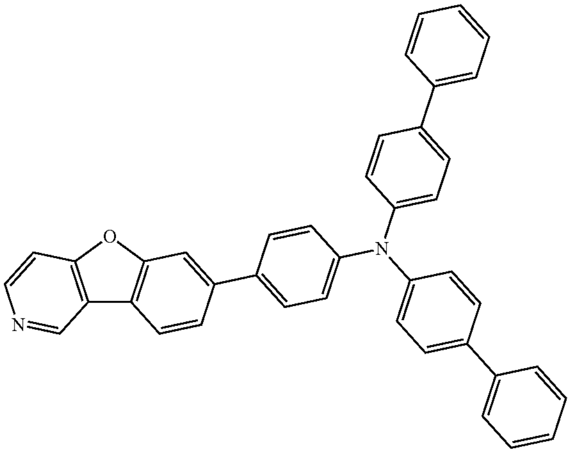
-continued -continued
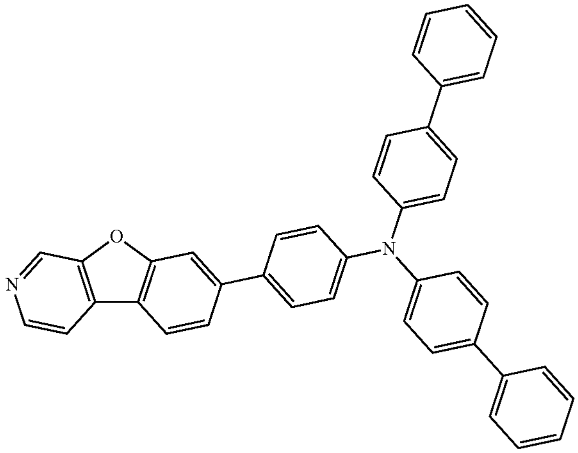
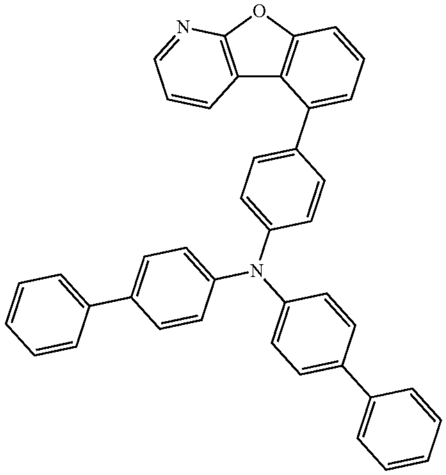
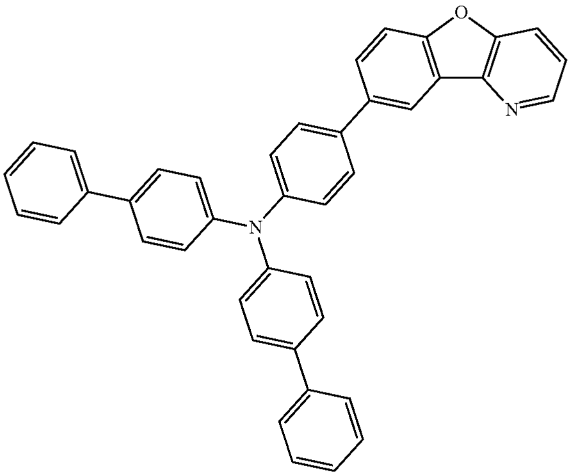
-continued
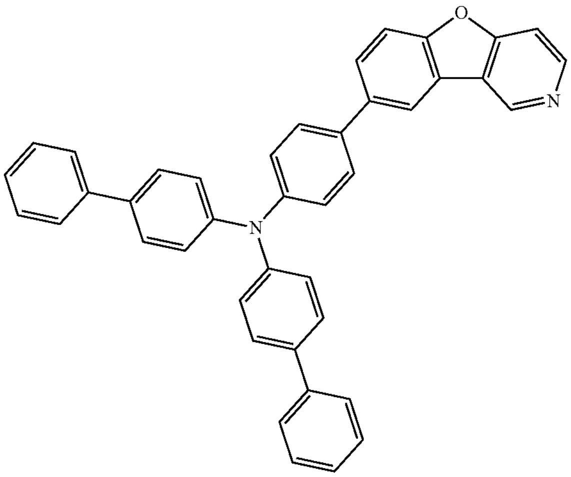
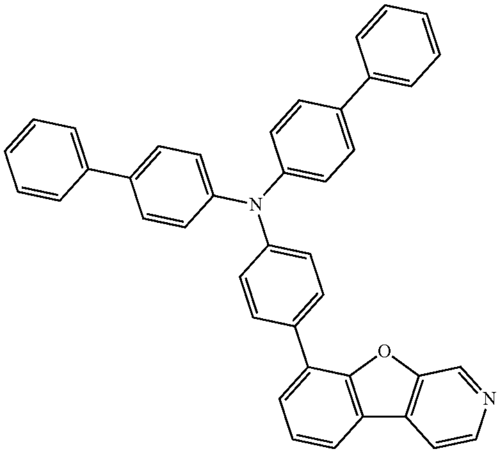
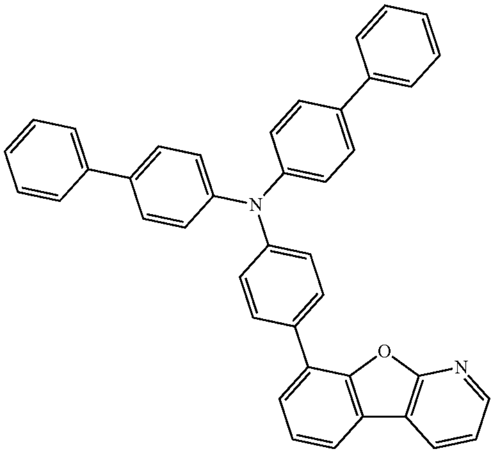

-continued
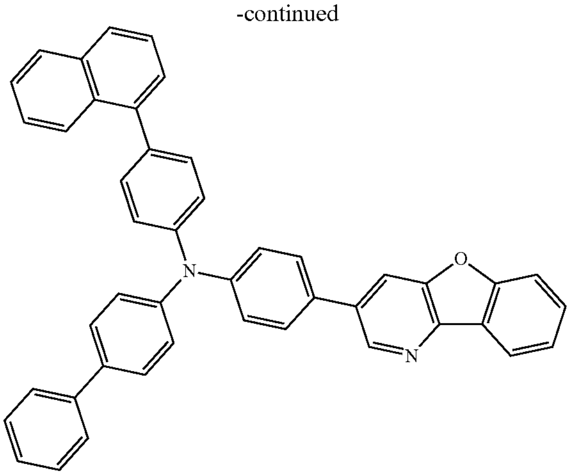
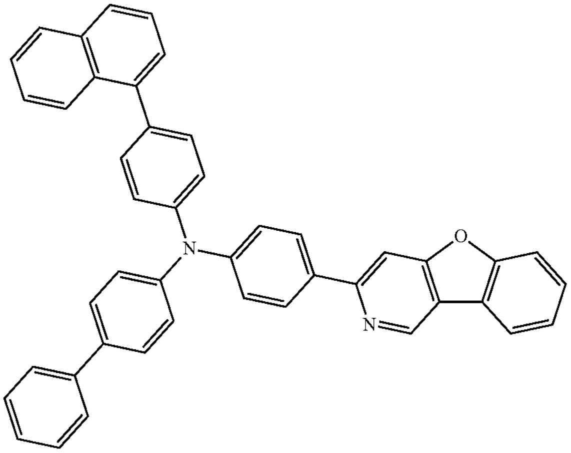
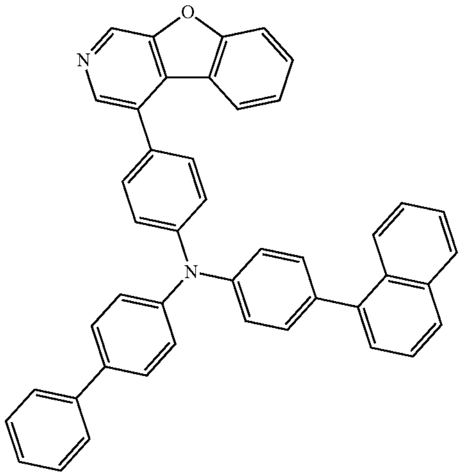
-continued
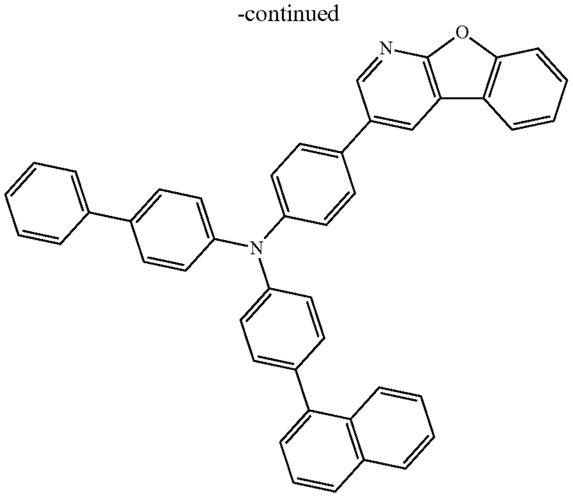
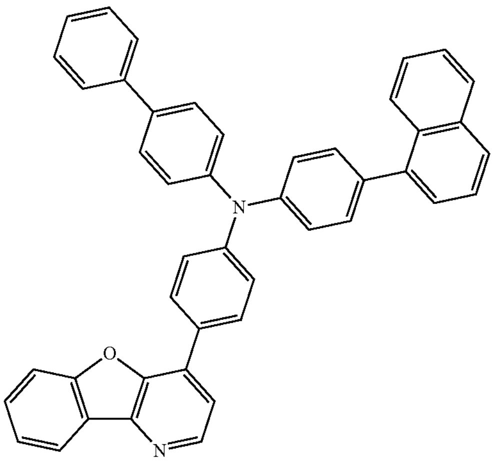
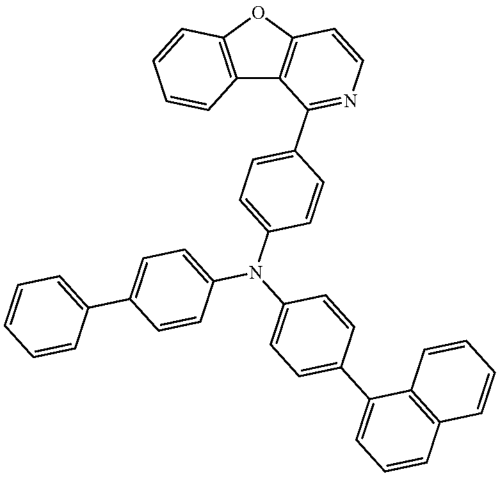

-continued
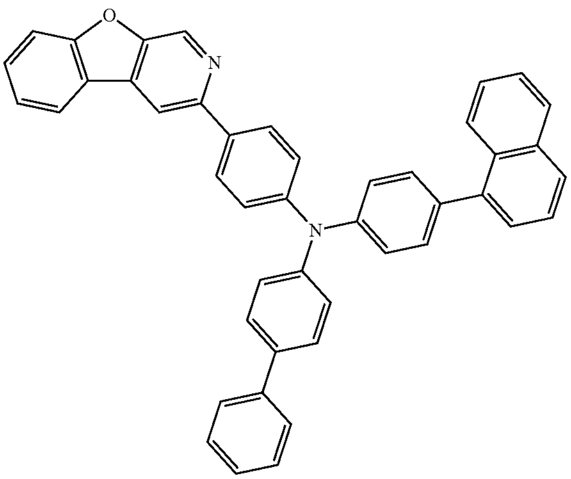
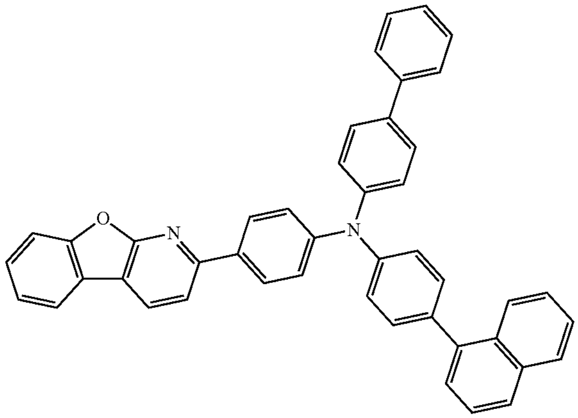
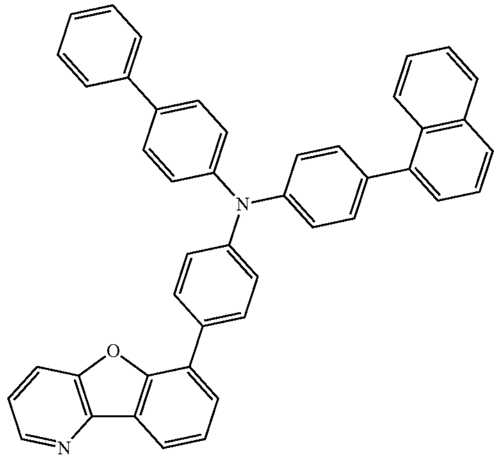
-continued
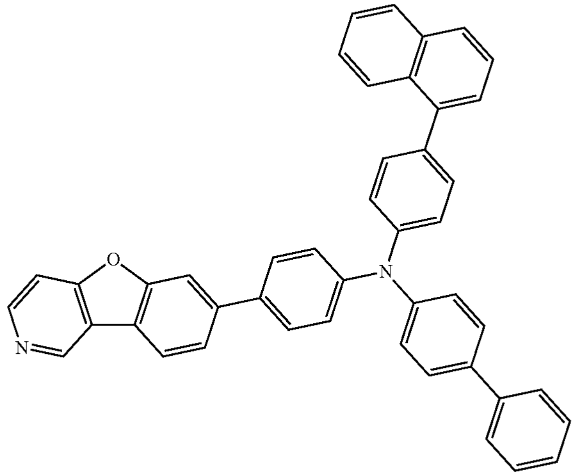
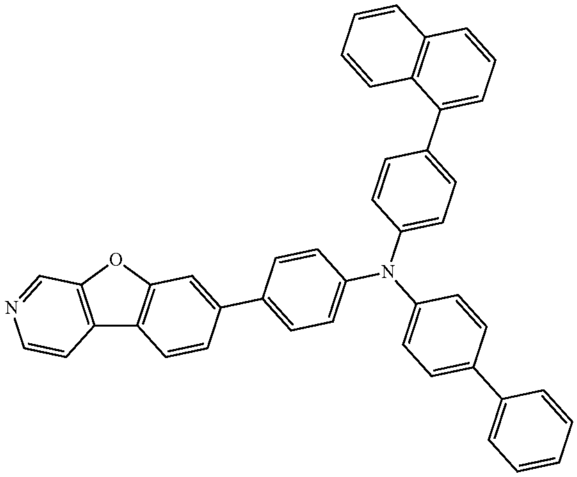
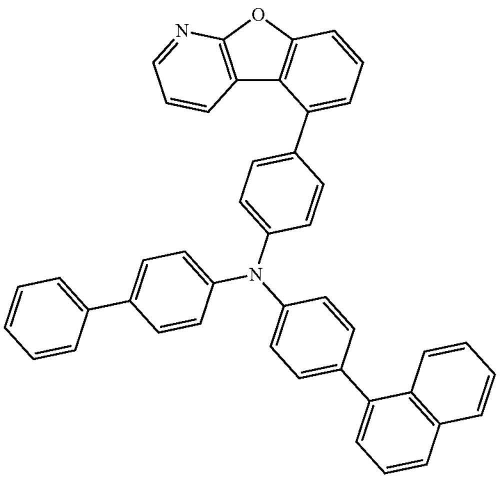

-continued
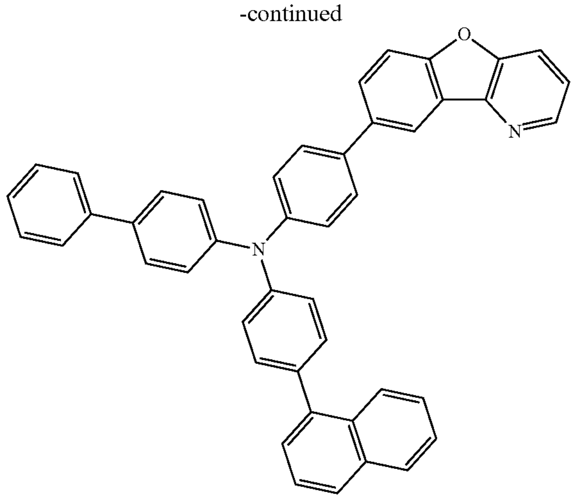
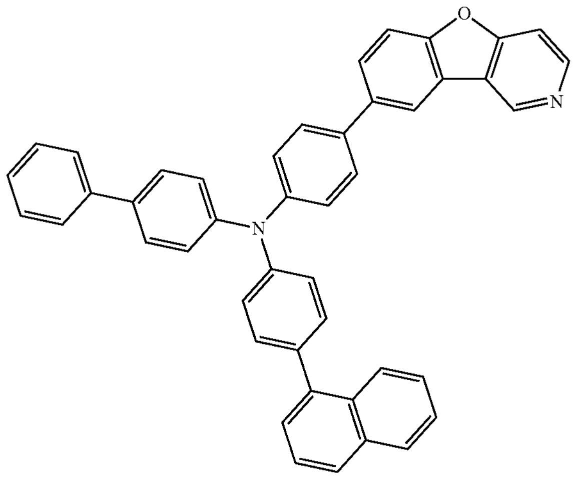
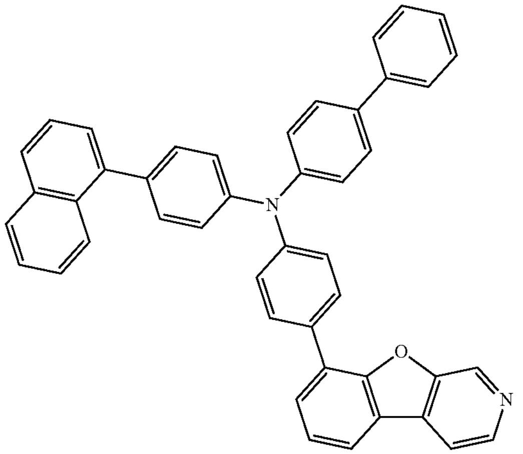
-continued
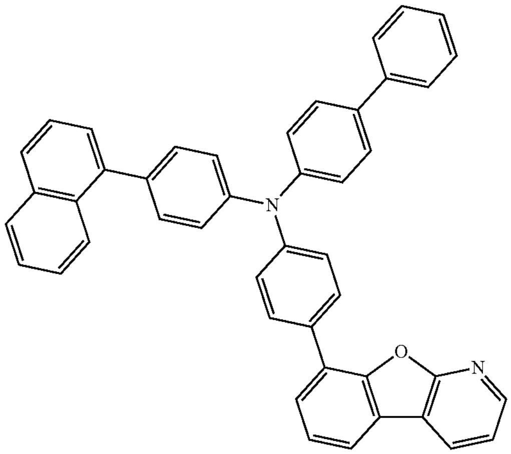
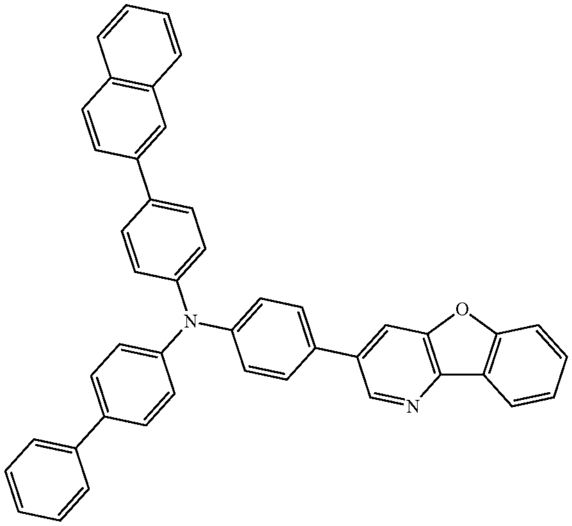
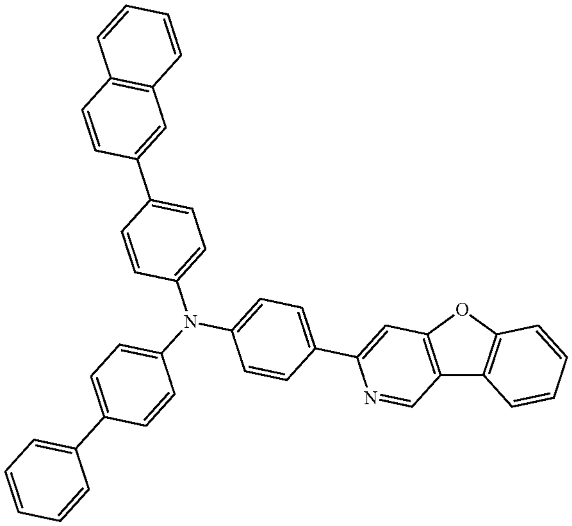

-continued
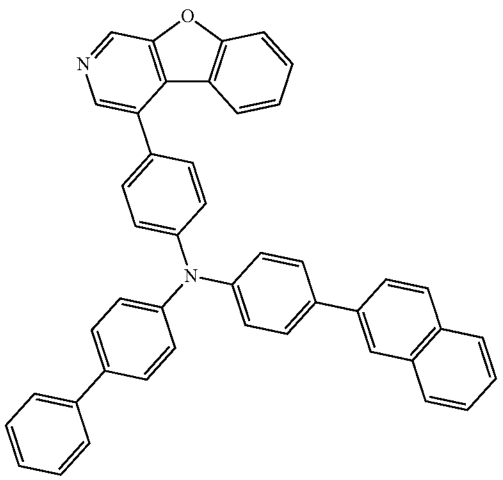
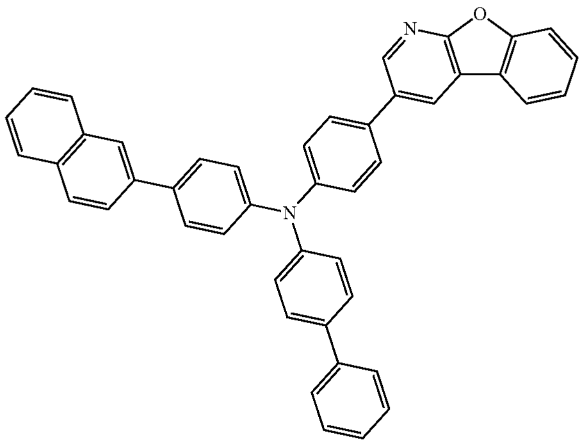
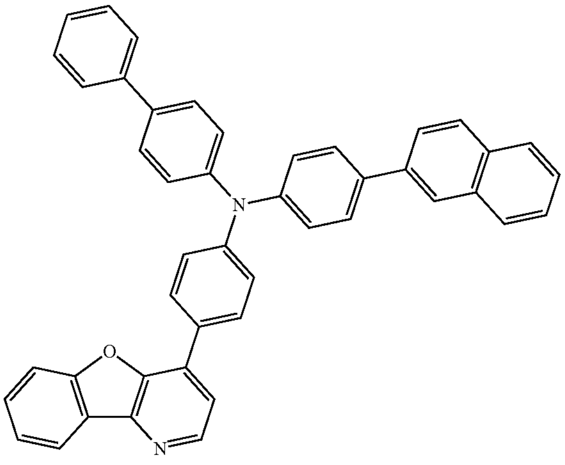
-continued
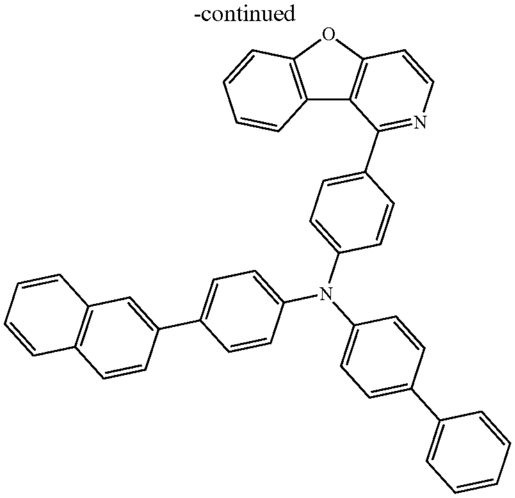
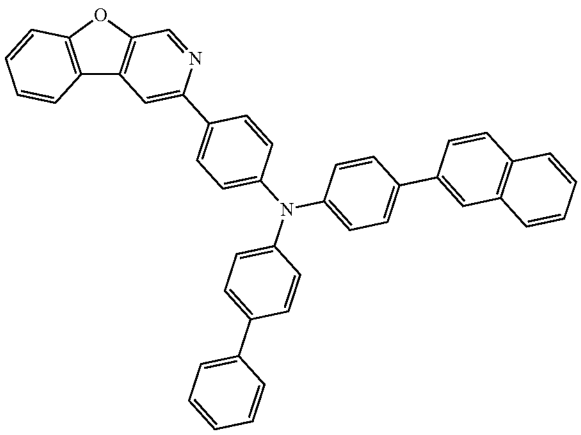
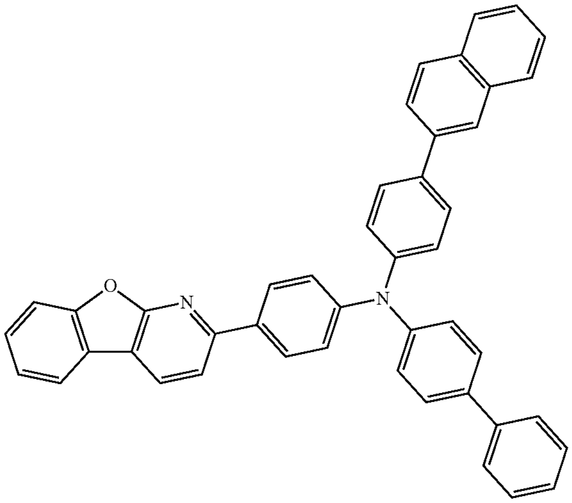

-continued
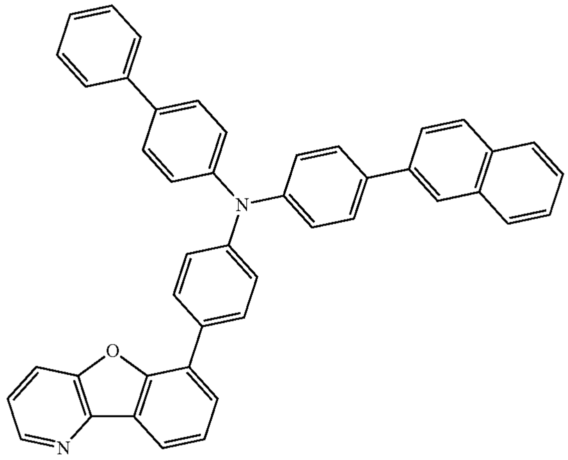
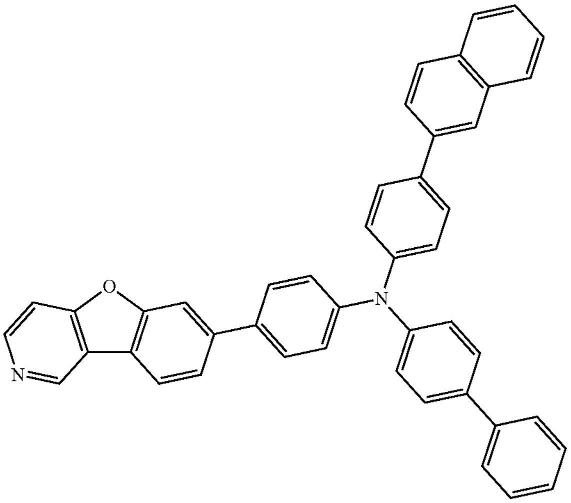
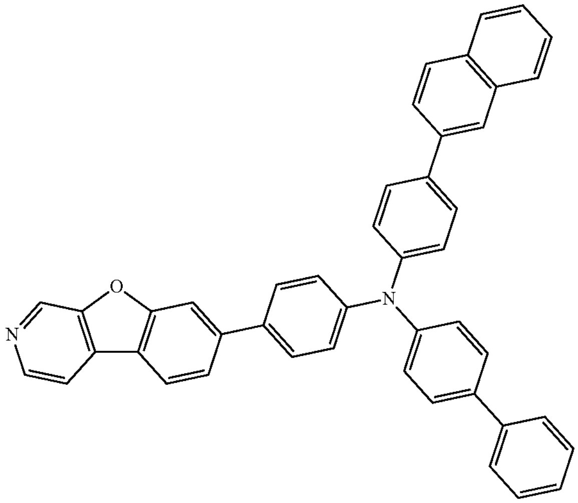
-continued
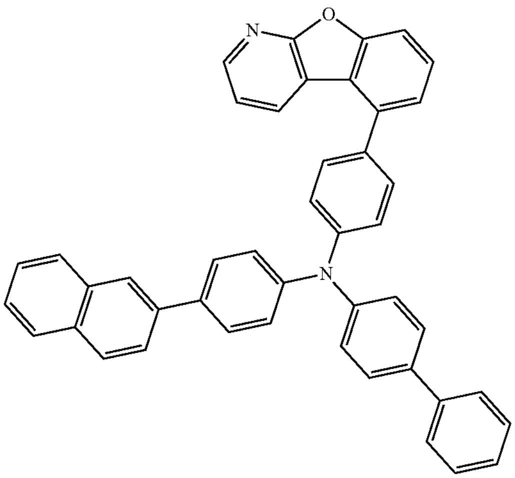
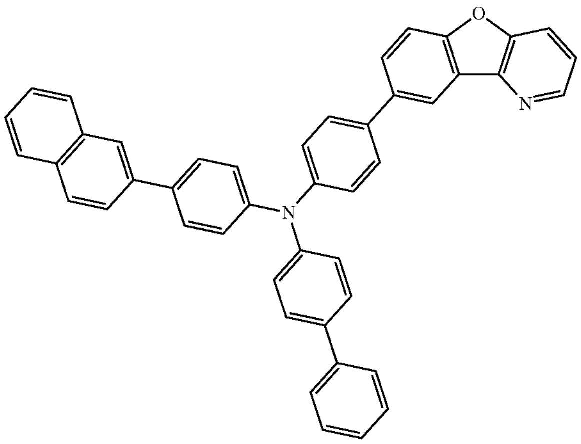
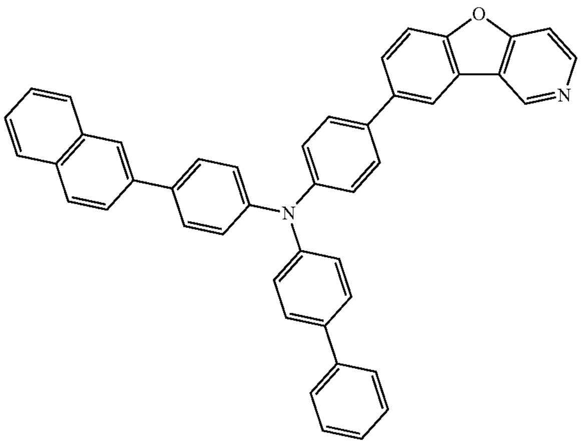

-continued
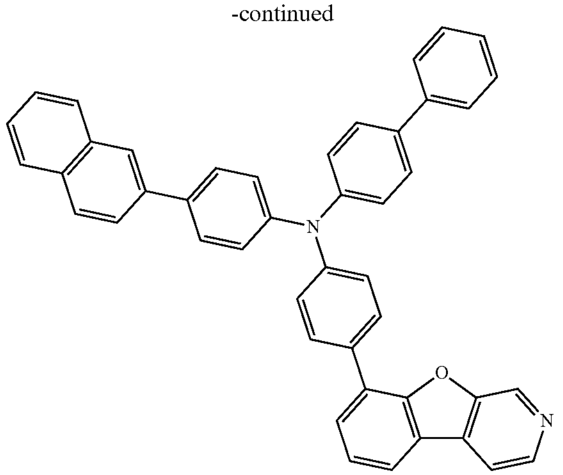
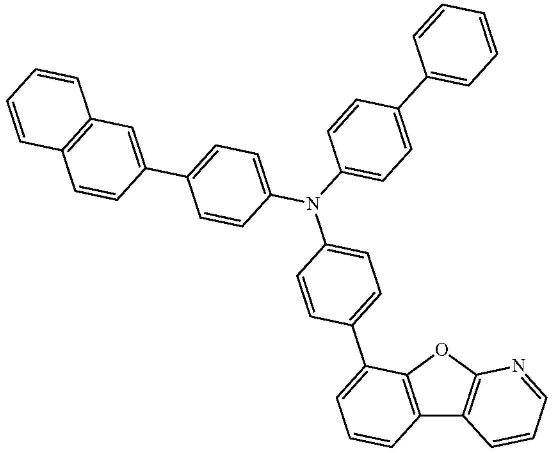
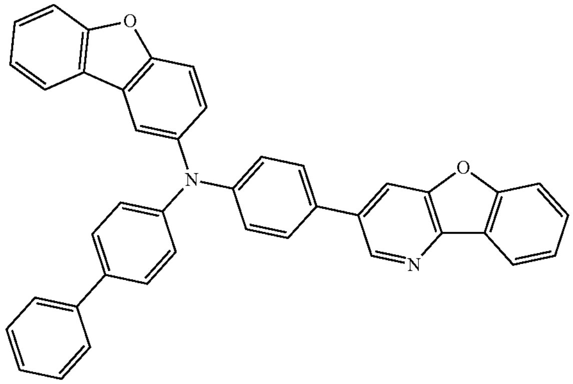
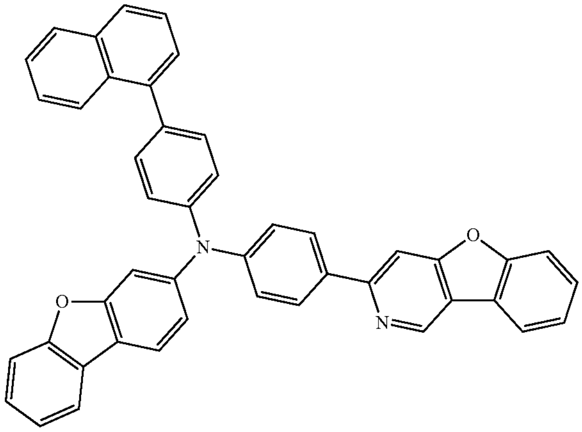
-continued
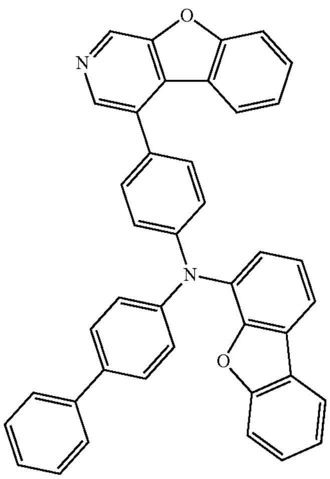
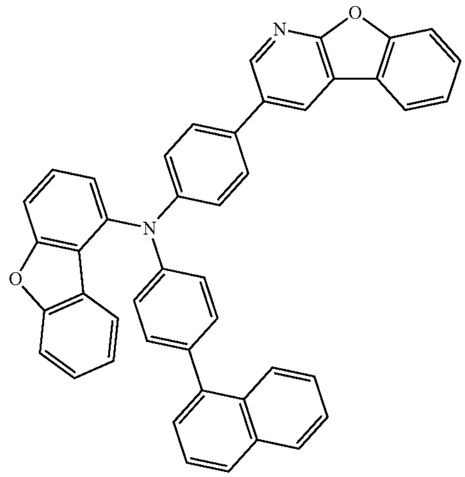
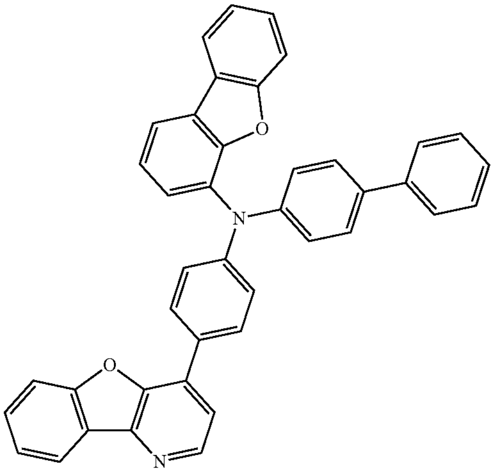

-continued
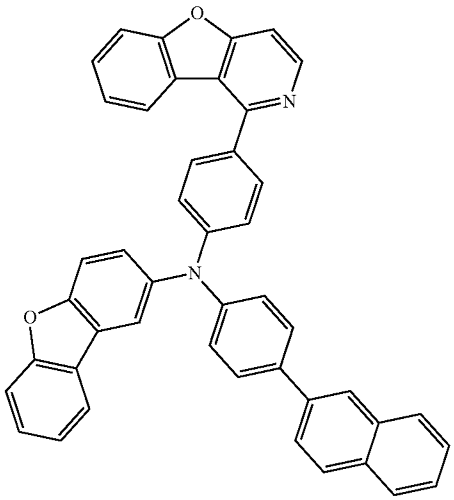
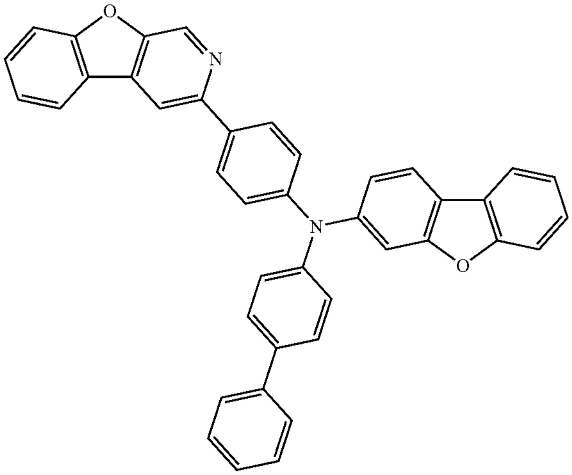
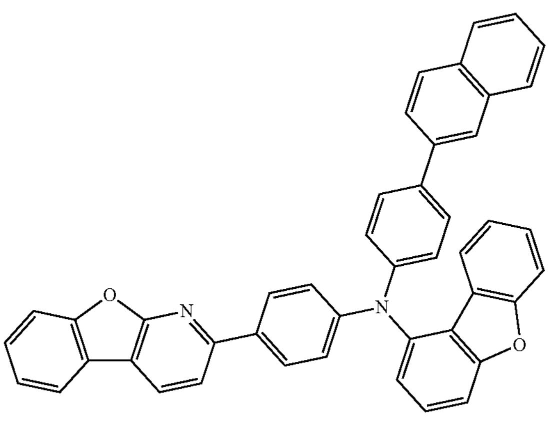
-continued
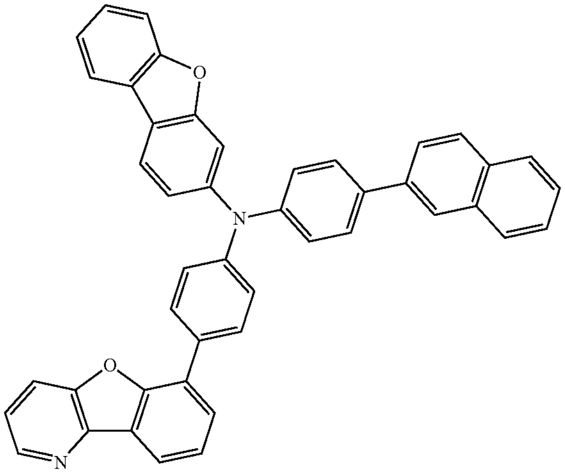
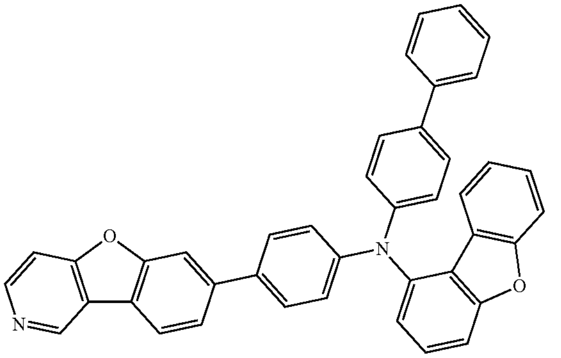
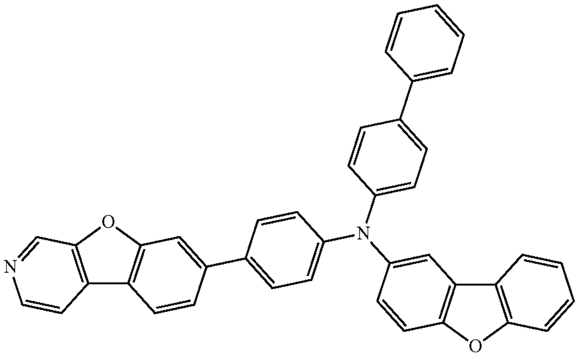
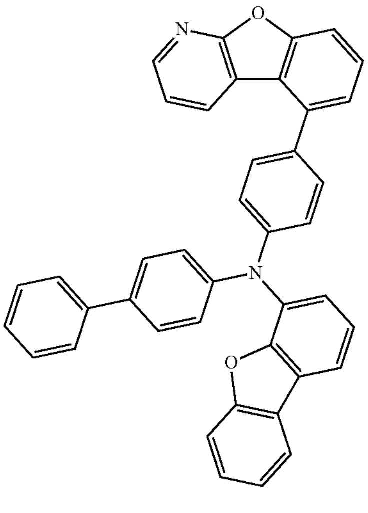

-continued
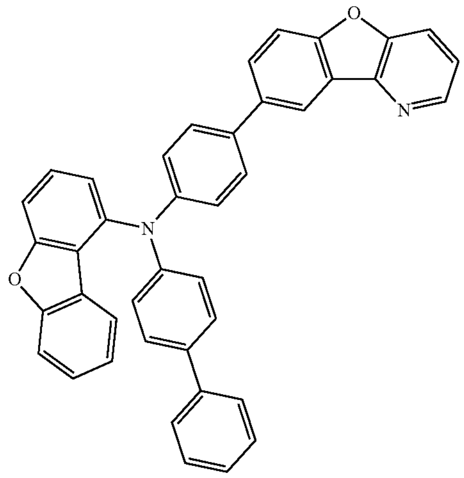
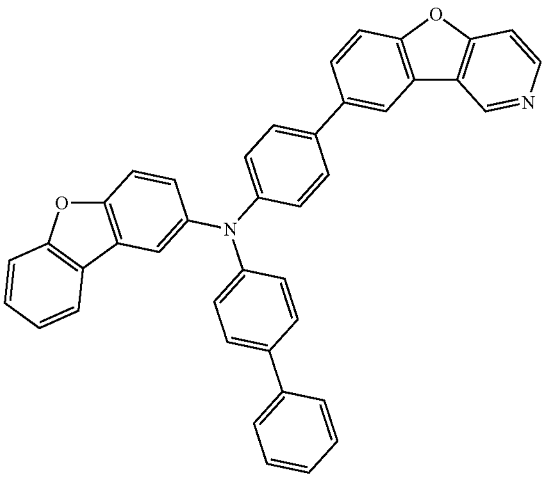
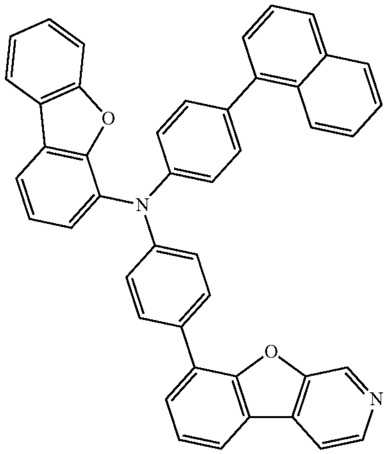
-continued
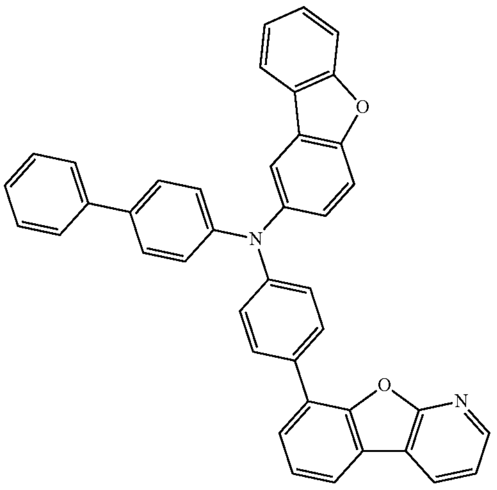
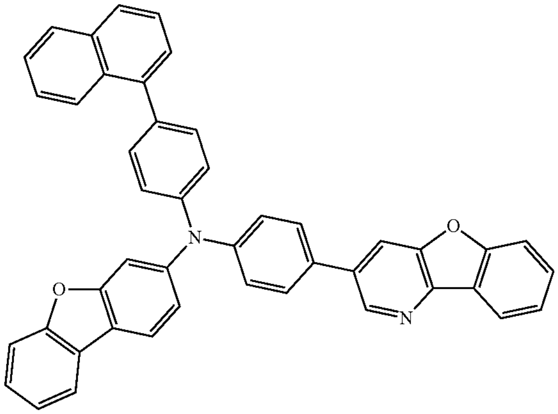
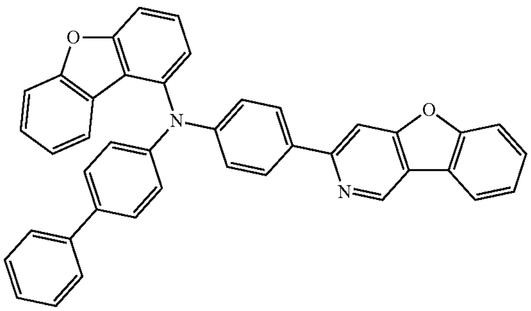

-continued
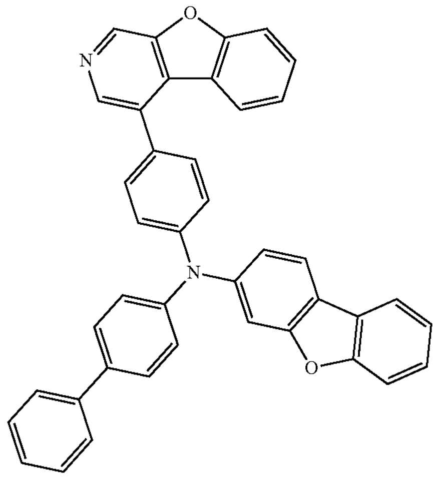
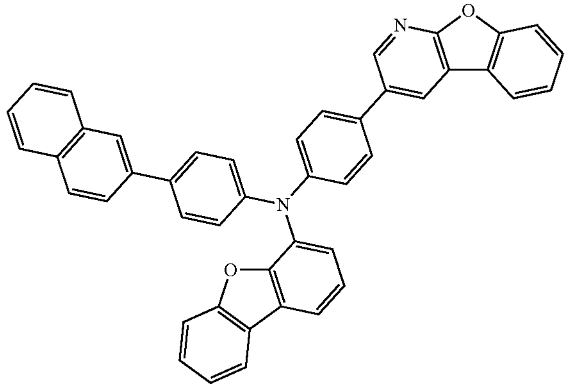
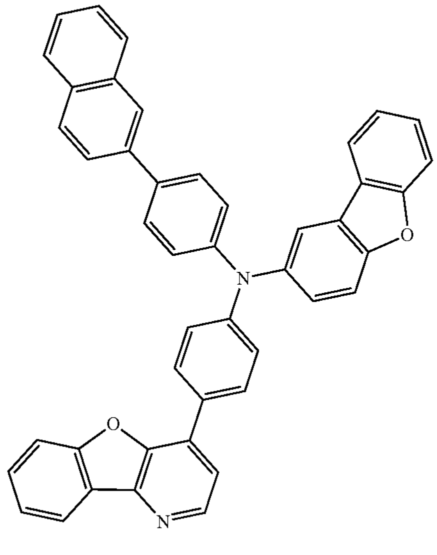
-continued
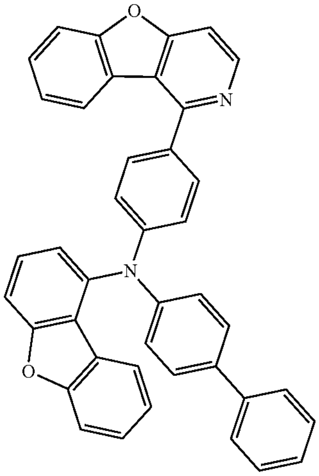
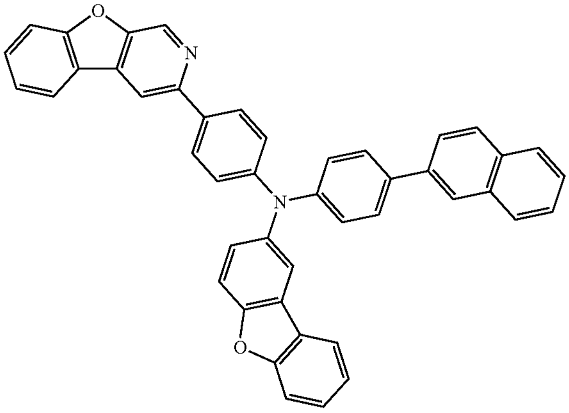
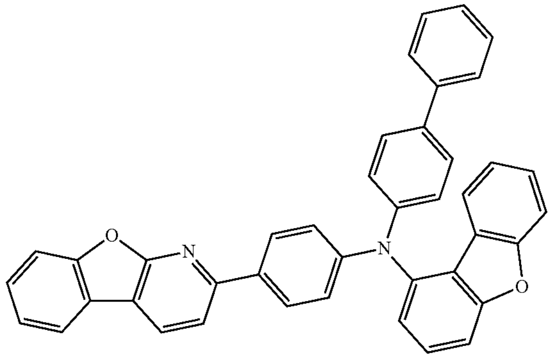
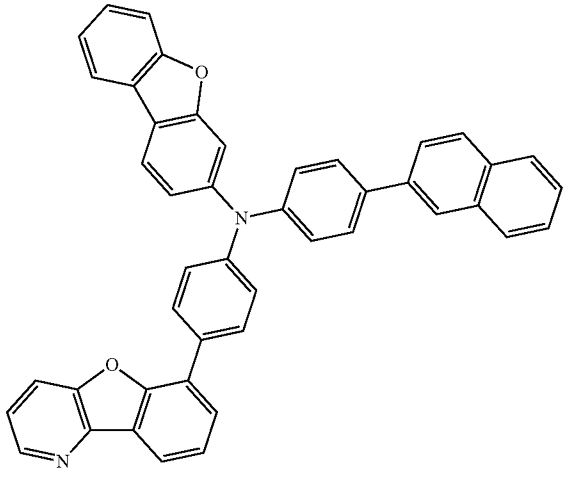

-continued
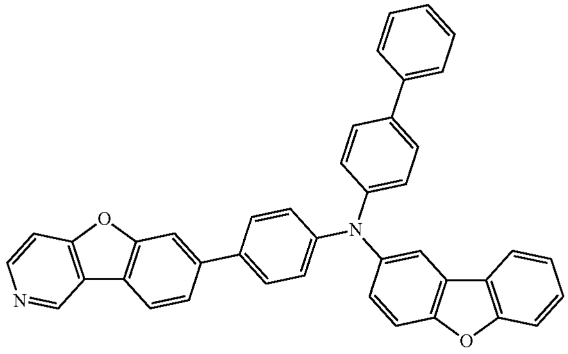
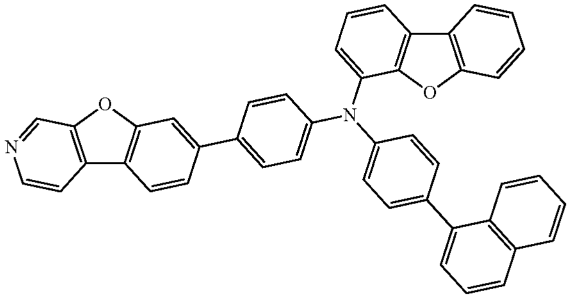
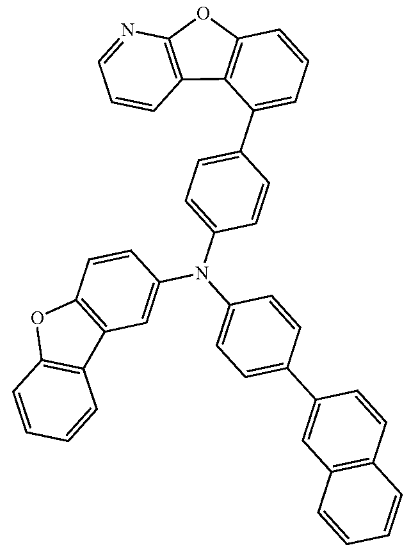
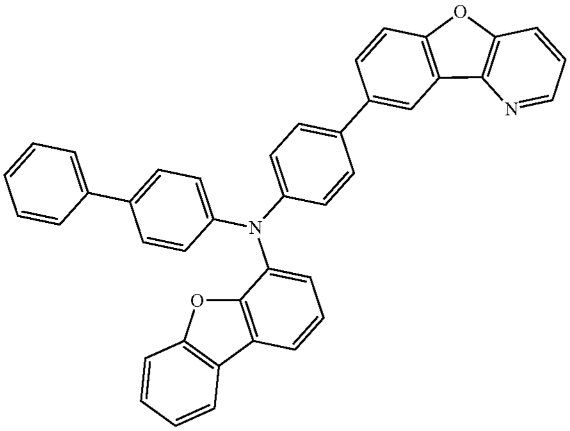
-continued
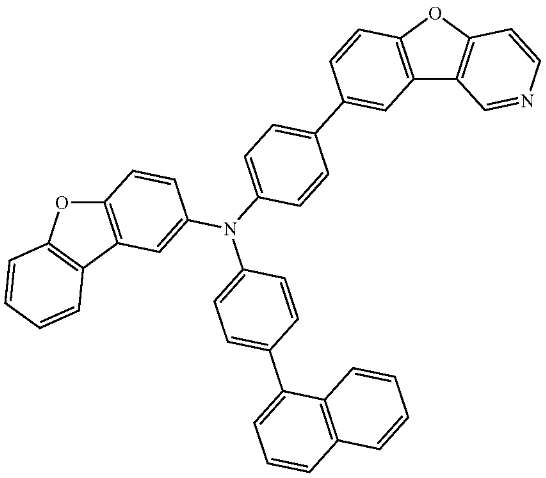
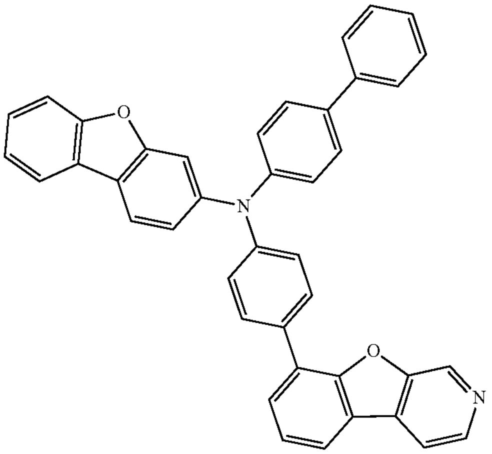
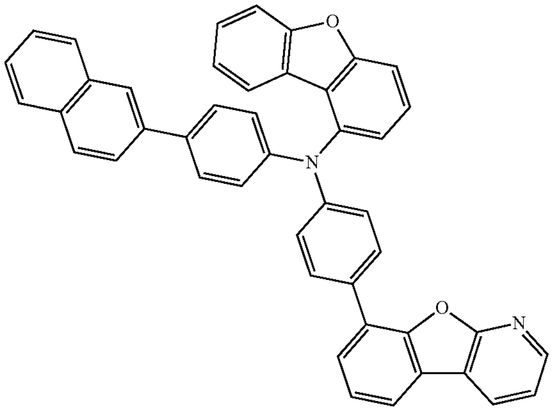
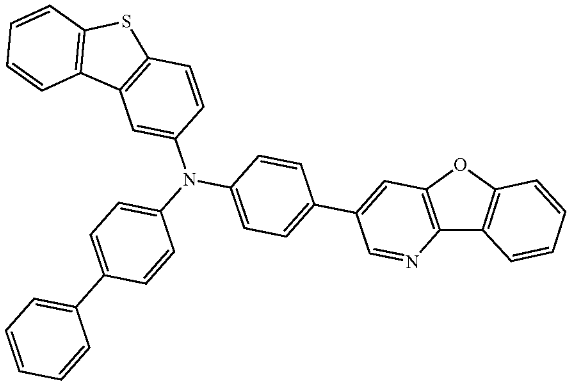

-continued
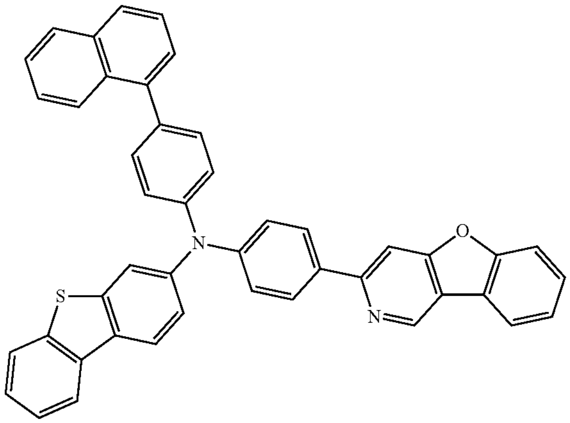
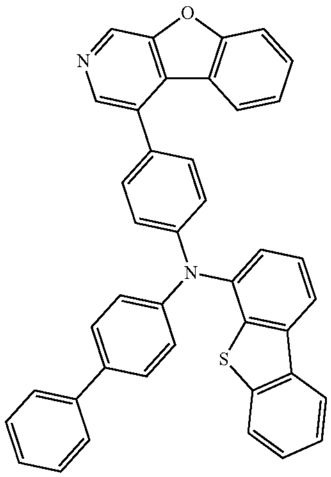
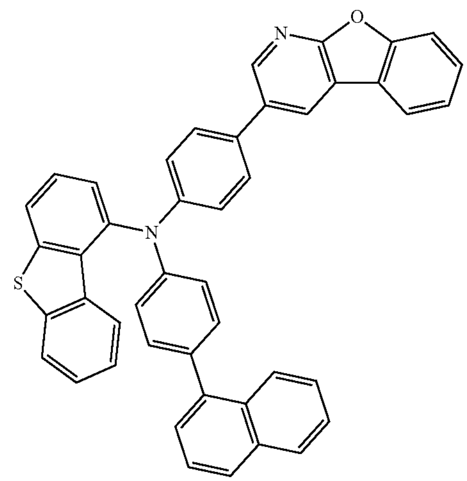
-continued
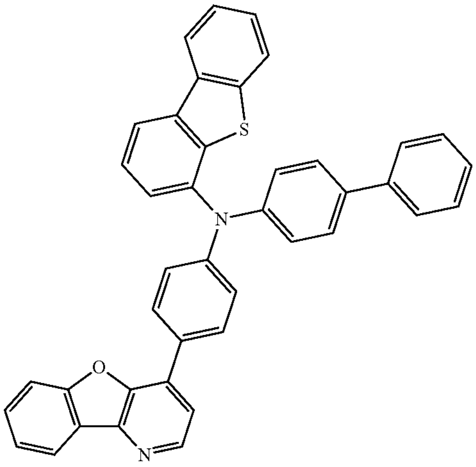
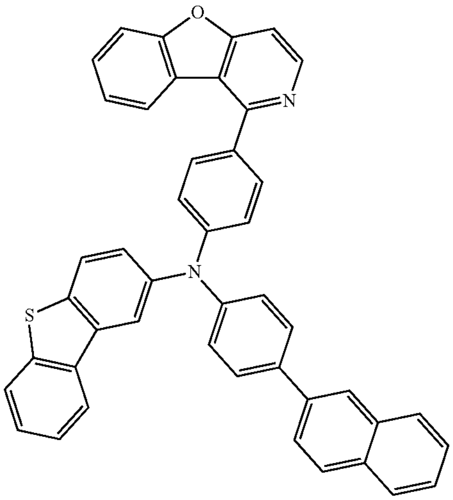
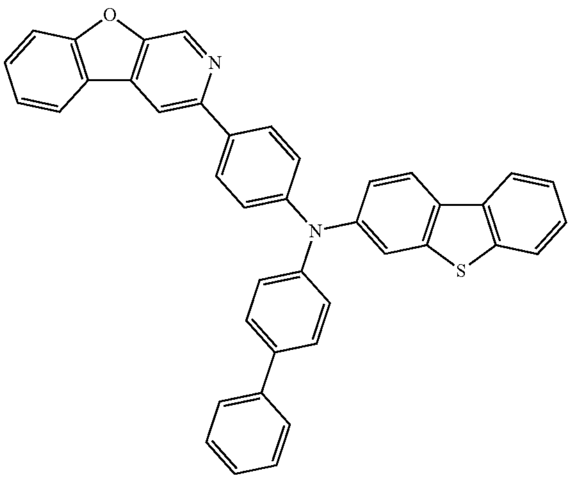

-continued
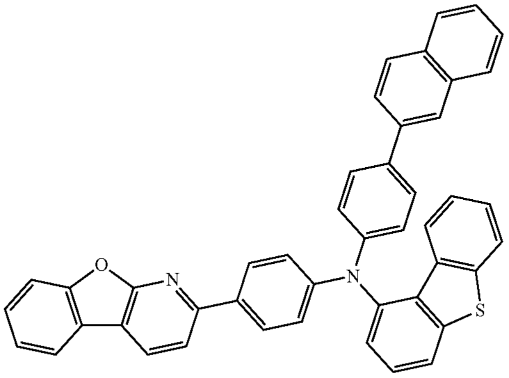
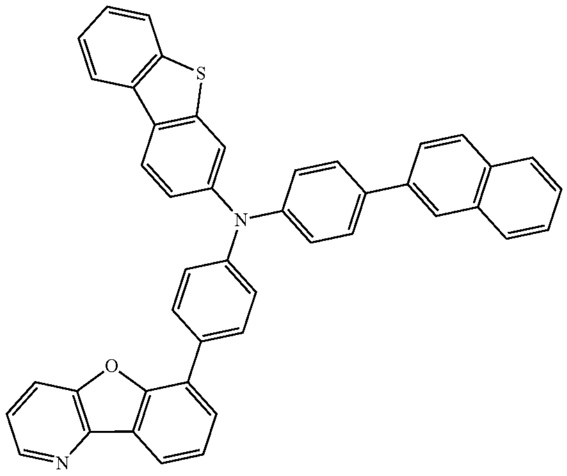
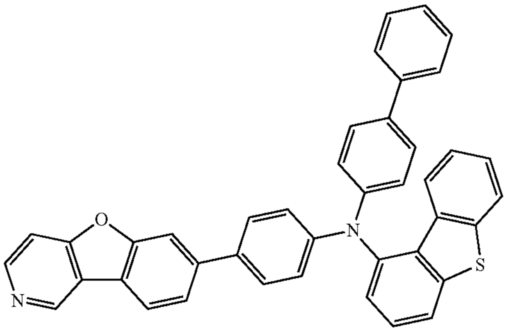
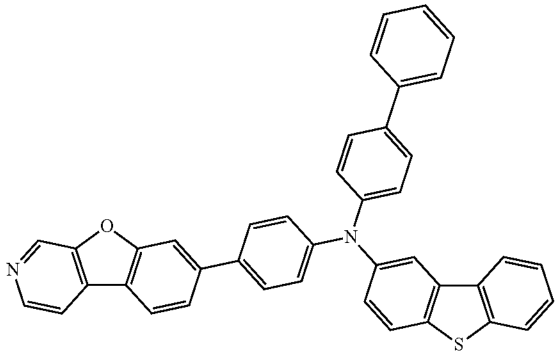
-continued
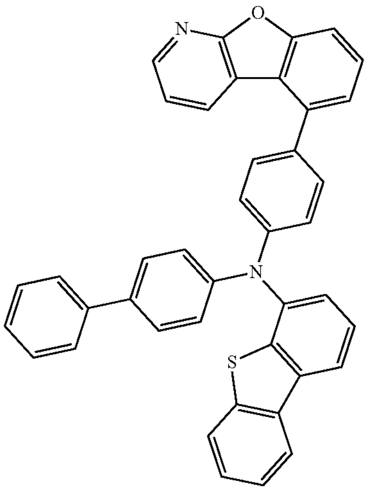
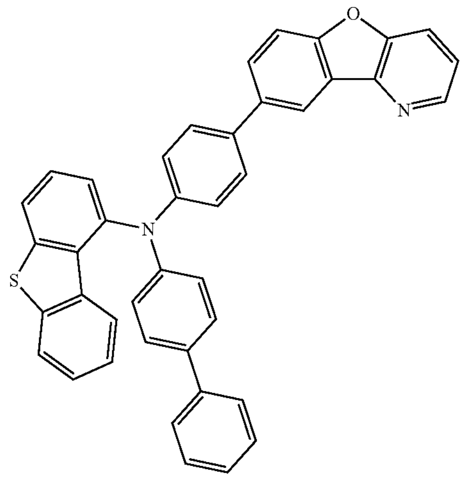
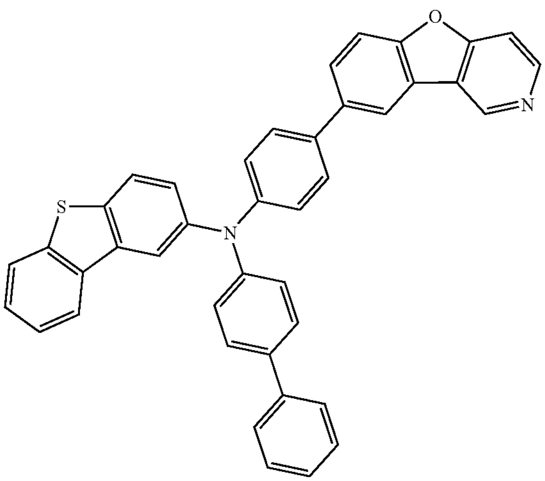

-continued
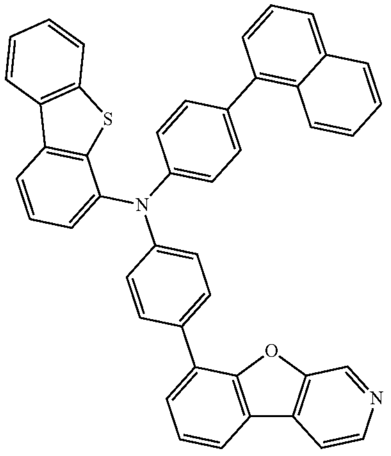
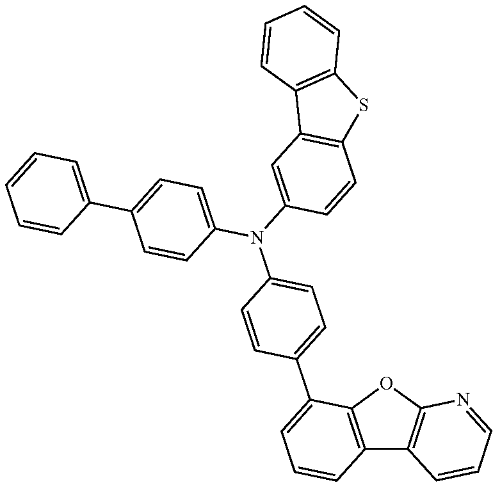
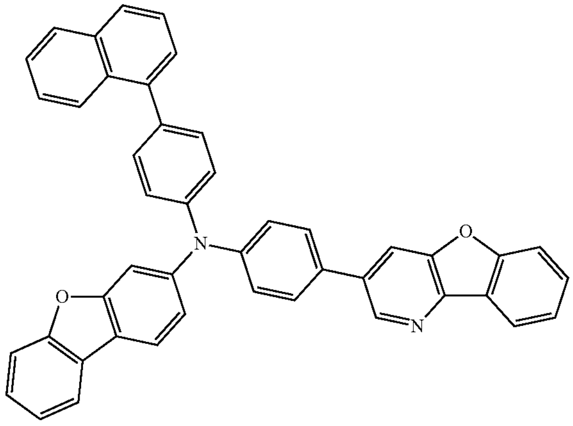
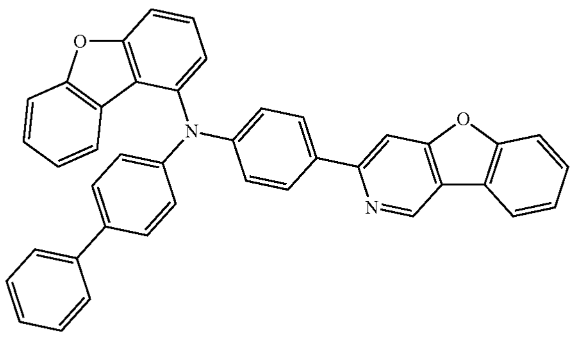
-continued
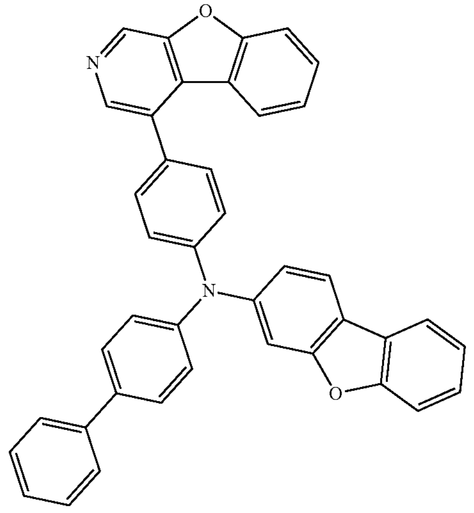
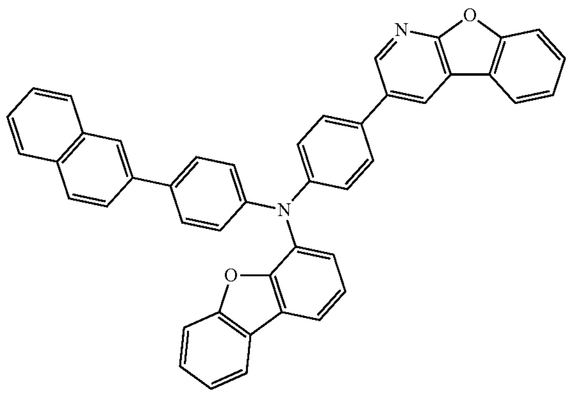
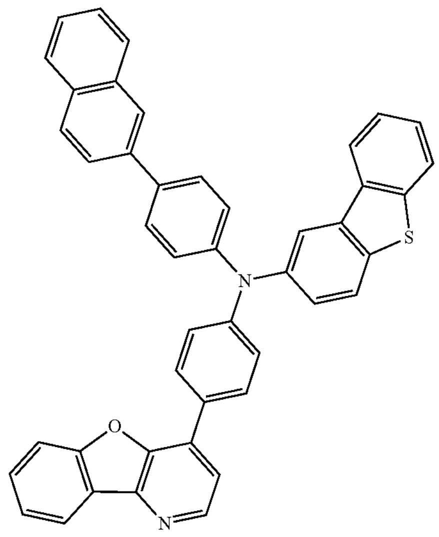

-continued
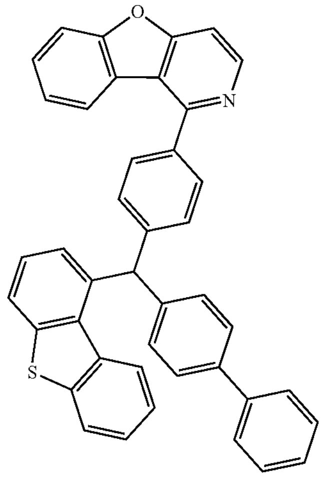
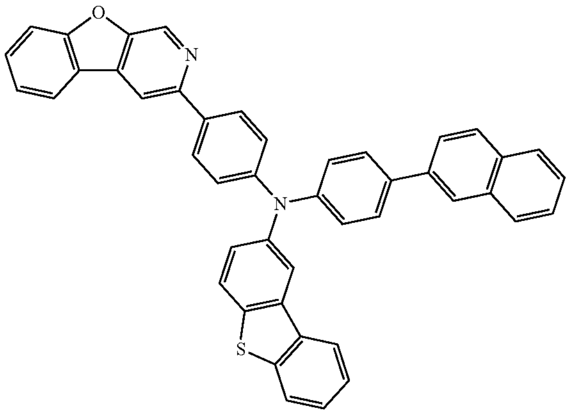
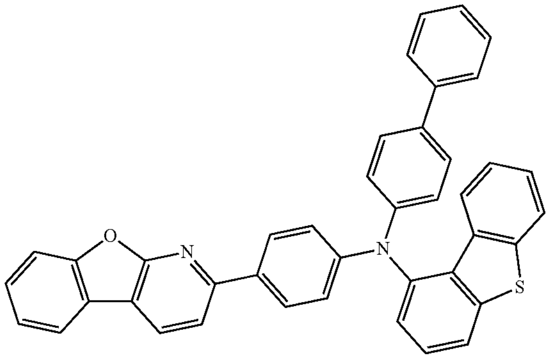
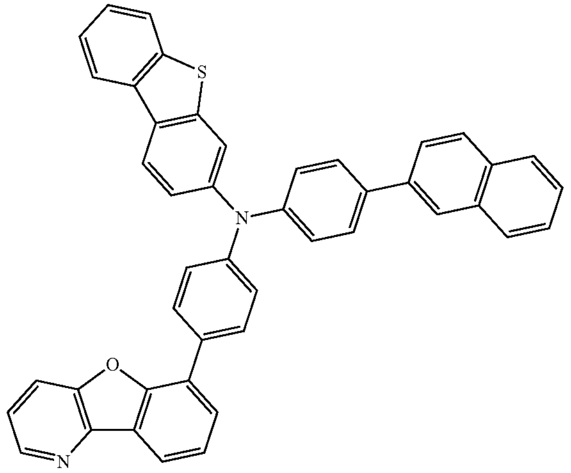
-continued
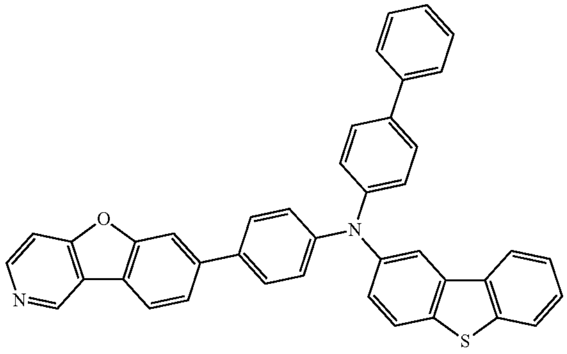
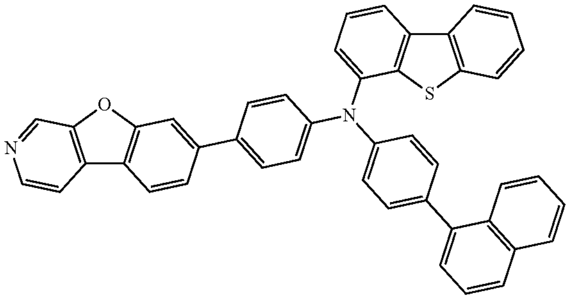
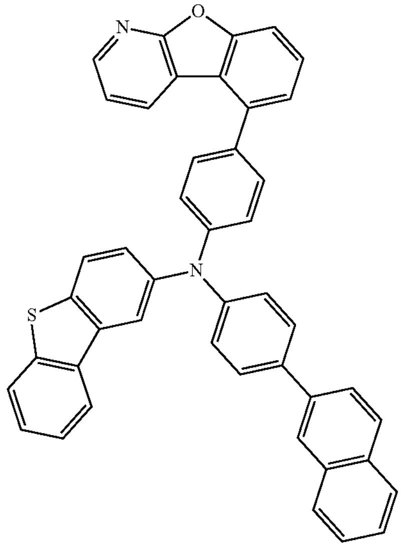
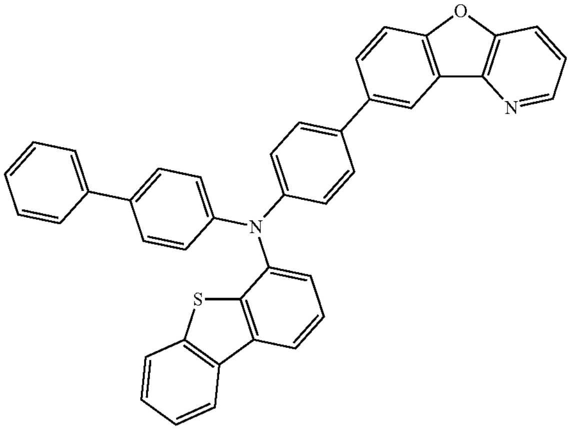

-continued
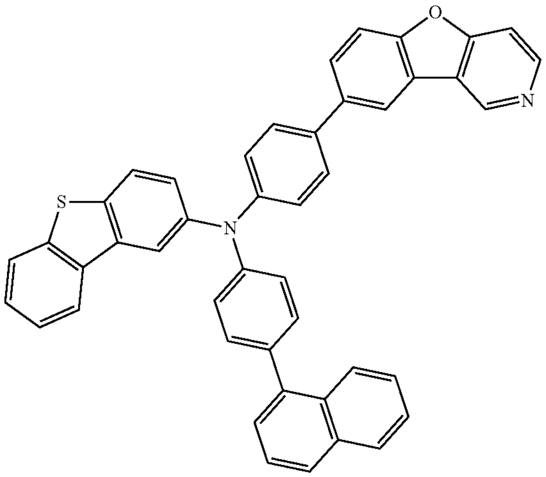
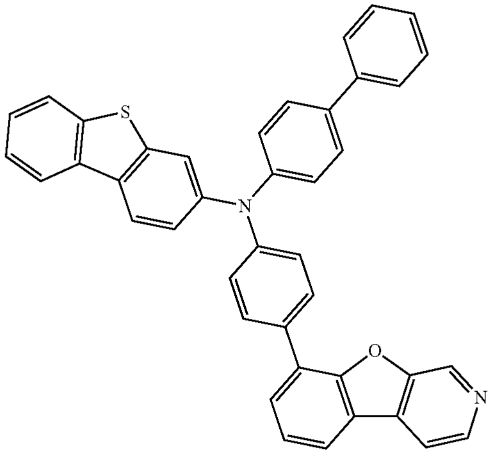
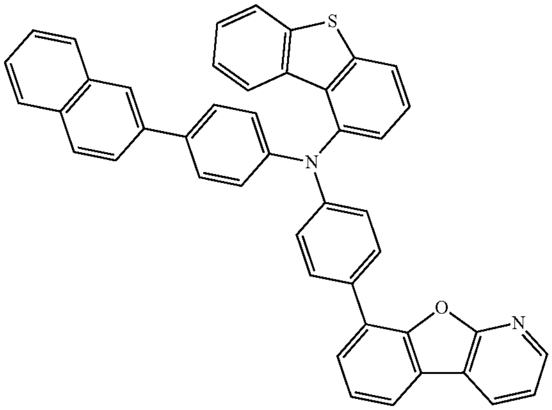
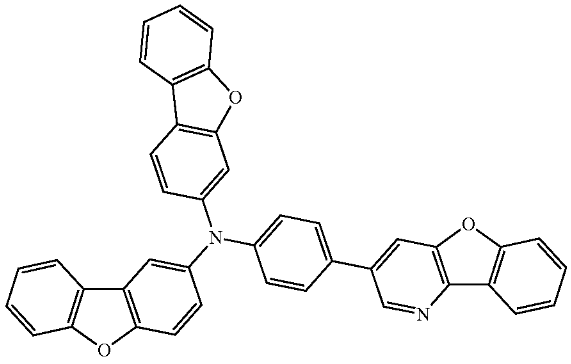
-continued
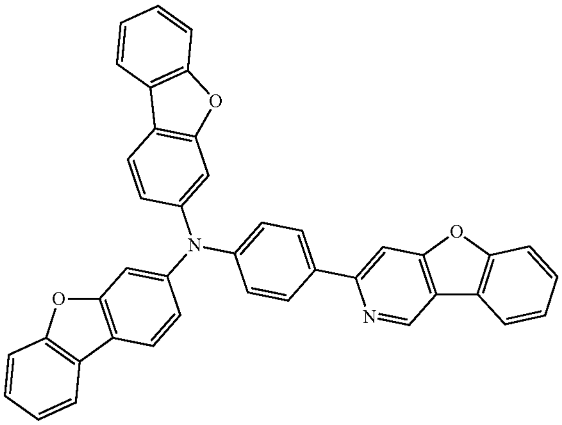
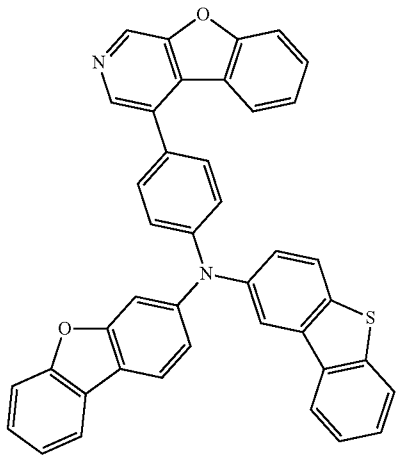
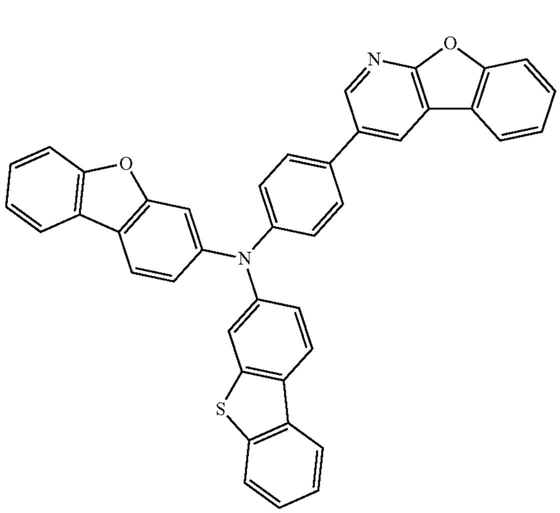

-continued
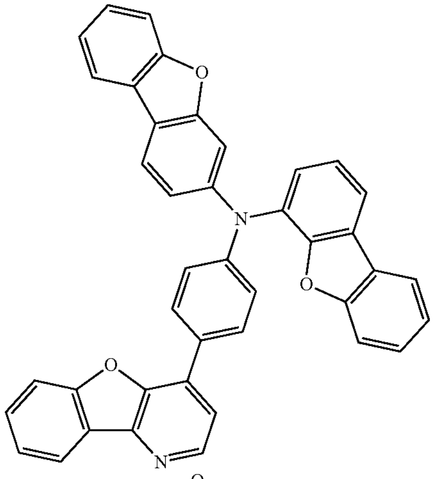
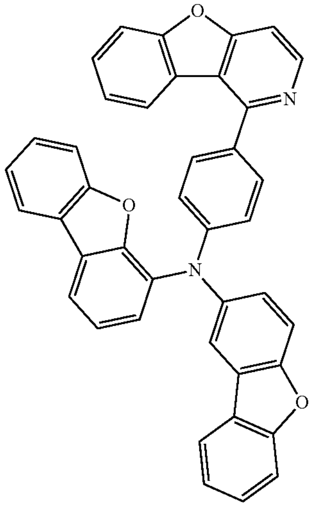
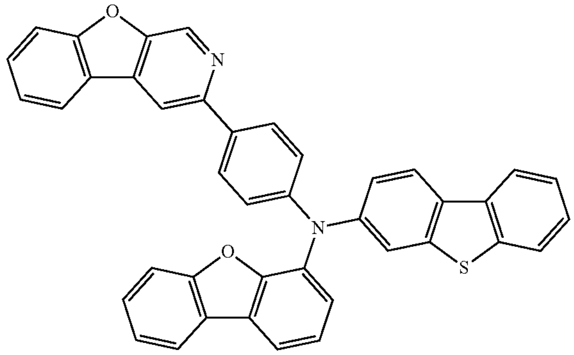
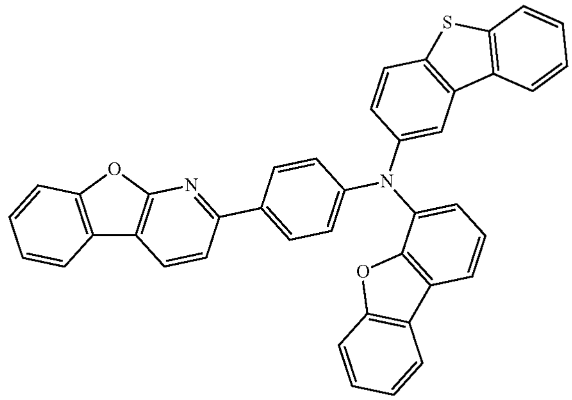
-continued
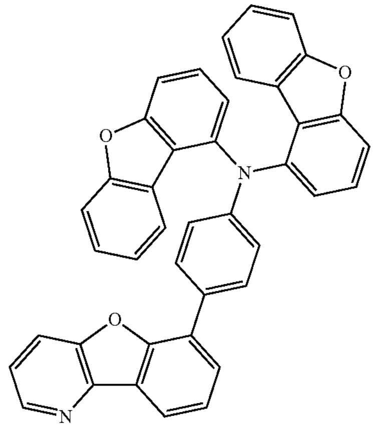
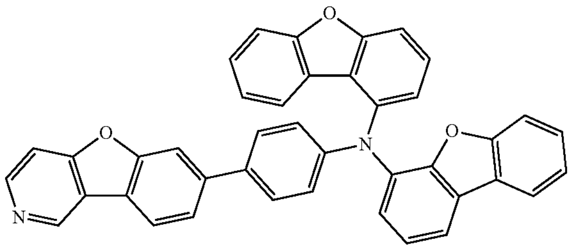
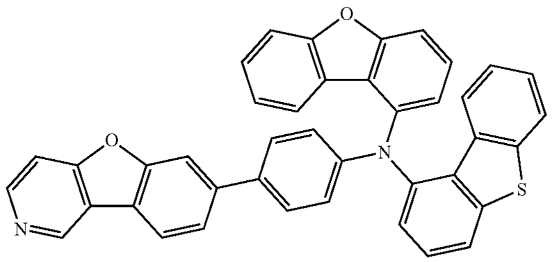
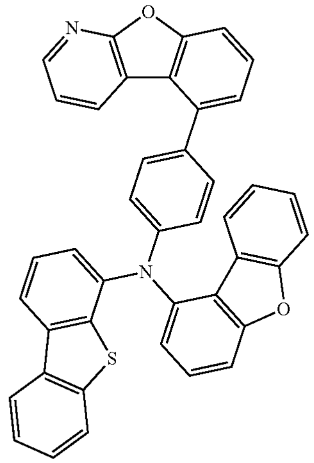

-continued
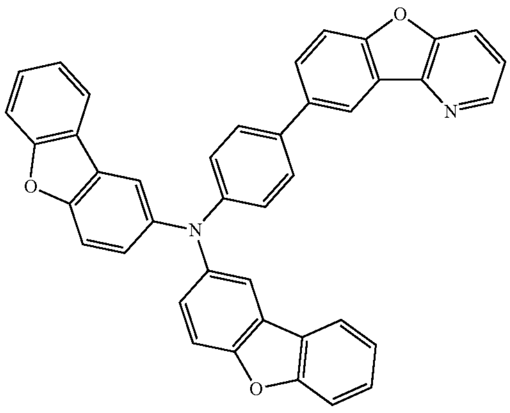
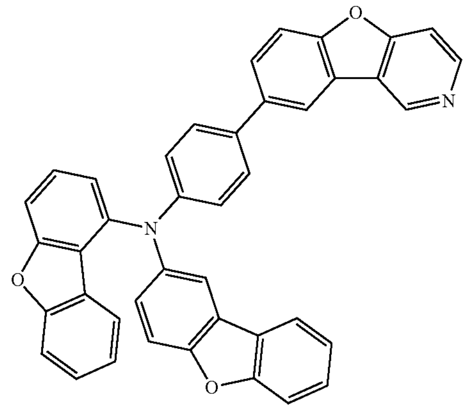
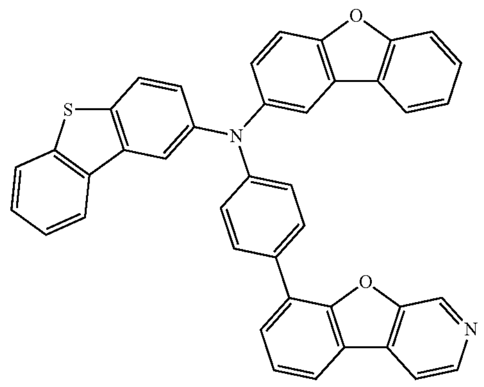
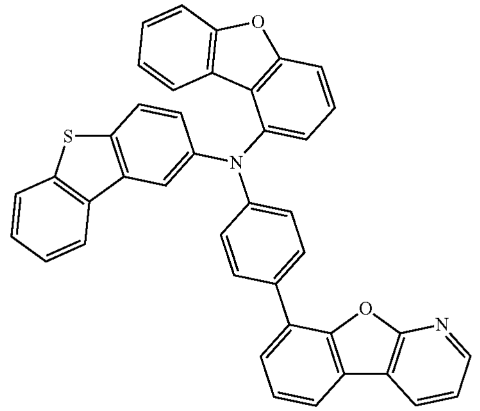
-continued
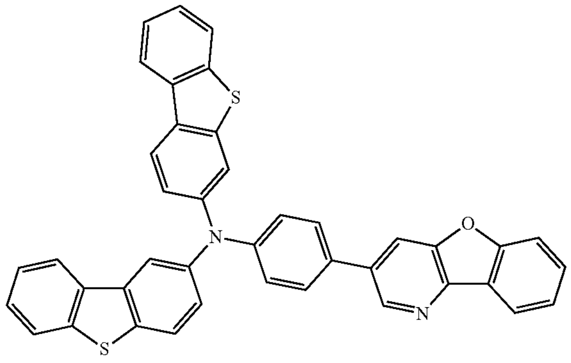
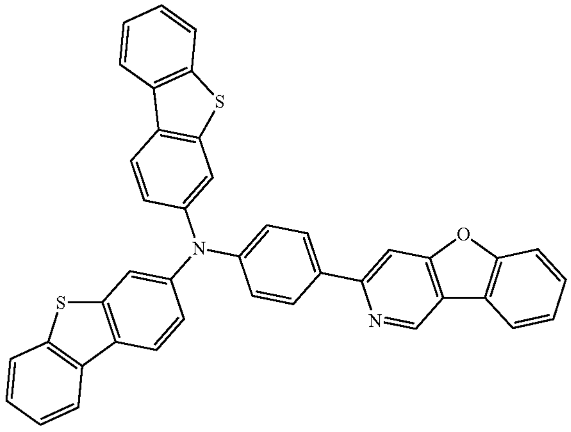
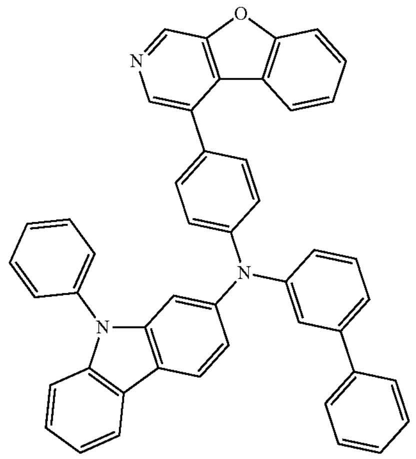
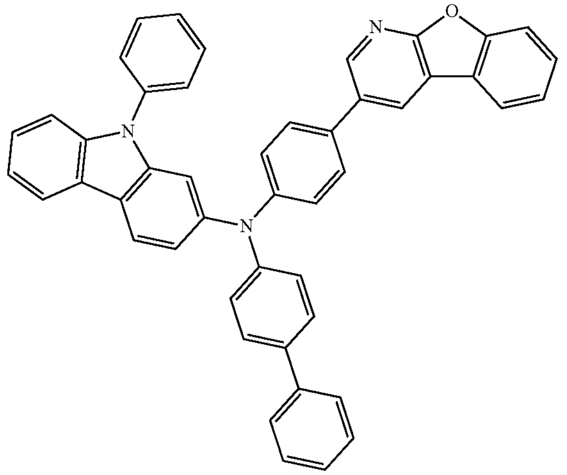

-continued
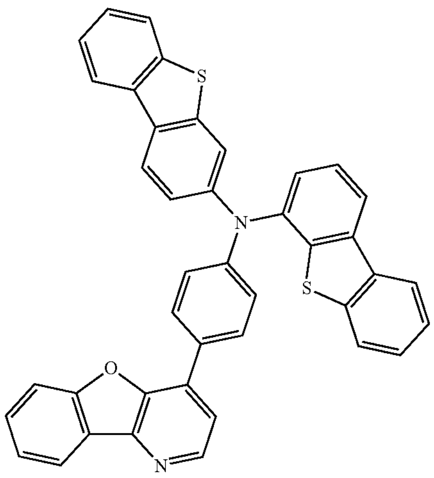
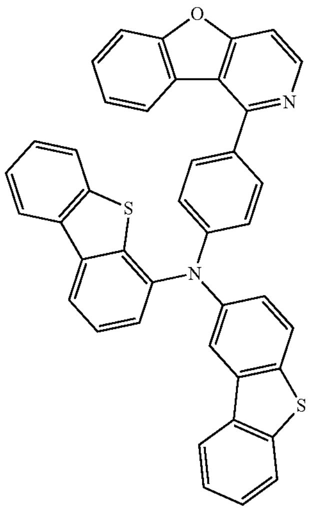
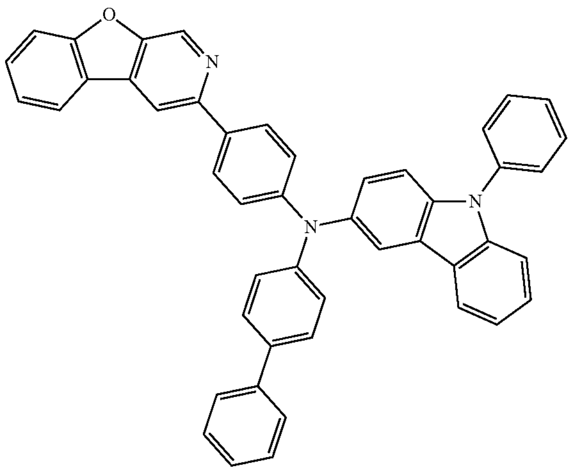
-continued
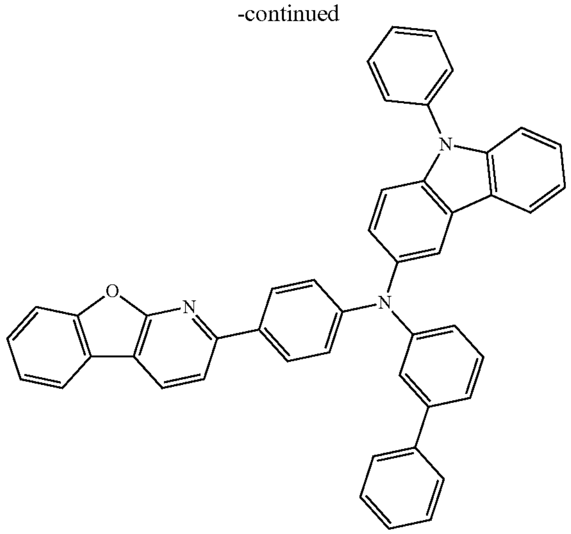
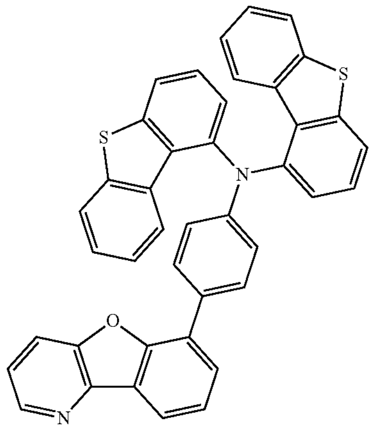
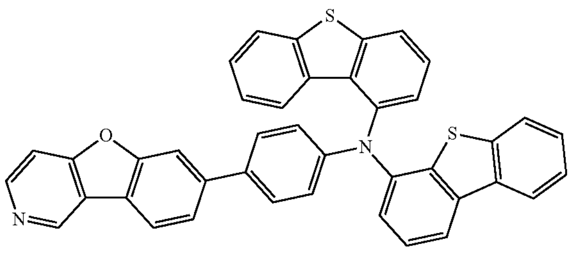
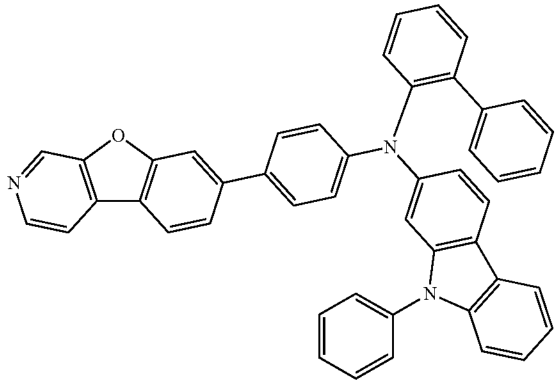

-continued
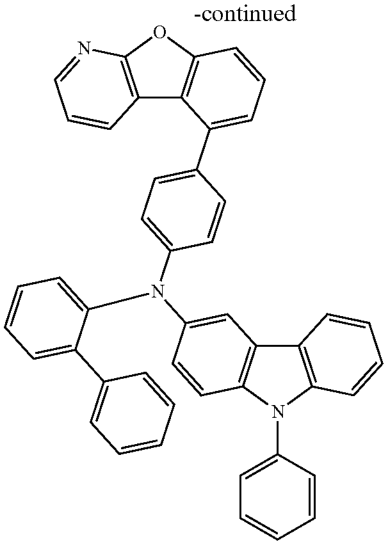
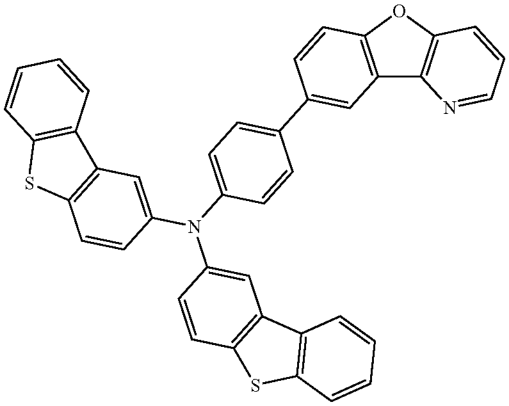
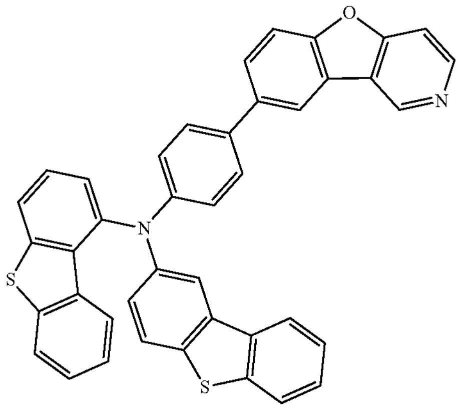
-continued
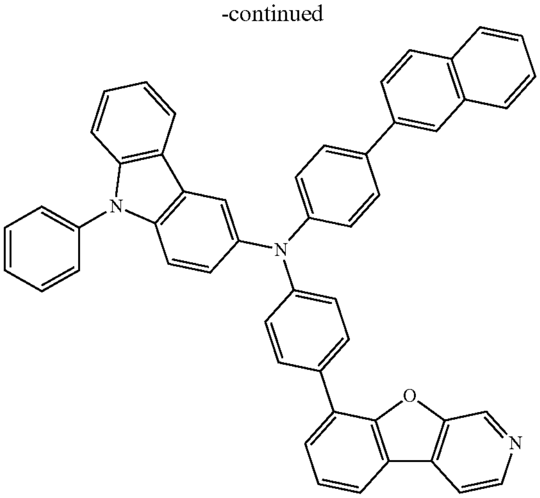
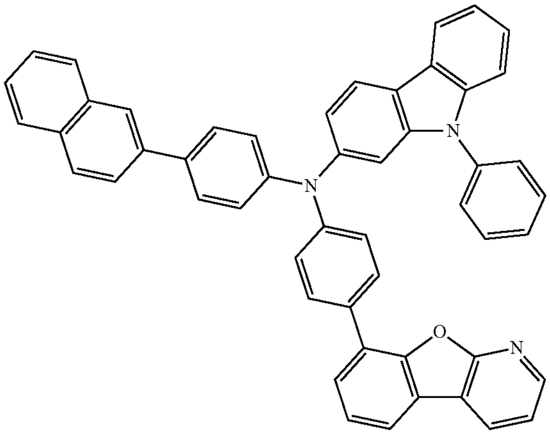
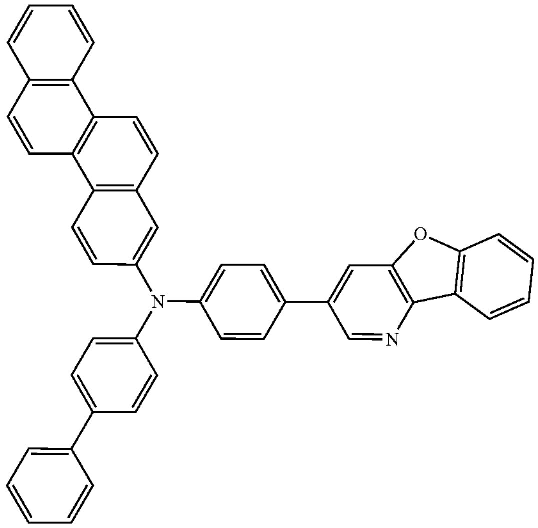

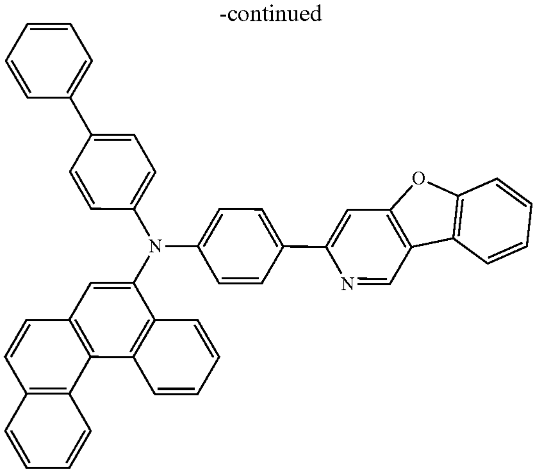
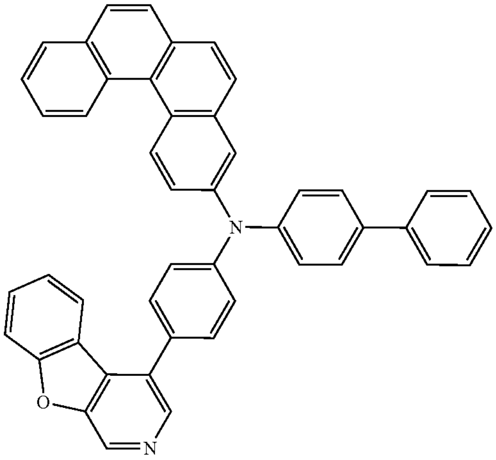
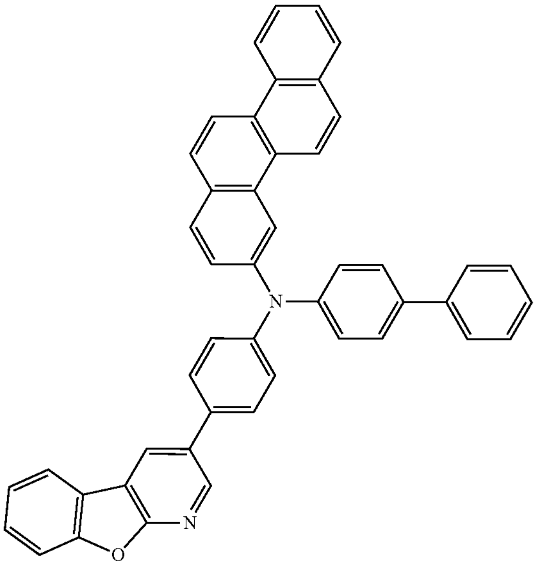
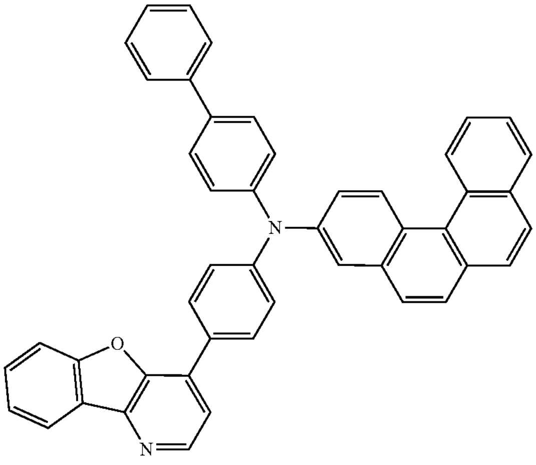
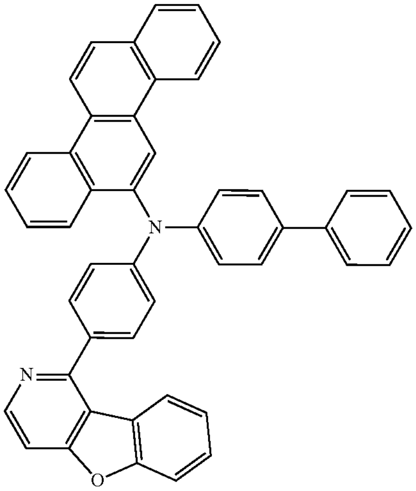
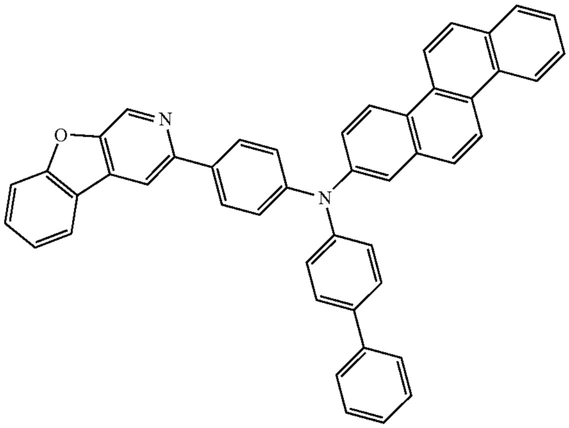

-continued
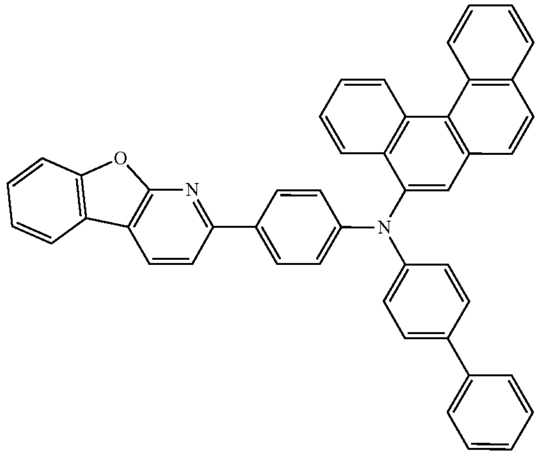
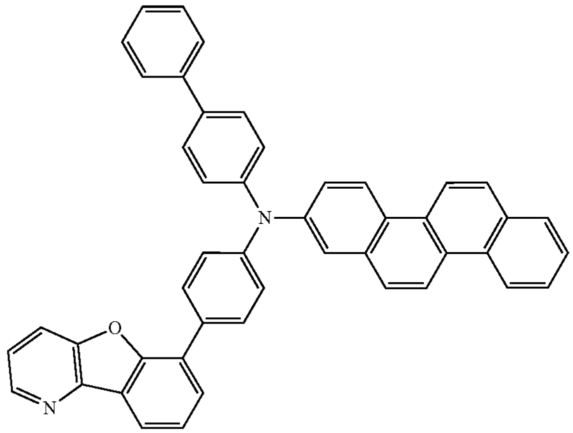
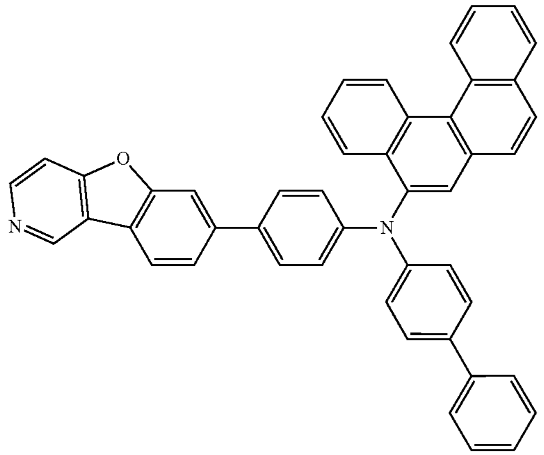
-continued
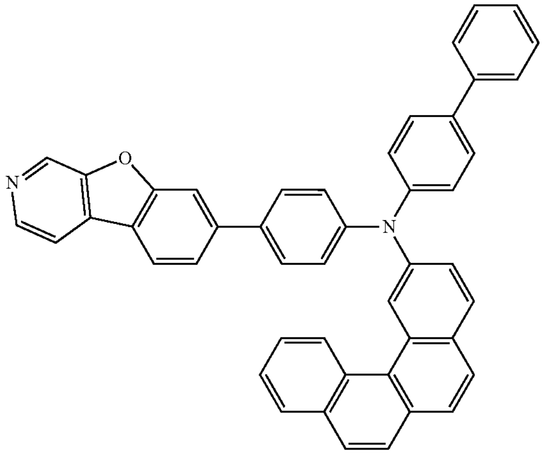
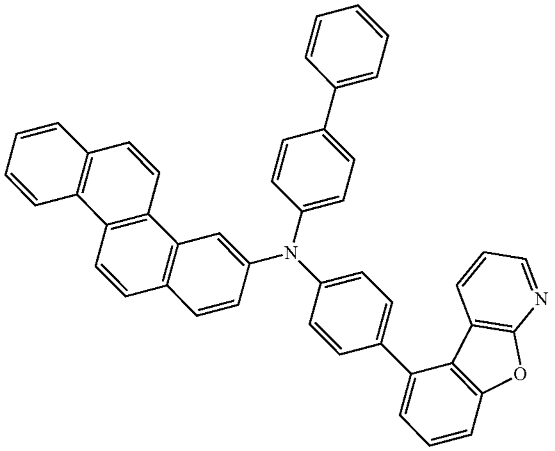
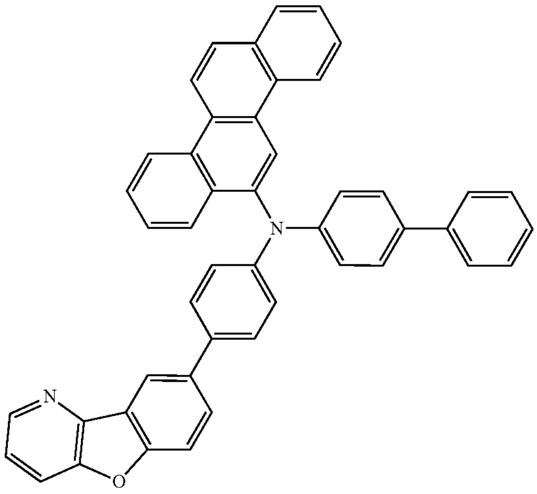

-continued
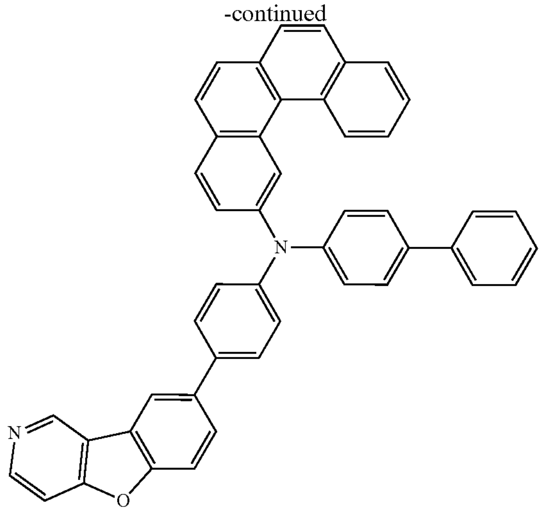
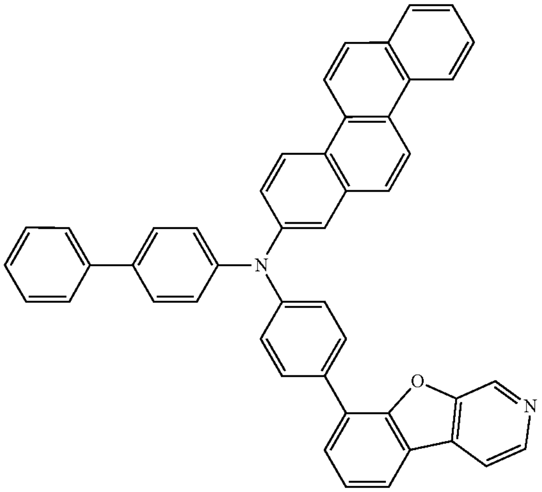
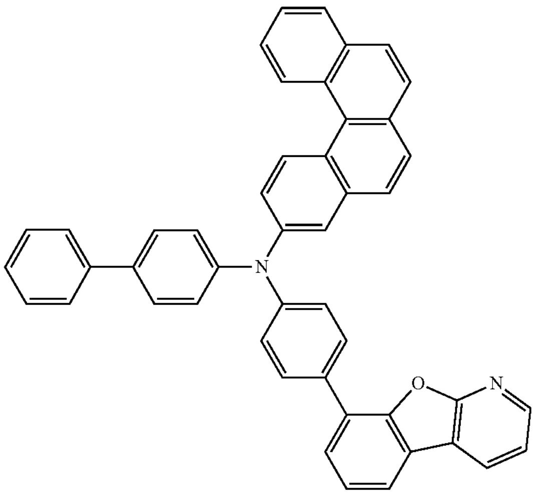
-continued
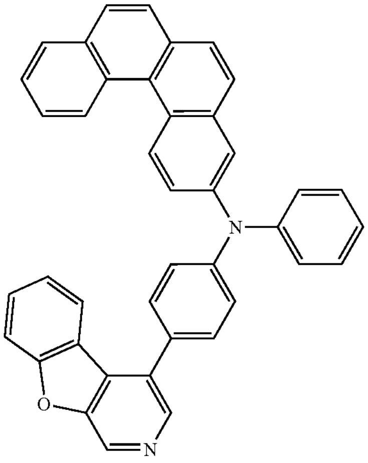
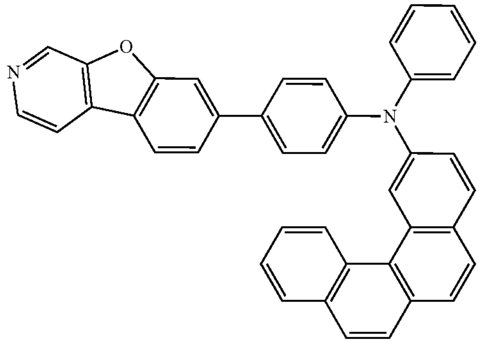
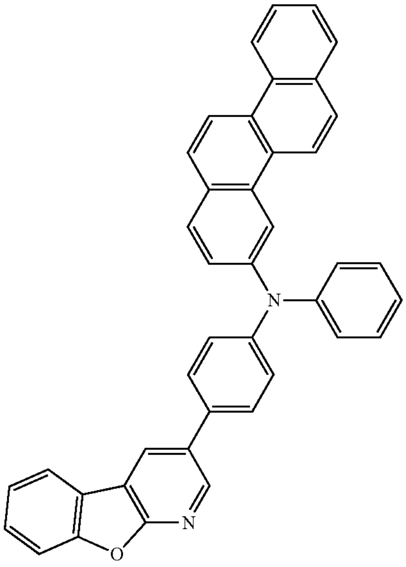
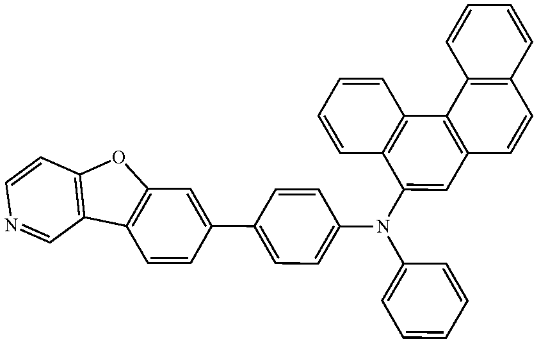

-continued
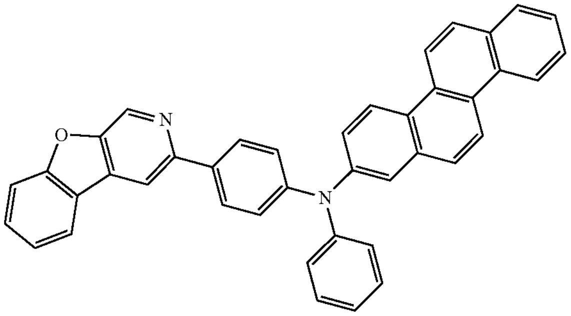
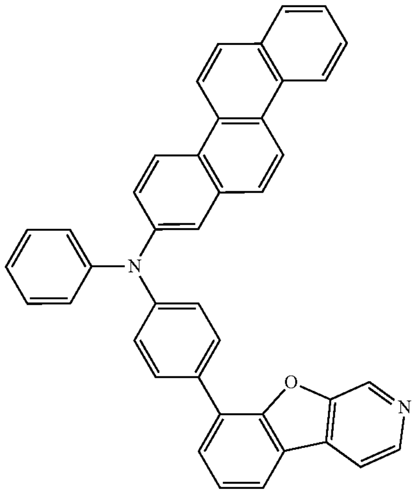
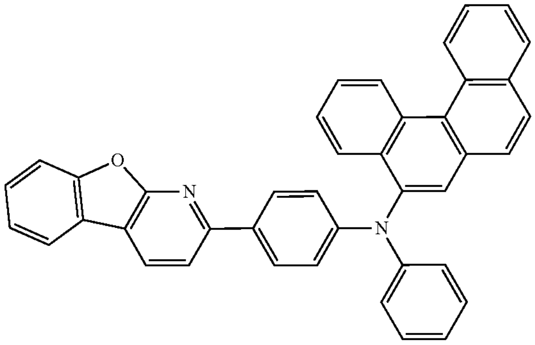
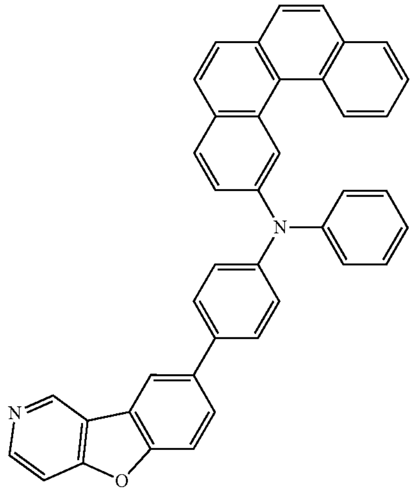
-continued
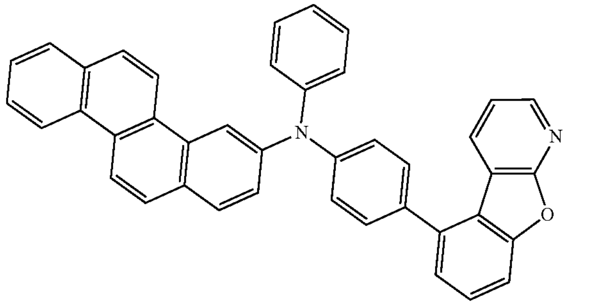
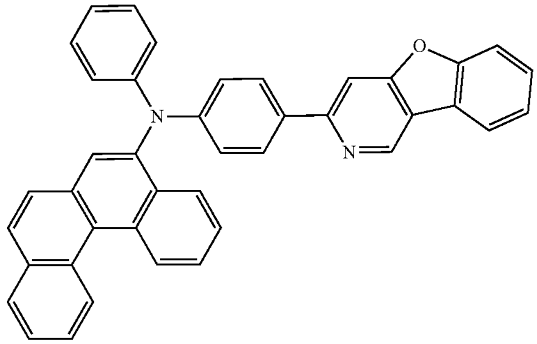
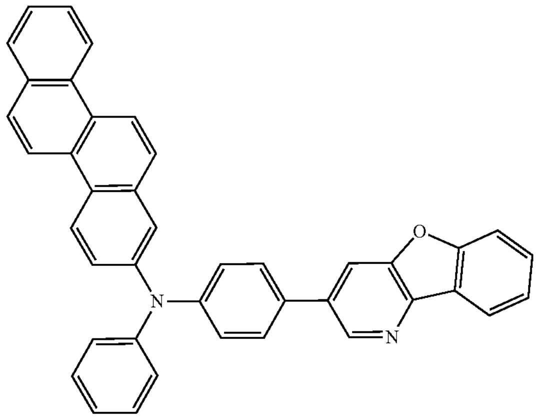
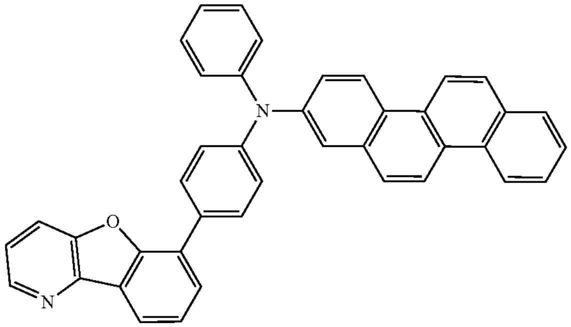

-continued
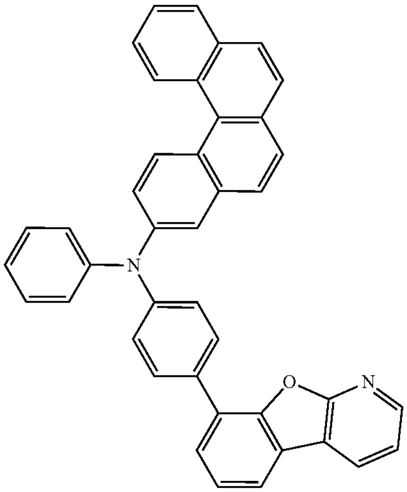
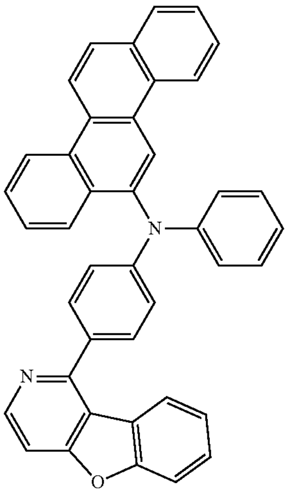
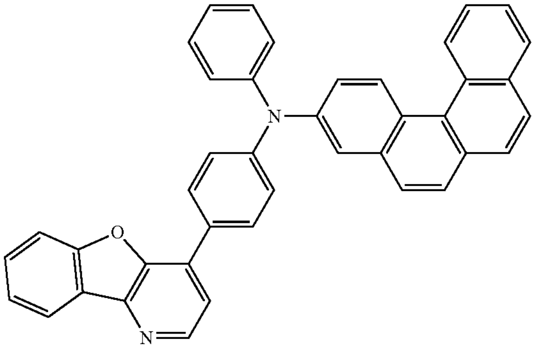
-continued
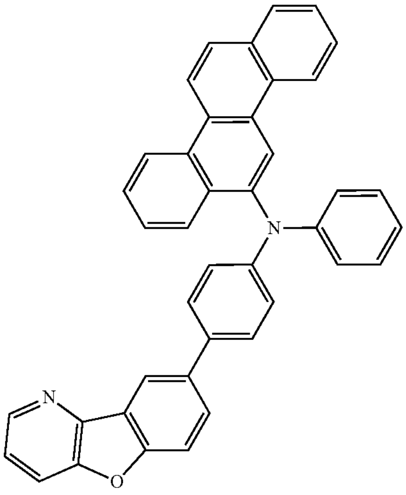
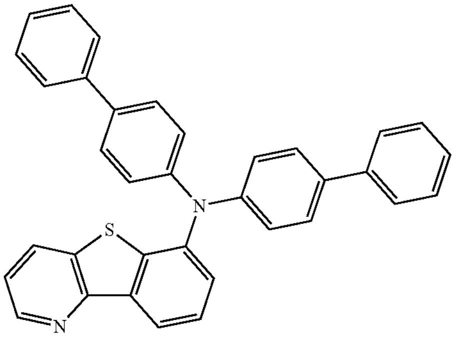
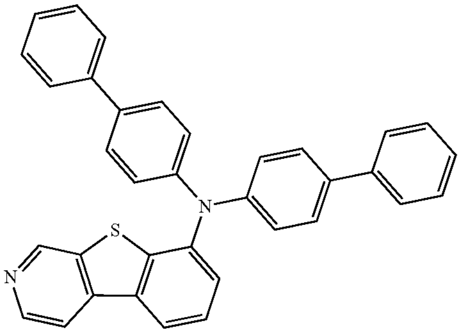
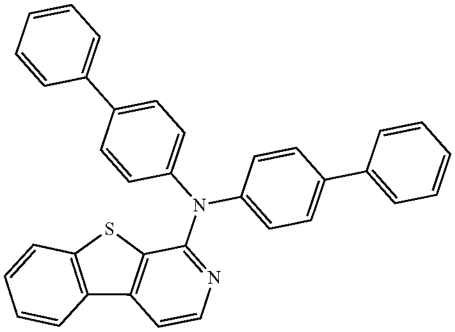

-continued
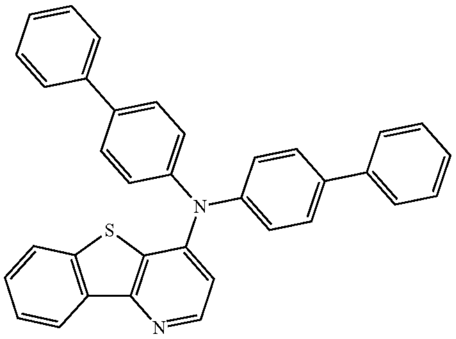
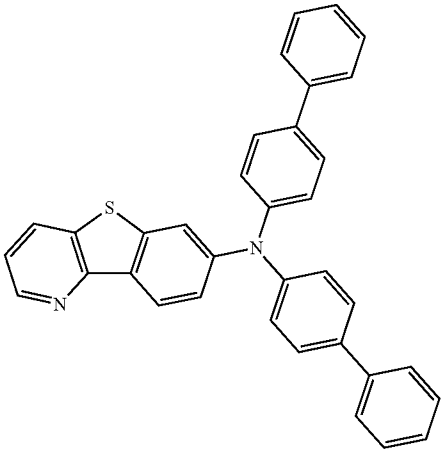
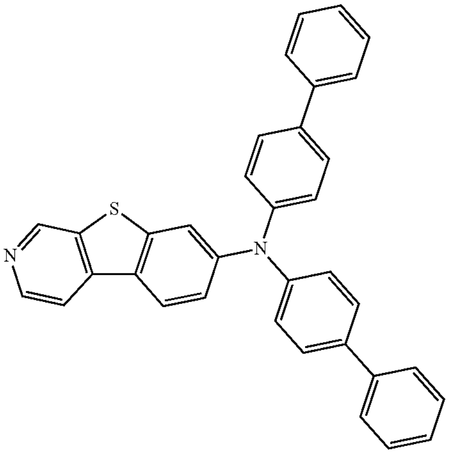
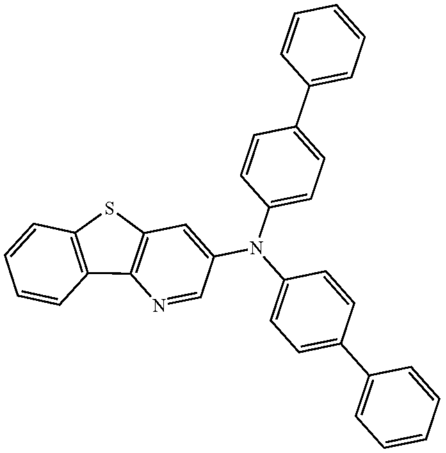
-continued
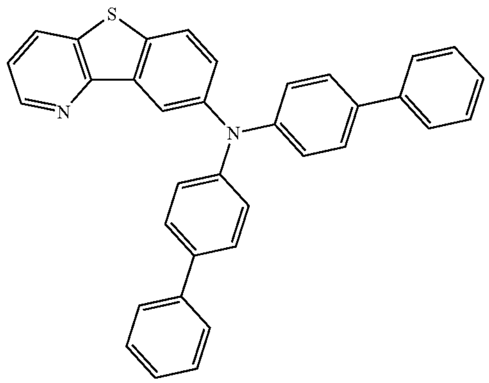
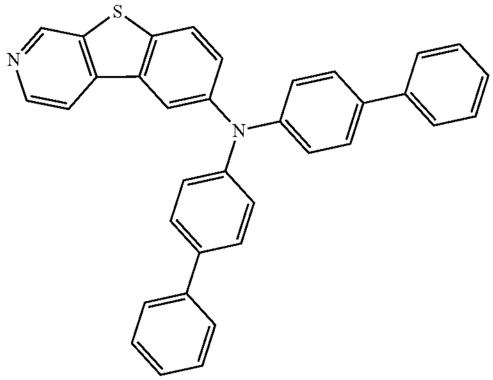
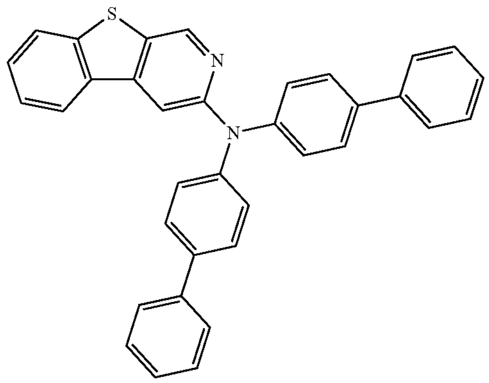
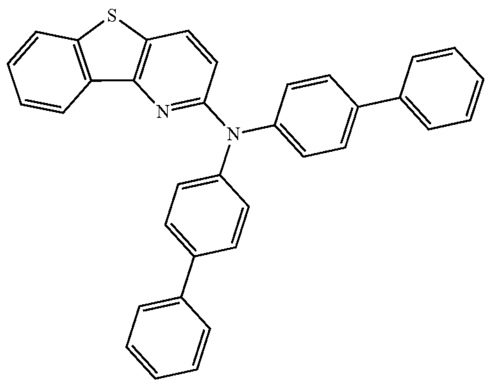

-continued
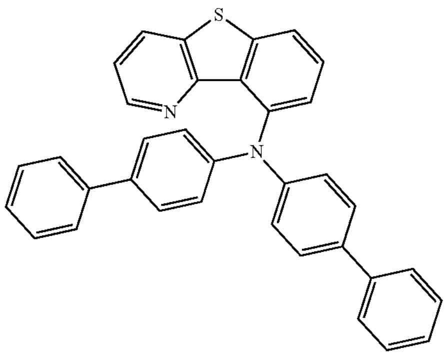
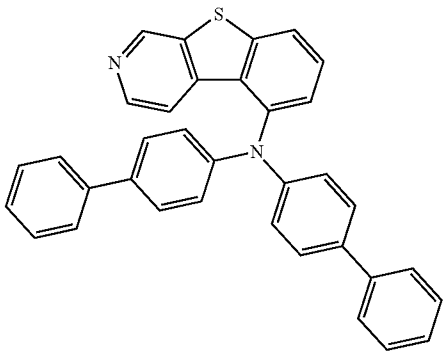
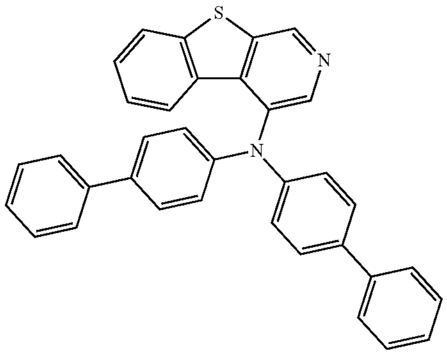
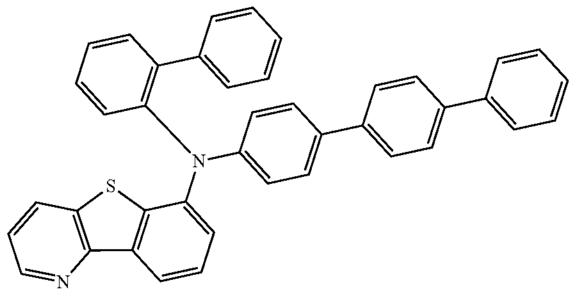
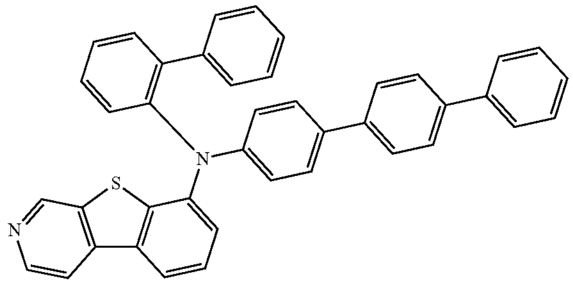
-continued
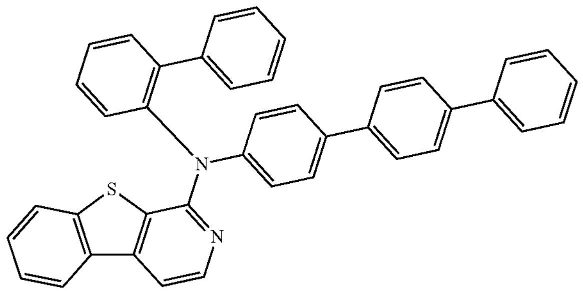
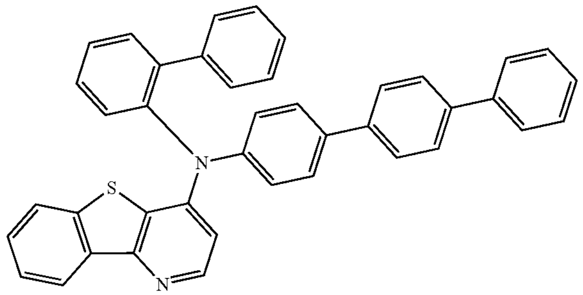
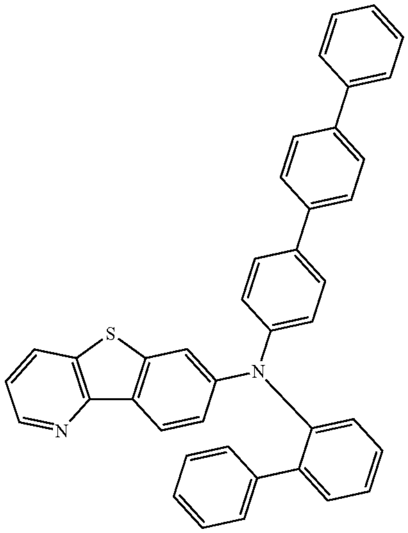
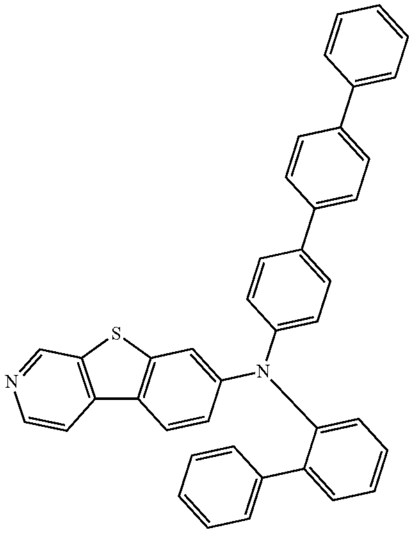

-continued
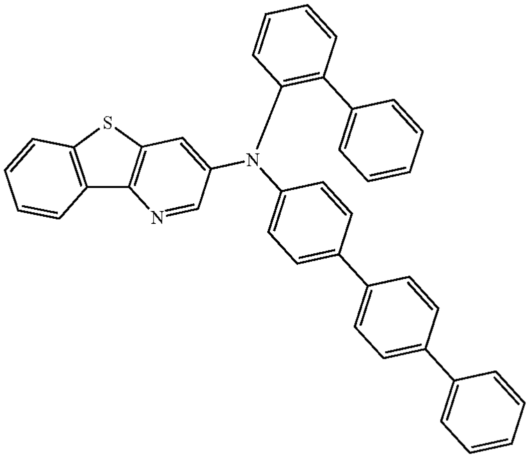
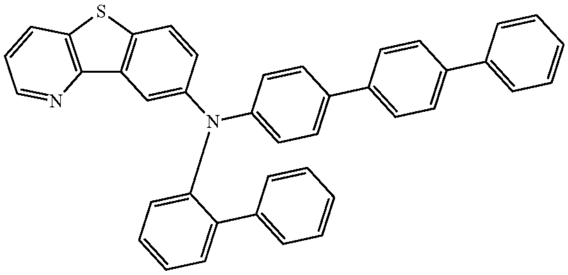
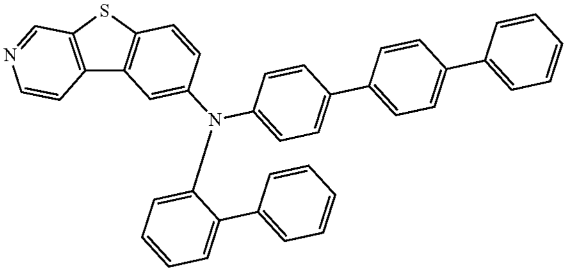
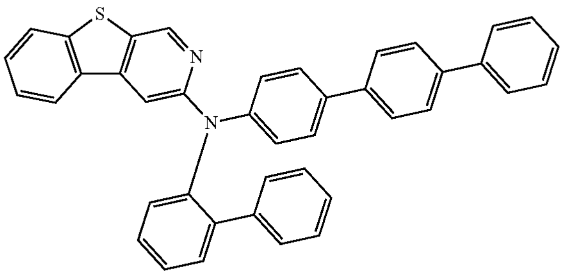
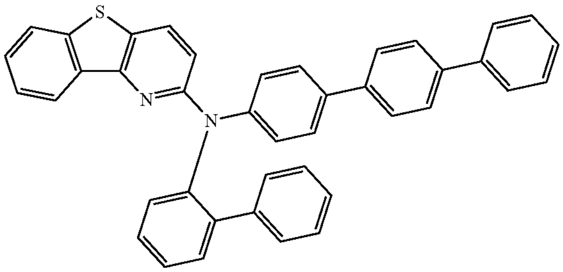
-continued
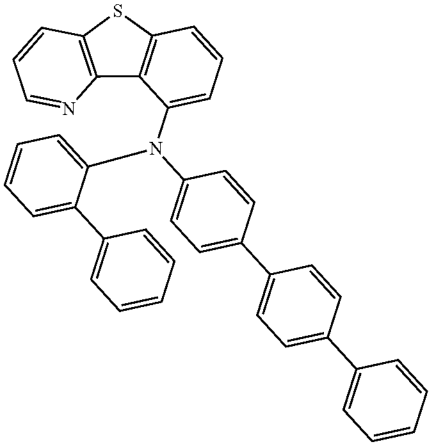
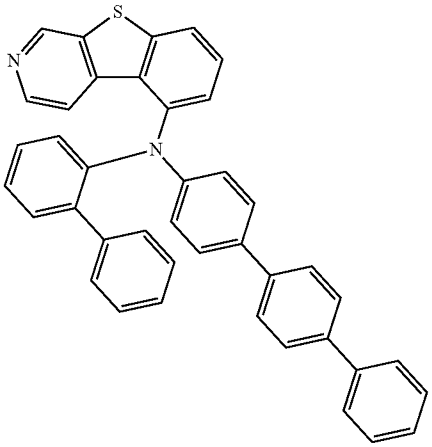
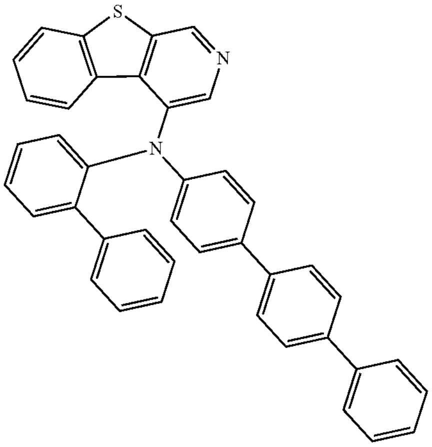
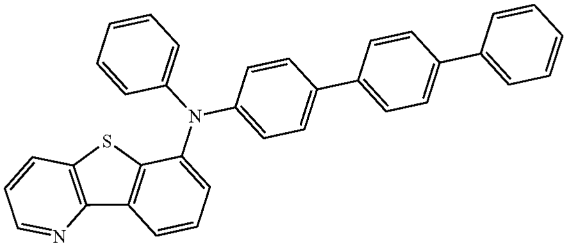

-continued
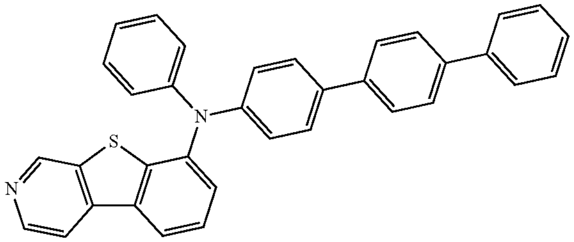
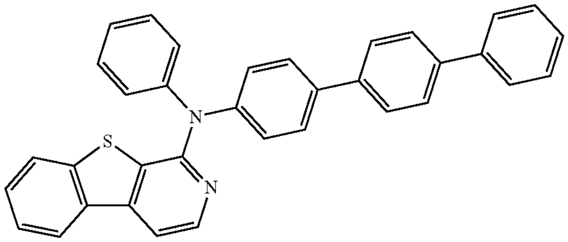
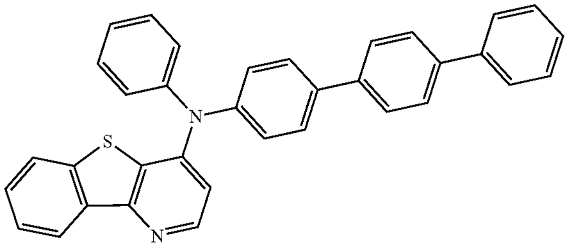
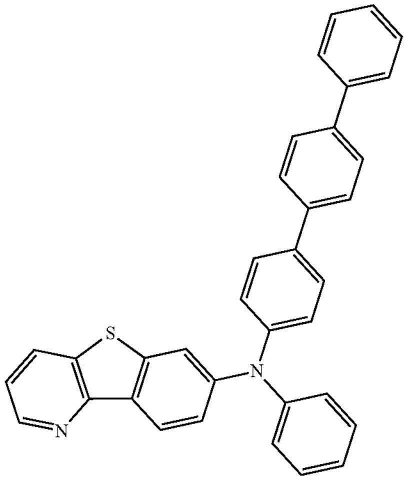
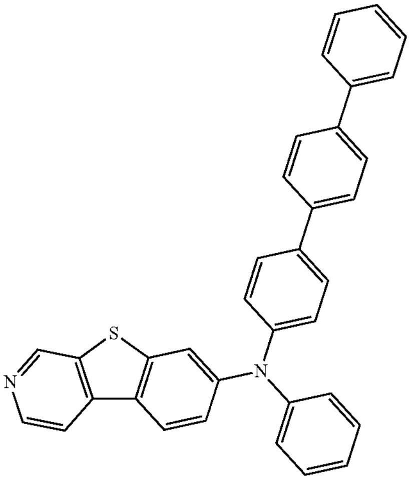
-continued
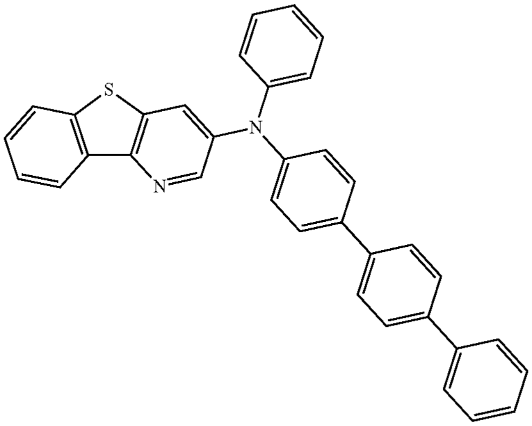
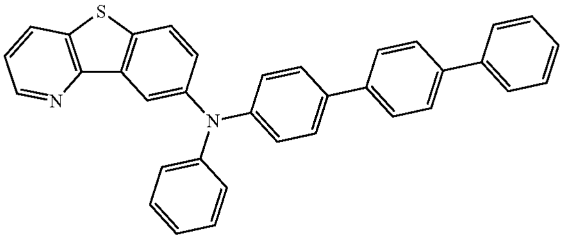
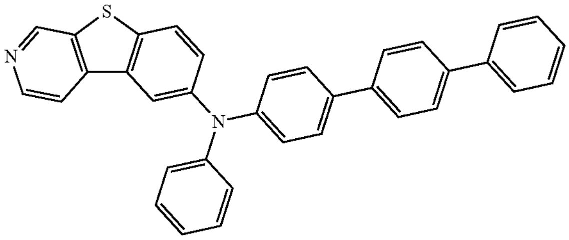
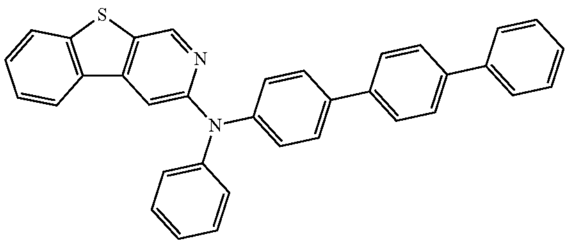
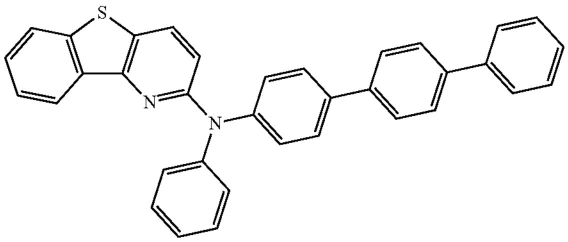

-continued
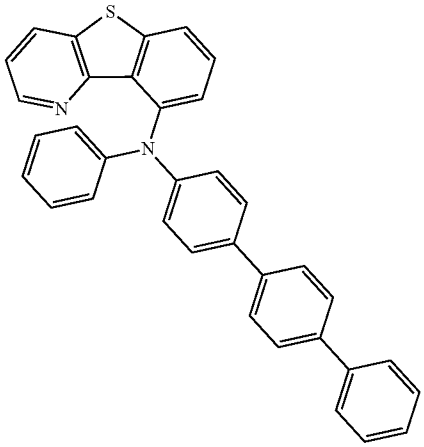
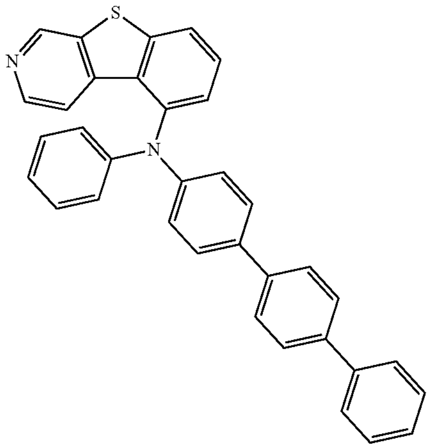
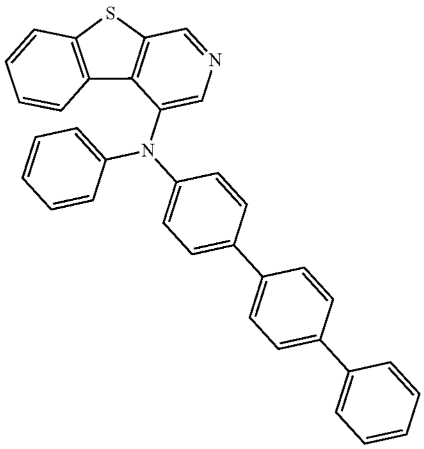
-continued
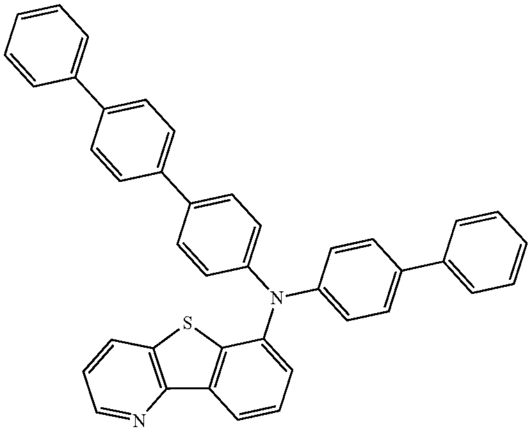
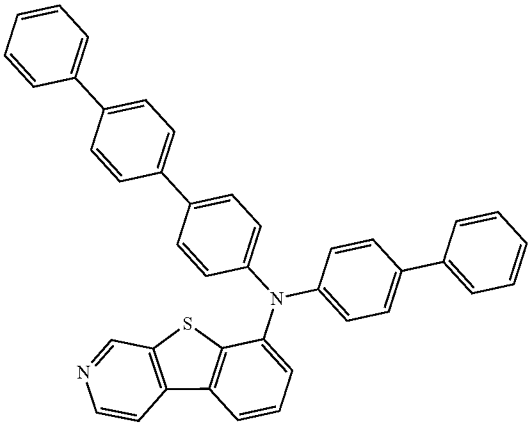
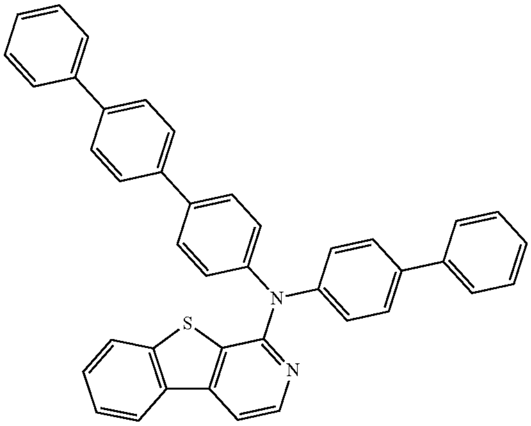
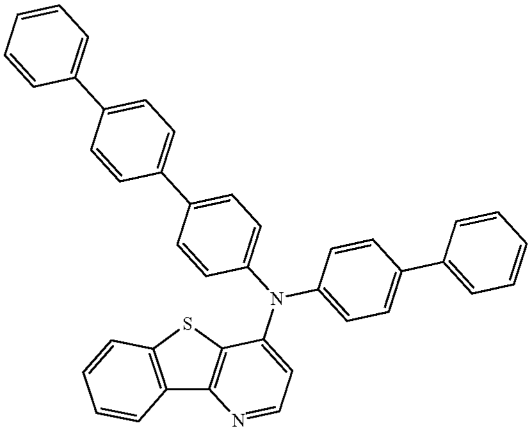

-continued
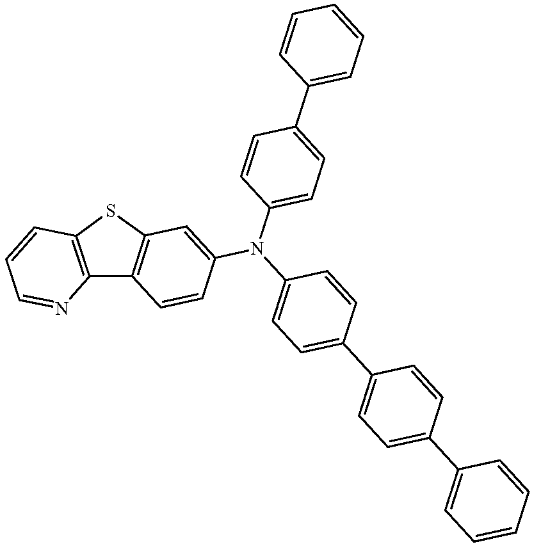
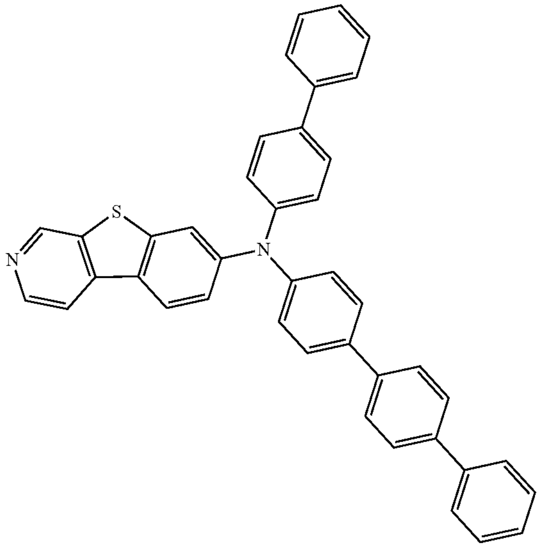
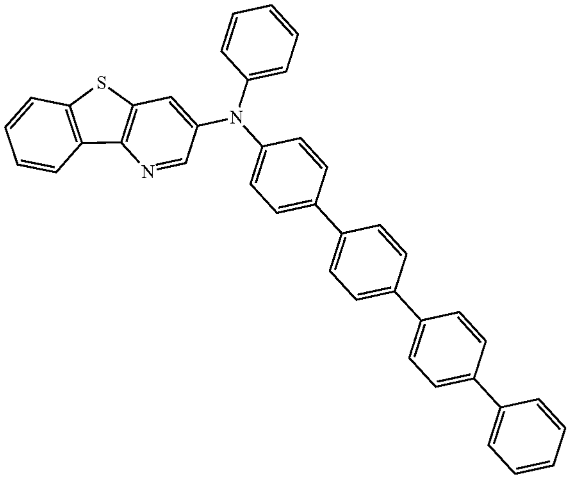
-continued
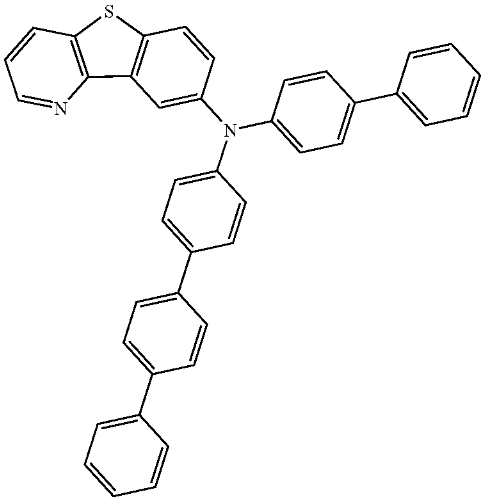
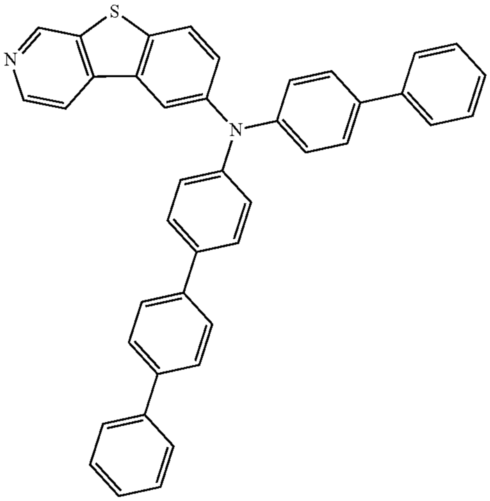
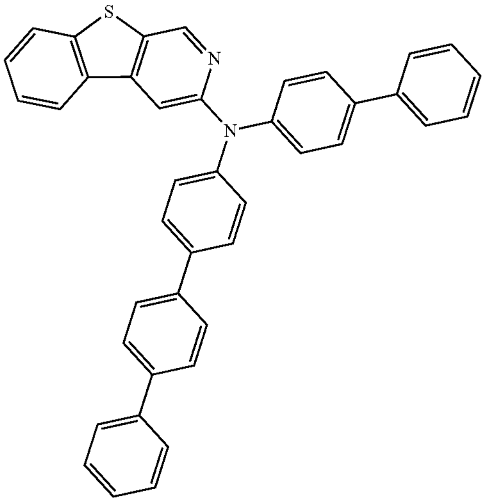

-continued
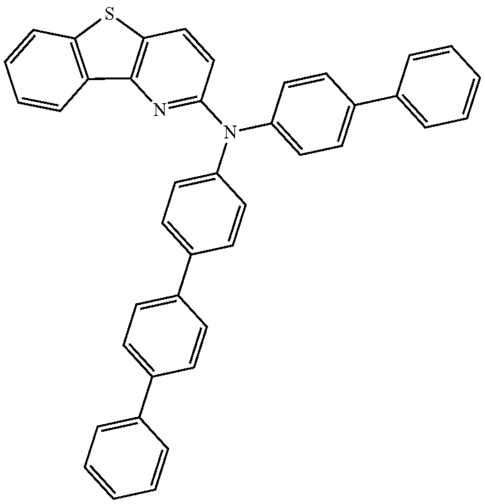
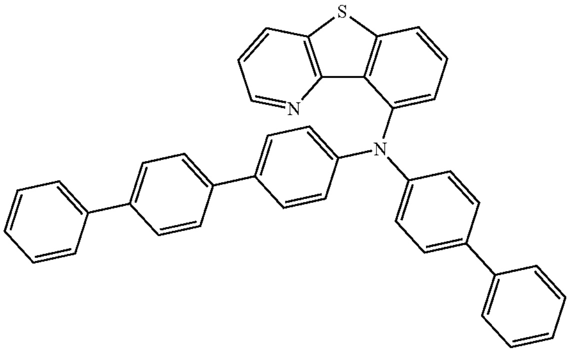
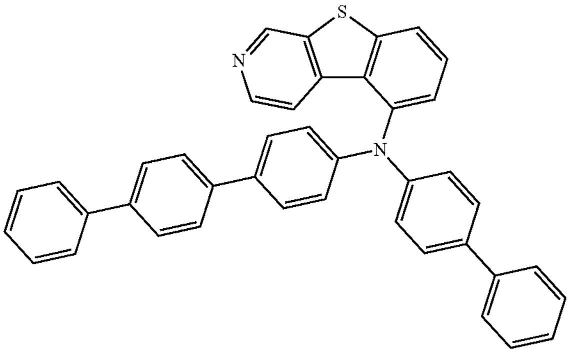
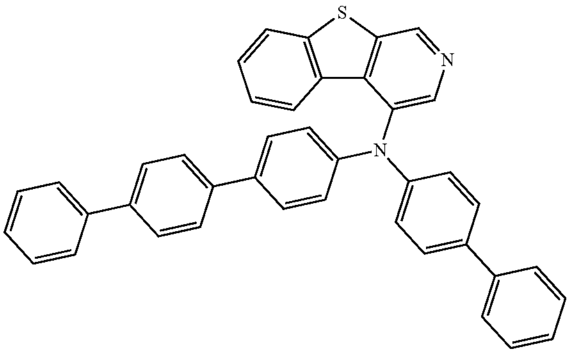
-continued
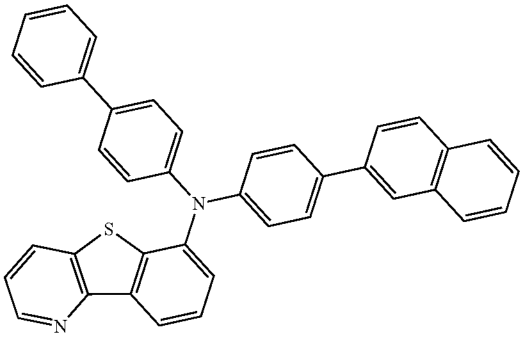
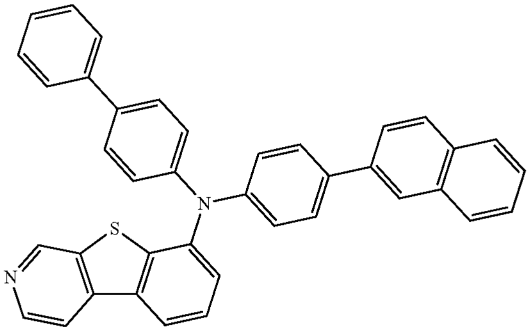
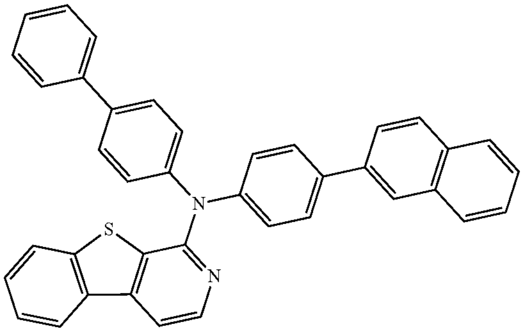
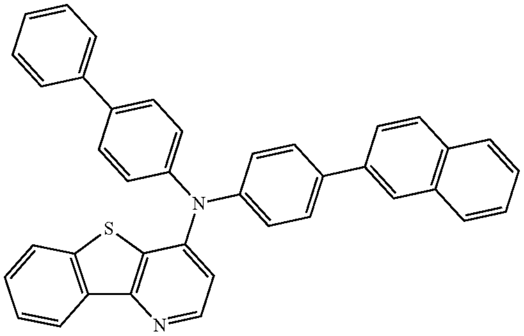

-continued
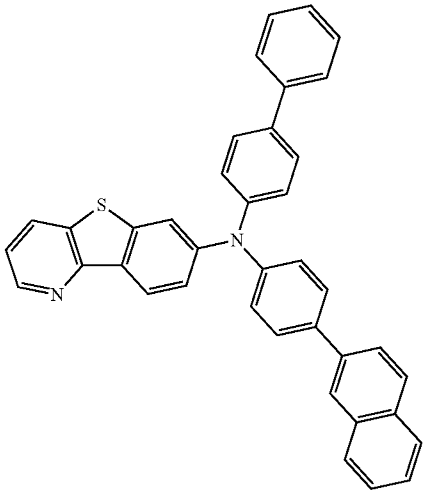
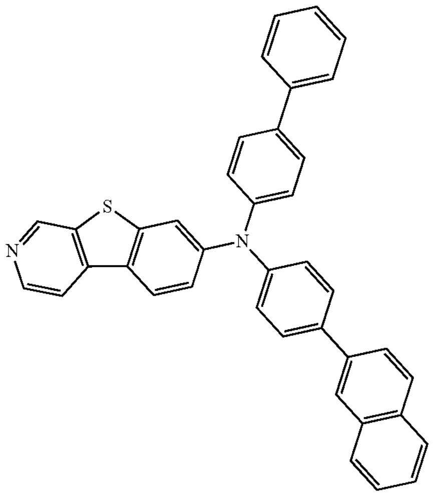
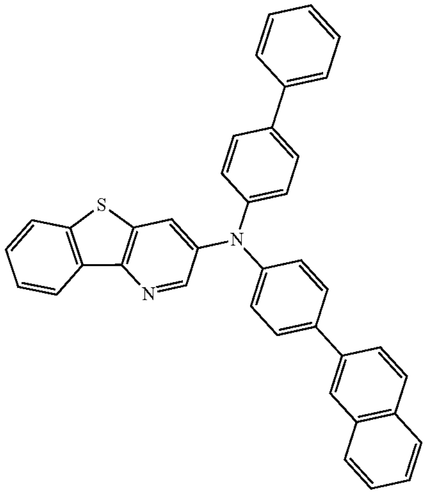
-continued
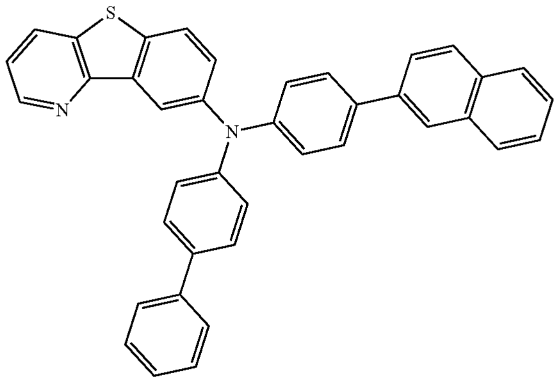
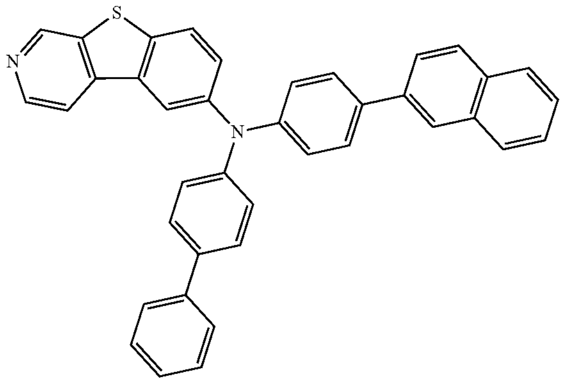
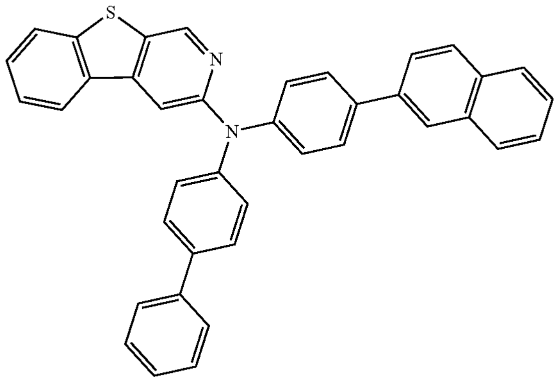
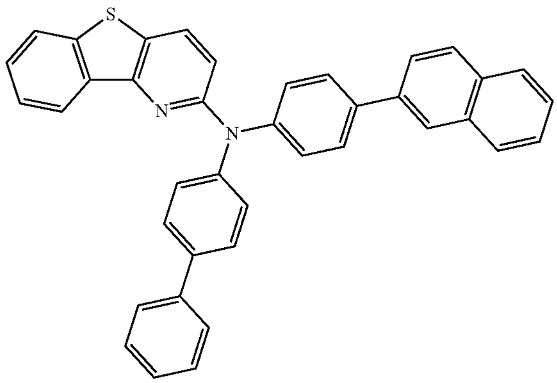

-continued
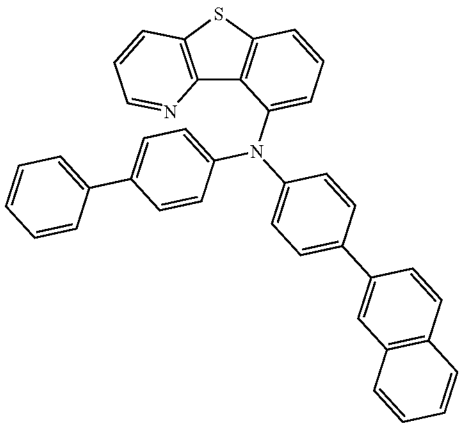
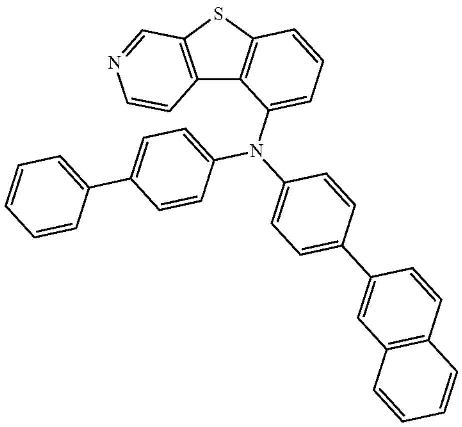
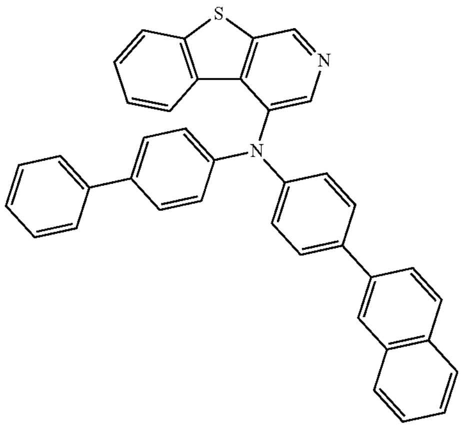
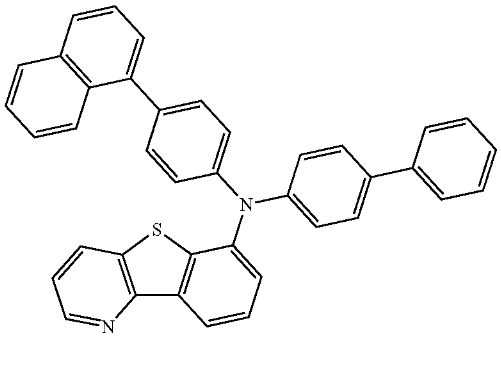
-continued
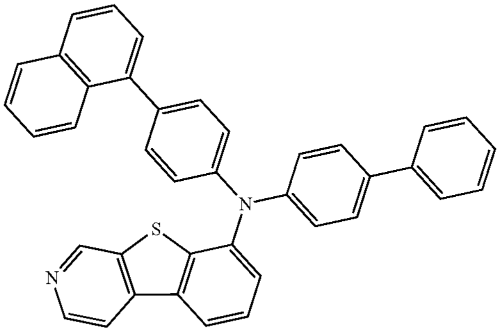
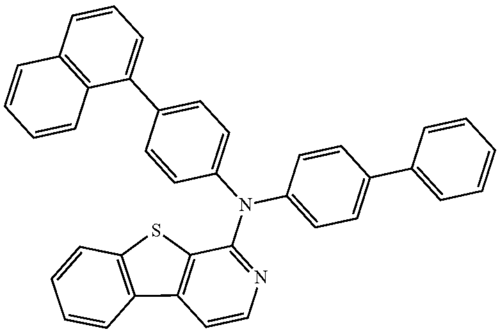
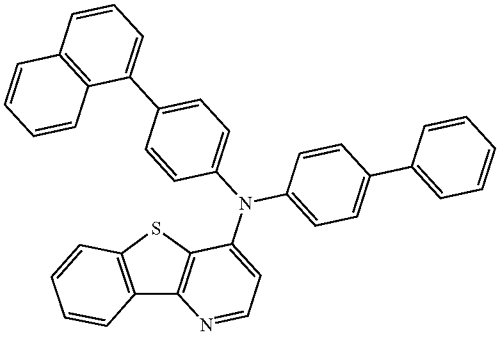
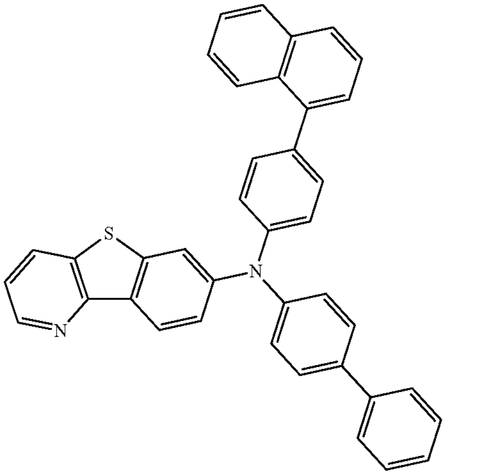

-continued
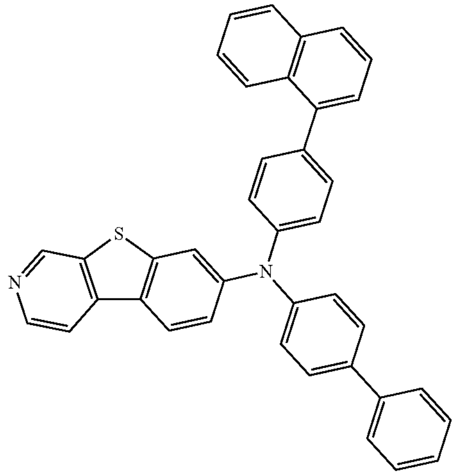
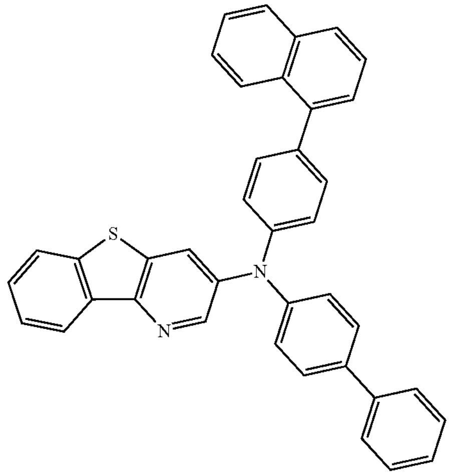
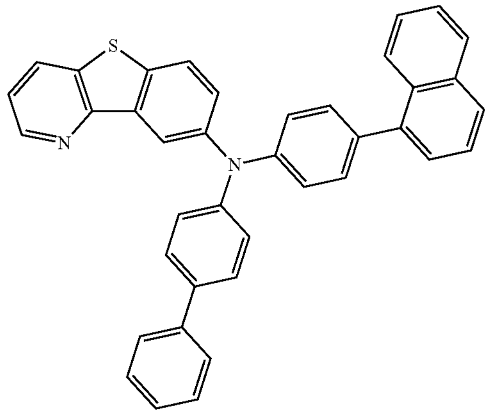
-continued
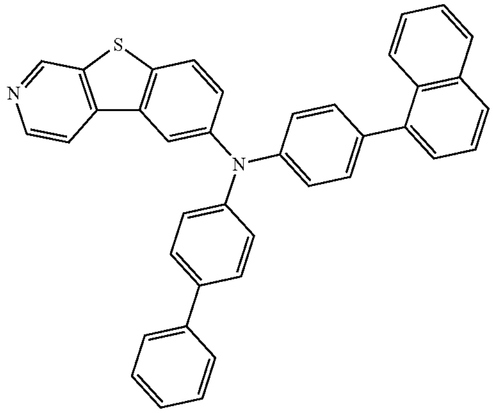
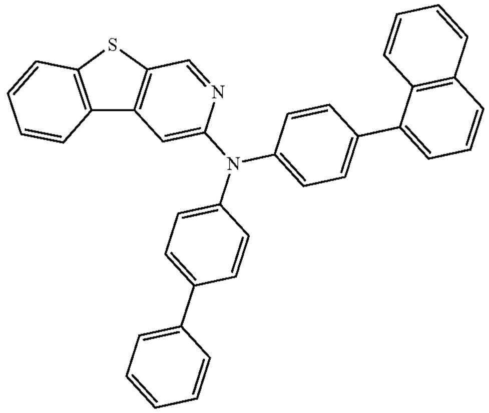
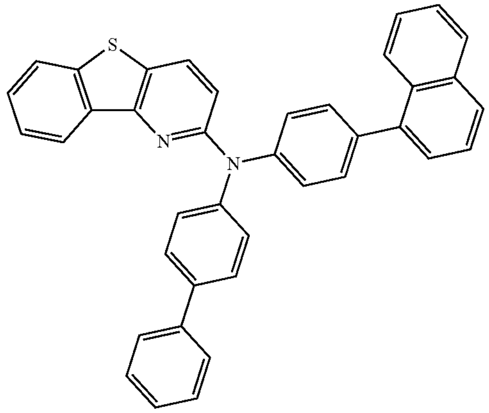
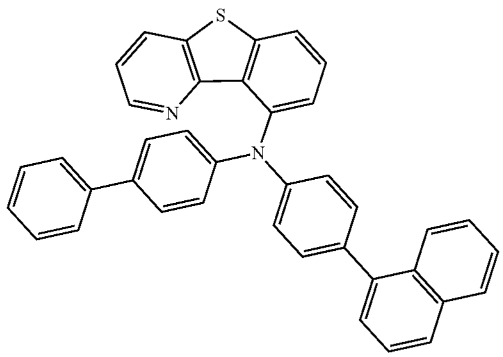

-continued
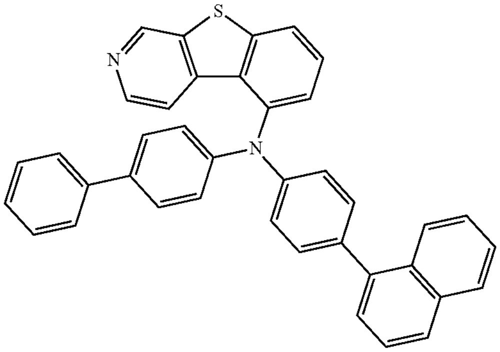
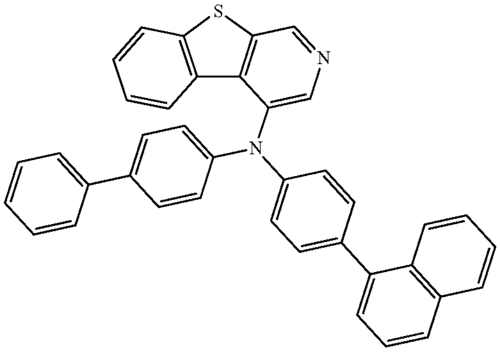
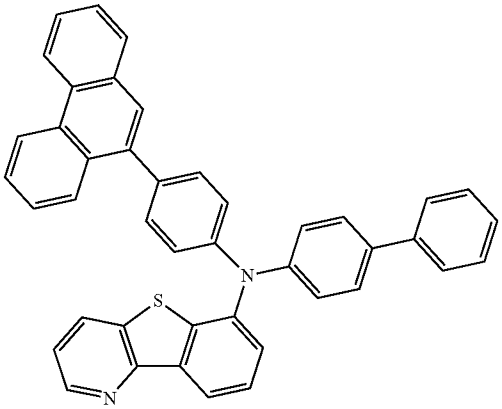
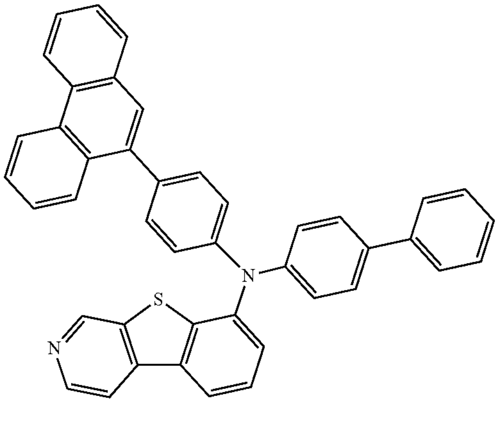
-continued
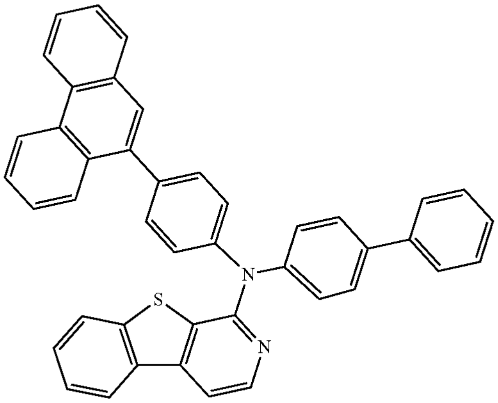
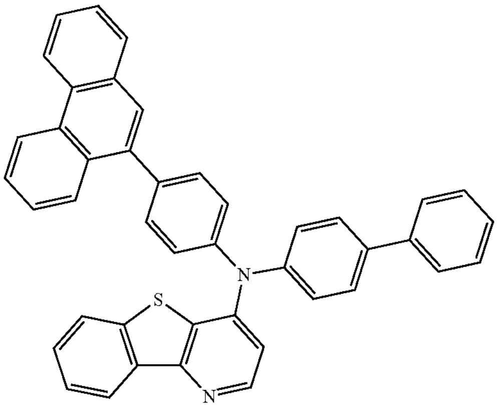
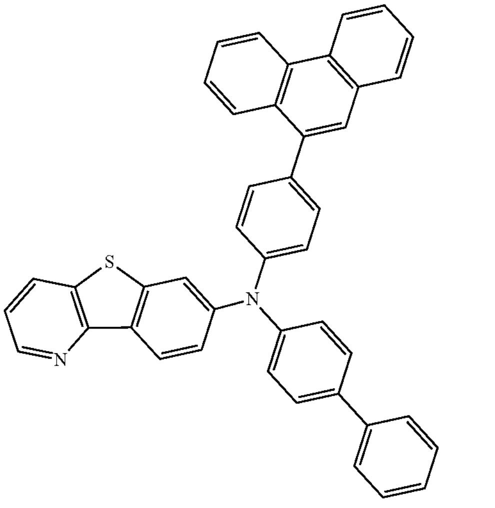

-continued
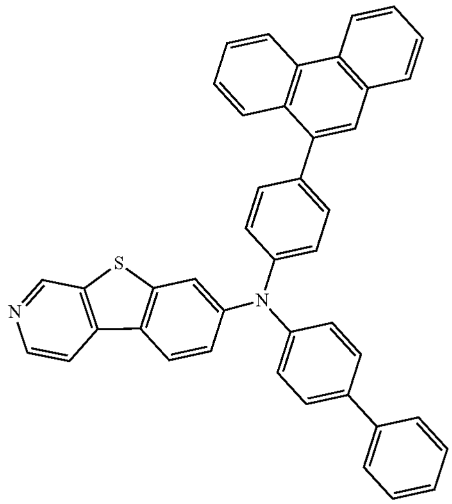
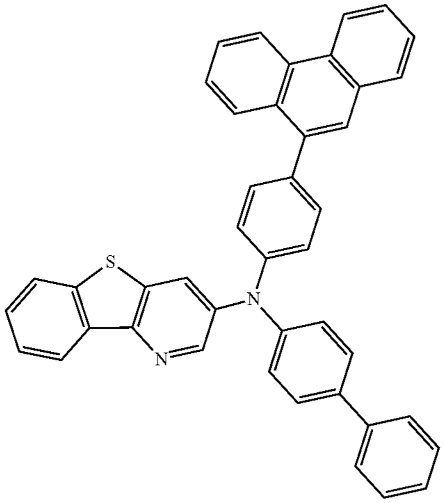
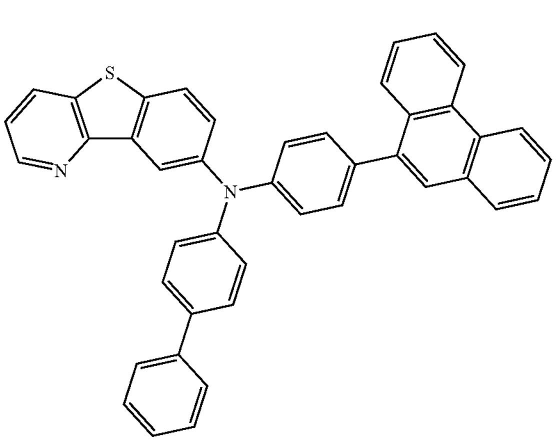
-continued
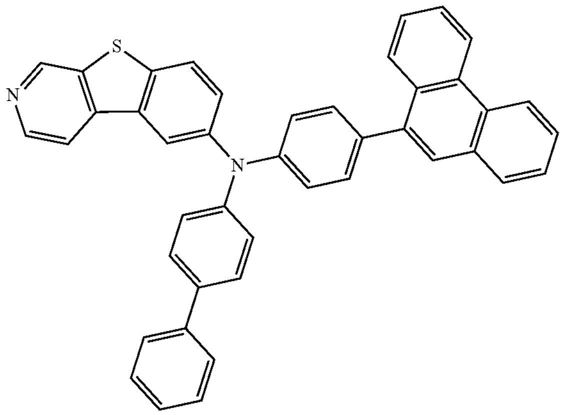
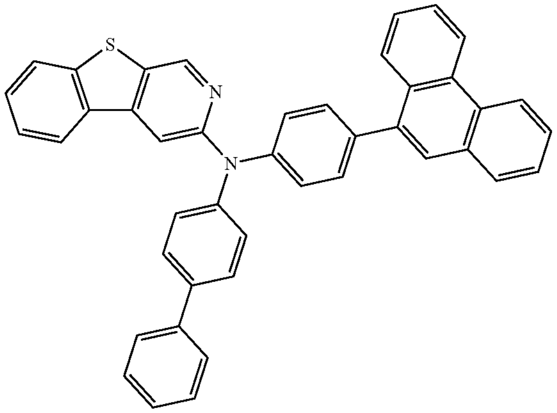
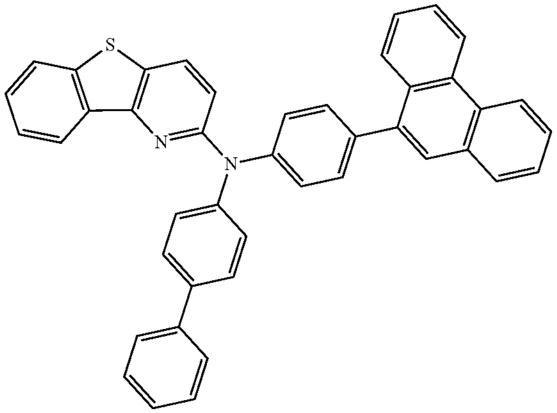
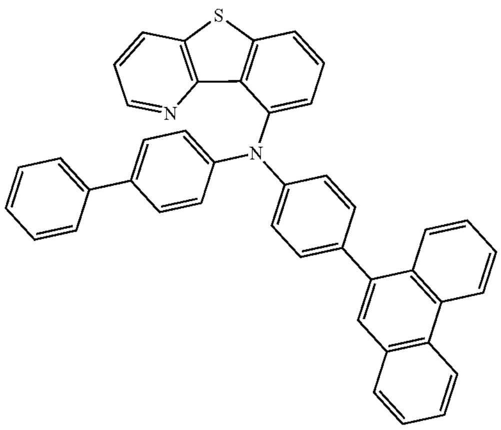

301
-continued
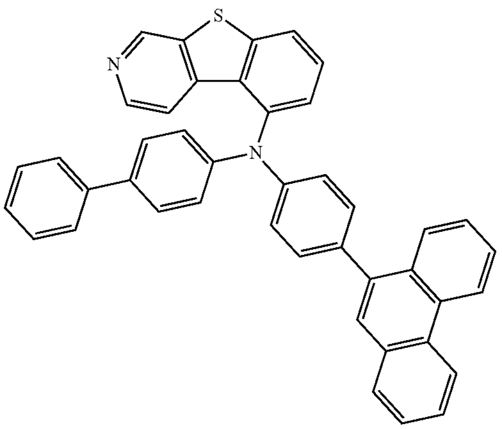
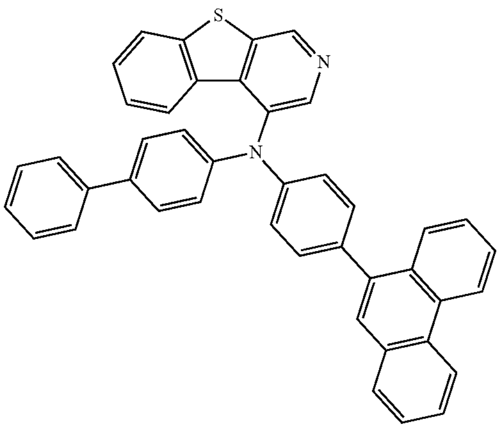
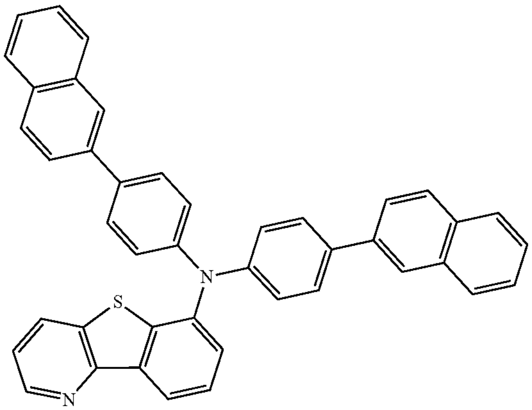
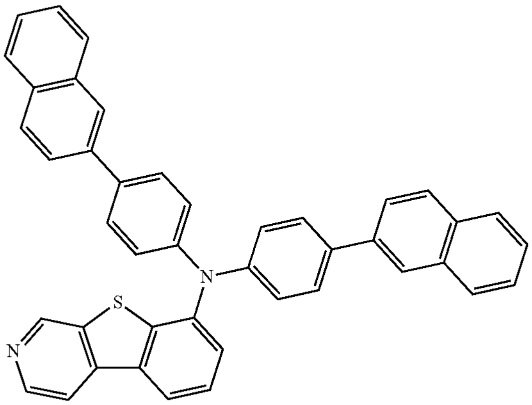
302
-continued
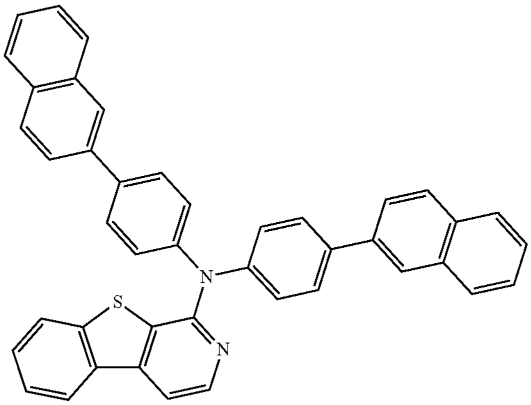
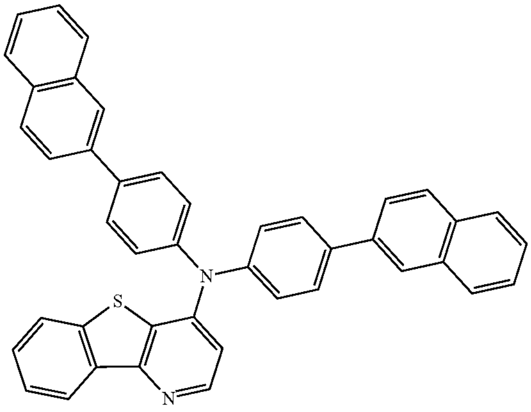
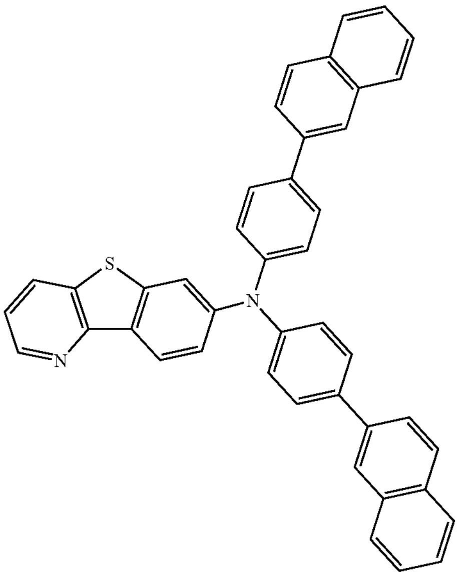

-continued
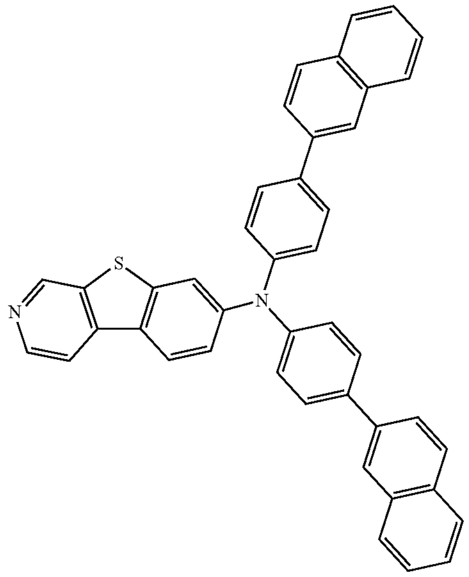
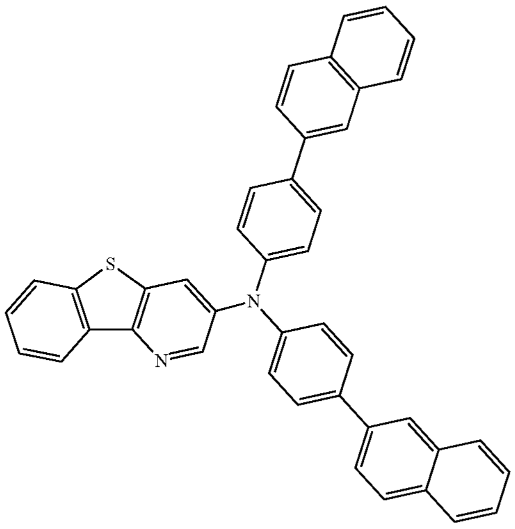
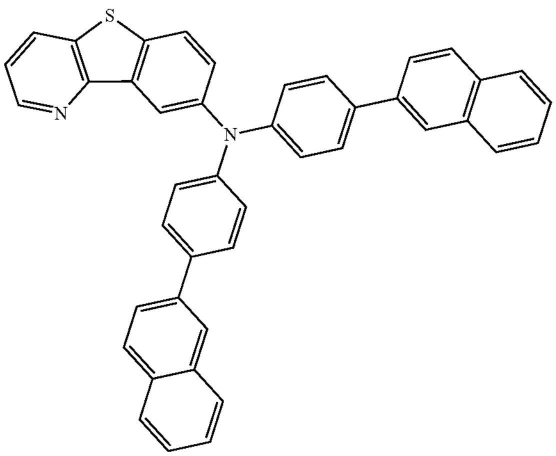
-continued
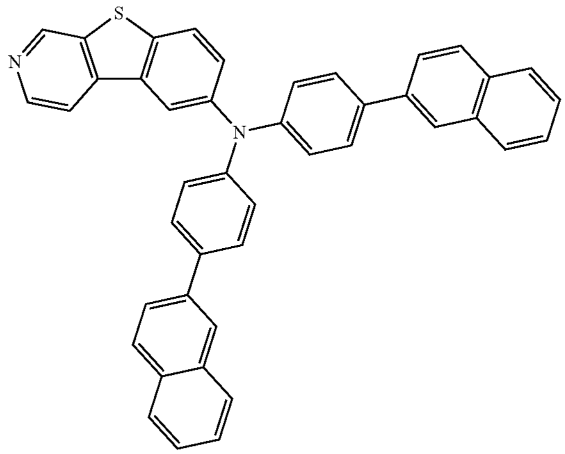
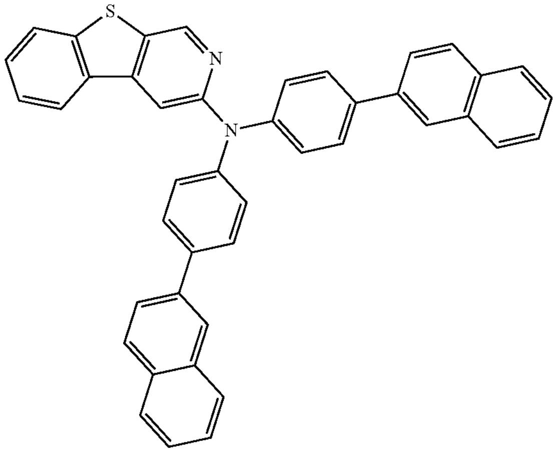
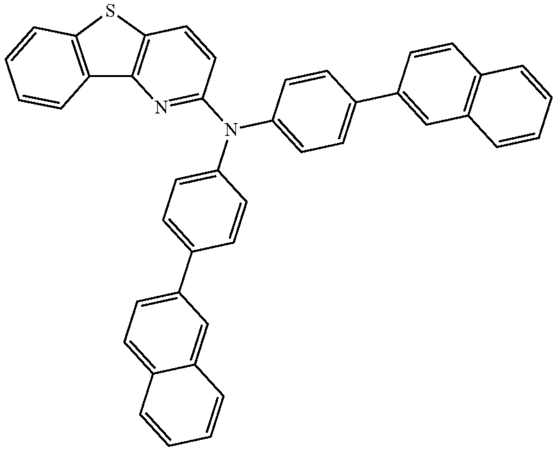
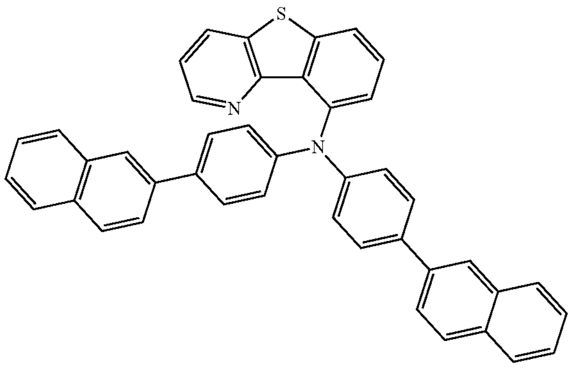

-continued
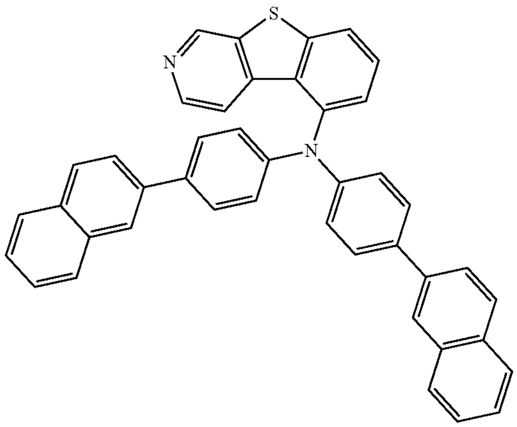
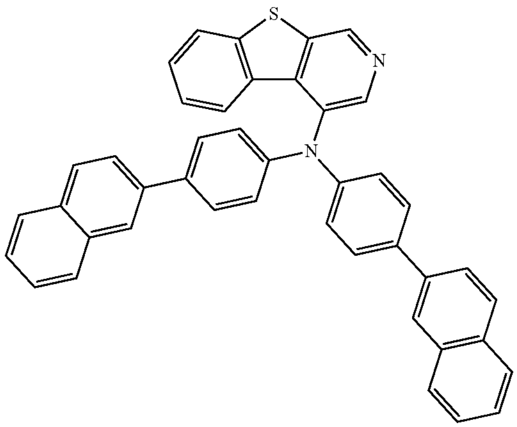
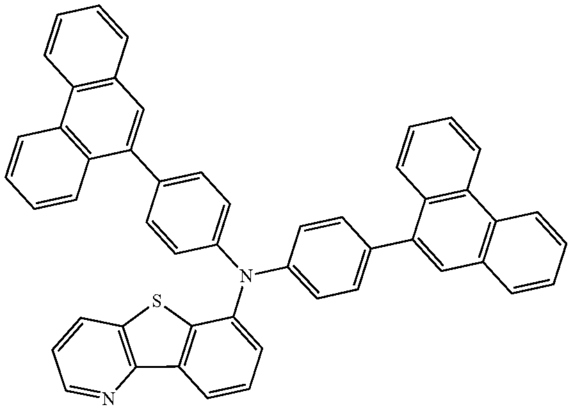
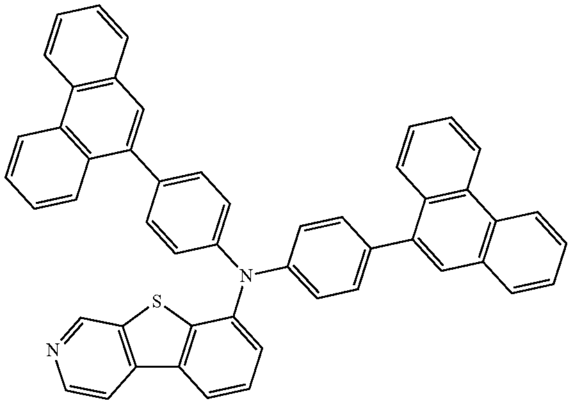
-continued
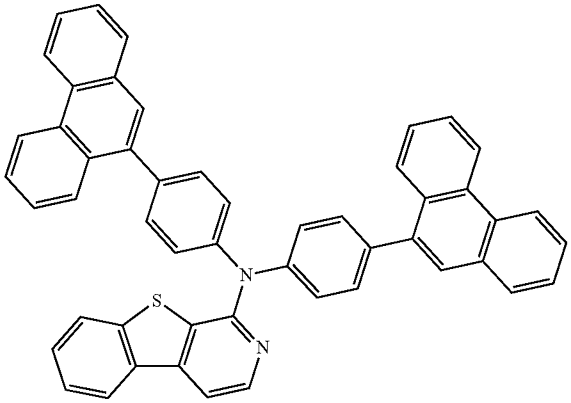
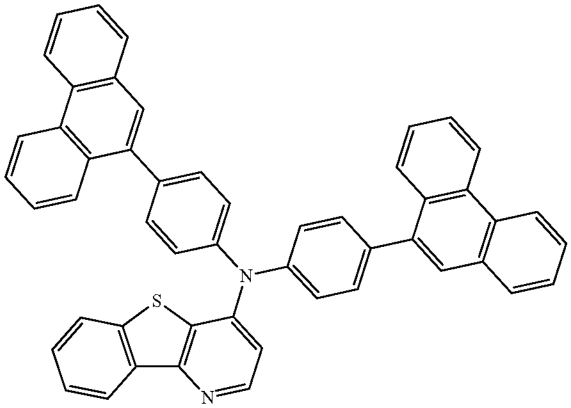
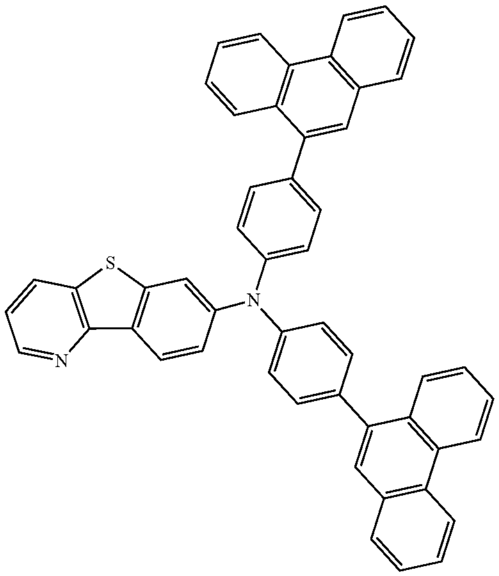

-continued
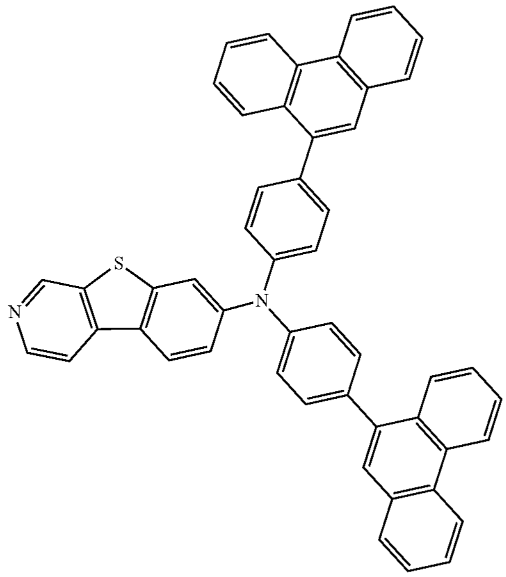
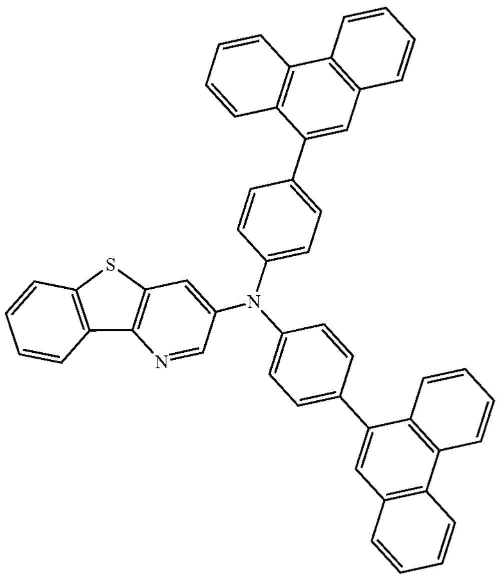
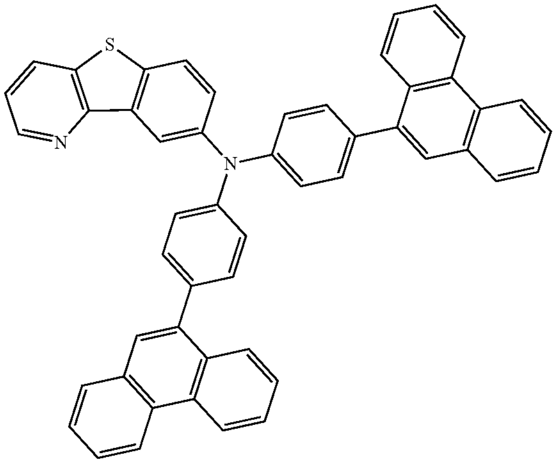
-continued
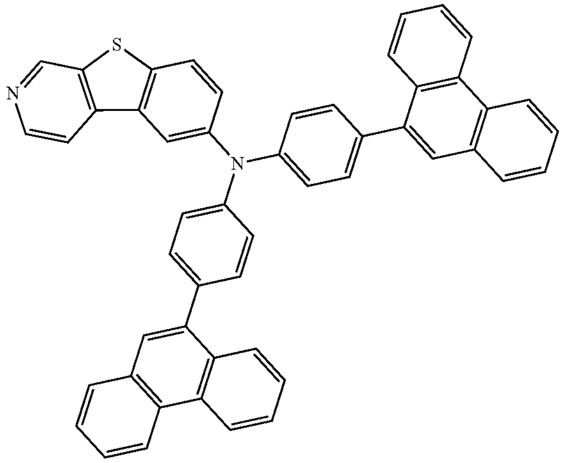
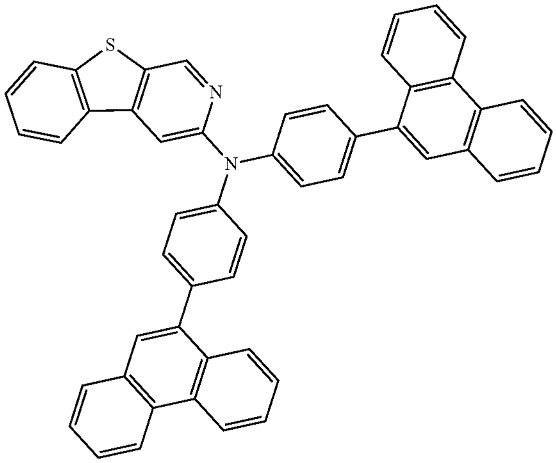
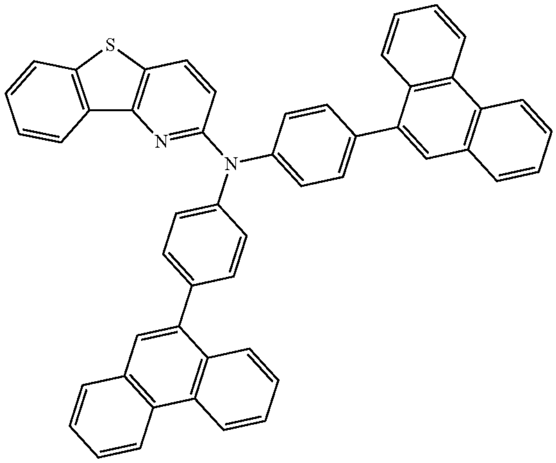

-continued
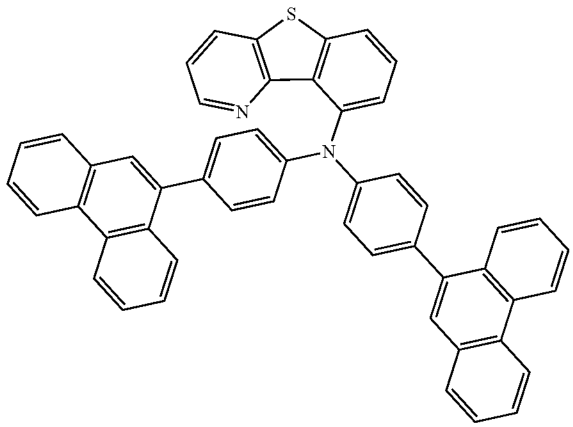
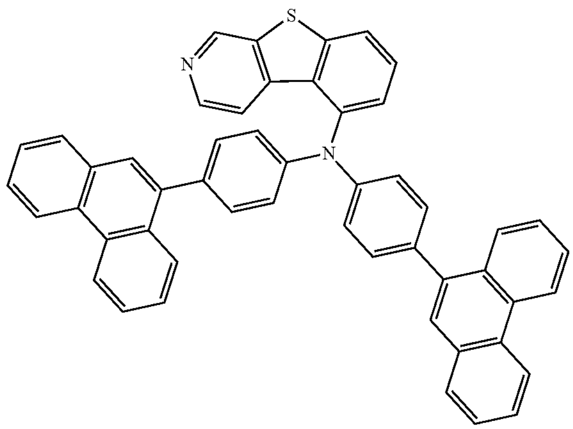
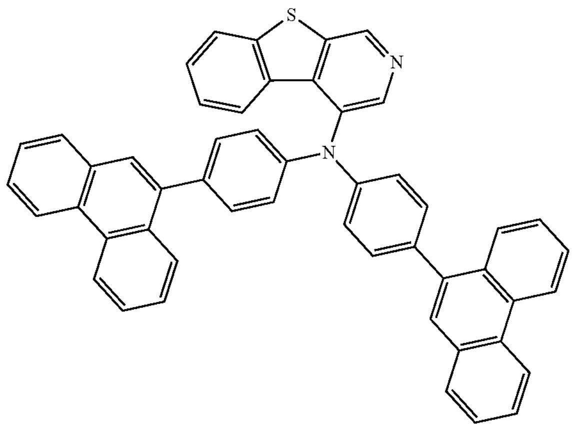
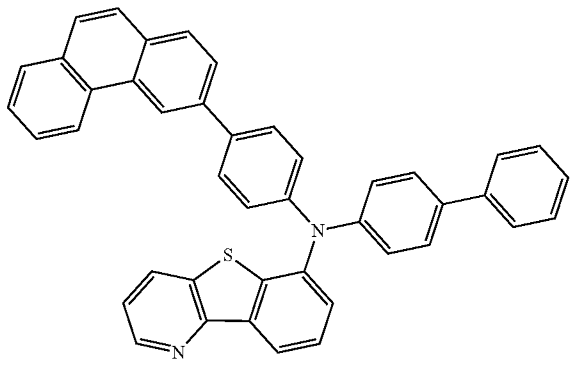
-continued
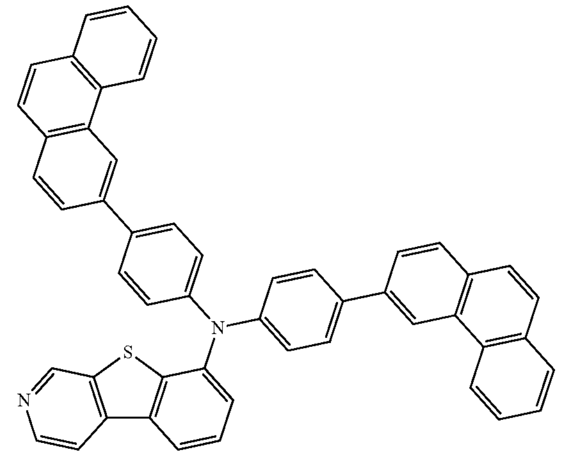
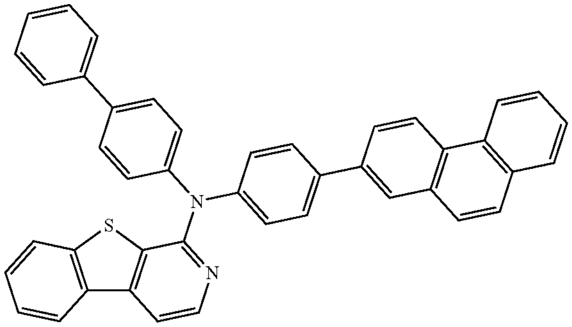
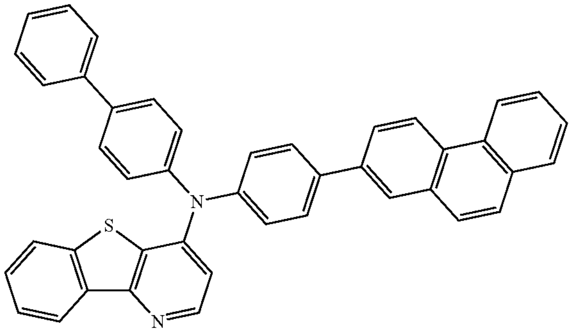
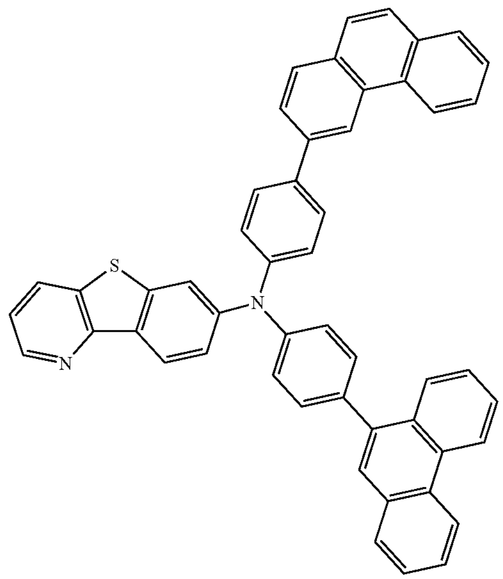

-continued
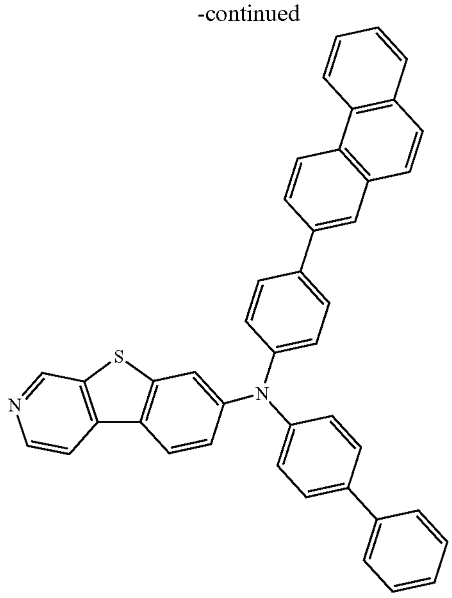
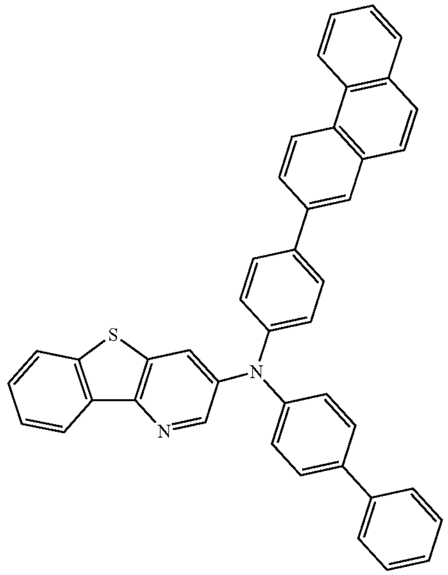
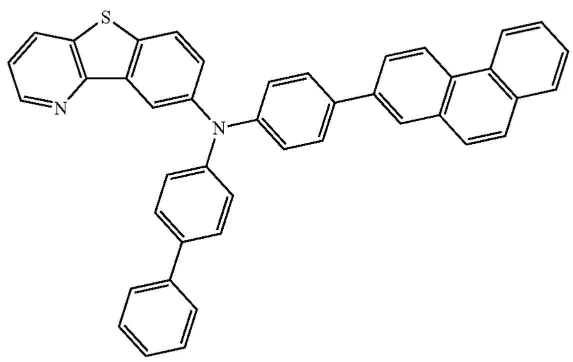
-continued
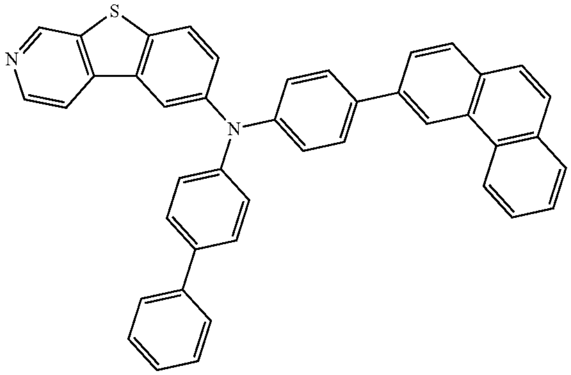
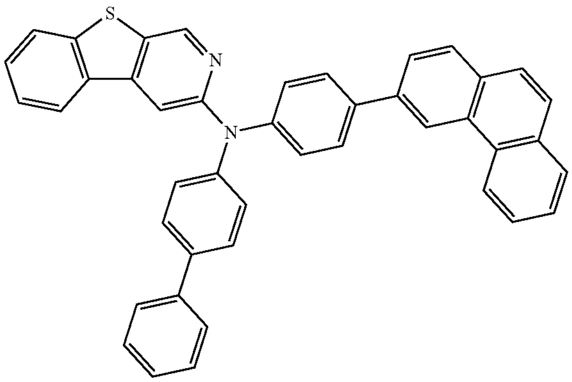
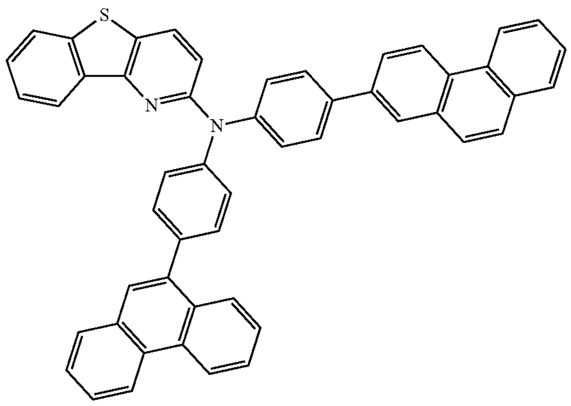
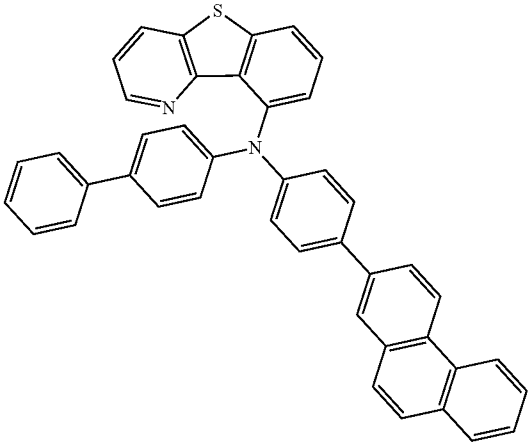

-continued
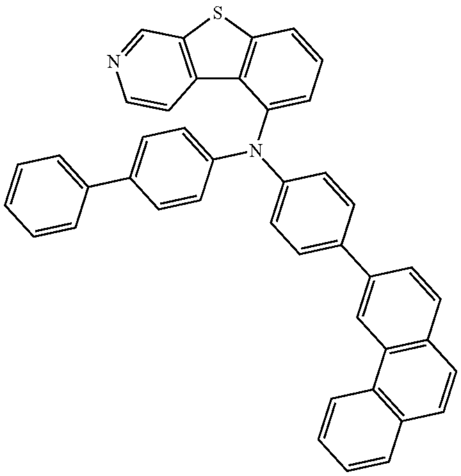
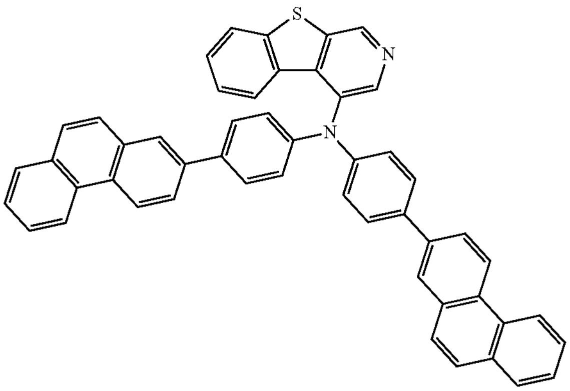
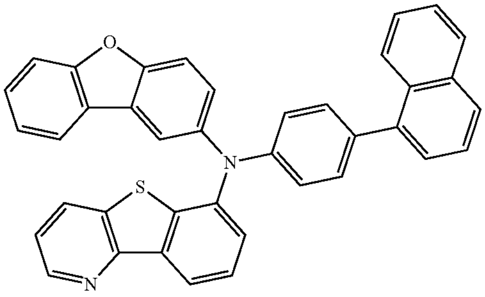
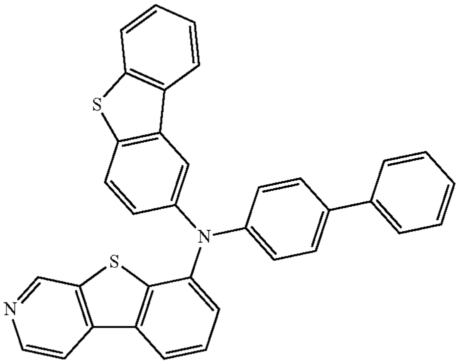
-continued
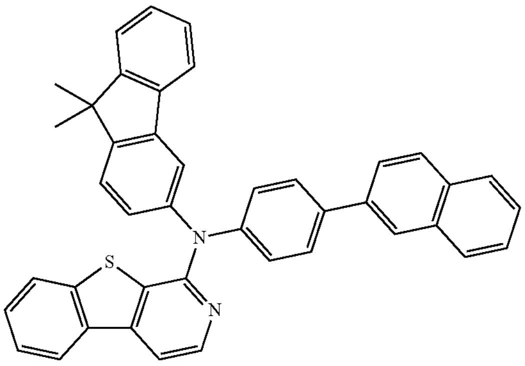
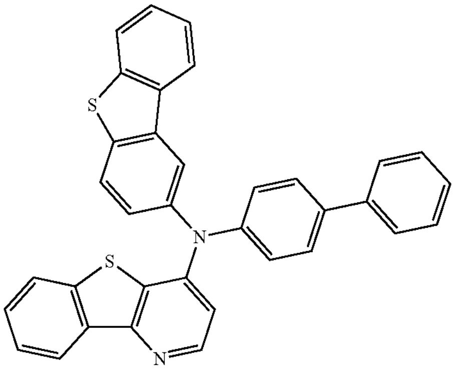
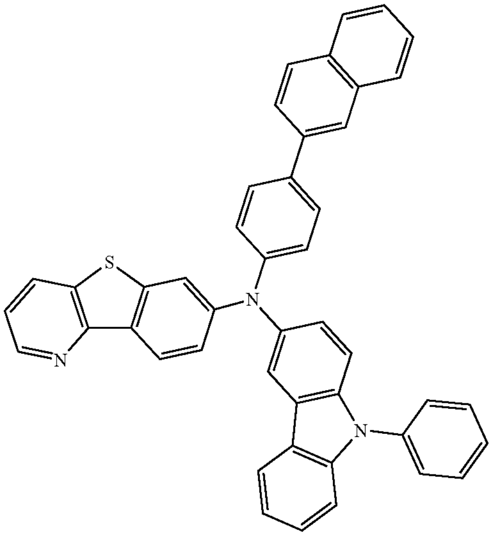

-continued
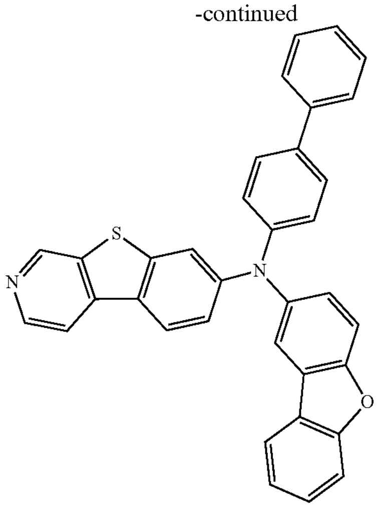
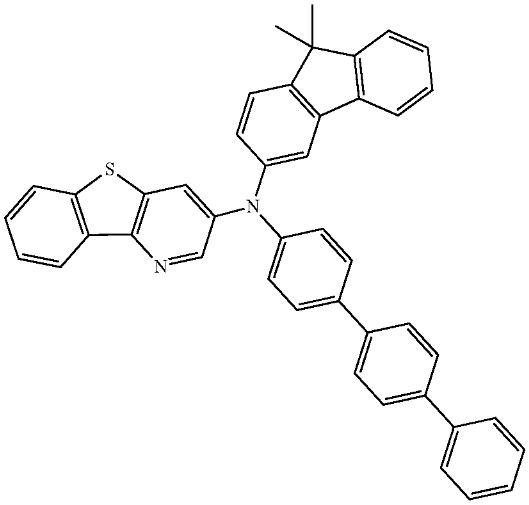
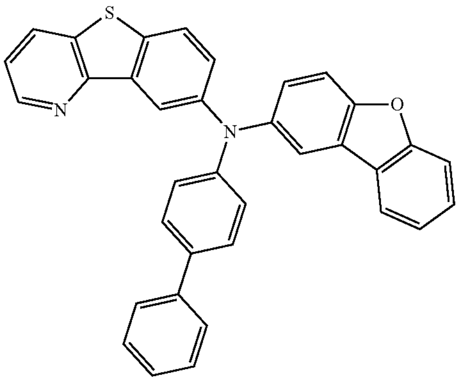
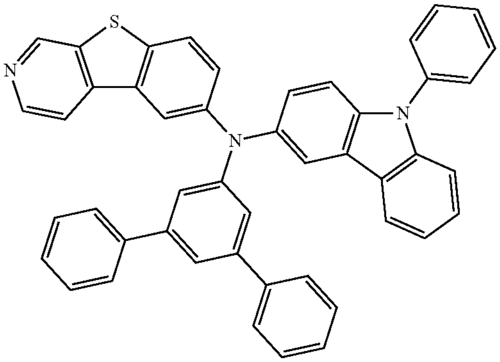
-continued
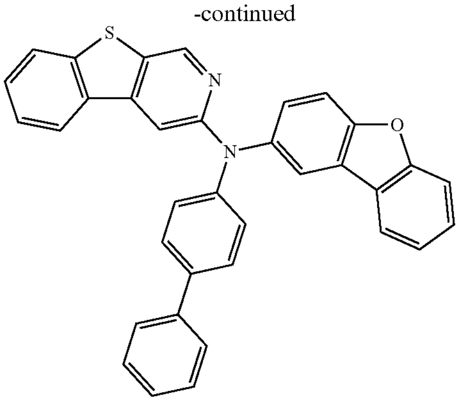
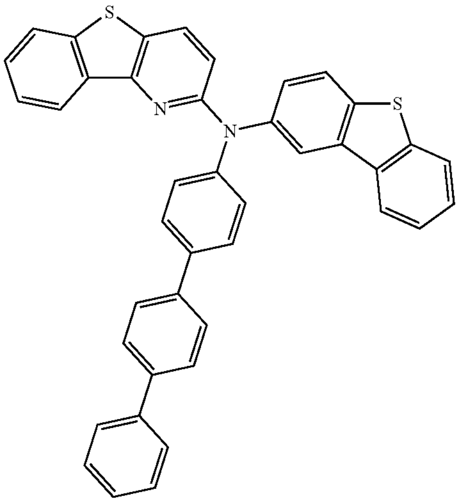
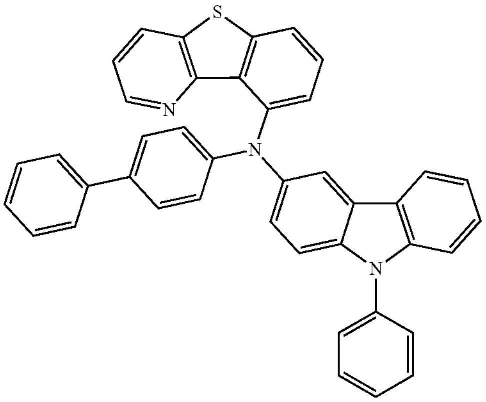
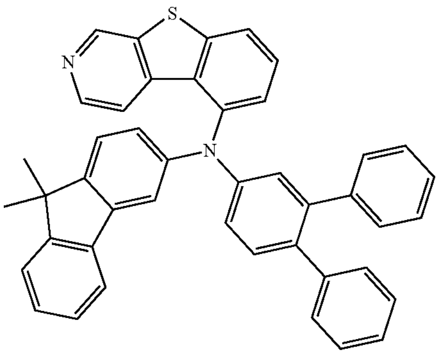

-continued
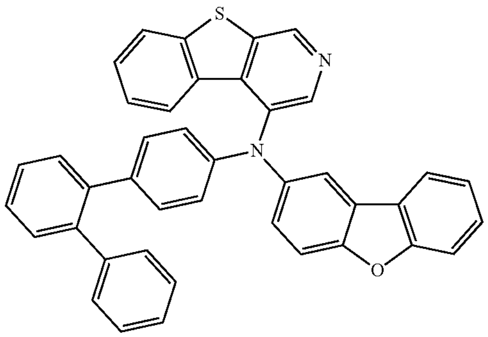
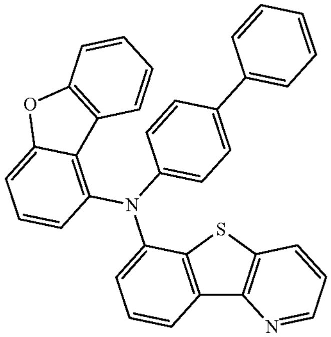
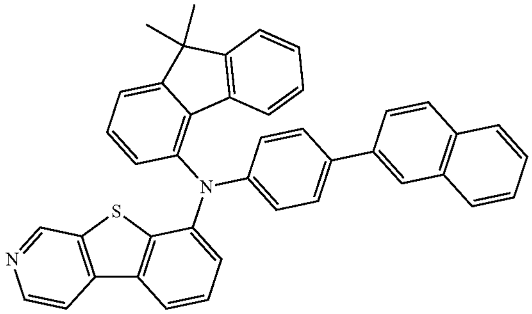
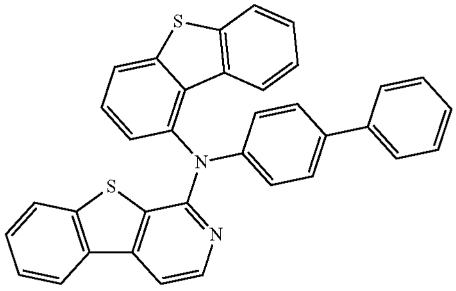
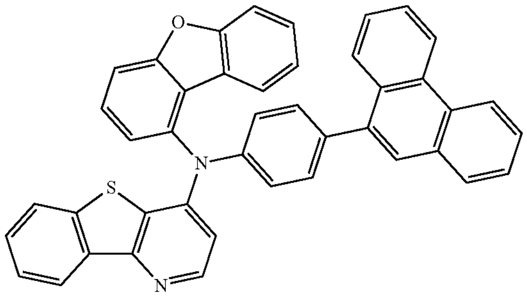
-continued
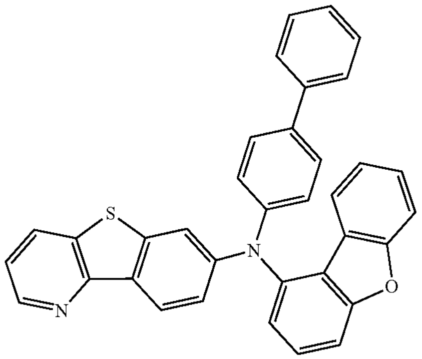
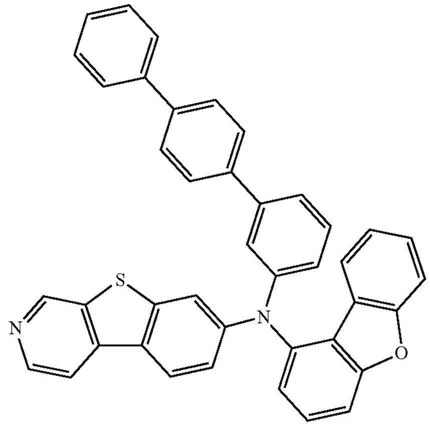
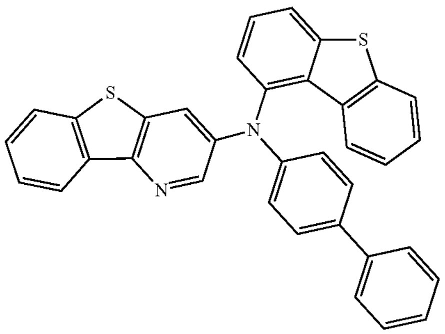
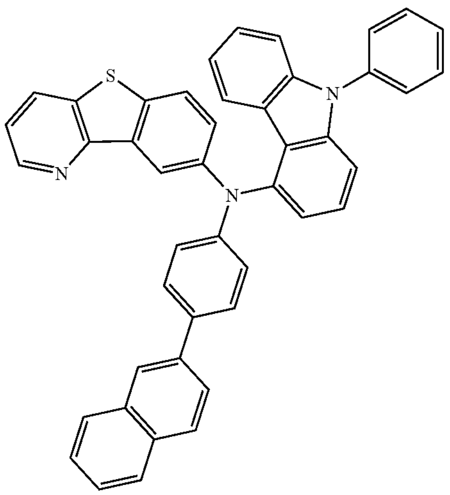

-continued
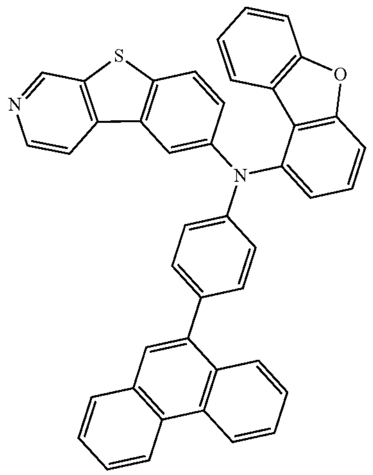
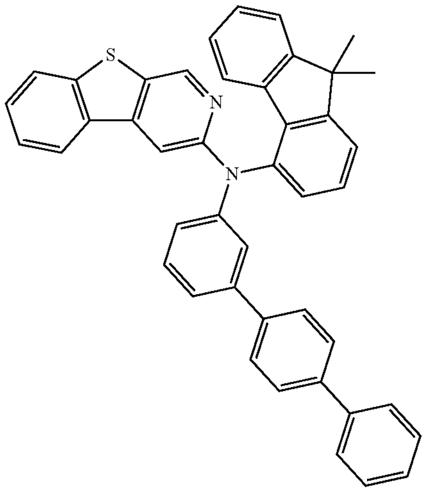
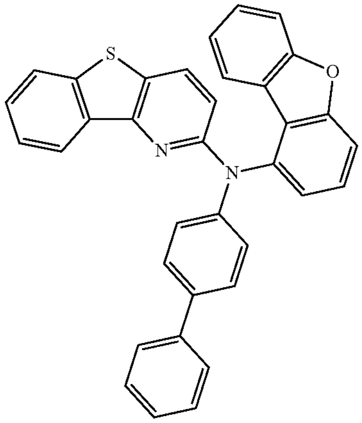
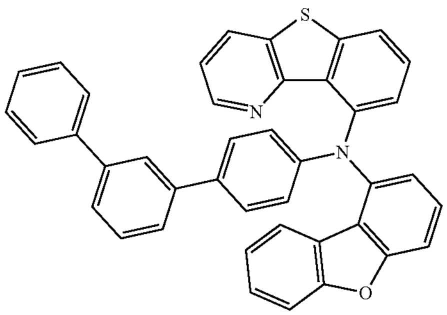
-continued
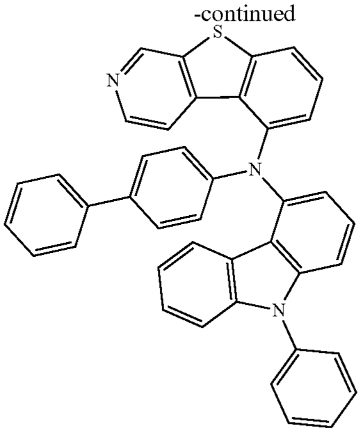
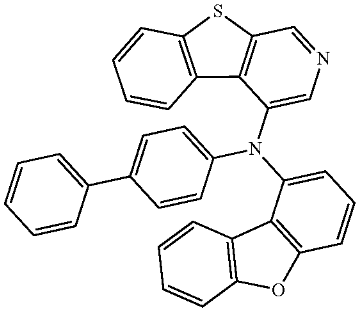
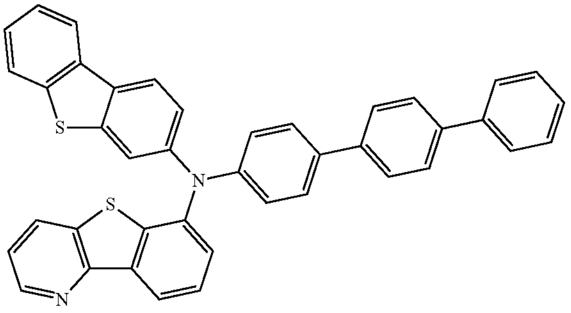
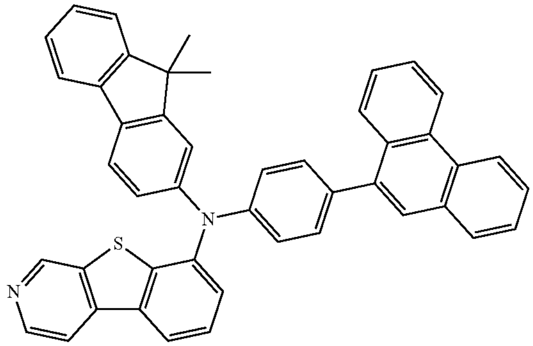
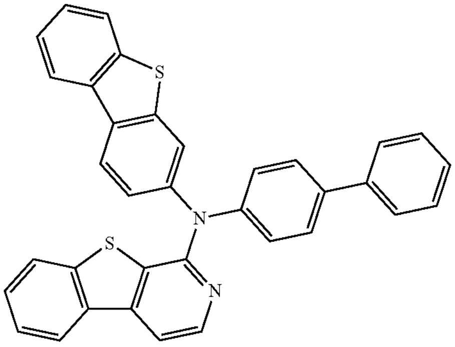

-continued
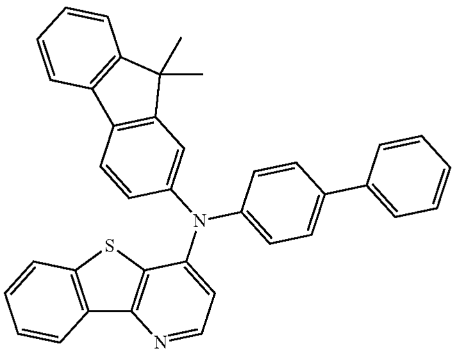
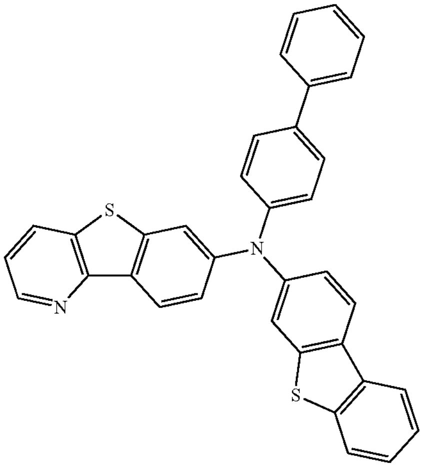
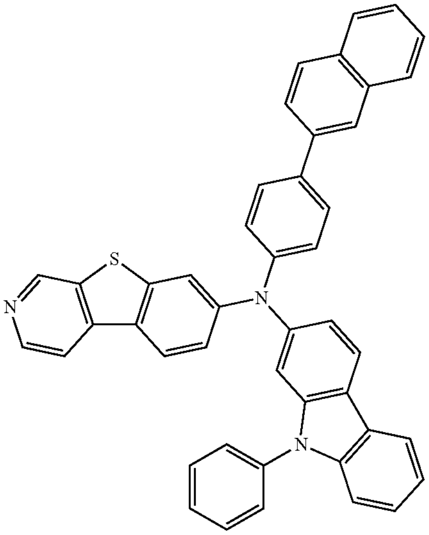
-continued
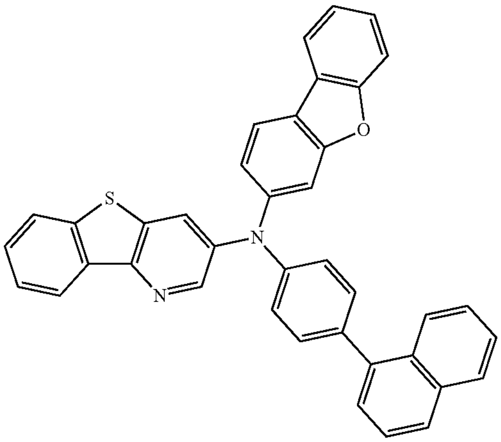
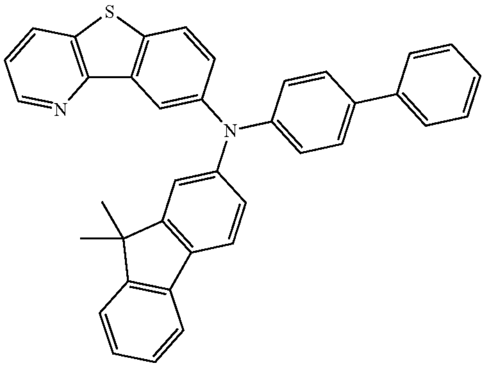
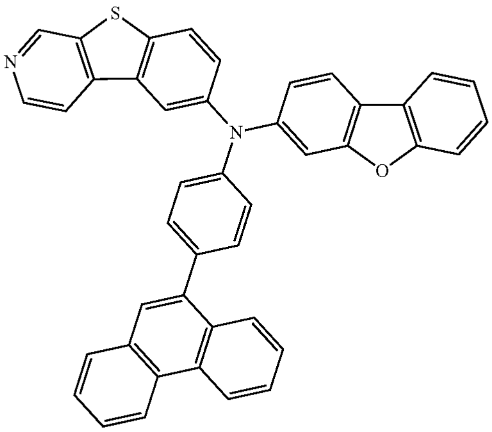
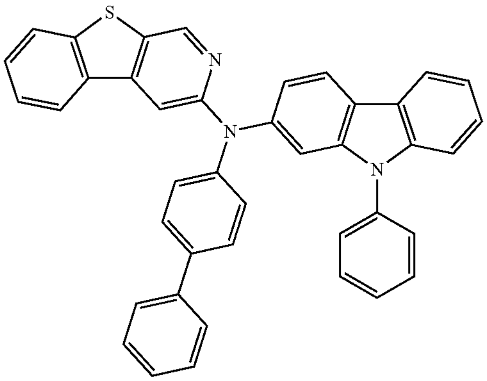

-continued
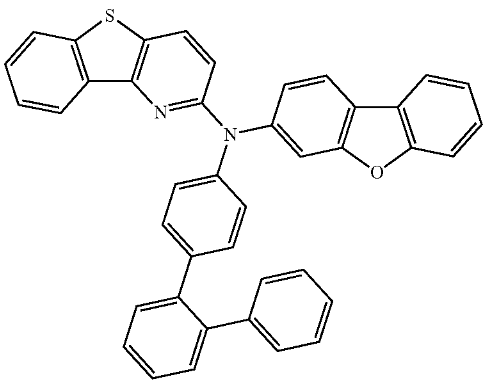
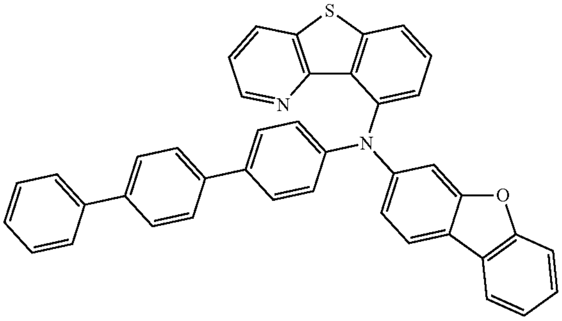
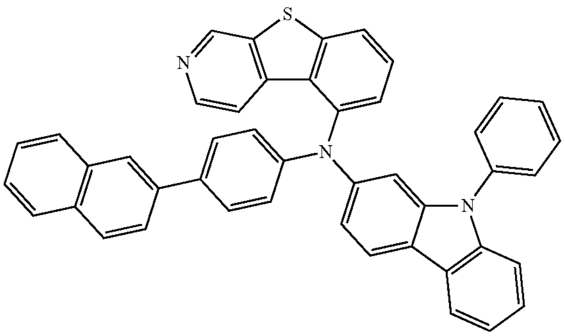
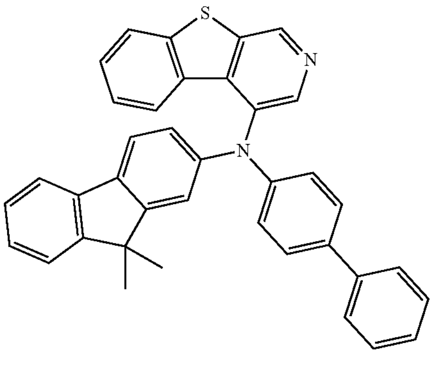
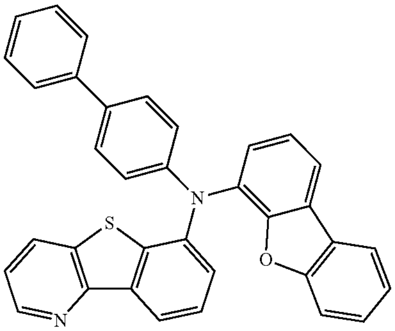
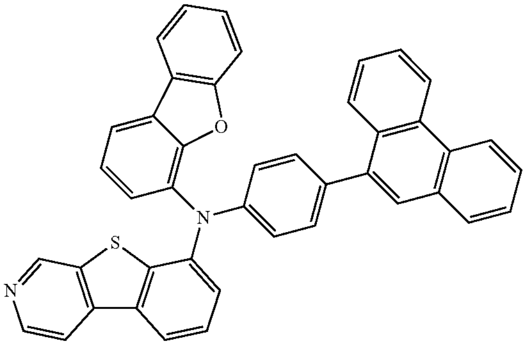
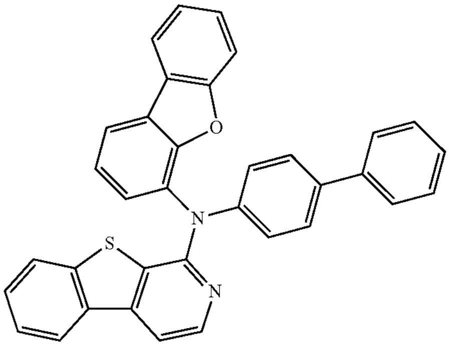
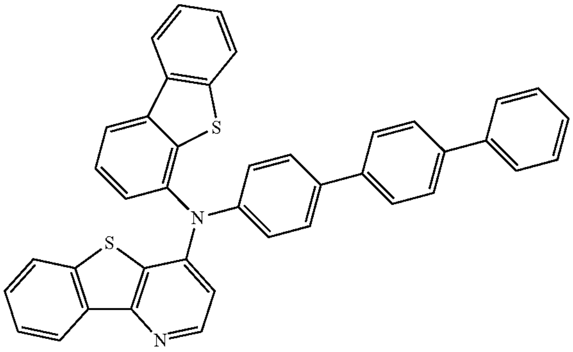
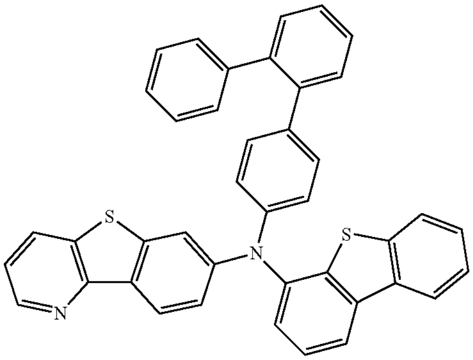

-continued
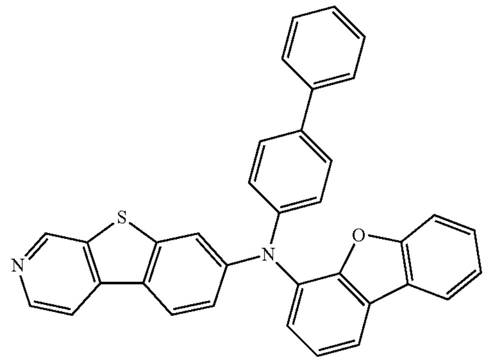
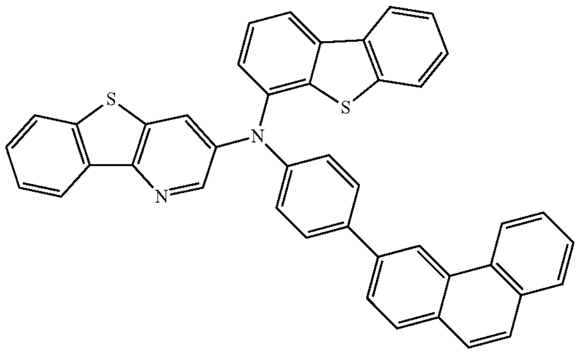
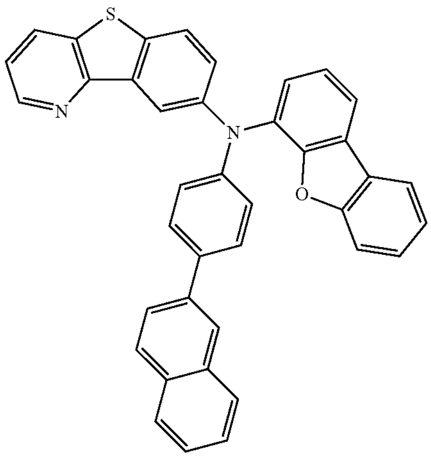
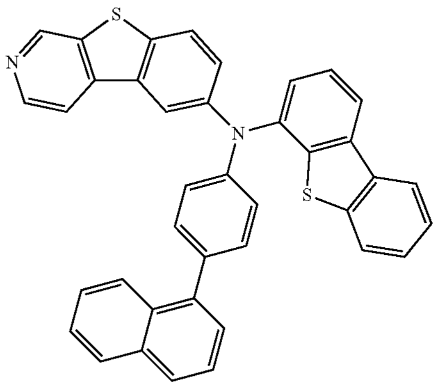
-continued
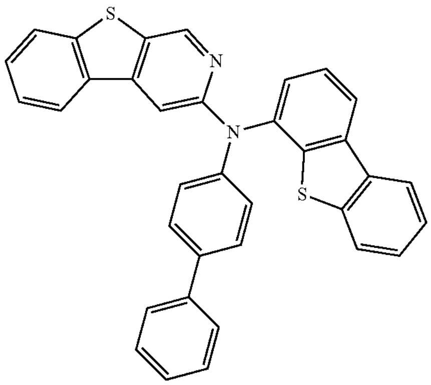
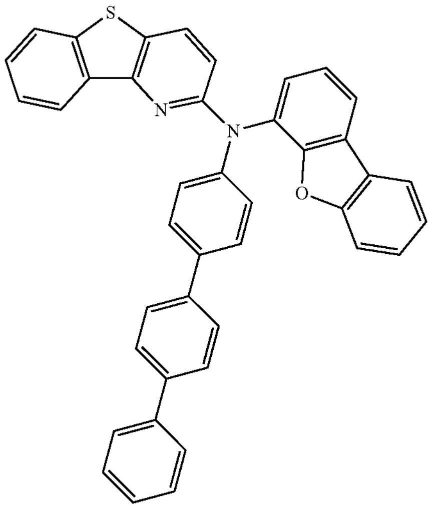
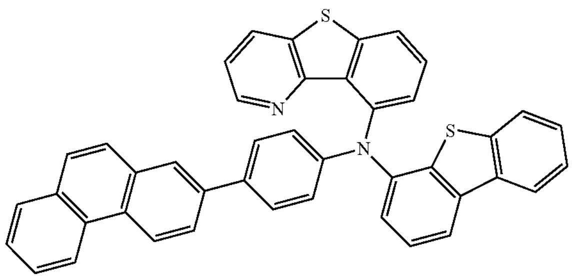
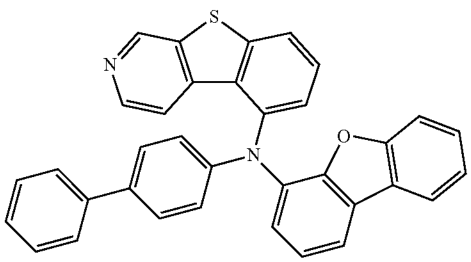

-continued
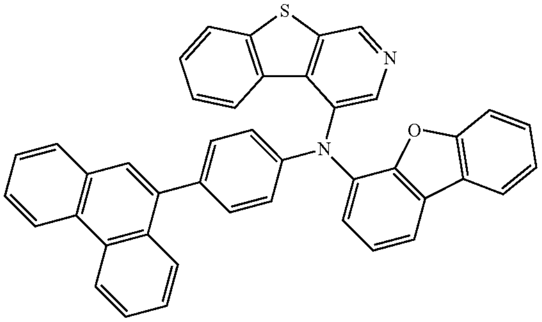
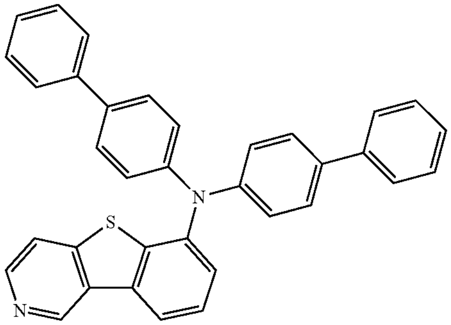
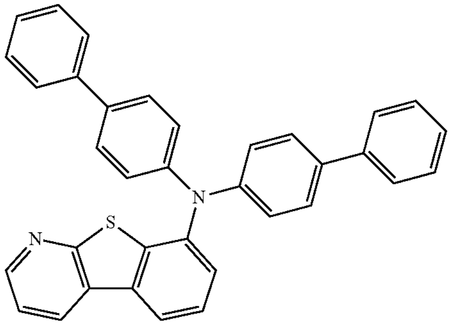
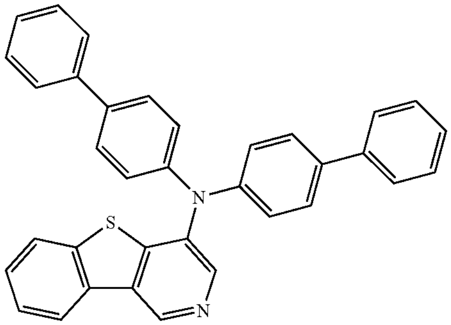
-continued
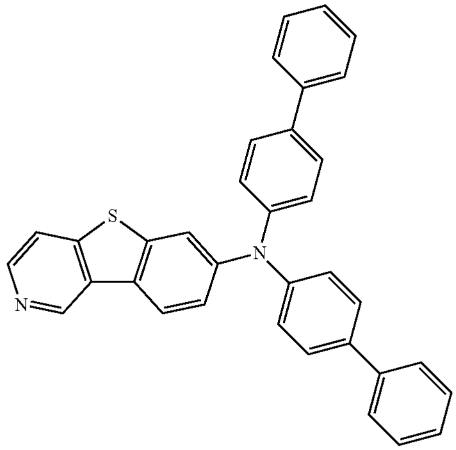
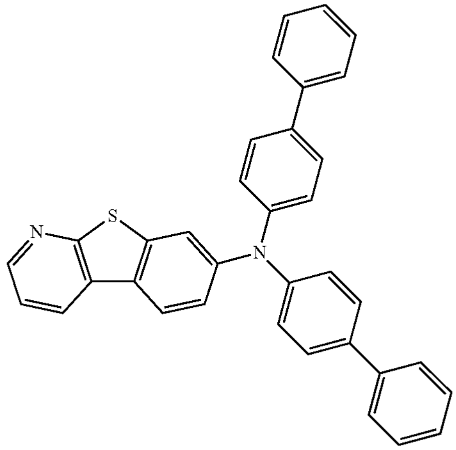
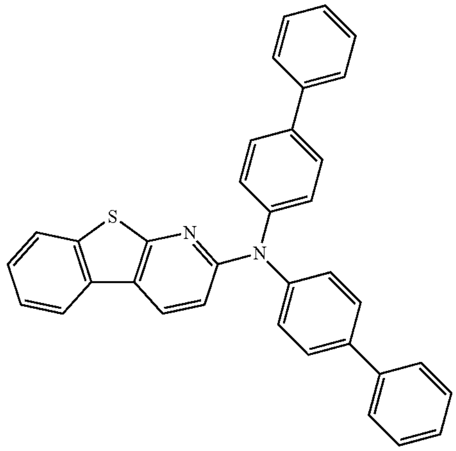

-continued
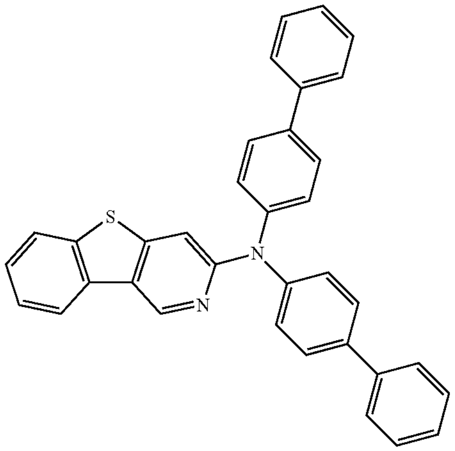
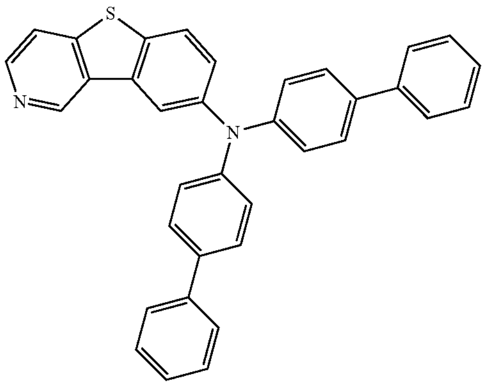
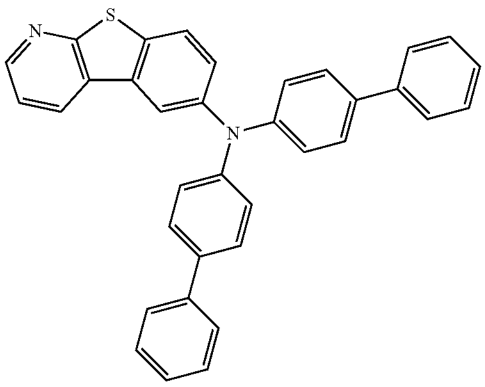
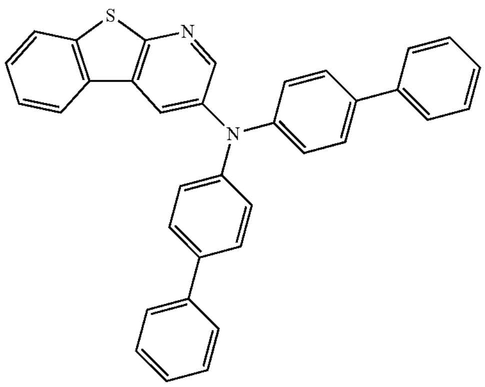
-continued
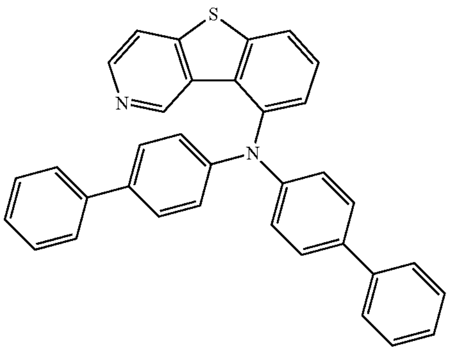
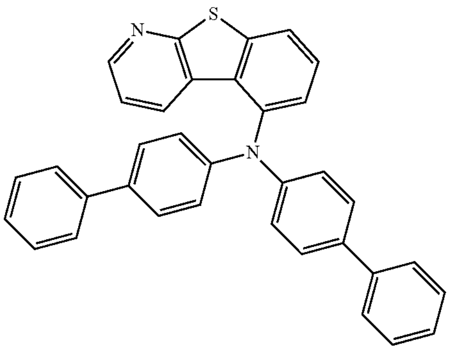
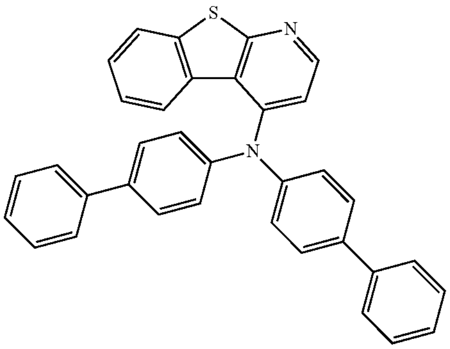
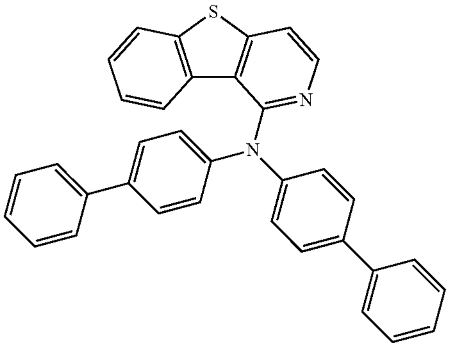
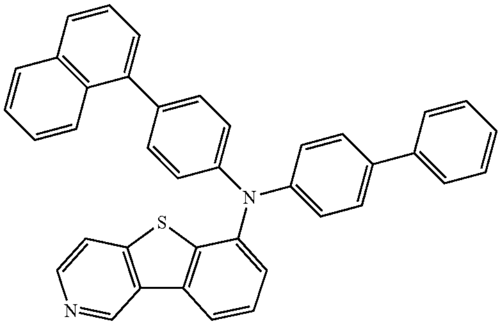

-continued
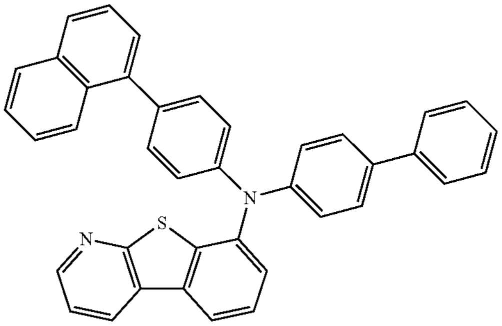
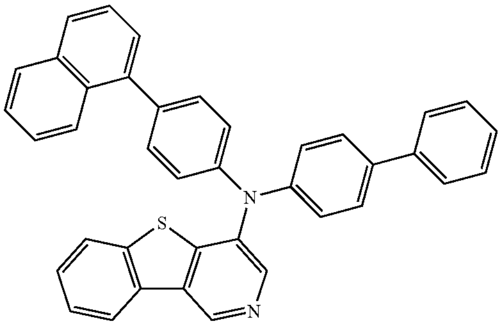
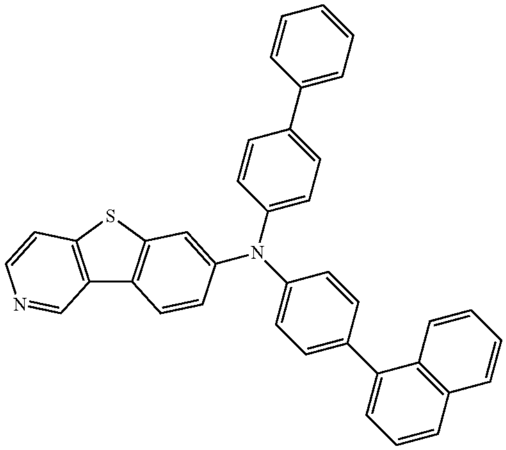
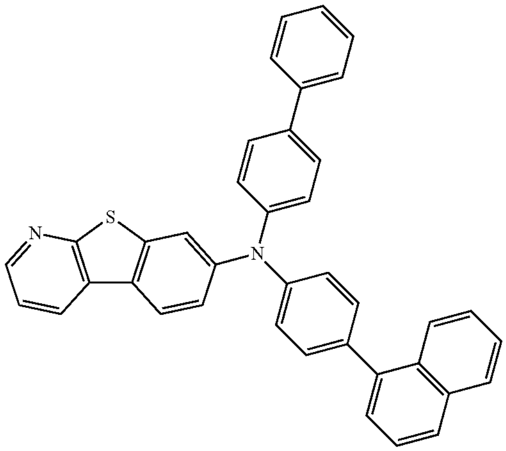
-continued
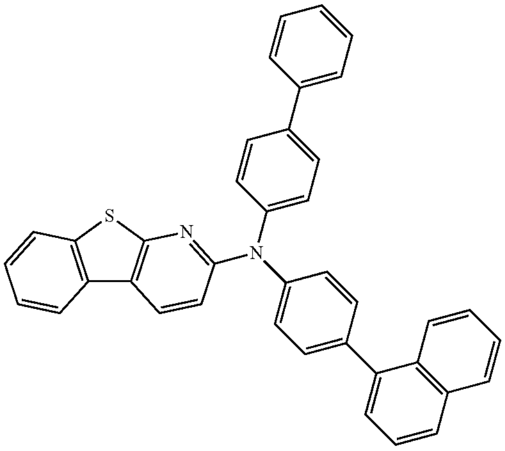
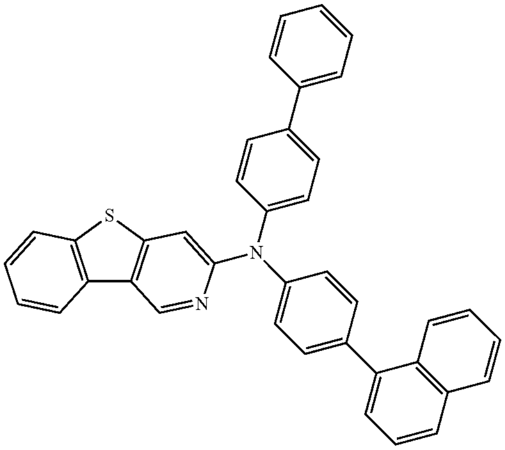
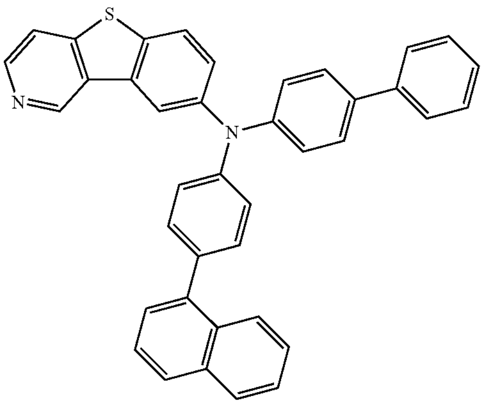
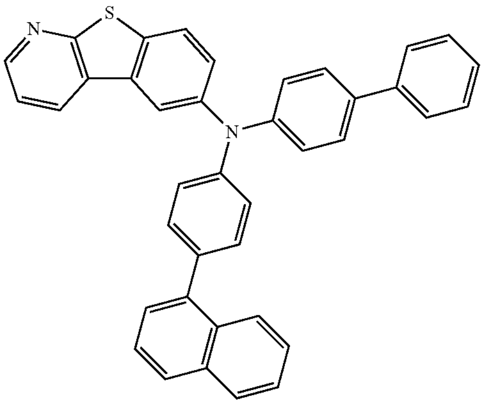

-continued
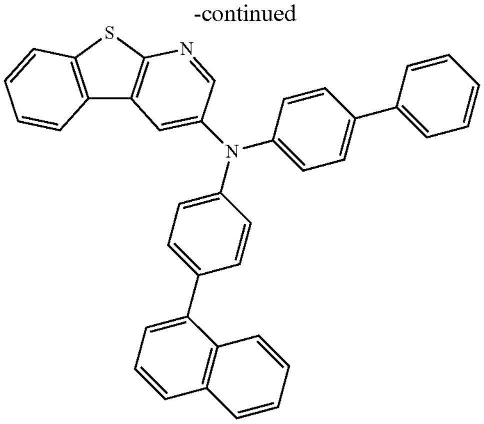
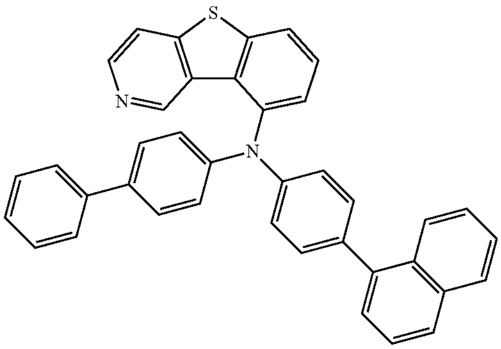
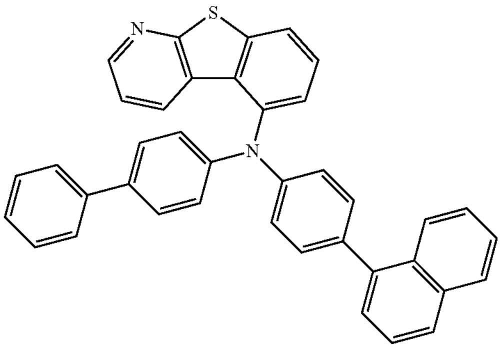
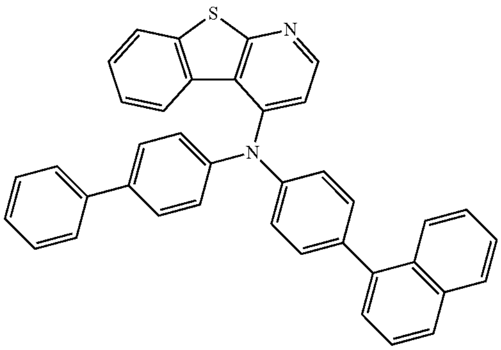
-continued
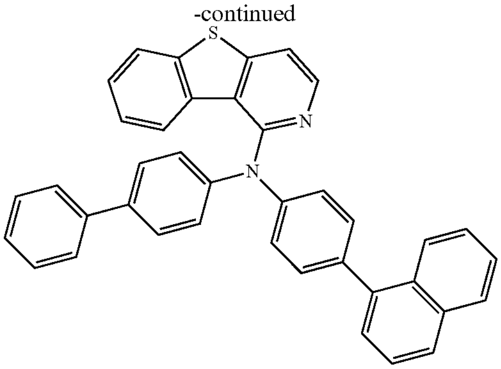
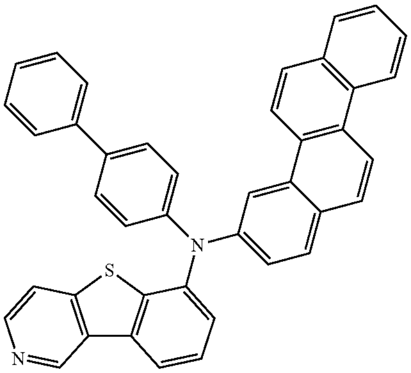
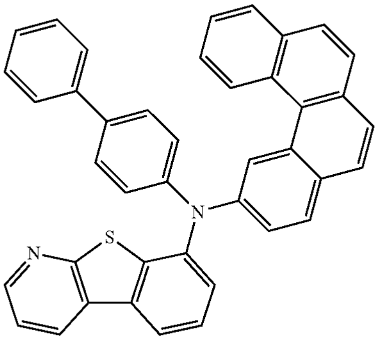
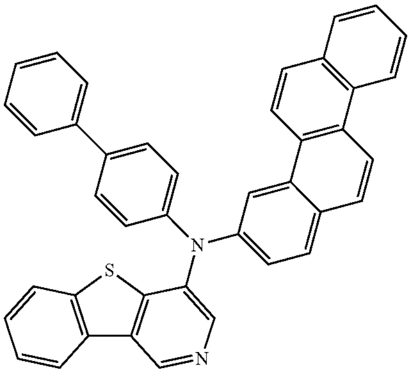

-continued
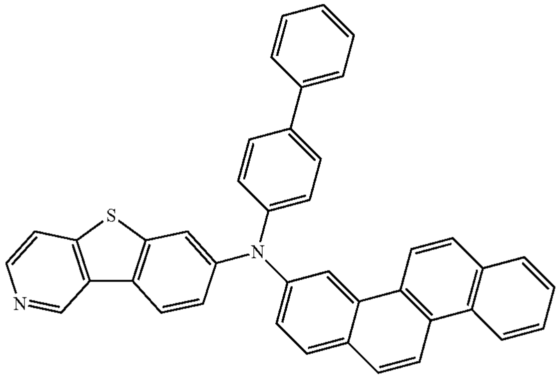
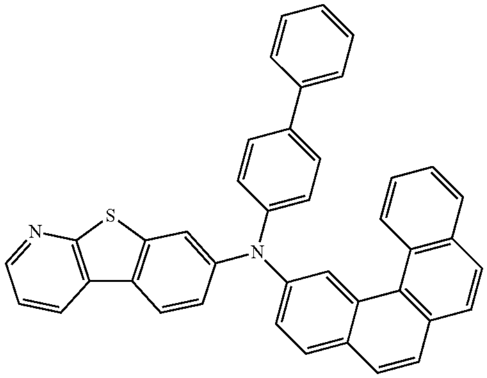
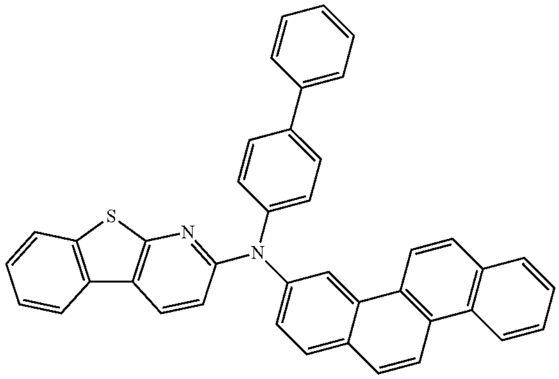
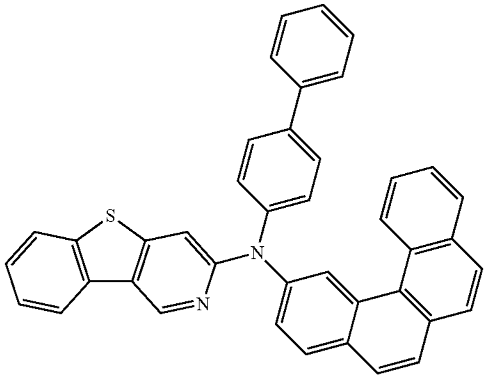
-continued
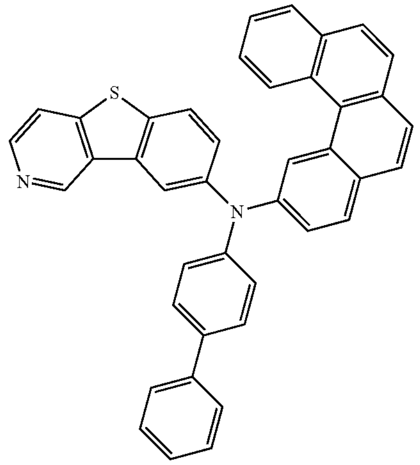
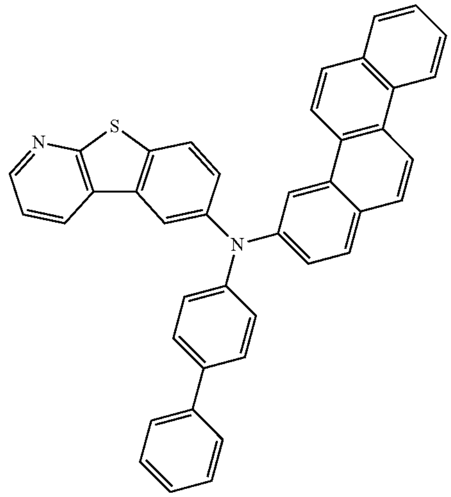
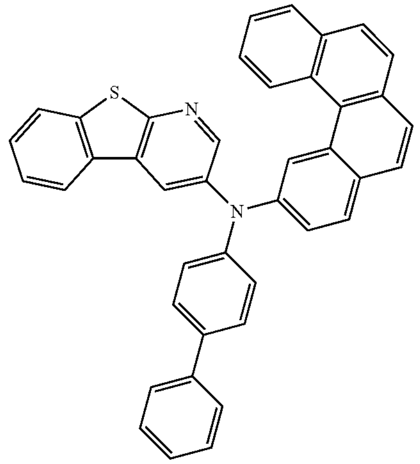
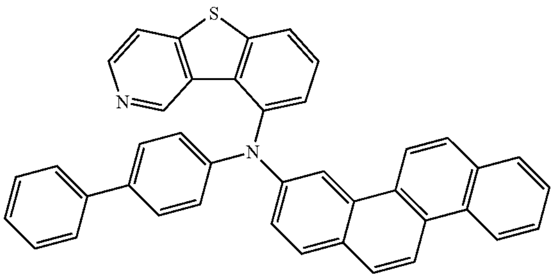

-continued
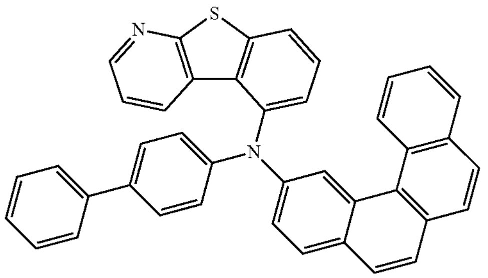
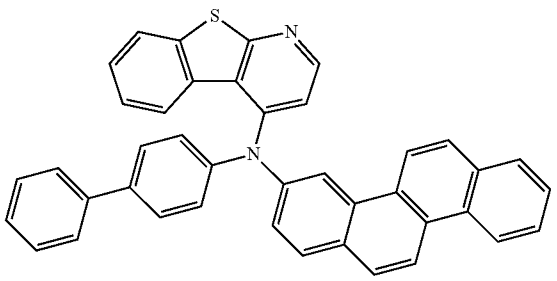
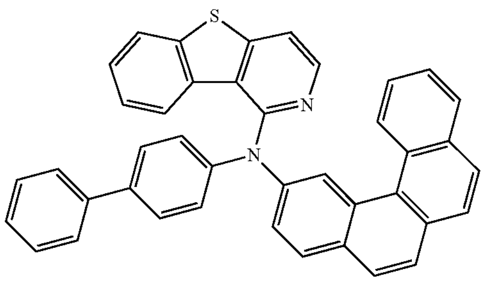
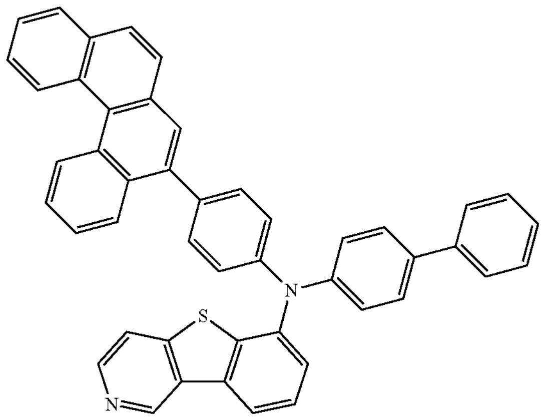
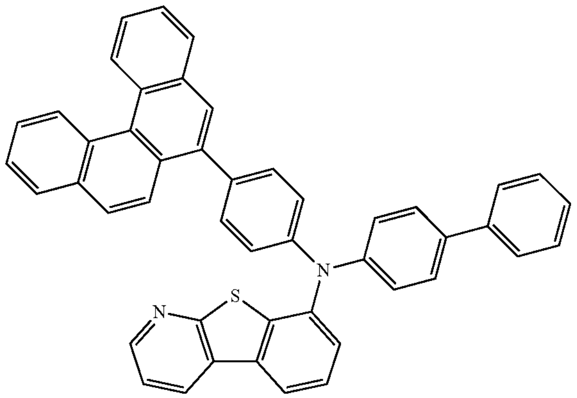
-continued
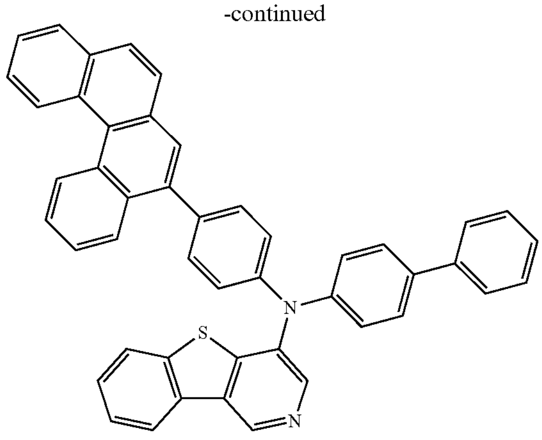
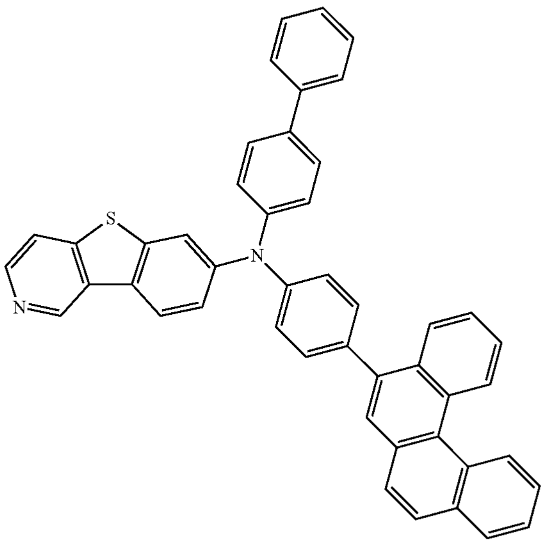
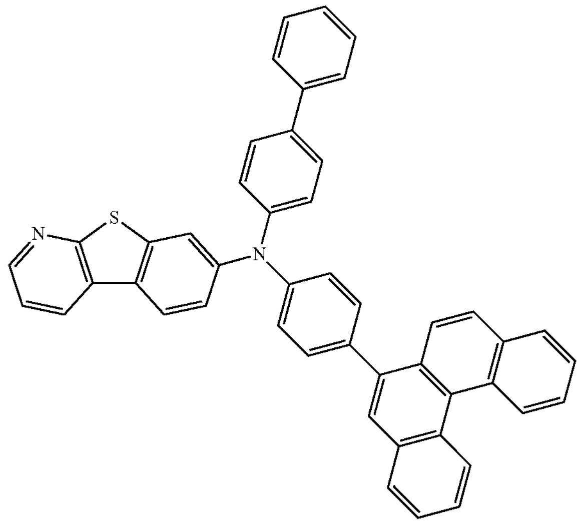

-continued
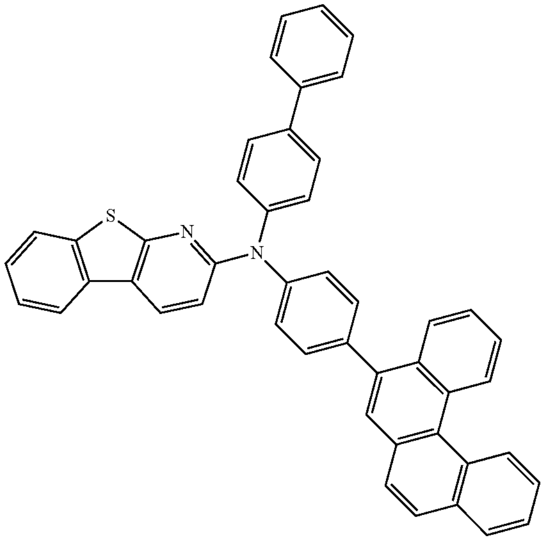
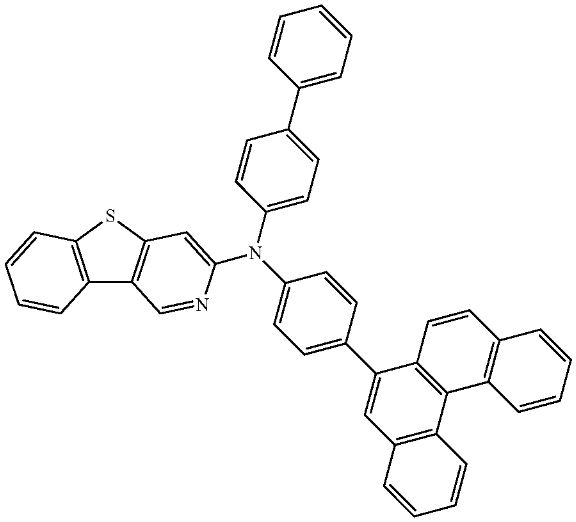
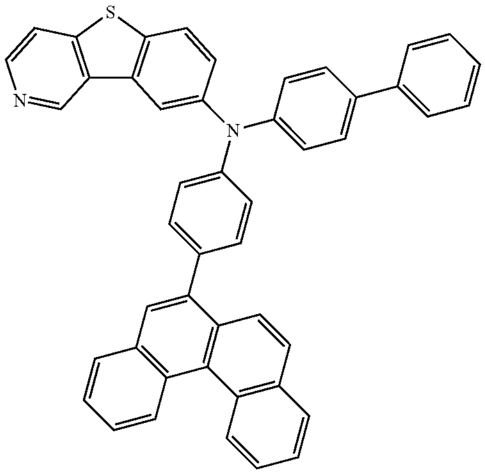
-continued
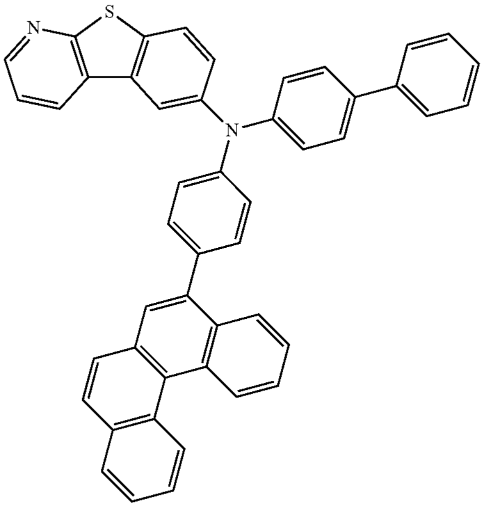
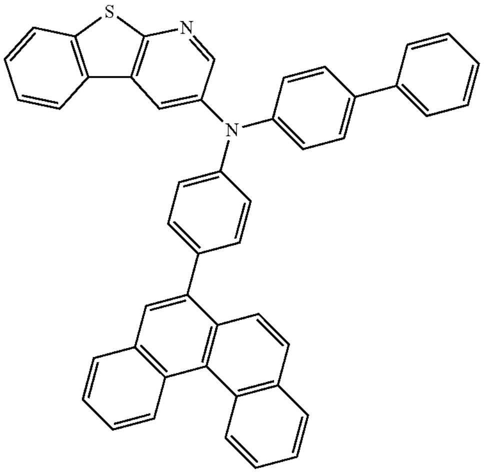
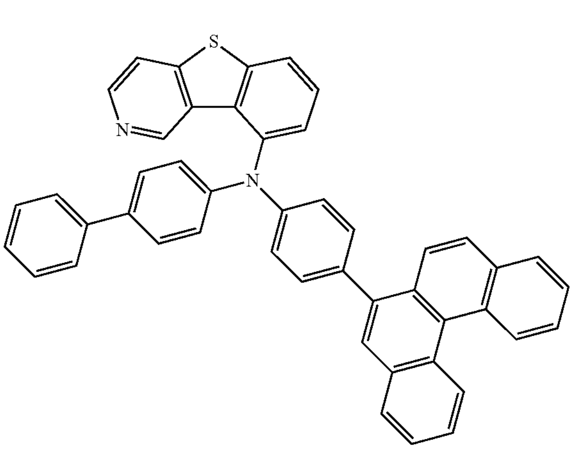

-continued
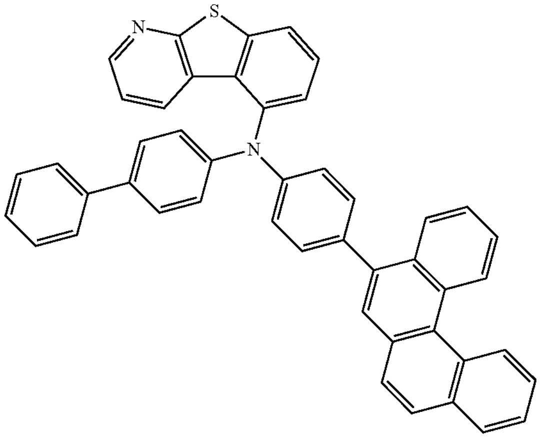
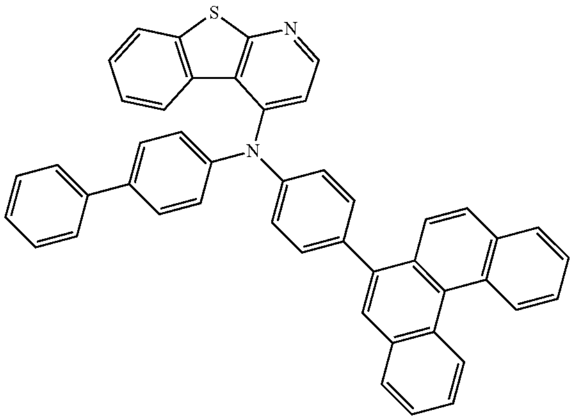
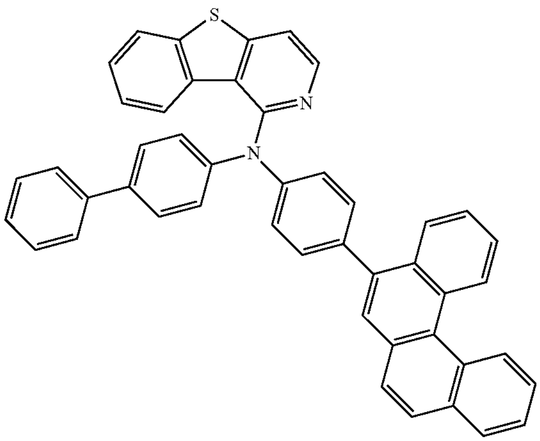
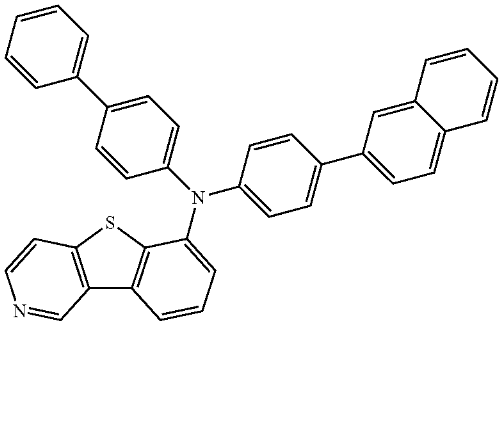
-continued
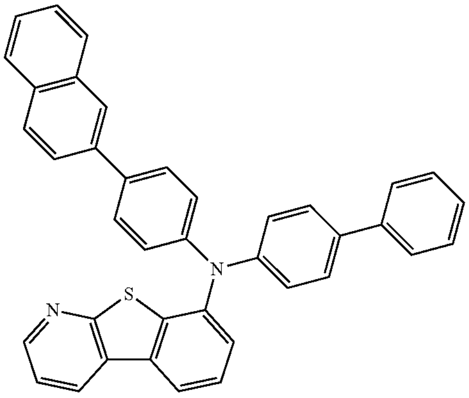
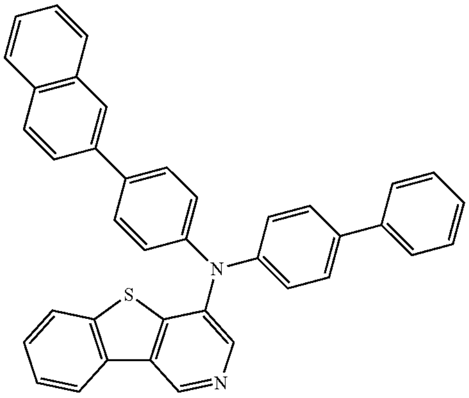
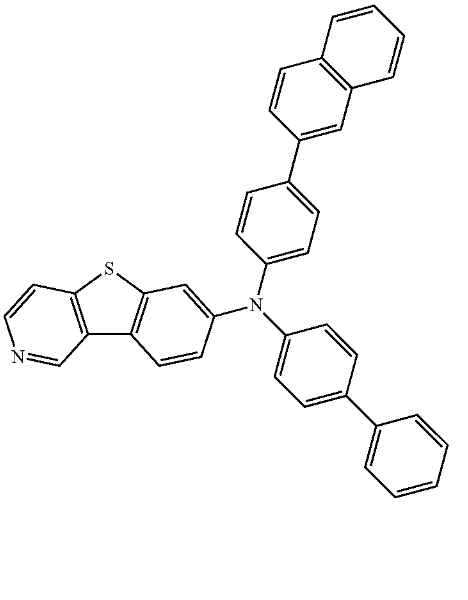

-continued
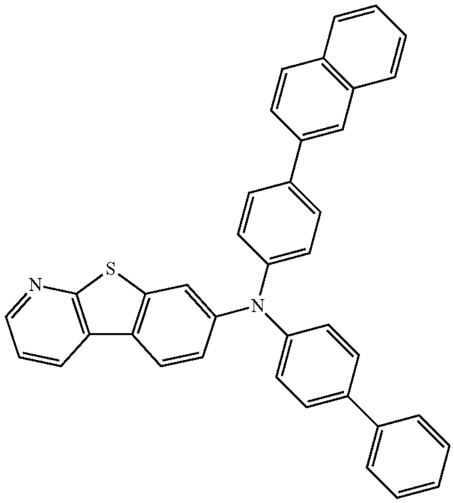
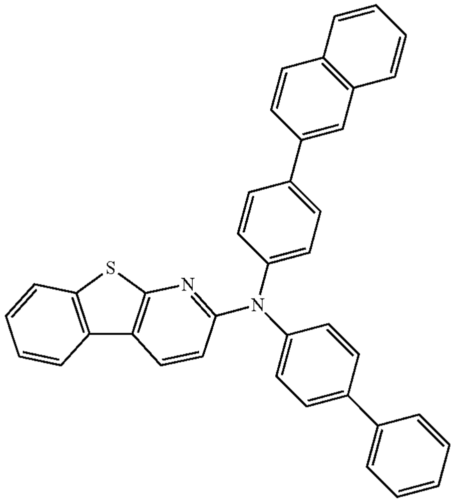
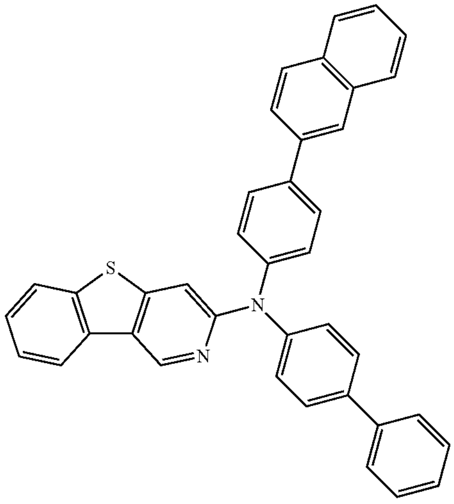
-continued
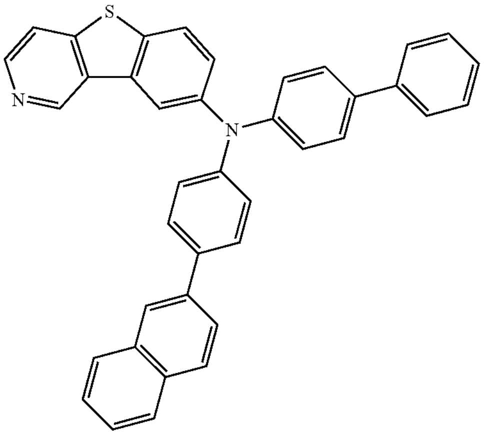
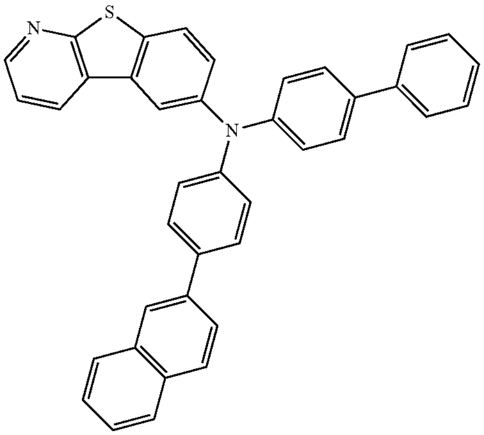
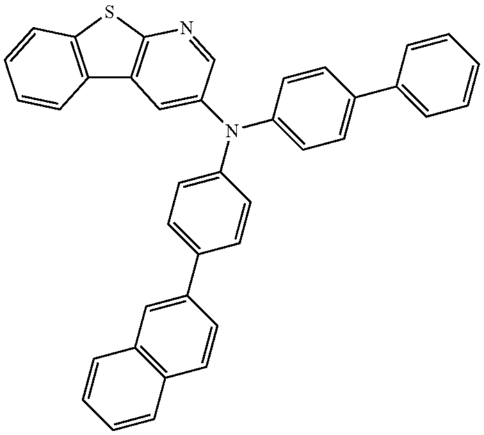
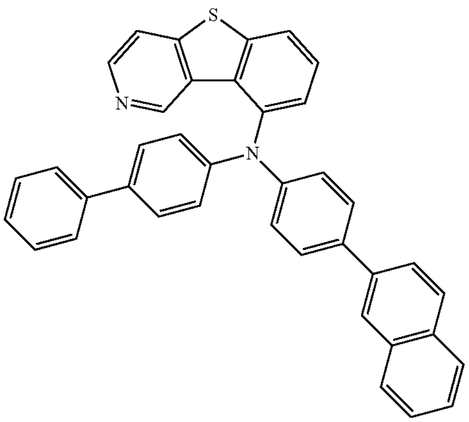

-continued
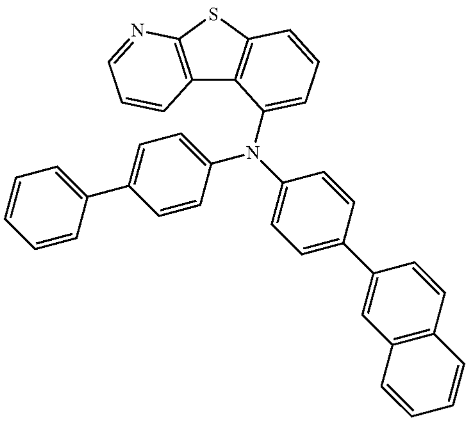
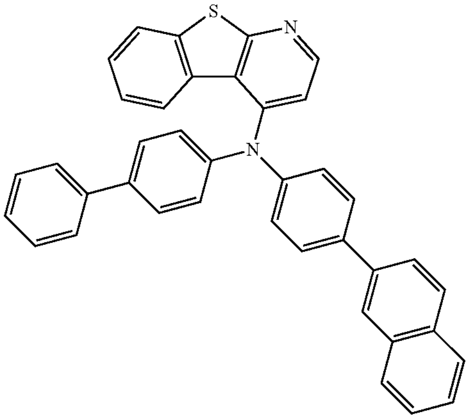
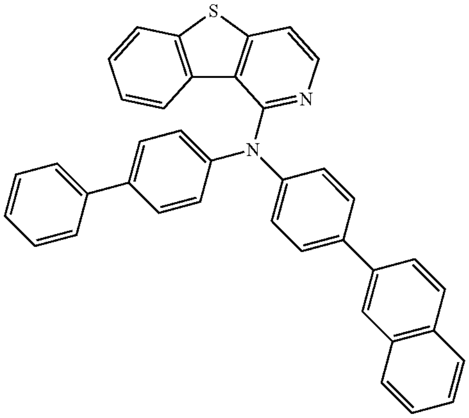
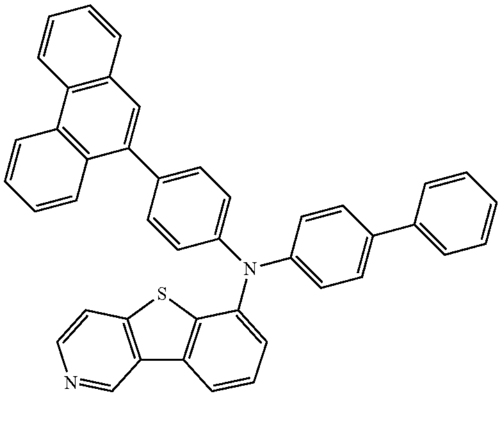
-continued
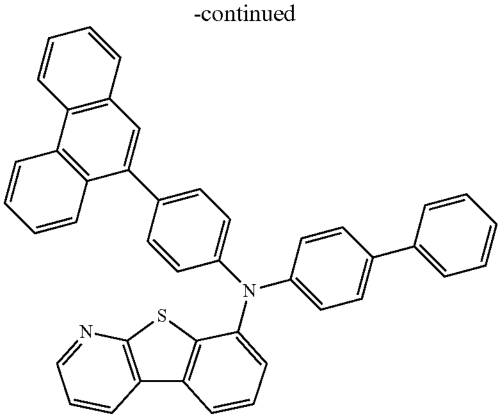
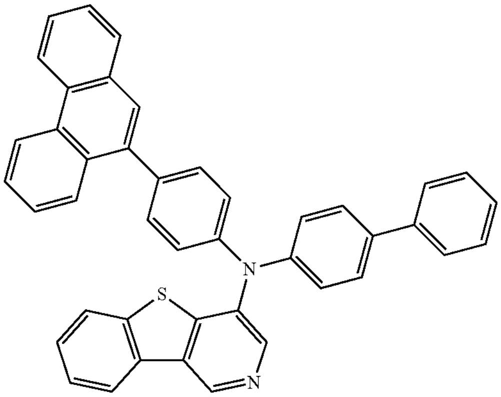
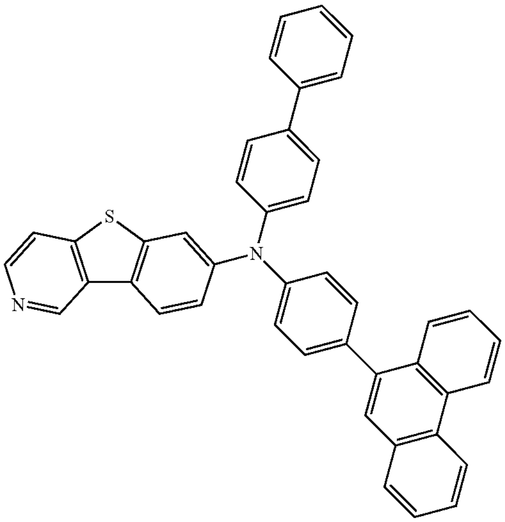

-continued
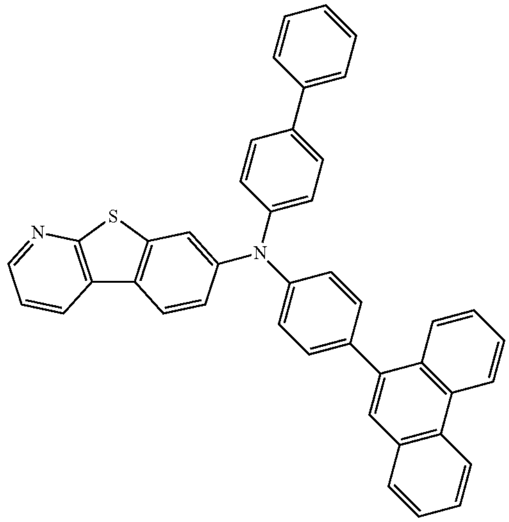
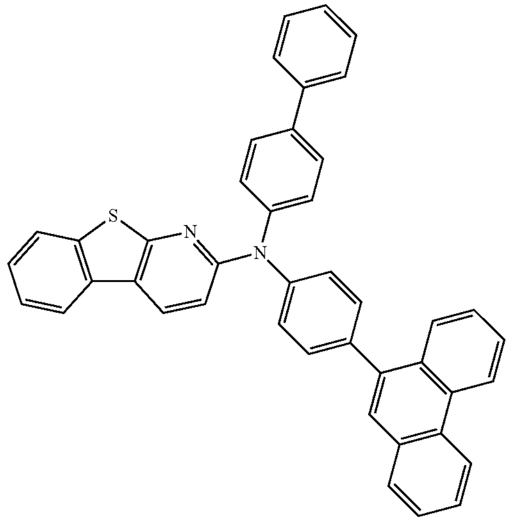
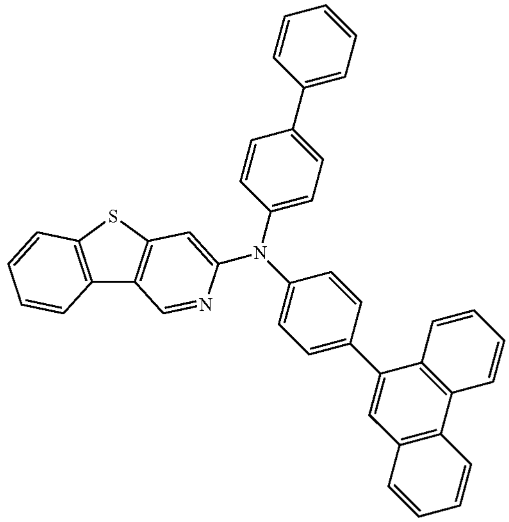
-continued
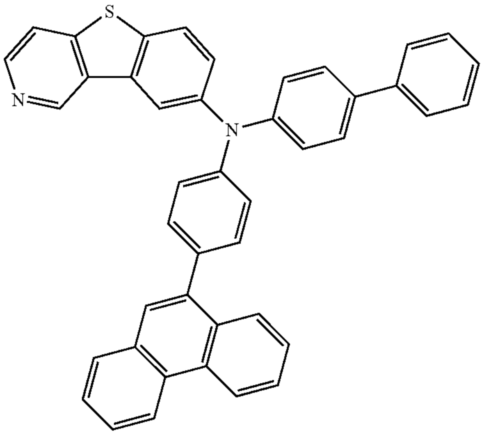
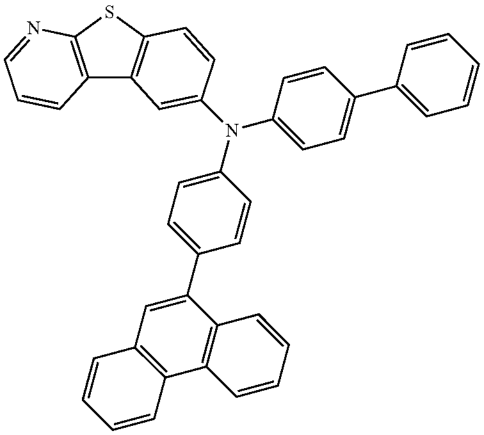
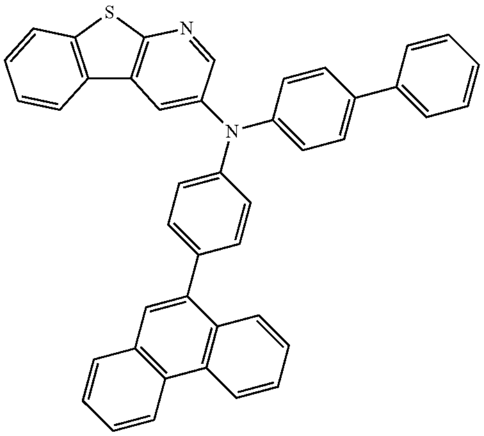
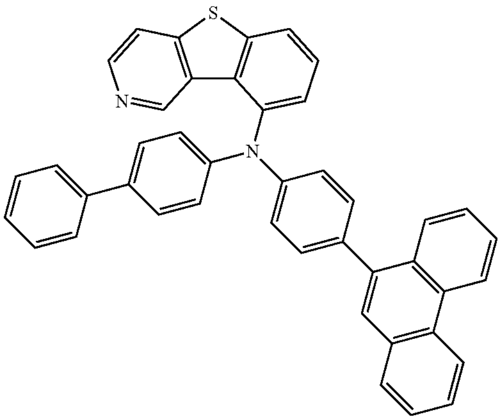

-continued
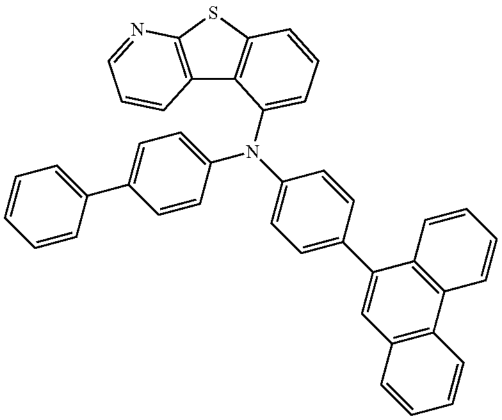
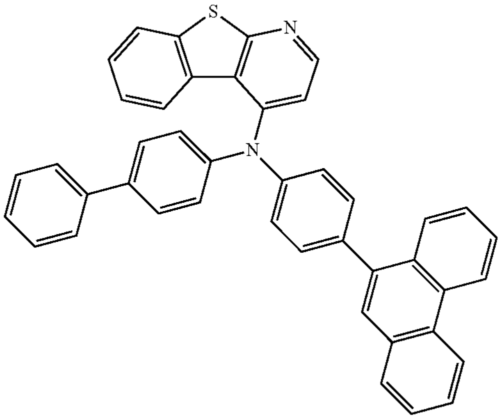
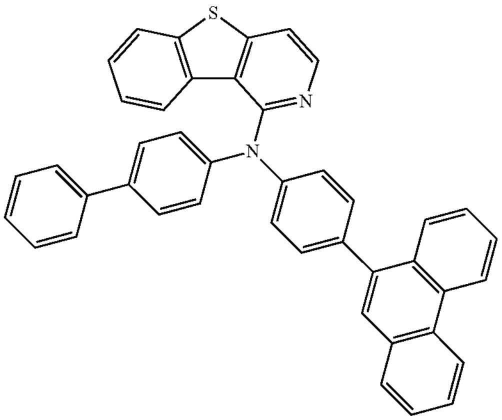
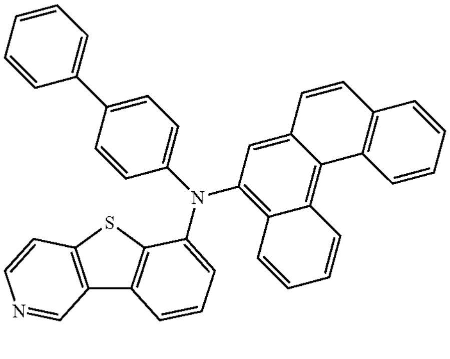
-continued
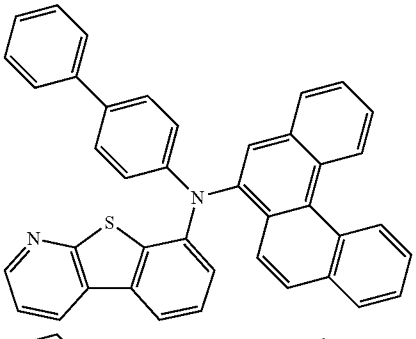
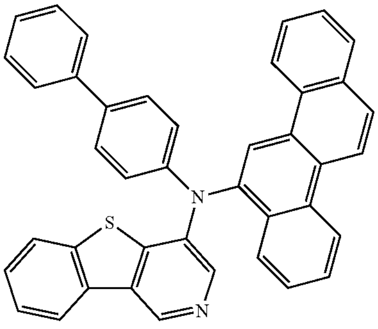
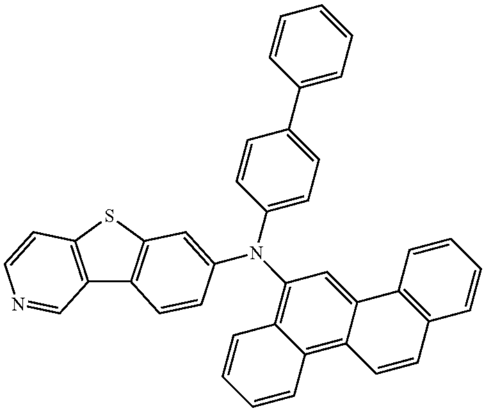
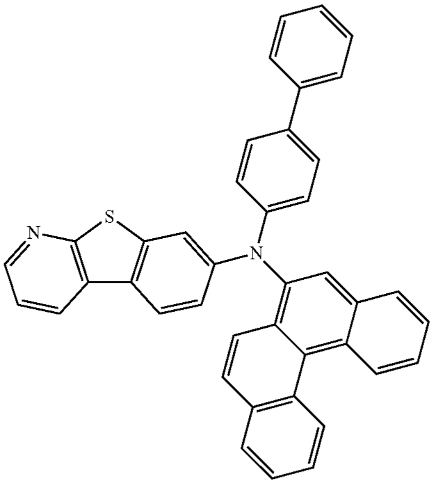

-continued
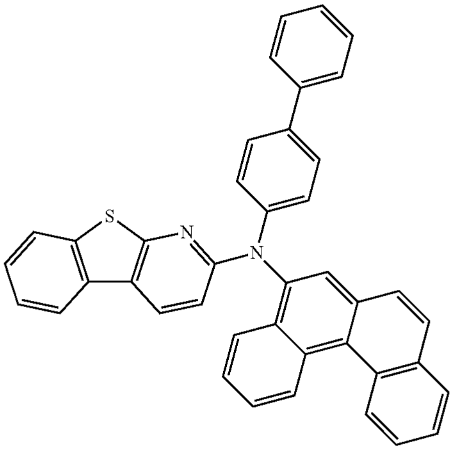
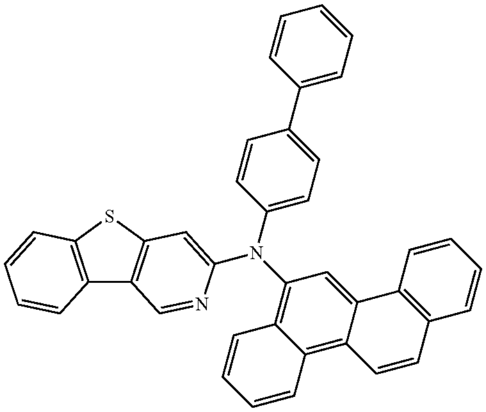
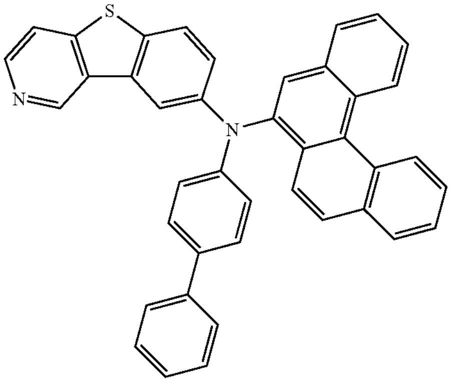
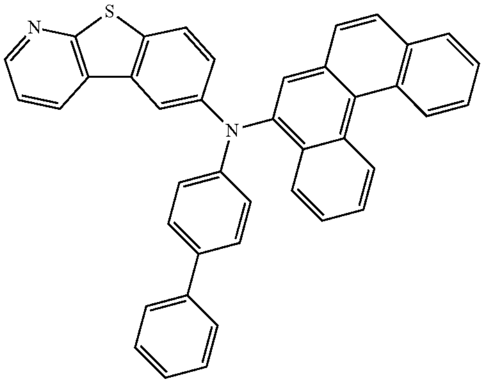
-continued
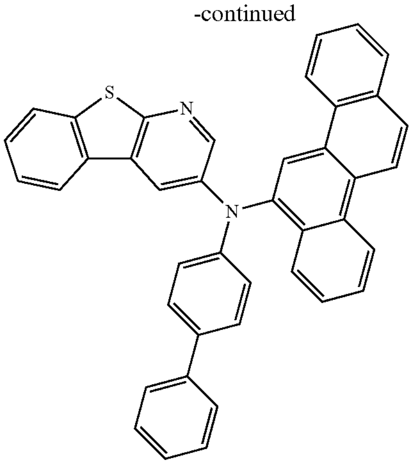
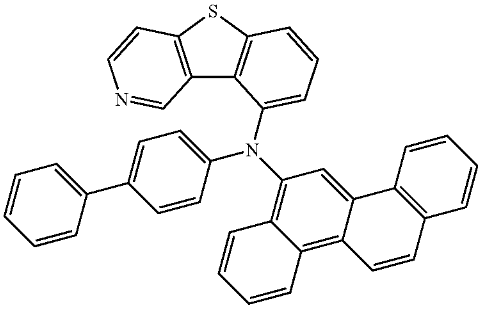
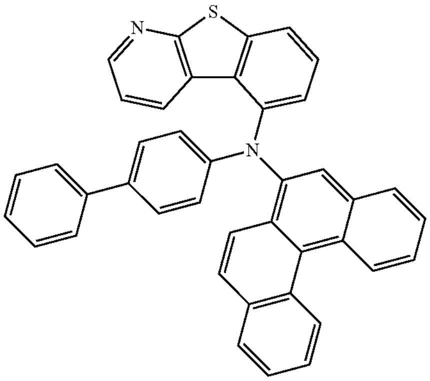
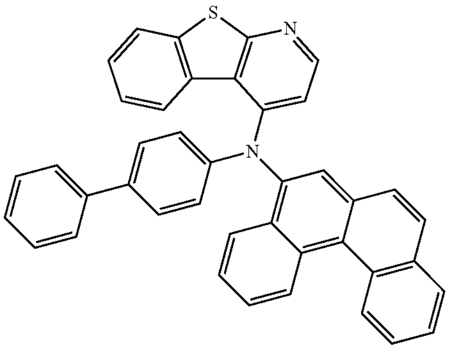

-continued
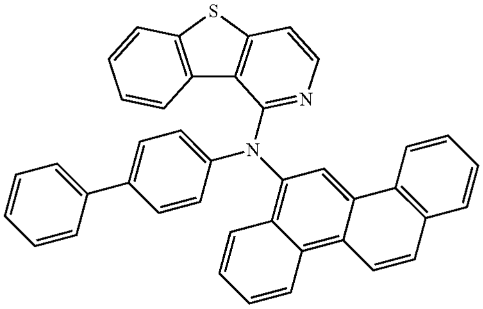
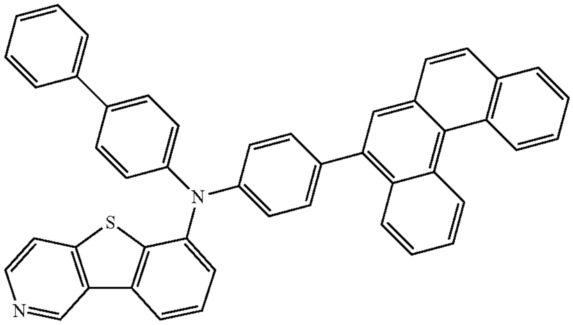
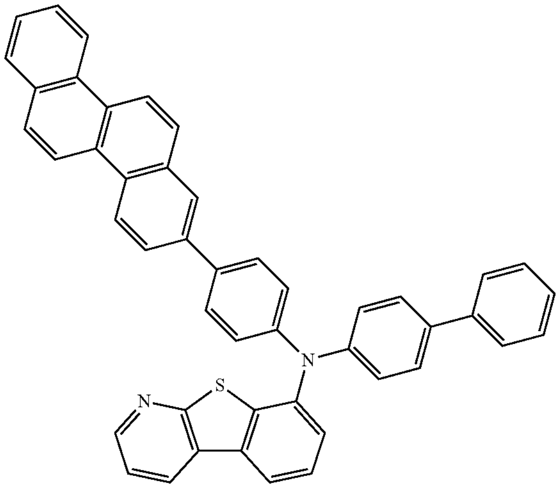
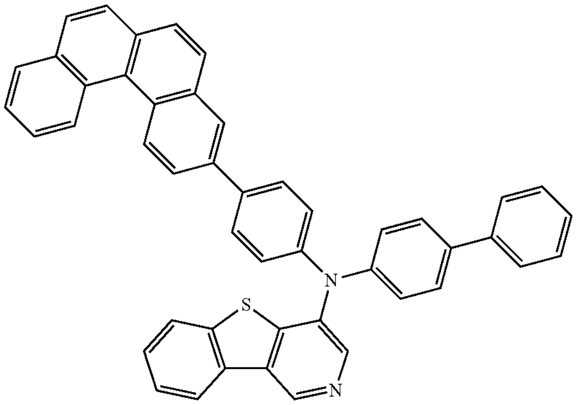
-continued
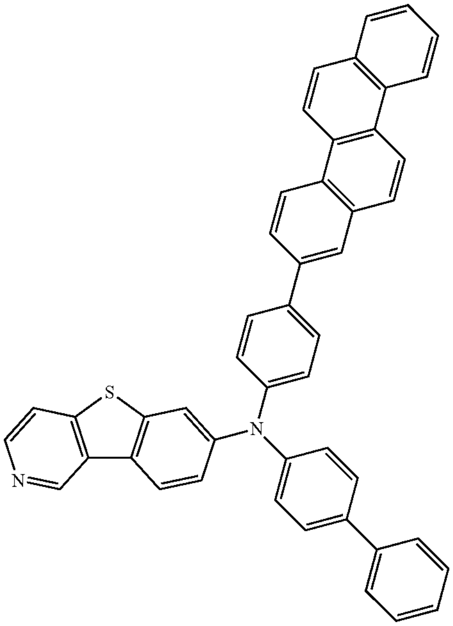
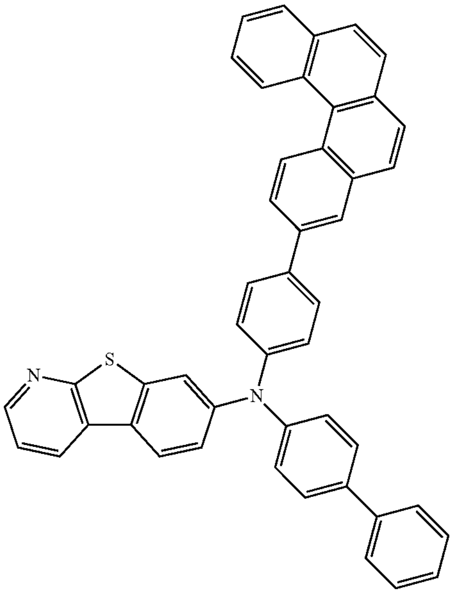

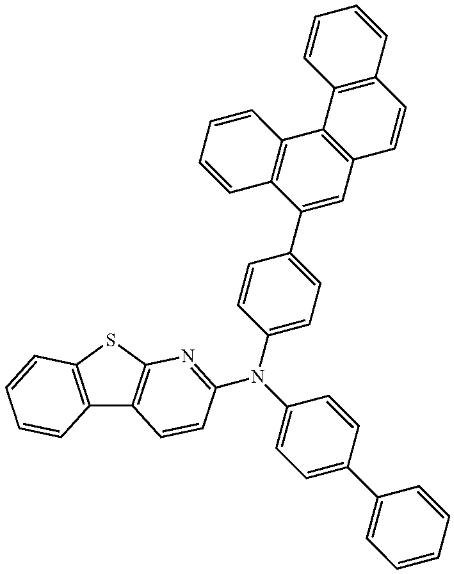
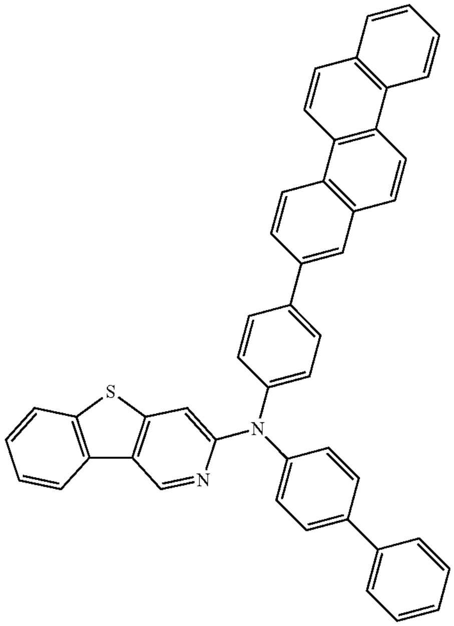
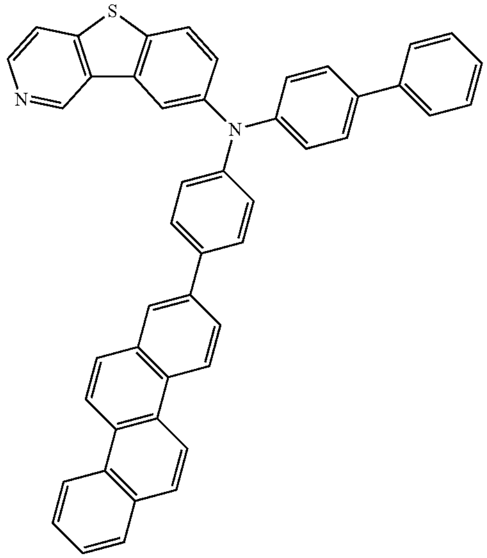
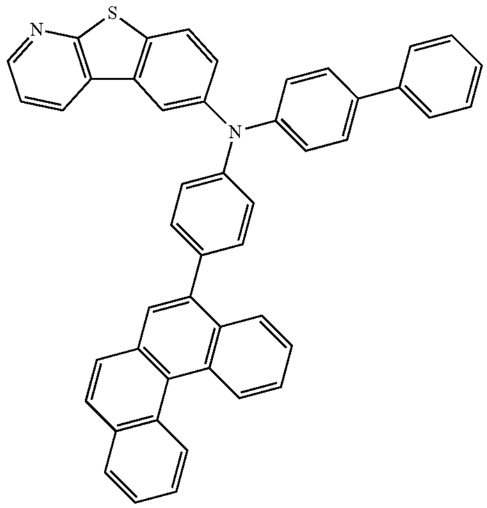
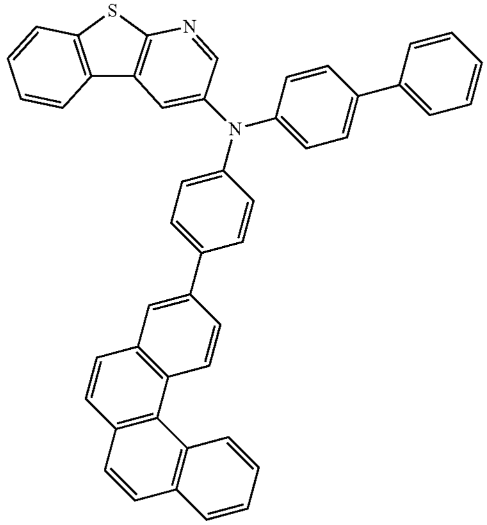

-continued
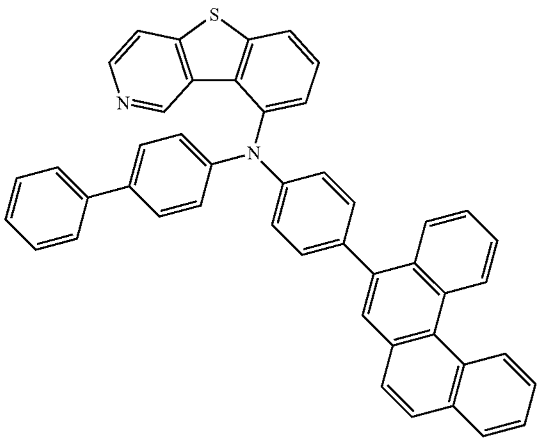
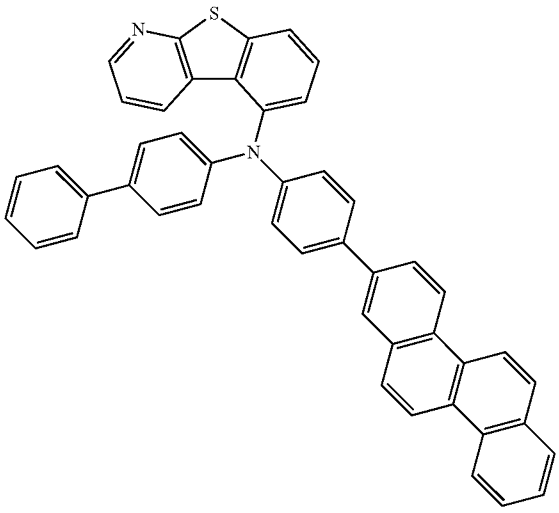
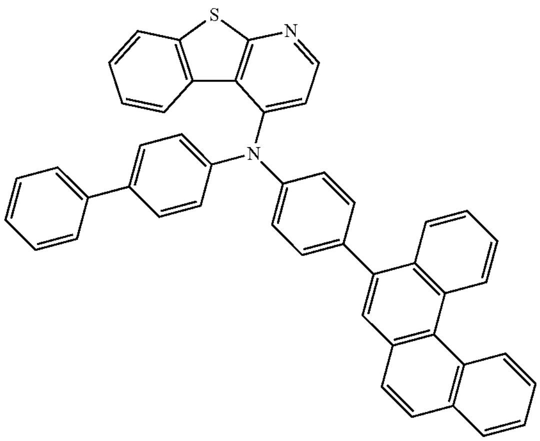
-continued
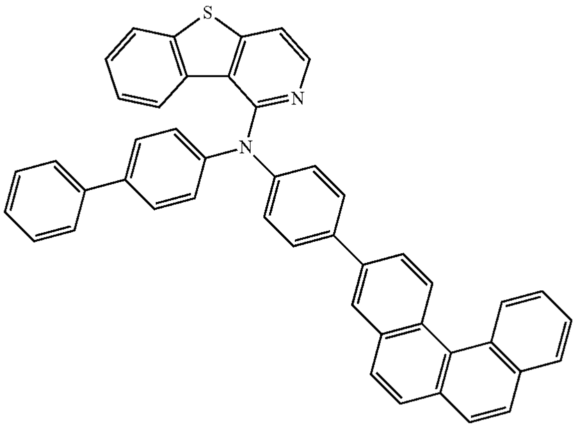
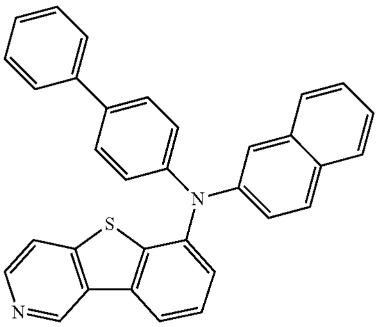
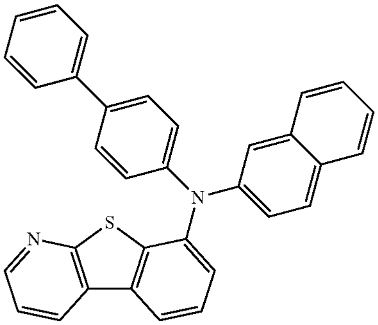
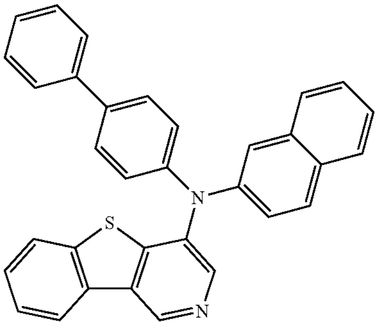

-continued
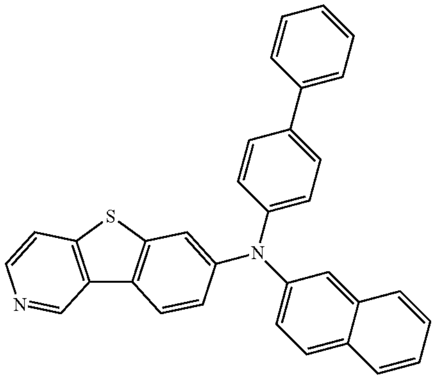
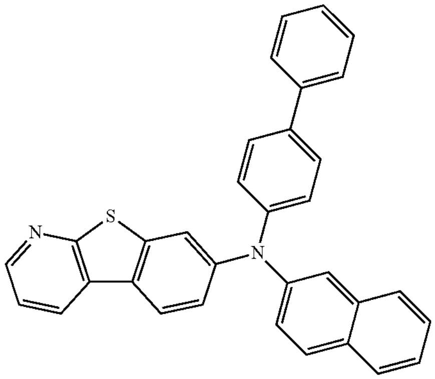
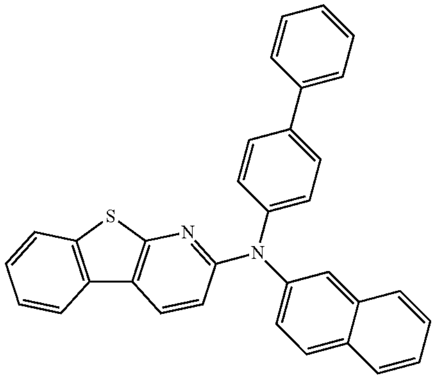
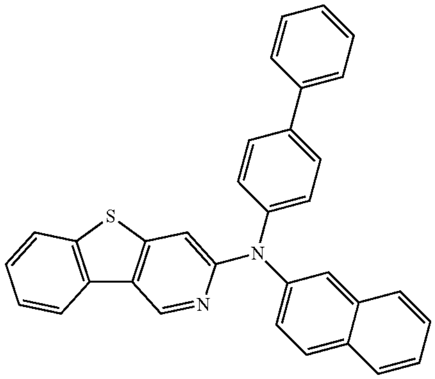
-continued
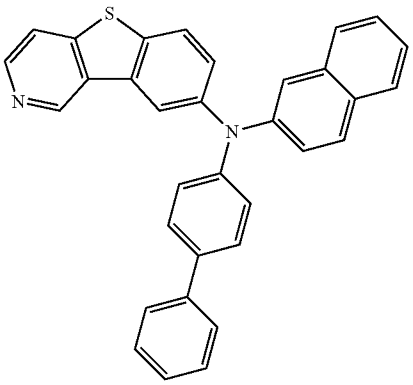
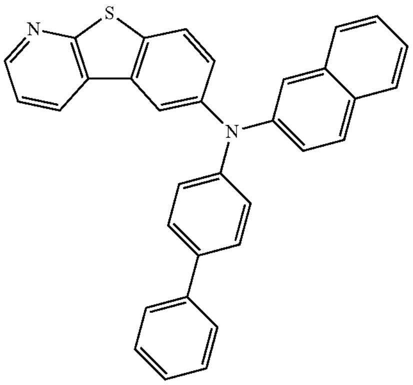
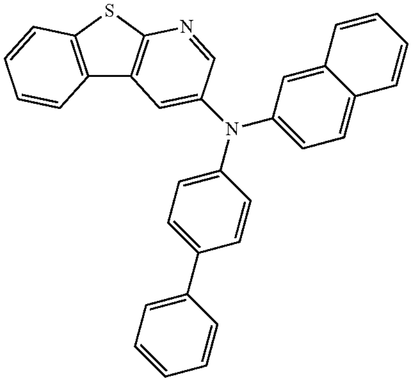
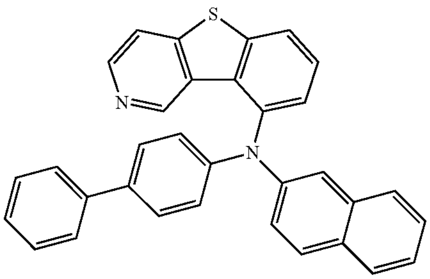
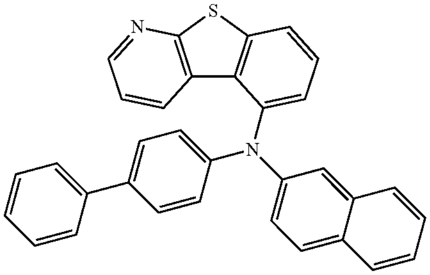

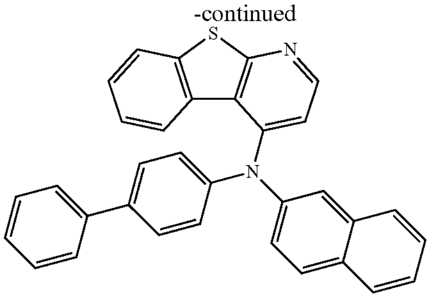
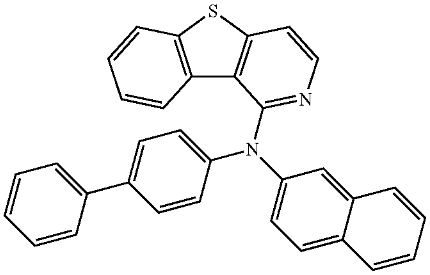
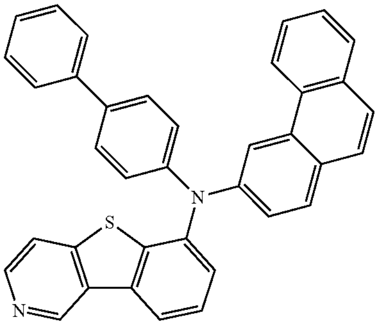
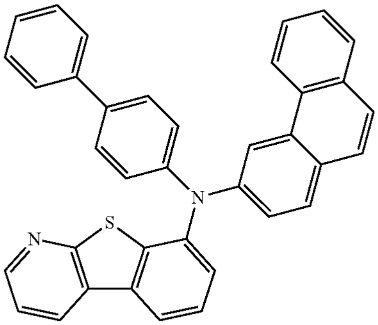
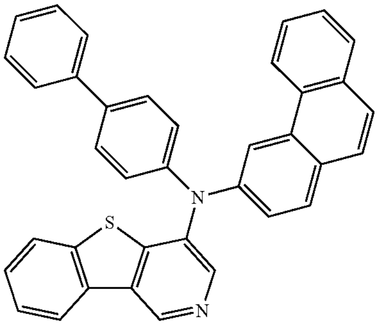
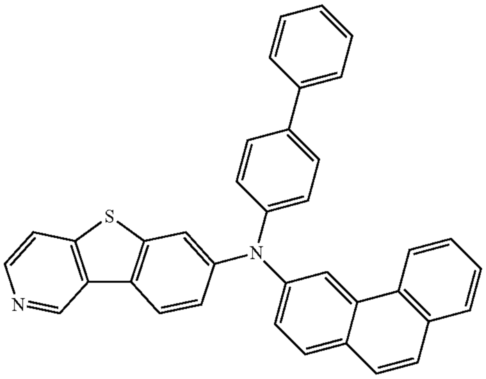
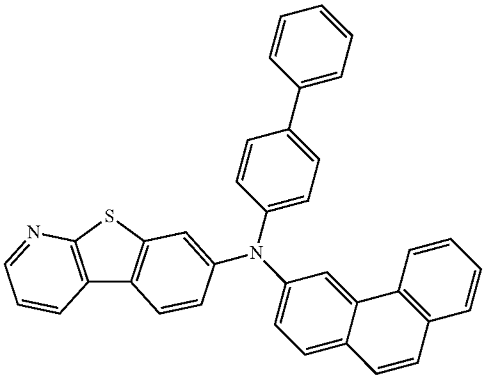
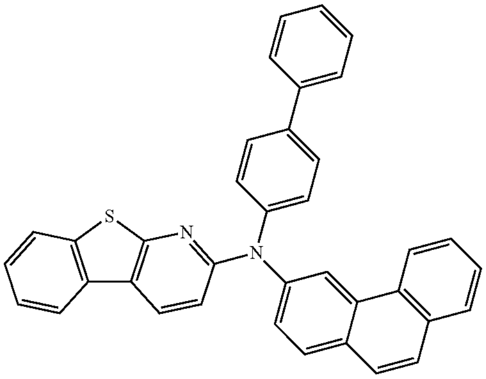
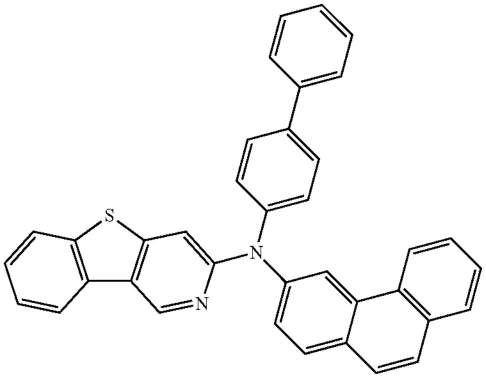

-continued
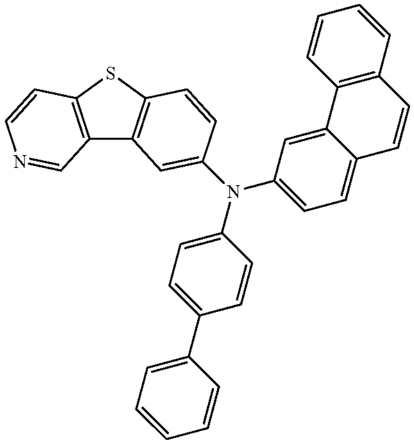
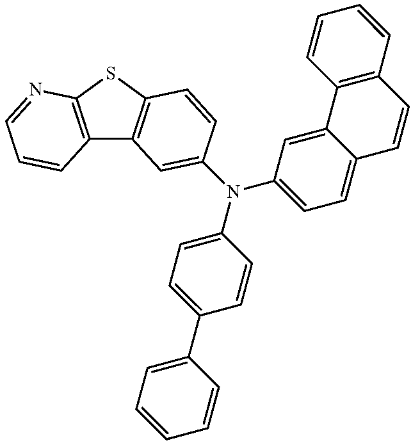
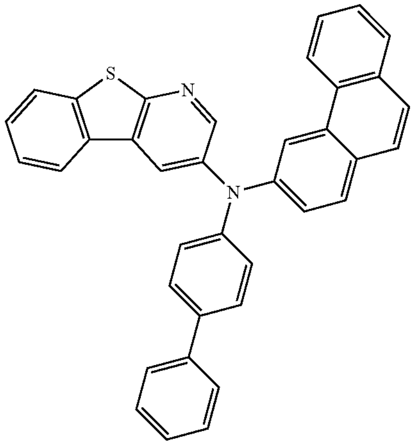
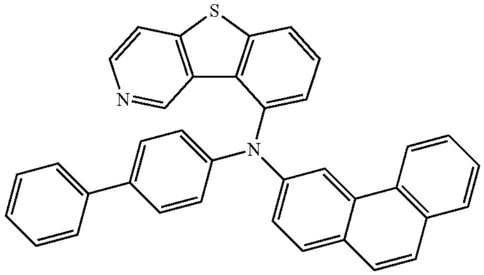
-continued
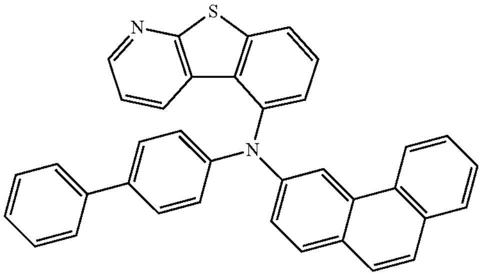
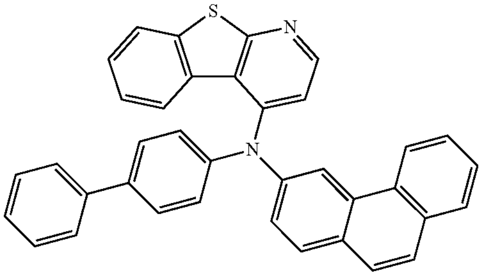
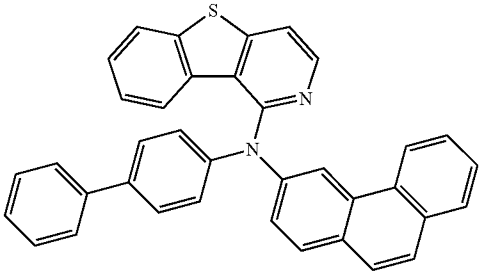
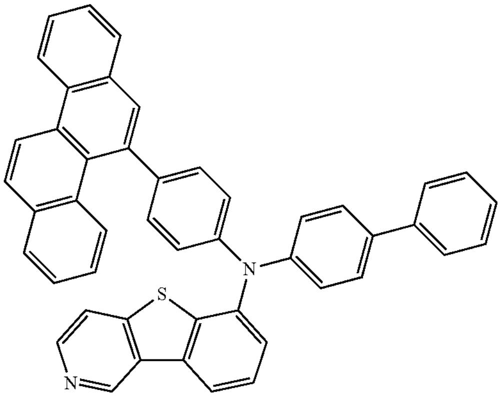
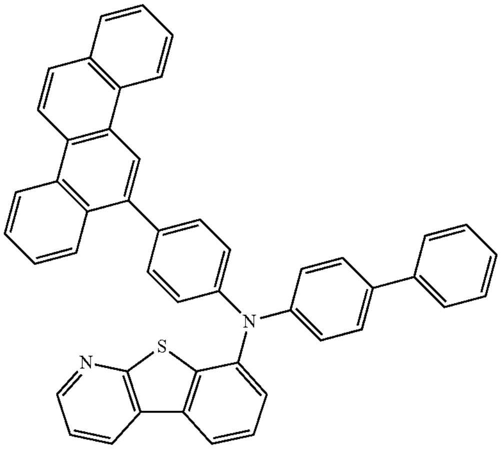

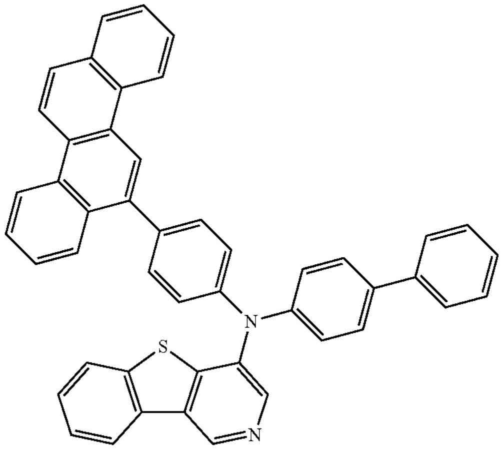
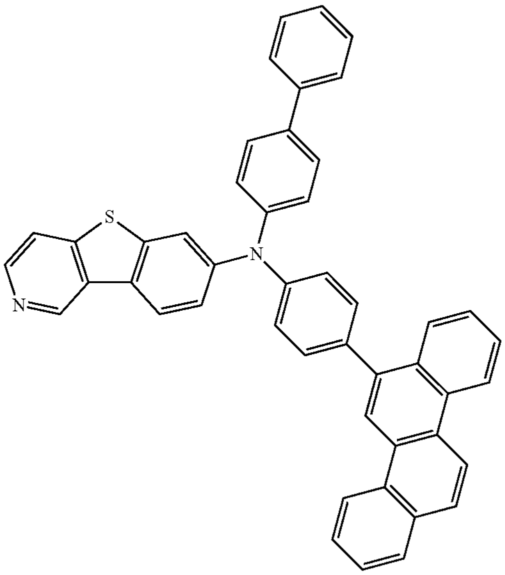
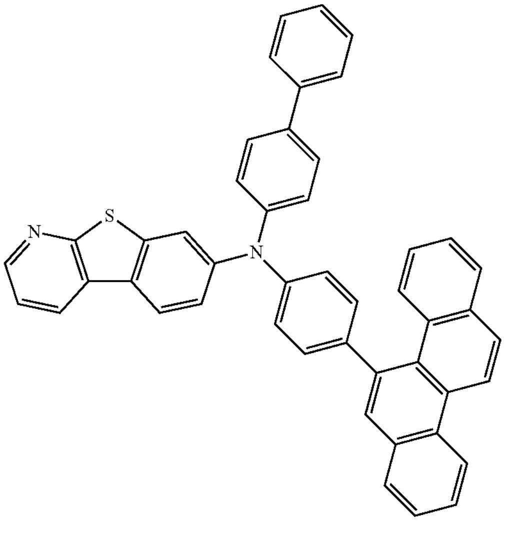
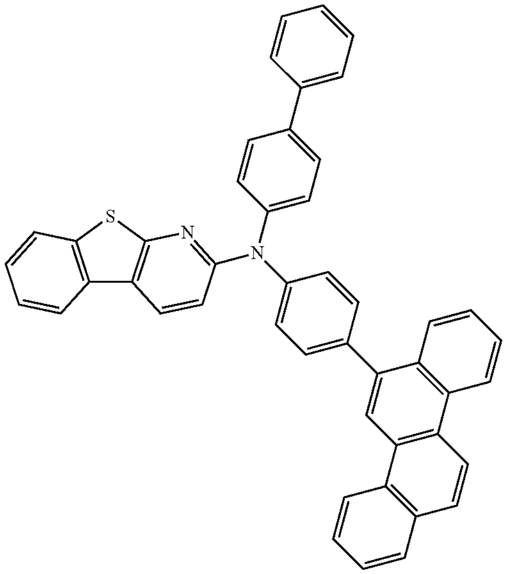
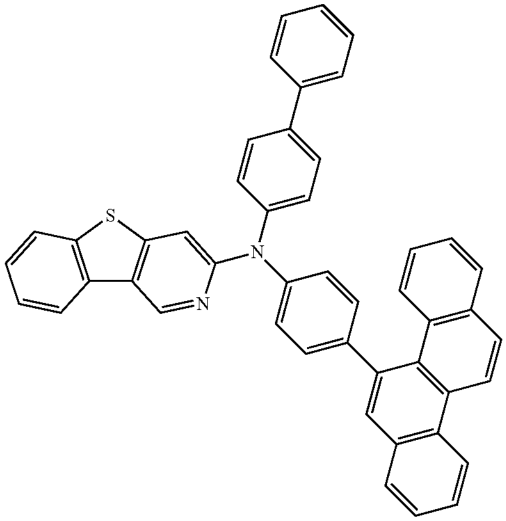
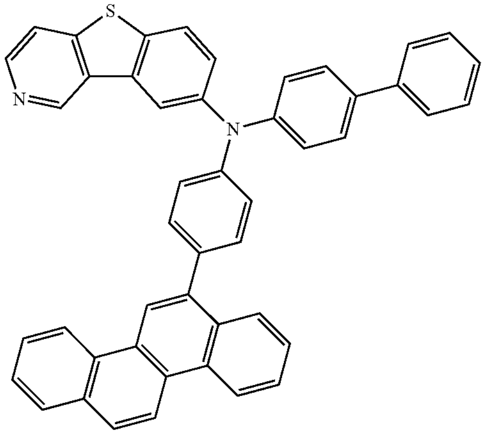

-continued
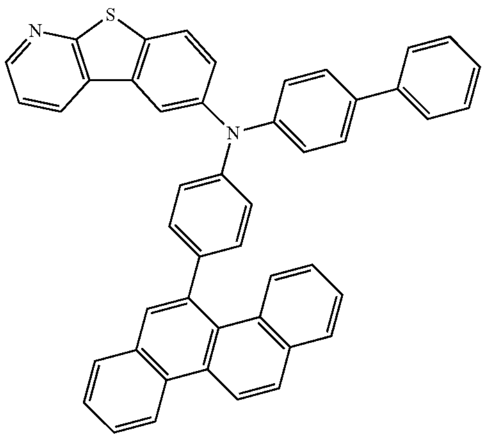
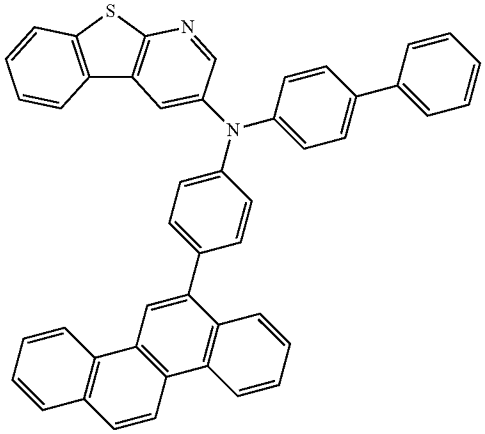
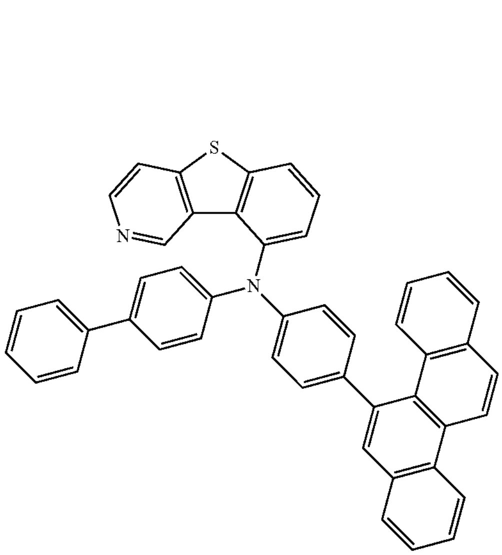
-continued
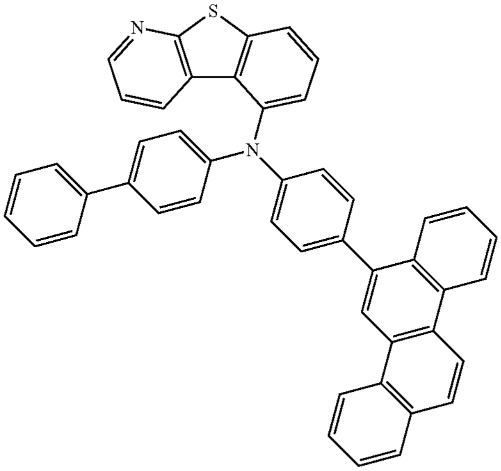
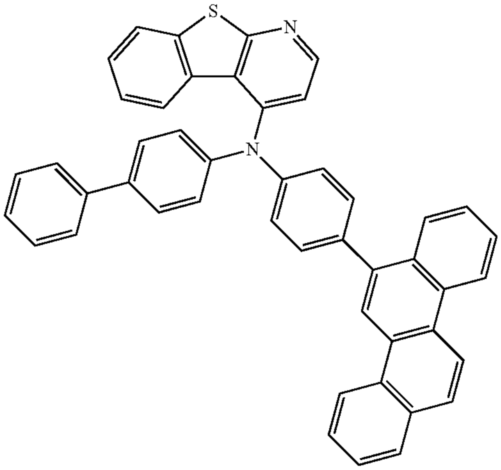
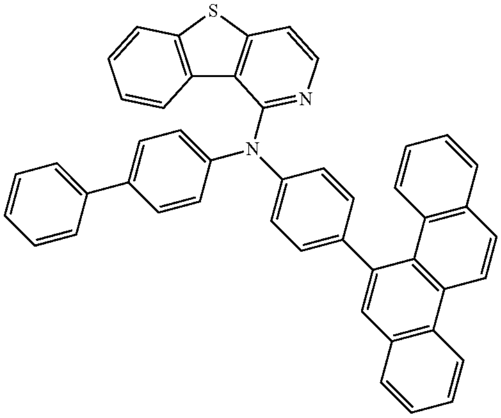
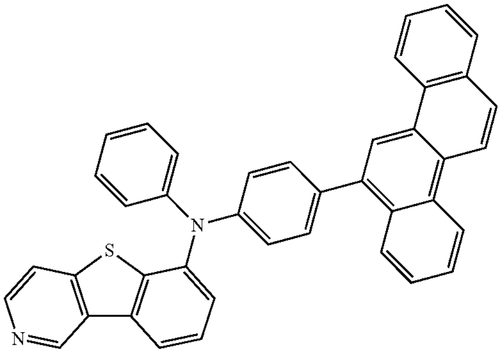

-continued
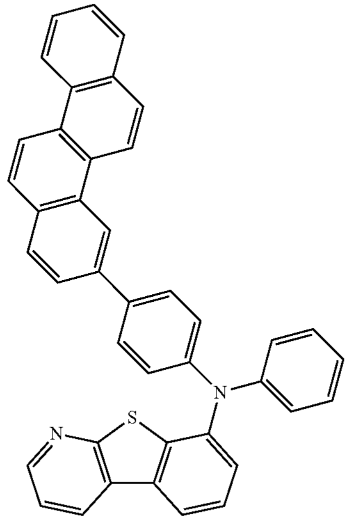
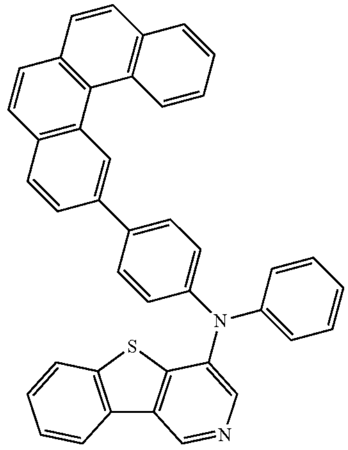
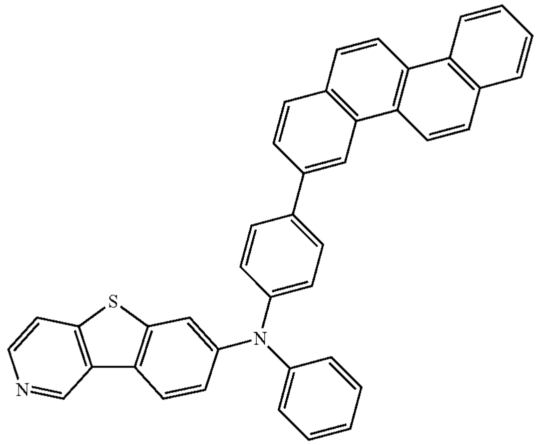
-continued
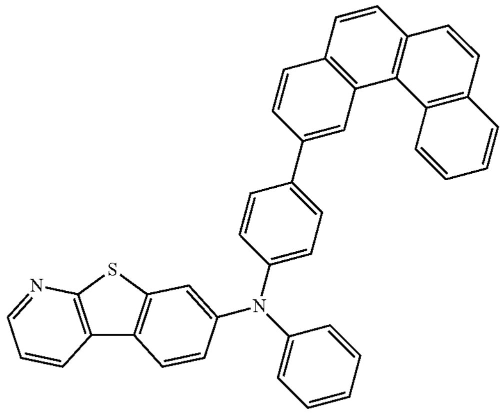
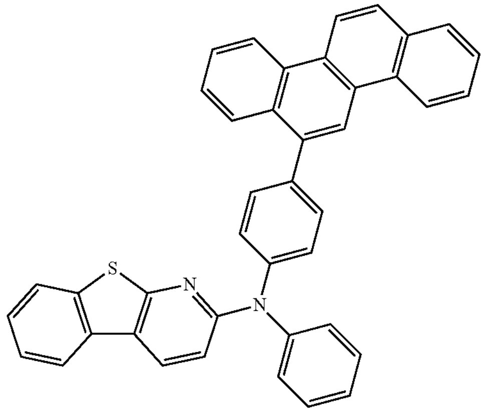
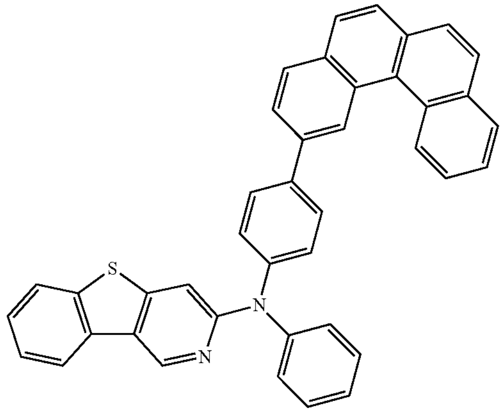
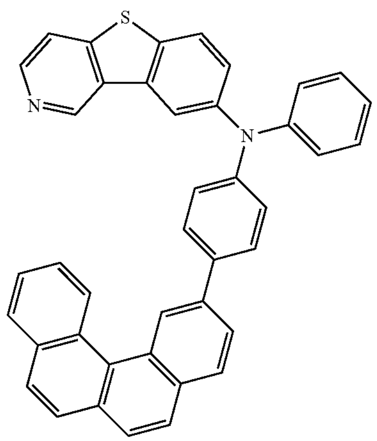

-continued
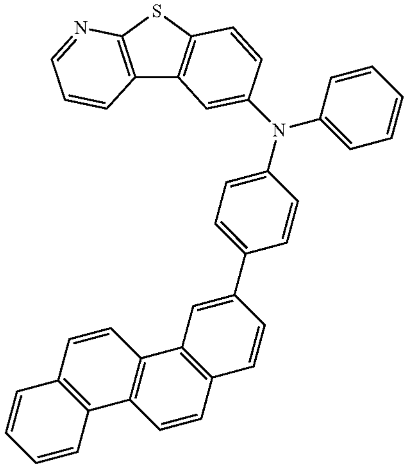
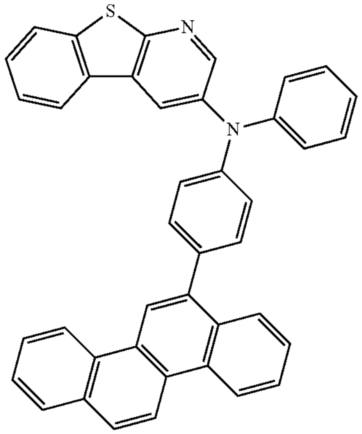
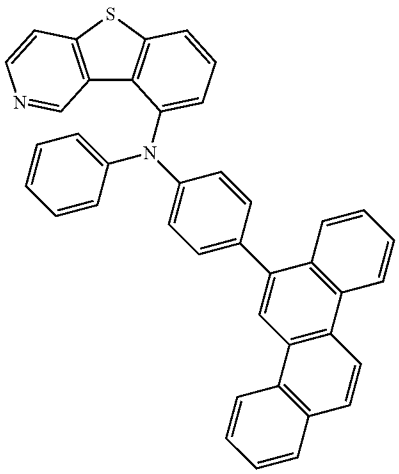
-continued
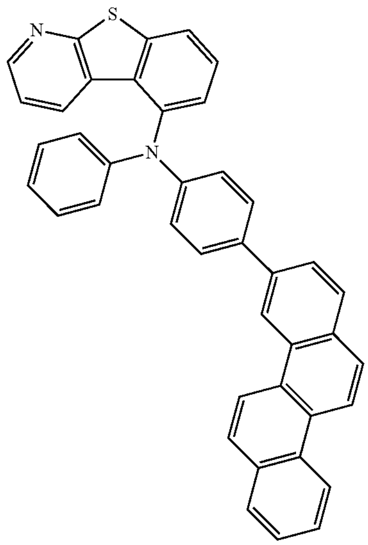
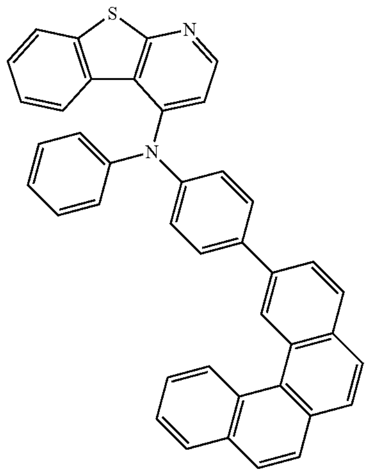
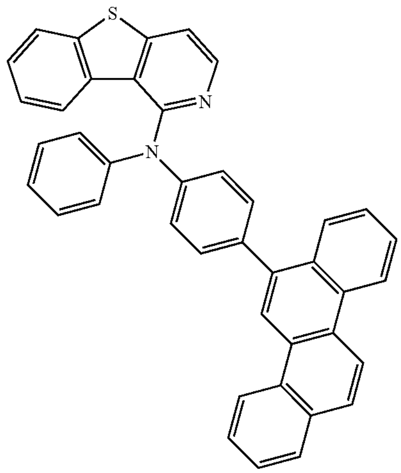

-continued
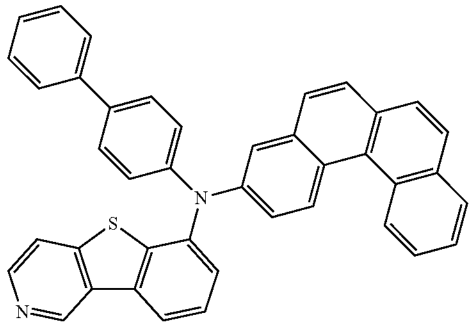
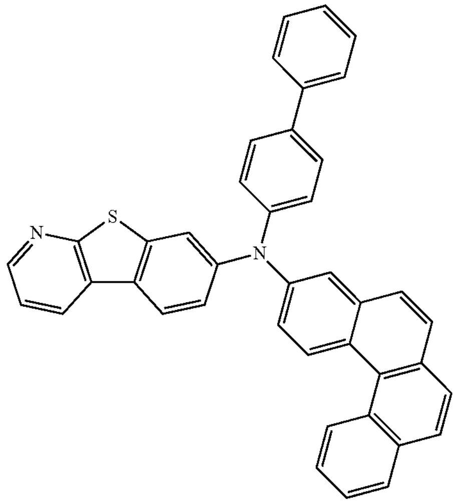
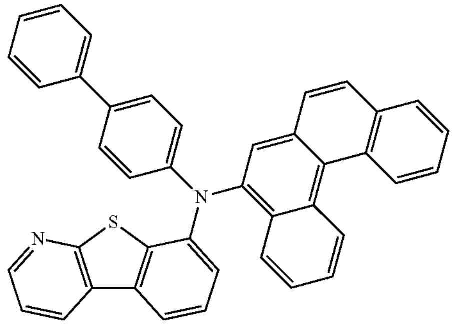
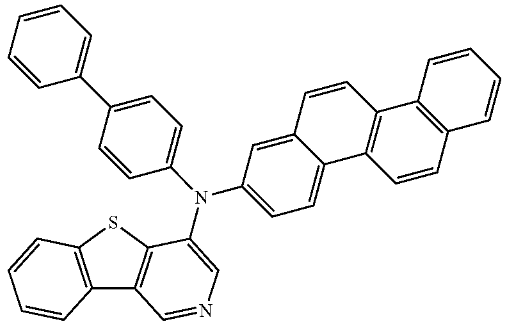
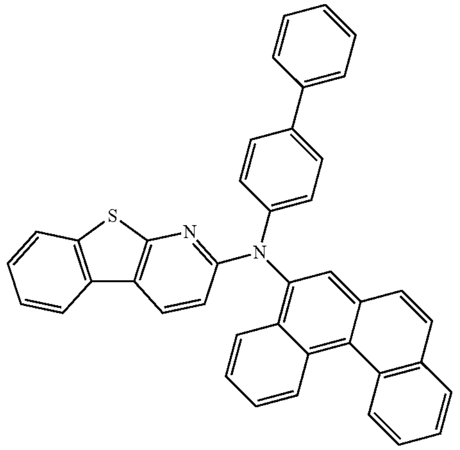
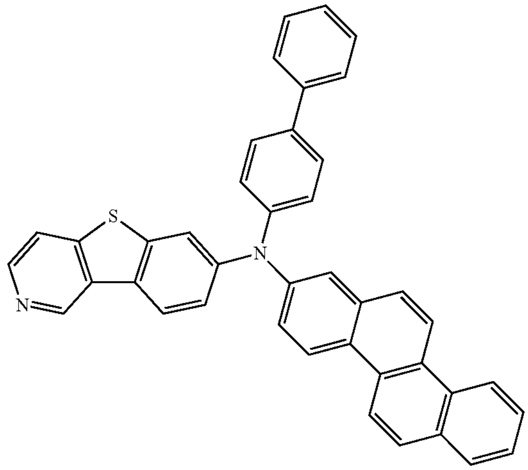
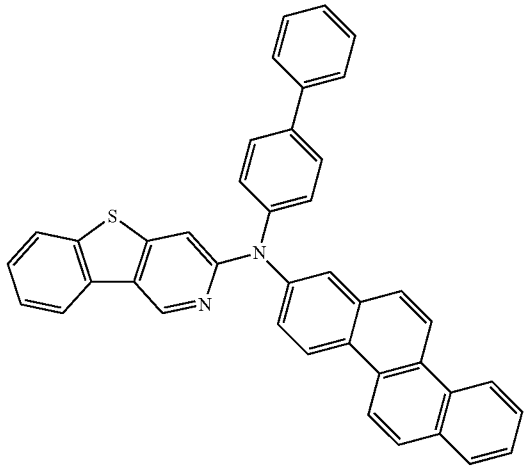

-continued
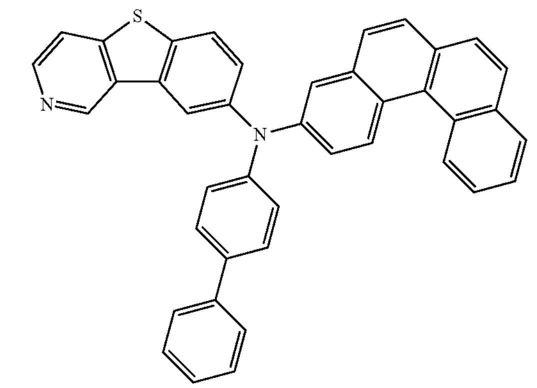
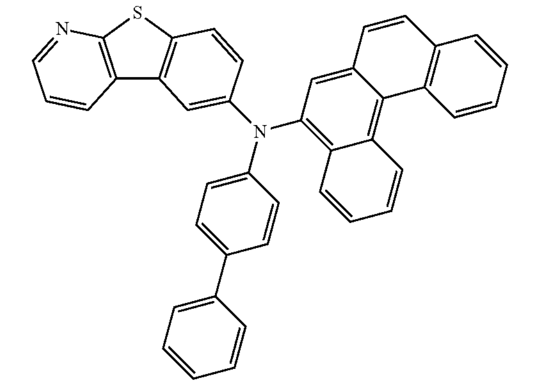
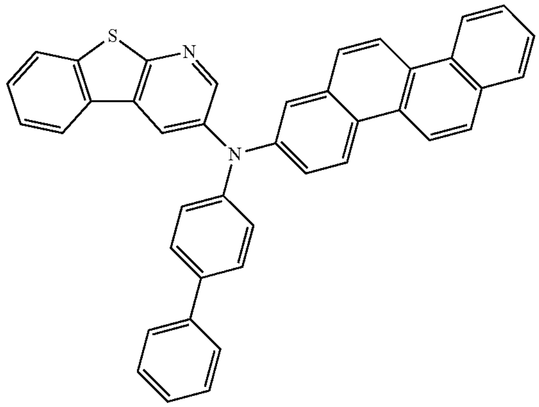
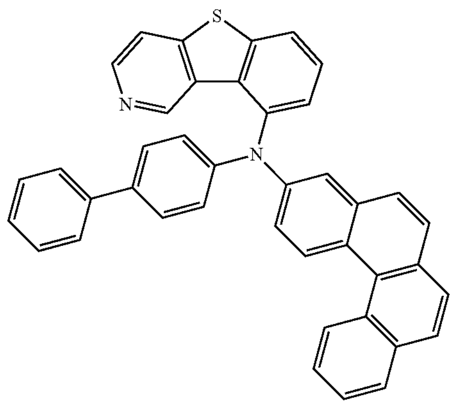
-continued
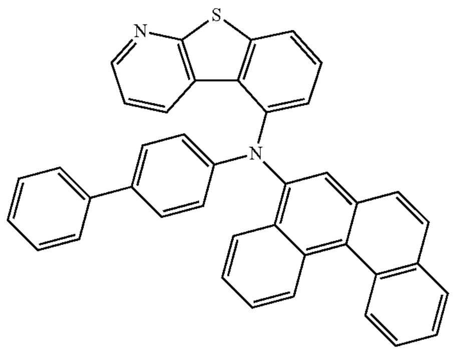
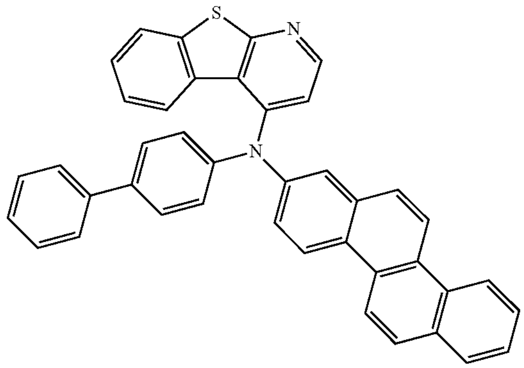
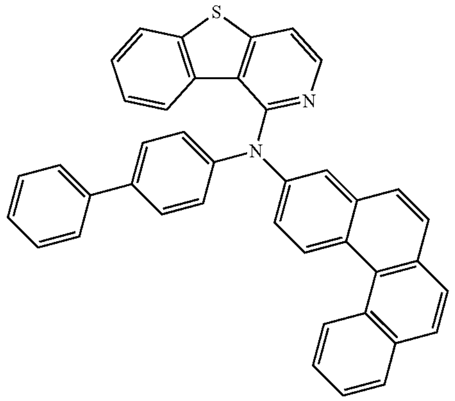
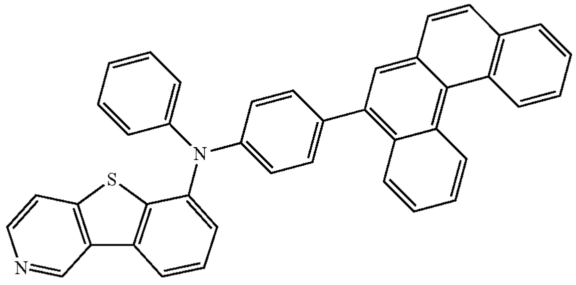

-continued
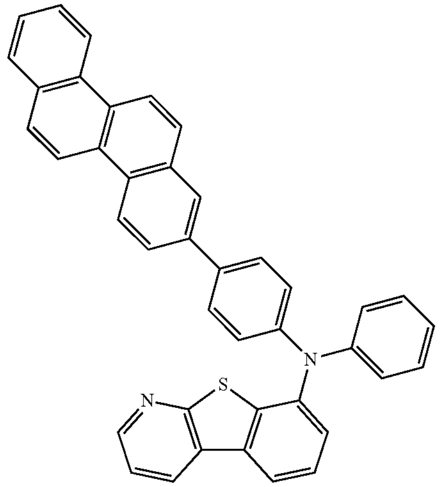
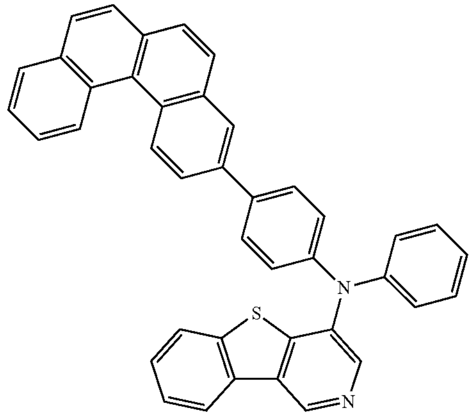
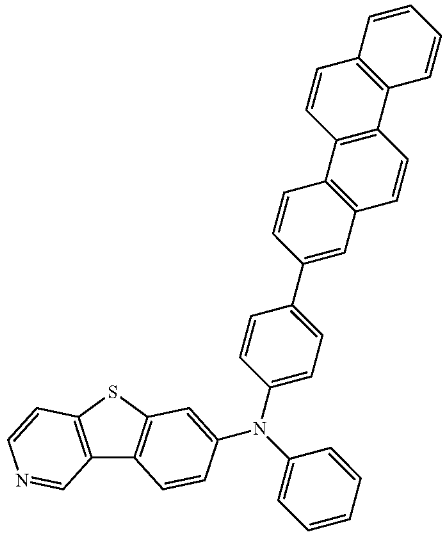
-continued
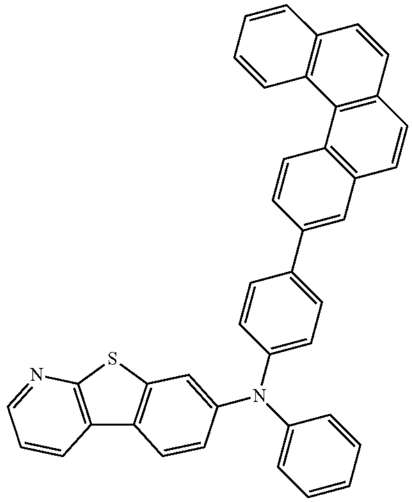
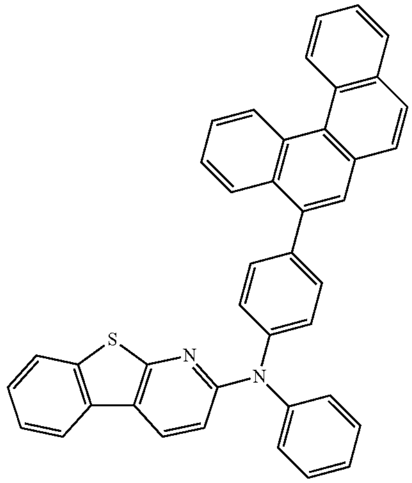
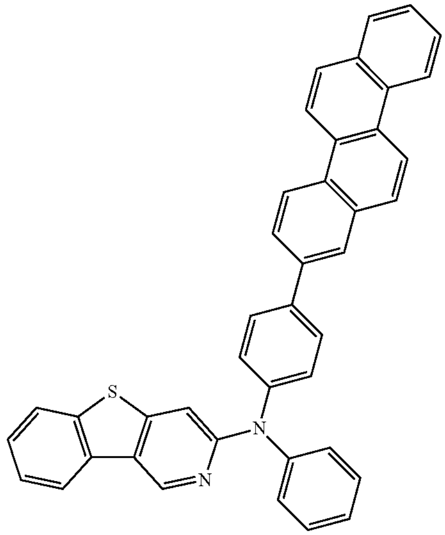

-continued
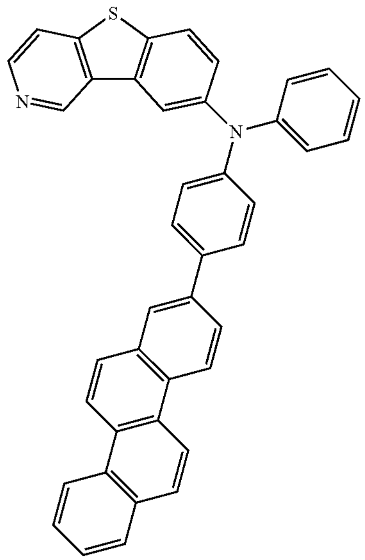
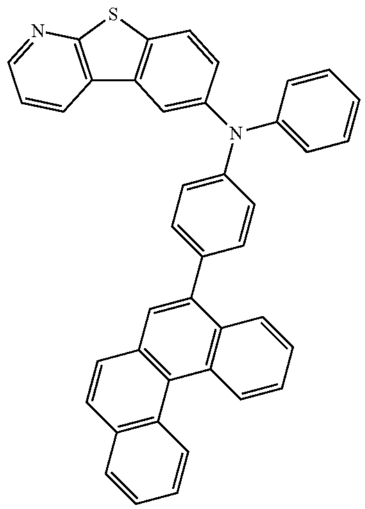
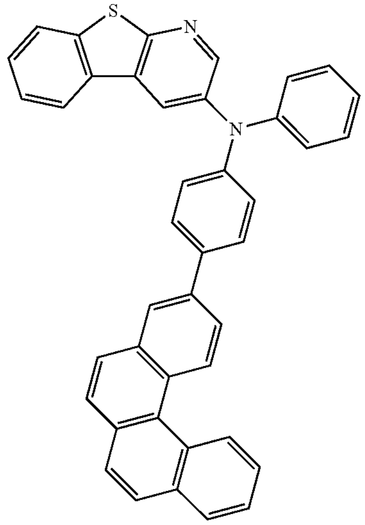
-continued
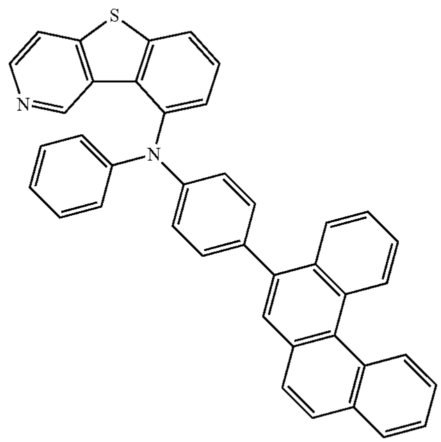
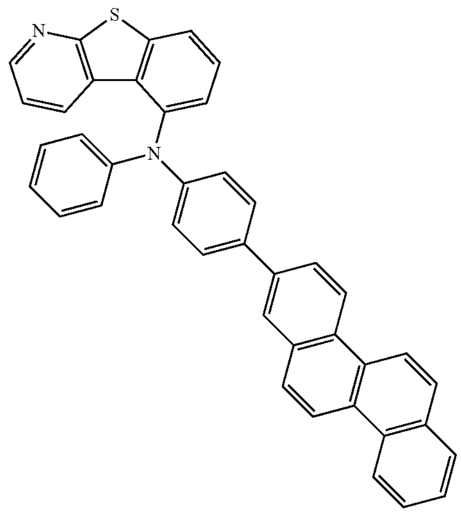
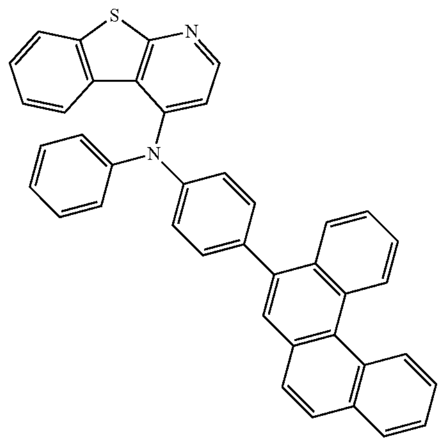

-continued
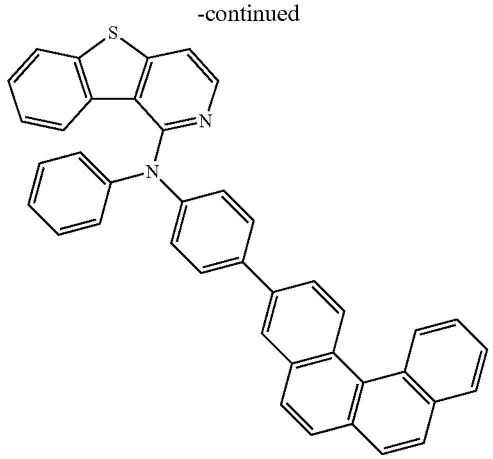
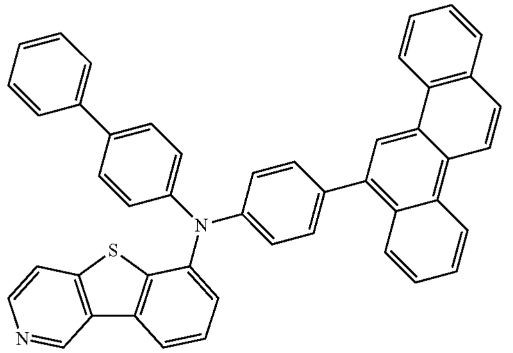
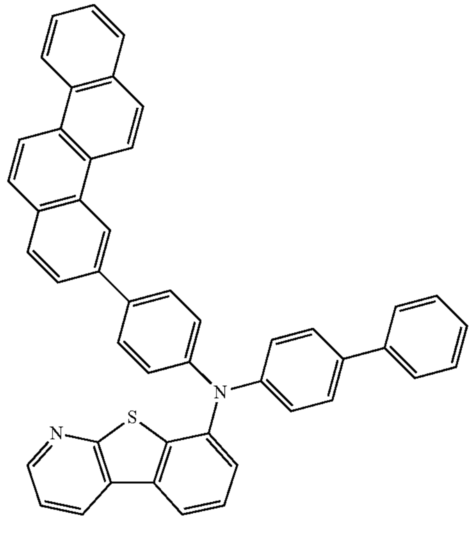
-continued
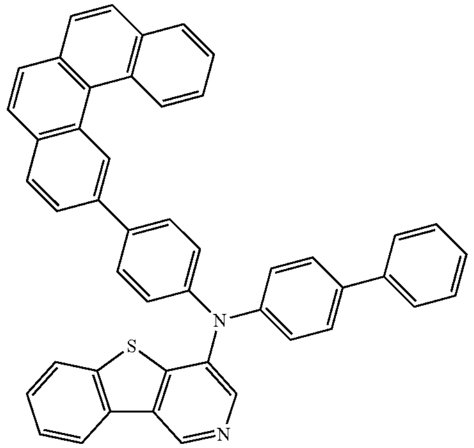
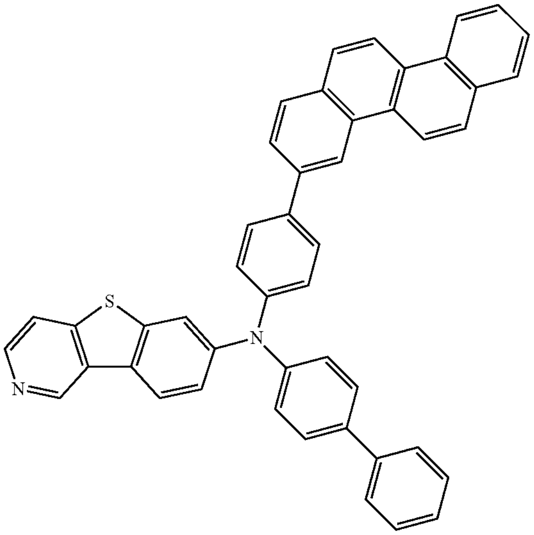
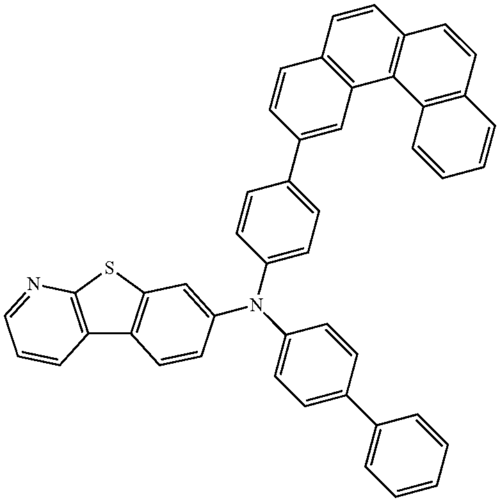

-continued
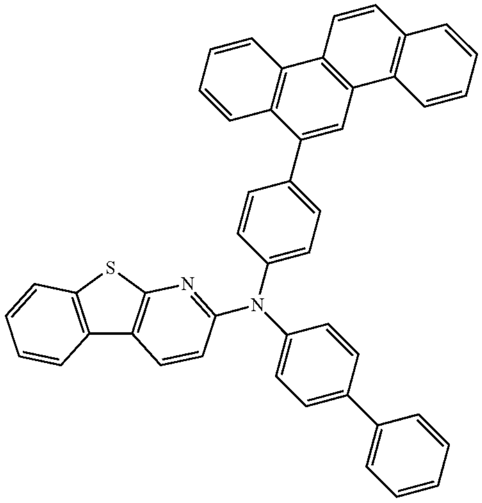
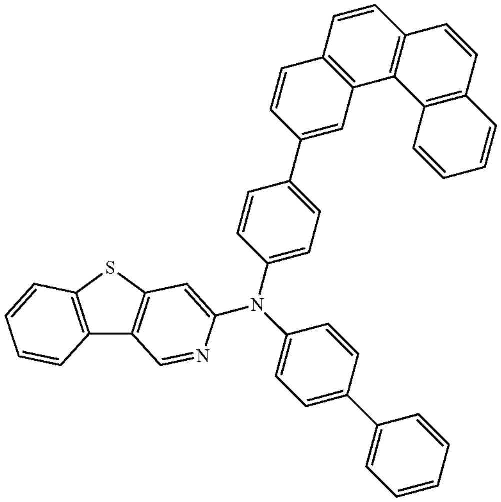
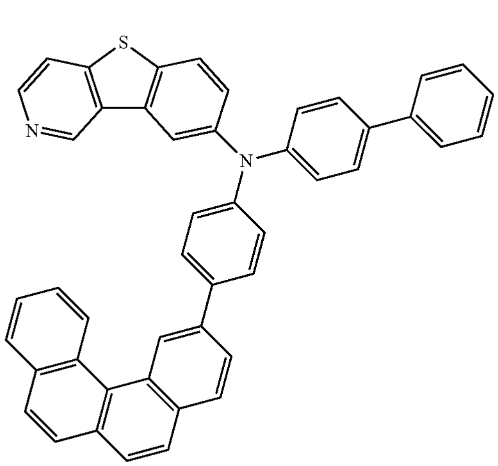
-continued
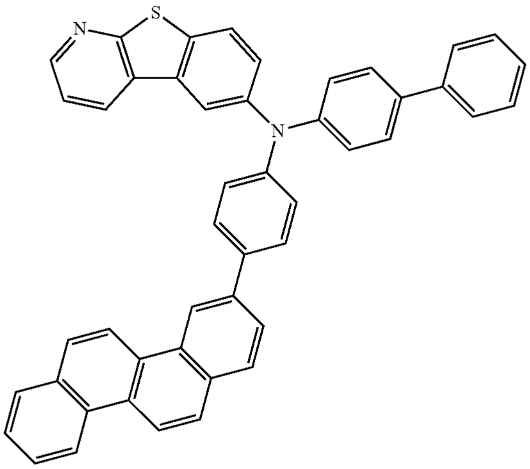
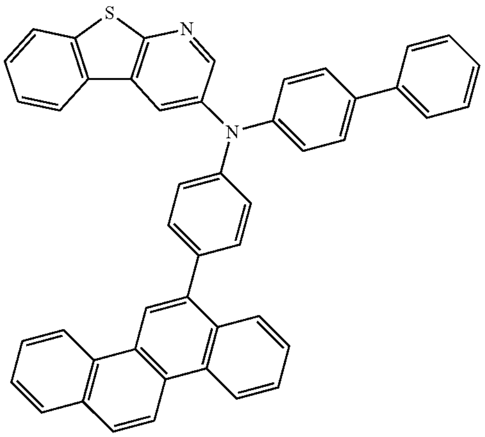
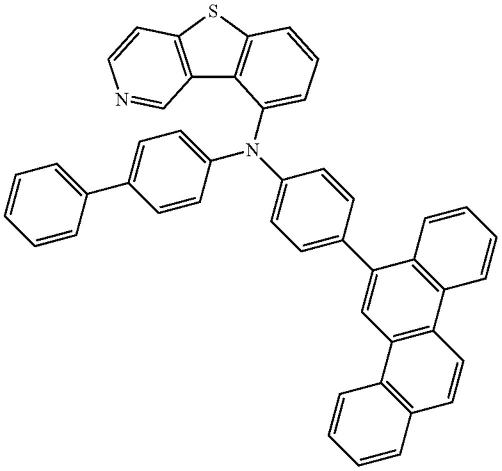

-continued
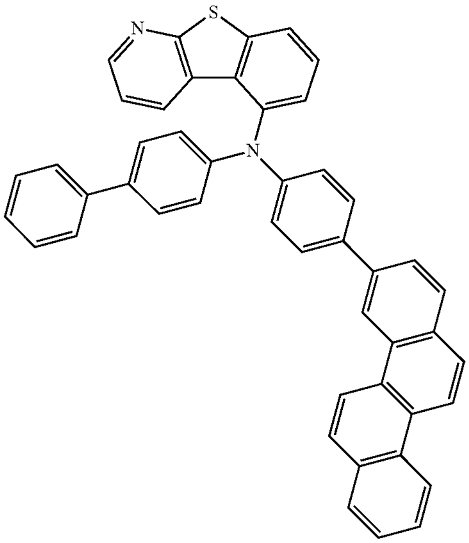
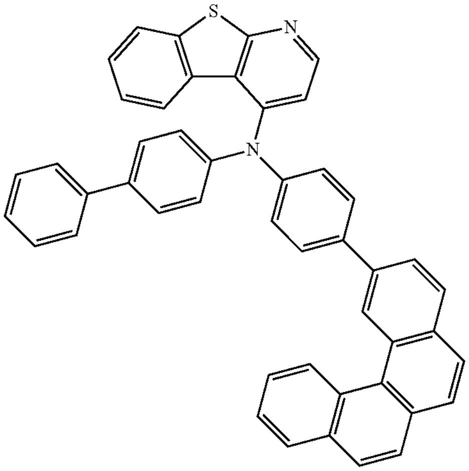
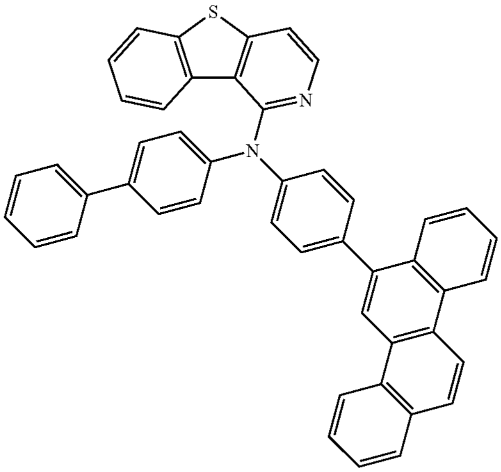
-continued
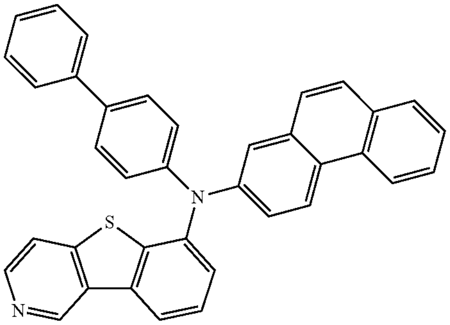
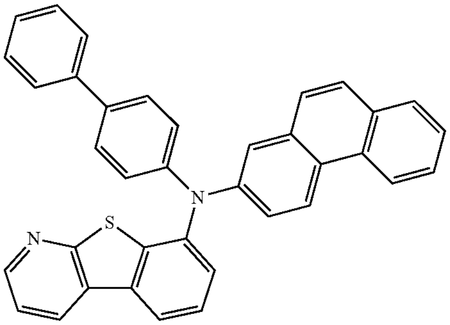
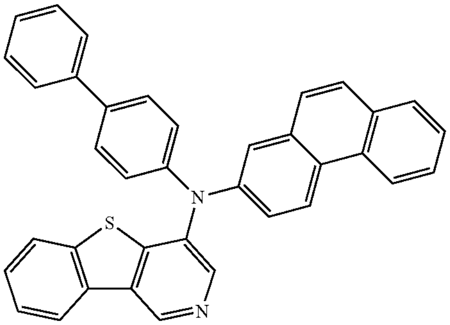
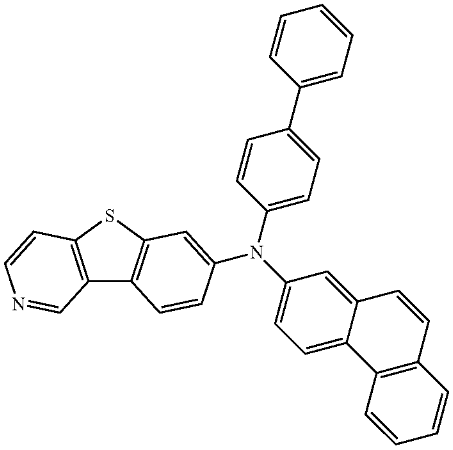

-continued
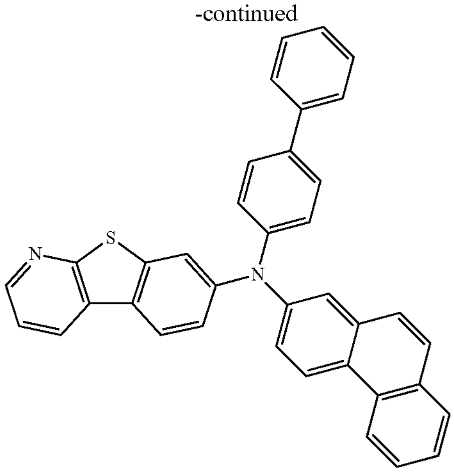
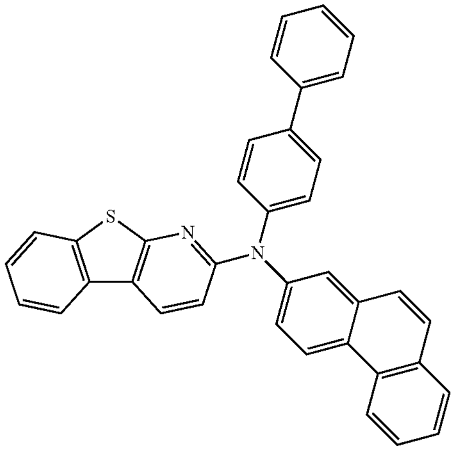
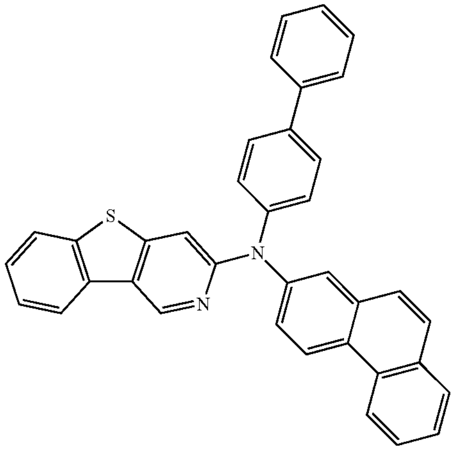
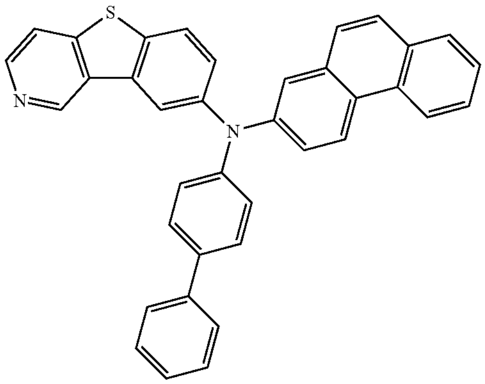
-continued
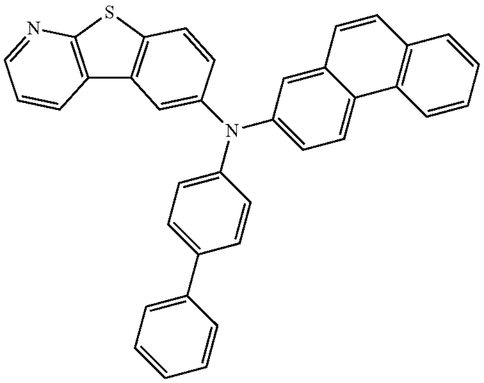
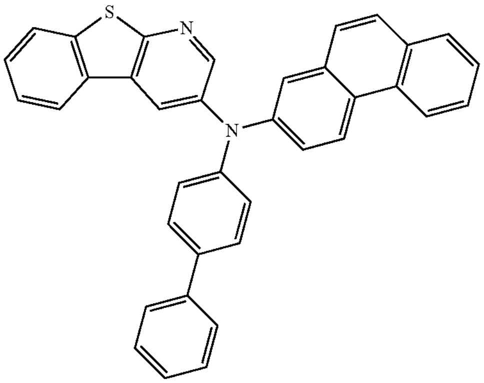
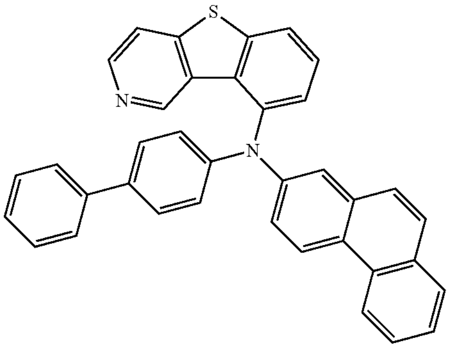
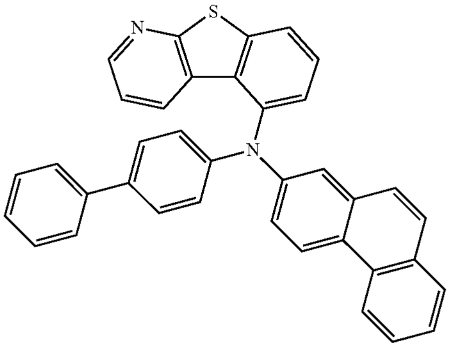

-continued
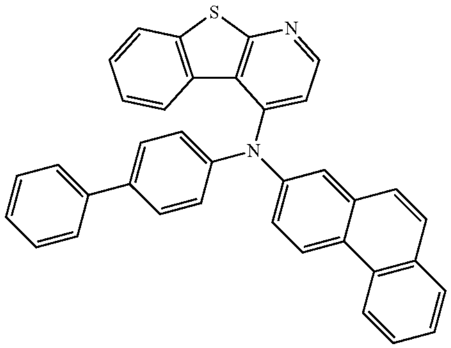
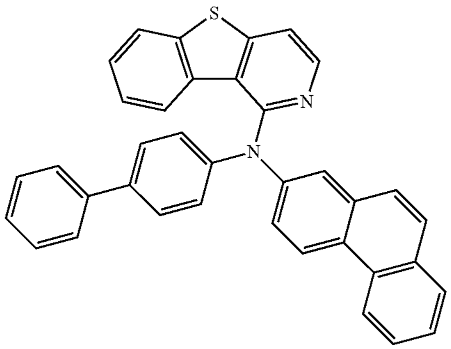
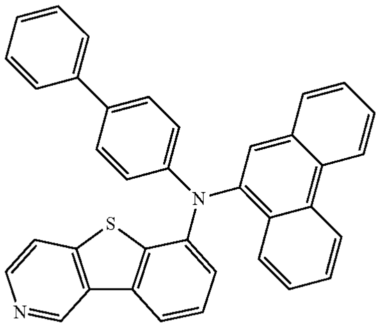
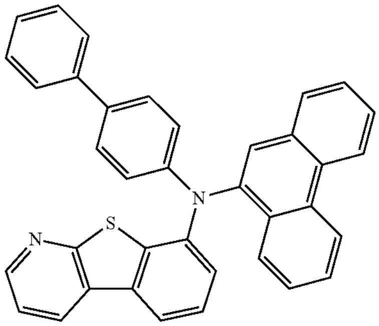
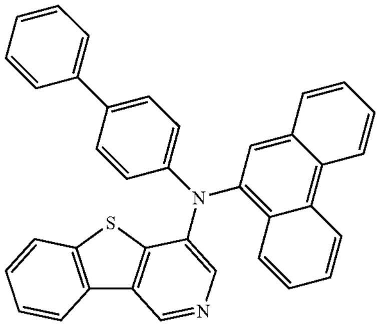
-continued
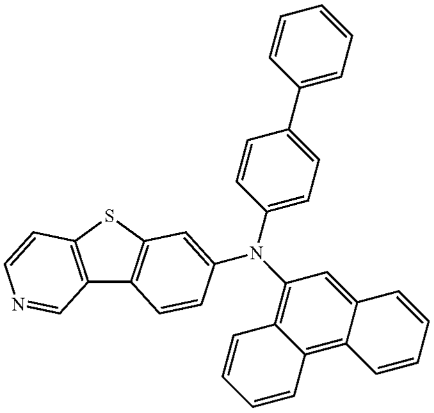
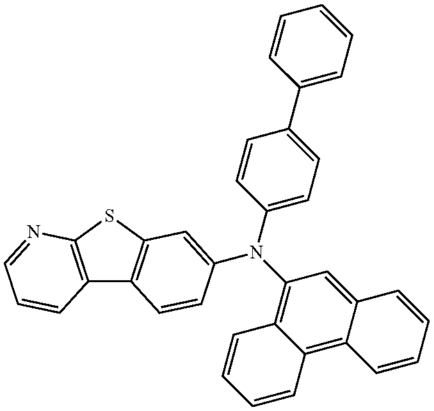
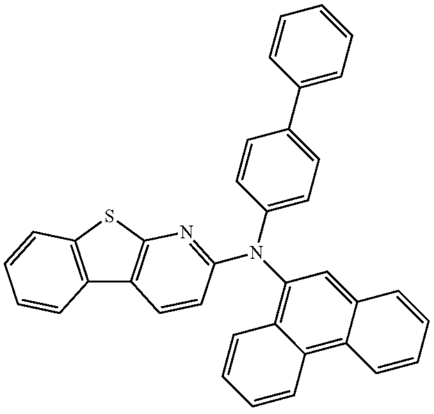
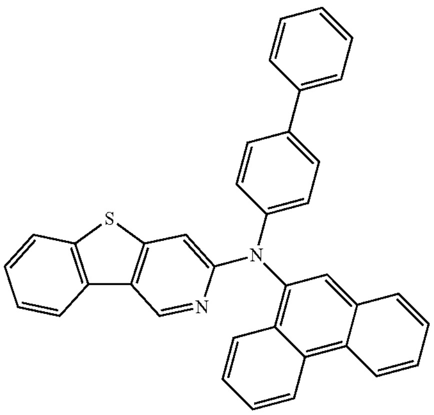

-continued
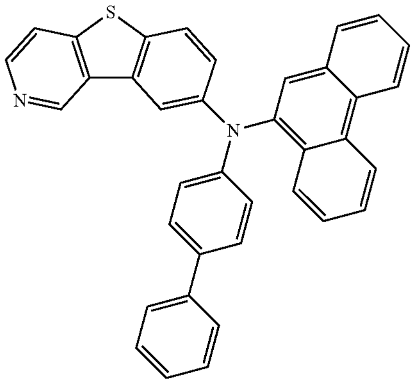
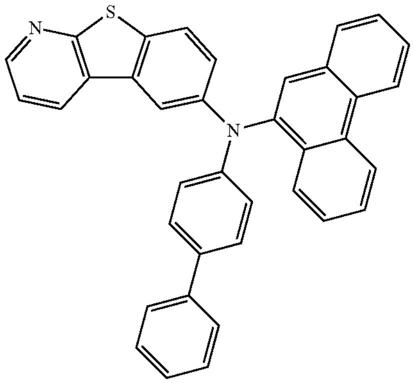
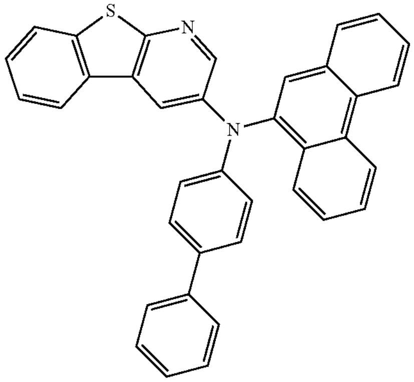
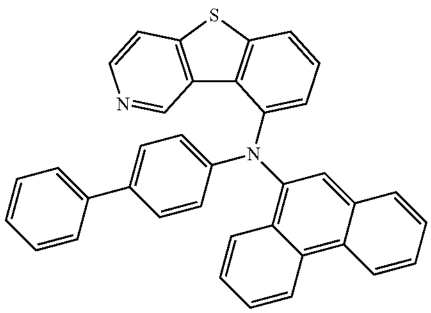
-continued
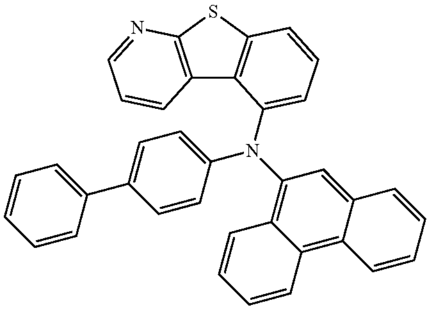
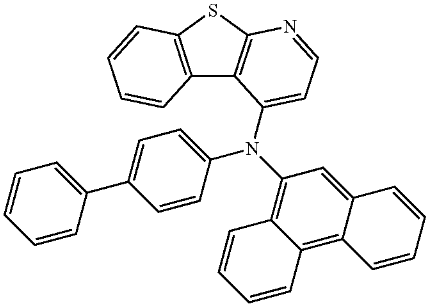
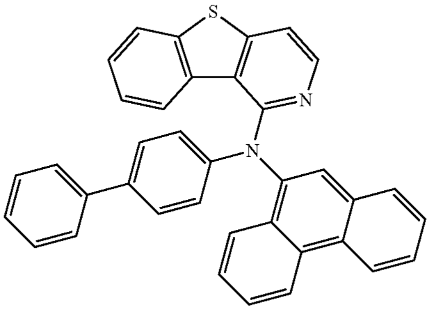
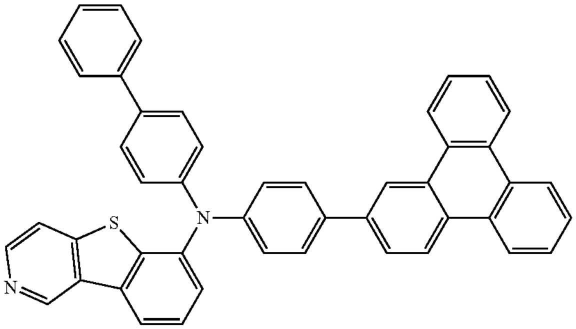
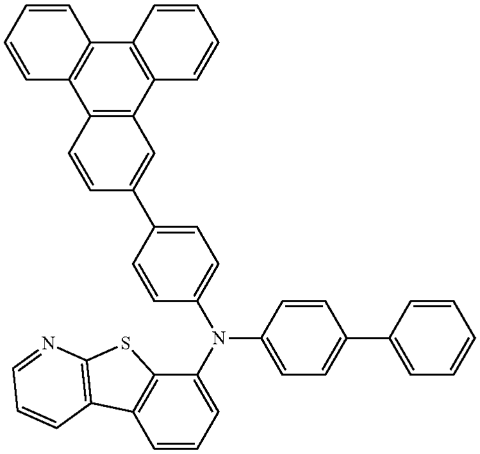

-continued
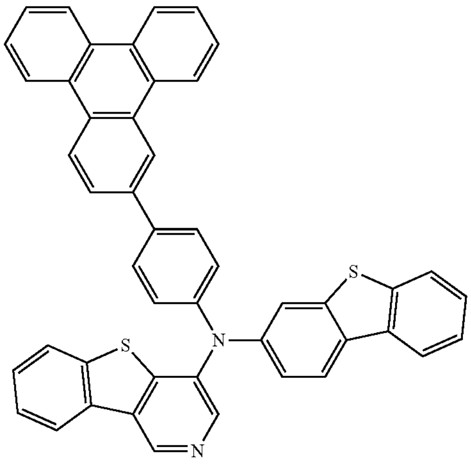
-continued
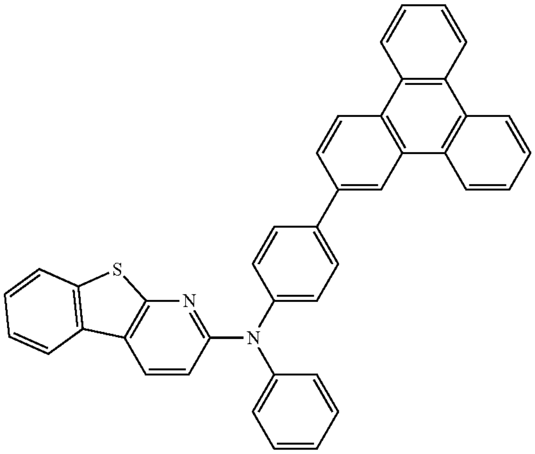
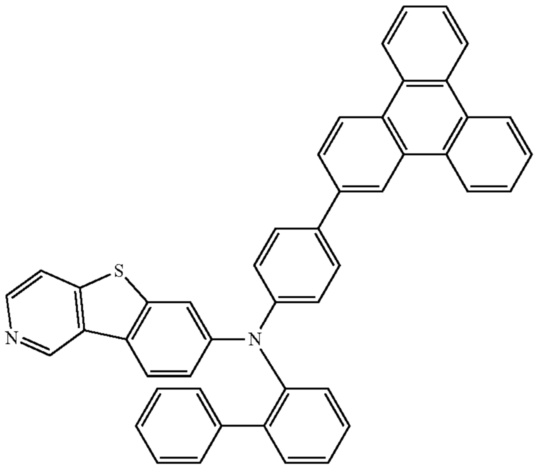
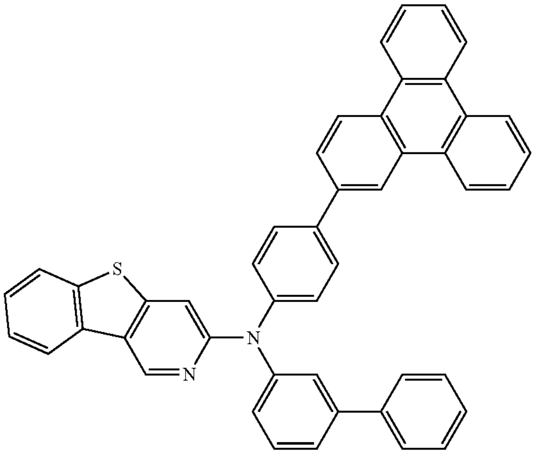
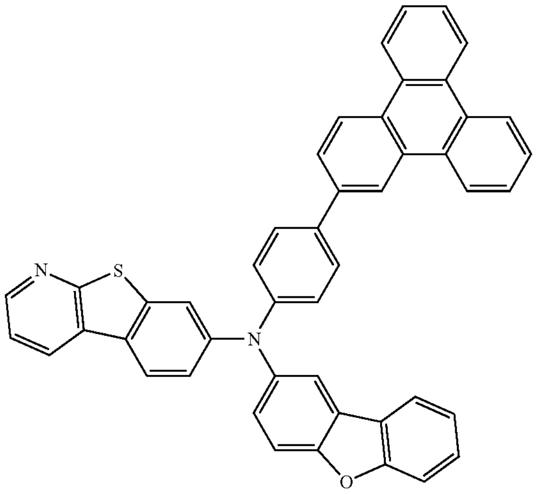
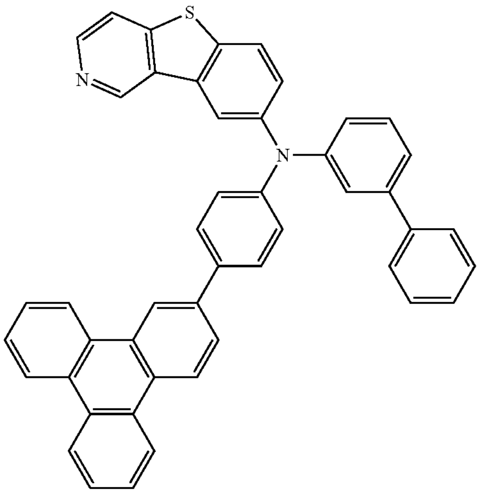

-continued
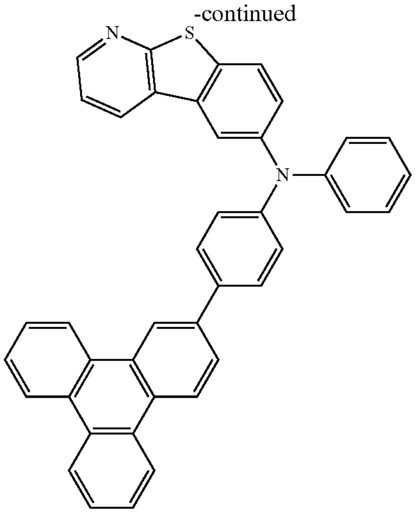
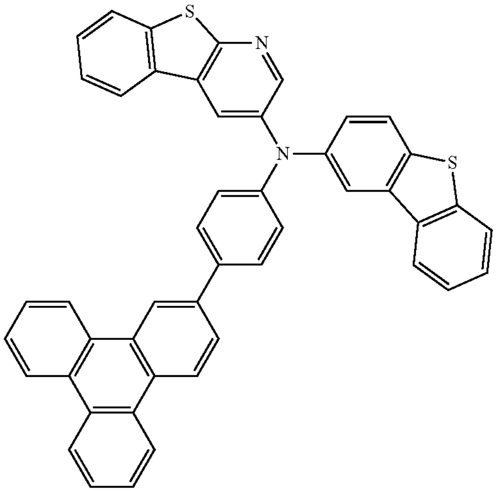
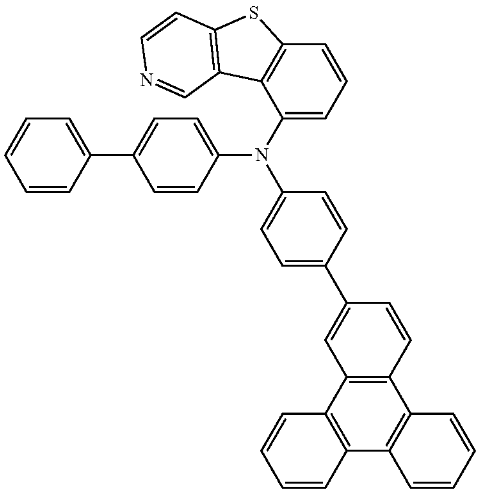
-continued
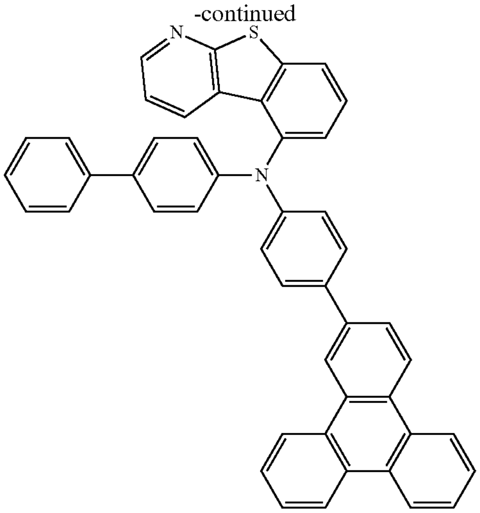
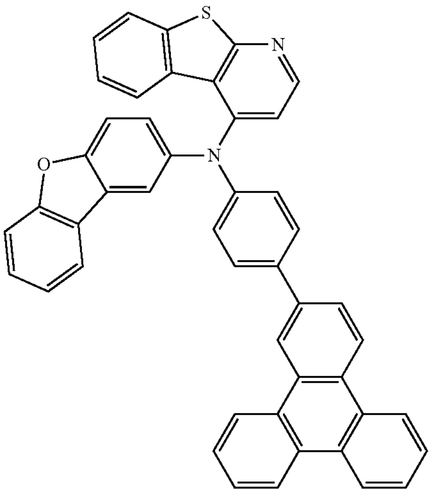
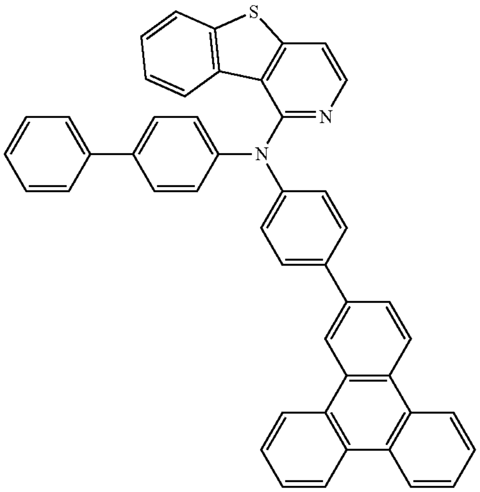

-continued
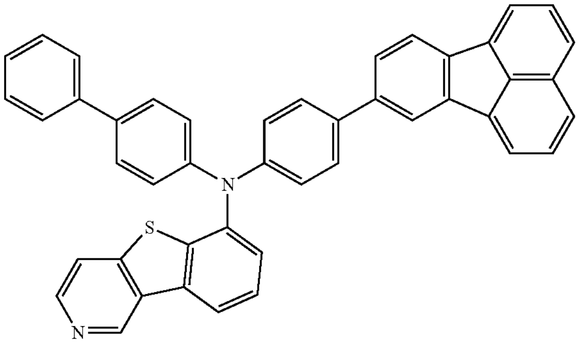
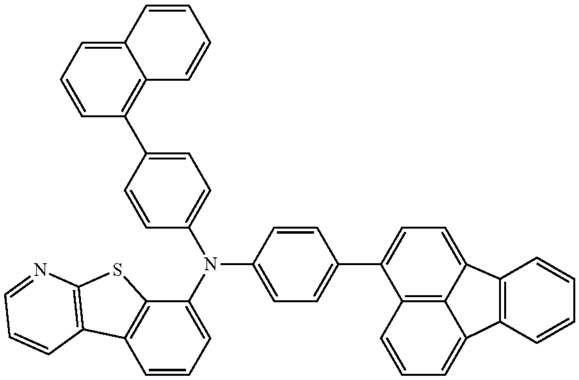
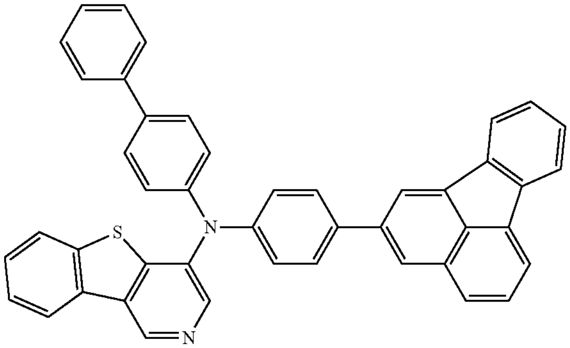
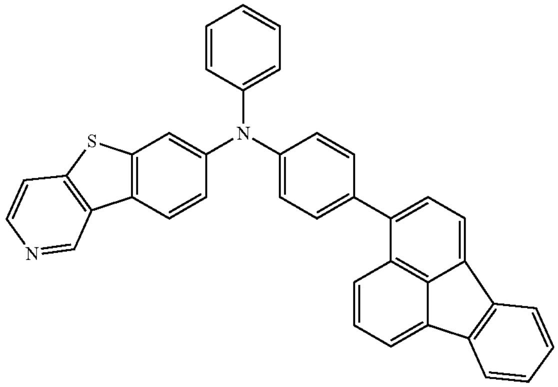
-continued
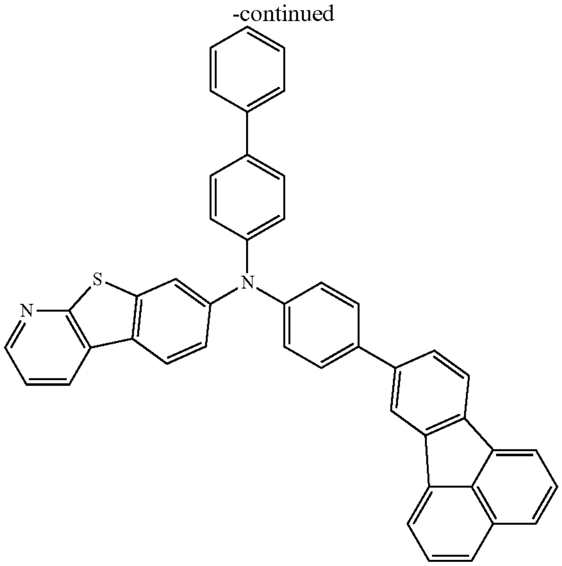
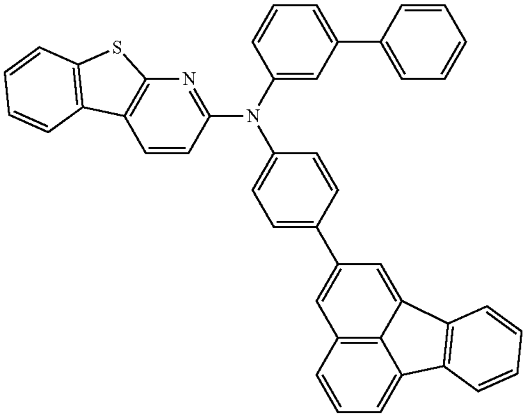
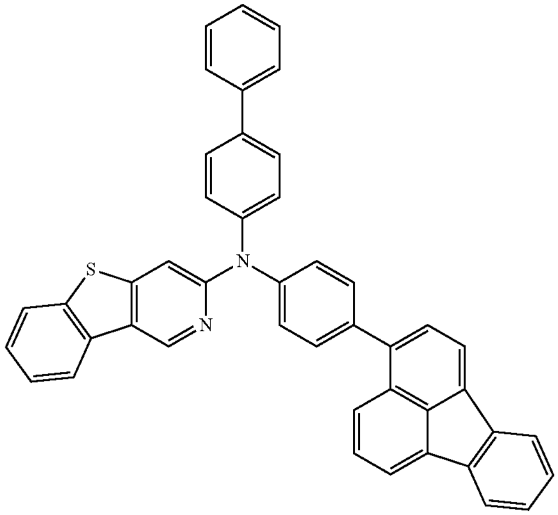

-continued
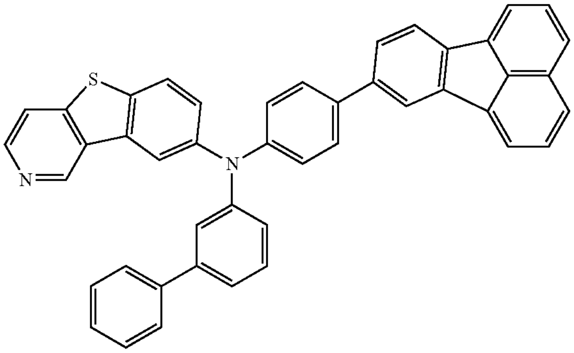
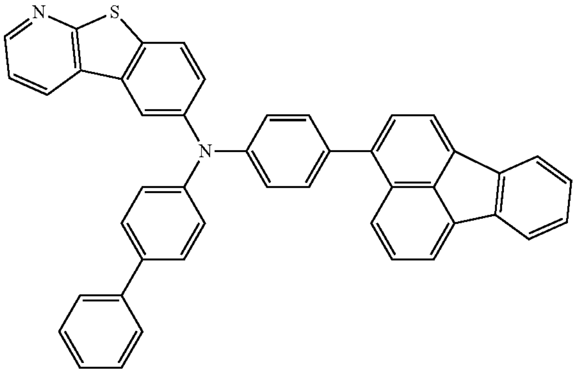
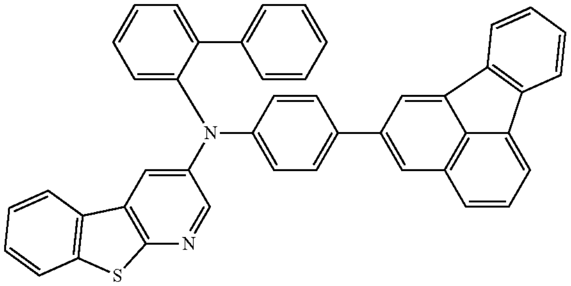
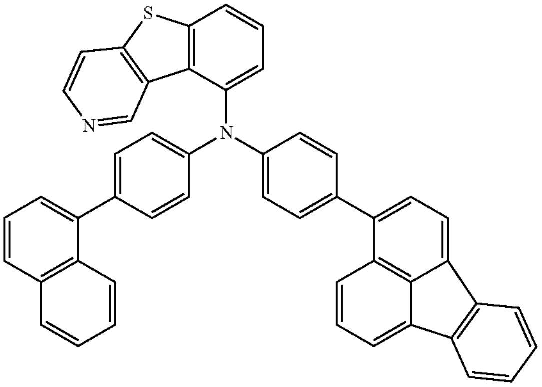
-continued
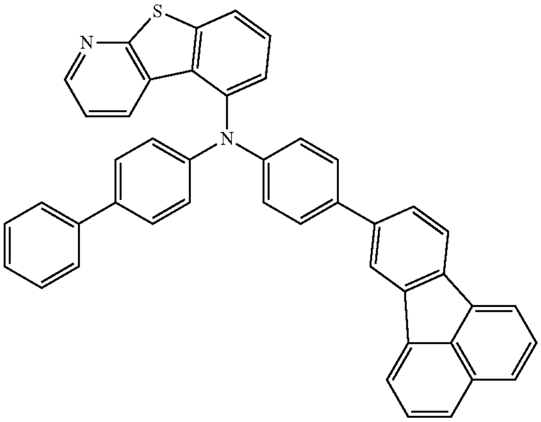
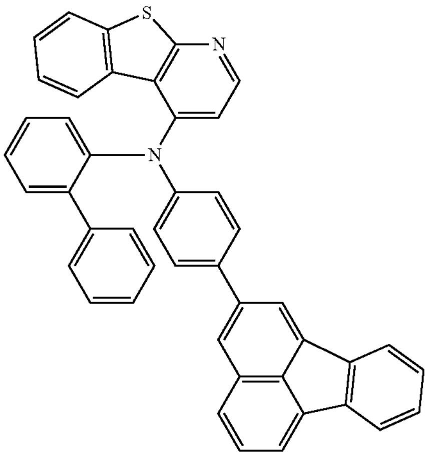
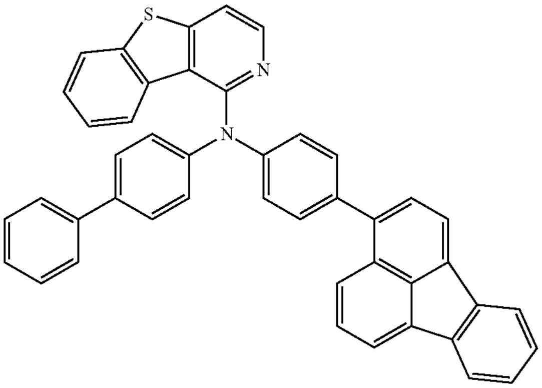
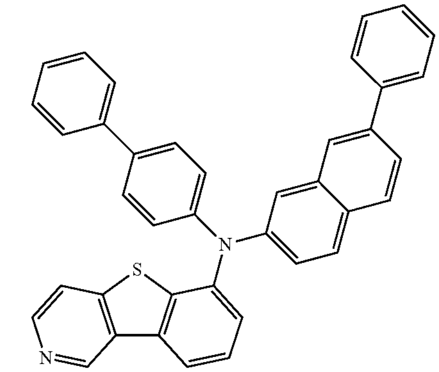

-continued
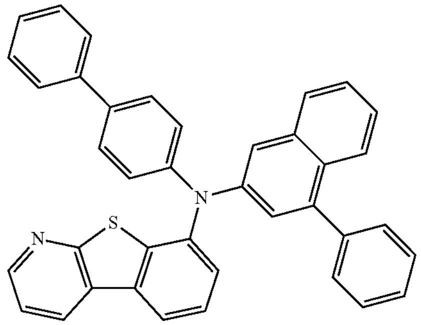
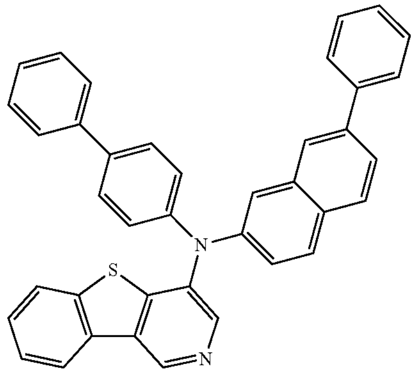
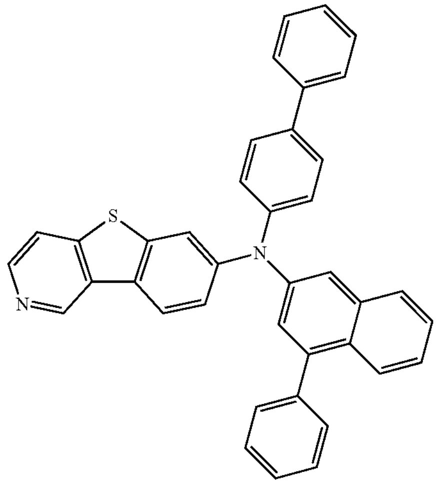
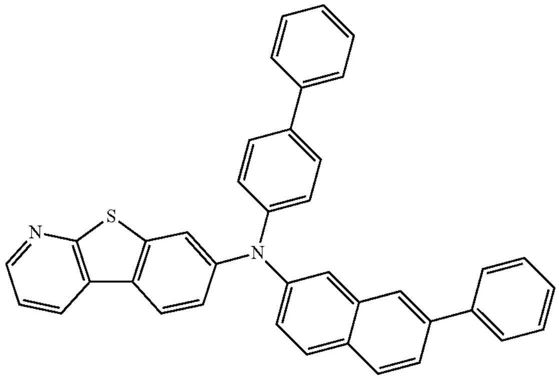
-continued
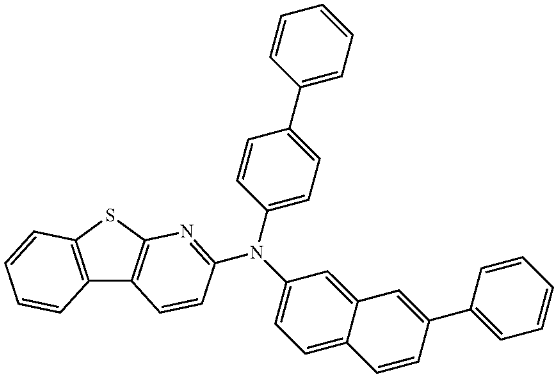
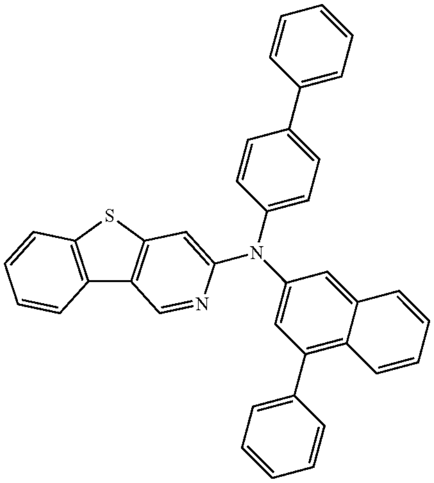
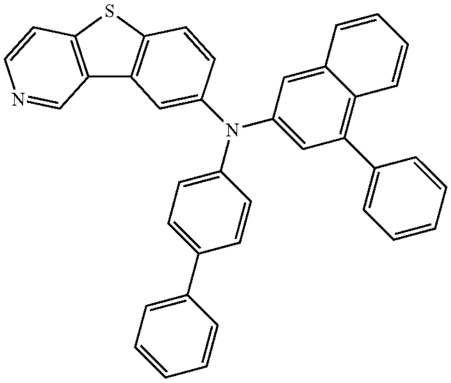

-continued
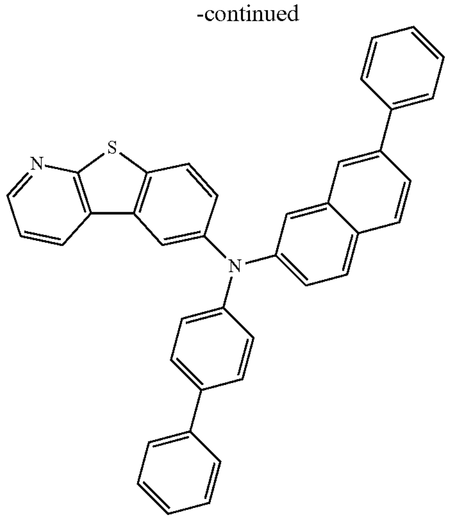
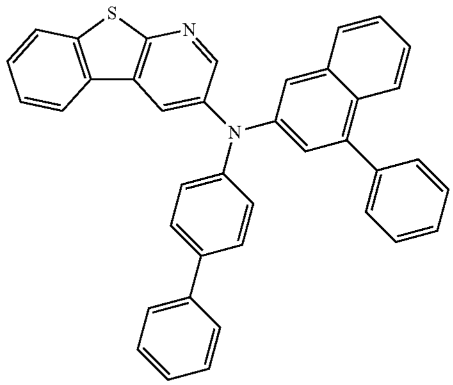
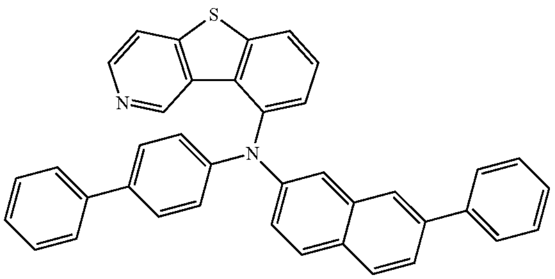
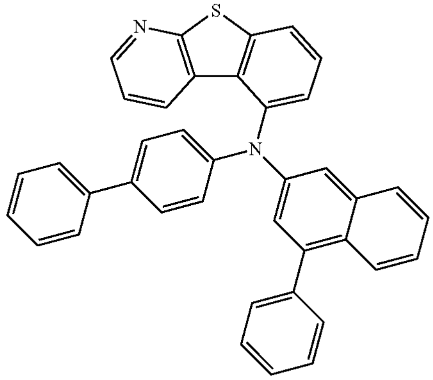
-continued
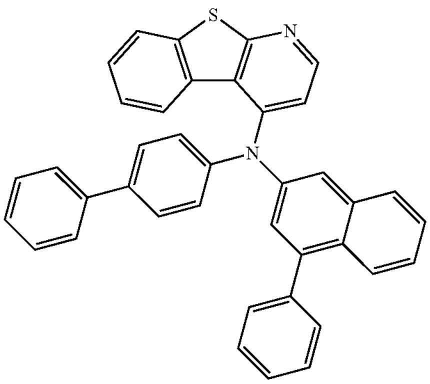
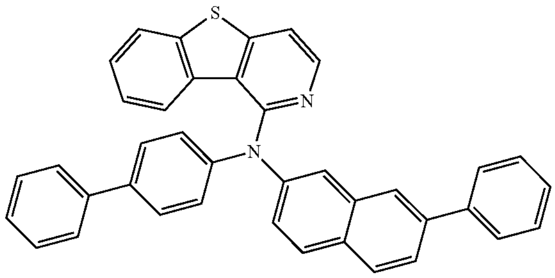
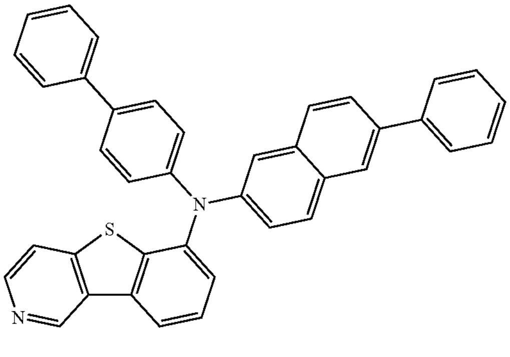
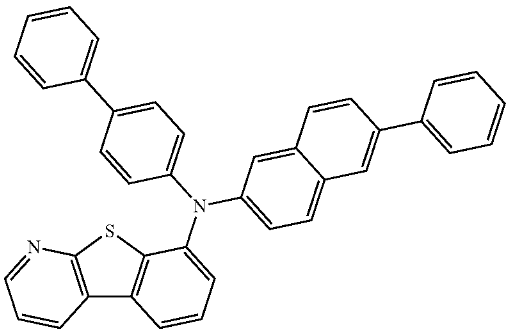

-continued
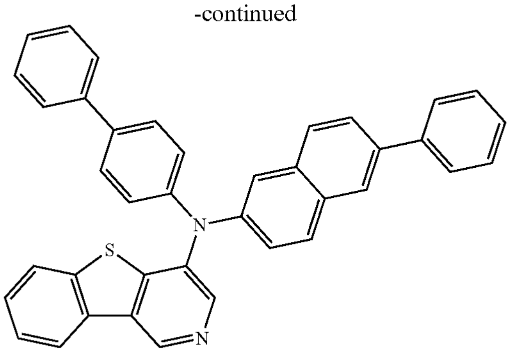
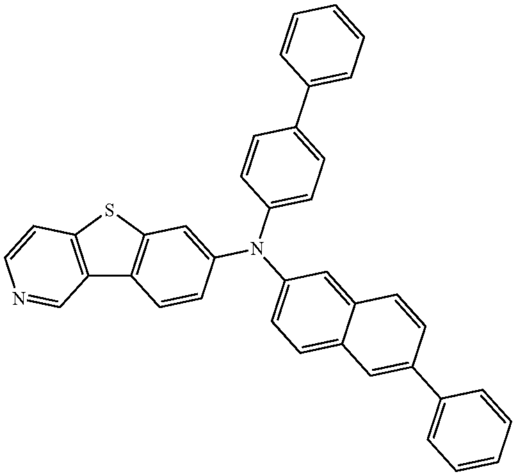
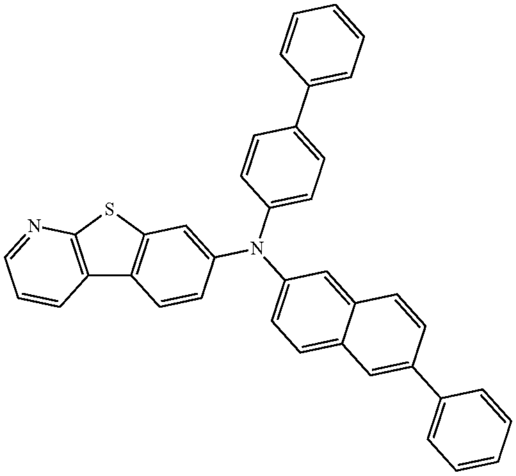
-continued
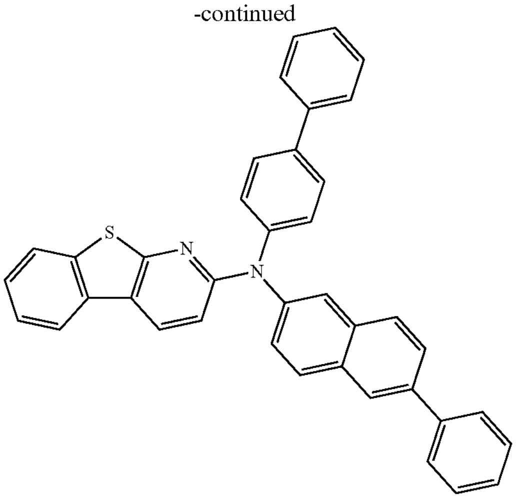
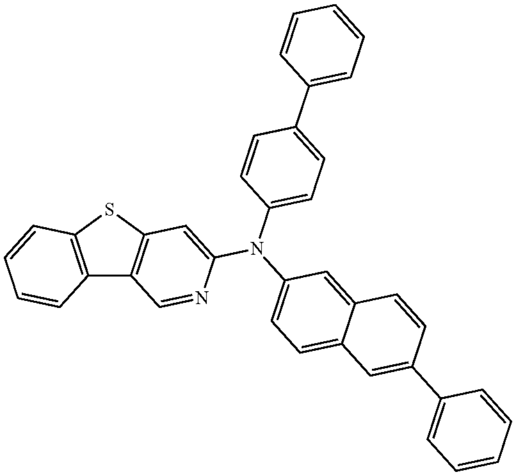
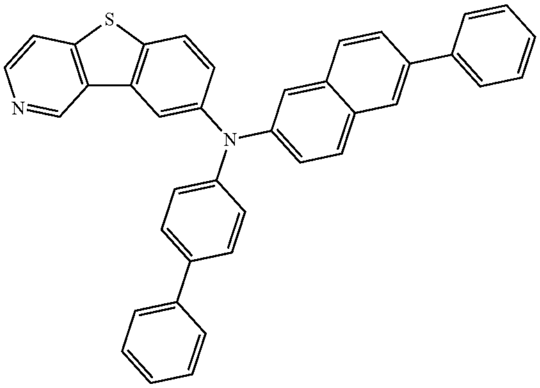
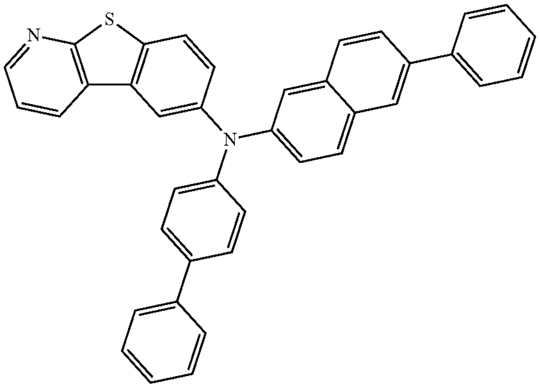

-continued
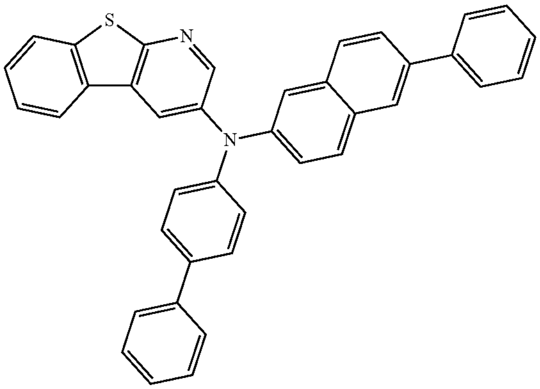
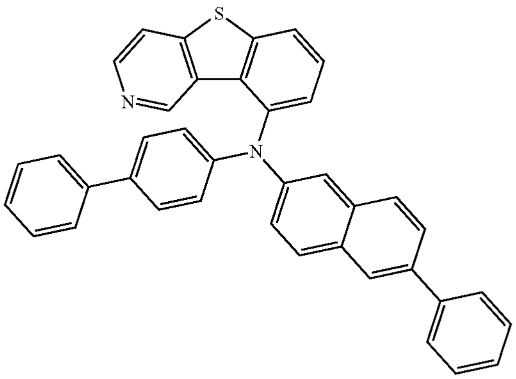
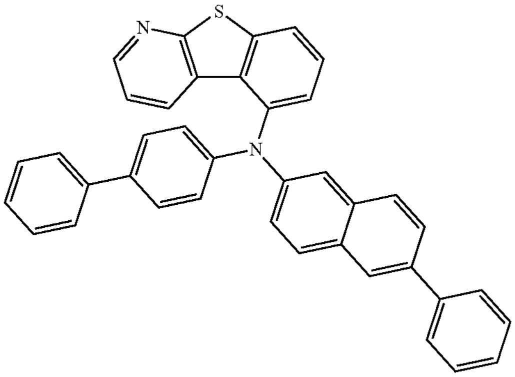
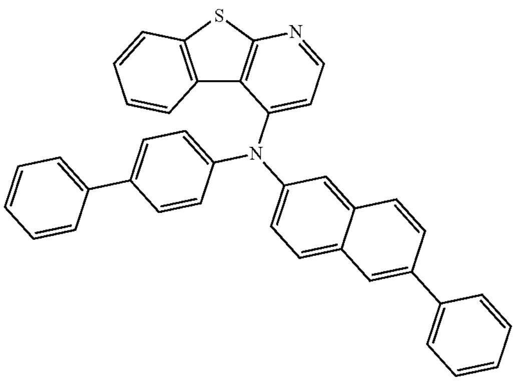
-continued
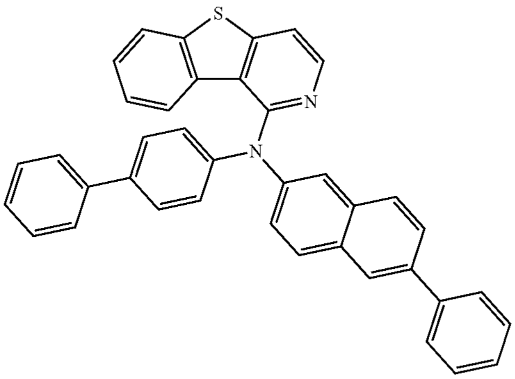 [SMILES: c1ccc(-c2ccc(N(c3ccc4cc(-c5ccccc5)ccc4c3)c3nccc4sc5ccccc5c34)cc2)cc1]
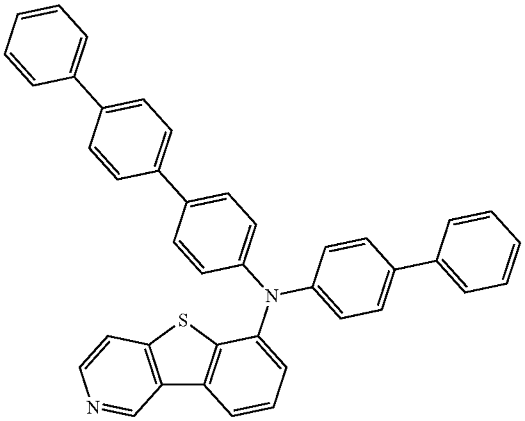
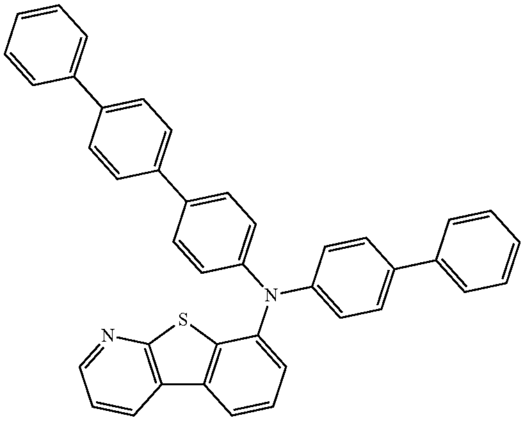
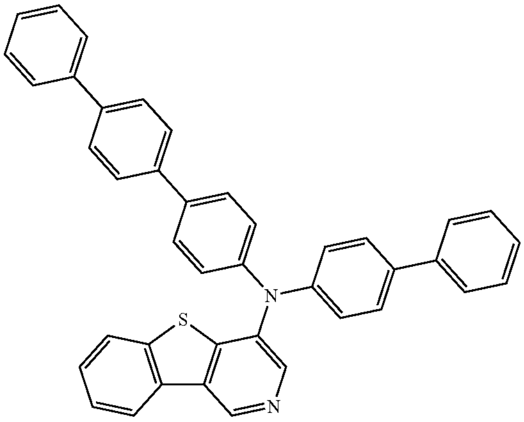

-continued
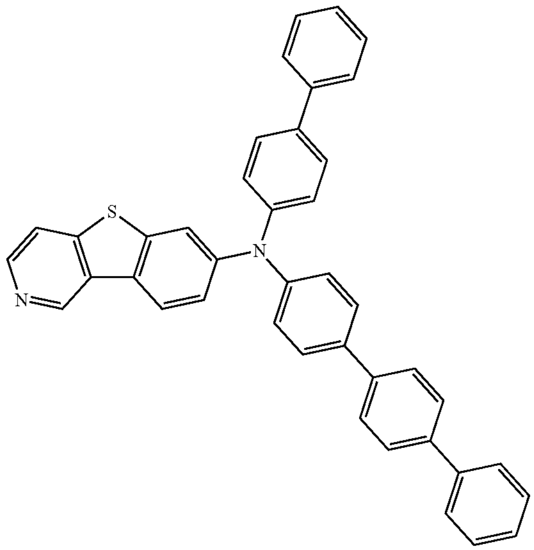
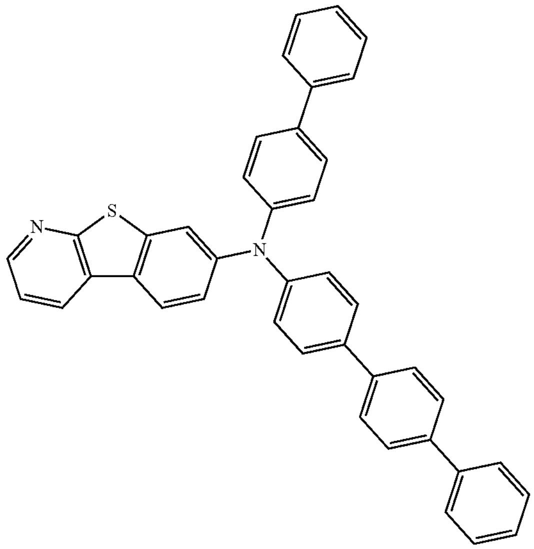
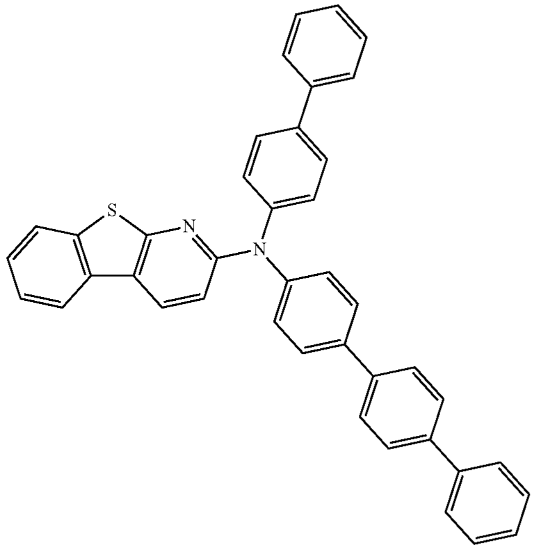
-continued
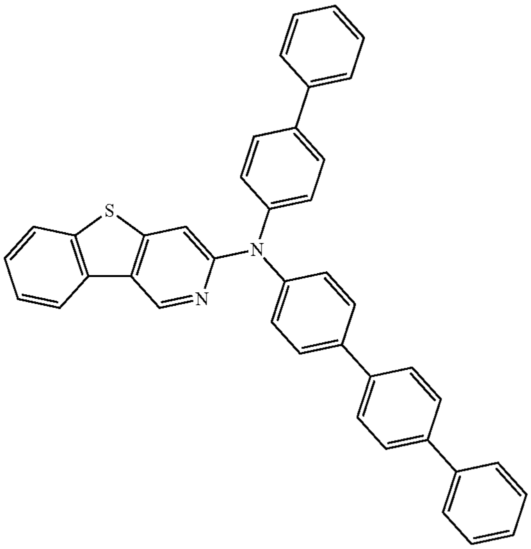 [SMILES: c1ccc(-c2ccc(-c3ccc(N(c4ccc(-c5ccccc5)cc4)c4cc5sc6ccccc6c5cn4)cc3)cc2)cc1]
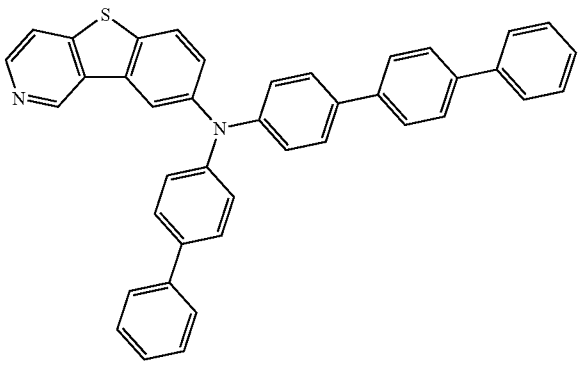
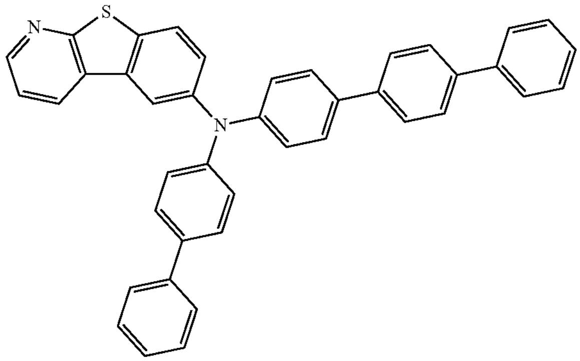
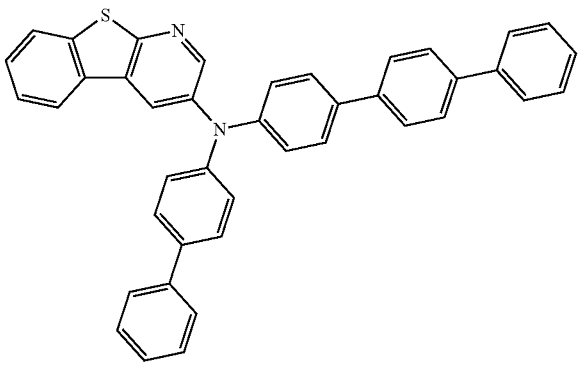

-continued
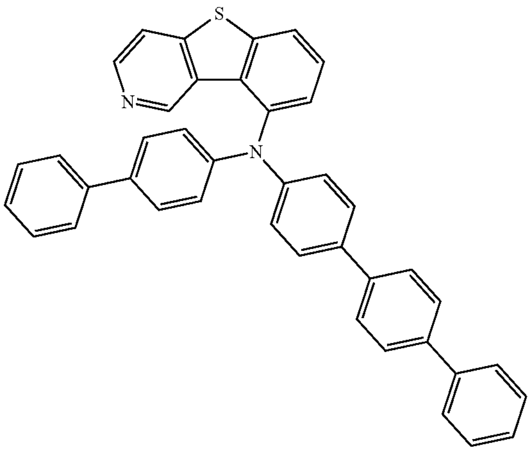 [SMILES: c1ccc(-c2ccc(-c3ccc(N(c4ccc(-c5ccccc5)cc4)c4nccc5sc6ccccc6c45)cc3)cc2)cc1]
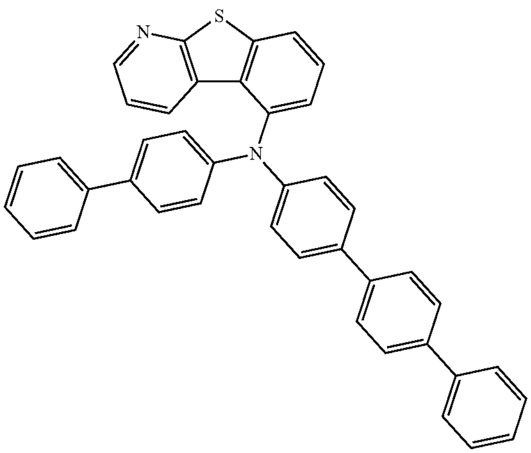
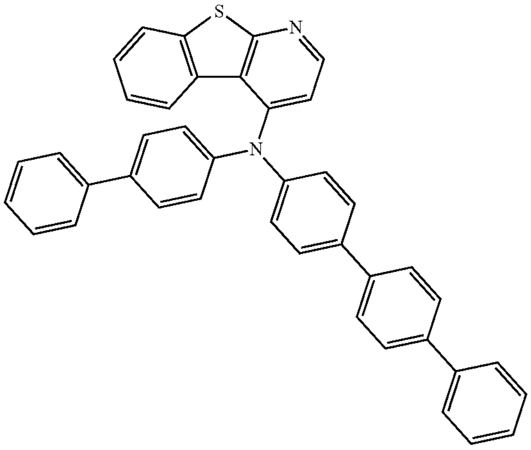
-continued
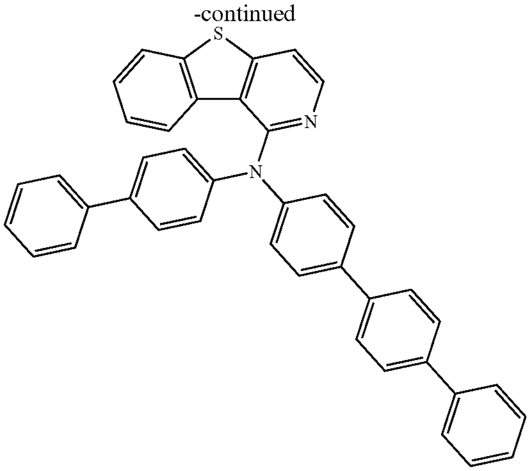
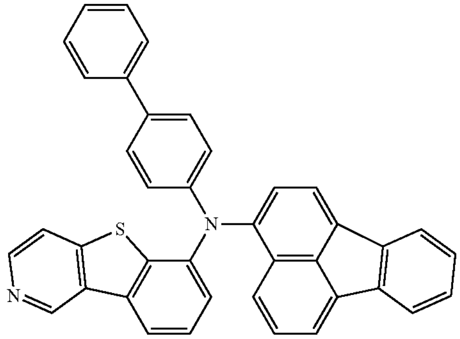
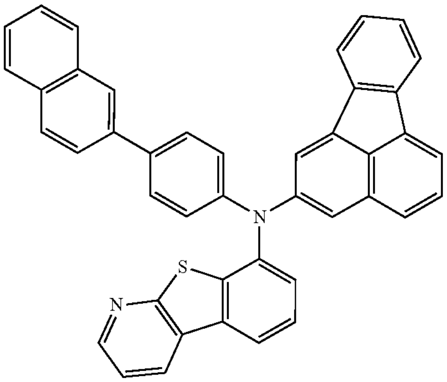
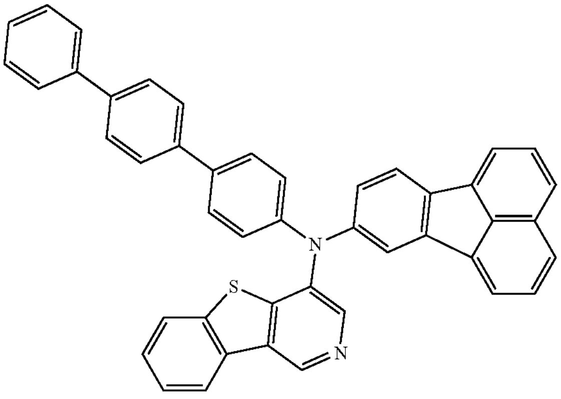

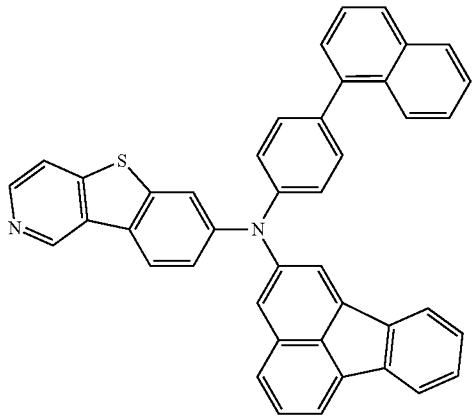
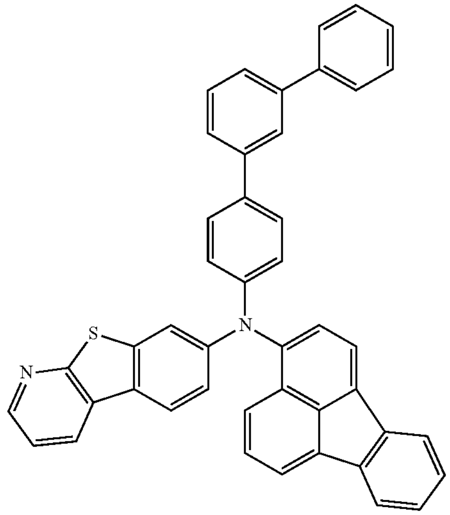
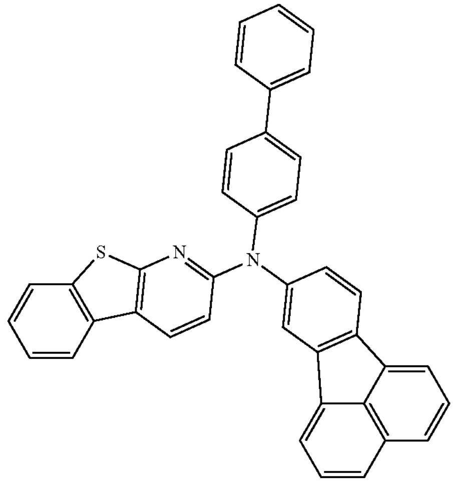
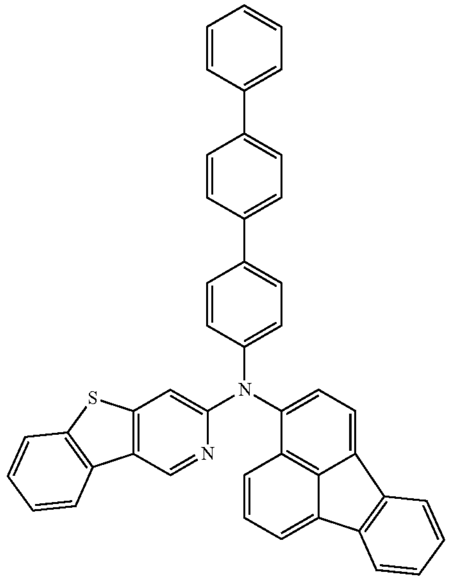
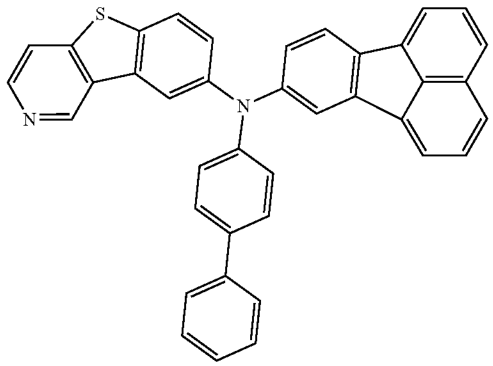
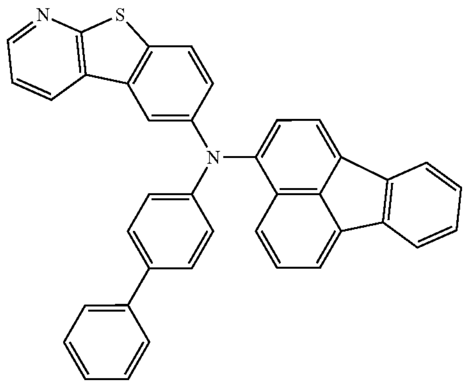

-continued
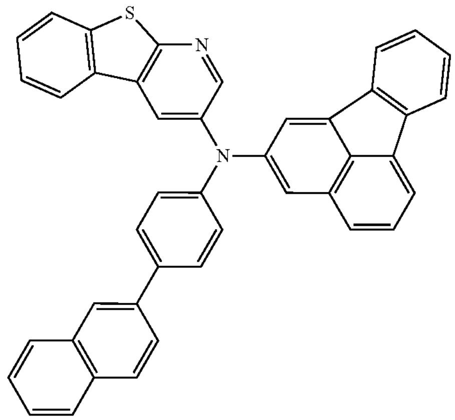
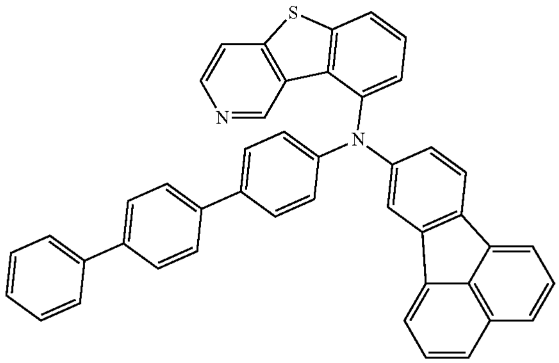
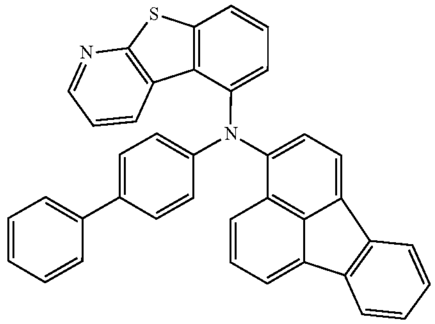
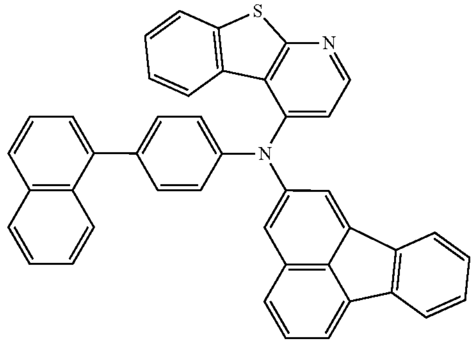
-continued
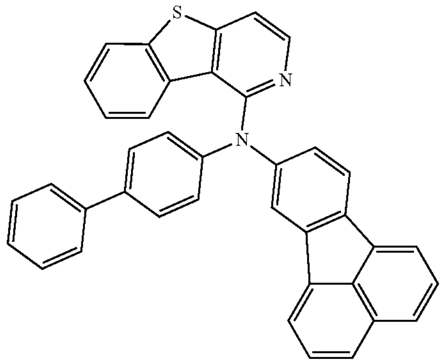 [SMILES: c1ccc(-c2ccc(N(c3ccc4c(c3)-c3cccc5cccc-4c35)c3nccc4sc5ccccc5c34)cc2)cc1]
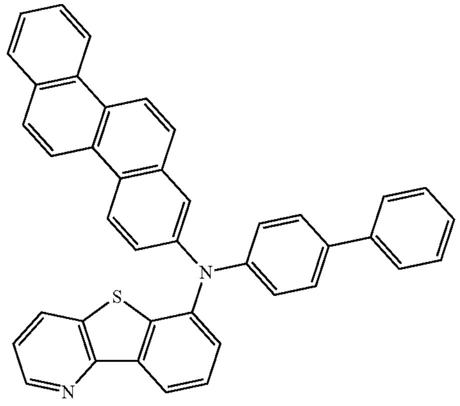
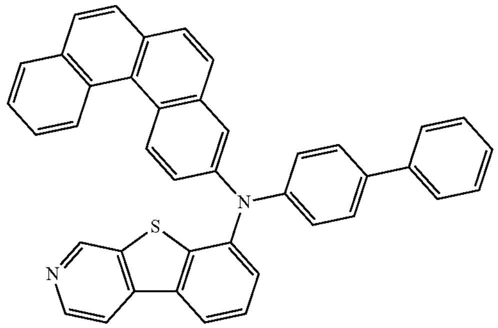
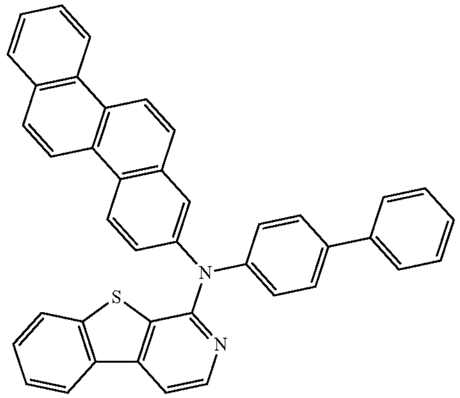

-continued
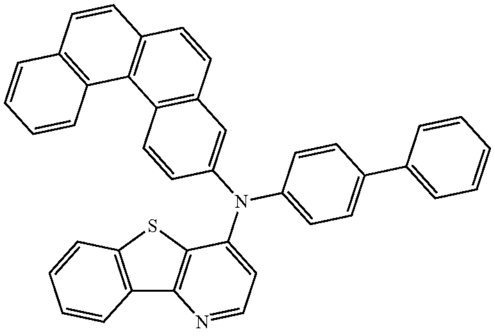 [SMILES: c1ccc(-c2ccc(N(c3ccc4c(ccc5ccc6ccccc6c54)c3)c3ccnc4c3sc3ccccc34)cc2)cc1]
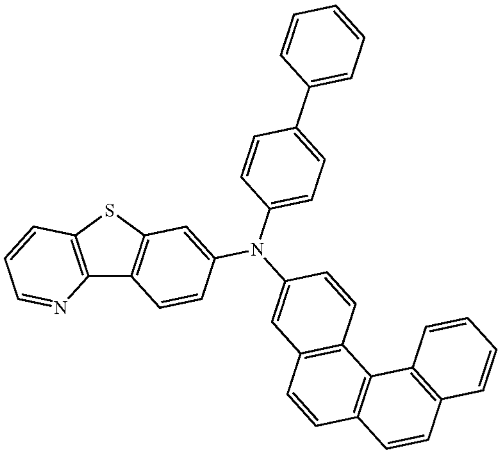
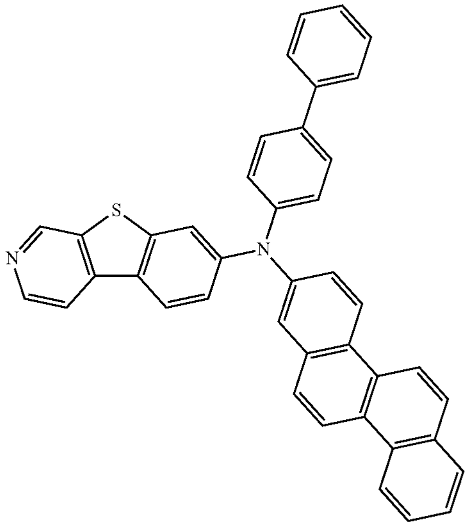
-continued
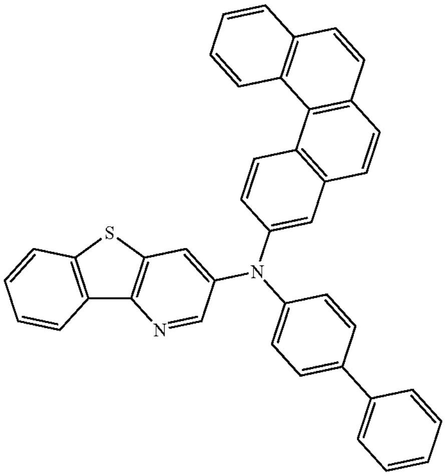
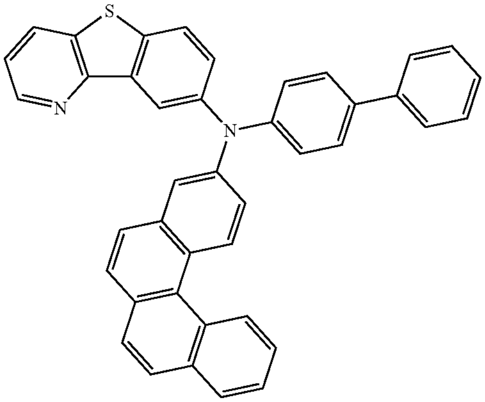
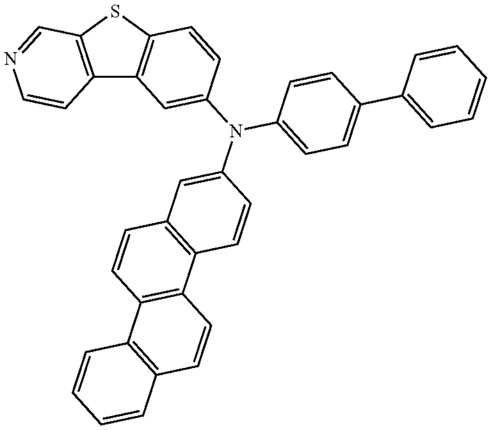
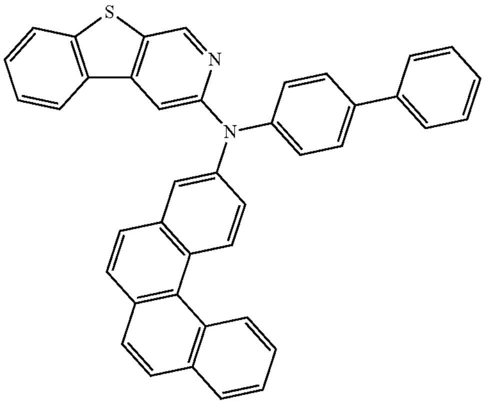

-continued
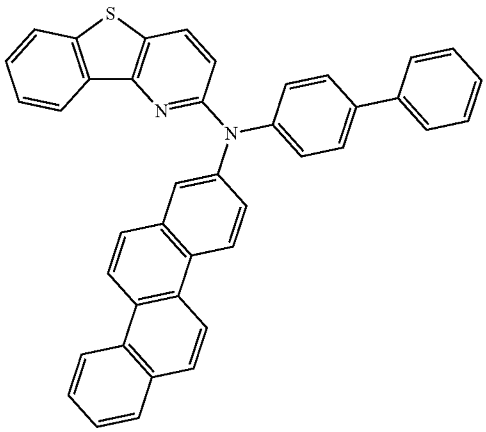 [SMILES: c1ccc(-c2ccc(N(c3ccc4c(ccc5c6ccccc6ccc45)c3)c3ccc4sc5ccccc5c4n3)cc2)cc1]
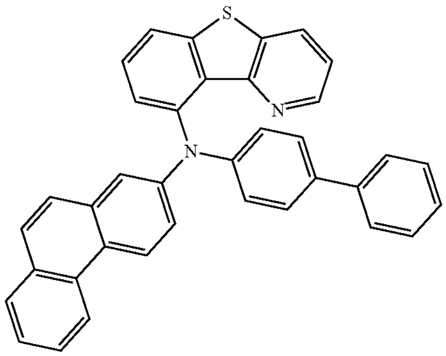
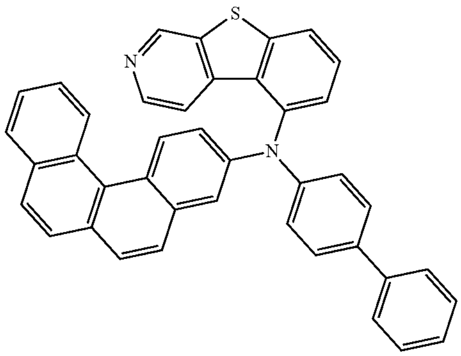
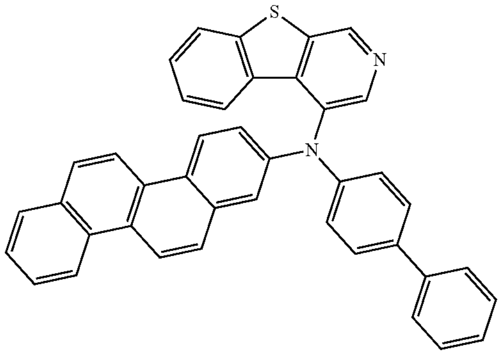
-continued
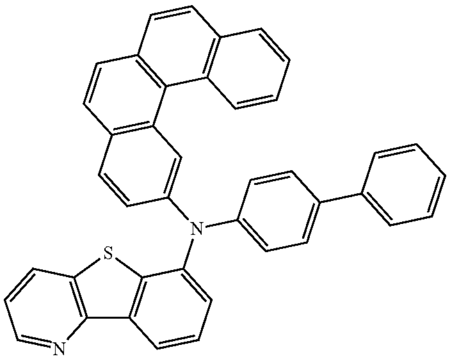
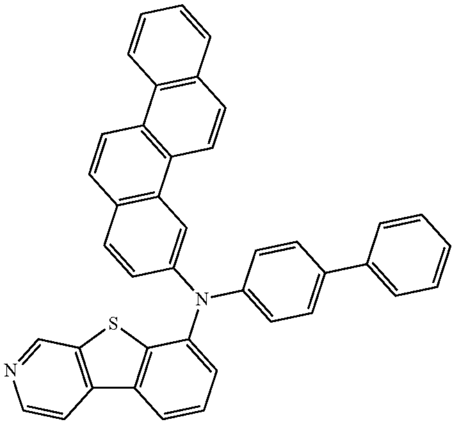
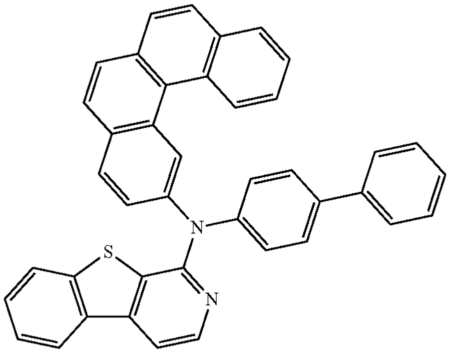
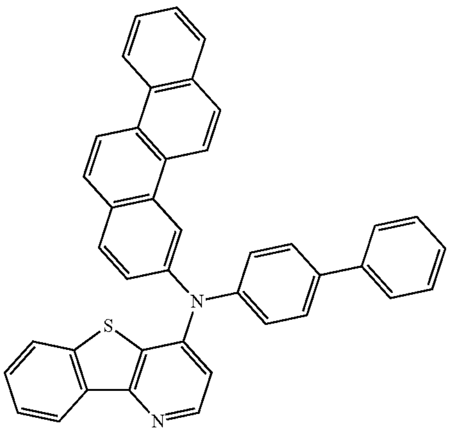 [SMILES: c1ccc(-c2ccc(N(c3ccc4ccc5c6ccccc6ccc5c4c3)c3ccnc4c3sc3ccccc34)cc2)cc1]

-continued
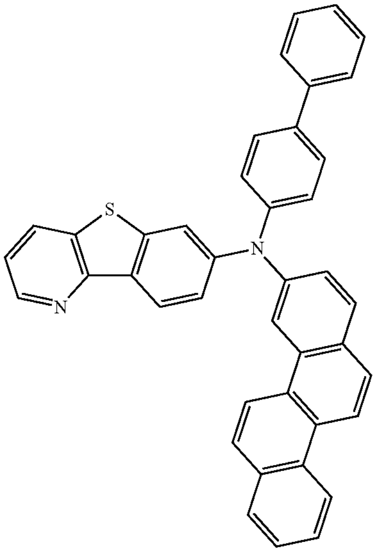
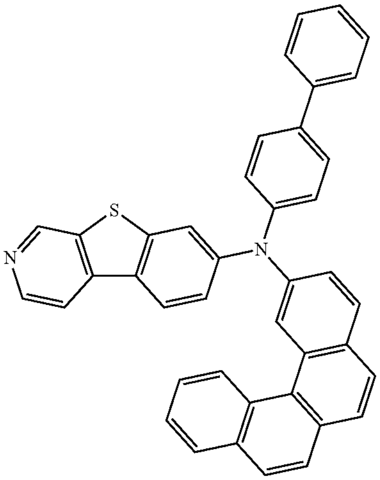
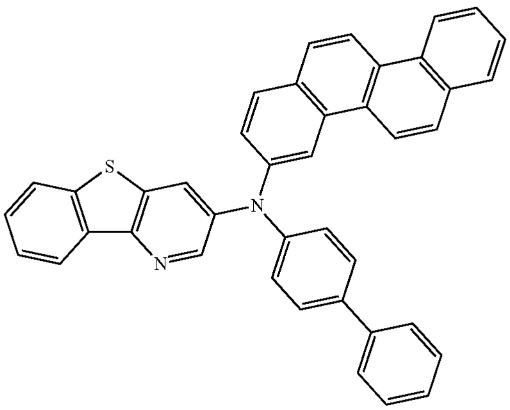
-continued
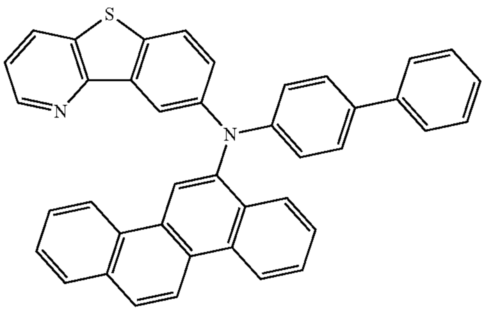
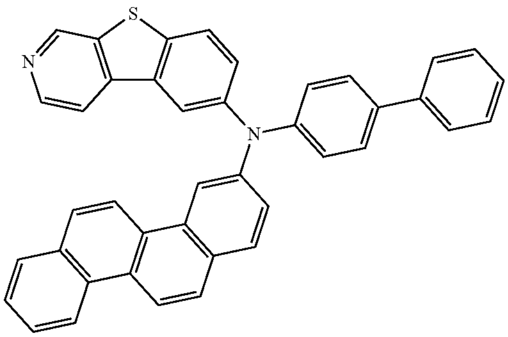
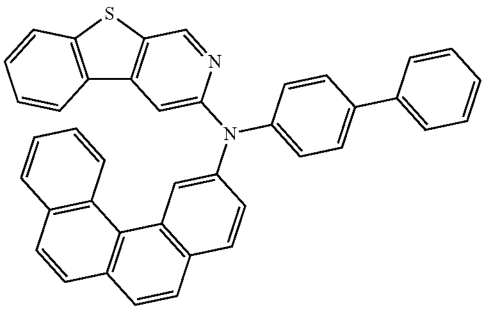
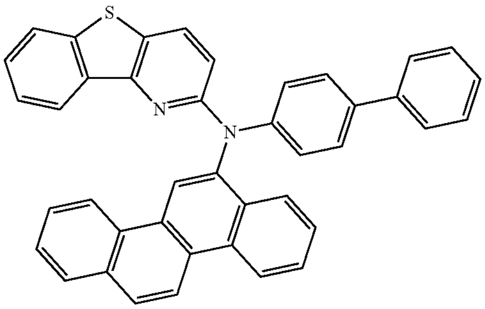 [SMILES: c1ccc(-c2ccc(N(c3ccc4sc5ccccc5c4n3)c3cc4c5ccccc5ccc4c4ccccc34)cc2)cc1]
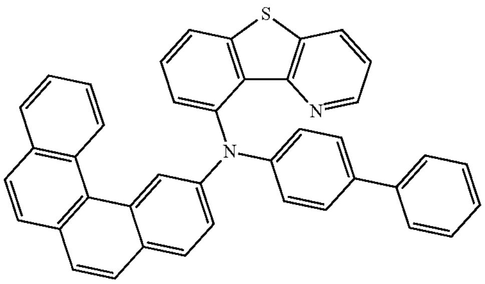

-continued
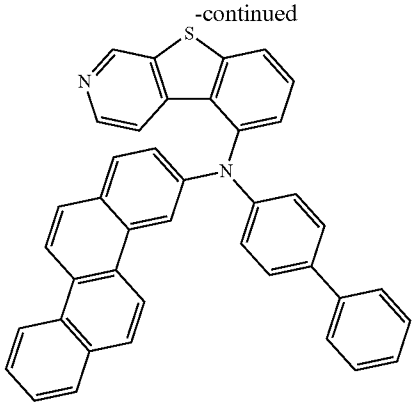
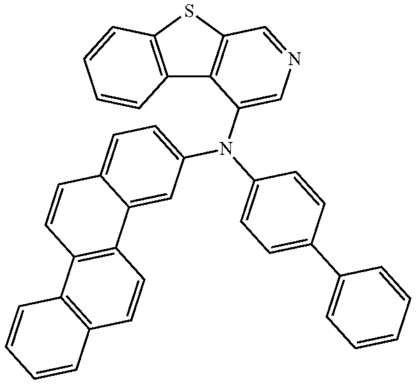
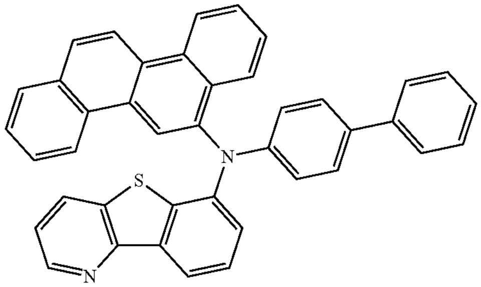
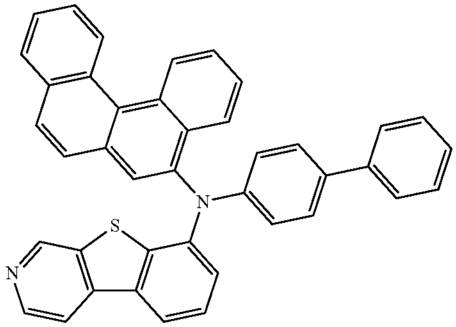
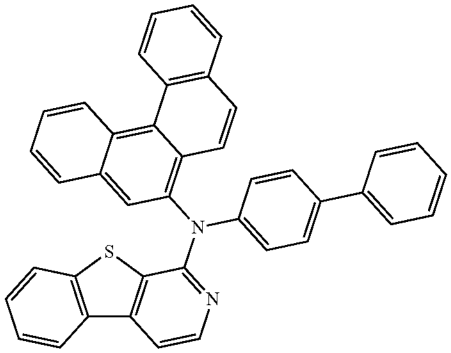
-continued
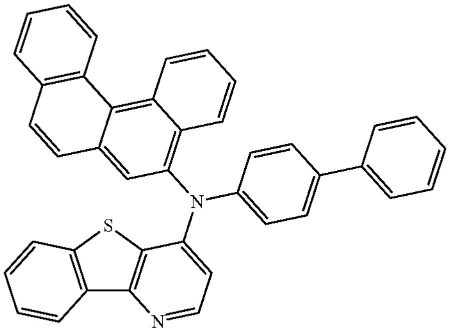 [SMILES: c1ccc(-c2ccc(N(c3cc4ccc5ccccc5c4c4ccccc34)c3ccnc4c3sc3ccccc34)cc2)cc1]
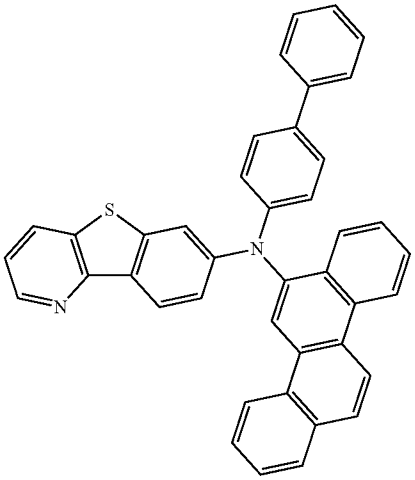
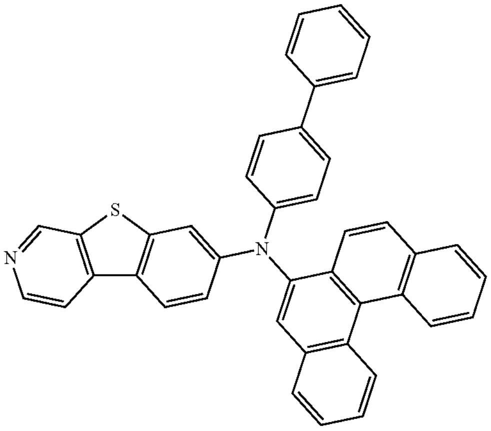
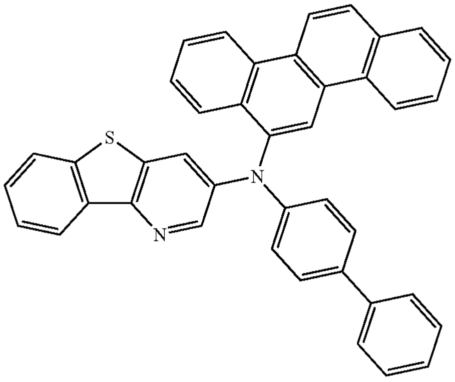

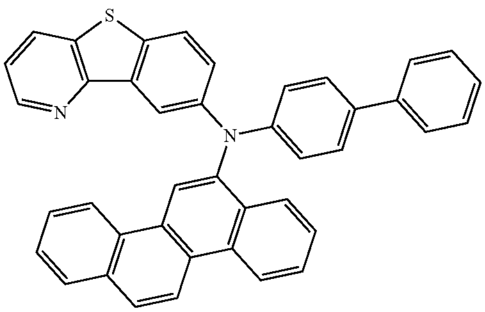
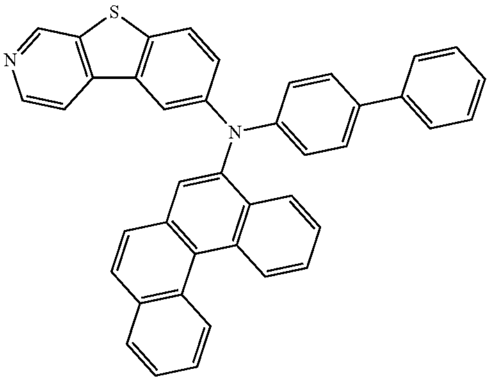
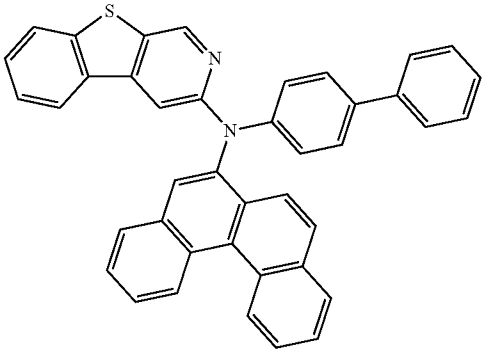
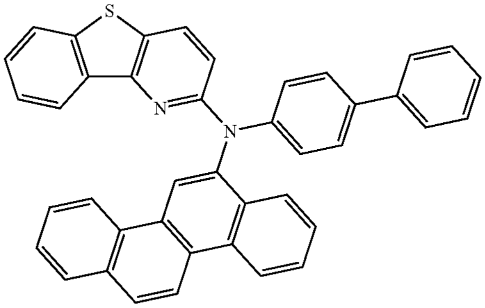 [SMILES: c1ccc(-c2ccc(N(c3ccc4sc5ccccc5c4n3)c3cc4c5ccccc5ccc4c4ccccc34)cc2)cc1]
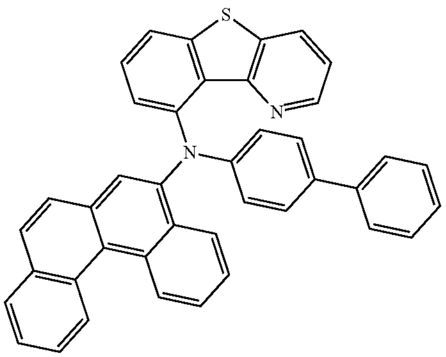
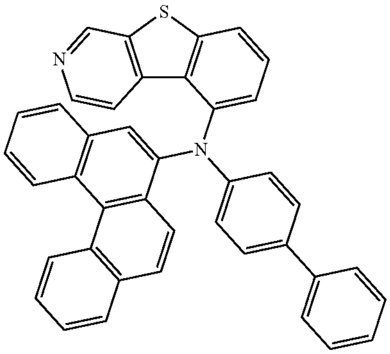
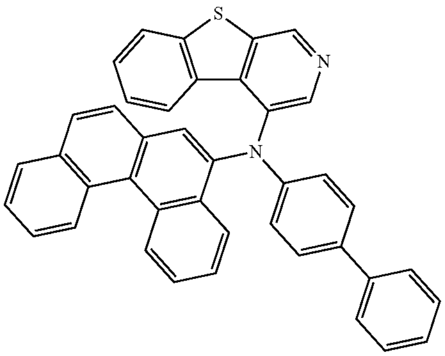
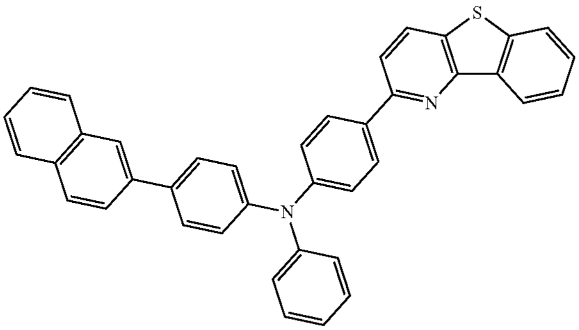
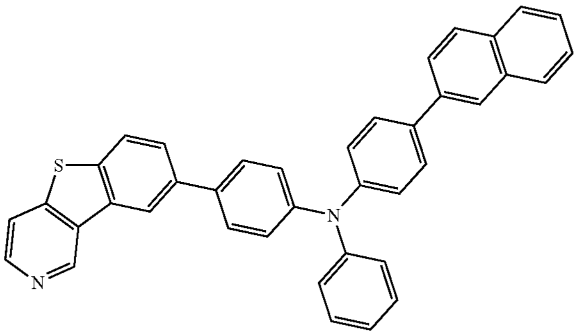

-continued
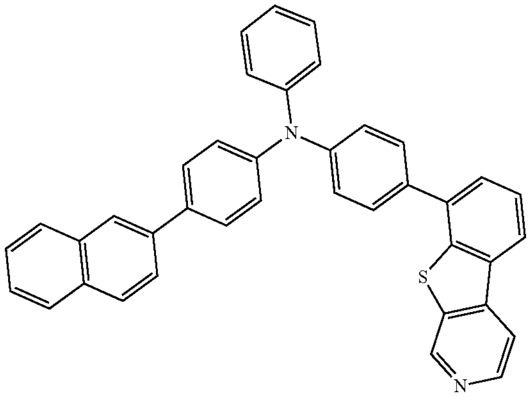
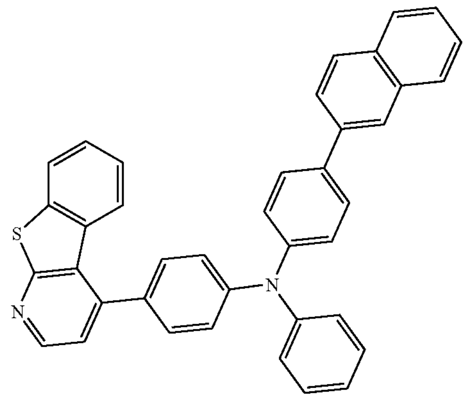
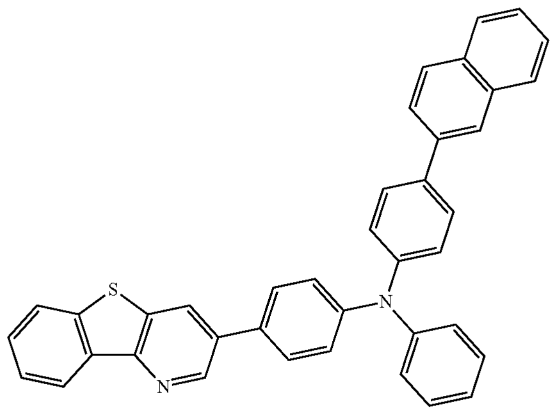
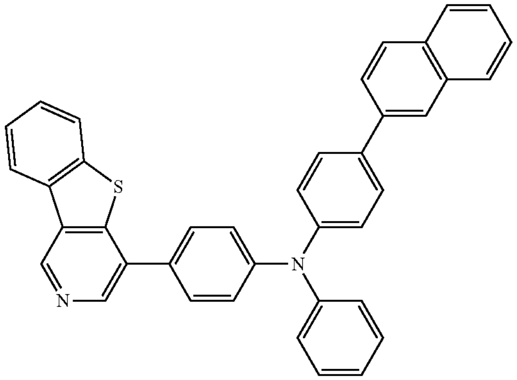
-continued
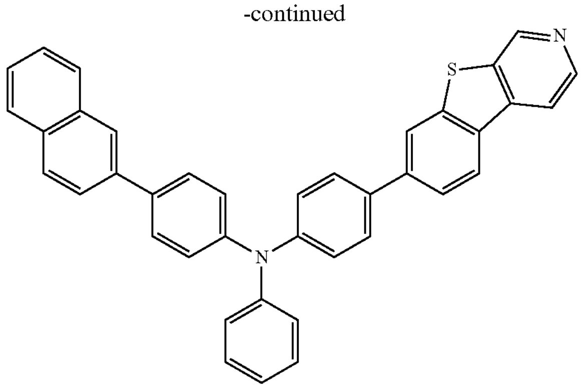
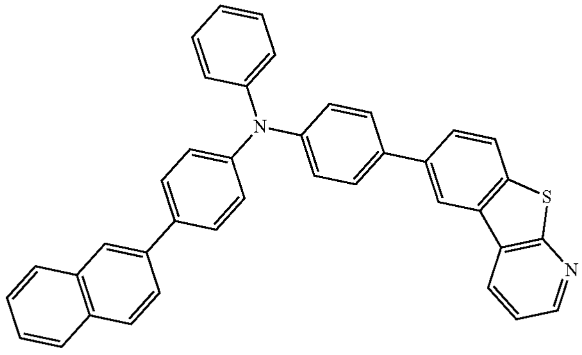
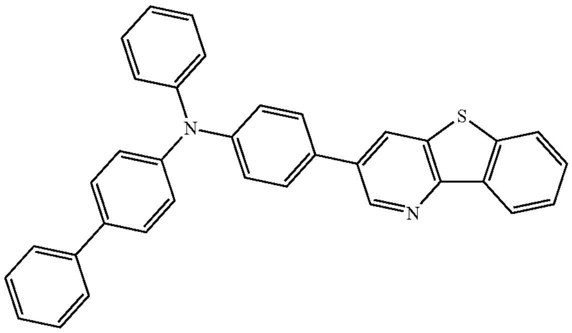
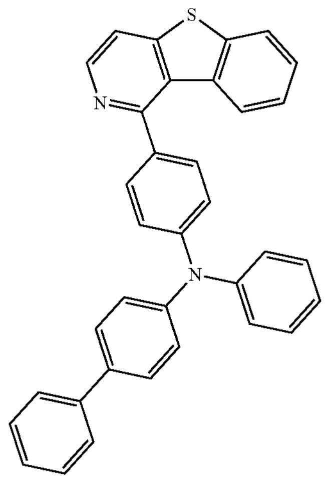

-continued
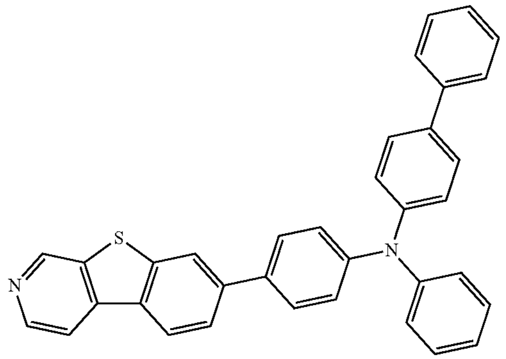
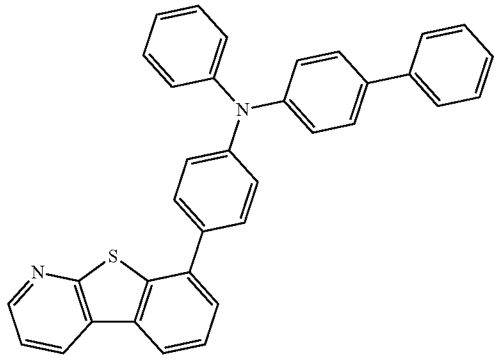 [SMILES: c1ccc(-c2ccc(N(c3ccccc3)c3ccc(-c4cccc5c4sc4ncccc45)cc3)cc2)cc1]
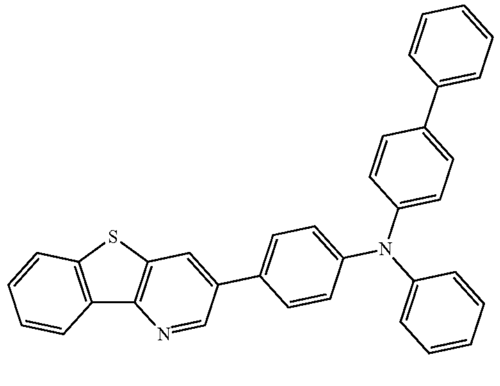
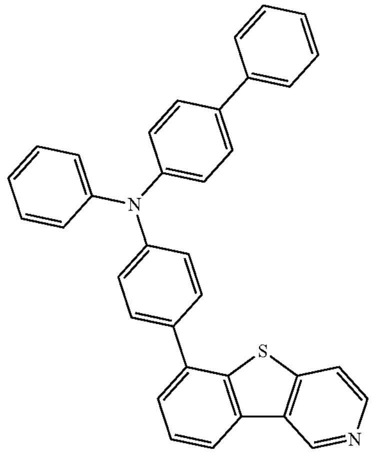
-continued
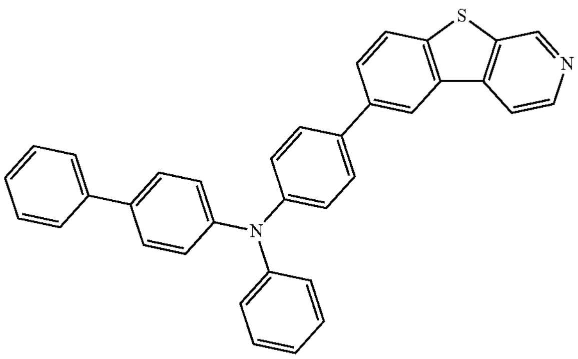
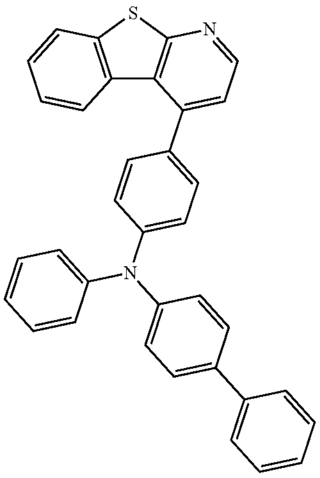 [SMILES: c1ccc(-c2ccc(N(c3ccccc3)c3ccc(-c4ccnc5sc6ccccc6c45)cc3)cc2)cc1]
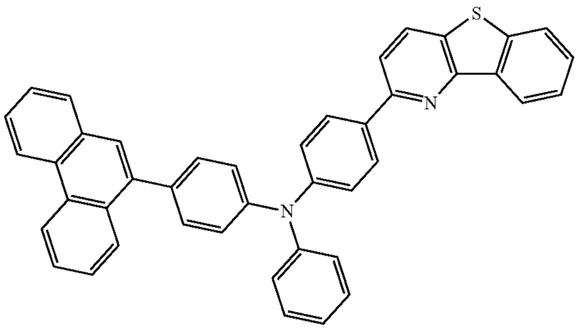
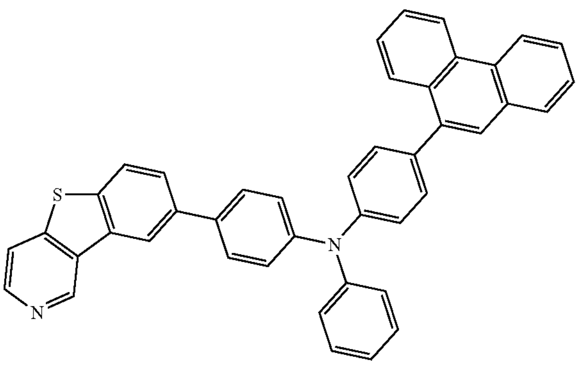

-continued
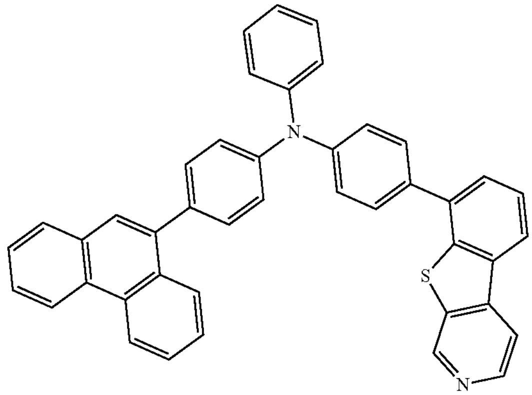
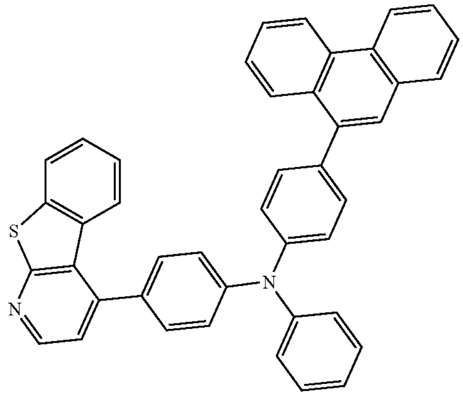
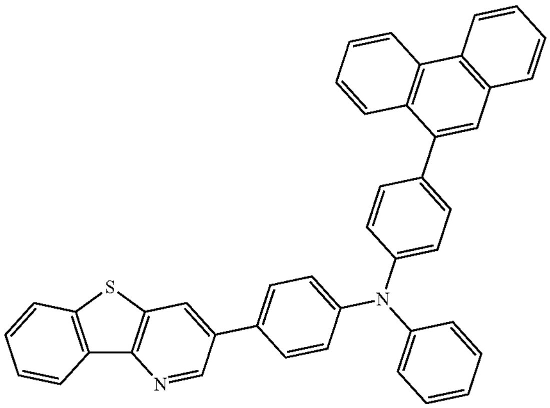
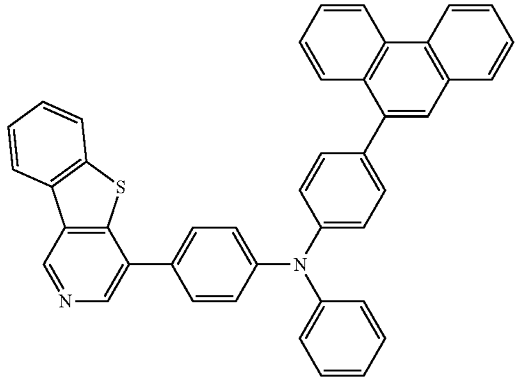
-continued
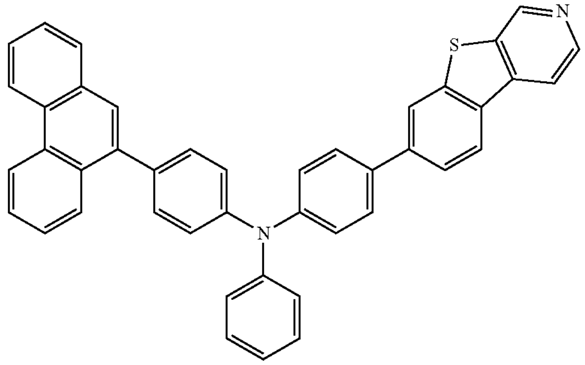
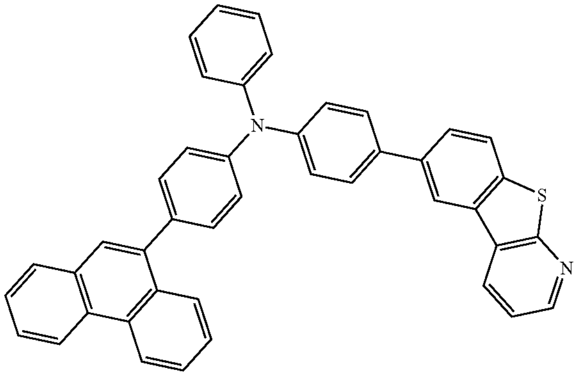
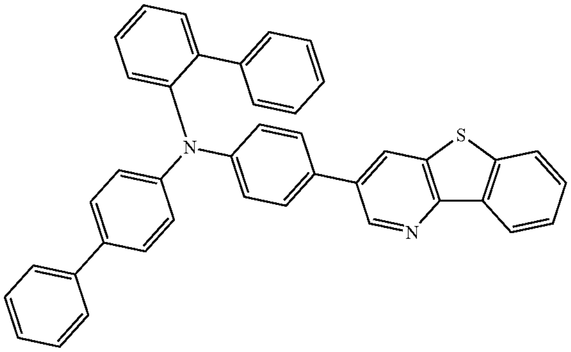
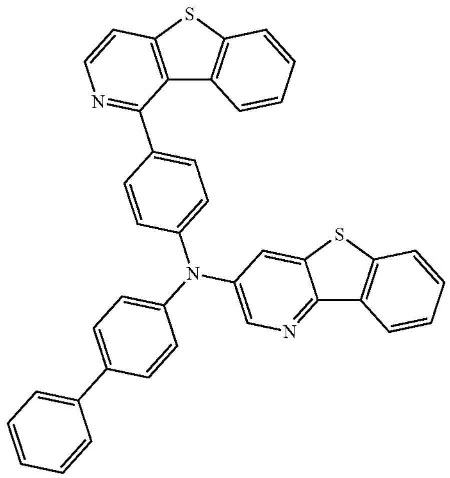

-continued
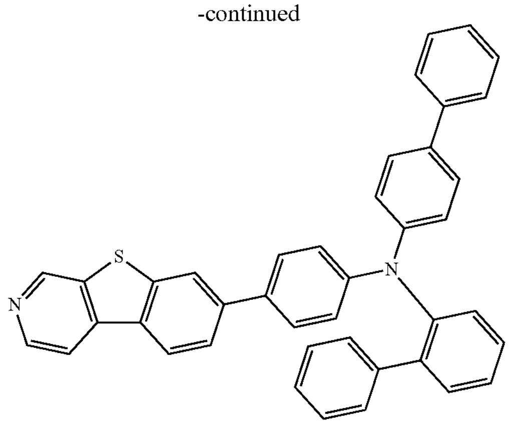
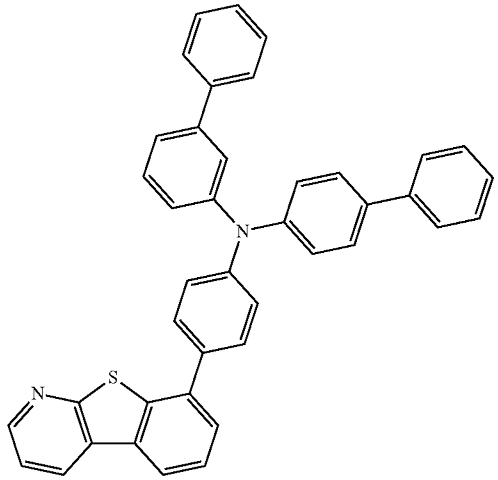
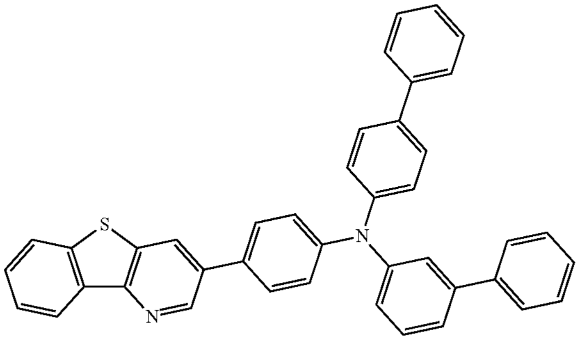
-continued
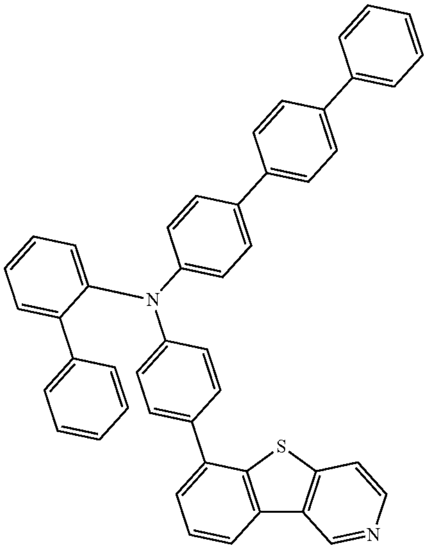
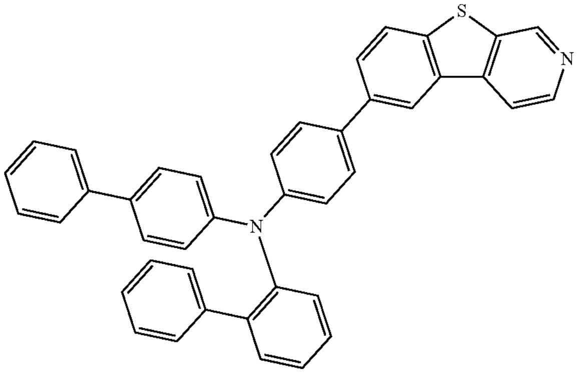
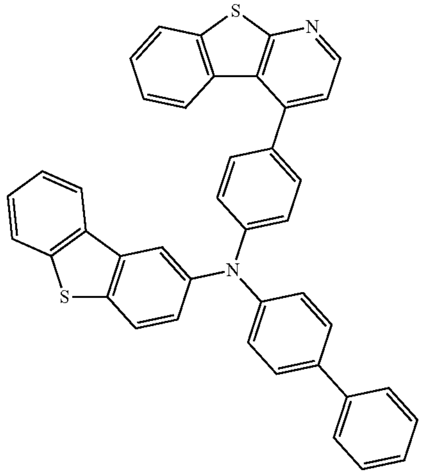

-continued
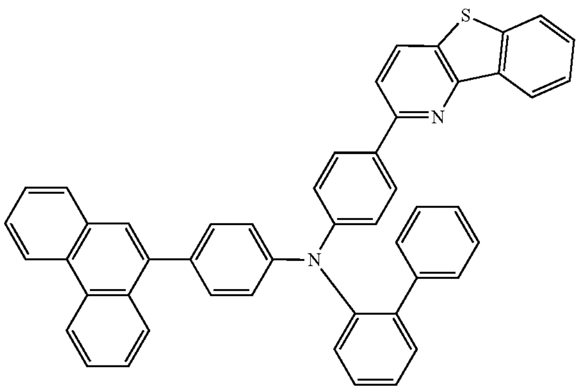
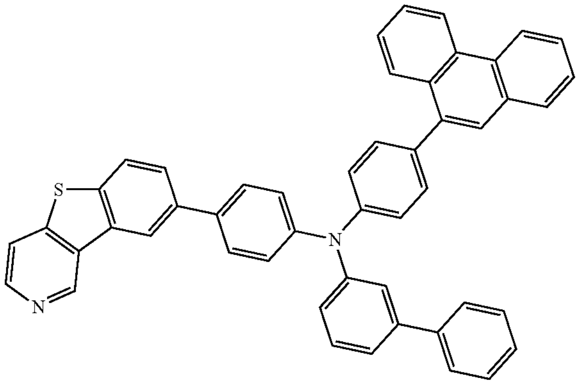
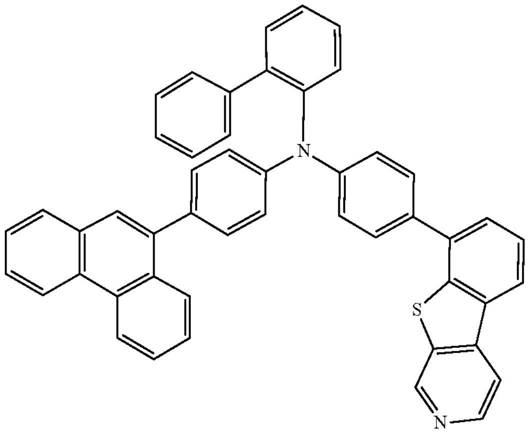
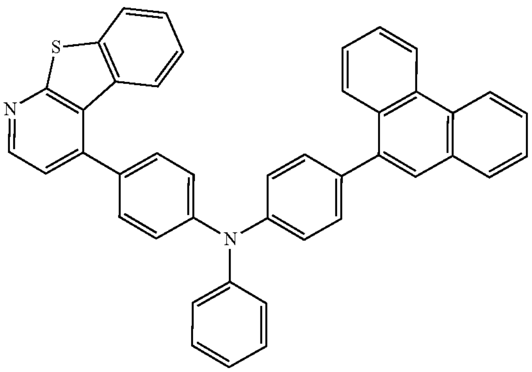
-continued
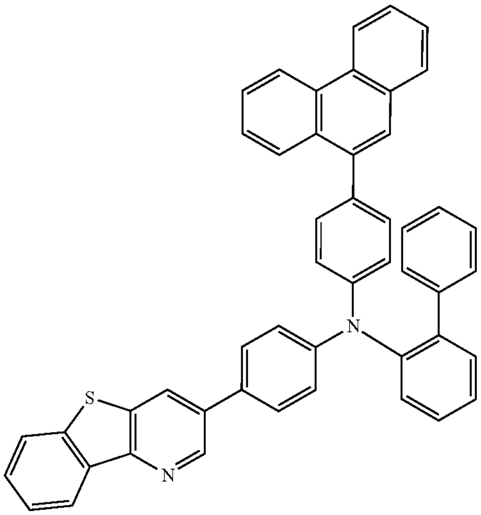
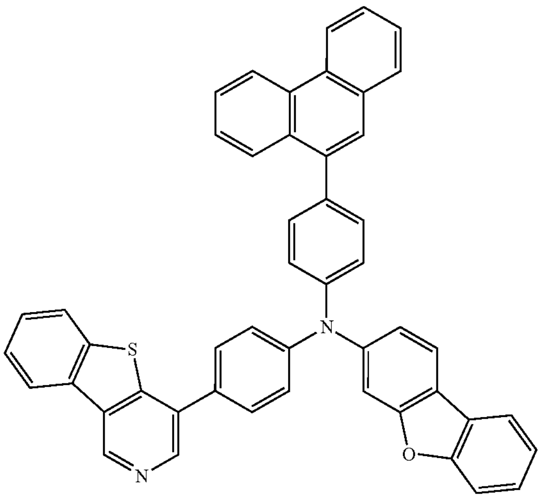
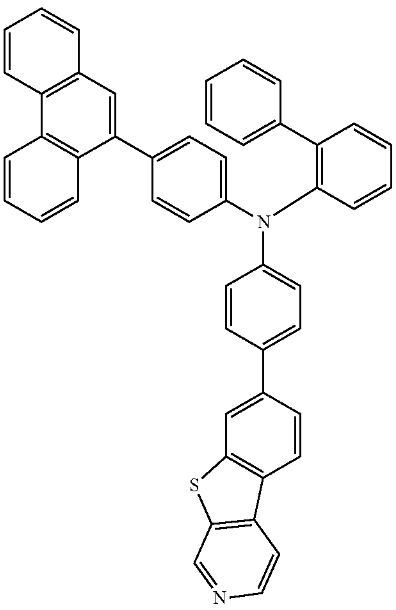

-continued
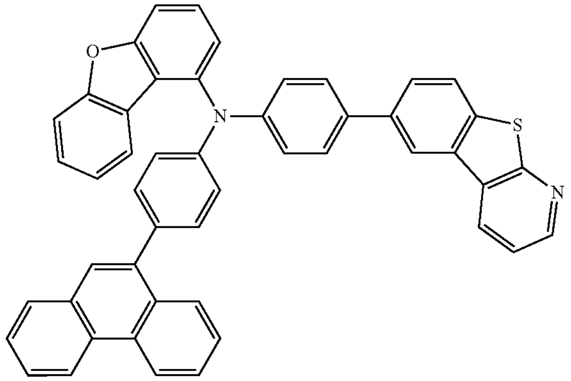 [SMILES: c1ccc2c(c1)cc(-c1ccc(N(c3ccc(-c4ccc5sc6ncccc6c5c4)cc3)c3cccc4oc5ccccc5c34)cc1)c1ccccc12]
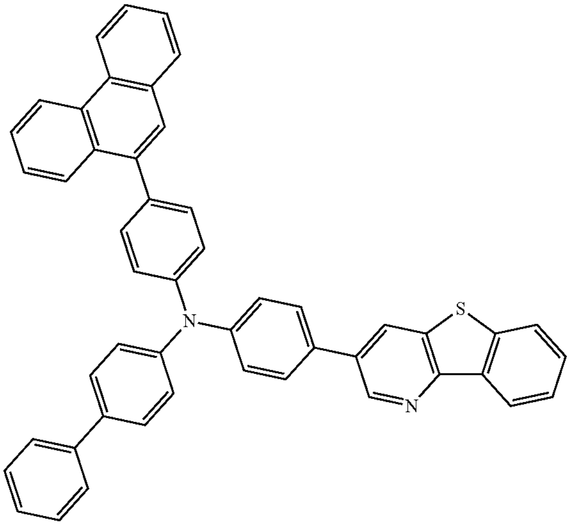
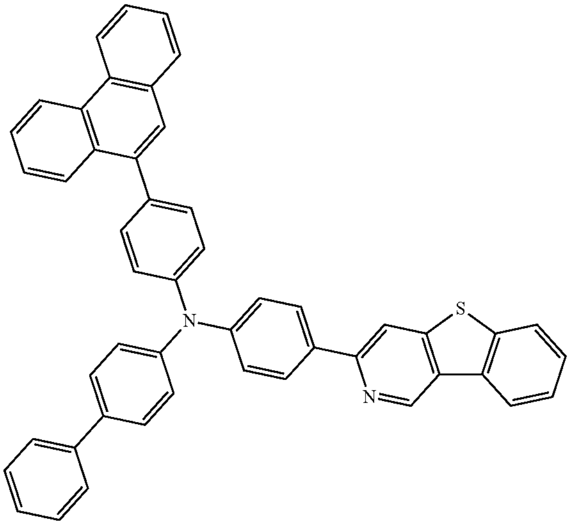
-continued
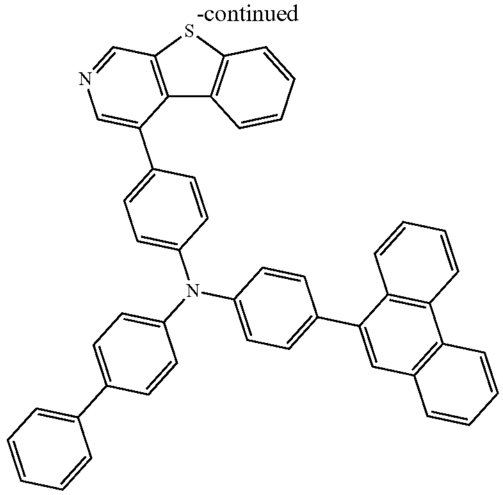
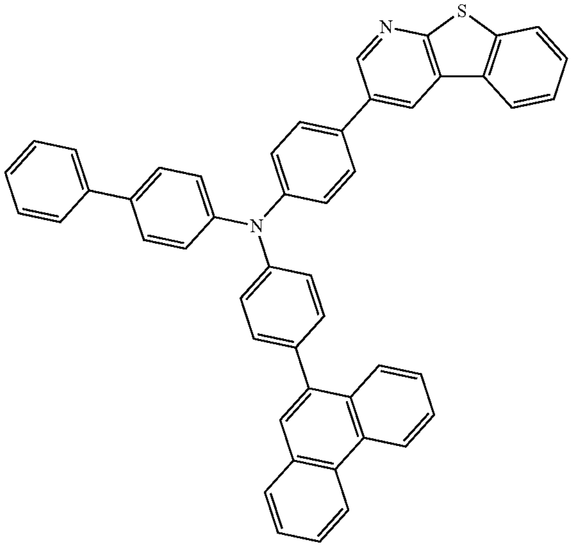
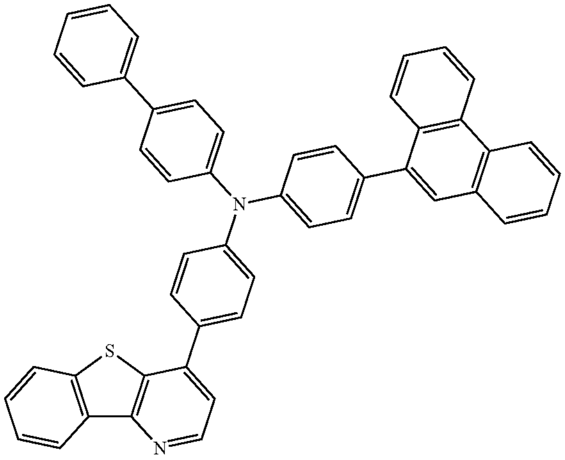

-continued
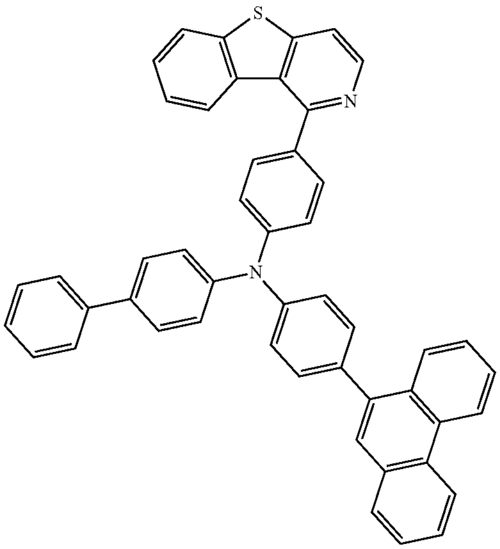
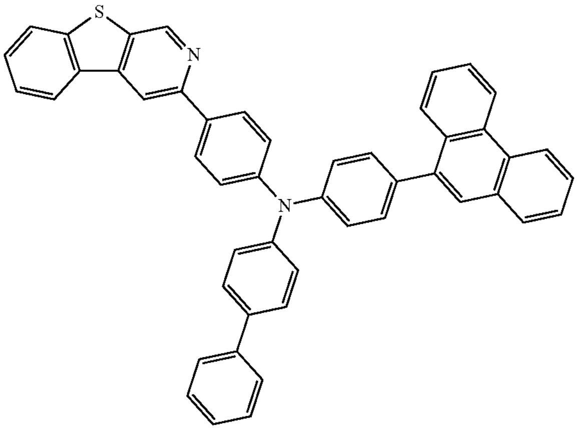
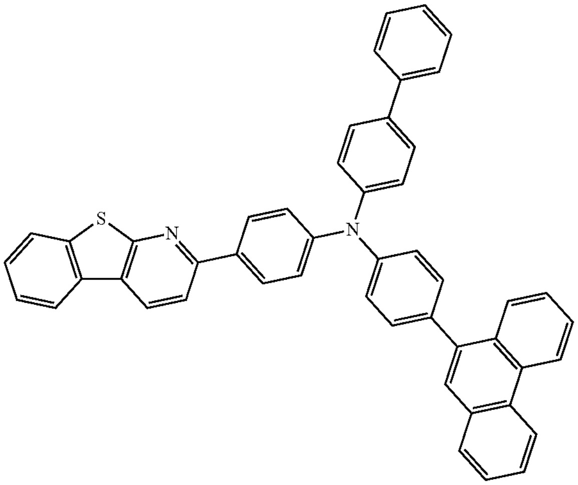 [SMILES: c1ccc(-c2ccc(N(c3ccc(-c4ccc5c(n4)sc4ccccc45)cc3)c3ccc(-c4cc5ccccc5c5ccccc45)cc3)cc2)cc1]
-continued
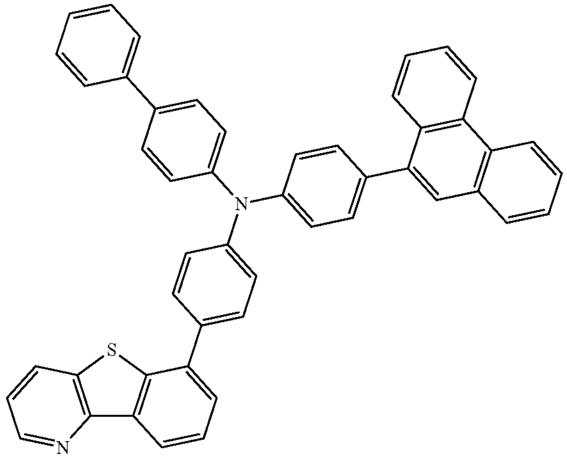
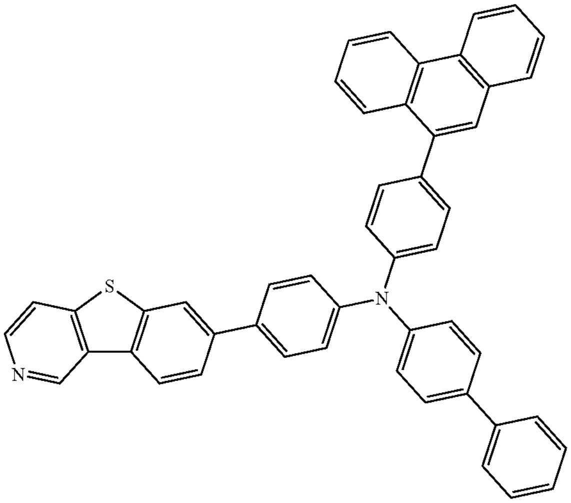
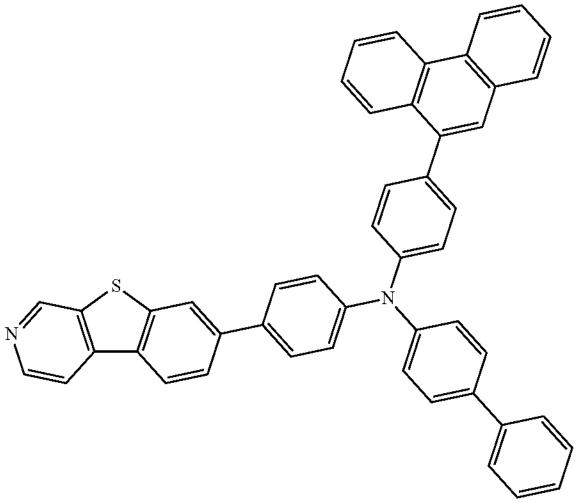

-continued
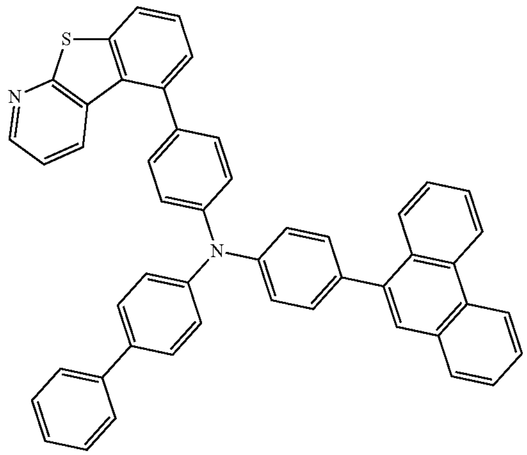 [SMILES: c1ccc(-c2ccc(N(c3ccc(-c4cc5ccccc5c5ccccc45)cc3)c3ccc(-c4cccc5sc6ncccc6c45)cc3)cc2)cc1]
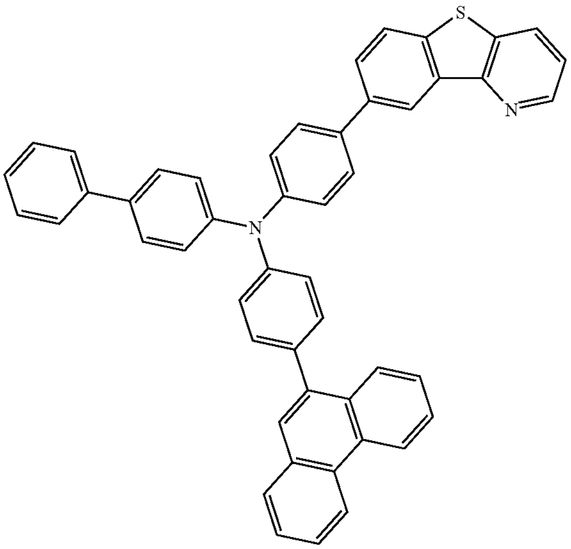
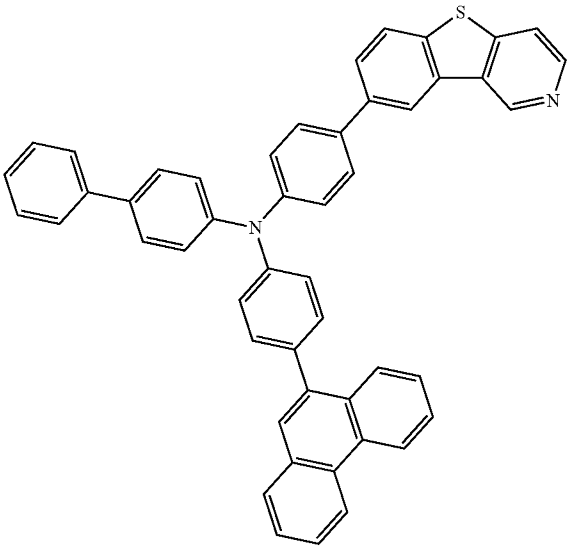
-continued
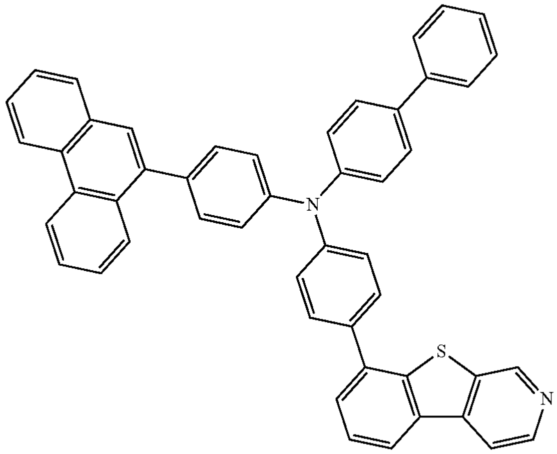
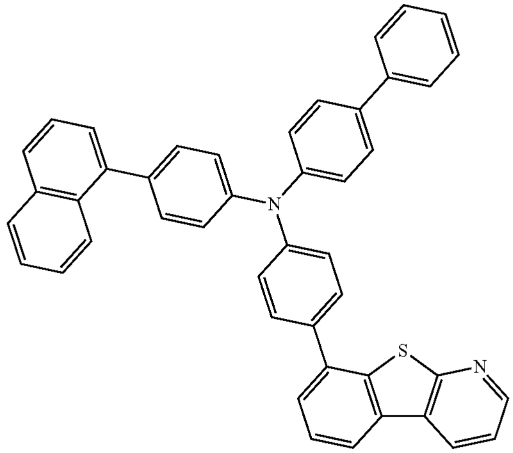 [SMILES: c1ccc(-c2ccc(N(c3ccc(-c4cccc5ccccc45)cc3)c3ccc(-c4cccc5c4sc4ncccc45)cc3)cc2)cc1]
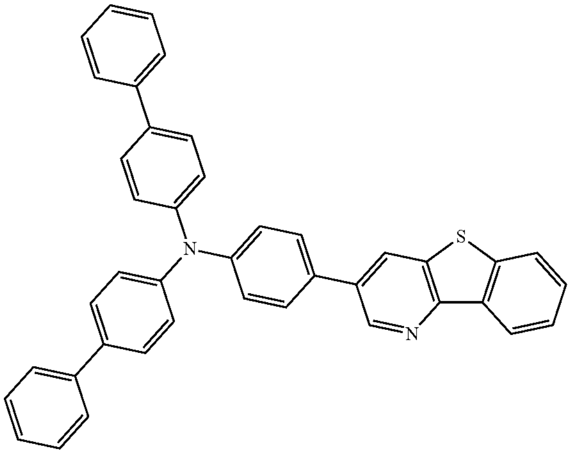

-continued
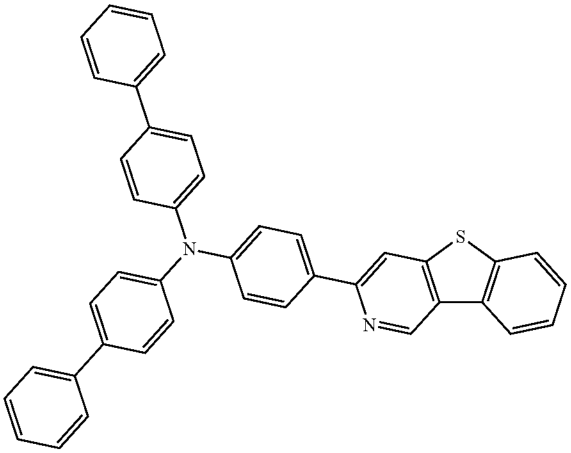
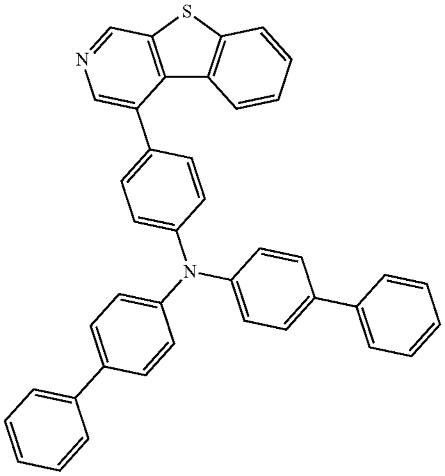
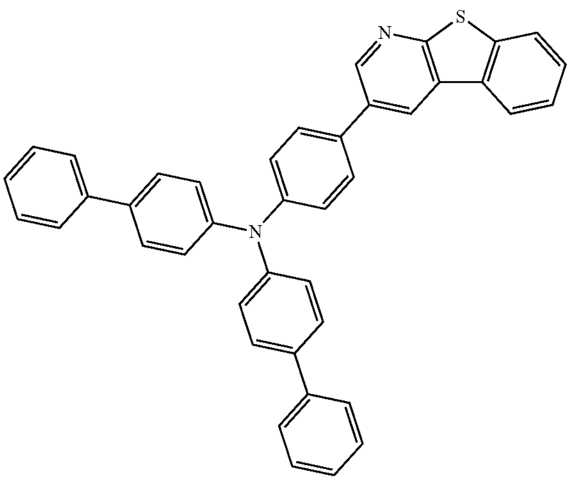 [SMILES: c1ccc(-c2ccc(N(c3ccc(-c4ccccc4)cc3)c3ccc(-c4cnc5sc6ccccc6c5c4)cc3)cc2)cc1]
-continued
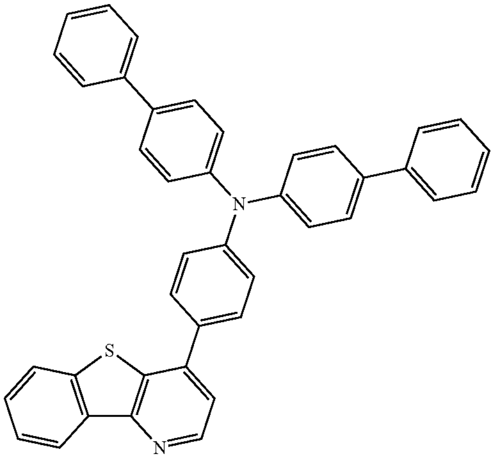
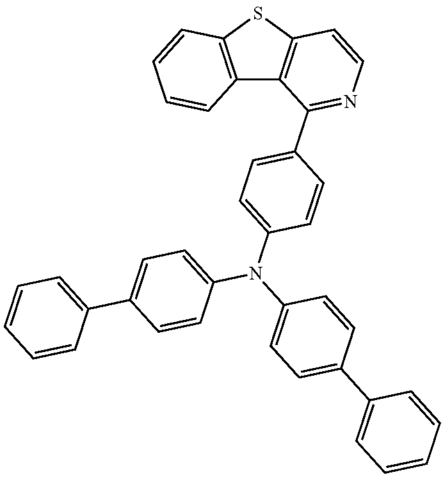
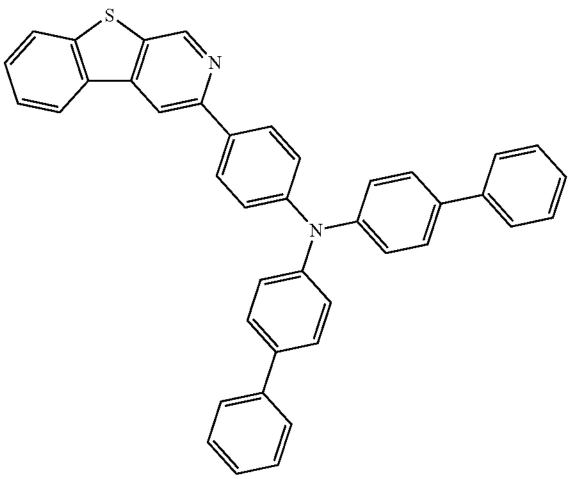

-continued
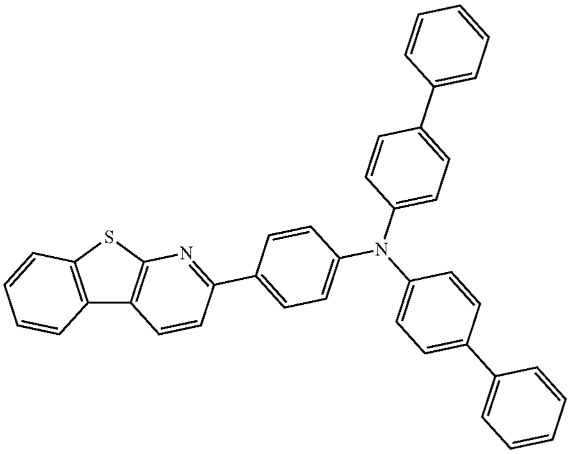
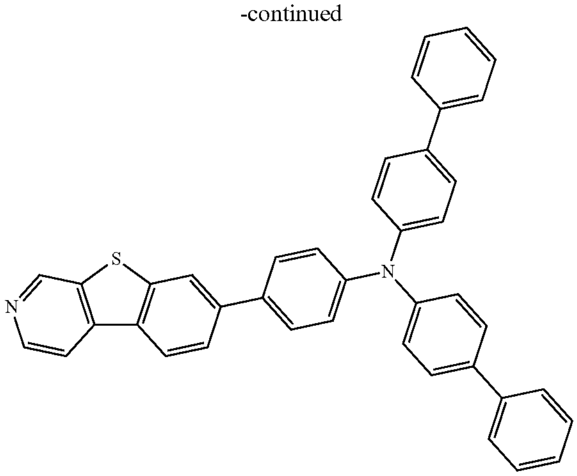
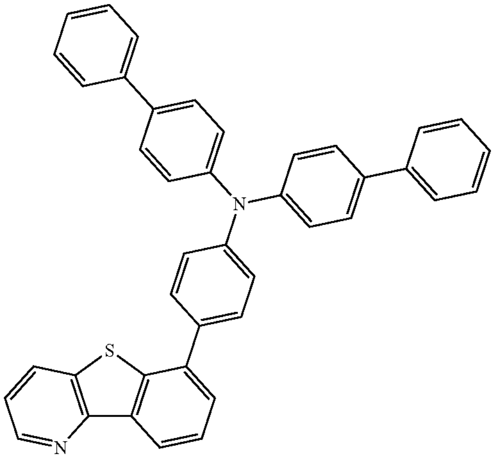
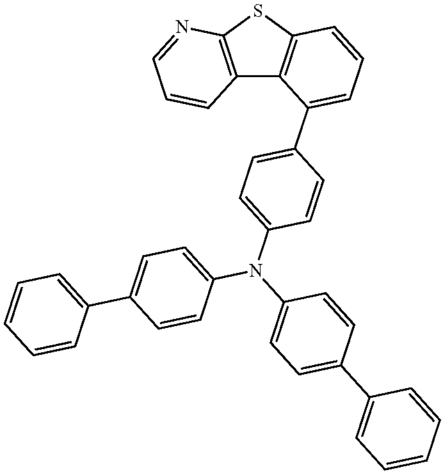 [SMILES: c1ccc(-c2ccc(N(c3ccc(-c4ccccc4)cc3)c3ccc(-c4cccc5sc6ncccc6c45)cc3)cc2)cc1]
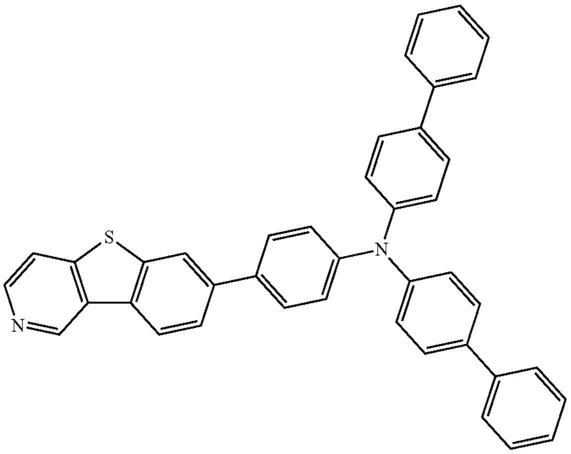
-continued
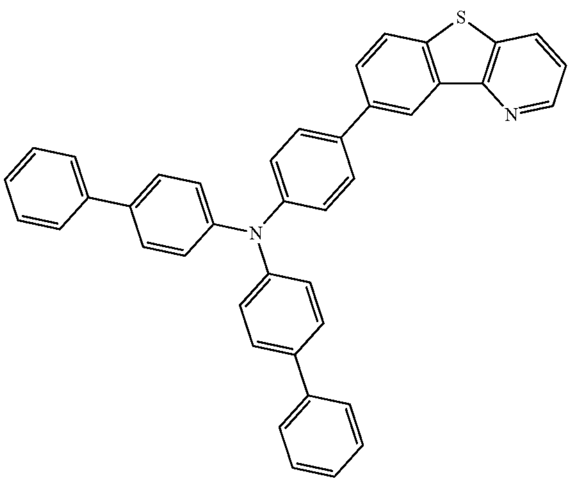

-continued
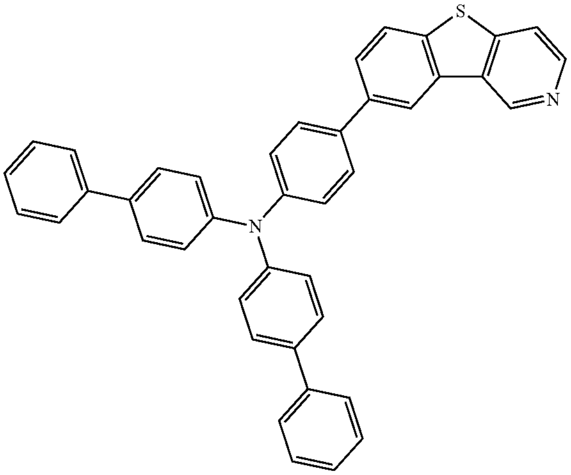
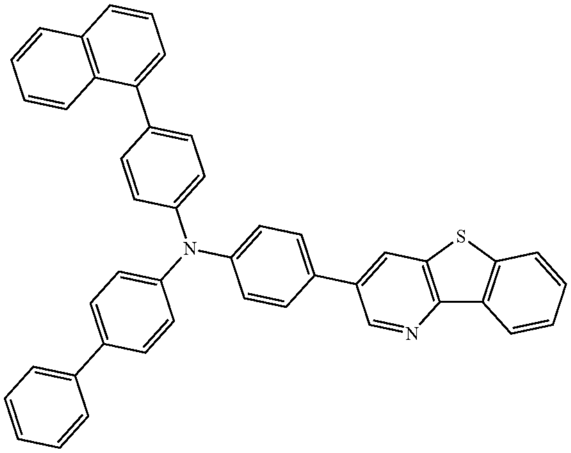
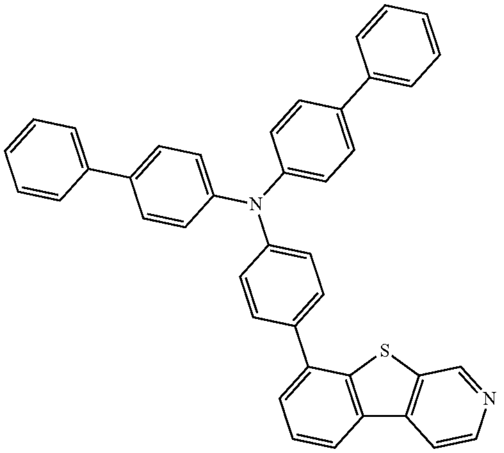
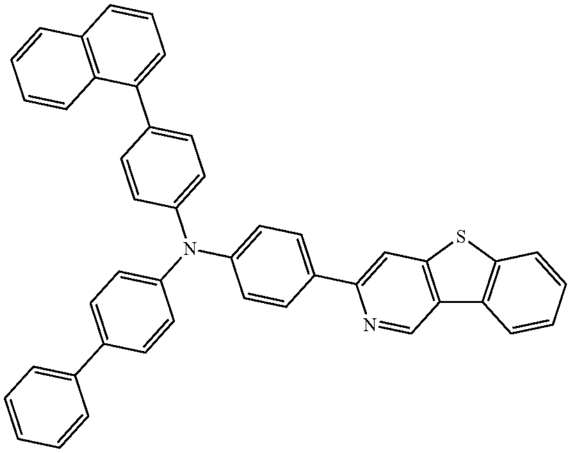
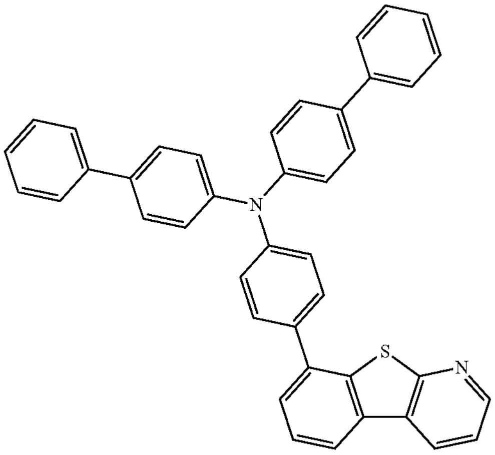 [SMILES: c1ccc(-c2ccc(N(c3ccc(-c4ccccc4)cc3)c3ccc(-c4cccc5c4sc4ncccc45)cc3)cc2)cc1]
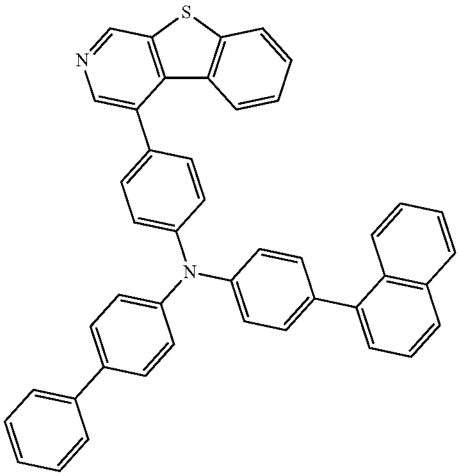
-continued -continued
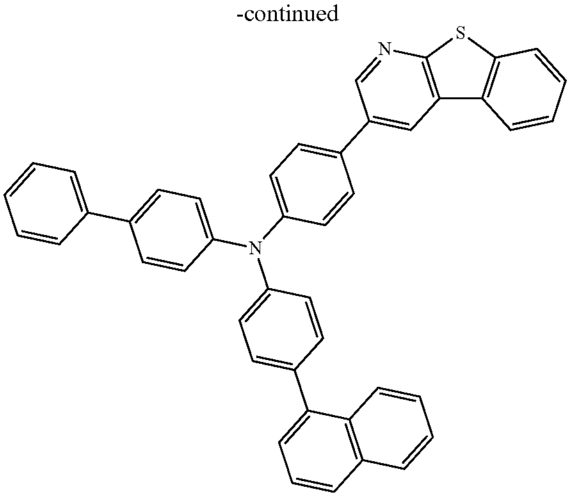
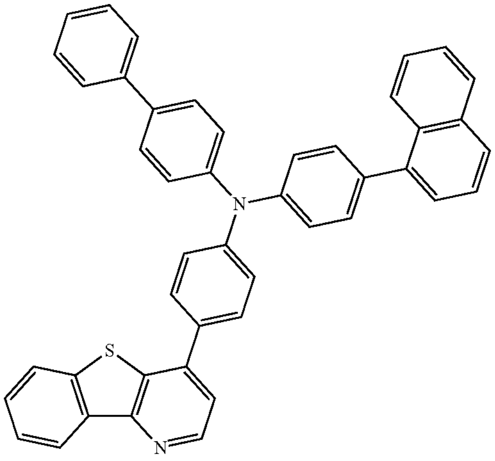
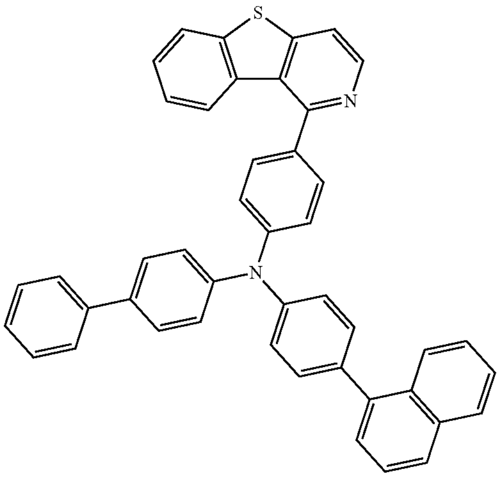
-continued
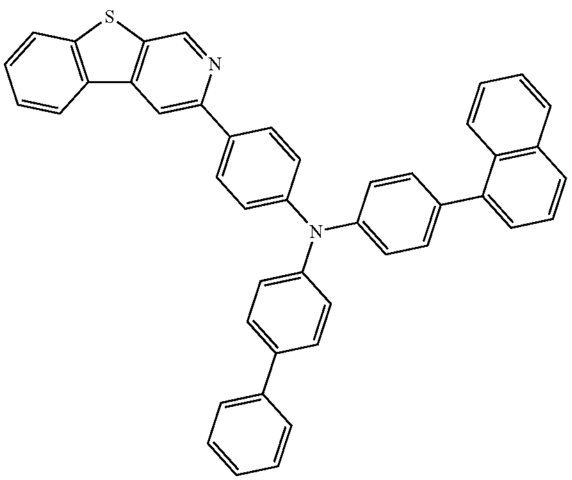
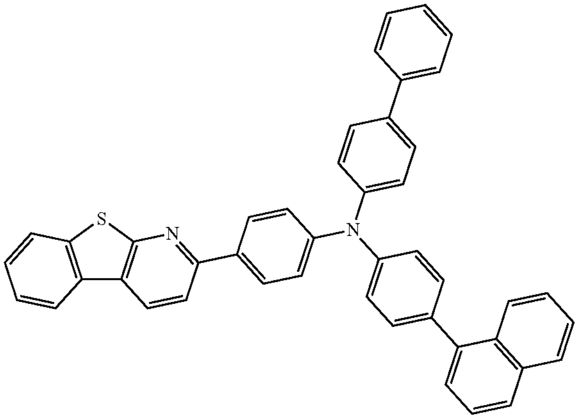 [SMILES: c1ccc(-c2ccc(N(c3ccc(-c4ccc5c(n4)sc4ccccc45)cc3)c3ccc(-c4cccc5ccccc45)cc3)cc2)cc1]
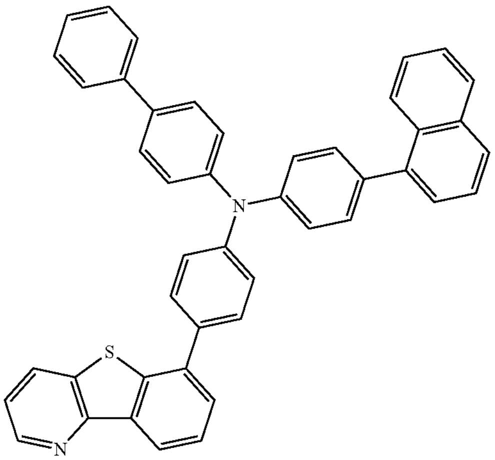

-continued
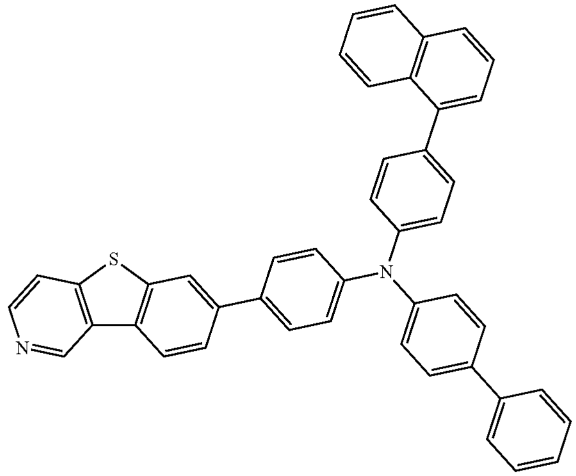
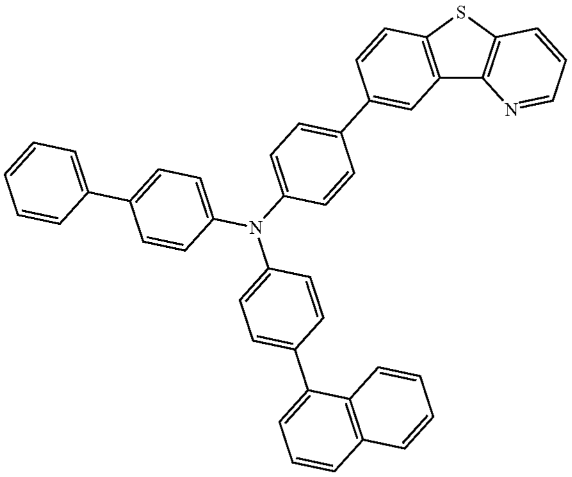
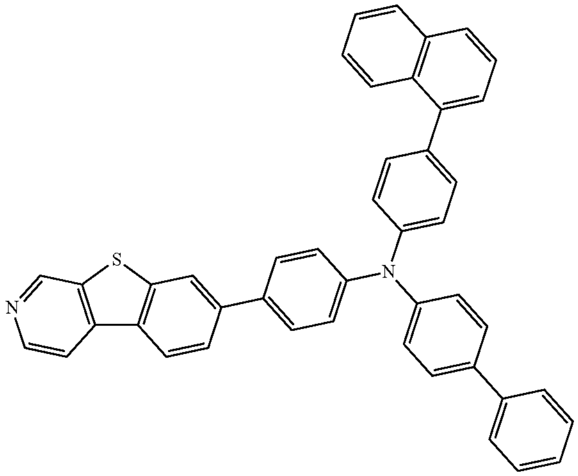
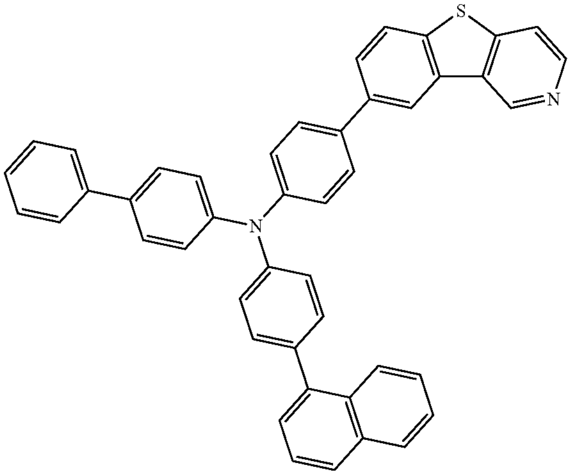
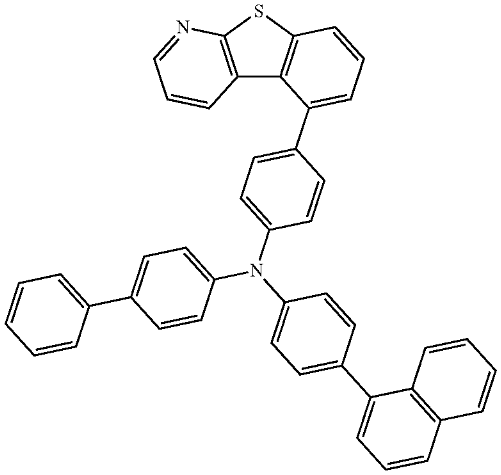
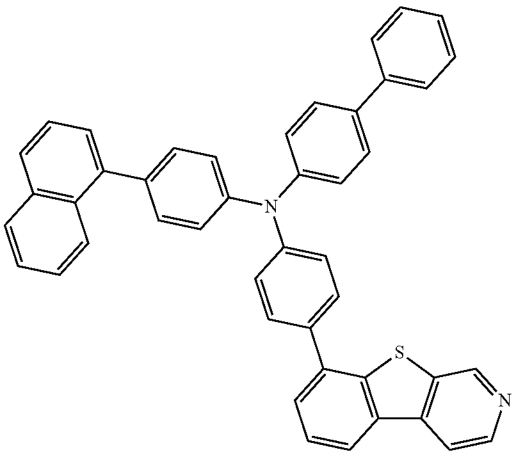
-continued -continued
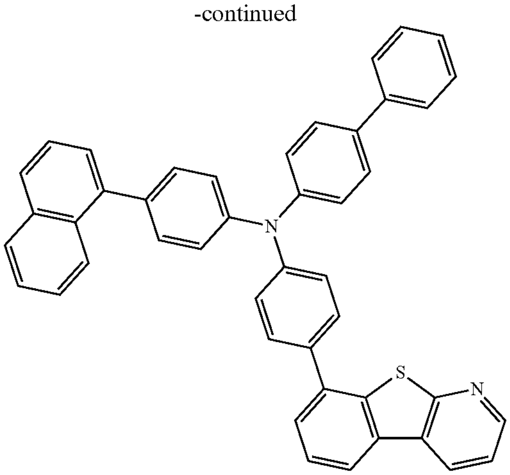
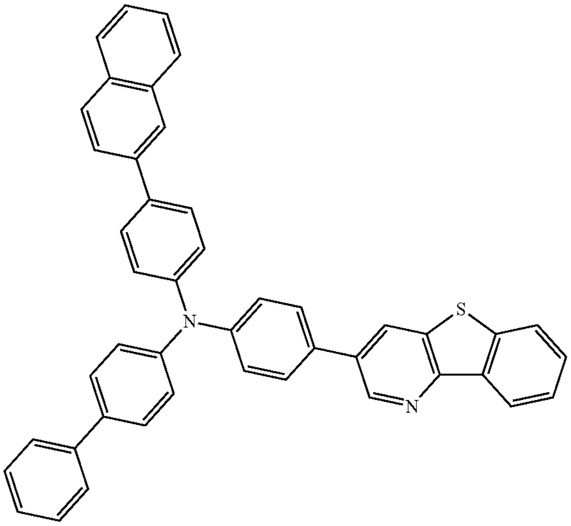
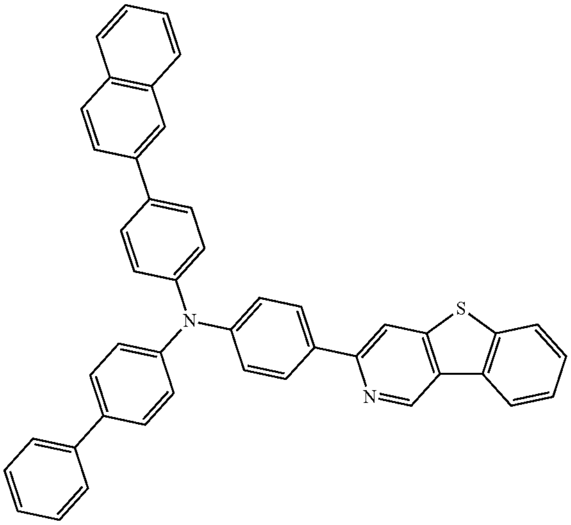
-continued
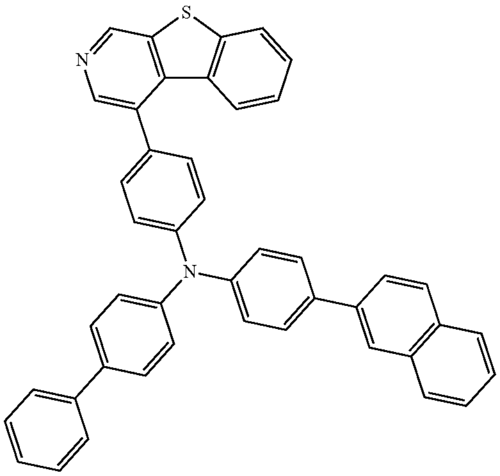
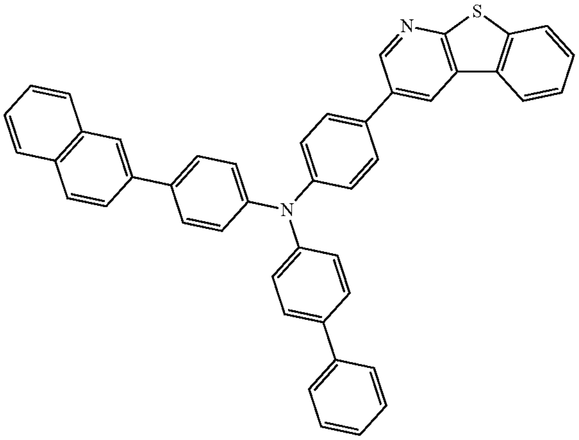
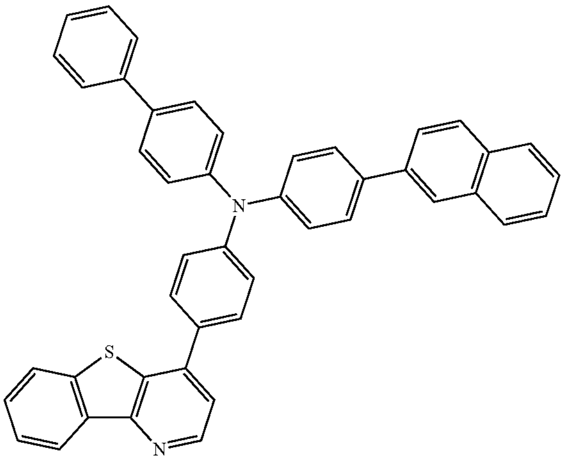

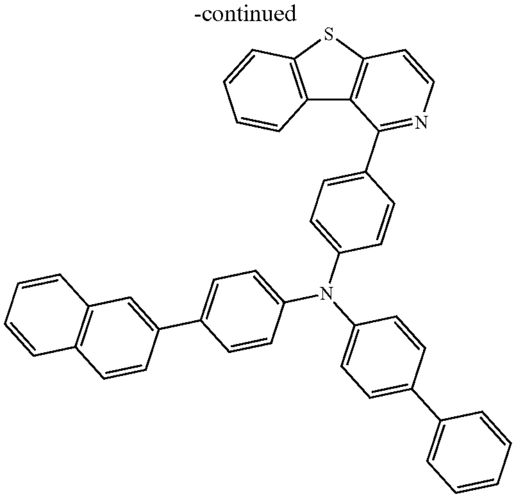
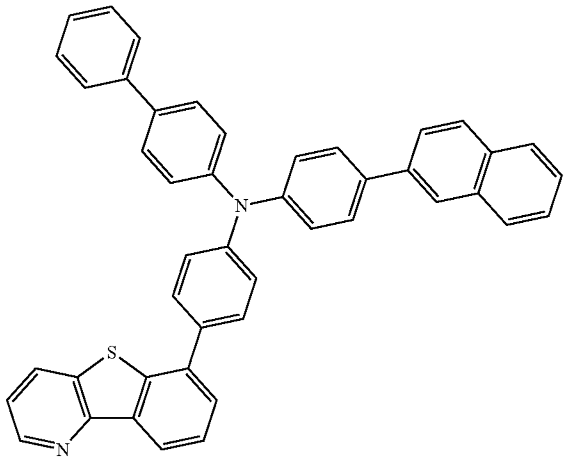
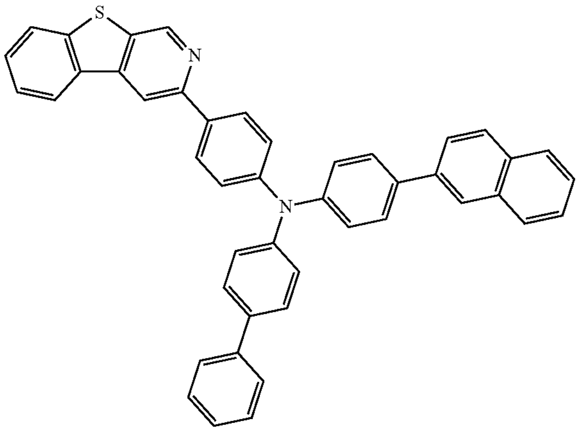
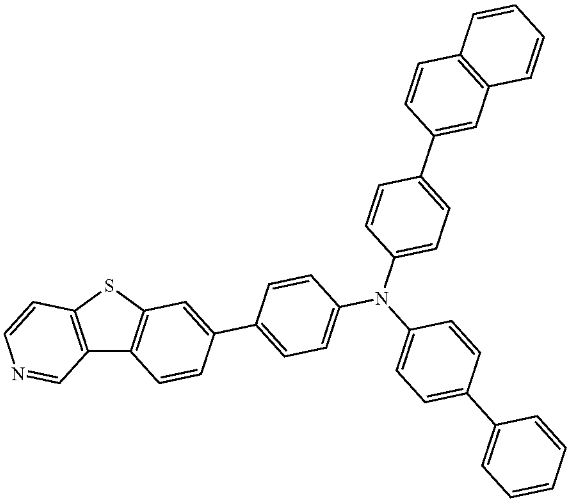
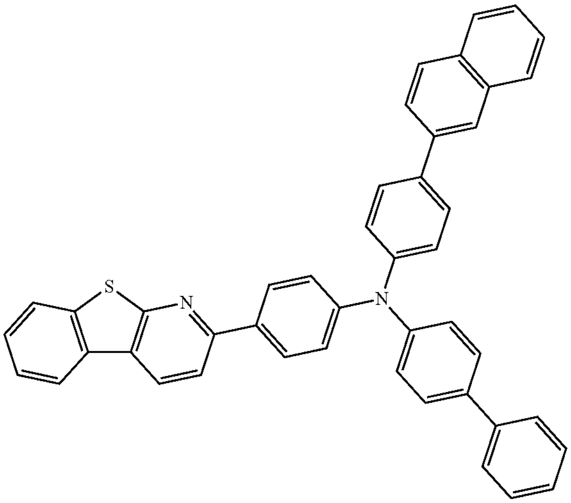
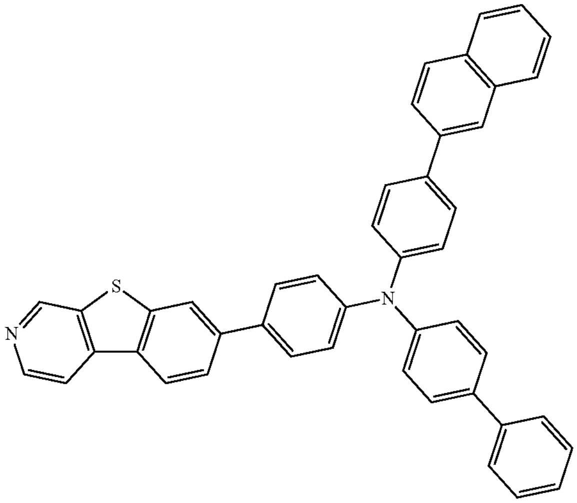

-continued
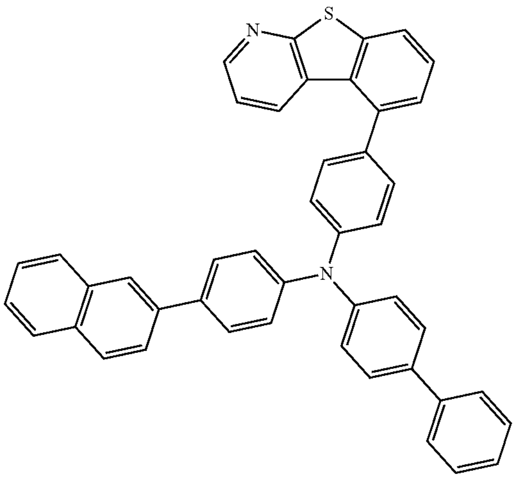 [SMILES: c1ccc(-c2ccc(N(c3ccc(-c4ccc5ccccc5c4)cc3)c3ccc(-c4cccc5sc6ncccc6c45)cc3)cc2)cc1]
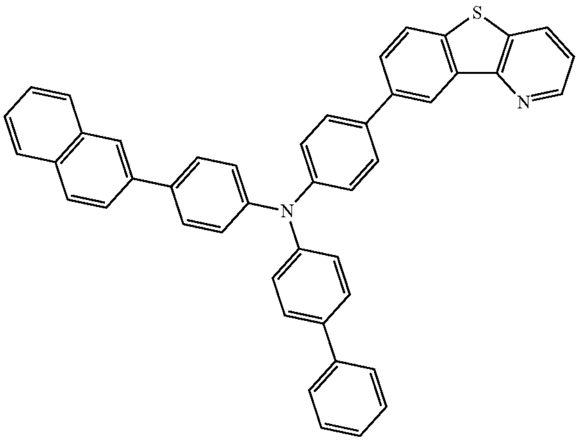
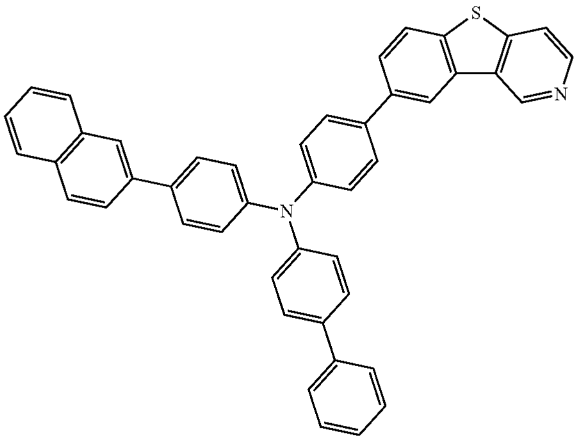
-continued
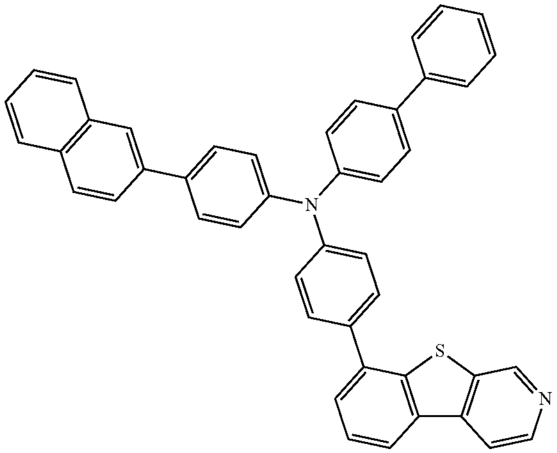
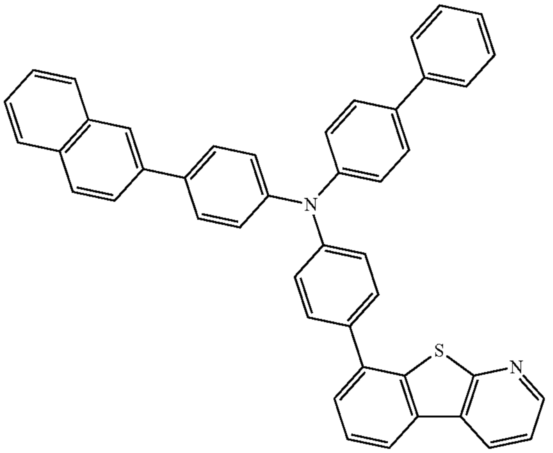
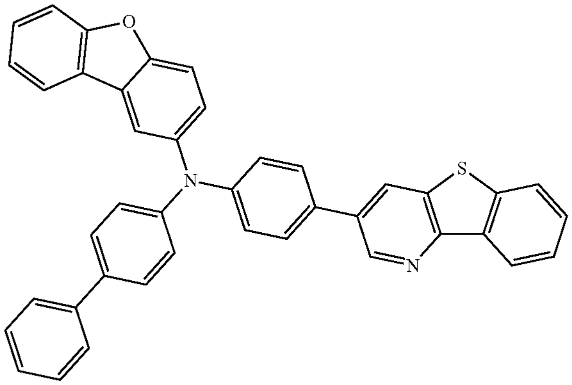
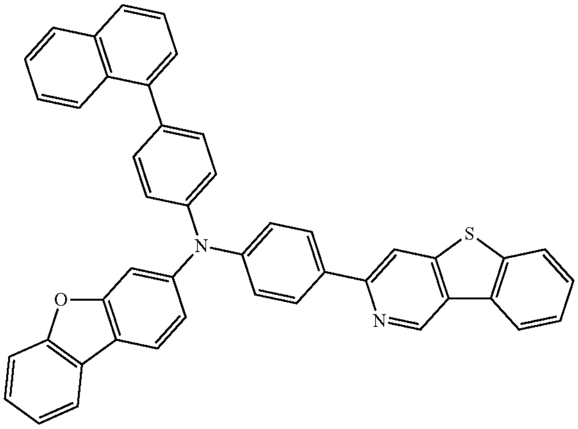

-continued
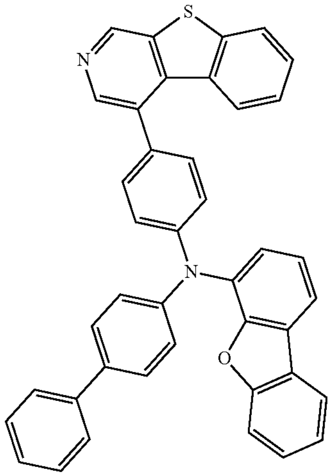
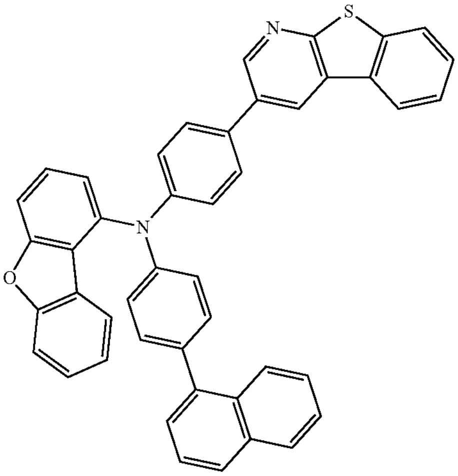 [SMILES: c1ccc2c(-c3ccc(N(c4ccc(-c5cnc6sc7ccccc7c6c5)cc4)c4cccc5oc6ccccc6c45)cc3)cccc2c1]
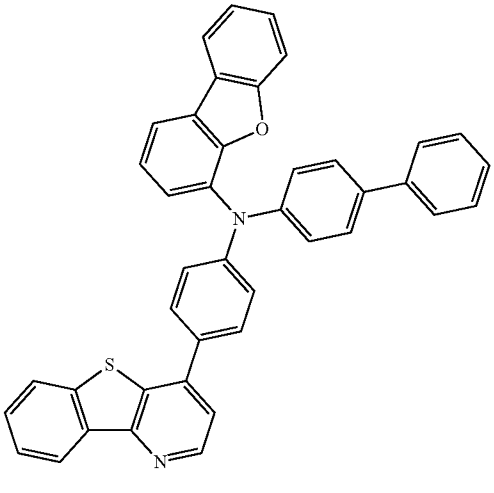
-continued
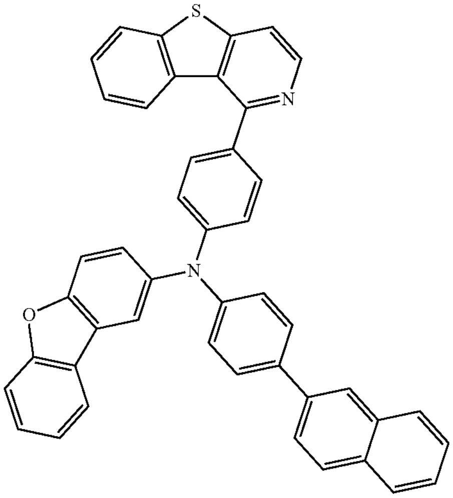
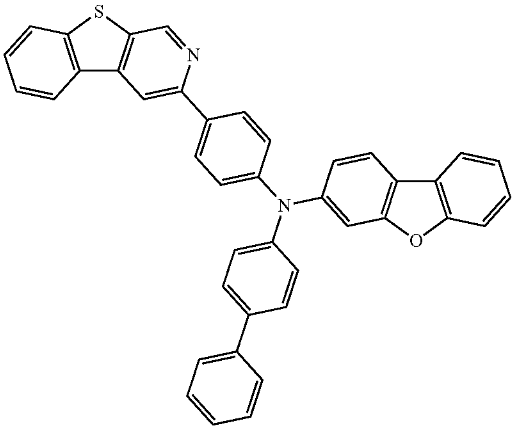
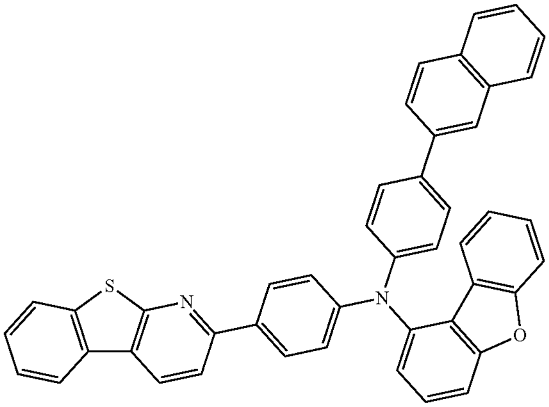 [SMILES: c1ccc2cc(-c3ccc(N(c4ccc(-c5ccc6c(n5)sc5ccccc56)cc4)c4cccc5oc6ccccc6c45)cc3)ccc2c1]

-continued
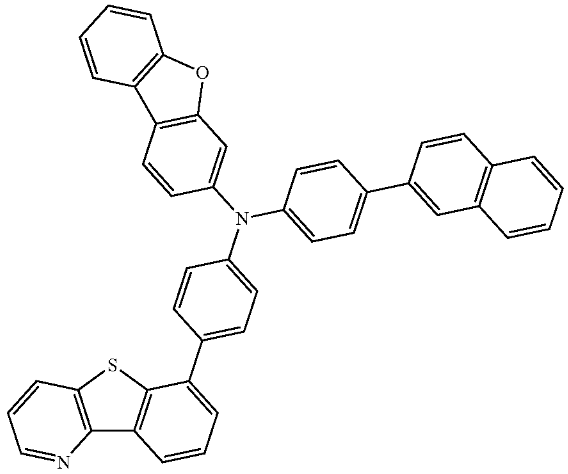
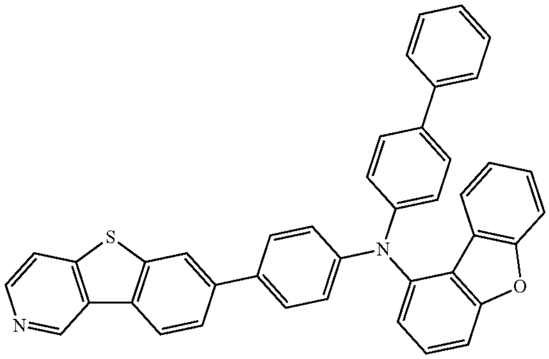
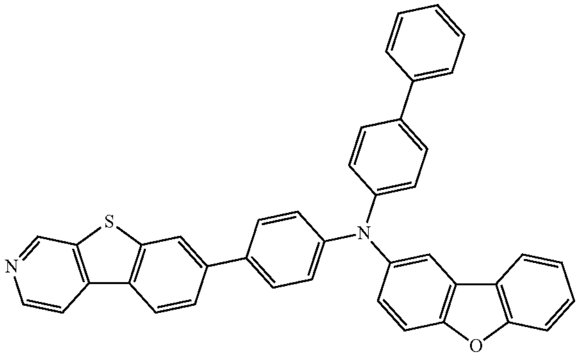
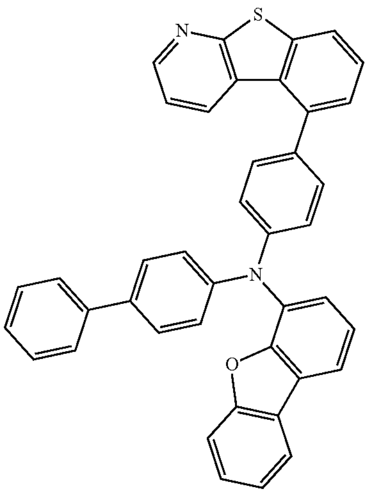 [SMILES: c1ccc(-c2ccc(N(c3ccc(-c4cccc5sc6ncccc6c45)cc3)c3cccc4c3oc3ccccc34)cc2)cc1]
-continued
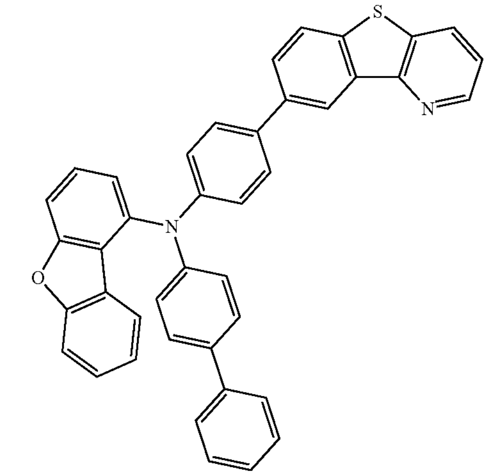
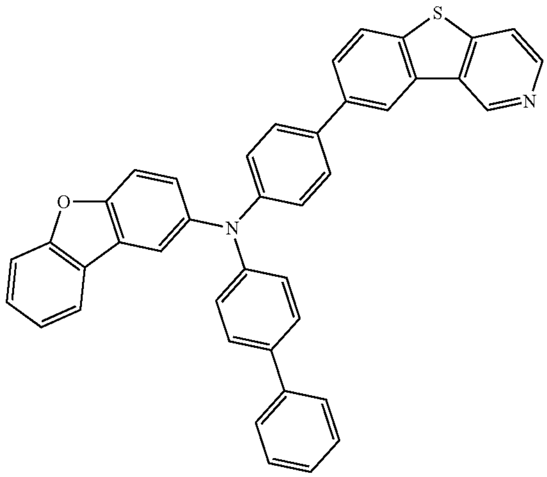
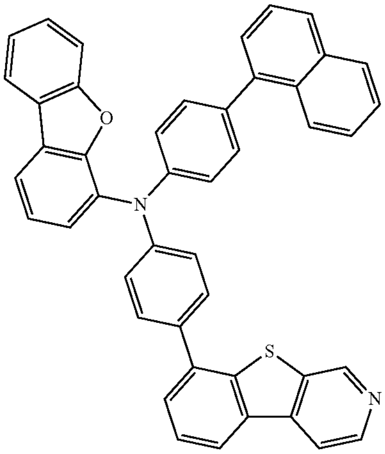

-continued
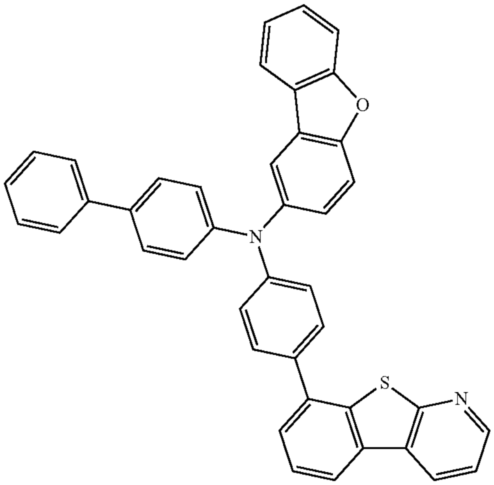 [SMILES: c1ccc(-c2ccc(N(c3ccc(-c4cccc5c4sc4ncccc45)cc3)c3ccc4oc5ccccc5c4c3)cc2)cc1]
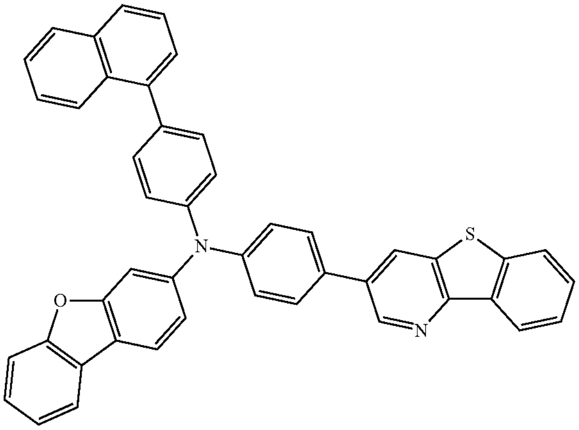
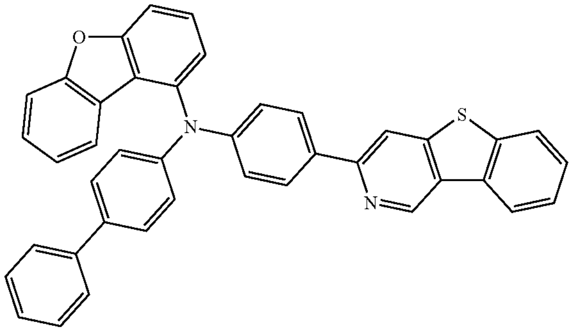
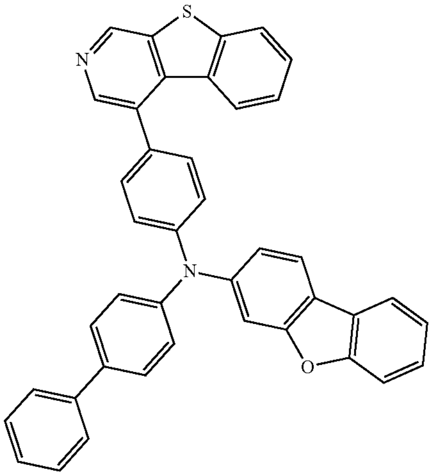
-continued
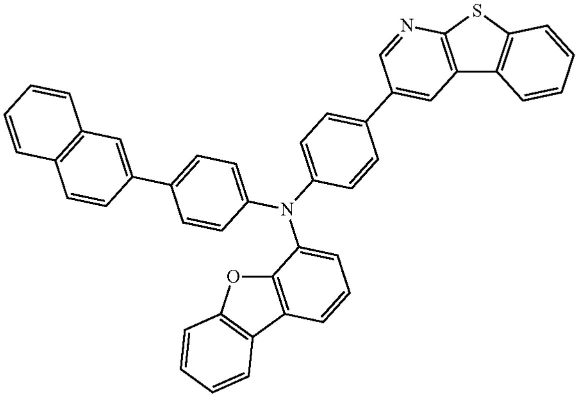 [SMILES: c1ccc2cc(-c3ccc(N(c4ccc(-c5cnc6sc7ccccc7c6c5)cc4)c4cccc5c4oc4ccccc45)cc3)ccc2c1]
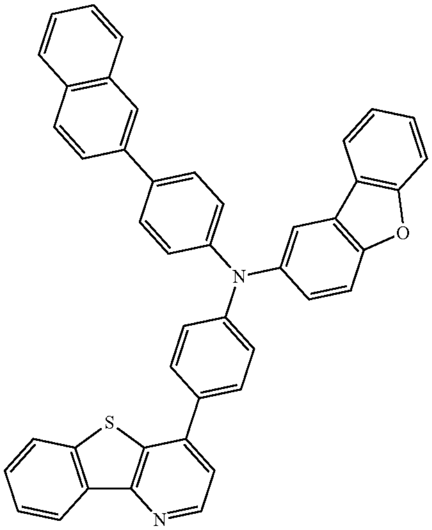
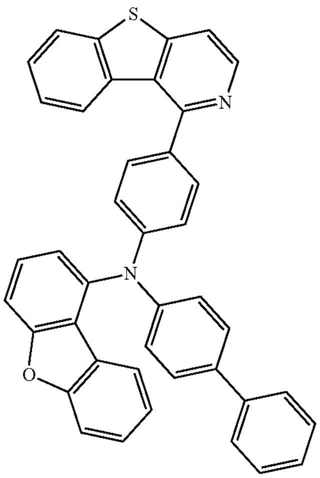

-continued
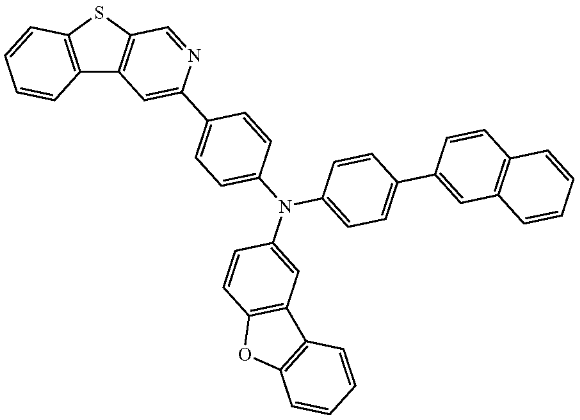
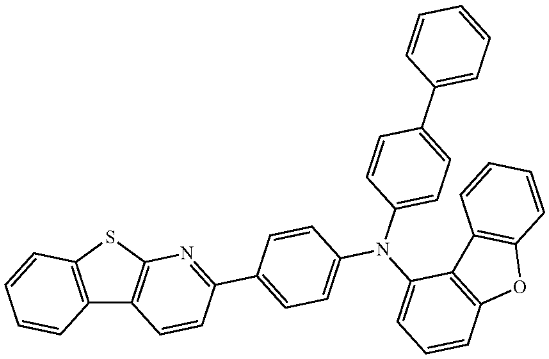 [SMILES: c1ccc(-c2ccc(N(c3ccc(-c4ccc5c(n4)sc4ccccc45)cc3)c3cccc4oc5ccccc5c34)cc2)cc1]
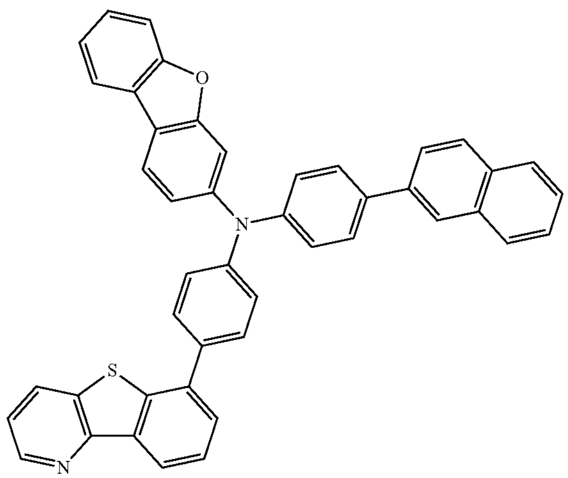
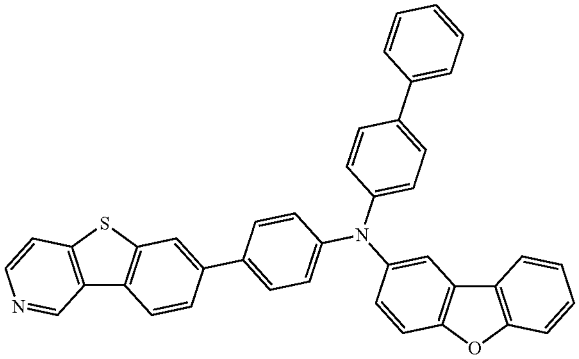
-continued
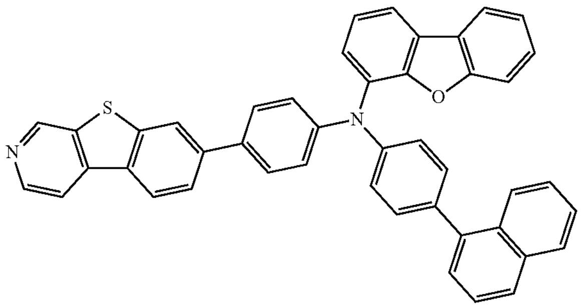
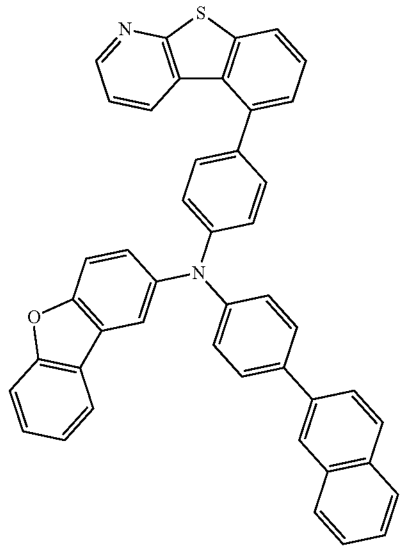 [SMILES: c1ccc2cc(-c3ccc(N(c4ccc(-c5cccc6sc7ncccc7c56)cc4)c4ccc5oc6ccccc6c5c4)cc3)ccc2c1]
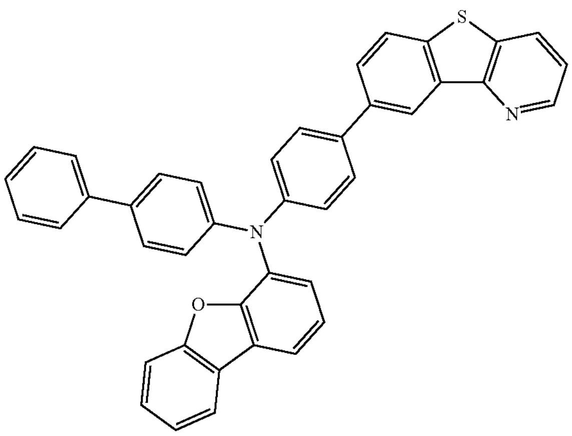

-continued
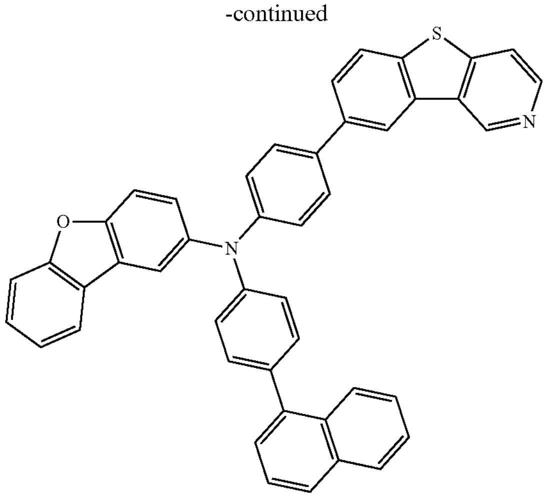
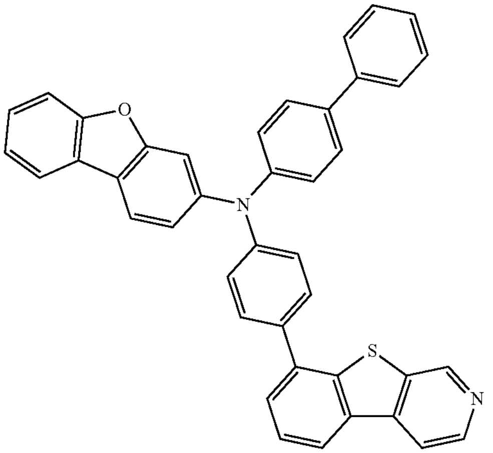
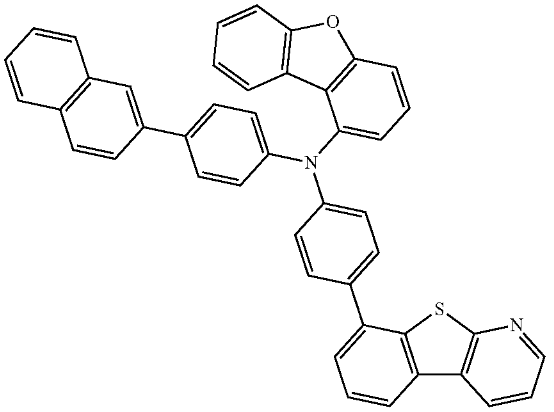
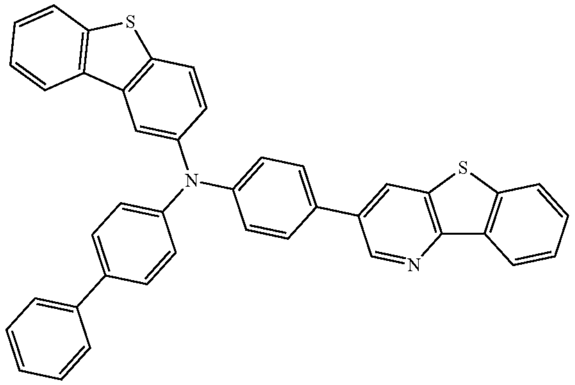
-continued
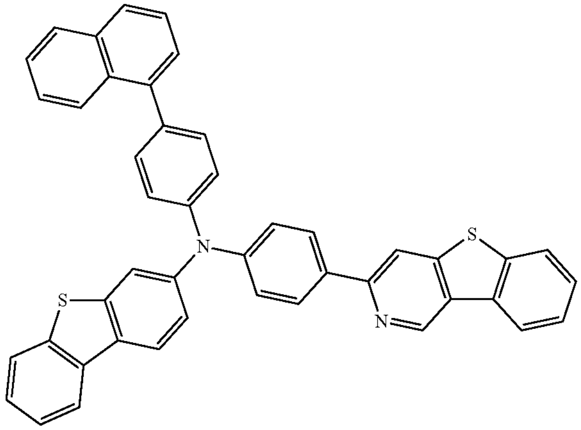
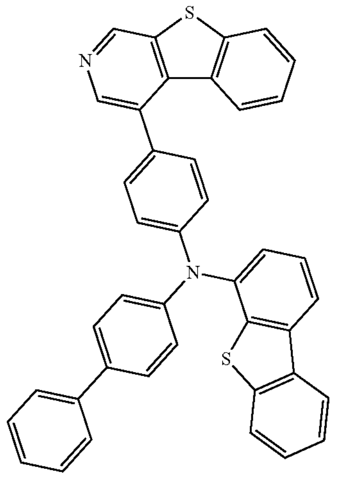
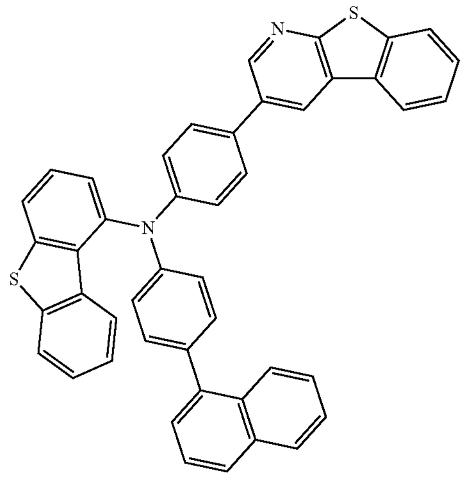 [SMILES: c1ccc2c(-c3ccc(N(c4ccc(-c5cnc6sc7ccccc7c6c5)cc4)c4cccc5sc6ccccc6c45)cc3)cccc2c1]

-continued
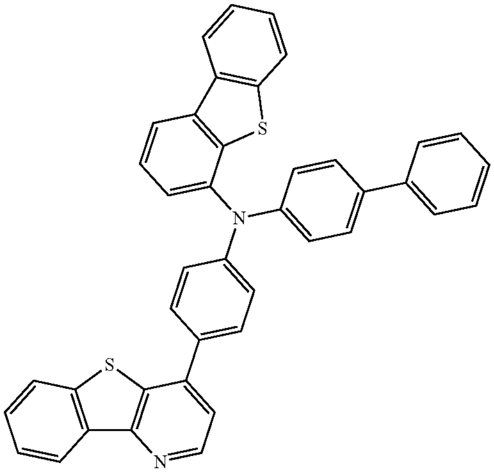
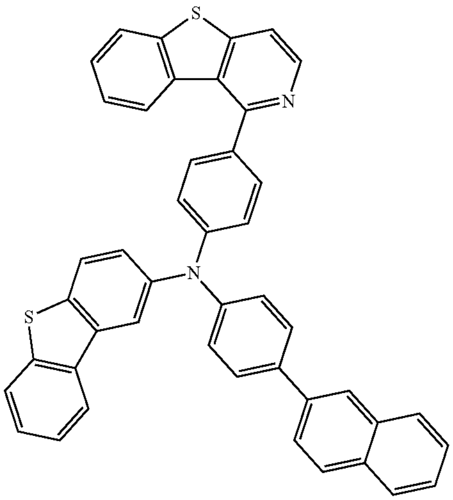
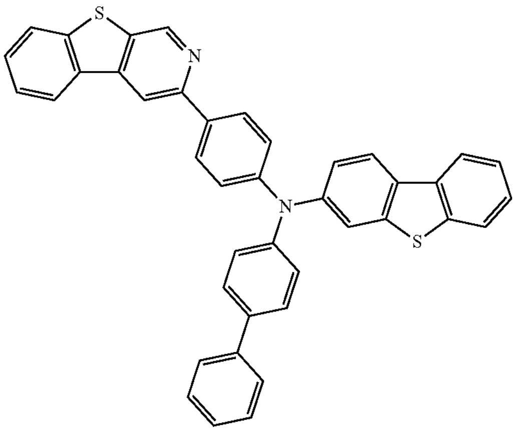
-continued
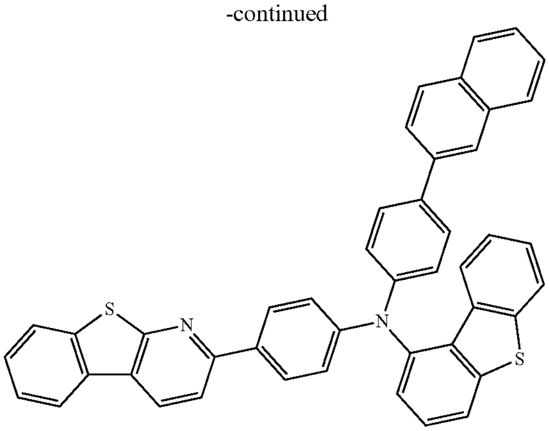
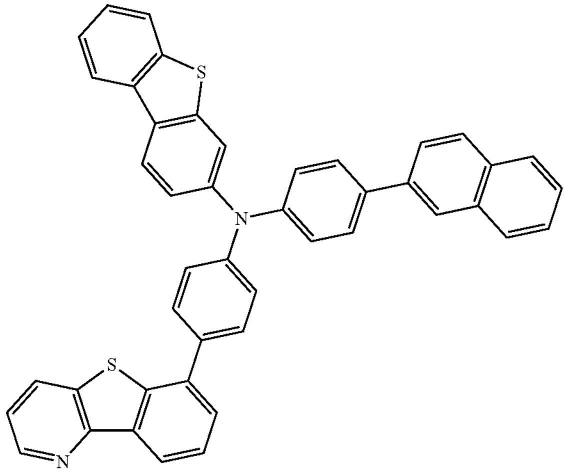
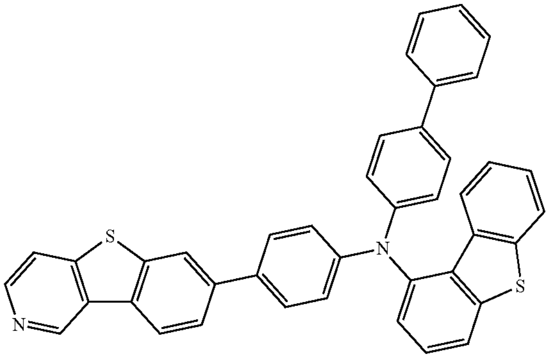
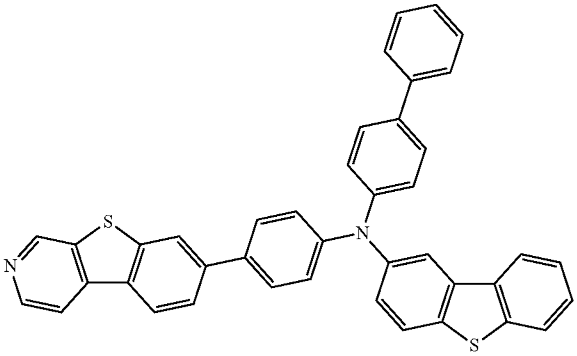

-continued
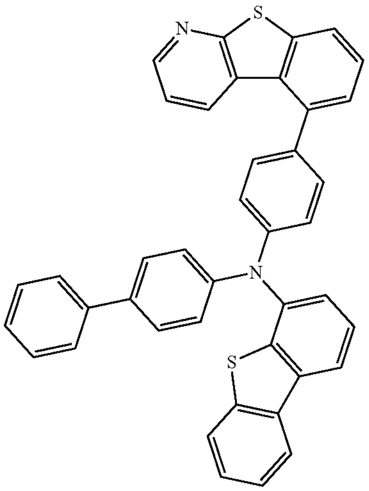
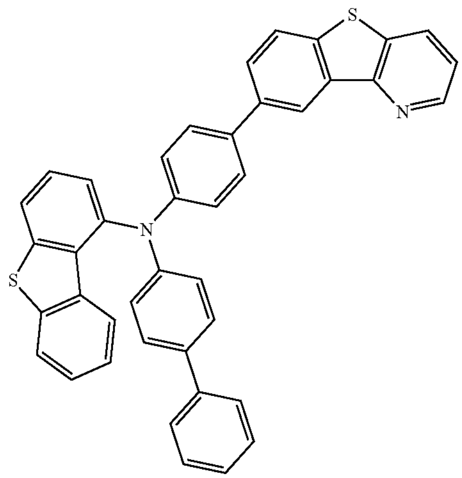
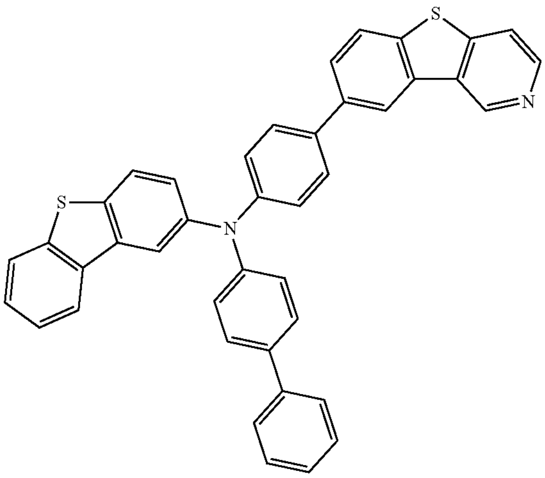
-continued
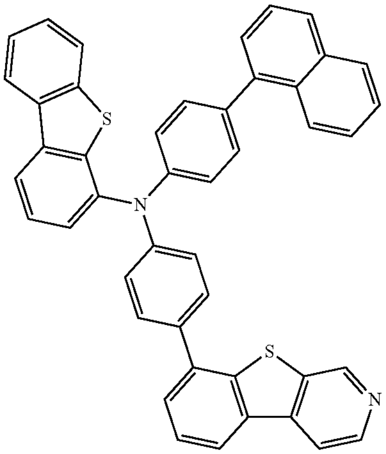
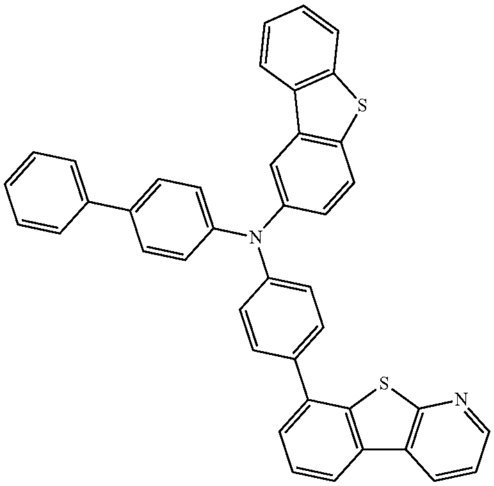 [SMILES: c1ccc(-c2ccc(N(c3ccc(-c4cccc5c4sc4ncccc45)cc3)c3ccc4sc5ccccc5c4c3)cc2)cc1]
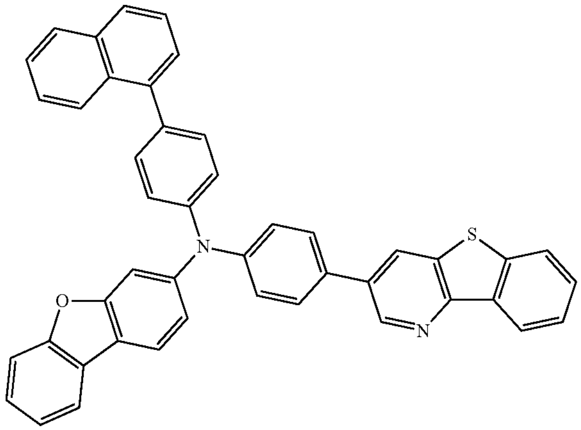
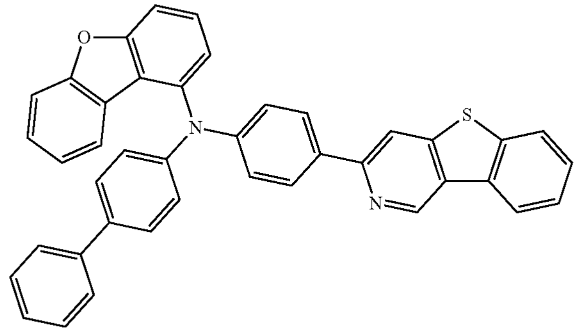

-continued
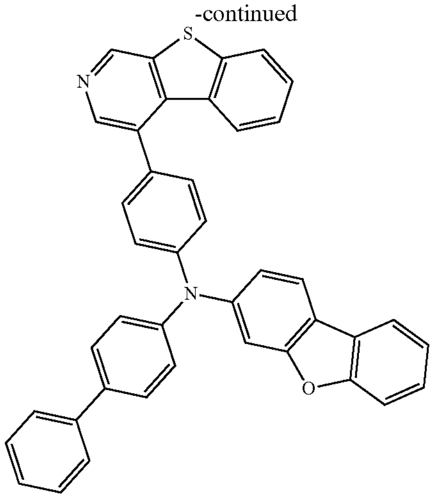
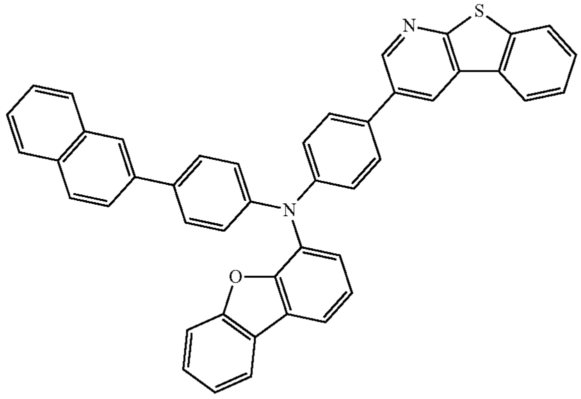 [SMILES: c1ccc2cc(-c3ccc(N(c4ccc(-c5cnc6sc7ccccc7c6c5)cc4)c4cccc5c4oc4ccccc45)cc3)ccc2c1]
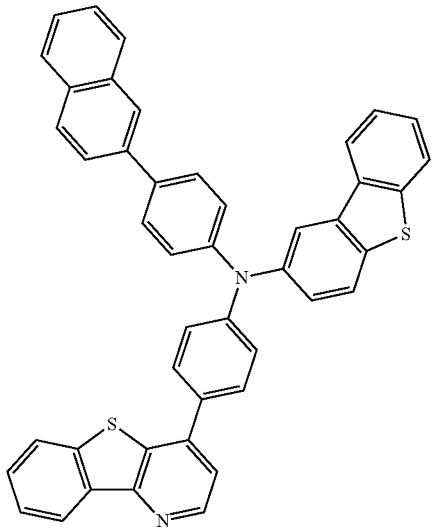
-continued
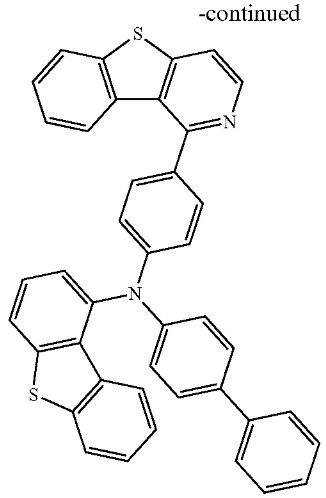
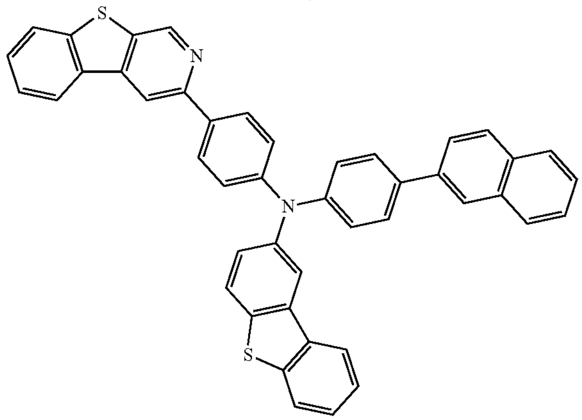
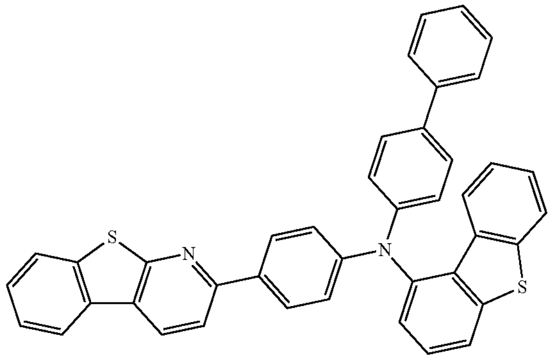
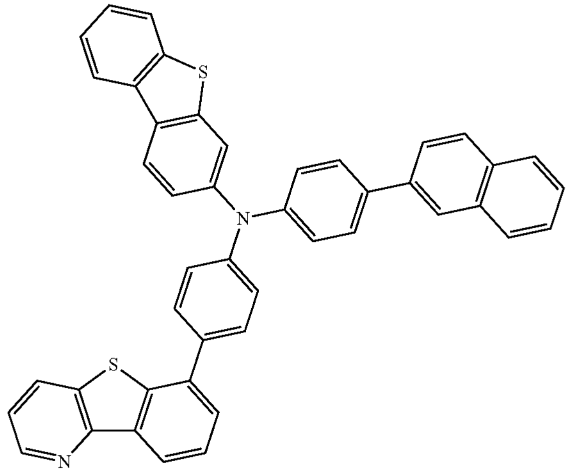

-continued
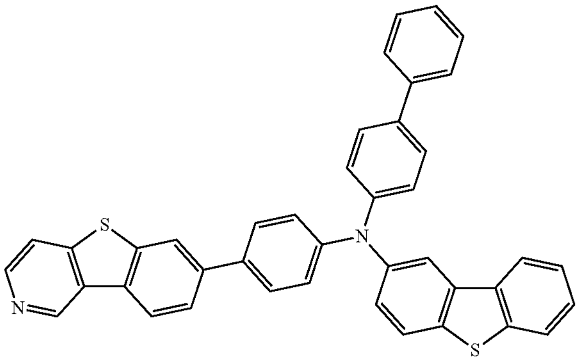
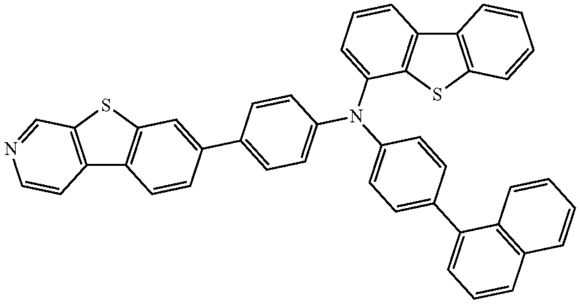
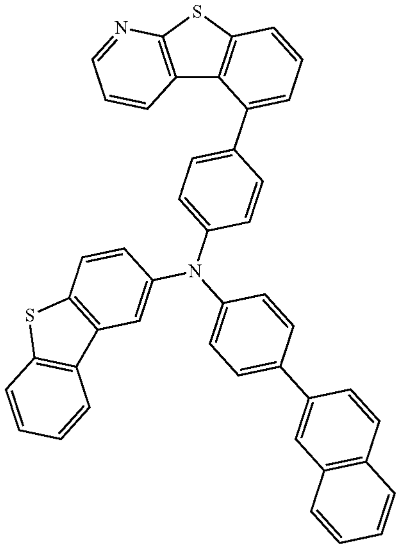
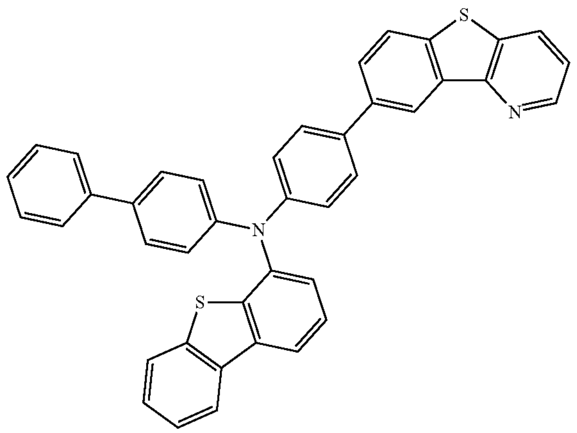
-continued
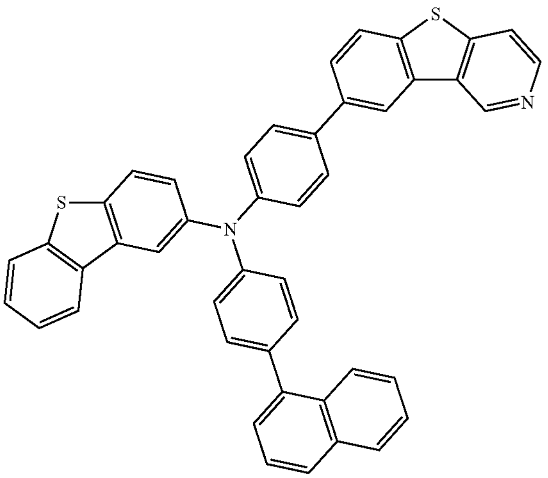
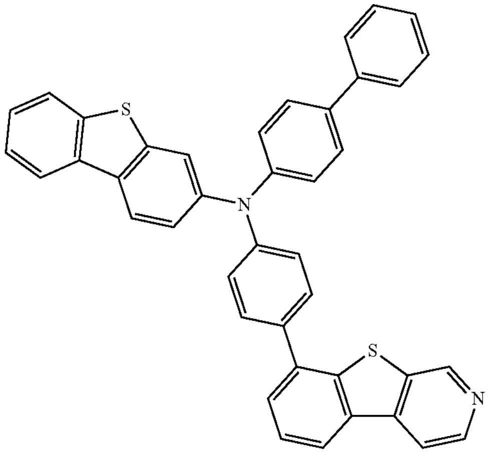
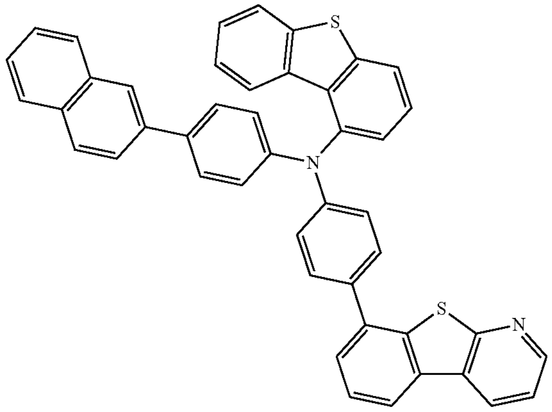 [SMILES: c1ccc2cc(-c3ccc(N(c4ccc(-c5cccc6c5sc5ncccc56)cc4)c4cccc5sc6ccccc6c45)cc3)ccc2c1]
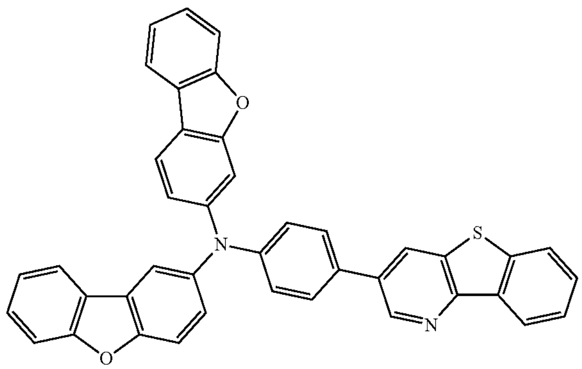

-continued
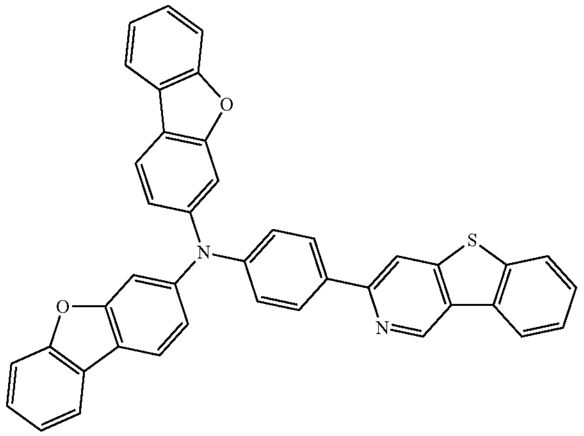
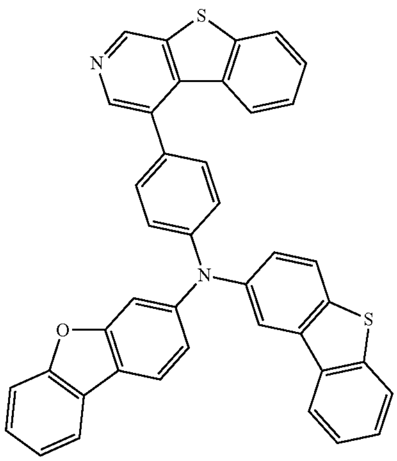
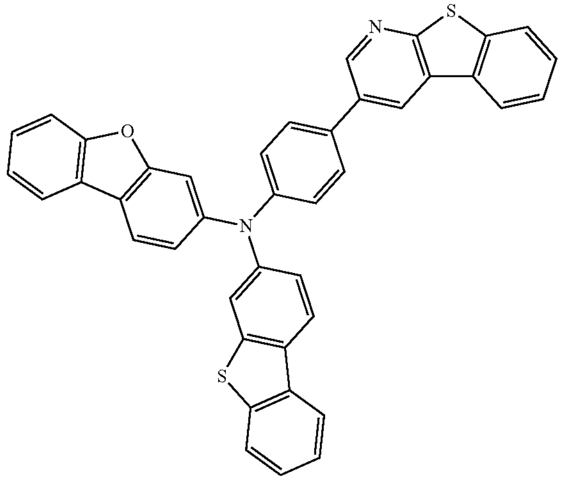 [SMILES: c1ccc2c(c1)oc1cc(N(c3ccc(-c4cnc5sc6ccccc6c5c4)cc3)c3ccc4c(c3)sc3ccccc34)ccc12]
-continued
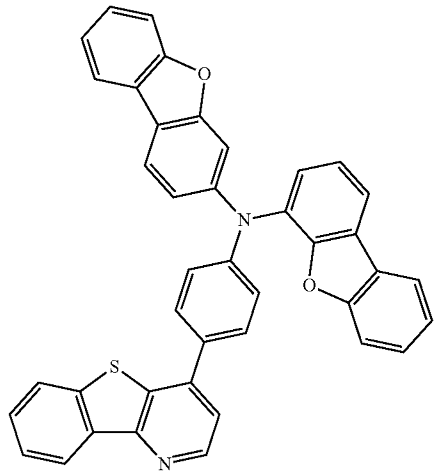
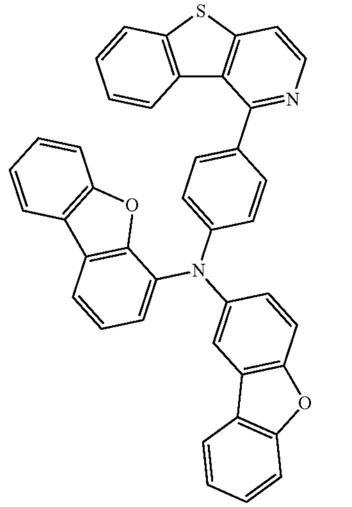
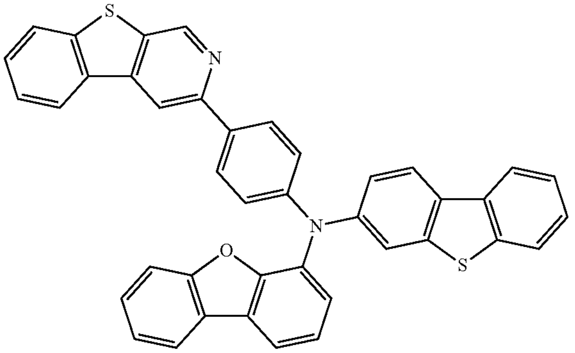
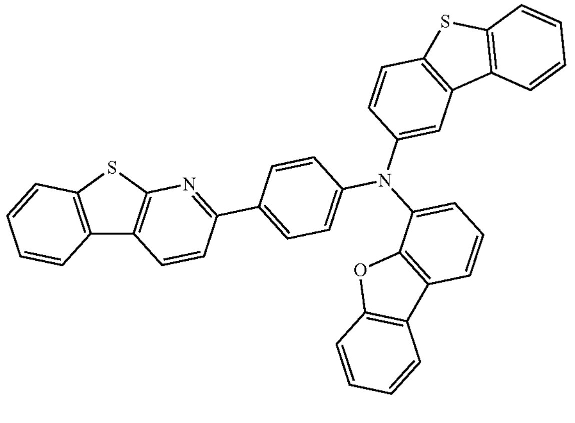 [SMILES: c1ccc2c(c1)oc1c(N(c3ccc(-c4ccc5c(n4)sc4ccccc45)cc3)c3ccc4sc5ccccc5c4c3)cccc12]

-continued
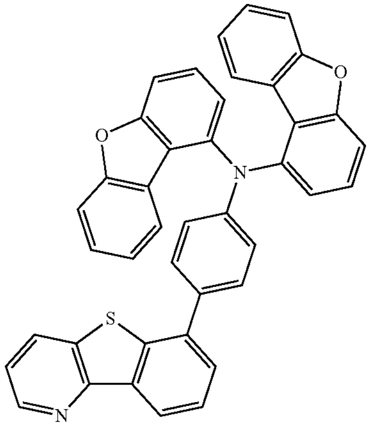
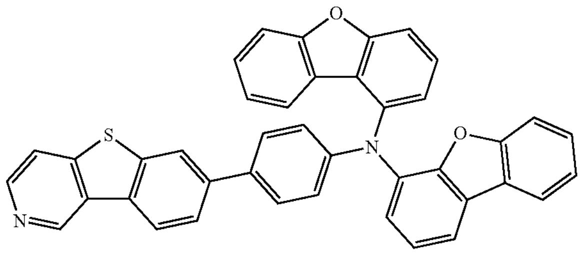
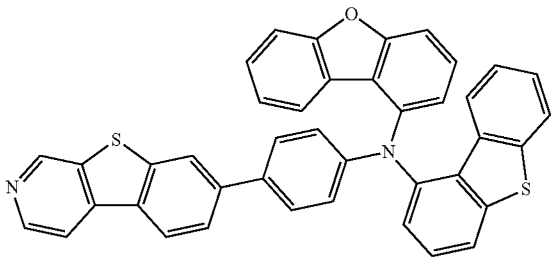
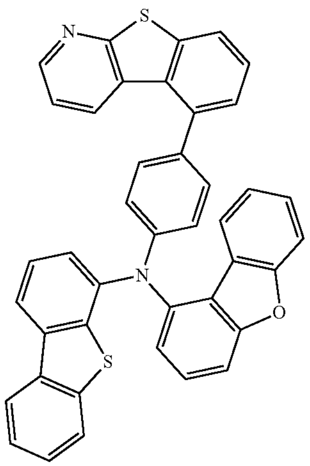 [SMILES: c1ccc2c(c1)oc1cccc(N(c3ccc(-c4cccc5sc6ncccc6c45)cc3)c3cccc4c3sc3ccccc34)c12]
-continued
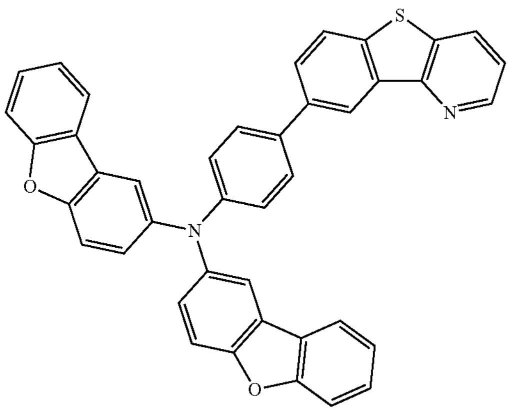
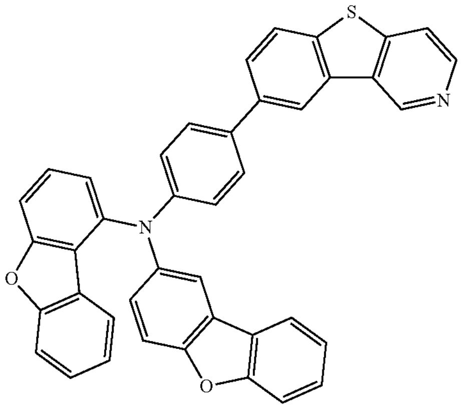
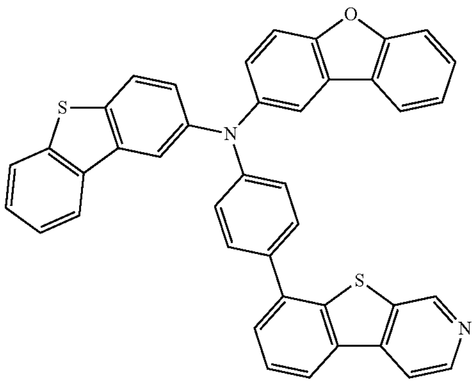
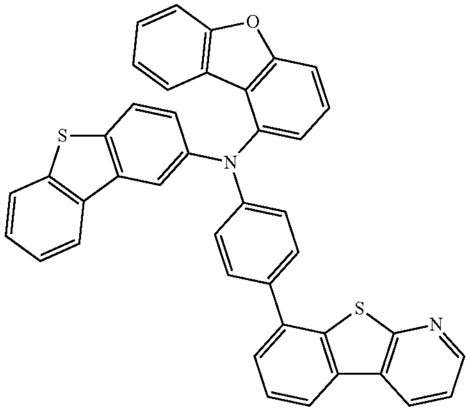 [SMILES: c1ccc2c(c1)oc1cccc(N(c3ccc(-c4cccc5c4sc4ncccc45)cc3)c3ccc4sc5ccccc5c4c3)c12]

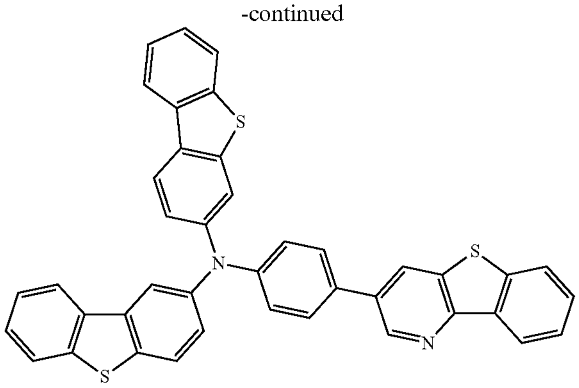
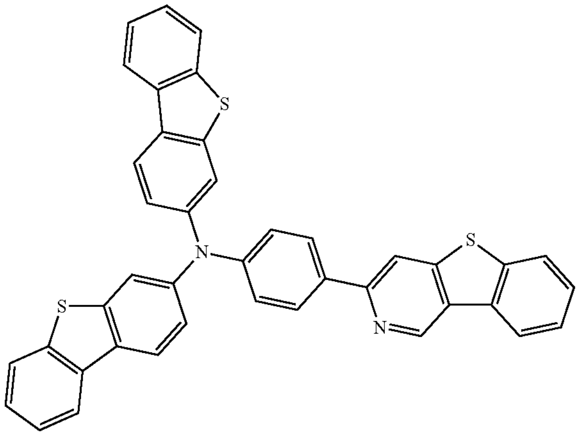
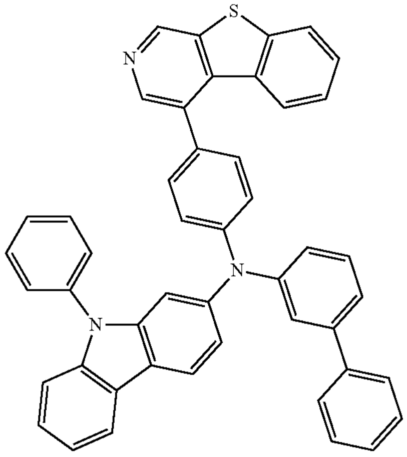
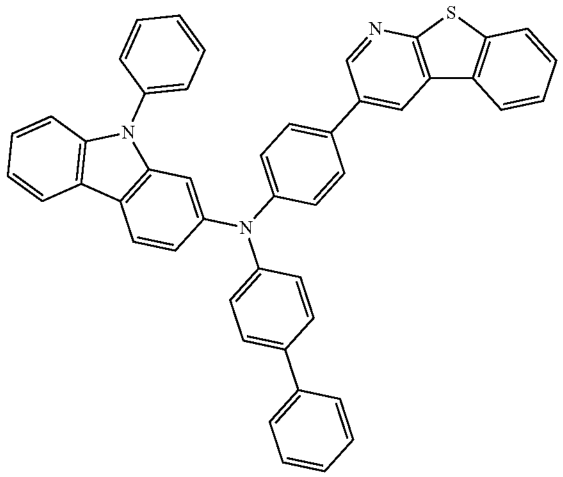 [SMILES: c1ccc(-c2ccc(N(c3ccc(-c4cnc5sc6ccccc6c5c4)cc3)c3ccc4c5ccccc5n(-c5ccccc5)c4c3)cc2)cc1]
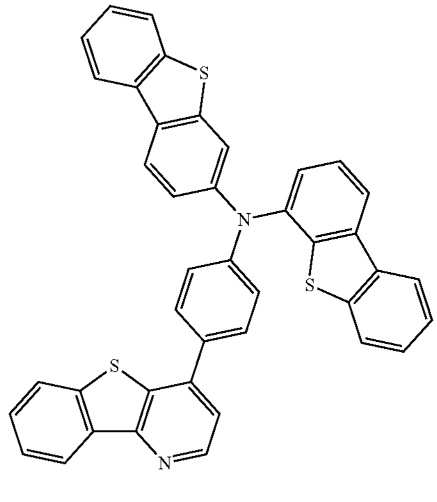
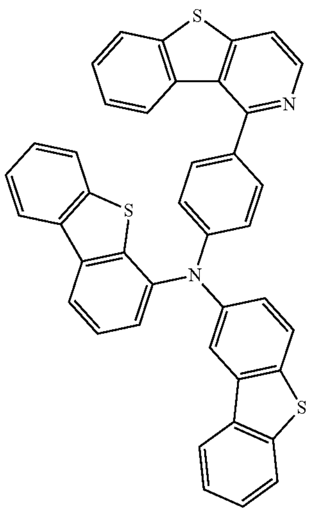
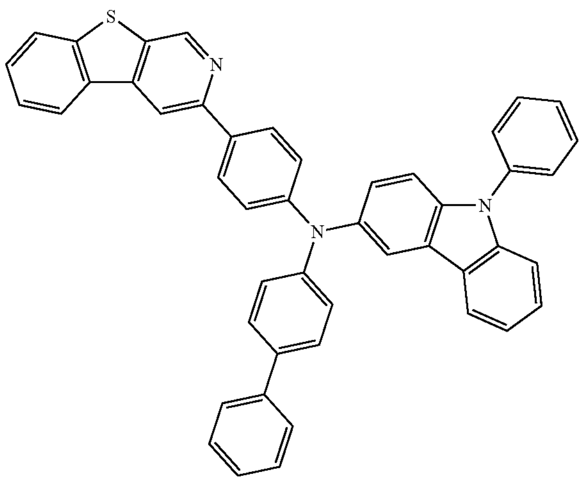

-continued
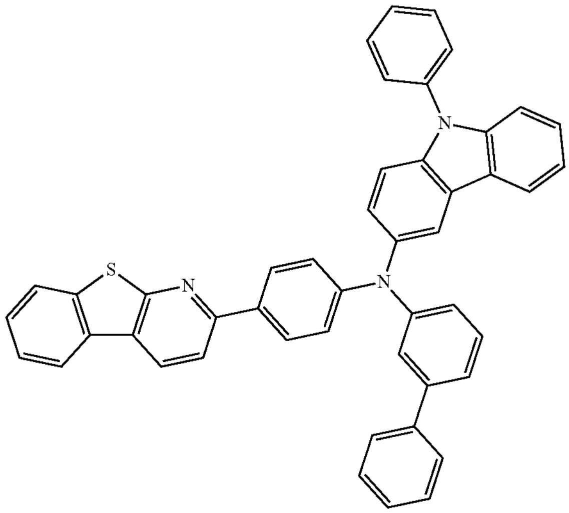 [SMILES: c1ccc(-c2cccc(N(c3ccc(-c4ccc5c(n4)sc4ccccc45)cc3)c3ccc4c(c3)c3ccccc3n4-c3ccccc3)c2)cc1]
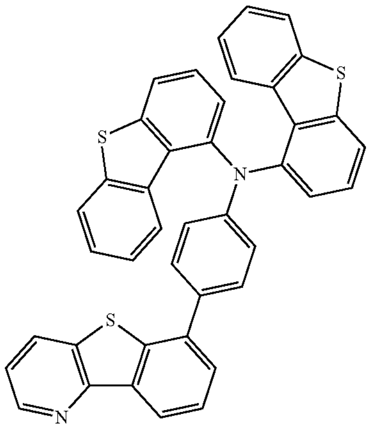
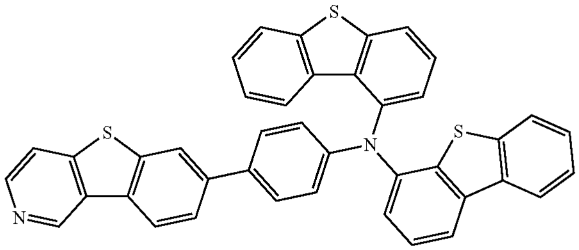
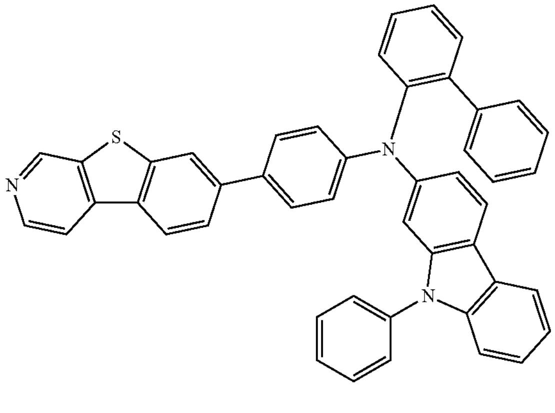
-continued
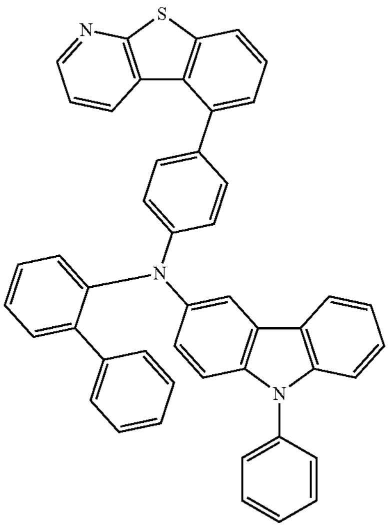 [SMILES: c1ccc(-c2ccccc2N(c2ccc(-c3cccc4sc5ncccc5c34)cc2)c2ccc3c(c2)c2ccccc2n3-c2ccccc2)cc1]
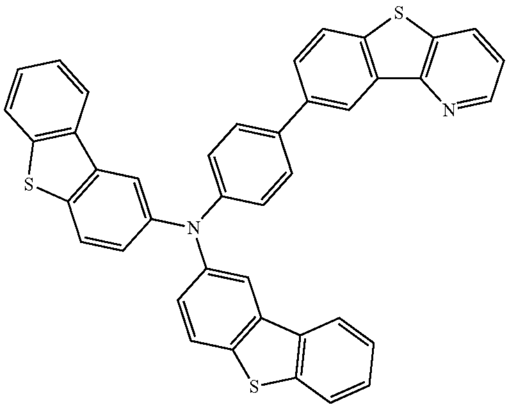
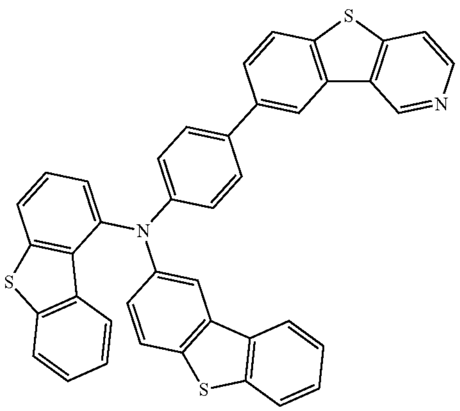

-continued
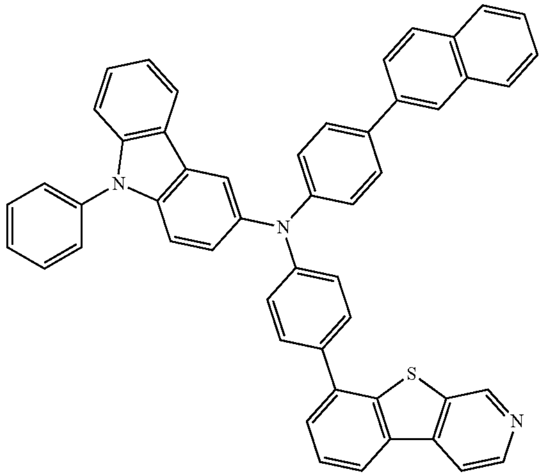
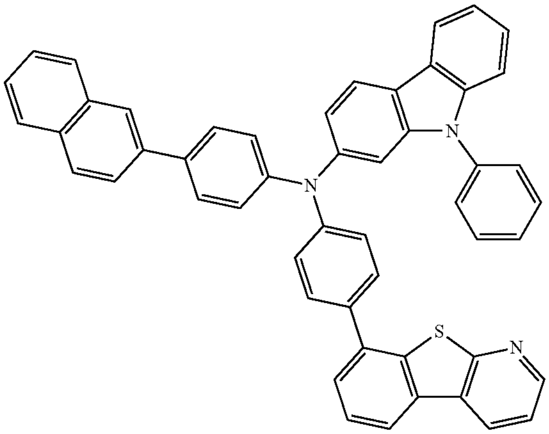 [SMILES: c1ccc(-n2c3ccccc3c3ccc(N(c4ccc(-c5ccc6ccccc6c5)cc4)c4ccc(-c5cccc6c5sc5ncccc56)cc4)cc32)cc1]
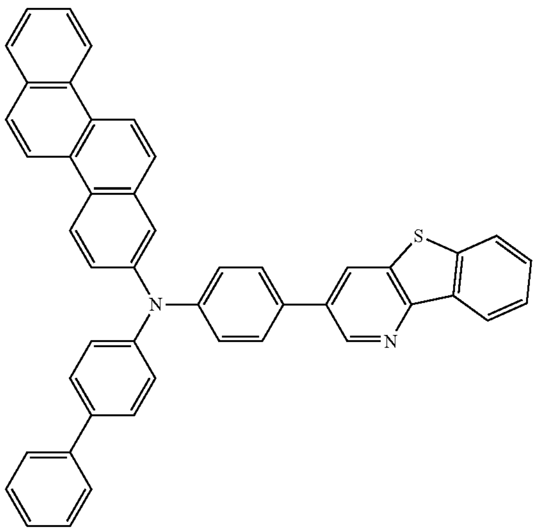
-continued
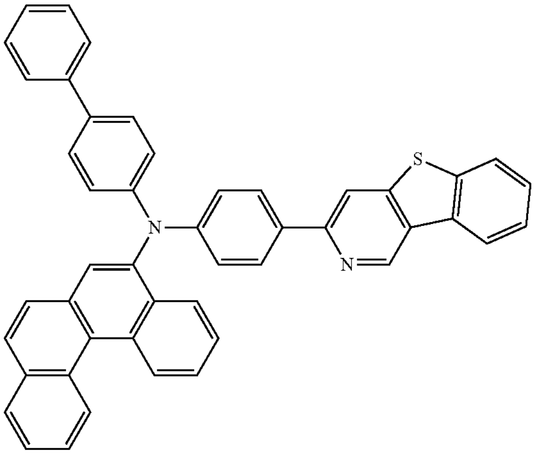
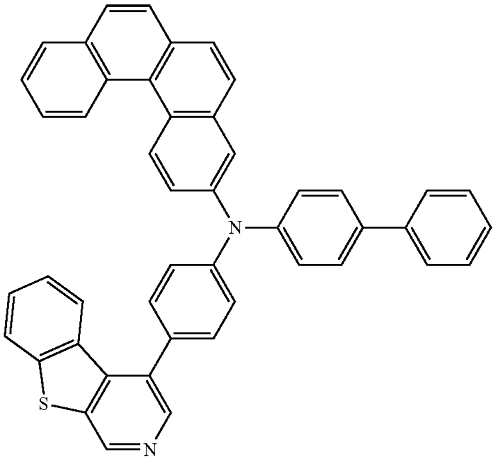
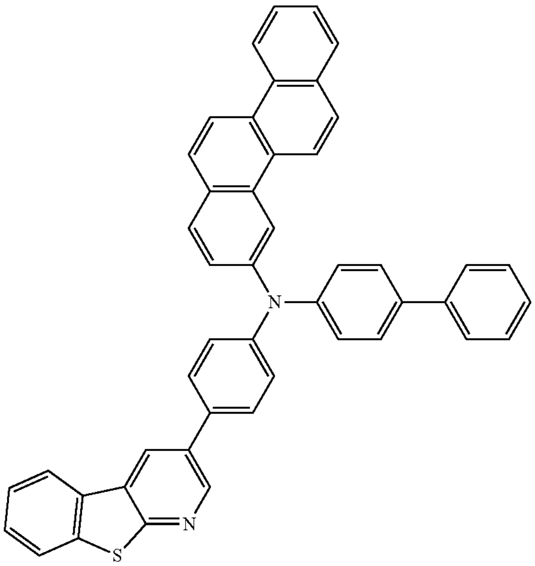

-continued
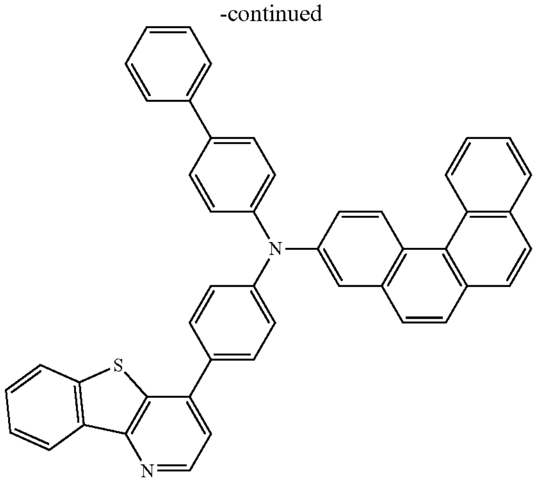
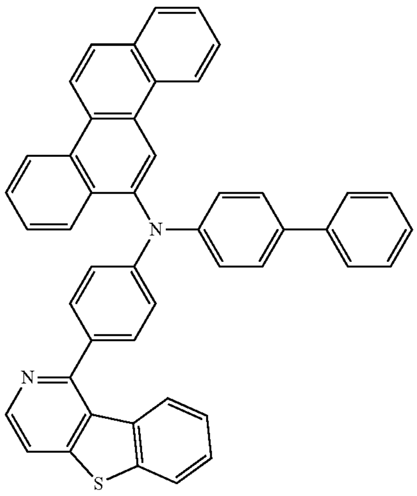
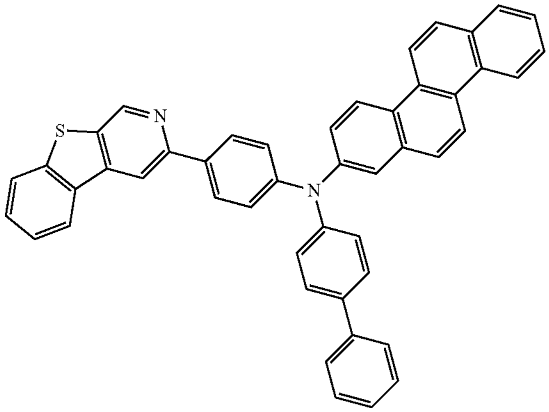
-continued
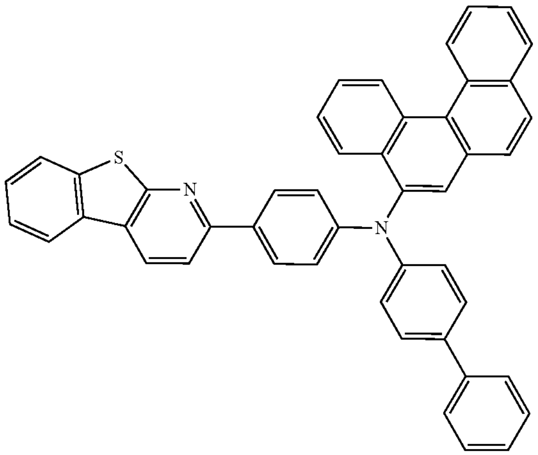
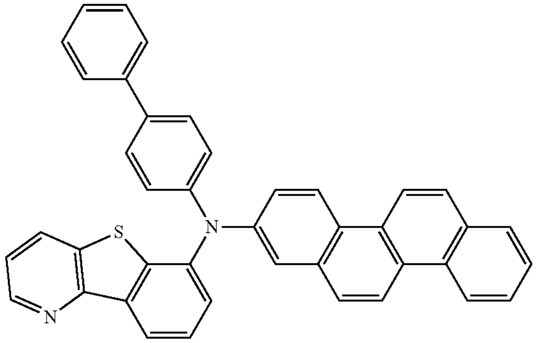
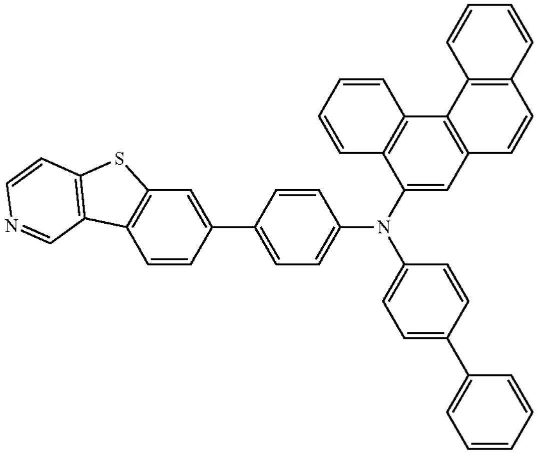
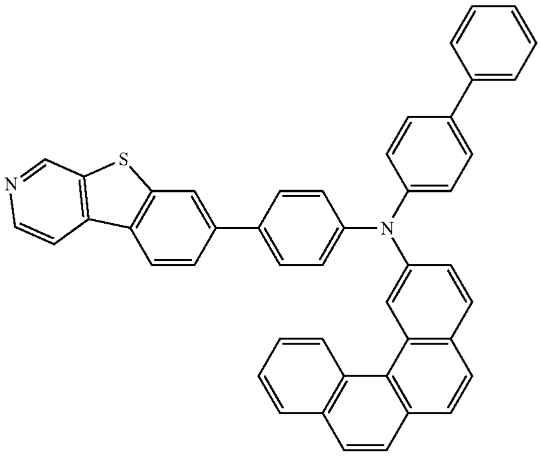

-continued
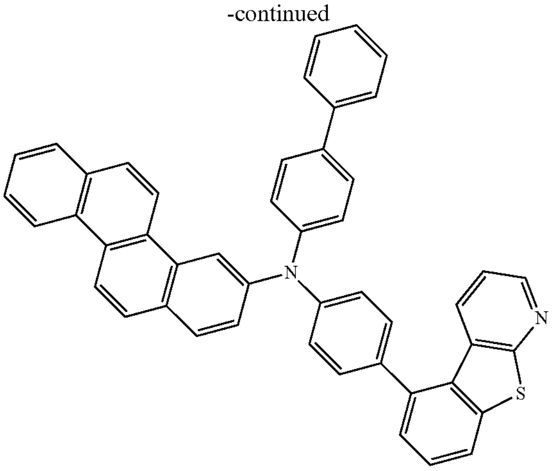
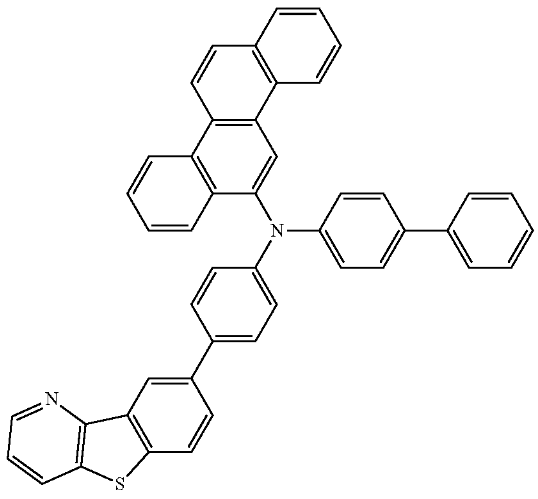
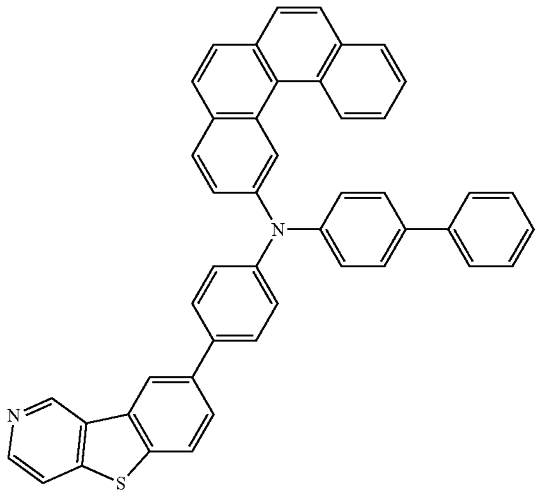
-continued
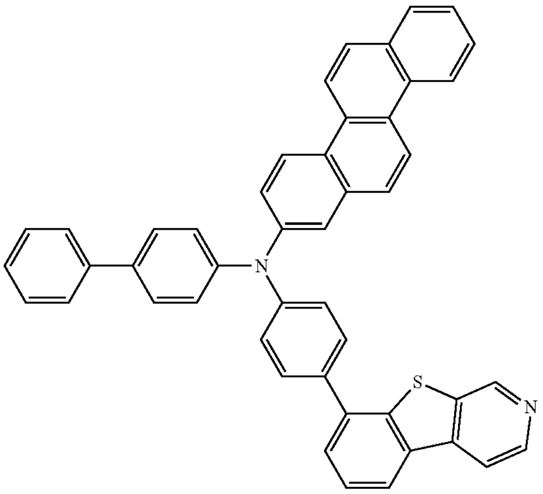
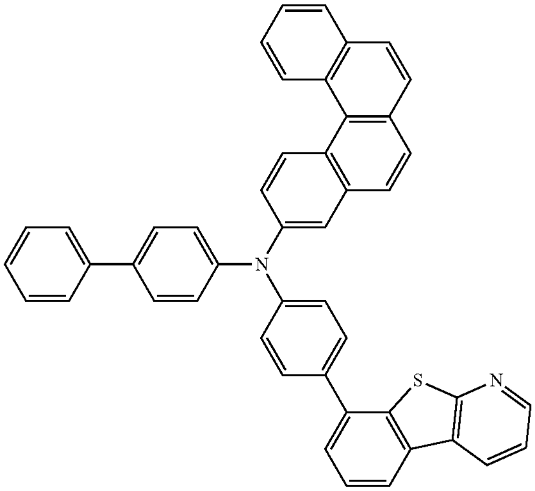
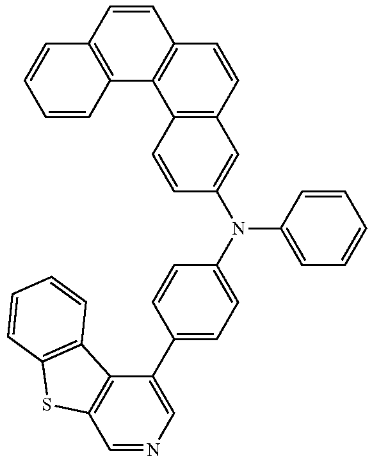

-continued
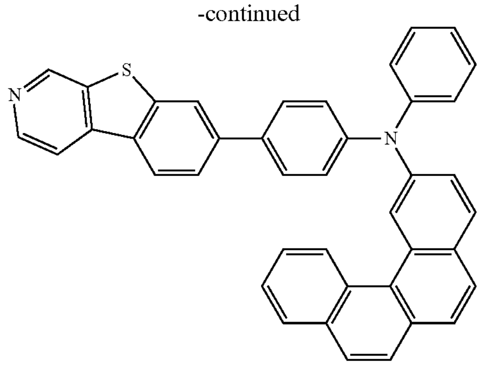
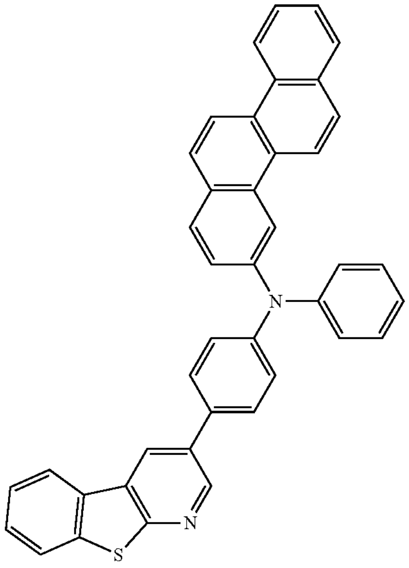
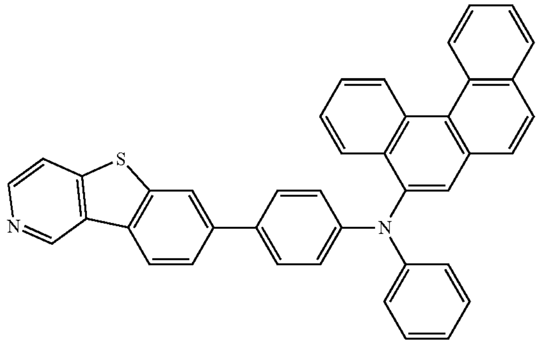
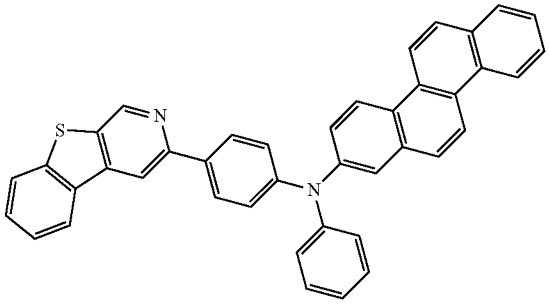
-continued
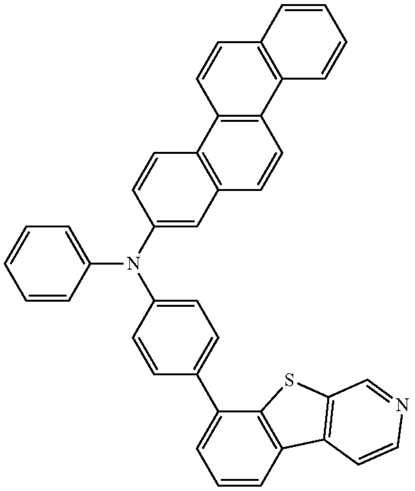
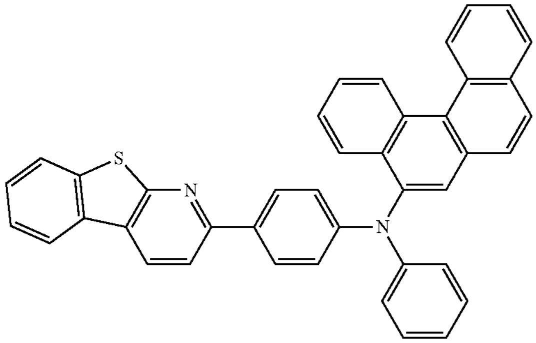
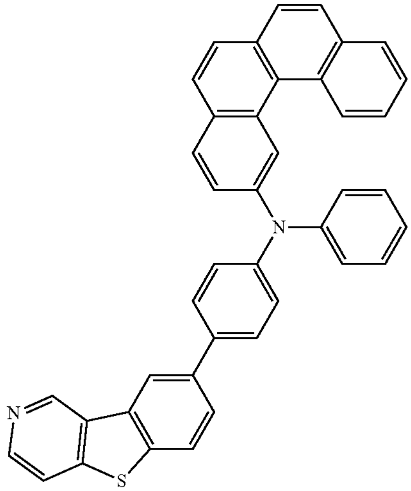
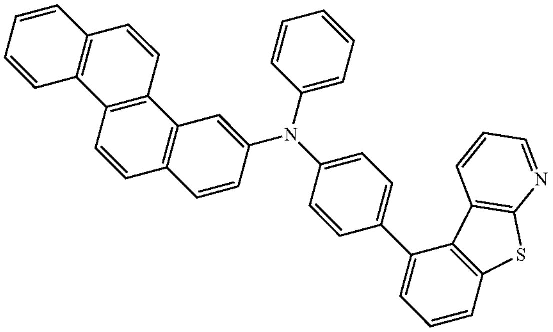

-continued

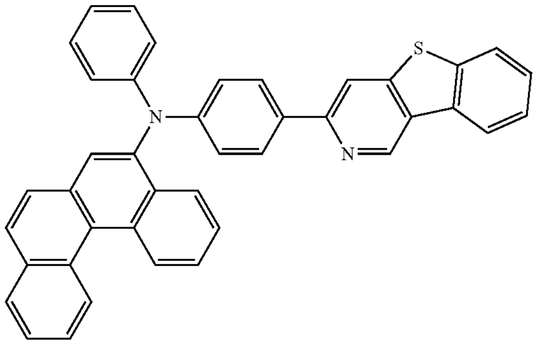

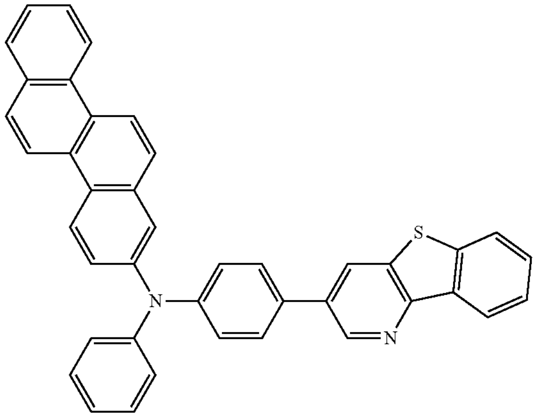

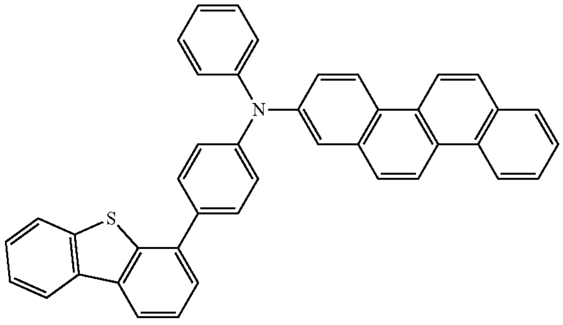

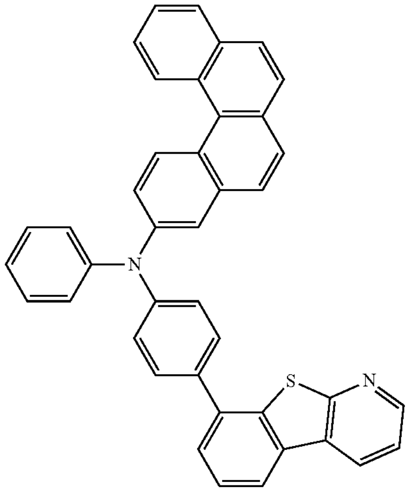

-continued

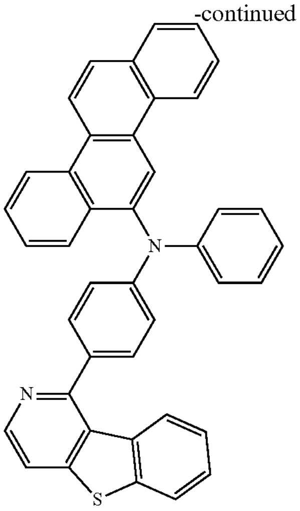

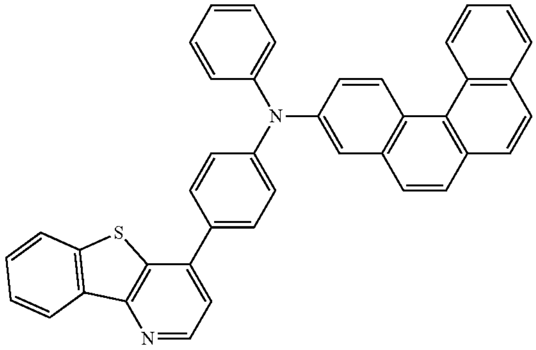

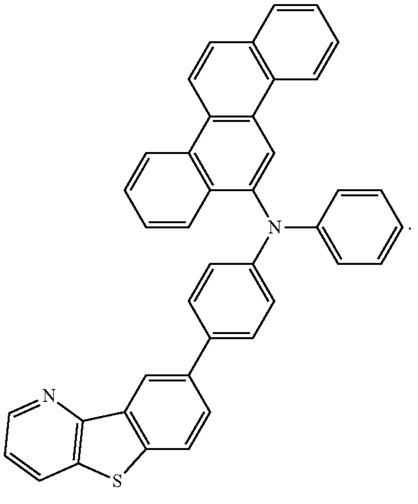

Meanwhile, the compound of Chemical Formula 1 can be prepared by subjecting a compound having a mother nucleus structure and a compound having an amino group structure bound to the mother nucleus structure to an amine substitution reaction or a Suzuki coupling reaction.

In one example, in the case of Compound (1a) in which $L_1$ is a single bond in Chemical Formula 1, it can be prepared by an amine substitution reaction as shown in the following Reaction Scheme 1.

[Reaction Scheme 1]

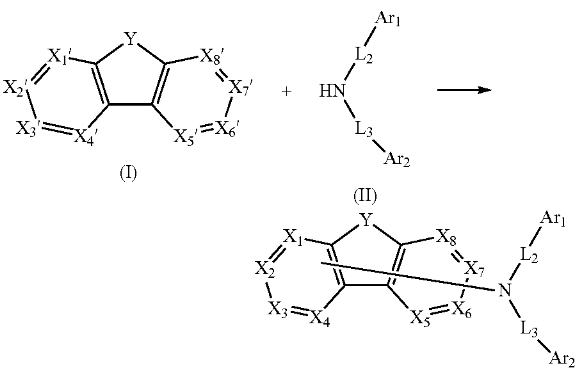

(I)

(II)

(1a)

In Reaction Scheme 1, Y, $L_2$, $L_3$, $Ar_1$, and $Ar_2$ are as defined in Chemical Formula 1;

one of $X_1$' to $X_8$' is N, one of the rest is CW, and the rest are each independently CR;

W is halogen, preferably W is chloro or bromo; and

R is hydrogen or deuterium.

Specifically, the Compound (1a) can be prepared by subjecting compound (I) having a mother nucleus structure to an amine substitution reaction with Compound (II) having an amino group structure in the presence of a palladium catalyst and a base.

Specifically, a palladium-based catalyst usable in the amine substitution reaction can include bis(dibenzylideneacetone)palladium(0) ($Pd(dba)_2$), bis(tri-tert-butylphosphine) palladium(0) ($Pd(P\text{-}tBu_3P)_2$), tetrakis(triphenyl-phosphine) palladium(0) ($Pd(PPh_3)_4$), tris(dibenzylideneacetone) dipalladium ($Pd_2(dba)_3$), bis(triphenylphosphine)palladium chloride ($Pd(PPh_3)_2Cl_2$), bis(acetonitrile)palladium(II) chloride ($Pd(CH_3CN)_2Cl_2$), palladium(II) acetate ($Pd(OAc)_2$), palladium(II) acetylacetonate ($Pd(acac)_2$), allylpalladium(II) chloride dimer ($[Pd(allyl)Cl]_2$), palladium on carbon (Pd/C), palladium(II) chloride ($PdCl_2$) or the like, and can use any one or a mixture of two or more thereof.

Further, the base can include inorganic bases such as sodium tert-butoxide (NaOtBu), potassium tert-butoxide, sodium tert-pentoxide, sodium ethoxide, sodium carbonate, potassium carbonate, cesium carbonate, sodium hydride, lithium hydride or potassium hydride; organic bases such as tetraethylammonium hydroxide ($Et_4NOH$), bis(tetraethylammonium)carbonate, and triethylamine; or inorganic salts such as cesium fluoride, and can use any one or a mixture of two or more thereof.

Further, the amine substitution reaction can be performed in water, an organic solvent, or a mixed solvent thereof, and the organic solvent can include ether solvents such diethyl ether, tetrahydrofuran, 1,4-dioxane, ethylene glycol diethyl ether, dimethoxyethane, bis(2-methoxyethyl)ether, diethylene glycol diethyl ether, tetrahydrofuran or anisole; aromatic hydrocarbon-based solvents such as benzene, toluene or xylene; halogenated aromatic solvents such as chlorobenzene, dimethylformamide, dimethylacetamide, N-methylpyrrolidone, dimethylimidazolidone or acetonitrile; or sulfoxide-based solvents such as dimethyl sulfoxide (DMSO), and the like, and can use any one or a mixture of two or more thereof.

In another example, in Chemical Formula 1, Compound (1b), in which $L_1$ is

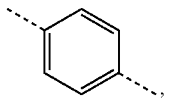

can be prepared by a Suzuki coupling reaction as shown in the following Reaction Scheme 2.

[Reaction Scheme 2]

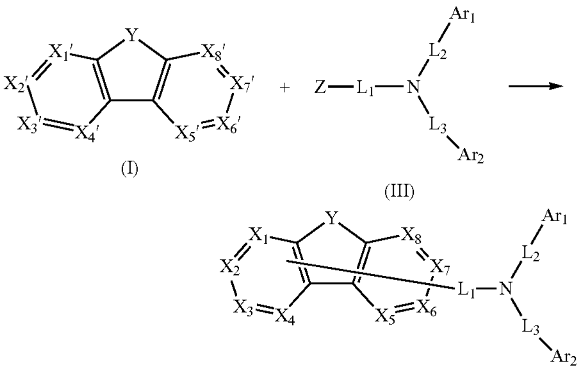

(I)

(III)

(1b)

In Reaction Scheme 2, Y, $L_2$, $L_3$, $Ar_1$, and $Ar_2$ are as defined in Chemical Formula 1, $L_1$ is

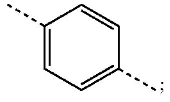

one of $X_1$' to $X_8$' is N, one of the rest is CW, and the rest are each independently CR;

W is halogen, preferably W is chloro or bromo;

R is hydrogen or deuterium; and

Z is a boron-containing organic group, and preferably can be a boronic acid group, a boronic acid ester group, a boronic acid pinacol ester group, or the like.

Specifically, the Compound (1b) can be prepared by subjecting the Compound (I) containing a mother nucleus structure and the Compound (III) bound to the mother nucleus structure and having an amino group structure to a Suzuki coupling reaction in the presence of a palladium catalyst and a base.

The palladium-based catalyst and base that can be used in the Suzuki coupling reaction are the same as those described in the amine substitution reaction.

Further, the Suzuki coupling reaction can be performed in water, an organic solvent, or a mixed solvent thereof, and the organic solvent is the same as described in the amine substitution reaction.

Further, the reactive group for the amine substitution reaction and the Suzuki coupling reaction can be modified as known in the art. Further, the reactants and Compounds (I) to (III) used in the preparation of Compounds (1a) and (1b) can be prepared using a conventional organic reaction, or alternatively, commercially available materials can be used. The above preparation method can be further embodied in Preparation Examples described hereinafter.

Further, the present disclosure provides an organic light emitting device comprising a compound of Chemical Formula 1. In one example, the present disclosure provides an organic light emitting device comprising: a first electrode; a second electrode opposite to the first electrode; and one or more organic material layers between the first electrode and the second electrode, wherein one or more layers of the organic material layers includes the compound of Chemical Formula 1.

In the organic light emitting device, the first electrode is an anode, and the second electrode is a cathode, or alternatively, the first electrode is a cathode and the second electrode is an anode.

Further, the organic material layer of the organic light emitting device of the present disclosure can have a single-layer structure, or it can have a multilayered structure in which two or more organic material layers are stacked. For example, the organic light emitting device of the present disclosure can have a structure comprising a hole injection layer, a hole transport layer, a light emitting layer, an electron transport layer, an electron injection layer, an electron injection and transport layer and the like as the organic material layer. However, the structure of the organic light emitting device is not limited thereto, and it can include a smaller number of organic layers.

In one embodiment, the organic material layer can include a light emitting layer, wherein the organic material layer including the above compound can be a light emitting layer.

In another embodiment, the organic material layer can include a hole injection layer, a hole transport layer, a light emitting layer and an electron injection and transport layer, wherein the organic material layer including the above compound can be a light emitting layer.

In another embodiment, the organic material layer can include a hole injection layer, a hole transport layer, an electron blocking layer, a light emitting layer and an electron injection and transport layer, wherein the organic material layer including the above compound can be a light emitting layer.

In yet another embodiment, the organic material layer can include a hole injection layer, a hole transport layer, an electron blocking layer, a light emitting layer, a hole blocking layer, and an electron injection and transport layer, wherein the organic material layer including the above compound can be a light emitting layer.

Further, the organic light emitting device according to the present disclosure can be a normal type organic light emitting device in which an anode, one or more organic material layers, and a cathode are sequentially stacked on a substrate. Further, the organic light emitting device according to the present disclosure can be an inverted type organic light emitting device in which a cathode, one or more organic material layers, and an anode are sequentially stacked on a substrate. For example, the structure of the organic light emitting device according to an embodiment of the present disclosure is illustrated in FIGS. 1 and 2.

FIG. 1 shows an example of an organic light emitting device comprising a substrate 1, an anode 2, an organic material layer 3, and a cathode 4. In such a structure, the compound of Chemical Formula 1 can be included in the organic material layer 3.

FIG. 2 shows an example of an organic light emitting device comprising a substrate 1, an anode 2, a hole injection layer 5, a hole transport layer 6, an electron blocking layer 7, a light emitting layer 8, a hole blocking layer 9, an electron injection and transport layer 10, and a cathode 4. In such a structure, the compound of Chemical Formula 1 can be included in at least one layer of the hole injection layer 5, the hole transport layer 6, the electron blocking layer 7, the light emitting layer 8, the hole blocking layer 9, and the electron injection and transport layer 10.

The organic light emitting device according to the present disclosure can be manufactured by materials and methods known in the art, except that at least one of the organic material layers includes the compound of Chemical Formula 1. Further, when the organic light emitting device includes a plurality of organic material layers, the organic material layers can be formed of the same material or different materials.

For example, the organic light emitting device according to the present disclosure can be manufactured by sequentially stacking an anode, an organic material layer and a cathode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the electron blocking layer, the light emitting layer, the hole blocking layer, and the electron injection and transport layer thereon, and then depositing a material that can be used as the cathode thereon.

Further, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and an anode material on a substrate (International Publication WO2003/012890). However, the manufacturing method is not limited thereto.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and further is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer refers to a layer which is formed on the hole transport layer, preferably provided in contact with the light emitting layer, and serves to adjust the hole mobility, prevent excessive movement of electrons, and increase the probability of hole-electron coupling, thereby improving the efficiency of the organic light emitting device. The electron blocking layer includes an electron blocking material, and examples of such electron blocking material can include or an arylamine-based organic material or the like, but is not limited thereto.

The light emitting layer can include a host material and a dopant material. The host material can be the compound of Chemical Formula 1. Further, the host material can be a fused aromatic ring derivative, a heterocycle-containing compound or the like in addition to the compound of Chemical Formula 1. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Further, the dopant material includes an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

More specifically, the dopant material can include compounds having the following structures, but is not limited thereto:

Dp-1

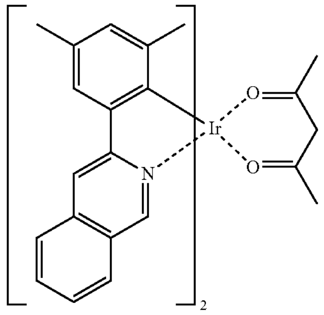

Dp-2

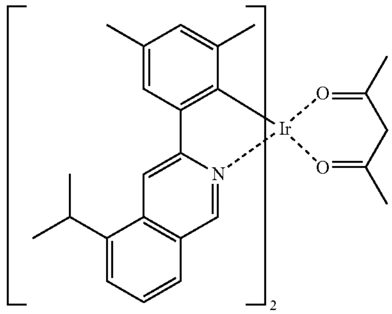

Dp-3

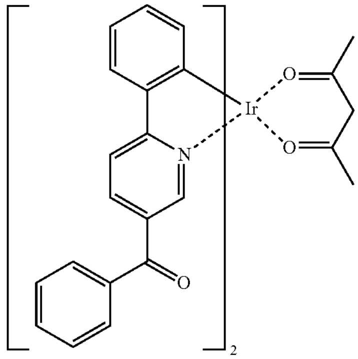

Dp-4

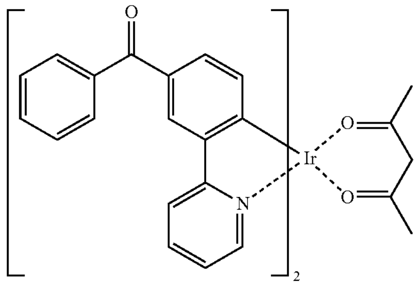

Dp-5

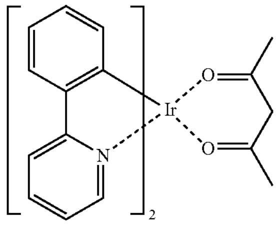

-continued
Dp-6
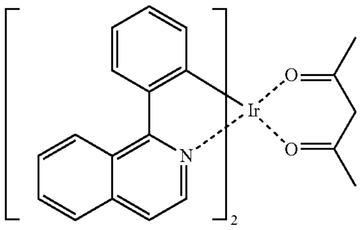
Dp-7
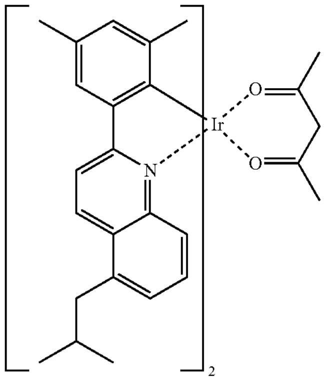
Dp-8
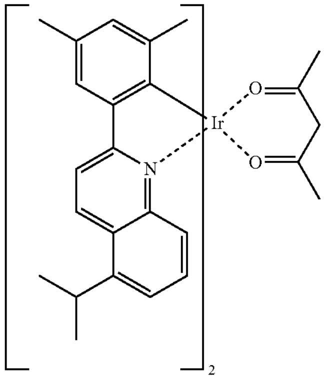
Dp-9
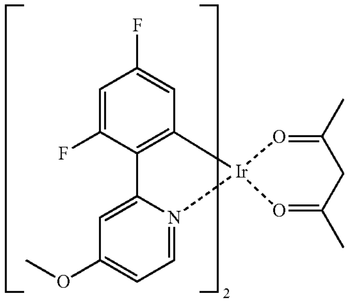
Dp-10
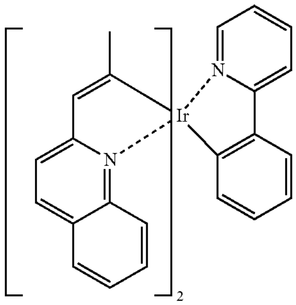
-continued
Dp-11
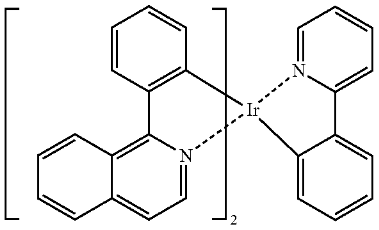
Dp-12
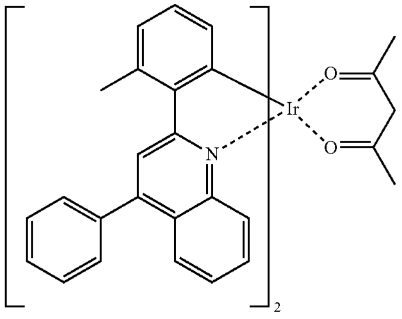
DP-13
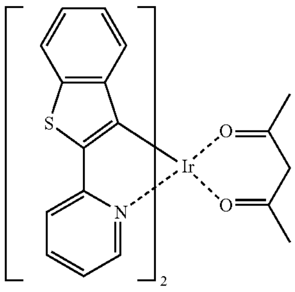
Dp-14
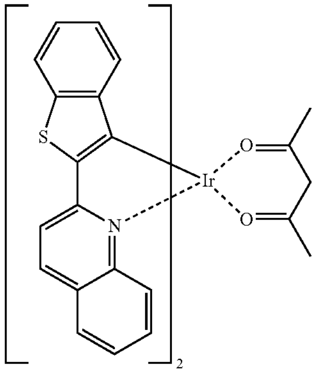
Dp-15
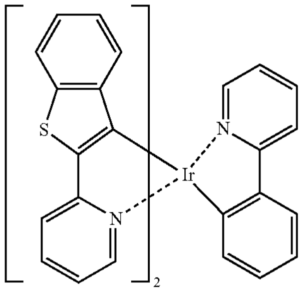

-continued
Dp-16
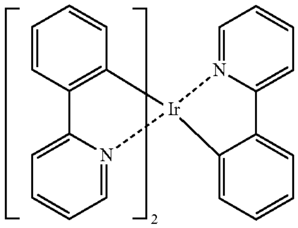
Dp-17
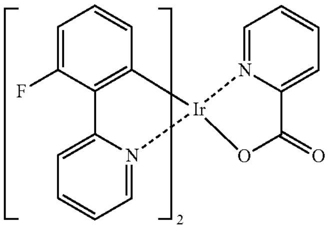
Dp-18
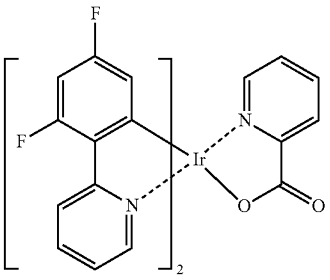
Dp-19
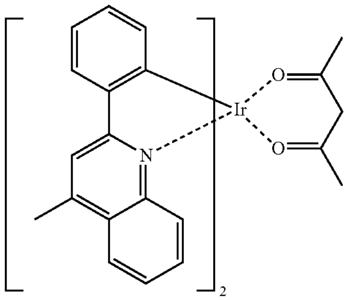
Dp-20
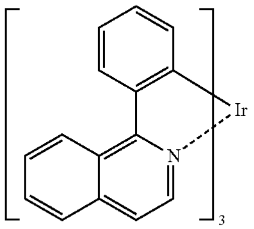
Dp-21
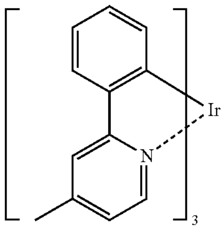
-continued
Dp-22
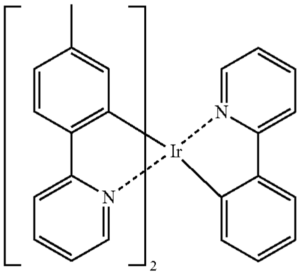
Dp-23
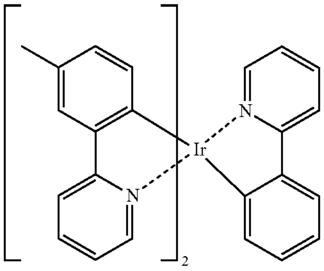
Dp-24
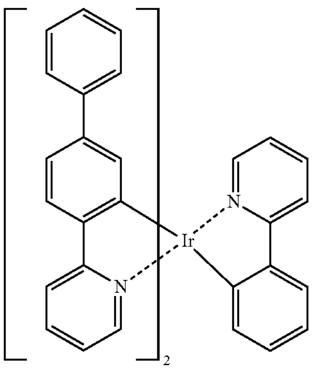
Dp-25
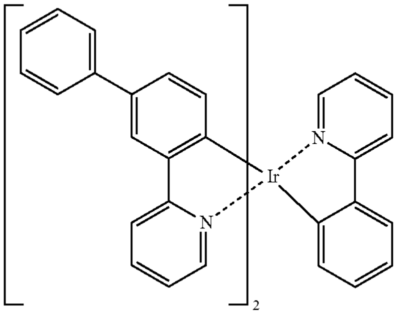
Dp-26
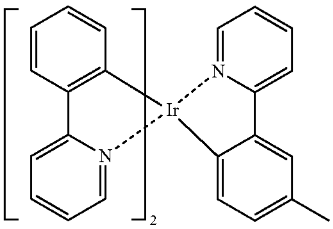

-continued
Dp-27
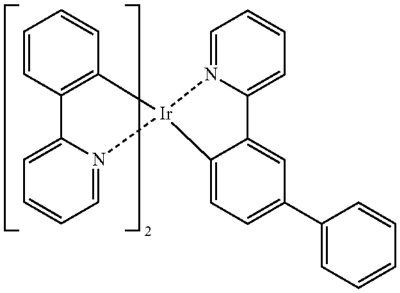
Dp-28
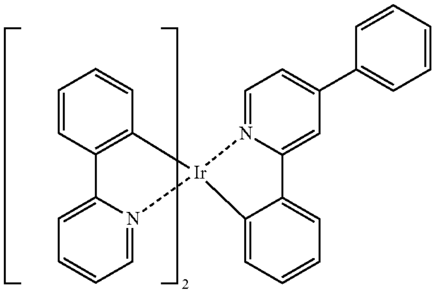
Dp-29
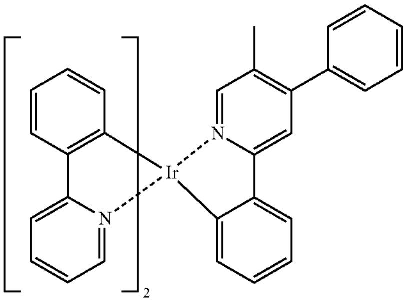
Dp-30
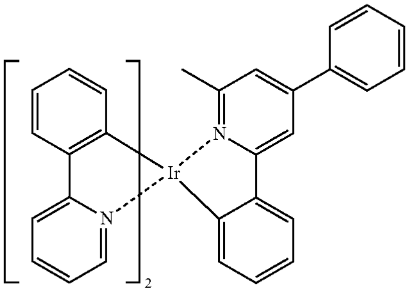
Dp-31
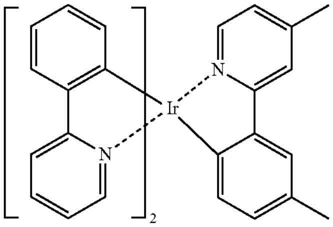
-continued
Dp-32
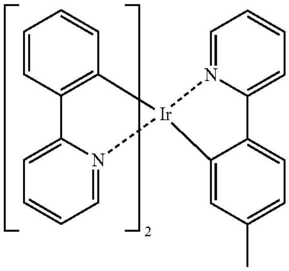
Dp-33
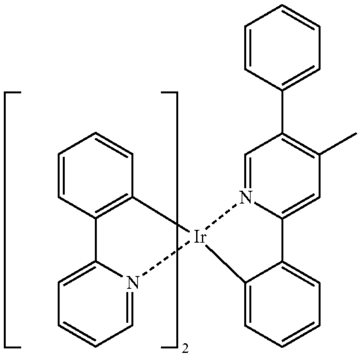
Dp-34
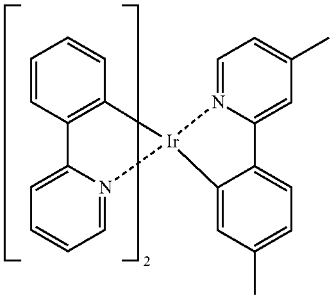
Dp-35
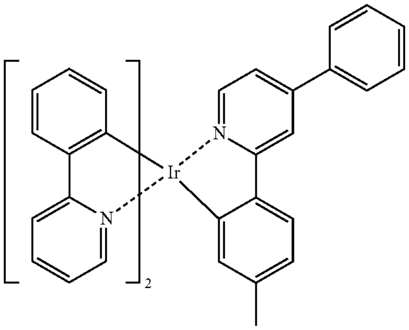

-continued

Dp-36

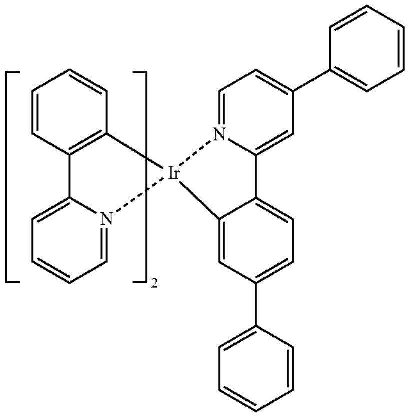

Dp-37

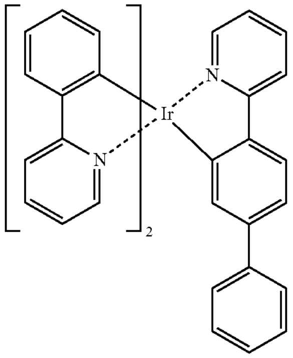

Dp-38

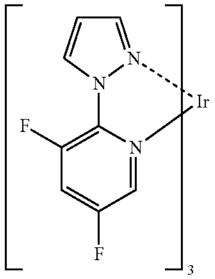

The hole blocking layer refers to a layer which is formed on the light emitting layer, preferably provided in contact with the light emitting layer, and serves to adjust the electron mobility, prevent excessive movement of holes, and increase the probability of hole-electron coupling, thereby improving the efficiency of the organic light emitting device. The hole blocking layer includes a hole blocking material, and examples of such hole blocking material can include a compound having an electron-withdrawing group introduced therein, such as azine derivatives including triazine; triazole derivatives; oxadiazole derivatives; phenanthroline derivatives; phosphine oxide derivatives, but is not limited thereto.

The electron injection and transport layer is a layer for simultaneously performing the roles of an electron transport layer and an electron injection layer that inject electrons from an electrode and transport the received electrons up to the light emitting layer, and is formed on the light emitting layer or the hole blocking layer. The electron injection and transport material is suitably a material which can receive electrons well from a cathode and transfer the electrons to a light emitting layer, and has a large mobility for electrons. Specific examples of the electron injection and transport material include: an Al complex of 8-hydroxyquinoline; a complex including $Alq_3$; an organic radical compound; a hydroxyflavone-metal complex, a triazine derivative, and the like, but are not limited thereto. Alternatively, it can be used together with fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)beryllium, bis (10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The electron injection and transport layer can also be formed as a separate layer such as an electron injection layer and an electron transport layer. In such a case, the electron transport layer is formed on the light emitting layer or the hole blocking layer, and the above-mentioned electron injection and transport material can be used as the electron transport material included in the electron transport layer. In addition, the electron injection layer is formed on the electron transport layer, and examples of the electron injection material included in the electron injection layer include LiF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like.

The organic light emitting device according to the present disclosure can be a bottom emission device, a top emission device, or a double-sided light emitting device, and in particular, can be a bottom emission device that requires relatively high luminous efficiency.

In addition, the compound of Chemical Formula 1 can be included in an organic solar cell or an organic transistor in addition to an organic light emitting device.

Hereinafter, preferred examples are presented to assist in the understanding of the present disclosure. However, the following examples are for illustrative purposes only, and is not intended to limit the content of the present disclosure.

Preparation Example 1: Preparation of Compound A-a-a

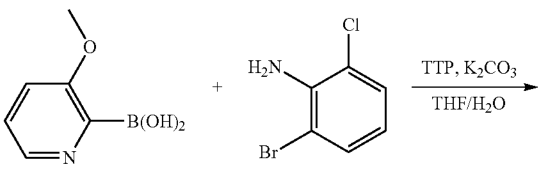

-continued

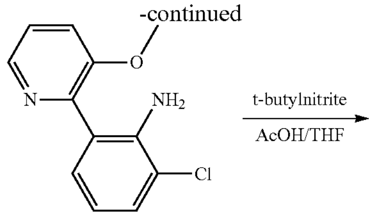

A-a-a-1

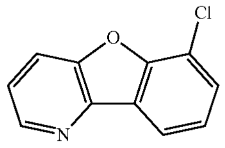

A-a-a

1) Preparation of Compound A-a-a-1

100.0 g (1.0 eq.) of (3-methoxypyridin-2-yl)boronic acid and 135 g (1.0 eq.) of 2-bromo-6-chloroaniline were added to 2000 ml of THF, and the mixture was stirred and refluxed. Then, 271.1 g (3.0 eq.) of potassium carbonate was dissolved in 813 ml of water, added thereto, sufficiently stirred, and then 22.7 g (0.03 eq.) of tetrakis(triphenylphosphine) palladium(0) (TTP) was added. After reacting for 5 hours, the reaction mixture was cooled to room temperature, and the organic layer and the aqueous layer were separated and then the organic layer was distilled. Then, the reaction mixture was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 127.4 g (yield: 83%) of Compound A-a-a-1. [M+H]=236

2) Preparation of Compound A-a-a 127.4 g (1.0 eq.) of Compound A-a-a-1 was added to 8000 ml of AcOH and 400 m of THF, and the mixture was stirred at 0° C. 84 g (1.5 eq.) of tert-butyl nitrite was slowly added thereto, and then stirred at room temperature for 4 hours. After completion of the reaction, the reaction solution was poured into water, crystals precipitated and were filtered. The filtered solid was completely dissolved in ethyl acetate, washed with water, and anhydrous magnesium sulfate was added, stirred, filtered, and the filtrate was distilled under reduced pressure. The concentrated compound was purified by silica gel column chromatography to give 73 g (yield: 66%) of Compound A-a-a. [M+H]=205

Preparation Example 2: Preparation of Compound A-a-b

Compound A-a-b was synthesized by the same method as the preparation method of Compound A-a-a, except that (4-methoxypyridin-3-yl)boronic acid was used instead of (3-methoxypyridin-2-yl)boronic acid.

A-a-b

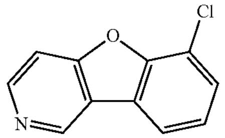

Preparation Example 3: Preparation of Compound A-a-c

Compound A-a-c was synthesized by the same method as the preparation method of Compound A-a-a, except that (3-methoxypyridin-4-yl)boronic acid was used instead of (3-methoxypyridin-2-yl)boronic acid.

A-a-c

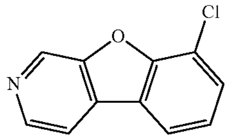

Preparation Example 4: Preparation of Compound A-a-d

Compound A-a-d was synthesized by the same method as the preparation method of Compound A-a-a, except that (2-methoxypyridin-3-yl)boronic acid was used instead of (3-methoxypyridin-2-yl)boronic acid.

A-a-d

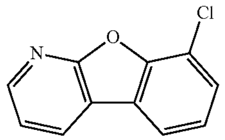

Preparation Example 5: Preparation of Compound A-a-e

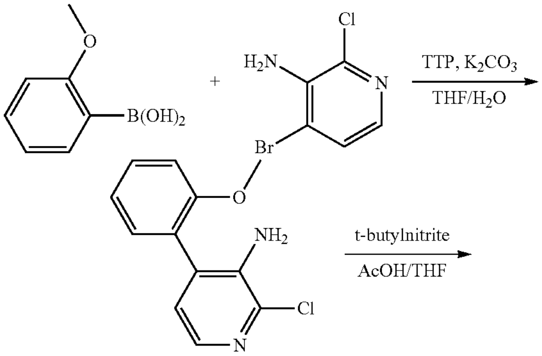

A-a-e-1

-continued

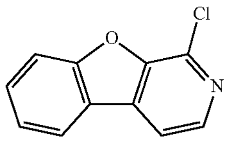

A-a-e

1) Preparation of Compound A-a-e-1

100.0 g (1.0 eq.) of (2-methoxyphenyl)boronic acid and 136.5 g (1.0 eq.) of 4-bromo-2-chloropyridin-3-amine were added to 2000 ml of THF, and the mixture was stirred and refluxed. Then, 272.9 g (3.0 eq.) of potassium carbonate was dissolved in 819 ml of water, added thereto, sufficiently stirred, and then 22.8 g (0.03 eq.) of tetrakis(triphenylphosphine)palladium(0) was added. After reacting for 6 hours, the reaction mixture was cooled to room temperature, and the organic layer and the aqueous layer were separated and then the organic layer was distilled. Then, the reaction mixture was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 103.5 g (yield: 67%) of Compound A-a-e-1. [M+H]=236

2) Preparation of Compound A-a-e 103.5 g (1.0 eq.) of Compound A-a-e-1 was added to 7000 ml of AcOH and 3500 ml of THF, and the mixture was stirred at 0° C. 68.2 g (1.5 eq.) of tert-butyl nitrite was slowly added thereto, and then stirred at room temperature for 3 hours. After completion of the reaction, the reaction solution was poured into water, crystals precipitated and were filtered. The filtered solid was completely dissolved in ethyl acetate, washed with water, and anhydrous magnesium sulfate was added, stirred, filtered, and the filtrate was distilled under reduced pressure. The concentrated compound was purified by silica gel column chromatography to give 55.7 g (yield: 62%) of Compound A-a-e. [M+H]=205

Preparation Example 6: Preparation of Compound A-a-f

Compound A-a-f was synthesized by the same method as the preparation method of Compound A-a-e, except that 3-bromo-5-chloropyridin-4-amine was used instead of 4-bromo-2-chloropyridin-3-amine.

A-a-f

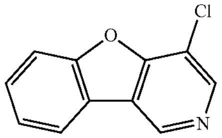

Preparation Example 7: Preparation of Compound A-a-g

Compound A-a-g was synthesized by the same method as the preparation method of Compound A-a-e, except that 2-bromo-4-chloropyridin-3-amine was used instead of 4-bromo-2-chloropyridin-3-amine.

A-a-g

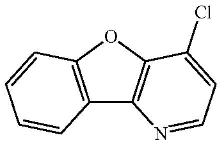

Preparation Example 8: Preparation of Compound A-b-a

Compound A-b-a was synthesized by the same method as the preparation method of Compound A-a-a, except that 2-bromo-5-chloroaniline was used instead of 2-bromo-6-chloroaniline.

A-b-a

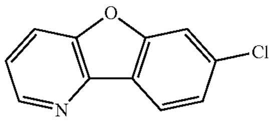

Preparation Example 9: Preparation of Compound A-b-b

Compound A-b-b was synthesized by the same method as the preparation method of Compound A-a-b, except that 2-bromo-5-chloroaniline was used instead of 2-bromo-6-chloroaniline.

A-b-b

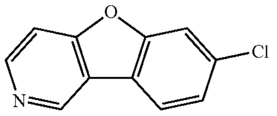

Preparation Example 10: Preparation of Compound A-b-c

Compound A-b-c was synthesized by the same method as the preparation method of Compound A-a-c, except that 2-bromo-5-chloroaniline was used instead of 2-bromo-6-chloroaniline.

A-b-c

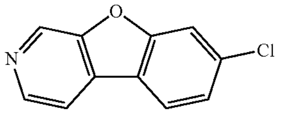

Preparation Example 11: Preparation of Compound A-b-d

Compound A-b-d was synthesized by the same method as the preparation method of Compound A-a-d, except that 2-bromo-5-chloroaniline was used instead of 2-bromo-6-chloroaniline.

A-b-d

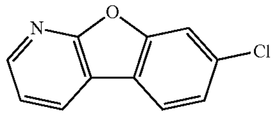

Preparation Example 12: Preparation of Compound A-b-e

Compound A-b-e was synthesized by the same method as the preparation method of Compound A-a-e, except that 3-bromo-6-chloropyridin-2-amine was used instead of 4-bromo-2-chloropyridin-3-amine.

A-b-e

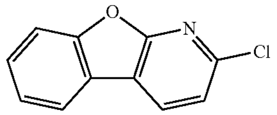

Preparation Example 13: Preparation of Compound A-b-f

Compound A-b-f was synthesized by the same method as the preparation method of Compound A-a-e, except that 5-bromo-2-chloropyridin-4-amine was used instead of 4-bromo-2-chloropyridin-3-amine.

A-b-f

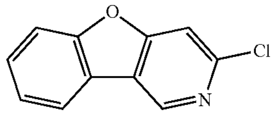

Preparation Example 14: Preparation of Compound A-b-g

Compound A-b-g was synthesized by the same method as the preparation method of Compound A-a-e, except that 2-bromo-5-chloropyridin-3-amine was used instead of 4-bromo-2-chloropyridin-3-amine.

A-b-g

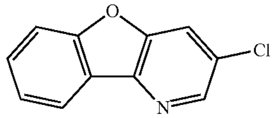

Preparation Example 15: Preparation of Compound A-c-a

Compound A-c-a was synthesized by the same method as the preparation method of Compound A-a-a, except that 2-bromo-4-chloroaniline was used instead of 2-bromo-6-chloroaniline.

A-c-a

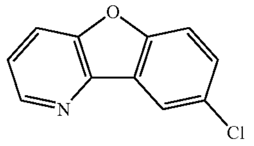

Preparation Example 16: Preparation of Compound A-c-b

Compound A-c-b was synthesized by the same method as the preparation method of Compound A-a-b, except that 2-bromo-4-chloroaniline was used instead of 2-bromo-6-chloroaniline.

A-c-b

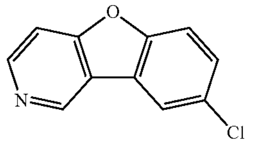

Preparation Example 17: Preparation of Compound A-c-c

Compound A-c-c was synthesized by the same method as the preparation method of Compound A-a-c, except that 2-bromo-4-chloroaniline was used instead of 2-bromo-6-chloroaniline.

A-c-c

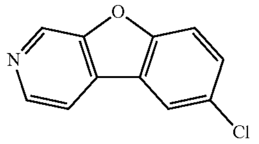

Preparation Example 18: Preparation of Compound A-c-d

Compound A-c-d was synthesized by the same method as the preparation method of Compound A-a-d, except that 2-bromo-4-chloroaniline was used instead of 2-bromo-6-chloroaniline.

A-c-d

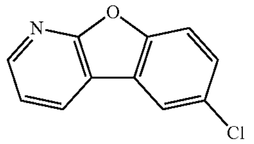

Preparation Example 19: Preparation of Compound A-c-e

Compound A-c-e was synthesized by the same method as the preparation method of Compound A-a-e, except that 3-bromo-5-chloropyridin-2-amine was used instead of 4-bromo-2-chloropyridin-3-amine.

A-c-e

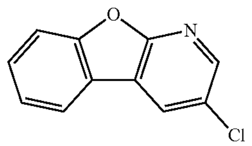

Preparation Example 20: Preparation of Compound A-c-f

Compound A-c-f was synthesized by the same method as the preparation method of Compound A-a-e, except that 4-bromo-6-chloropyridin-3-amine was used instead of 4-bromo-2-chloropyridin-3-amine.

A-c-f

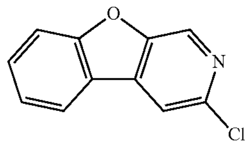

Preparation Example 21: Preparation of Compound A-c-g

Compound A-c-g was synthesized by the same method as the preparation method of Compound A-a-e, except that 2-bromo-6-chloropyridin-3-amine was used instead of 4-bromo-2-chloropyridin-3-amine.

A-c-g

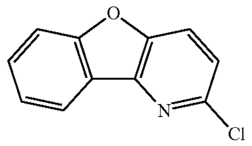

Preparation Example 22: Preparation of Compound A-d-a

Compound A-d-a was synthesized by the same method as the preparation method of Compound A-a-a, except that 2-bromo-3-chloroaniline was used instead of 2-bromo-6-chloroaniline.

A-d-a

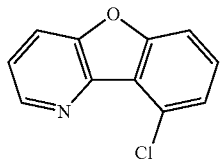

Preparation Example 23: Preparation of Compound A-d-b

Compound A-d-b was synthesized by the same method as the preparation method of Compound A-a-b, except that 2-bromo-3-chloroaniline was used instead of 2-bromo-6-chloroaniline.

A-d-b

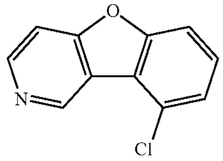

Preparation Example 24: Preparation of Compound A-d-c

Compound A-d-c was synthesized by the same method as the preparation method of Compound A-a-c, except that 2-bromo-3-chloroaniline was used instead of 2-bromo-6-chloroaniline.

A-d-c

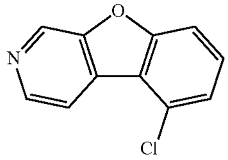

Preparation Example 25: Preparation of Compound A-d-d

Compound A-d-d was synthesized by the same method as the preparation method of Compound A-a-d, except that 2-bromo-3-chloroaniline was used instead of 2-bromo-6-chloroaniline.

A-d-d

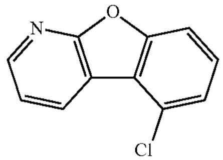

Preparation Example 26: Preparation of Compound A-d-e

Compound A-d-e was synthesized by the same method as the preparation method of Compound A-a-e, except that 3-bromo-4-chloropyridin-2-amine was used instead of 4-bromo-2-chloropyridin-3-amine.

A-d-e

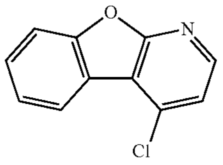

Preparation Example 27: Preparation of Compound A-d-f

Compound A-d-f was synthesized by the same method as the preparation method of Compound A-a-e, except that 4-bromo-5-chloropyridin-3-amine was used instead of 4-bromo-2-chloropyridin-3-amine.

A-d-f

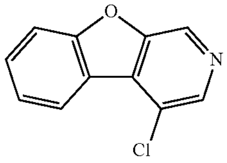

Preparation Example 28: Preparation of Compound A-d-g

Compound A-d-g was synthesized by the same method as the preparation method of Compound A-a-e, except that 3-bromo-2-chloropyridin-4-amine was used instead of 4-bromo-2-chloropyridin-3-amine.

A-d-g

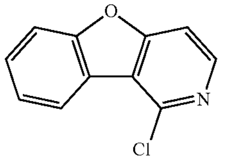

Preparation Example 29: Preparation of Compound B-a-a

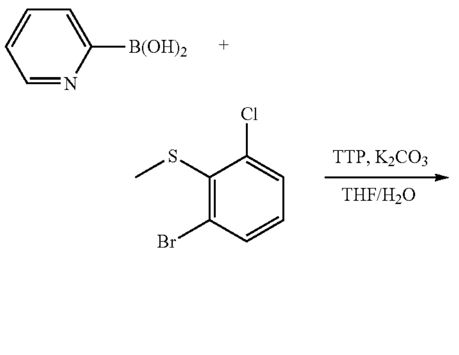

-continued

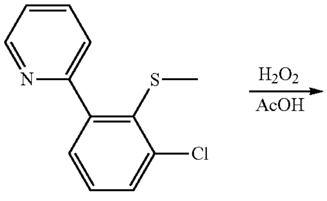

B-a-a-2

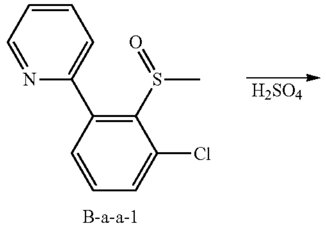

B-a-a-1

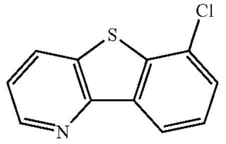

B-a-a

1) Preparation of Compound B-a-a-2

200.0 g (1.0 eq.) of pyridin-2-ylboronic acid and 386.5 g (1.0 eq.) of (2-bromo-6-chlorophenyl)(methyl)sulfane were added to 4000 ml of THF, and the mixture was stirred and refluxed. Then, 674.6 g (3.0 eq.) of potassium carbonate was dissolved in 2024 ml of water, added thereto, sufficiently stirred, and then 56.4 g (0.03 eq.) of tetrakis(triphenylphosphine)palladium(0) was added. After reacting for 3 hours, the reaction mixture was cooled to room temperature, and the organic layer and the aqueous layer were separated and then the organic layer was distilled. Then, the reaction mixture was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 306.8 g (yield: 80%) of Compound B-a-a-2. [M+H]=237

2) Preparation of Compound B-a-a-1

306.8 g (1.0 eq) of Compound B-a-a-2 and 88.5 g (2.00 eq) of $H_2O_2$ were added to 1500 ml of acetic acid, and the mixture was stirred under reflux. After 1 hour, the reaction solution was poured into water, crystals precipitated and were filtered. The filtered solid was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 131 g (yield: 40%) of Compound B-a-a-1. [M+H]=253

3) Preparation of Compound B-a-a 131 g (1.0 eq) of Compound B-a-a-1 was added to 600 ml of $H_2SO_4$, and then dissolved while stirring under reflux. When the reaction was completed after 2 hours, the reaction solution was poured into water, crystals precipitated and were filtered. The filtered solid was completely dissolved in $CHCl_3$, washed with water, and the solution in which the product was dissolved was concentrated under reduced pressure to remove about 80% of the solvent. Under reflux again, crystals formed and precipitated while adding hexane thereto, and the result was cooled and then filtered to give 43.4 g (yield: 38%) of Compound B-a-a. [M+H]=221

Preparation Example 30: Preparation of Compound B-a-b

Compound B-a-b was synthesized by the same method as the preparation method of Compound B-a-a, except that pyridin-3-ylboronic acid was used instead of pyridin-2-ylboronic acid.

B-a-c

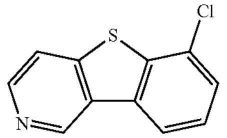

Preparation Example 31: Preparation of Compound B-a-c

Compound B-a-c was synthesized by the same method as the preparation method of Compound B-a-a, except that pyridin-4-ylboronic acid was used instead of pyridin-2-ylboronic acid.

B-a-c

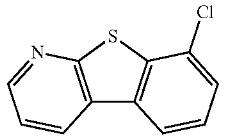

Preparation Example 32: Preparation of Compound B-a-d

Compound B-a-d was synthesized by the same method as the preparation method of Compound B-a-a, except that pyridin-5-ylboronic acid was used instead of pyridin-2-ylboronic acid.

B-a-d

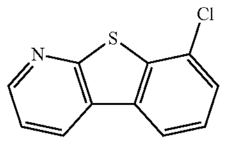

Preparation Example 33: Preparation of Compound B-a-e

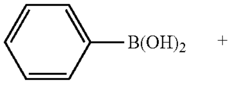

-continued

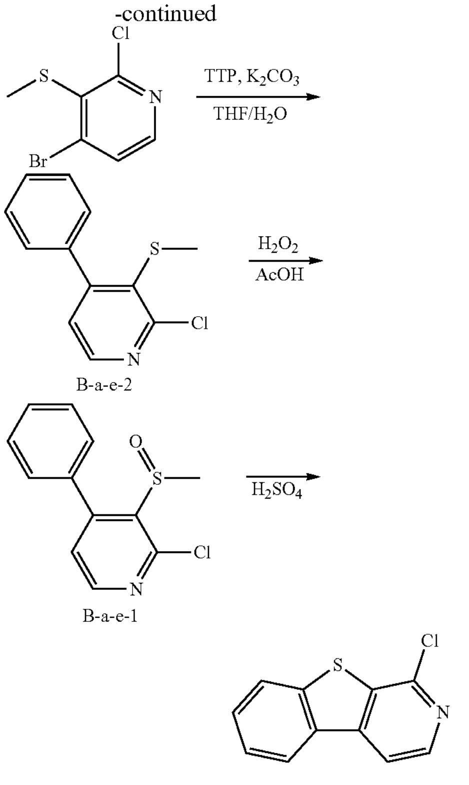

B-a-e-2

B-a-e-1

B-a-e

1) Preparation of Compound B-a-e-2

200.0 g (1.0 eq.) of phenylboronic acid and 391.3 g (1.0 eq.) of 4-bromo-2-chloro-3-(methylthio)pyridine were added to 4000 ml of THF, and the mixture was stirred and refluxed. Then, 680.1 g (3.0 eq.) of potassium carbonate was dissolved in 2040 ml of water, added thereto, sufficiently stirred, and then 56.9 g (0.03 eq.) of tetrakis(triphenylphosphine)palladium(0) was added. After reacting for 5 hours, the reaction mixture was cooled to room temperature, and the organic layer and the aqueous layer were separated and then the organic layer was distilled. Then, the reaction mixture was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 274.5 g (yield: 71%) of Compound B-a-e-2. [M+H]=237

2) Preparation of Compound B-a-e-1

274.5 g (1.0 eq) of Compound B-a-e-2 and 79.2 g (2.00 eq) of $H_2O_2$ were added to 1200 ml of acetic acid, and the mixture was stirred under reflux. After 1 hour, the reaction solution was poured into water, crystals precipitated and were filtered. The filtered solid was completely dissolved in ethyl acetate, washed with water, and then approximately 80% of the solvent was removed under reduced pressure again. Under reflux again, crystals formed and precipitated while adding hexane thereto, and the result was cooled and then filtered. This was subjected to column chromatography to give 131.9 g (yield: 45%) of Compound B-a-e-1. [M+H]=253

3) Preparation of Compound B-a-e 131.9 g (1.0 eq) of Compound B-a-e-1 was added 600 ml of $H_2SO_4$, and then dissolved and stirred under reflux. When the reaction was completed after 2 hours, the reaction solution was poured into water, crystals precipitated and were filtered. The filtered solid was completely dissolved in $CHCl_3$, washed with water, and the solution in which the product was dissolved was concentrated under reduced pressure to remove about 80% of the solvent. Under reflux again, crystals formed and precipitated while adding hexane thereto, and the result was cooled and then filtered to give 44.6 g (yield: 39%) of Compound B-a-e. [M+H]=221

Preparation Example 34: Preparation of Compound B-a-f

Compound B-a-f was synthesized by the same method as the preparation method of Compound B-a-e, except that 3-bromo-5-chloro-4-(methylthio)pyridine was used instead of 4-bromo-2-chloro-3-(methylthio)pyridine.

B-a-f

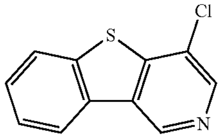

Preparation Example 35: Preparation of Compound B-a-g

Compound B-a-g was synthesized by the same method as the preparation method of Compound B-a-e, except that 2-bromo-4-chloro-3-(methylthio)pyridine was used instead of 4-bromo-2-chloro-3-(methylthio)pyridine.

B-a-g

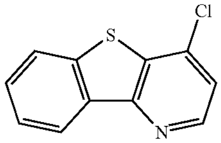

Preparation Example 36: Preparation of Compound B-b-a

Compound B-b-a was synthesized by the same method as the preparation method of Compound B-a-a, except that (2-bromo-5-chlorophenyl)(methyl)sulfane was used instead of (2-bromo-6-chlorophenyl)(methyl)sulfane.

B-b-a

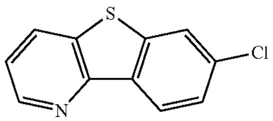

Preparation Example 37: Preparation of Compound B-b-b

Compound B-b-b was synthesized by the same method as the preparation method of Compound B-a-b, except that (2-bromo-5-chlorophenyl)(methyl)sulfane was used instead of (2-bromo-6-chlorophenyl)(methyl)sulfane.

B-b-b

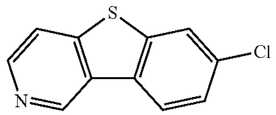

Preparation Example 38: Preparation of Compound B-b-c

Compound B-b-c was synthesized by the same method as the preparation method of Compound B-a-c, except that (2-bromo-5-chlorophenyl)(methyl)sulfane was used instead of (2-bromo-6-chlorophenyl)(methyl)sulfane.

B-b-c

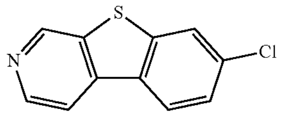

Preparation Example 39: Preparation of Compound B-b-d

Compound B-b-d was synthesized by the same method as the preparation method of Compound B-a-d, except that (2-bromo-5-chlorophenyl)(methyl)sulfane was used instead of (2-bromo-6-chlorophenyl)(methyl)sulfane.

B-b-d

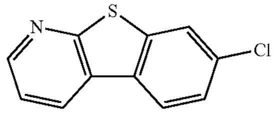

Preparation Example 40: Preparation of Compound B-b-e

Compound B-b-e was synthesized by the same method as the preparation method of Compound B-a-e, except that 3-bromo-6-chloro-2-(methylthio)pyridine was used instead of 4-bromo-2-chloro-3-(methylthio)pyridine.

B-b-e

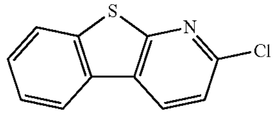

Preparation Example 41: Preparation of Compound B-b-f

Compound B-b-f was synthesized by the same method as the preparation method of Compound B-a-e, except that 5-bromo-2-chloro-4-(methylthio)pyridine was used instead of 4-bromo-2-chloro-3-(methylthio)pyridine.

B-b-f

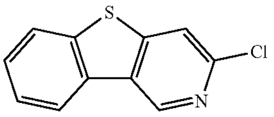

Preparation Example 42: Preparation of Compound B-b-g

Compound B-b-g was synthesized by the same method as the preparation method of Compound B-a-e, except that 2-bromo-5-chloro-3-(methylthio)pyridine was used instead of 4-bromo-2-chloro-3-(methylthio)pyridine.

B-b-g

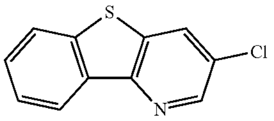

Preparation Example 43: Preparation of Compound B-c-a

Compound B-c-a was synthesized by the same method as the preparation method of Compound B-a-a, except that (2-bromo-4-chlorophenyl)(methyl)sulfane was used instead of (2-bromo-6-chlorophenyl)(methyl)sulfane.

B-c-a

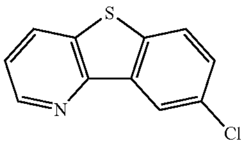

Preparation Example 44: Preparation of Compound B-c-b

Compound B-c-b was synthesized by the same method as the preparation method of Compound B-a-b, except that (2-bromo-4-chlorophenyl)(methyl)sulfane was used instead of (2-bromo-6-chlorophenyl)(methyl)sulfane.

B-c-b

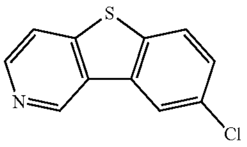

Preparation Example 45: Preparation of Compound B-c-c

Compound B-c-c was synthesized by the same method as the preparation method of Compound B-a-c, except that (2-bromo-4-chlorophenyl)(methyl)sulfane was used instead of (2-bromo-6-chlorophenyl)(methyl)sulfane.

B-c-c

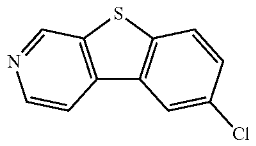

Preparation Example 46: Preparation of Compound B-c-d

Compound B-c-d was synthesized by the same method as the preparation method of Compound B-a-d, except that (2-bromo-4-chlorophenyl)(methyl)sulfane was used instead of (2-bromo-6-chlorophenyl)(methyl)sulfane.

B-c-d

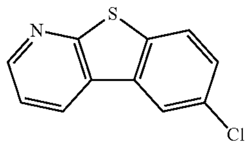

Preparation Example 47: Preparation of Compound B-c-e

Compound B-c-e was synthesized by the same method as the preparation method of Compound B-a-e, except that 3-bromo-5-chloro-2-(methylthio)pyridine was used instead of 4-bromo-2-chloro-3-(methylthio)pyridine.

B-c-e

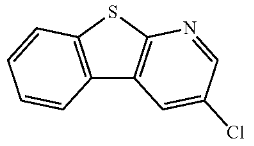

Preparation Example 48: Preparation of Compound B-c-f

Compound B-c-f was synthesized by the same method as the preparation method of Compound B-a-e, except that 4-bromo-2-chloro-5-(methylthio)pyridine was used instead of 4-bromo-2-chloro-3-(methylthio)pyridine.

B-c-f

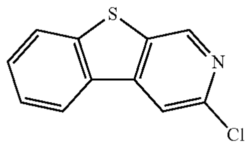

Preparation Example 49: Preparation of Compound B-c-g

Compound B-c-g was synthesized by the same method as the preparation method of Compound B-a-e, except that 2-bromo-6-chloro-3-(methylthio)pyridine was used instead of 4-bromo-2-chloro-3-(methylthio)pyridine.

B-c-g

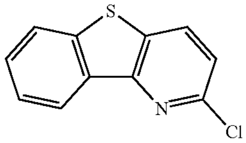

Preparation Example 50: Preparation of Compound B-d-a

Compound B-d-a was synthesized by the same method as the preparation method of Compound B-a-a, except that (2-bromo-3-chlorophenyl)(methyl)sulfane was used instead of (2-bromo-6-chlorophenyl)(methyl)sulfane.

B-d-a

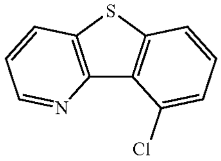

Preparation Example 51: Preparation of Compound B-d-b

Compound B-d-b was synthesized by the same method as the preparation method of Compound B-a-b, except that (2-bromo-3-chlorophenyl)(methyl)sulfane was used instead of (2-bromo-6-chlorophenyl)(methyl)sulfane.

B-d-b

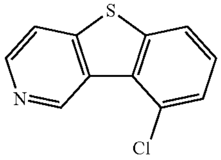

Preparation Example 52: Preparation of Compound B-d-c

Compound B-d-c was synthesized by the same method as the preparation method of Compound B-a-c, except that (2-bromo-3-chlorophenyl)(methyl)sulfane was used instead of (2-bromo-6-chlorophenyl)(methyl)sulfane.

B-d-c

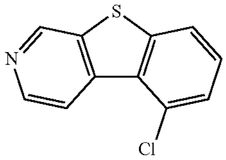

Preparation Example 53: Preparation of Compound B-d-d

Compound B-d-d was synthesized by the same method as the preparation method of Compound B-a-d, except that (2-bromo-3-chlorophenyl)(methyl)sulfane was used instead of (2-bromo-6-chlorophenyl)(methyl)sulfane.

B-d-d

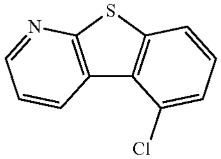

Preparation Example 54: Preparation of Compound B-d-e

Compound B-d-e was synthesized by the same method as the preparation method of Compound B-a-e, except that 3-bromo-4-chloro-2-(methylthio)pyridine was used instead of 4-bromo-2-chloro-3-(methylthio)pyridine.

B-d-e

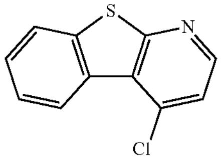

Preparation Example 55: Preparation of Compound B-d-f

Compound B-d-f was synthesized by the same method as the preparation method of Compound B-a-e, except that 4-bromo-3-chloro-5-(methylthio)pyridine was used instead of 4-bromo-2-chloro-3-(methylthio)pyridine.

B-d-f

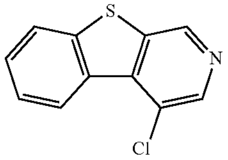

Preparation Example 56: Preparation of Compound B-d-g

Compound B-d-g was synthesized by the same method as the preparation method of Compound B-a-e, except that 3-bromo-2-chloro-4-(methylthio)pyridine was used instead of 4-bromo-2-chloro-3-(methylthio)pyridine.

B-d-g

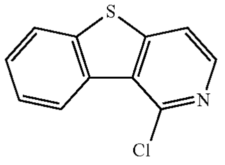

Synthesis Example 1

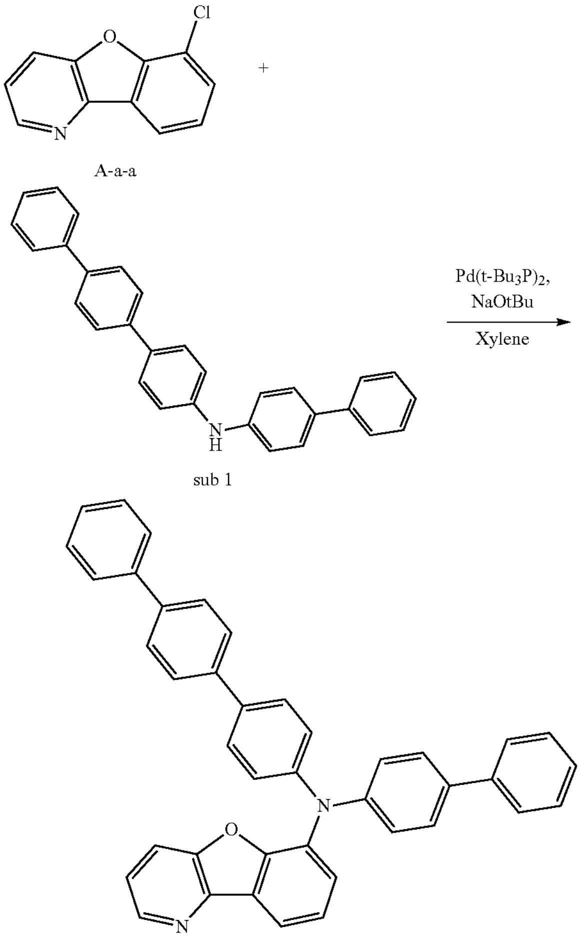

A-a-a sub 1

1

Compound A-a-a (15 g, 73.7 mmol) and Compound sub 1 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 12.5 g of Compound 1. (Yield: 30%, MS: $[M+H]^+=566$)

Synthesis Example 2

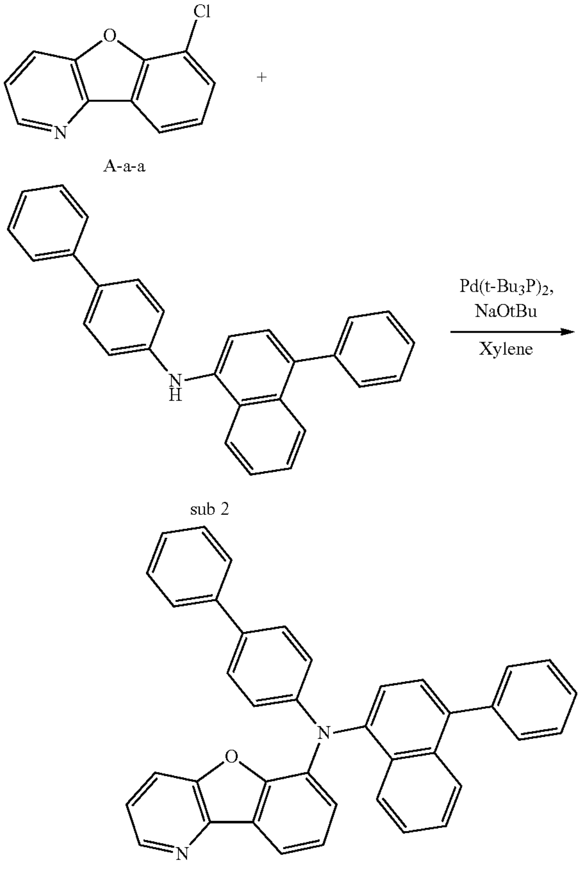

A-a-a sub 2

2

Compound A-a-a (15 g, 73.7 mmol) and Compound sub 2 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 14.7 g of Compound 2. (Yield: 37%, MS: $[M+H]^+=540$)

Synthesis Example 3

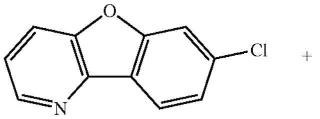

A-b-a

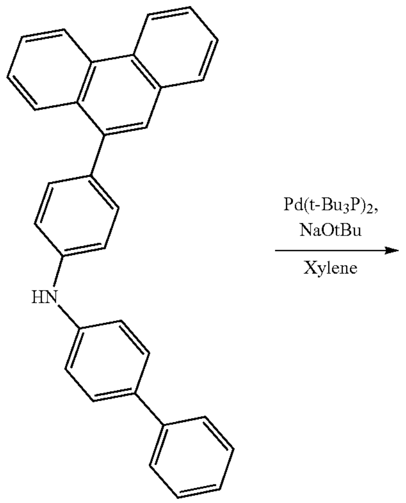

sub 3

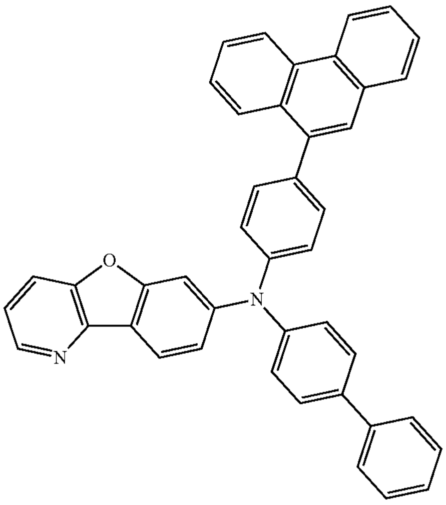

3

Compound A-b-a (15 g, 73.7 mmol) and Compound sub 3 (34.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.3 g of Compound 3. (Yield: 40%, MS: $[M+H]^+=590$)

Synthesis Example 4

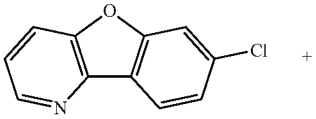

A-b-a

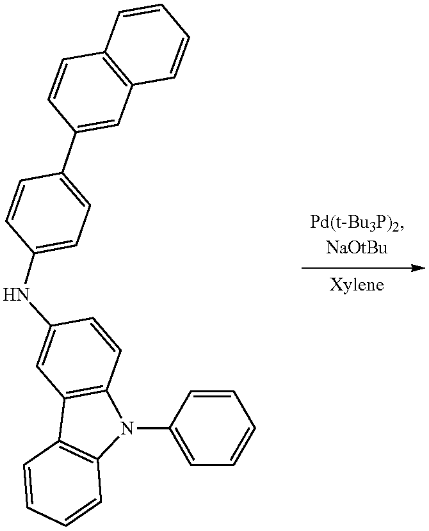

sub 4

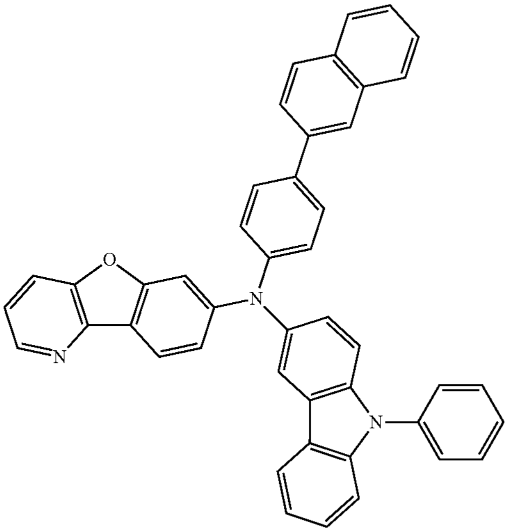

4

Compound A-b-a (15 g, 73.7 mmol) and Compound sub 4 (37.3 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19 g of Compound 4. (Yield: 41%, MS: $[M+H]^+=629$)

Synthesis Example 5

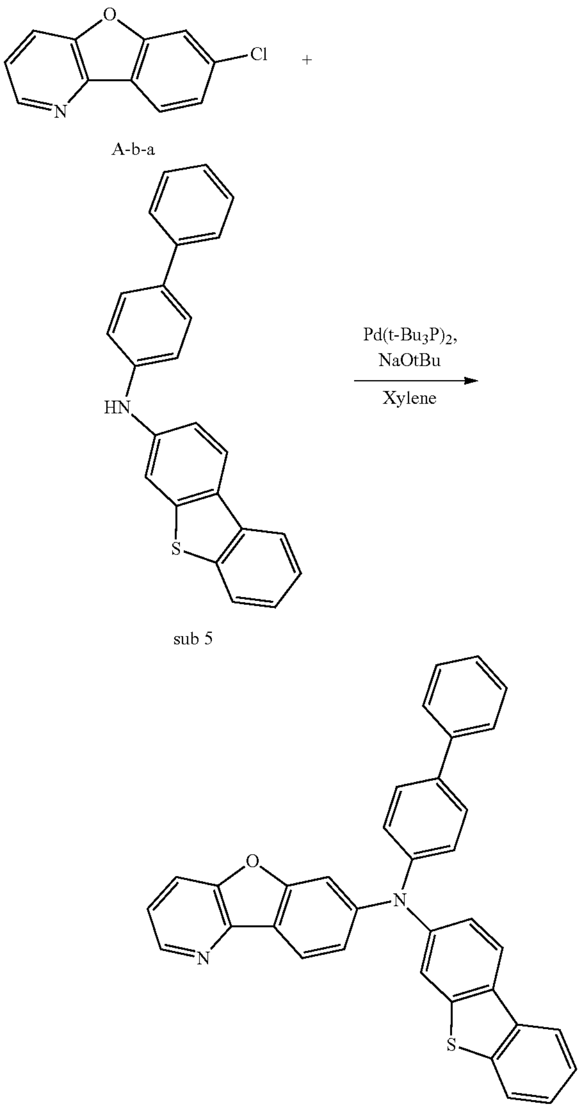

A-b-a sub 5

5

Compound A-b-a (15 g, 73.7 mmol) and Compound sub 5 (28.5 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 16 g of Compound 5. (Yield: 42%, MS: $[M+H]^+=520$)

Synthesis Example 6

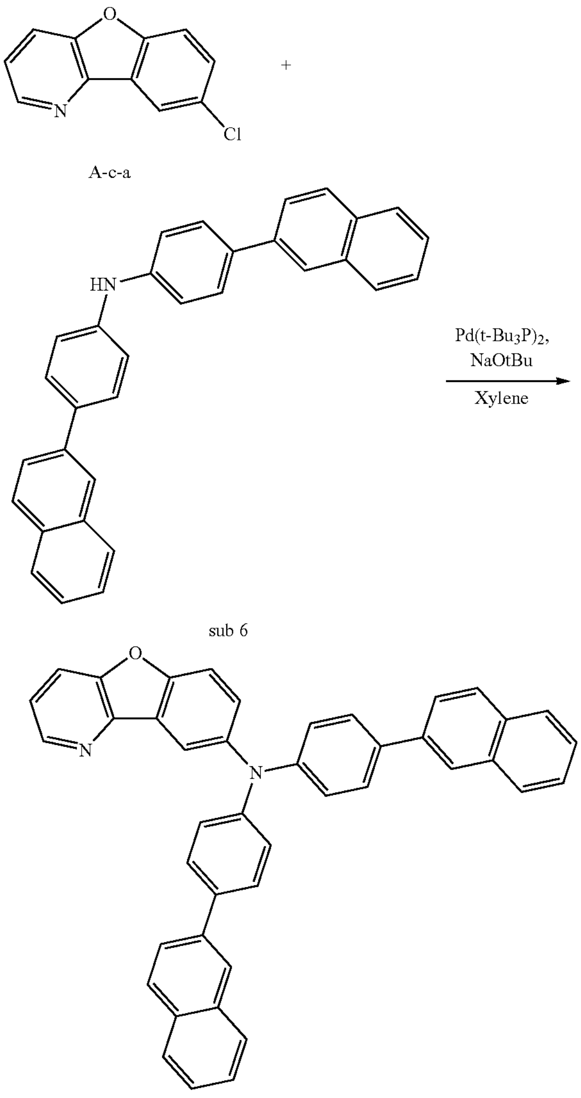

A-c-a sub 6

6

Compound A-c-a (15 g, 73.7 mmol) and Compound sub 6 (34.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.8 g of Compound 6. (Yield: 41%, MS: $[M+H]^+=590$)

Synthesis Example 7

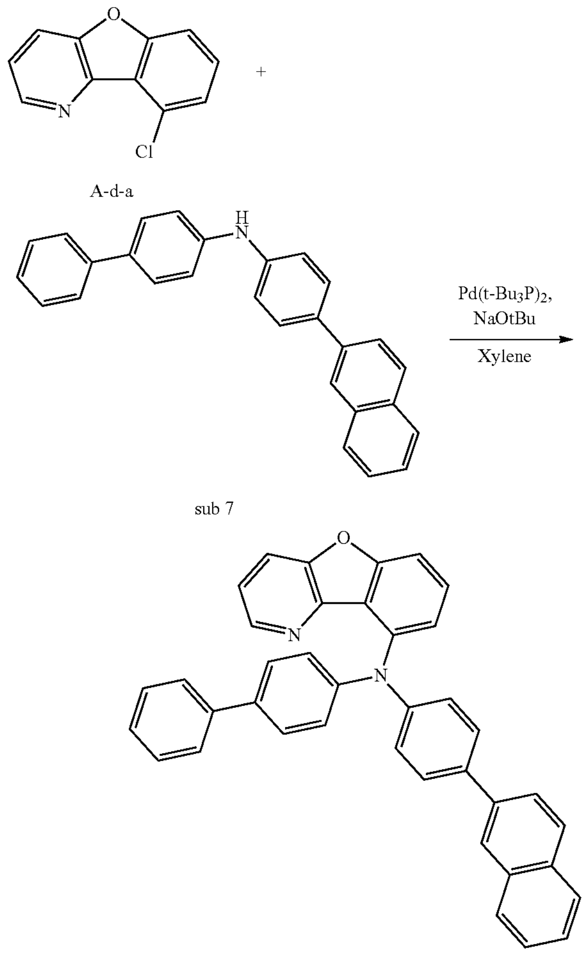

A-d-a sub 7

7

Compound A-d-a (15 g, 73.7 mmol) and Compound sub 7 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 18.3 g of Compound 7. (Yield: 46%, MS: $[M+H]^+=540$)

Synthesis Example 8

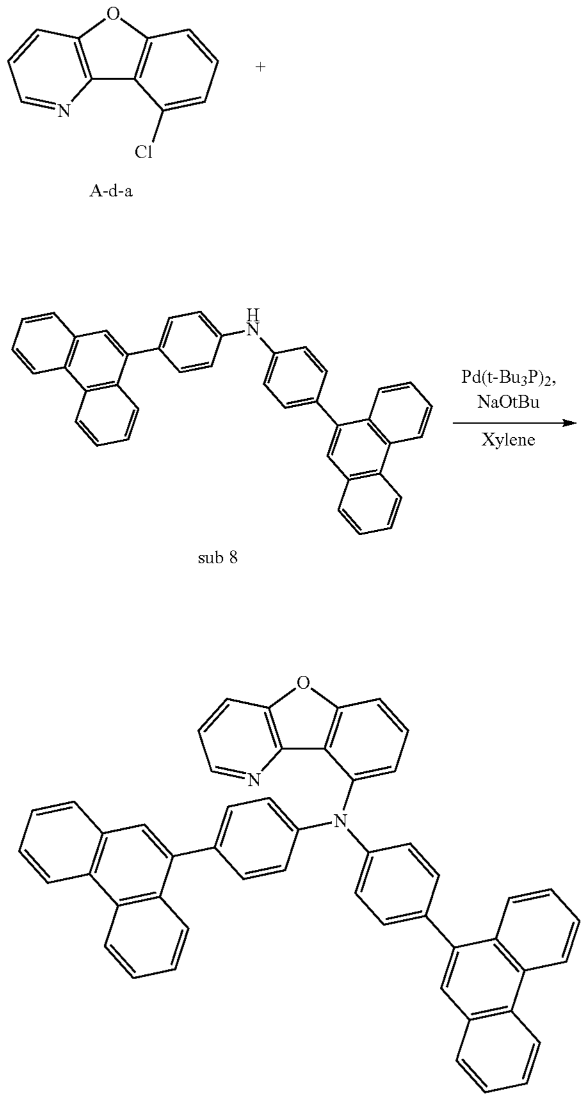

A-d-a sub 8

8

Compound A-d-a (15 g, 73.7 mmol) and Compound sub 8 (42.3 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.8 g of Compound 8. (Yield: 41%, MS: $[M+H]^+=690$)

Synthesis Example 9

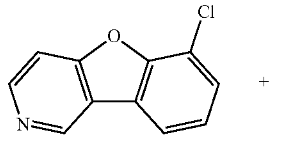

A-a-b

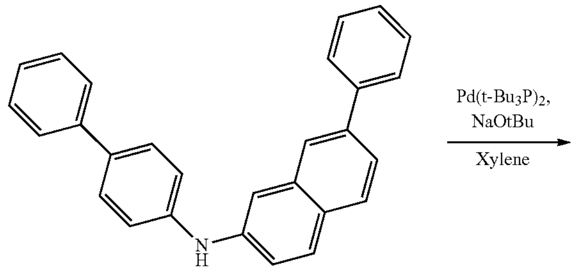

sub 9

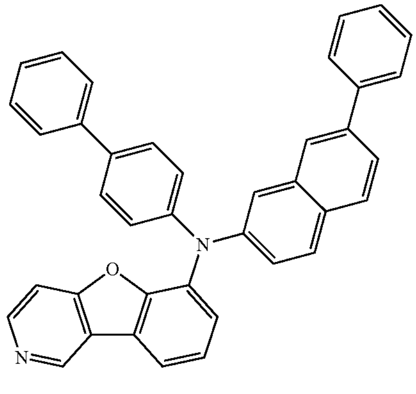

9

Compound A-a-b (15 g, 73.7 mmol) and Compound sub 9 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 24.2 g of Compound 9. (Yield: 61%, MS: $[M+H]^+=540$)

Synthesis Example 10

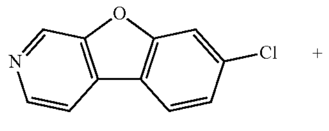

A-b-c

-continued

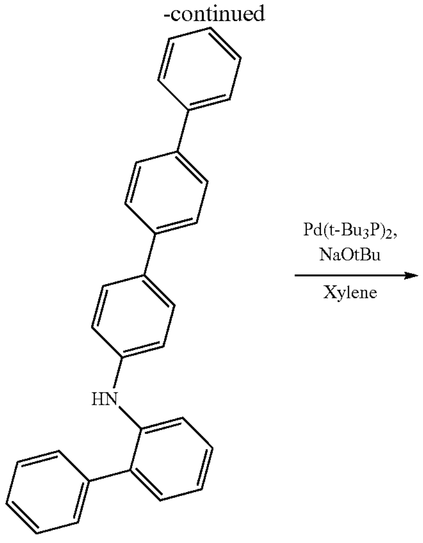

sub 10

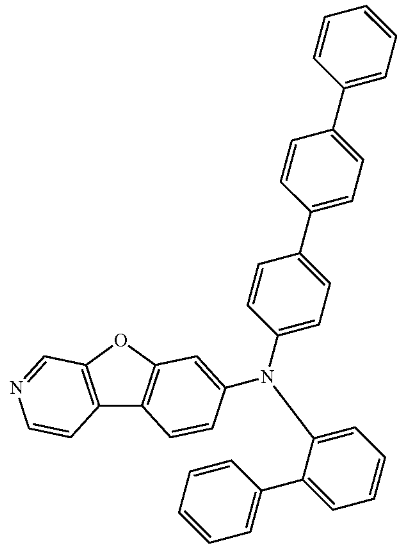

10

Compound A-b-c (15 g, 73.7 mmol) and Compound sub 10 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 27.5 g of Compound 10. (Yield: 66%, MS: $[M+H]^+=566$)

Synthesis Example 11

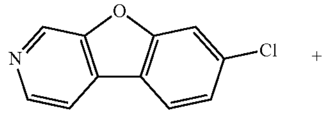

A-b-c

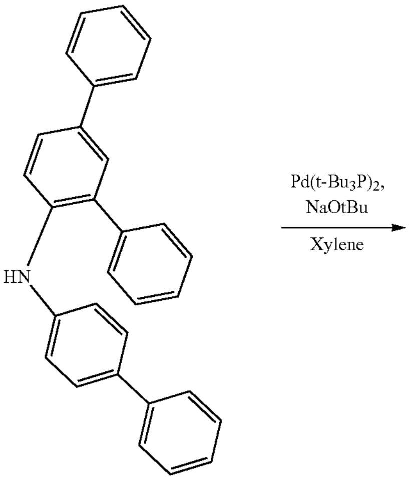

sub 11

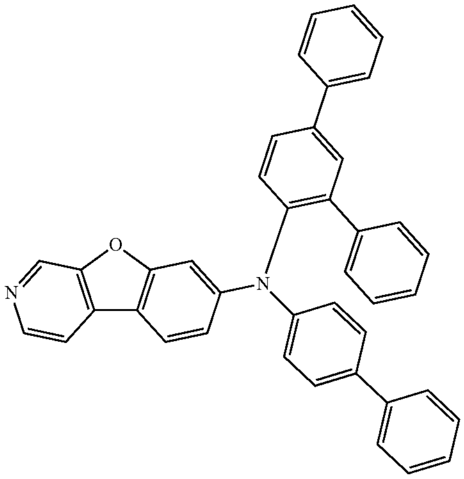

11

Compound A-b-c (15 g, 73.7 mmol) and Compound sub 11 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 27 g of Compound 11. (Yield: 65%, MS: $[M+H]^+=566$)

Synthesis Example 12

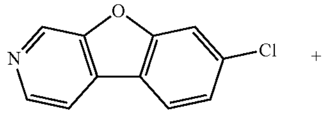

A-b-c

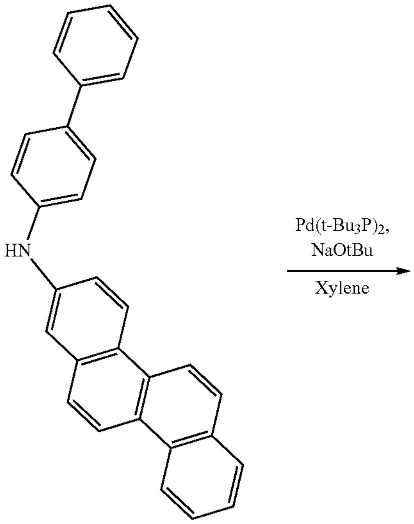

sub 12

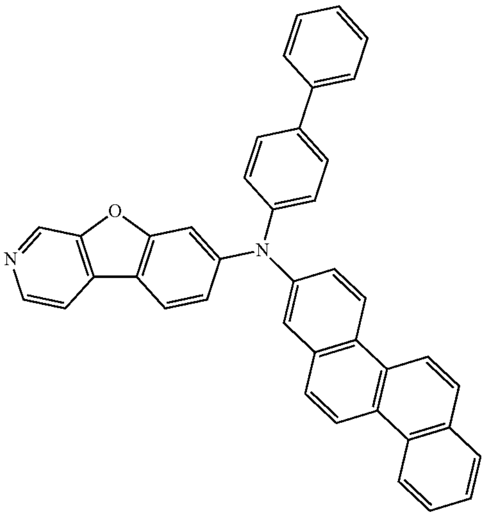

12

Compound A-b-c (15 g, 73.7 mmol) and Compound sub 12 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.9 g of Compound 12. (Yield: 48%, MS: $[M+H]^+=564$)

Synthesis Example 13

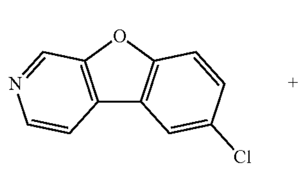

A-c-c

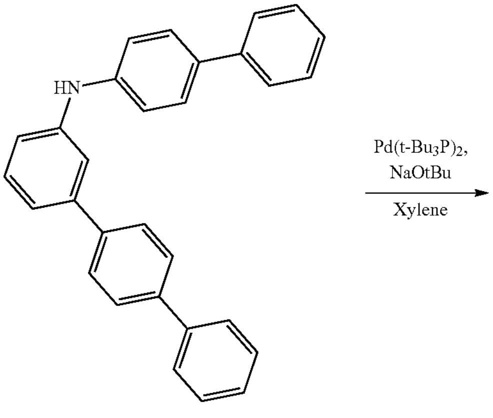

sub 13

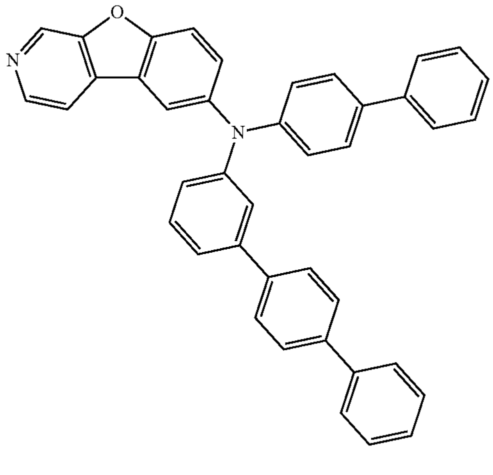

13

Compound A-c-c (15 g, 73.7 mmol) and Compound sub 13 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 24.1 g of Compound 13. (Yield: 58%, MS: $[M+H]^+=566$)

Synthesis Example 14

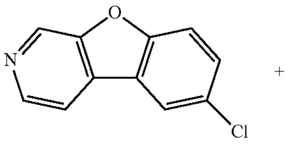

A-c-c

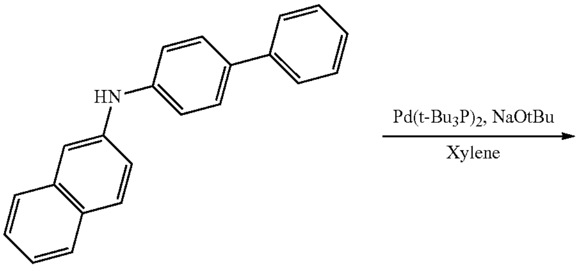

sub 14

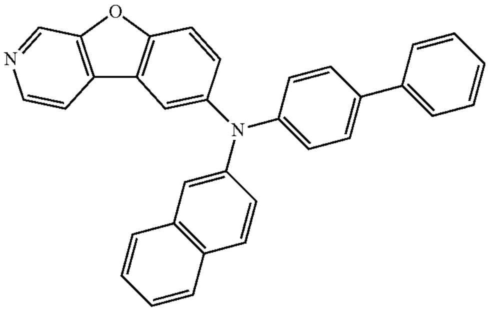

14

Compound A-c-c (15 g, 73.7 mmol) and Compound sub 14 (23.9 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 13.6 g of Compound 14. (Yield: 40%, MS: $[M+H]^+=464$)

Synthesis Example 15

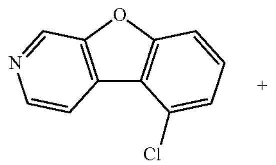

A-d-c

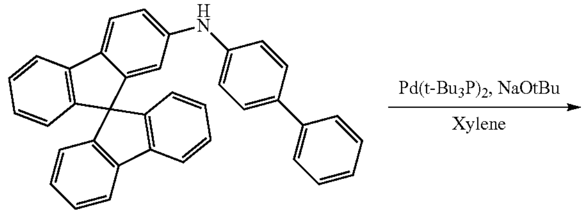

sub 15

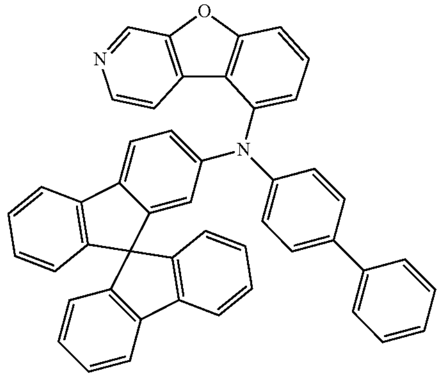

15

Compound A-d-c (15 g, 73.7 mmol) and Compound sub 15 (39.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 28.8 g of Compound 15. (Yield: 60%, MS: $[M+H]^+=652$)

Synthesis Example 16

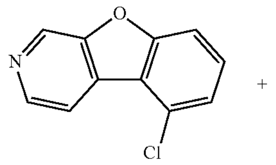

A-d-c

-continued

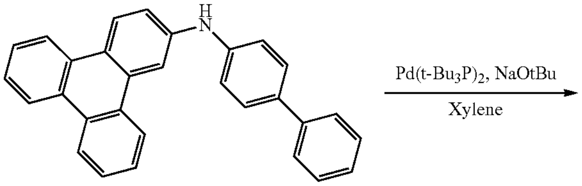

sub 16

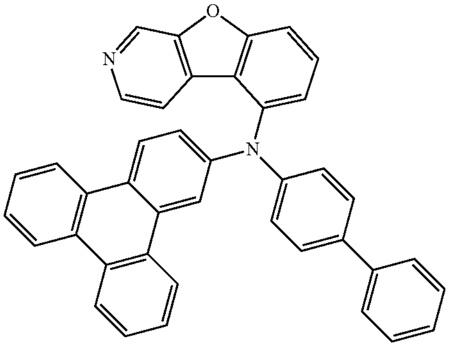

16

Compound A-d-c (15 g, 73.7 mmol) and Compound sub 16 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.2 g of Compound 16. (Yield: 56%, MS: $[M+H]^+=564$)

Synthesis Example 17

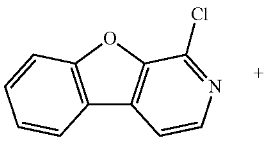

A-a-e

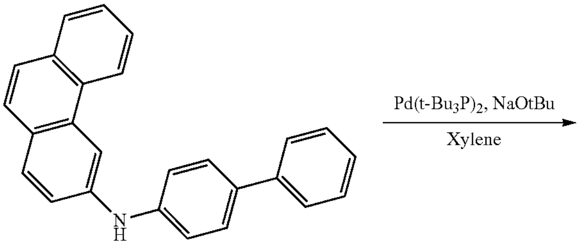

sub 17

-continued

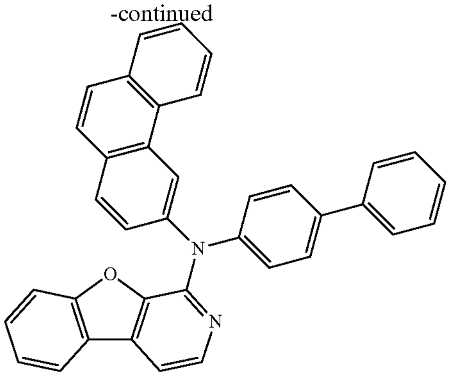

17

Compound A-a-e (15 g, 73.7 mmol) and Compound sub 17 (28 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.7 g of Compound 17. (Yield: 60%, MS: $[M+H]^+=514$)

Synthesis Example 18

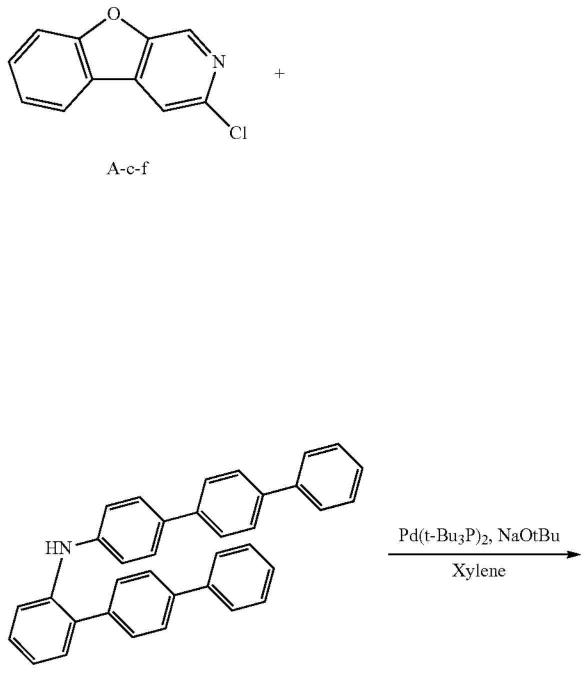

A-c-f

+ sub 18

-continued

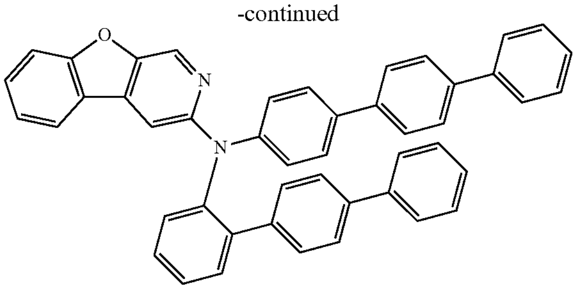

18

Compound A-c-f (15 g, 73.7 mmol) and Compound sub 18 (38.4 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 28.8 g of Compound 18. (Yield: 61%, MS: $[M+H]^+=642$)

Synthesis Example 19

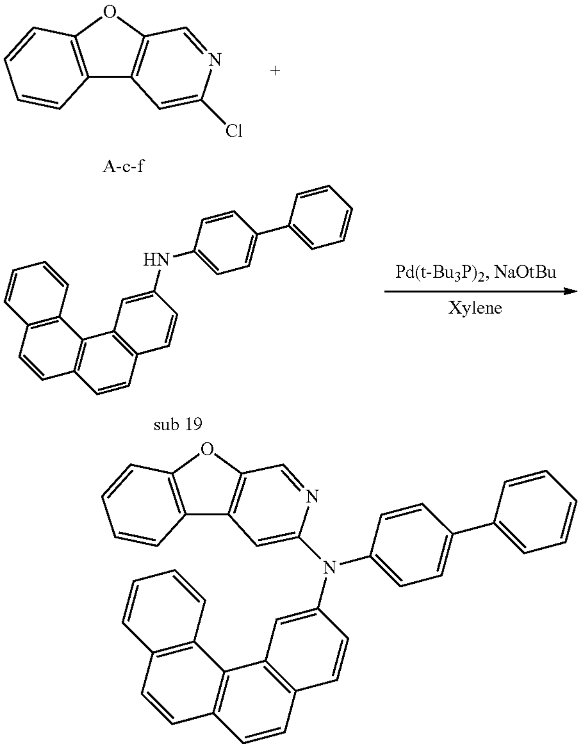

+

A-c-f sub 19

19

Compounds A-c-f (15 g, 73.7 mmol) and Compound sub 19 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22 g of Compound 19. (Yield: 53%, MS: $[M+H]^+$=564)

Synthesis Example 20

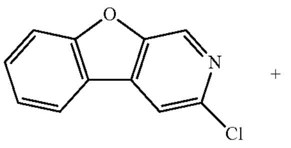

A-c-f

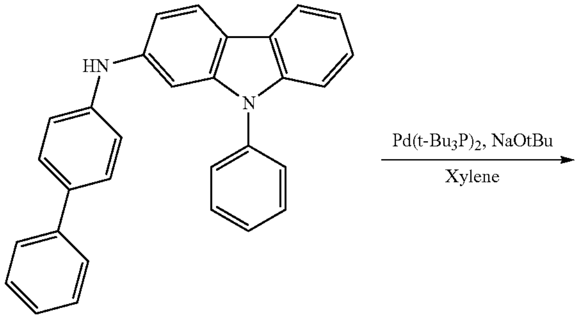

sub 20

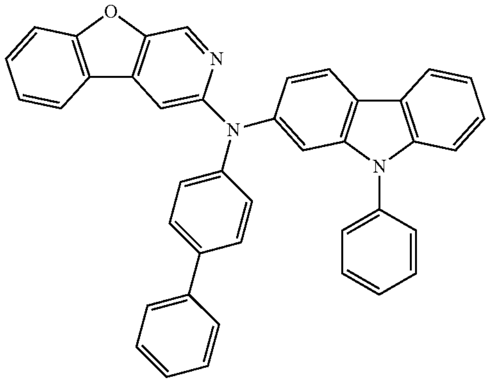

20

Compound A-c-f (15 g, 73.7 mmol) and Compound sub 20 (33.3 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.4 g of Compound 20. (Yield: 41%, MS: $[M+H]^+$=579)

Synthesis Example 21

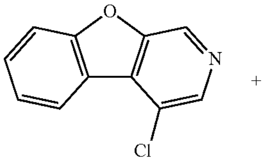

A-d-f

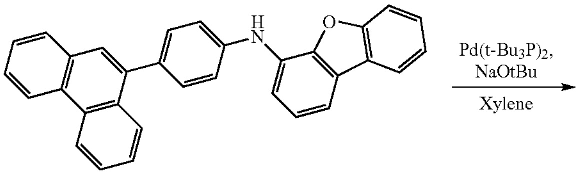

sub 21

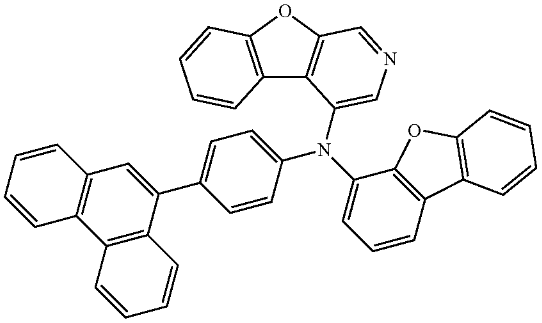

21

Compound A-d-f (15 g, 73.7 mmol) and Compound sub 21 (35.3 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 26.2 g of Compound 21. (Yield: 59%, MS: $[M+H]^+$=604)

Synthesis Example 22

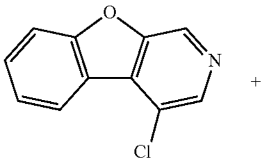

A-d-f

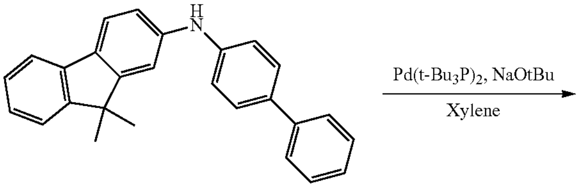

sub 22

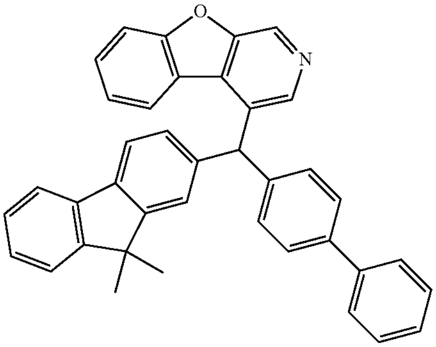

22

Compound A-d-f (15 g, 73.7 mmol) and Compound sub 22 (29.3 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 16.4 g of Compound 22. (Yield: 42%, MS: $[M+H]^+=530$)

Synthesis Example 23

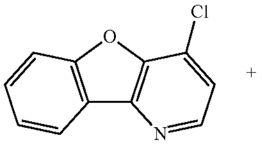

A-a-g

-continued

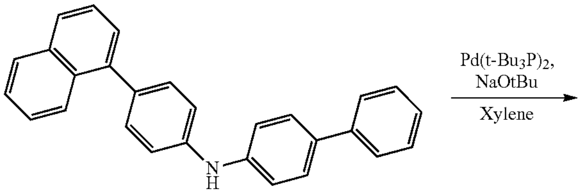

sub 23

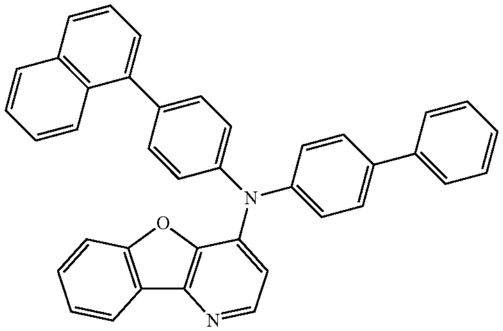

23

Compound A-a-g (15 g, 73.7 mmol) and Compound sub 23 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19 g of Compound 23. (Yield: 48%, MS: $[M+H]^+=540$)

Synthesis Example 24

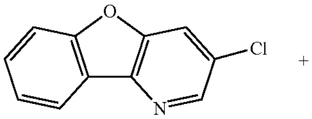

A-b-g

-continued

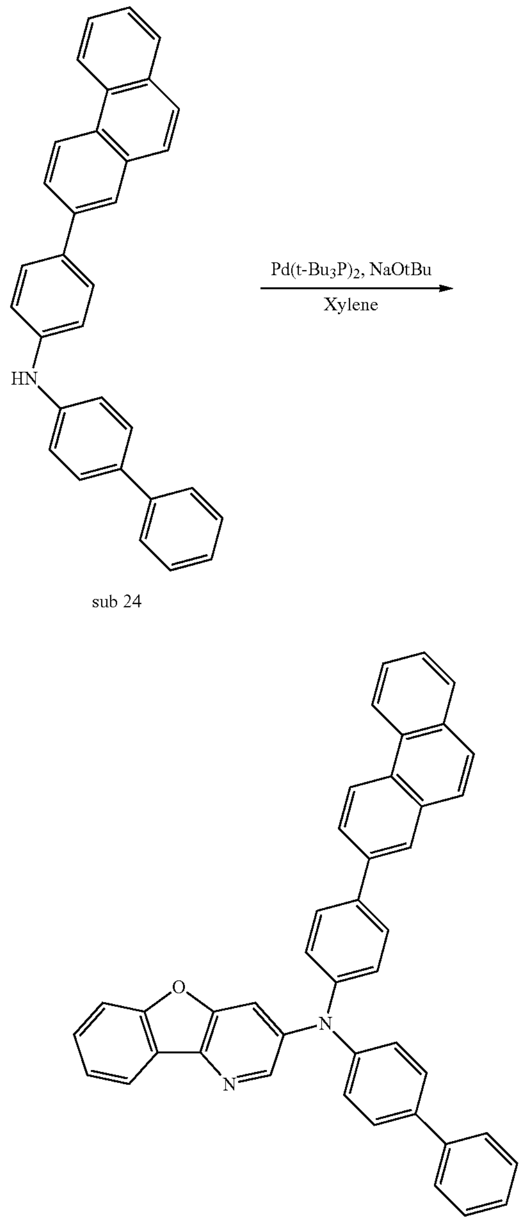

sub 24

24

Synthesis Example 25

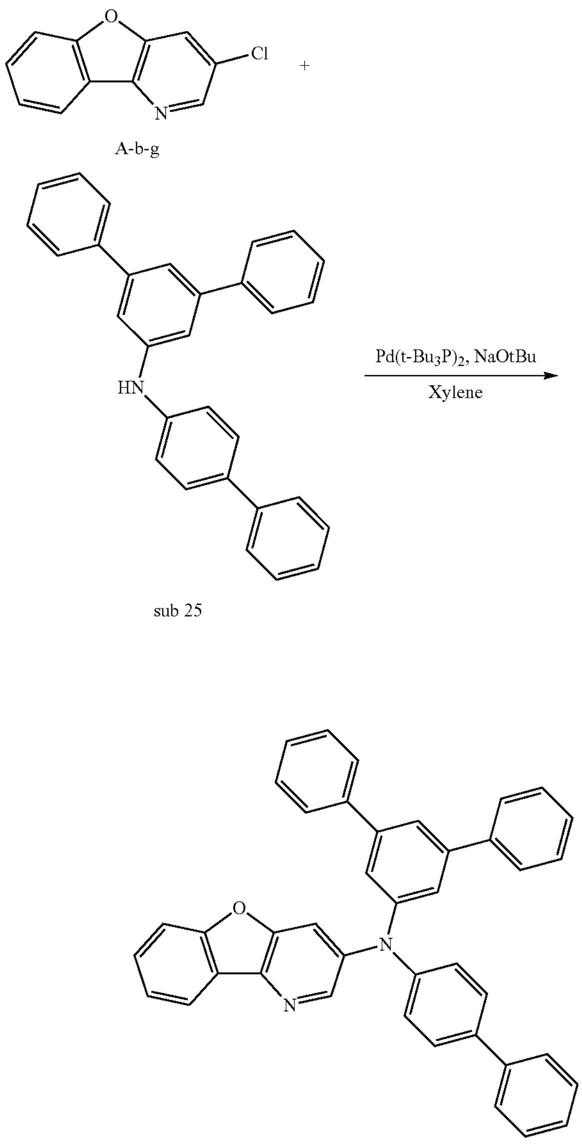

A-b-g sub 25

25

Compounds A-b-g (15 g, 73.7 mmol) and Compound sub 24 (34.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.1 g of Compound 24. (Yield: 44%, MS: $[M+H]^+$=590)

Compound A-b-g (15 g, 73.7 mmol) and Compound sub 25 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.3 g of Compound 25. (Yield: 56%, MS: $[M+H]^+$=566)

Synthesis Example 26

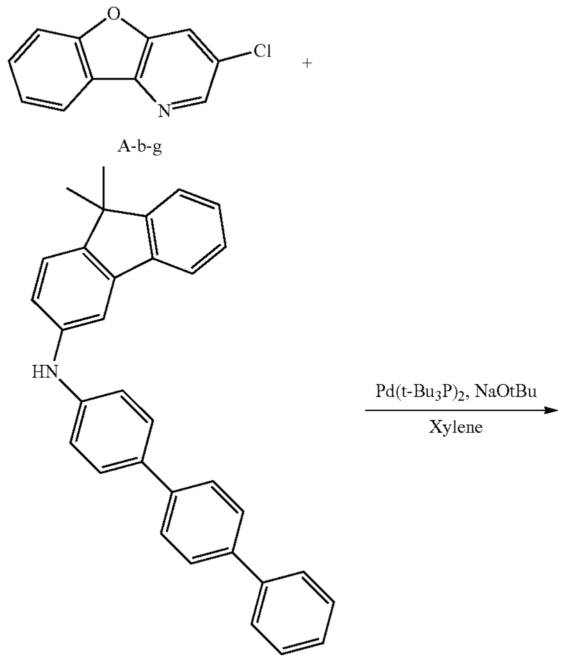

A-b-g sub 26

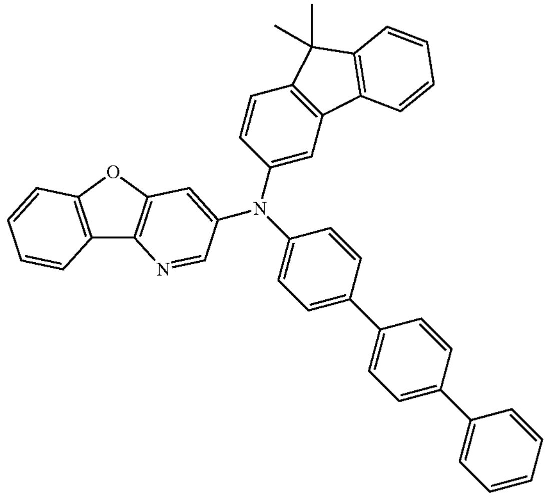

26

Compound A-b-g (15 g, 73.7 mmol) and Compound sub 26 (35.5 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.3 g of Compound 26. (Yield: 50%, MS: $[M+H]^+$=606)

Synthesis Example 27

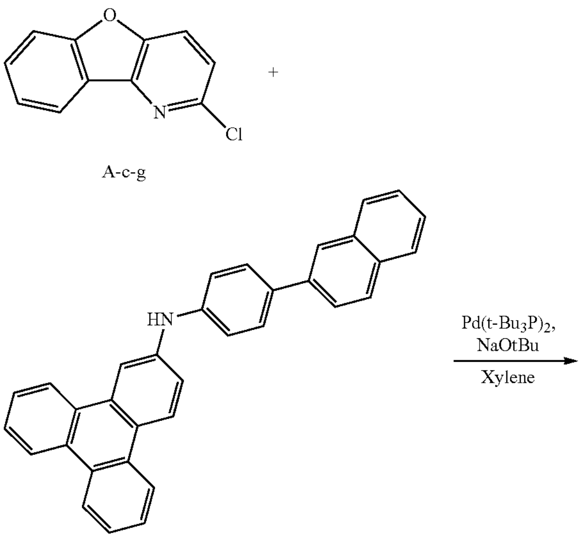

A-c-g sub 27

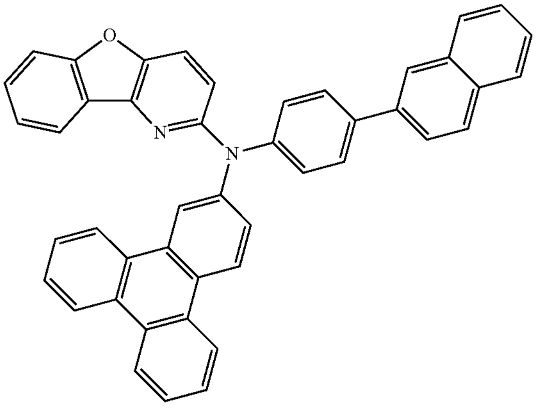

27

Compound A-c-g (15 g, 73.7 mmol) and Compound sub 27 (36.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 24.4 g of Compound 27. (Yield: 54%, MS: $[M+H]^+$=614)

Synthesis Example 28

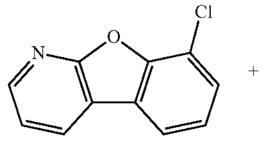

A-a-d

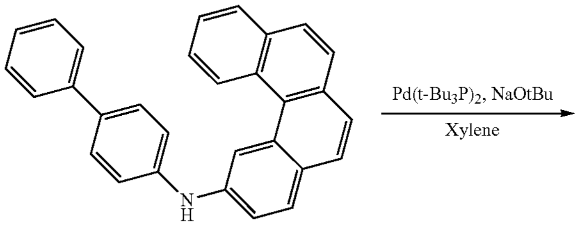

sub 28

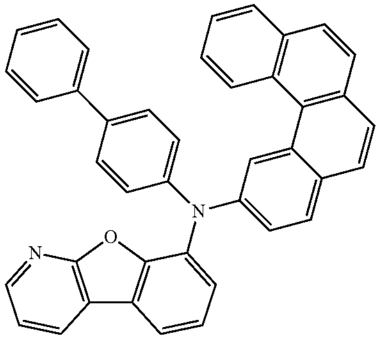

28

Compound A-a-d (15 g, 73.7 mmol) and Compound sub 28 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.9 g of Compound 28. (Yield: 48%, MS: $[M+H]^+$=564)

Synthesis Example 29

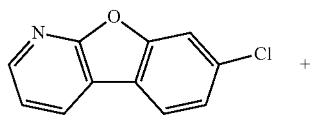

A-b-d

-continued

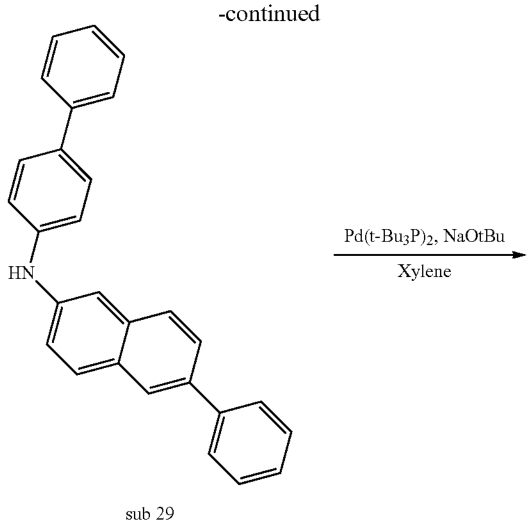

sub 29

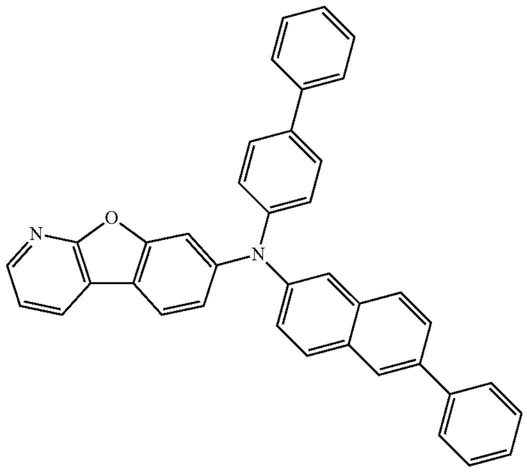

29

Compound A-b-d (15 g, 73.7 mmol) and Compound sub 29 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.4 g of Compound 29. (Yield: 49%, MS: $[M+H]^+$=540)

Synthesis Example 30

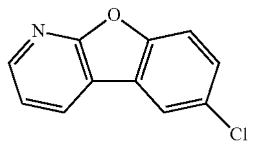

A-c-d

+

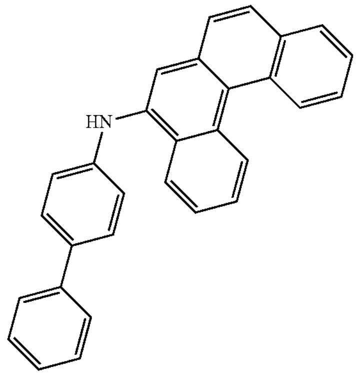

sub 30

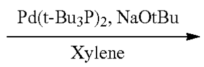

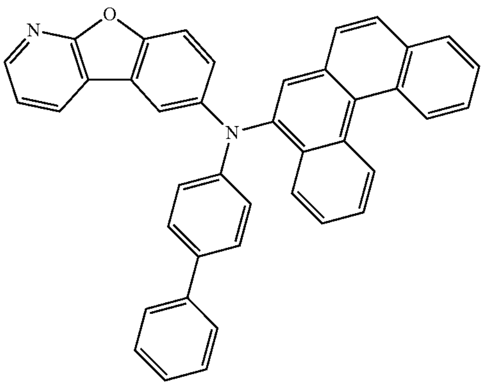

30

Compound A-c-d (15 g, 73.7 mmol) and Compound sub 30 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.2 g of Compound 30. (Yield: 56%, MS: $[M+H]^+=564$)

Synthesis Example 31

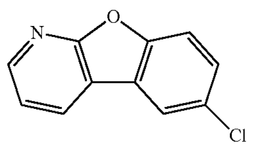

A-c-d

+

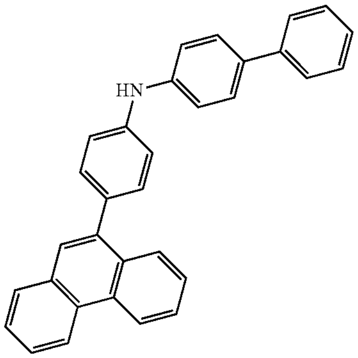

sub 31

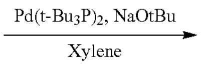

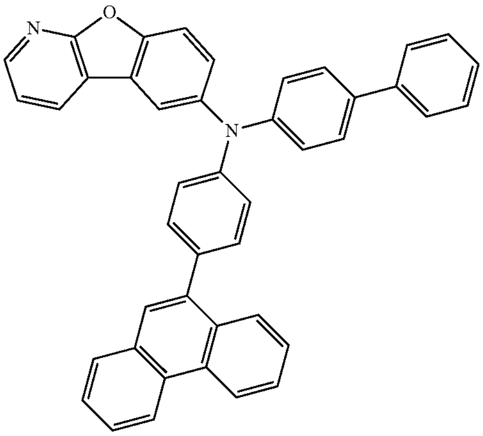

31

Compound A-c-d (15 g, 73.7 mmol) and Compound sub 31 (34.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23 g of Compound 31. (Yield: 53%, MS: $[M+H]^+=590$)

Synthesis Example 32

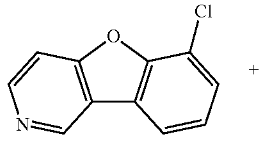

A-a-b

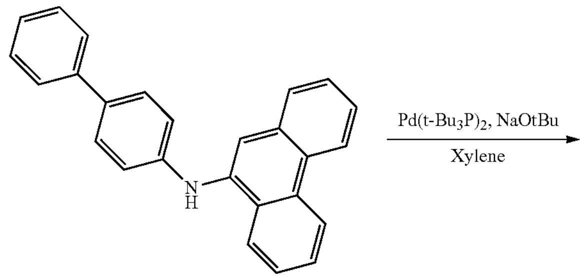

sub 32

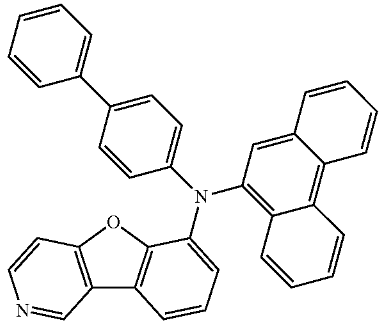

32

Compound A-a-b (15 g, 73.7 mmol) and Compound sub 32 (28 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 15.1 g of Compound 32. (Yield: 40%, MS: $[M+H]^+=514$)

Synthesis Example 33

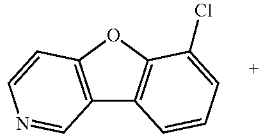

A-a-b

-continued

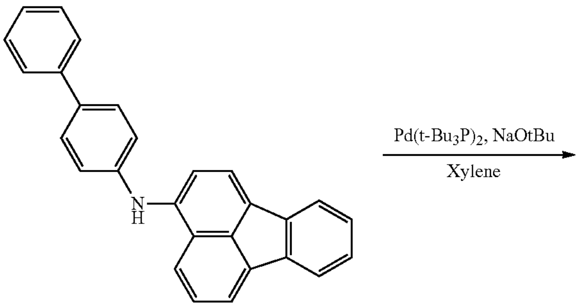

sub 33

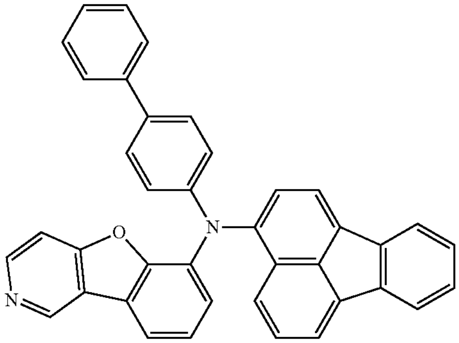

33

Compound A-a-b (15 g, 73.7 mmol) and Compound sub 33 (29.9 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21.7 g of Compound 33. (Yield: 55%, MS: $[M+H]^+=538$)

Synthesis Example 34

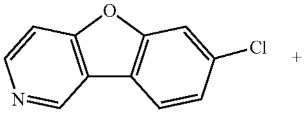

A-b-b

-continued

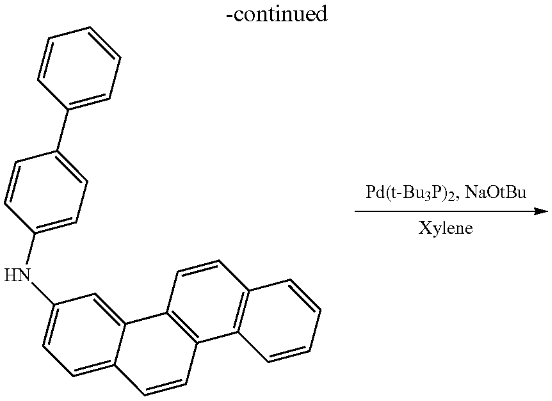

sub 34

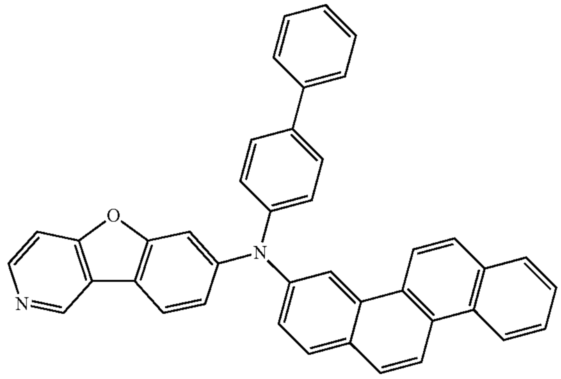

34

Compound A-b-b (15 g, 73.7 mmol) and Compound sub 34 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 28.6 g of Compound 34. (Yield: 69%, MS: $[M+H]^+=564$)

Synthesis Example 35

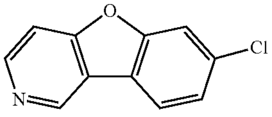

+

A-b-b

-continued

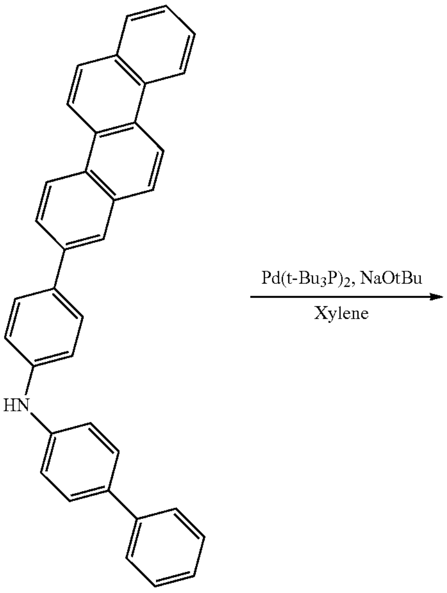

sub 35

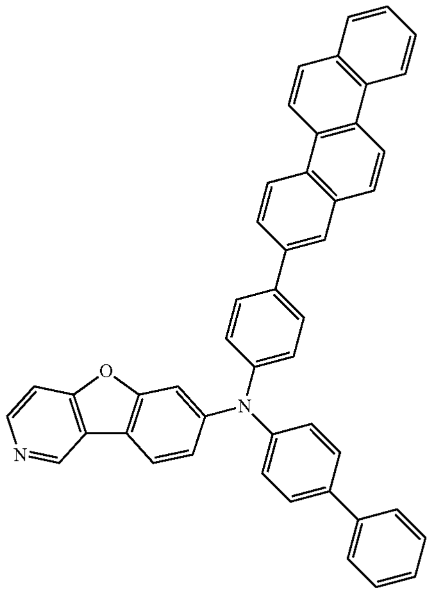

35

Compound A-b-b (15 g, 73.7 mmol) and Compound sub 35 (38.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 29.6 g of Compound 35. (Yield: 63%, MS: $[M+H]^+=640$)

Synthesis Example 36

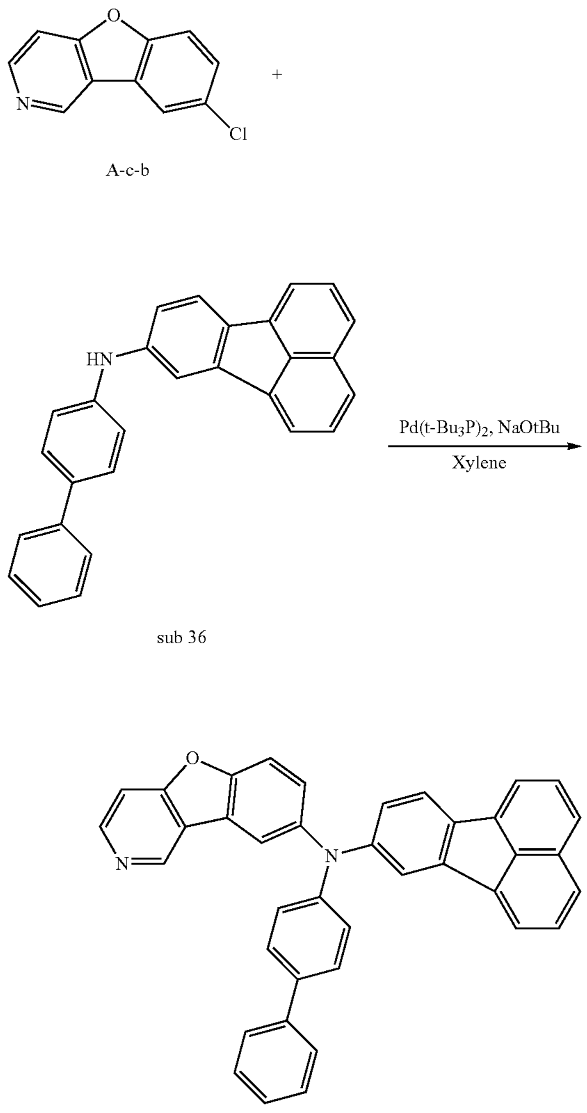

A-c-b sub 36

36

Compounds A-c-b (15 g, 73.7 mmol) and Compound sub 36 (29.9 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 16.2 g of Compound 36. (Yield: 41%, MS: $[M+H]^+=538$)

Synthesis Example 37

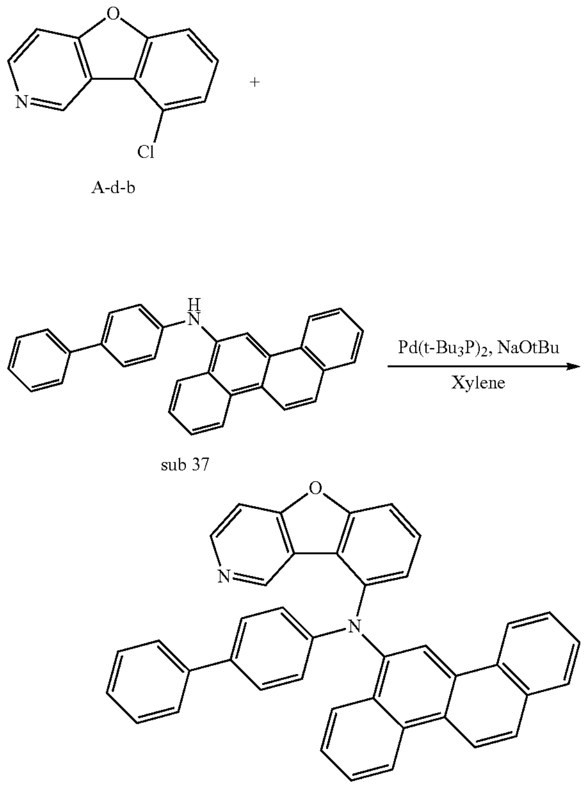

A-d-b sub 37

37

Compound A-d-b (15 g, 73.7 mmol) and Compound sub 37 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.2 g of Compound 37. (Yield: 56%, MS: $[M+H]^+=564$)

Synthesis Example 38

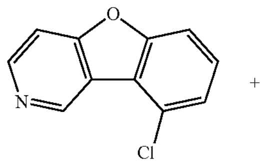

A-d-b

-continued

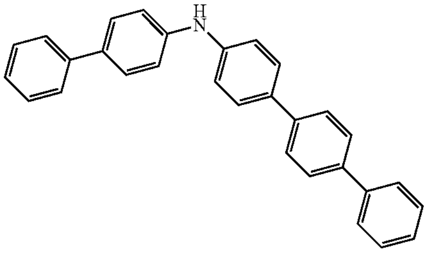

sub 38

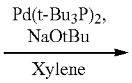

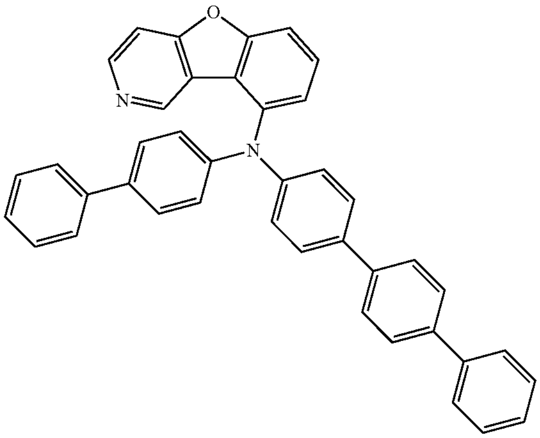

38

-continued

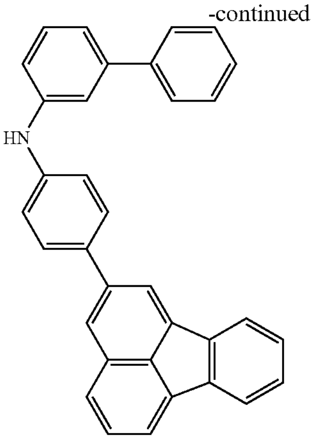

sub 39

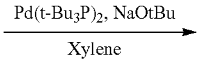

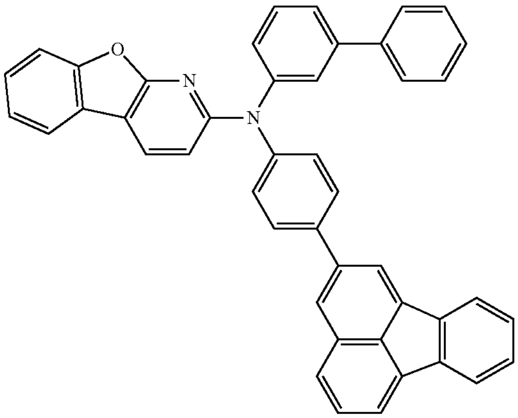

39

Compound A-d-b (15 g, 73.7 mmol) and Compound sub 38 (32.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 16.6 g of Compound 38. (Yield: 40%, MS: $[M+H]^+=566$)

Synthesis Example 39

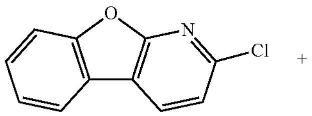

A-b-e

Compound A-b-e (15 g, 73.7 mmol) and Compound sub 39 (36.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 27.1 g of Compound 39. (Yield: 60%, MS: $[M+H]^+=614$)

Synthesis Example 40

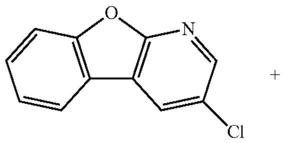

A-c-e

-continued

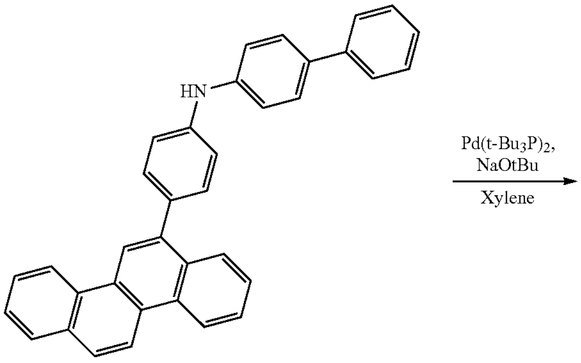

sub 40

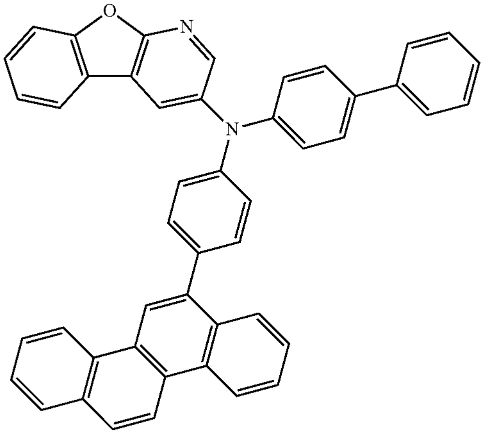

40

Compound A-c-e (15 g, 73.7 mmol) and Compound sub 40 (38.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 24 g of Compound 40. (Yield: 51%, MS: $[M+H]^+=640$)

Synthesis Example 41

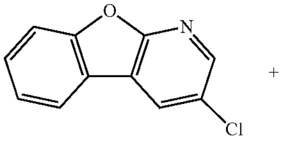

A-c-e

-continued

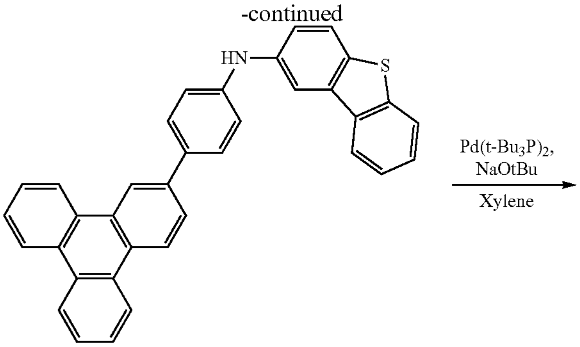

sub 41

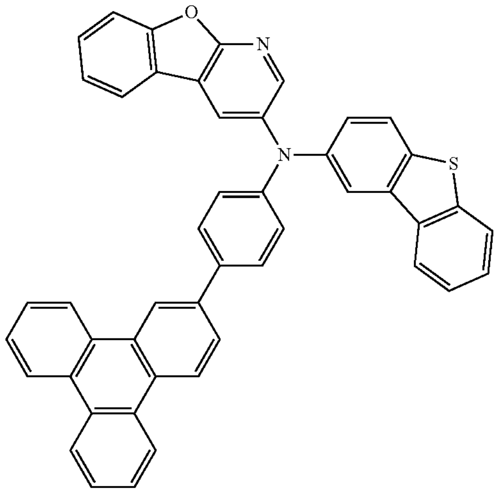

41

Compound A-c-e (15 g, 73.7 mmol) and Compound sub 41 (40.6 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.7 g of Compound 41. (Yield: 46%, MS: $[M+H]^+=670$)

Synthesis Example 42

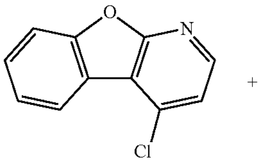

A-d-e

-continued

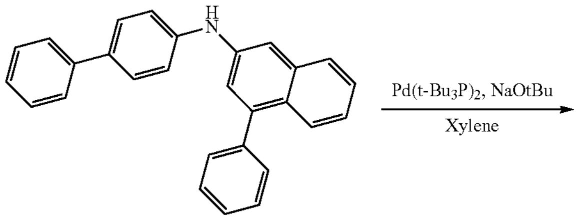

sub 42

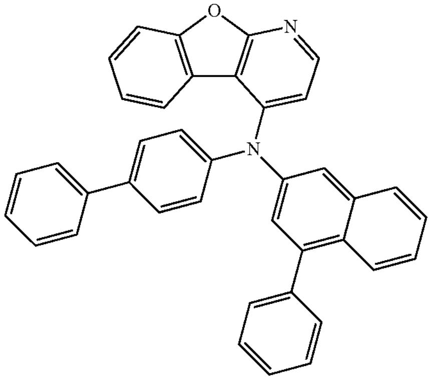

42

Compound A-d-e (15 g, 73.7 mmol) and Compound sub 42 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.5 g of Compound 42. (Yield: 49%, MS: $[M+H]^+=541$)

Synthesis Example 43

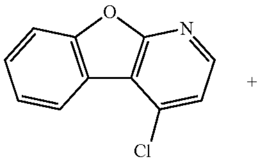

A-d-e

-continued

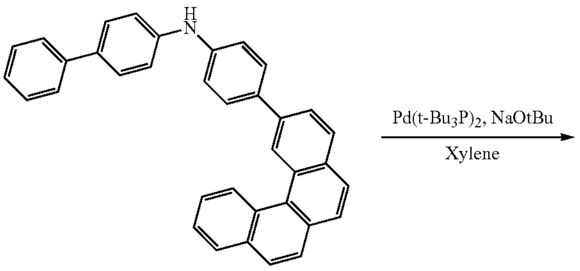

sub 43

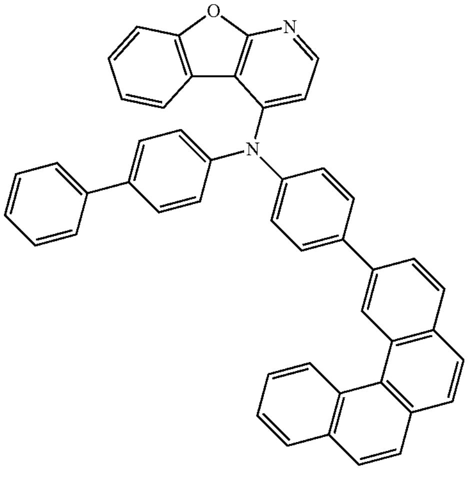

43

Compound A-d-e (15 g, 73.7 mmol) and Compound sub 43 (38.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21.6 g of Compound 43. (Yield: 46%, MS: $[M+H]^+=640$)

Synthesis Example 44

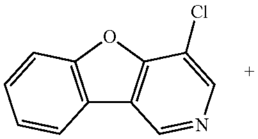

A-a-f

-continued

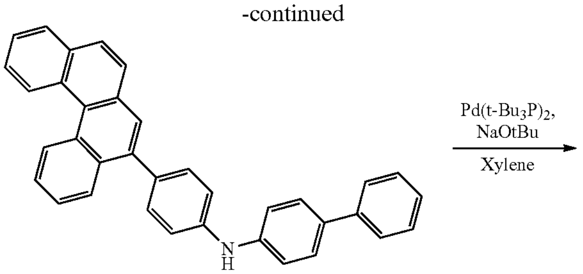

sub 44

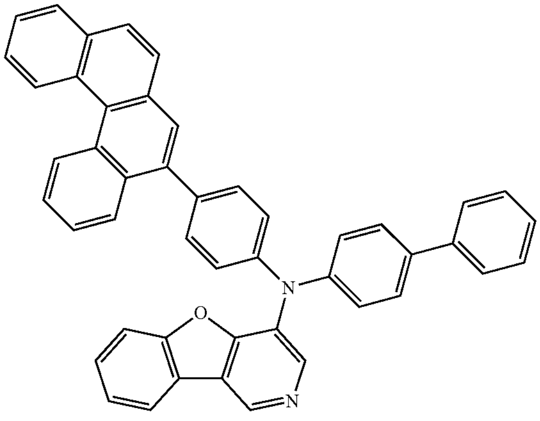

44

Compound A-a-f (15 g, 73.7 mmol) and Compound sub 44 (38.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.2 g of Compound 44. (Yield: 43%, MS: $[M+H]^+=640$)

Synthesis Example 45

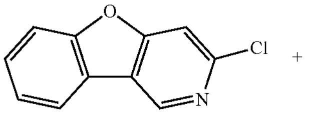

A-b-f

-continued

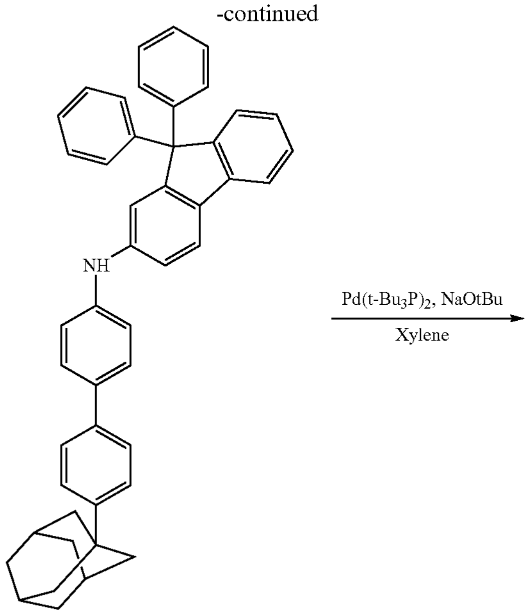

sub 45

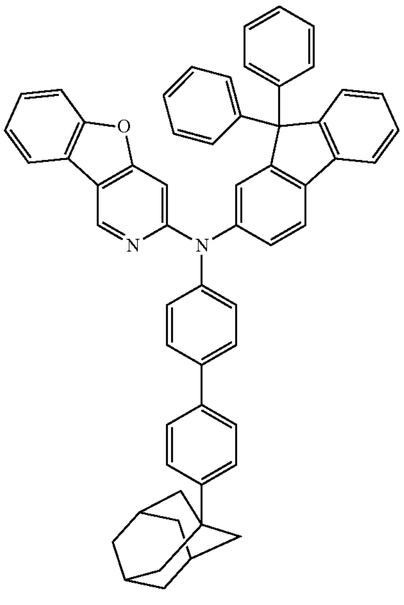

45

Compound A-b-f (15 g, 73.7 mmol) and Compound sub 45 (50.2 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 34.8 g of Compound 45. (Yield: 60%, MS: $[M+H]^+=788$)

Synthesis Example 46

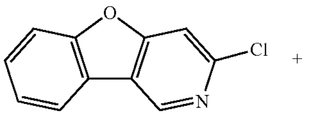

A-b-f

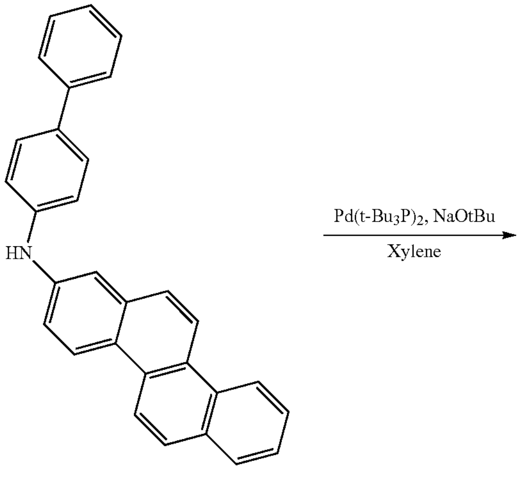

sub 46

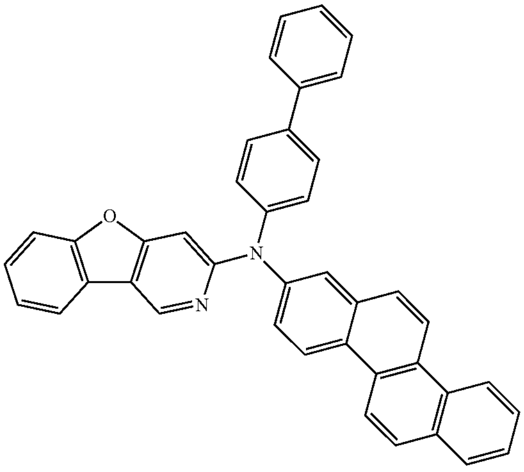

46

Compound A-b-f (15 g, 73.7 mmol) and Compound sub 46 (32 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.3 g of Compound 46. (Yield: 49%, MS: $[M+H]^+=564$)

Synthesis Example 47

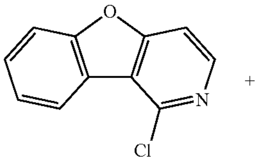

A-d-g

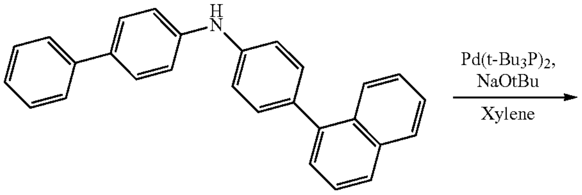

sub 47

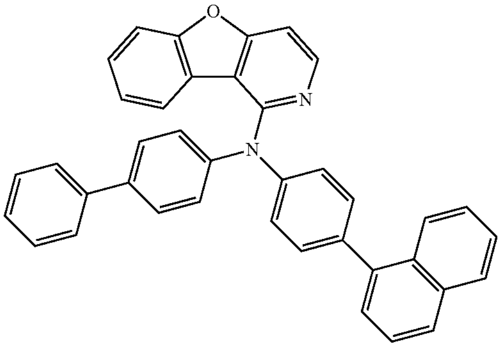

47

Compound A-d-g (15 g, 73.7 mmol) and Compound sub 47 (30.1 g, 81 mmol) were added to 300 ml of xylene under a nitrogen atmosphere, and the mixture was stirred and refluxed. Then, sodium tert-butoxide (10.6 g, 110.5 mmol) and bis(tri-tert-butylphosphine)palladium(0) (1.1 g, 2.2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 26.6 g of Compound 47. (Yield: 67%, MS: $[M+H]^+=540$)

Synthesis Example 48

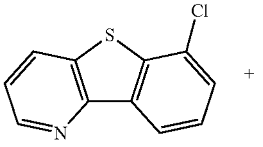

B-a-a

-continued

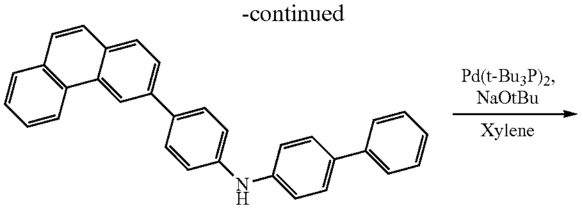

sub 48

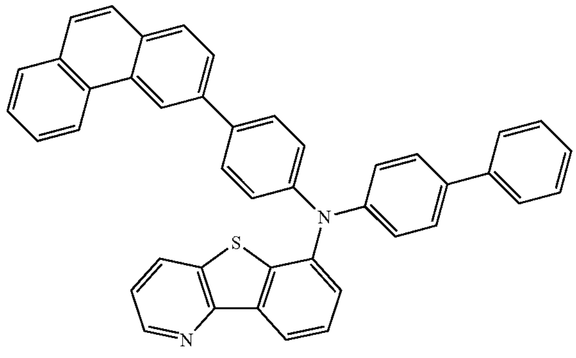

48

Compound B-a-a (15 g, 68.3 mmol) and Compound sub 48 (31.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.1 g of Compound 48. (Yield: 56%, MS: $[M+H]^+=606$)

Synthesis Example 49

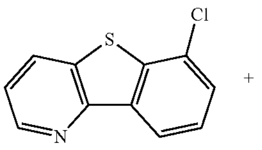

B-a-a

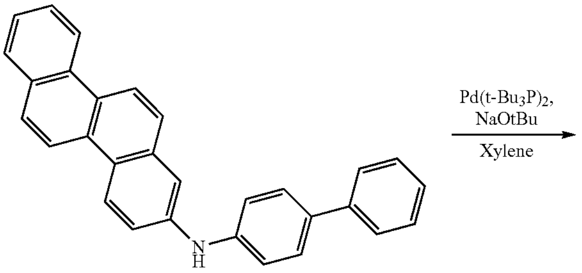

sub 49

-continued

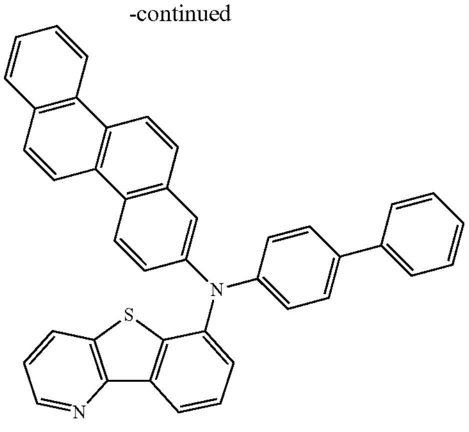

49

Compound B-a-a (15 g, 68.3 mmol) and Compound sub 49 (29.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.8 g of Compound 49. (Yield: 45%, MS: $[M+H]^+=580$)

Synthesis Example 50

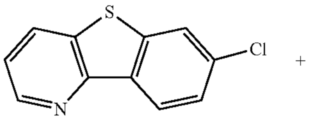

B-b-a

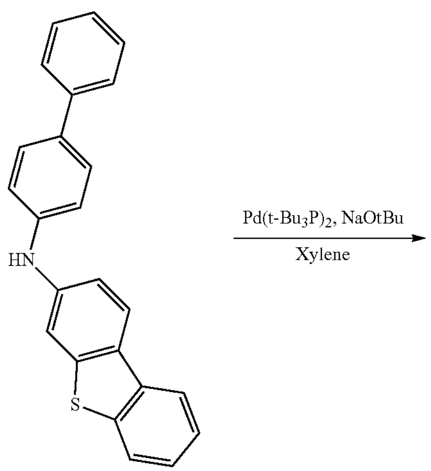

sub 50

-continued

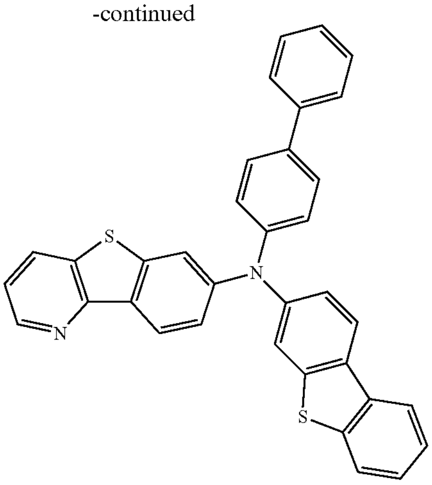

50

-continued

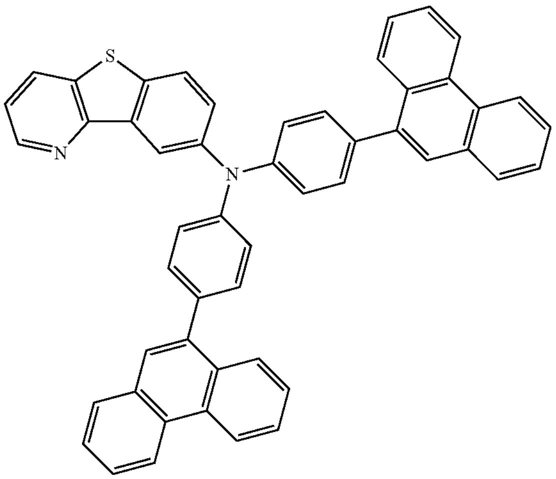

51

Compound B-b-a (15 g, 68.3 mmol) and Compound sub 50 (26.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 24.5 g of Compound 50. (Yield: 67%, MS: $[M+H]^+=536$)

Synthesis Example 51

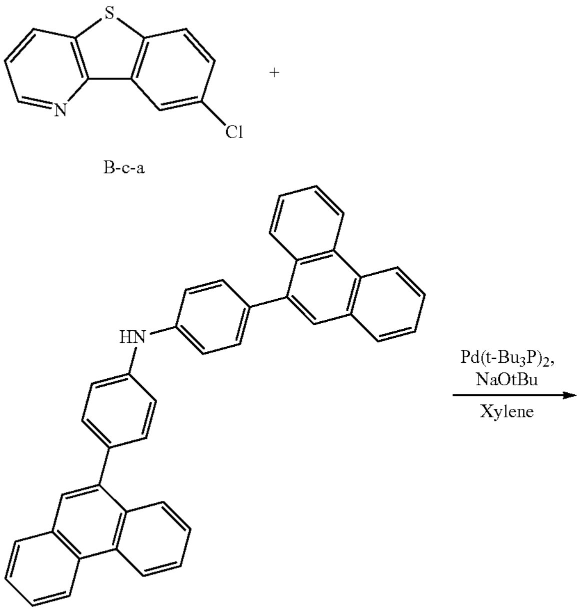

B-c-a sub 51

Compound B-c-a (15 g, 68.3 mmol) and Compound sub 51 (39.2 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 33.2 g of Compound 51. (Yield: 69%, MS: $[M+H]^+=706$)

Synthesis Example 52

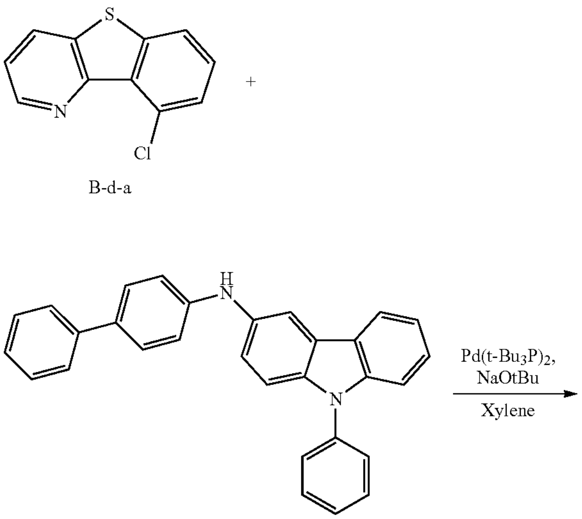

B-d-a sub 52

-continued

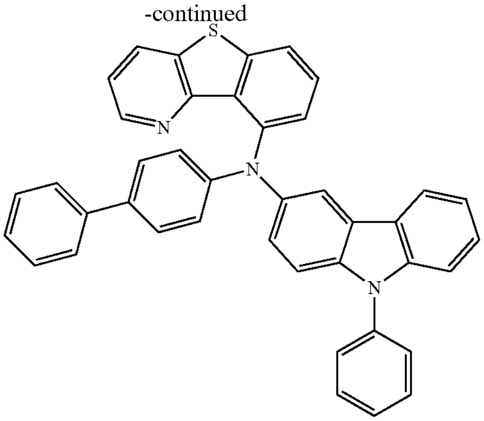

52

Compound B-d-a (15 g, 68.3 mmol) and Compound sub 52 (30.8 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 26.8 g of Compound 52. (Yield: 66%, MS: $[M+H]^+=595$)

Synthesis Example 53

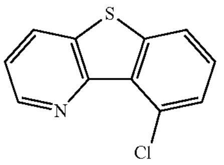

B-d-a

+

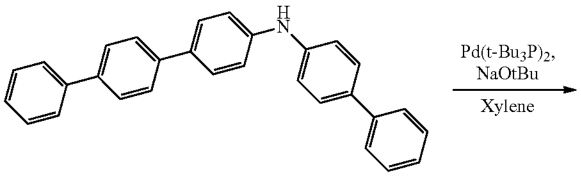

sub 53

-continued

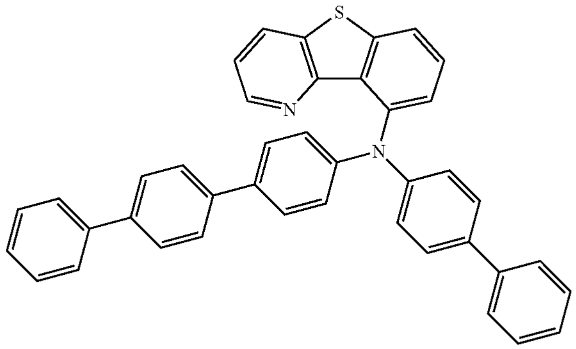

53

Compound B-d-a (15 g, 68.3 mmol) and Compound sub 53 (29.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23 g of Compound 53. (Yield: 58%, MS: $[M+H]^+=582$)

Synthesis Example 54

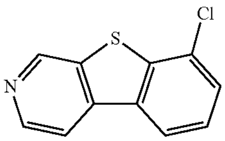

B-a-c

+

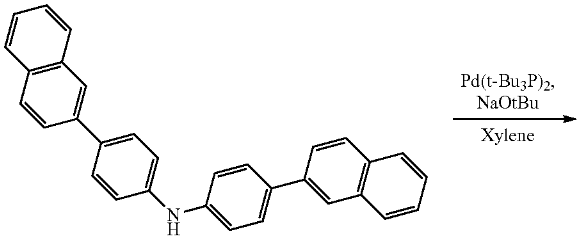

sub 54

-continued

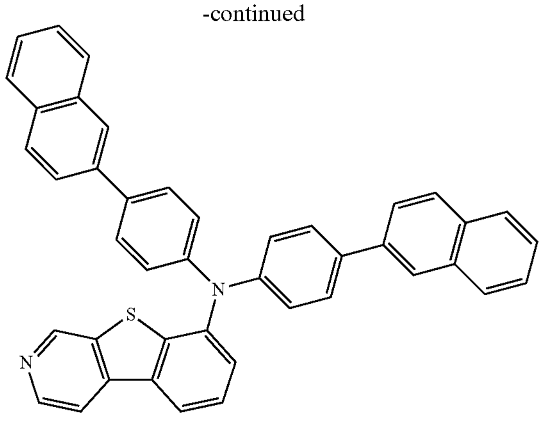

54

Compound B-a-c (15 g, 68.3 mmol) and Compound sub 54 (31.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 28.9 g of Compound 54. (Yield: 70%, MS: $[M+H]^+=606$)

Synthesis Example 55

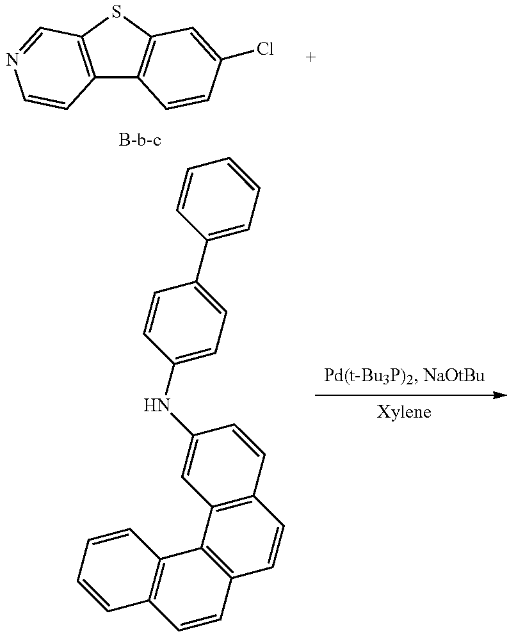

B-b-c sub 55

-continued

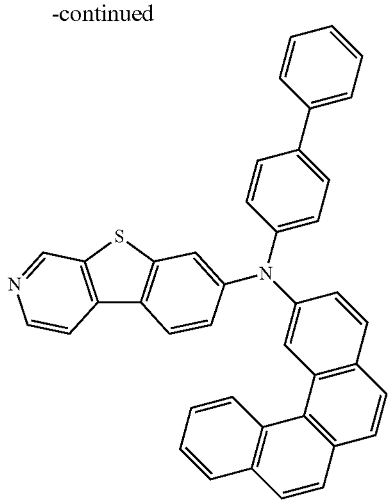

55

Compound B-b-c (15 g, 68.3 mmol) and Compound sub 55 (29.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.9 g of Compound 55. (Yield: 58%, MS: $[M+H]^+=580$)

Synthesis Example 56

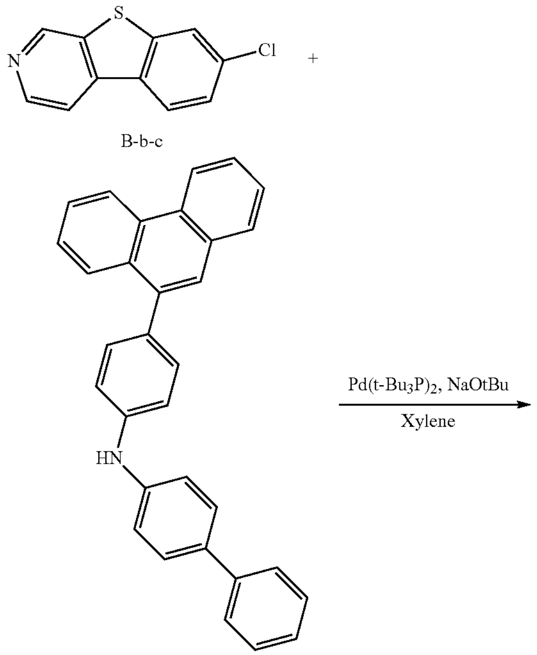

B-b-c sub 56

-continued

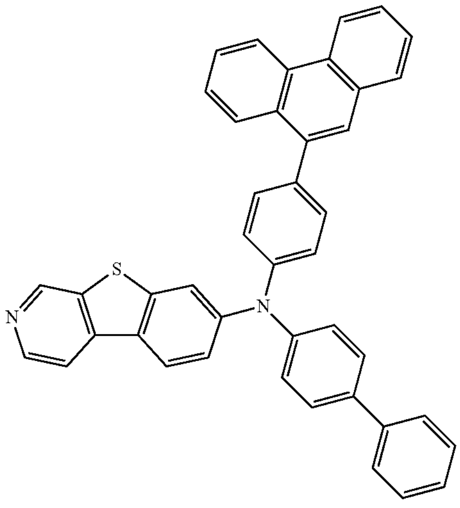

56

Compound B-b-c (15 g, 68.3 mmol) and Compound sub 56 (31.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 26.8 g of Compound 56. (Yield: 65%, MS: $[M+H]^+=606$)

Synthesis Example 57

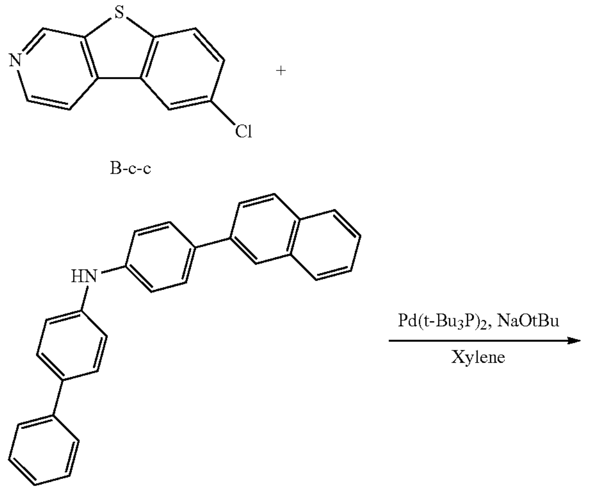

B-c-c sub 57

-continued

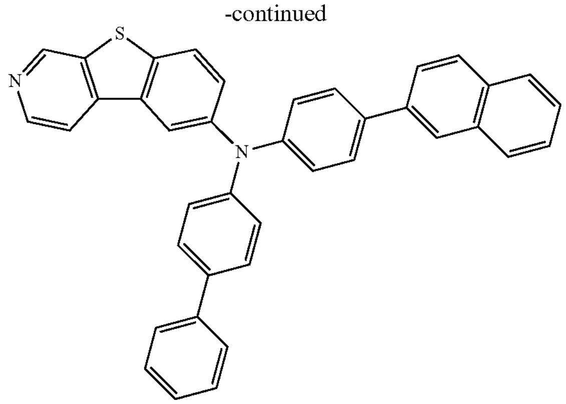

57

Compound B-c-c (15 g, 68.3 mmol) and Compound sub 57 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.3 g of Compound 57. (Yield: 51%, MS: $[M+H]^+=556$)

Synthesis Example 58

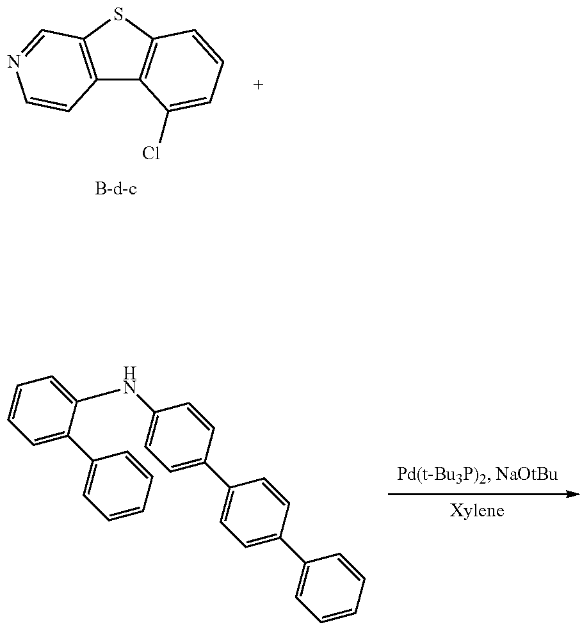

B-d-c sub 58

-continued

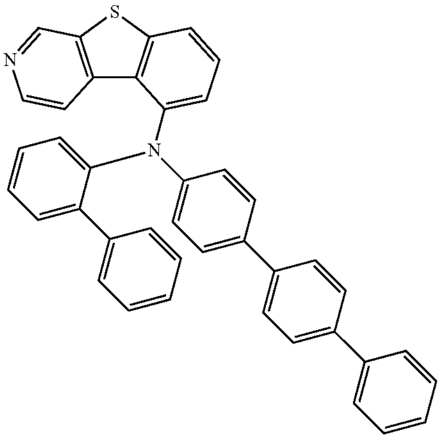

58

Compound B-d-c (15 g, 68.3 mmol) and Compound sub 58 (29.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.2 g of Compound 58. (Yield: 51%, MS: $[M+H]^+=582$)

Synthesis Example 59

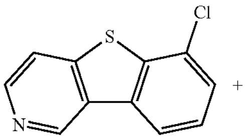

B-a-b

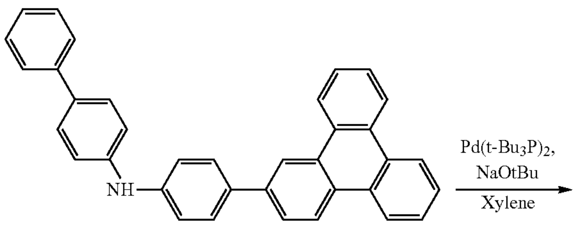

sub59

-continued

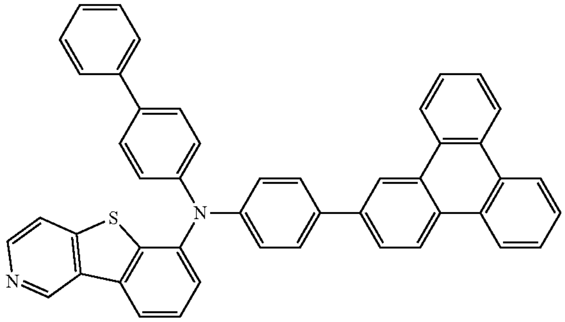

59

Compound B-a-b (15 g, 68.3 mmol) and Compound sub 59 (35.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.7 g of Compound 59. (Yield: 53%, MS: $[M+H]^+=656$)

Synthesis Example 60

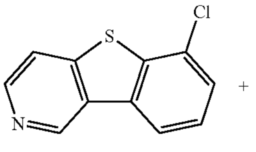

B-a-b

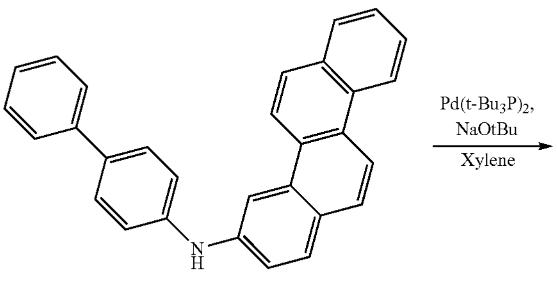

sub 60

-continued

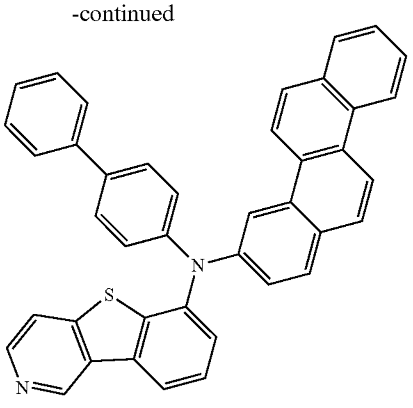

60

Compound B-a-b (15 g, 68.3 mmol) and Compound sub 60 (29.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.5 g of Compound 60. (Yield: 57%, MS: $[M+H]^+=580$)

Synthesis Example 61

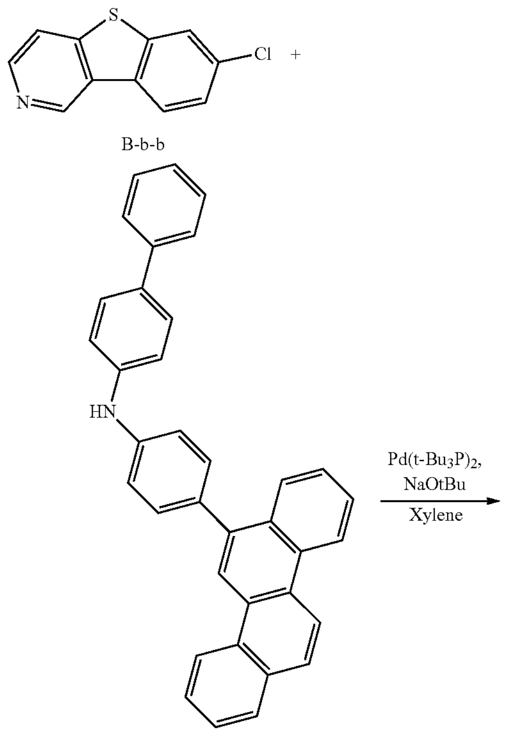

B-b-b sub 61

-continued

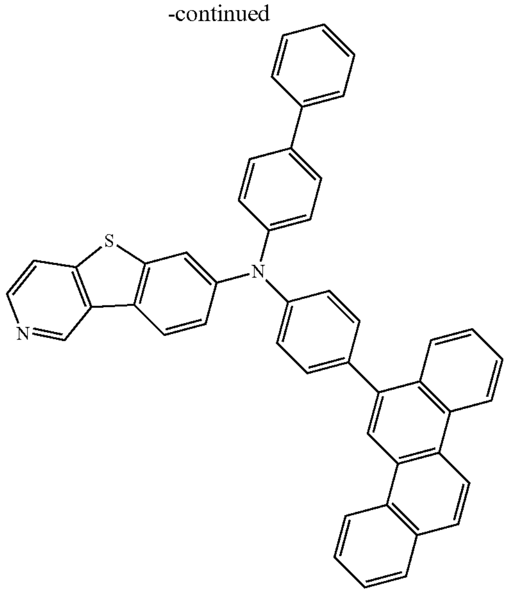

61

Compound B-b-b (15 g, 68.3 mmol) and Compound sub 61 (35.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After the reaction for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.4 g of Compound 61. (Yield: 50%, MS: $[M+H]^+=656$)

Synthesis Example 62

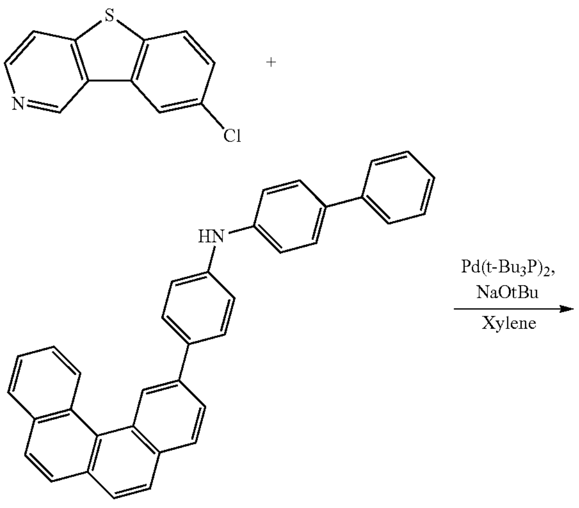

sub 62

-continued

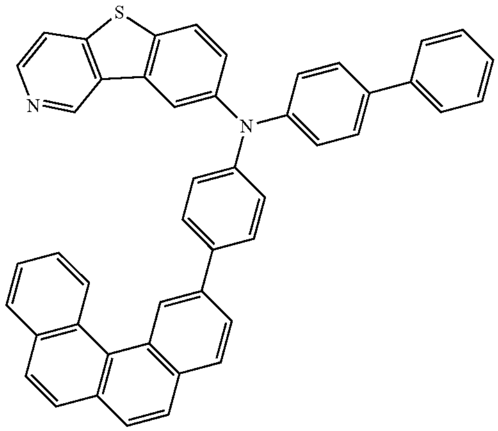

62

Compound B-c-b (15 g, 68.3 mmol) and Compound sub 62 (35.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 26.4 g of Compound 62. (Yield: 59%, MS: $[M+H]^+=656$)

Synthesis Example 63

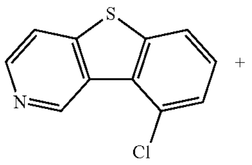

B-d-b

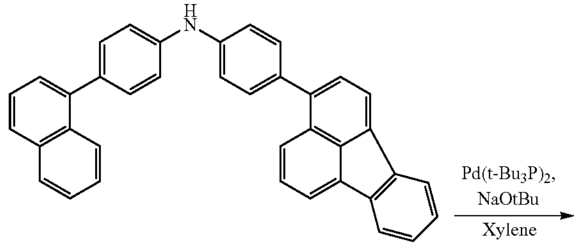

sub 63

-continued

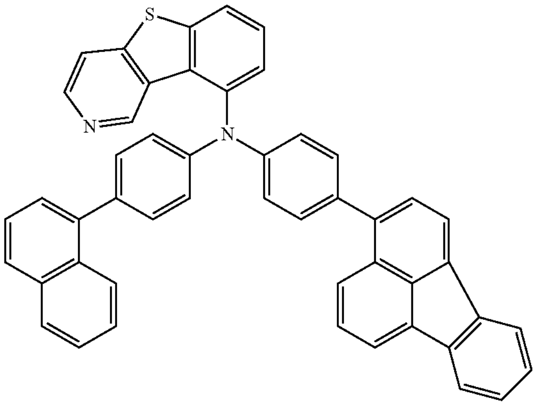

63

Compound B-d-b (15 g, 68.3 mmol) and Compound sub 63 (37.2 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 27.8 g of Compound 63. (Yield: 60%, MS: $[M+H]^+=680$)

Synthesis Example 64

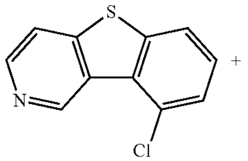

B-d-b

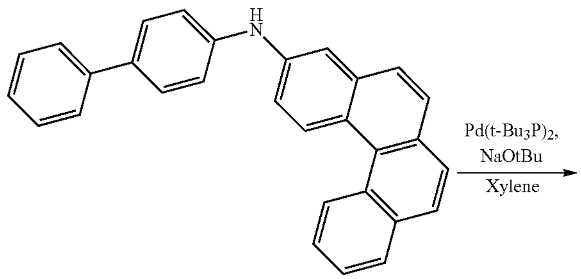

sub 64

-continued

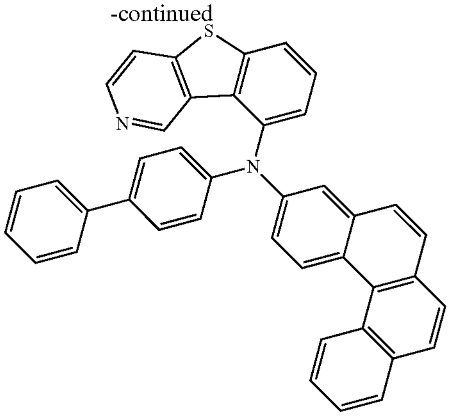

64

Compound B-d-b (15 g, 68.3 mmol) and Compound sub 64 (29.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 15.8 g of Compound 64. (Yield: 40%, MS: $[M+H]^+=580$)

Synthesis Example 65

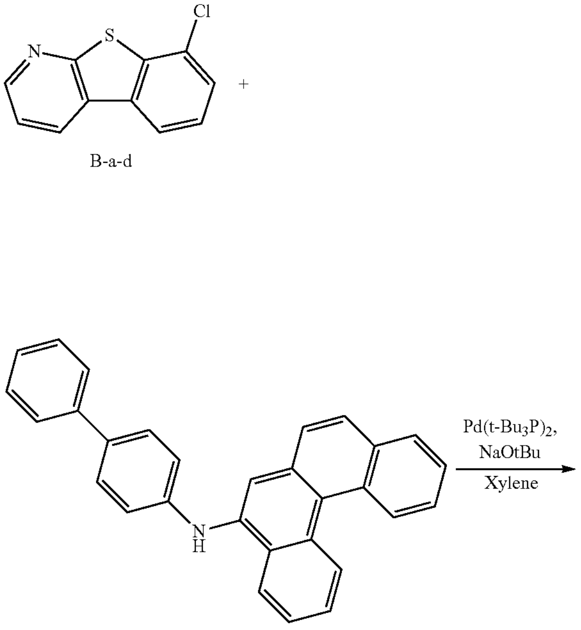

B-a-d sub 65

-continued

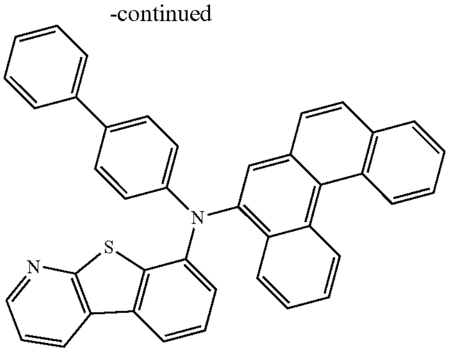

65

Compound B-a-d (15 g, 68.3 mmol) and Compound sub 65 (29.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 19.8 g of Compound 65. (Yield: 50%, MS: $[M+H]^+=580$)

Synthesis Example 66

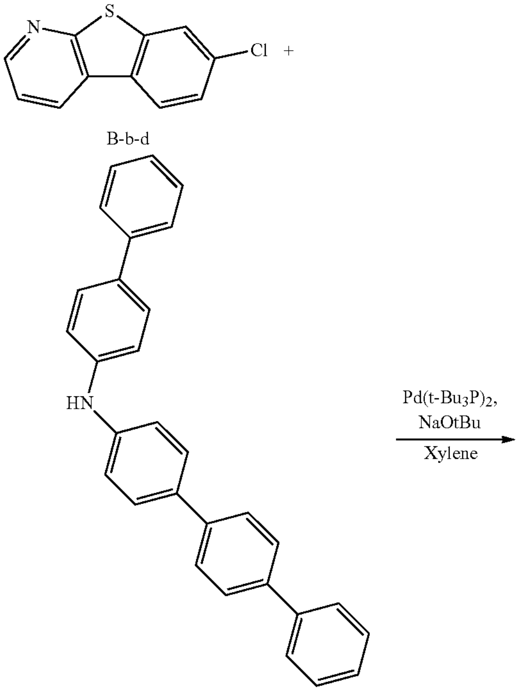

B-b-d sub 66

-continued

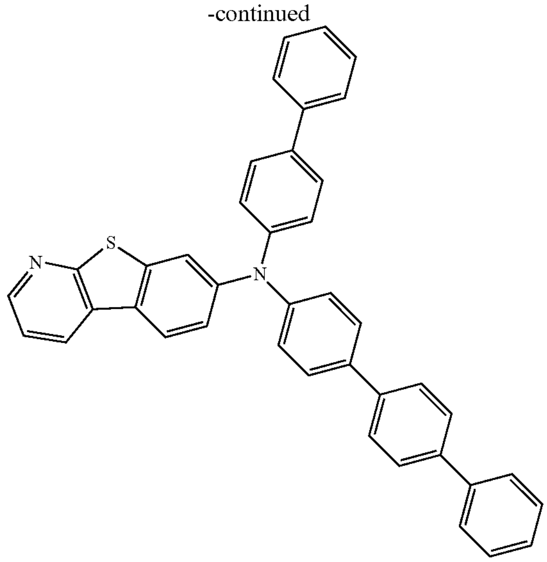

66

Compound B-b-d (15 g, 68.3 mmol) and Compound sub 66 (29.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21 g of Compound 66. (Yield: 53%, MS: $[M+H]^+$=582)

Synthesis Example 67

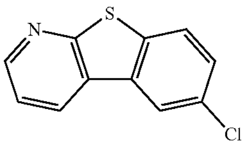

+

B-c-d

-continued

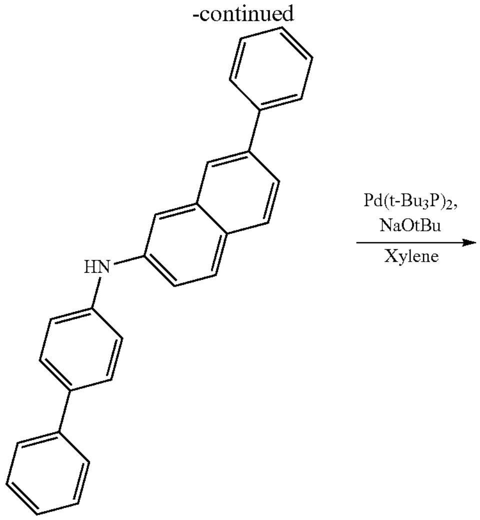

sub 67

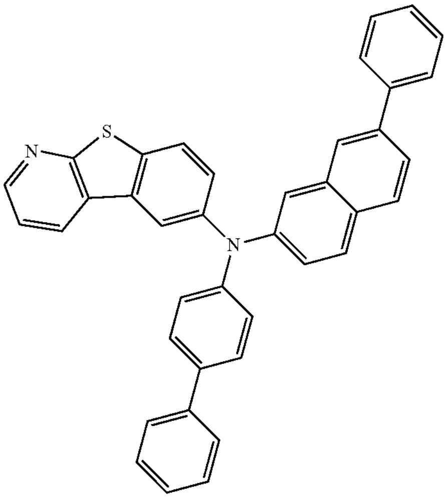

67

Compound B-c-d (15 g, 68.3 mmol) and Compound sub 67 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.5 g of Compound 67. (Yield: 62%, MS: $[M+H]^+$=556)

Synthesis Example 68

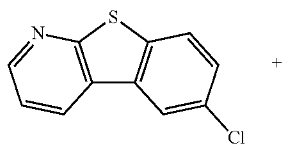

B-c-d

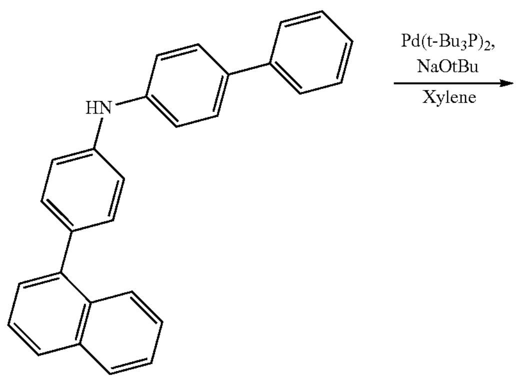

sub 68

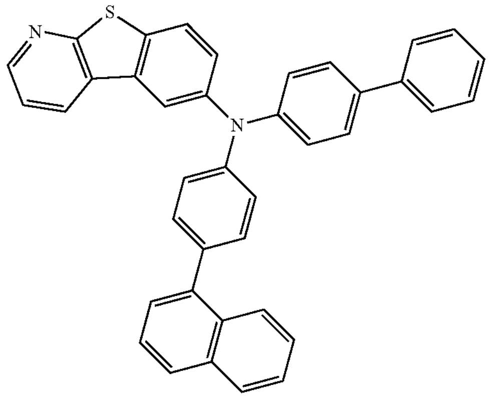

68

Compound B-c-d (15 g, 68.3 mmol) and Compound sub 68 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21.6 g of Compound 68. (Yield: 57%, MS: $[M+H]^+=556$)

Synthesis Example 69

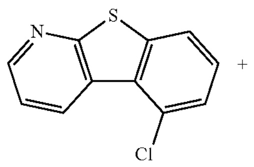

B-d-d

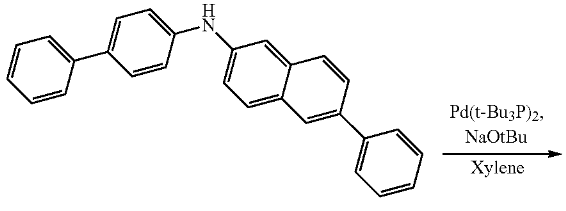

sub 69

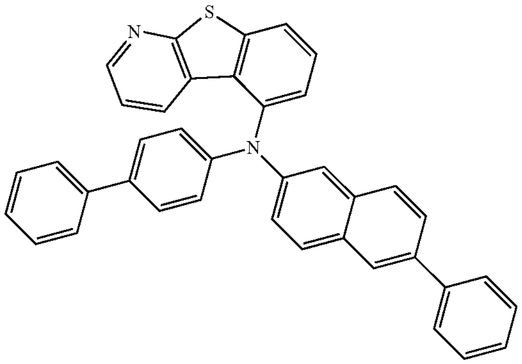

69

Compound B-d-d (15 g, 68.3 mmol) and Compound sub 69 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.5 g of Compound 69. (Yield: 54%, MS: $[M+H]^+=556$)

Synthesis Example 70

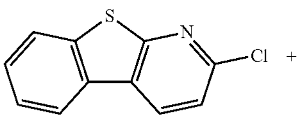

B-b-e

-continued

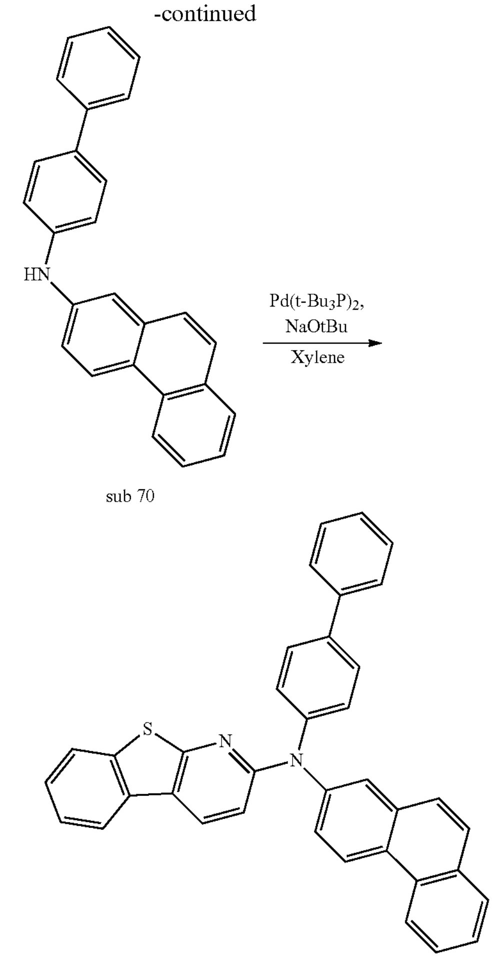

sub 70

70

Compound B-b-e (15 g, 68.3 mmol) and Compound sub 70 (25.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 16.2 g of Compound 70. (Yield: 45%, MS: $[M+H]^+=530$)

Synthesis Example 71

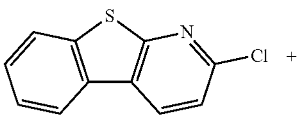

B-b-e

-continued

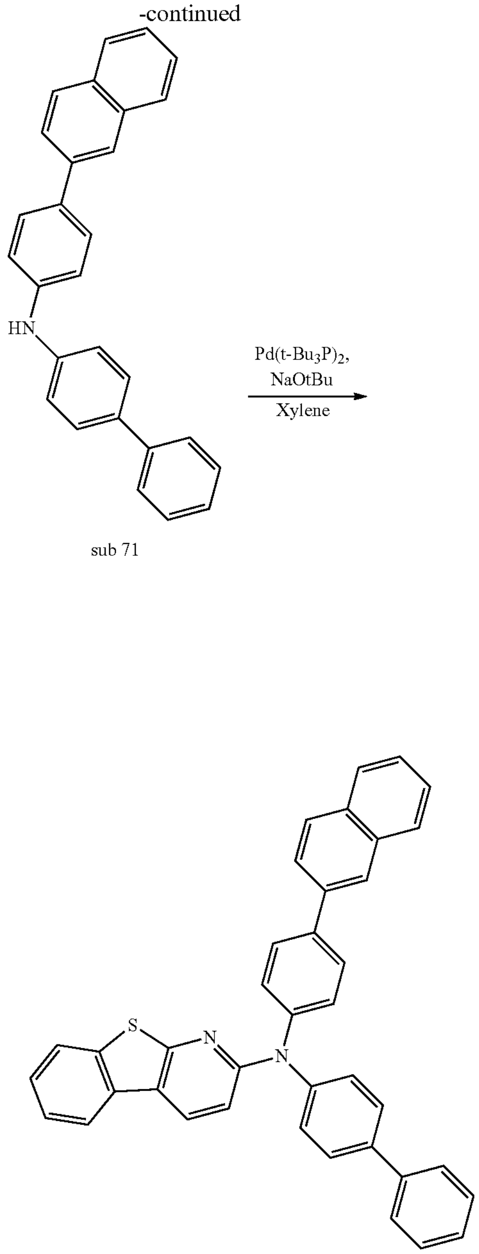

sub 71

71

Compound B-b-e (15 g, 68.3 mmol) and Compound sub 71 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.4 g of Compound 71. (Yield: 46%, MS: $[M+H]^+=556$)

Synthesis Example 72

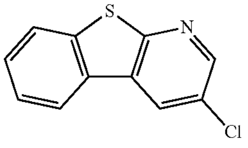

+

B-c-e

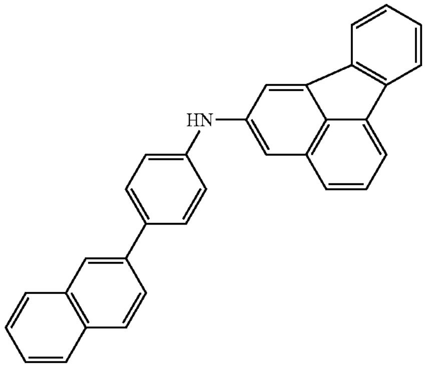

Pd(t-$Bu_3P)_2$,
NaOtBu
Xylene sub 72

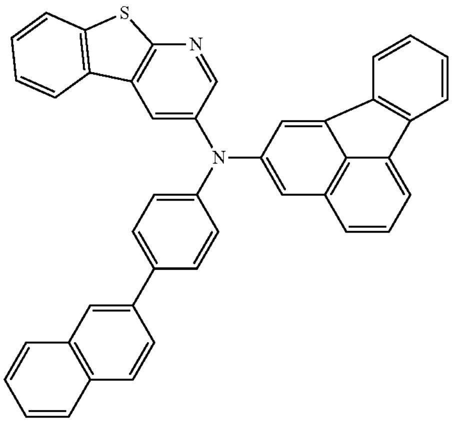

72

Compound B-c-e (15 g, 68.3 mmol) and Compound sub 72 (31.5 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.2 g of Compound 72. (Yield: 54%, MS: $[M+H]^+$=604)

Synthesis Example 73

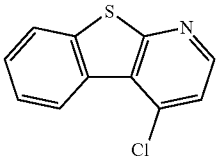

+

B-d-e

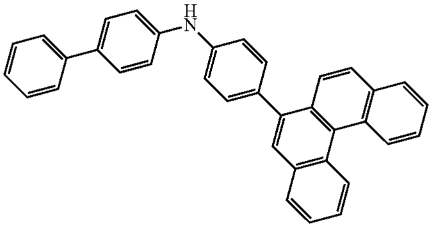

sub 73

Pd(t-$Bu_3P)_2$,
NaOtBu
Xylene

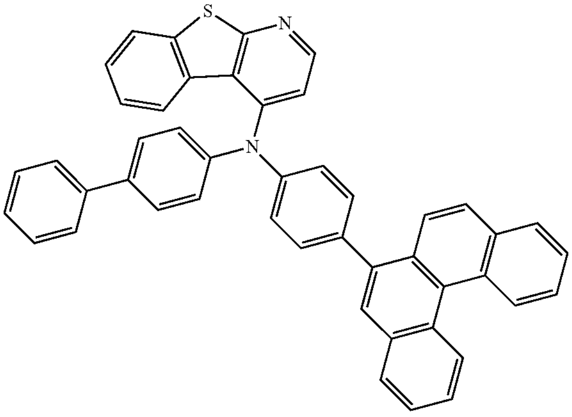

73

Compound B-d-e (15 g, 68.3 mmol) and Compound sub 73 (35.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 9 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 20.1 g of Compound 73. (Yield: 45%, MS: $[M+H]^+$=656)

Synthesis Example 74

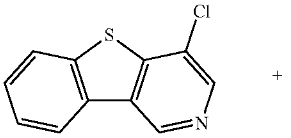

B-a-f

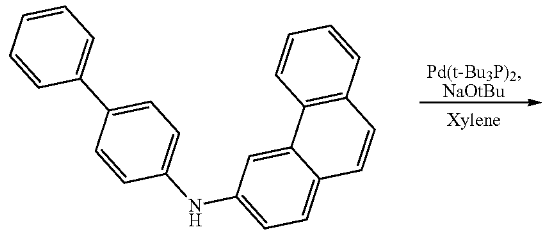

sub 74

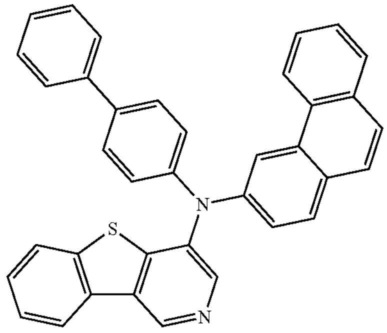

74

Compound B-a-f (15 g, 68.3 mmol) and Compound sub 74 (25.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.1 g of Compound 74. (Yield: 64%, MS: $[M+H]^+=530$)

Synthesis Example 75

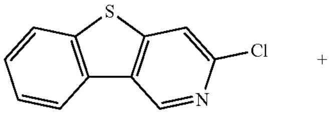

B-b-f

-continued

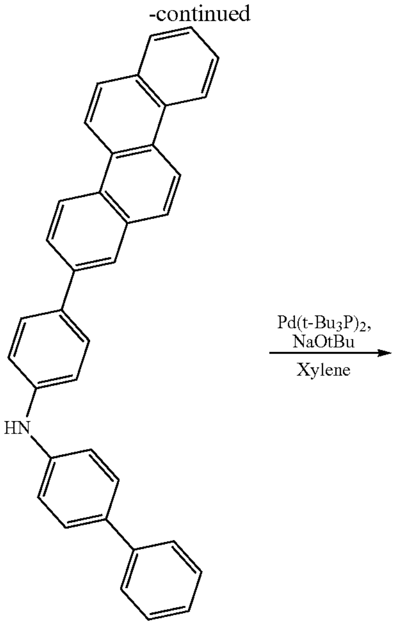

sub 75

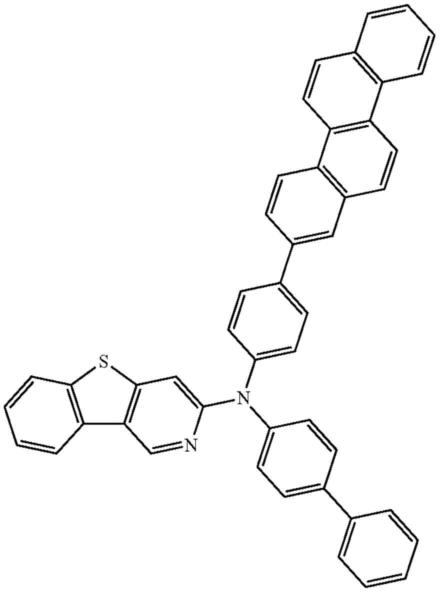

75

Compound B-b-f (15 g, 68.3 mmol) and Compound sub 75 (35.4 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.8 g of Compound 75. (Yield: 51%, MS: $[M+H]^+=656$)

Synthesis Example 76

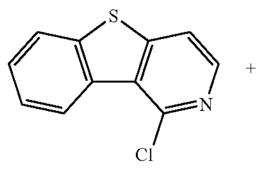

B-d-g

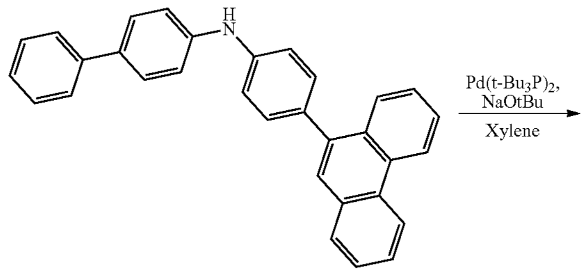

sub 76

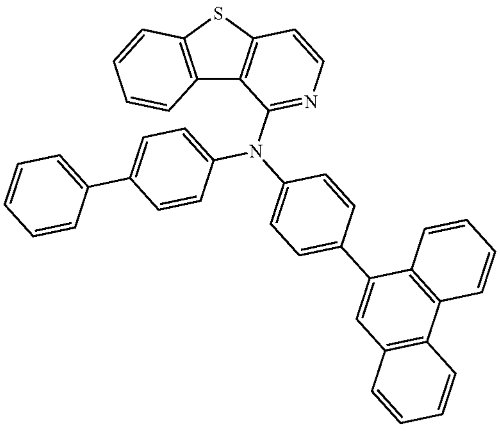

76

Compound B-d-g (15 g, 68.3 mmol) and Compound sub 76 (31.7 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.8 g of Compound 76. (Yield: 43%, MS: $[M+H]^+=606$)

Synthesis Example 77

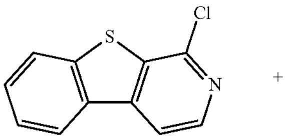

B-a-e

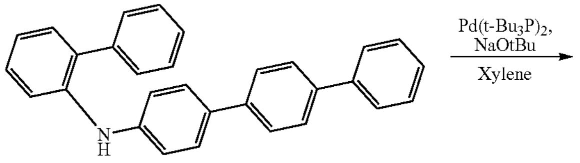

sub 77

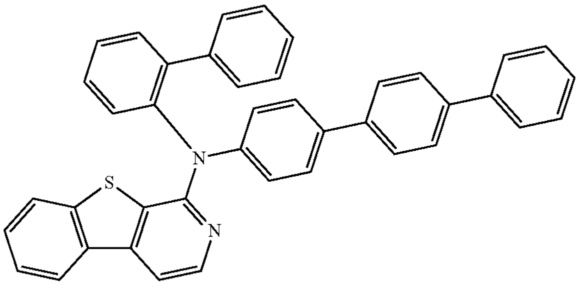

77

Compound B-a-e (15 g, 68.3 mmol) and Compound sub 77 (29.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 10 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23 g of Compound 77. (Yield: 58%, MS: $[M+H]^+=582$)

Synthesis Example 78

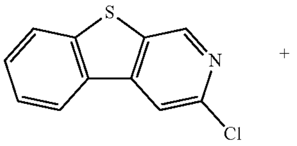

B-c-f

-continued

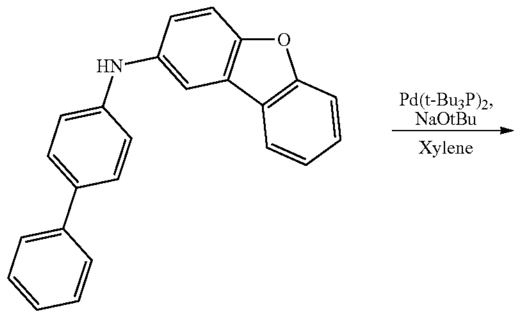

sub 78

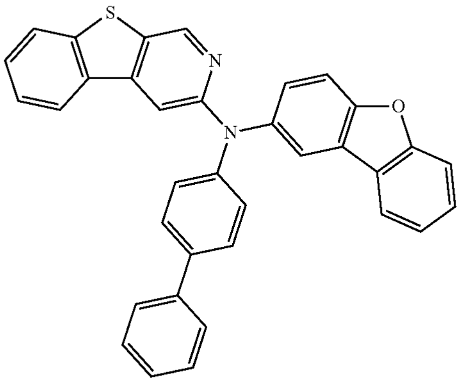

78

Compound B-c-f (15 g, 68.3 mmol) and Compound sub 78 (25.2 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21.2 g of Compound 78. (Yield: 60%, MS: $[M+H]^+=520$)

Synthesis Example 79

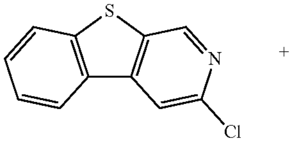

B-c-f

-continued

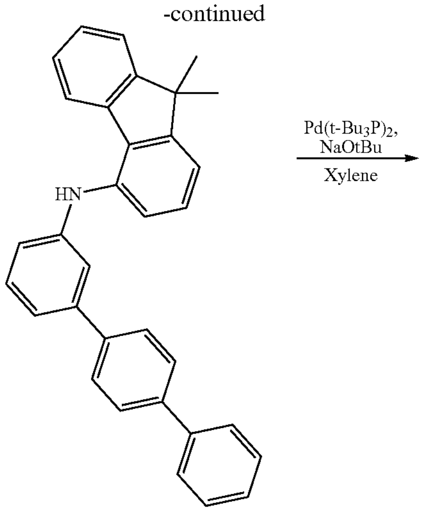

sub 79

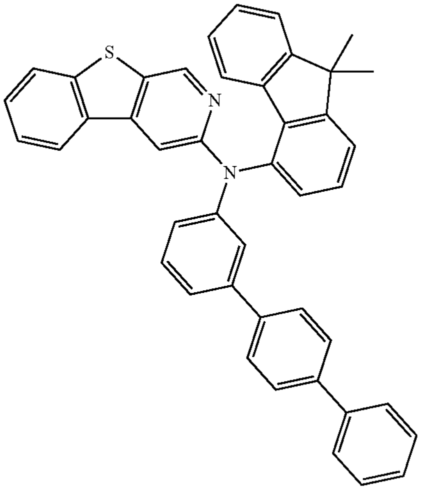

79

Compound B-c-f (15 g, 68.3 mmol) and Compound sub 79 (32.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 8 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 28.4 g of Compound 79. (Yield: 67%, MS: $[M+H]^+=622$)

Synthesis Example 80

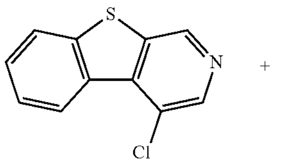

B-d-f

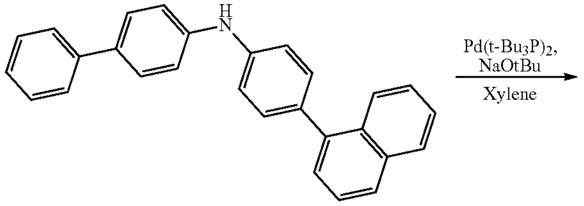

sub 80

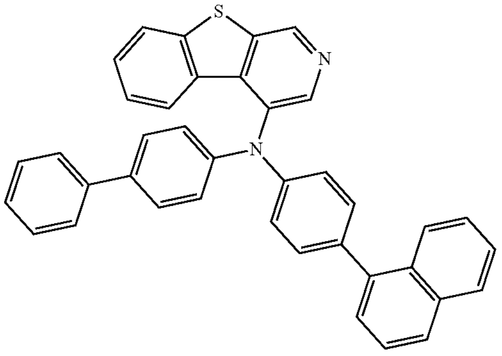

80

Compound B-d-f (15 g, 68.3 mmol) and Compound sub 80 (27.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 12 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 23.9 g of Compound 80. (Yield: 63%, MS: $[M+H]^+=556$)

Synthesis Example 81

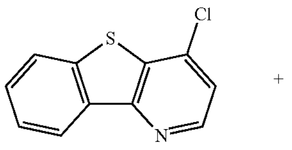

B-a-g

-continued

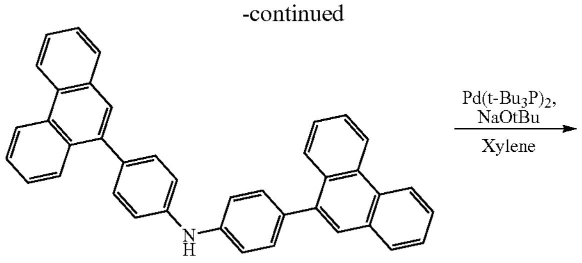

sub 81

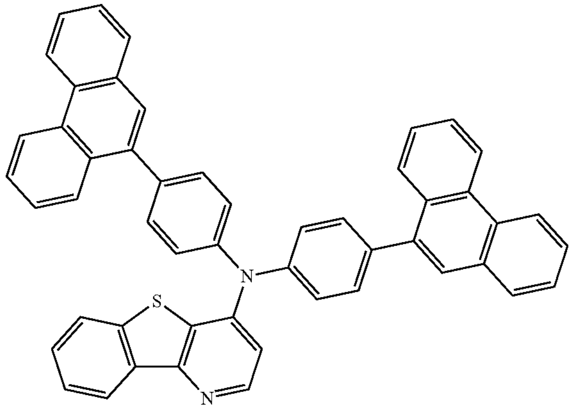

81

Compound B-a-g (15 g, 68.3 mmol) and Compound sub 81 (39.2 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 6 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 22.1 g of Compound 81. (Yield: 46%, MS: $[M+H]^+=706$)

Synthesis Example 82

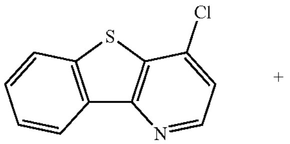

B-a-g

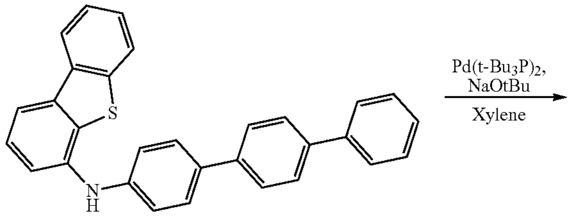

sub 82

-continued

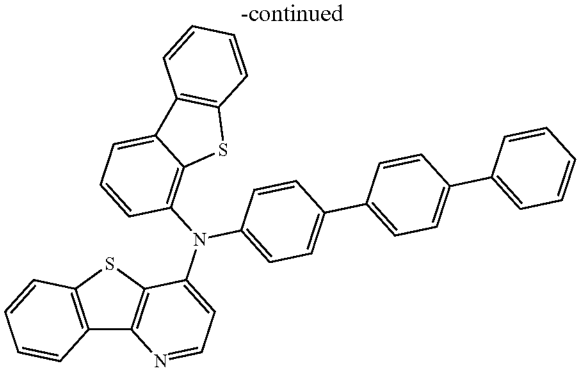

82

Compound B-a-g (15 g, 68.3 mmol) and Compound sub 82 (32.1 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 17.5 g of Compound 82. (Yield: 42%, MS: $[M+H]^+=612$)

Synthesis Example 83

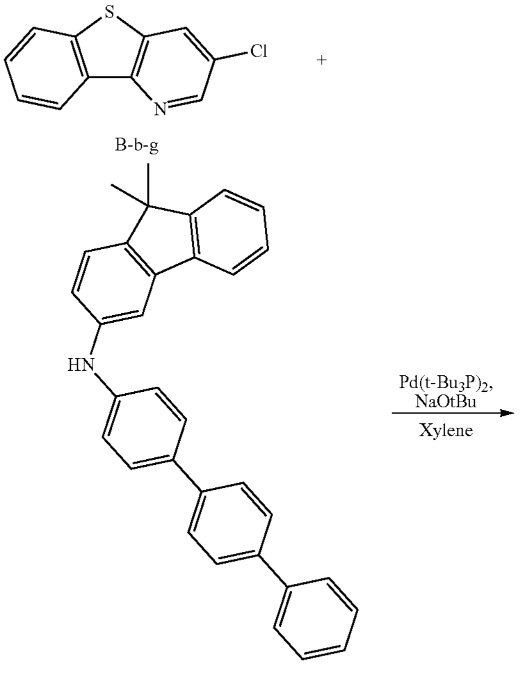

B-b-g sub 83

-continued

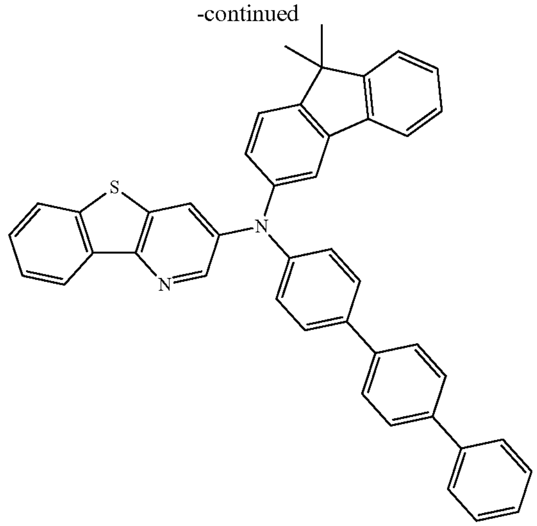

83

Compound B-b-g (15 g, 68.3 mmol) and Compound sub 83 (32.9 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 11 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 21.2 g of Compound 83. (Yield: 50%, MS: $[M+H]^+=622$)

Synthesis Example 84

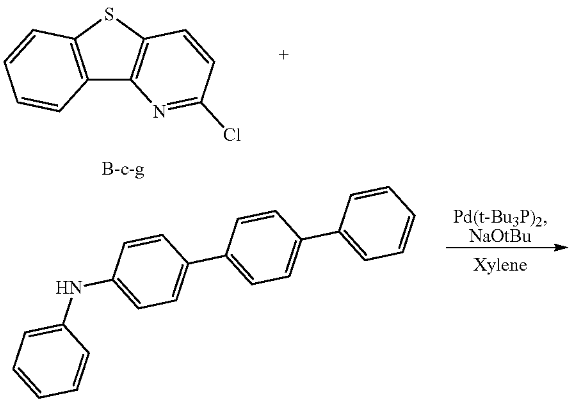

B-c-g sub 84

-continued

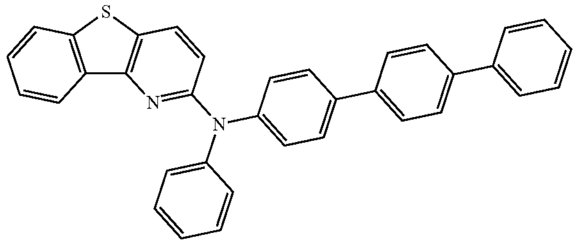

84

Compound B-c-g (15 g, 68.3 mmol) and Compound sub 84 (24.1 g, 75.1 mmol) were added to 300 ml of xylene under a nitrogen atmosphere, and the mixture was stirred and refluxed. Then, sodium tert-butoxide (9.8 g, 102.4 mmol) and bis(tri-tert-butylphosphine)palladium(0) (1 g, 2 mmol) were added thereto. After reacting for 7 hours, the reaction mixture was cooled to room temperature, and the organic layer was separated using chloroform and water, and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography and then subjected to sublimation purification to give 15.5 g of Compound 84. (Yield: 45%, MS: $[M+H]^+$=506)

Synthesis Example 85

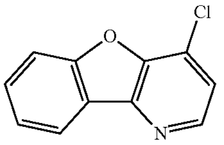

+

A-a-g

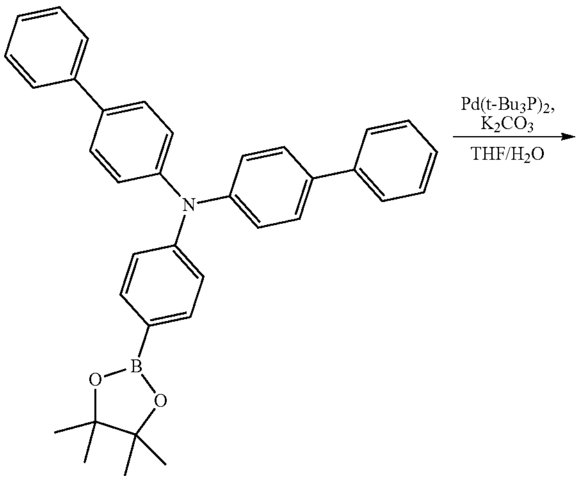

sub 85

-continued

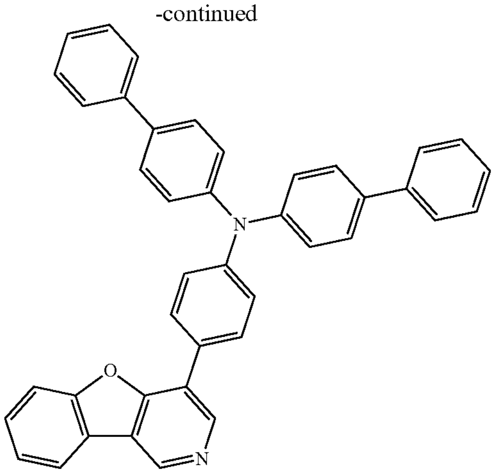

85

Compound A-a-g (15 g, 73.7 mmol) and Compound sub 85 (42.4 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 11 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 26.2 g of Compound 85. (Yield: 63%, MS: $[M+H]^+$=566)

Synthesis Example 86

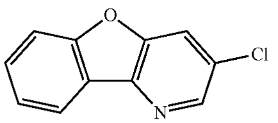

+

A-b-g

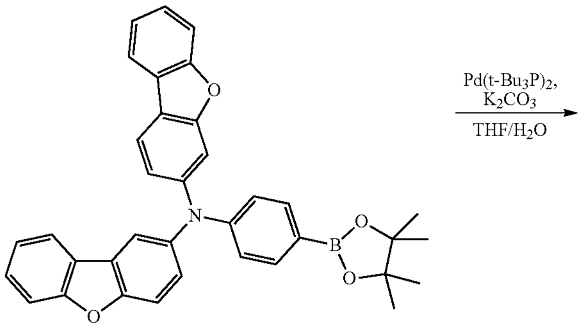

sub 86

-continued

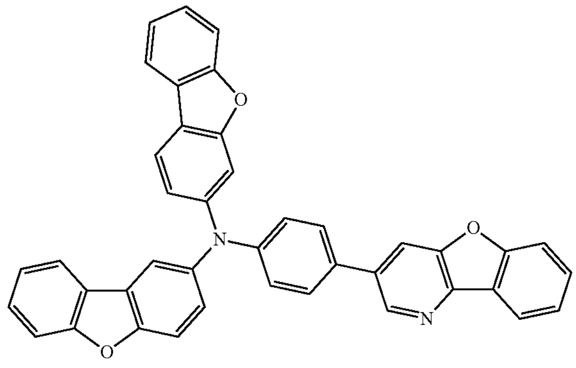

86

Compound A-b-g (15 g, 73.7 mmol) and Compound sub 86 (44.7 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 27.9 g of Compound 86. (Yield: 64%, MS: $[M+H]^+=594$)

Synthesis Example 87

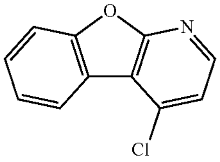

A-d-e

+

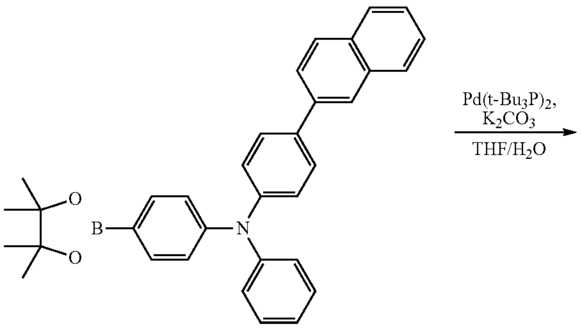

sub 87

-continued

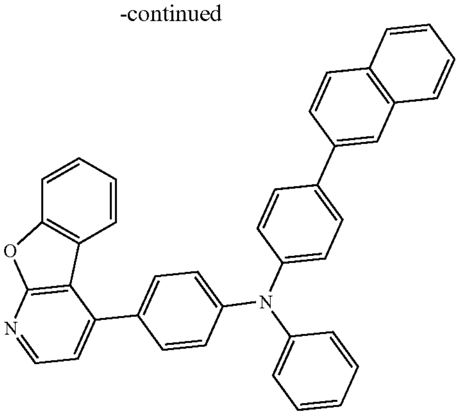

87

Compound A-d-e (15 g, 73.7 mmol) and Compound sub 87 (40.3 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.3 g of Compound 87. (Yield: 46%, MS: $[M+H]^+=540$)

Synthesis Example 88

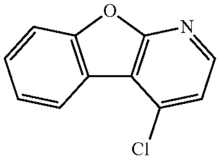

A-d-e

+

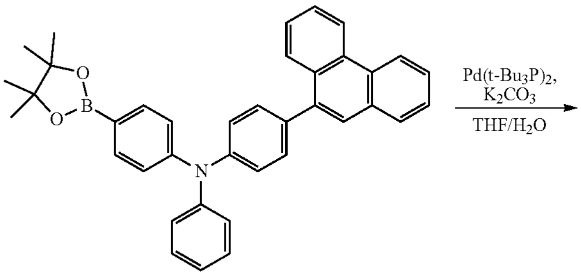

sub 88

-continued

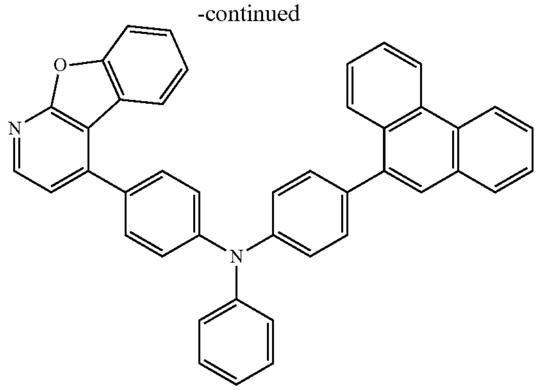

88

Compound A-d-e (15 g, 73.7 mmol) and Compound sub 88 (44.4 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 21.2 g of Compound 88. (Yield: 49%, MS: $[M+H]^+$=590)

Synthesis Example 89

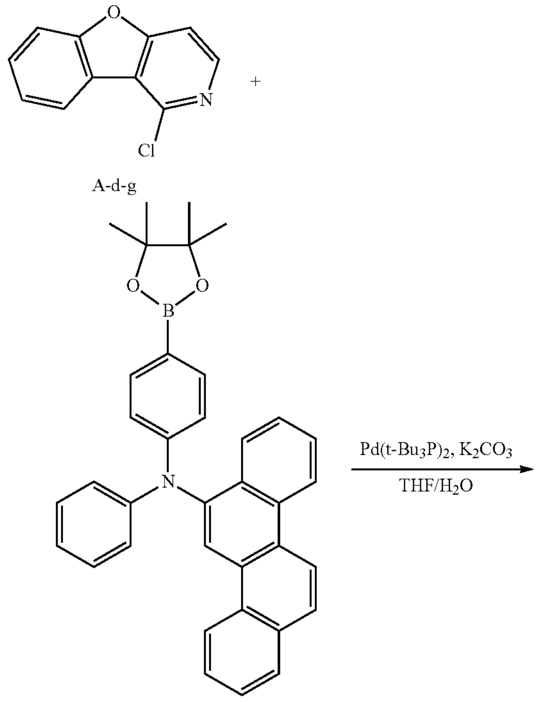

A-d-g sub 89

-continued

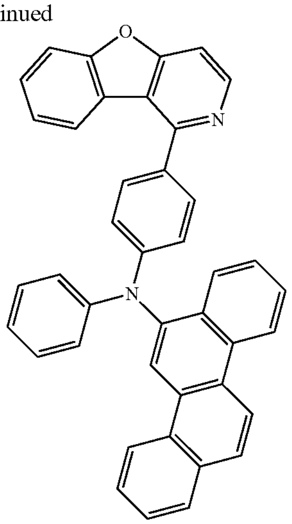

89

Compound A-d-g (15 g, 73.7 mmol) and Compound sub 89 (42.3 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24 g of Compound 89. (Yield: 58%, MS: $[M+H]^+$=564)

Synthesis Example 90

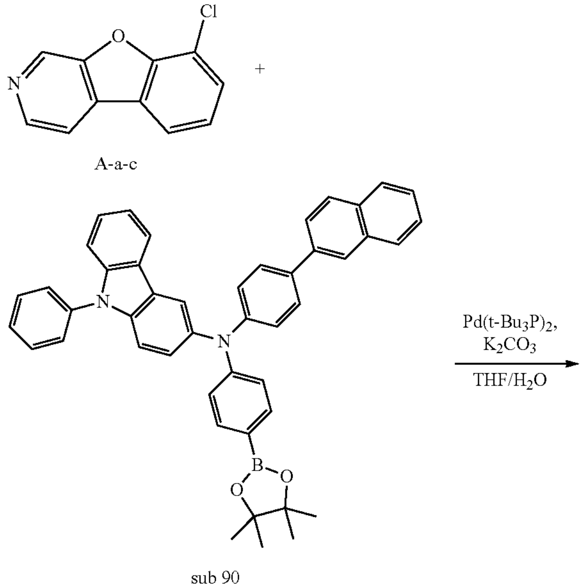

A-a-c sub 90

-continued

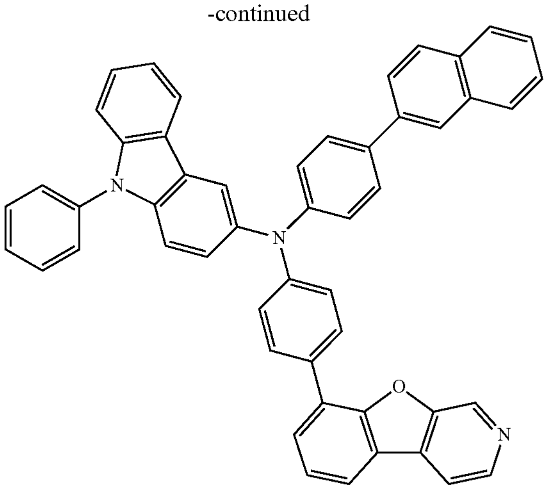

90

Compound A-a-c (15 g, 73.7 mmol) and Compound sub 90 (53.7 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 38.9 g of Compound 90. (Yield: 75%, MS: $[M+H]^+$=705)

Synthesis Example 91

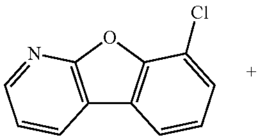

A-a-d

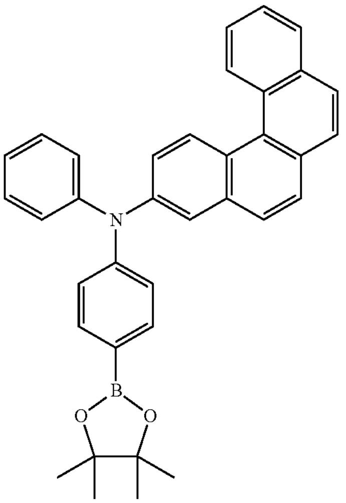

sub 91

Pd(t-Bu$_3$P)$_2$, K$_2$CO$_3$

THF/H$_2$O

-continued

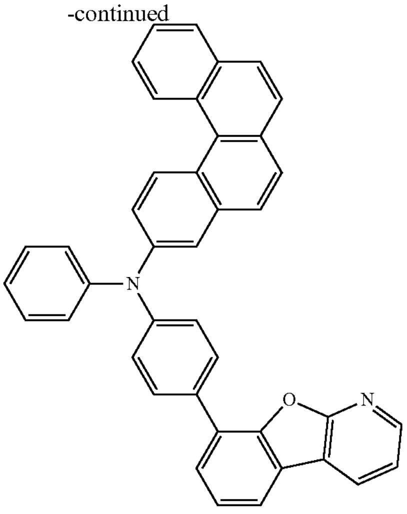

91

Compound A-a-d (15 g, 73.7 mmol) and Compound sub 91 (42.3 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 18.2 g of Compound 91. (Yield: 44%, MS: $[M+H]^+$=564)

Synthesis Example 92

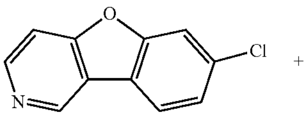

A-b-b

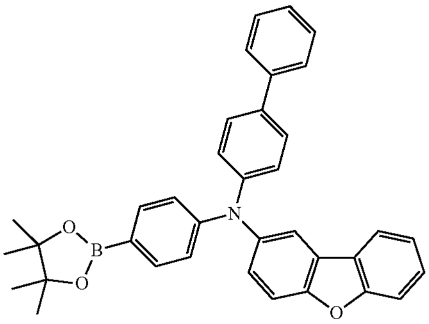

sub 92

Pd(t-Bu$_3$P)$_2$,
K$_2$CO$_3$

THF/H$_2$O

-continued

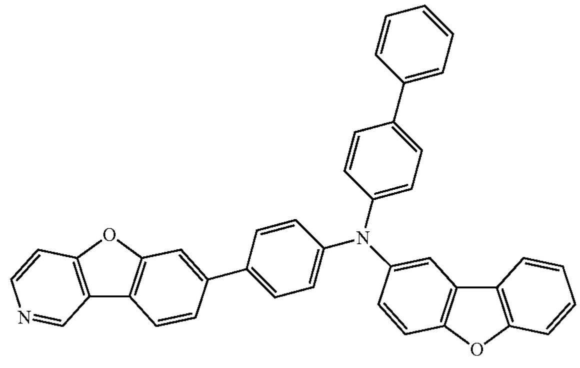

92

Compound A-b-b (15 g, 73.7 mmol) and Compound sub 92 (43.6 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24.3 g of Compound 92. (Yield: 57%, MS: $[M+H]^+=580$)

Synthesis Example 93

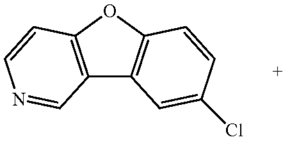

A-c-b

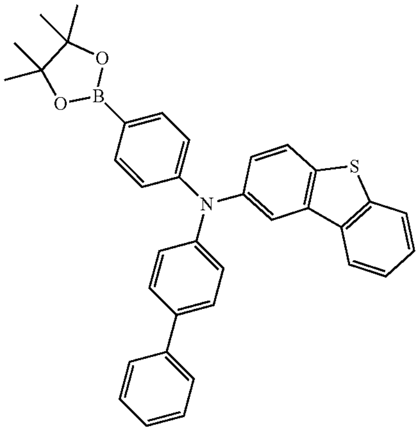

sub 93

$Pd(t\text{-}Bu_3P)_2$,
$K_2CO_3$
$THF/H_2O$

-continued

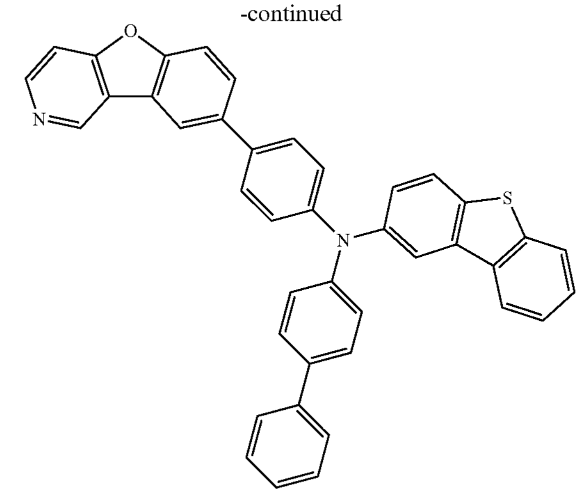

93

Compound A-c-b (15 g, 73.7 mmol) and Compound sub 93 (44.9 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 31.1 g of Compound 93. (Yield: 71%, MS: $[M+H]^+=596$)

Synthesis Example 94

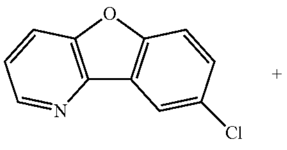

A-c-a

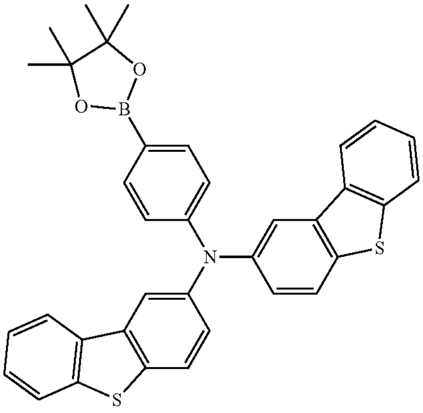

sub 94

$Pd(t\text{-}Bu_3P)_2$,
$K_2CO_3$
$THF/H_2O$

-continued

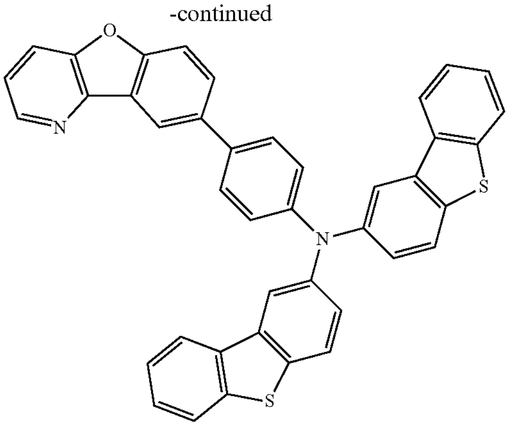

94

Compound A-c-a (15 g, 73.7 mmol) and Compound sub 94 (47.3 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 9 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 33.1 g of Compound 94. (Yield: 72%, MS: $[M+H]^+$=626)

Synthesis Example 95

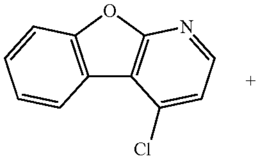

A-d-e

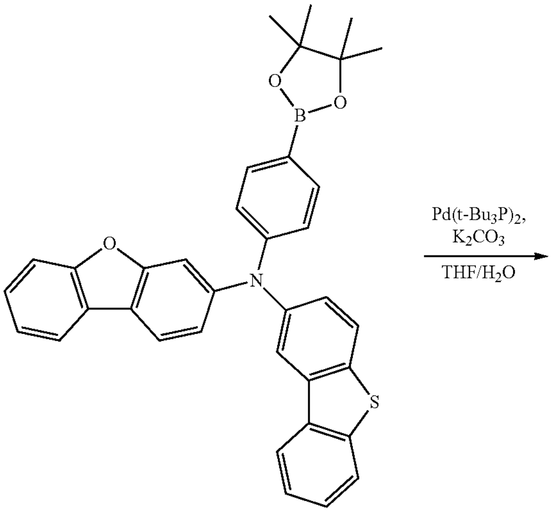

sub 95

-continued

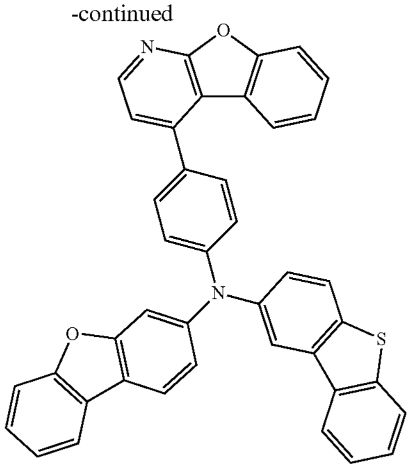

95

Compound A-d-e (15 g, 73.7 mmol) and Compound sub 95 (46 g, 81 mmol) were added to 300 ml of THF, and the mixture was stirred and refluxed. Then, potassium carbonate (40.7 g, 294.7 mmol) was dissolved in 122 ml of water, added thereto and sufficiently stirred, and then bis(tri-tert-butylphosphine)palladium(0) (0.4 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 29.6 g of Compound 95. (Yield: 66%, MS: $[M+H]^+$=610)

Synthesis Example 96

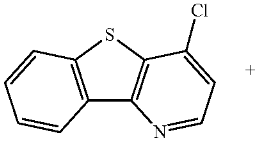

B-a-g

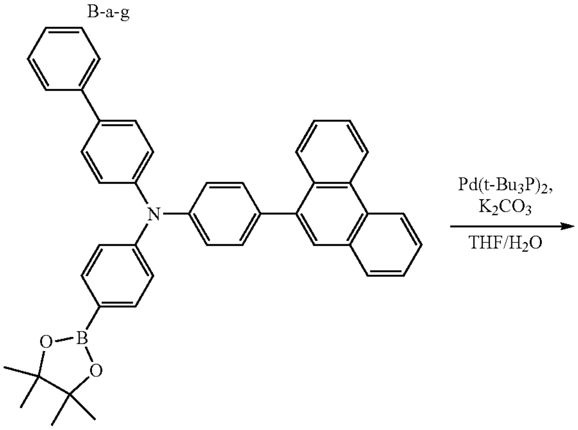

sub 96

-continued

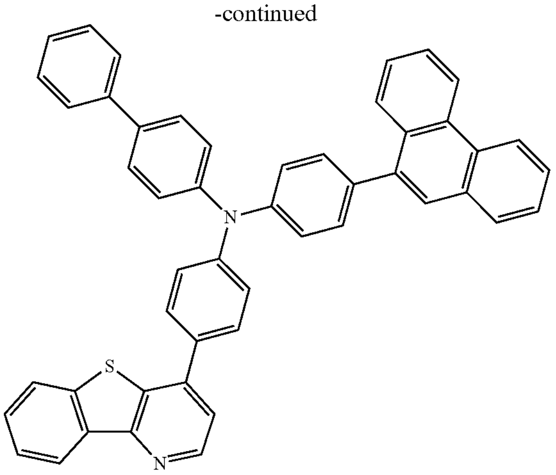

96

Compound B-a-g (15 g, 68.3 mmol) and Compound sub 96 (46.8 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 27.4 g of Compound 96. (Yield: 59%, MS: $[M+H]^+$=682)

Synthesis Example 97

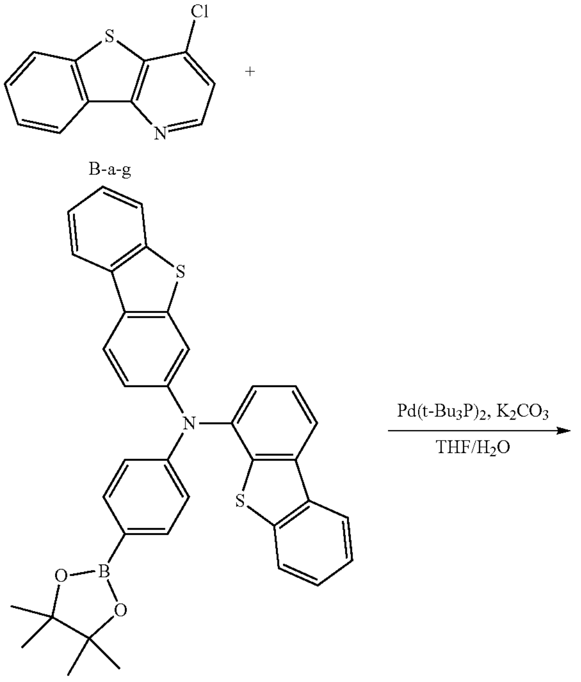

B-a-g sub 97

-continued

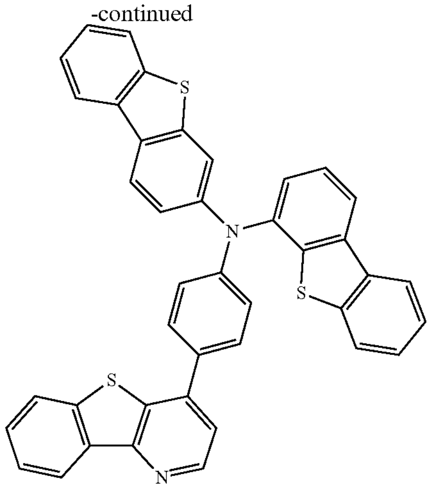

97

Compound B-a-g (15 g, 68.3 mmol) and Compound sub 97 (43.8 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 24.1 g of Compound 97. (Yield: 55%, MS: $[M+H]^+$=642)

Synthesis Example 98

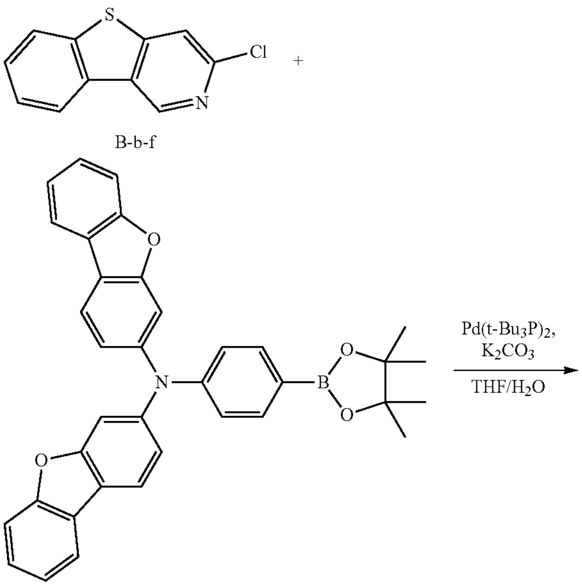

B-b-f sub 98

-continued

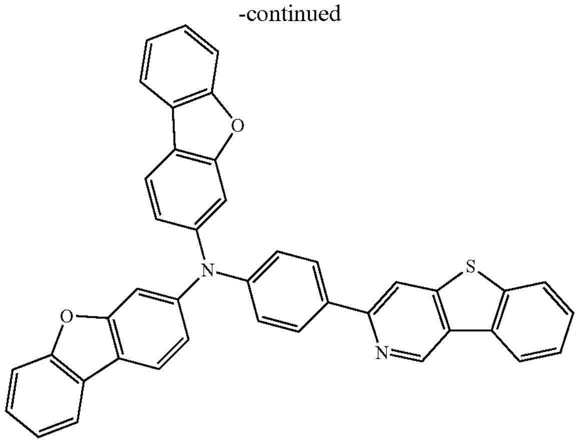

98

Compound B-b-f (15 g, 68.3 mmol) and Compound sub 98 (41.4 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 19.5 g of Compound 98. (Yield: 47%, MS: $[M+H]^+=610$)

Synthesis Example 99

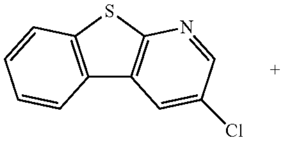

B-c-e

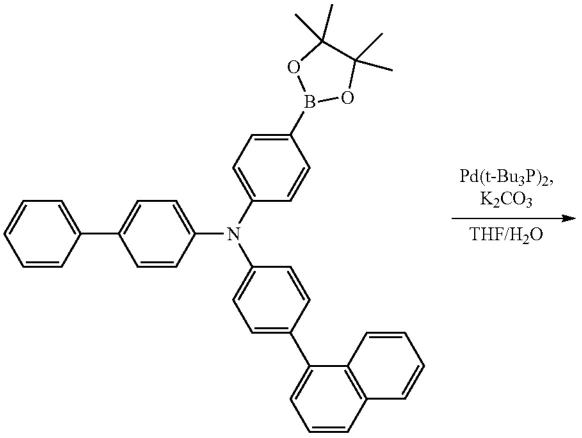

sub 99

-continued

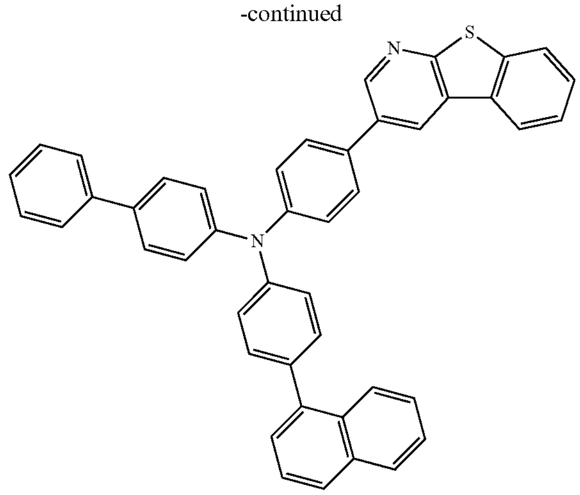

99

Compound B-c-e (15 g, 68.3 mmol) and Compound sub 99 (43.1 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 23.7 g of Compound 99. (Yield: 55%, MS: $[M+H]^+=632$)

Synthesis Example 100

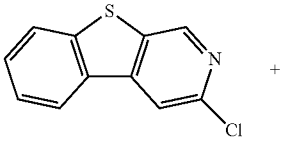

B-c-f

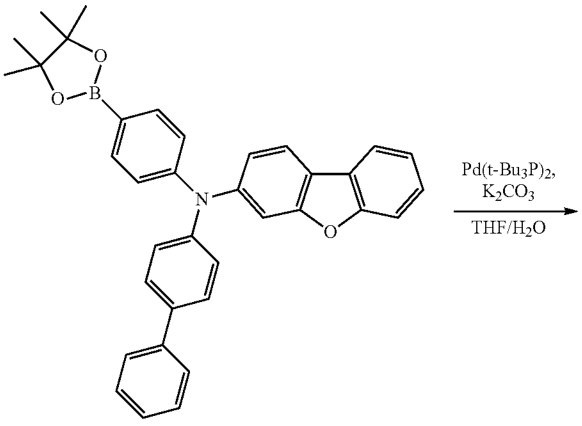

sub 100

-continued

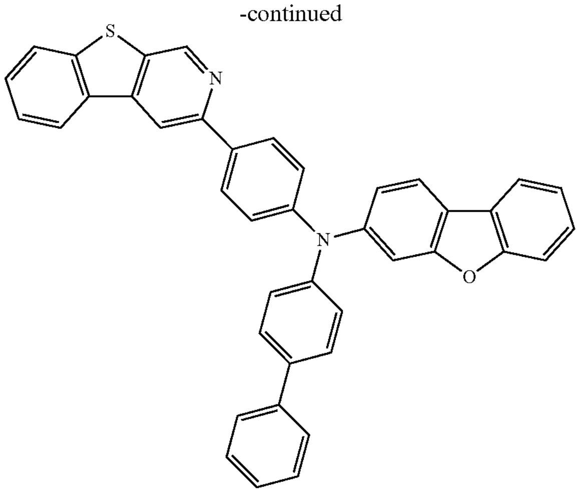

100

Compound B-c-f (15 g, 68.3 mmol) and Compound sub 100 (40.4 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis(tri-tert-butylphosphine)palladium(0) (0.3 g, 0.7 mmol) was added. After reacting for 10 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 20.7 g of Compound 100. (Yield: 51%, MS: $[M+H]^+$=596)

Synthesis Example 101

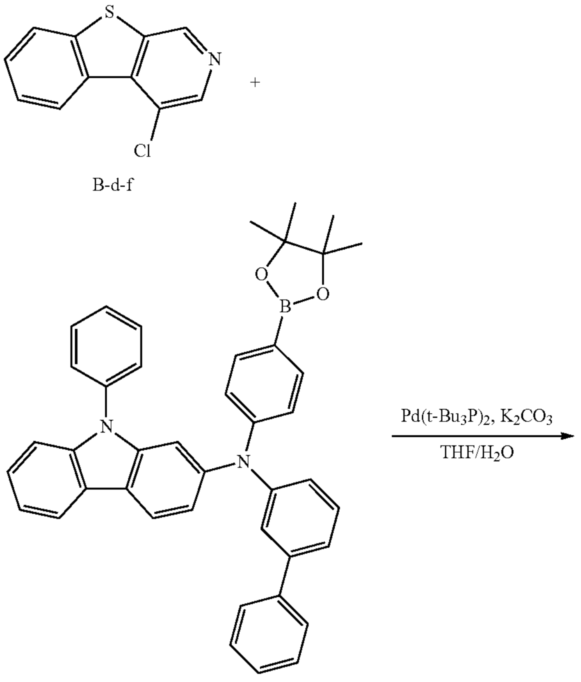

B-d-f sub 101

-continued

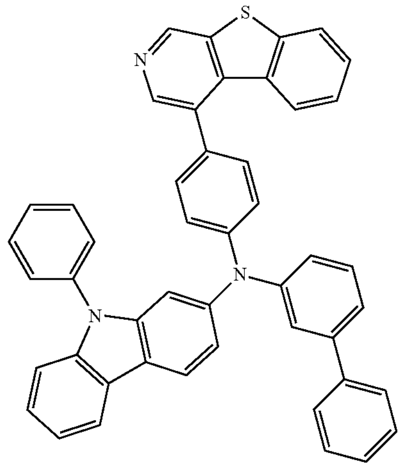

101

Compound B-d-f (15 g, 68.3 mmol) and Compound sub 101 (46 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis(tri-tert-butylphosphine)palladium(0) (0.3 g, 0.7 mmol) was added. After reacting for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 31.1 g of Compound 101. (Yield: 68%, MS: $[M+H]^+$=671)

Synthesis Example 102

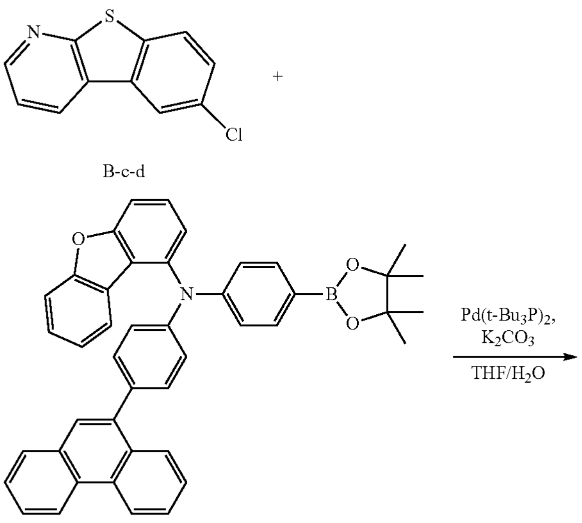

B-c-d sub 102

-continued

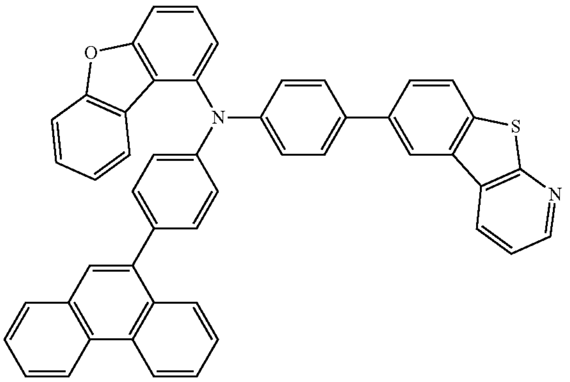

102

-continued

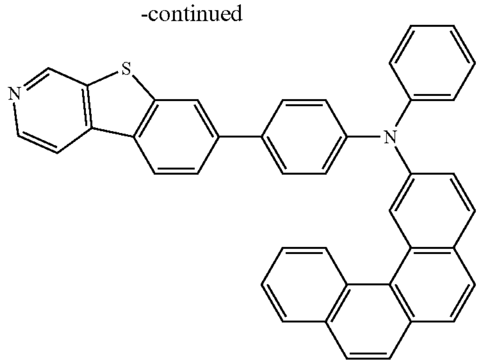

103

Compound B-c-d (15 g, 68.3 mmol) and Compound sub 102 (47.9 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 12 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 28.5 g of Compound 102. (Yield: 60%, MS: $[M+H]^+=696$)

Synthesis Example 103

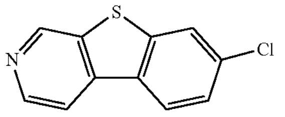

+

B-b-c

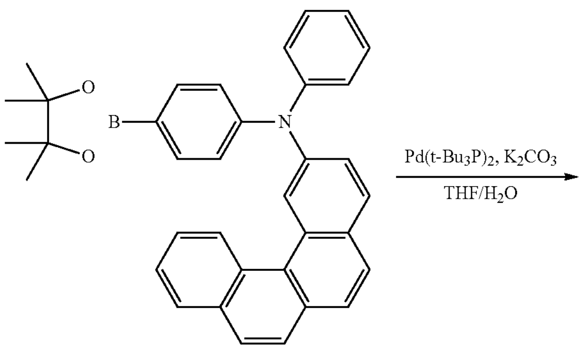

sub 103

Compound B-b-c (15 g, 68.3 mmol) and Compound sub 103 (39.2 g, 75.1 mmol) were added to 300 ml of THF, and the mixture was stirred and refluxed. Then, potassium carbonate (37.7 g, 273.1 mmol) was dissolved in 113 ml of water, added thereto and sufficiently stirred, and then bis (tri-tert-butylphosphine)palladium(0) (0.3 g, 0.7 mmol) was added. After reacting for 8 hours, the reaction mixture was cooled to room temperature, and the organic layer and the aqueous layer were separated and then the organic layer was distilled. This was again dissolved in chloroform, washed twice with water, and then the organic layer was separated, anhydrous magnesium sulfate was added thereto, stirred, and then filtered, and the filtrate was distilled under reduced pressure. The concentrated compound was purified by silica gel column chromatography to give 31.2 g of Compound 103. (Yield: 79%, MS: $[M+H]^+=580$)

Example 1

A glass substrate on which a thin film of ITO (indium tin oxide) was coated in a thickness of 1,000 Å was put into distilled water containing a detergent dissolved therein and ultrasonically washed. In this case, the detergent used was a product commercially available from Fisher Co. and the distilled water was one which had been twice filtered by using a filter commercially available from Millipore Co. The ITO was washed for 30 minutes, and ultrasonic washing was then repeated twice for 10 minutes by using distilled water. After the washing with distilled water was completed, the substrate was ultrasonically washed with isopropyl alcohol, acetone, and methanol solvent, and dried, after which it was transported to a plasma cleaner. Then, the substrate was cleaned with oxygen plasma for 5 minutes, and then transferred to a vacuum evaporator.

On the ITO transparent electrode thus prepared, the following Compound HI-1 was formed to a thickness of 1150 Å as a hole injection layer, but the following Compound A-1 was p-doped at a concentration of 1.5 wt. %. The following Compound HT-1 was vacuum deposited to a film thickness of 800 Å on the hole injection layer to form a hole transport layer. Then, the following Compound EB-1 was vacuum deposited to a film thickness of 150 Å on the hole transport layer to form an electron blocking layer. Then, the following Compound RH-1, the Compound 1 prepared in Synthesis Example 1 as a host, and the following Compound Dp-7 as a dopant were vacuum deposited in a weight ratio of 49:49:2 on the EB-1-deposited layer to form a red light emitting layer with a thickness of 400 Å. The following Compound HB-1 was vacuum deposited to a film thickness of 30 Å on the light emitting layer to form a hole blocking layer. The following Compound ET-1 and the following Compound LiQ were vacuum deposited in a ratio of 2:1 on the hole blocking layer to form an electron injection and transport layer with a film thickness of 300 Å. Lithium fluoride (LiF) and aluminum were sequentially deposited to have a thickness of 12 Å and 1,000 Å, respectively, on the electron injection and transport layer, thereby forming a cathode,

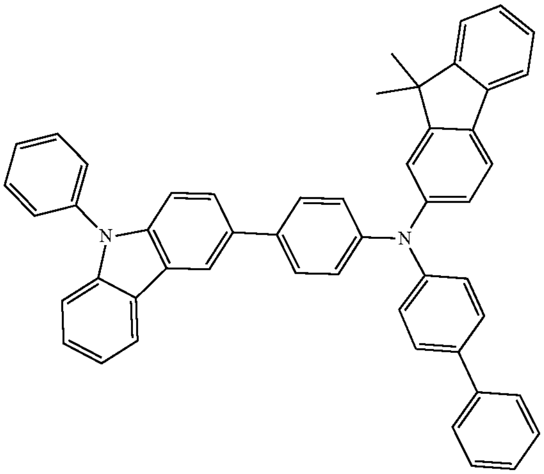

HI-1

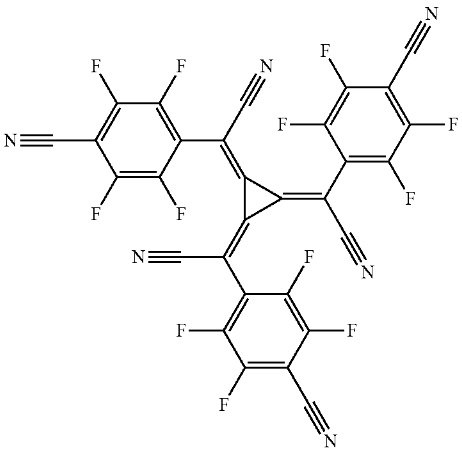

A-1

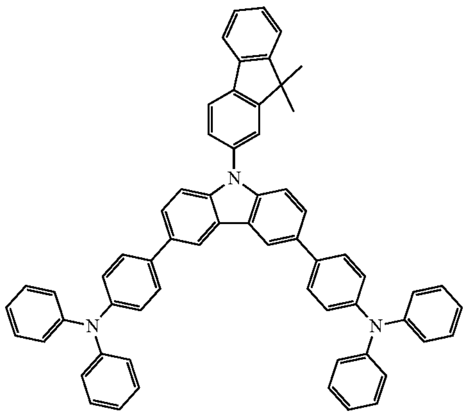

HT-1

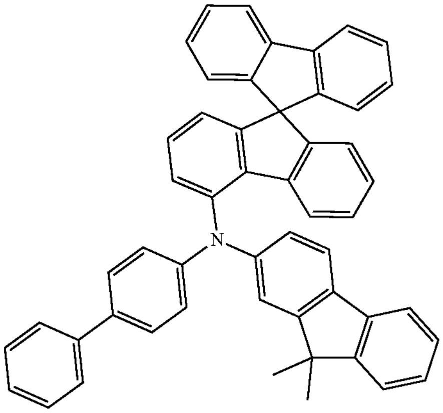

EB-1

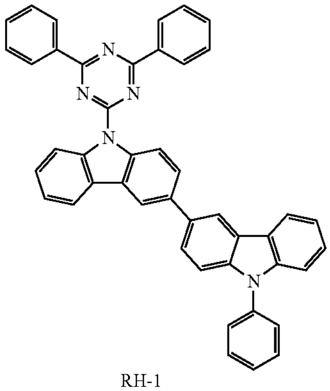

RH-1

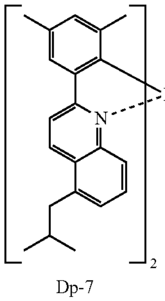

Dp-7

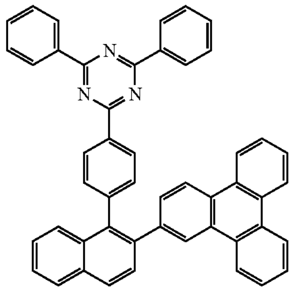

HB-1

-continued

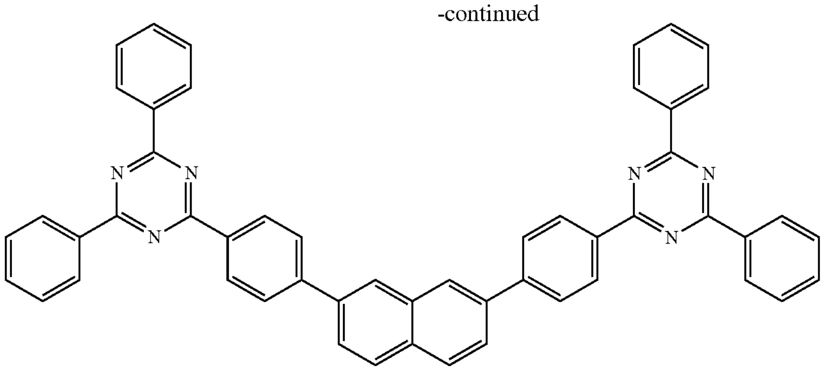

ET-1

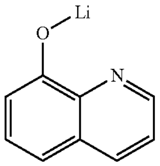

LiQ

In the above-mentioned processes, the deposition rates of the organic materials were maintained at 0.4 to 0.7 Å/sec, the deposition rates of lithium fluoride and the aluminum of the cathode were maintained at 0.3 Å/sec and 2 Å/sec, respectively, and the degree of vacuum during the deposition was maintained at $2\times10^{-7}$ to $5\times10^{-6}$ torr, thereby manufacturing an organic light emitting device.

Examples 2 to 103

The organic light emitting devices were manufactured in the same manner as in Example 1, except that the compounds shown in Tables 1 to 3 below were used instead of Compound 1 in the organic light emitting device of Example 1.

Comparative Examples 1 to 8

The organic light emitting devices were manufactured in the same manner as in Example 1, except that the compounds shown in Table 4 below were used instead of Compound 1 in the organic light emitting device of Example 1. The compounds used in the Comparative Examples 1 to 8 are as follows:

C-1

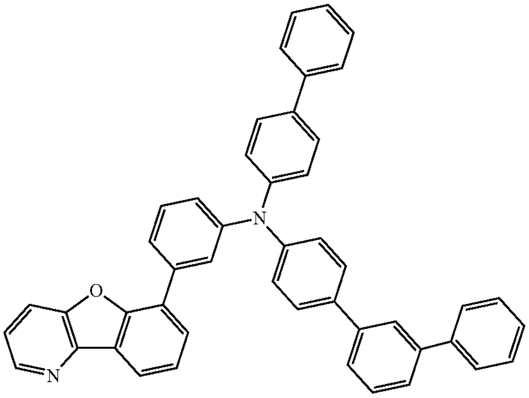

-continued

C-2

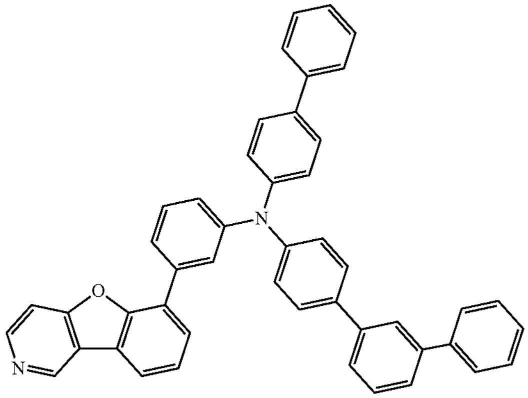

C-3

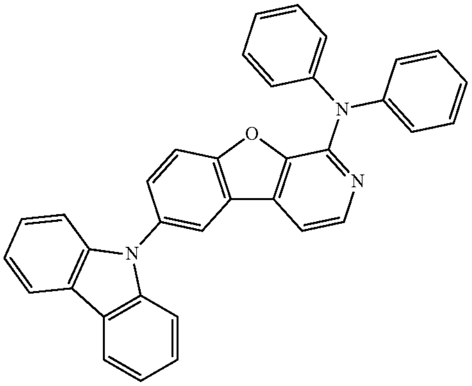

-continued

C-4

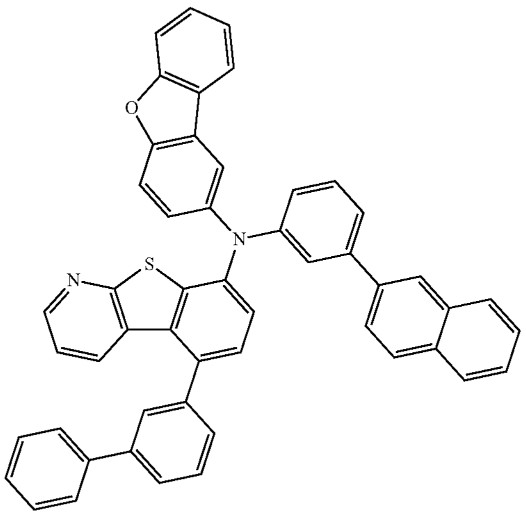

C-5

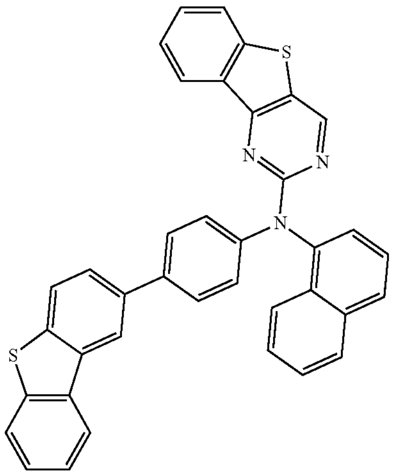

C-6

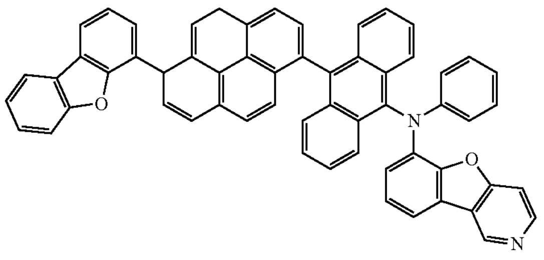

-continued

C-7

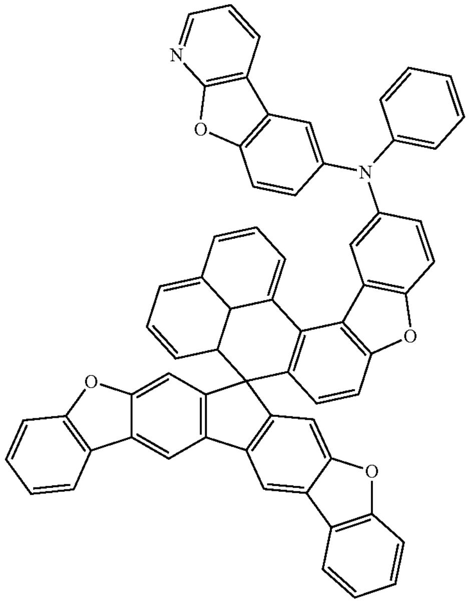

C-8

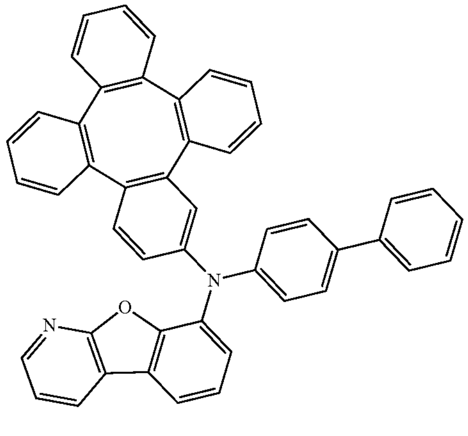

Experimental Example

The driving voltage and efficiency were measured by applying a current of 15 mA/cm$^2$ to the organic light emitting devices manufactured in the Examples 1 to 103 and Comparative Examples 1 to 8, and the results are shown in Tables 1 to 4 below. T95 means the time required for the luminance to be reduced to 95% of the initial luminance (6000 nit).

TABLE 1

| Category | Material | Driving voltage (V) | Efficiency (cd/A) | Lifetime T95 (hr) | Luminescent color |
|---|---|---|---|---|---|
| Example 1 | Compound 1 | 3.79 | 19.15 | 249 | Red |
| Example 2 | Compound 2 | 3.84 | 19.37 | 245 | Red |
| Example 3 | Compound | 3.88 | 18.97 | 244 | Red |
| Example 4 | Compound 4 | 3.76 | 18.48 | 234 | Red |
| Example 5 | Compound 5 | 3.76 | 18.40 | 228 | Red |

TABLE 1-continued

| Category | Material | Driving voltage (V) | Efficiency (cd/A) | Lifetime T95 (hr) | Luminescent color |
|---|---|---|---|---|---|
| Example 6 | Compound 6 | 3.86 | 18.40 | 234 | Red |
| Example 7 | Compound 7 | 3.85 | 19.49 | 227 | Red |
| Example 8 | Compound 8 | 3.77 | 19.26 | 222 | Red |
| Example 9 | Compound 9 | 3.86 | 18.93 | 240 | Red |
| Example 10 | Compound 10 | 3.76 | 18.55 | 227 | Red |
| Example 11 | Compound 11 | 3.86 | 18.71 | 236 | Red |
| Example 12 | Compound 12 | 3.88 | 18.87 | 211 | Red |
| Example 13 | Compound 13 | 3.78 | 18.04 | 218 | Red |
| Example 14 | Compound 14 | 3.84 | 18.33 | 231 | Red |
| Example 15 | Compound 15 | 3.89 | 18.35 | 250 | Red |
| Example 16 | Compound 16 | 3.75 | 18.09 | 213 | Red |
| Example 17 | Compound 17 | 3.81 | 18.52 | 243 | Red |
| Example 18 | Compound 18 | 3.83 | 18.55 | 225 | Red |
| Example 19 | Compound 19 | 3.85 | 19.31 | 238 | Red |
| Example 20 | Compound 20 | 3.78 | 18.89 | 217 | Red |
| Example 21 | Compound 21 | 3.78 | 19.12 | 248 | Red |
| Example 22 | Compound 22 | 3.79 | 19.57 | 248 | Red |
| Example 23 | Compound 23 | 3.72 | 19.34 | 276 | Red |
| Example 24 | Compound 24 | 3.70 | 19.88 | 246 | Red |
| Example 25 | Compound 25 | 3.76 | 20.25 | 274 | Red |
| Example 26 | Compound 26 | 3.70 | 19.06 | 277 | Red |
| Example 27 | Compound 27 | 3.71 | 19.00 | 261 | Red |
| Example 28 | Compound 28 | 3.70 | 20.37 | 245 | Red |
| Example 29 | Compound 29 | 3.71 | 20.39 | 271 | Red |
| Example 30 | Compound 30 | 3.77 | 20.17 | 276 | Red |
| Example 31 | Compound 31 | 3.70 | 20.40 | 258 | Red |
| Example 32 | Compound 32 | 3.76 | 19.74 | 270 | Red |
| Example 33 | Compound 33 | 3.72 | 19.17 | 280 | Red |
| Example 34 | Compound 34 | 3.69 | 19.05 | 280 | Red |
| Example 35 | Compound 35 | 3.78 | 20.08 | 251 | Red |

TABLE 2

| Category | Material | Driving voltage (V) | Efficiency (cd/A) | Lifetime T95 (hr) | Luminescent color |
|---|---|---|---|---|---|
| Example 36 | Compound 36 | 3.76 | 19.58 | 261 | Red |
| Example 37 | Compound 37 | 3.78 | 19.93 | 250 | Red |

TABLE 2-continued

| Category | Material | Driving voltage (V) | Efficiency (cd/A) | Lifetime T95 (hr) | Luminescent color |
|---|---|---|---|---|---|
| Example 38 | Compound 38 | 3.79 | 19.10 | 254 | Red |
| Example 39 | Compound 39 | 3.68 | 19.69 | 257 | Red |
| Example 40 | Compound 40 | 3.68 | 19.01 | 261 | Red |
| Example 41 | Compound 41 | 3.60 | 17.80 | 301 | Red |
| Example 42 | Compound 42 | 3.65 | 17.27 | 296 | Red |
| Example 43 | Compound 43 | 3.64 | 17.87 | 306 | Red |
| Example 44 | Compound 44 | 3.63 | 18.48 | 283 | Red |
| Example 45 | Compound 45 | 3.64 | 18.01 | 292 | Red |
| Example 46 | Compound 46 | 3.61 | 17.36 | 277 | Red |
| Example 47 | Compound 47 | 3.96 | 18.14 | 197 | Red |
| Example 48 | Compound 48 | 3.94 | 18.28 | 181 | Red |
| Example 49 | Compound 49 | 3.97 | 18.47 | 182 | Red |
| Example 50 | Compound 50 | 3.90 | 17.06 | 189 | Red |
| Example 51 | Compound 51 | 3.97 | 17.97 | 189 | Red |
| Example 52 | Compound 52 | 3.97 | 17.19 | 187 | Red |
| Example 53 | Compound 53 | 3.99 | 17.19 | 190 | Red |
| Example 54 | Compound 54 | 3.94 | 17.52 | 195 | Red |
| Example 55 | Compound 55 | 3.91 | 17.13 | 197 | Red |
| Example 56 | Compound 56 | 3.94 | 17.91 | 188 | Red |
| Example 57 | Compound 57 | 3.95 | 17.11 | 193 | Red |
| Example 58 | Compound 58 | 3.99 | 17.25 | 196 | Red |
| Example 59 | Compound 59 | 3.95 | 18.09 | 196 | Red |
| Example 60 | Compound 60 | 3.91 | 17.49 | 196 | Red |
| Example 61 | Compound 61 | 3.96 | 18.09 | 181 | Red |
| Example 62 | Compound 62 | 3.93 | 18.41 | 181 | Red |
| Example 63 | Compound 63 | 3.93 | 18.26 | 199 | Red |
| Example 64 | Compound 64 | 3.92 | 17.04 | 197 | Red |
| Example 65 | Compound 65 | 3.96 | 18.35 | 193 | Red |
| Example 66 | Compound 66 | 3.97 | 18.29 | 200 | Red |
| Example 67 | Compound 67 | 3.55 | 21.07 | 191 | Red |
| Example 68 | Compound 68 | 3.61 | 21.70 | 194 | Red |
| Example 69 | Compound 69 | 3.65 | 20.90 | 198 | Red |
| Example 70 | Compound 70 | 3.62 | 19.53 | 194 | Red |

TABLE 3

| Category | Material | Driving voltage (V) | Efficiency (cd/A) | Lifetime T95 (hr) | Luminescent color |
|---|---|---|---|---|---|
| Example 71 | Compound 71 | 3.57 | 20.58 | 181 | Red |
| Example 72 | Compound 72 | 3.62 | 22.08 | 190 | Red |
| Example 73 | Compound 73 | 3.56 | 22.05 | 196 | Red |
| Example 74 | Compound 74 | 3.64 | 21.20 | 190 | Red |
| Example 75 | Compound 75 | 3.65 | 20.10 | 183 | Red |
| Example 76 | Compound 76 | 3.51 | 21.43 | 196 | Red |
| Example 77 | Compound 77 | 3.56 | 21.70 | 194 | Red |
| Example 78 | Compound 78 | 3.60 | 21.13 | 196 | Red |
| Example 79 | Compound 79 | 3.63 | 19.86 | 182 | Red |
| Example 80 | Compound 80 | 3.63 | 21.56 | 187 | Red |
| Example 81 | Compound 81 | 3.60 | 22.70 | 181 | Red |
| Example 82 | Compound 82 | 3.56 | 20.09 | 196 | Red |
| Example 83 | Compound 83 | 3.65 | 19.78 | 180 | Red |
| Example 84 | Compound 84 | 3.67 | 17.26 | 309 | Red |
| Example 85 | Compound 85 | 3.61 | 17.95 | 288 | Red |
| Example 86 | Compound 86 | 3.67 | 17.98 | 274 | Red |
| Example 87 | Compound 87 | 3.69 | 18.48 | 288 | Red |
| Example 88 | Compound 88 | 3.63 | 17.32 | 297 | Red |
| Example 89 | Compound 89 | 3.61 | 17.73 | 287 | Red |
| Example 90 | Compound 90 | 3.63 | 17.96 | 289 | Red |
| Example 91 | Compound 91 | 3.64 | 18.07 | 290 | Red |
| Example 92 | Compound 92 | 3.60 | 17.17 | 296 | Red |
| Example 93 | Compound 93 | 3.61 | 17.16 | 292 | Red |
| Example 94 | Compound 94 | 3.61 | 17.70 | 296 | Red |
| Example 95 | Compound 95 | 3.50 | 21.97 | 195 | Red |
| Example 96 | Compound 96 | 3.65 | 20.59 | 184 | Red |
| Example 97 | Compound 97 | 3.58 | 20.26 | 190 | Red |
| Example 98 | Compound 98 | 3.59 | 22.62 | 196 | Red |
| Example 99 | Compound 99 | 3.63 | 20.43 | 191 | Red |
| Example 100 | Compound 100 | 3.62 | 20.51 | 192 | Red |
| Example 101 | Compound 101 | 3.55 | 21.25 | 181 | Red |
| Example 102 | Compound 102 | 3.64 | 22.21 | 184 | Red |
| Example 103 | Compound 103 | 3.60 | 19.89 | 181 | Red |

TABLE 4

| Category | Material | Driving voltage (V) | Efficiency (cd/A) | Lifetime T95 (hr) | Luminescent color |
|---|---|---|---|---|---|
| Comparative Example 1 | C-1 | 4.03 | 16.57 | 161 | Red |
| Comparative Example 2 | C-2 | 4.09 | 16.83 | 172 | Red |
| Comparative Example 3 | C-3 | 4.02 | 15.36 | 138 | Red |
| Comparative Example 4 | C-4 | 4.13 | 16.62 | 167 | Red |
| Comparative Example 5 | C-5 | 4.57 | 8.45 | 23 | Red |
| Comparative Example 6 | C-6 | 4.46 | 6.03 | 11 | Red |
| Comparative Example 7 | C-7 | 4.32 | 12.25 | 74 | Red |
| Comparative Example 8 | C-8 | 4.21 | 13.74 | 122 | Red |

As a result of the experiment, it can be seen that the organic light emitting devices of the Examples using the compounds according to the present disclosure exhibited a driving voltage that was greatly reduced and also exhibited greatly increased efficiency, as compared with the Comparative Examples. From this, it can be seen that energy transfer from the host to the red dopant was well performed. In addition, the organic light emitting devices of the Examples exhibited greatly improved lifetime characteristics while maintaining high efficiency compared to the Comparative Examples, which is considered to be because the compounds of the present disclosure have higher stability to electrons and holes than the compounds used in the Comparative Examples.

In conclusion, when the compounds of the present disclosure are used as hosts for the red light emitting layer, it can be confirmed that the driving voltage, luminous efficiency, and lifetime characteristics of the organic light emitting device can be improved. In general, considering that the luminous efficiency and lifetime characteristics of an organic light emitting devices have a trade-off relationship with each other, this can be considered that the organic light emitting devices of the Examples exhibit remarkably improved device characteristics as compared with the devices of the Comparative Examples.

| [Description of Symbols] | |
|---|---|
| 1: substrate | 2: anode |
| 3: organic material layer | 4: cathode |
| 5: hole injection layer | 6: hole transport layer |
| 7: electron blocking layer | 8: light emitting layer |
| 9: hole blocking layer | 10: electron injection and transport layer |

The invention claimed is:

1. A compound of Chemical Formula 1:

[Chemical Formula 1]

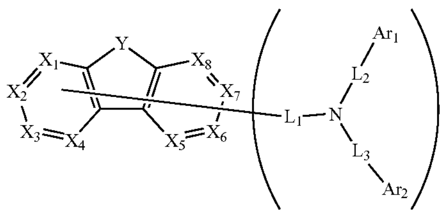

wherein:

one of $X_1$ to $X_8$ is N, and one of the rest is C bonded to $L_1$, and the rest are each independently CR;

R is hydrogen or deuterium;

Y is O or S;

$L_1$ is a single bond or

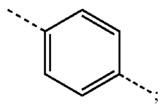

$L_2$ and $L_3$ are each independently a single bond, phenylene, or naphthylene;

$Ar_1$ and $Ar_2$ are each independently phenyl, biphenyl, terphenyl, quaterphenyl, naphthyl, binaphthyl, (naphthyl)phenyl, (phenyl)naphthyl, phenanthrenyl, triphenylenyl, chrysenyl, tetracenyl, benz[a]anthracenyl, benzo[c]phenanthrenyl, fluorenyl, 9,9-dimethylfluorenyl, 9,9-diphenylfluorenyl, spirobifluorenyl, fluoranthenyl, dibenzothiophenyl, dibenzofuranyl, carbazolyl or 9-phenylcarbazolyl, with the proviso that $Ar_1$ and $Ar_2$ are not phenyl at the same time; and $Ar_1$ and $Ar_2$ are each independently unsubstituted or substituted with at least one of deuterium, a $C_{1-20}$ alkyl, a $C_{3-20}$ cycloalkyl, or phenyl.

2. The compound of claim 1, wherein:

the Chemical Formula 1 is the following Chemical Formula 1-1 or 1-2:

[Chemical Formula 1-1]

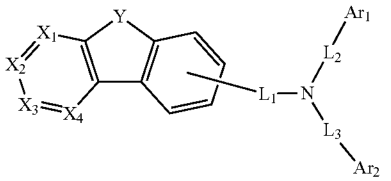

wherein, in Chemical Formula 1-1:

one of $X_1$ to $X_4$ is N, and one of the rest is C bonded to $L_1$, and the rest are each independently CR; and R, Y, $L_1$, $L_2$, $L_3$, $Ar_1$, and $Ar_2$ are as defined in claim 1;

[Chemical Formula 1-2]

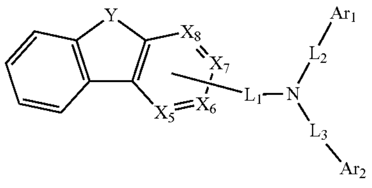

wherein, in Chemical Formula 1-2:

one of $X_5$ to $X_8$ is N, and one of the rest is C bonded to $L_1$, and the rest are each independently CR; and R, Y, $L_1$, $L_2$, $L_3$, $Ar_1$, and $Ar_2$ are as defined in claim 1.

3. The compound of claim 1, wherein:

R is hydrogen.

4. The compound of claim 1, wherein:

$Ar_1$ is phenyl, biphenyl, terphenyl, quaterphenyl, naphthyl, binaphthyl, (naphthyl)phenyl, (phenyl)naphthyl, phenanthrenyl, or triphenylenyl; and $Ar_2$ is phenyl, biphenyl, terphenyl, quaterphenyl, naphthyl, binaphthyl, (naphthyl)phenyl, (phenyl)naphthyl, phenanthrenyl, triphenylenyl, chrysenyl, tetracenyl, benz[a]anthracenyl, benzo[c]phenanthrenyl, fluorenyl, 9,9-dimethylfluorenyl, 9,9-diphenylfluorenyl, spirobifluorenyl, fluoranthenyl, dibenzothiophenyl, dibenzofuranyl, carbazolyl or 9-phenylcarbazolyl.

5. The compound of claim 1, wherein:

$Ar_1$ and $Ar_2$ are each independently unsubstituted or substituted with one or two of deuterium, methyl, adamantyl, or phenyl.

6. The compound of claim 1, wherein:

the compound of Chemical Formula 1 is any one compound selected from the group consisting of the following:

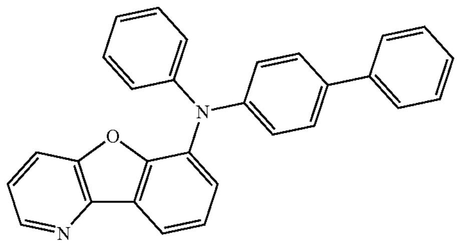

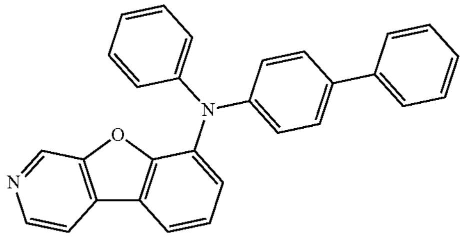

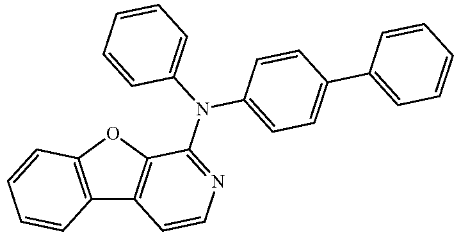

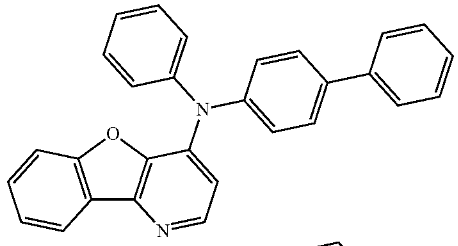

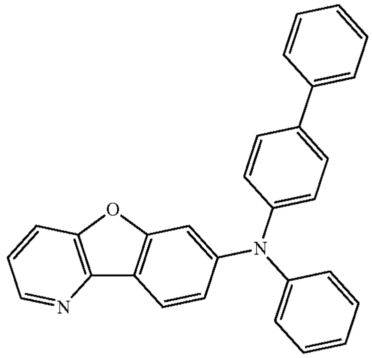

-continued
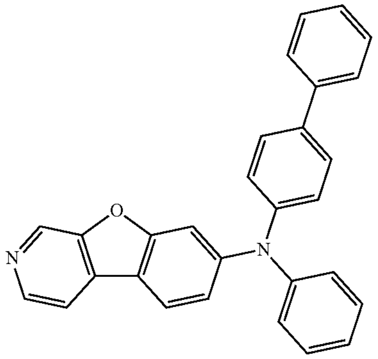
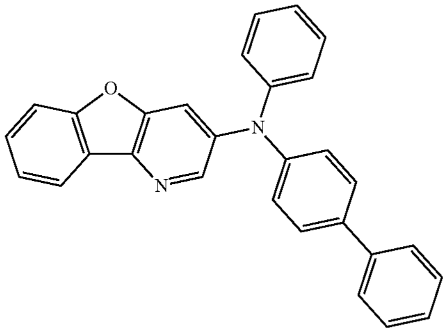
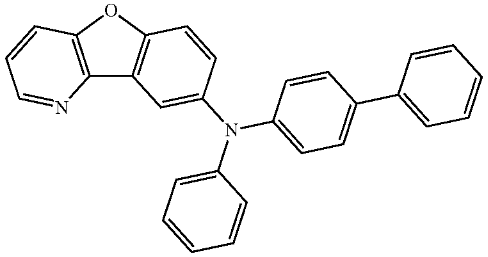
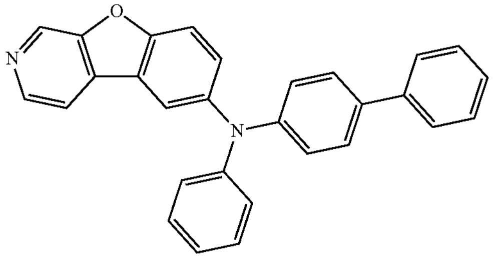
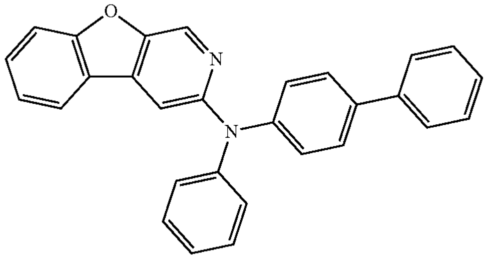
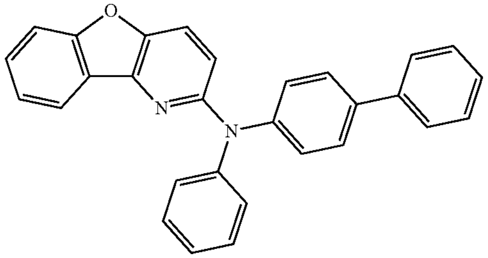
-continued
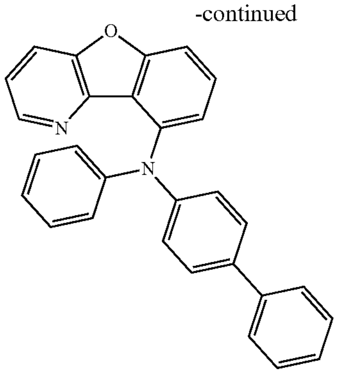
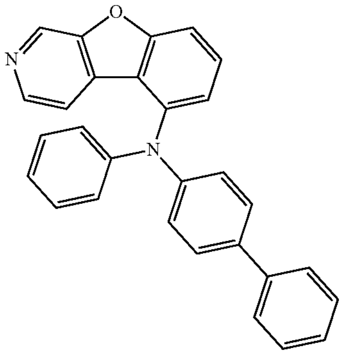
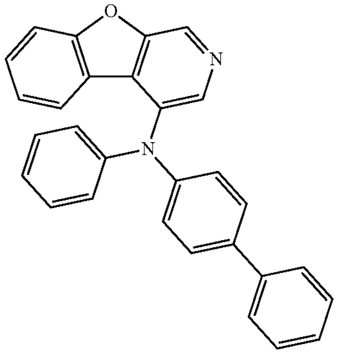
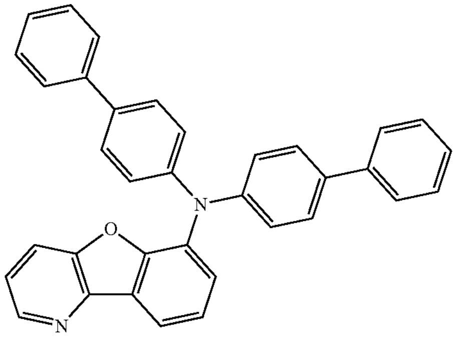
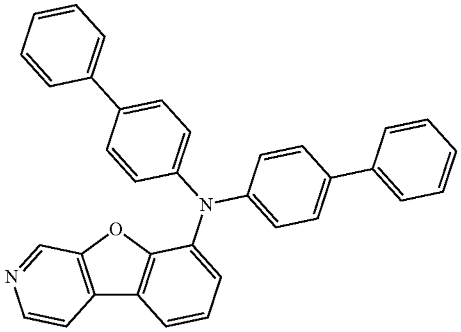

-continued
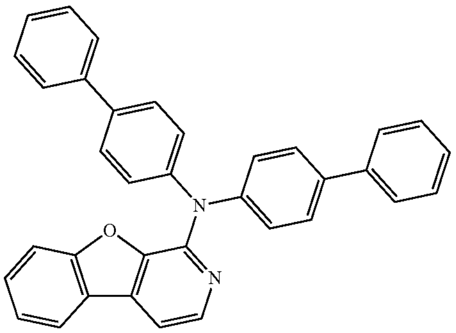
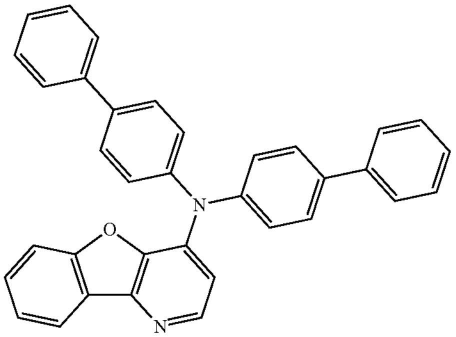
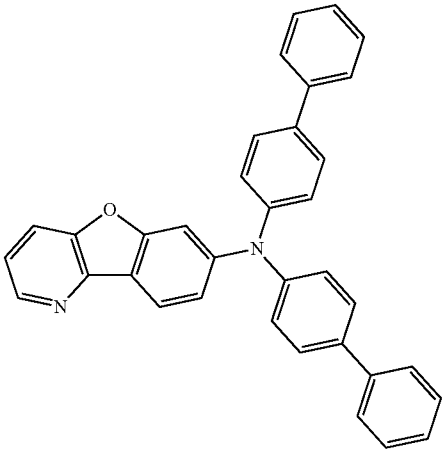
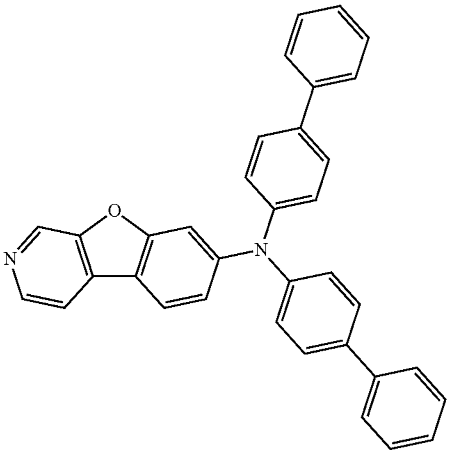
-continued
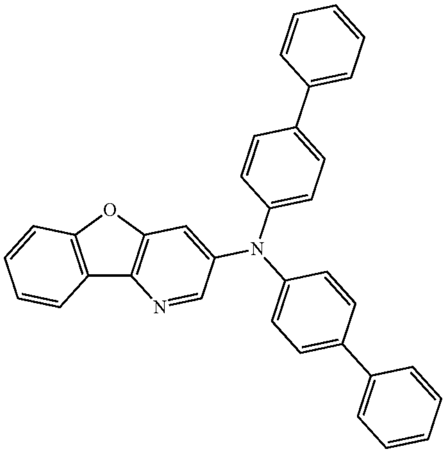
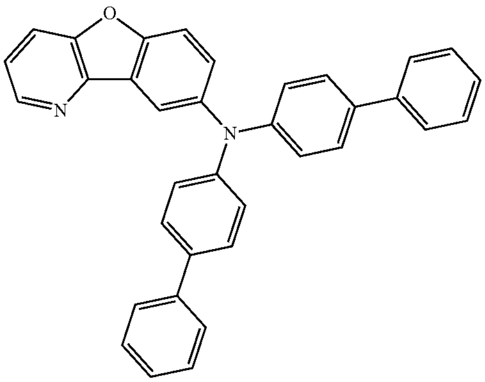
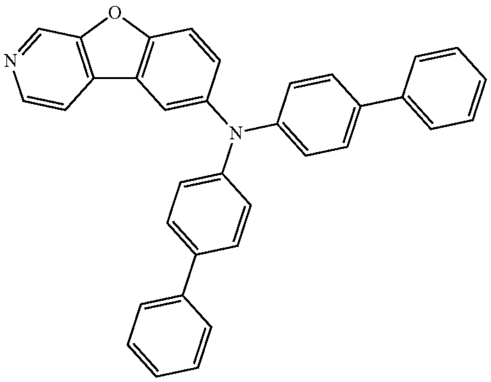
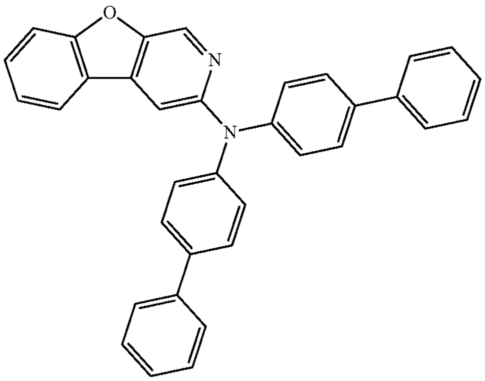

-continued
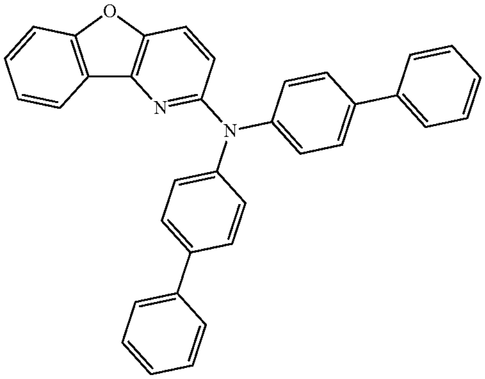
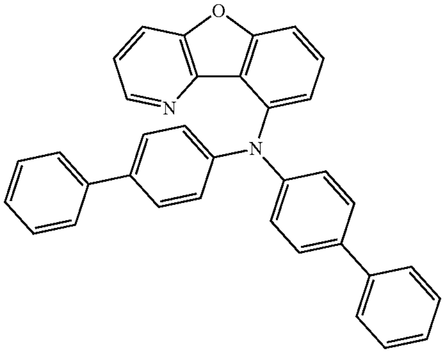
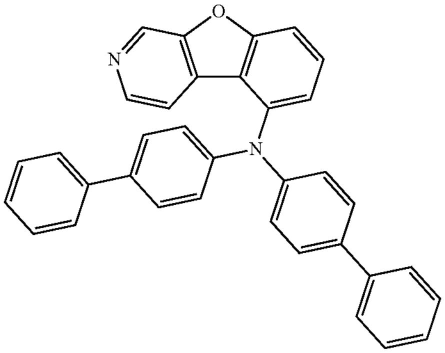
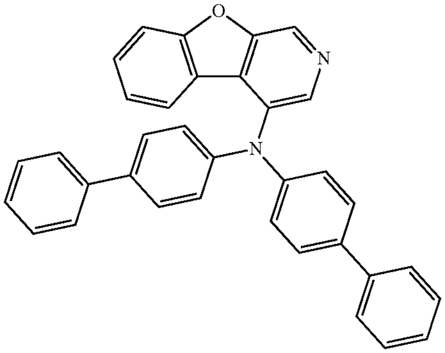
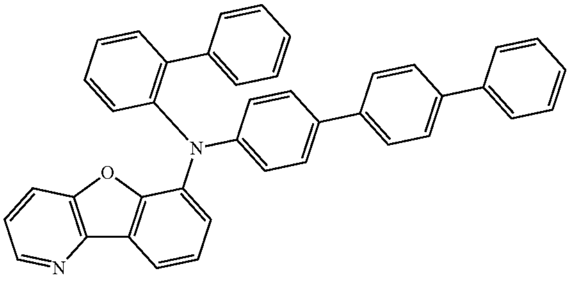
-continued
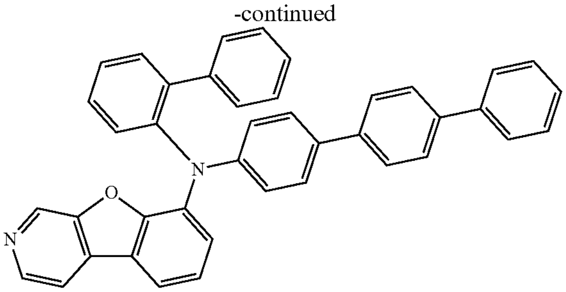
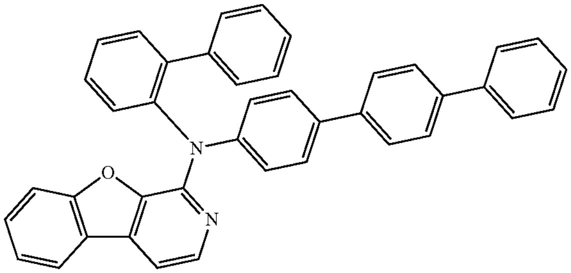
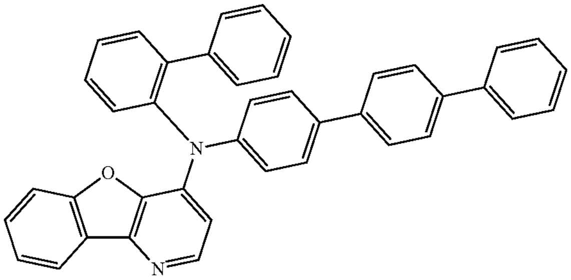
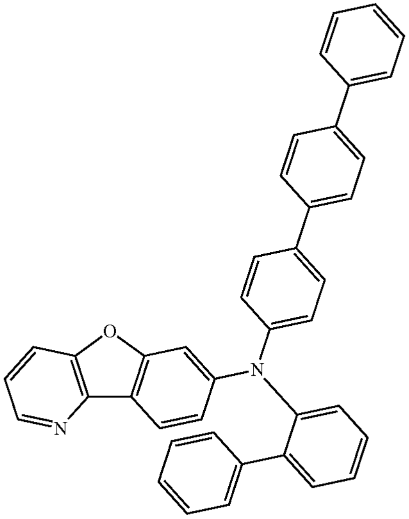

-continued
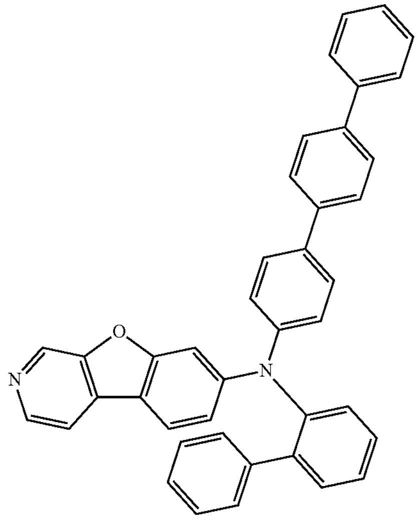
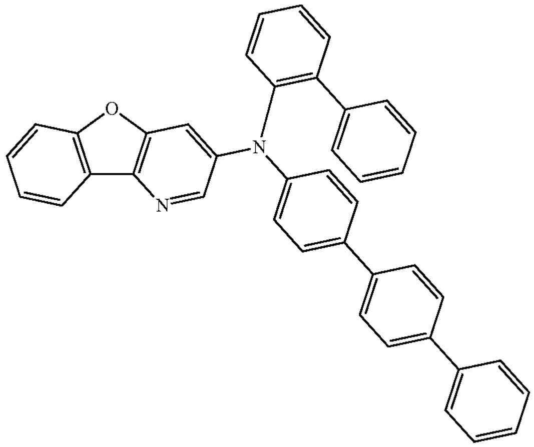
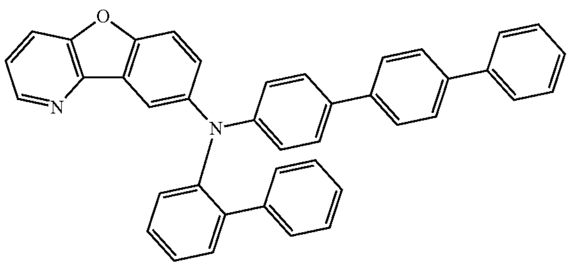
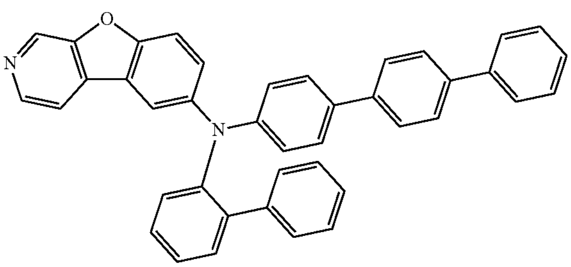
-continued
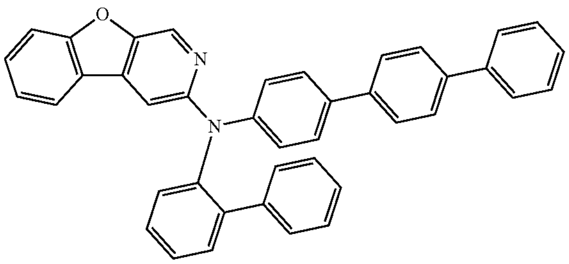
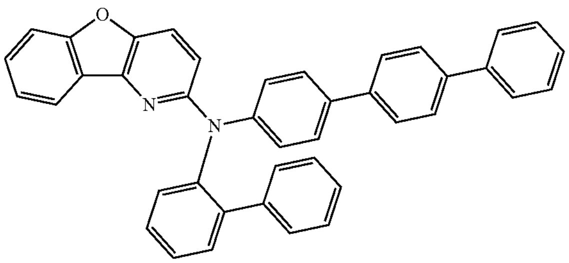
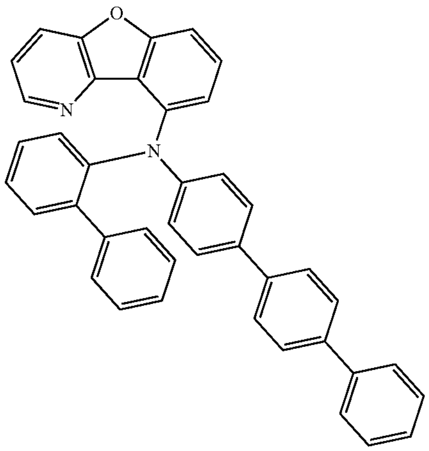
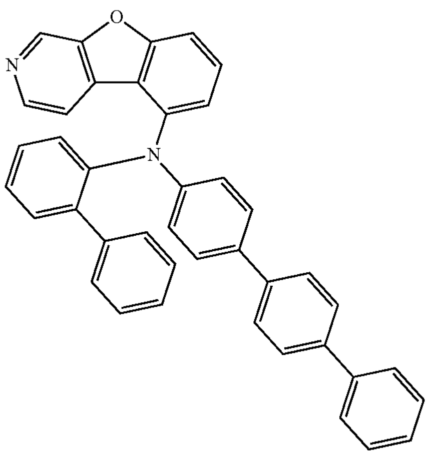

-continued
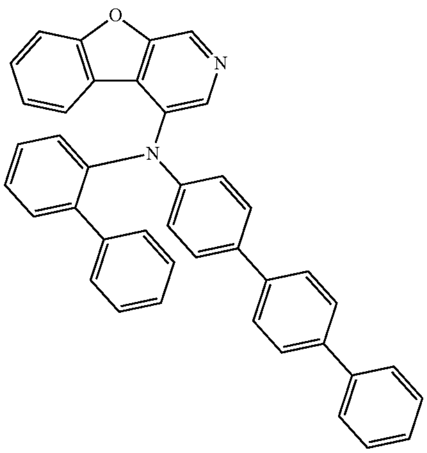
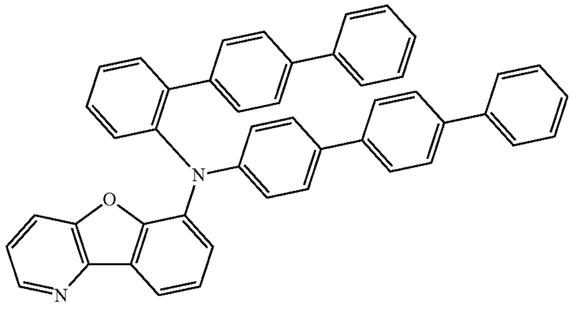
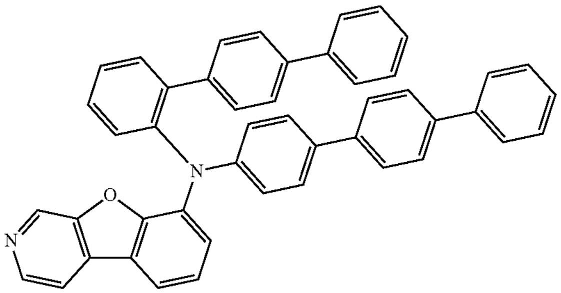
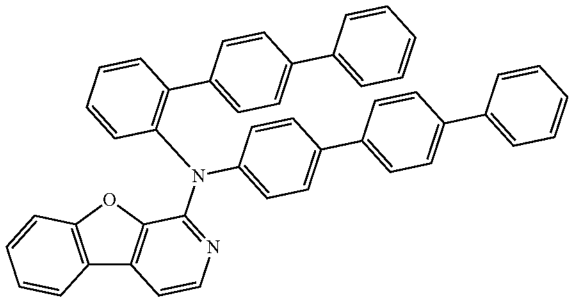
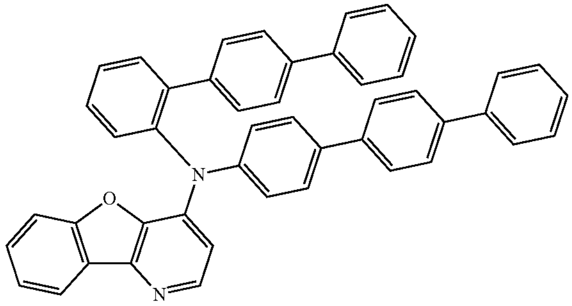
-continued
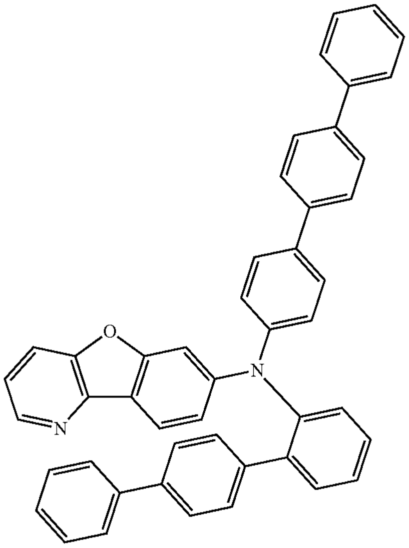
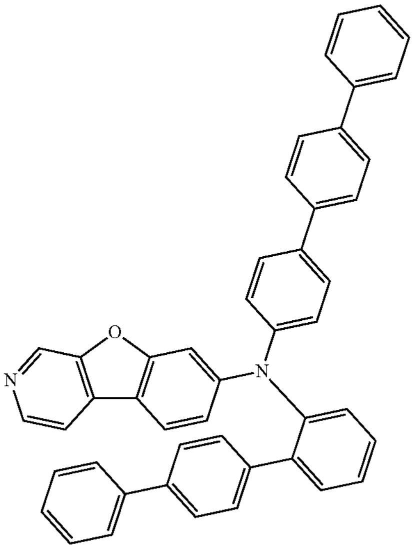
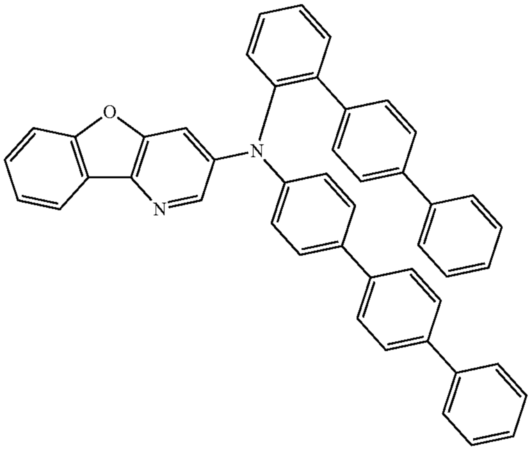

-continued
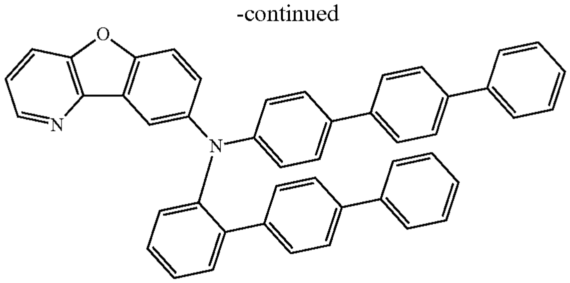
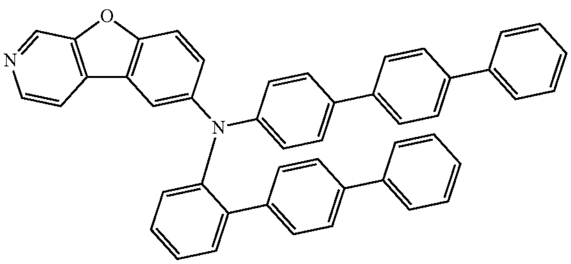
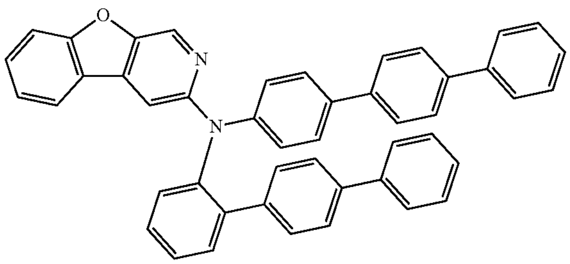
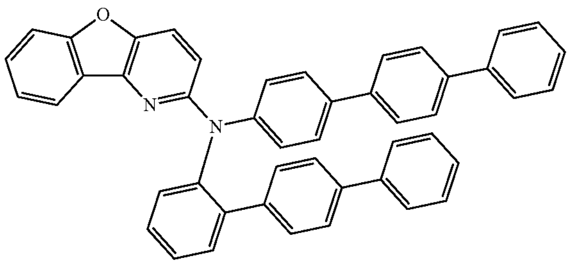
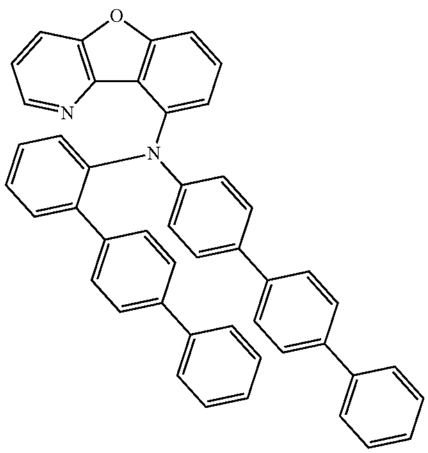
-continued
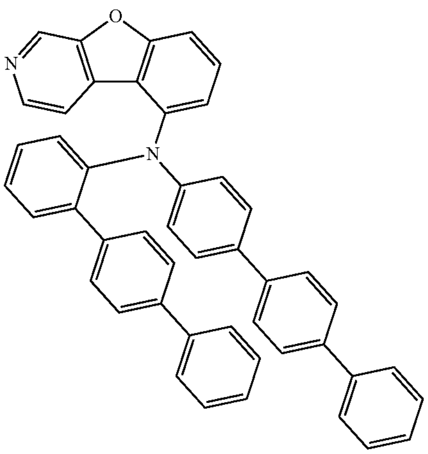
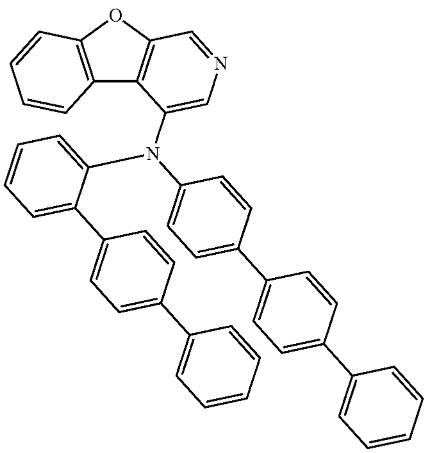
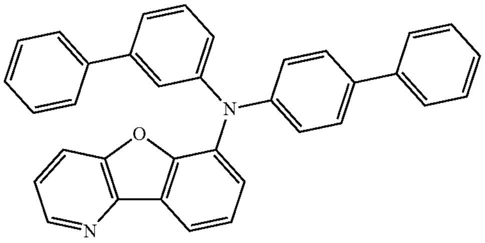
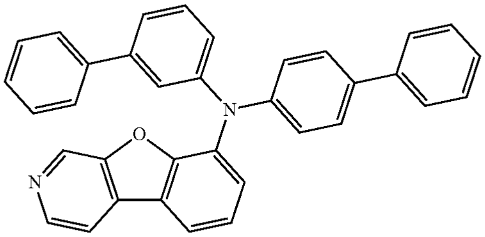
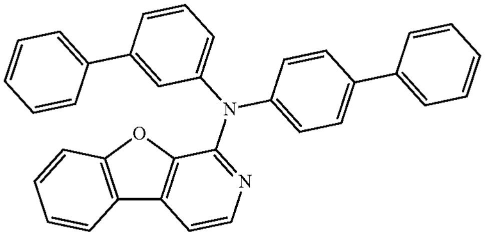

-continued
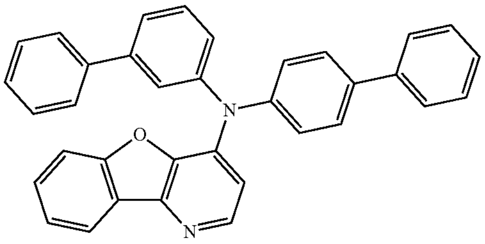
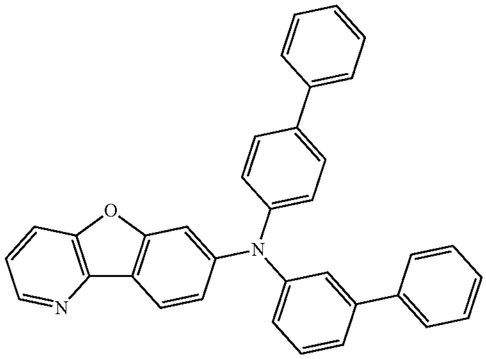
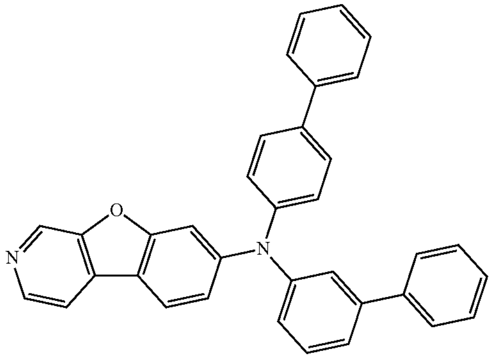
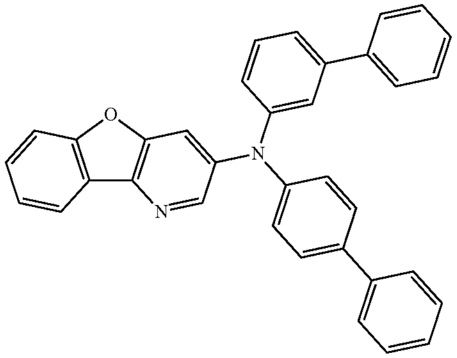
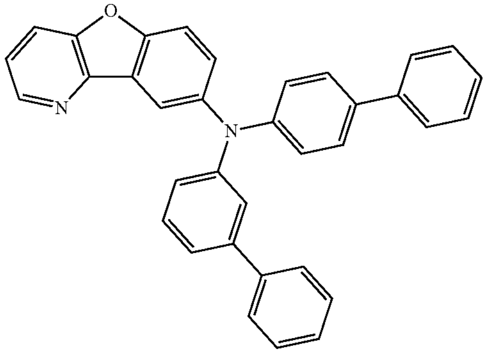
-continued
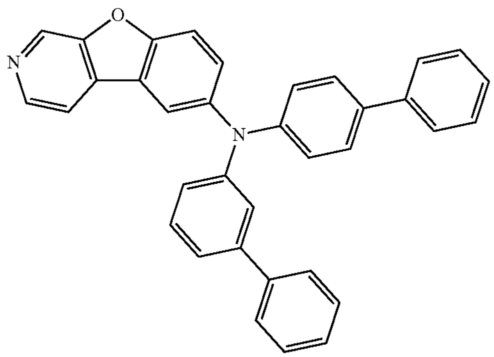
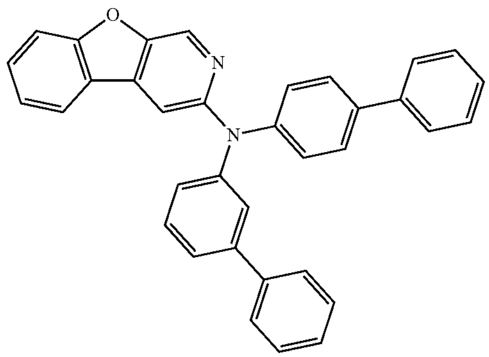
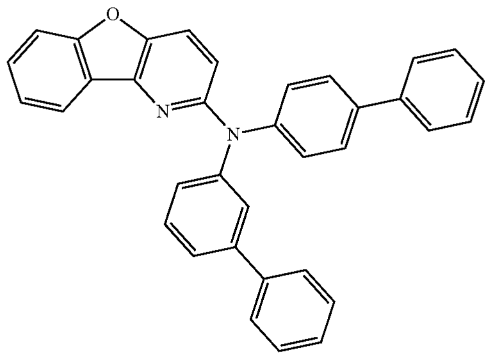
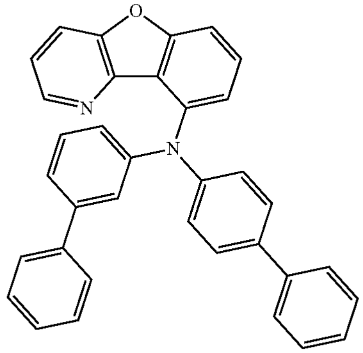

-continued
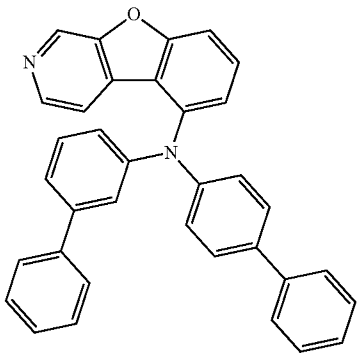
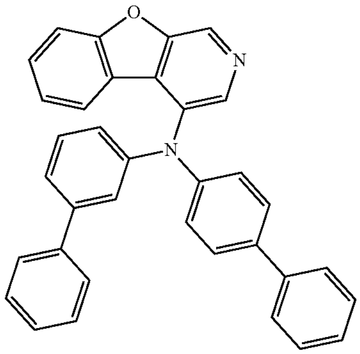
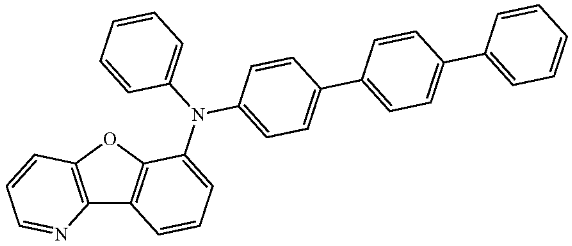
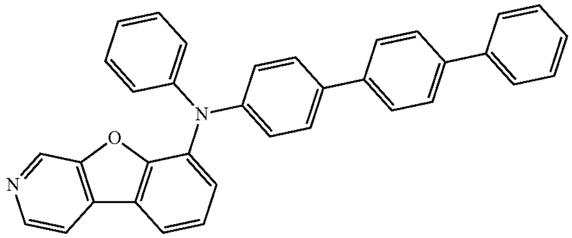
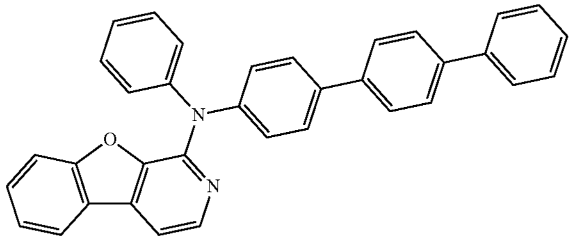
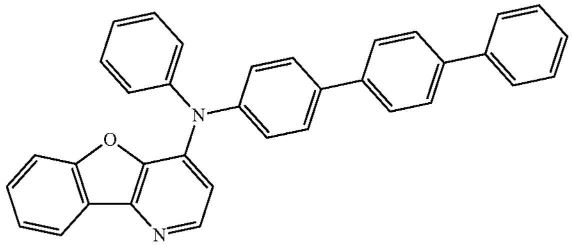
-continued
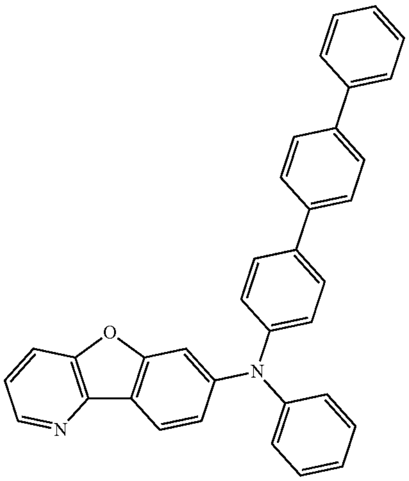
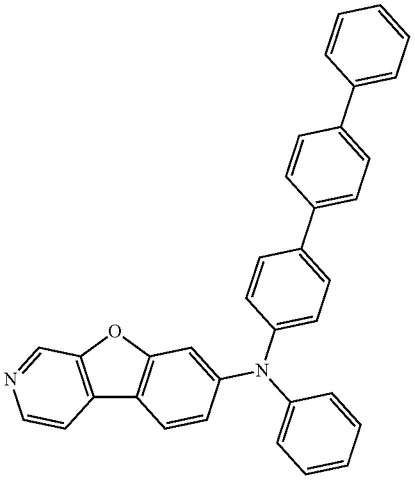
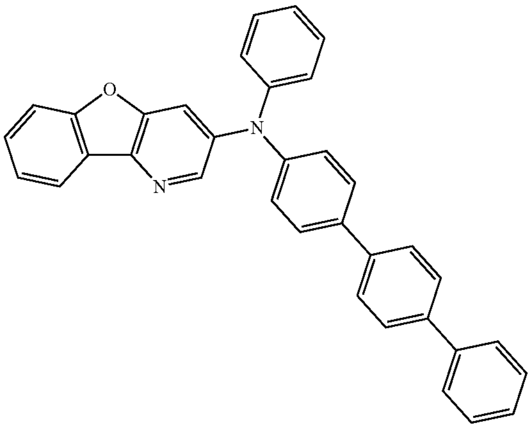
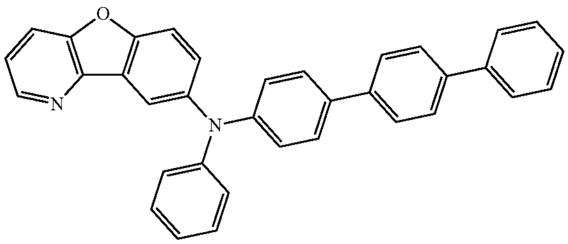

-continued
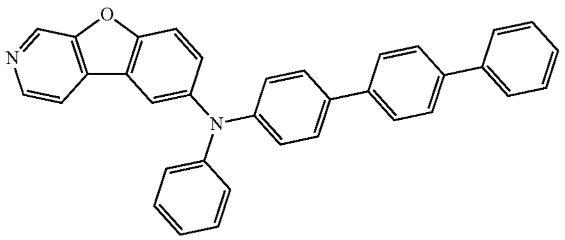
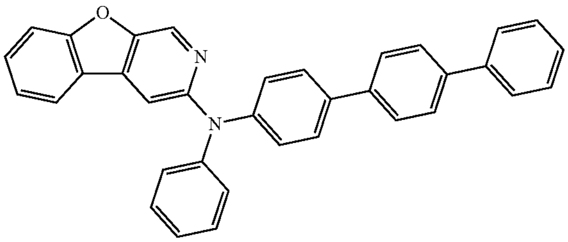
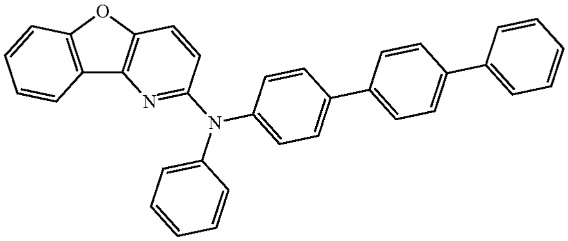
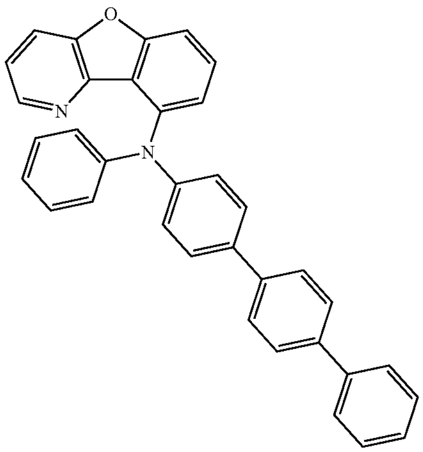
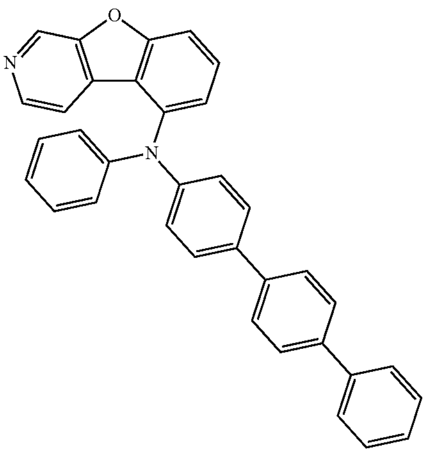
-continued
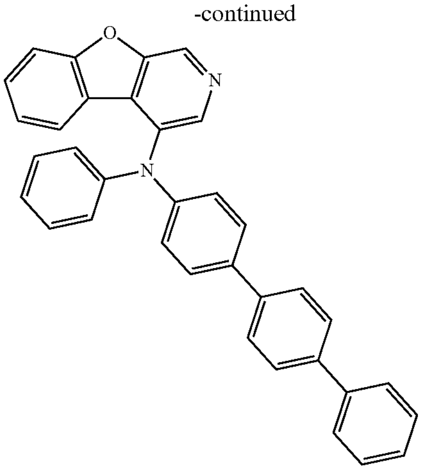
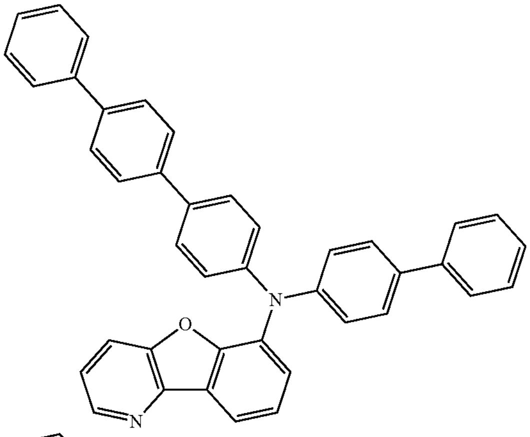
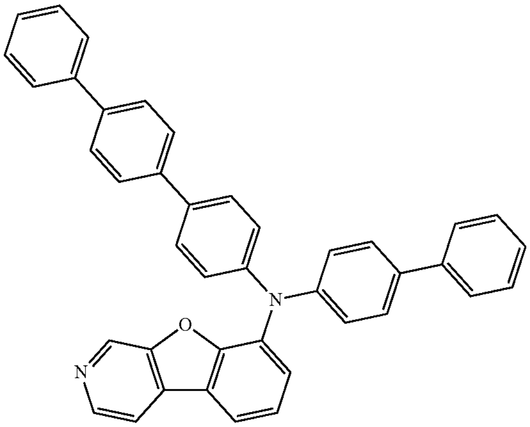
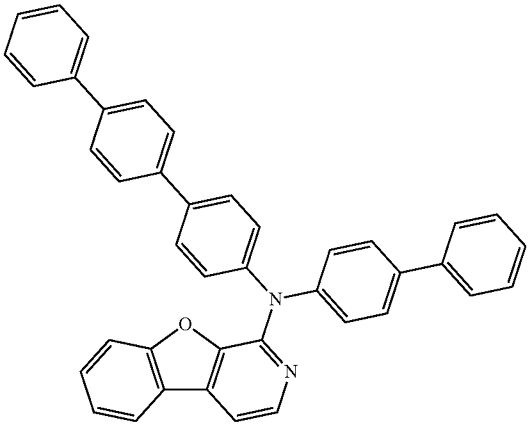

-continued
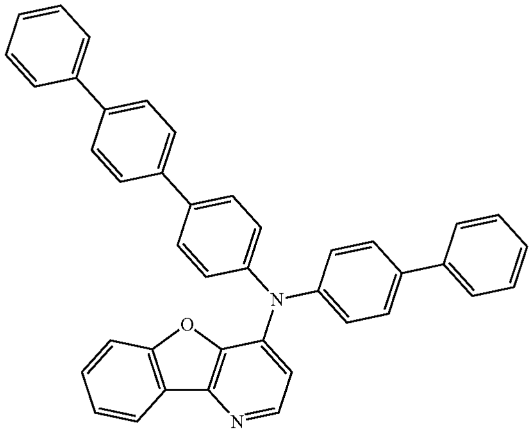
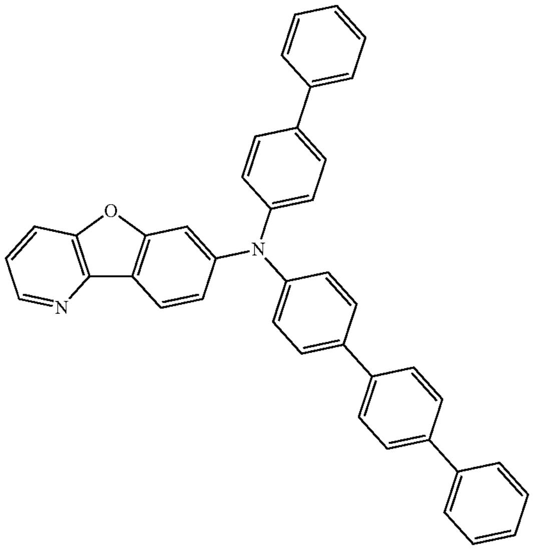
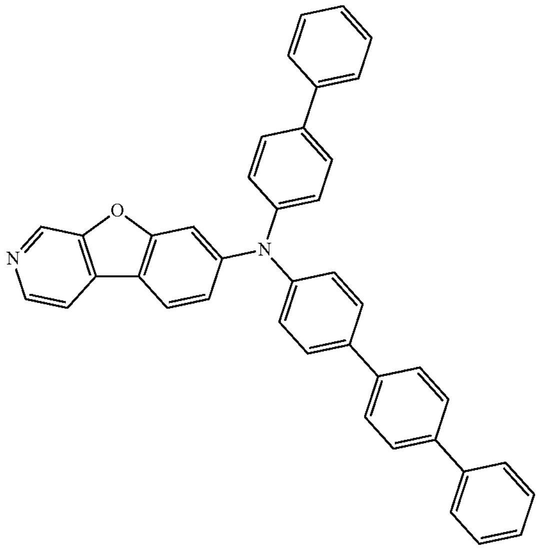
-continued
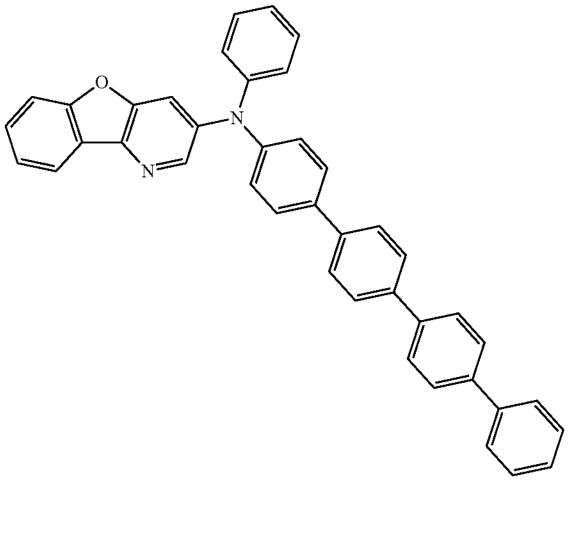
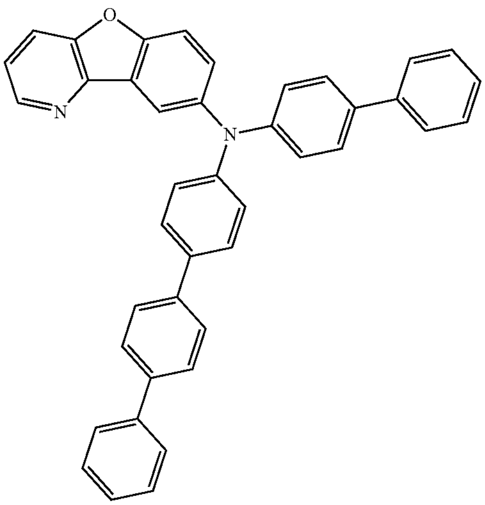
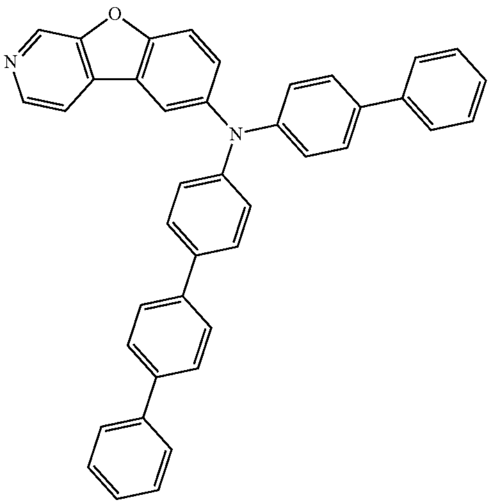

-continued
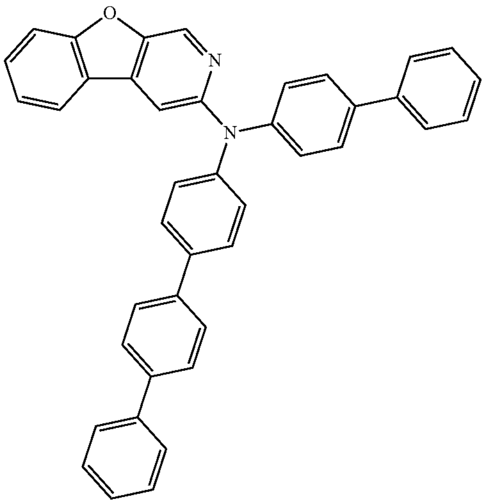
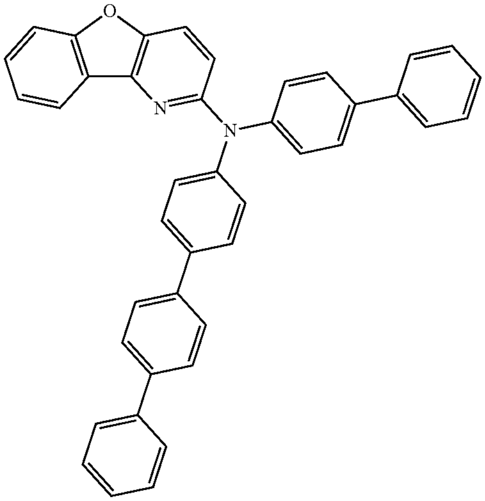
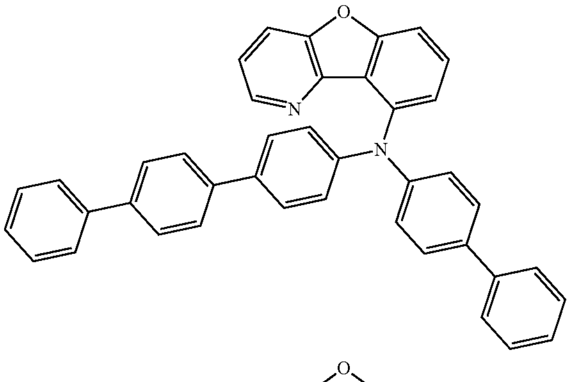
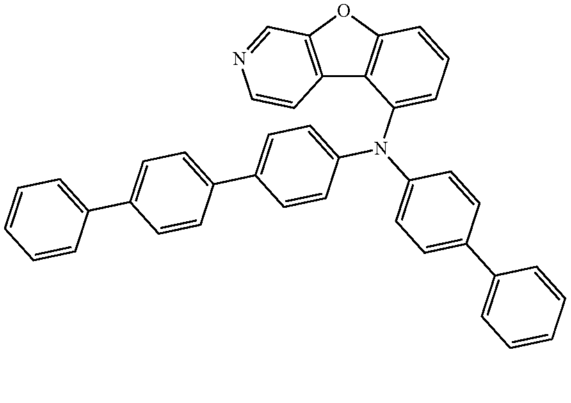
-continued
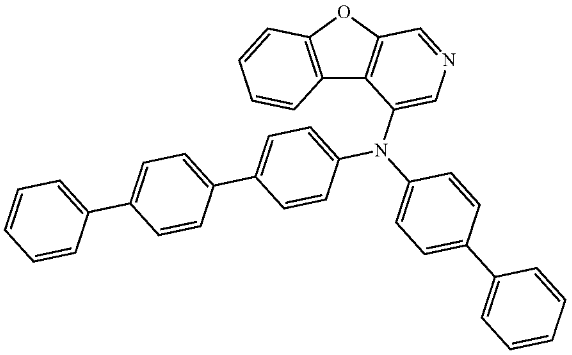
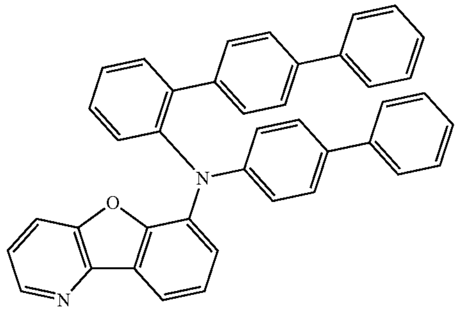
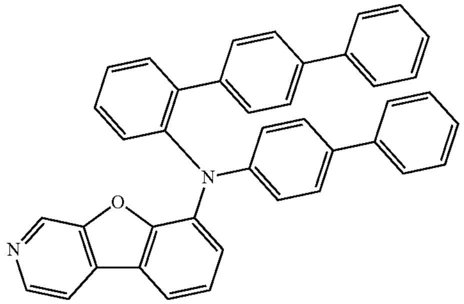
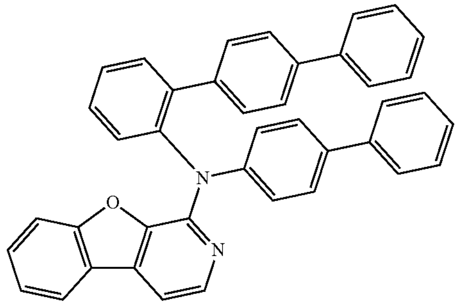
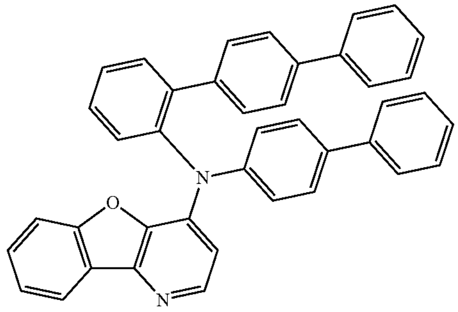

-continued
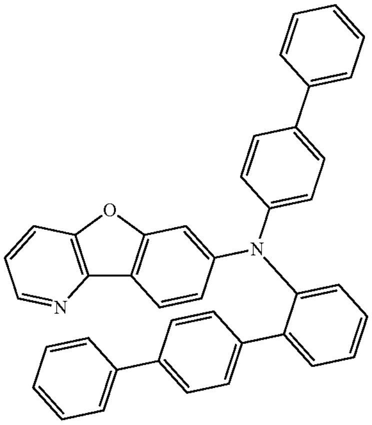
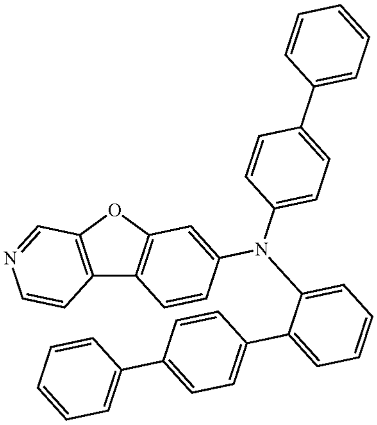
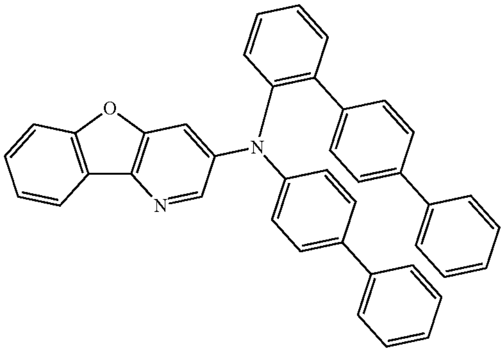
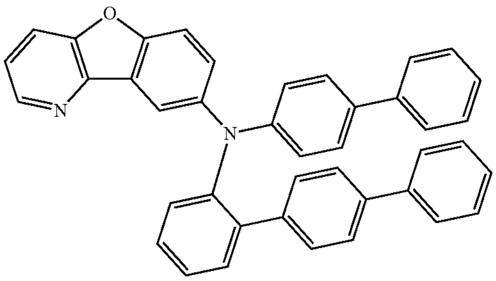
-continued
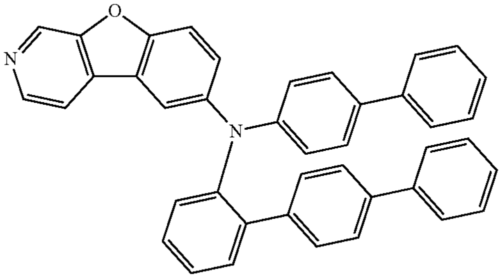
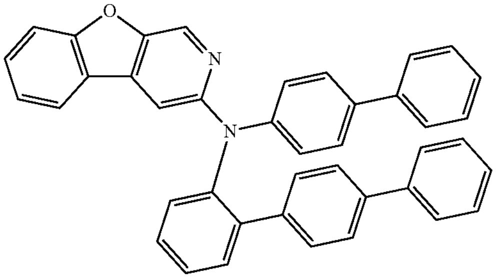
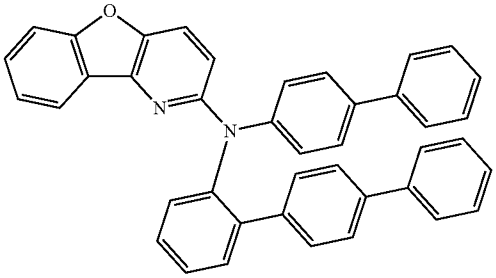
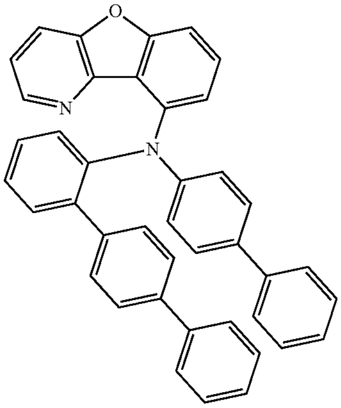
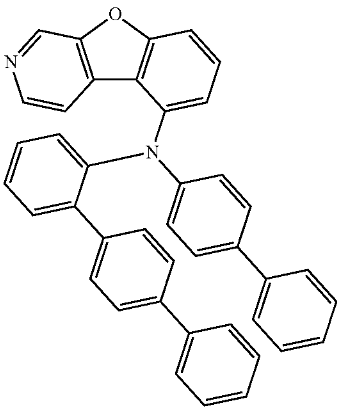

-continued
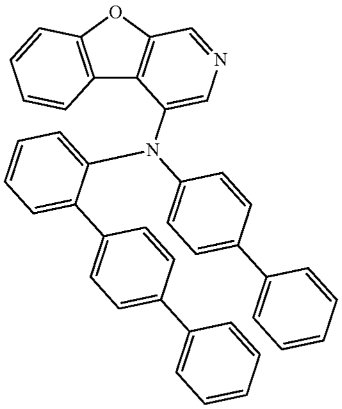
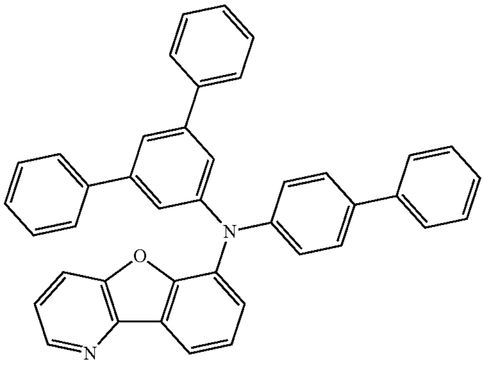
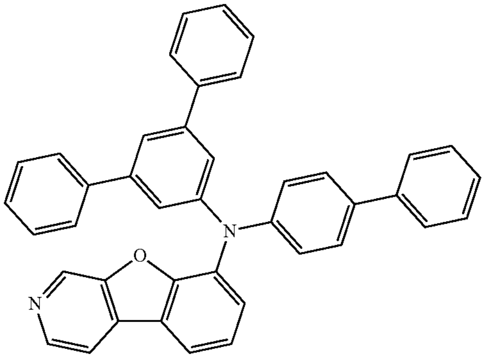
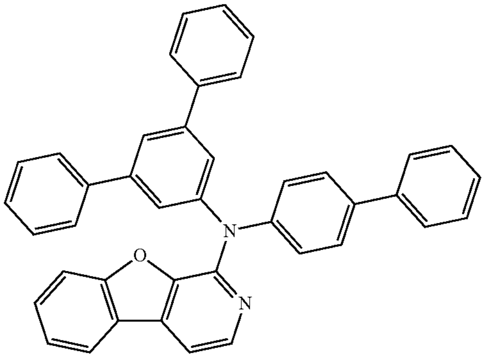
-continued
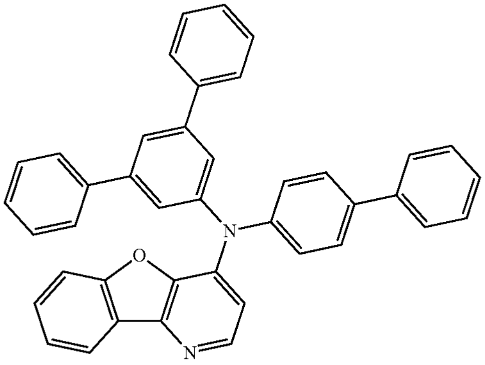
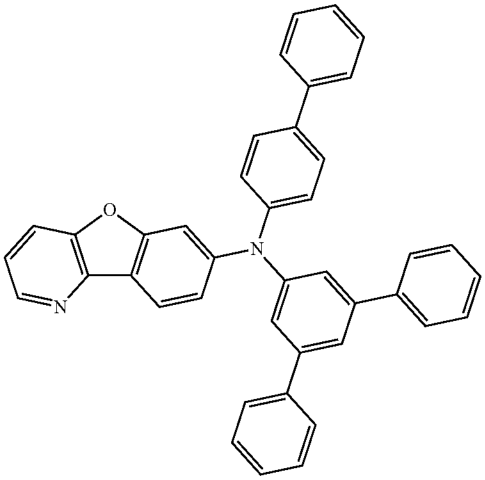
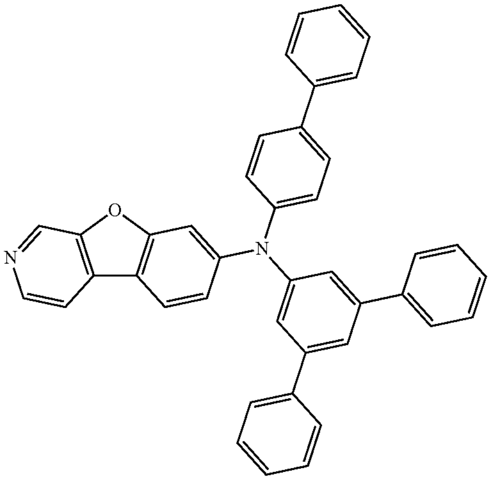

-continued
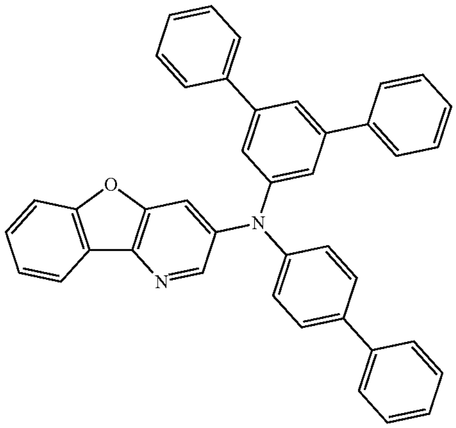
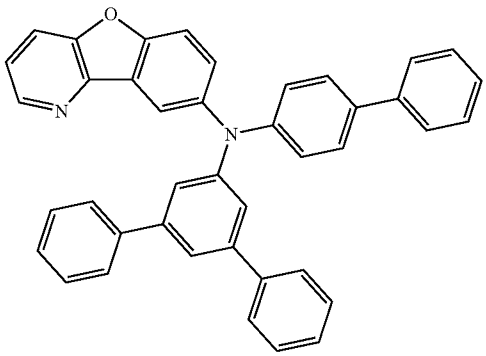
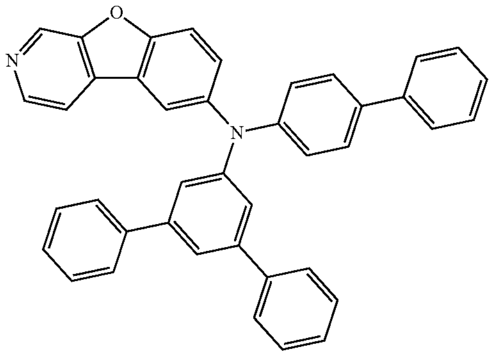
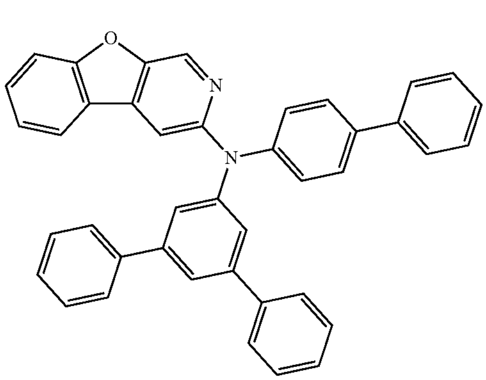
-continued
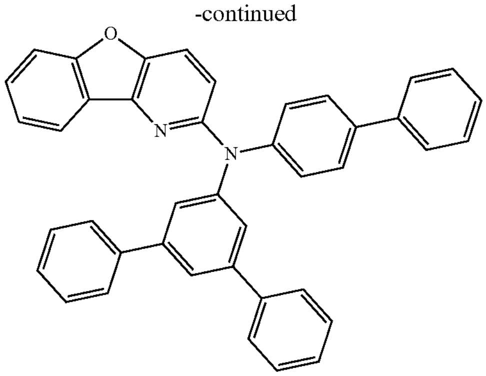
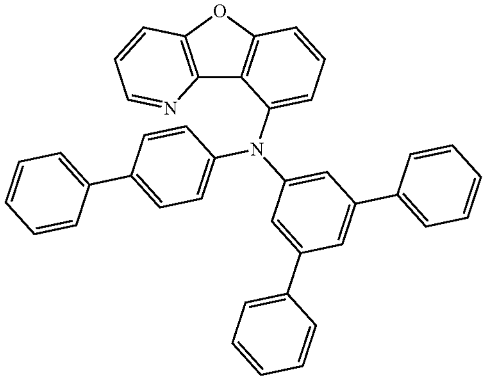
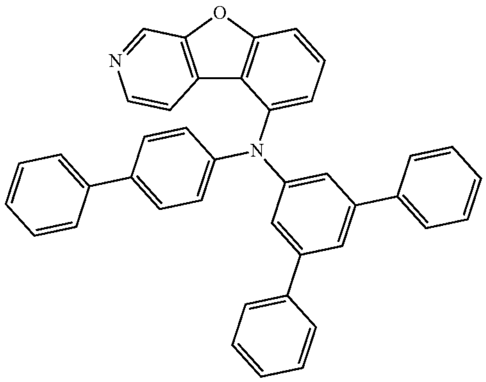
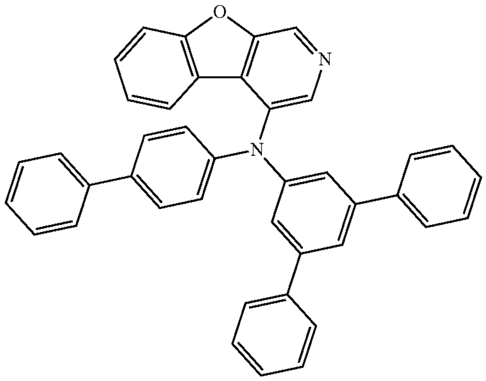

-continued
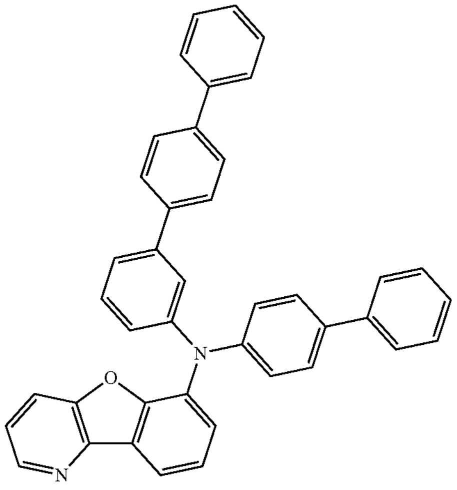
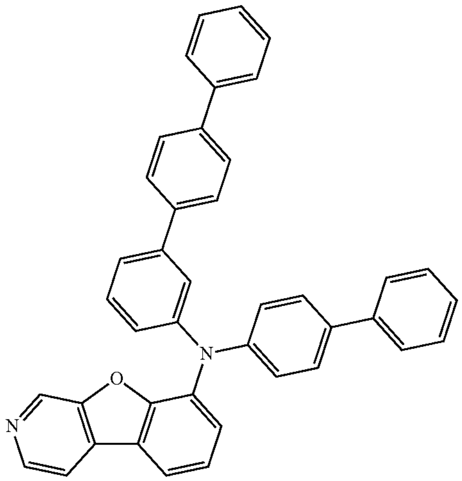
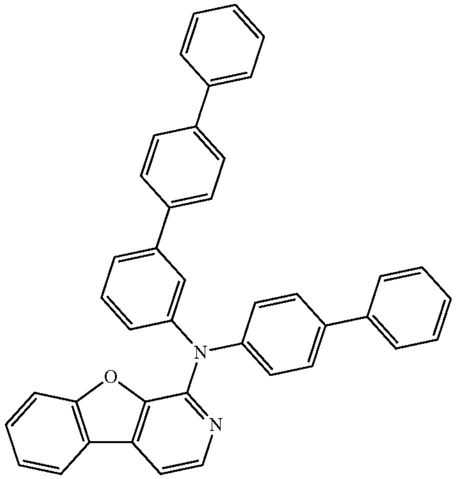
-continued
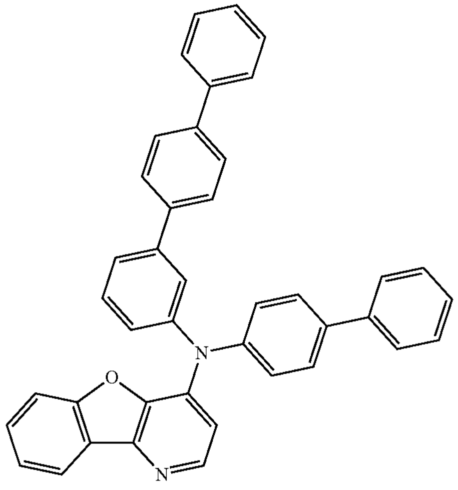
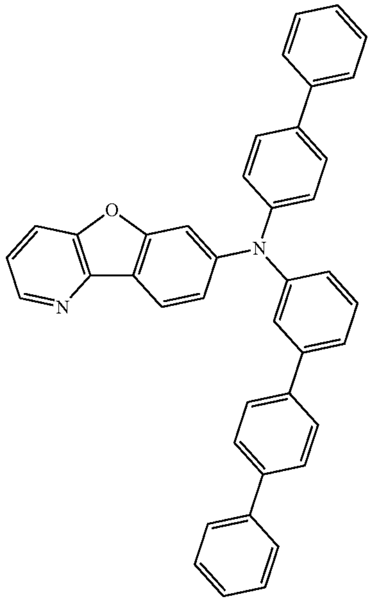
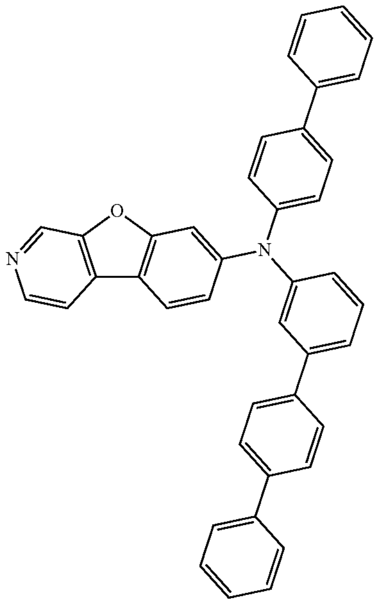

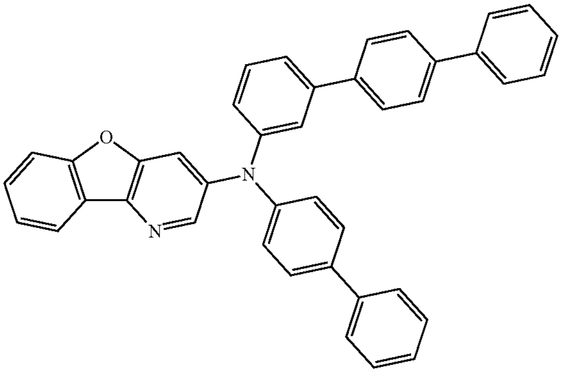
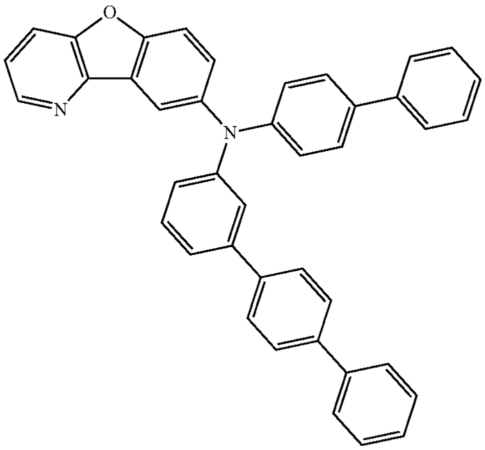
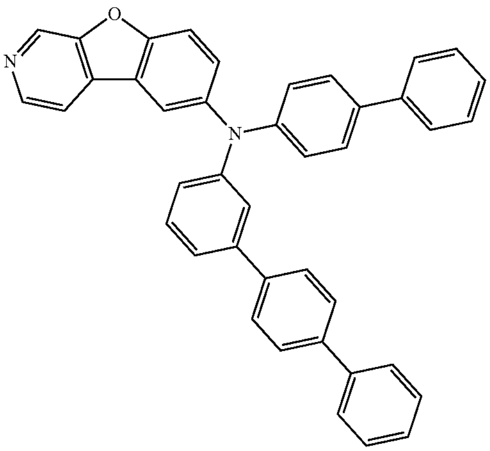
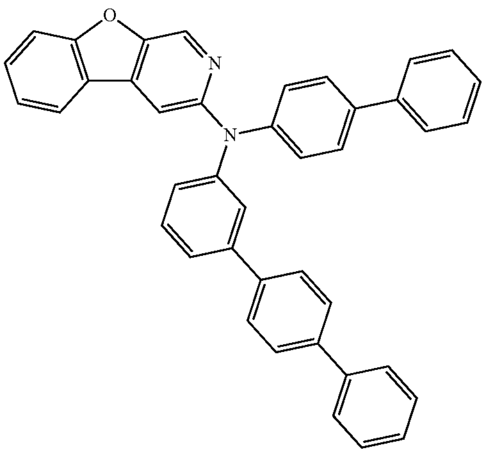
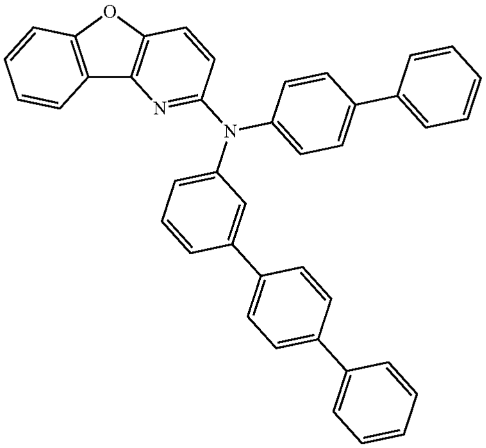
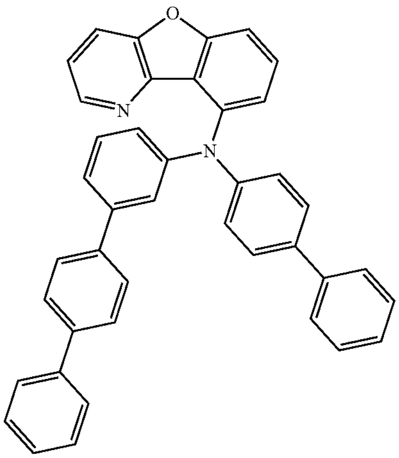
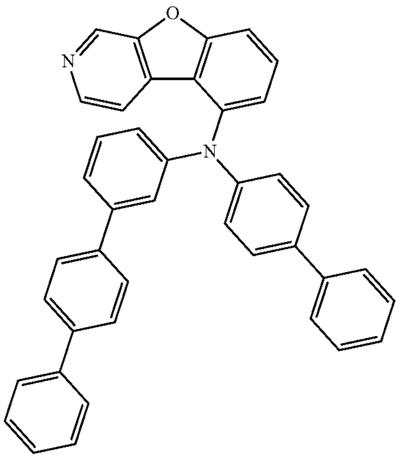

-continued
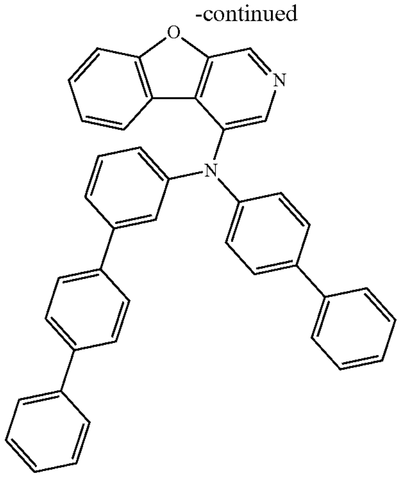
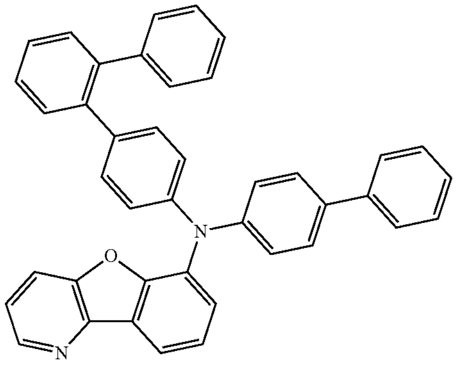
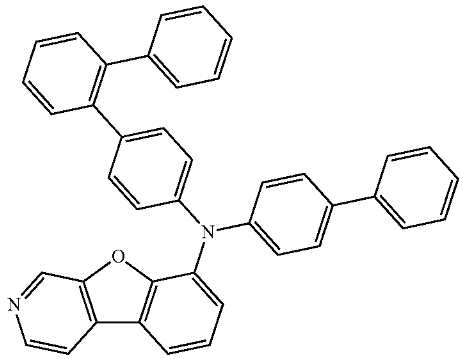
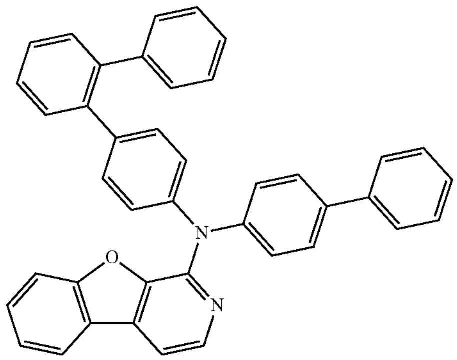
-continued
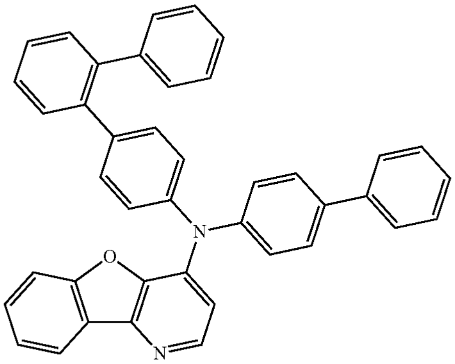
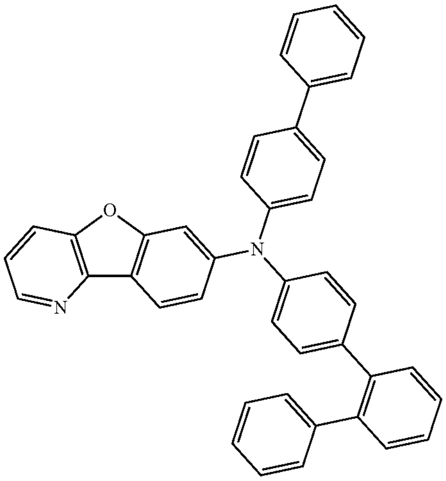
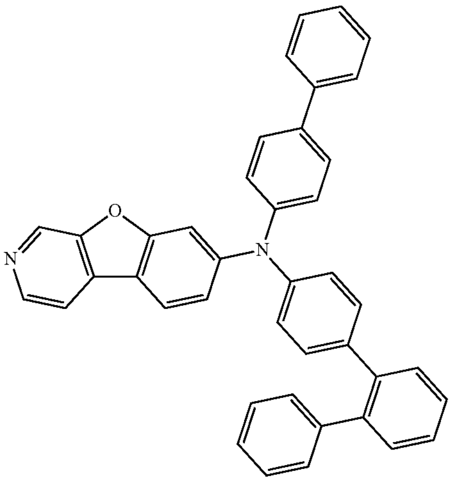

-continued
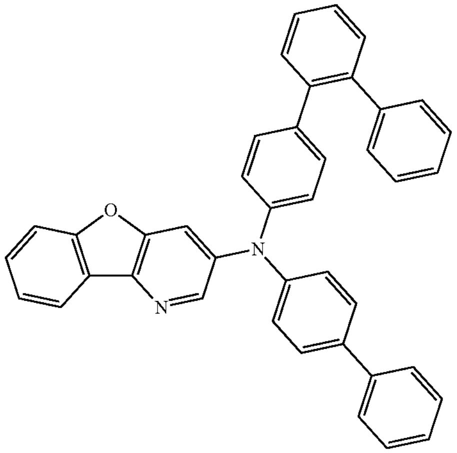
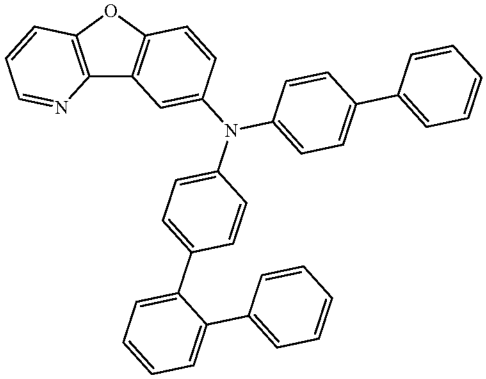
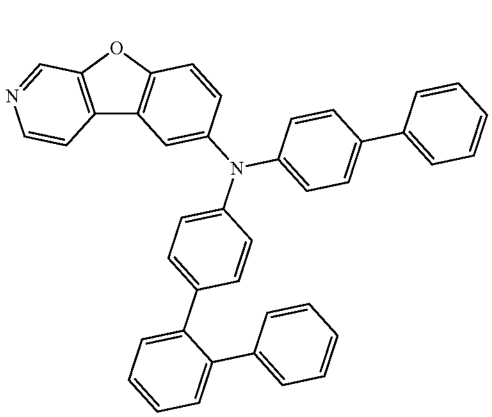
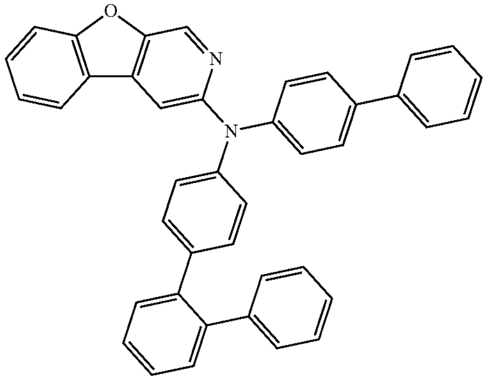
-continued
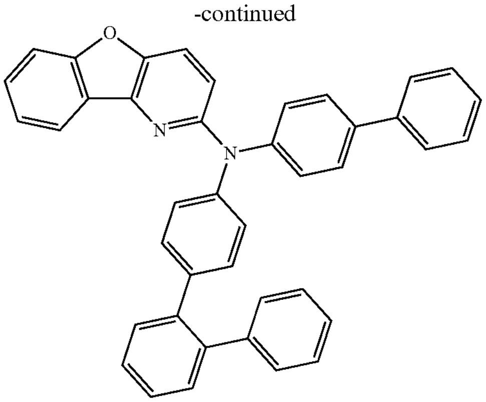
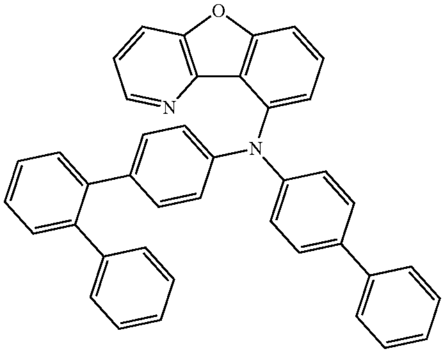
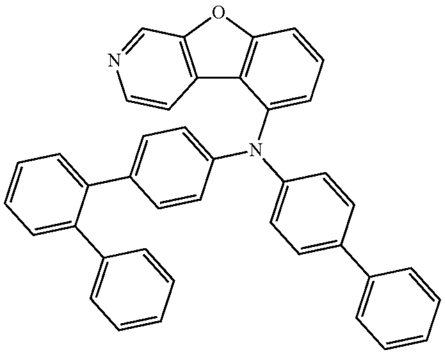
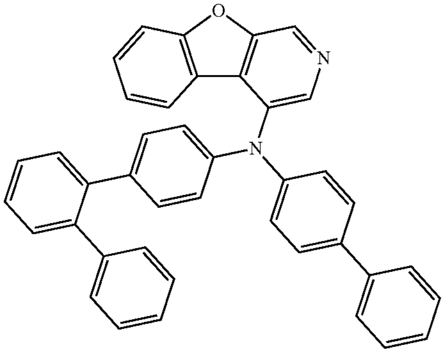

-continued
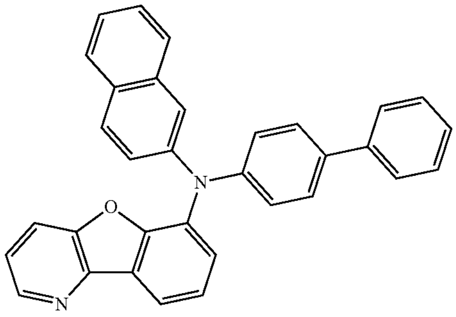
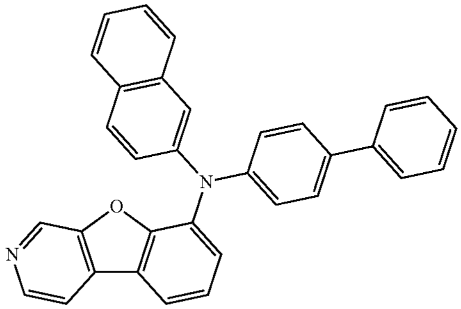
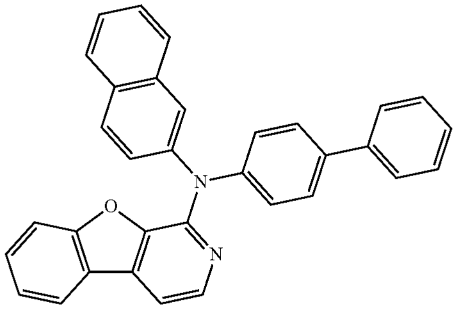
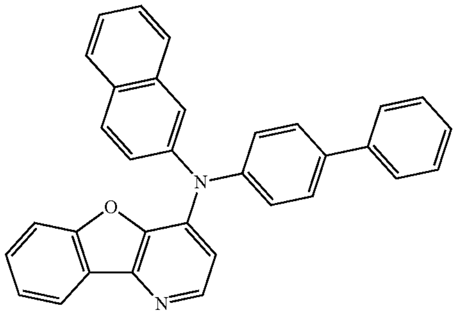
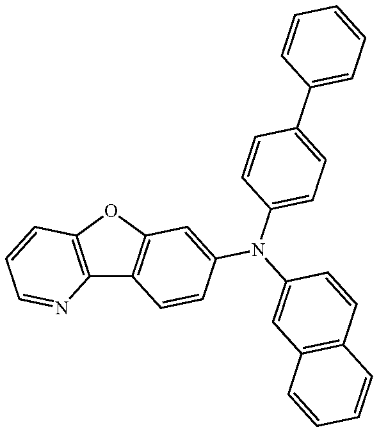
-continued
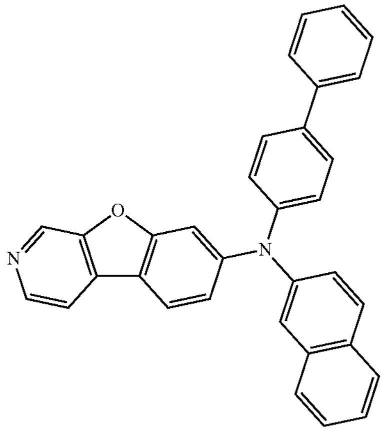
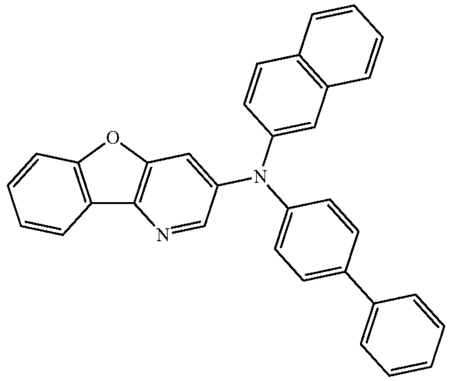
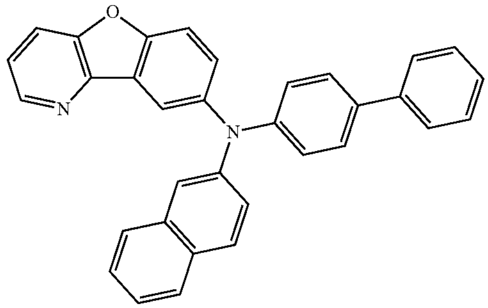
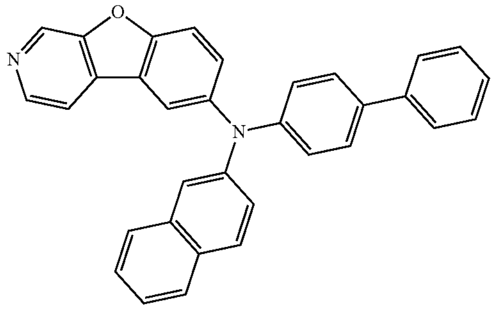
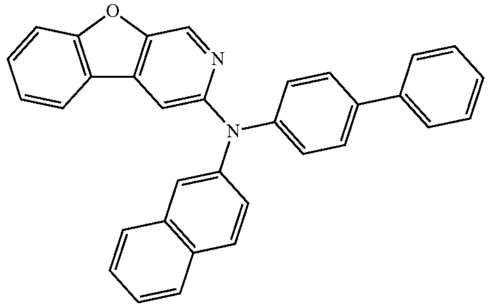

-continued
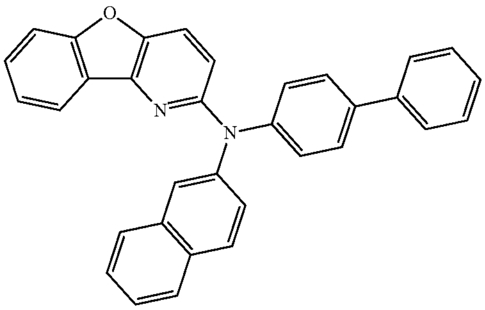
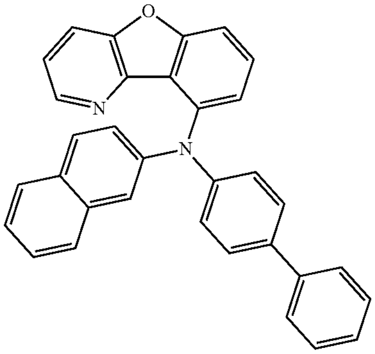
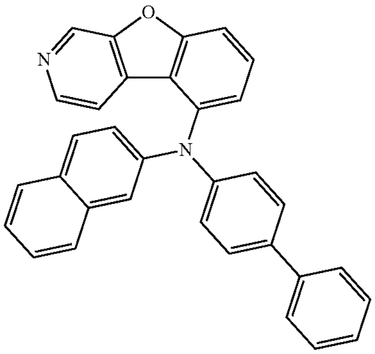
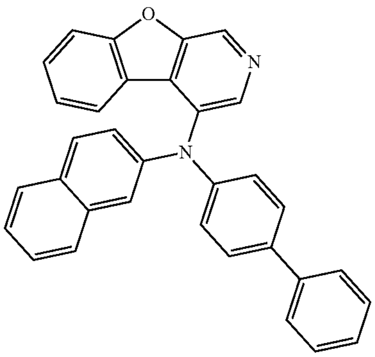
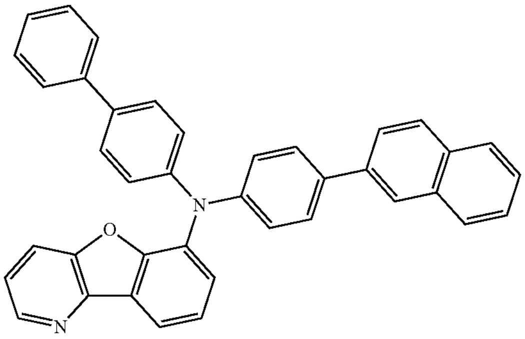
-continued
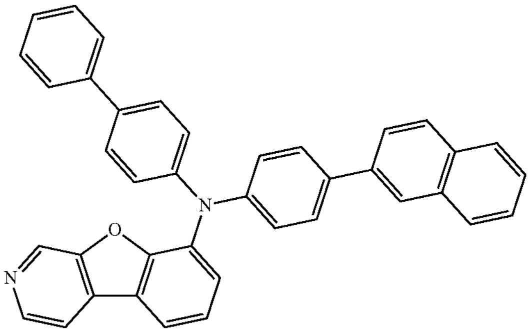
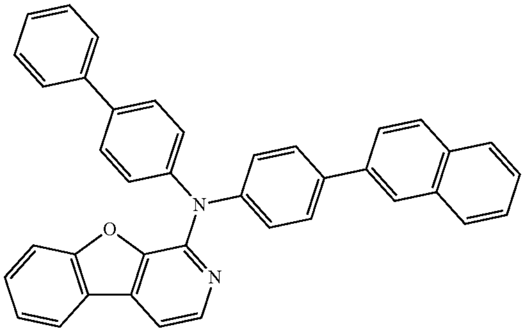
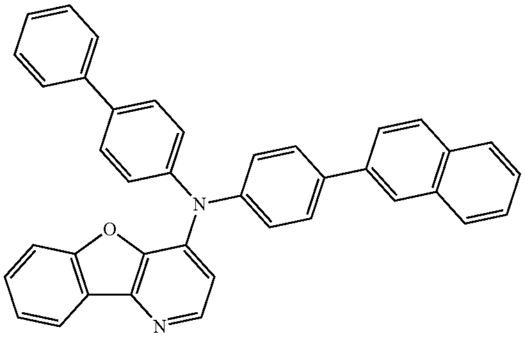
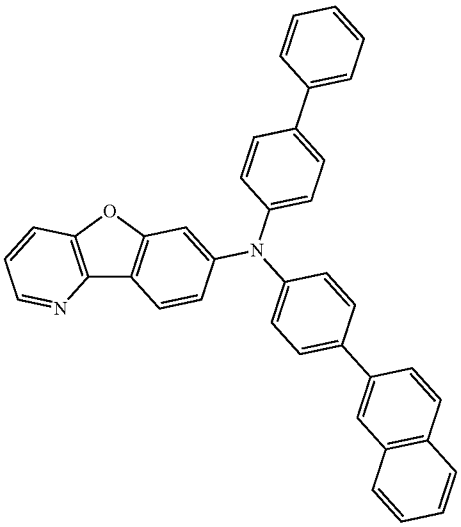

-continued
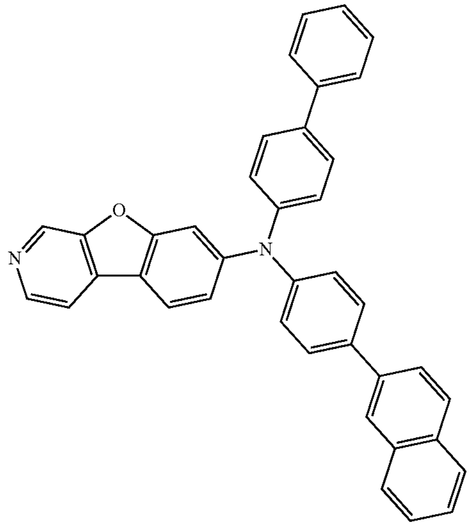
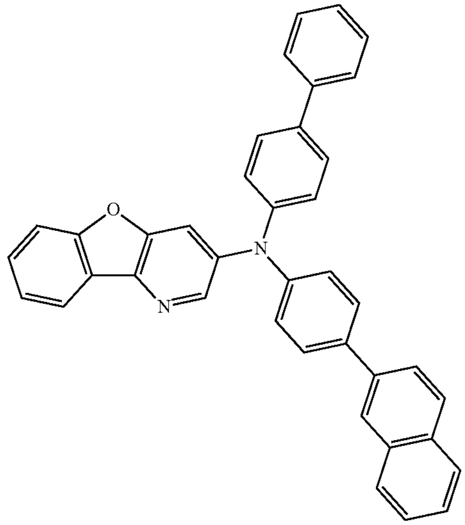
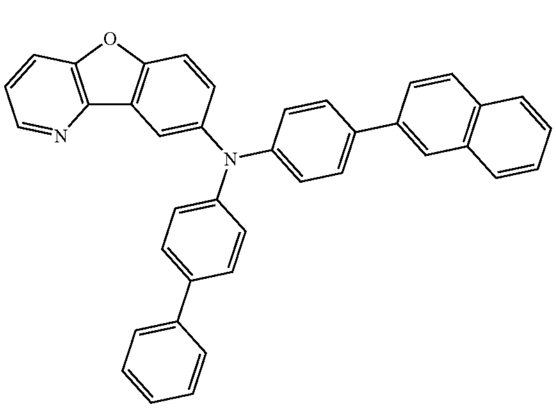
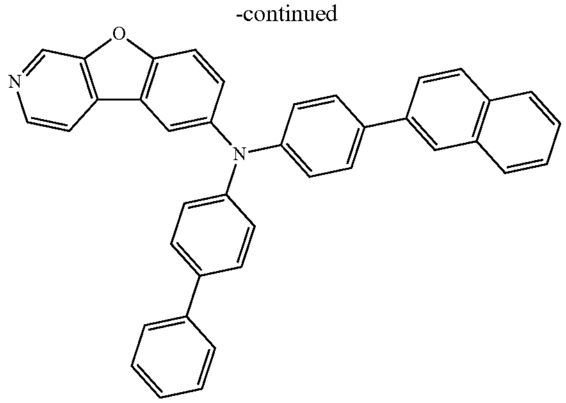
-continued
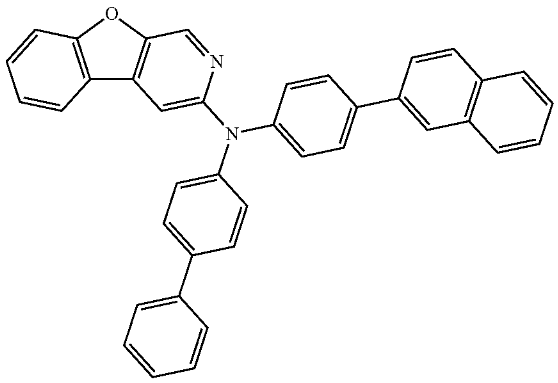
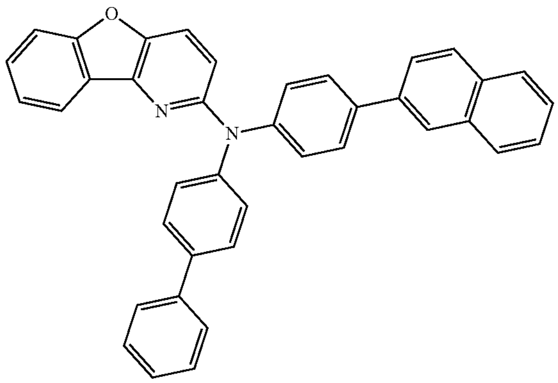
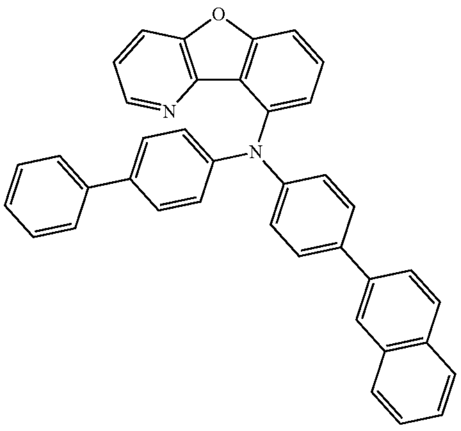

-continued
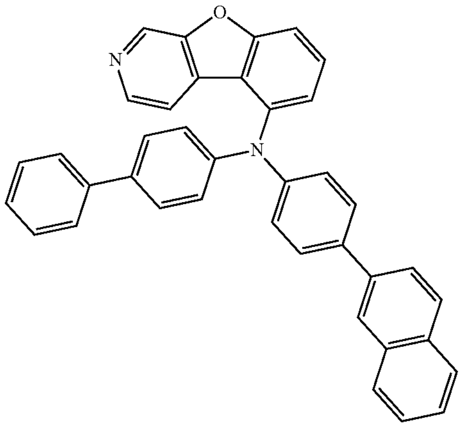
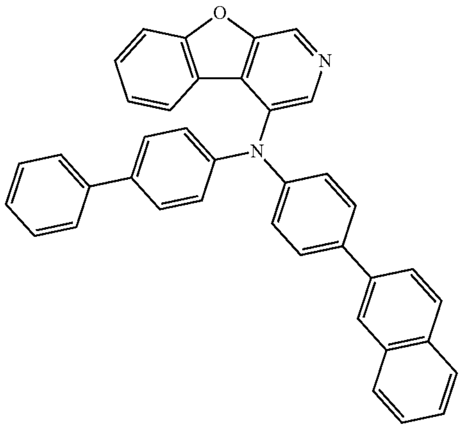
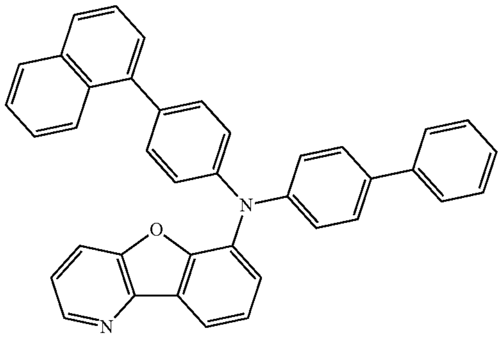
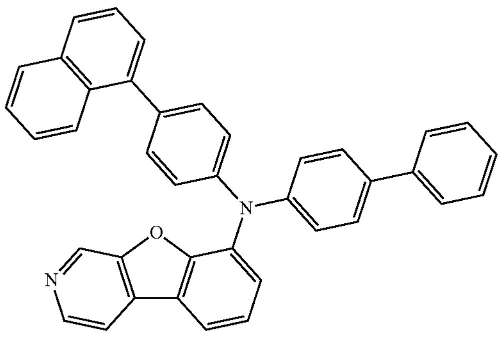
-continued
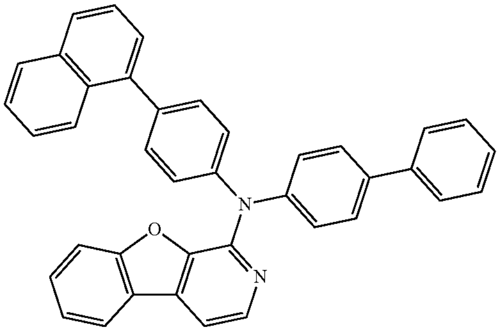
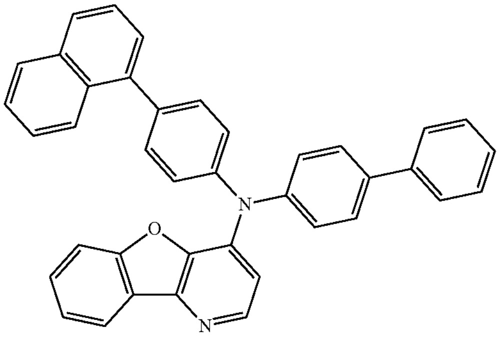
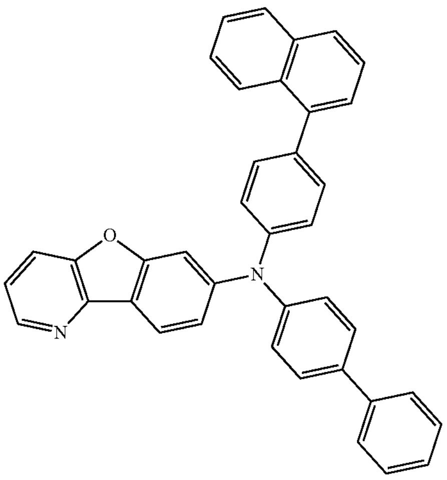
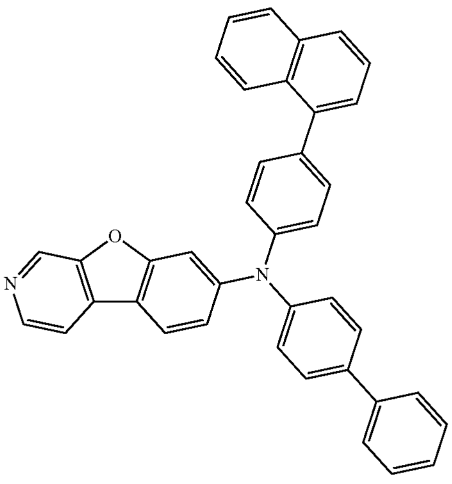

-continued
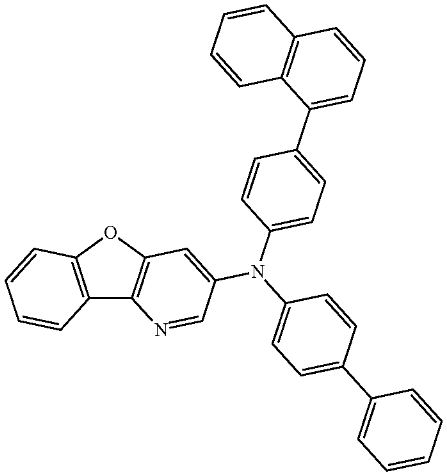
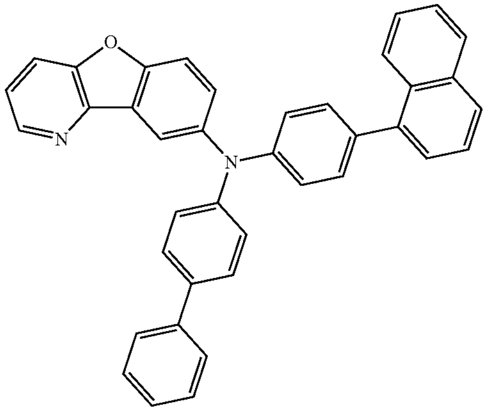
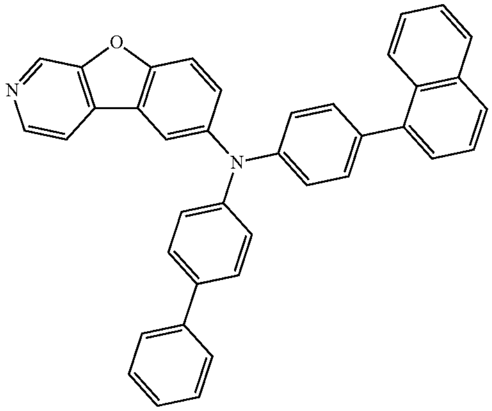
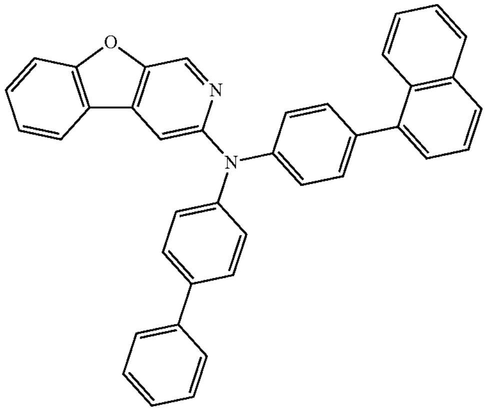
-continued
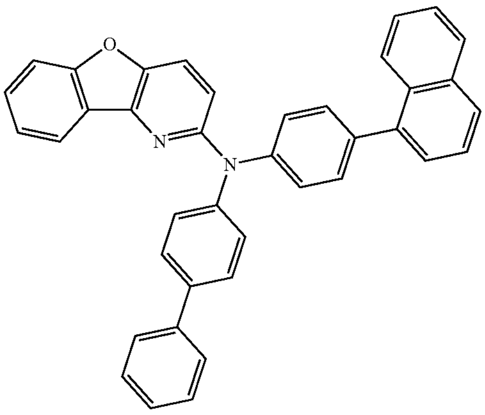
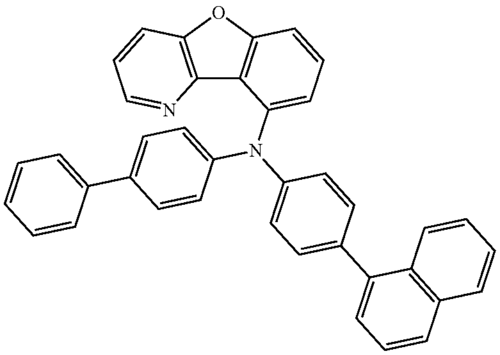
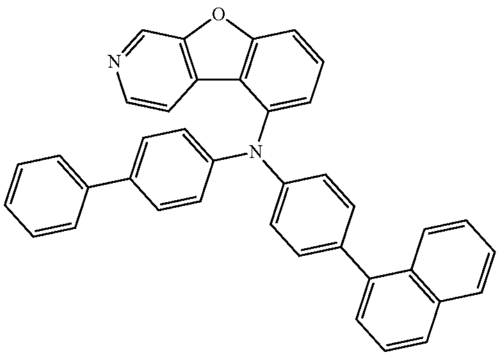
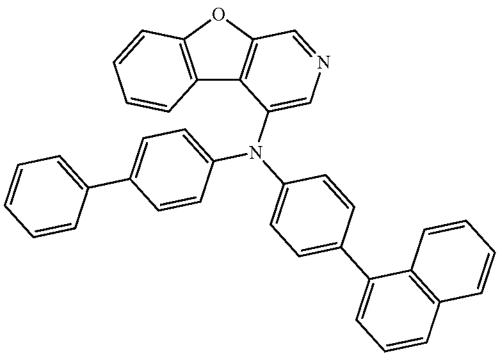

-continued
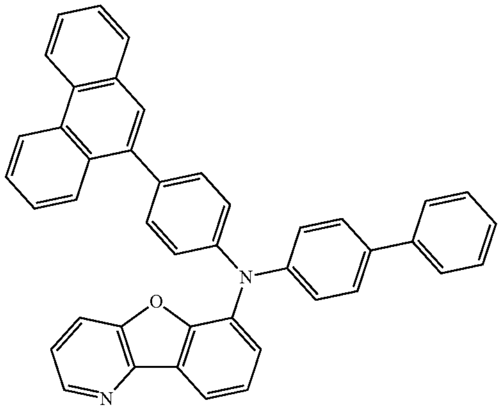
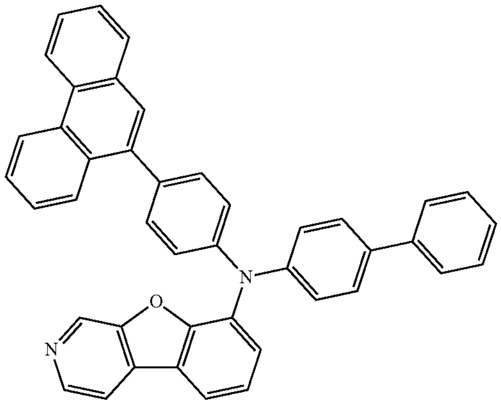
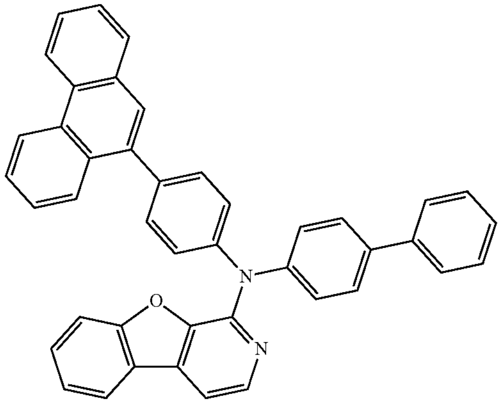
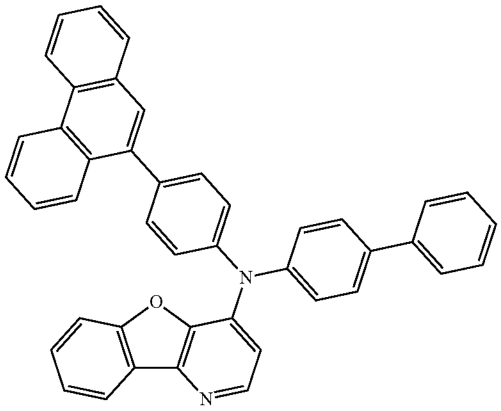
-continued
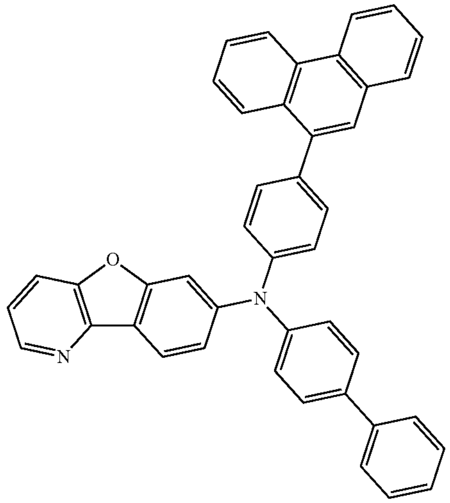
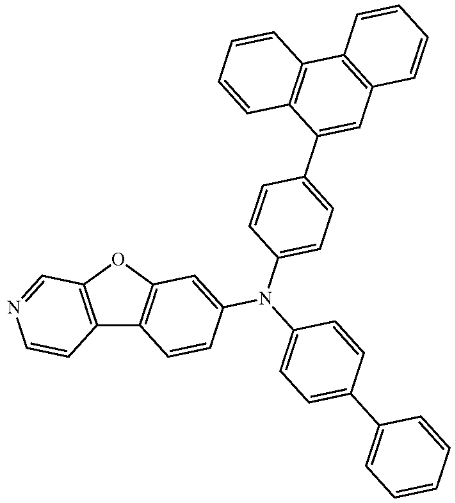
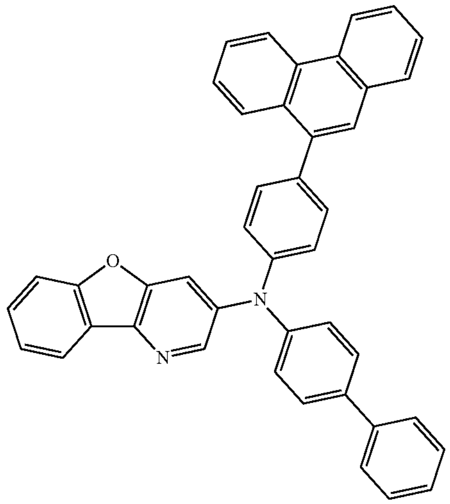

-continued
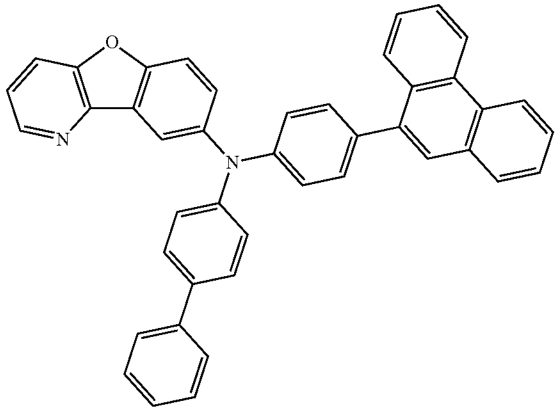
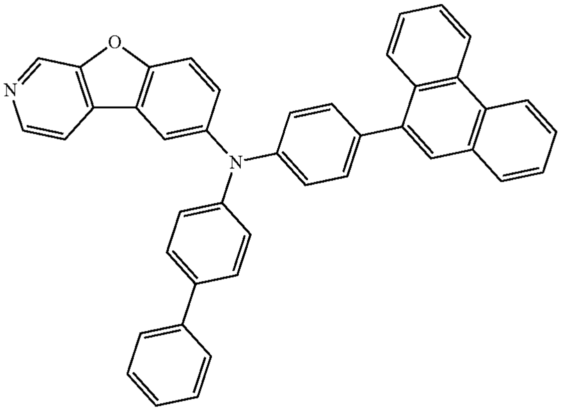
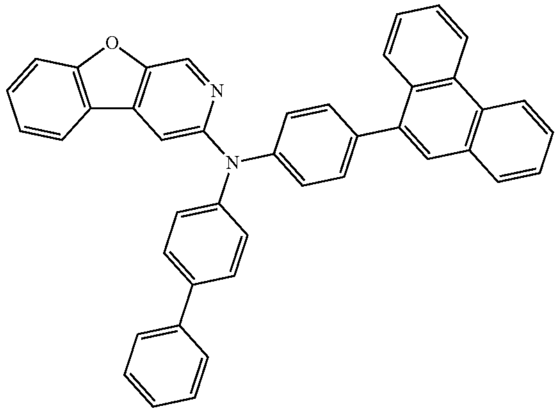
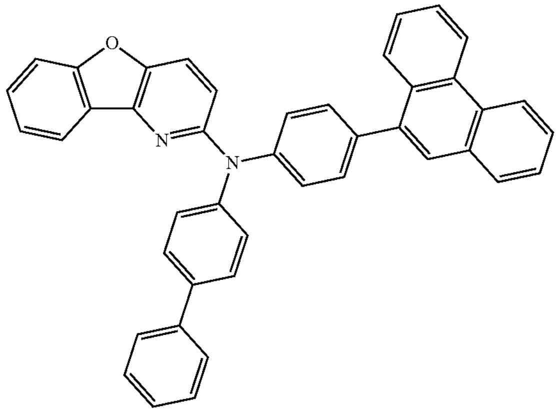
-continued
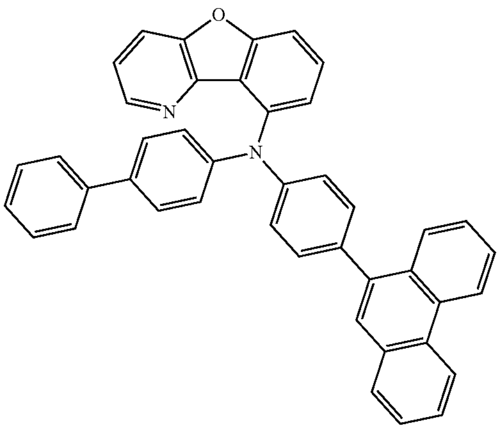
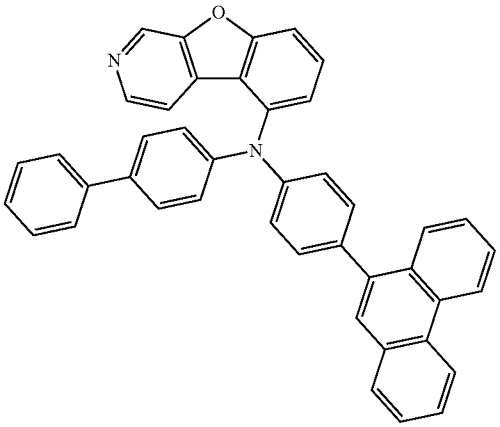
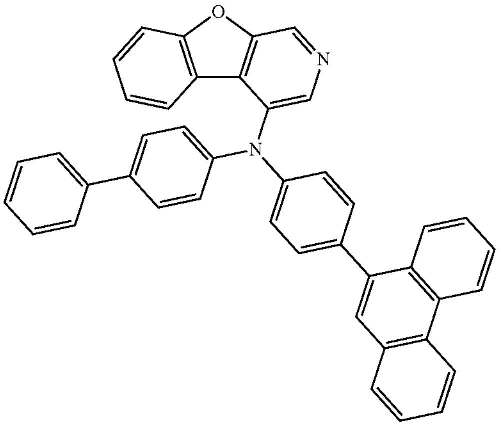
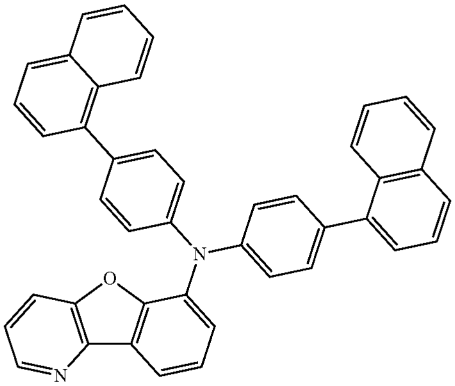

-continued
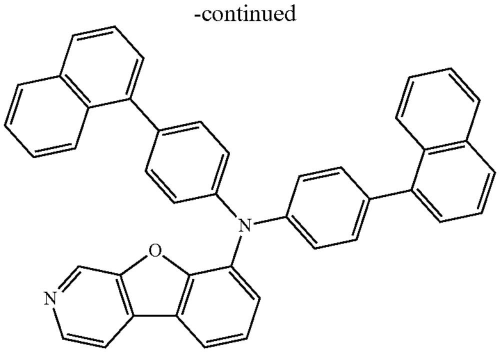
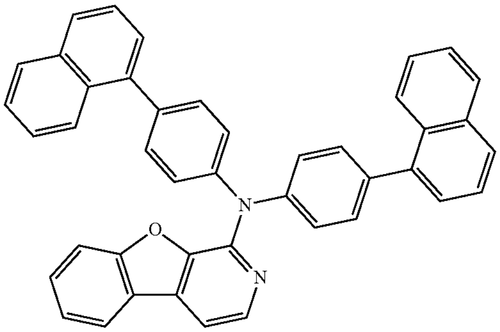
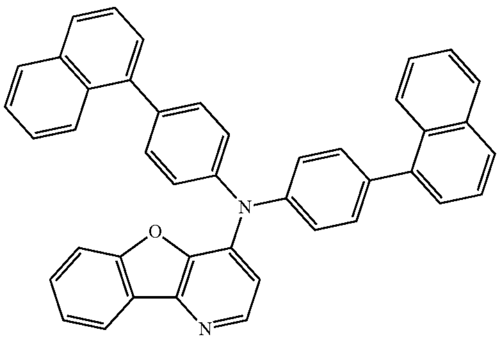
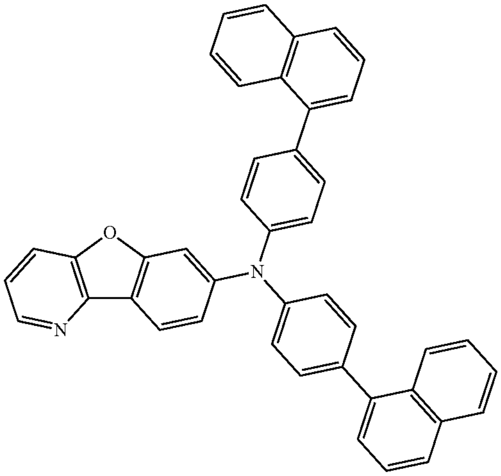
-continued
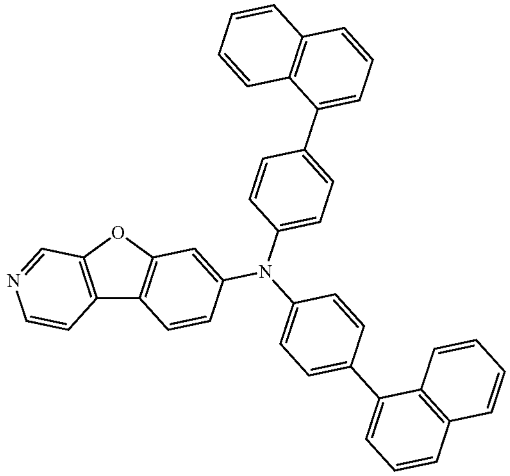
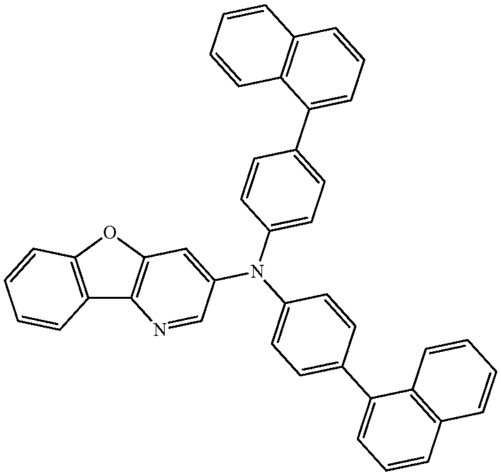
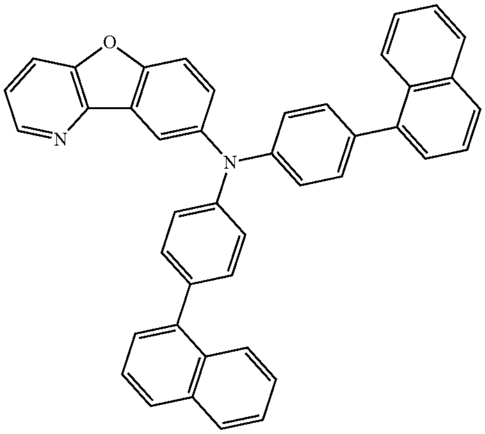

-continued
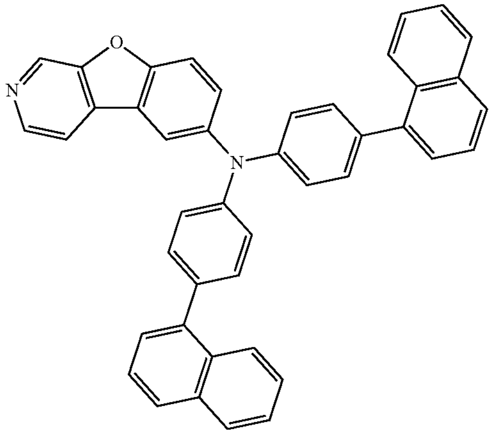
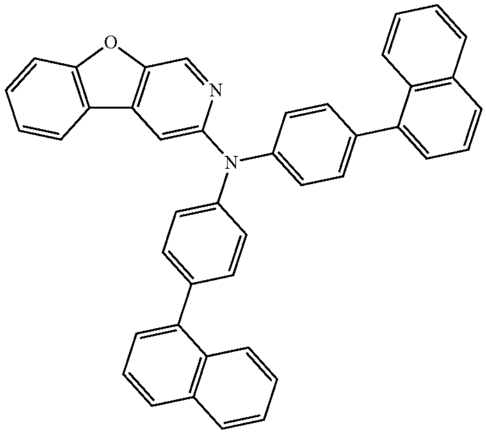
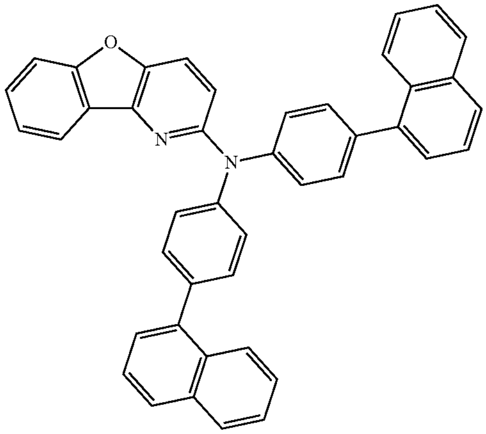
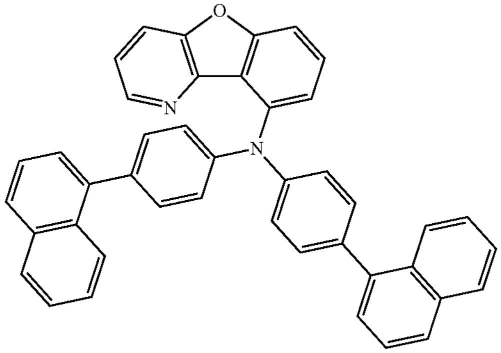
-continued
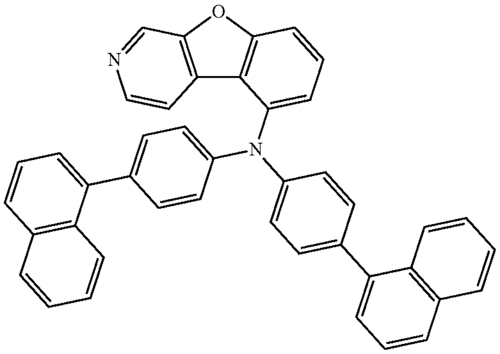
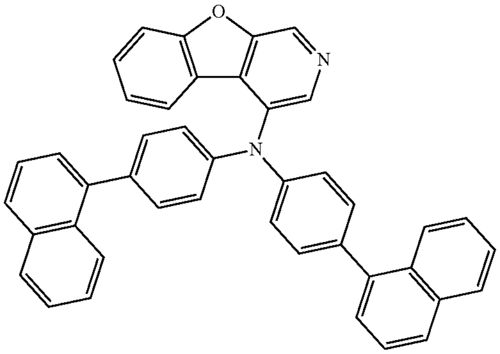
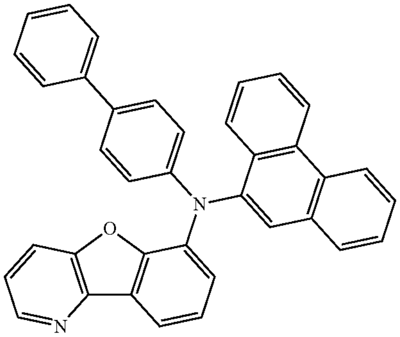
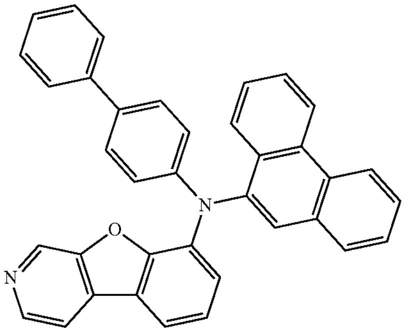
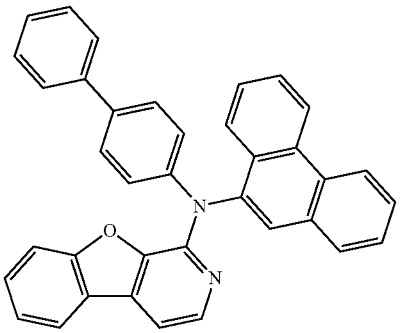

-continued
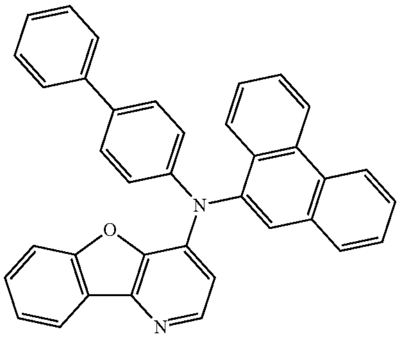
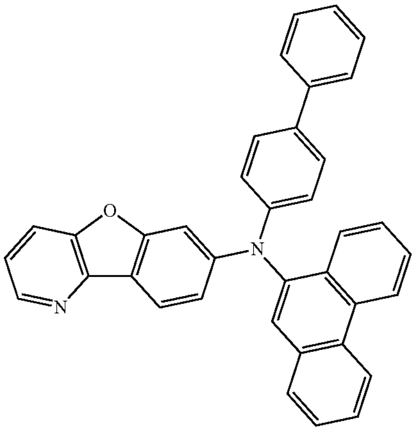
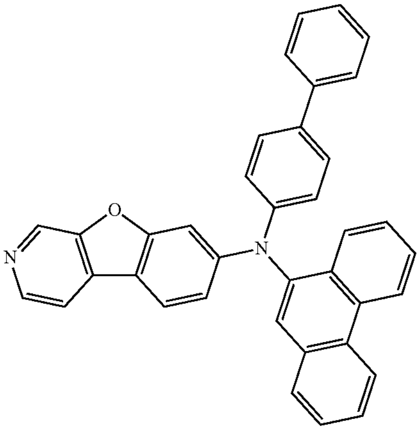
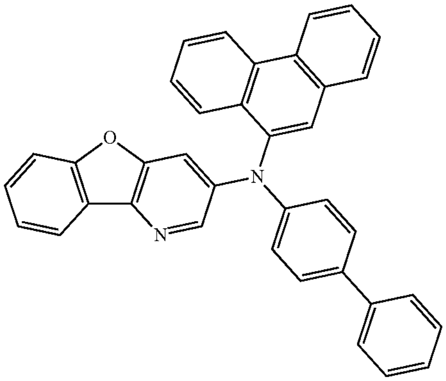
-continued
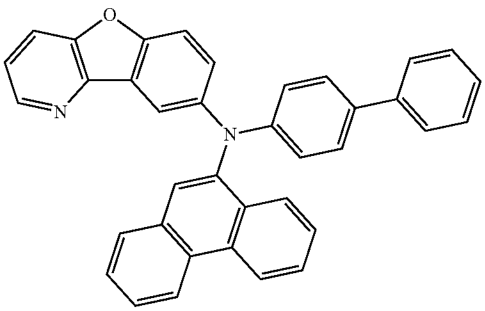
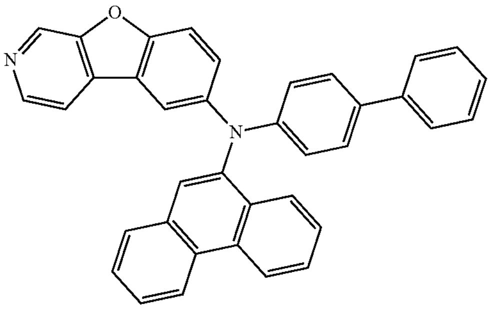
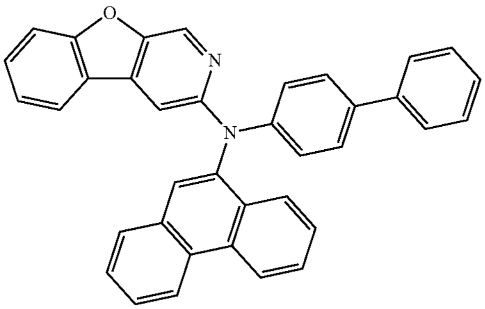
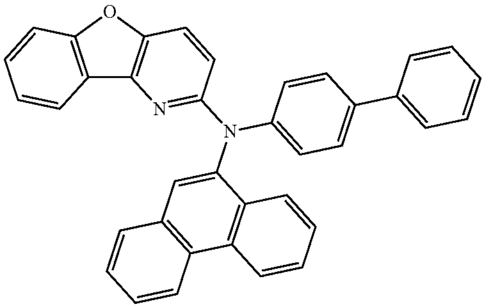
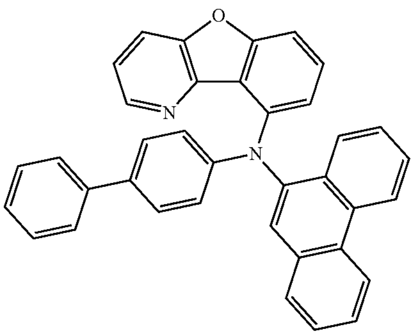

-continued
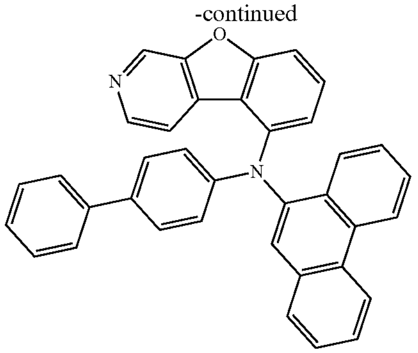
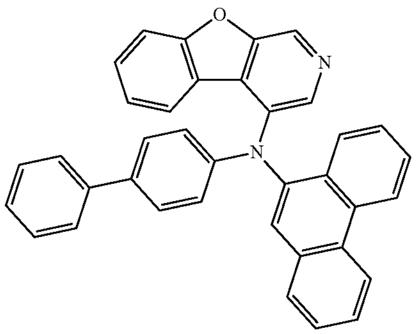
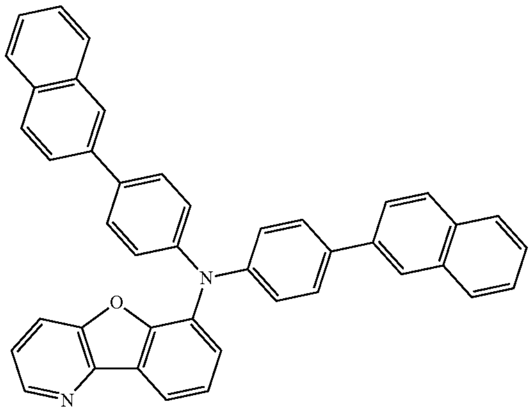
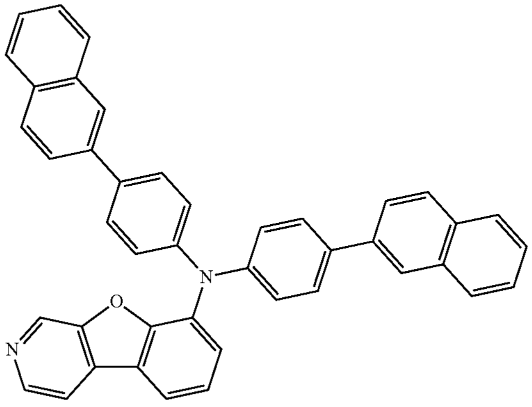
-continued
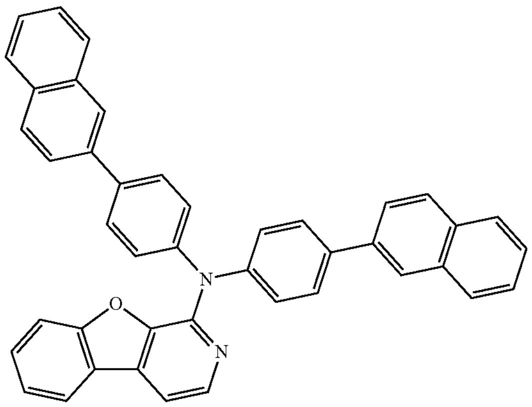
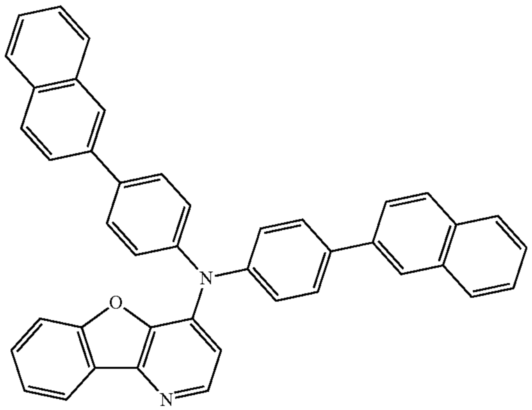
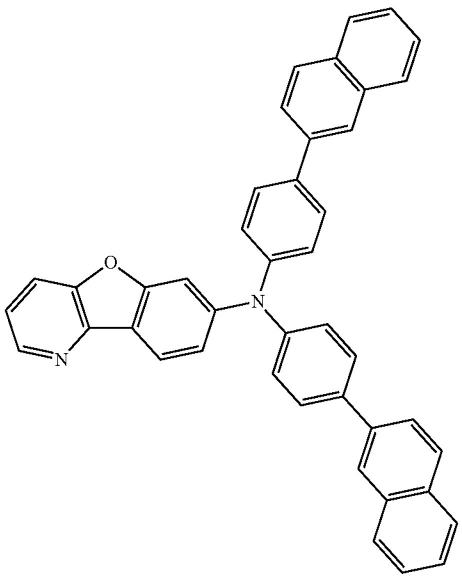

-continued
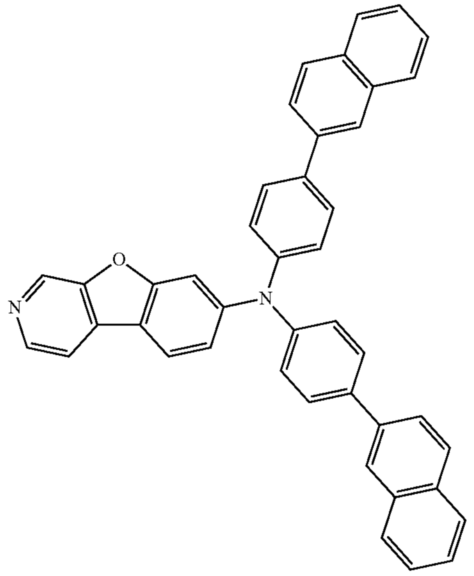
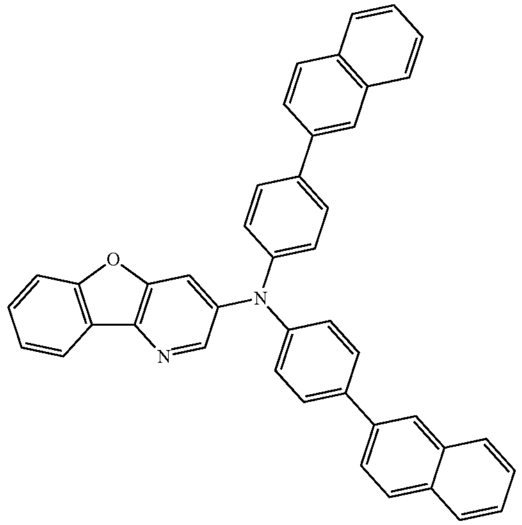
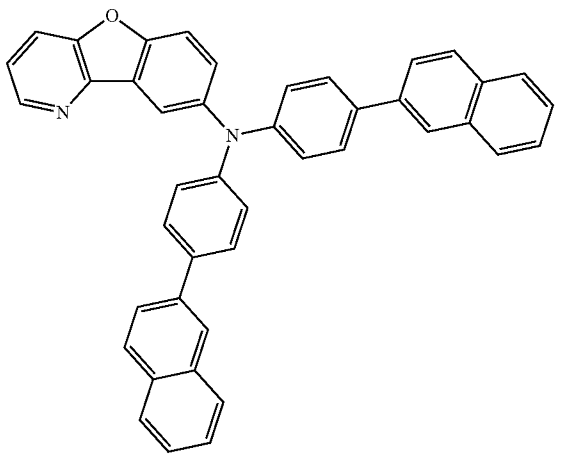
-continued
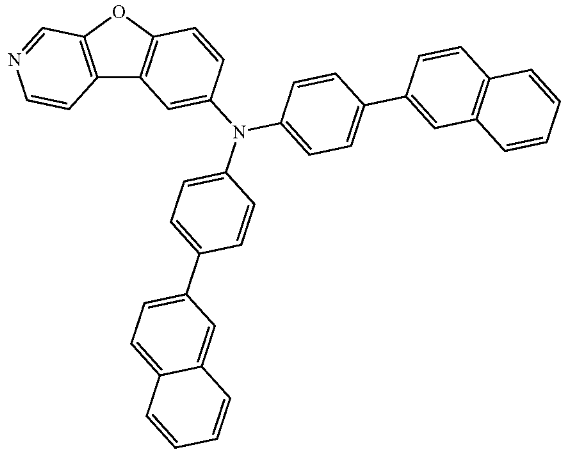
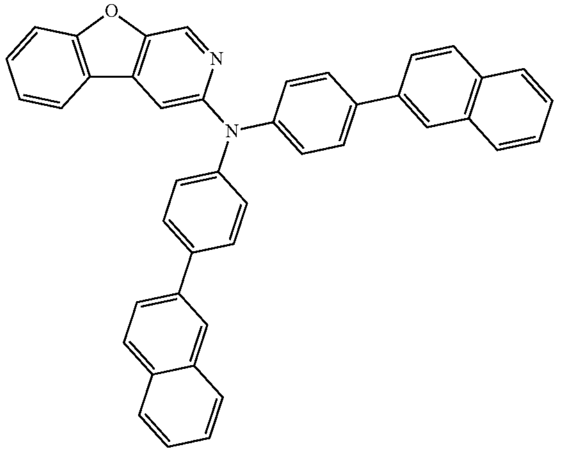
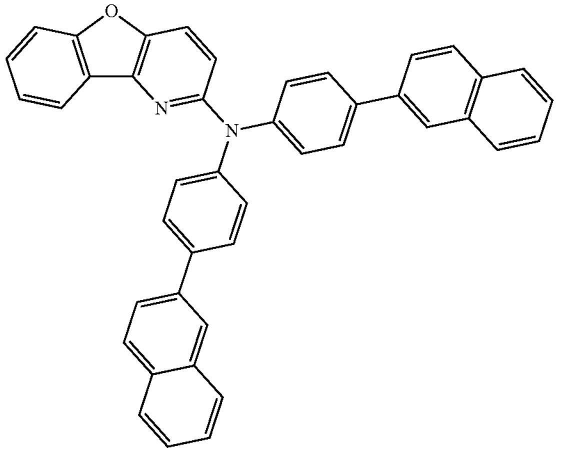
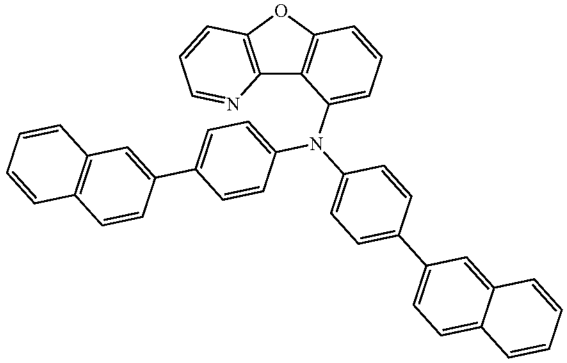

-continued
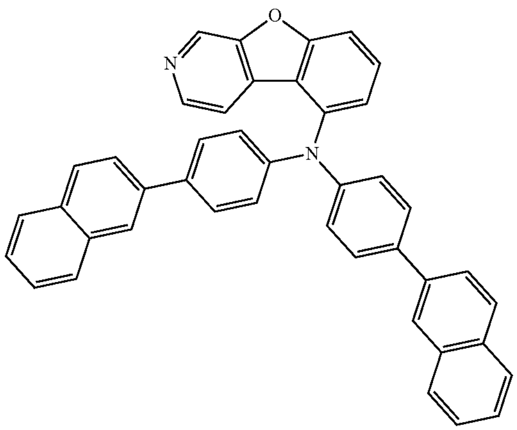
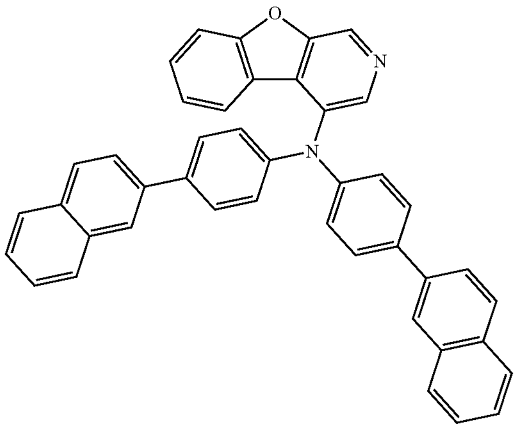
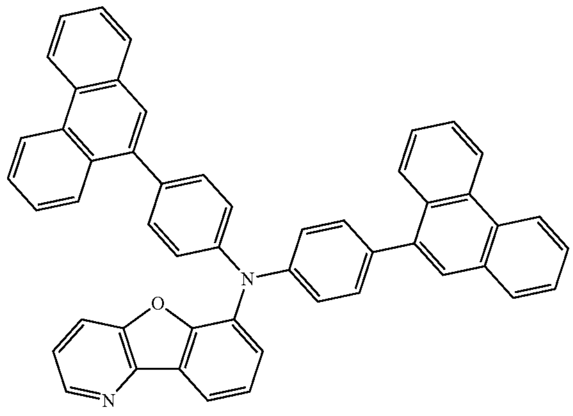
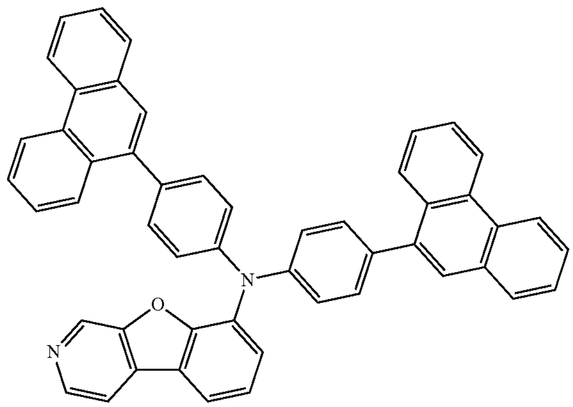
-continued
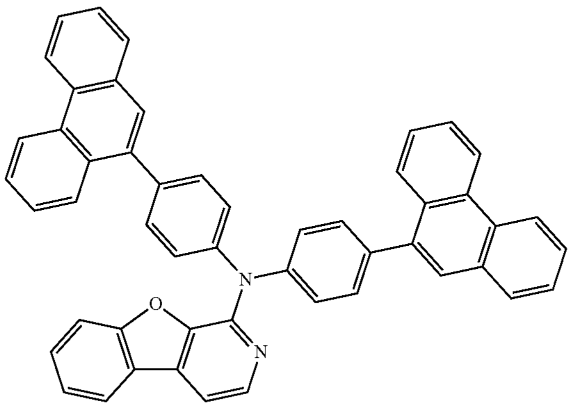
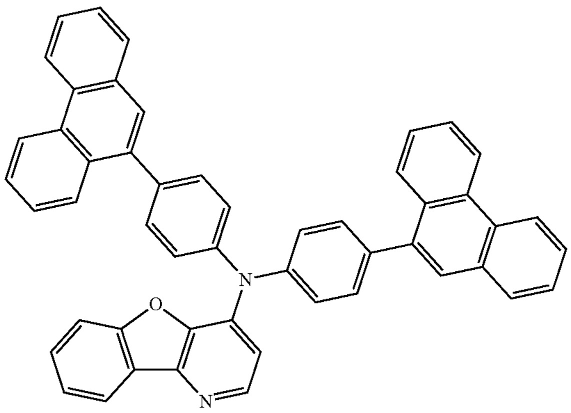
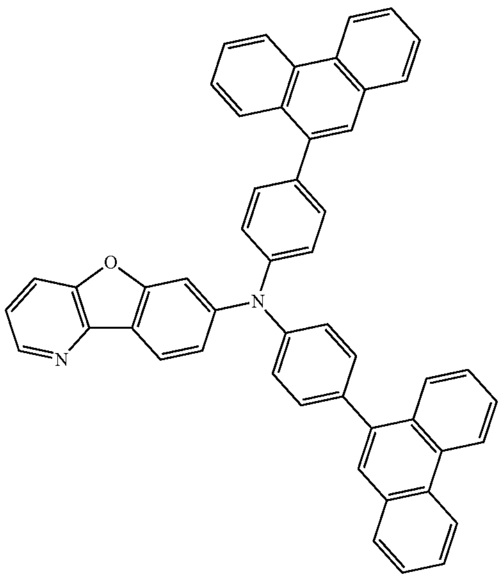

-continued
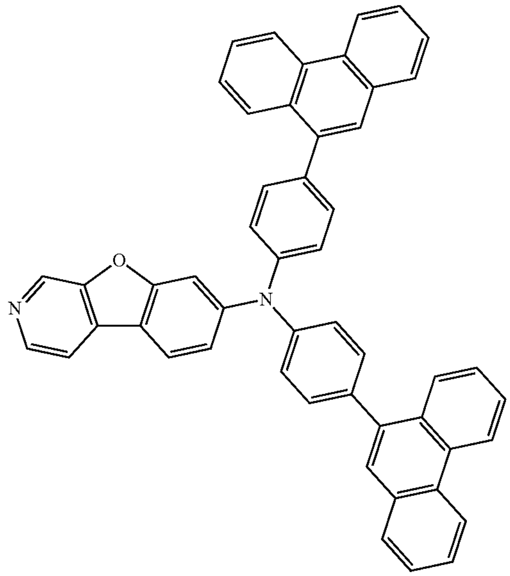
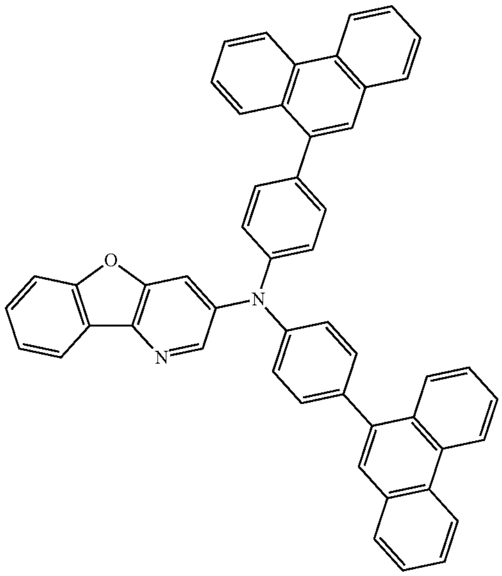
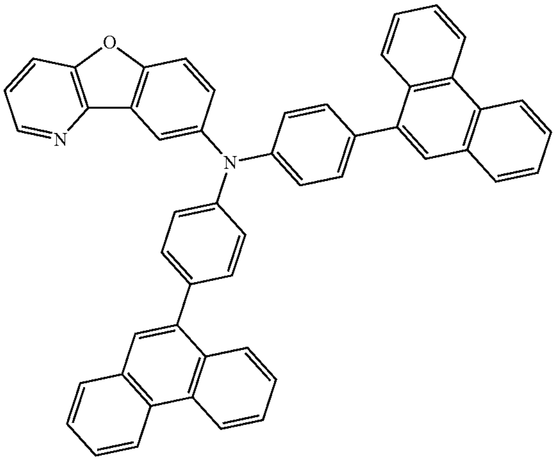
-continued
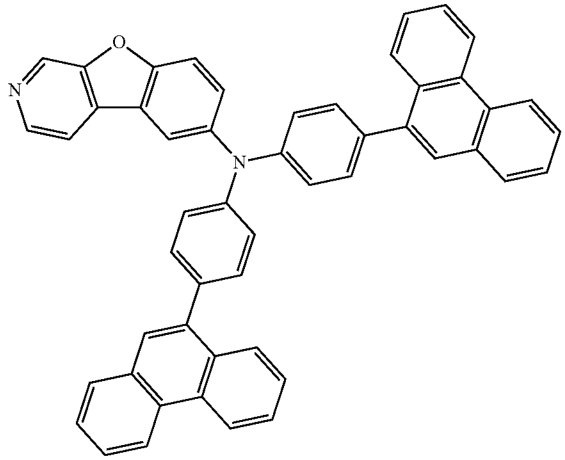
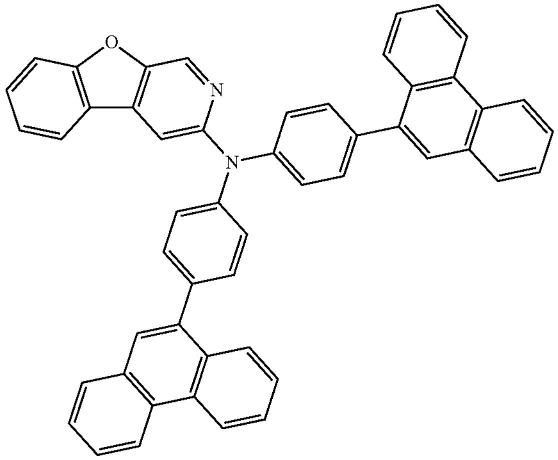
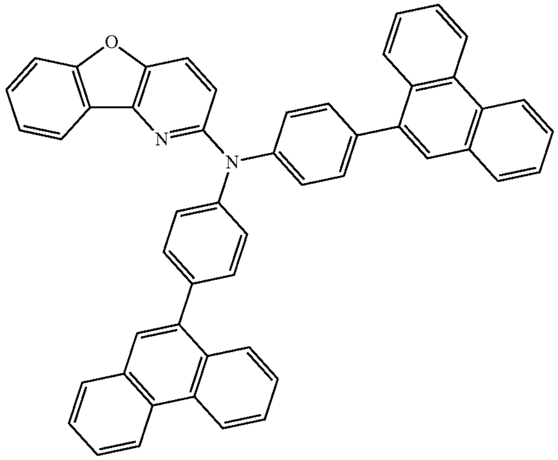

-continued
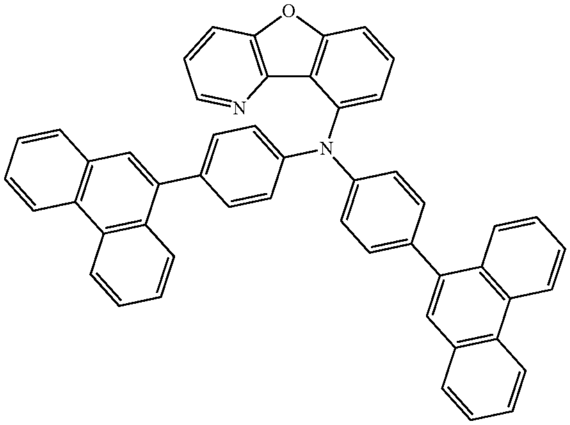
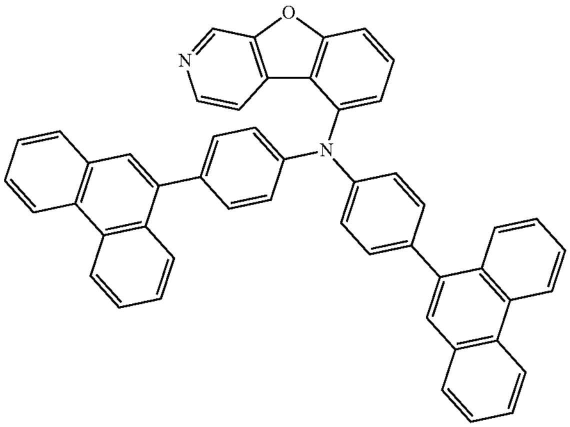
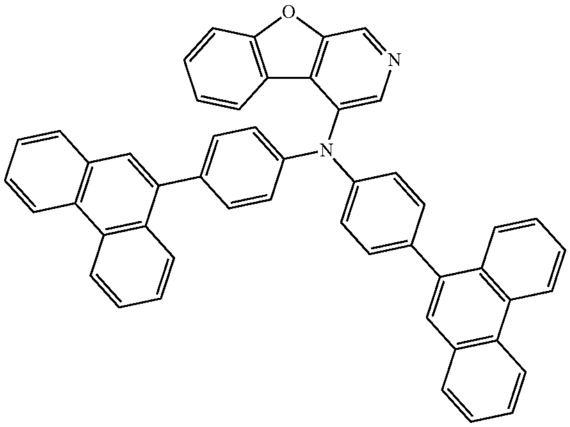
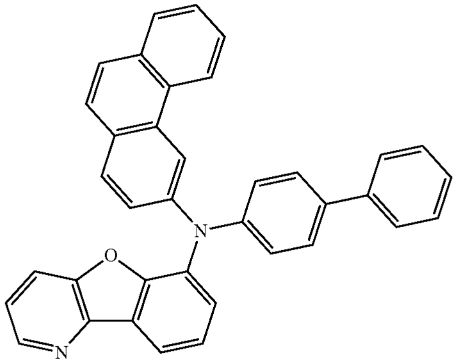
-continued
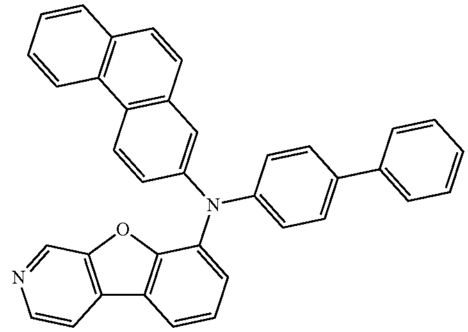
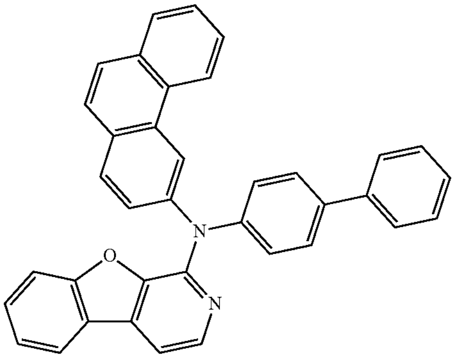
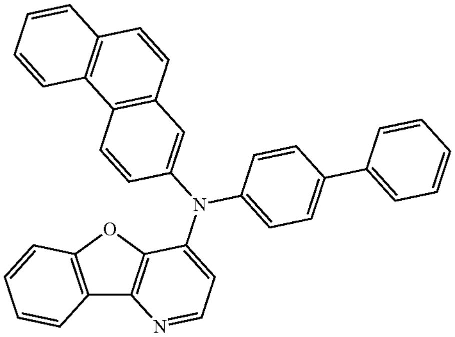
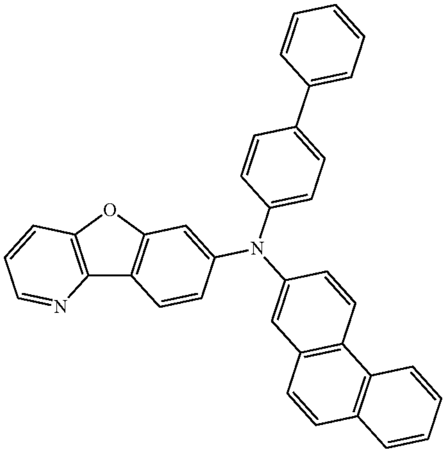

-continued
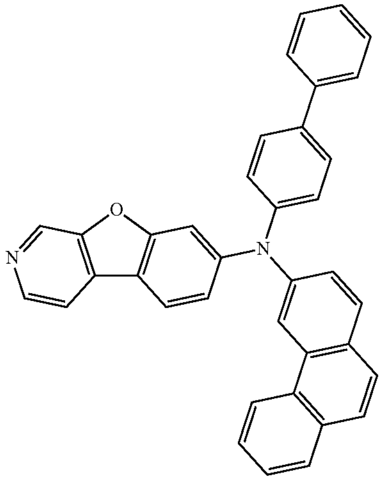
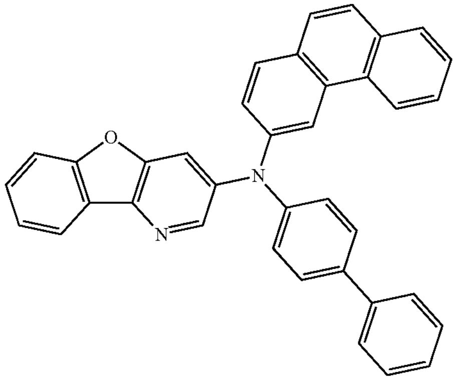
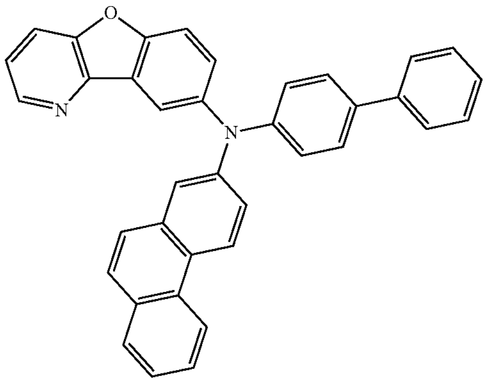
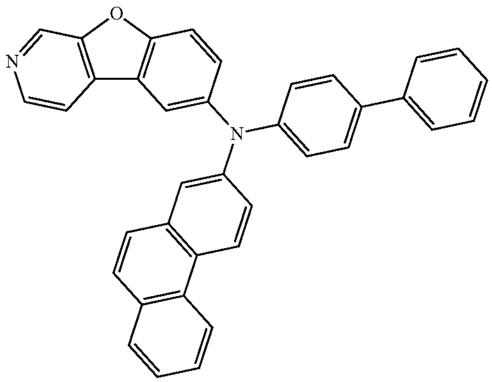
-continued
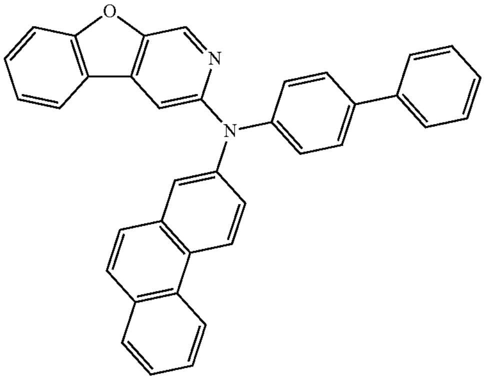
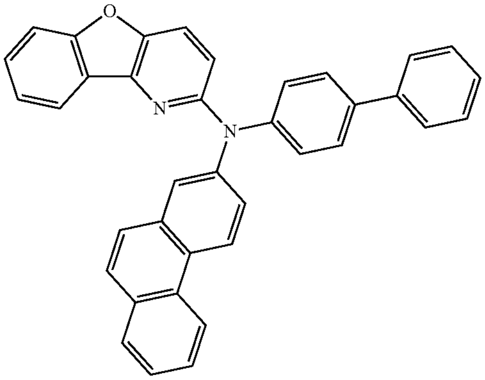
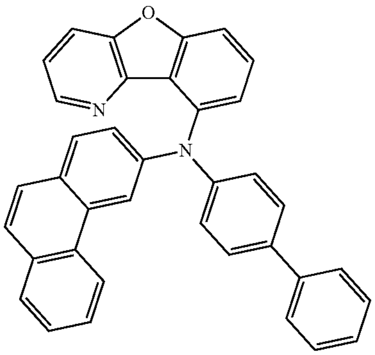
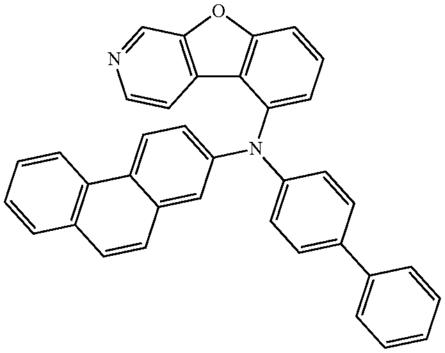

-continued
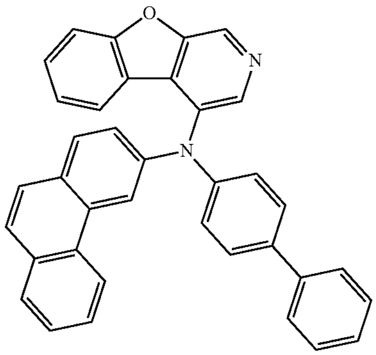
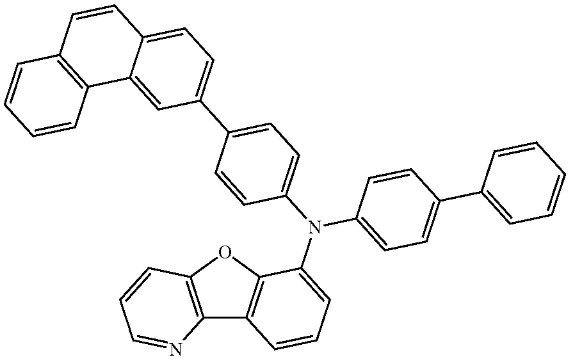
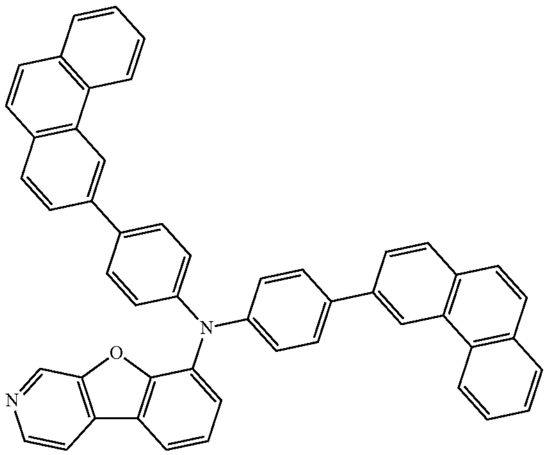
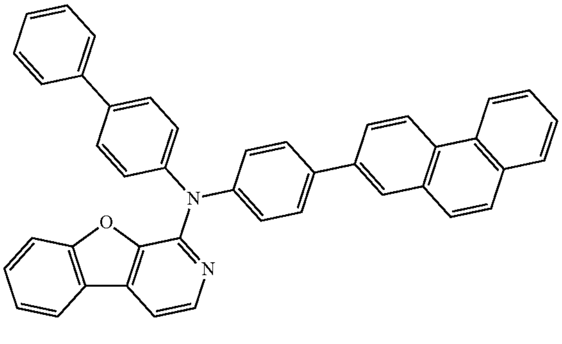
-continued
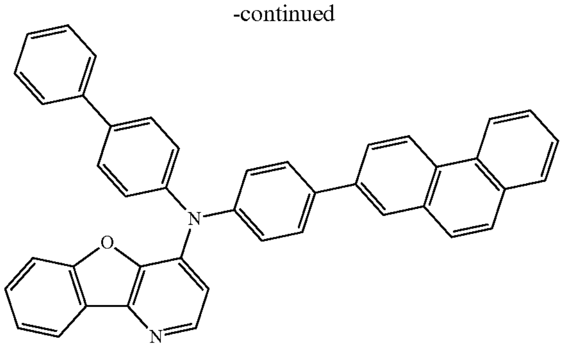
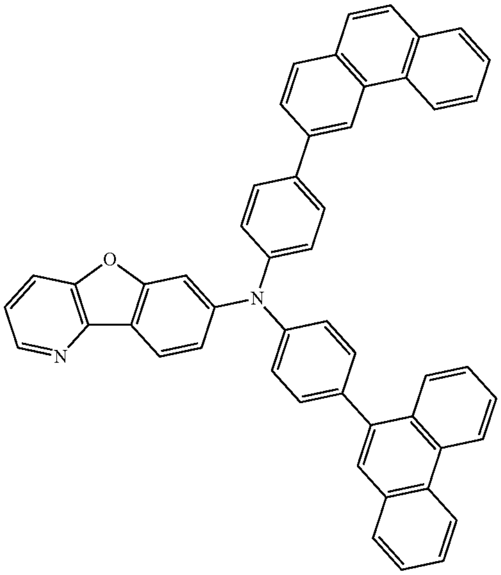
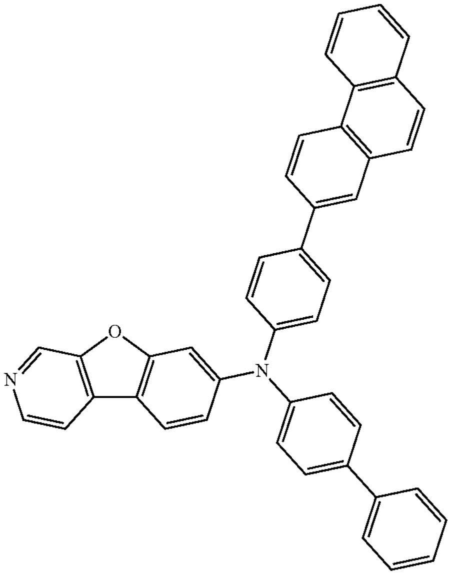

-continued
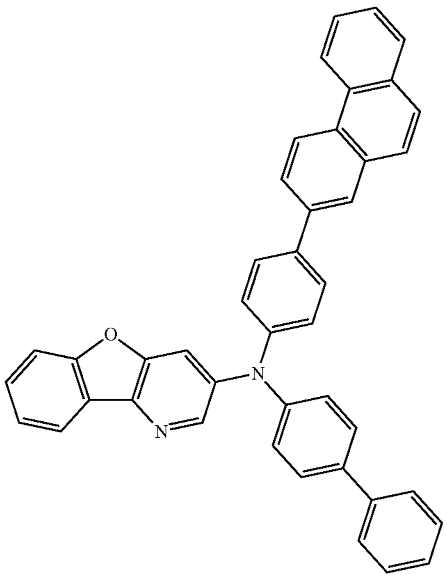
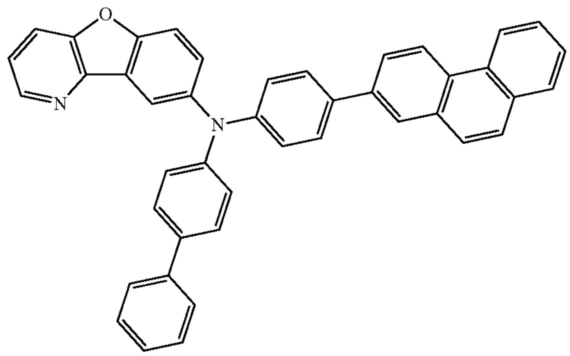
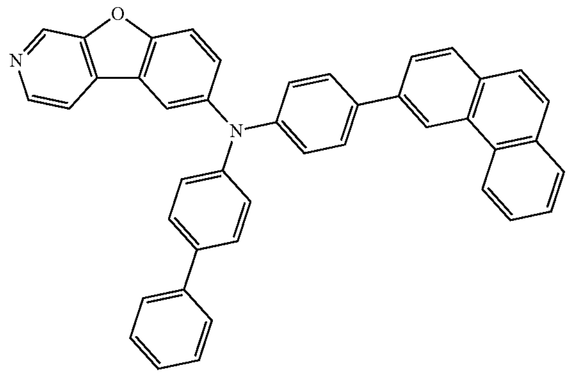
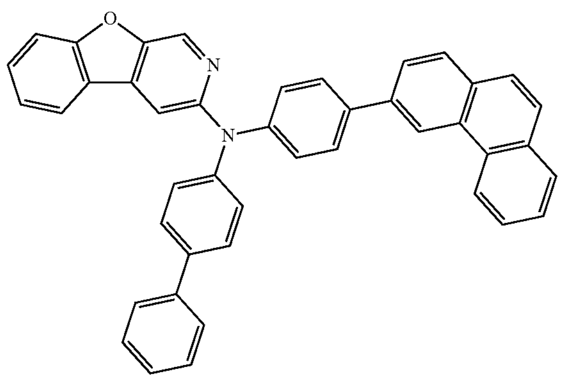
-continued
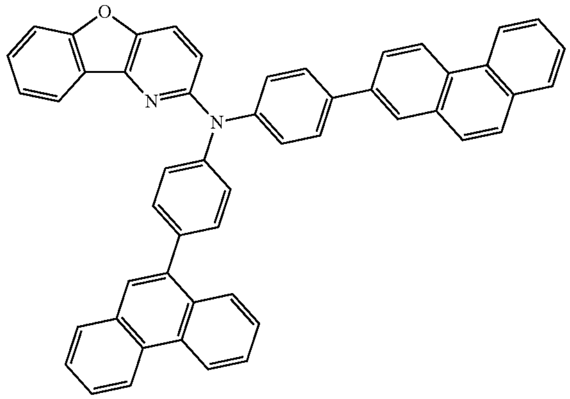
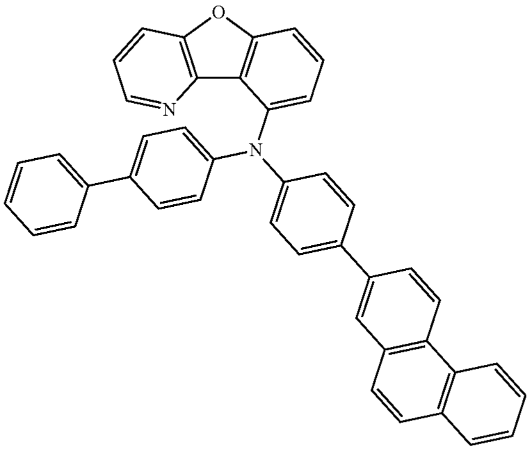
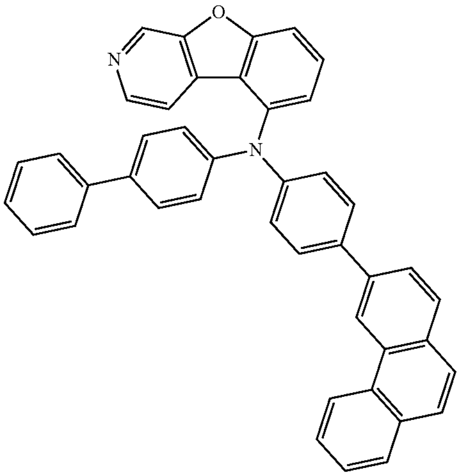
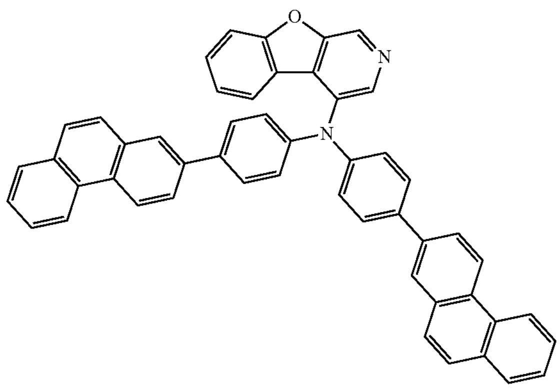 [SMILES: c1ccc2c(c1)ccc1cc(-c3ccc(N(c4ccc(-c5ccc6c(ccc7ccccc76)c5)cc4)c4cncc5oc6ccccc6c45)cc3)ccc12]

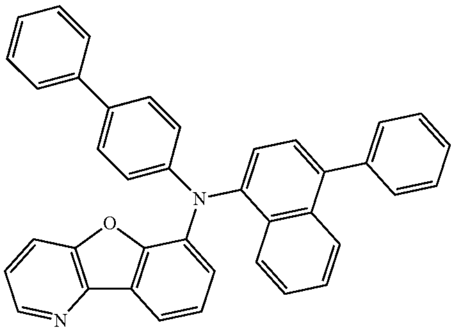
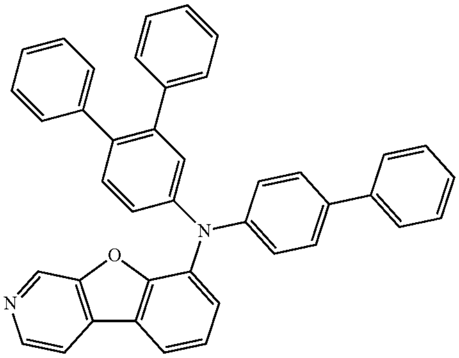
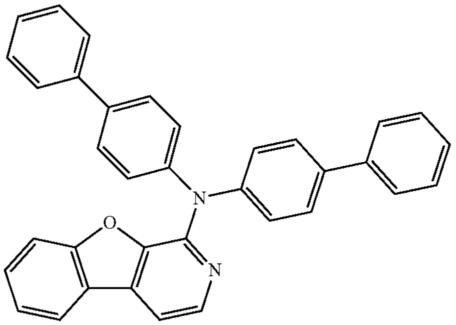
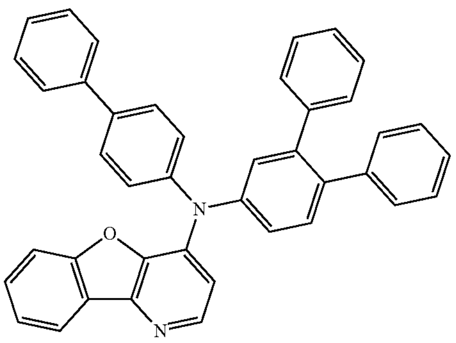
-continued
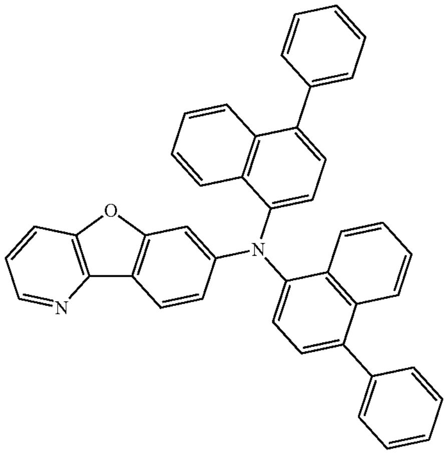
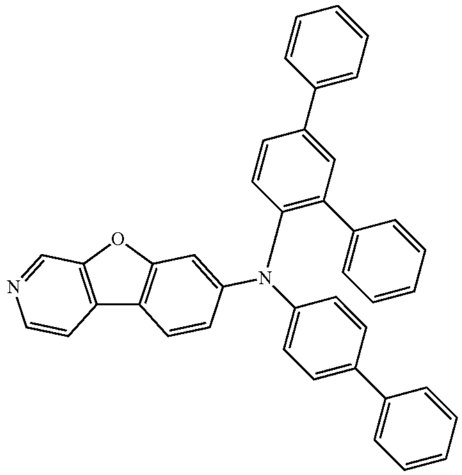
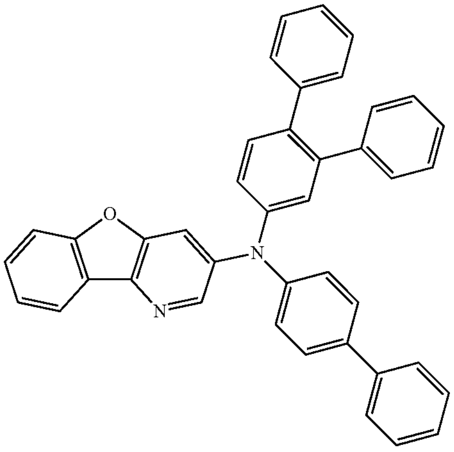

-continued
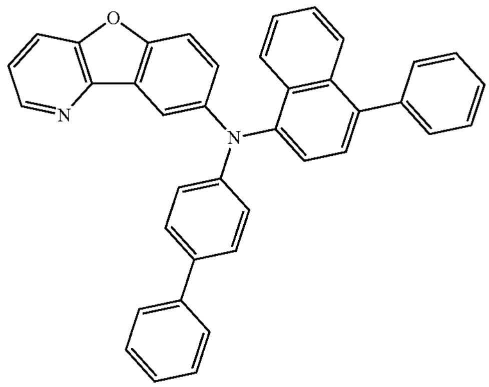
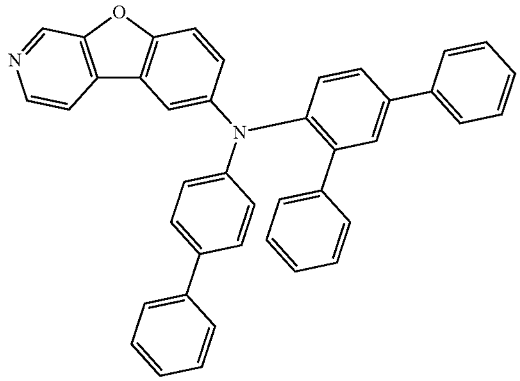
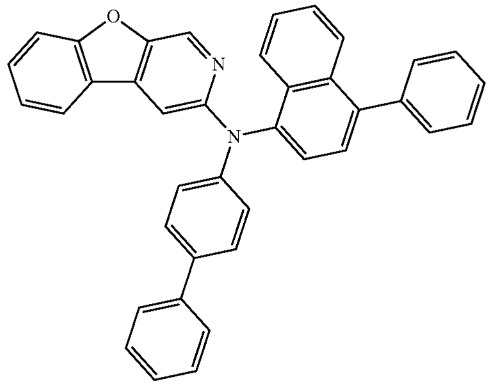
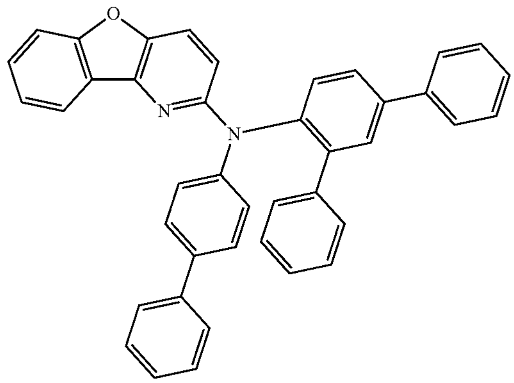
-continued
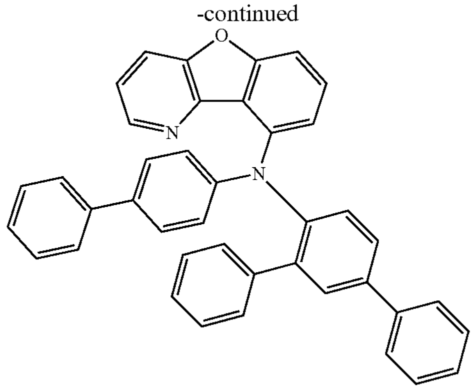
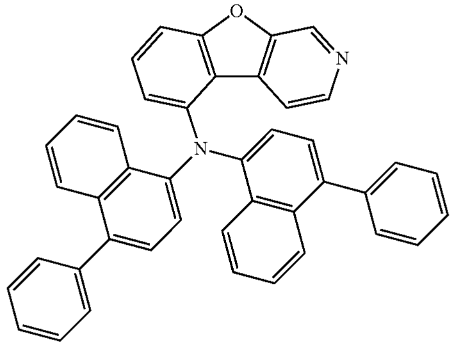
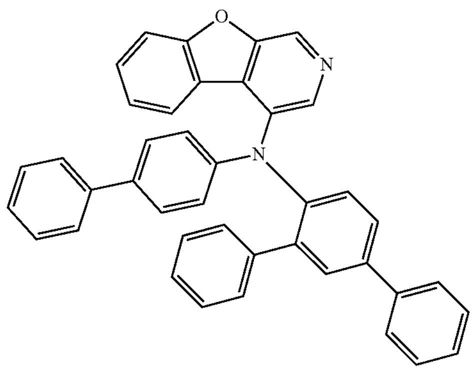
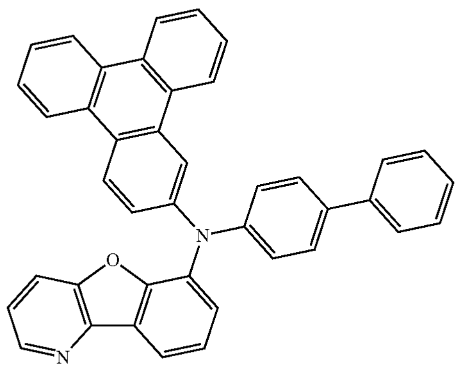

-continued
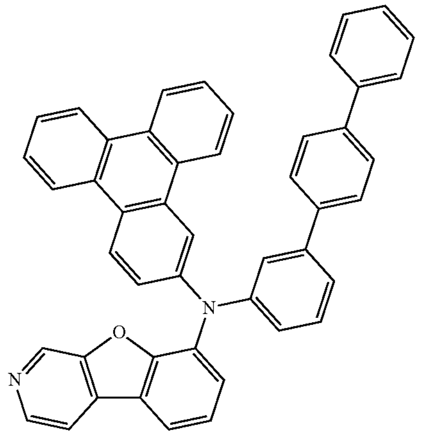
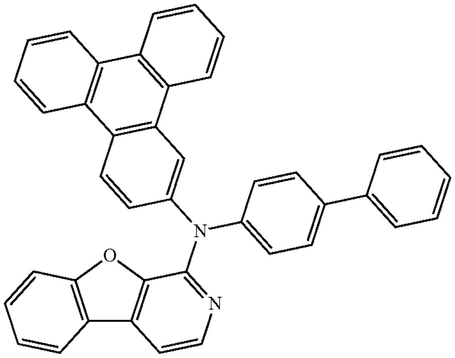
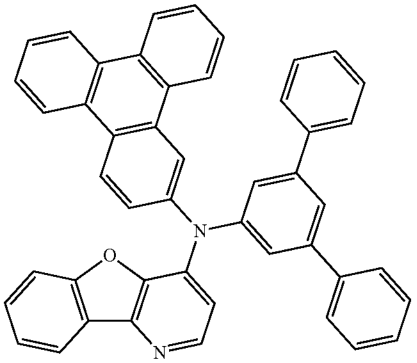
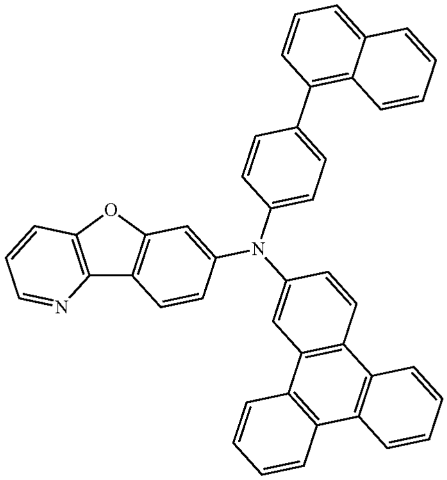
-continued
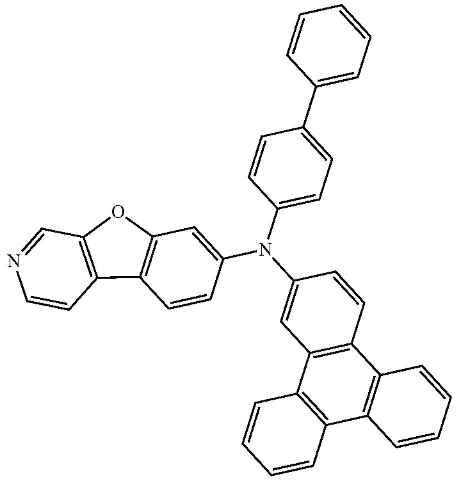
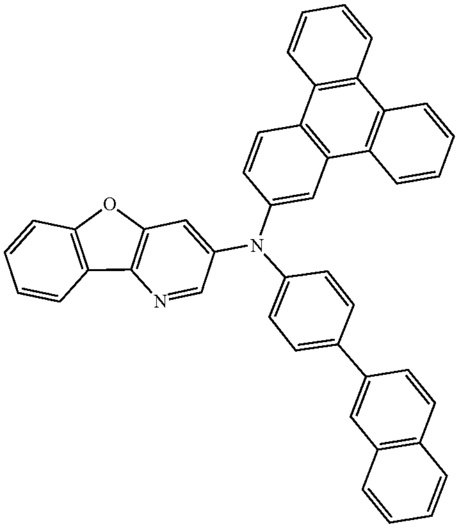
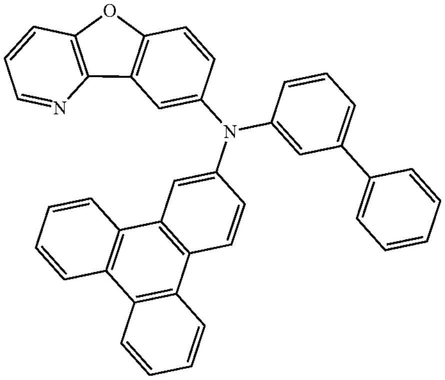

-continued
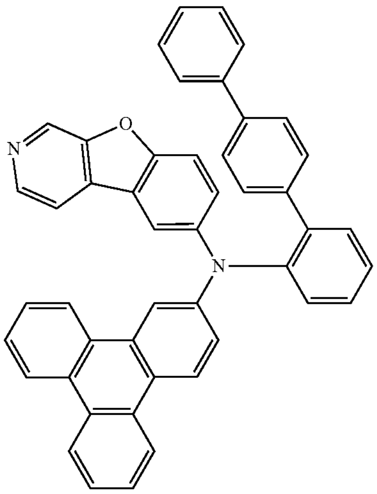
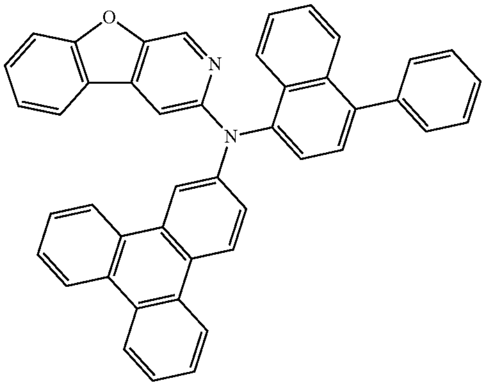
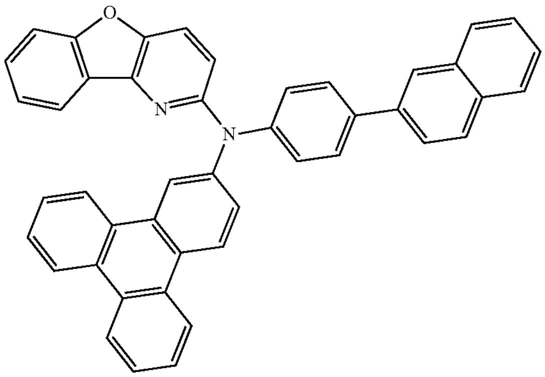
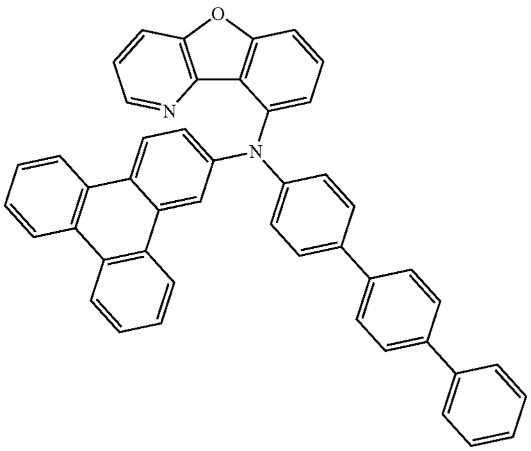
-continued
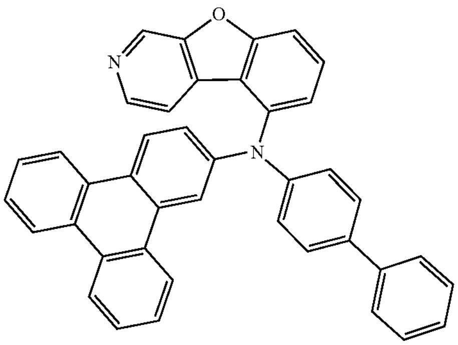
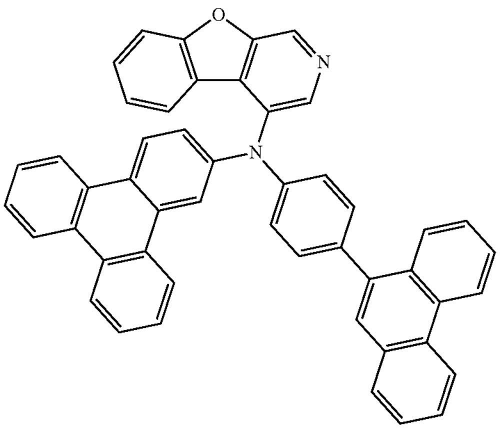
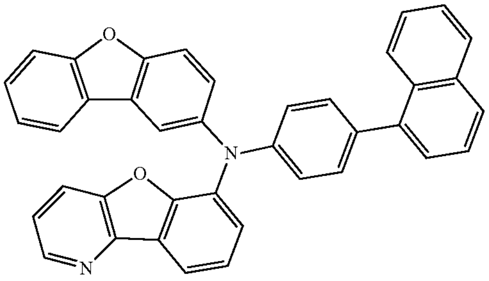
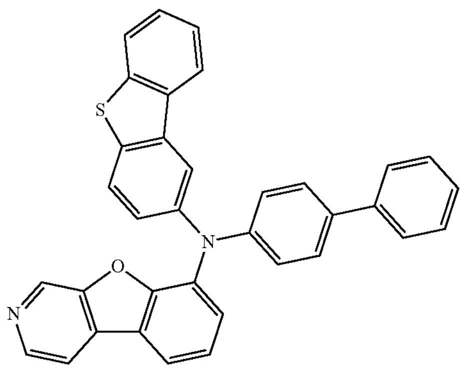

-continued
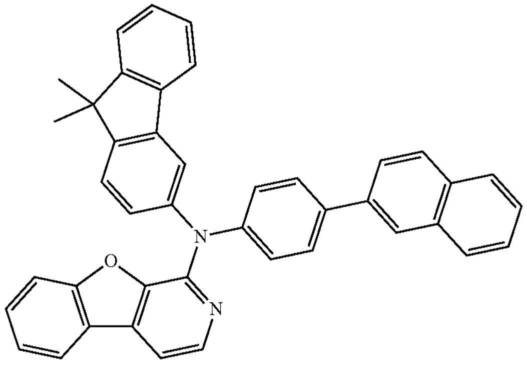
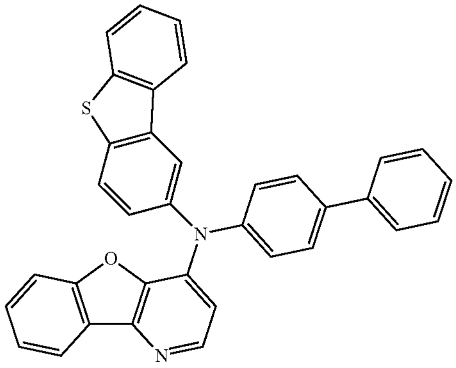
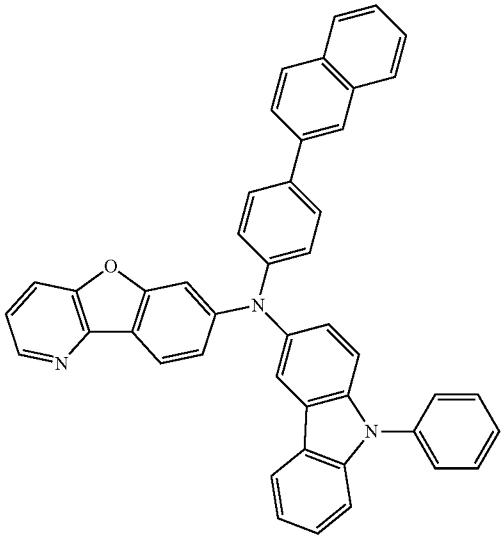
-continued
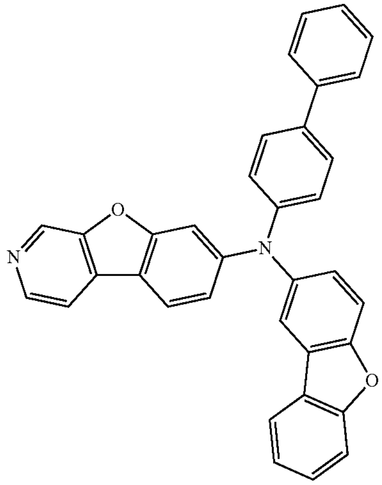
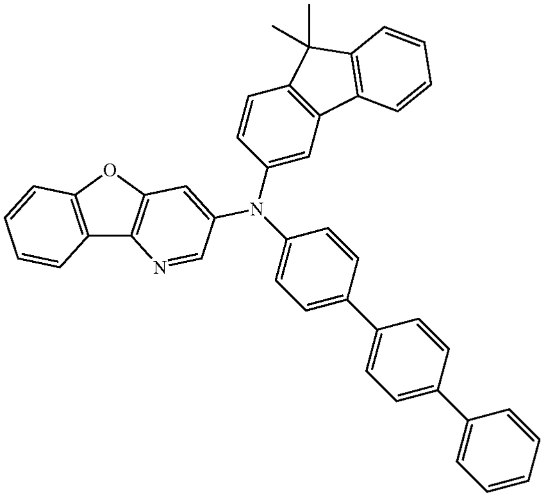
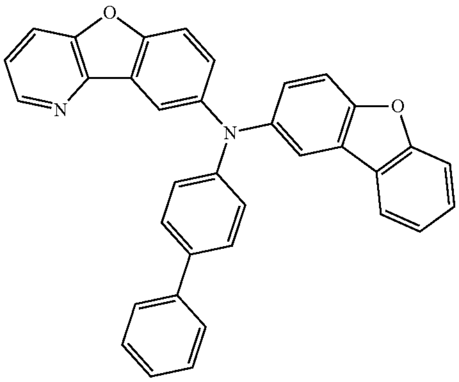
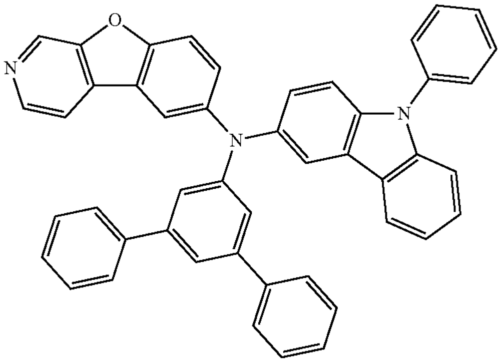

-continued
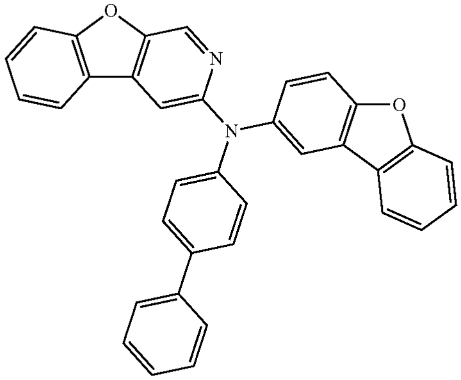
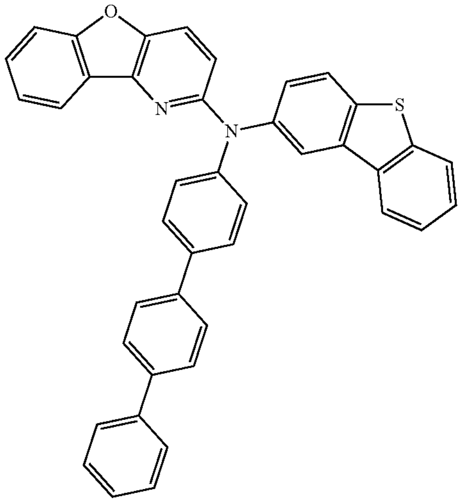
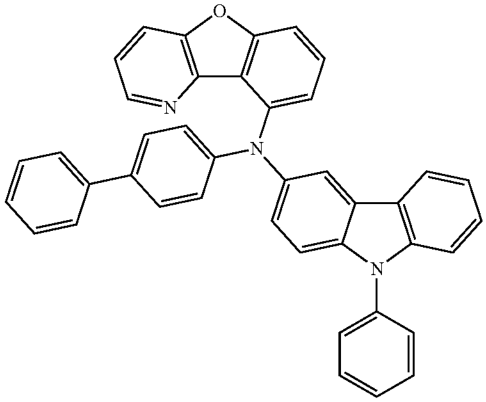
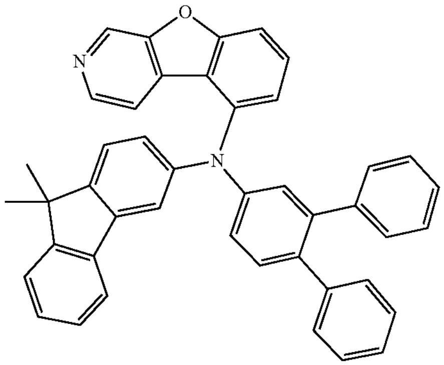
-continued
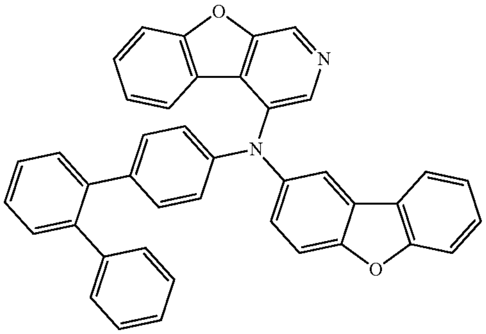
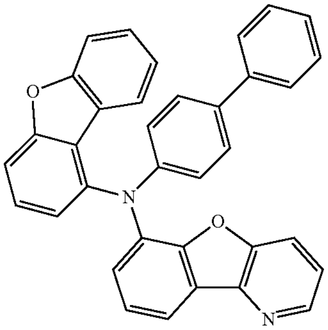
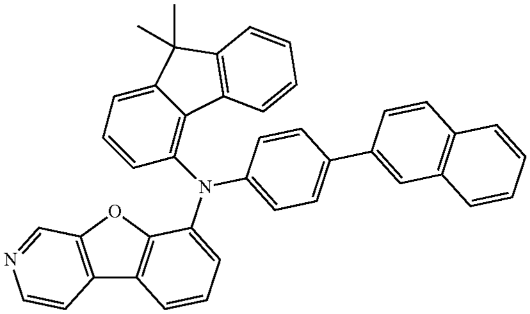
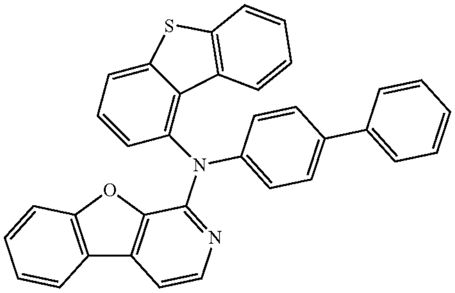
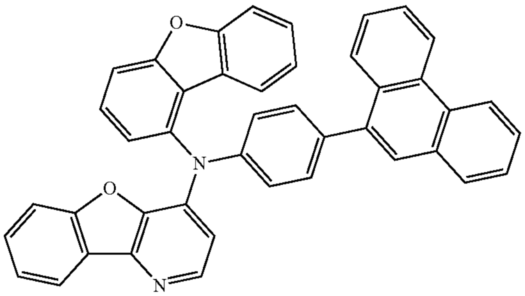

-continued
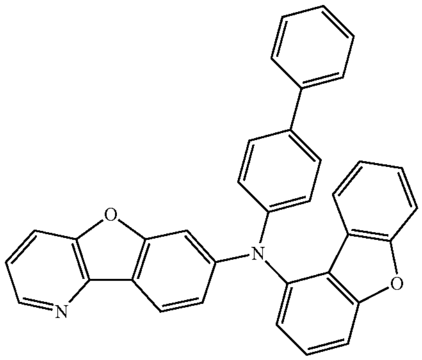
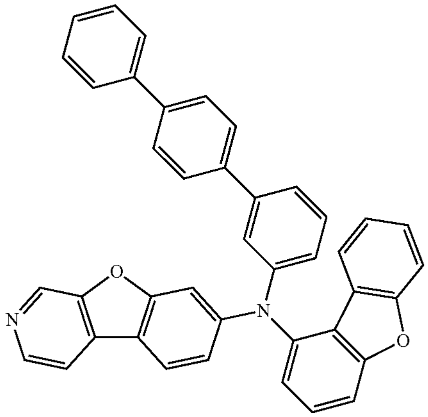
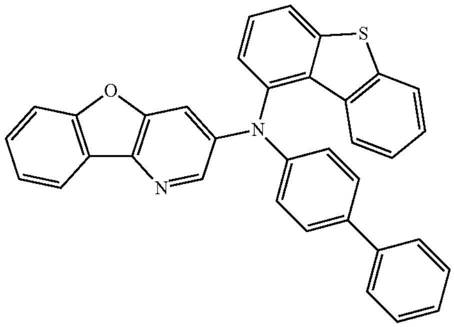
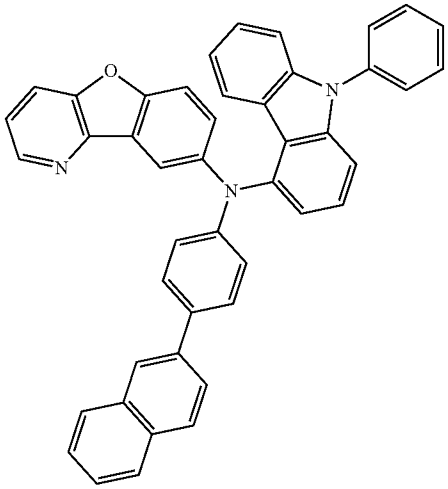
-continued
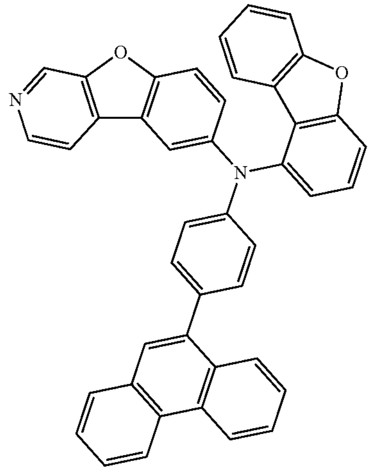
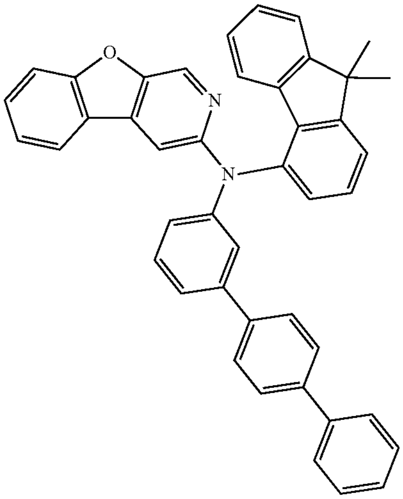
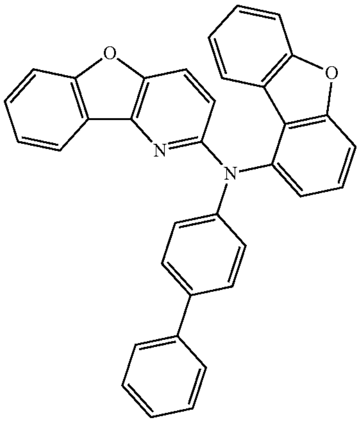
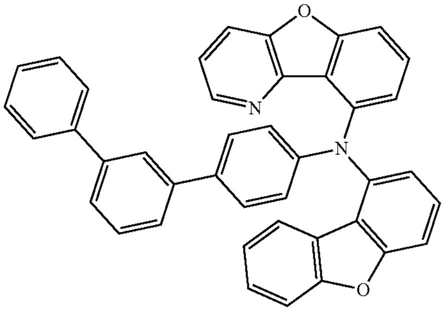

-continued
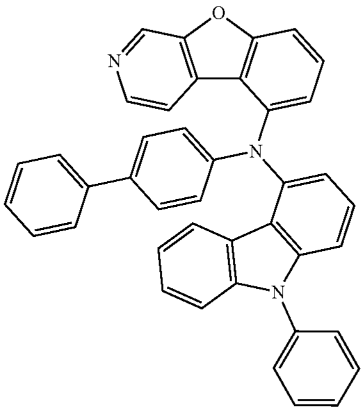
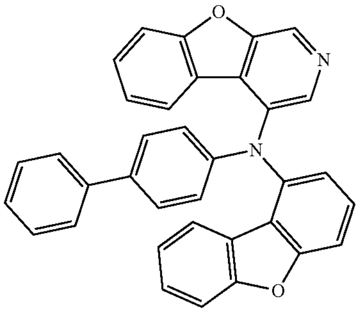
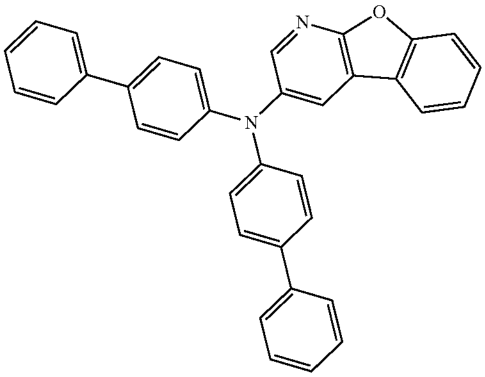
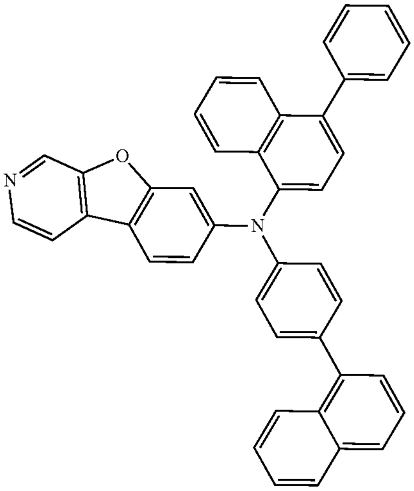
-continued
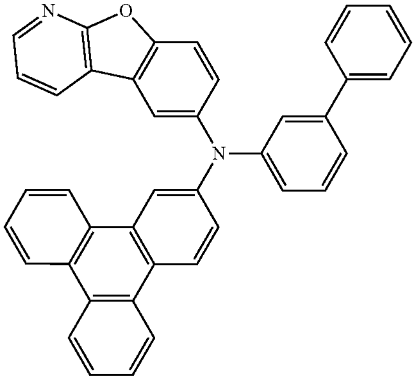
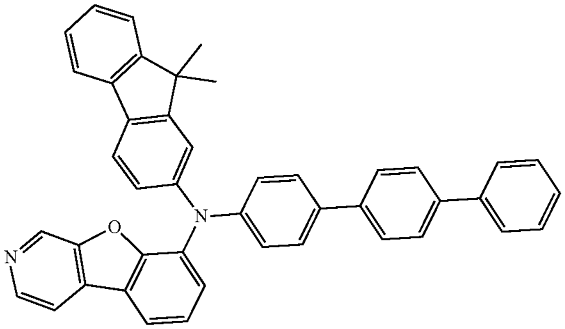
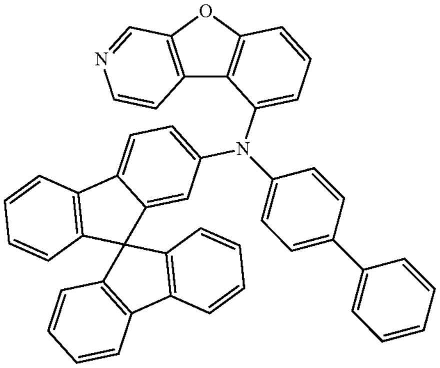
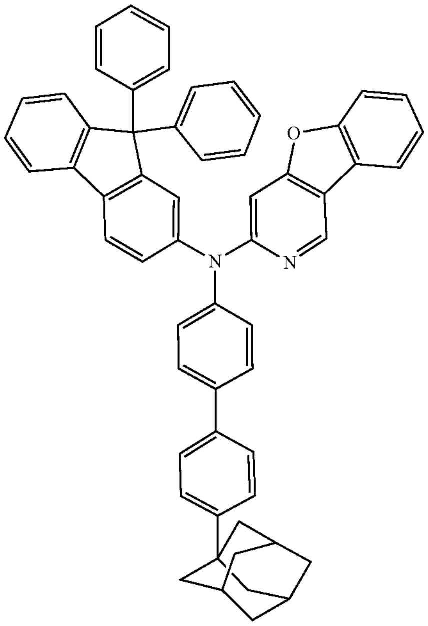

-continued
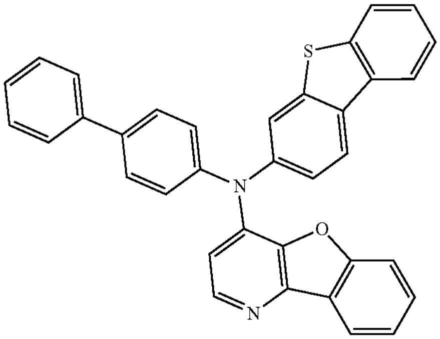
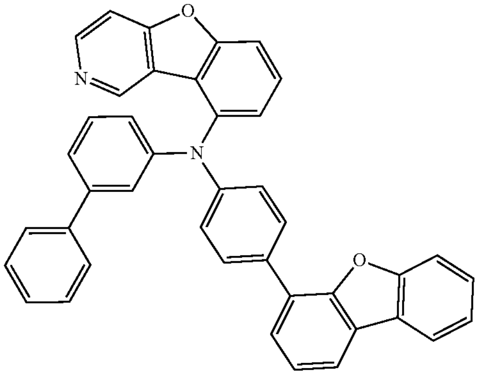
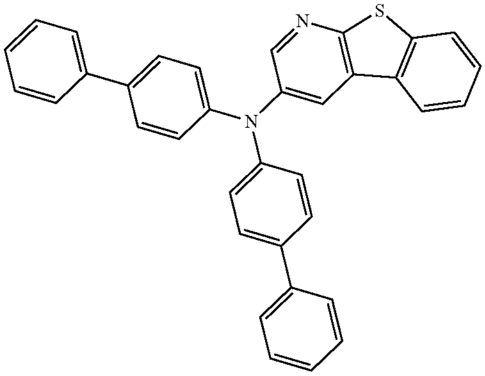
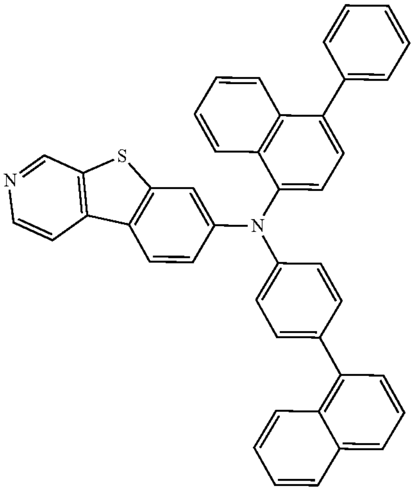
-continued
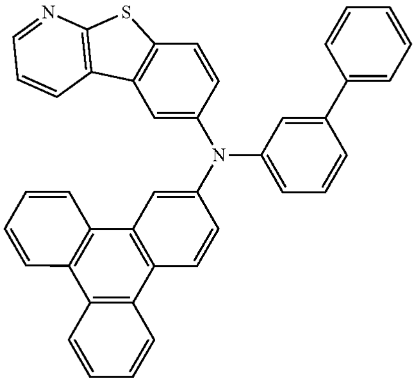
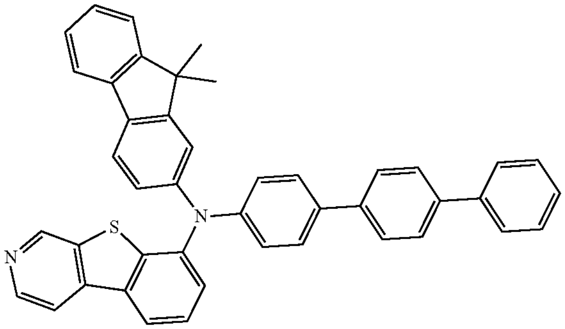
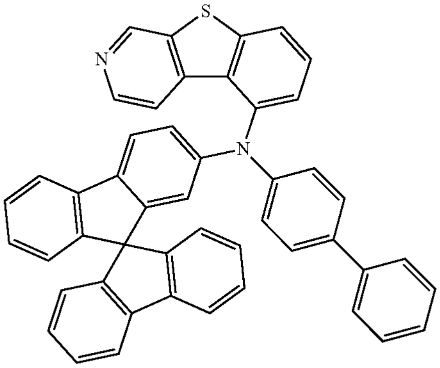
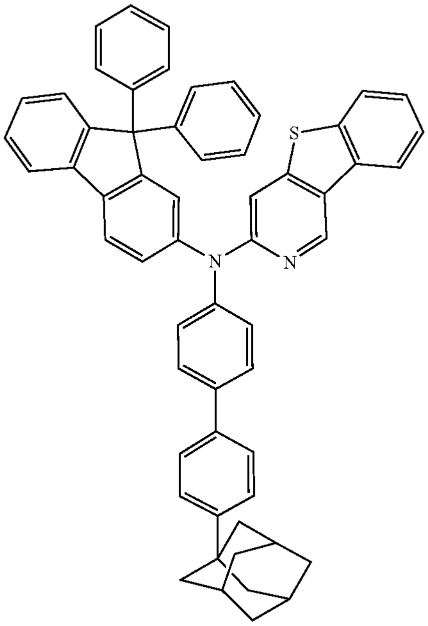

-continued
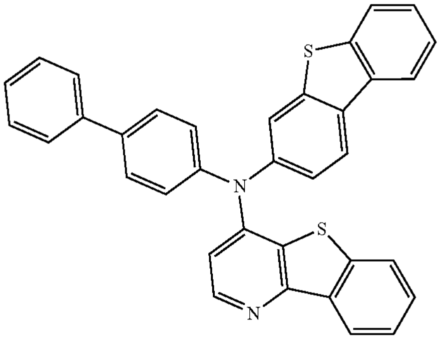
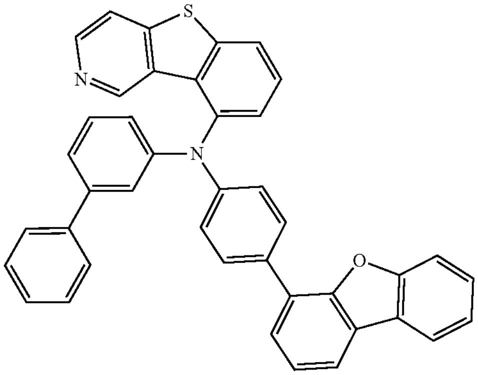
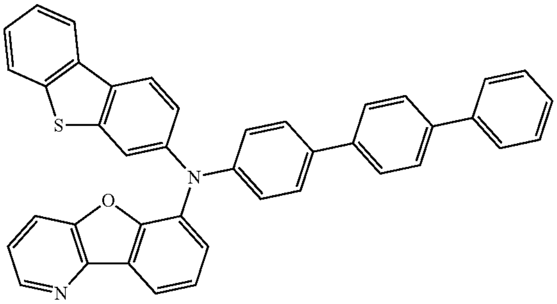
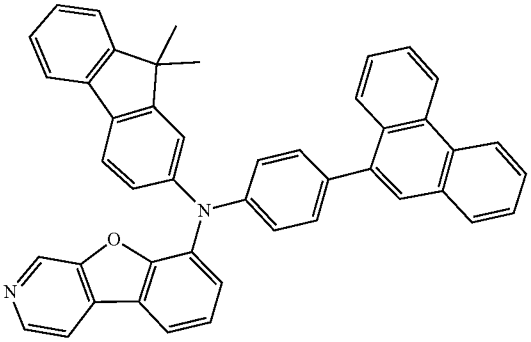
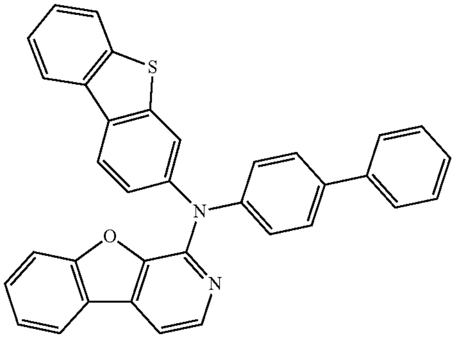
-continued
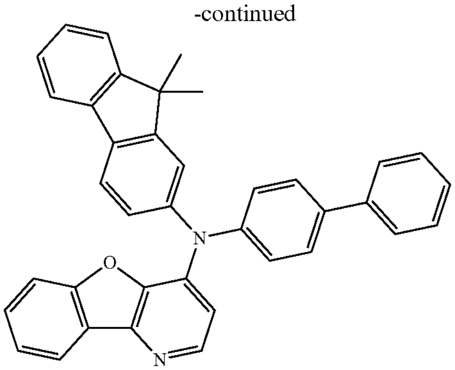
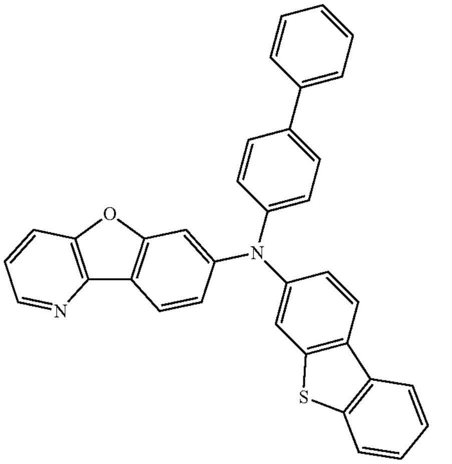
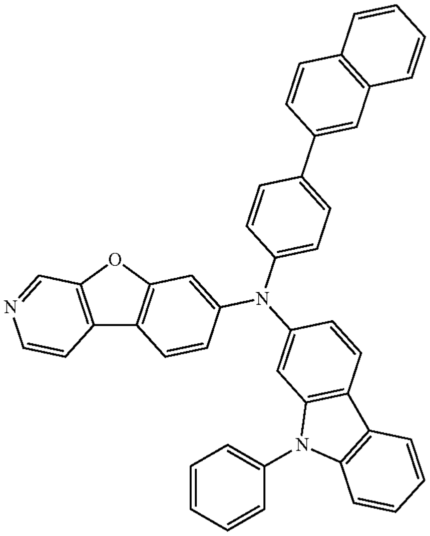

-continued
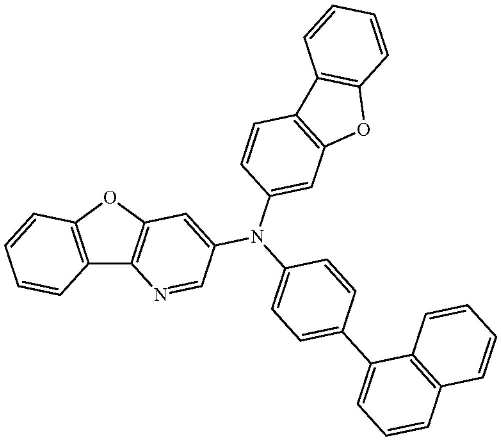
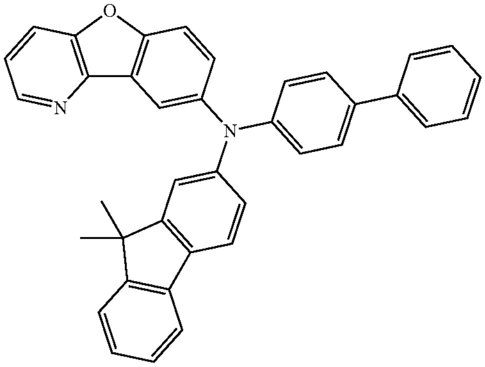
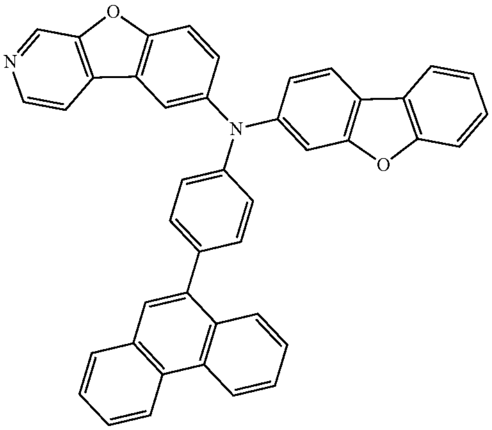
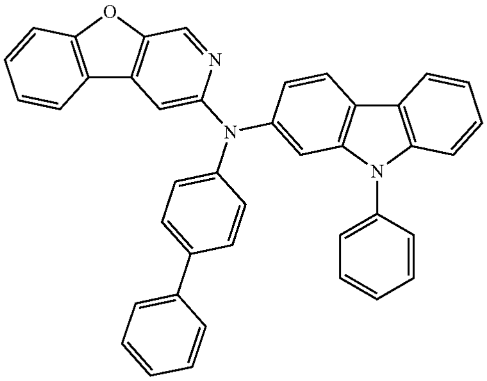
-continued
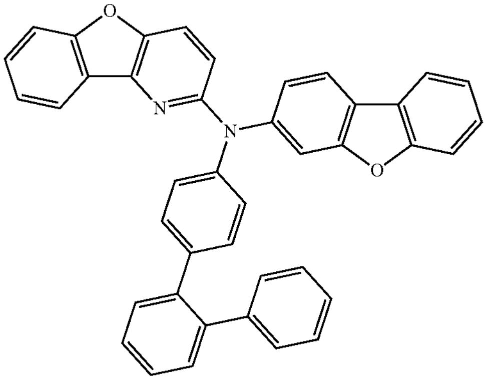
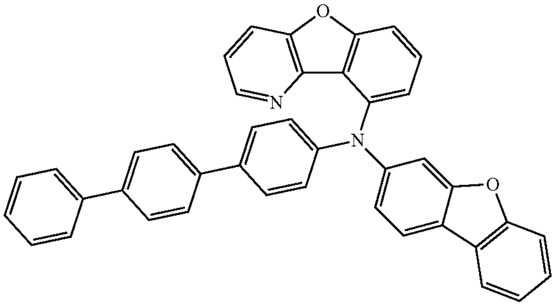
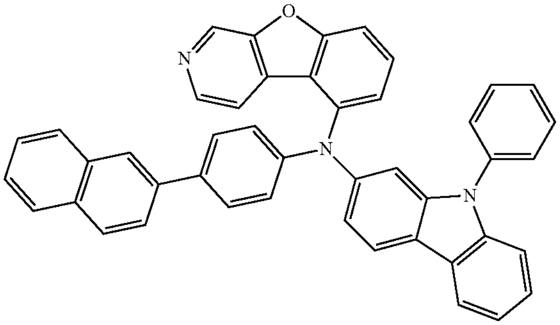
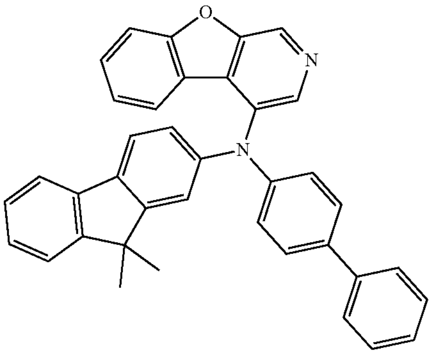
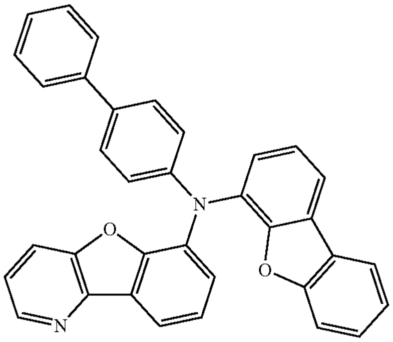

-continued
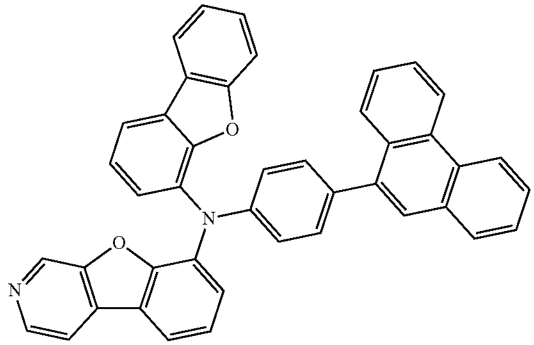
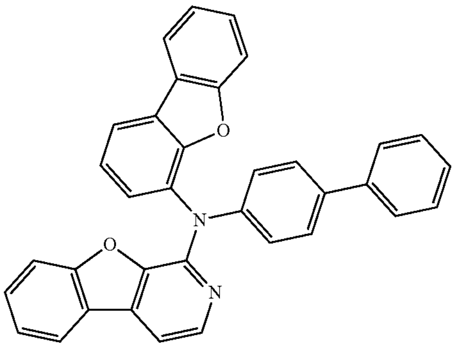
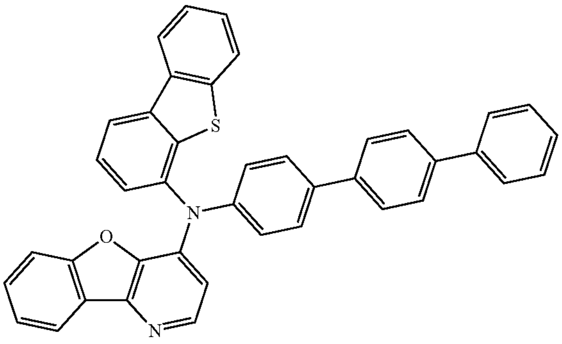
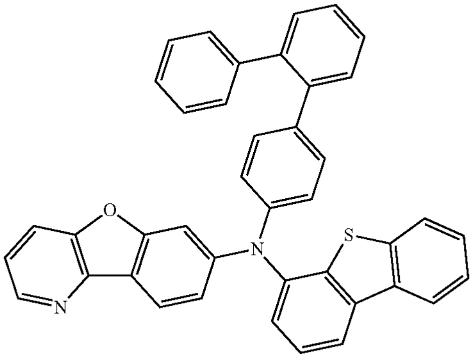
-continued
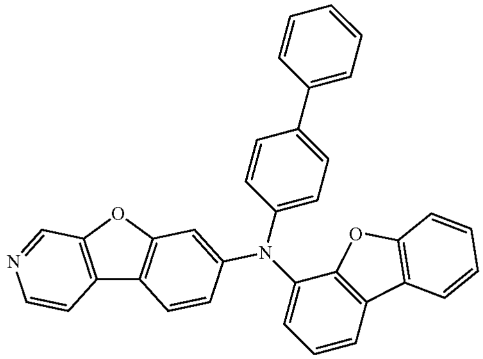
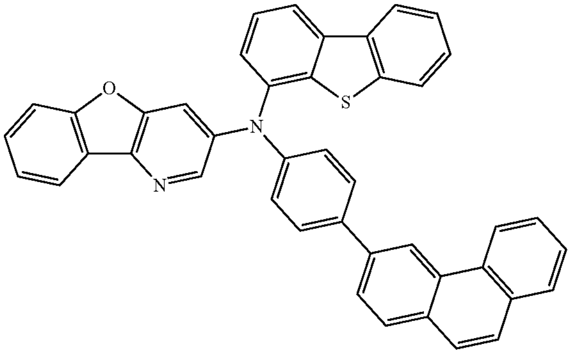
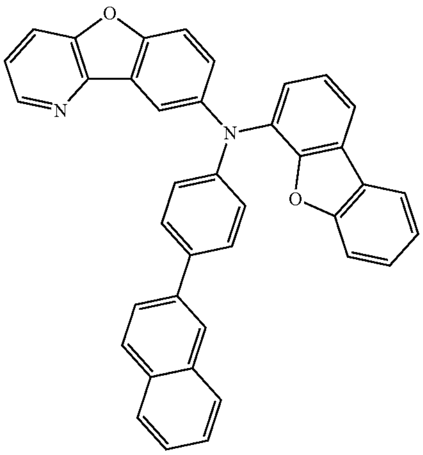
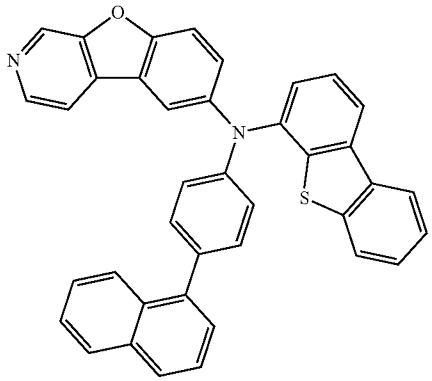

-continued
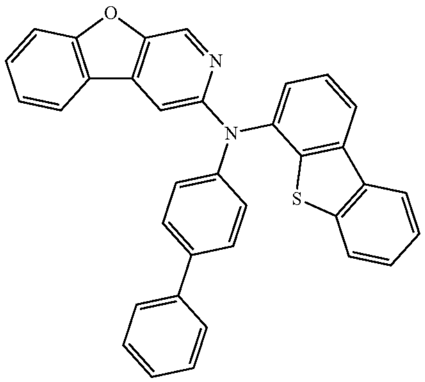
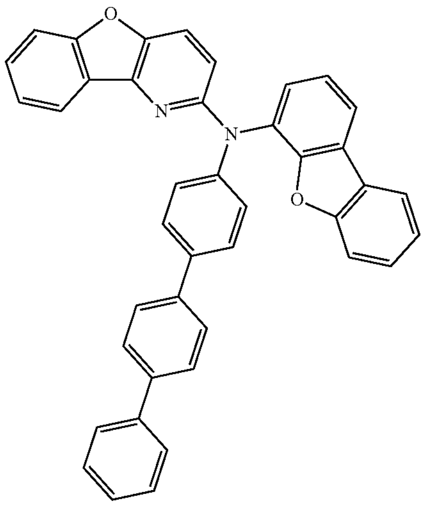
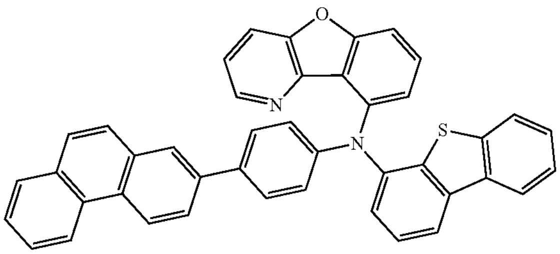
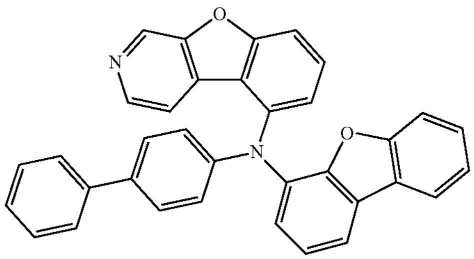
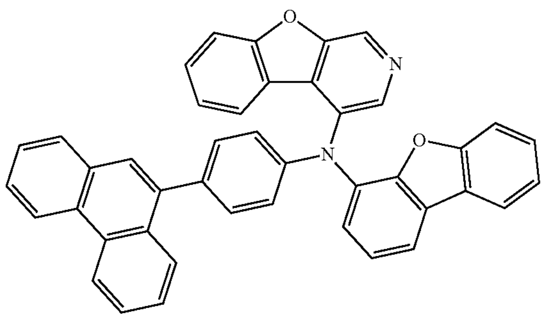
-continued
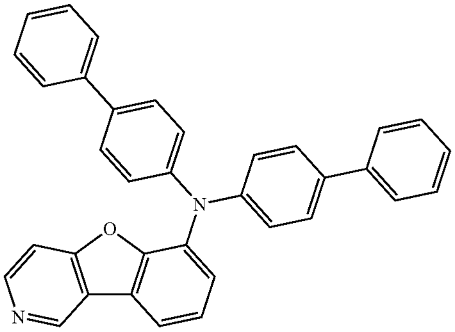
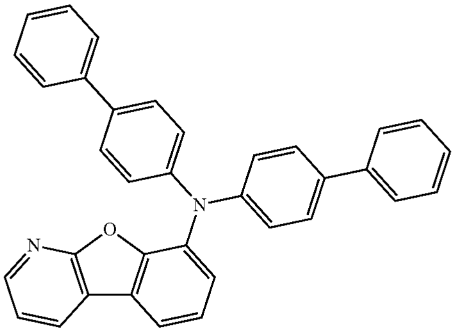
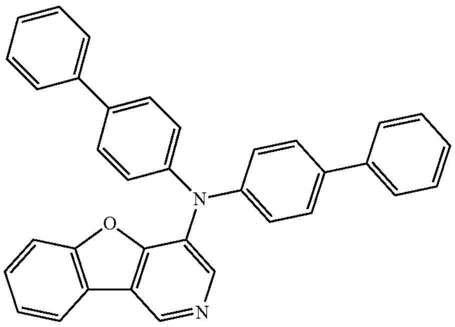
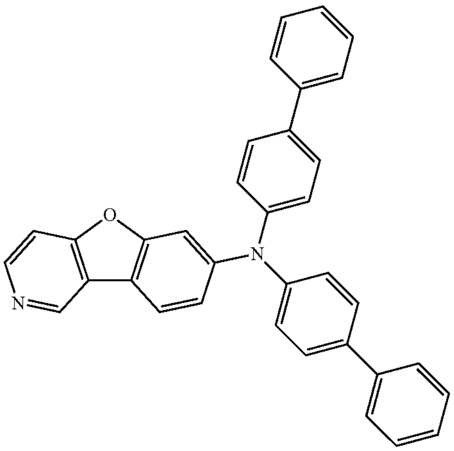

-continued
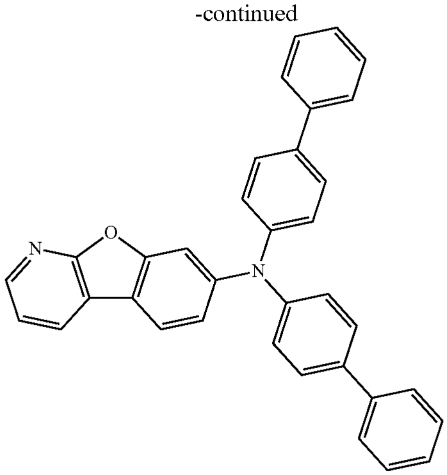
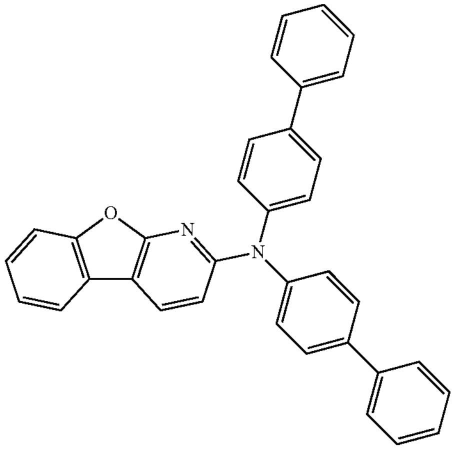
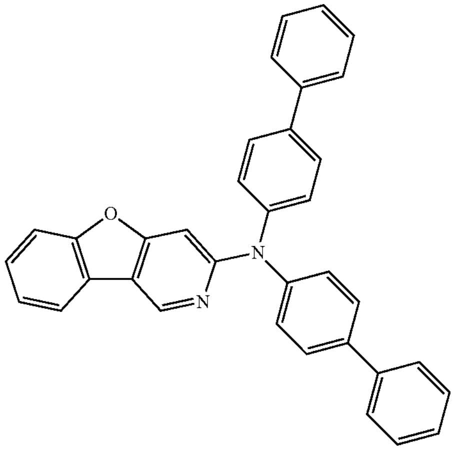
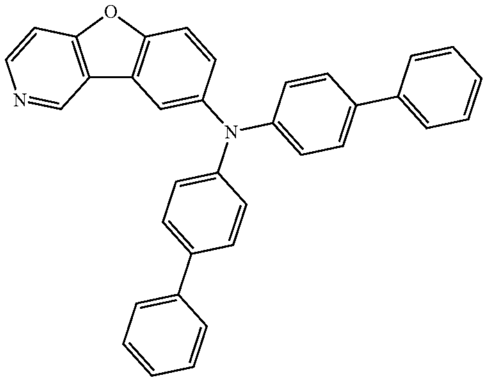
-continued
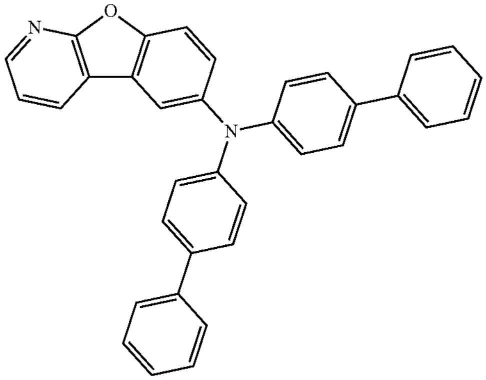
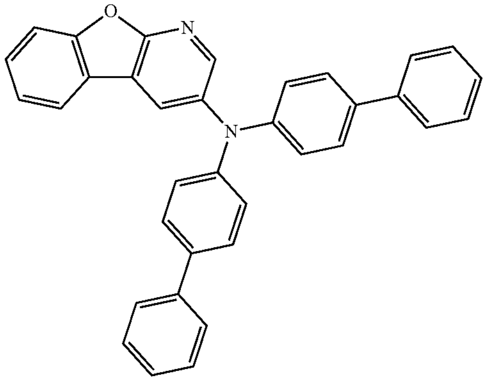
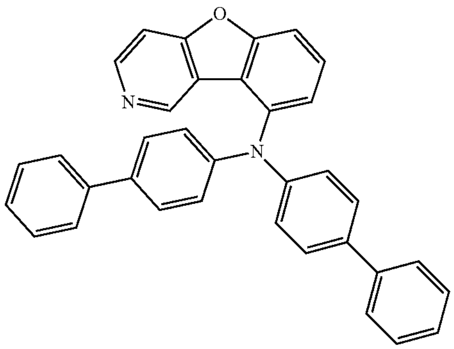
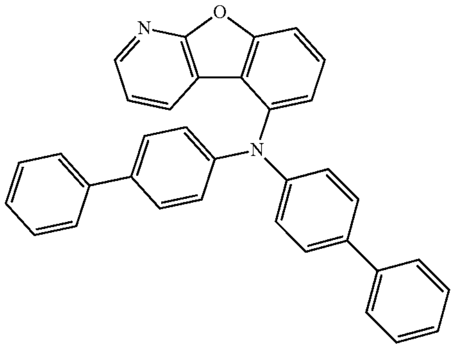

-continued
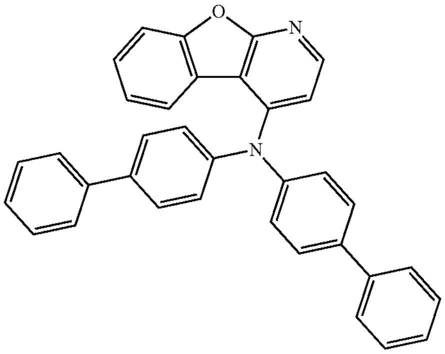
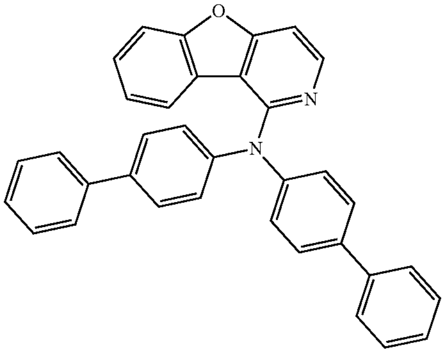
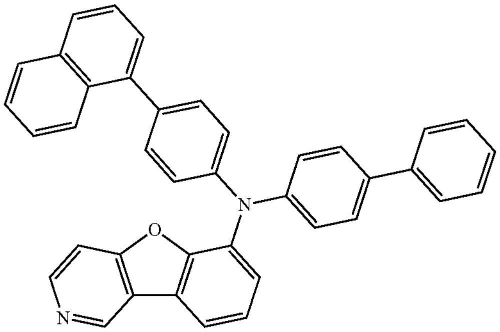
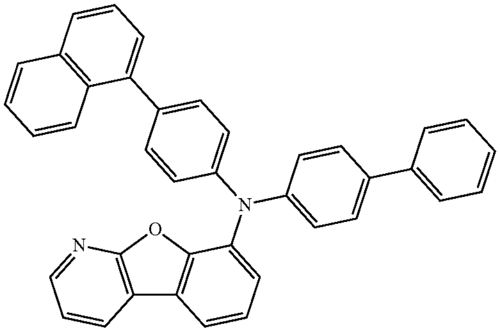
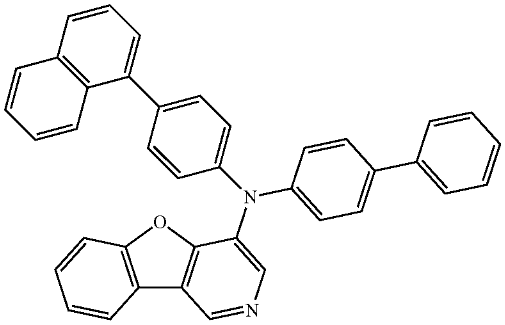
-continued
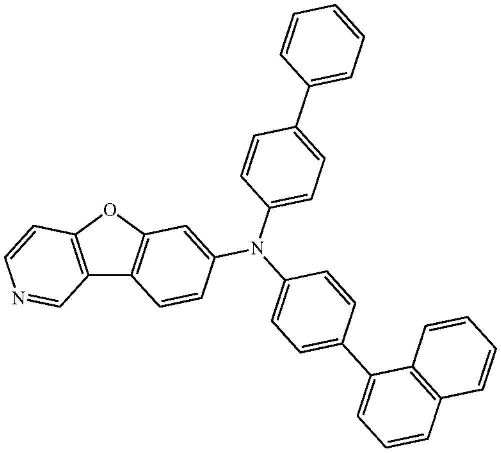
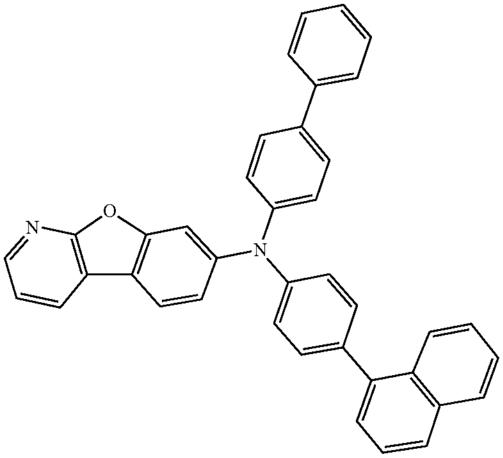
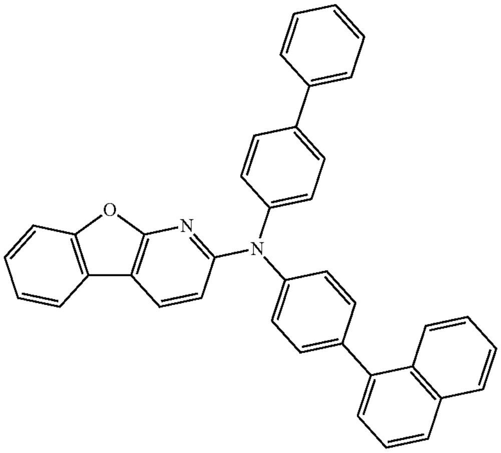

-continued
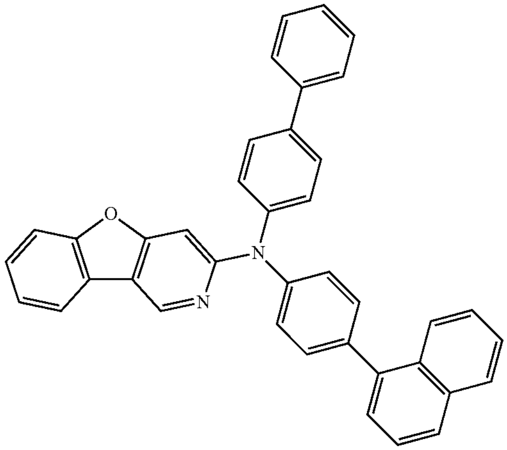
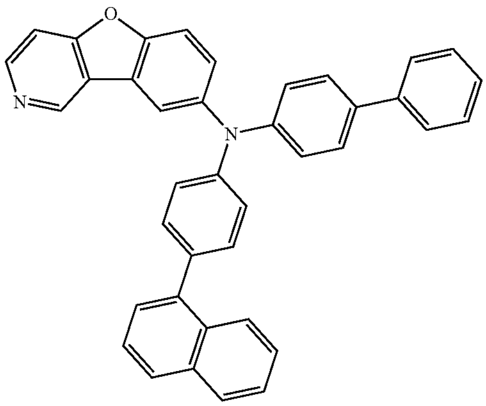
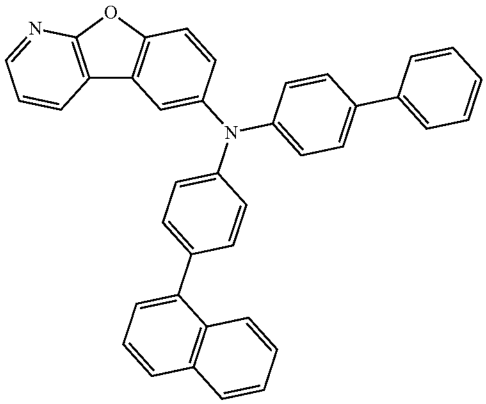
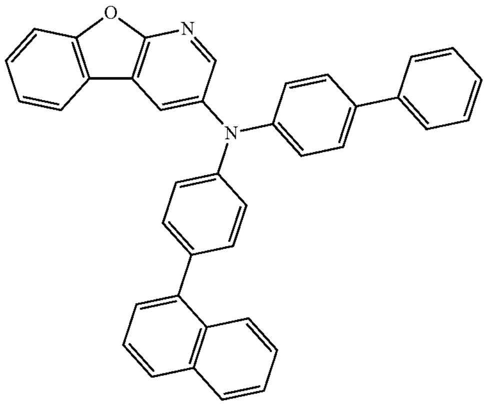
-continued
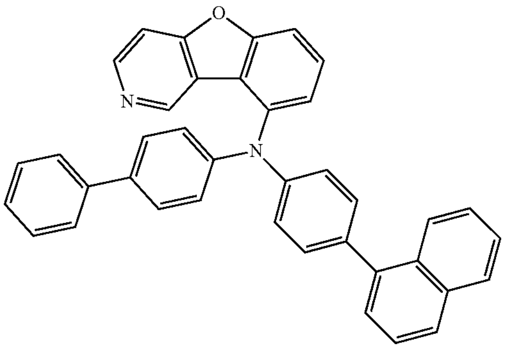
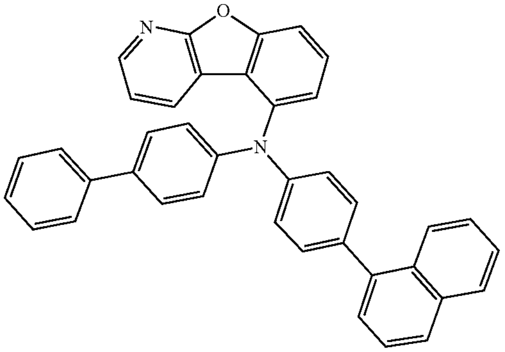
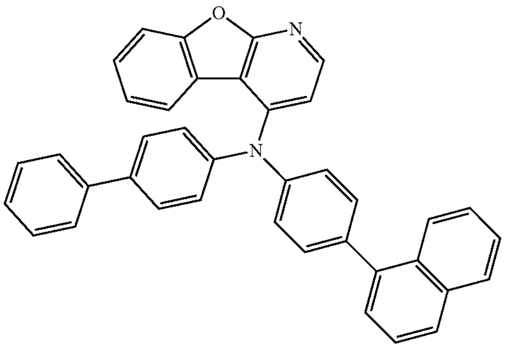
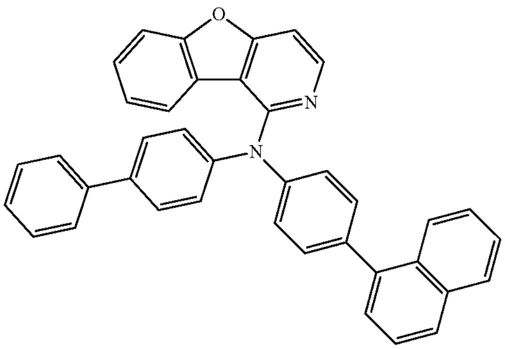

-continued
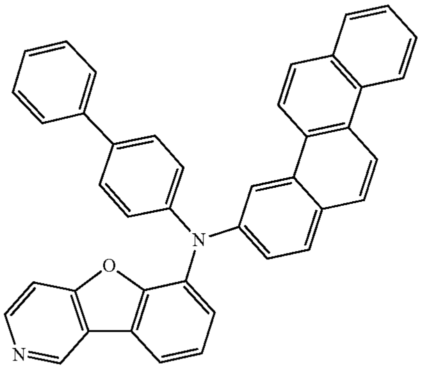
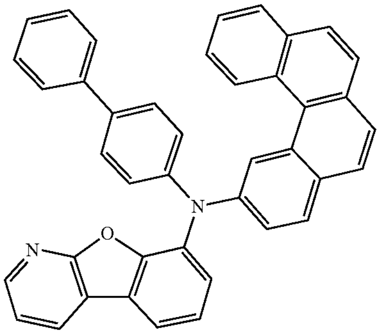
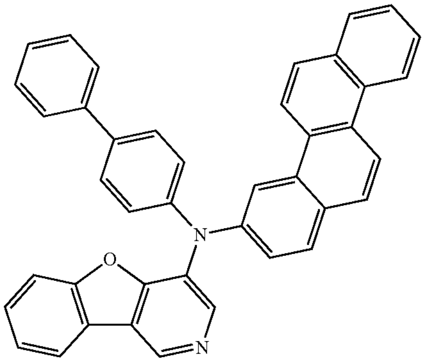
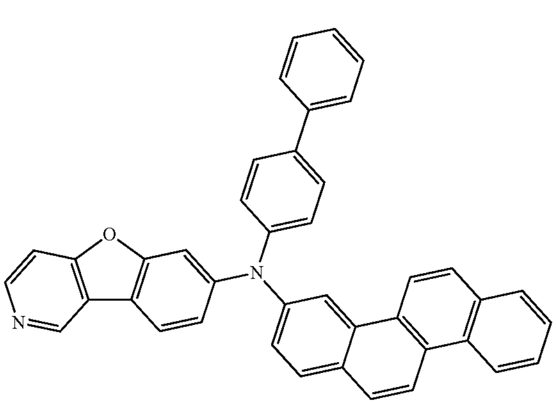
-continued
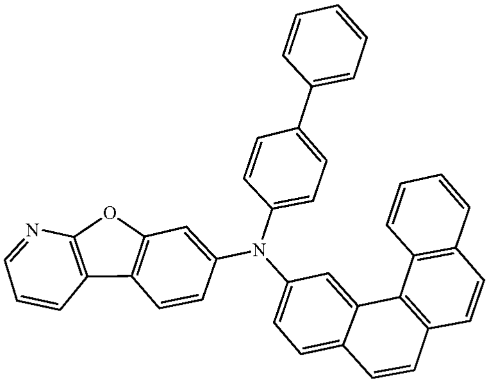
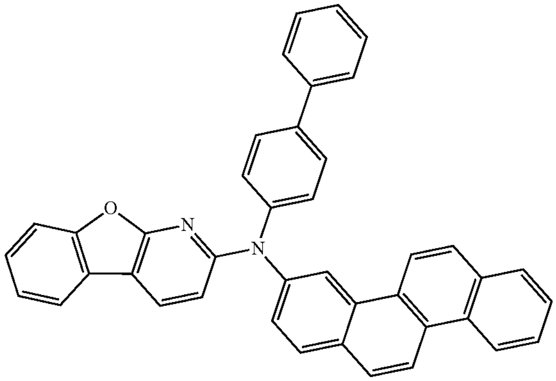
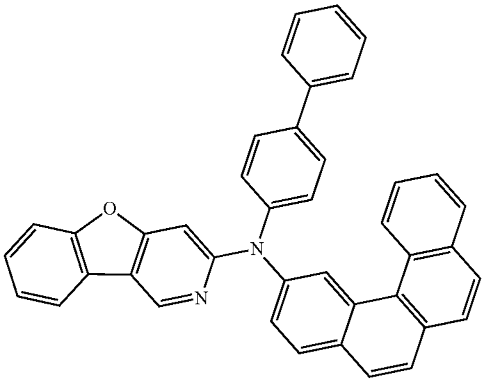
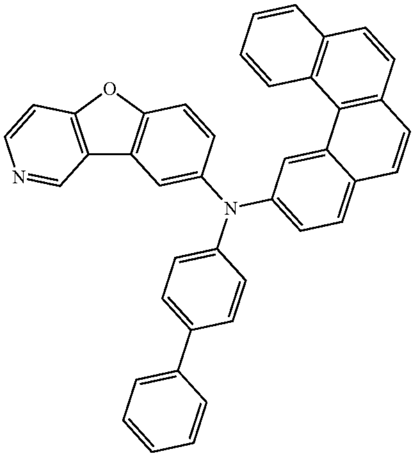

-continued
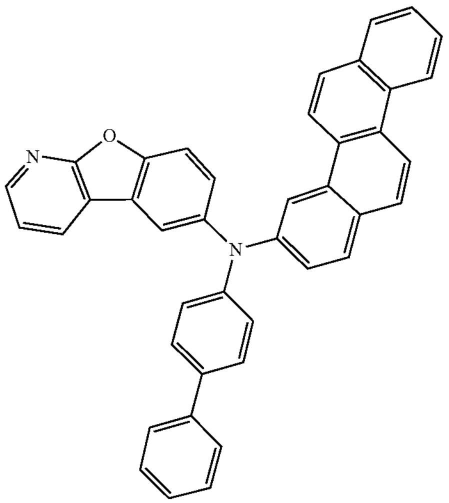
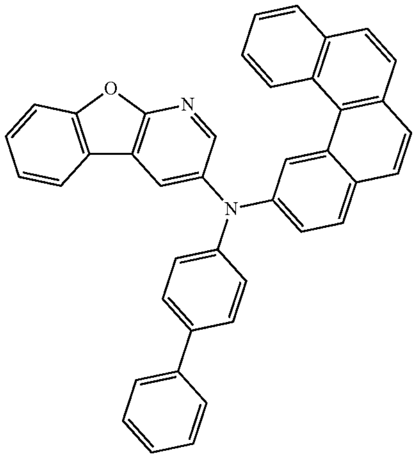
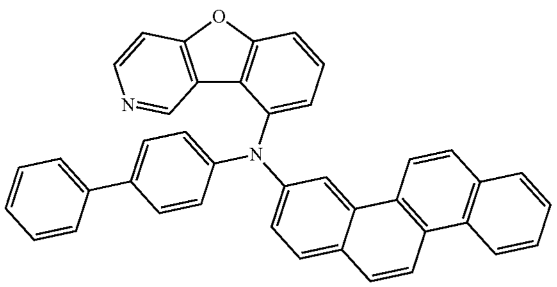
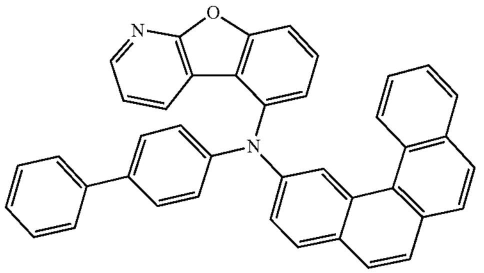
-continued
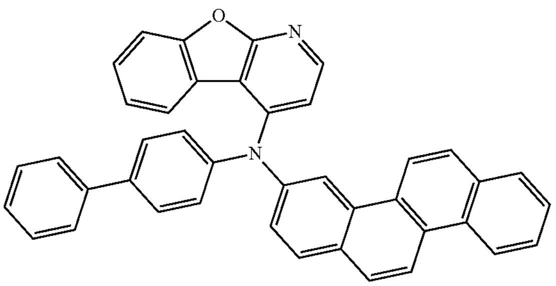
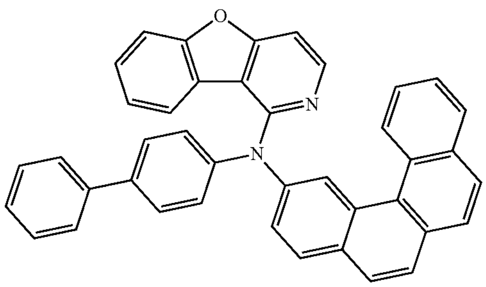
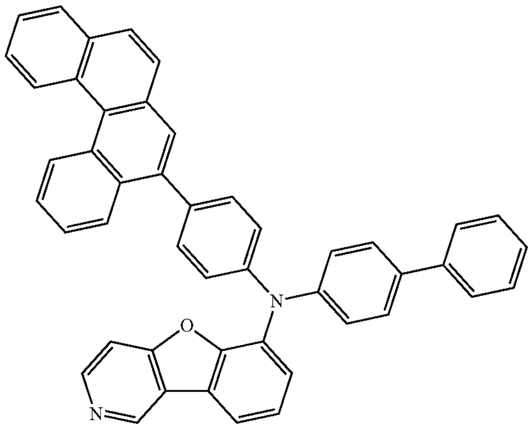
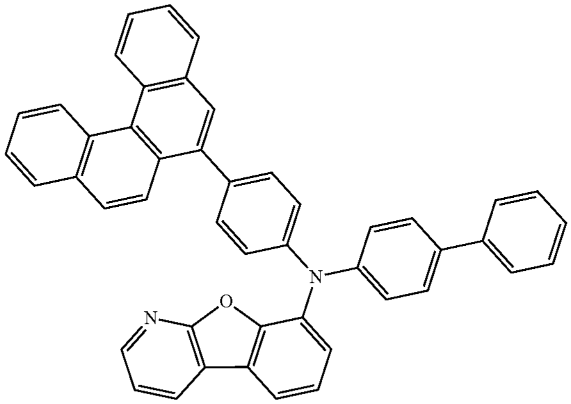

-continued
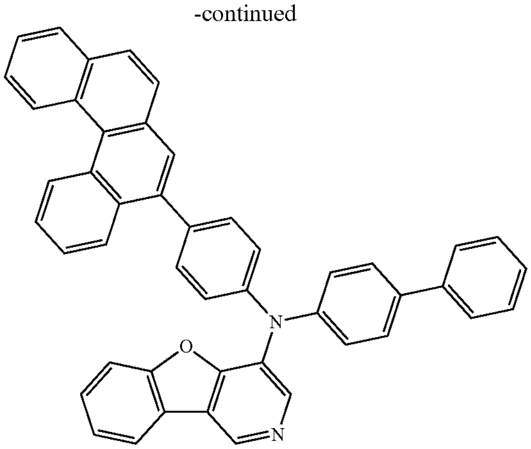
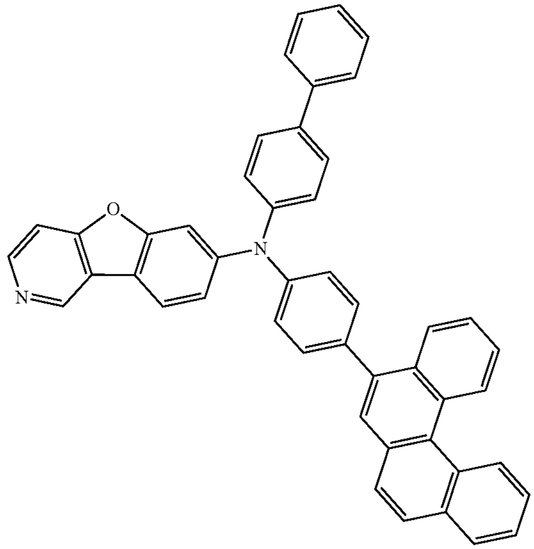
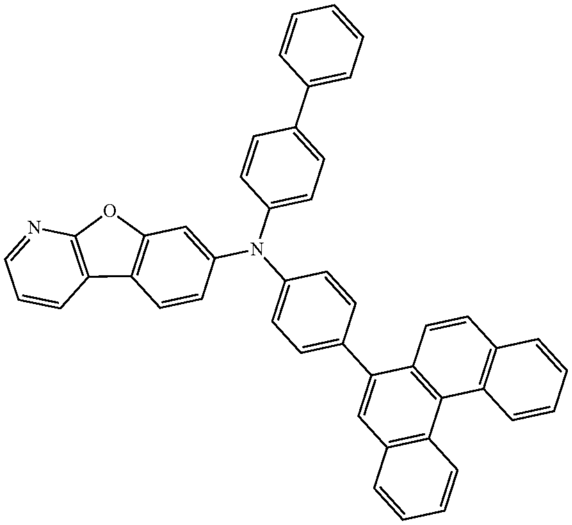
-continued
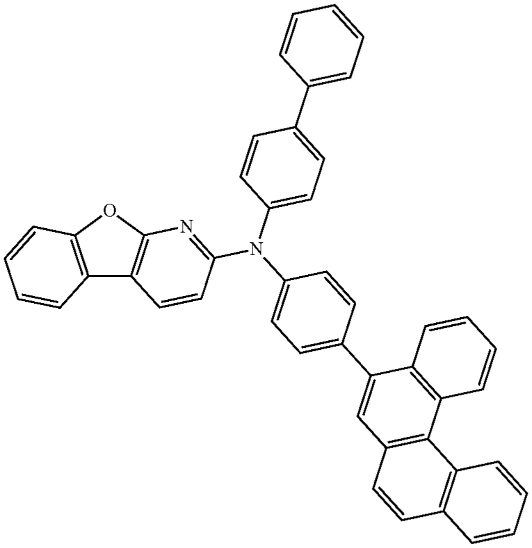
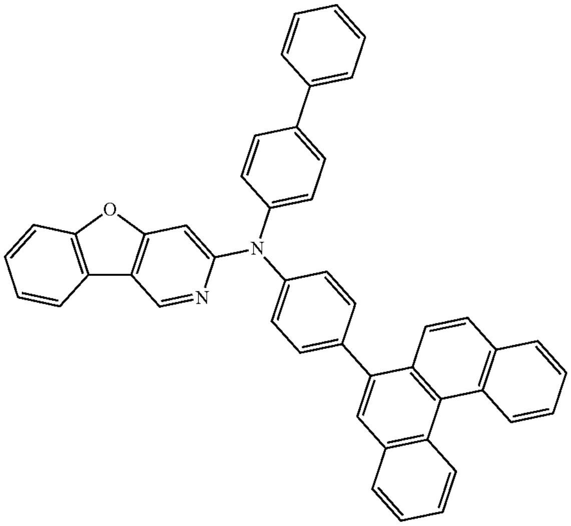
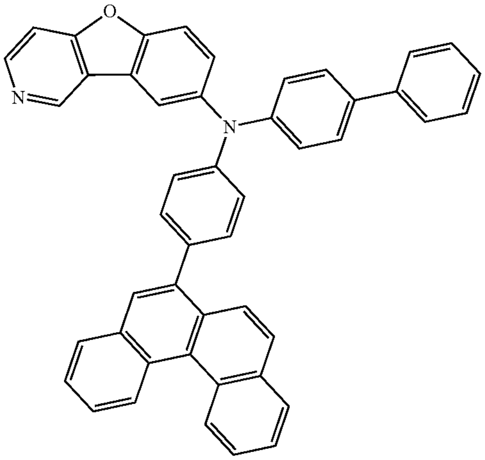

-continued
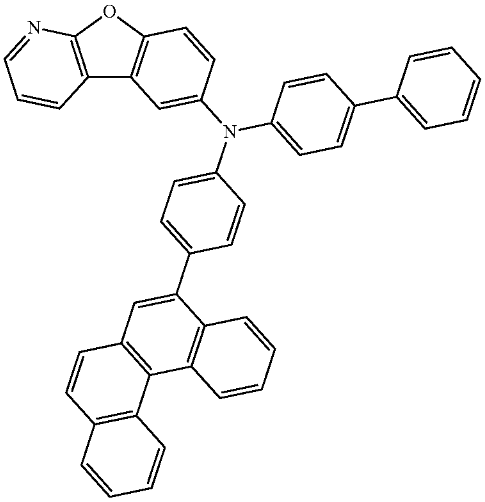
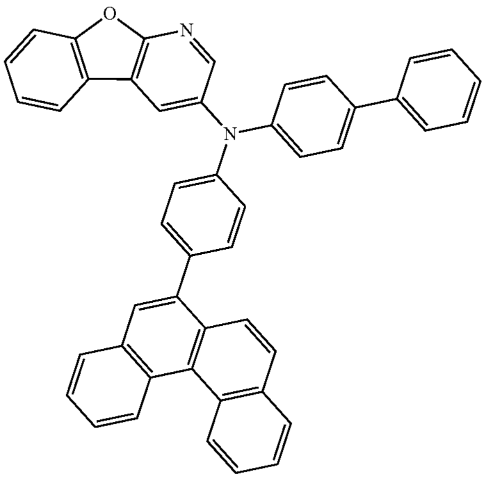
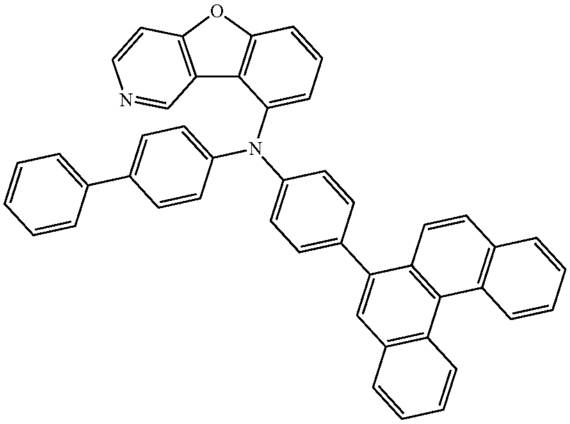
-continued
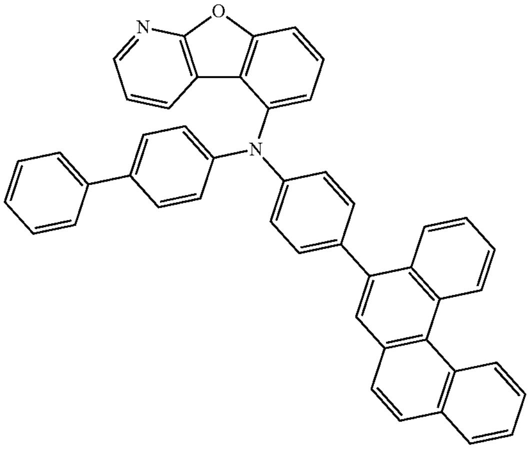
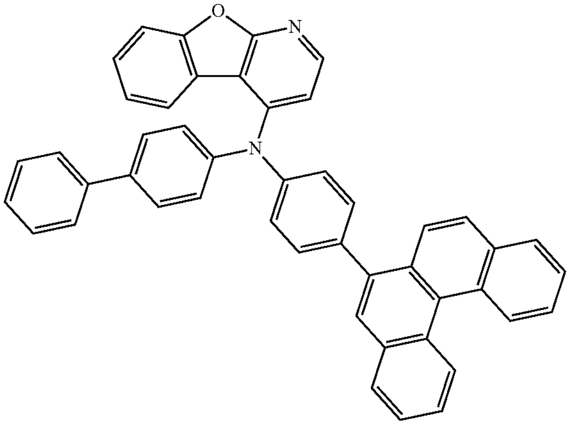
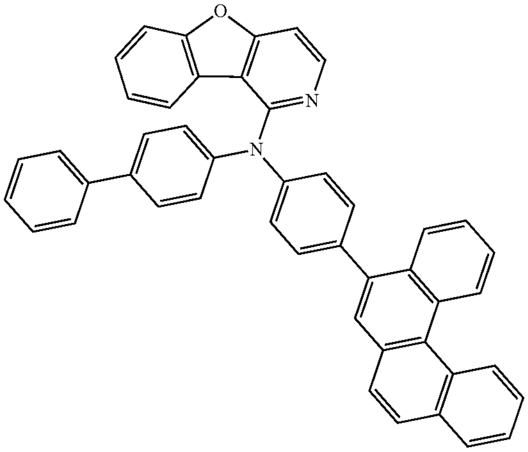
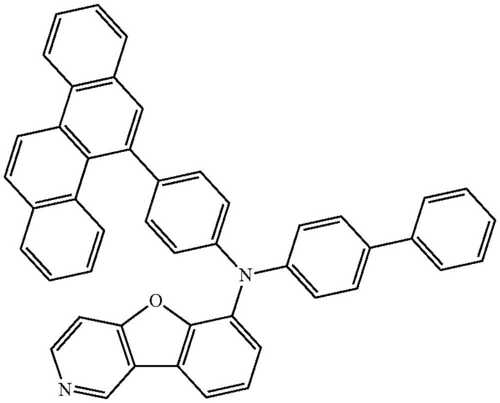

-continued
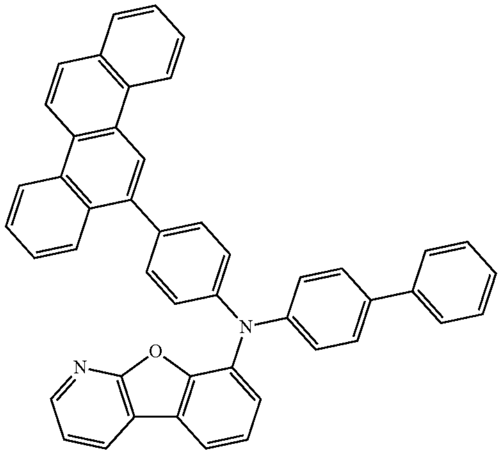
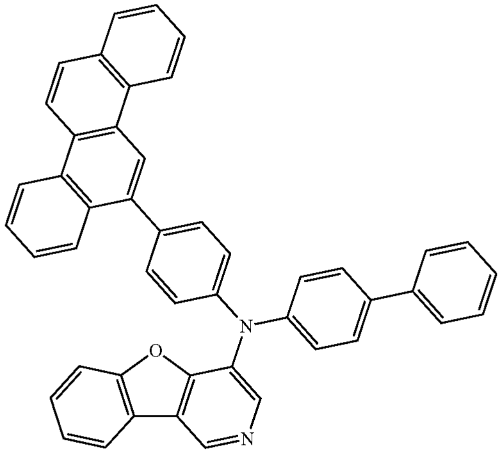
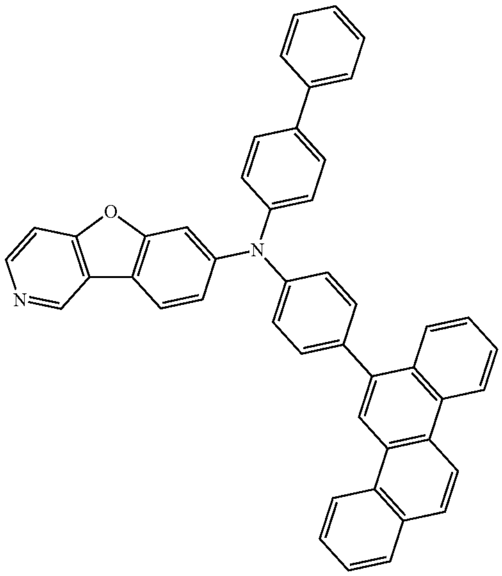
-continued
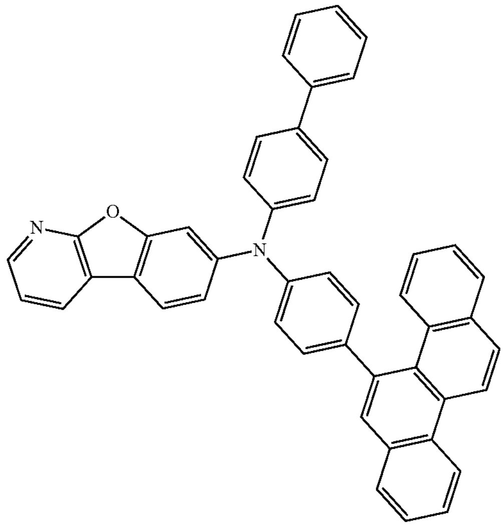
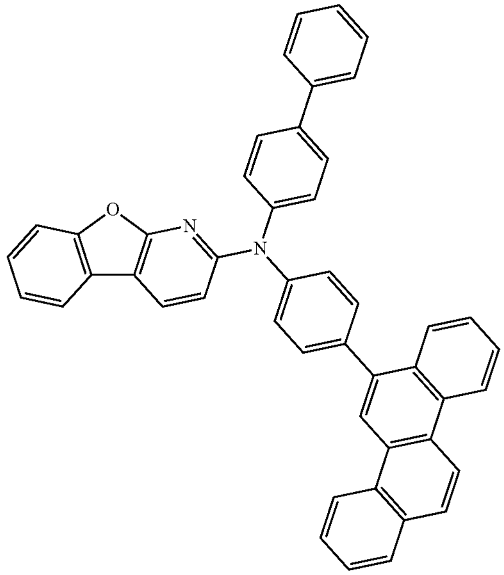
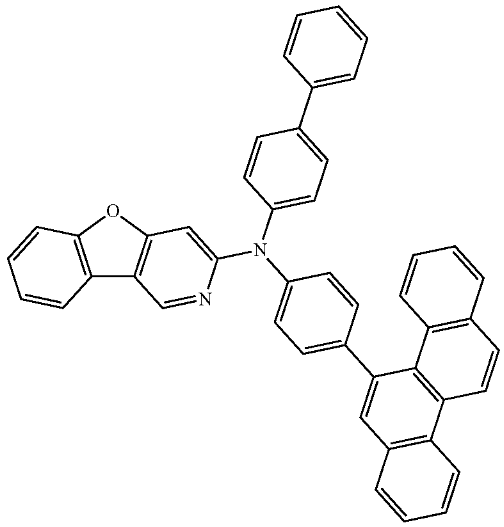 [SMILES: c1ccc(-c2ccc(N(c3ccc(-c4cc5ccccc5c5ccc6ccccc6c45)cc3)c3cc4oc5ccccc5c4cn3)cc2)cc1]

-continued
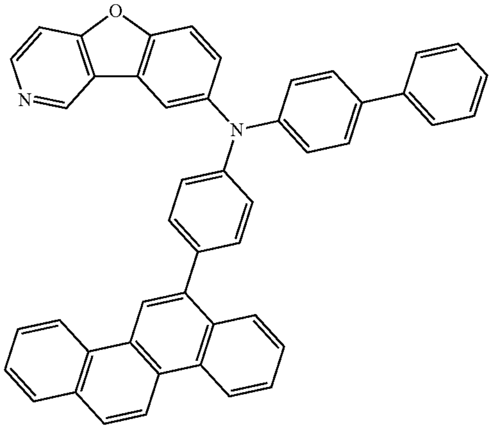
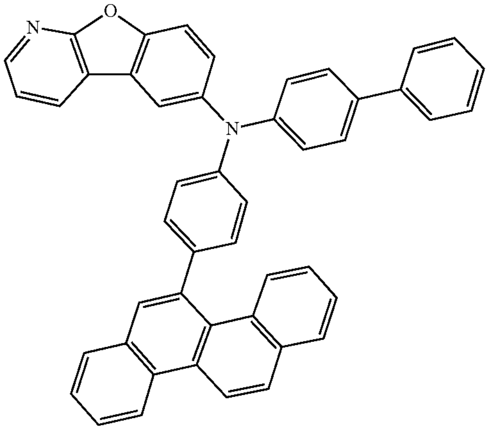
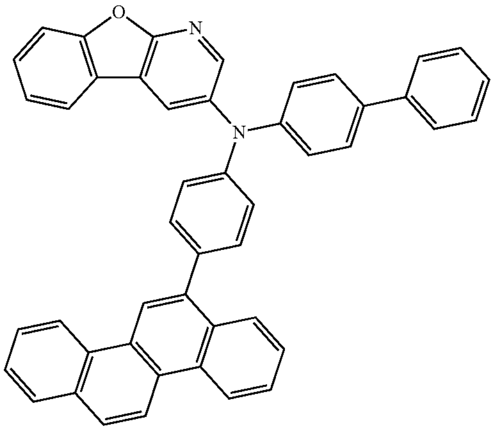
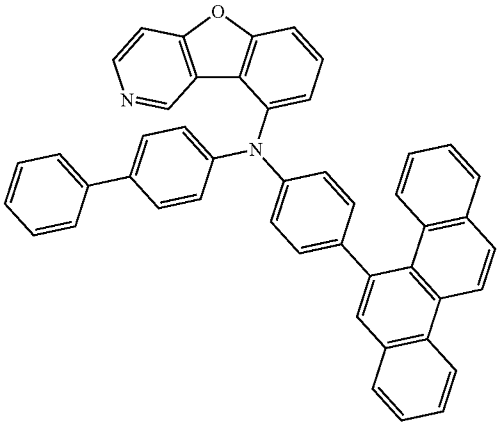
-continued
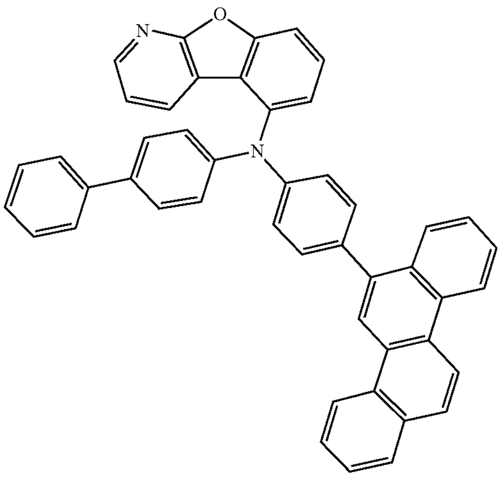
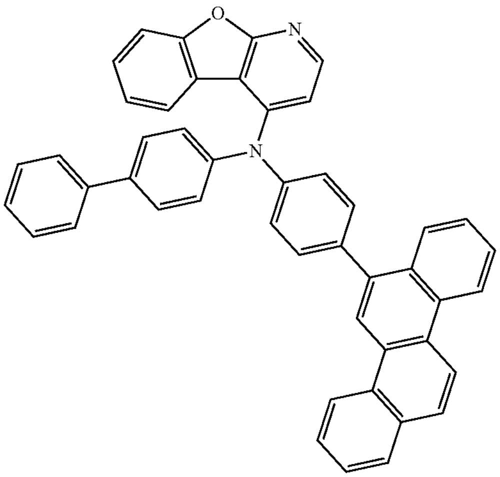
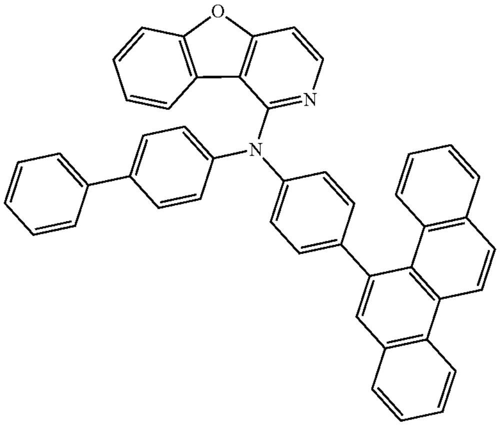
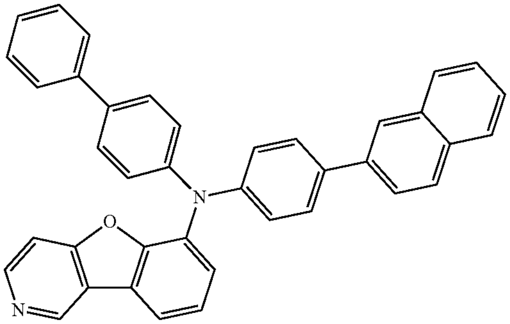

-continued
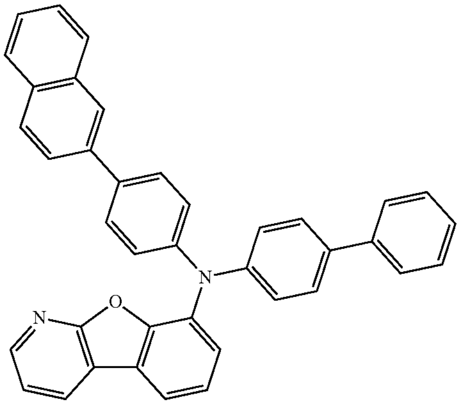
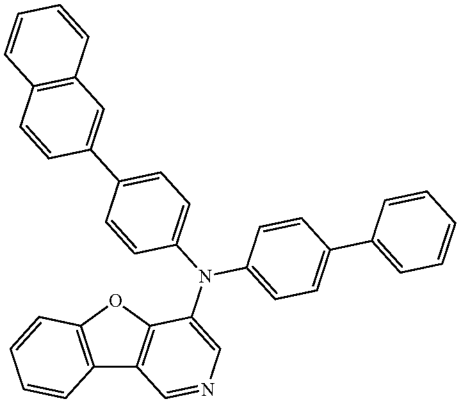
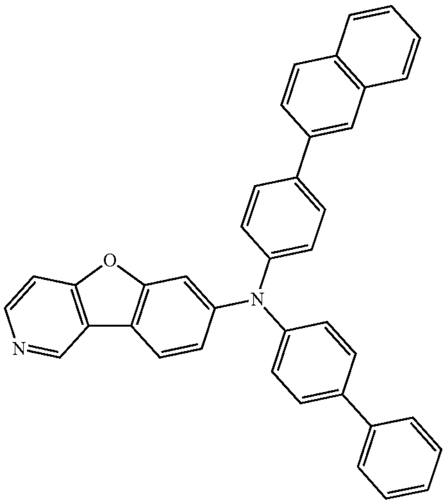
-continued
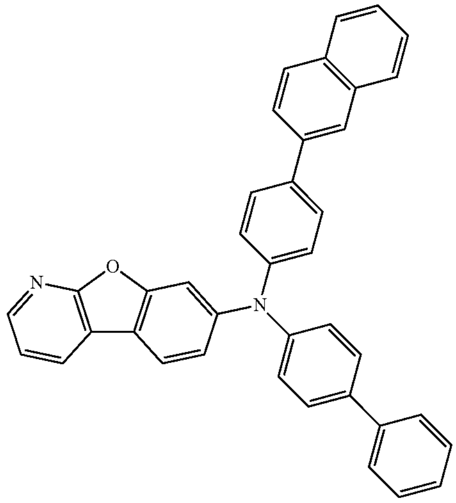
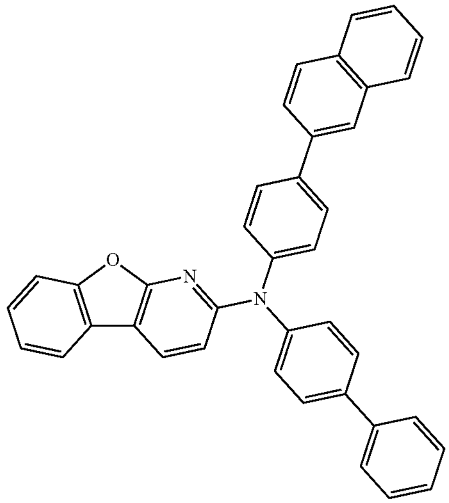
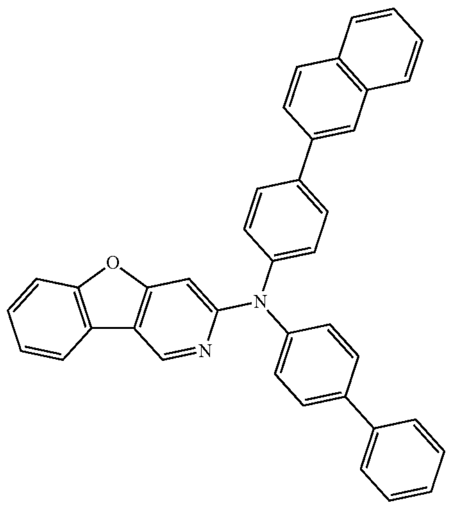 [SMILES: c1ccc(-c2ccc(N(c3ccc(-c4ccc5ccccc5c4)cc3)c3cc4oc5ccccc5c4cn3)cc2)cc1]

-continued
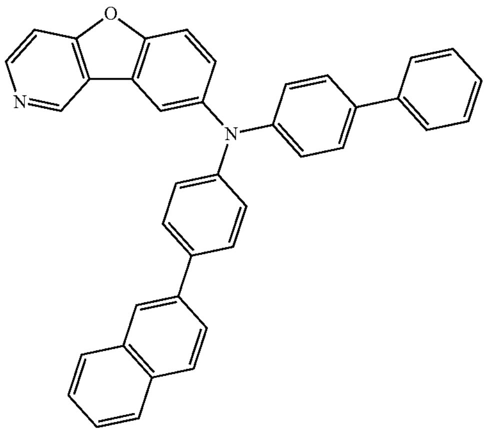
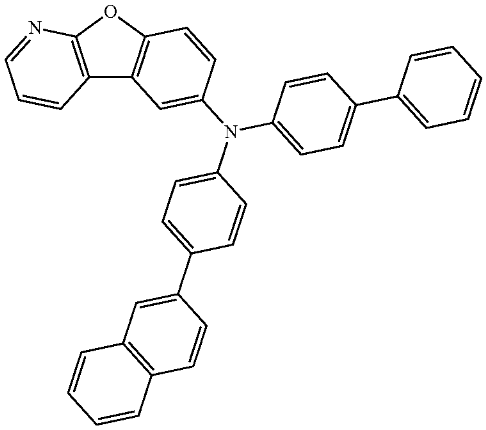
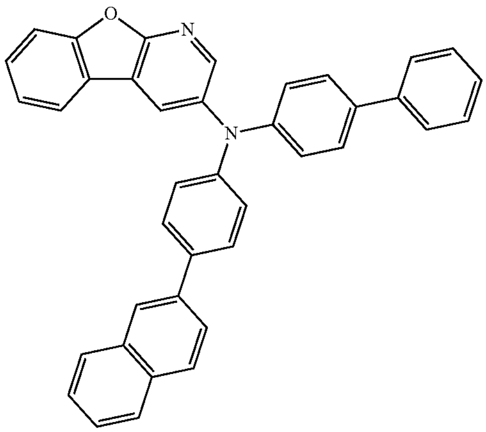
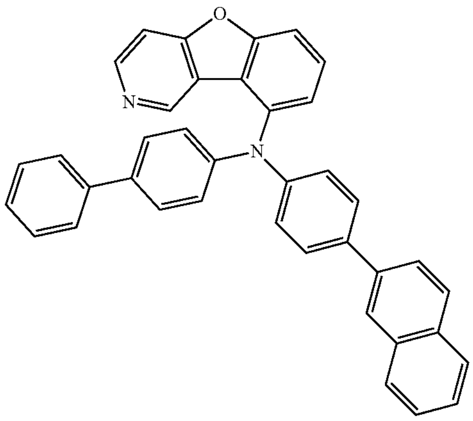
-continued
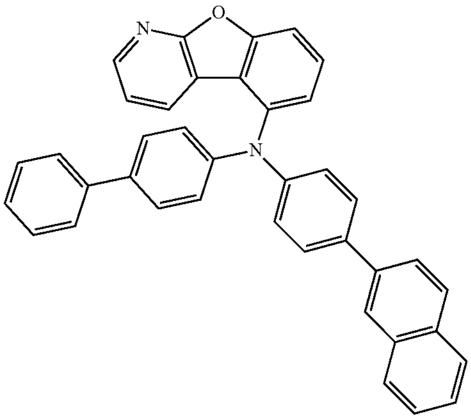
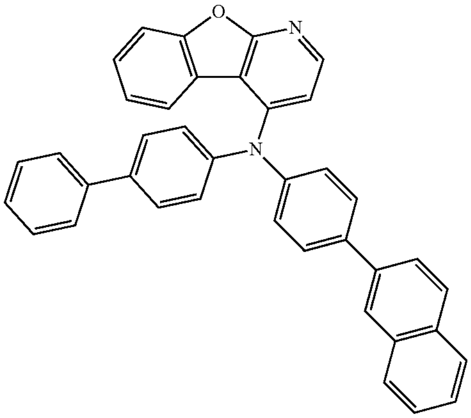
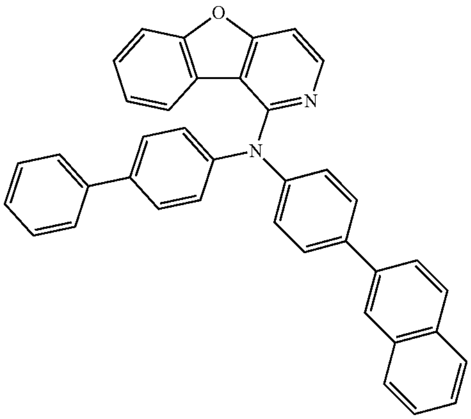
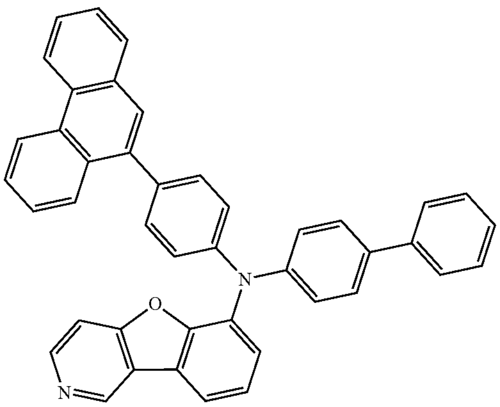

-continued
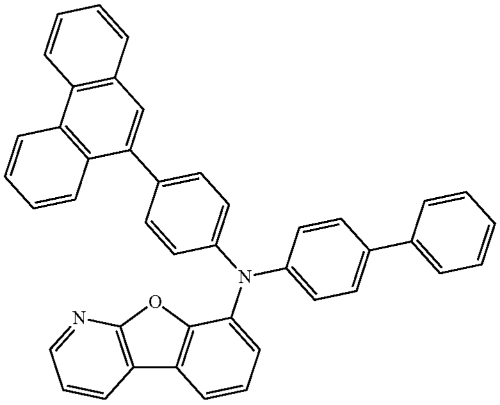
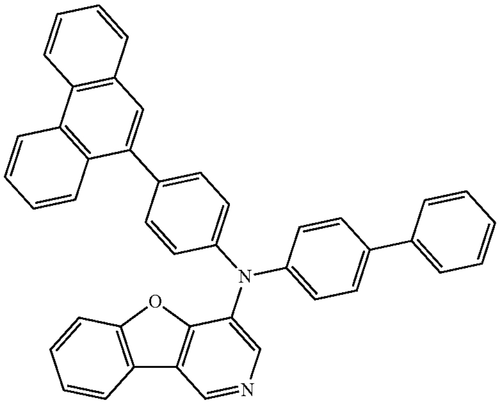
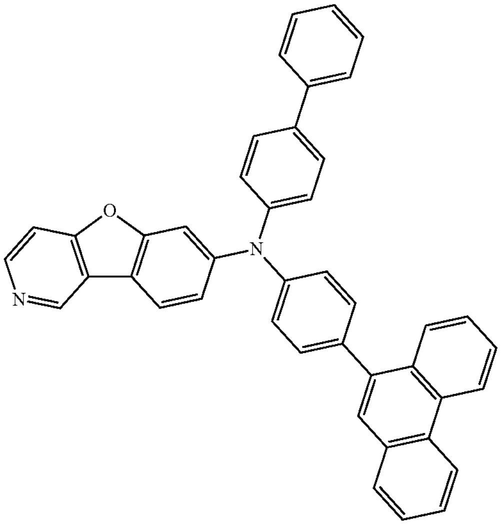
-continued
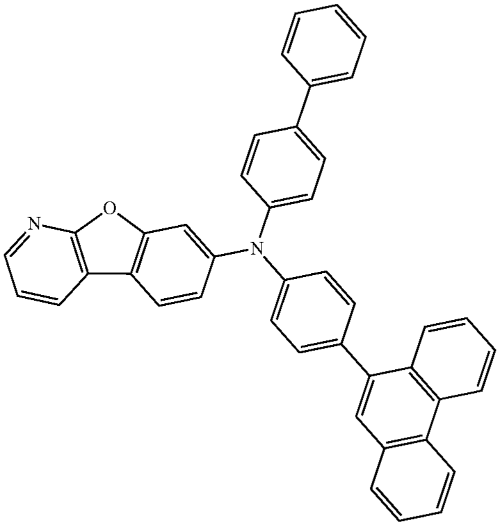
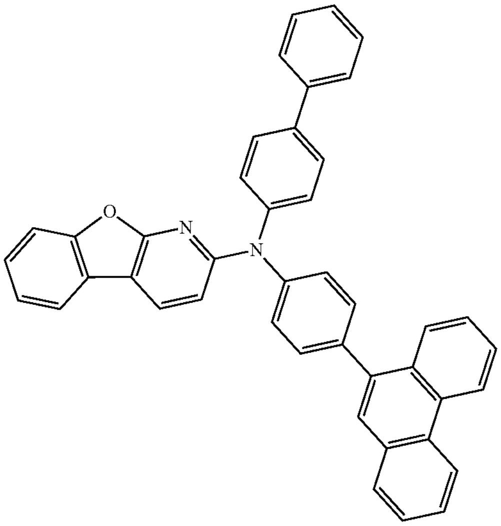
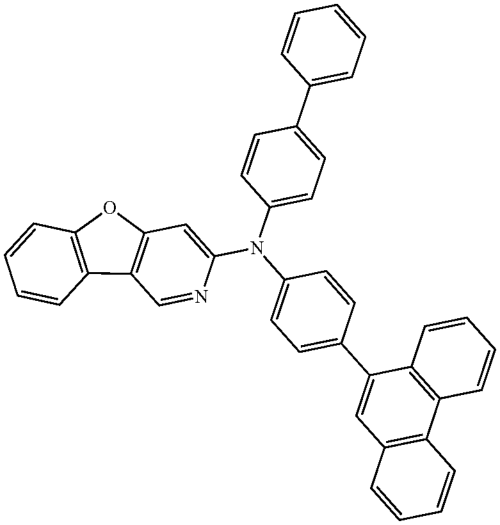

-continued
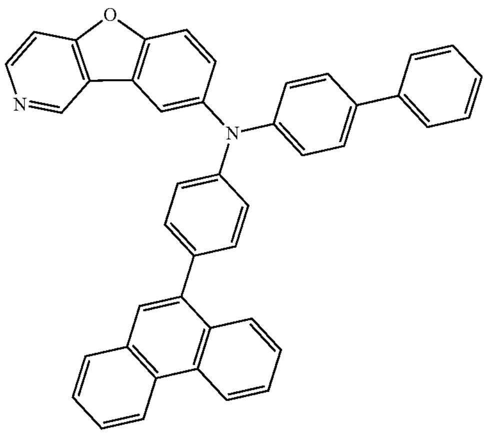
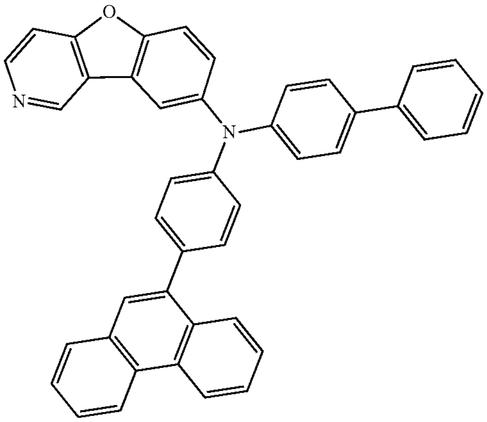
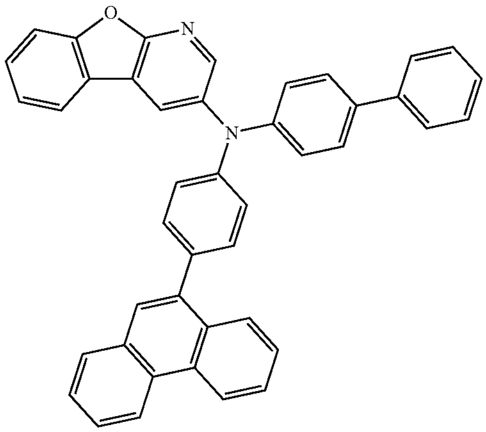
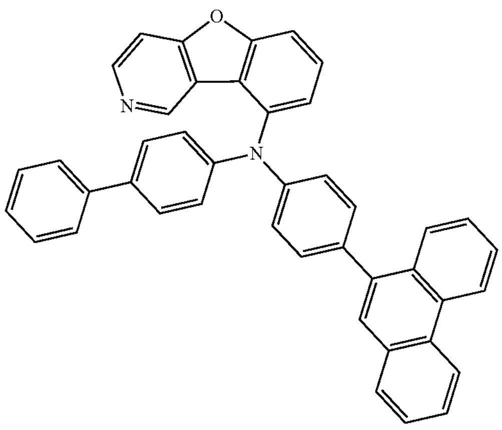
-continued
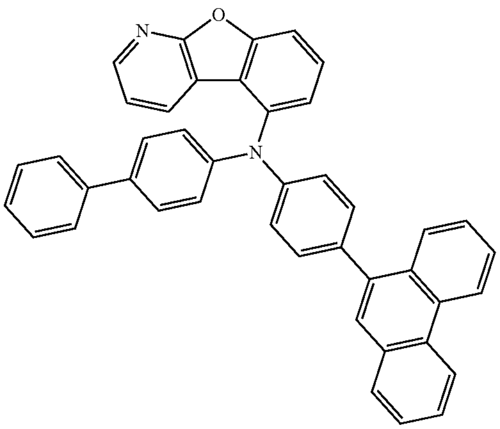
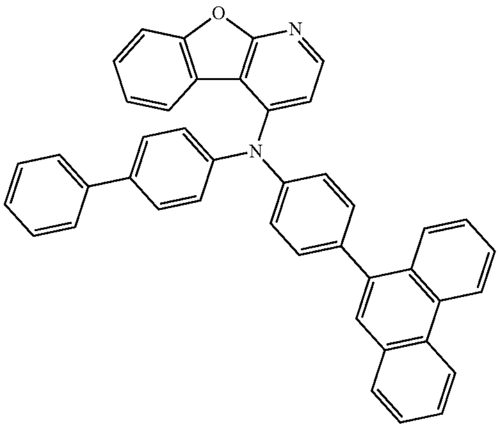
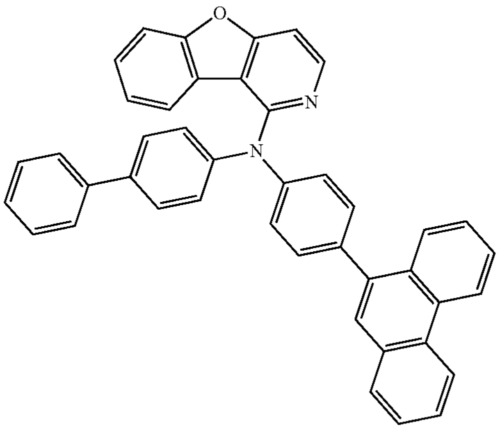
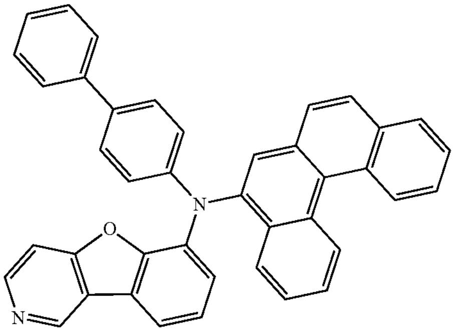

-continued
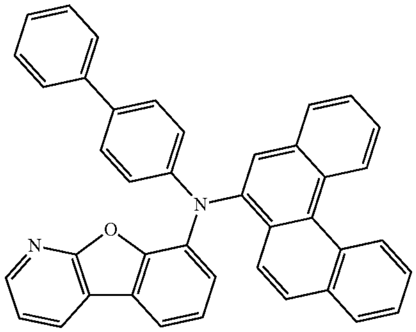
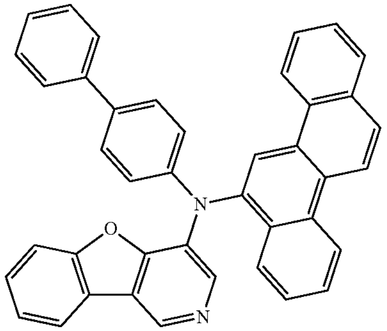
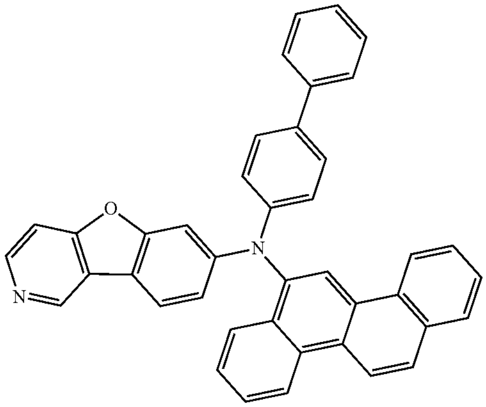
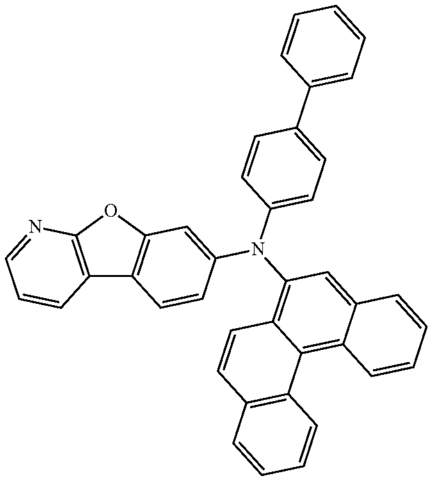
-continued
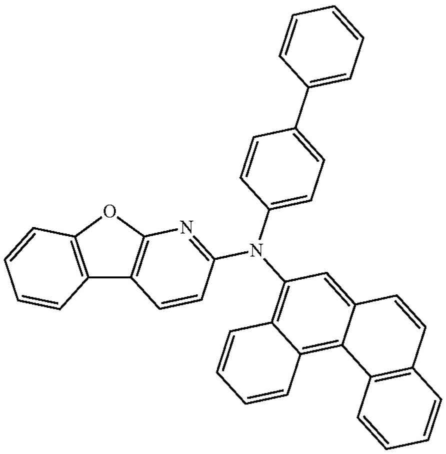
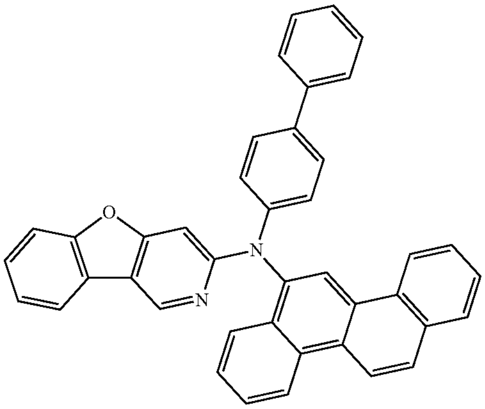
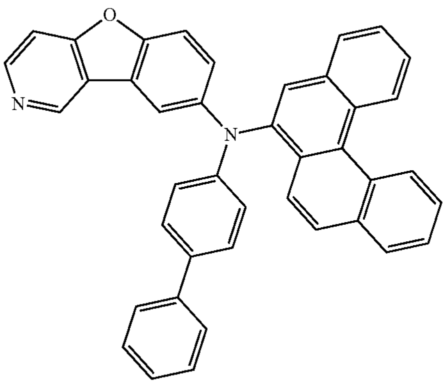
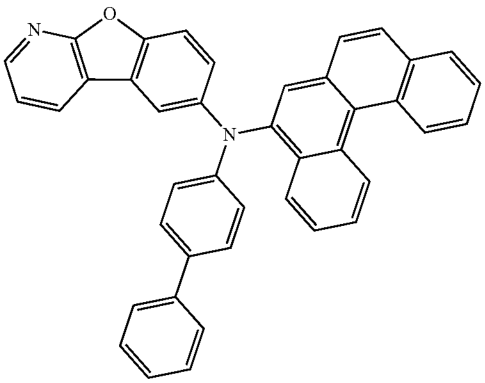

-continued
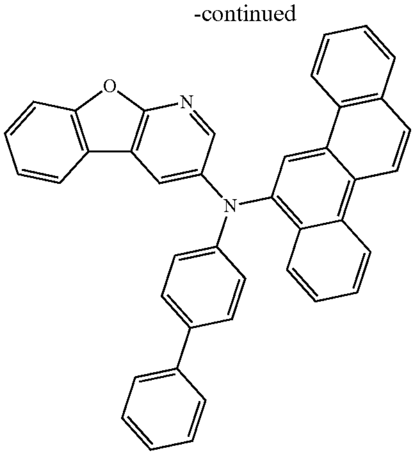
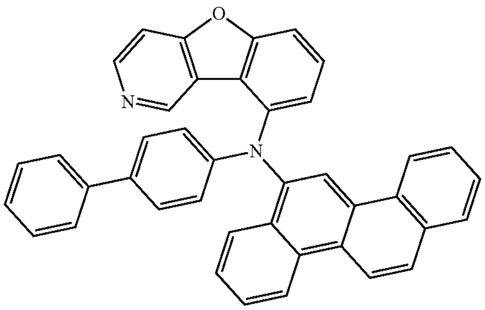
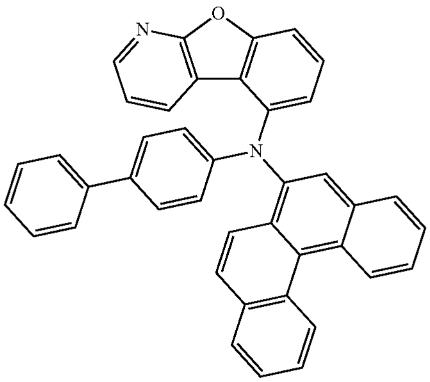
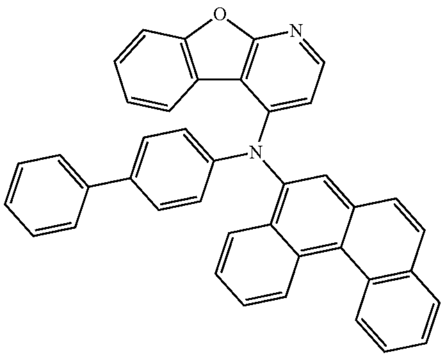
-continued
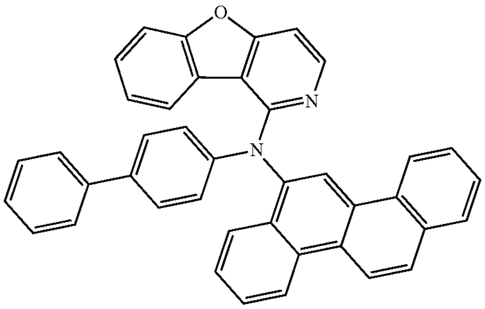
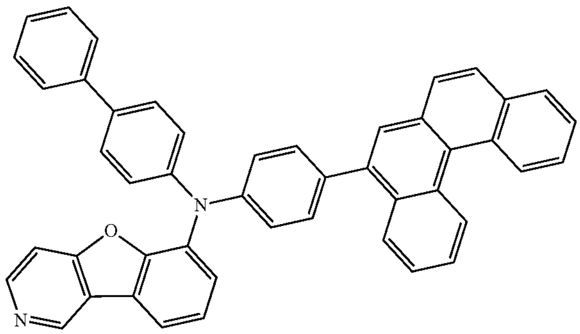
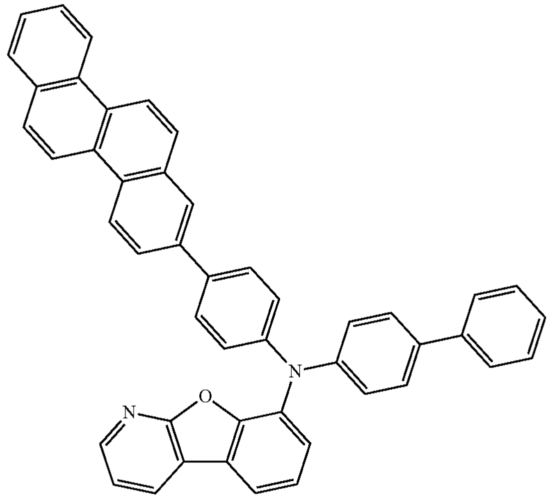
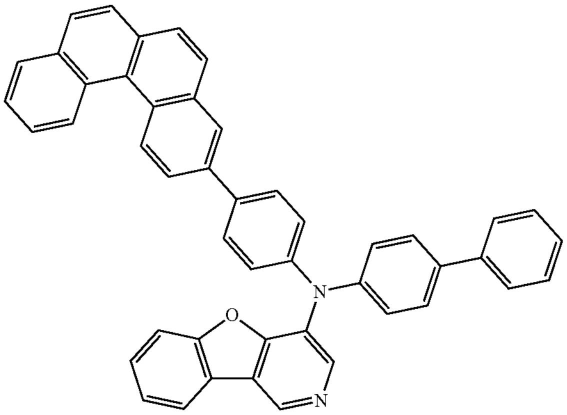

-continued
-continued
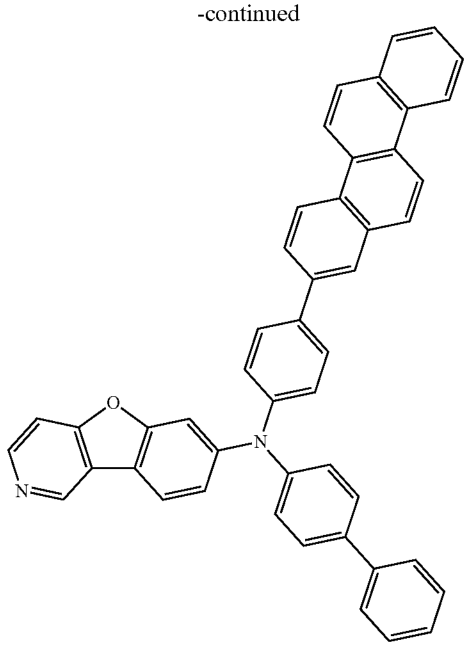
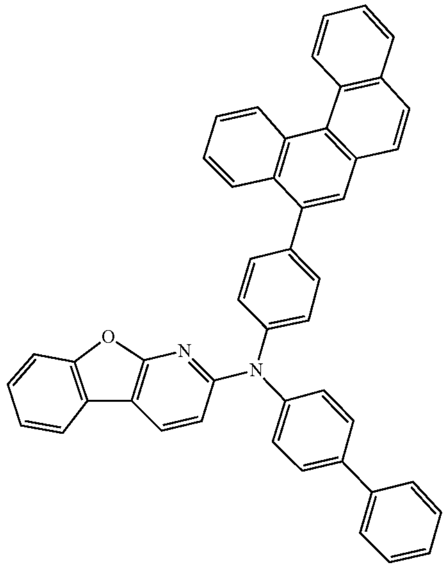
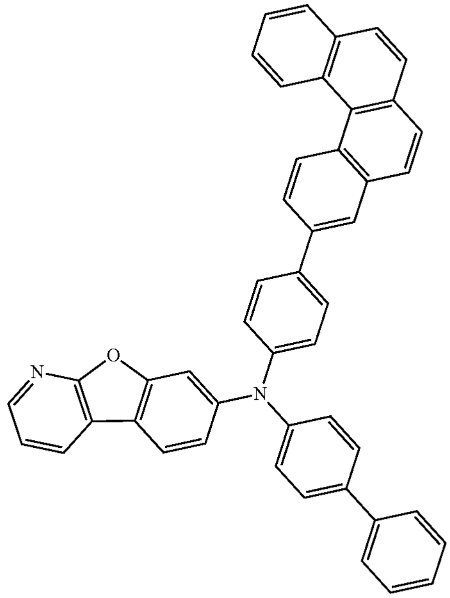
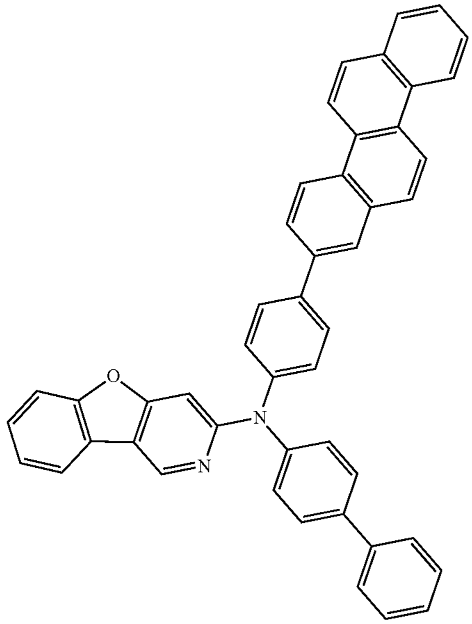

771
-continued
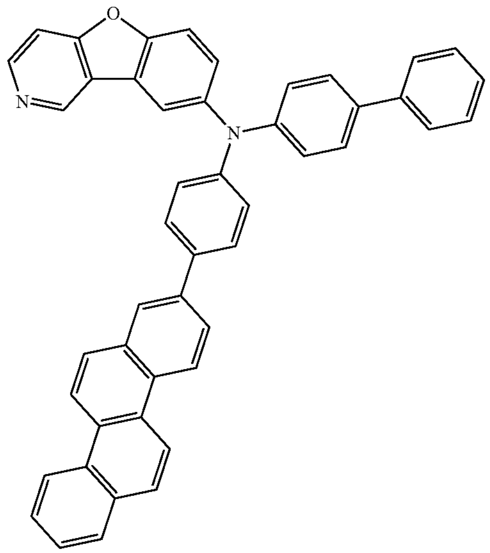
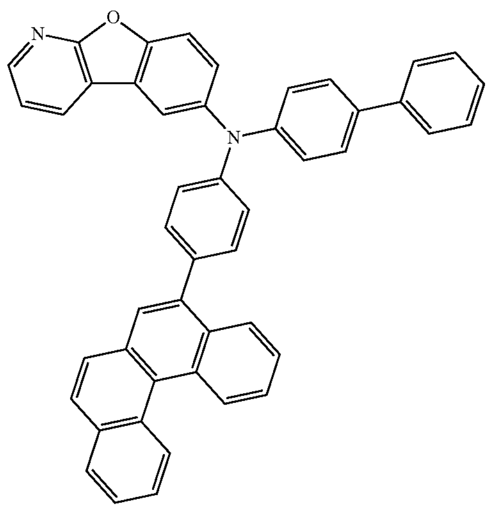
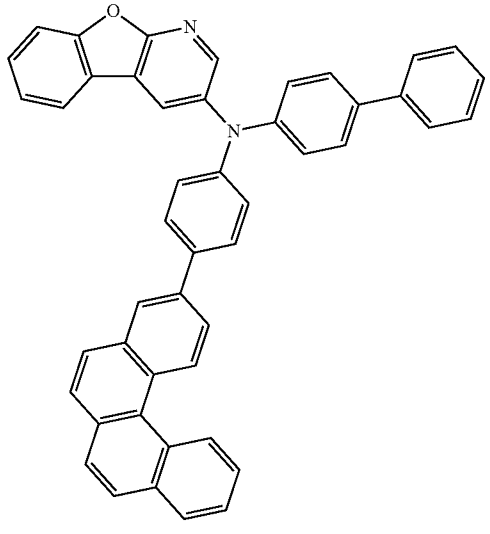
772
-continued
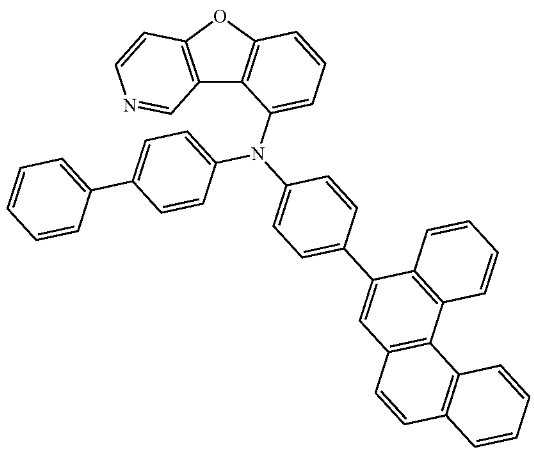
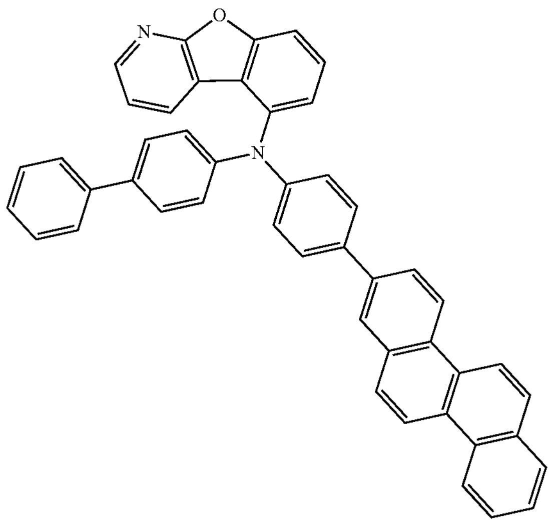
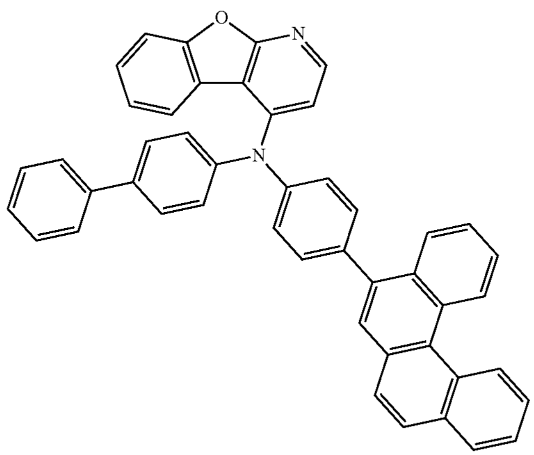

-continued
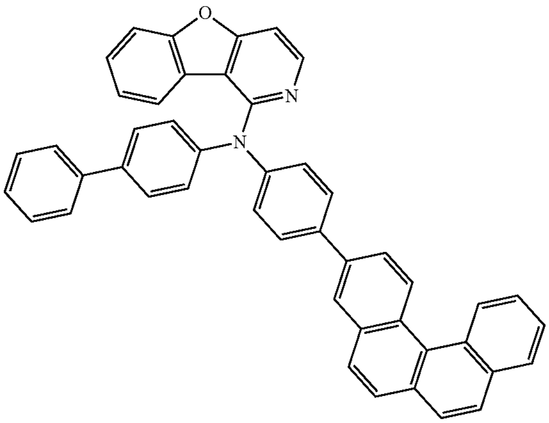
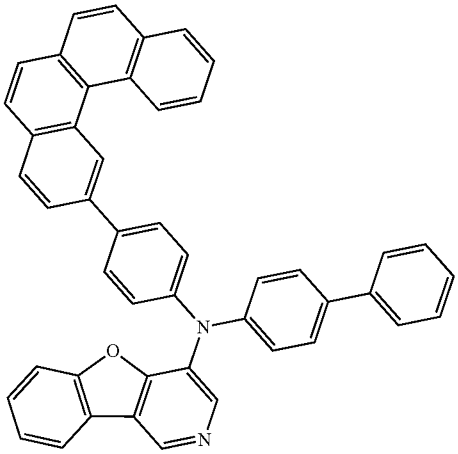
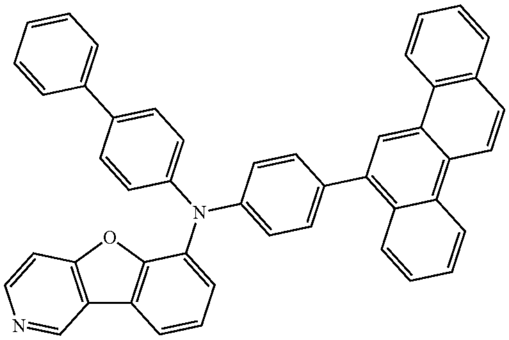
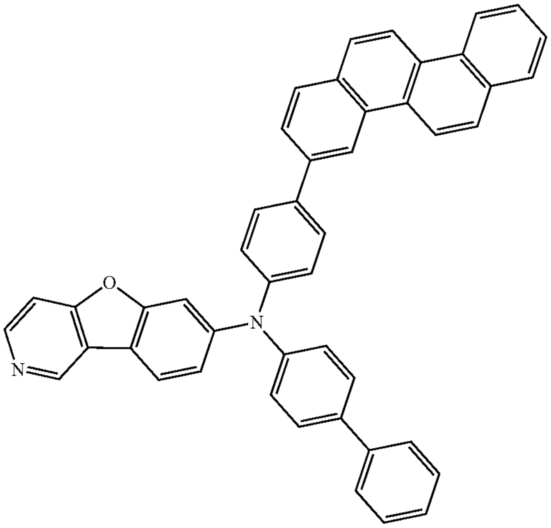
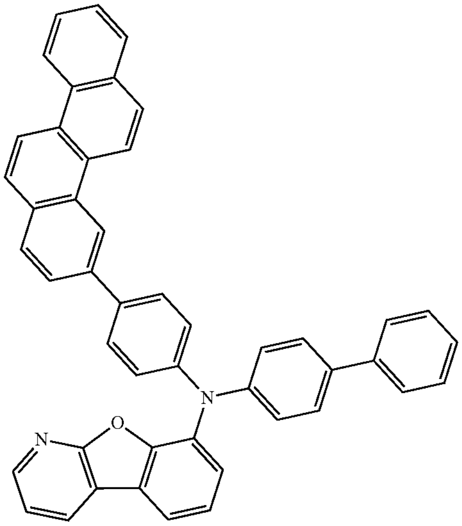
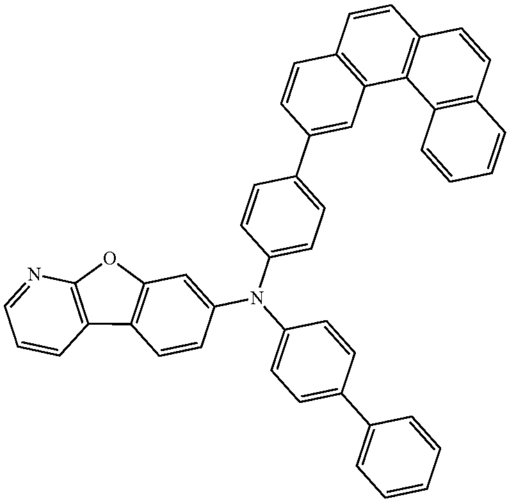
-continued -continued
-continued
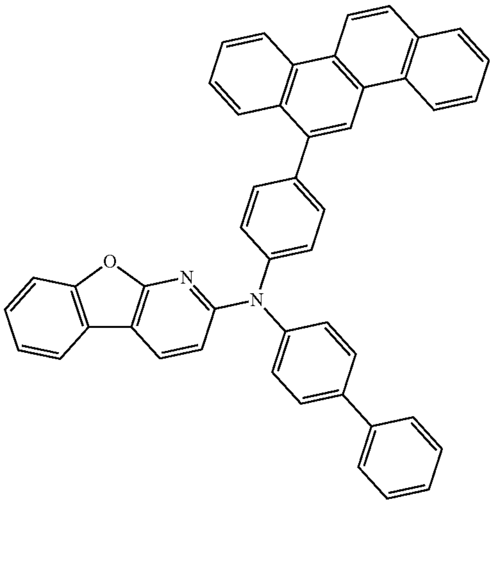
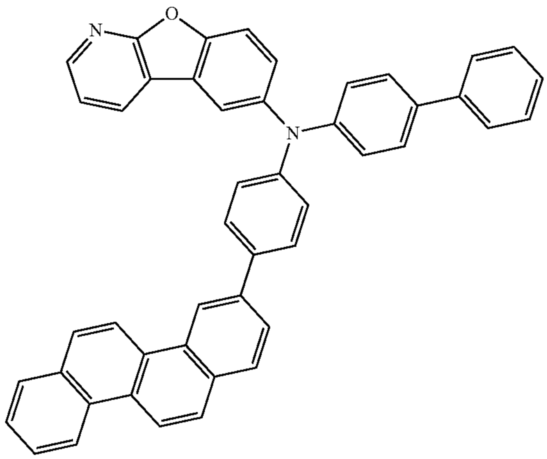
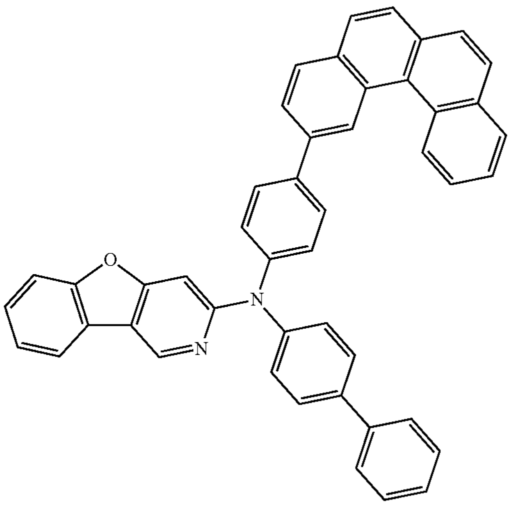
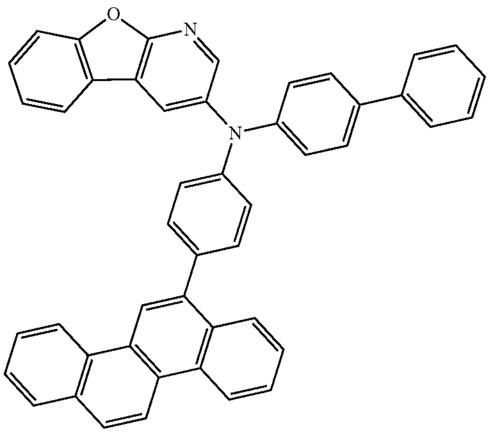
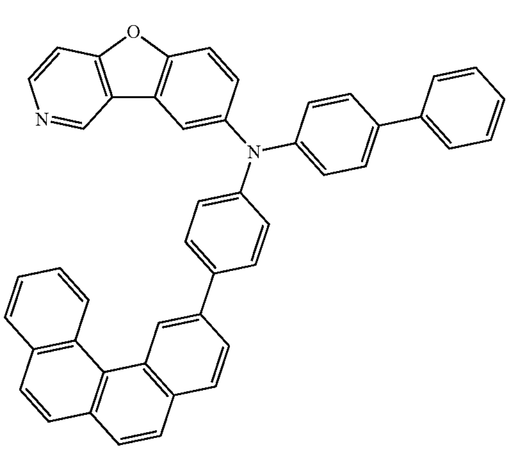
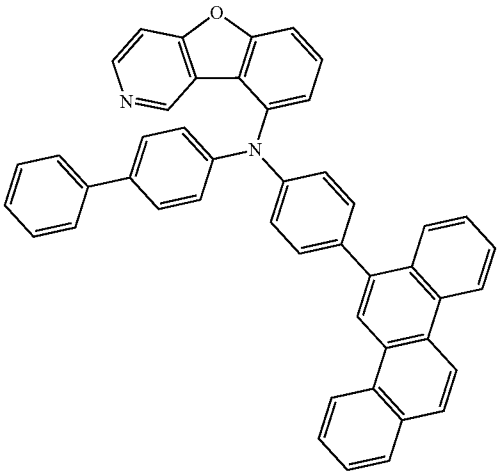

-continued
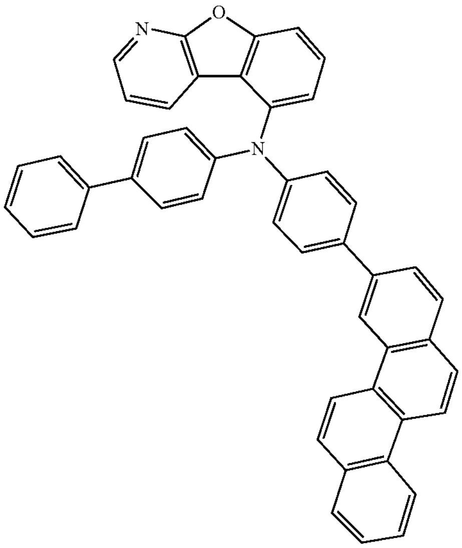
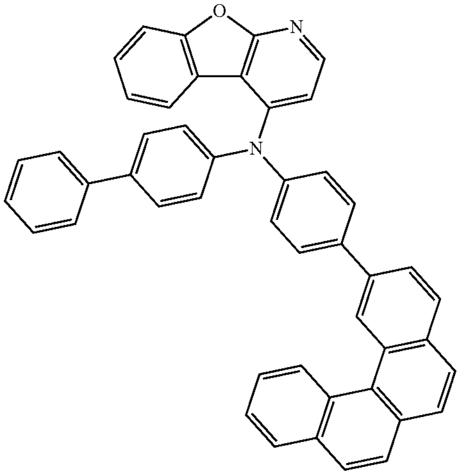
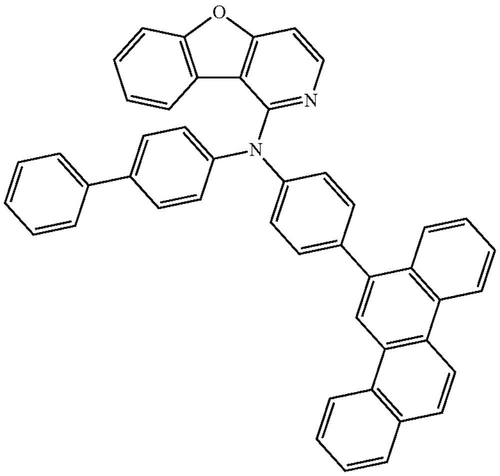
-continued
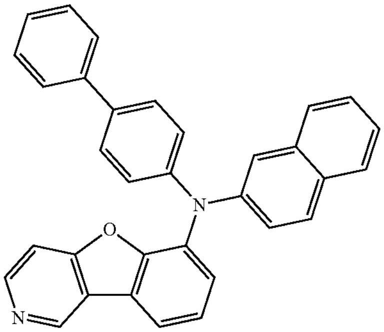
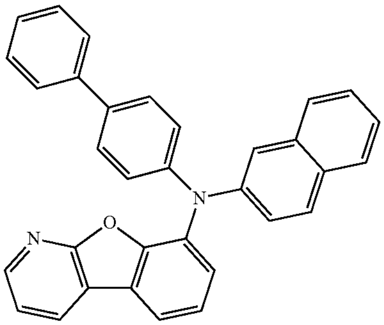
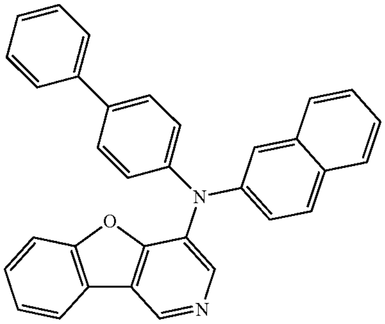
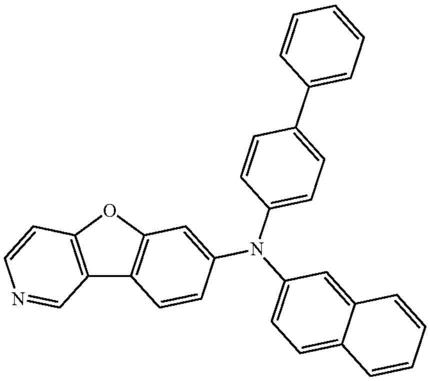

-continued
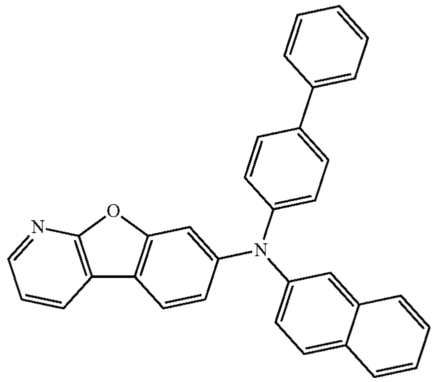
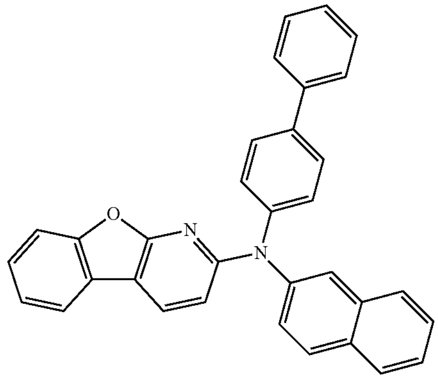
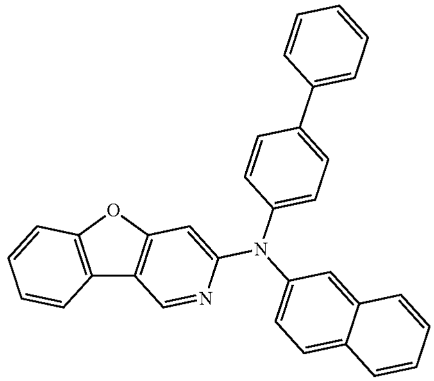
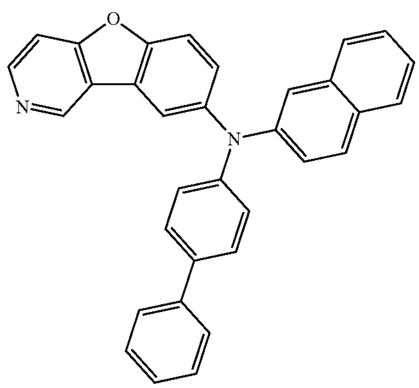
-continued
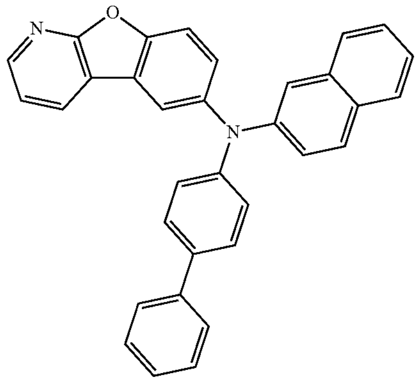
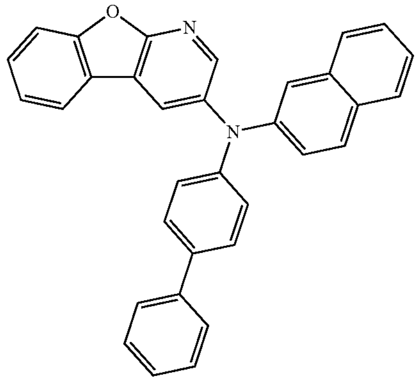
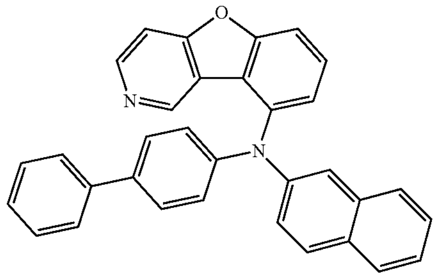
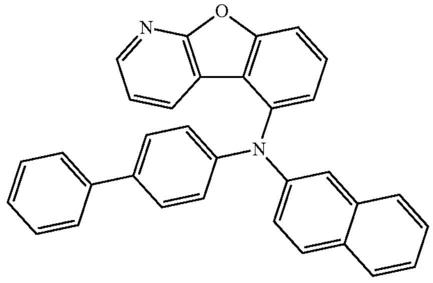
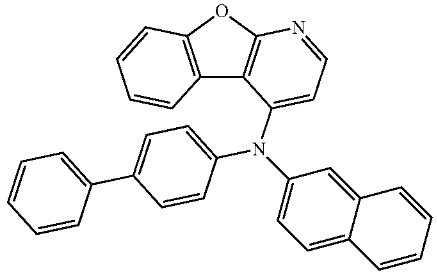

-continued
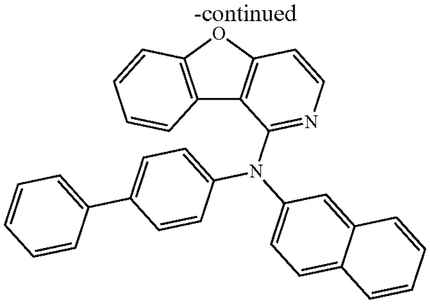
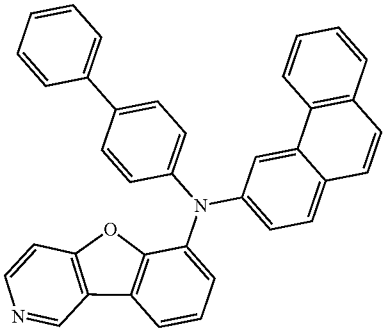
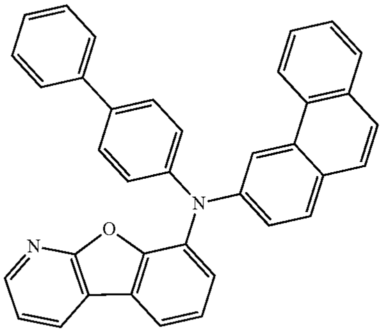
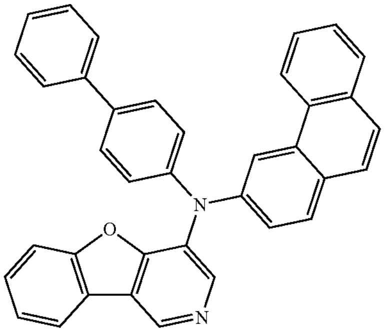
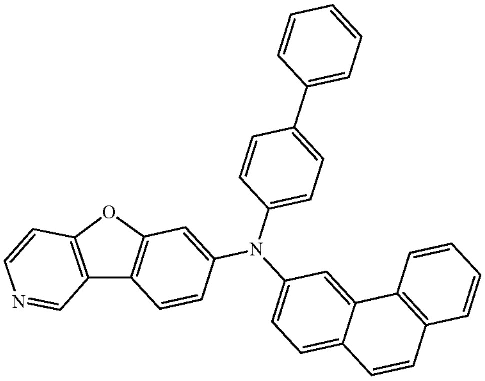
-continued
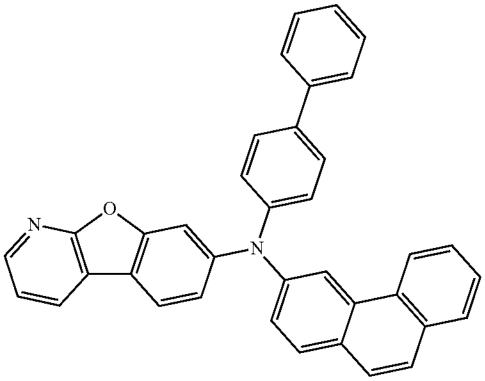
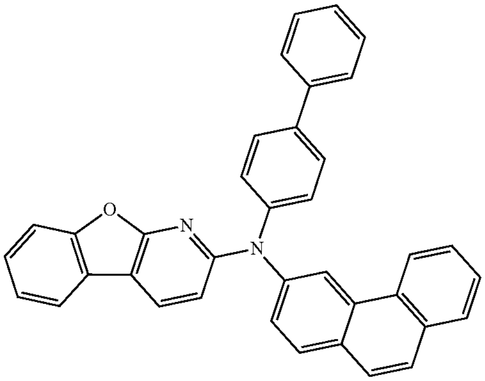
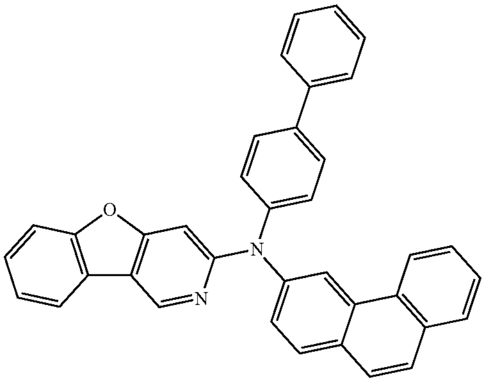
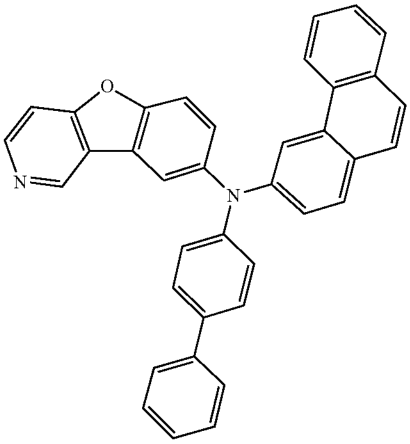

-continued
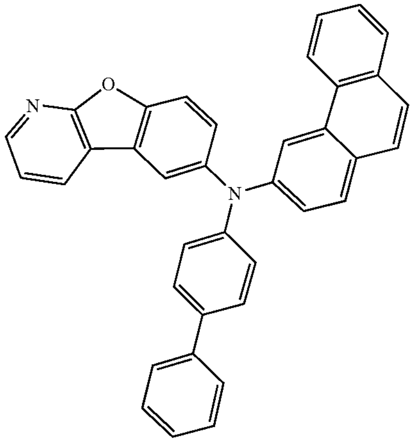
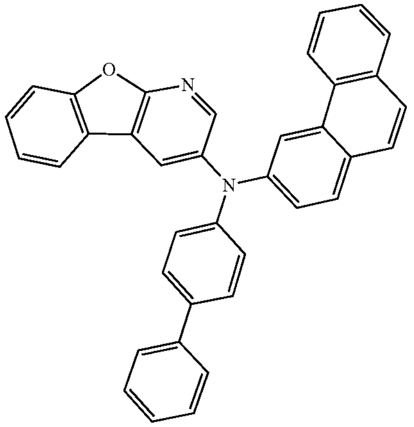
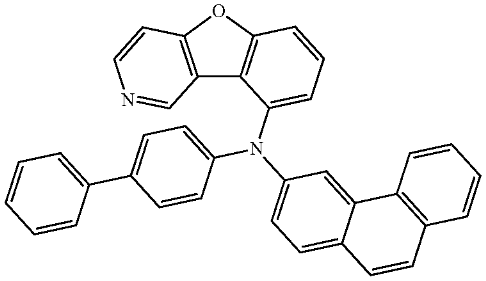
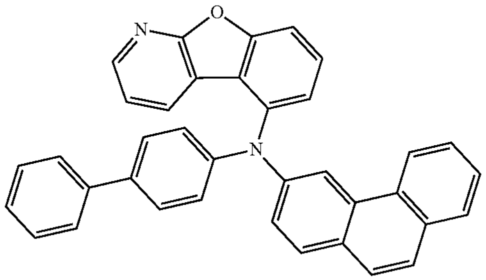
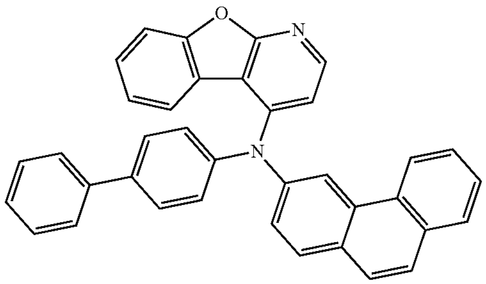
-continued
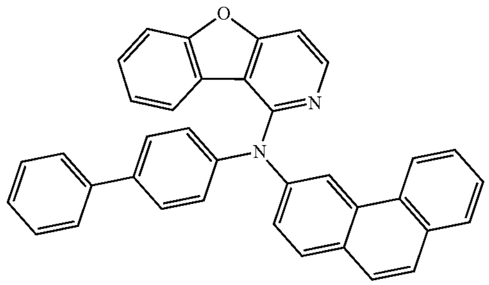
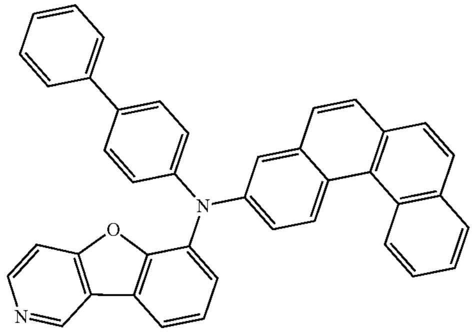
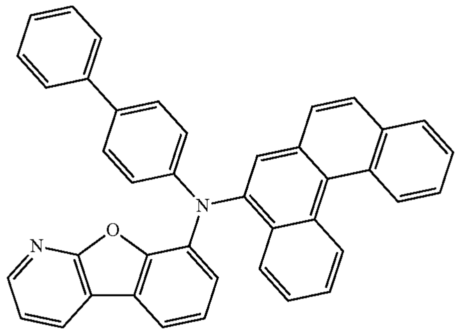
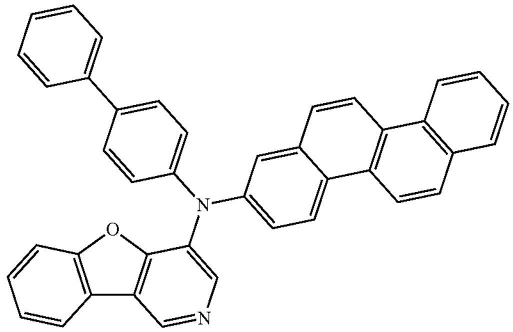

-continued
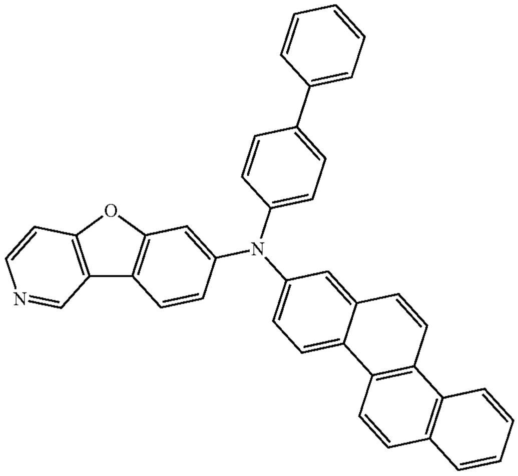
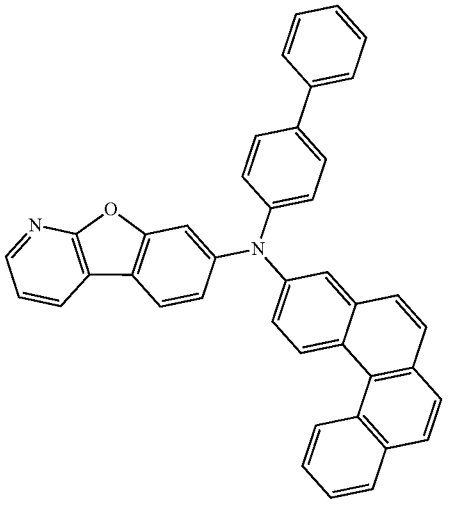
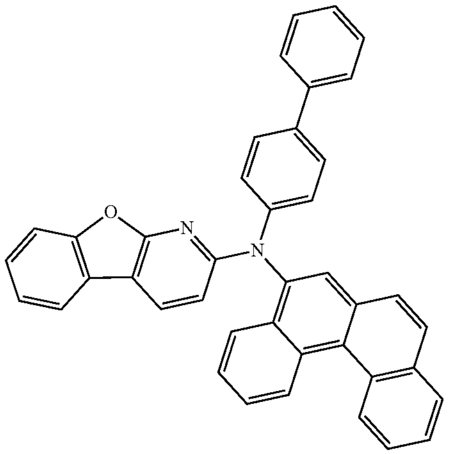
-continued
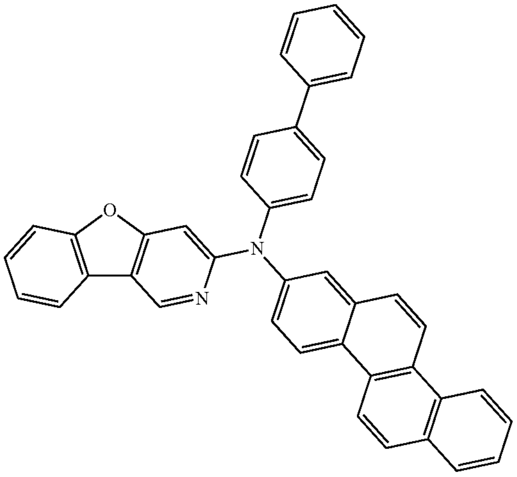
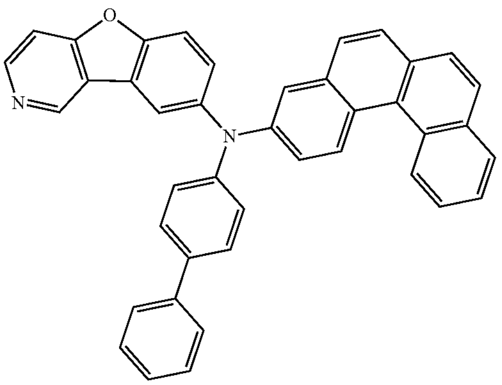
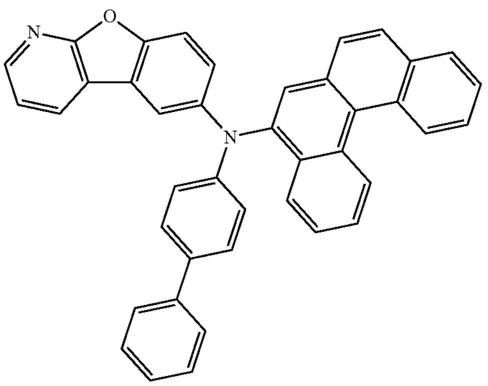
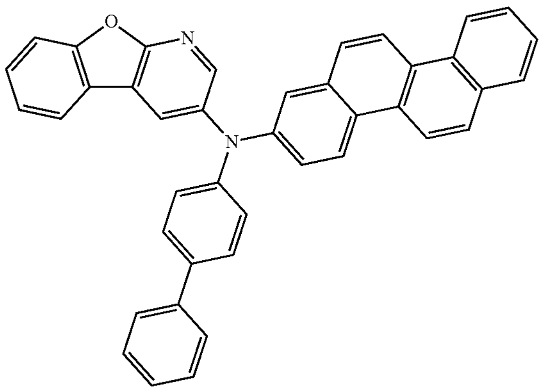

-continued
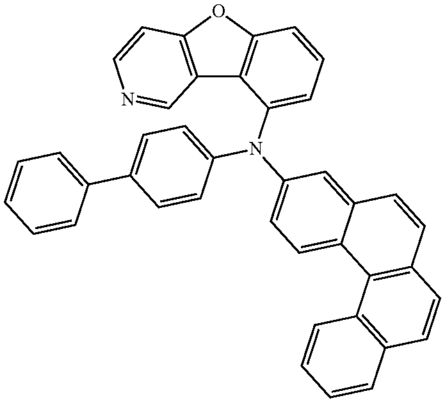
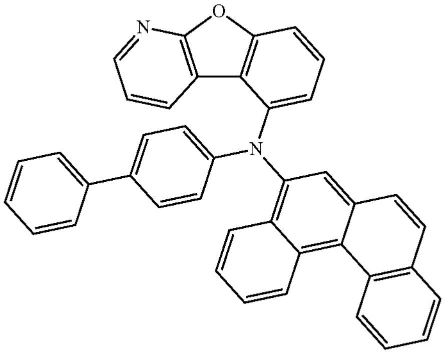
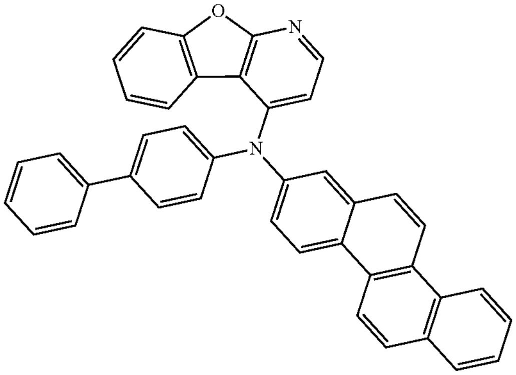
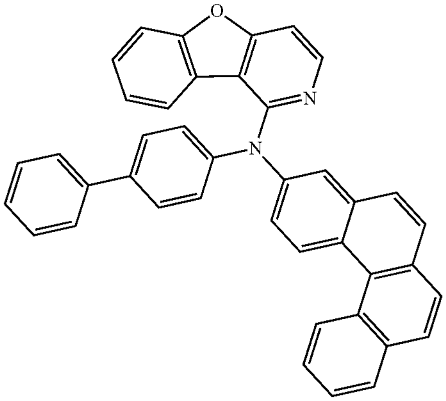
-continued
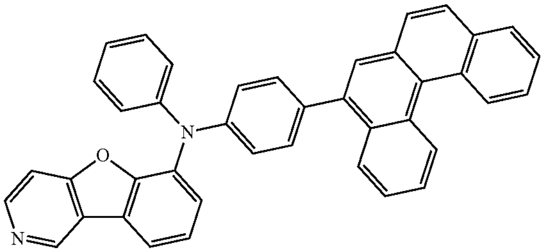
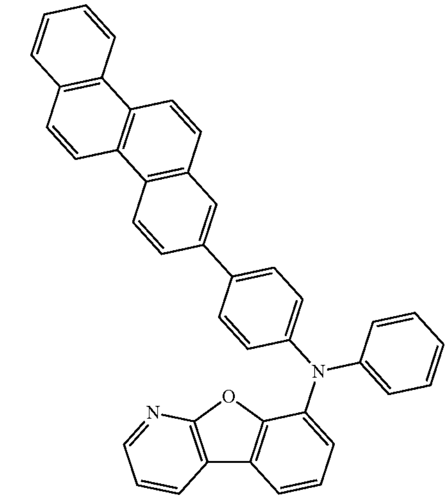
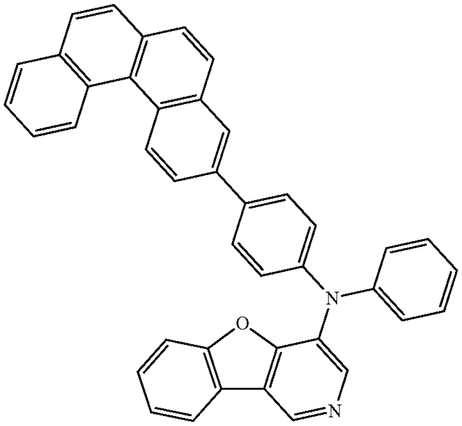
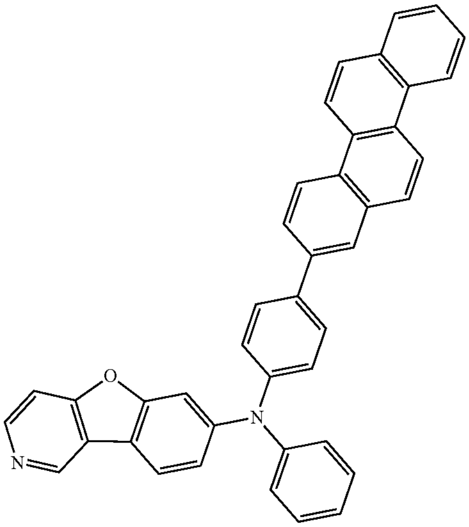

-continued
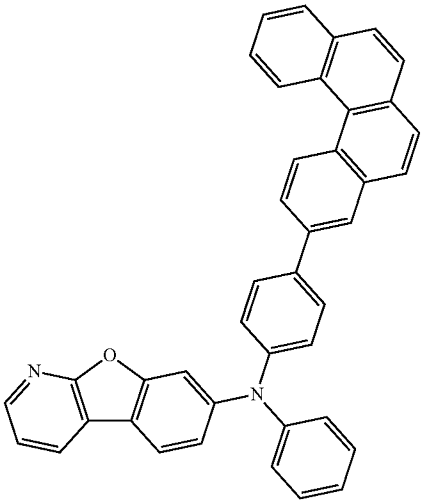
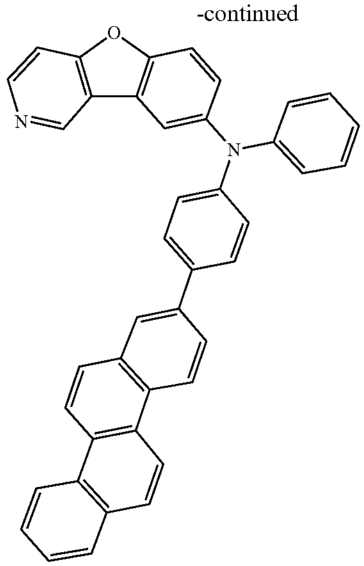
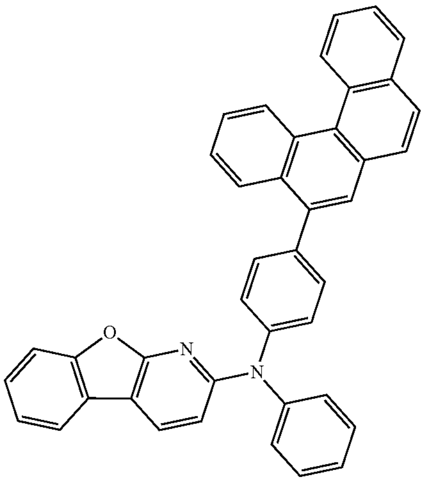
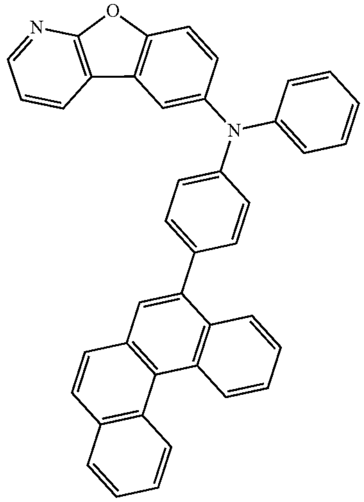
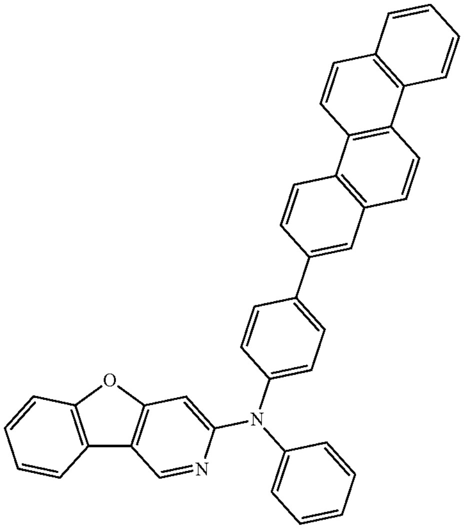
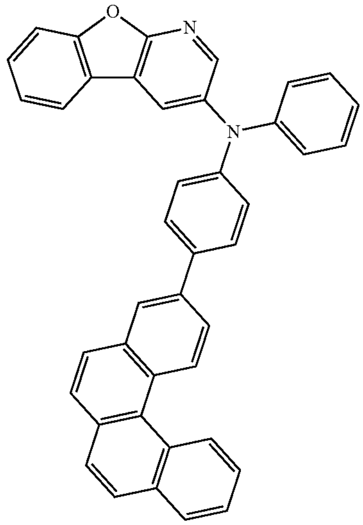
-continued -continued
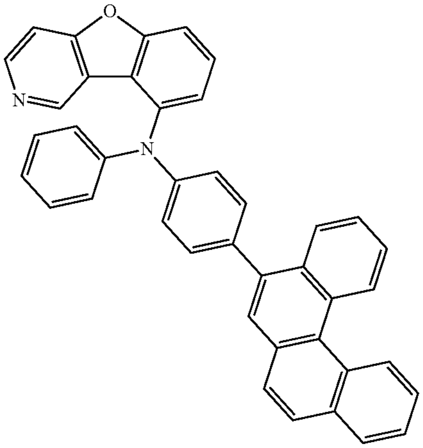
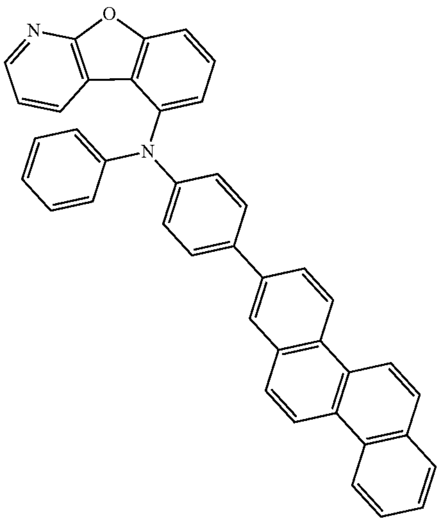
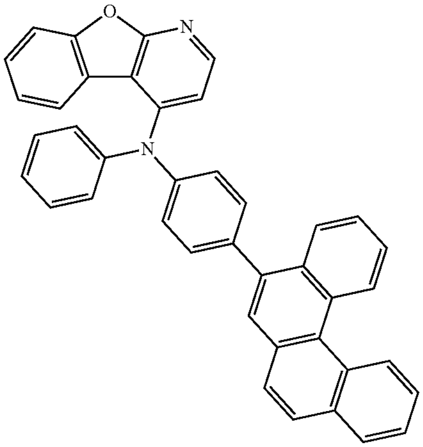
-continued
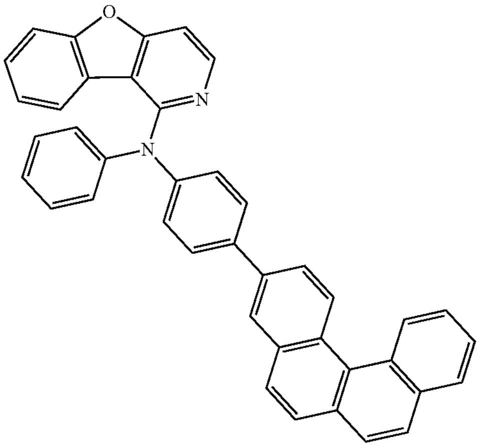
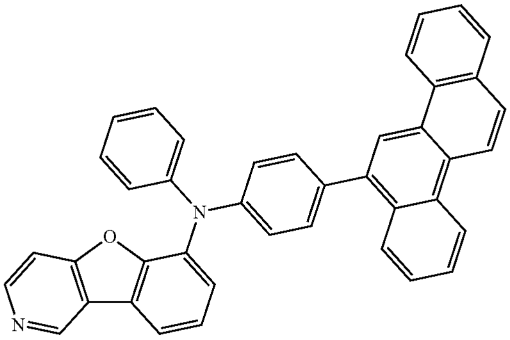
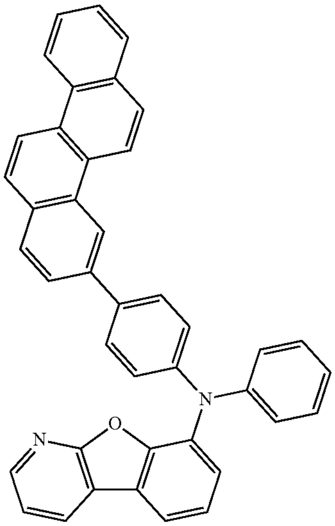

-continued
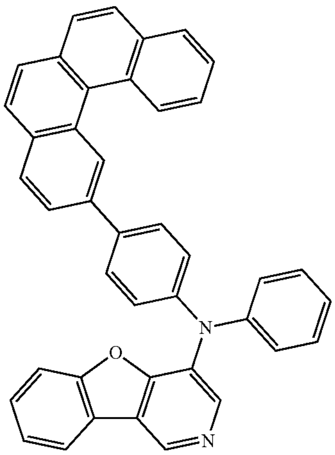
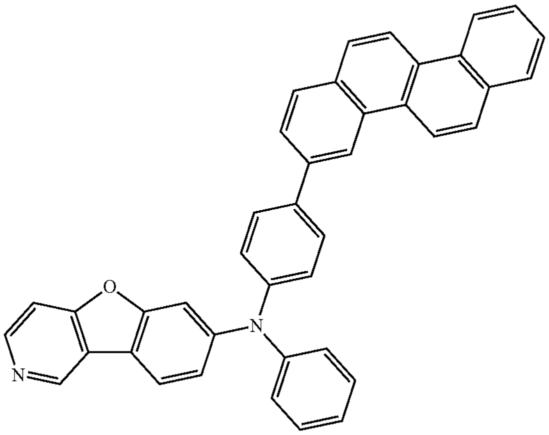
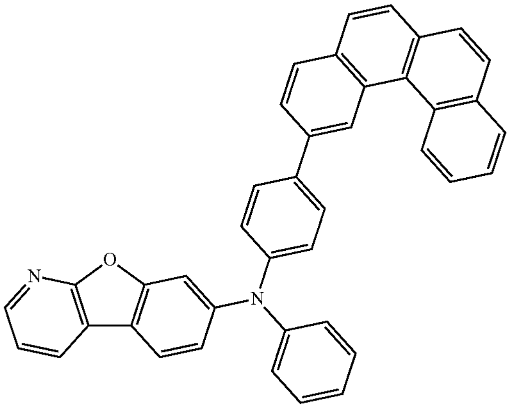
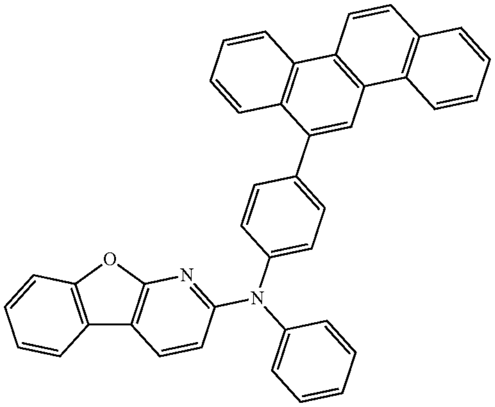
-continued
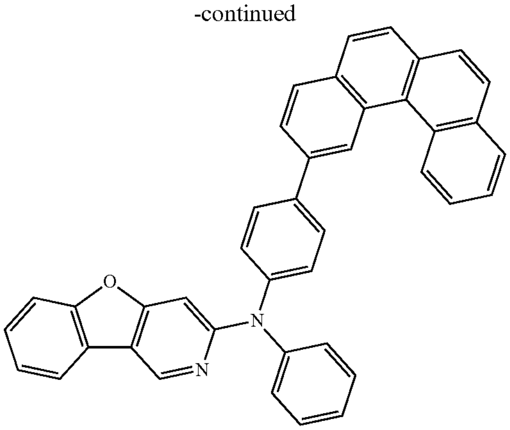
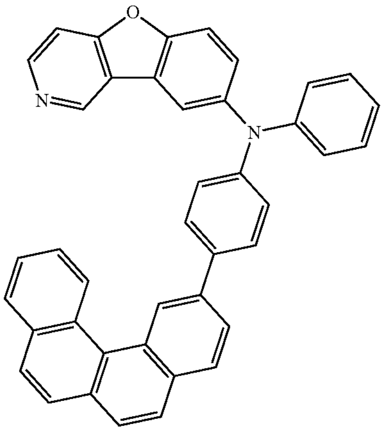
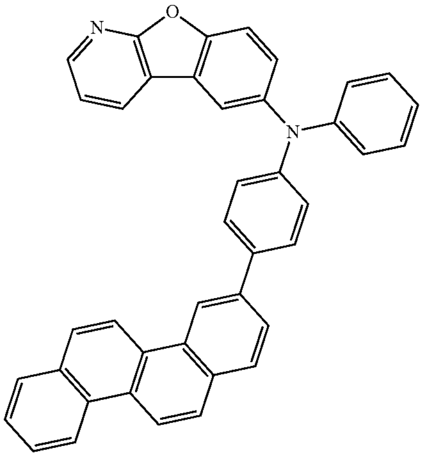
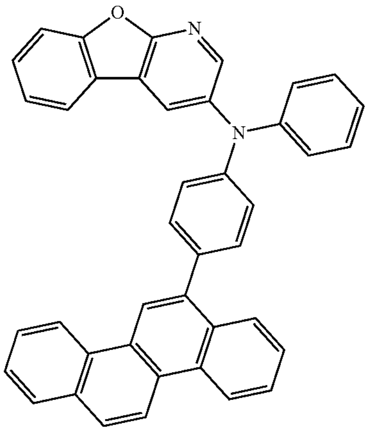

-continued
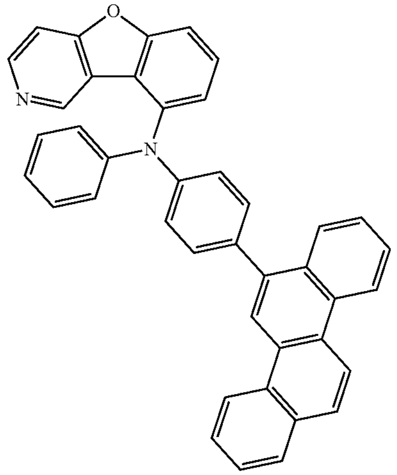
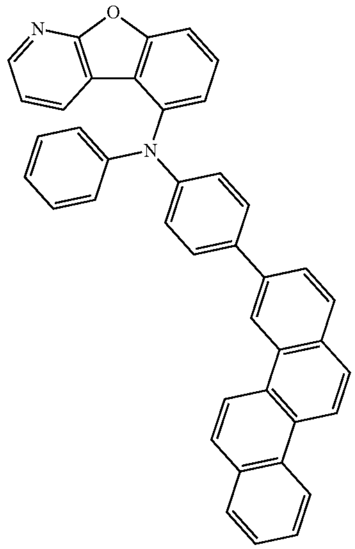
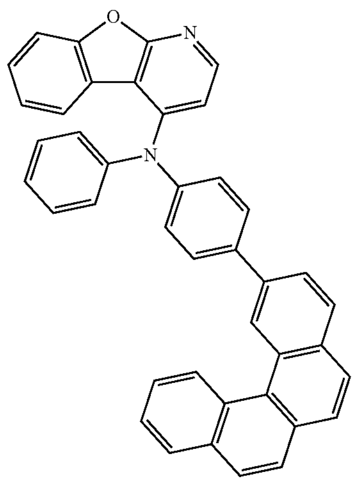
-continued
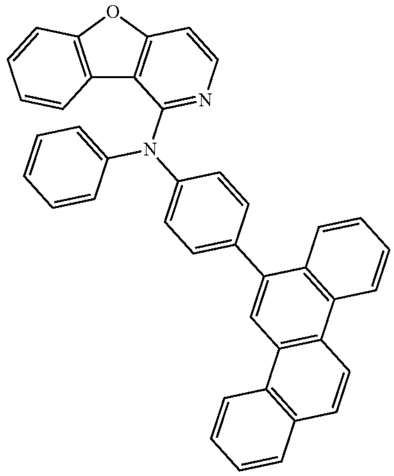 [SMILES: c1ccc(N(c2ccc(-c3cc4c5ccccc5ccc4c4ccccc34)cc2)c2nccc3oc4ccccc4c23)cc1]
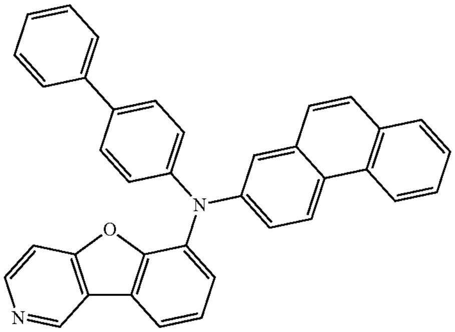
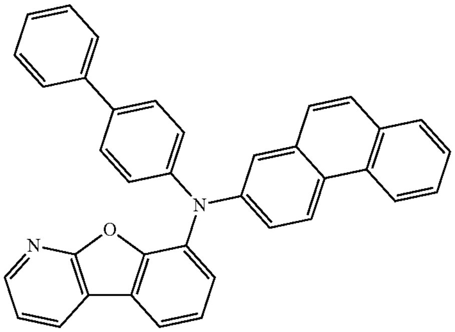
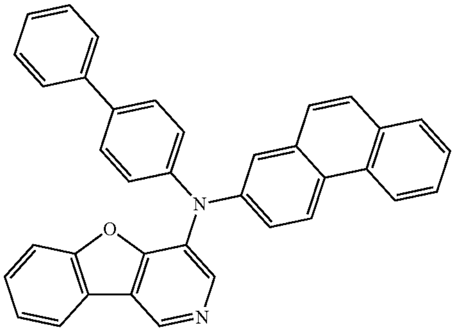

-continued
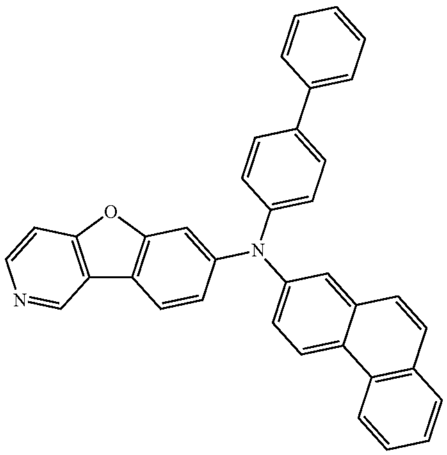
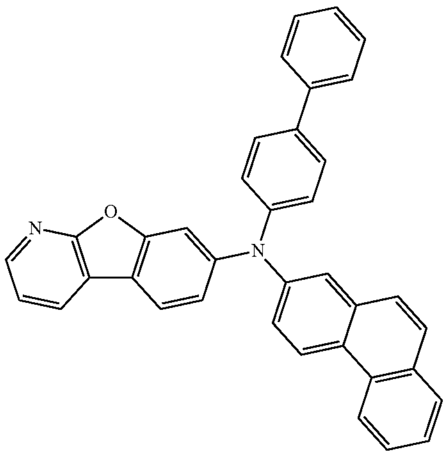
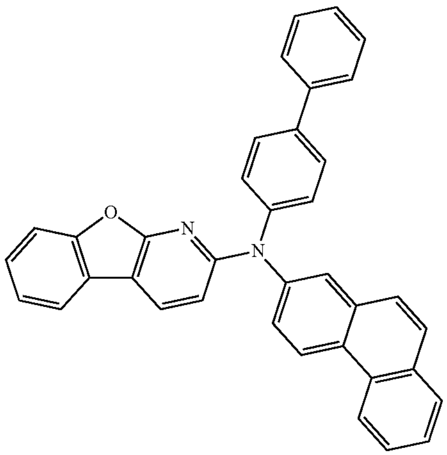
-continued
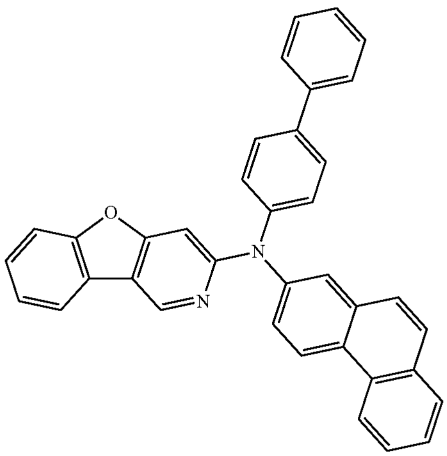
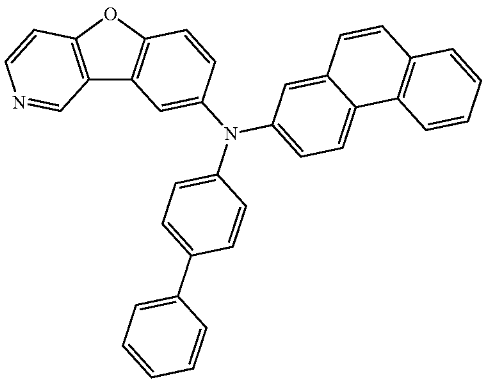
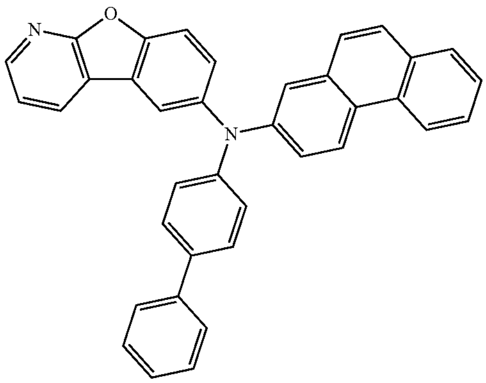
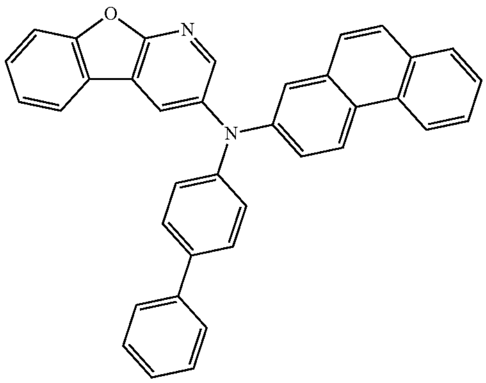

-continued
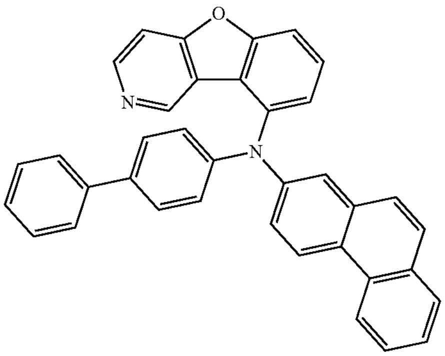
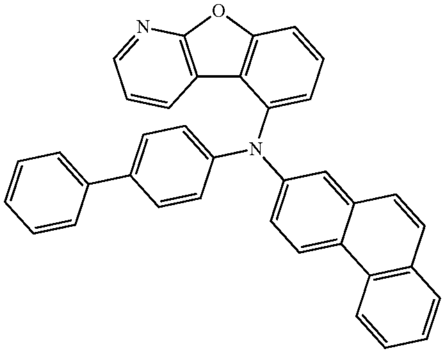
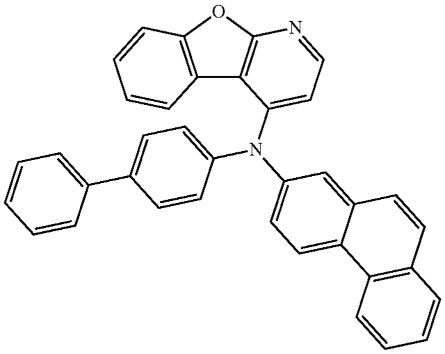
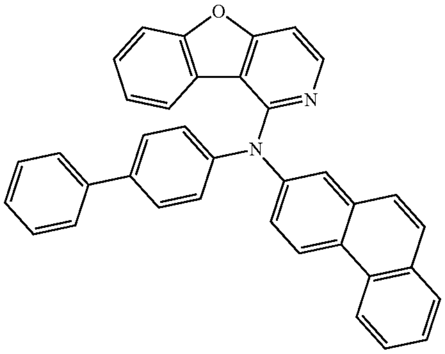
-continued
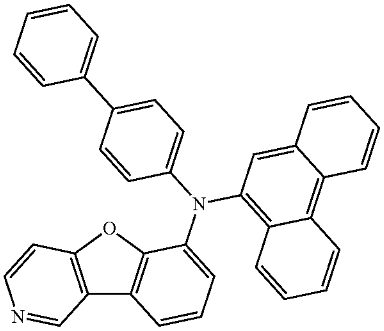
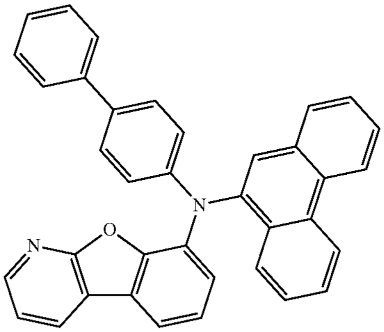
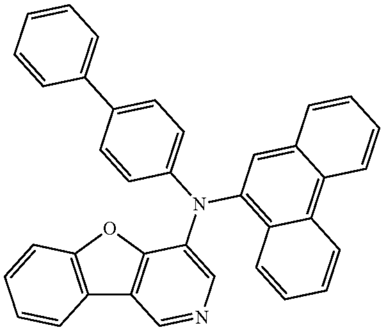
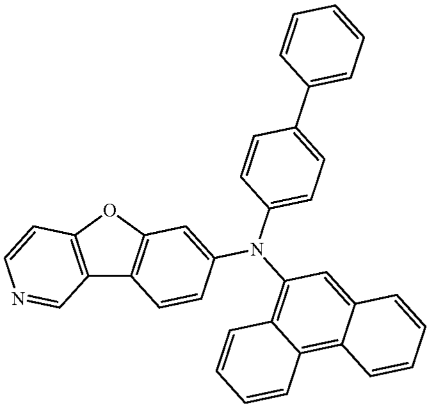

-continued
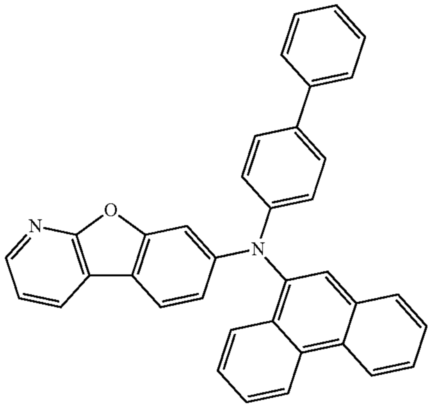
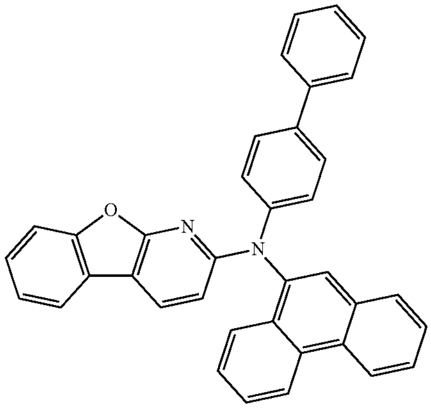
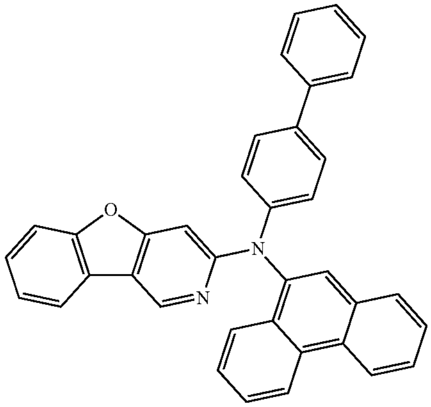
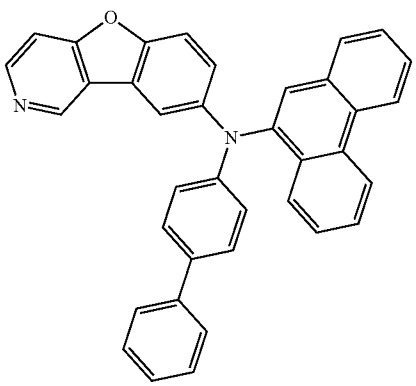
-continued
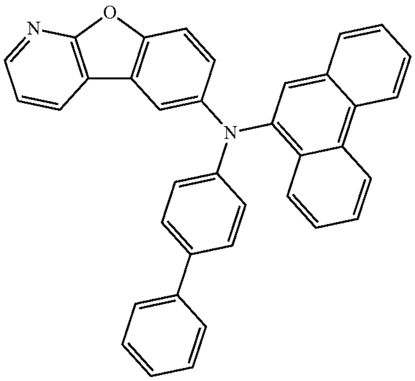
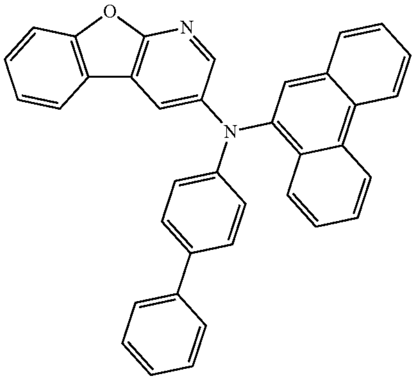
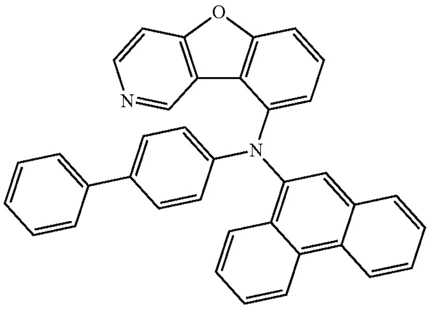
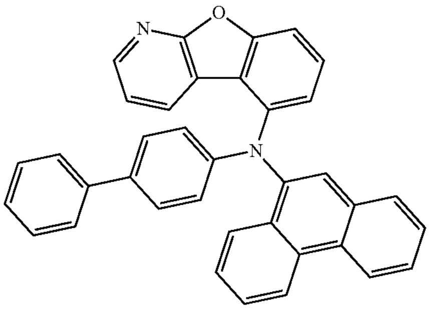
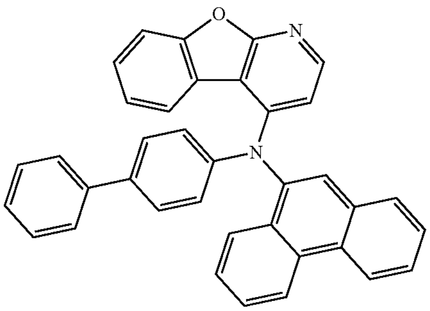

-continued
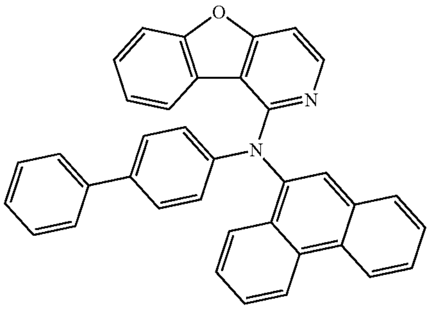
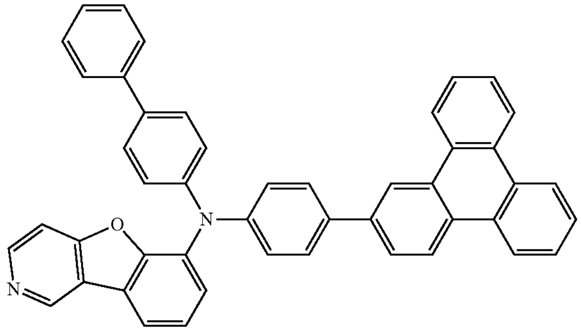
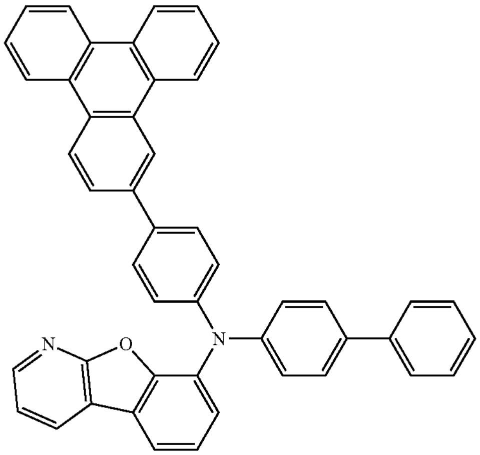
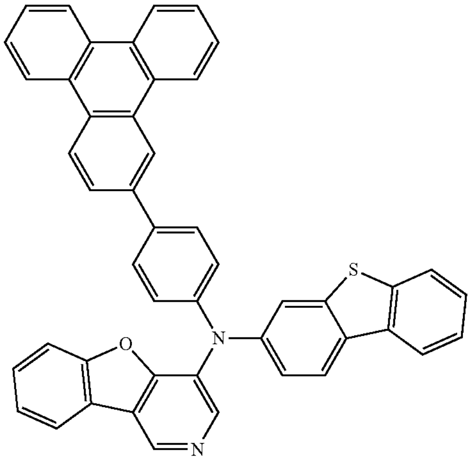
-continued
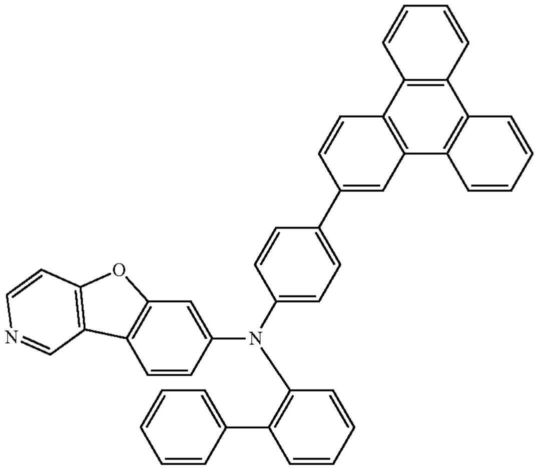
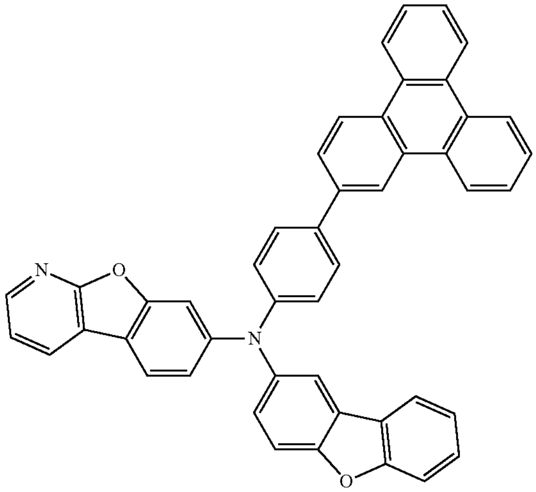
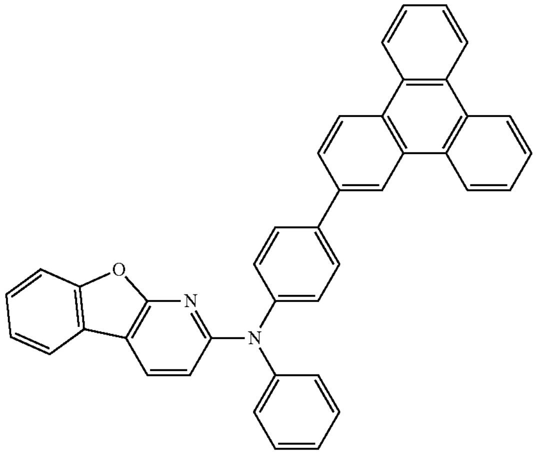

-continued
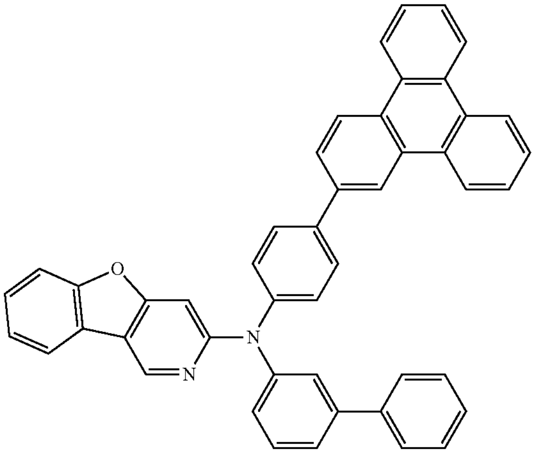 [SMILES: c1ccc(-c2cccc(N(c3ccc(-c4ccc5c6ccccc6c6ccccc6c5c4)cc3)c3cc4oc5ccccc5c4cn3)c2)cc1]
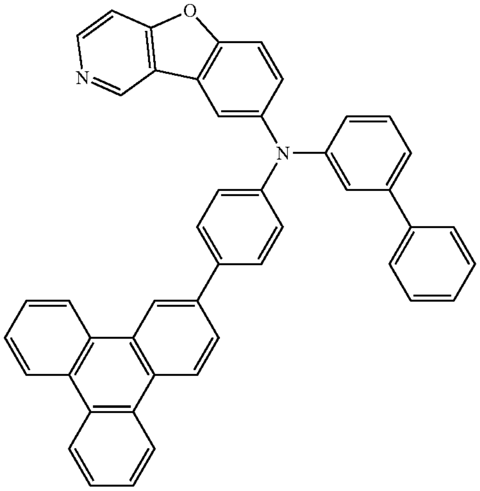
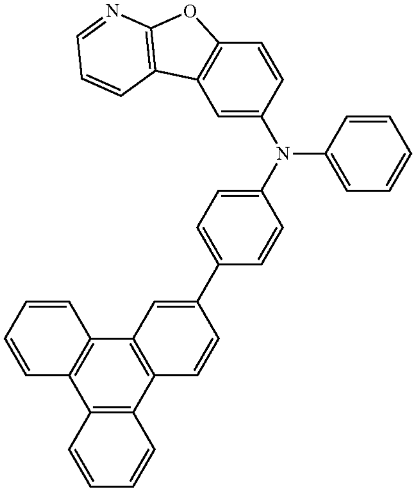
-continued
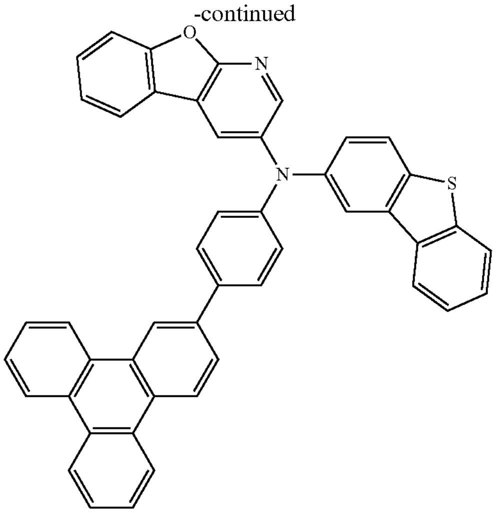
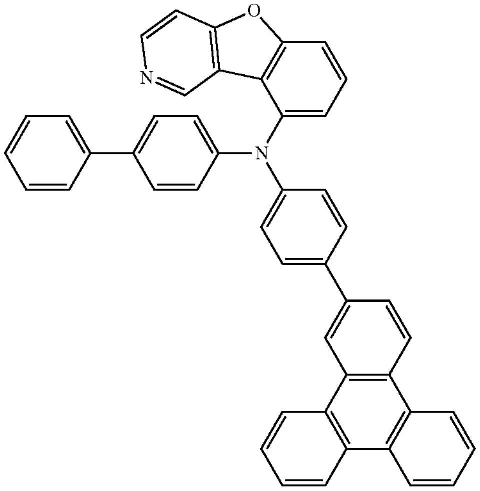
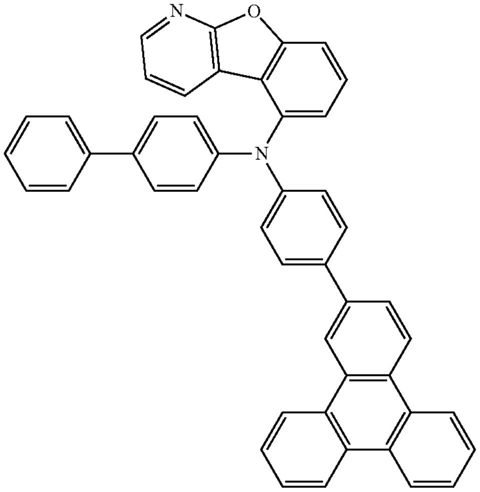

-continued
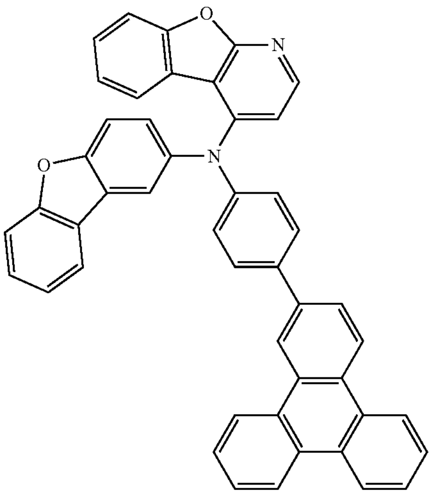
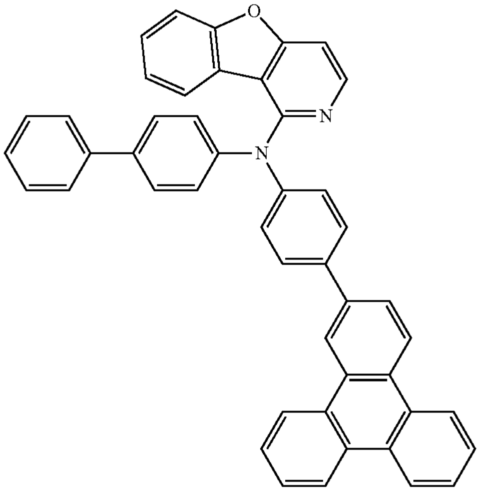
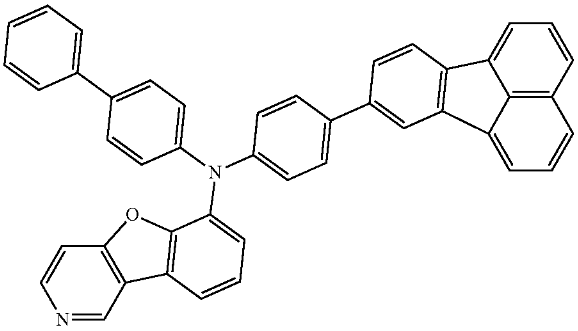
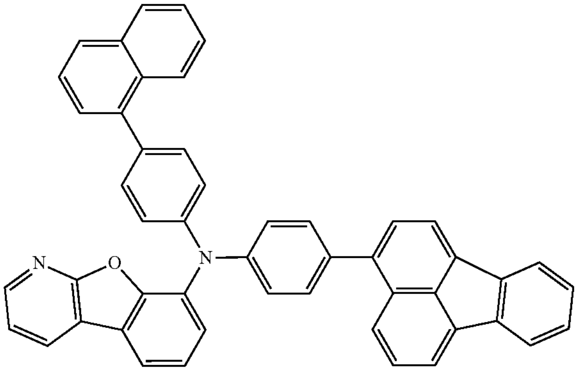
-continued
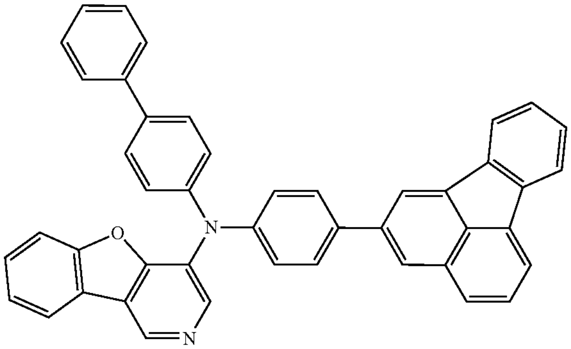
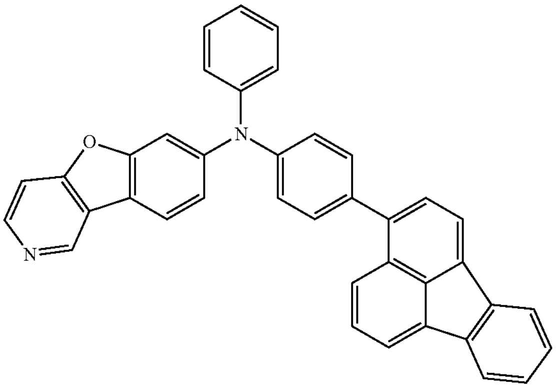
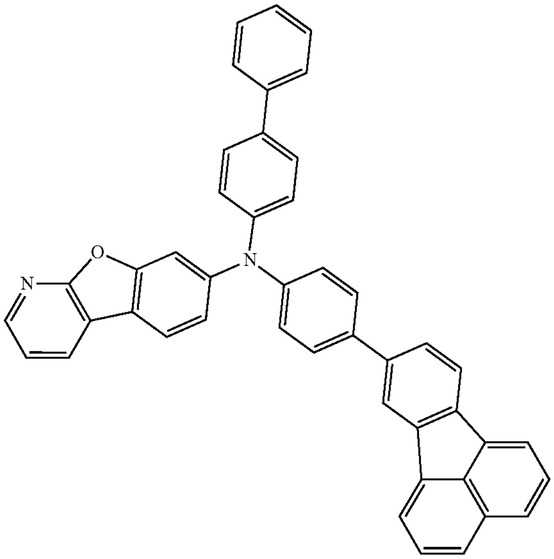
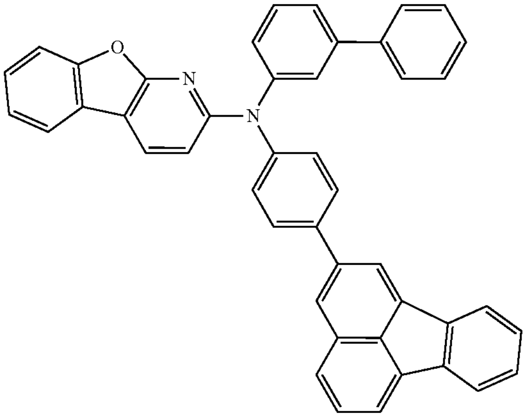

-continued
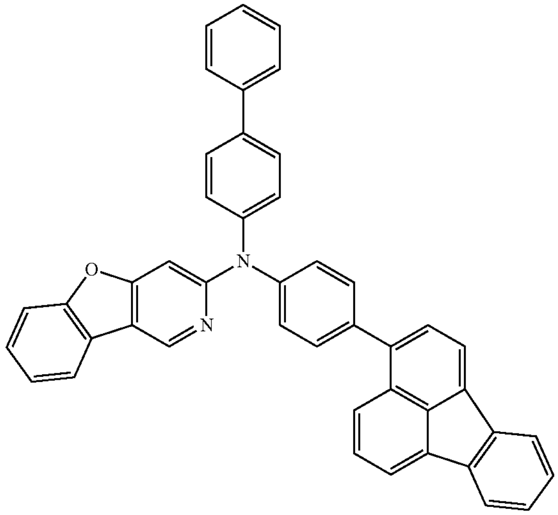 [SMILES: c1ccc(-c2ccc(N(c3ccc(-c4ccc5c6c(cccc46)-c4ccccc4-5)cc3)c3cc4oc5ccccc5c4cn3)cc2)cc1]
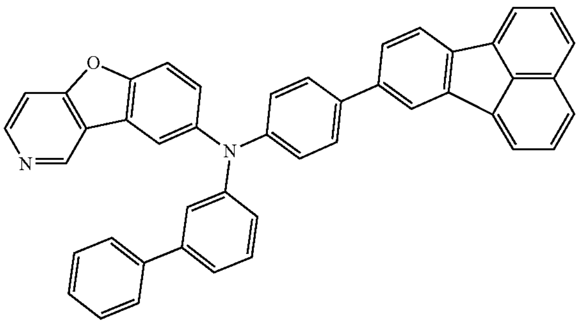
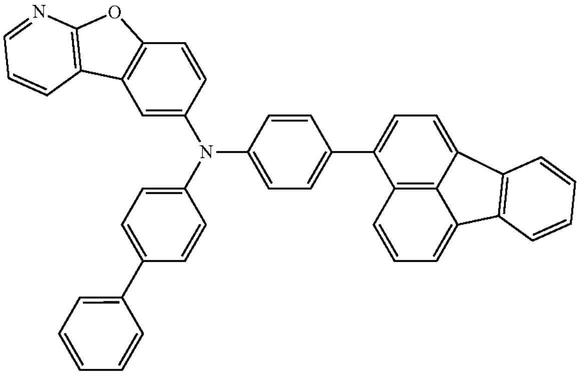
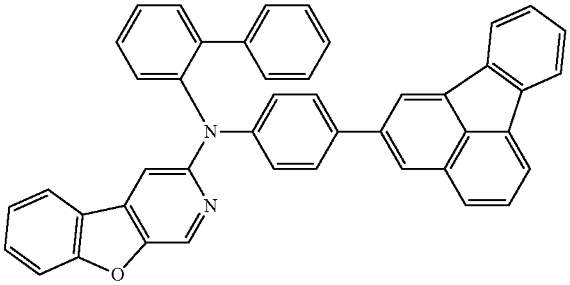
-continued
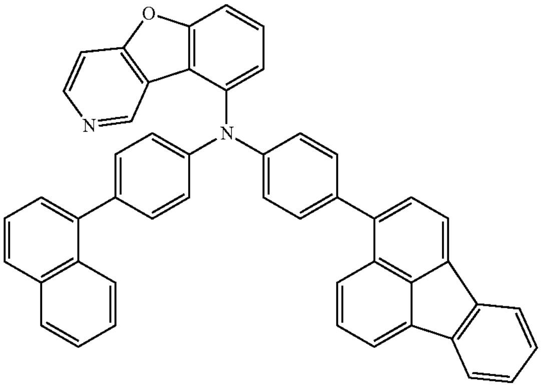
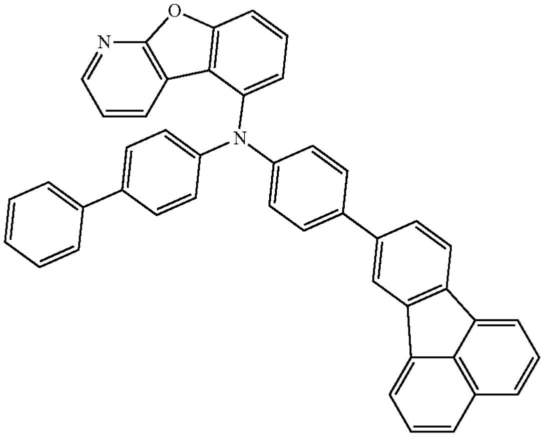
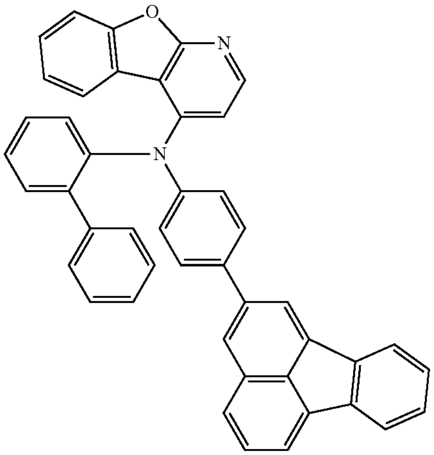
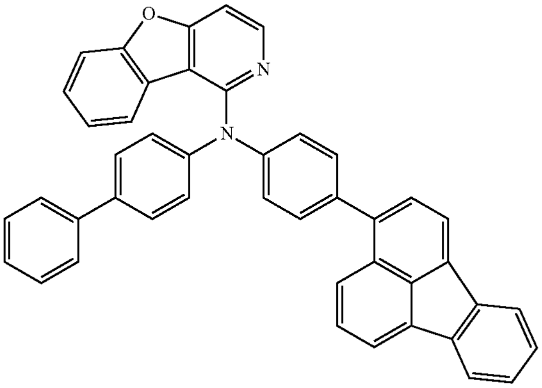

-continued
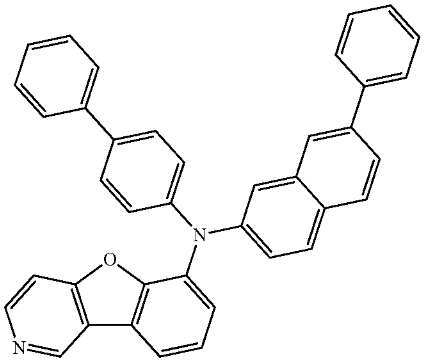
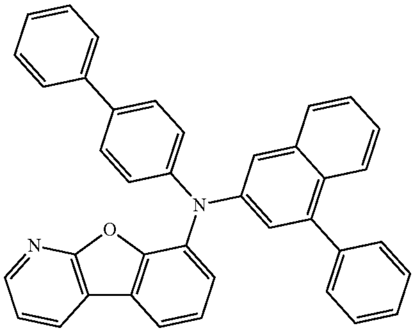
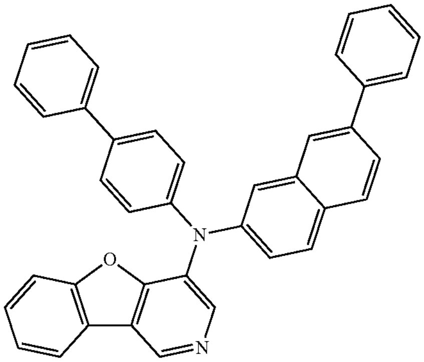
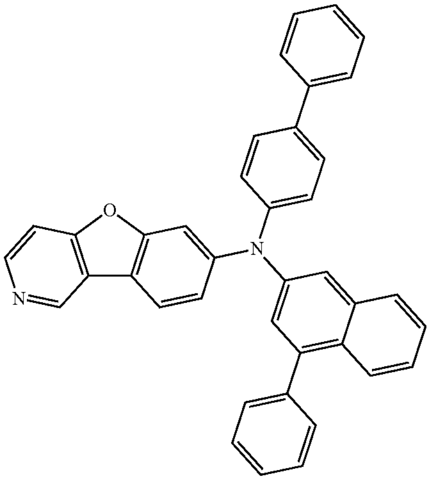
-continued
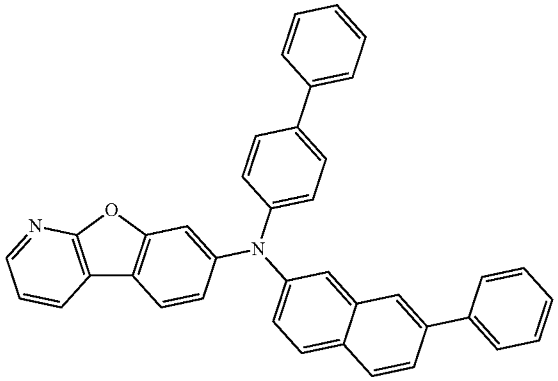
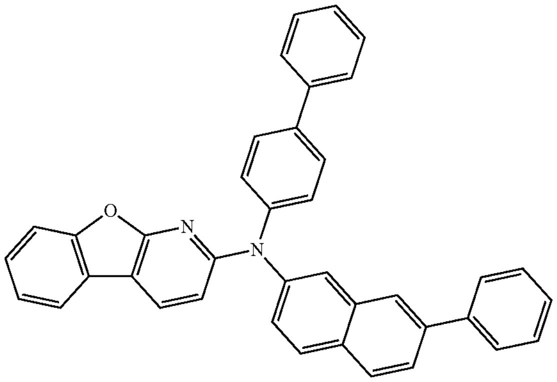
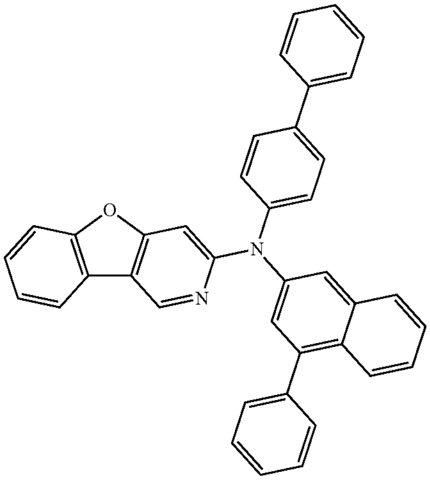
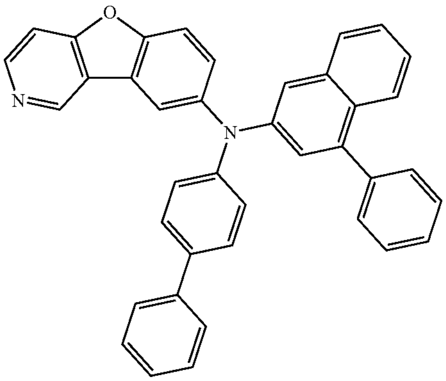

-continued
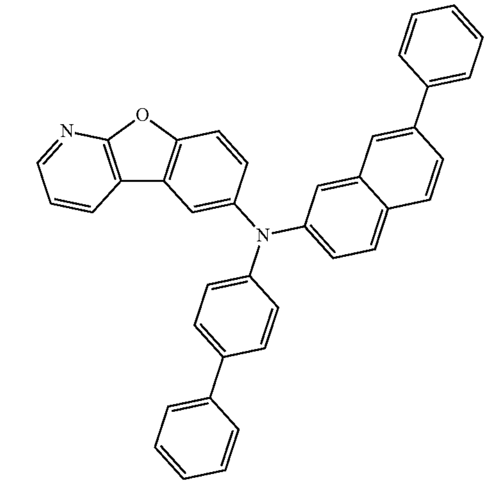
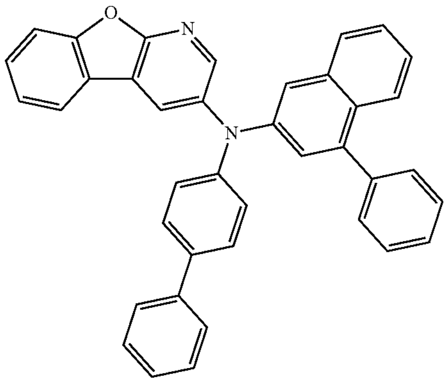
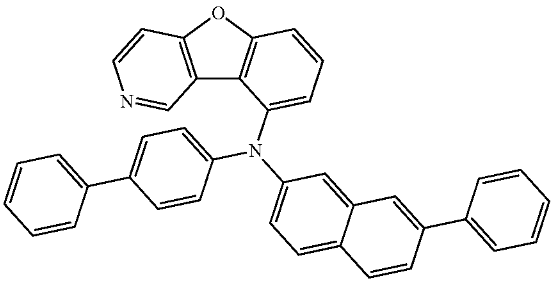
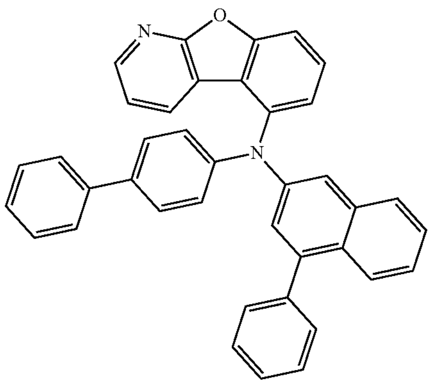
-continued
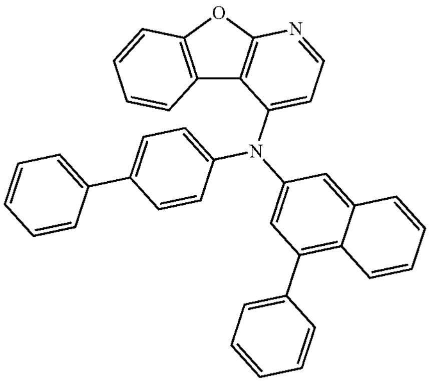
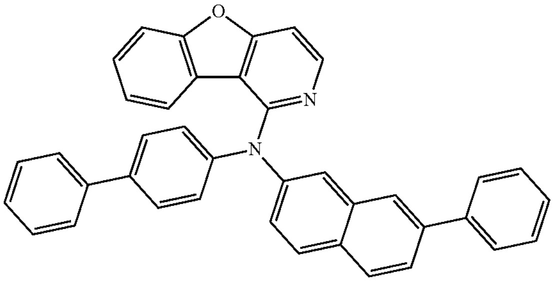
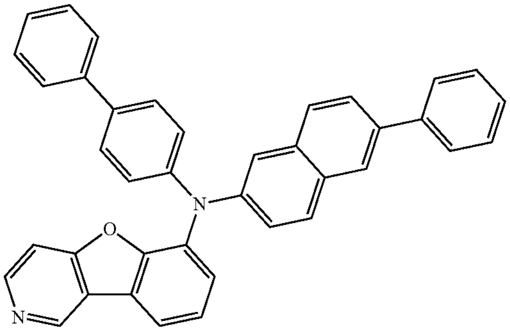
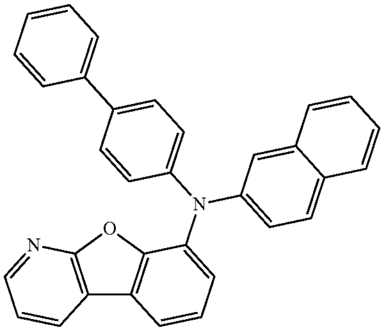
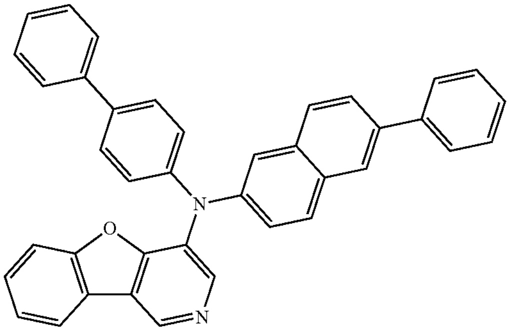

-continued
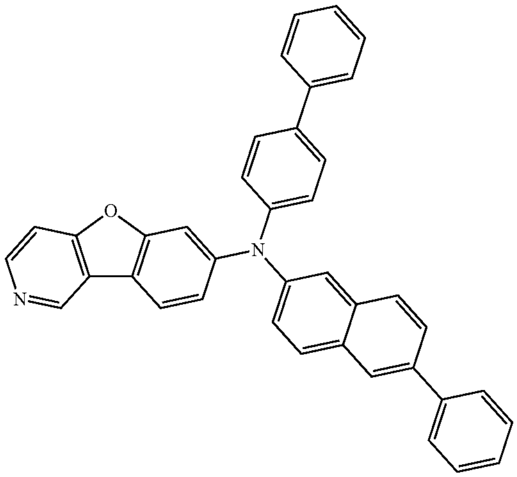
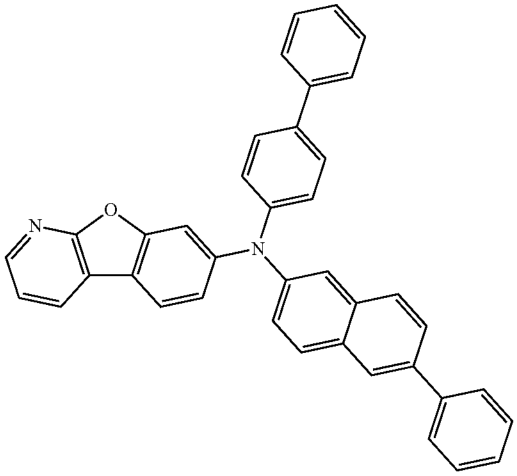
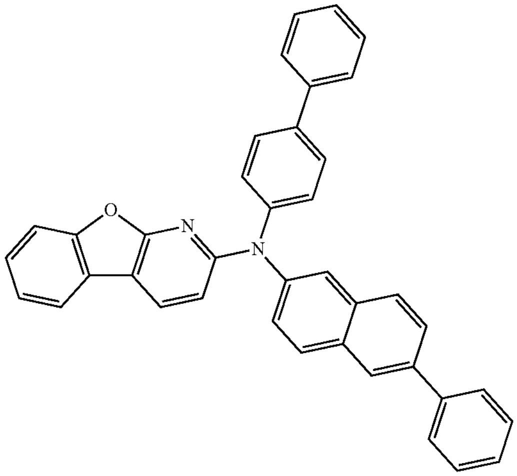
-continued
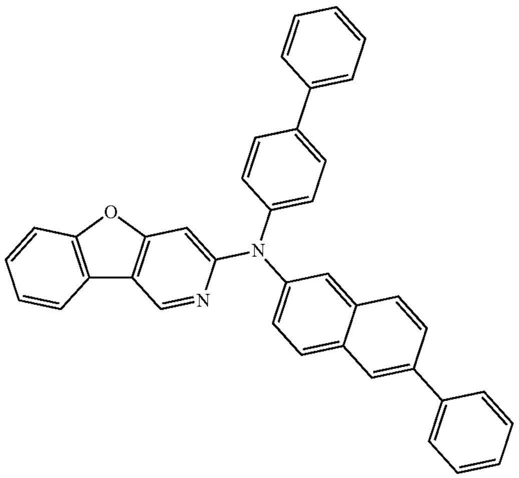 [SMILES: c1ccc(-c2ccc(N(c3ccc4cc(-c5ccccc5)ccc4c3)c3cc4oc5ccccc5c4cn3)cc2)cc1]
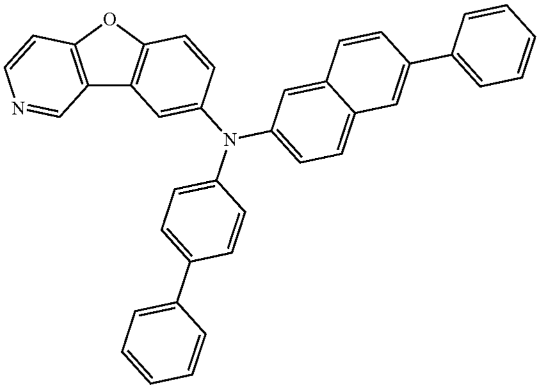
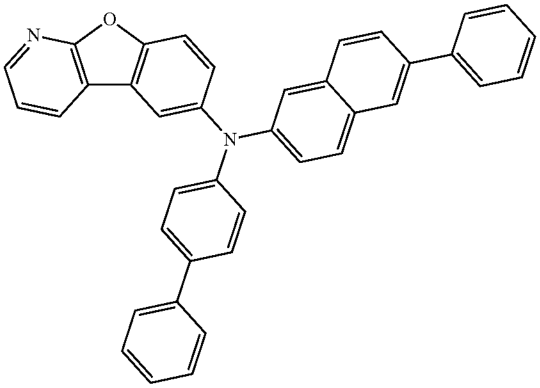
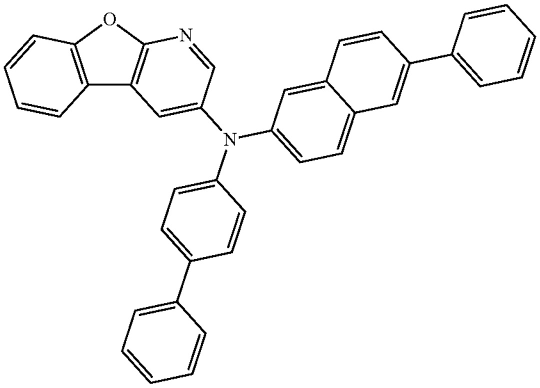

-continued
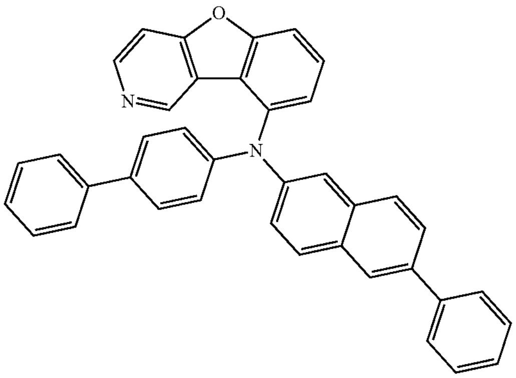
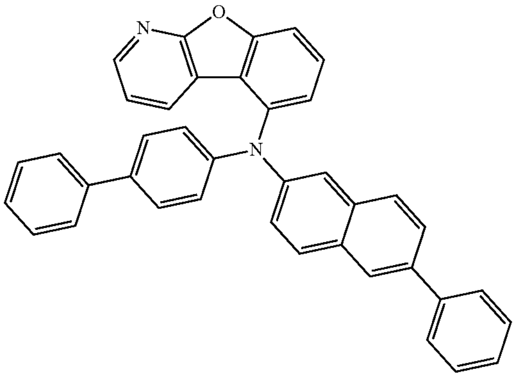
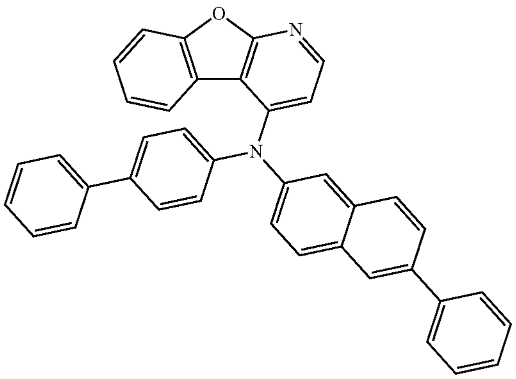
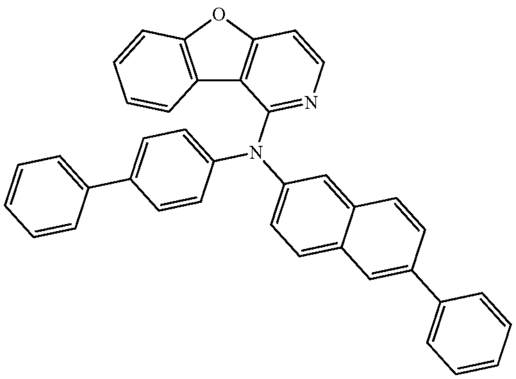
-continued
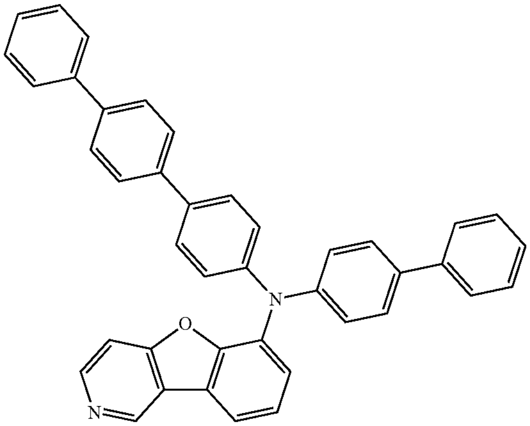
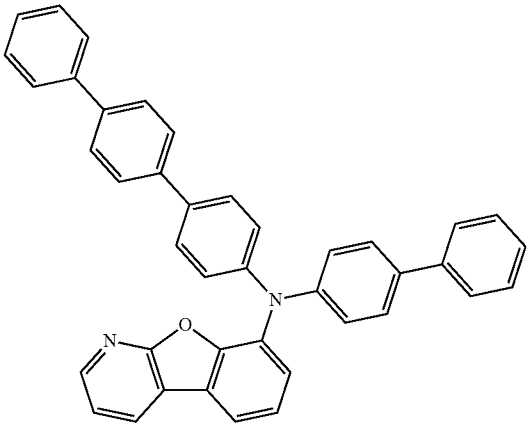
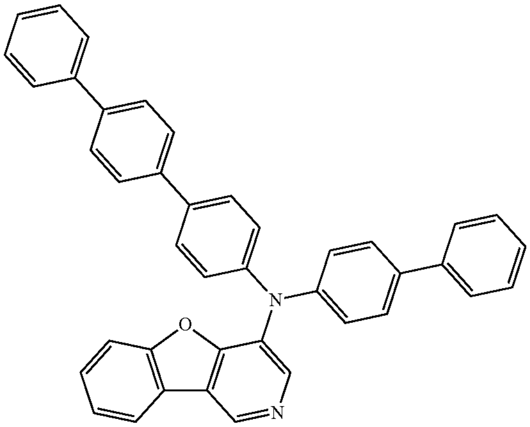

-continued
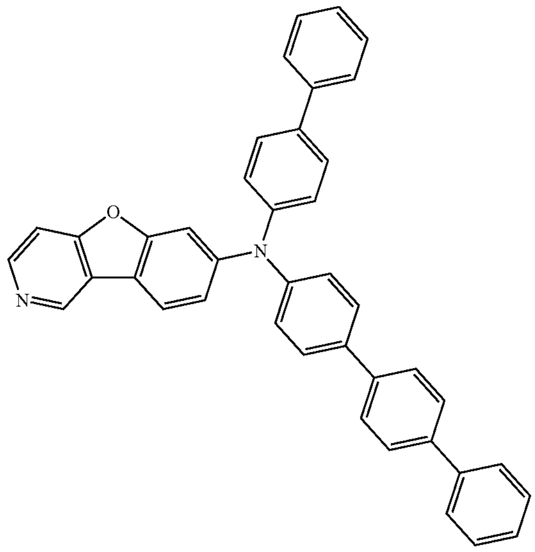
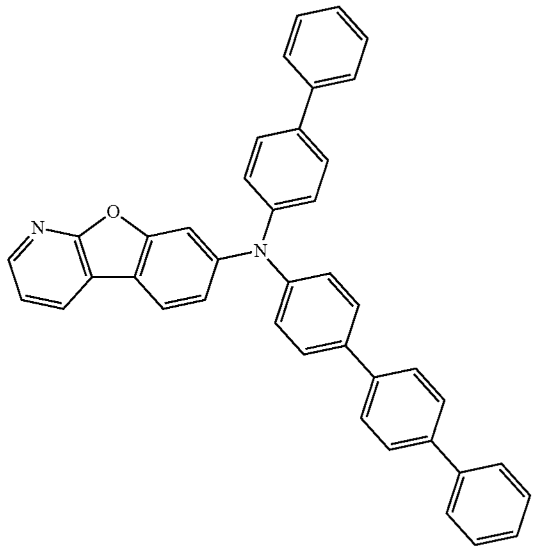
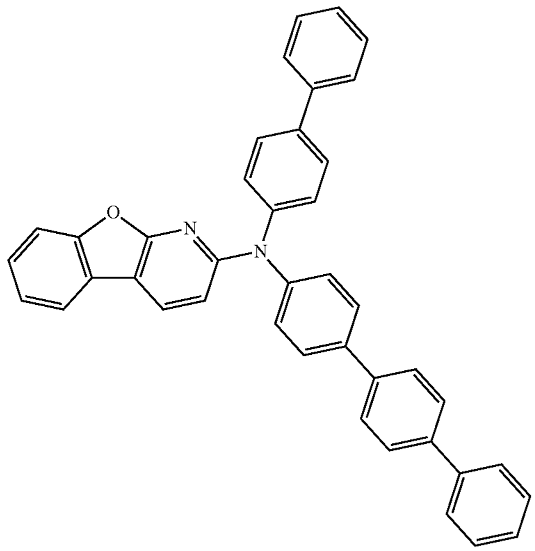
-continued
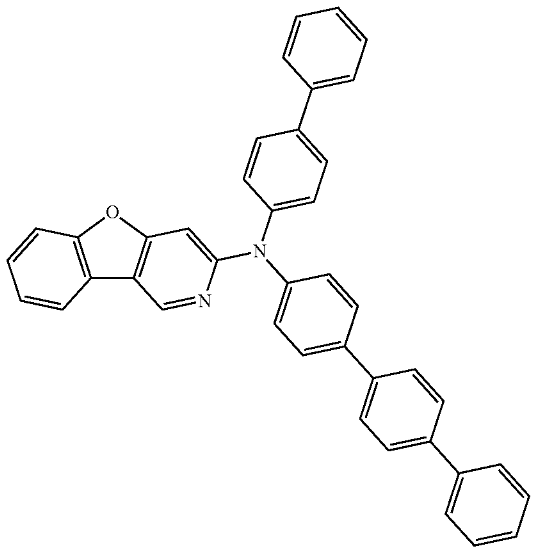 [SMILES: c1ccc(-c2ccc(-c3ccc(N(c4ccc(-c5ccccc5)cc4)c4cc5oc6ccccc6c5cn4)cc3)cc2)cc1]
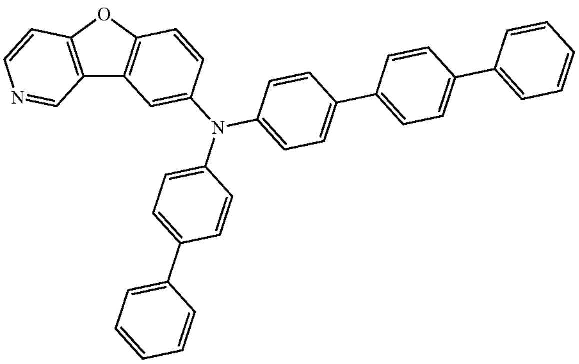
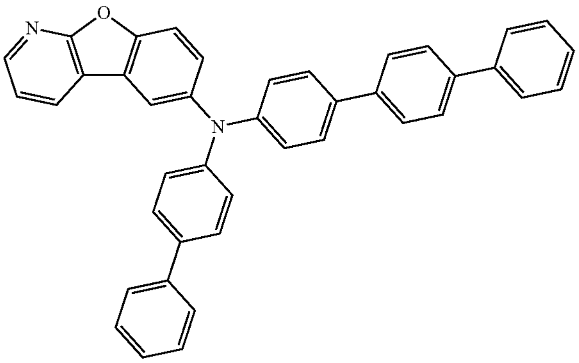
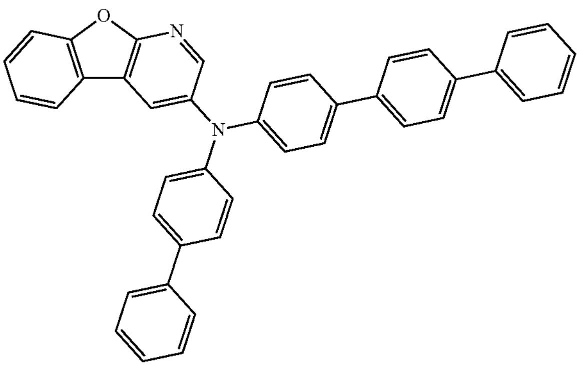

-continued
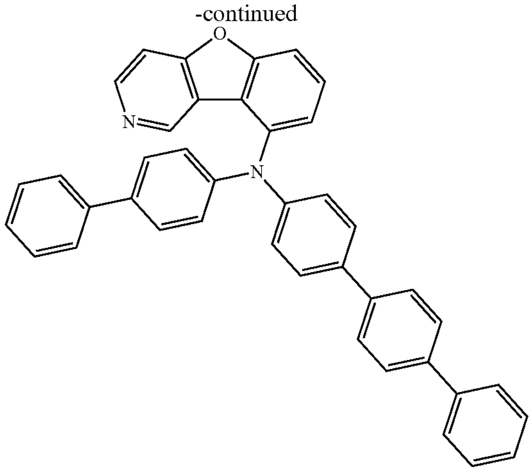
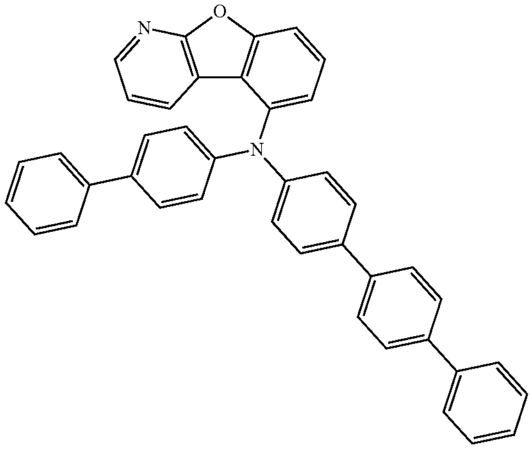
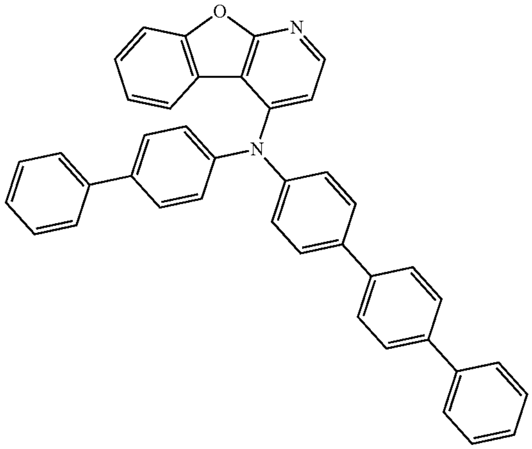
-continued
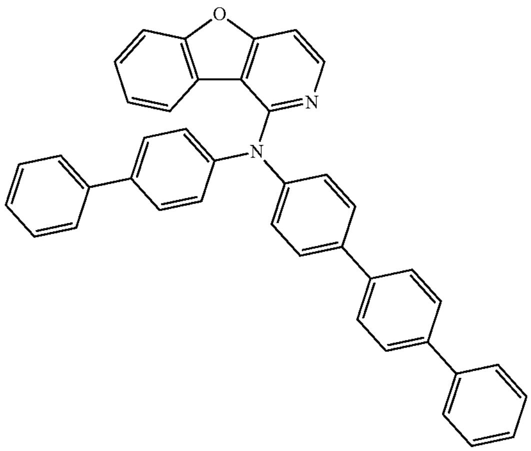
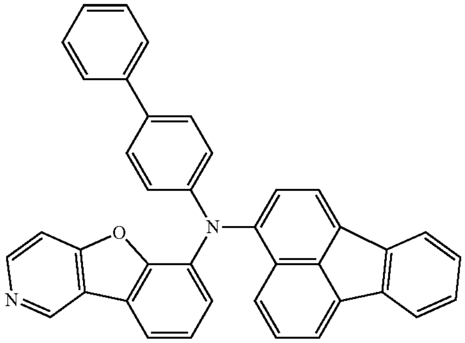
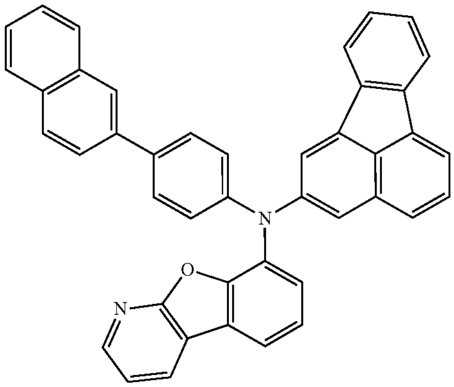
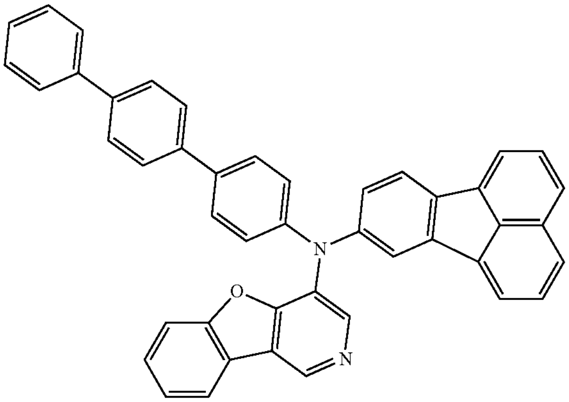

-continued
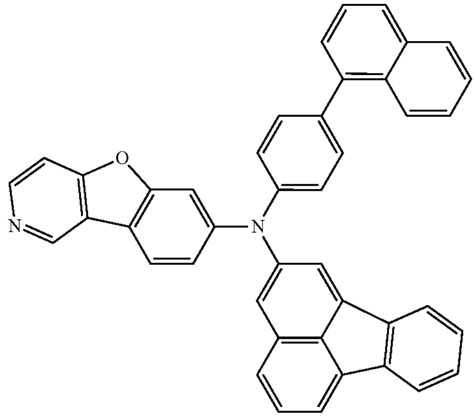
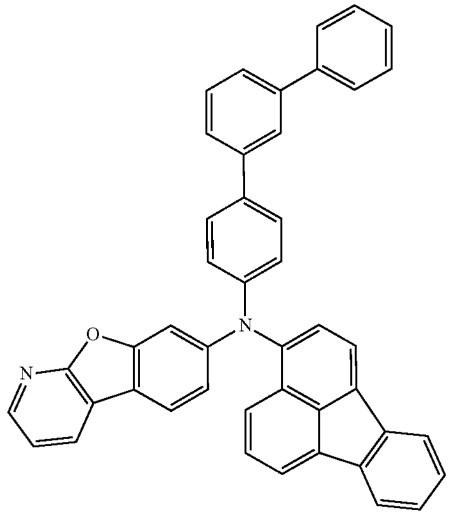
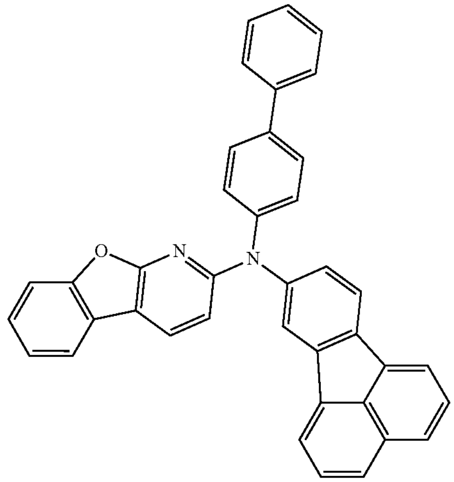
-continued
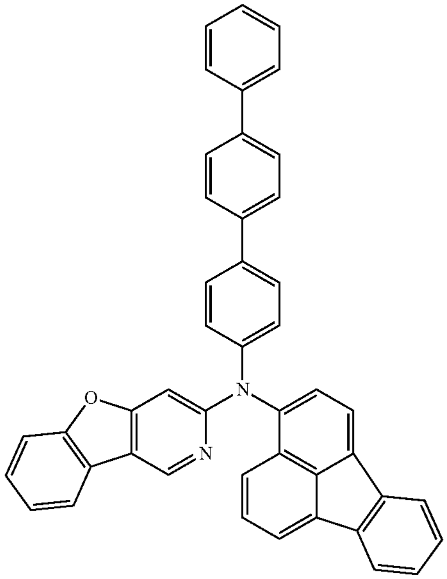 [SMILES: c1ccc(-c2ccc(-c3ccc(N(c4cc5oc6ccccc6c5cn4)c4ccc5c6c(cccc46)-c4ccccc4-5)cc3)cc2)cc1]
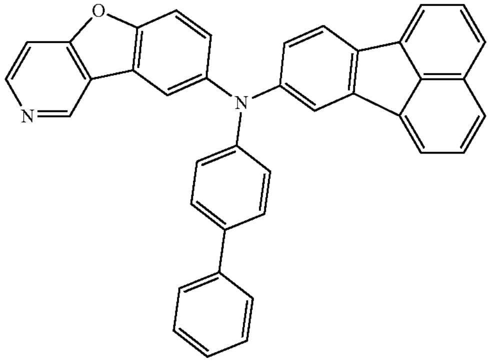
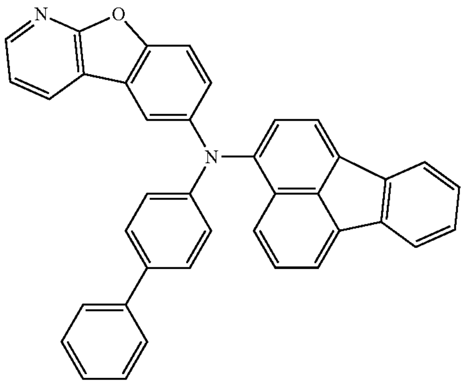

-continued
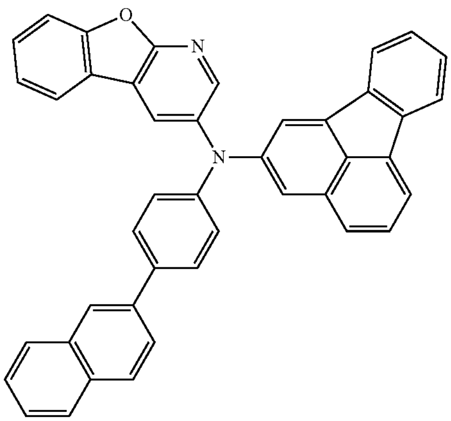
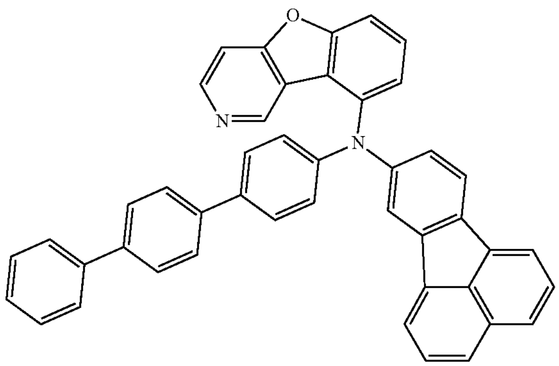
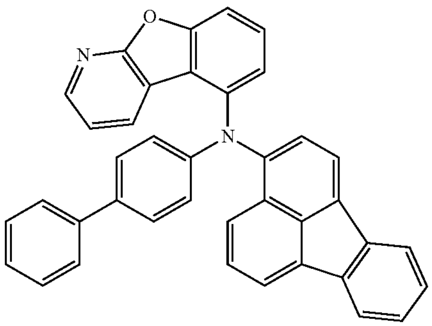
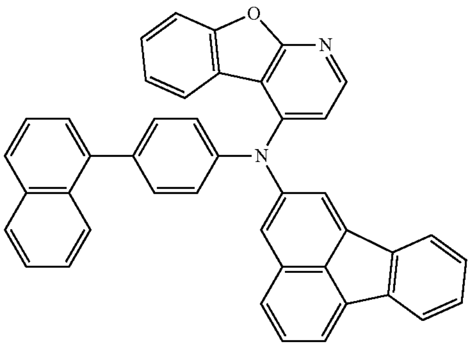
-continued
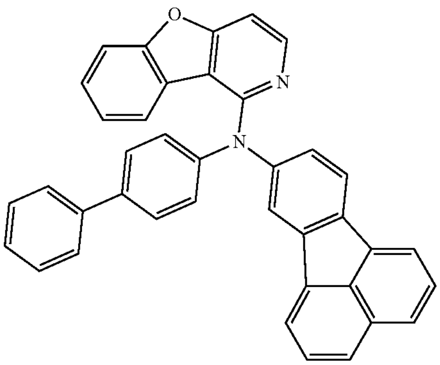
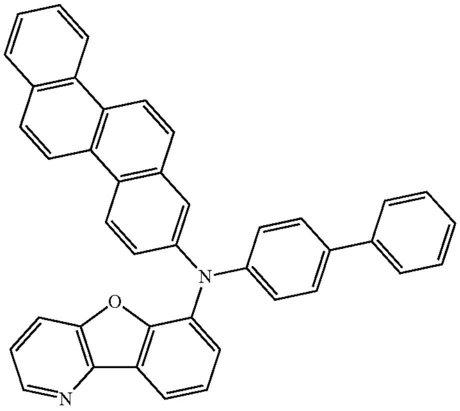
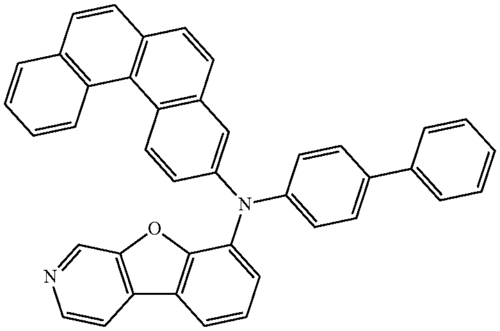
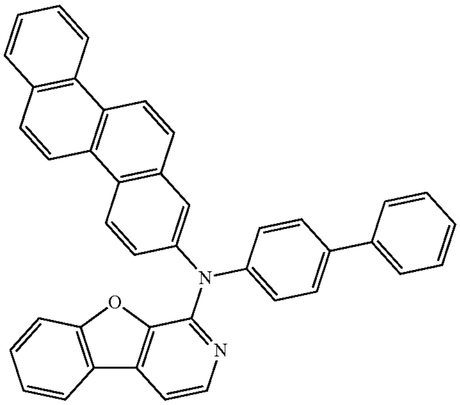

-continued
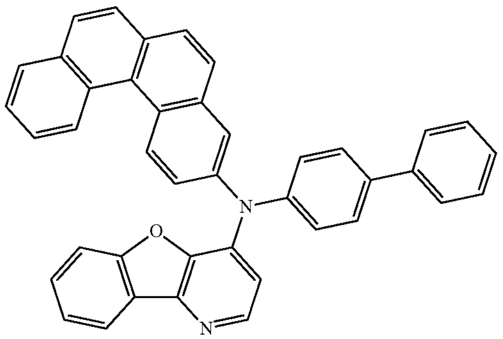 [SMILES: c1ccc(-c2ccc(N(c3ccc4c(ccc5ccc6ccccc6c54)c3)c3ccnc4c3oc3ccccc34)cc2)cc1]
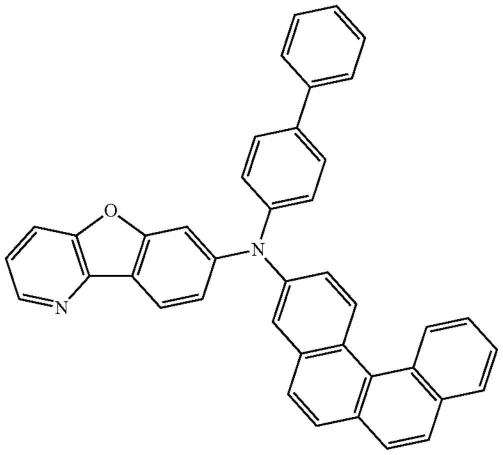
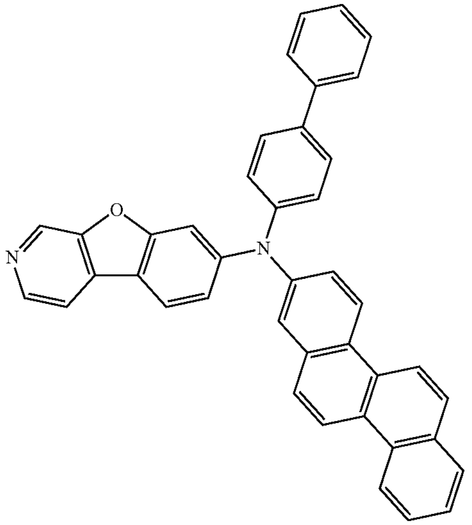
-continued
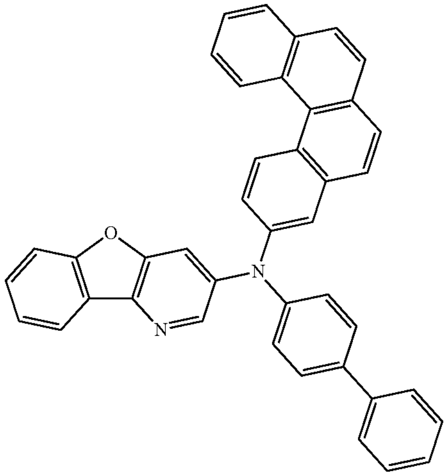
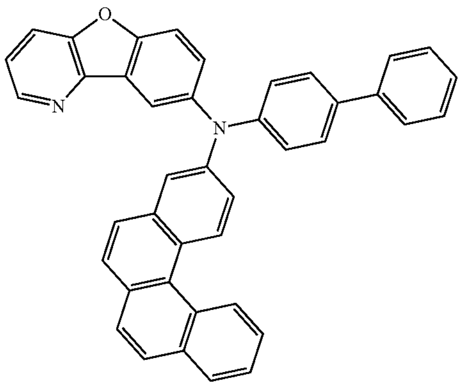
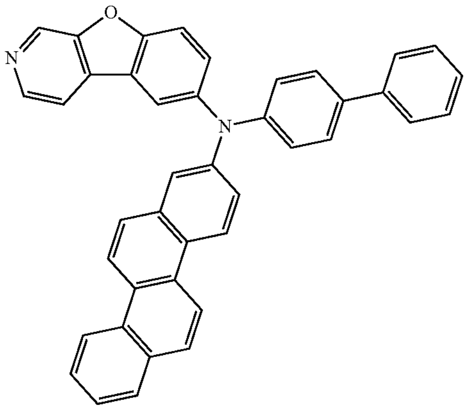
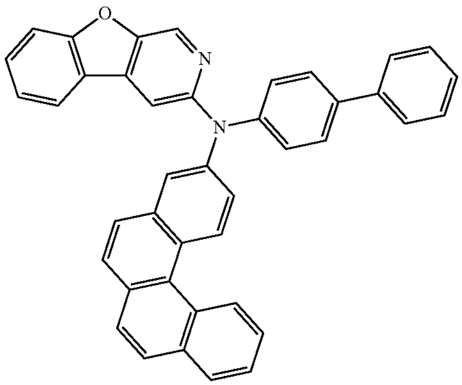

-continued
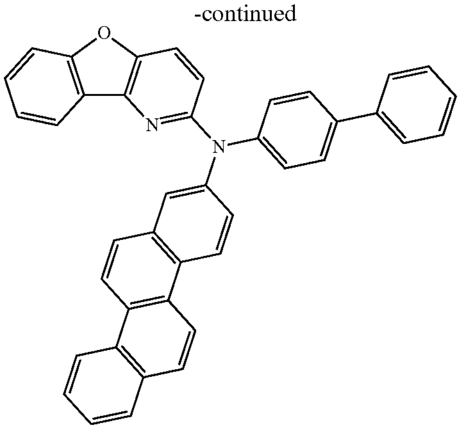
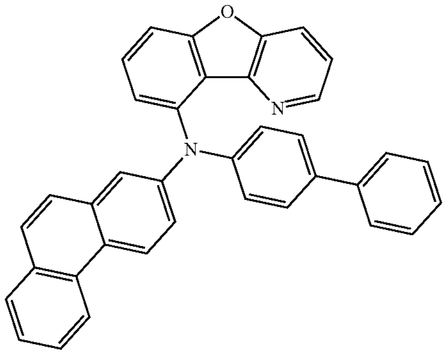
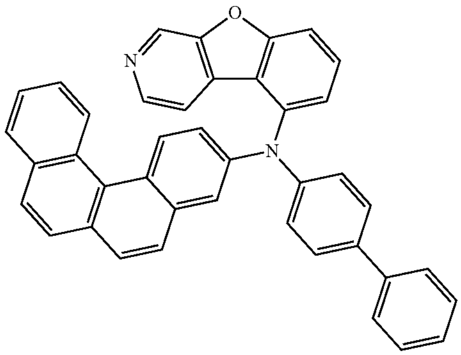
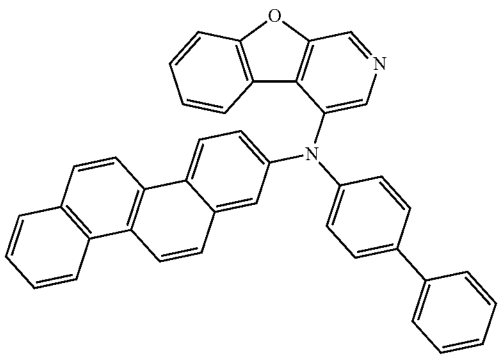
-continued
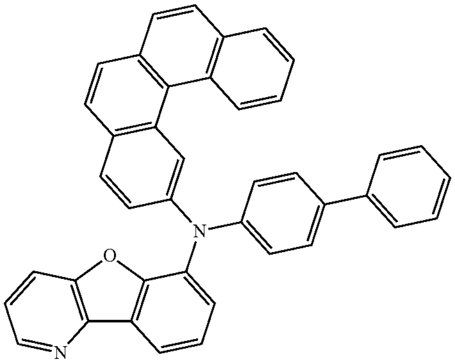
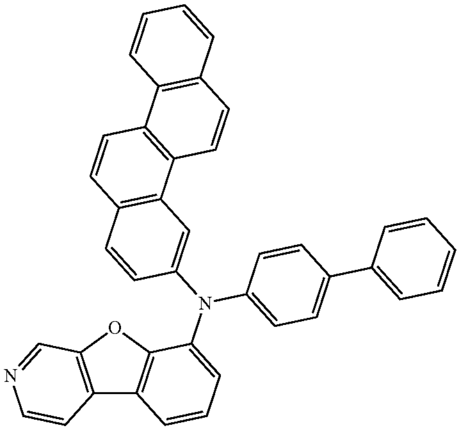
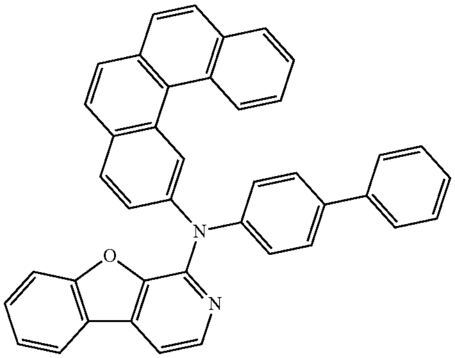
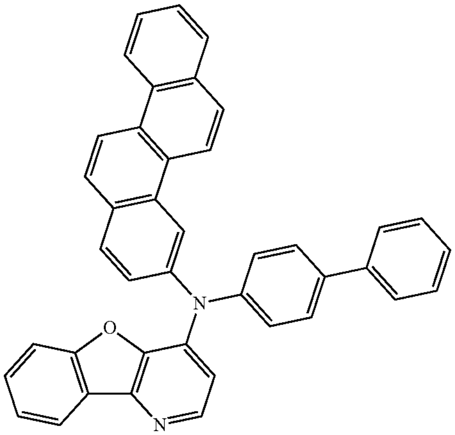 [SMILES: c1ccc(-c2ccc(N(c3ccc4ccc5c6ccccc6ccc5c4c3)c3ccnc4c3oc3ccccc34)cc2)cc1]

-continued
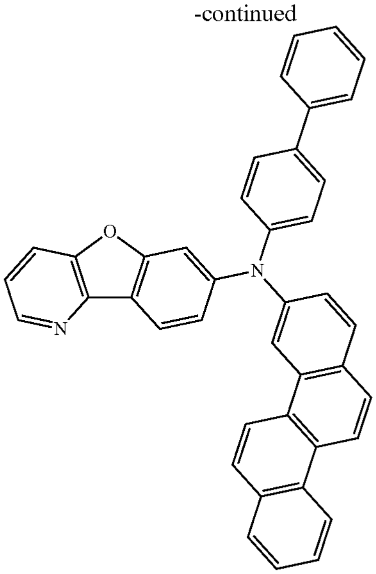
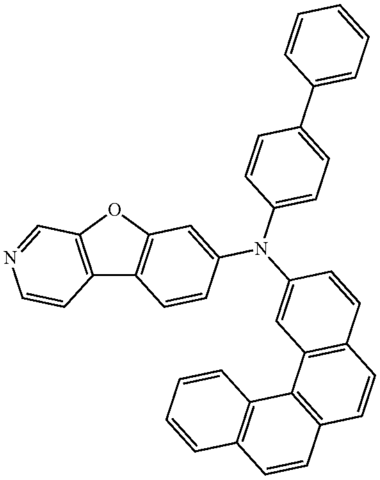
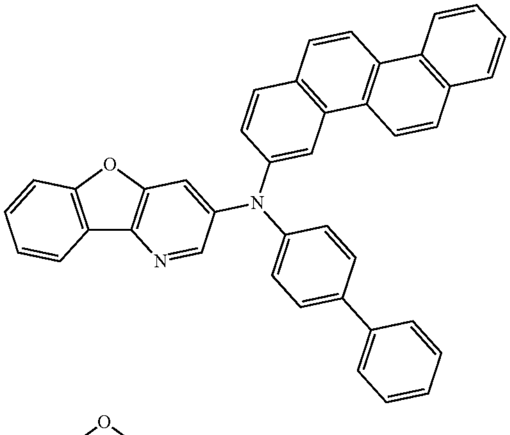
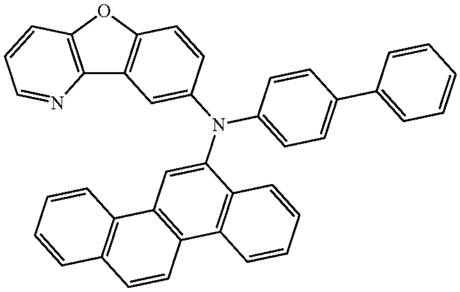
-continued
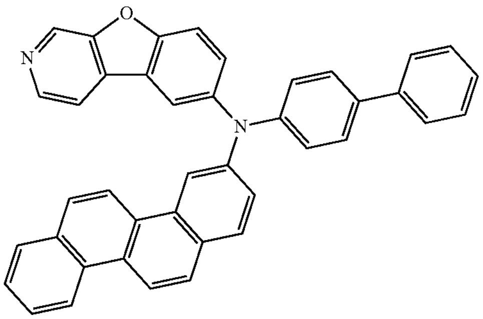
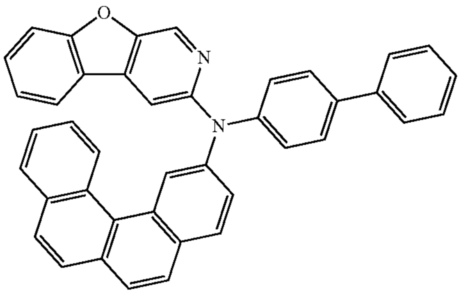
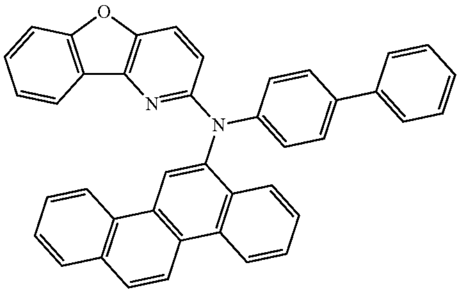
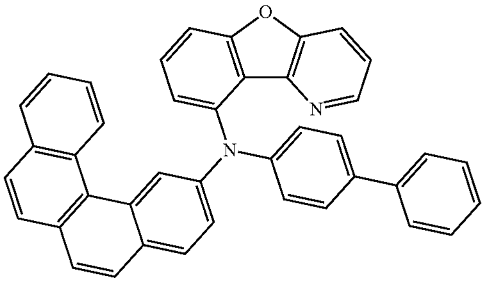
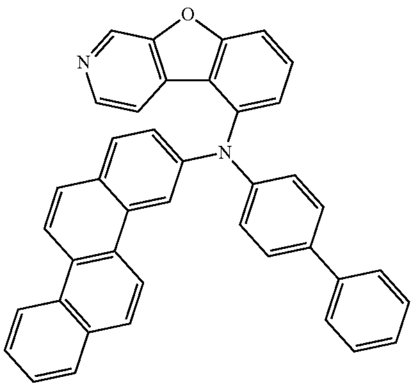

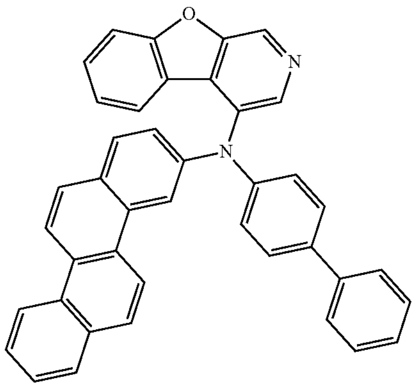
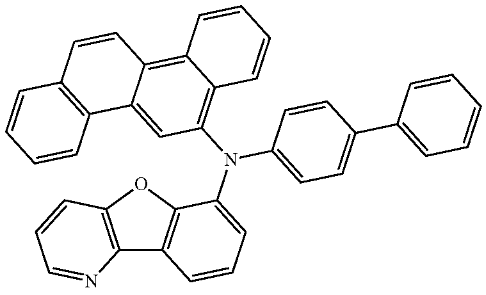
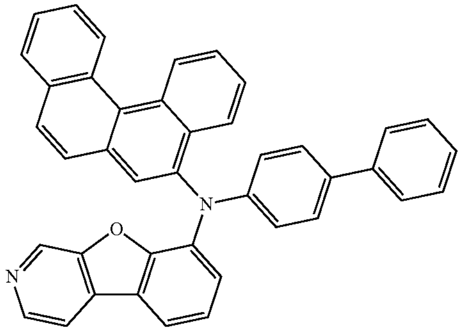
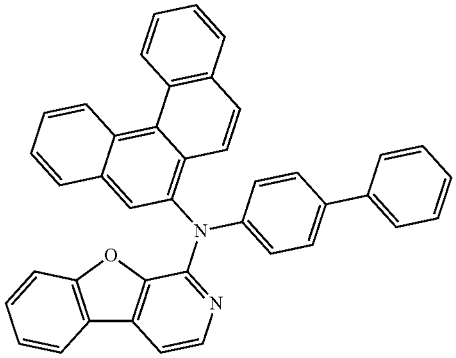
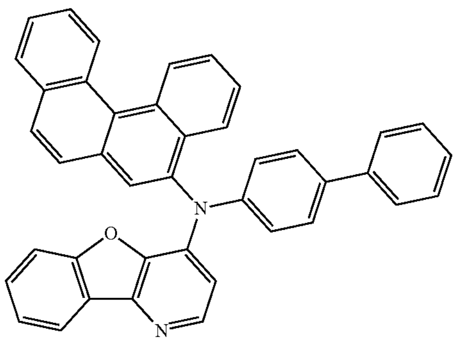 [SMILES: c1ccc(-c2ccc(N(c3cc4ccc5ccccc5c4c4ccccc34)c3ccnc4c3oc3ccccc34)cc2)cc1]
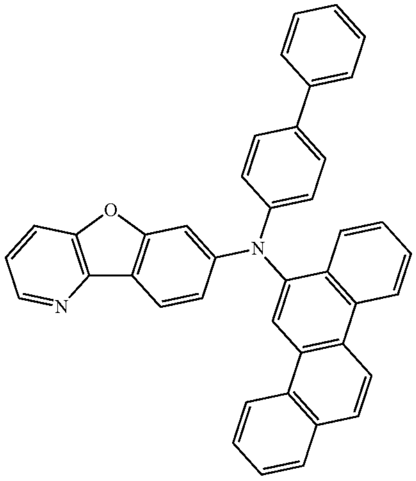
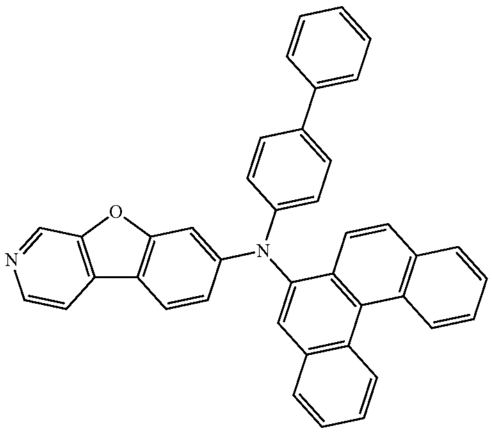
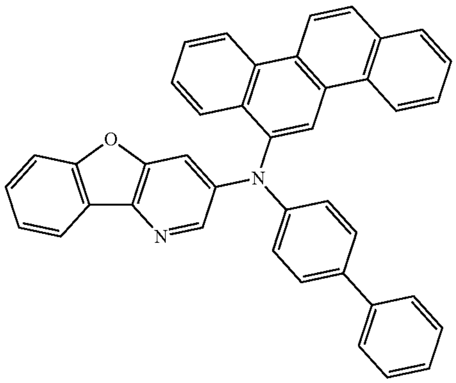
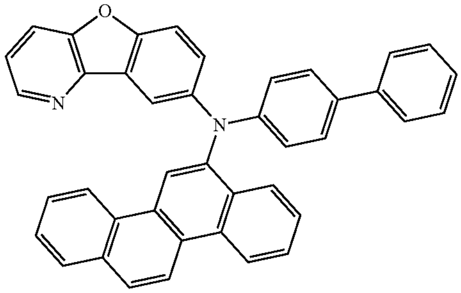

-continued
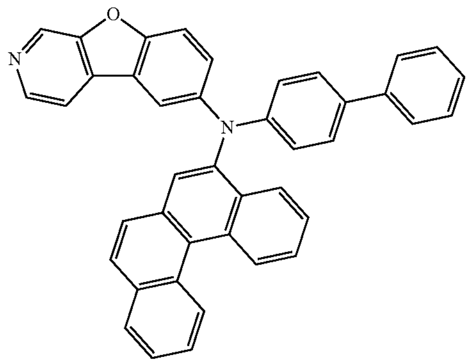
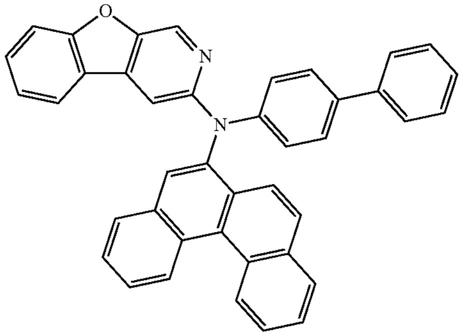
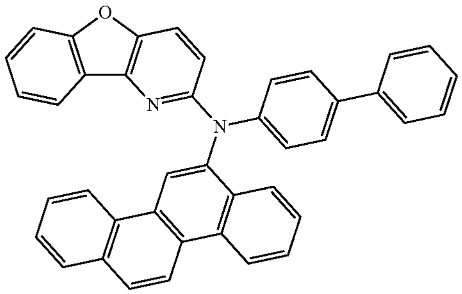
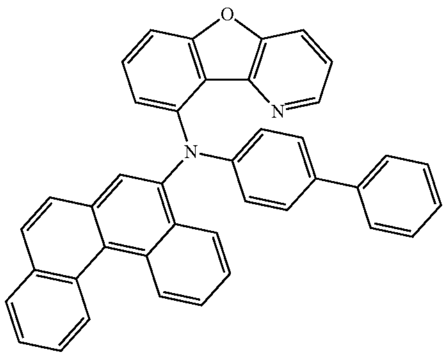
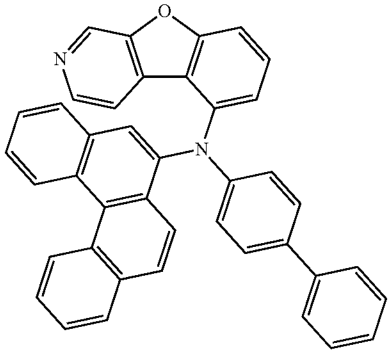
-continued
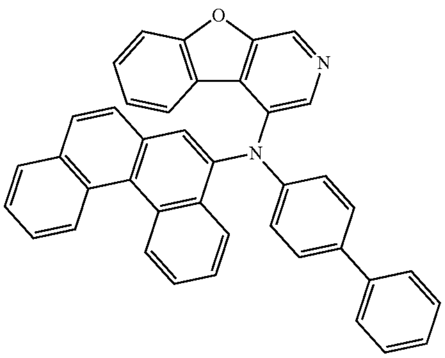
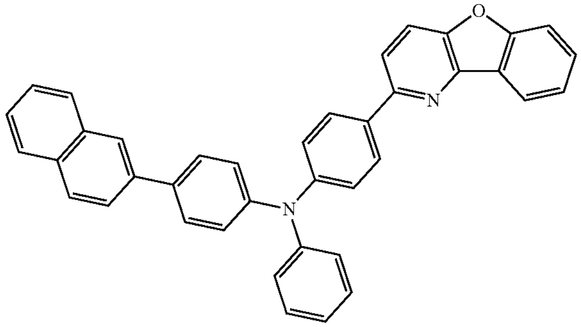
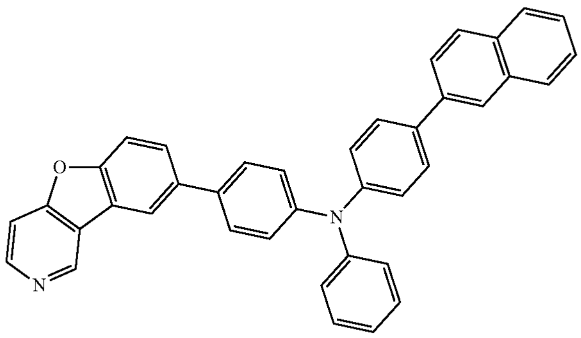
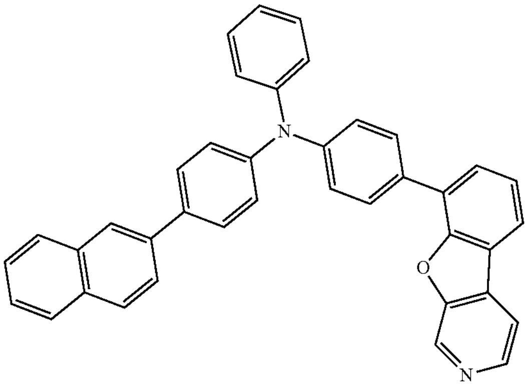

-continued
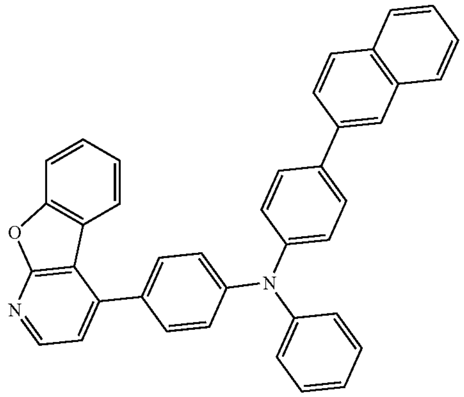
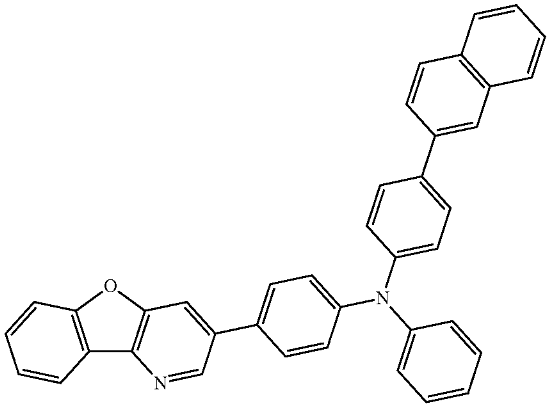
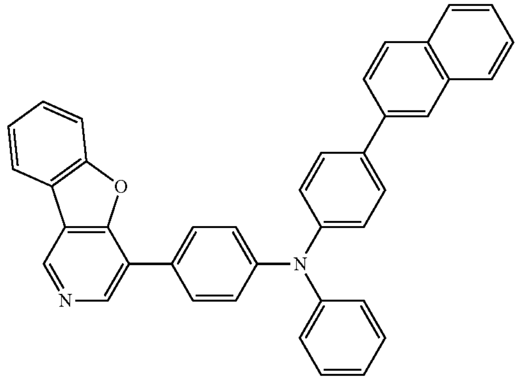
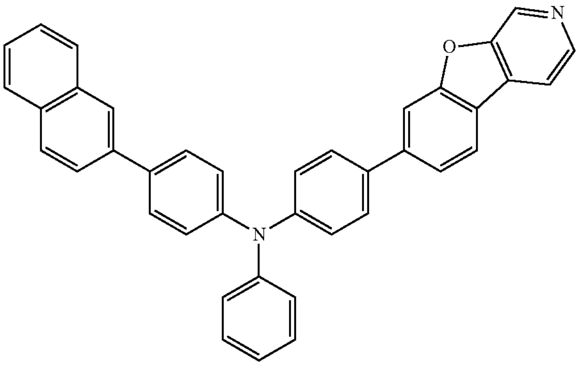
-continued
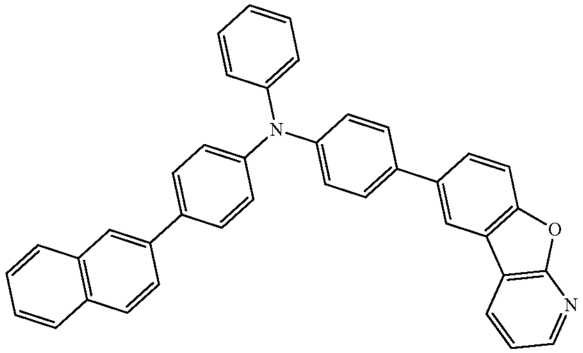
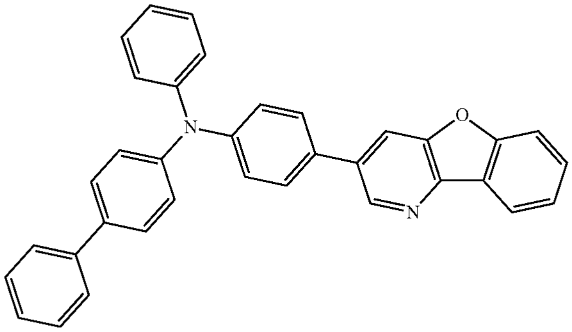
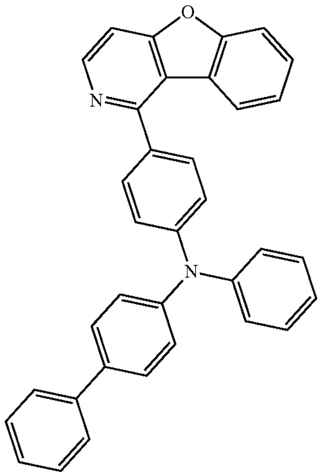
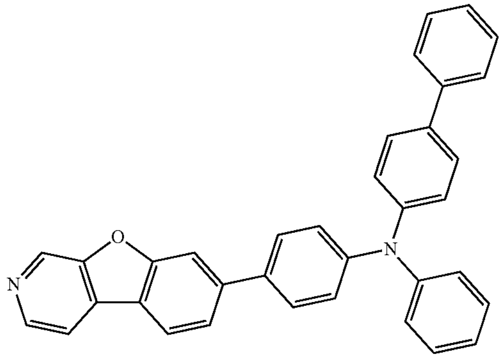

-continued
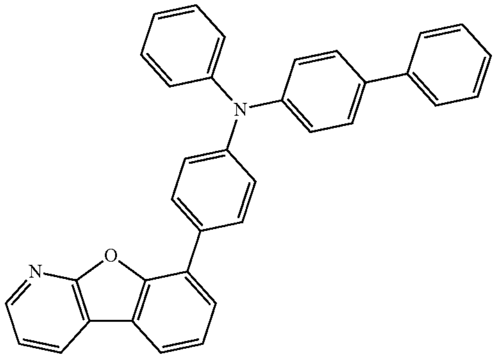
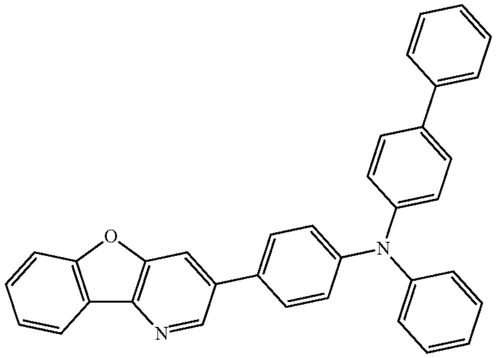
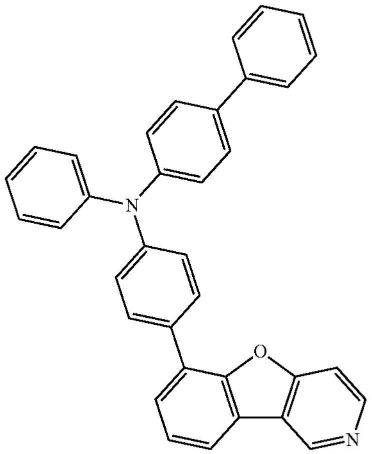
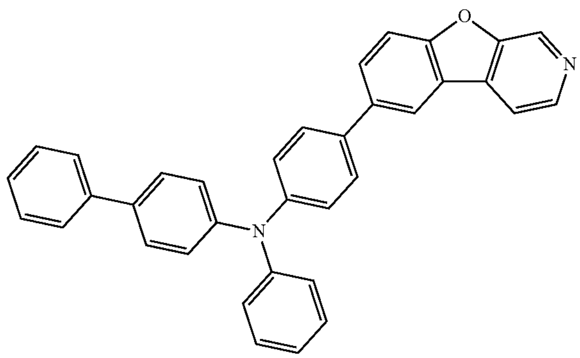
-continued
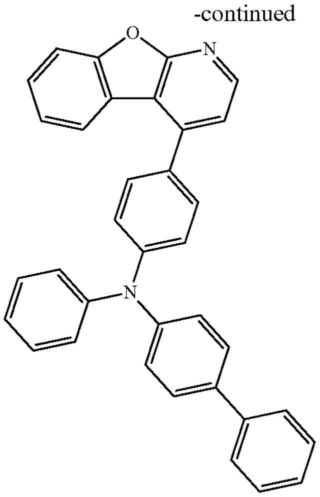
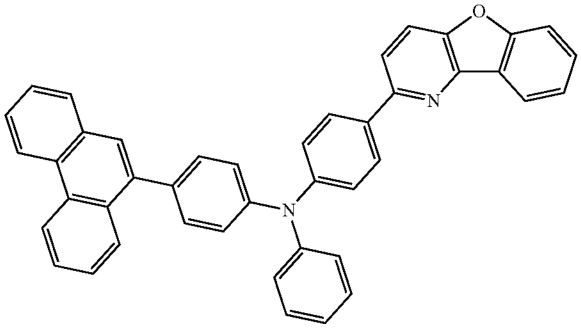
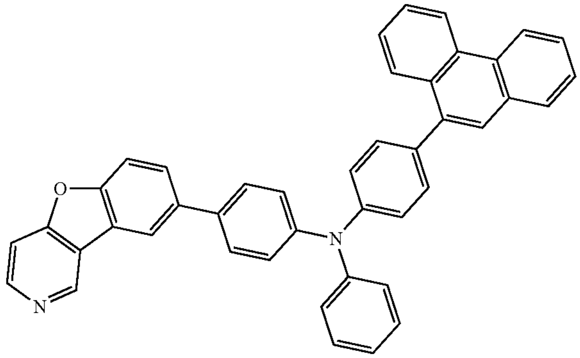
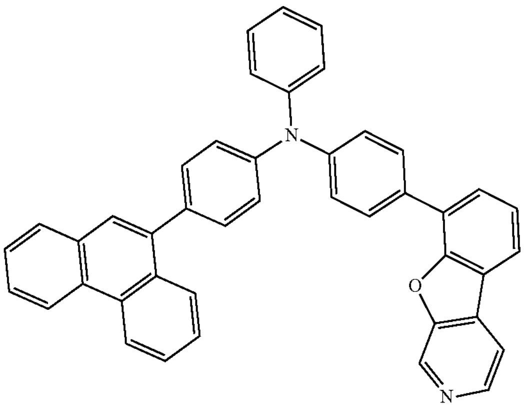

-continued
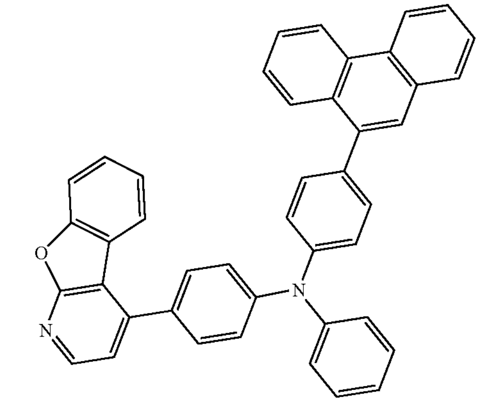
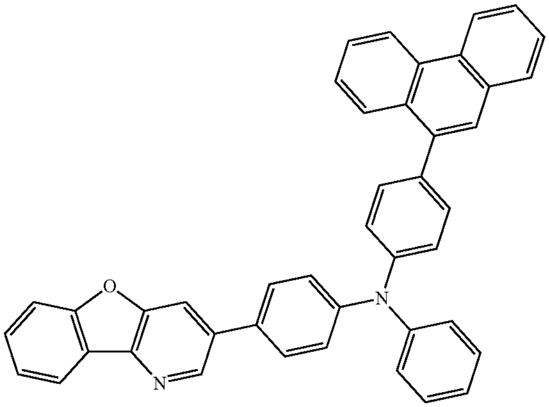
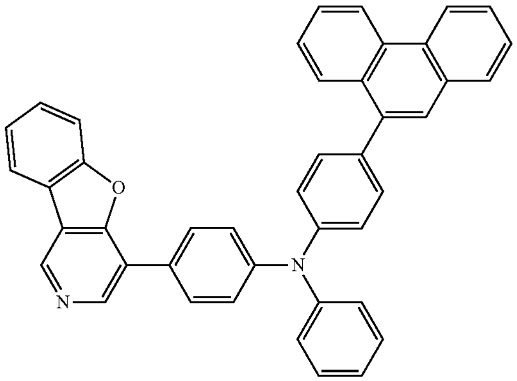
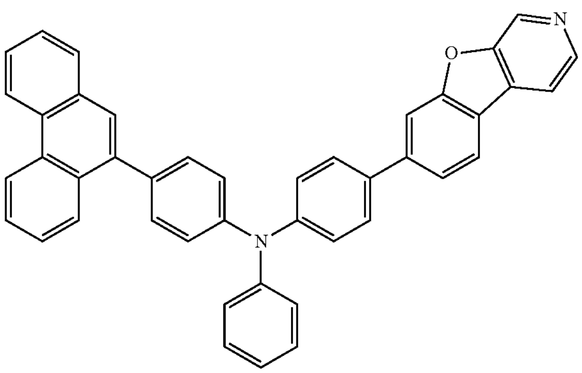
-continued
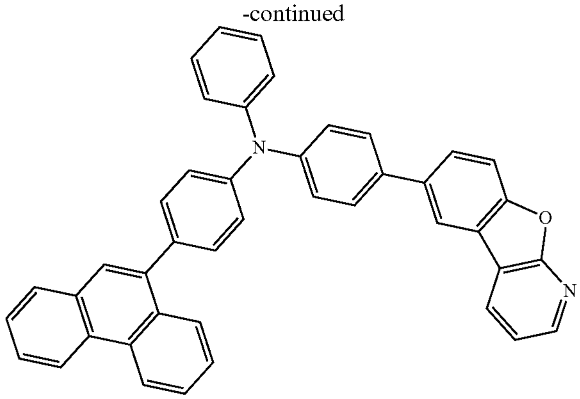
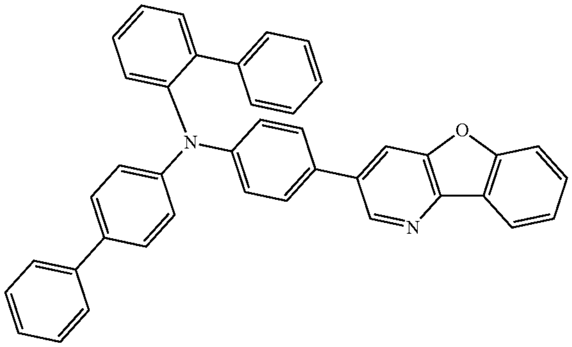
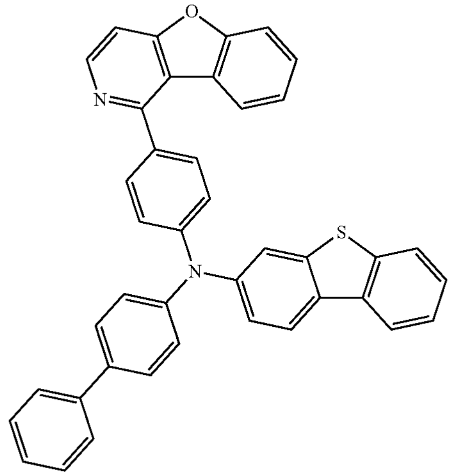
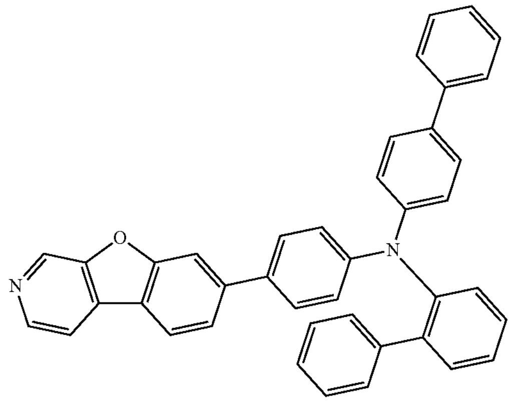

-continued
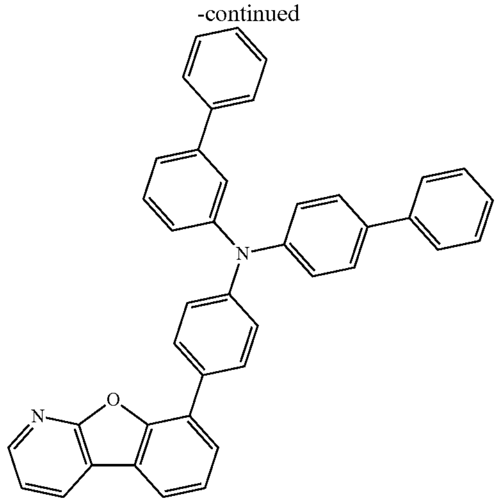
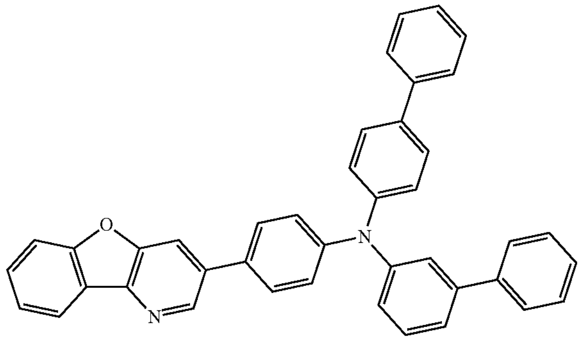
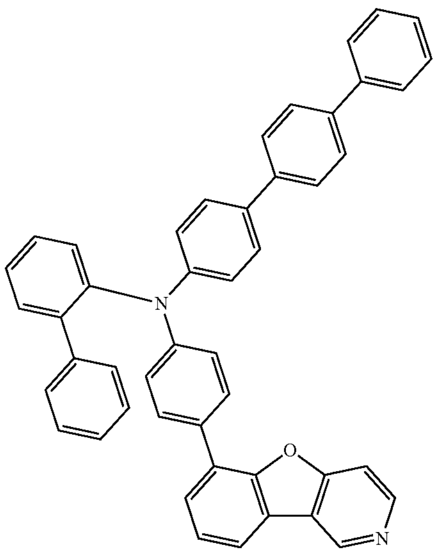
-continued
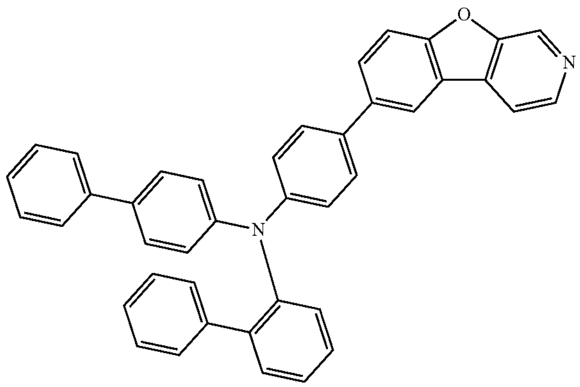
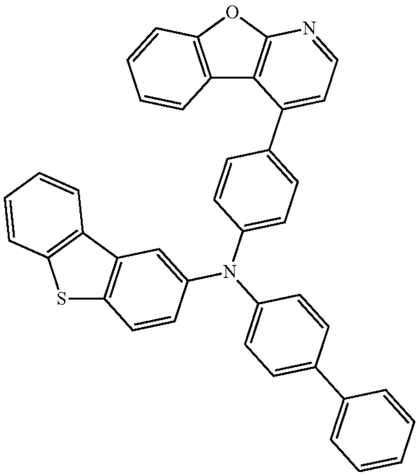
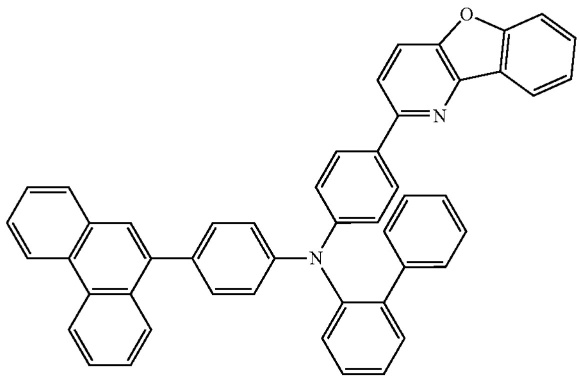
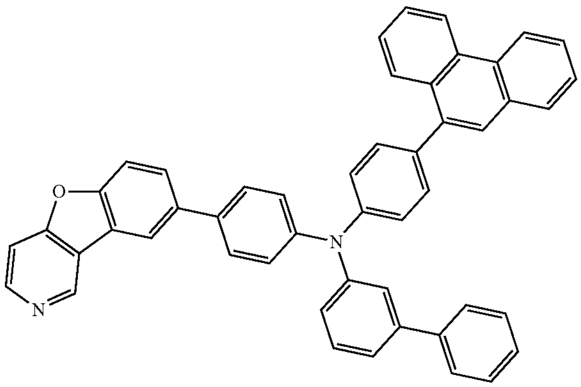

-continued
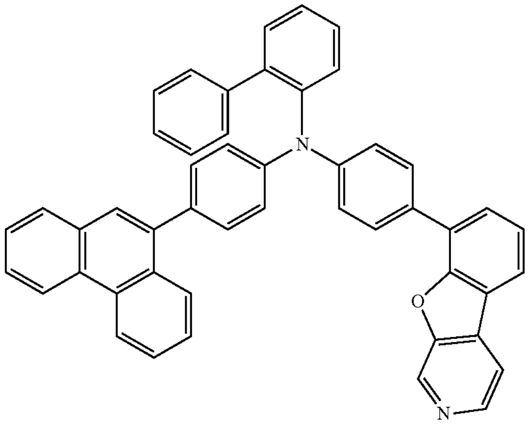
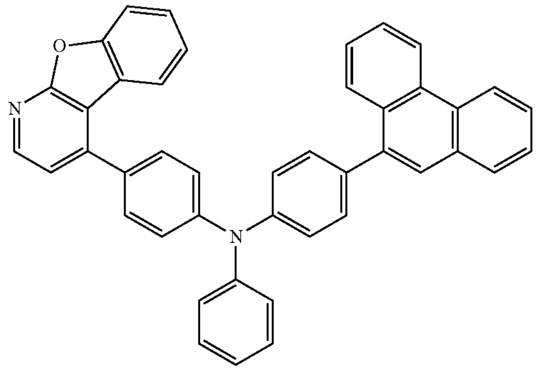
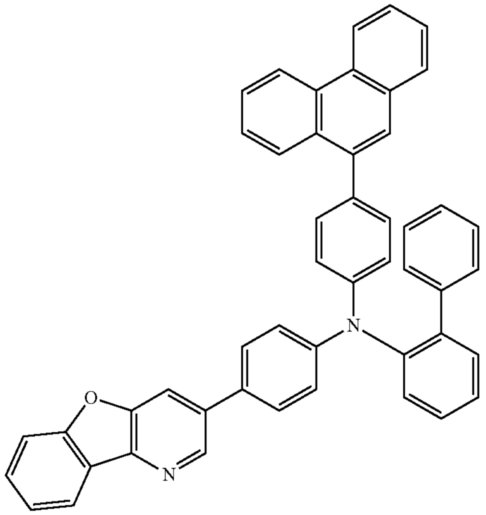
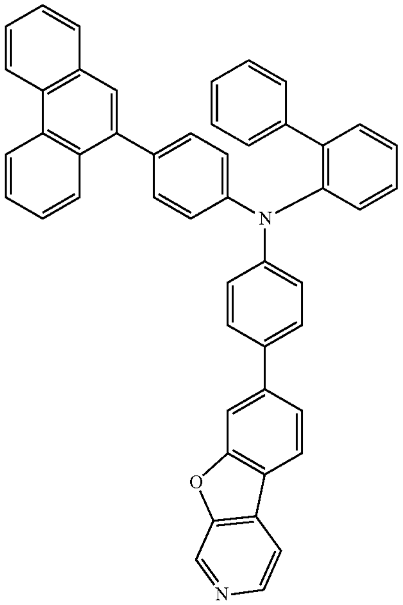
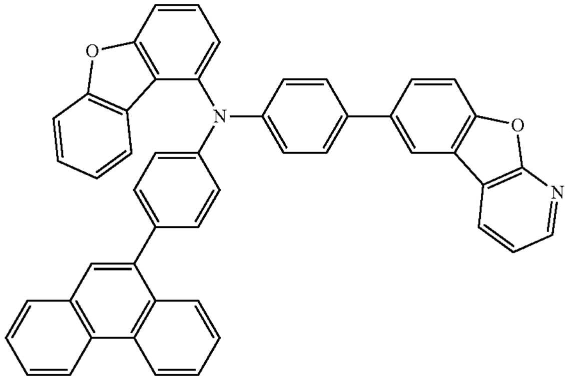
-continued
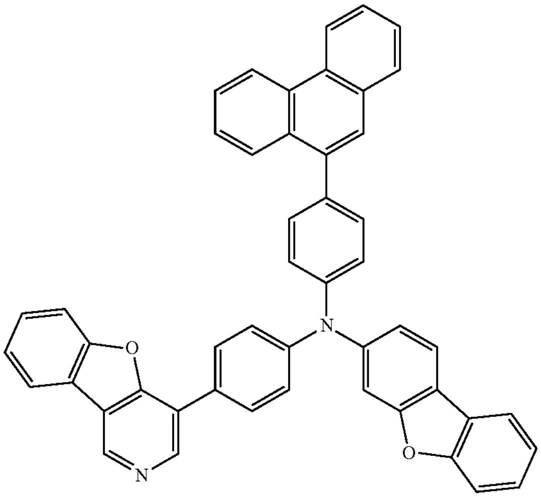

-continued
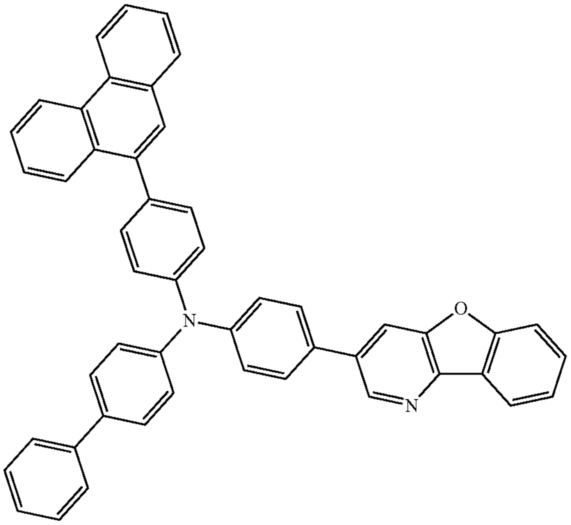
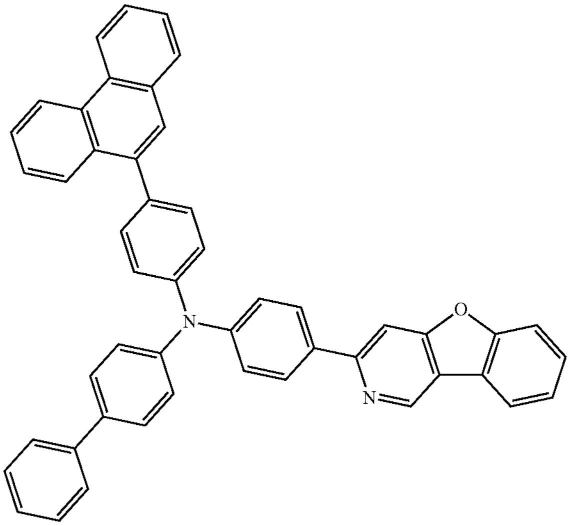
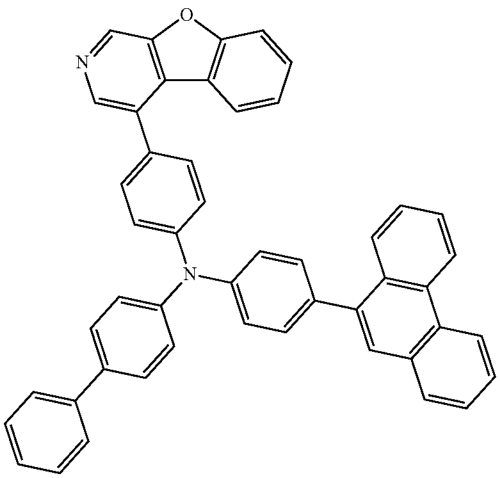
-continued
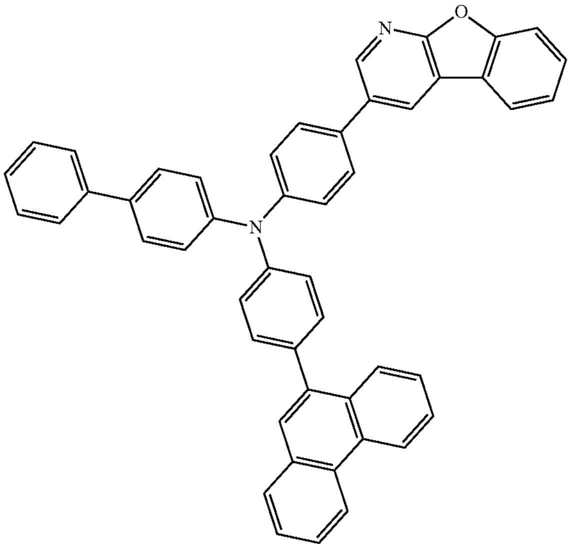 [SMILES: c1ccc(-c2ccc(N(c3ccc(-c4cnc5oc6ccccc6c5c4)cc3)c3ccc(-c4cc5ccccc5c5ccccc45)cc3)cc2)cc1]
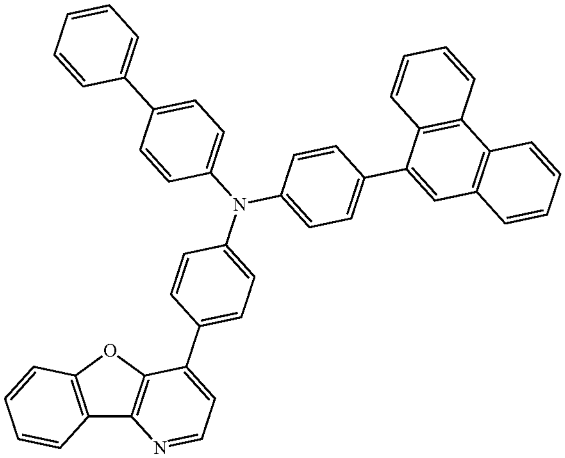
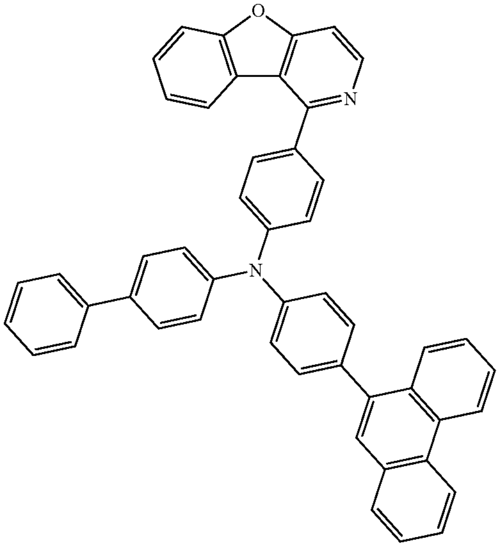

-continued
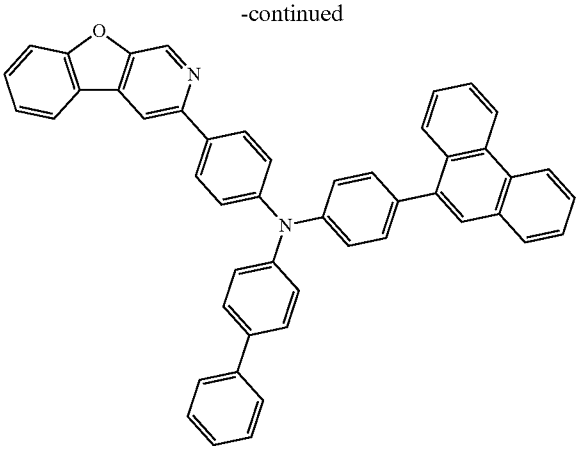
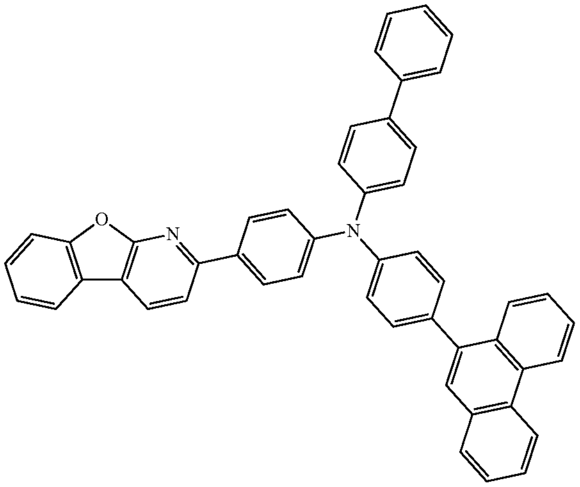
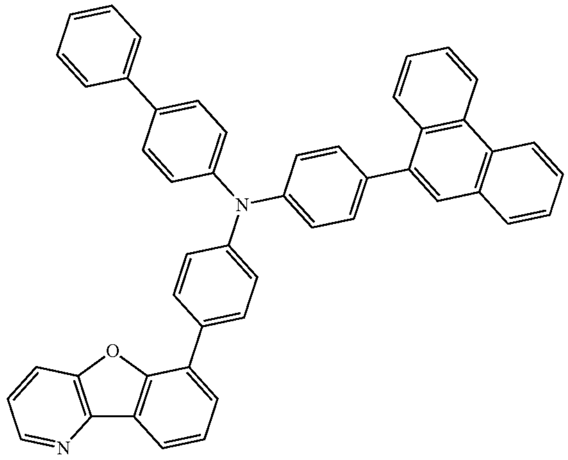
-continued
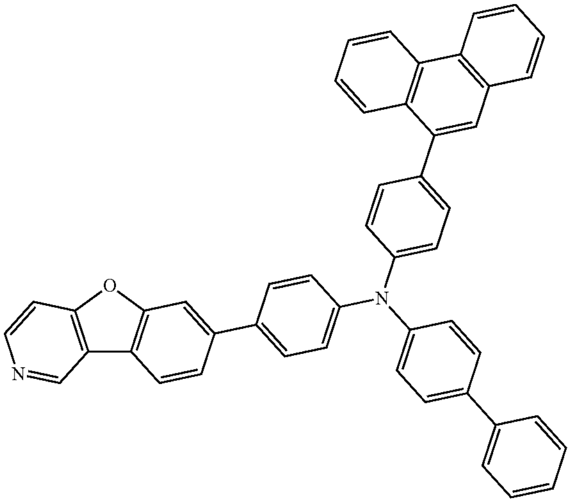
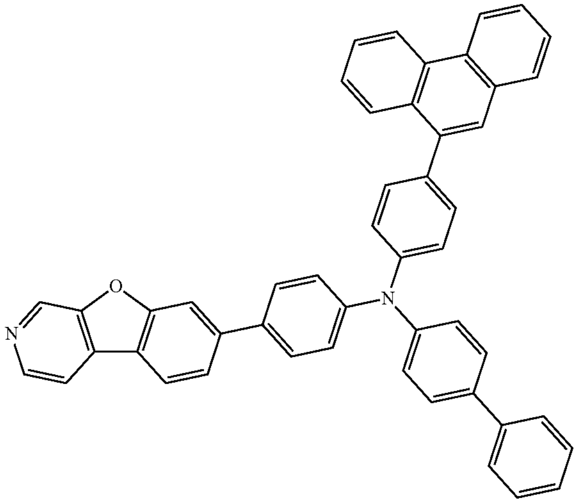
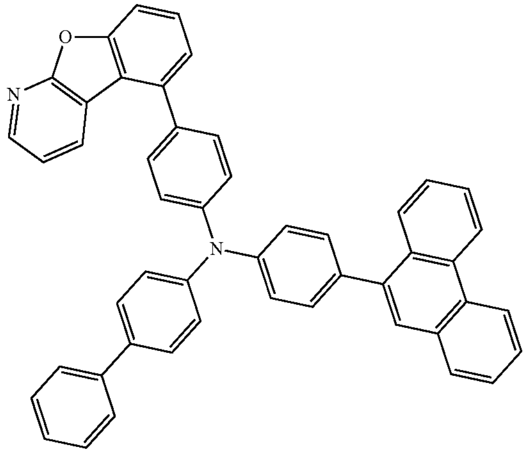

-continued
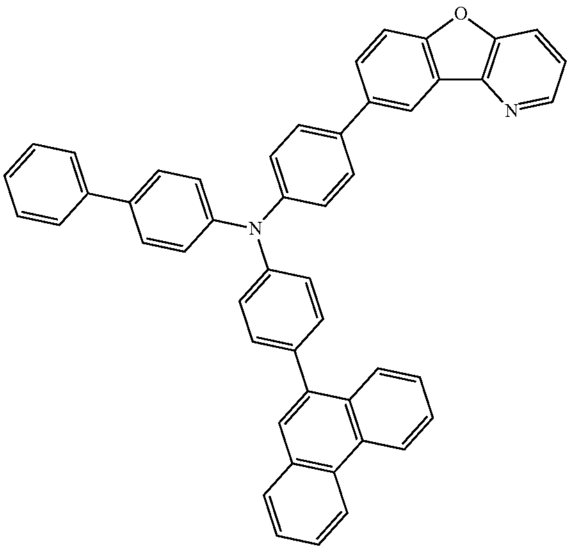
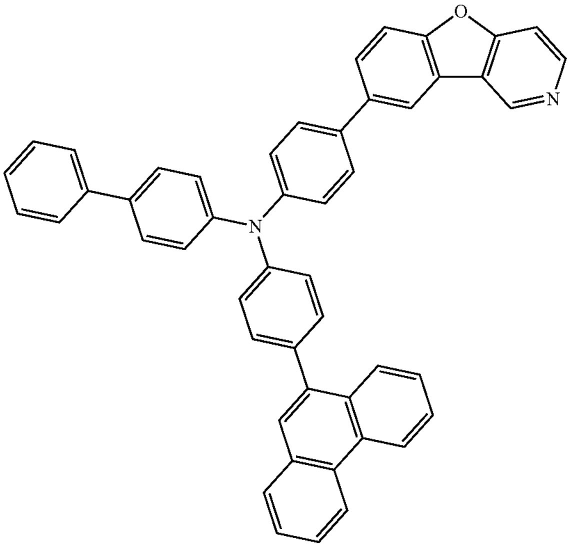
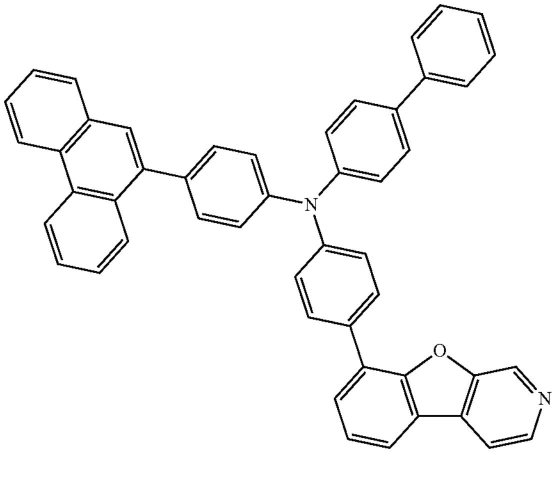
-continued
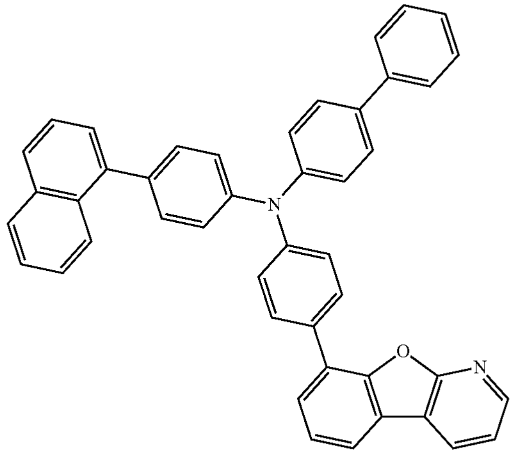 [SMILES: c1ccc(-c2ccc(N(c3ccc(-c4cccc5ccccc45)cc3)c3ccc(-c4cccc5c4oc4ncccc45)cc3)cc2)cc1]
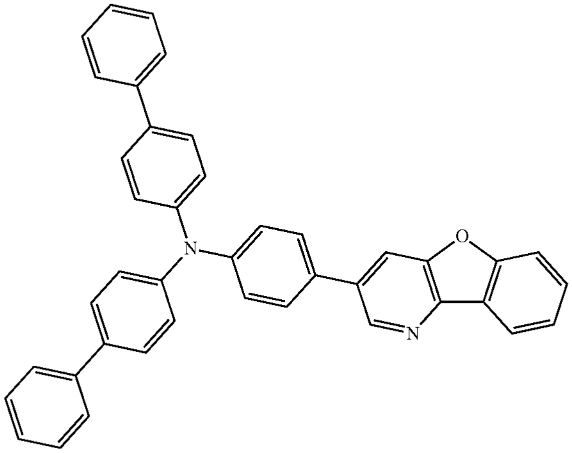
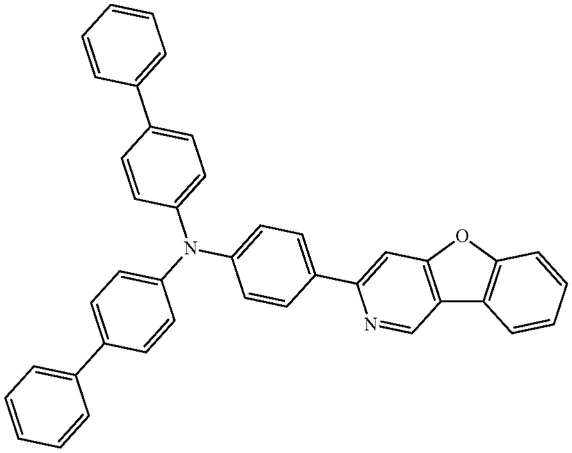

-continued
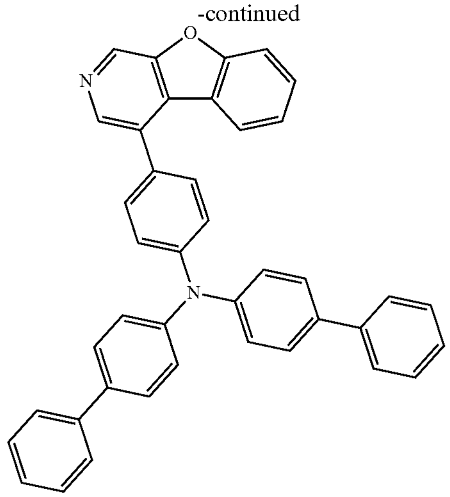
-continued
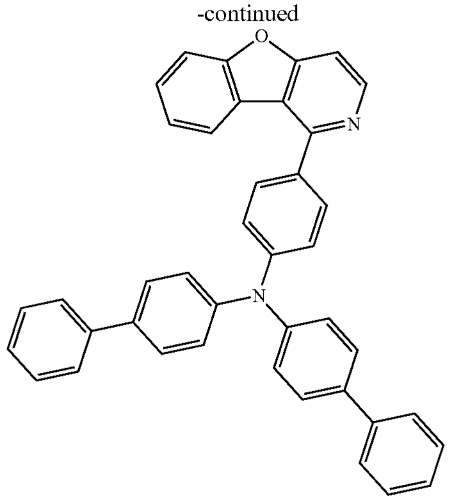
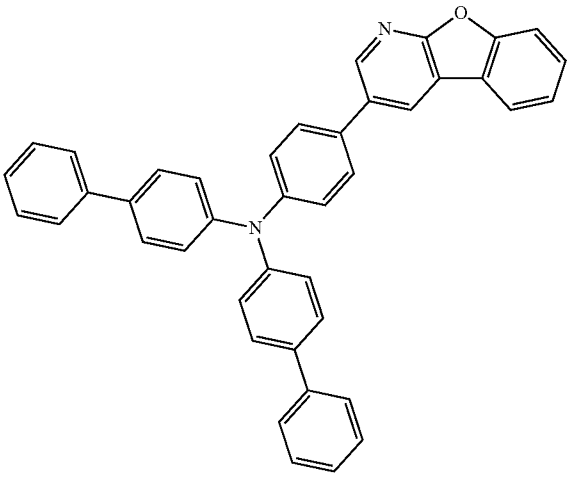
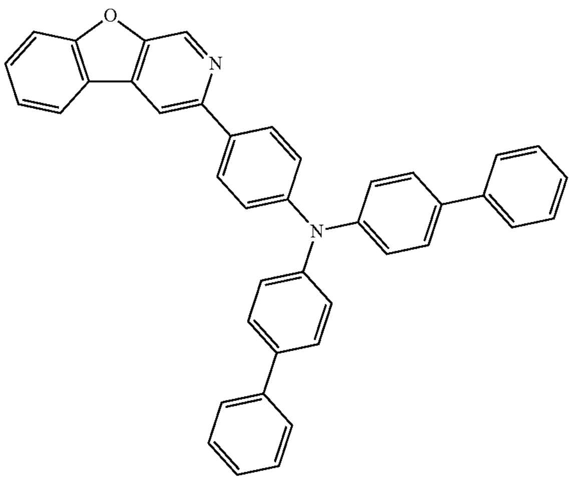
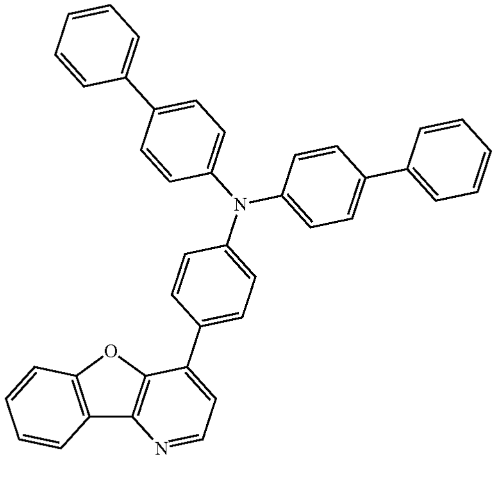
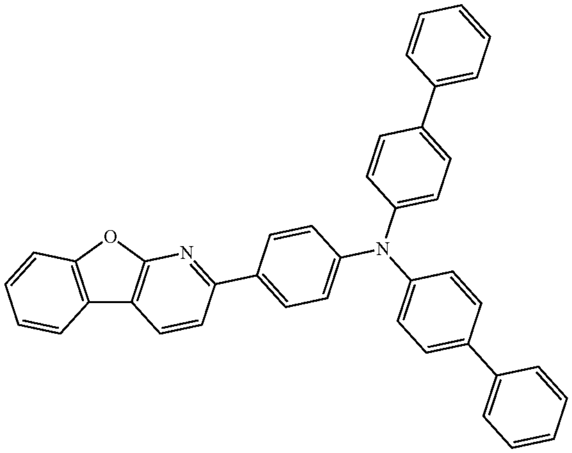 [SMILES: c1ccc(-c2ccc(N(c3ccc(-c4ccccc4)cc3)c3ccc(-c4ccc5c(n4)oc4ccccc45)cc3)cc2)cc1]

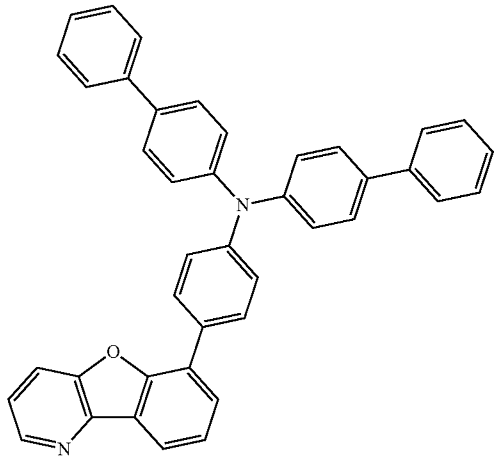
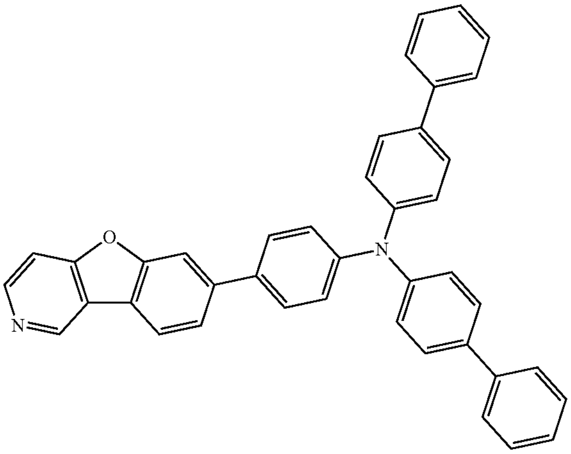
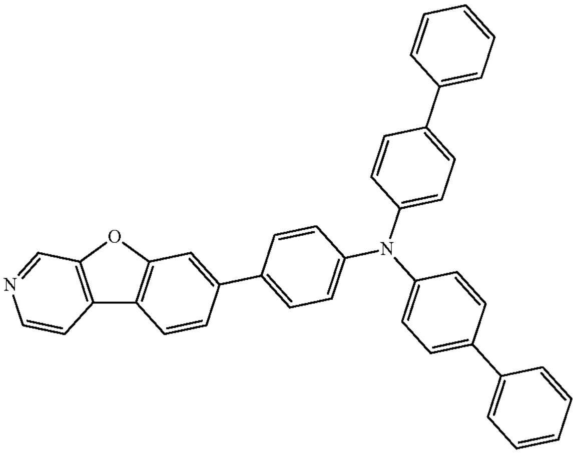
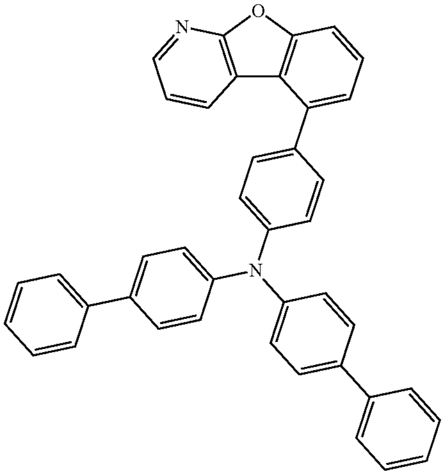 [SMILES: c1ccc(-c2ccc(N(c3ccc(-c4ccccc4)cc3)c3ccc(-c4cccc5oc6ncccc6c45)cc3)cc2)cc1]
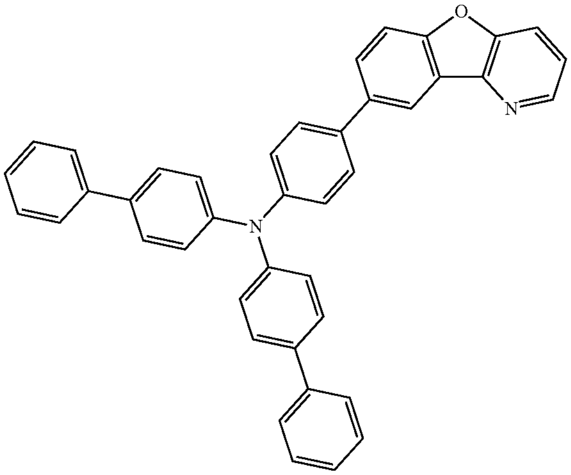
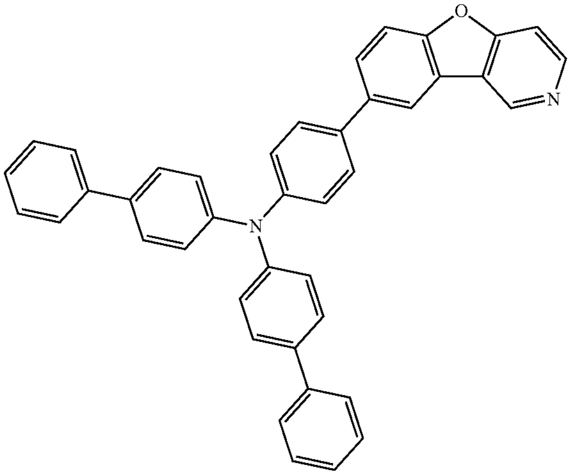

-continued
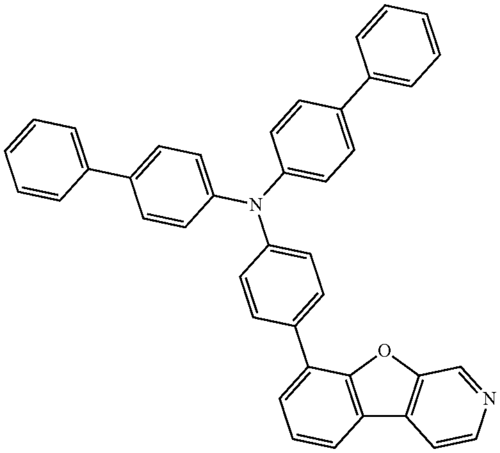
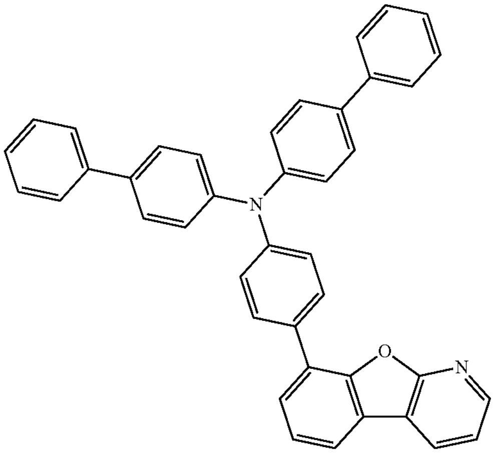
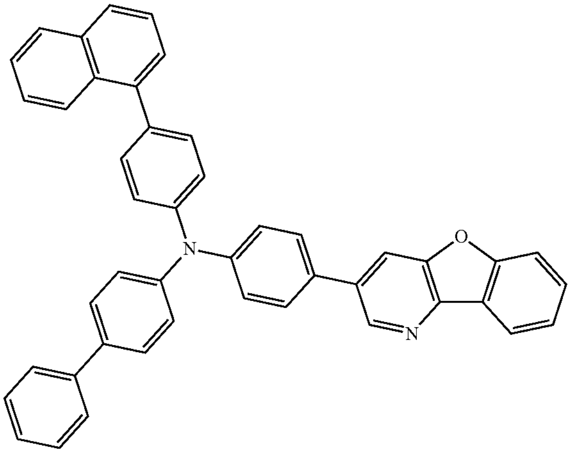
-continued
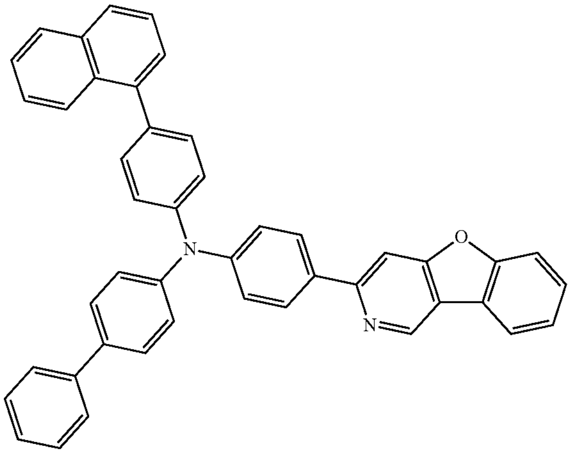
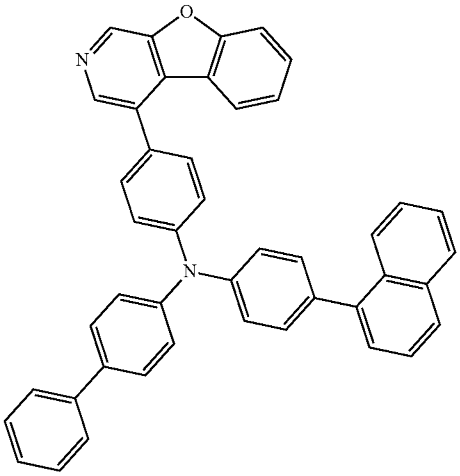
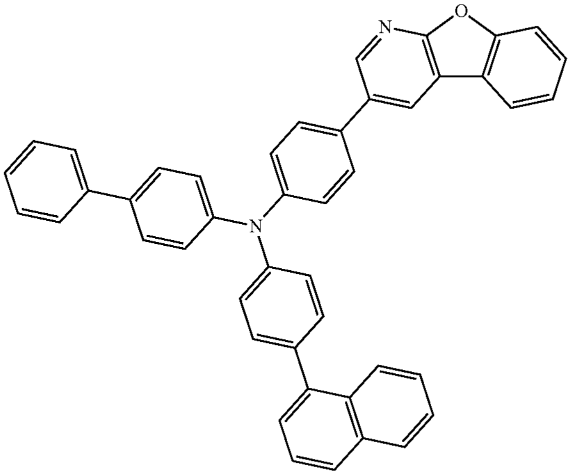 [SMILES: c1ccc(-c2ccc(N(c3ccc(-c4cnc5oc6ccccc6c5c4)cc3)c3ccc(-c4cccc5ccccc45)cc3)cc2)cc1]

-continued
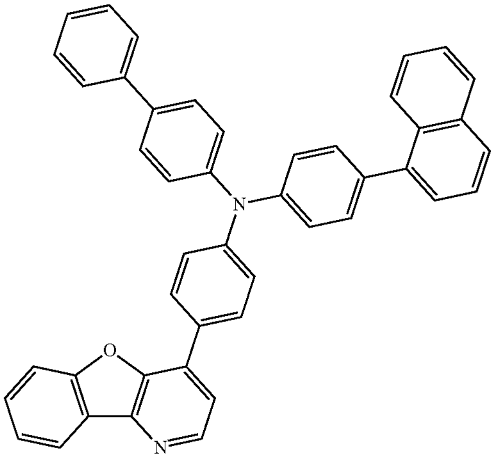
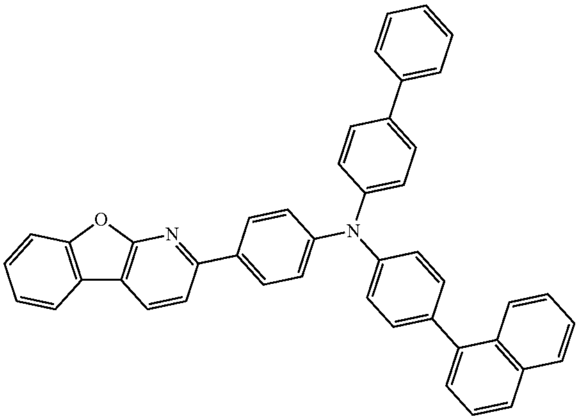 [SMILES: c1ccc(-c2ccc(N(c3ccc(-c4ccc5c(n4)oc4ccccc45)cc3)c3ccc(-c4cccc5ccccc45)cc3)cc2)cc1]
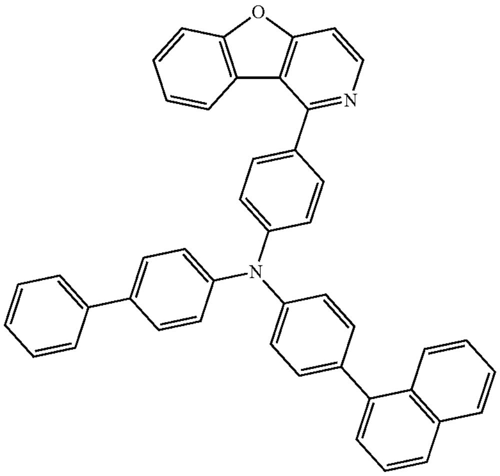
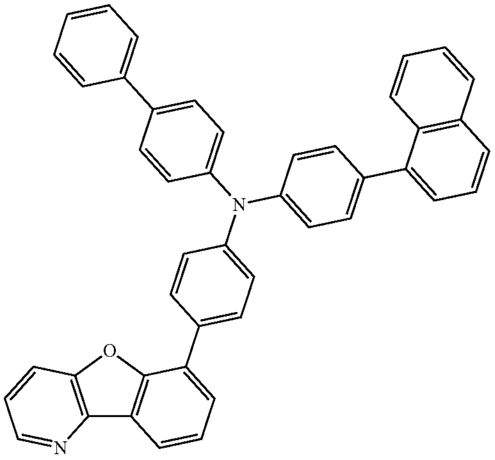
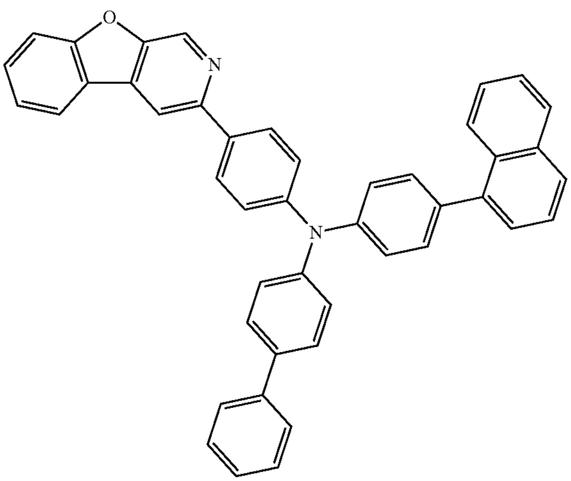
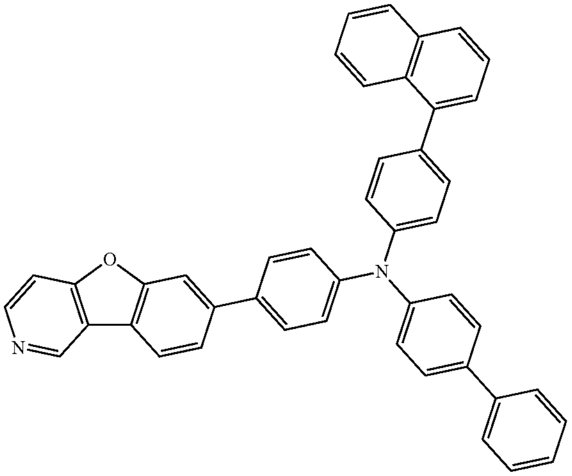
-continued -continued
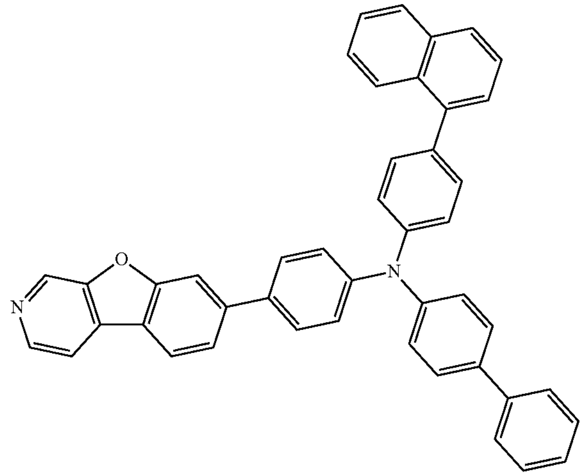
-continued
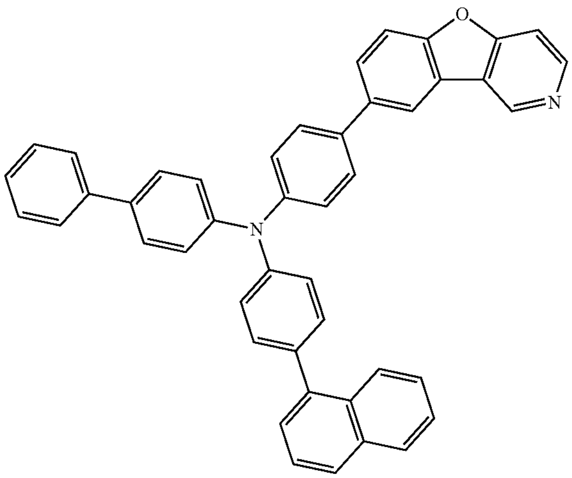
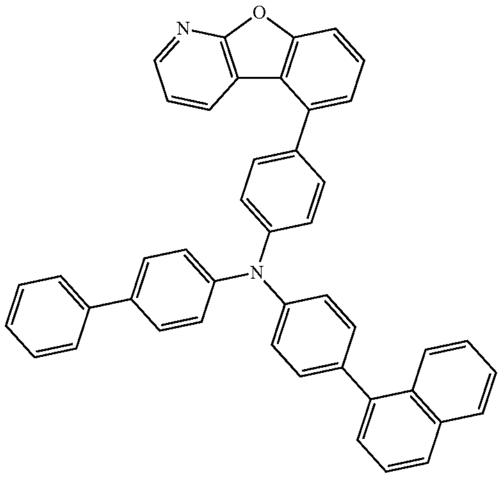 [SMILES: c1ccc(-c2ccc(N(c3ccc(-c4cccc5ccccc45)cc3)c3ccc(-c4cccc5oc6ncccc6c45)cc3)cc2)cc1]
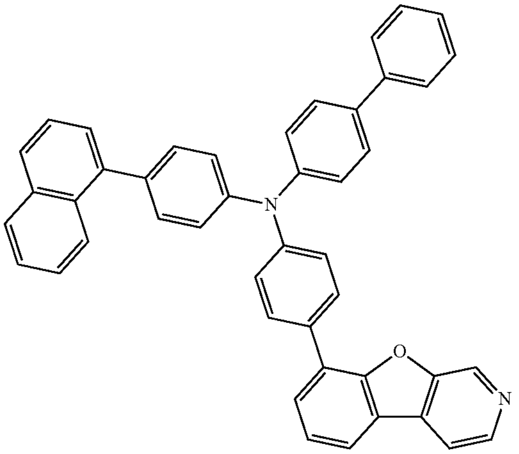
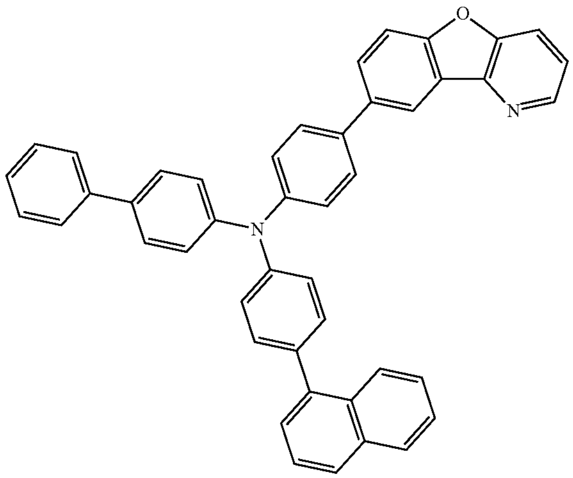
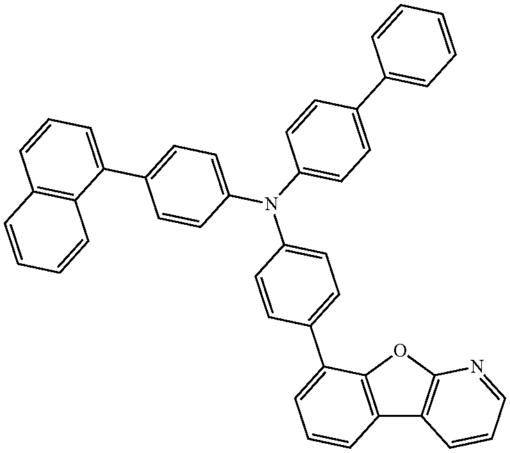

-continued
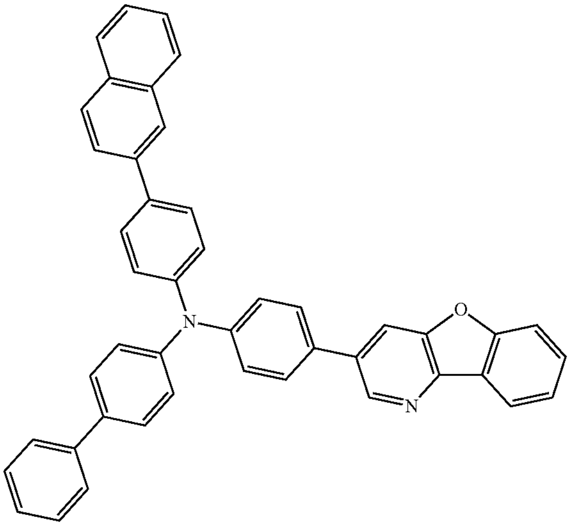
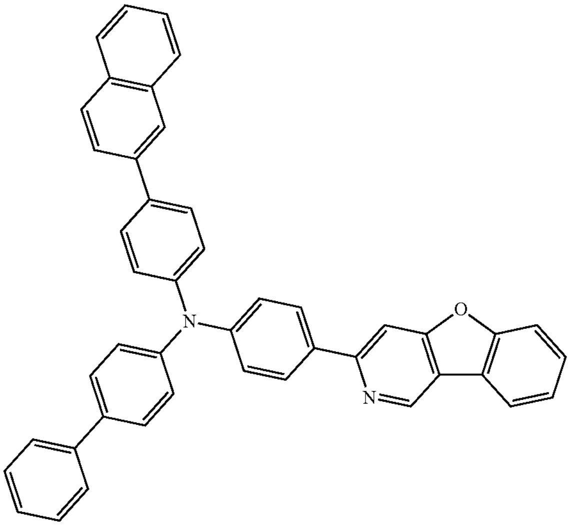
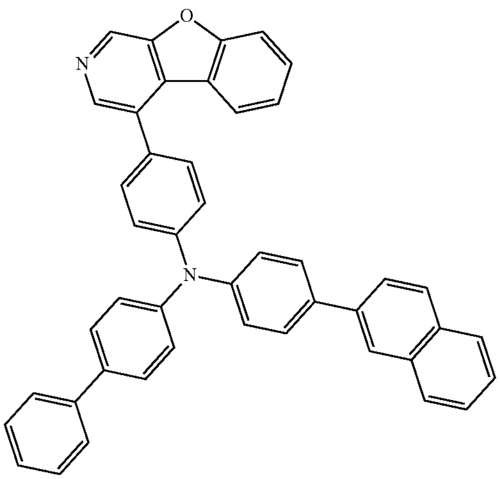
-continued
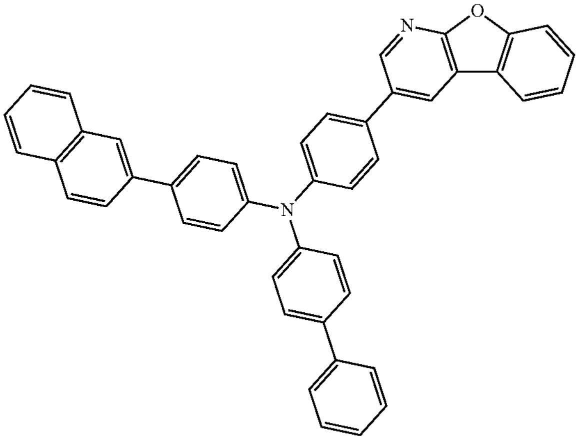 [SMILES: c1ccc(-c2ccc(N(c3ccc(-c4ccc5ccccc5c4)cc3)c3ccc(-c4cnc5oc6ccccc6c5c4)cc3)cc2)cc1]
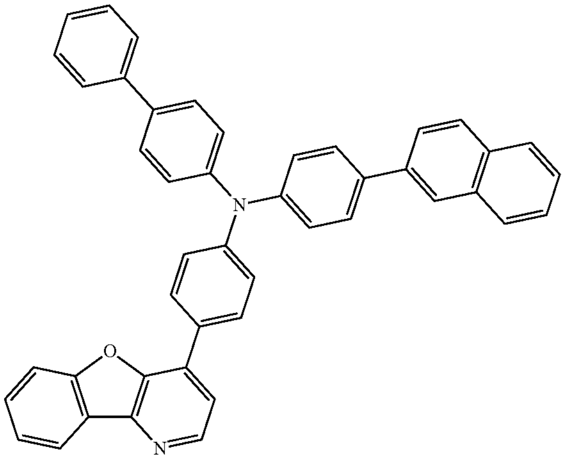
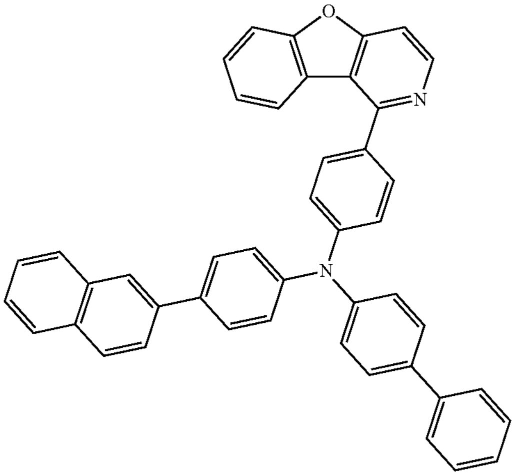

-continued
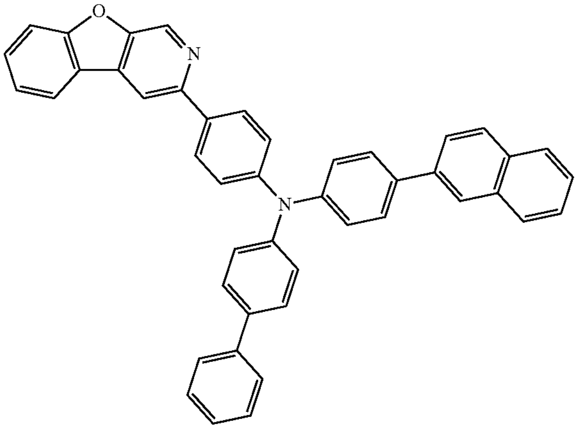
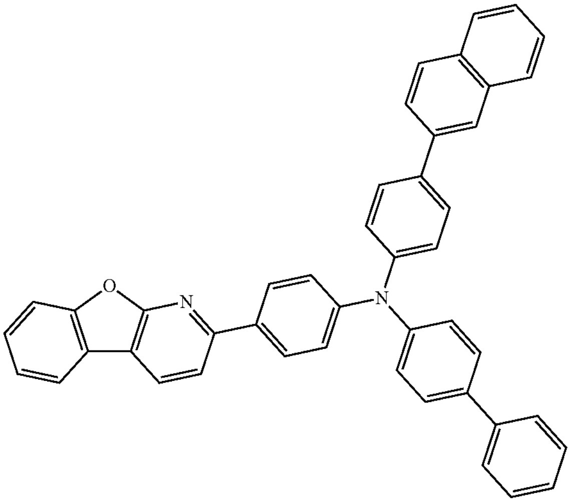 [SMILES: c1ccc(-c2ccc(N(c3ccc(-c4ccc5ccccc5c4)cc3)c3ccc(-c4ccc5c(n4)oc4ccccc45)cc3)cc2)cc1]
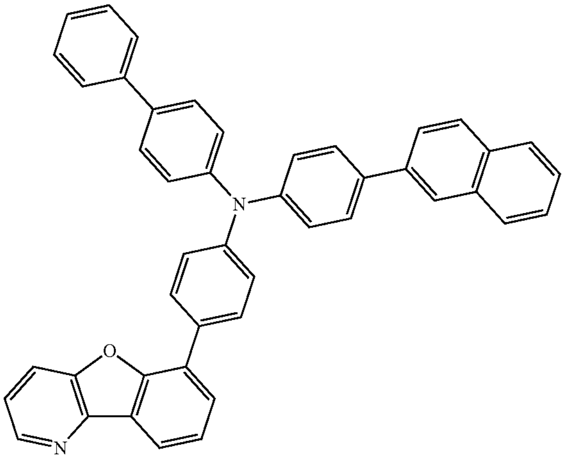
-continued
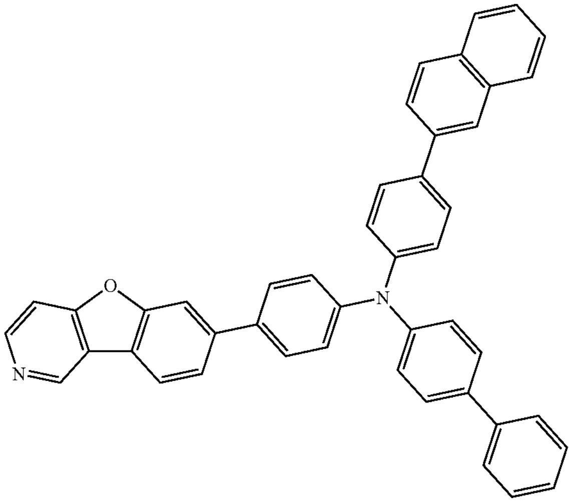
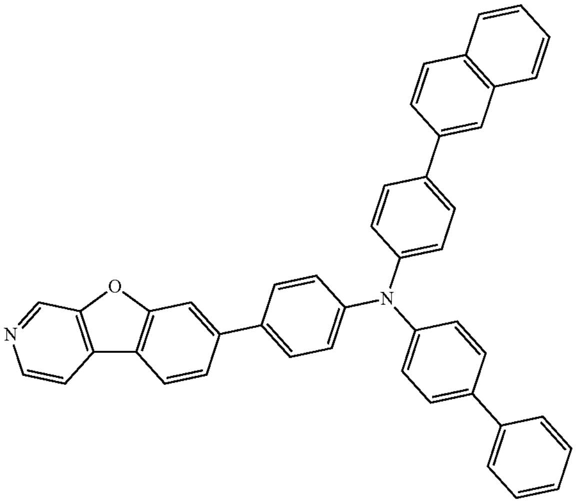
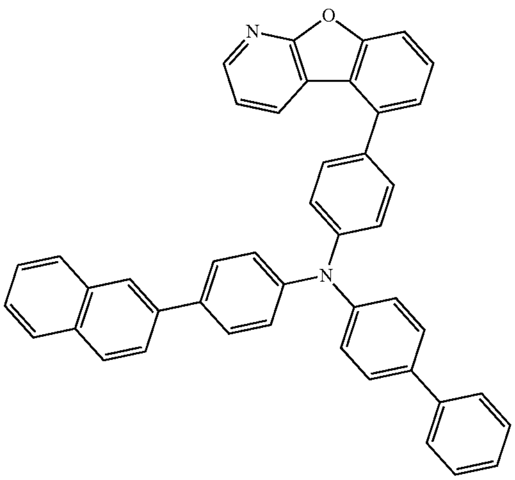 [SMILES: c1ccc(-c2ccc(N(c3ccc(-c4ccc5ccccc5c4)cc3)c3ccc(-c4cccc5oc6ncccc6c45)cc3)cc2)cc1]

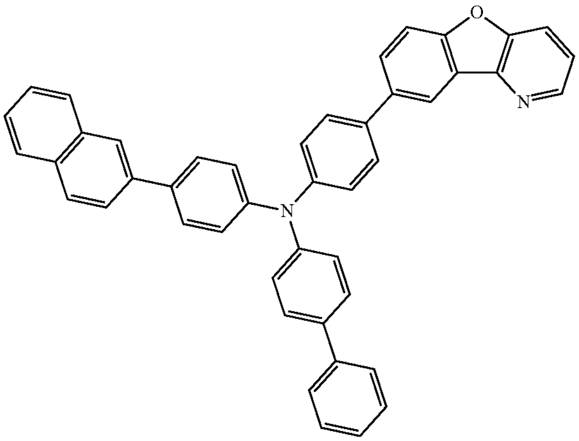
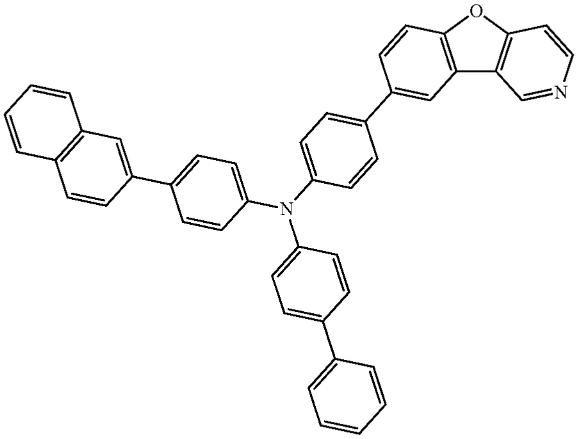
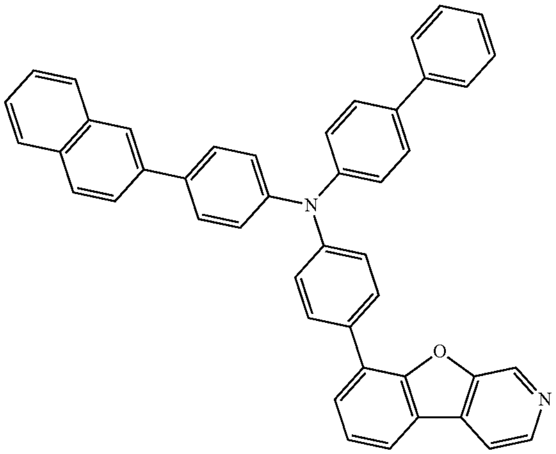
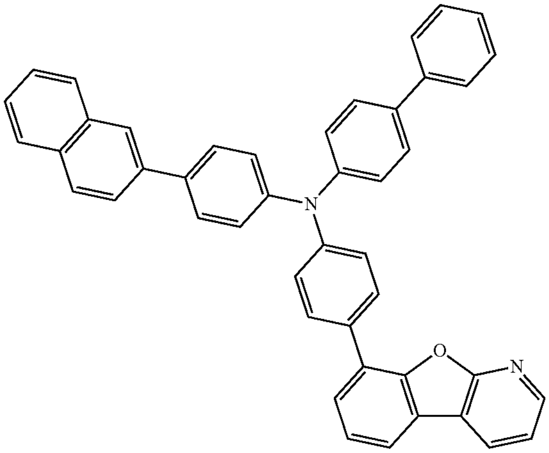
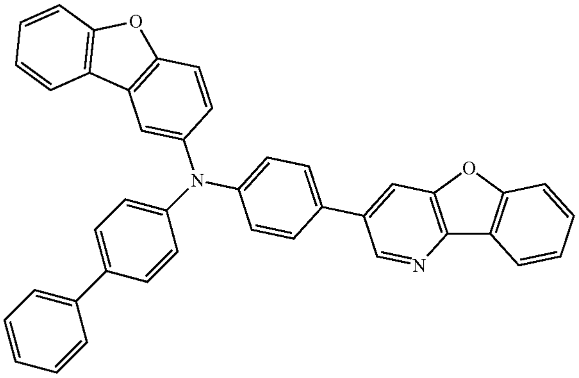
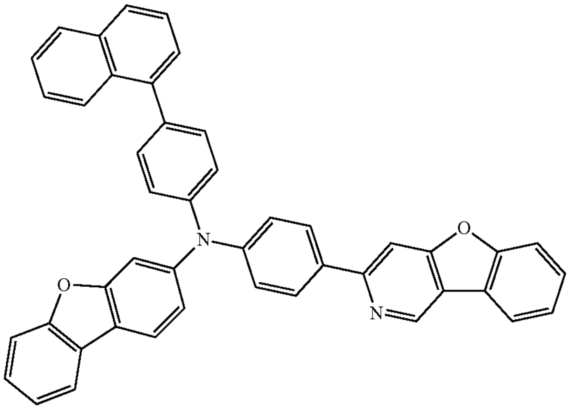

-continued
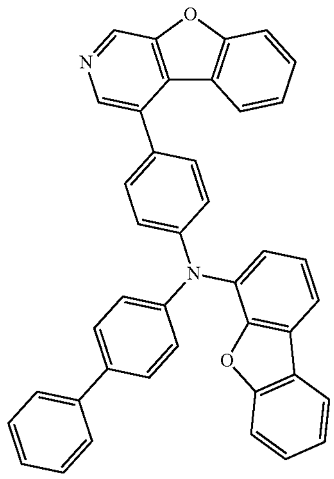
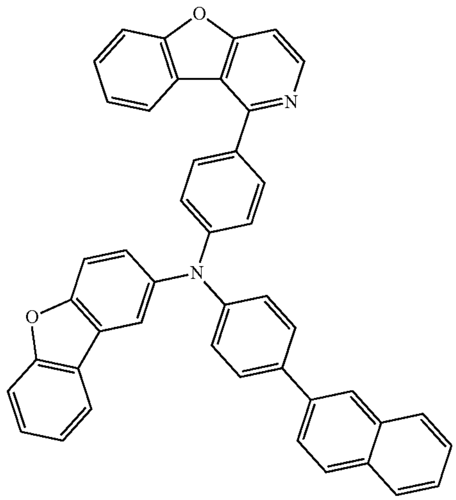
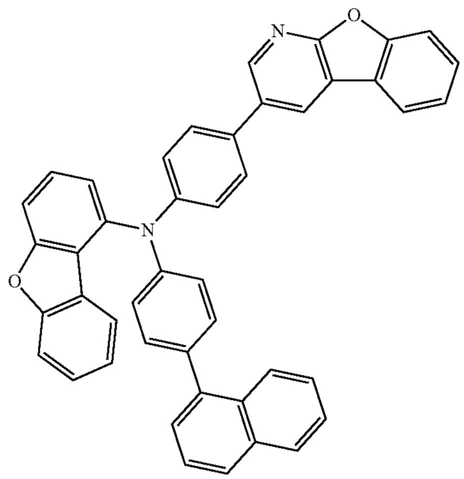
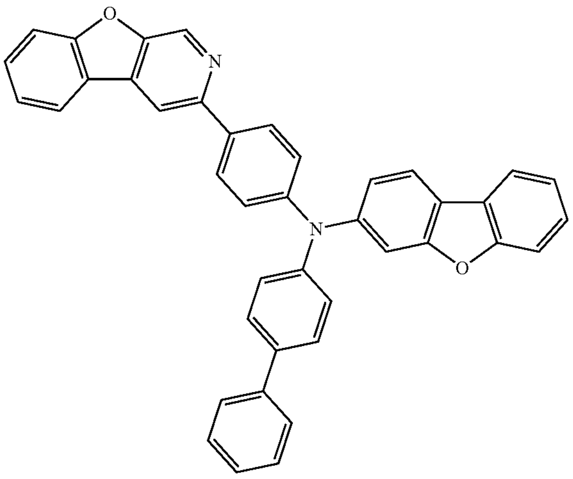
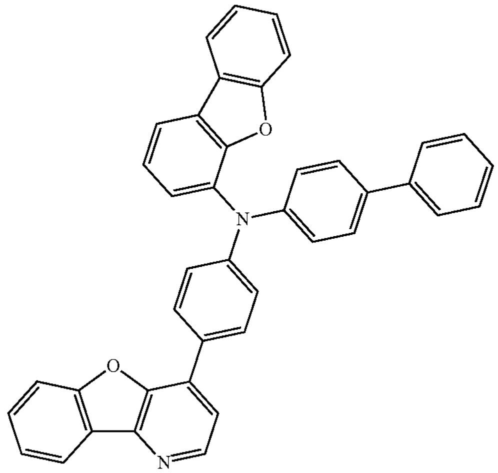
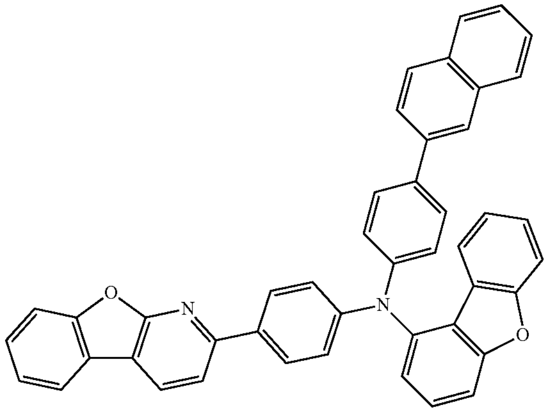

-continued
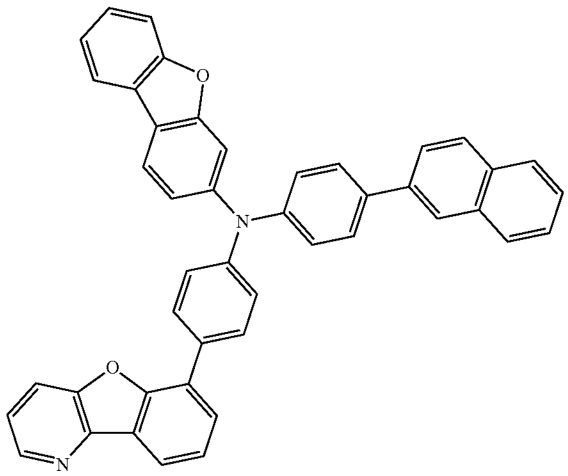
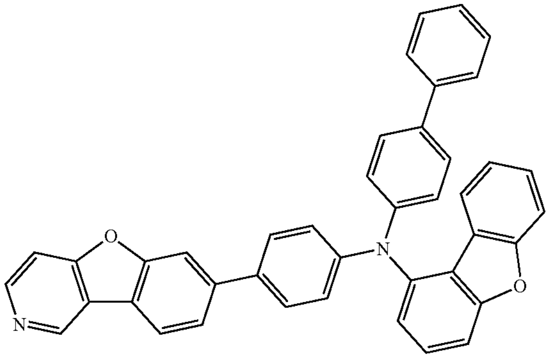
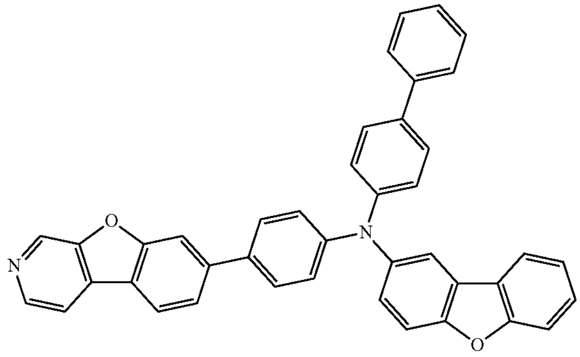
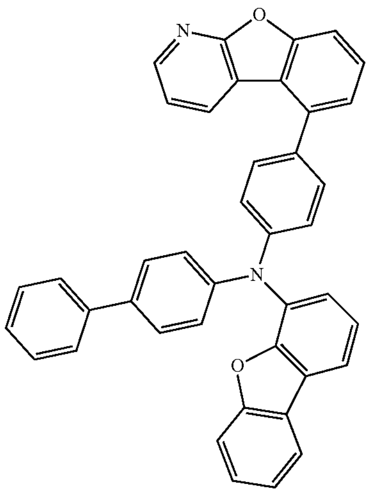
-continued
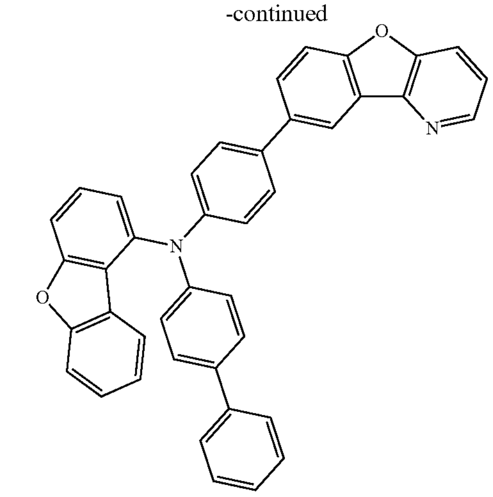
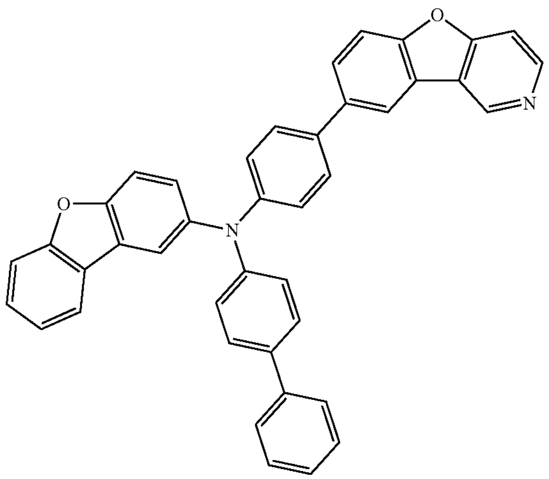
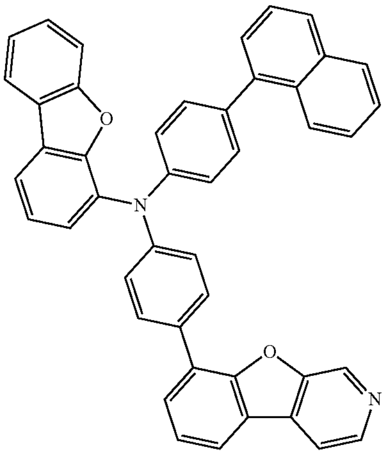

-continued
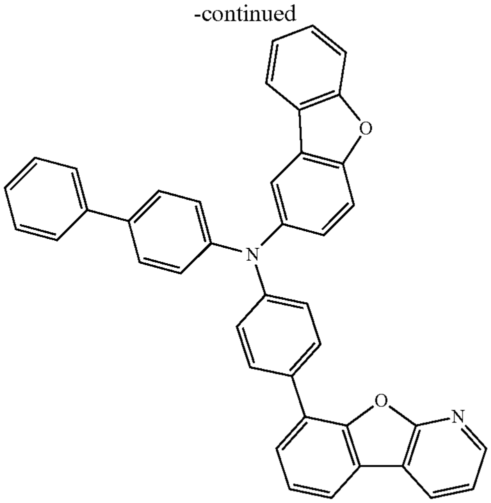
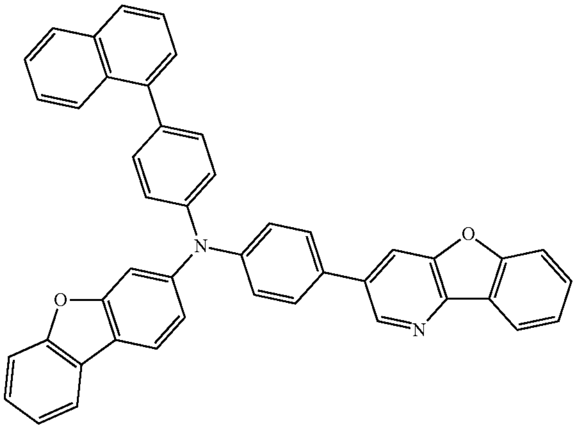
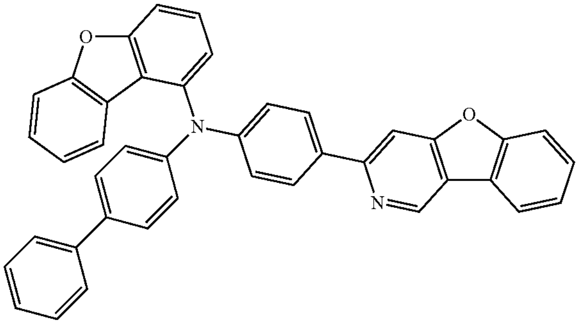
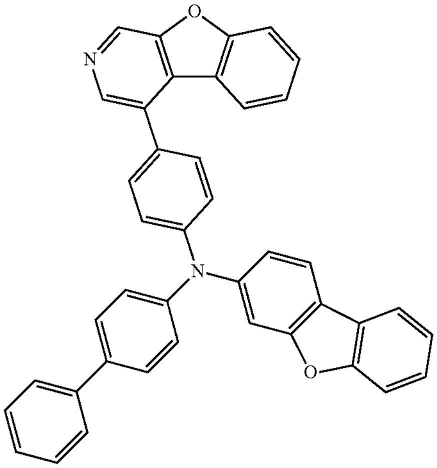
-continued
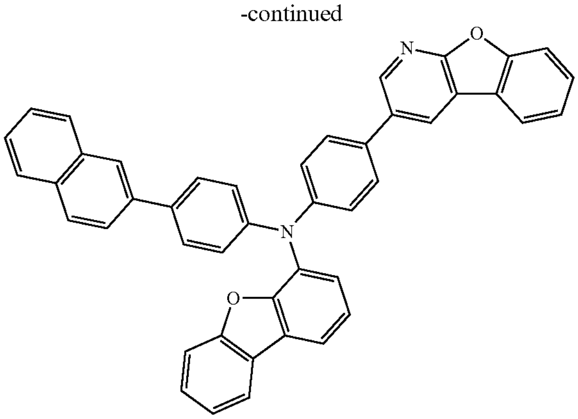
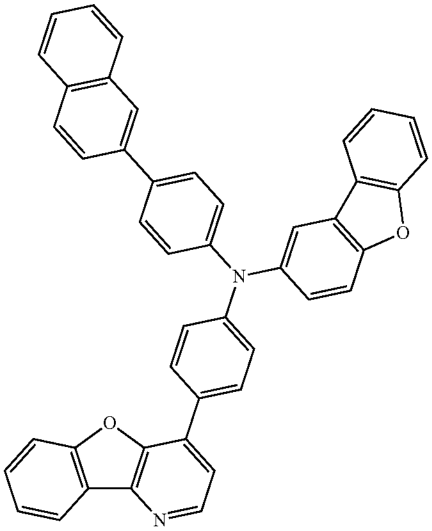
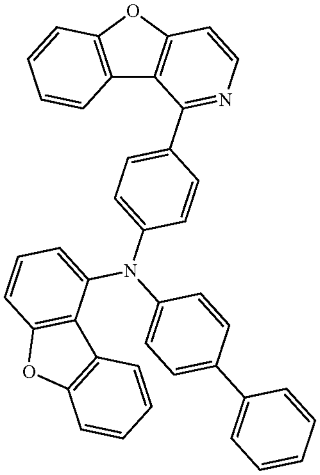

-continued
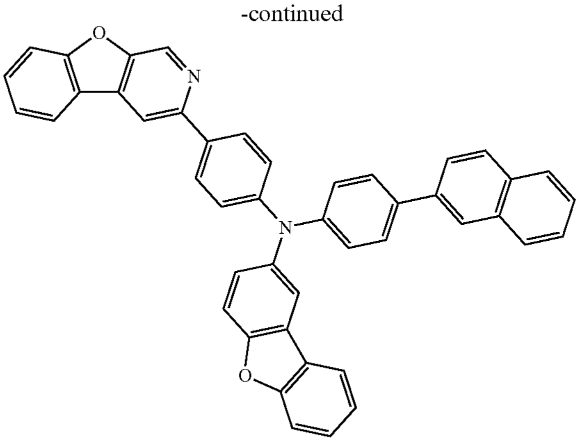
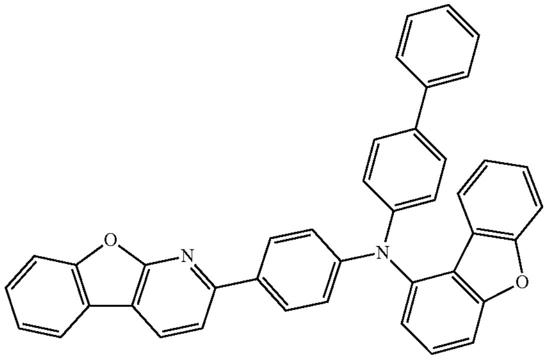
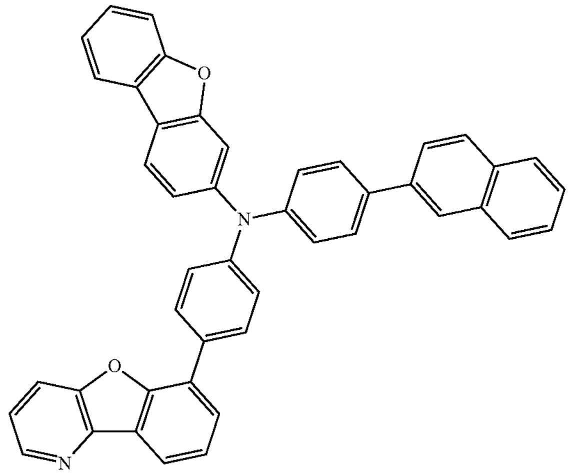
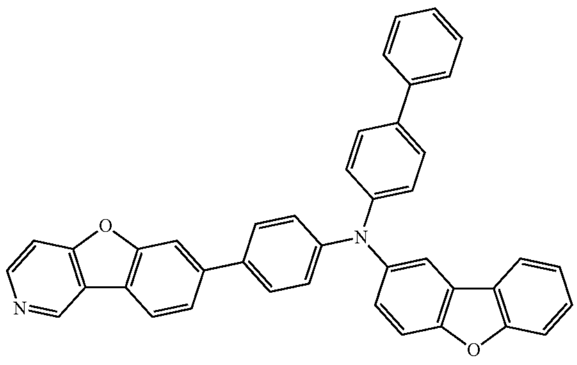
-continued
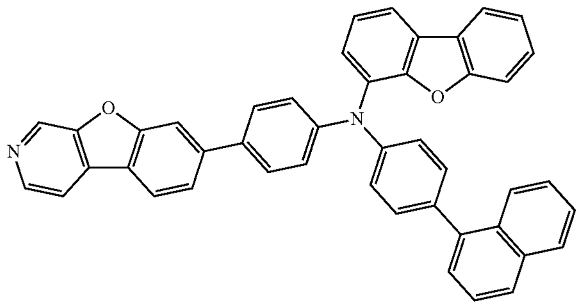
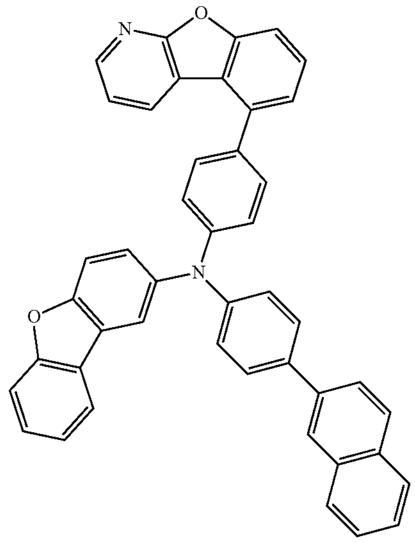
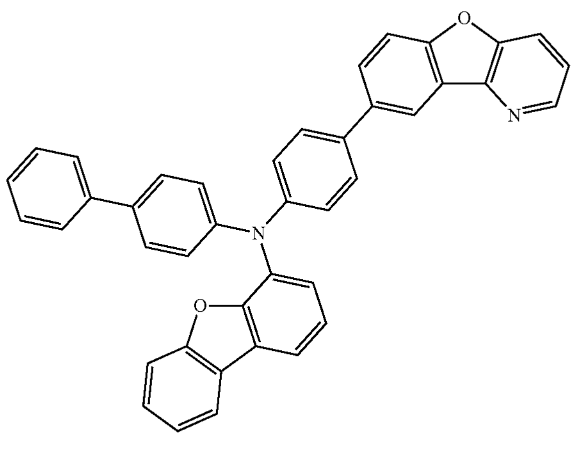

-continued
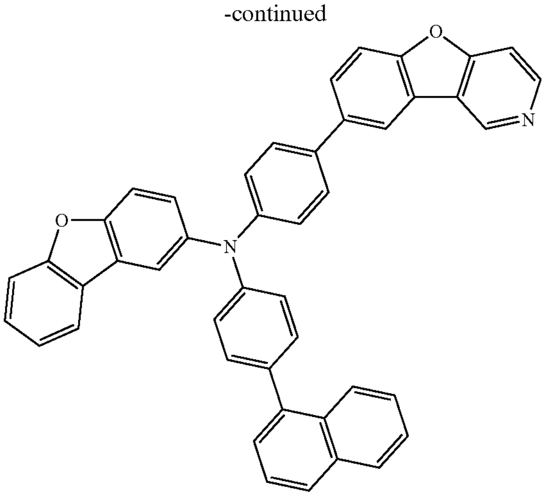
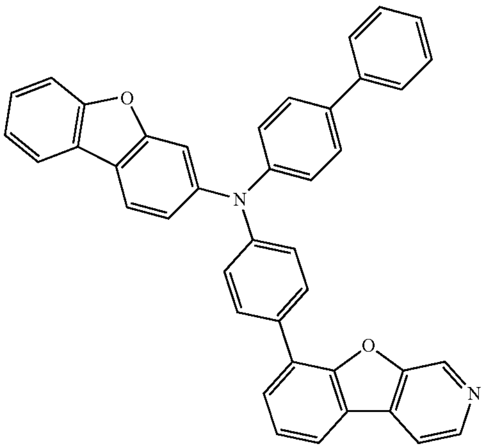
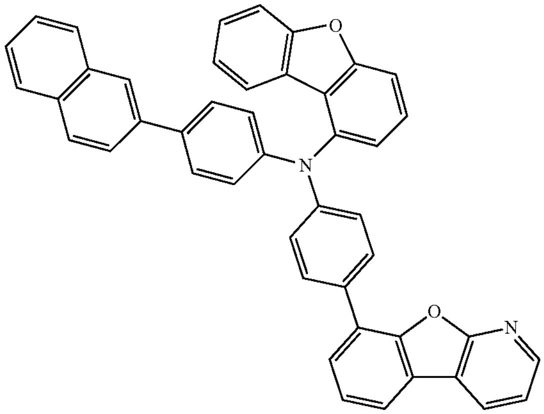
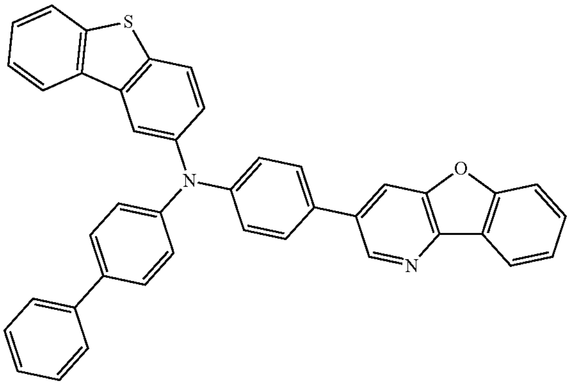
-continued
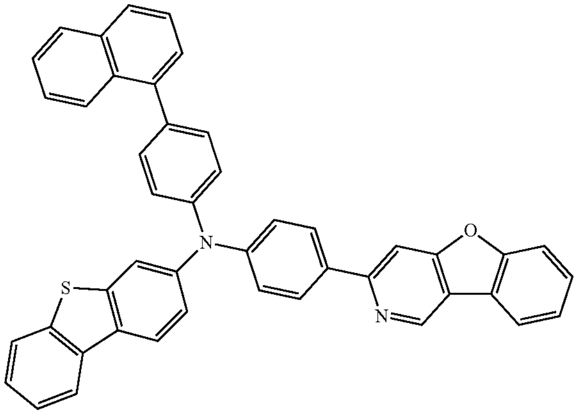
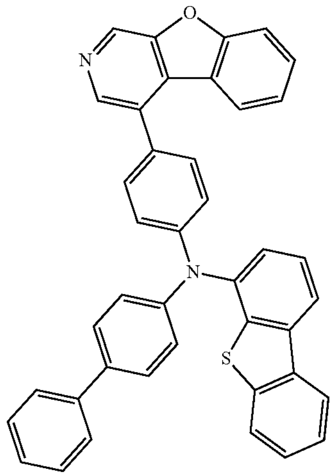
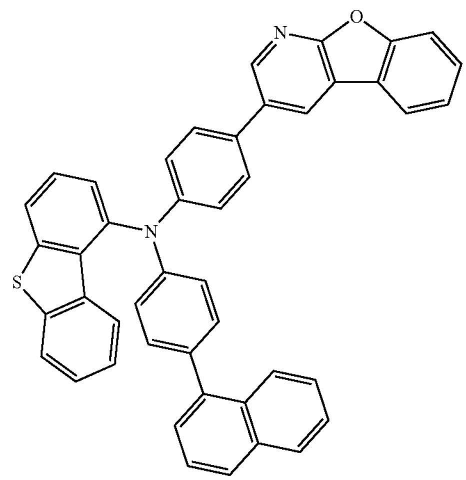

-continued
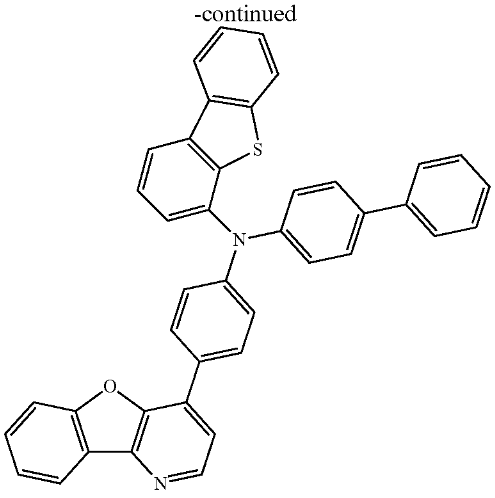
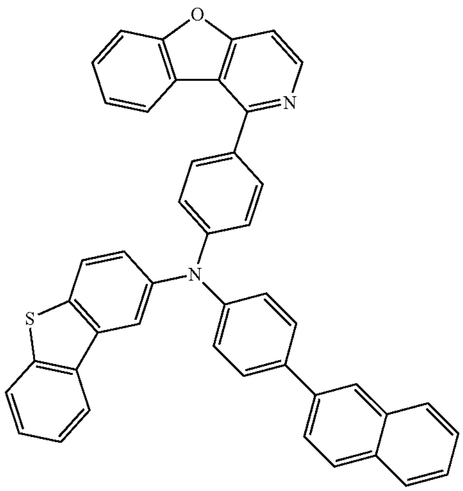
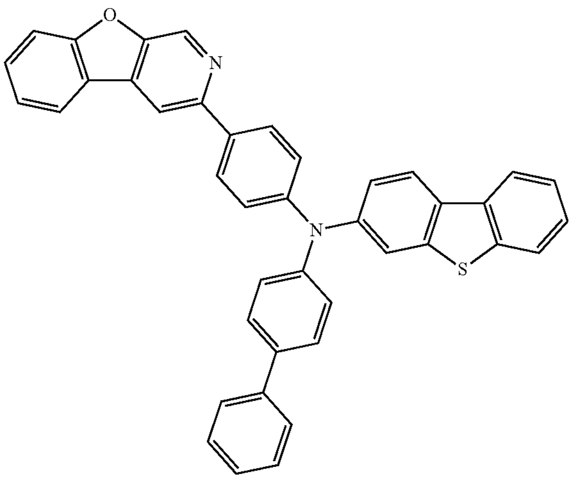
-continued
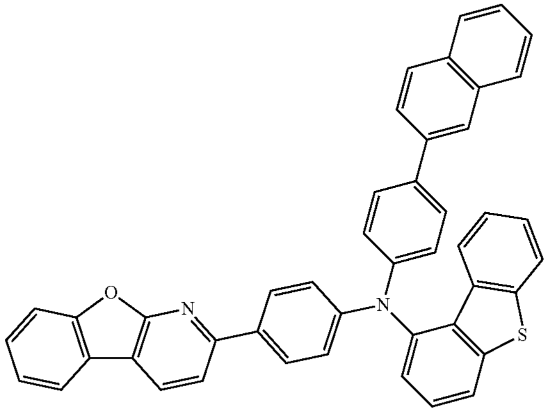
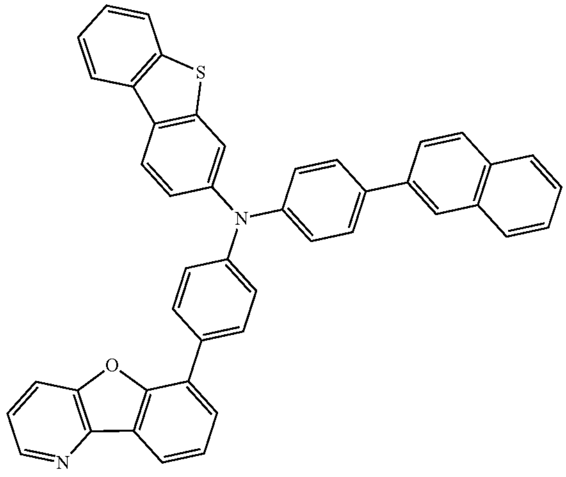
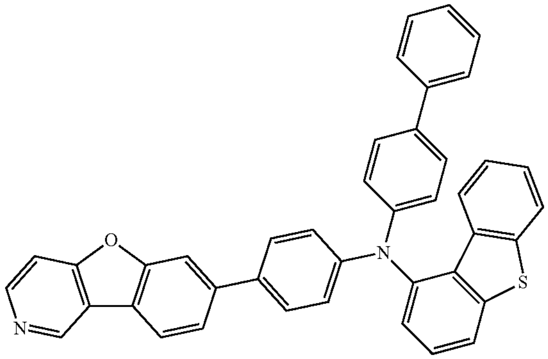
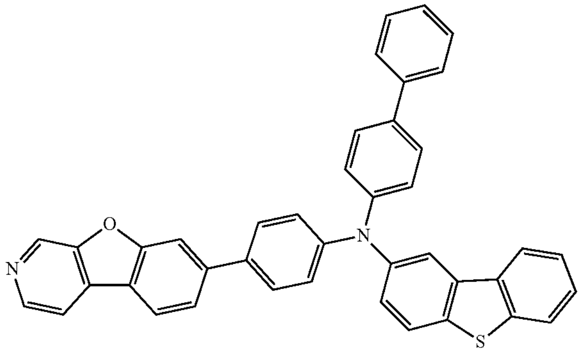

-continued
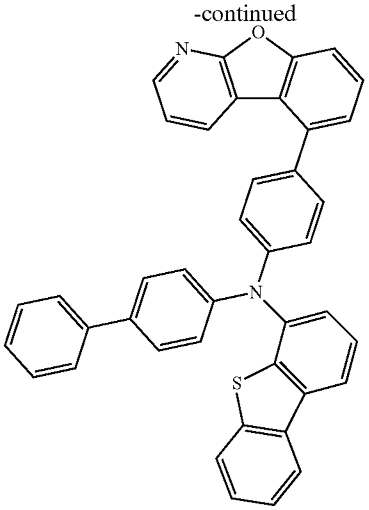
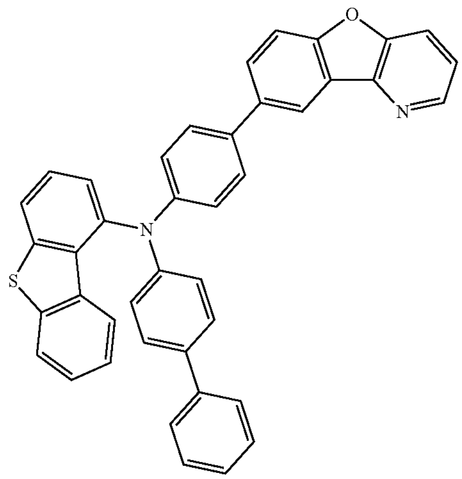
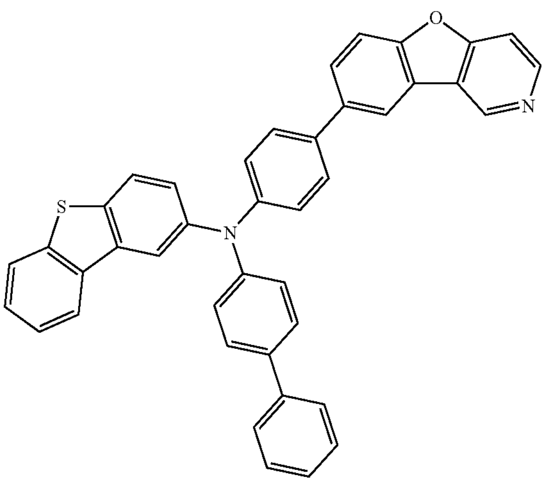
-continued
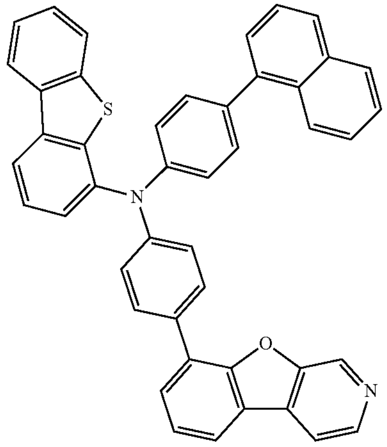
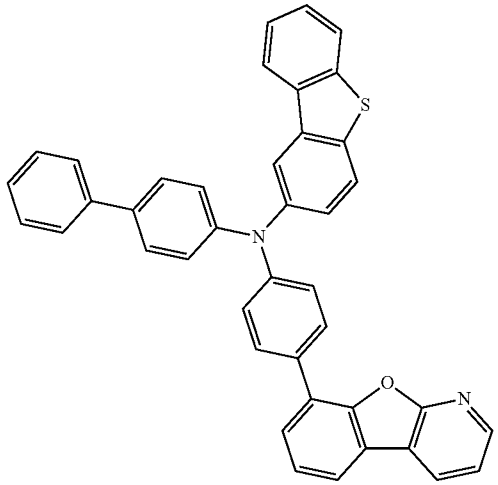
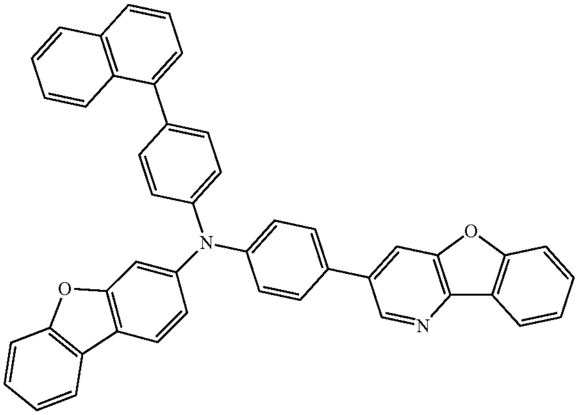
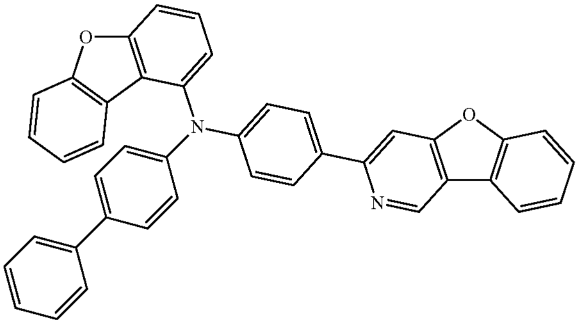

-continued
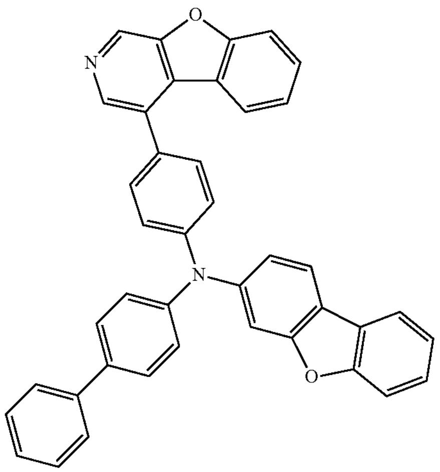
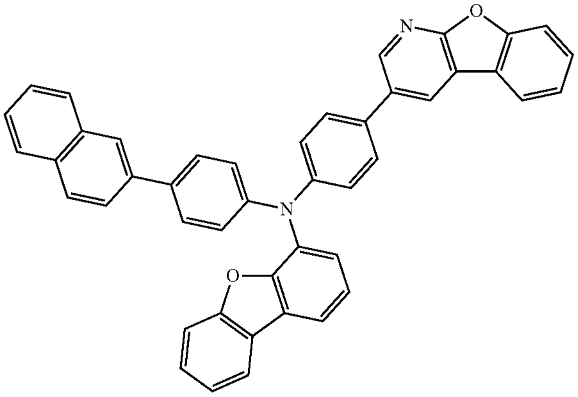
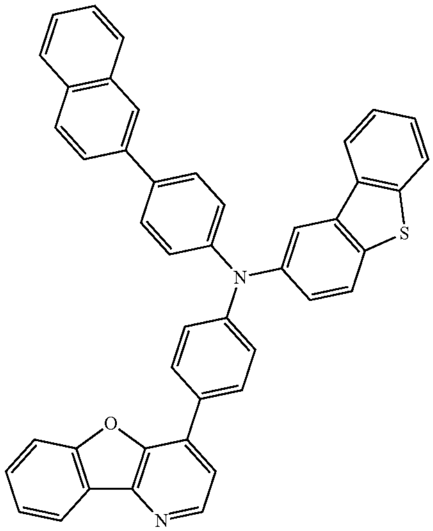
-continued
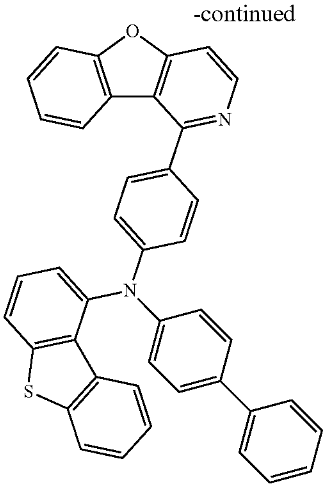
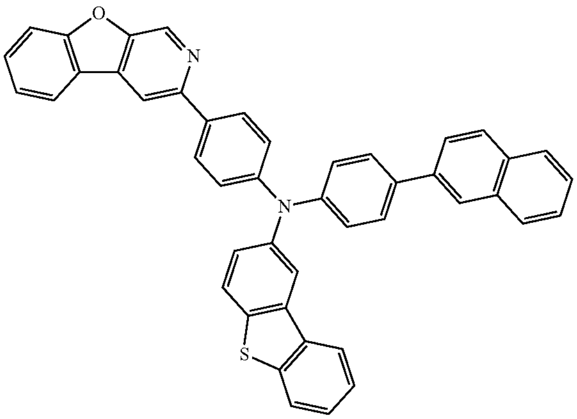
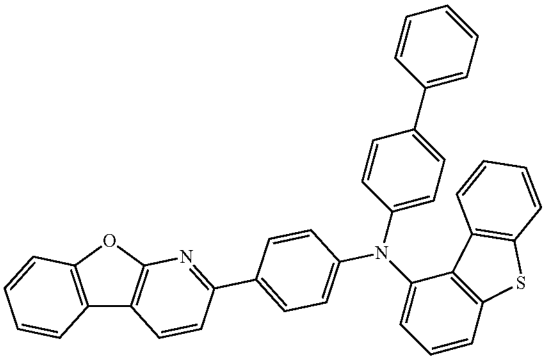
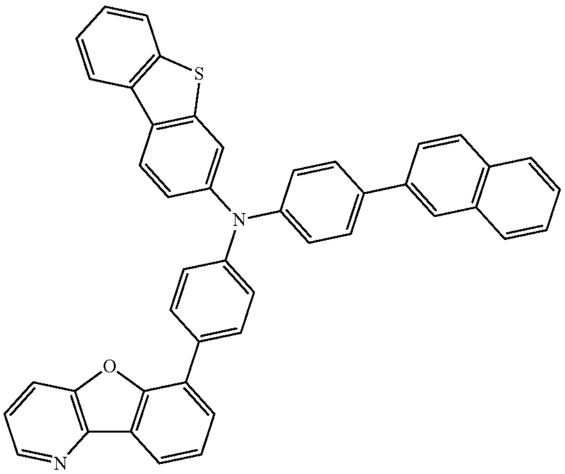

-continued
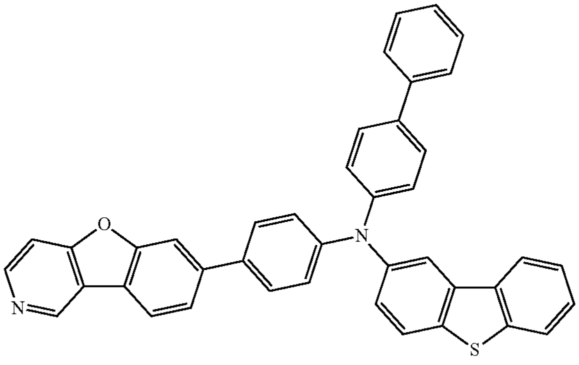
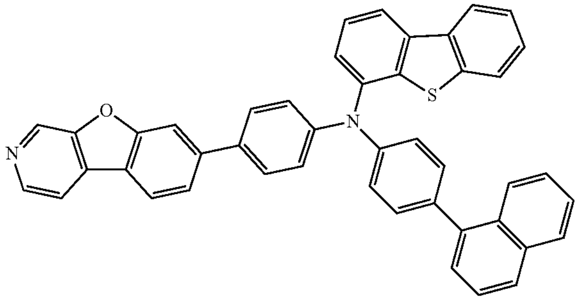
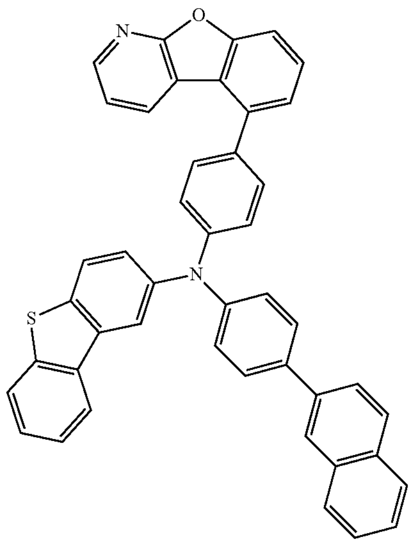
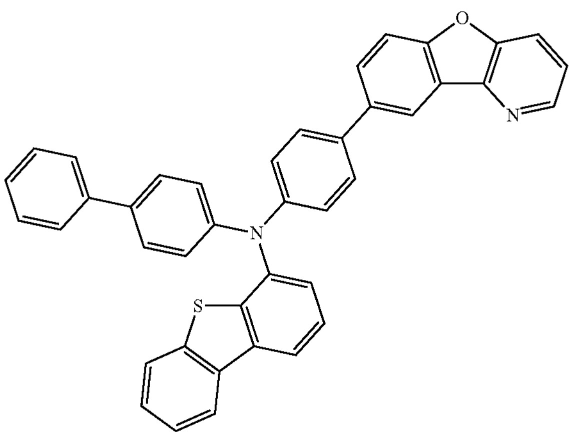
-continued
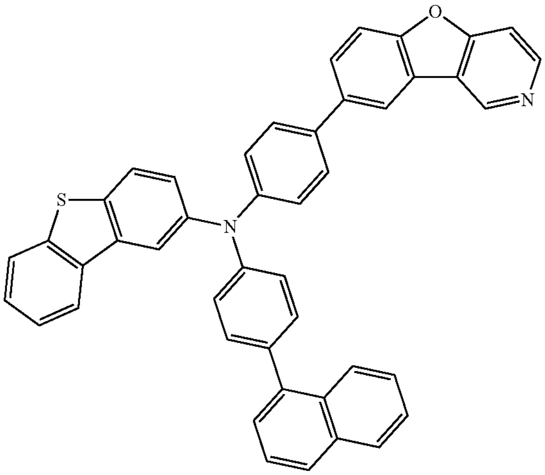
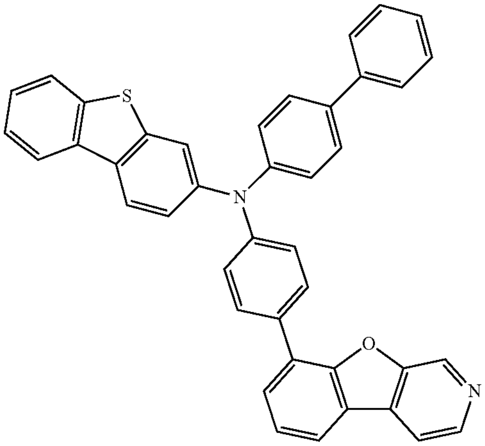
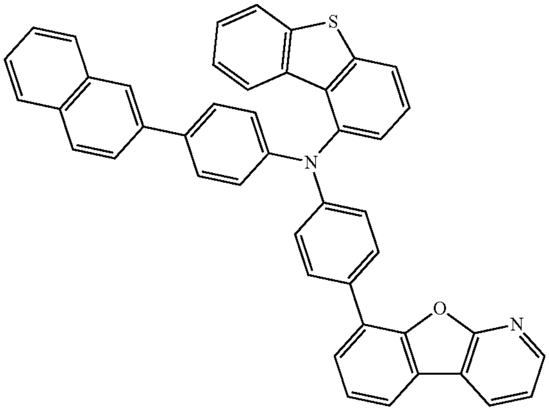
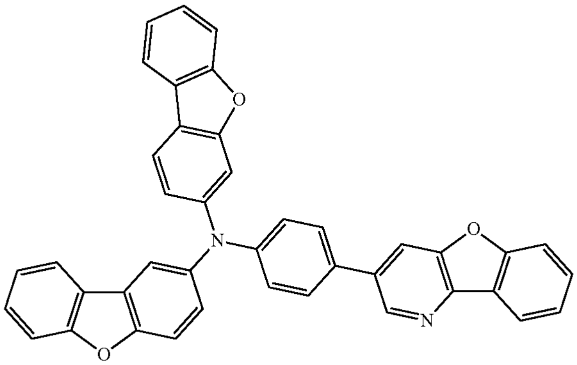

-continued
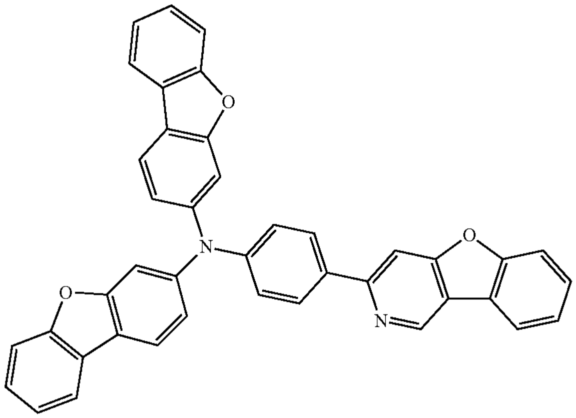
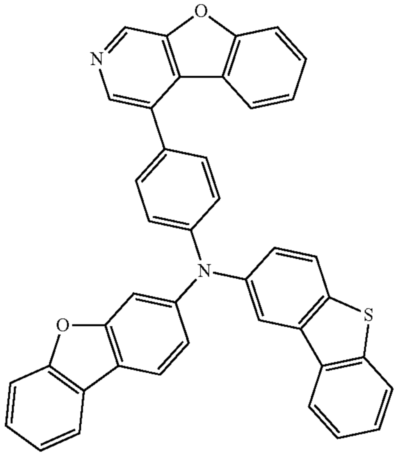
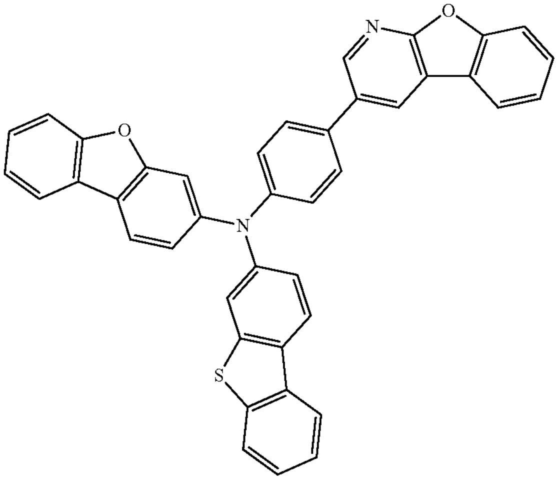
-continued
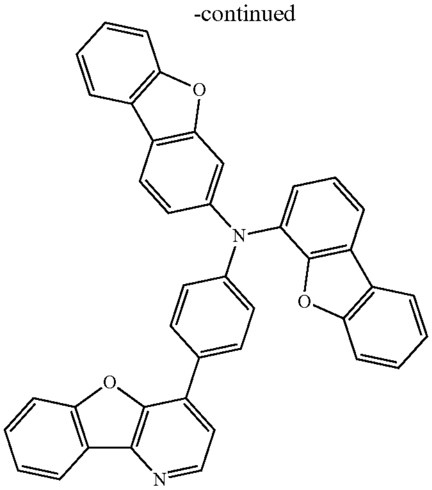
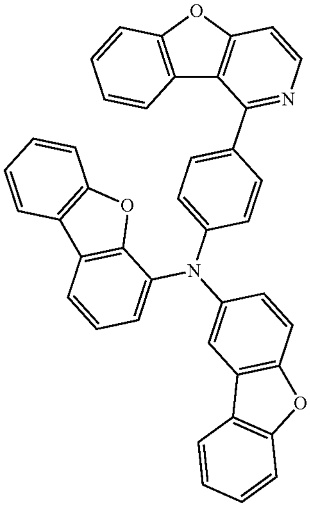
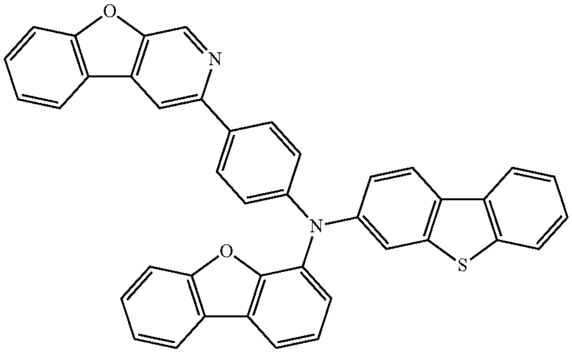
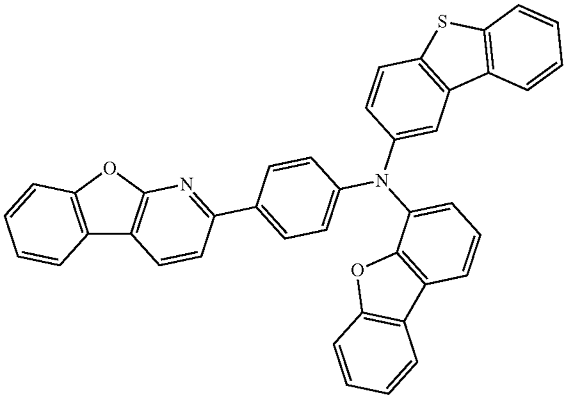

-continued
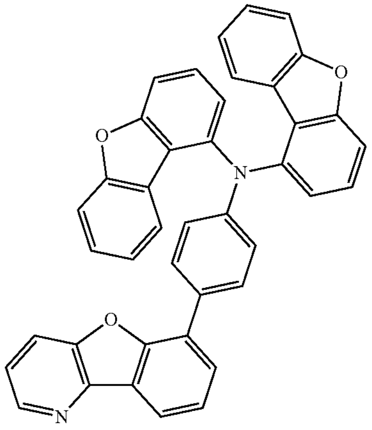
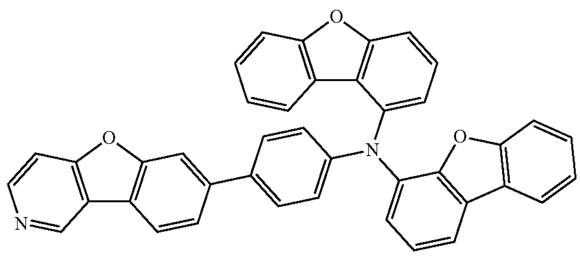
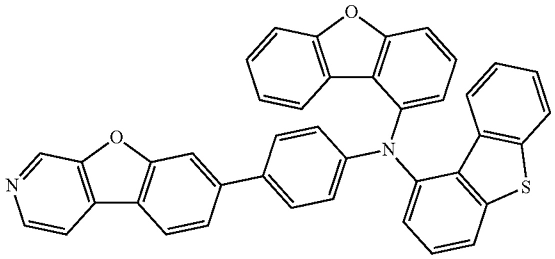
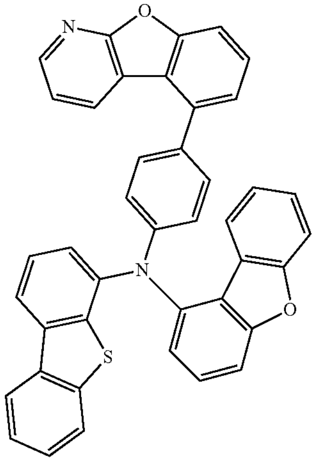
-continued
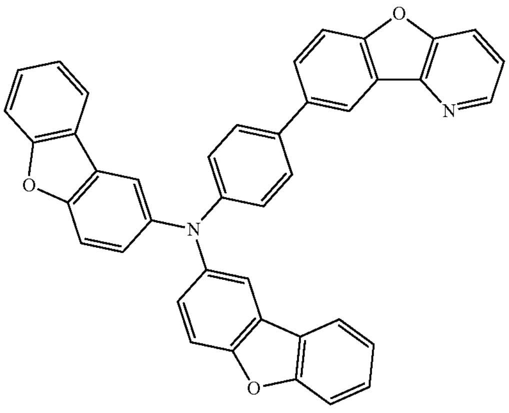
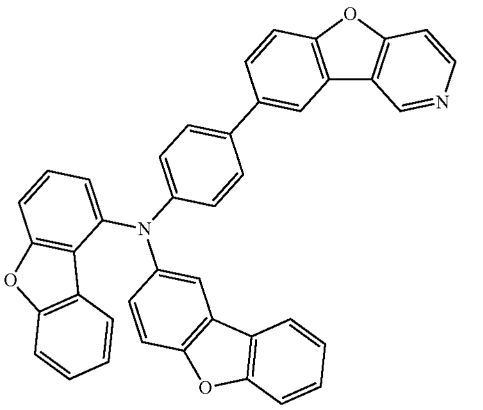
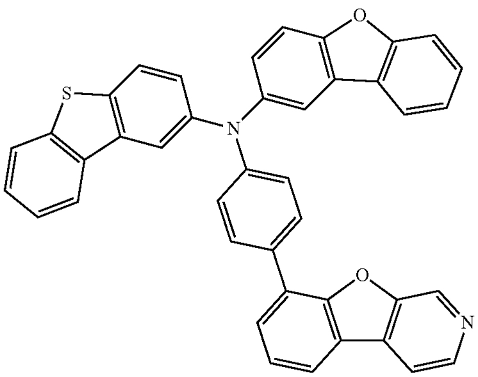
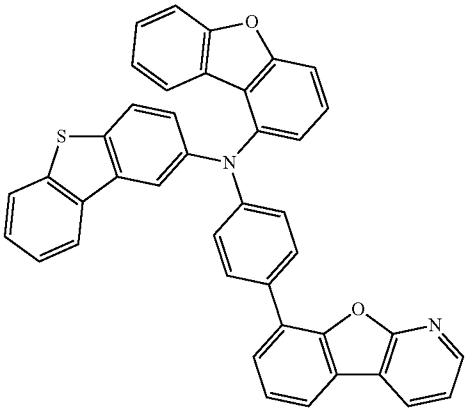

-continued
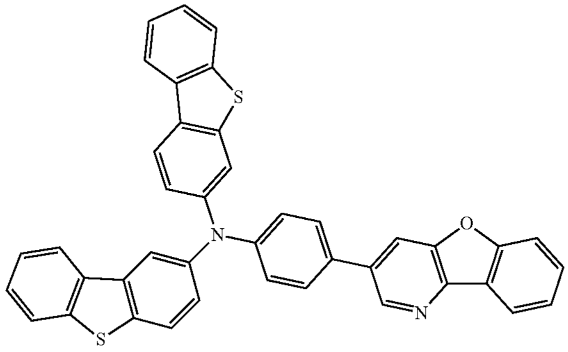
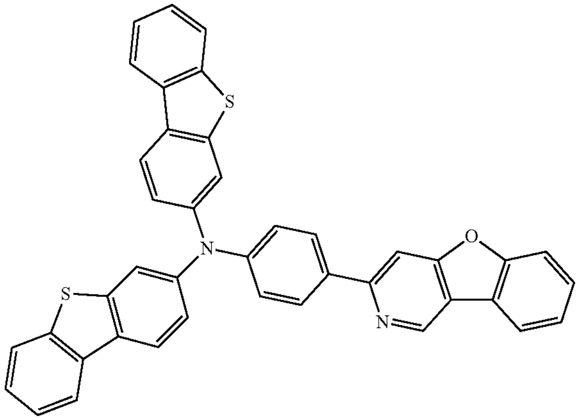
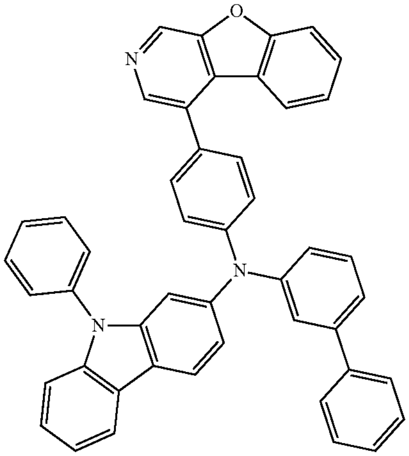
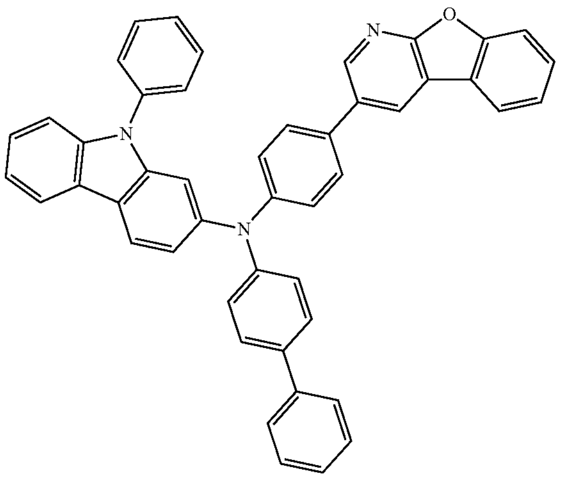
-continued
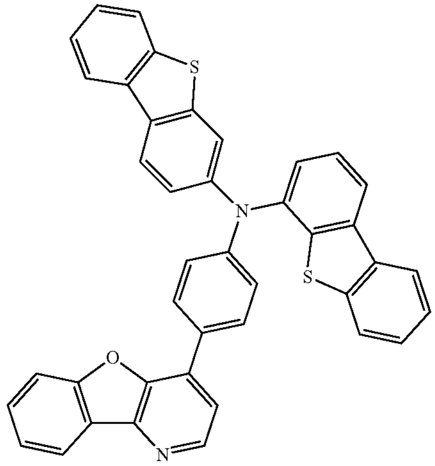
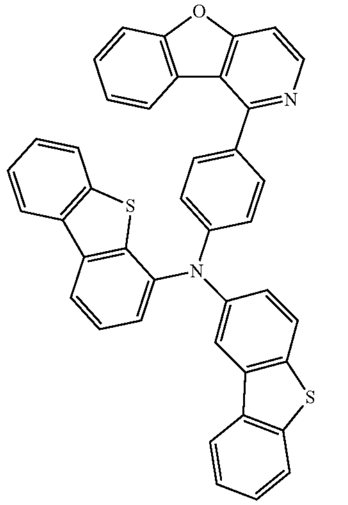
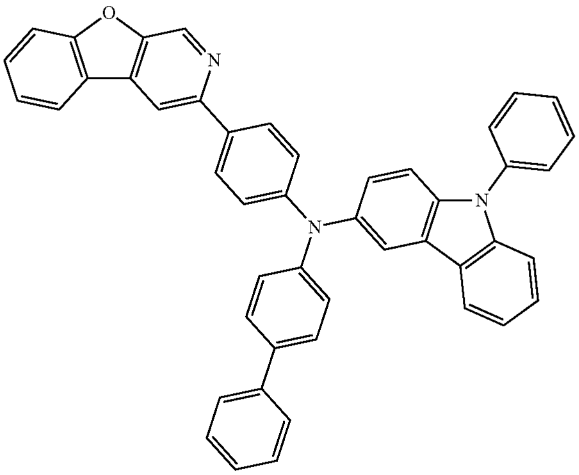

-continued
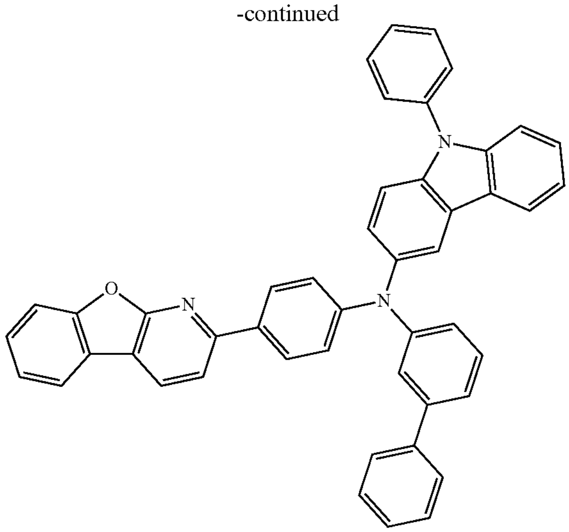
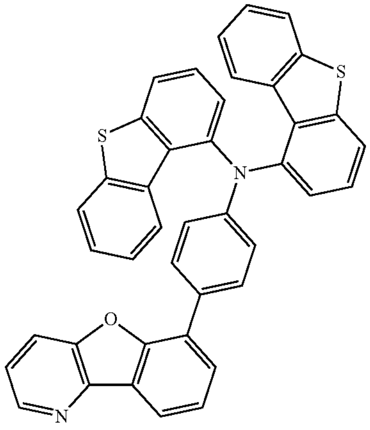
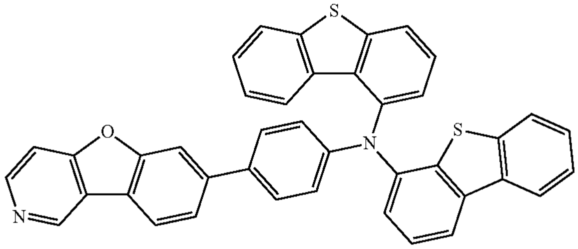
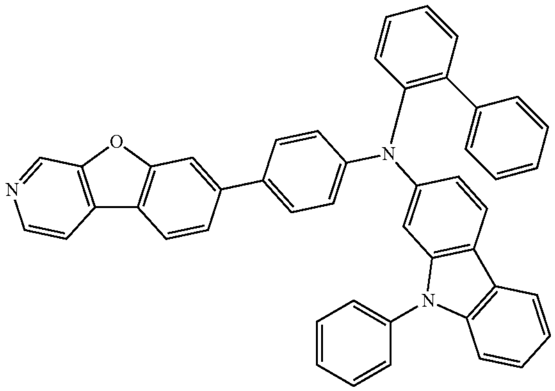
-continued
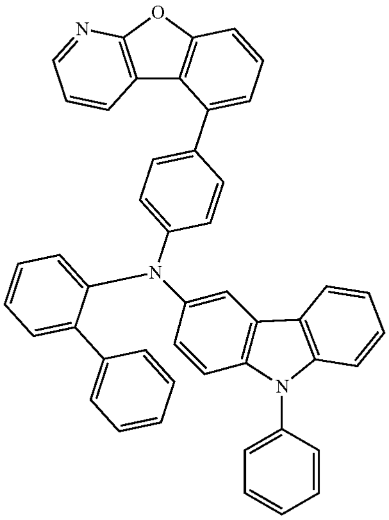
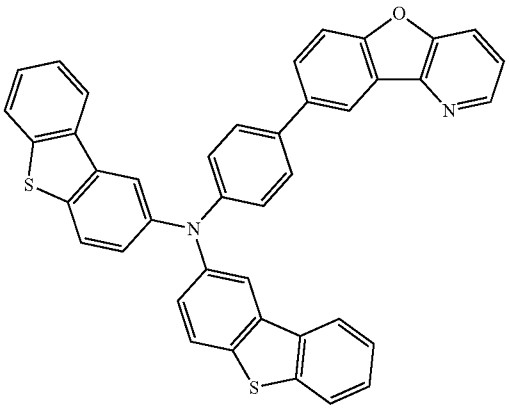
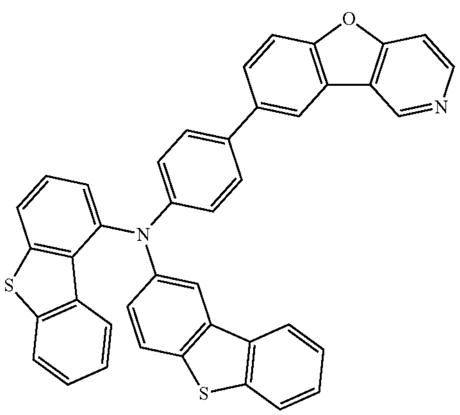

-continued
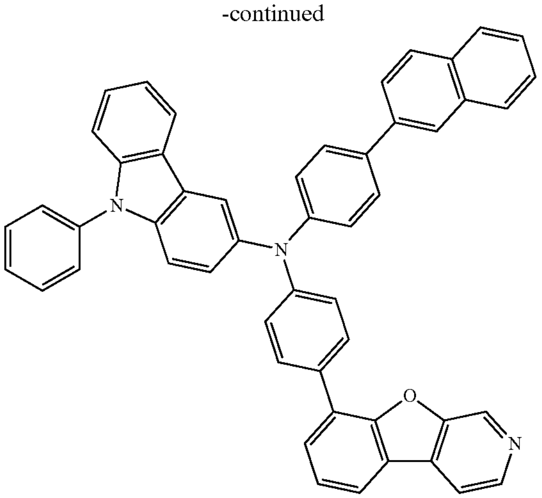
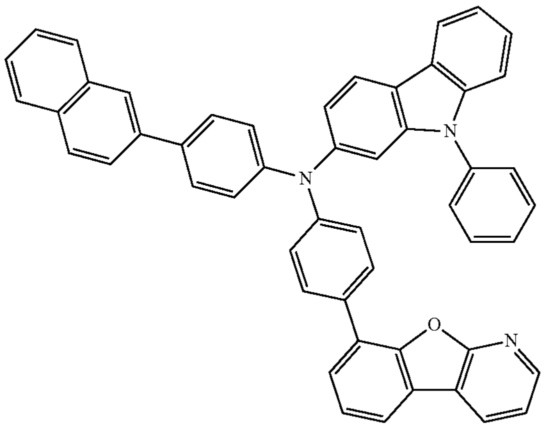
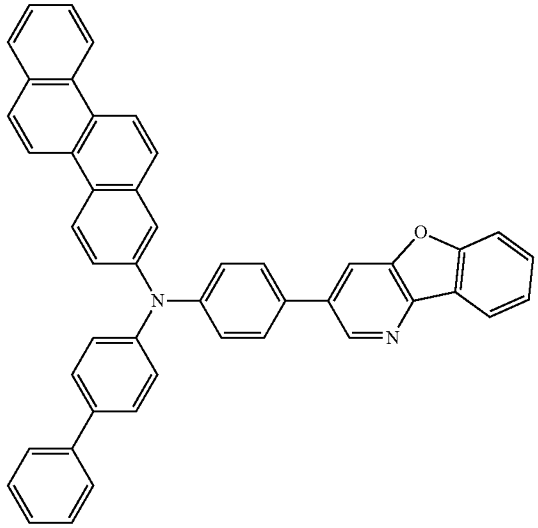
-continued
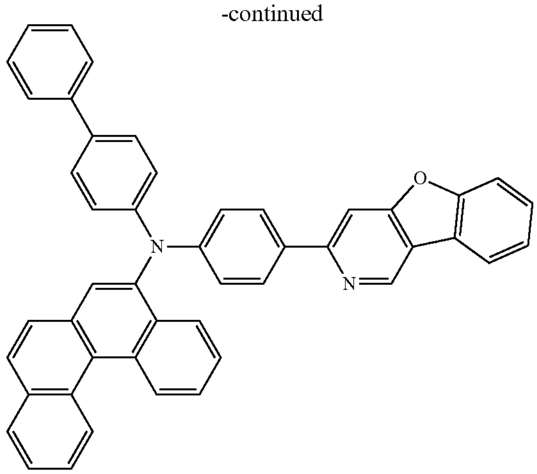
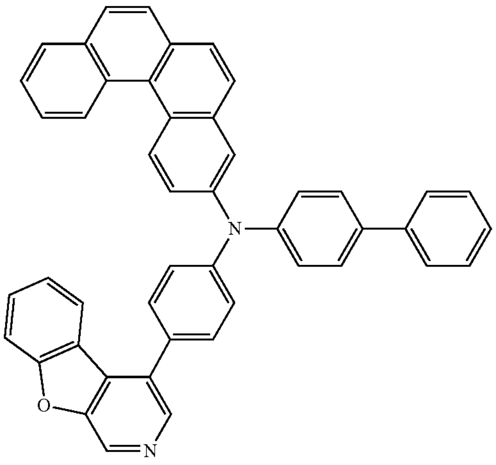
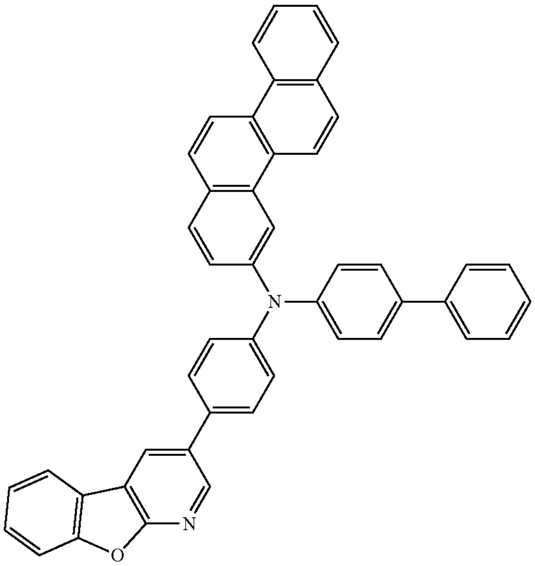

-continued
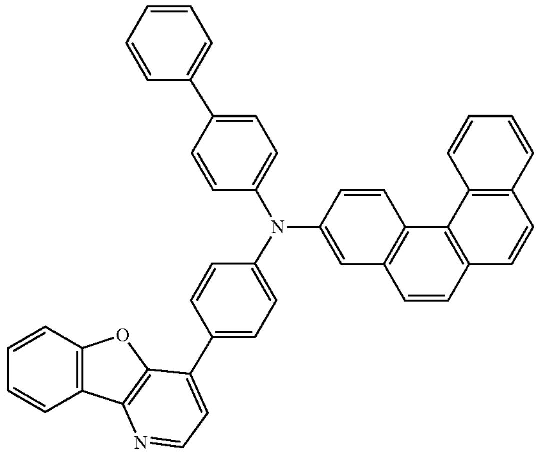
-continued
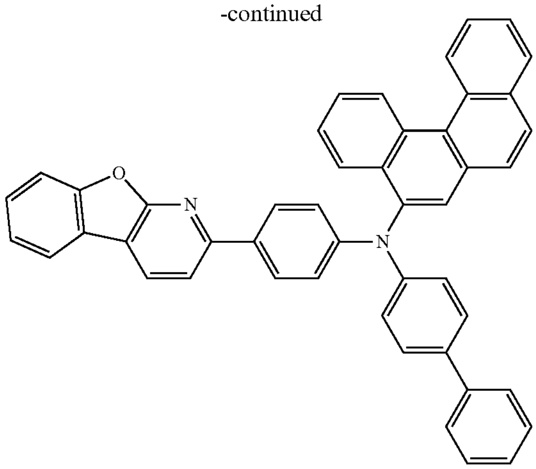
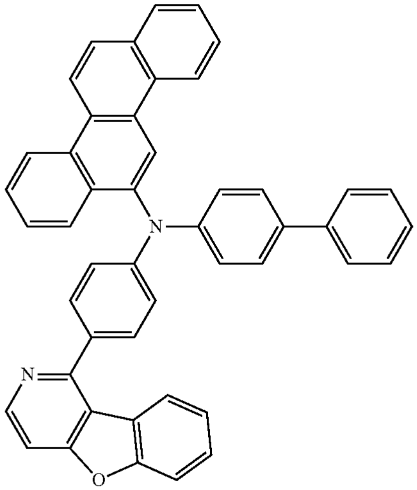
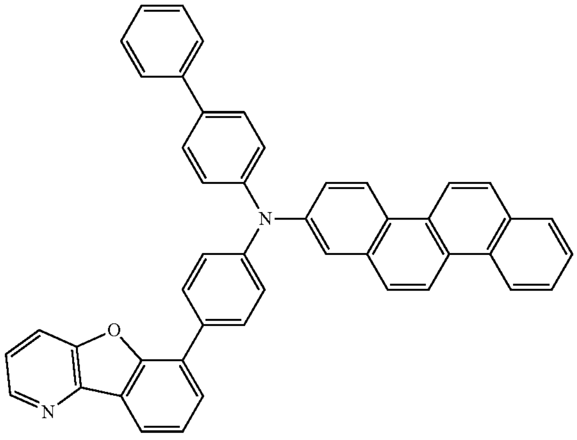
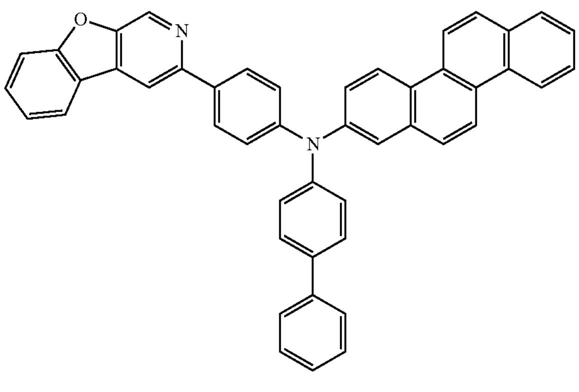
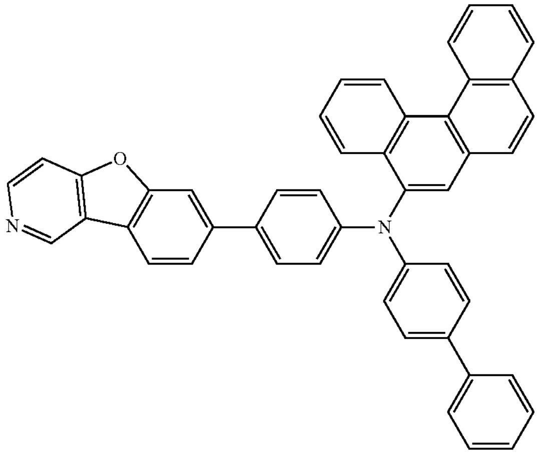

-continued
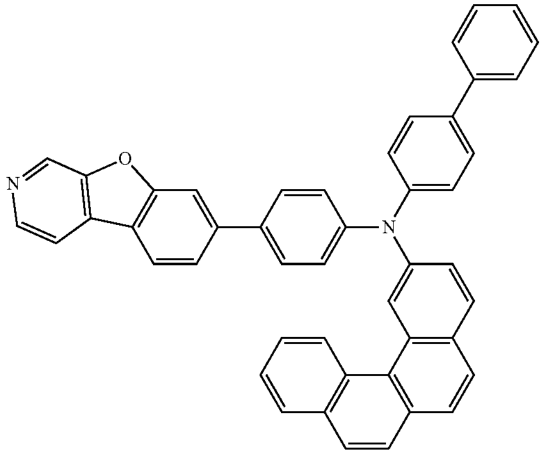
-continued
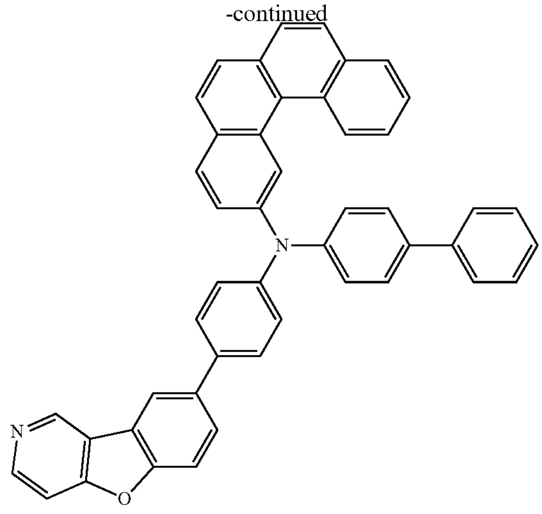
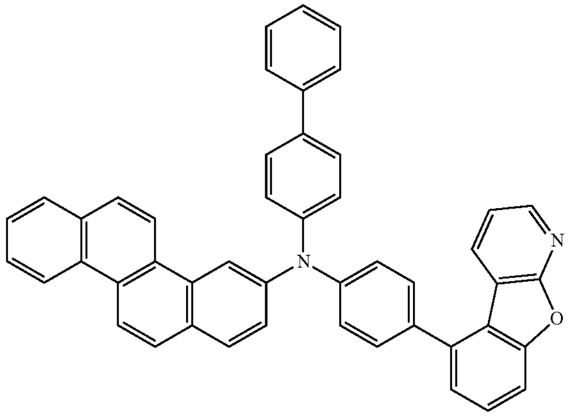
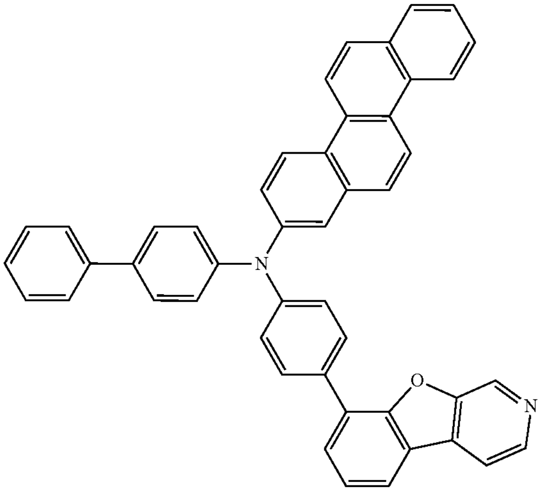
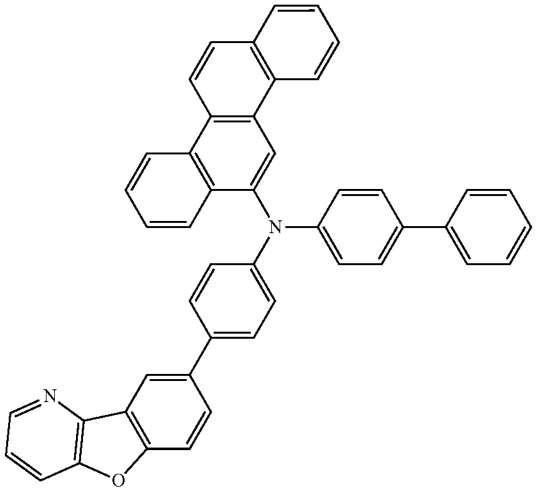
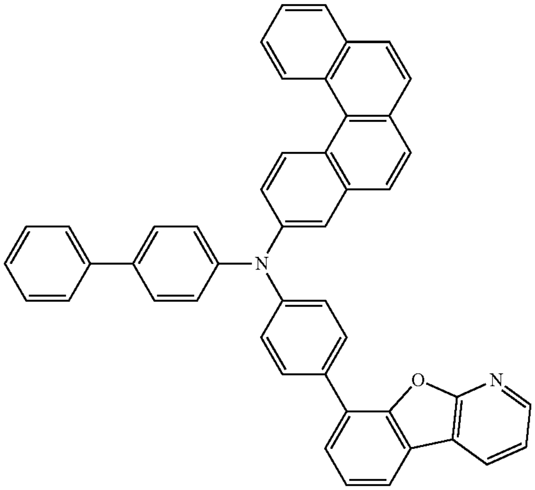

-continued
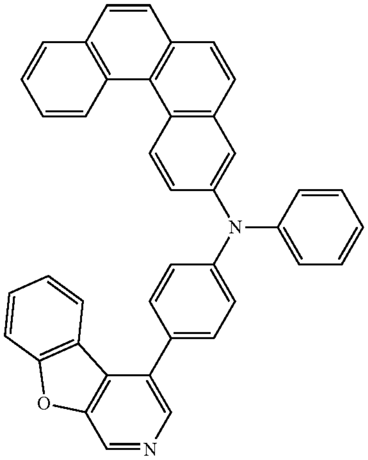
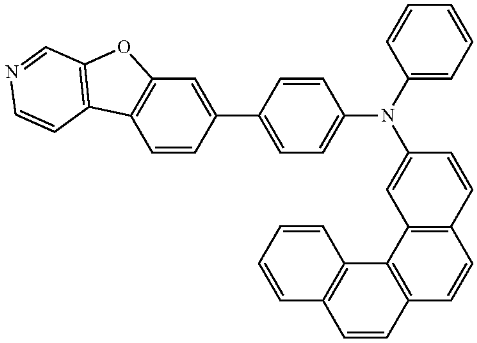
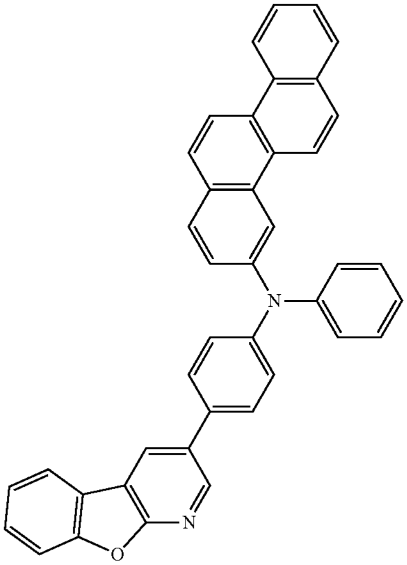
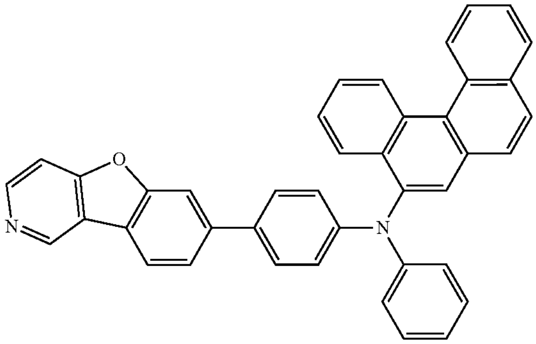
-continued
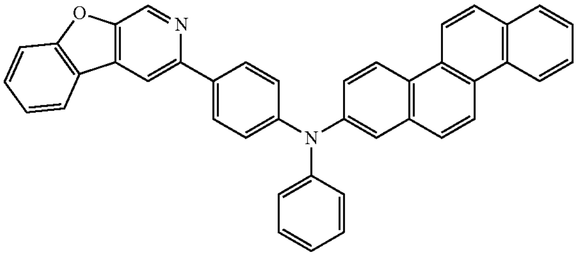
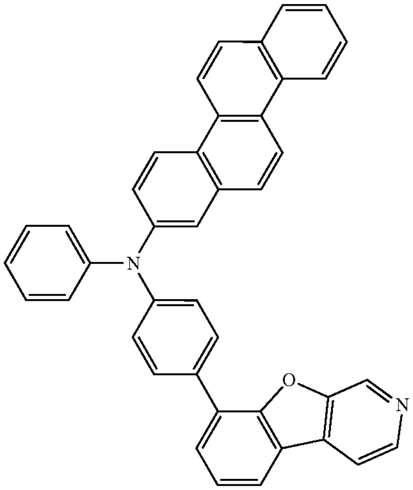
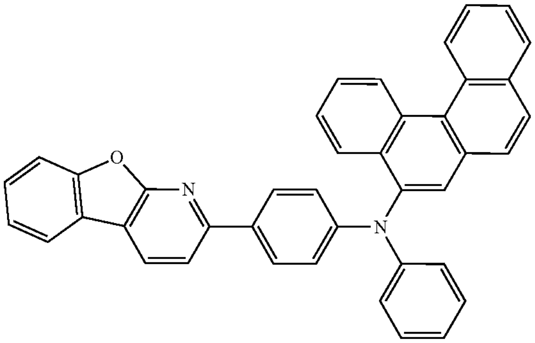
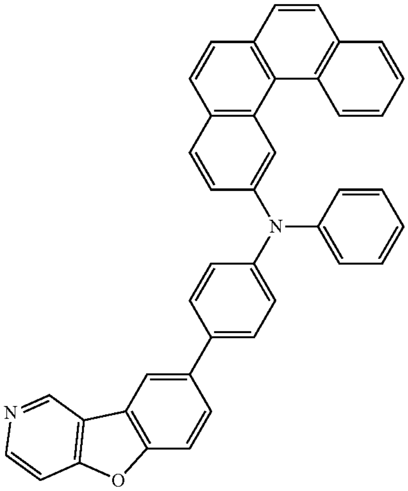

-continued
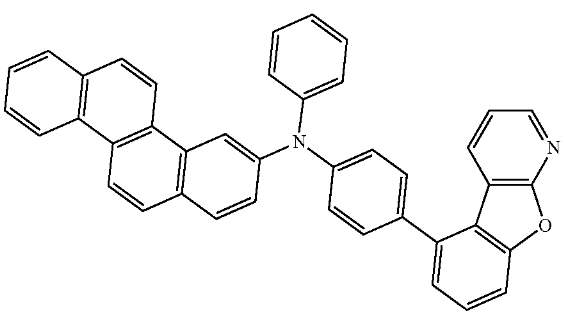
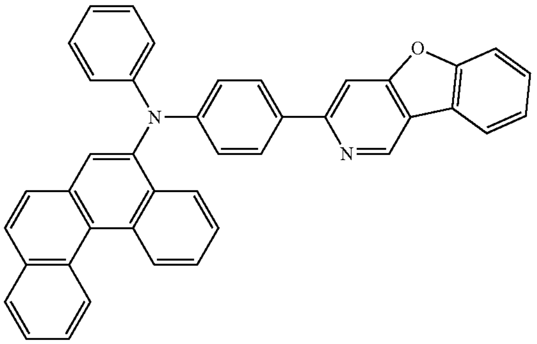
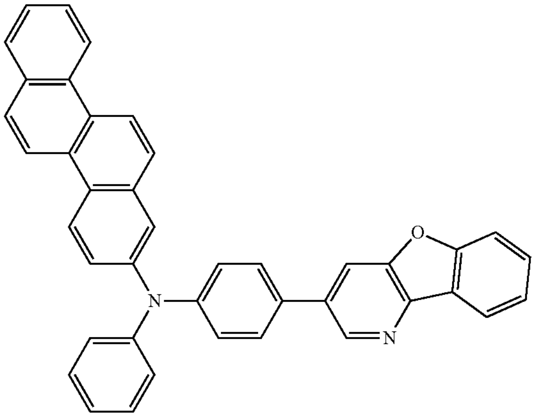
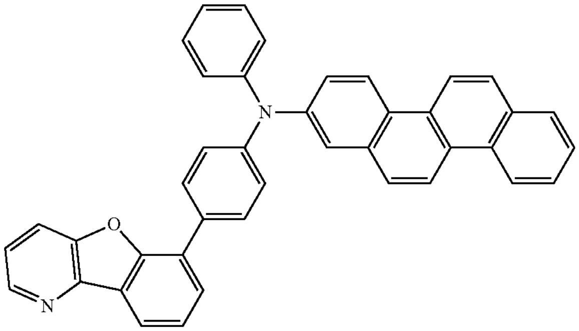
-continued
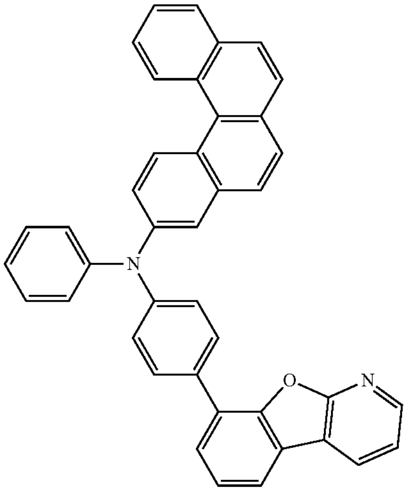
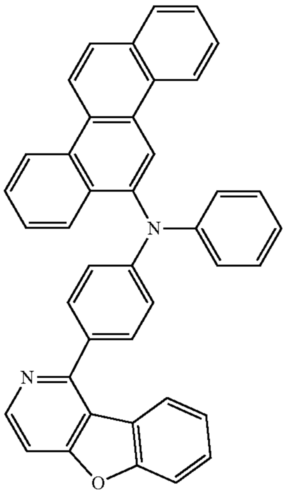
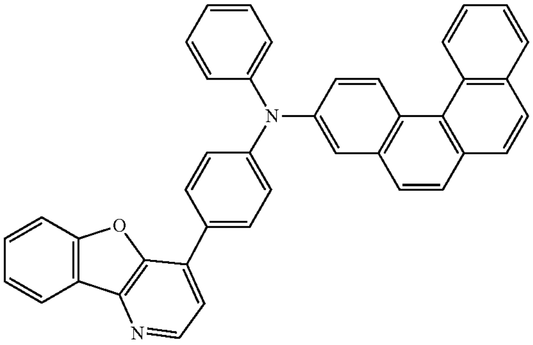

-continued
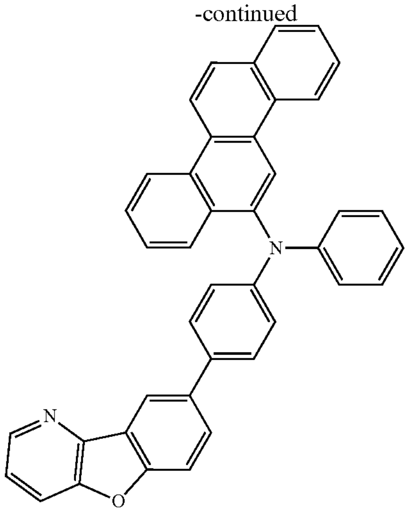
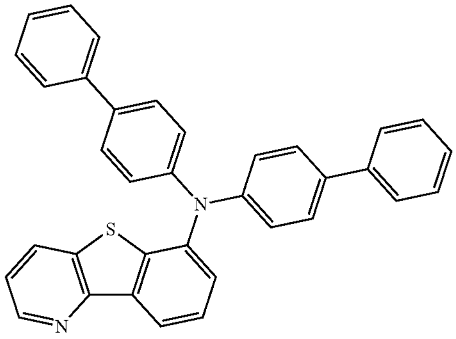
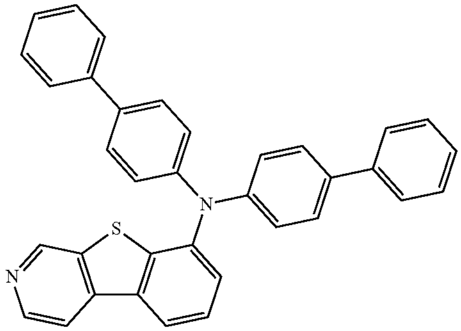
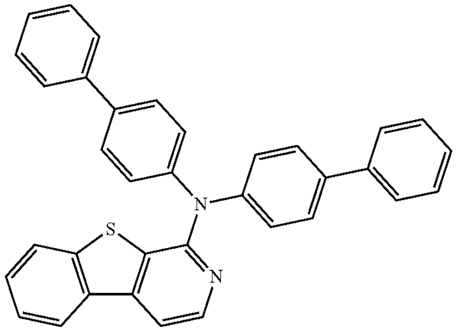
-continued
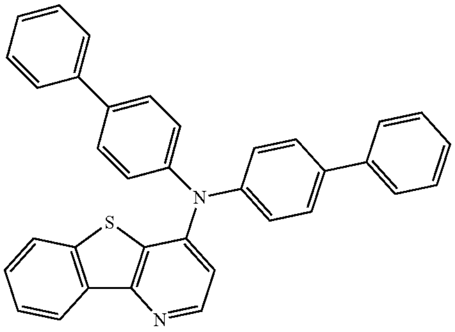
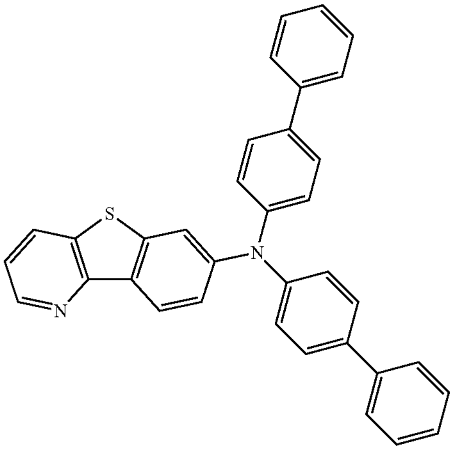
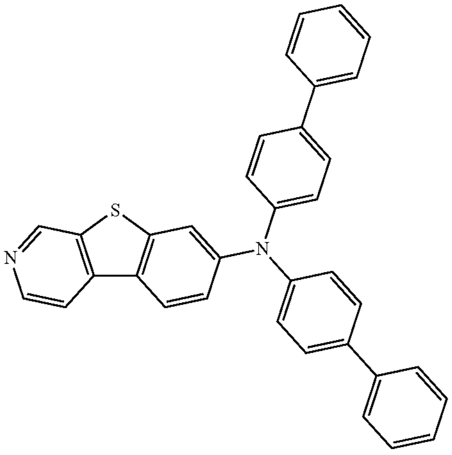
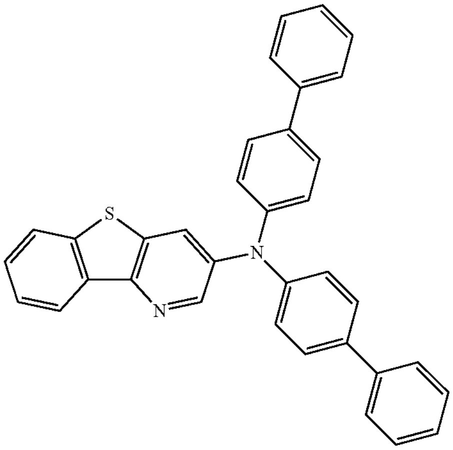

-continued
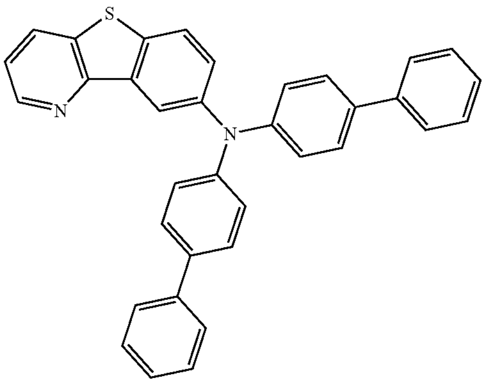
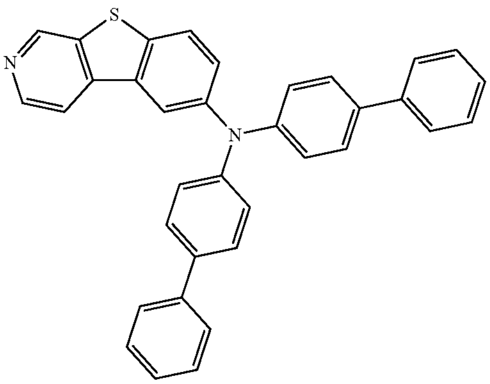
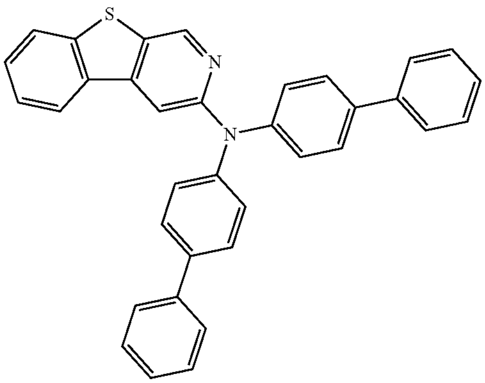
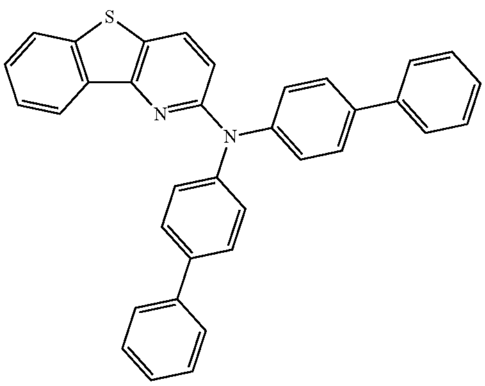
-continued
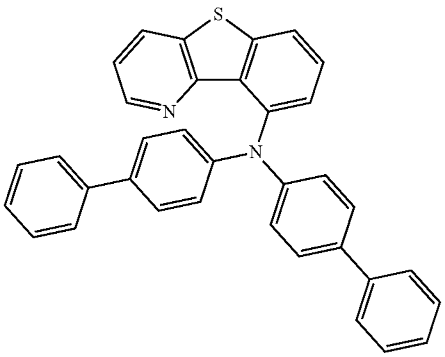
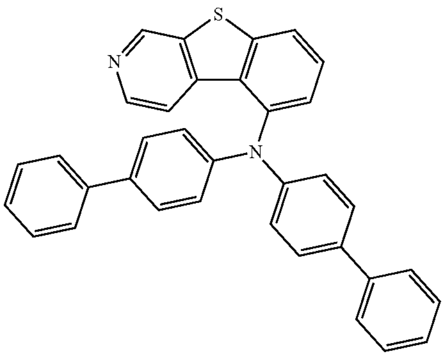
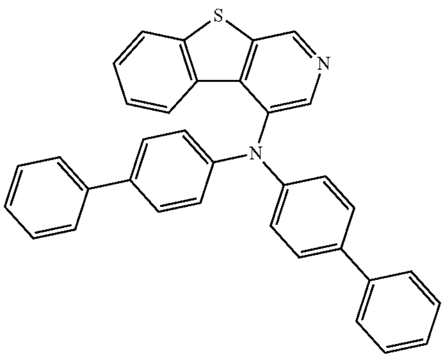
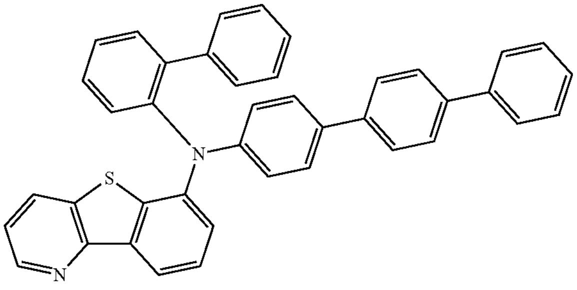
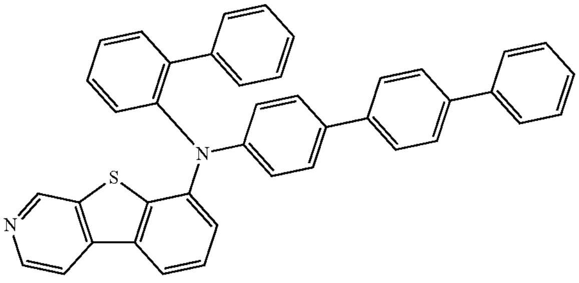

-continued
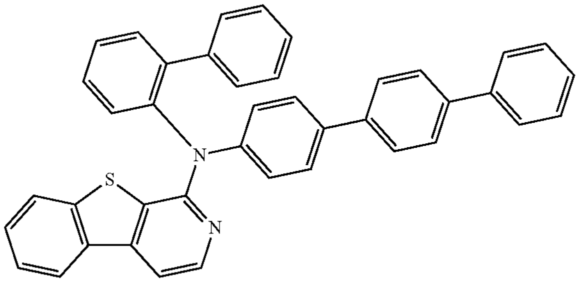
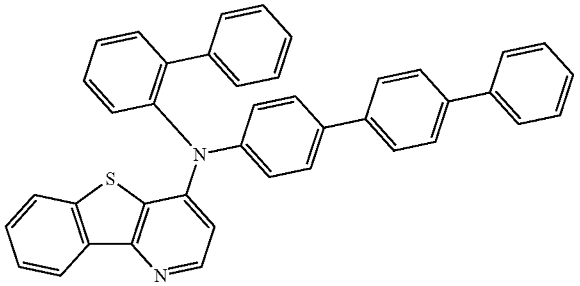
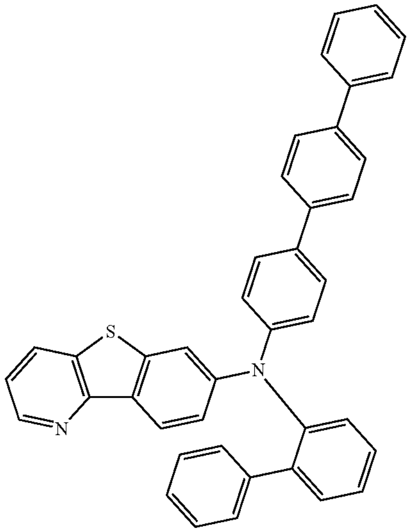
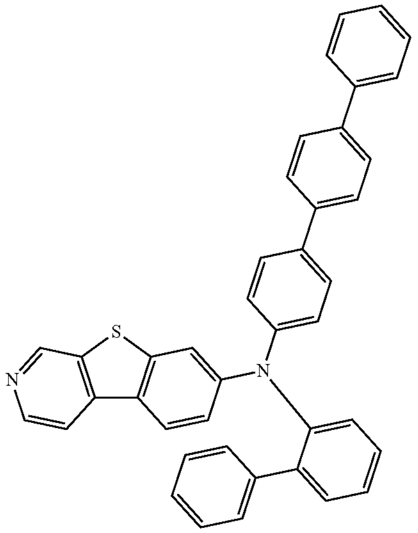
-continued
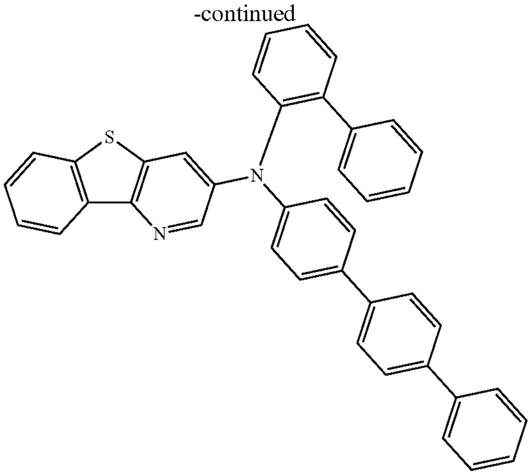
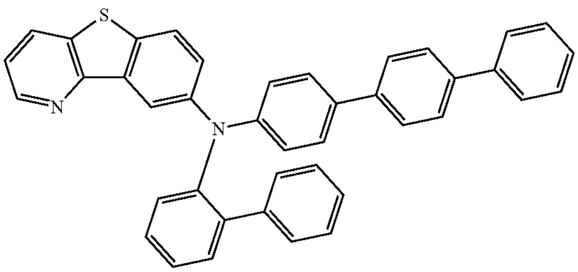
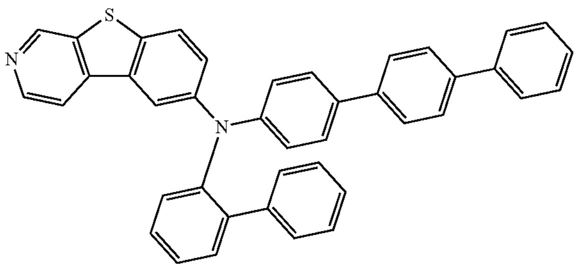
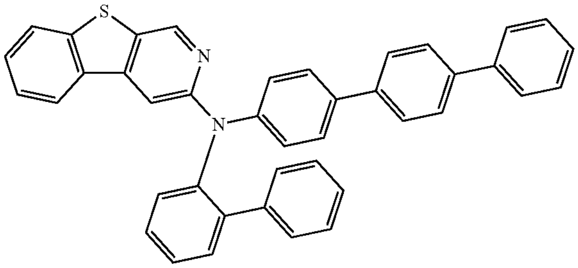
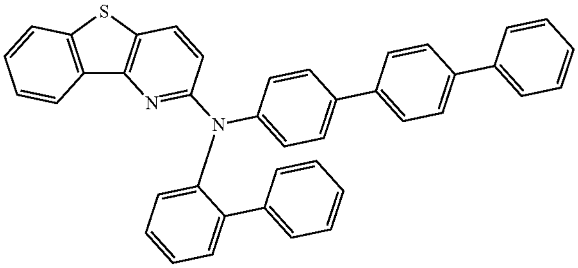

-continued
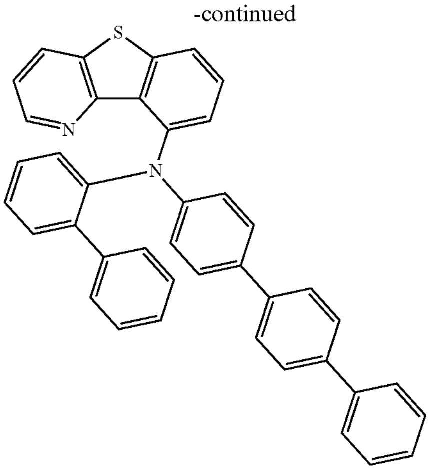
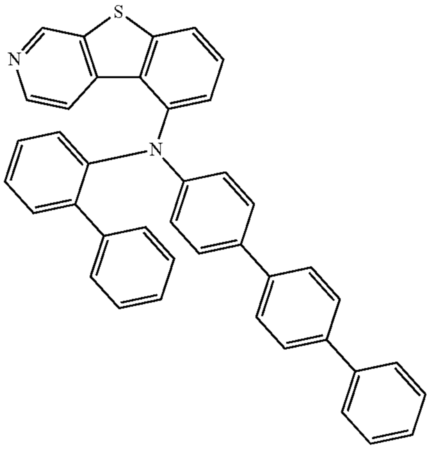
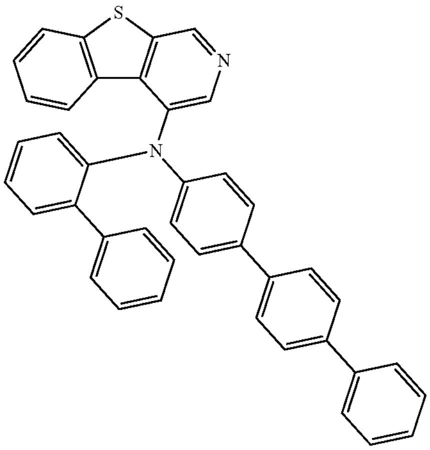
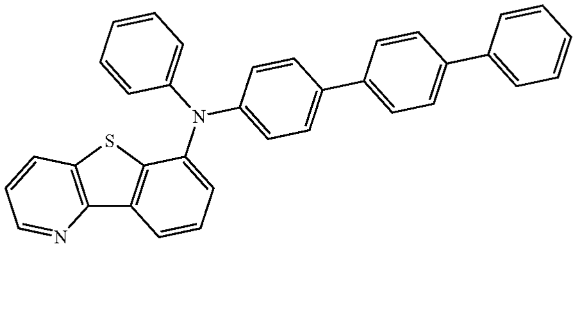
-continued
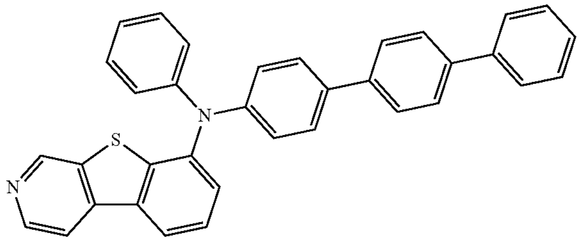
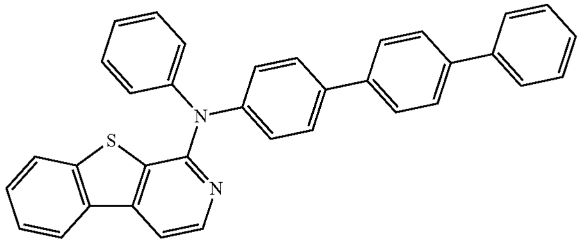
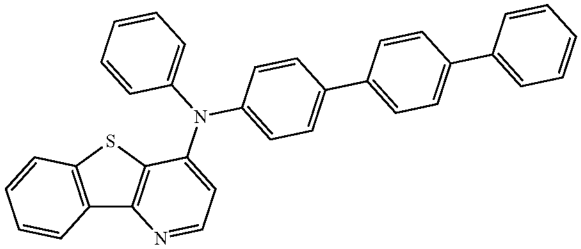
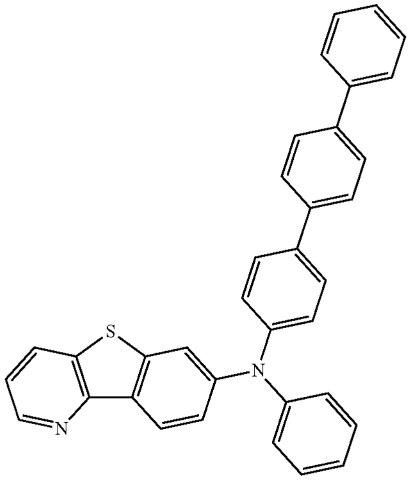
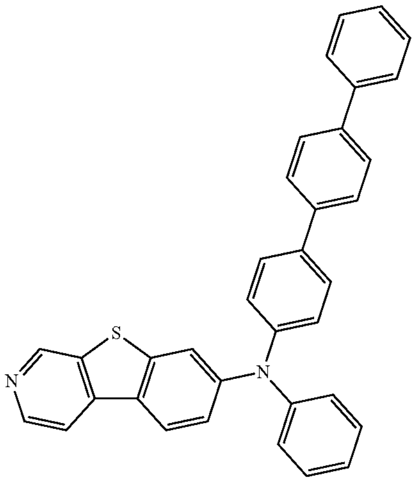

-continued
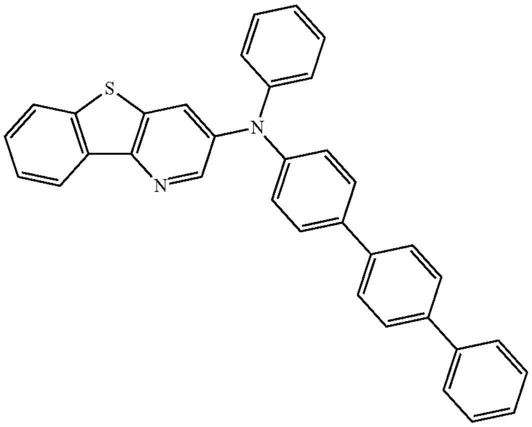
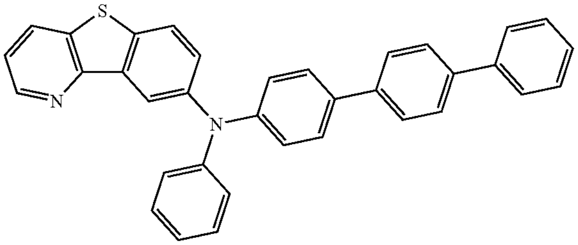
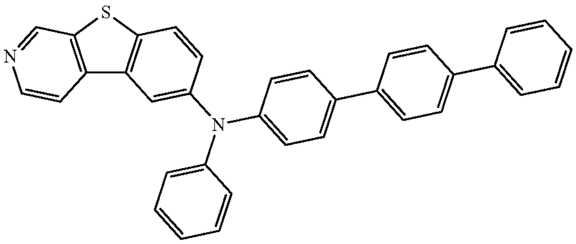
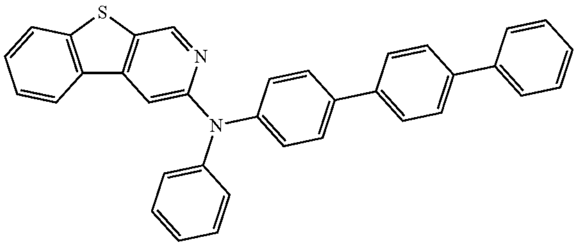
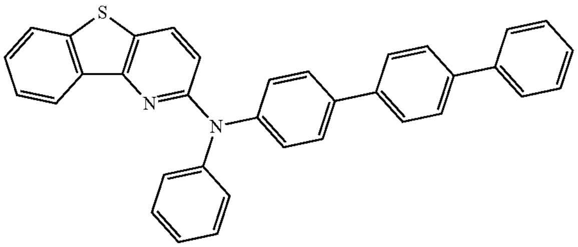
-continued
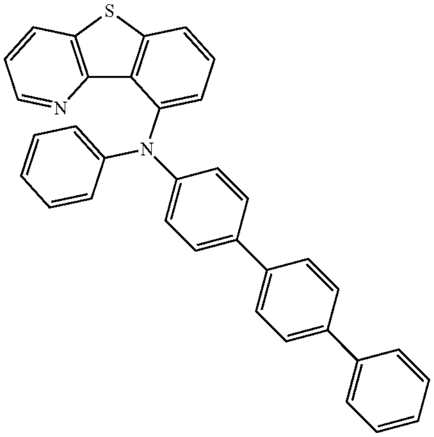
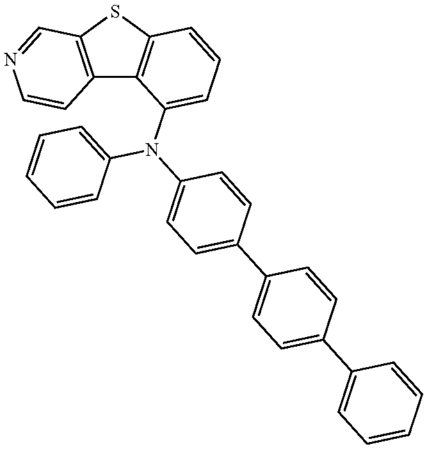
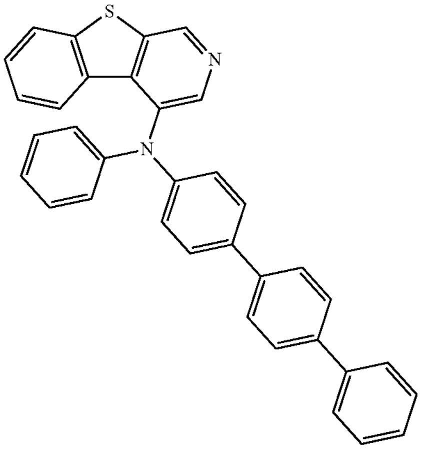

-continued
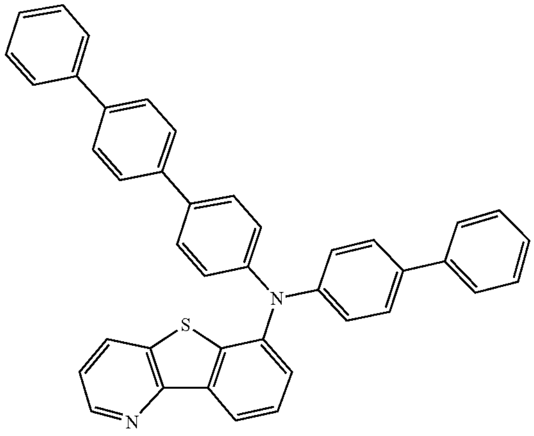
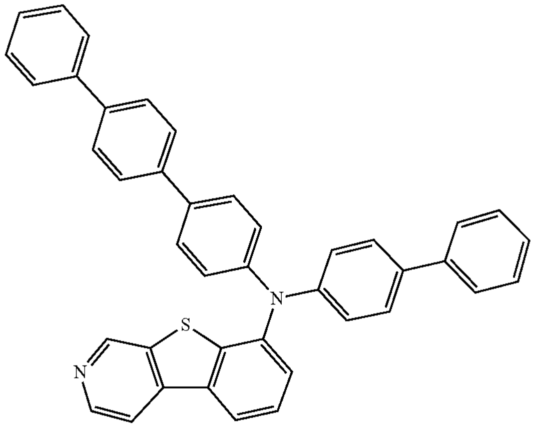
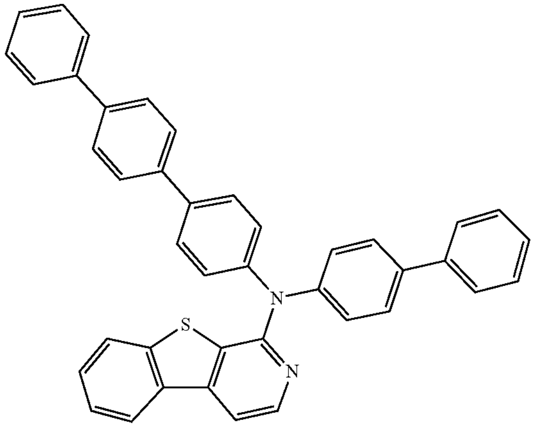
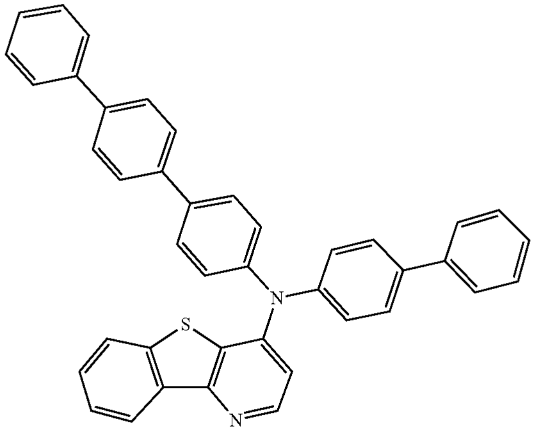
-continued
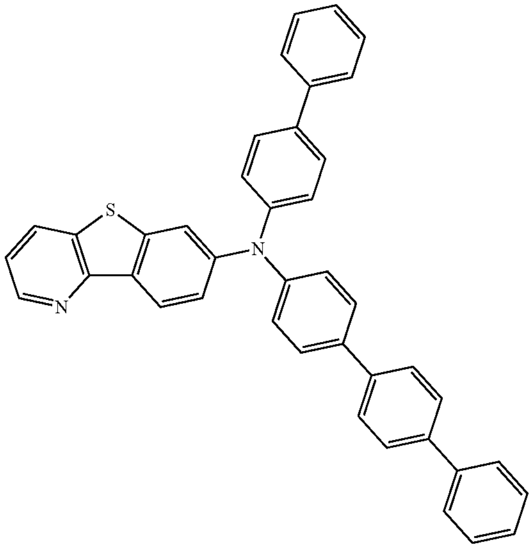
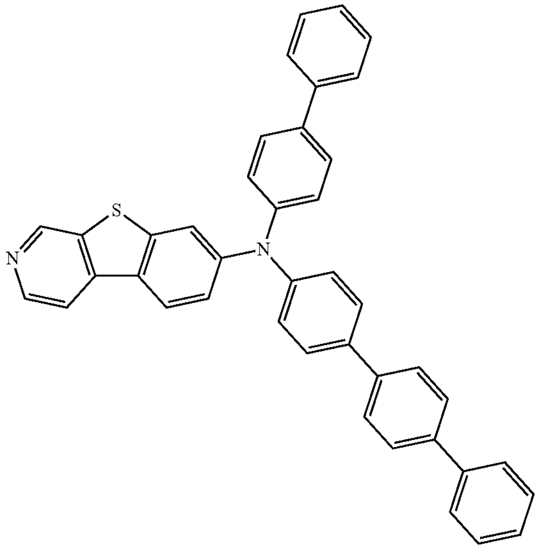
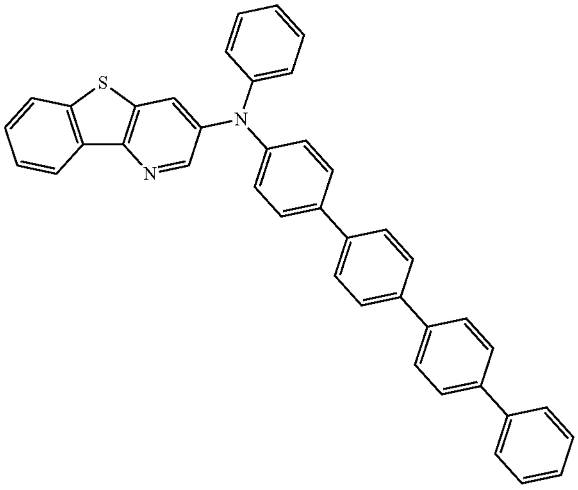

-continued
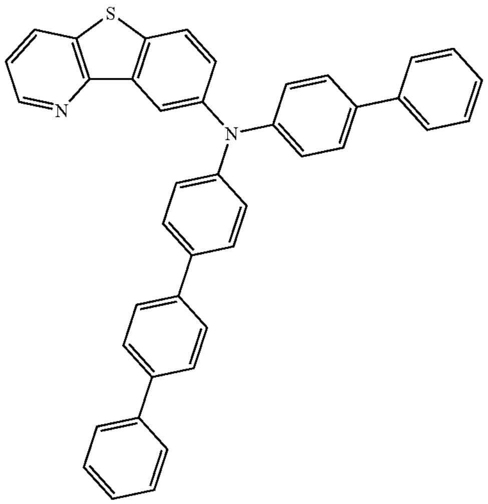
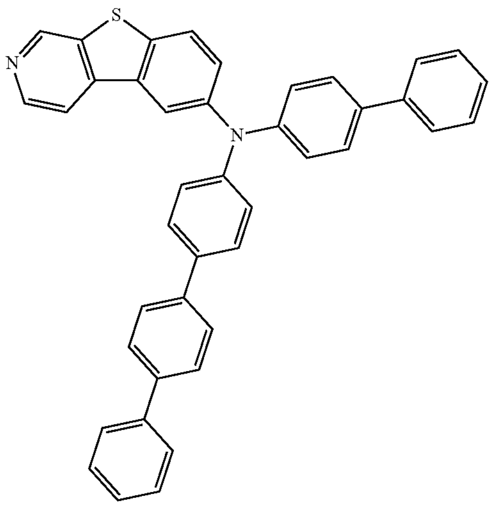
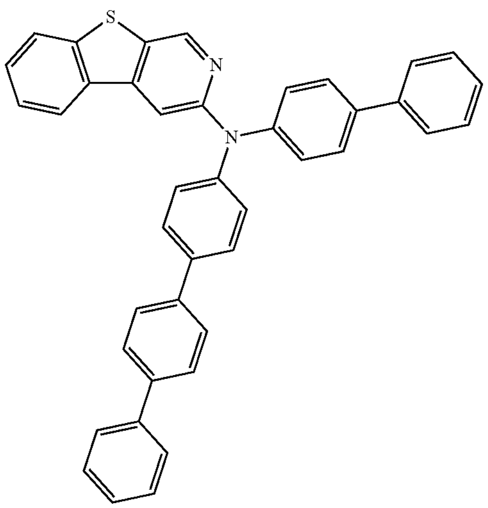
-continued
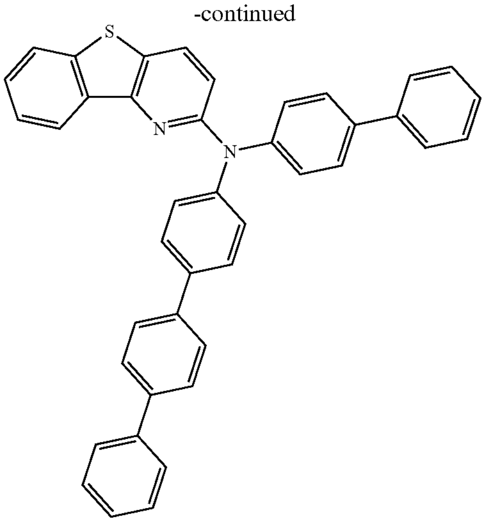
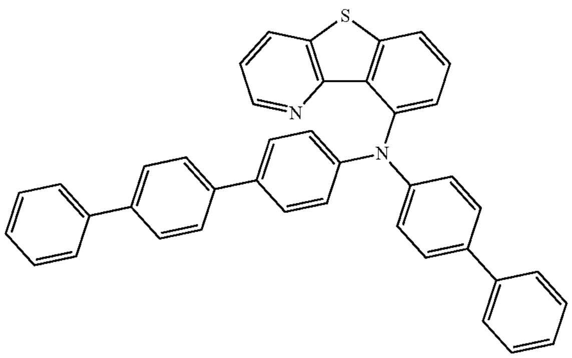
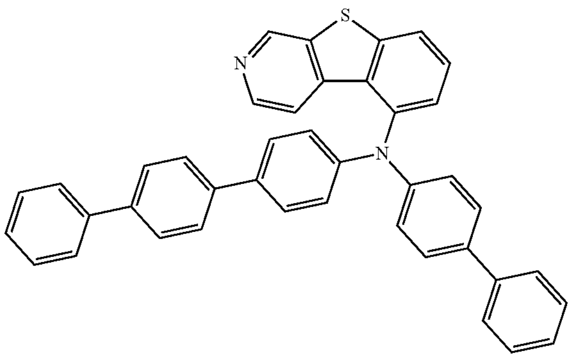
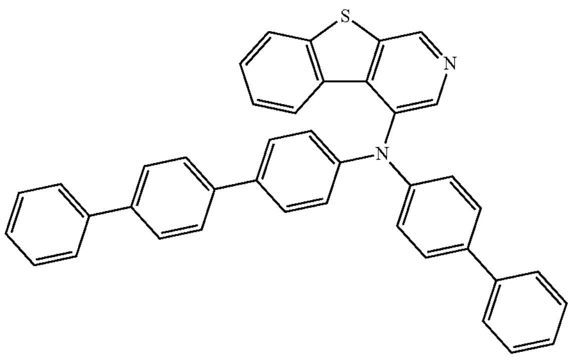

-continued
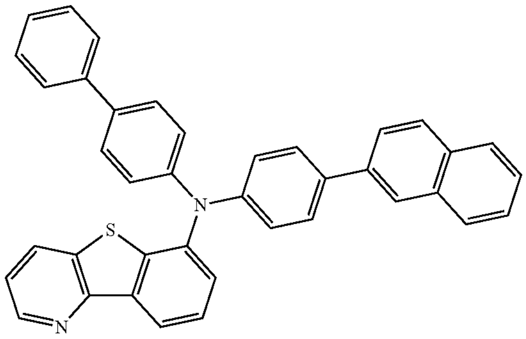
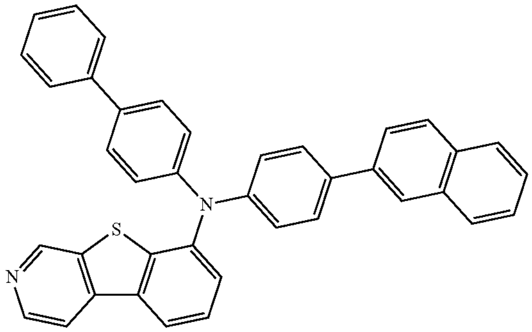
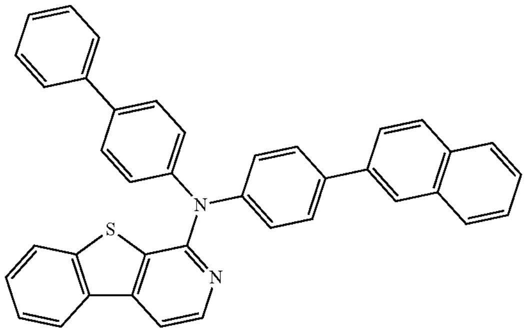
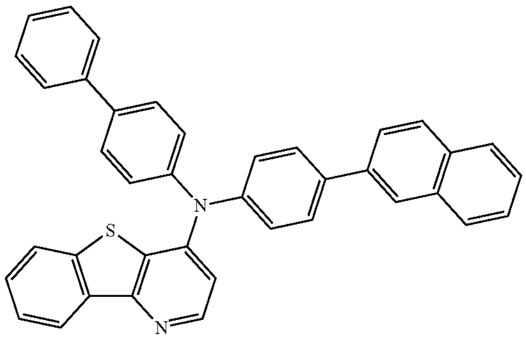
-continued
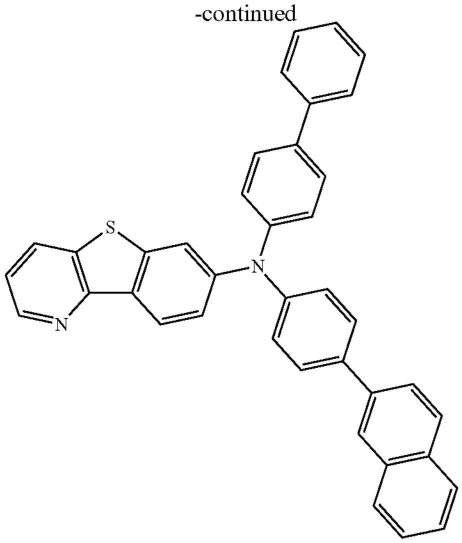
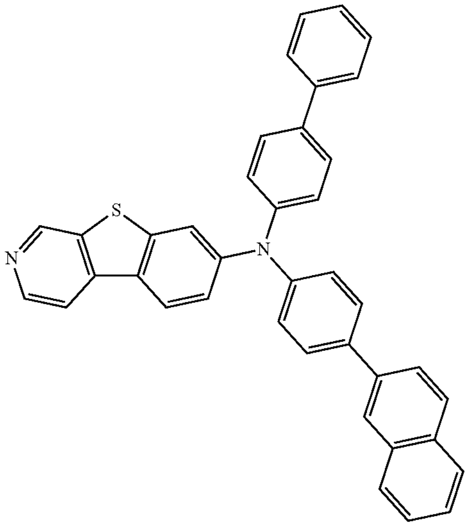
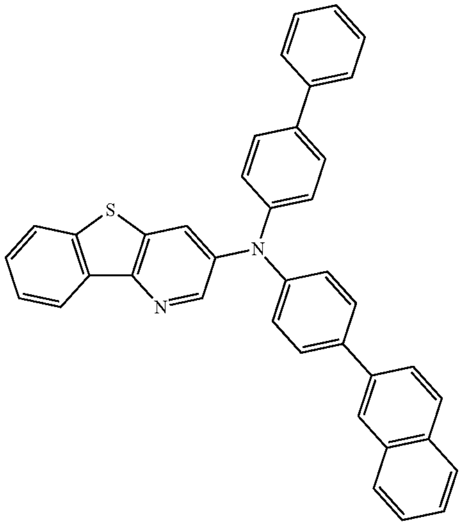

-continued
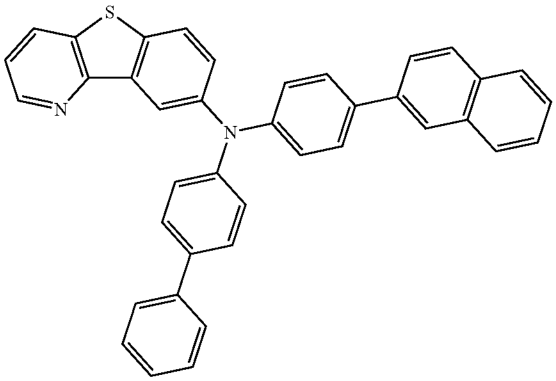
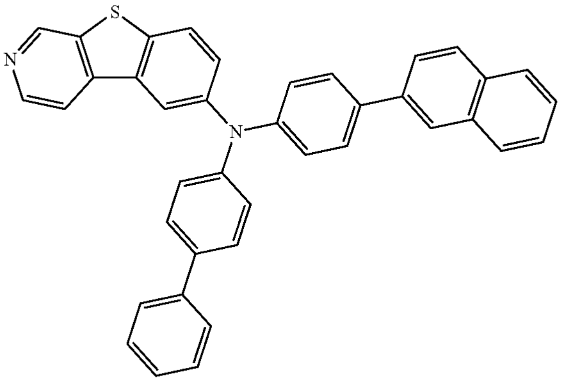
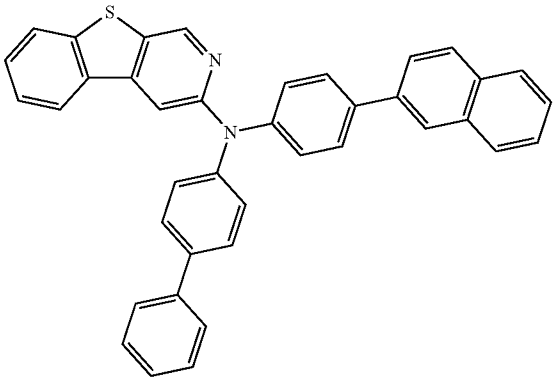
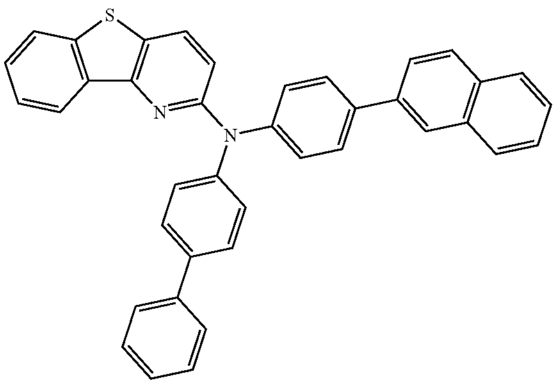
-continued
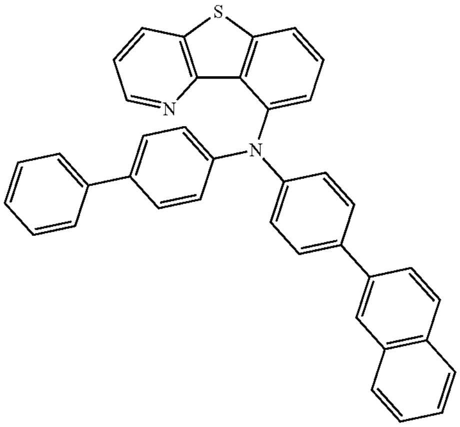
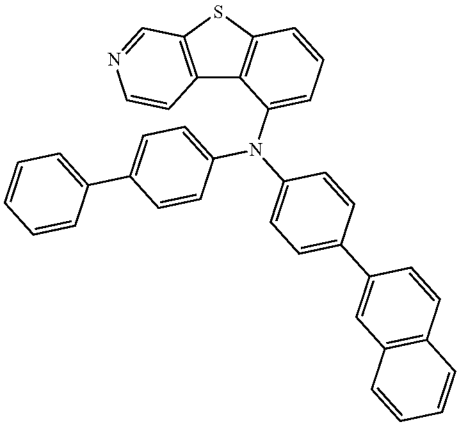
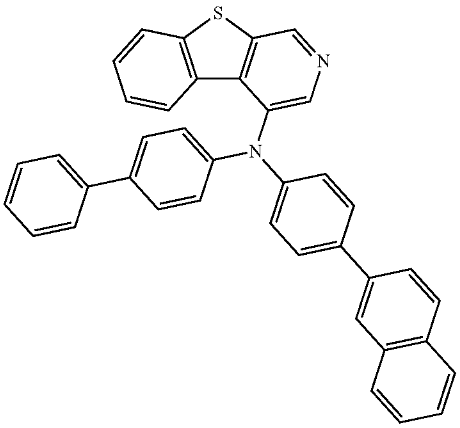
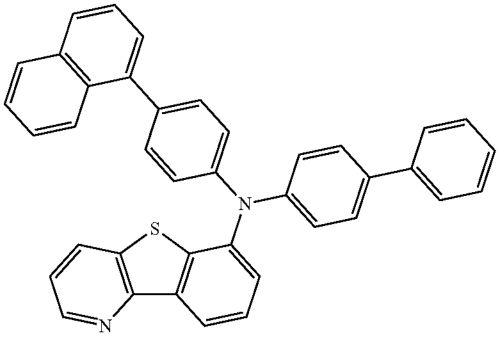

-continued
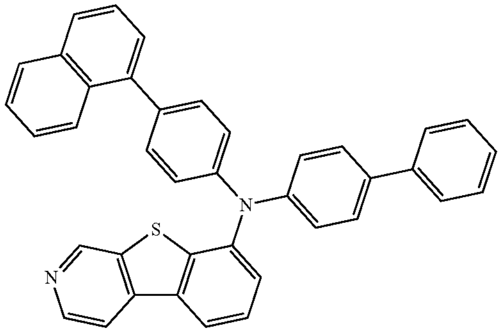
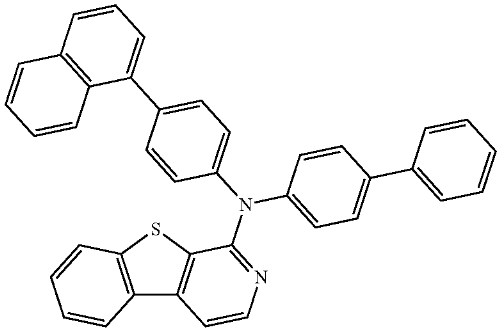
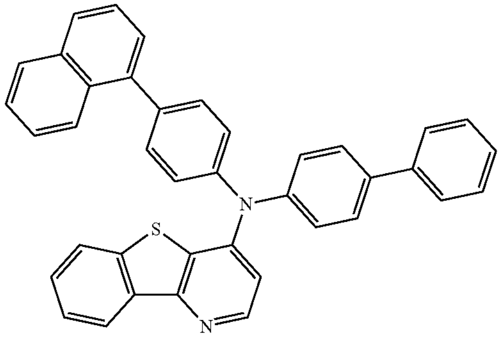
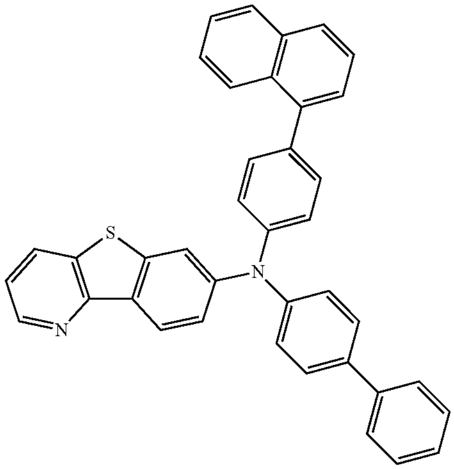
-continued
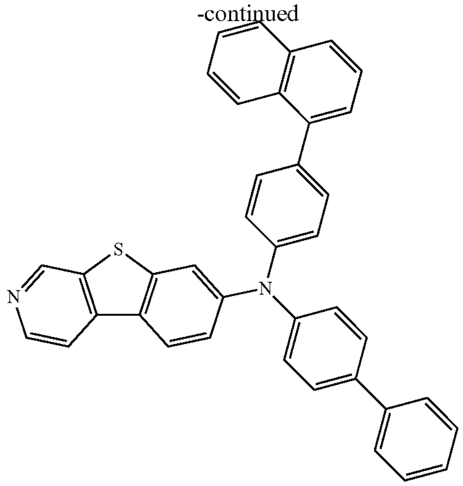
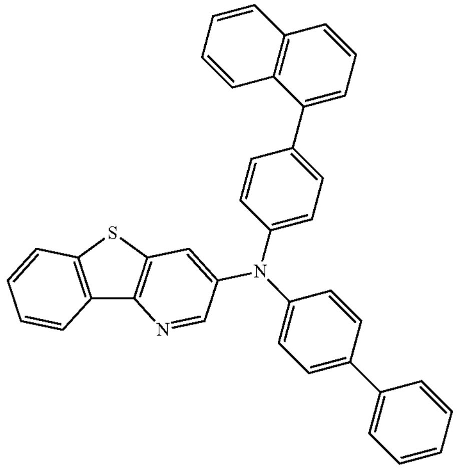
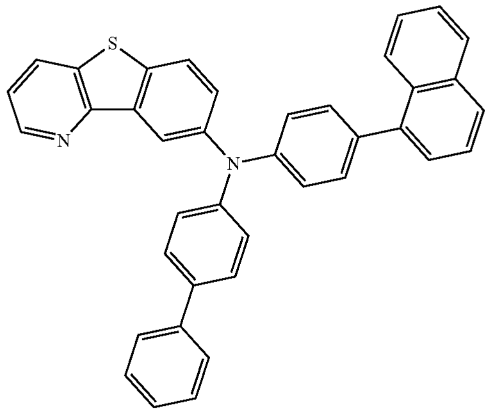

-continued
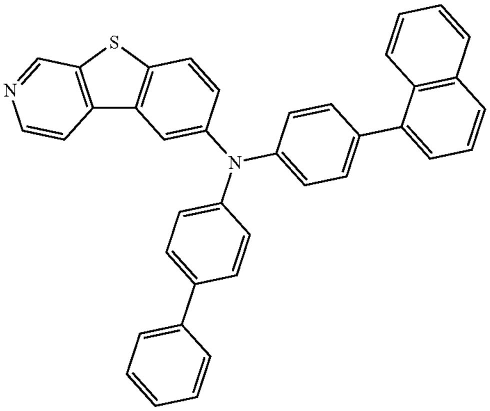
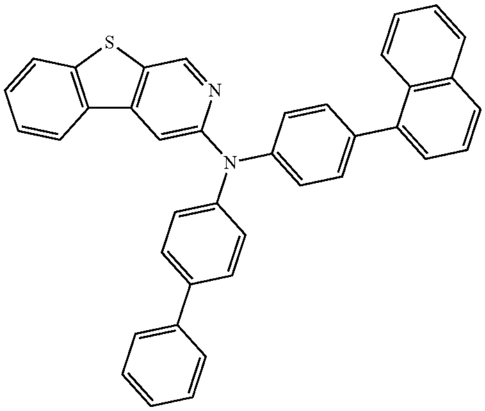
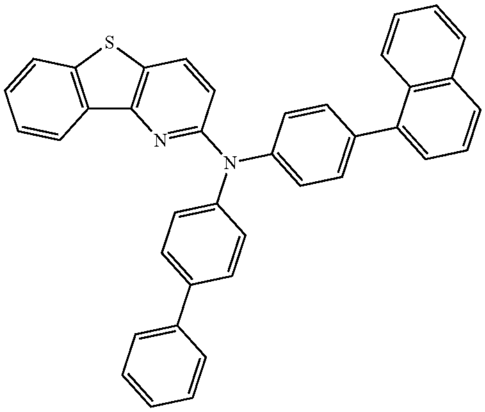
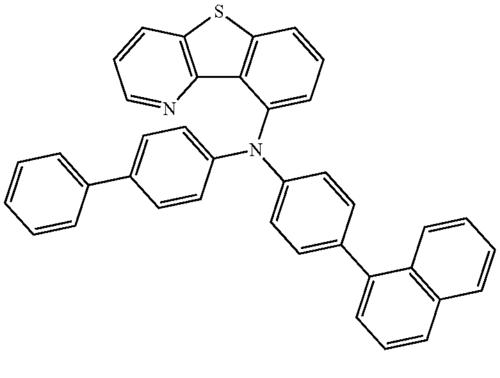
-continued
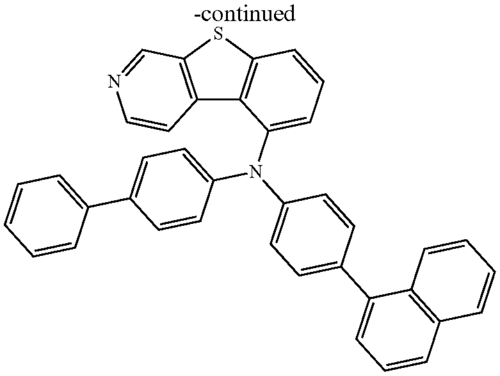
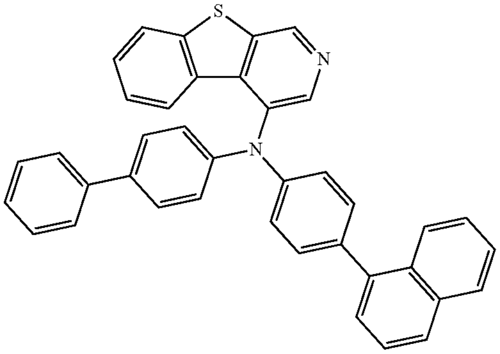
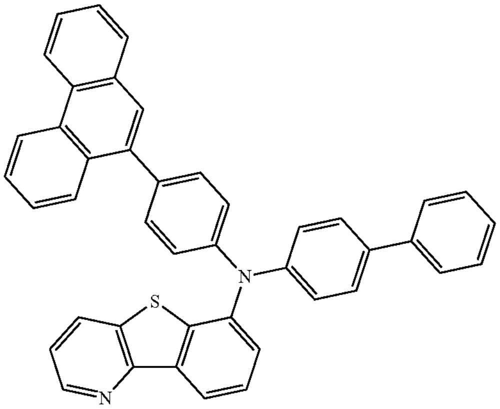
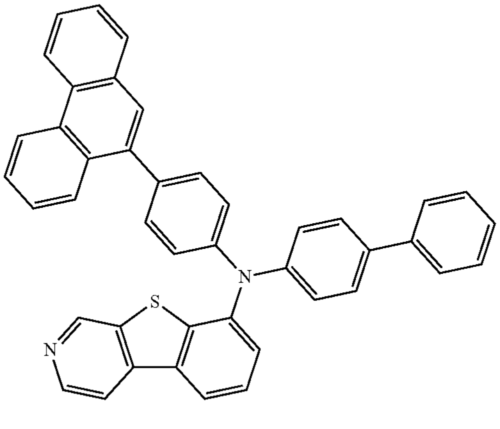

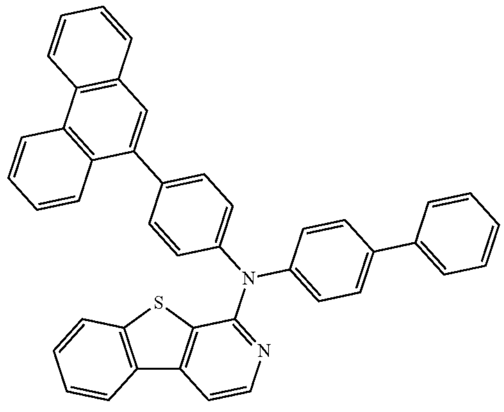
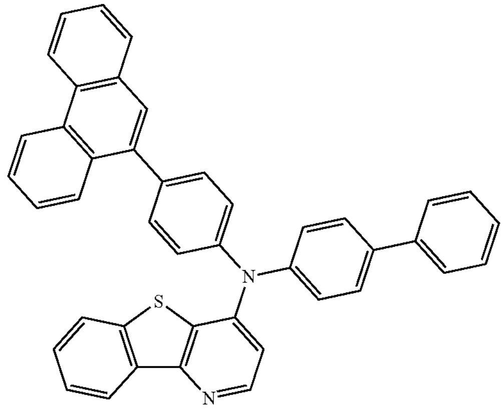
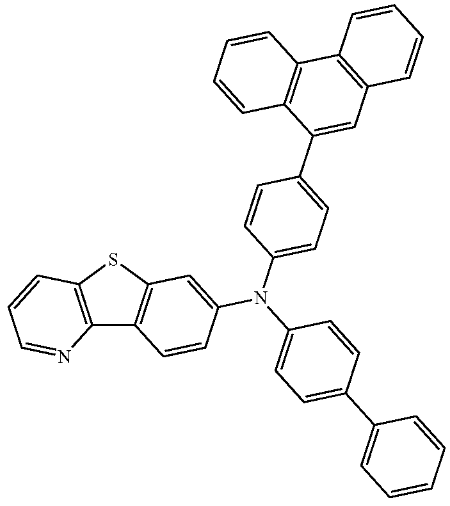
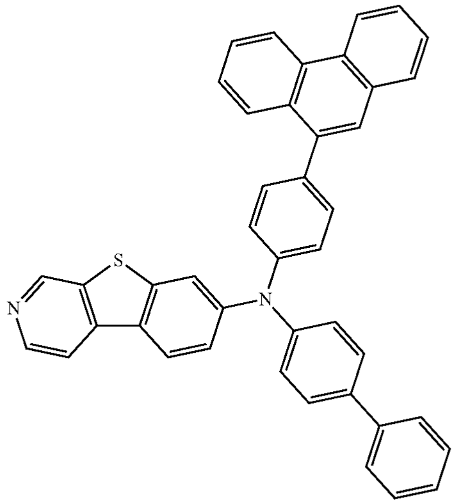
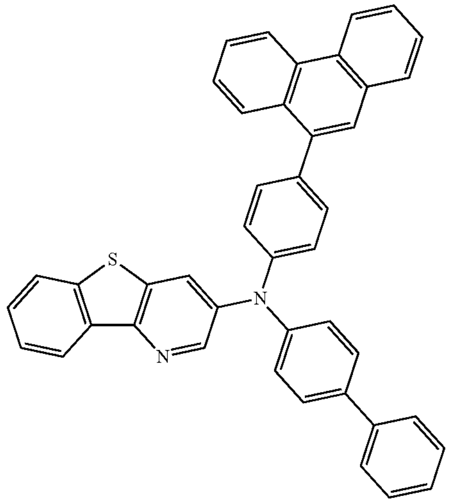
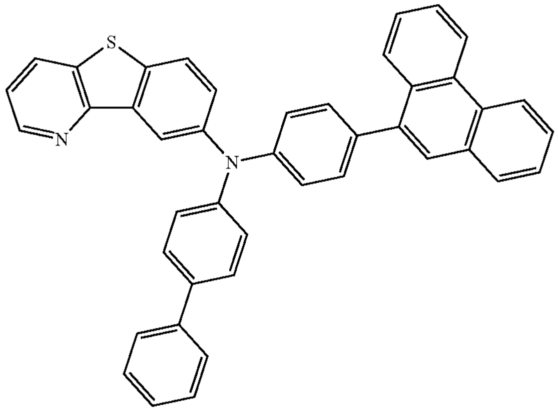

-continued
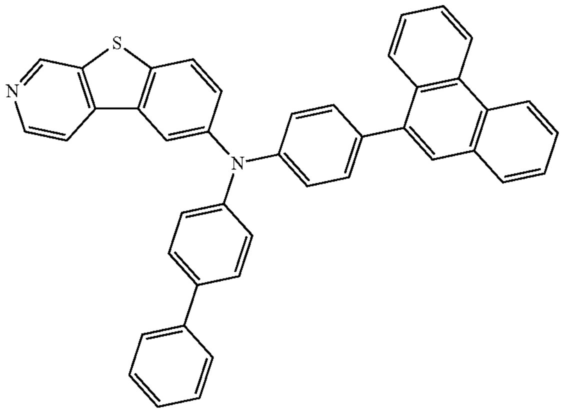
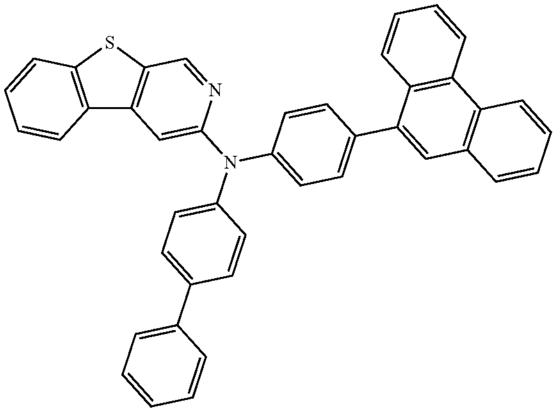
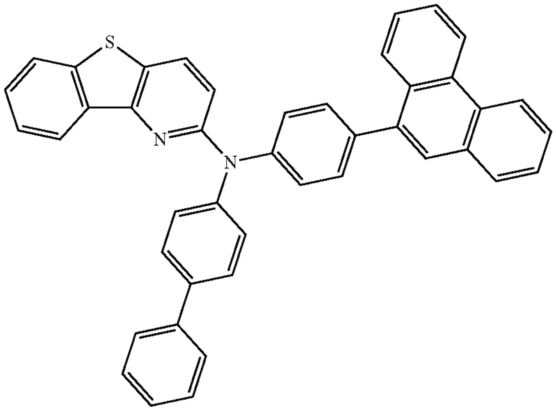
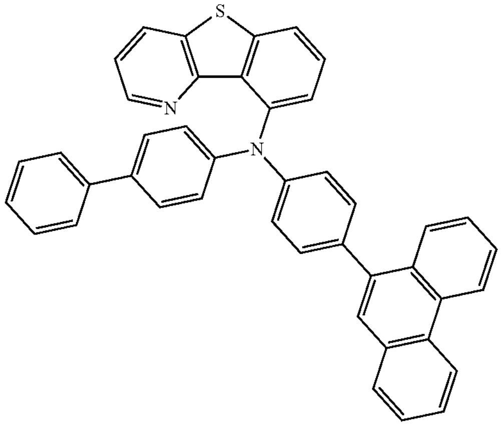
-continued
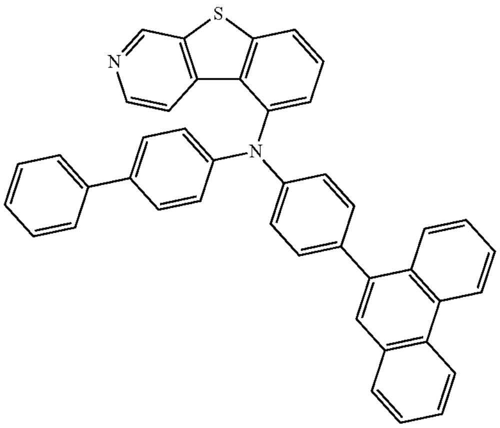
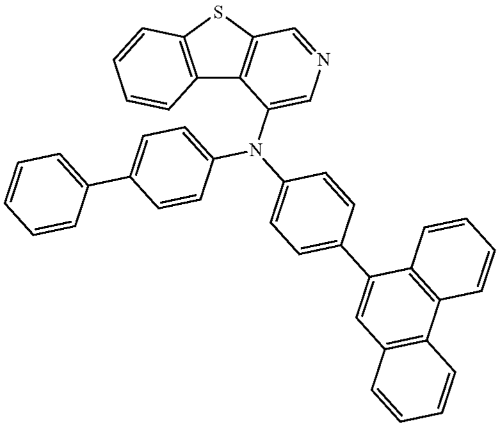
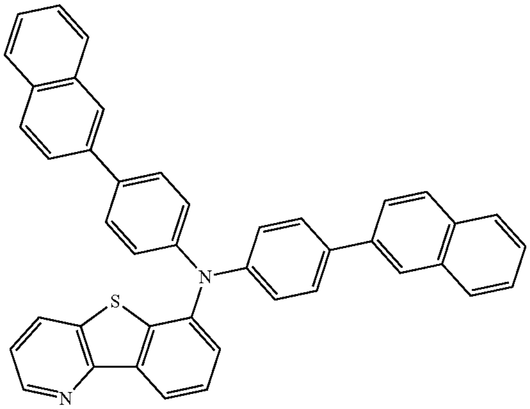
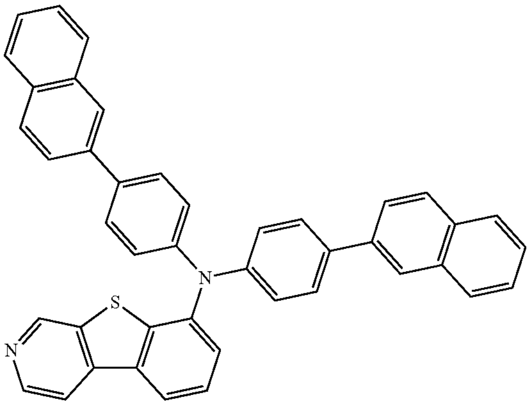

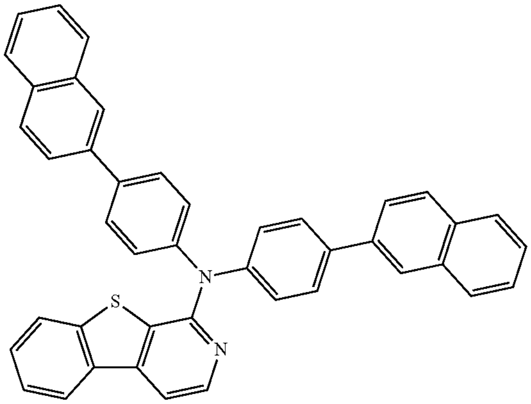
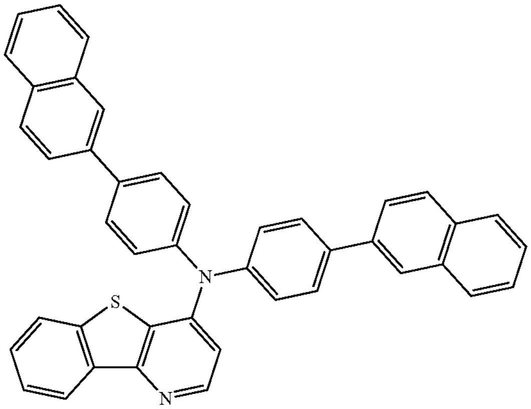
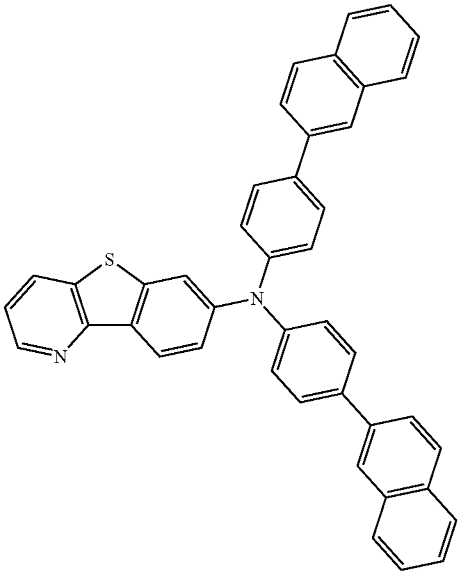
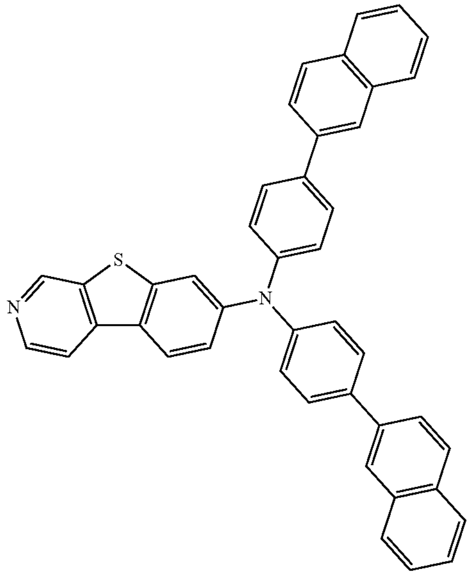
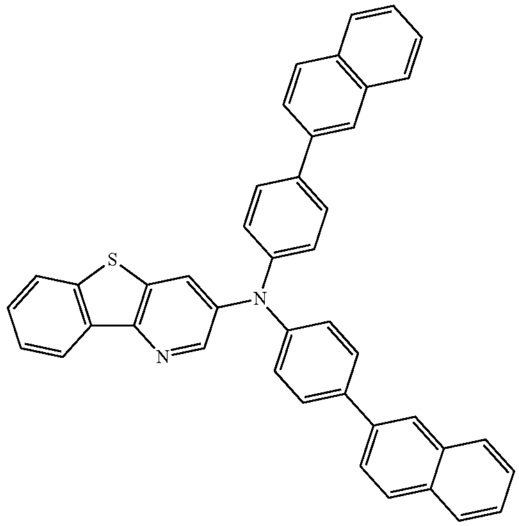
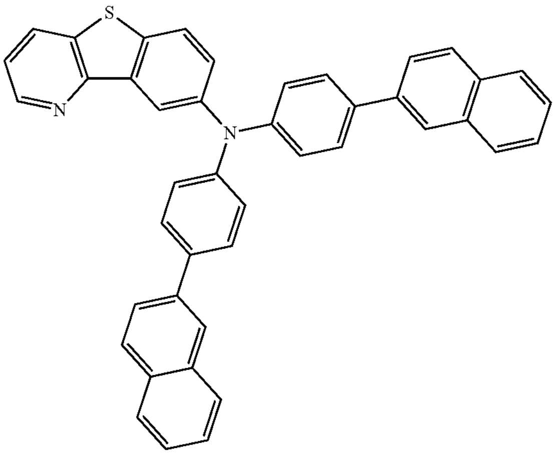

-continued
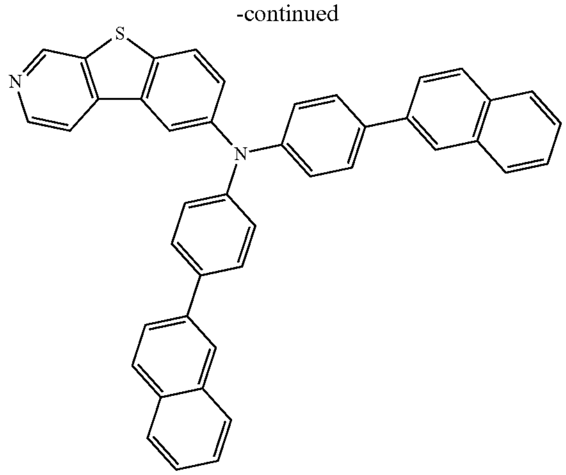
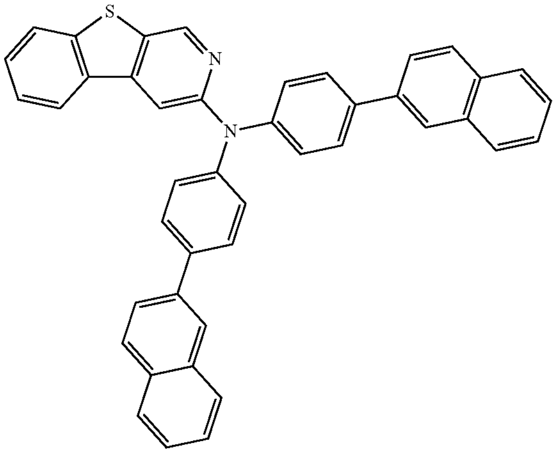
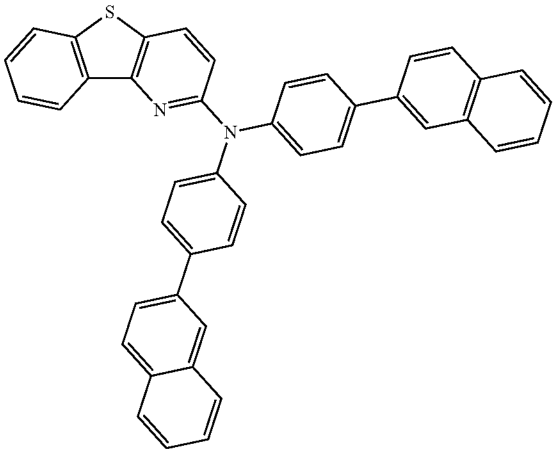
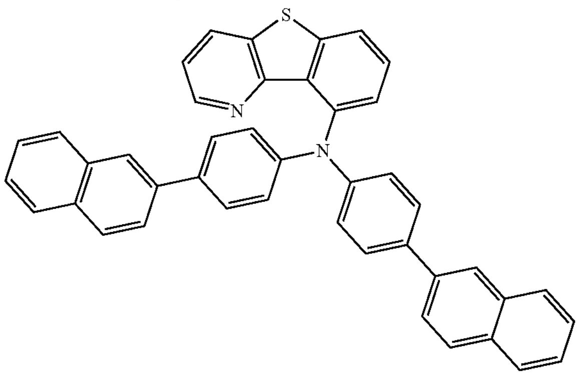
-continued
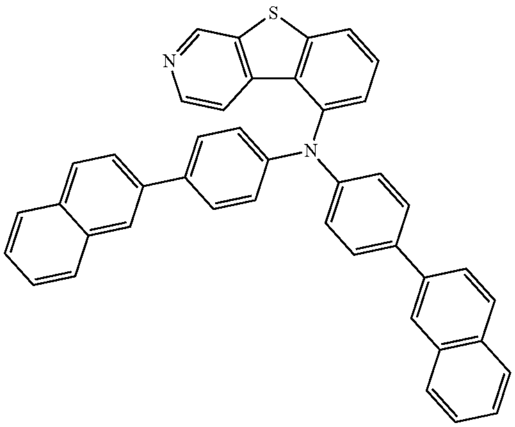
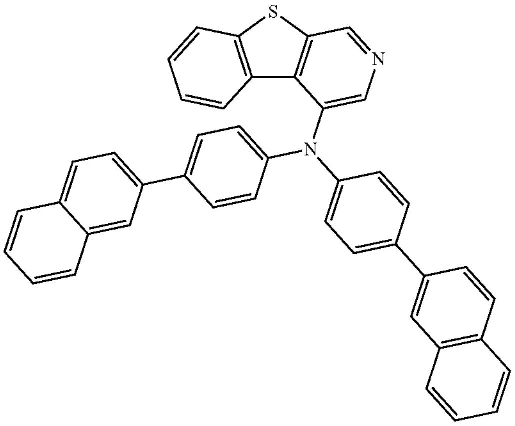
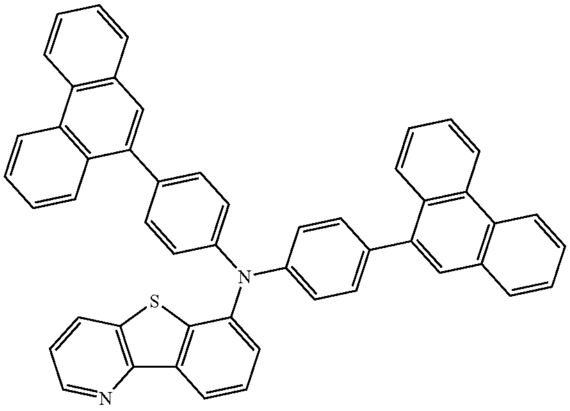
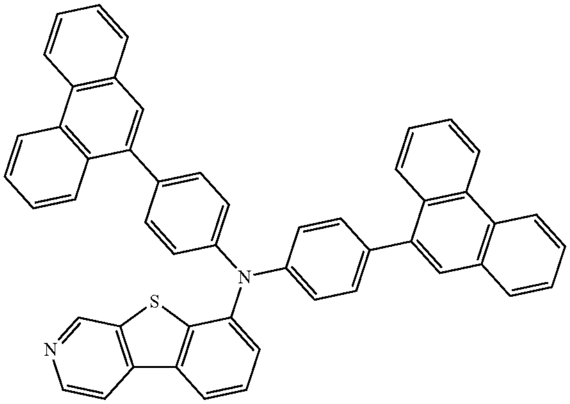

-continued
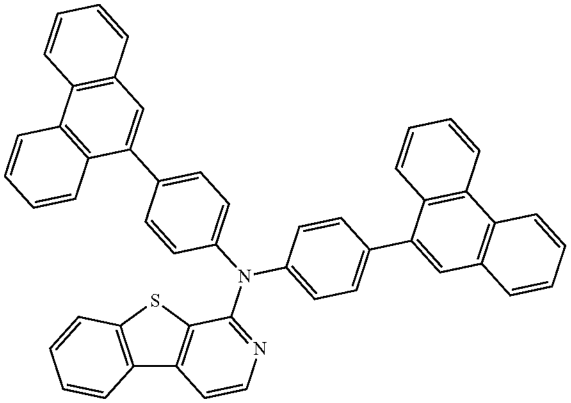
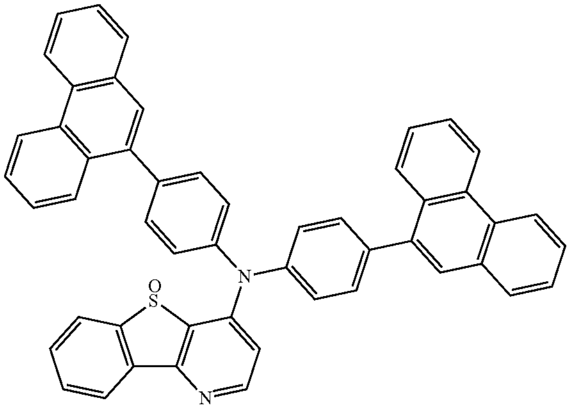
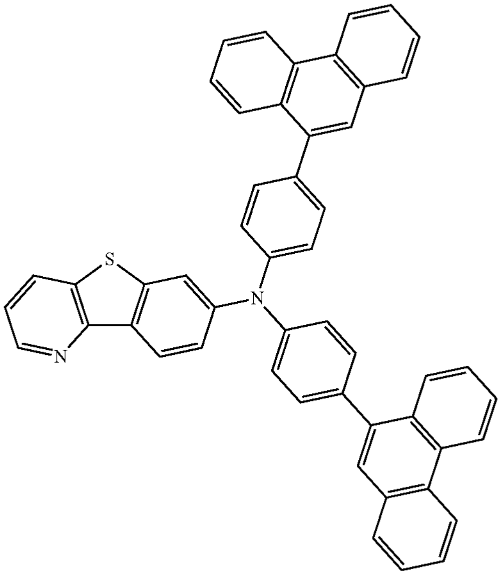
-continued
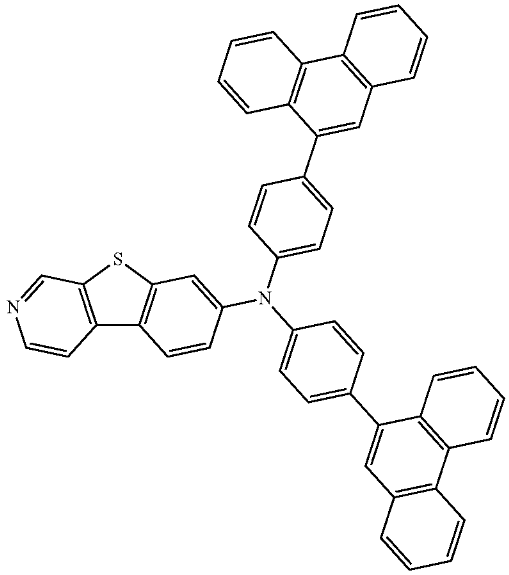
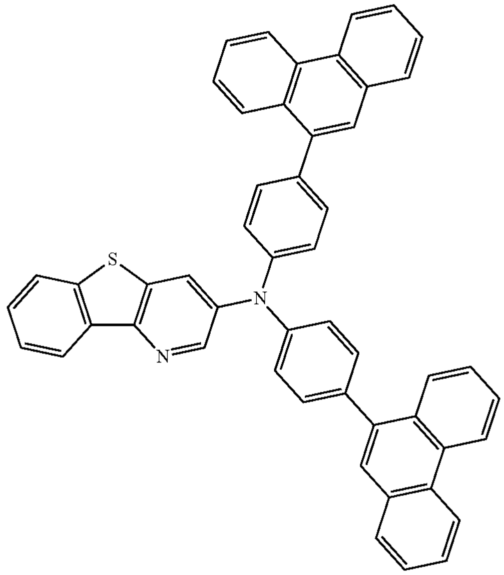
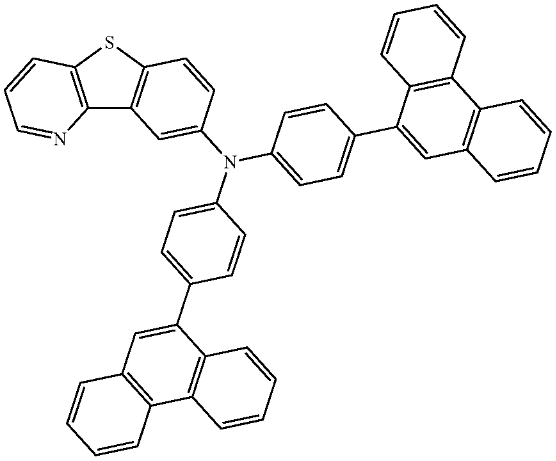

-continued
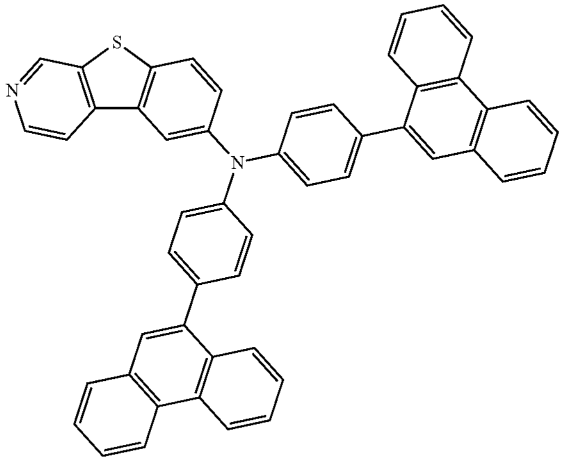
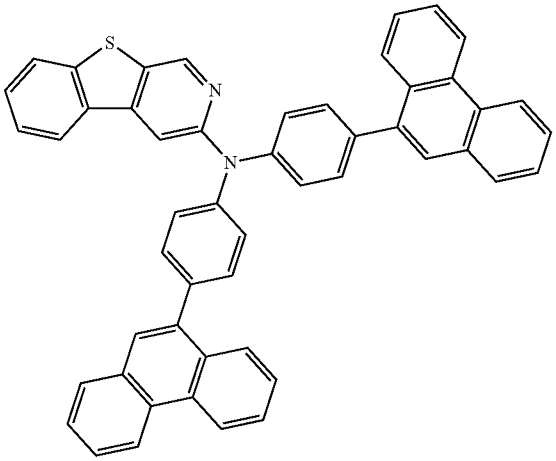
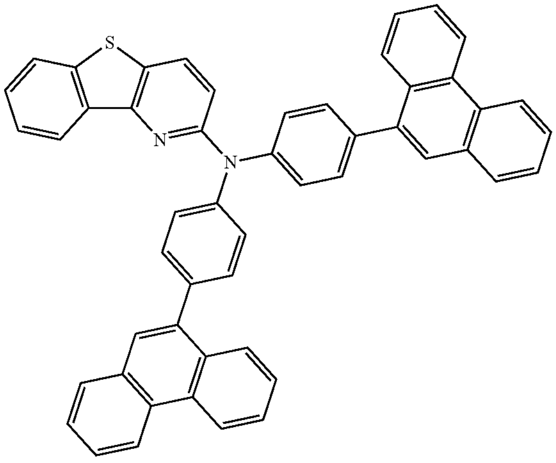
-continued
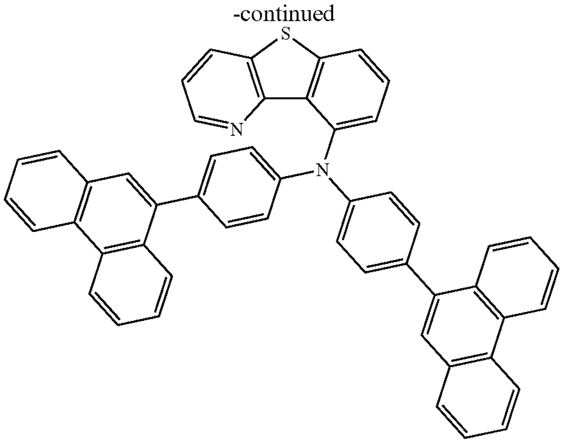
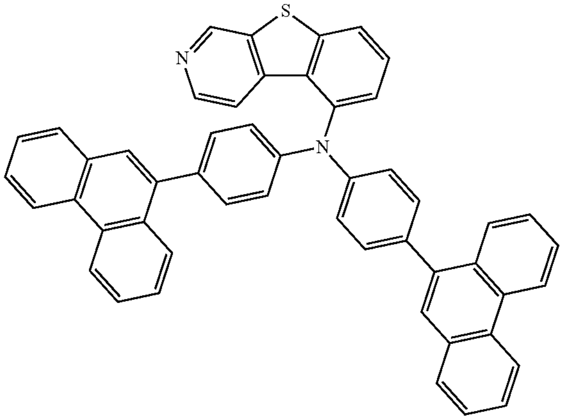
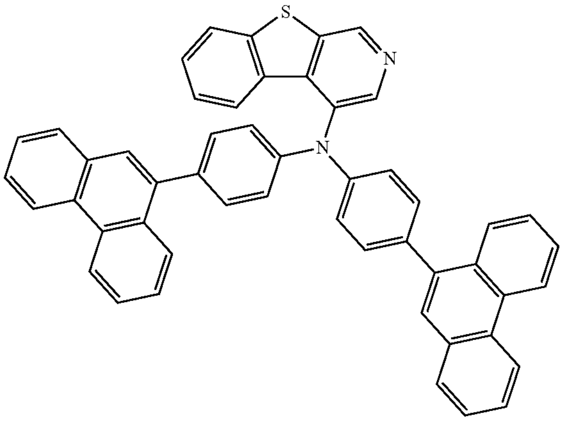
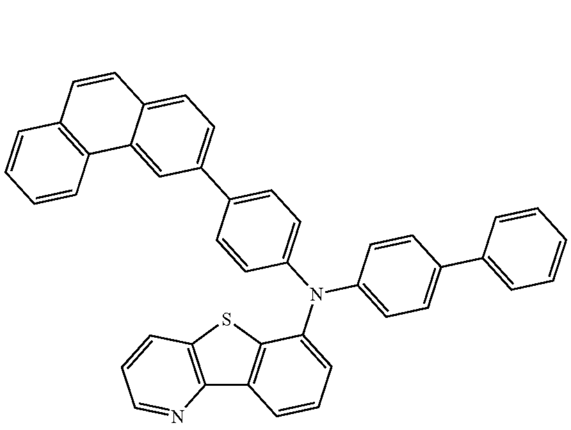

-continued
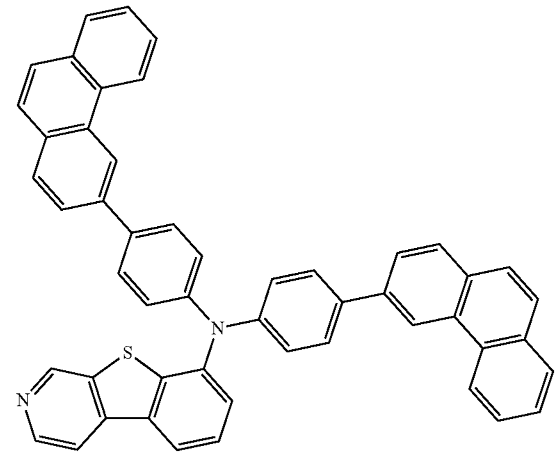
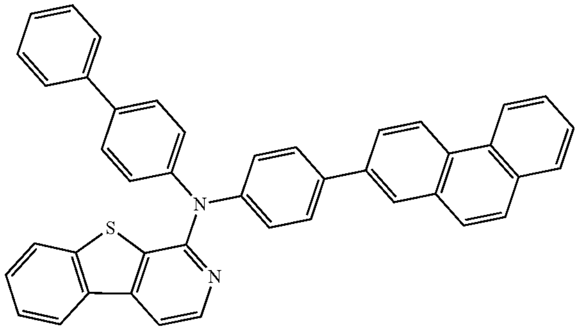
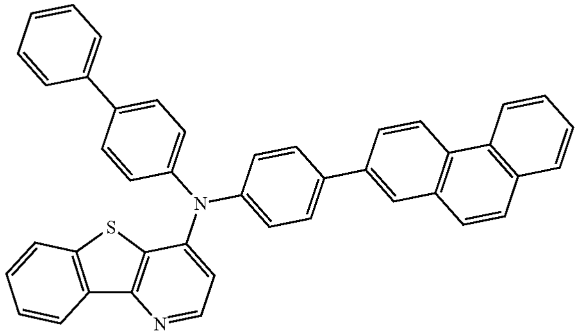
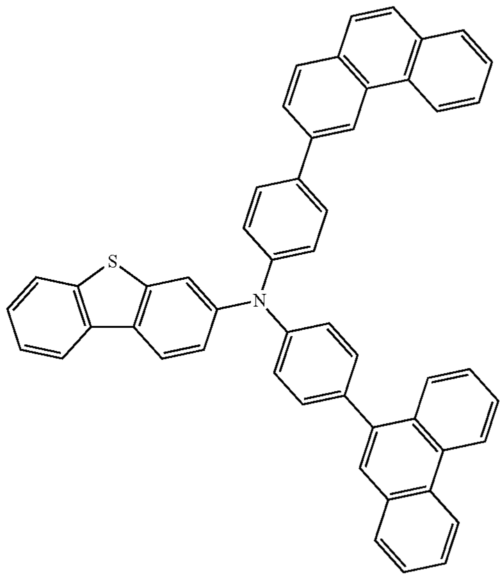
-continued
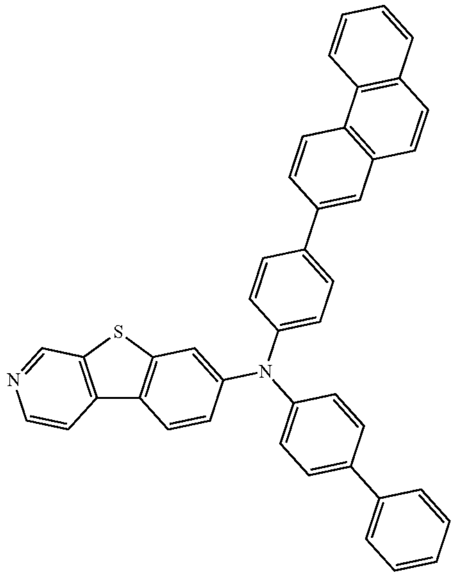
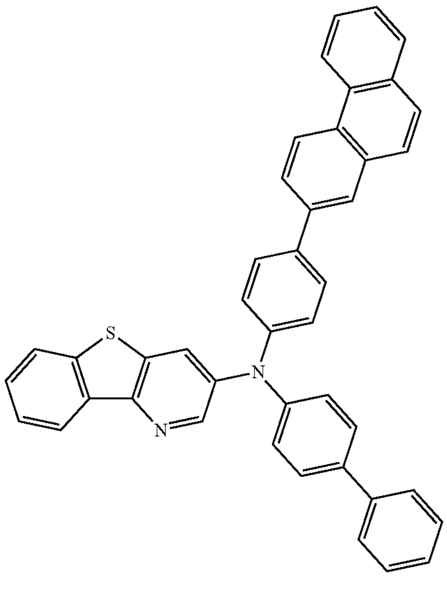
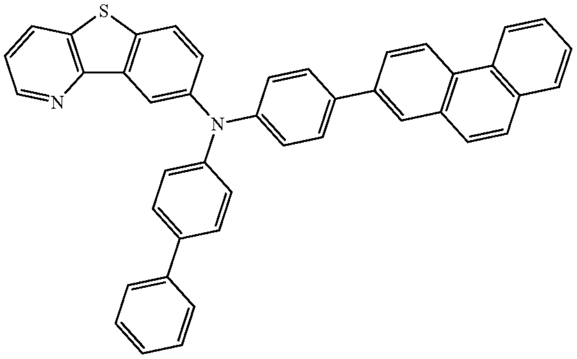

-continued
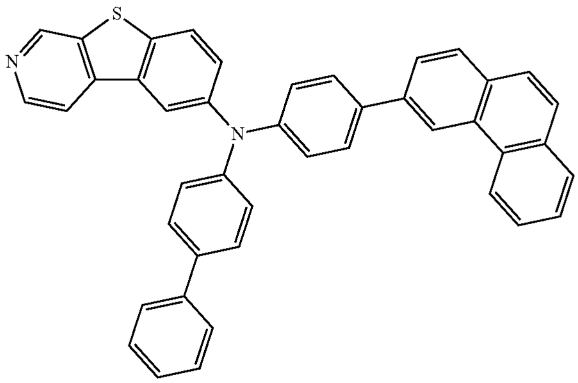
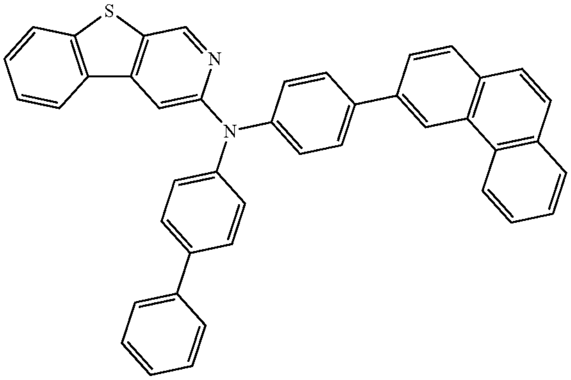
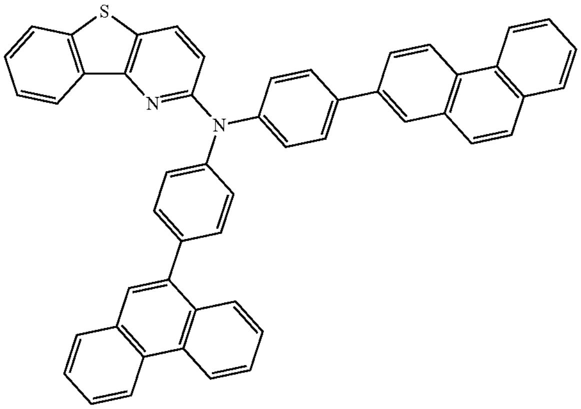
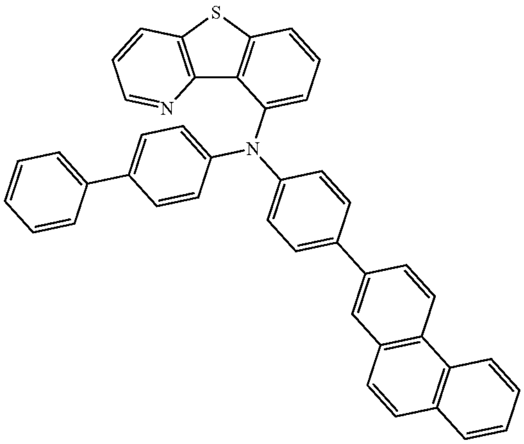
-continued
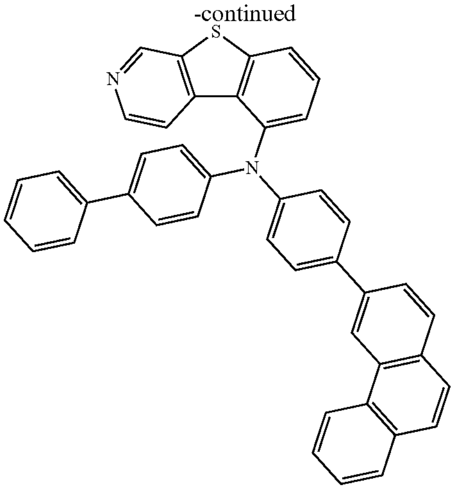
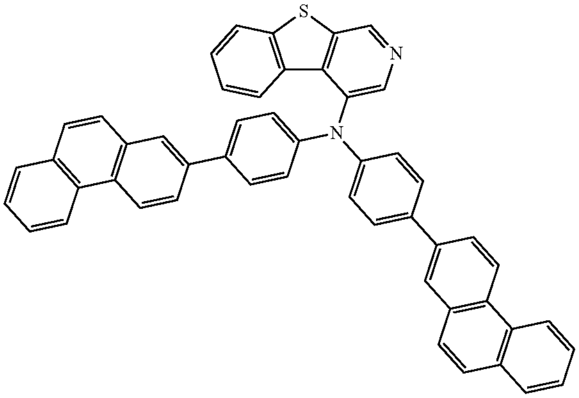
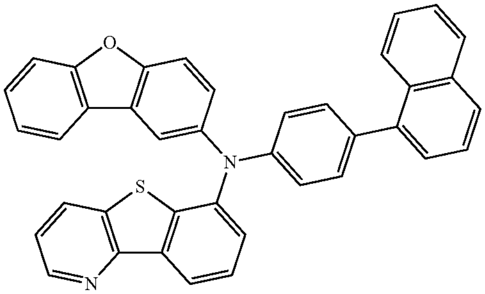
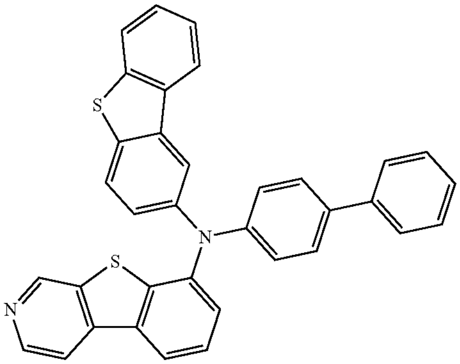

-continued
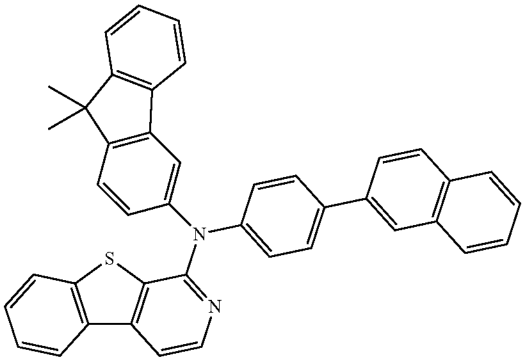
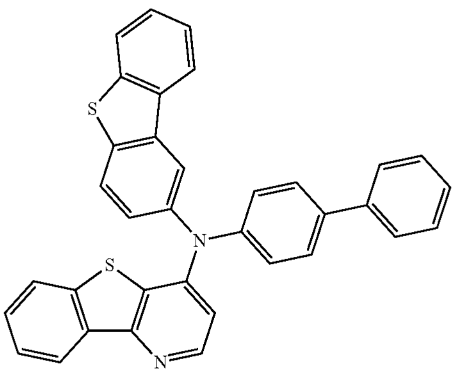
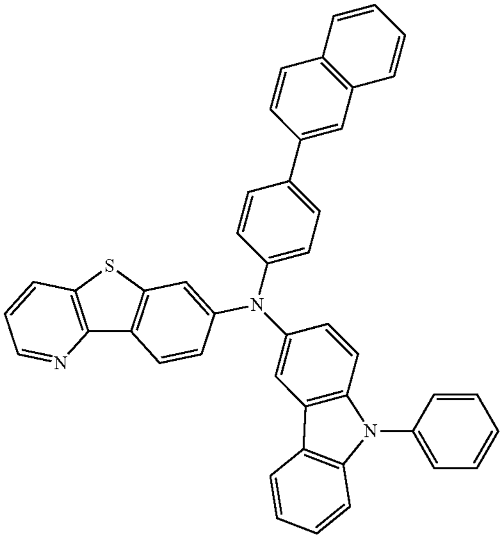
-continued
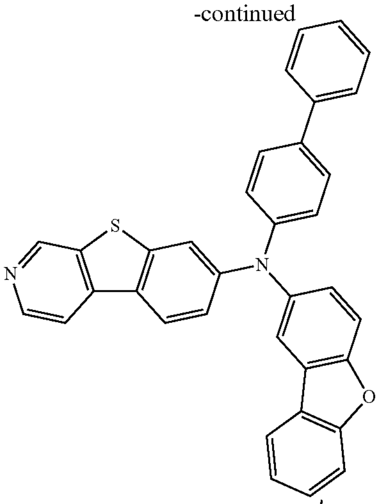
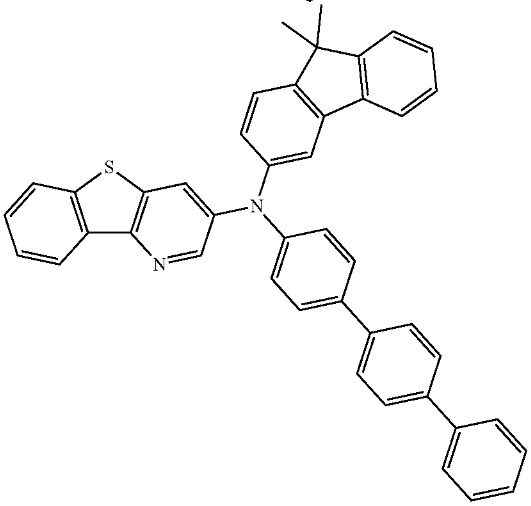
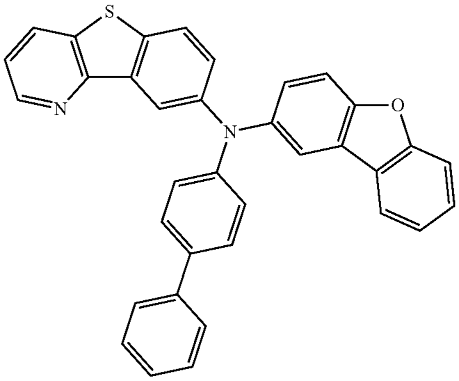
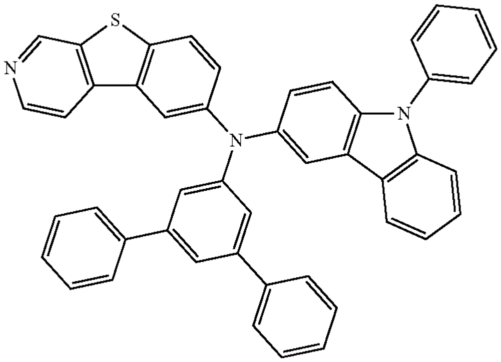

-continued
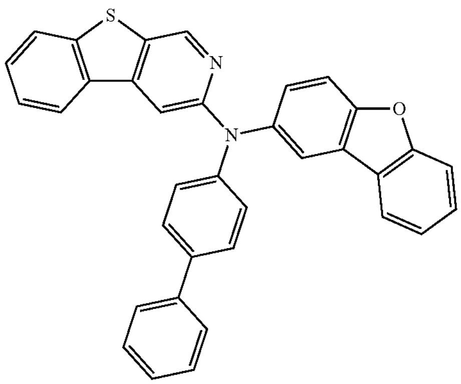
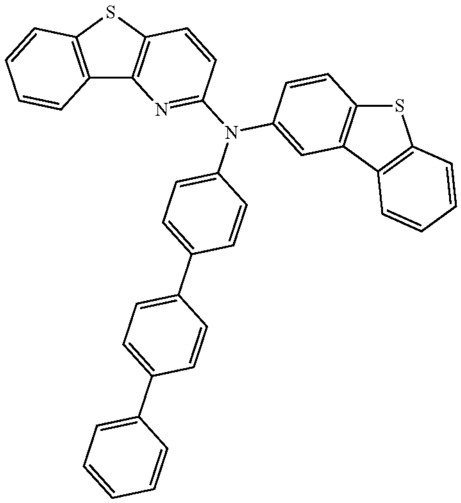
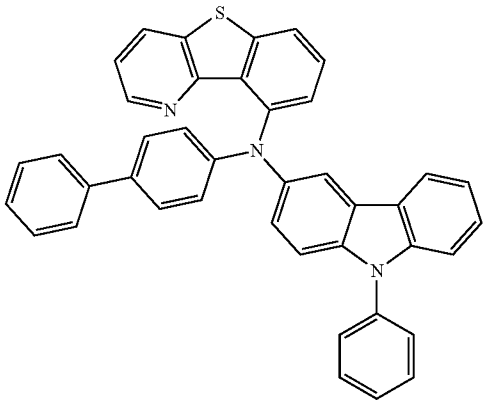
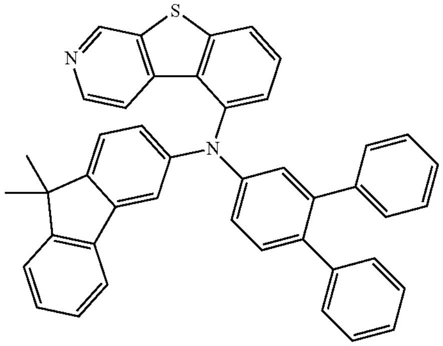
-continued
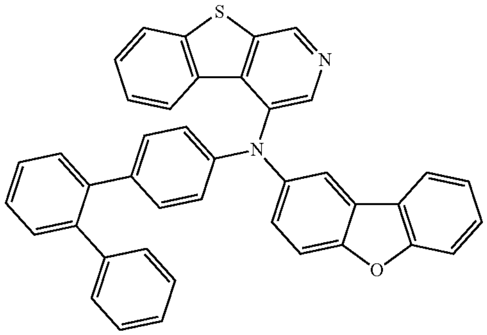
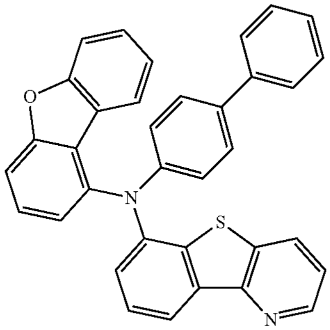
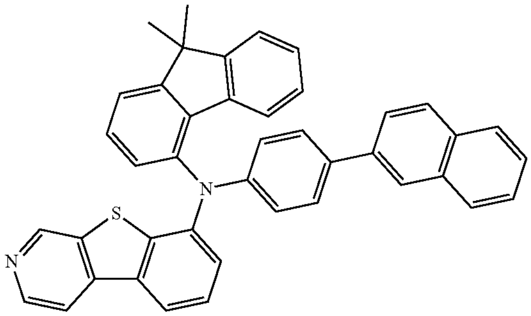
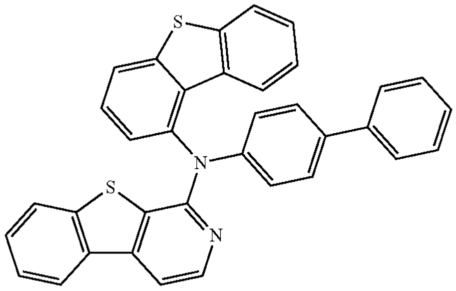
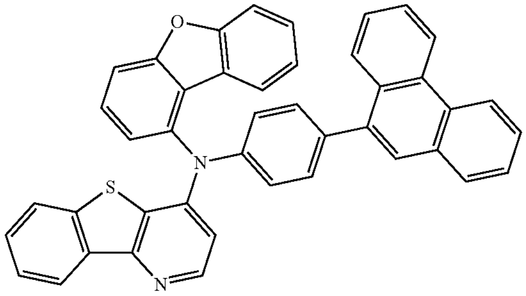

-continued
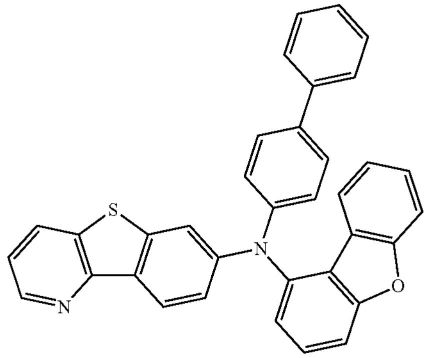
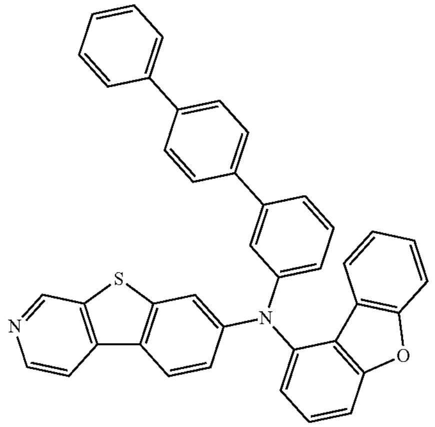
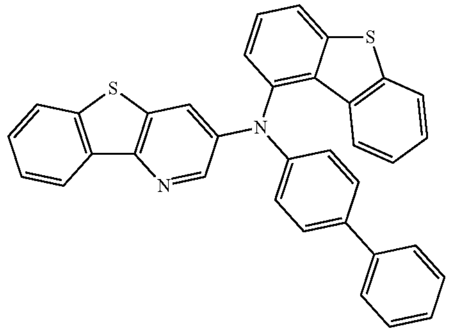
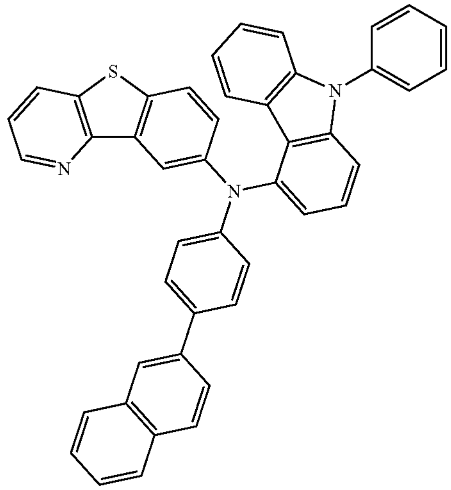
-continued
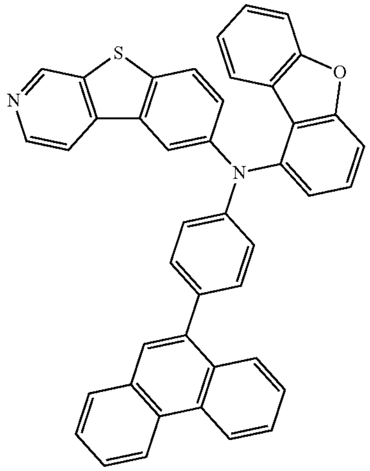
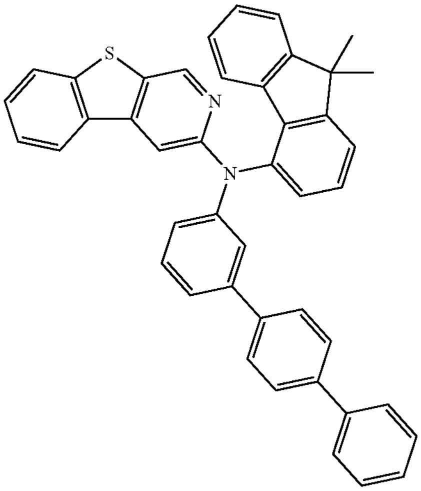
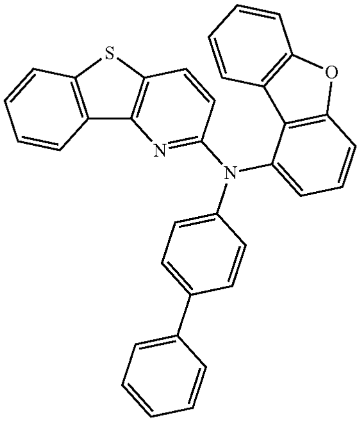
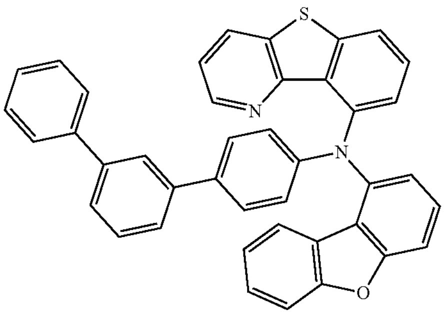

-continued
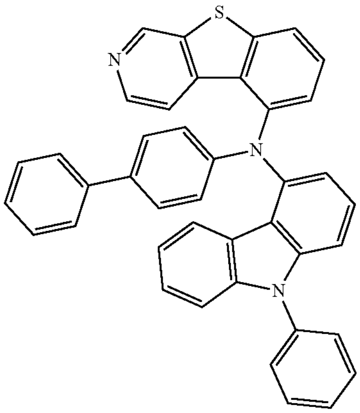
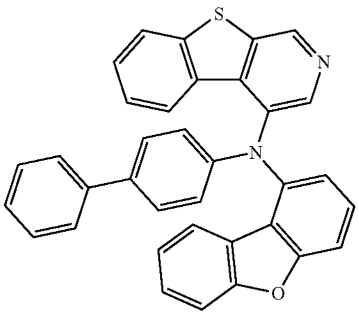
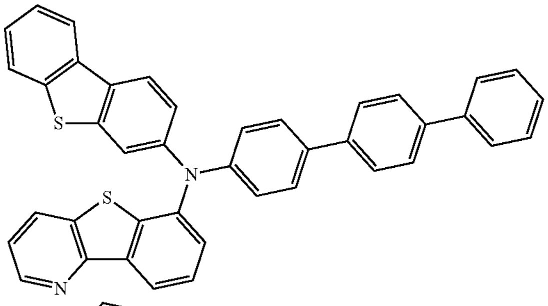
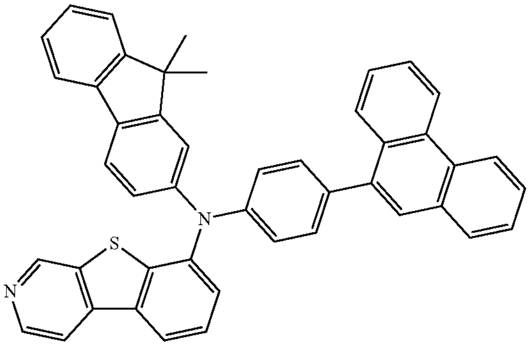
-continued
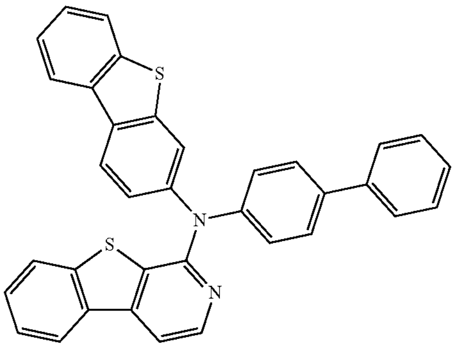
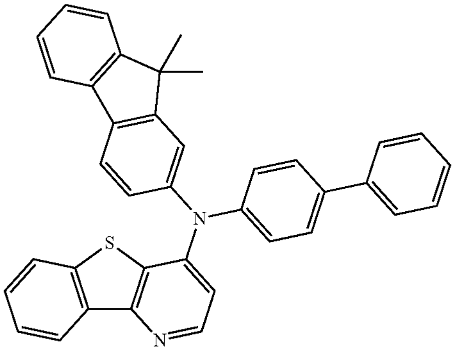
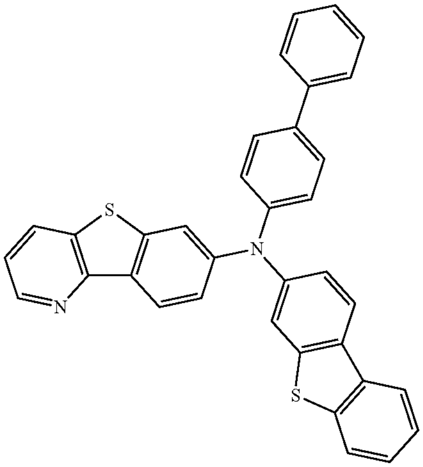
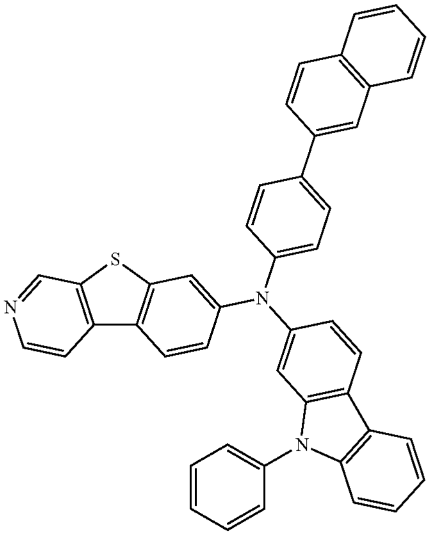

-continued
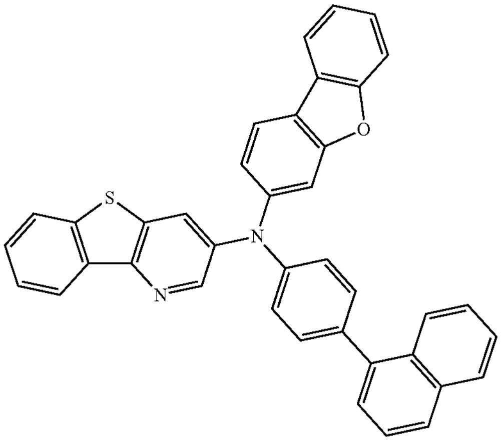
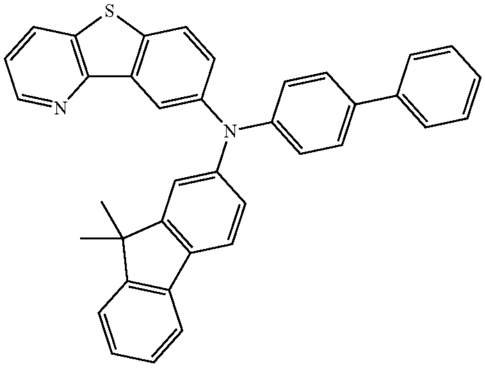
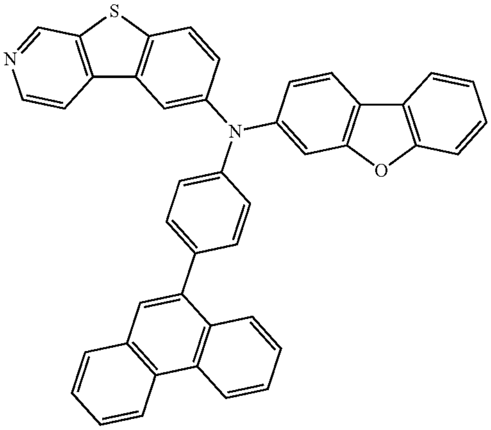
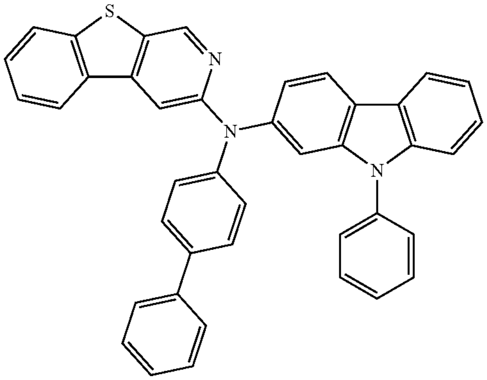
-continued
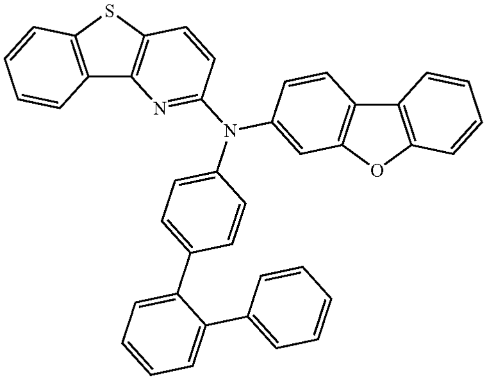
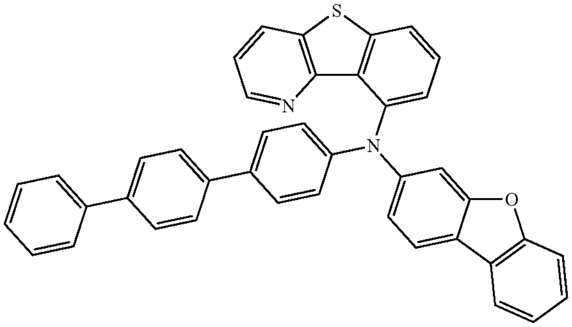
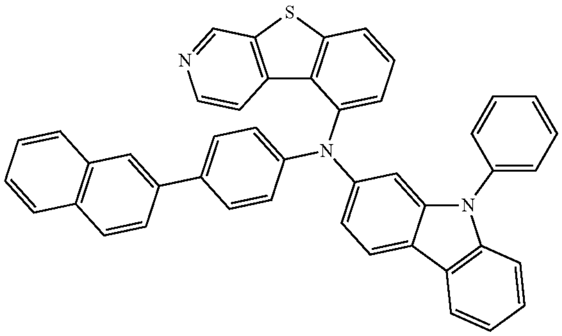
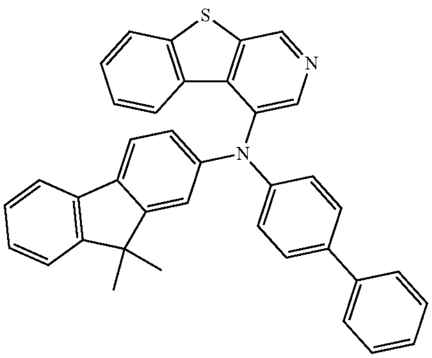

-continued
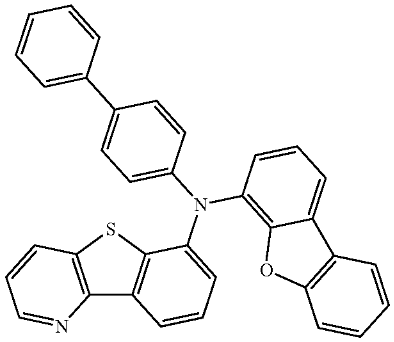
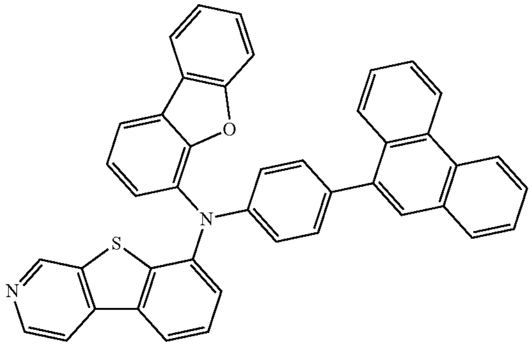
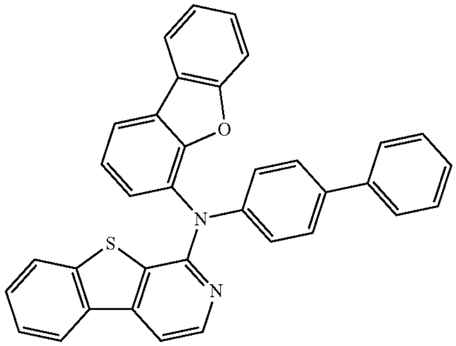
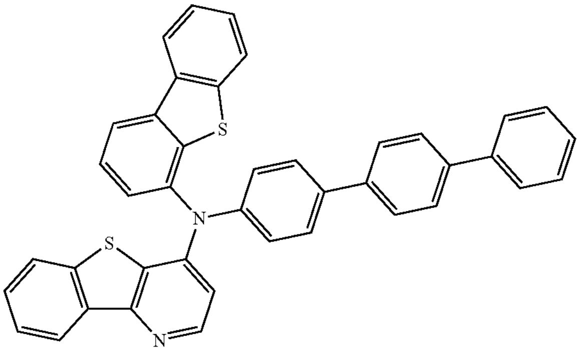
-continued
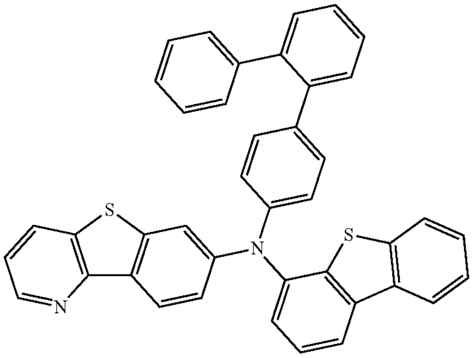
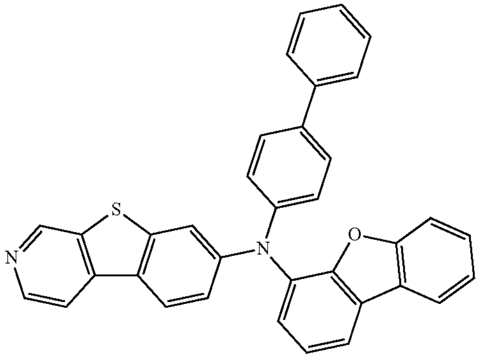
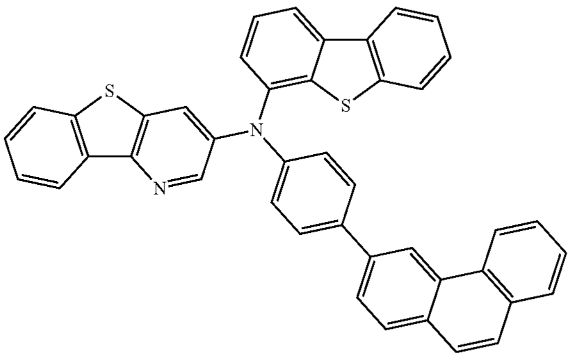
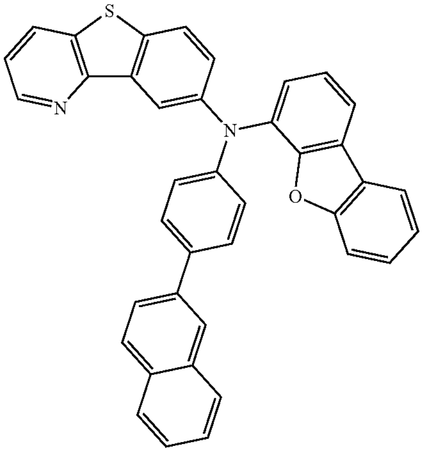

-continued
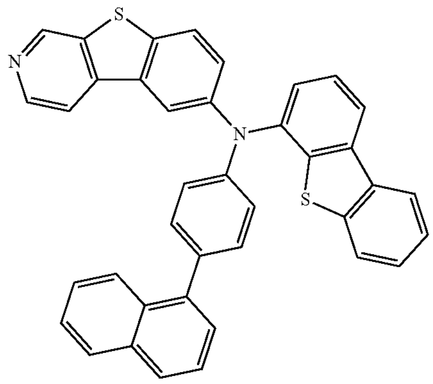
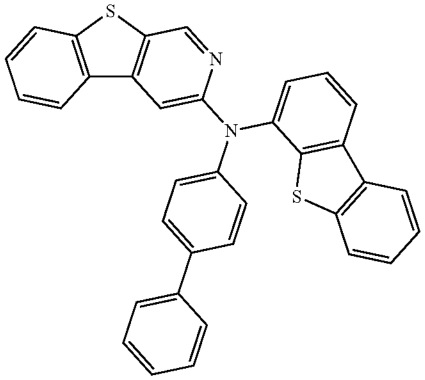
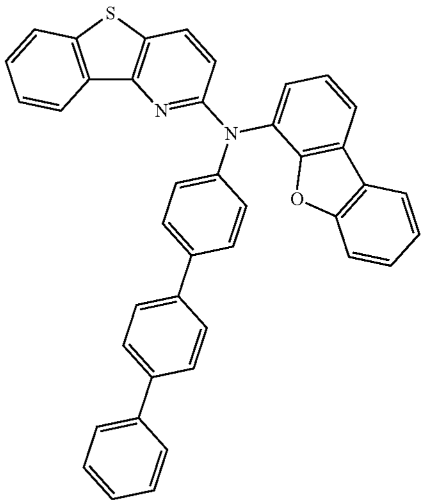
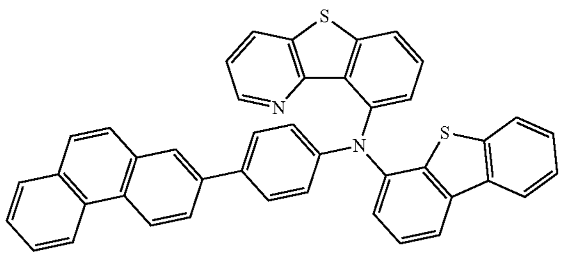
-continued
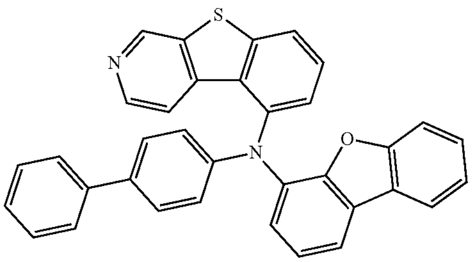
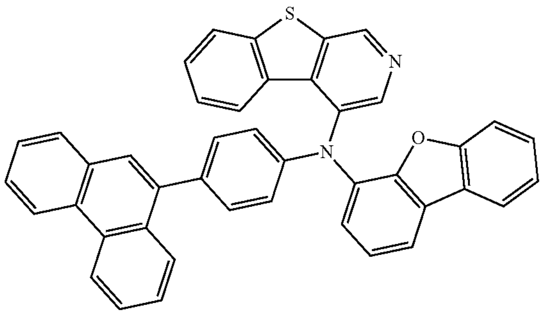
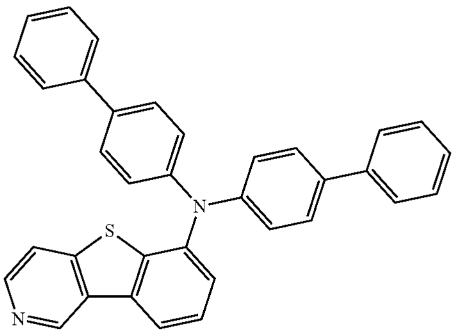
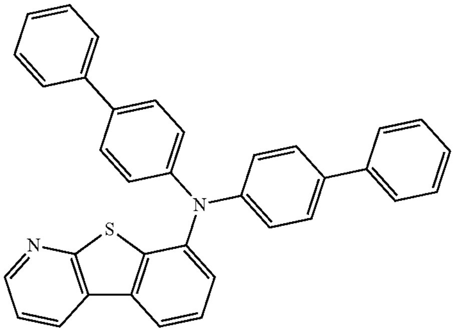
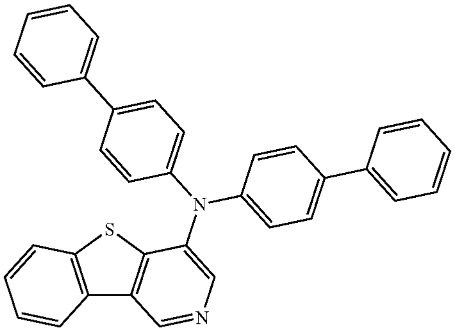

-continued
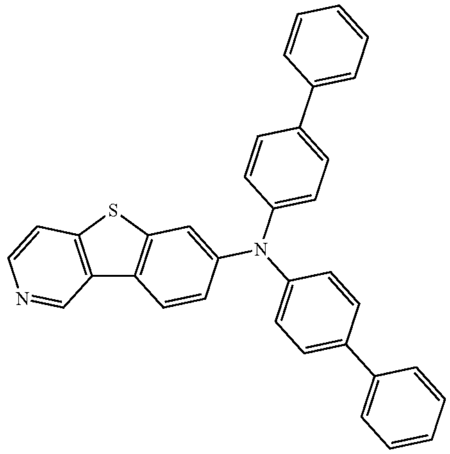
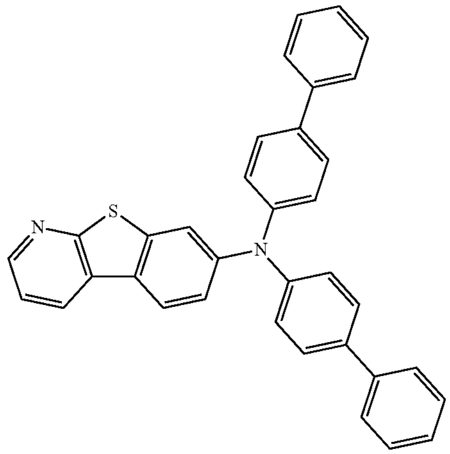
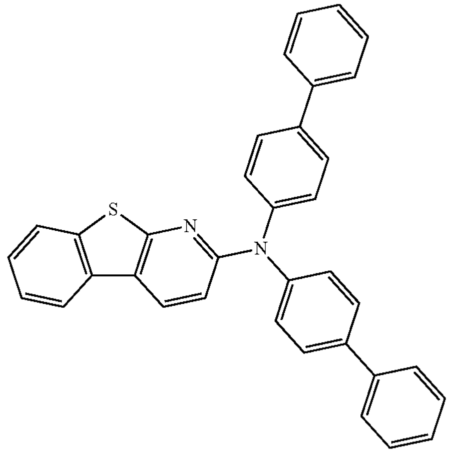
-continued
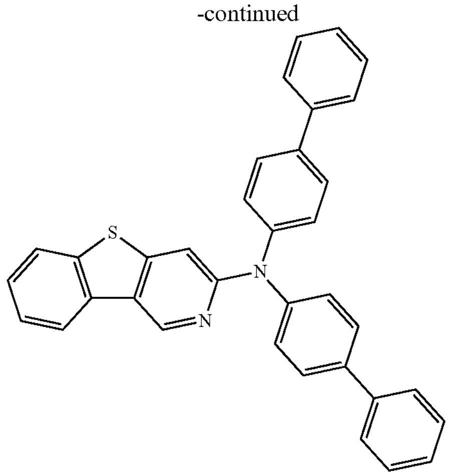
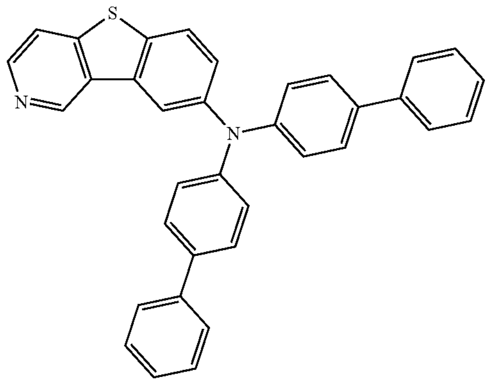
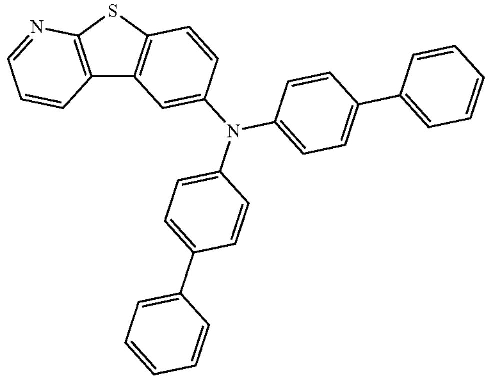
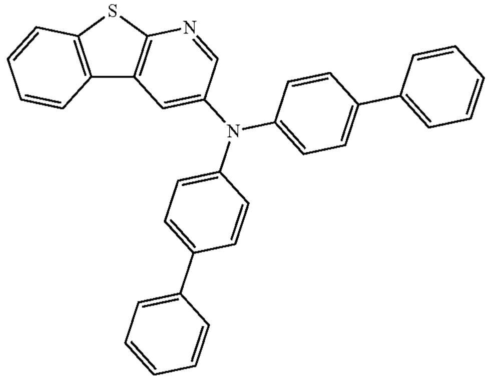

-continued
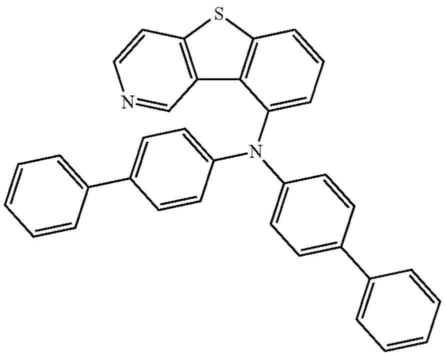
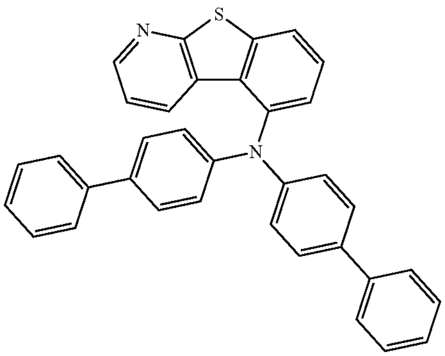
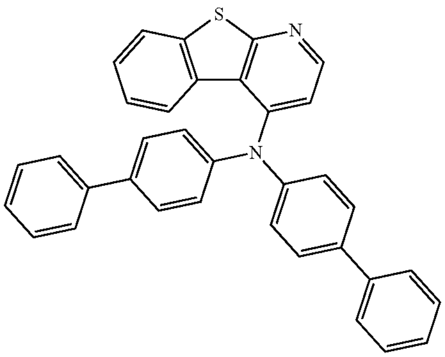
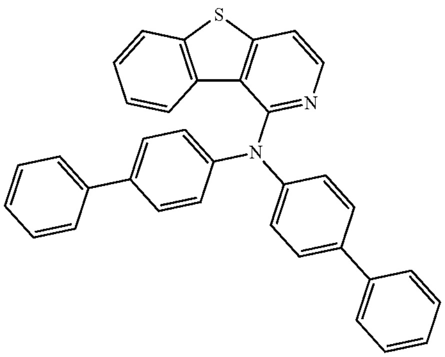
-continued
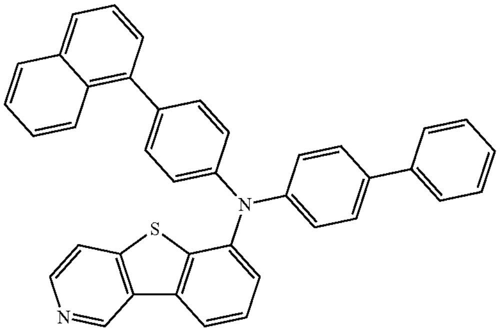
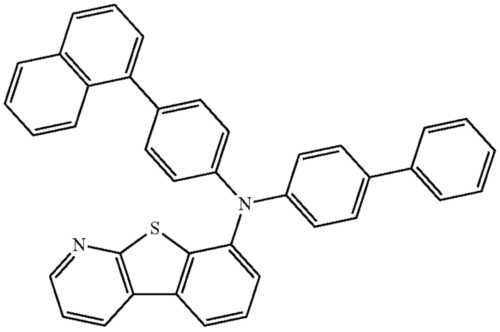
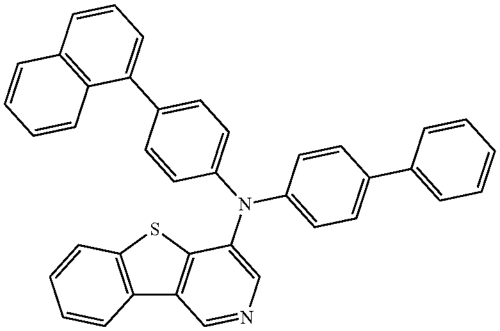
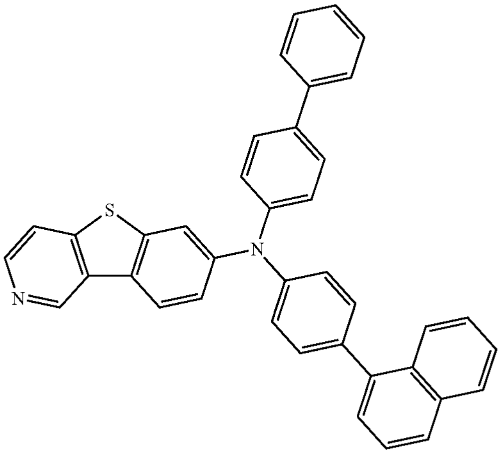

-continued
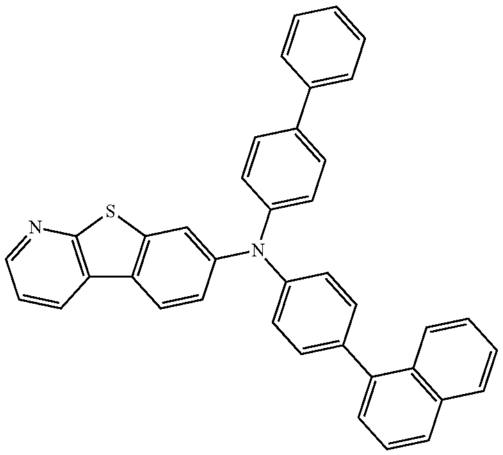
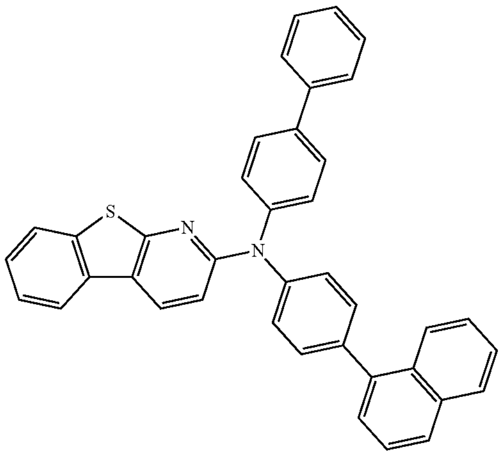
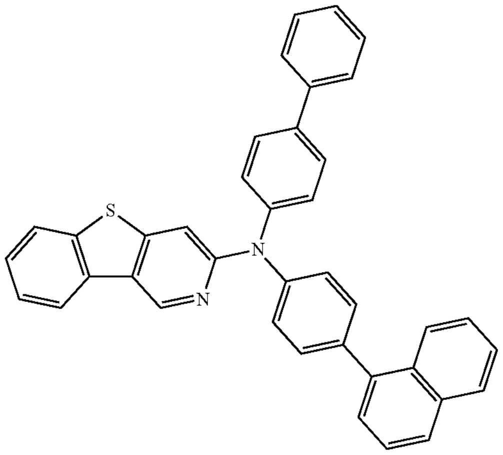
-continued
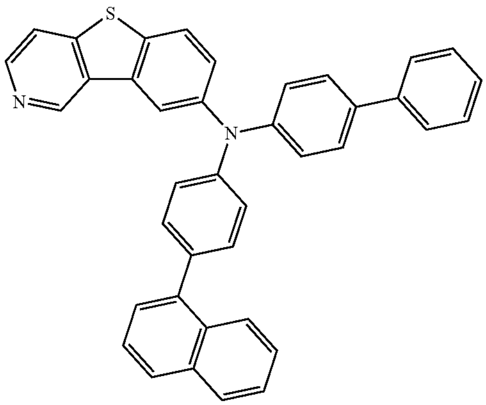
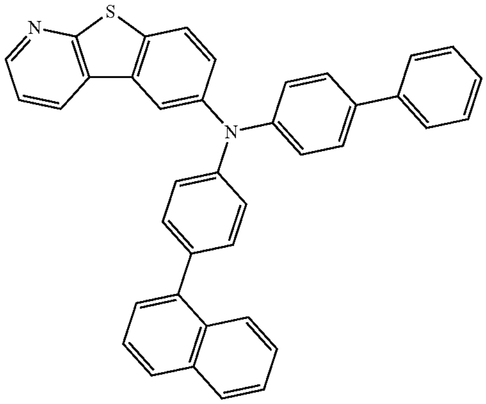
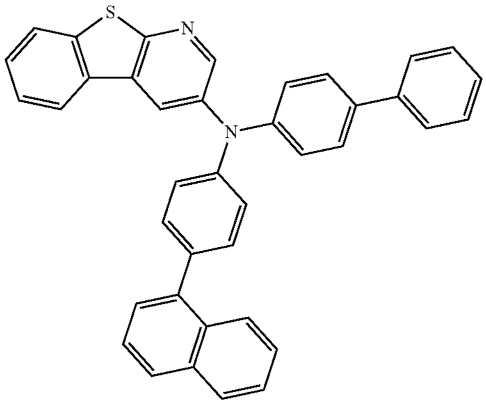
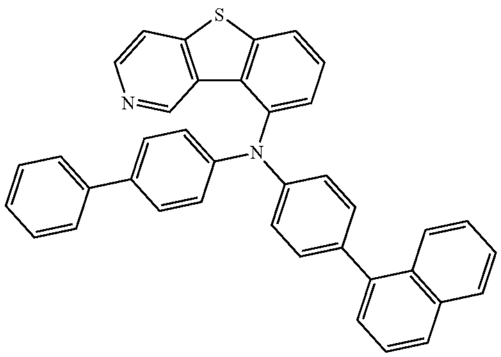

-continued
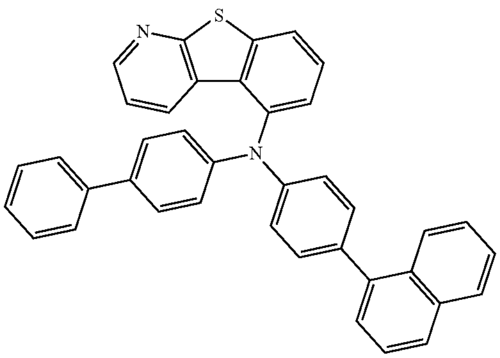
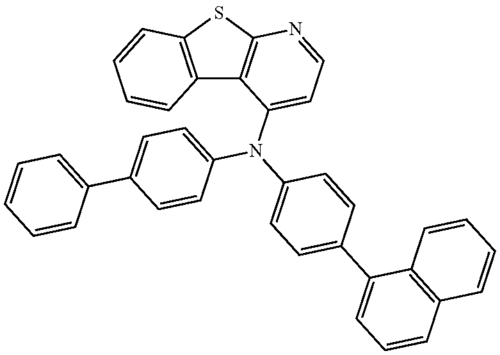
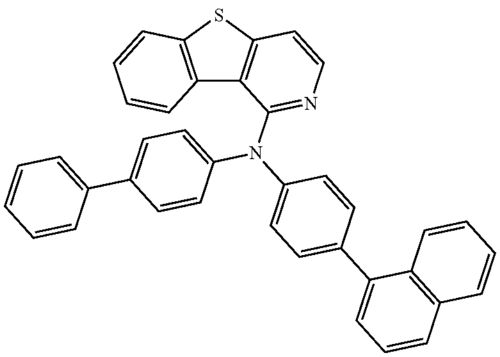
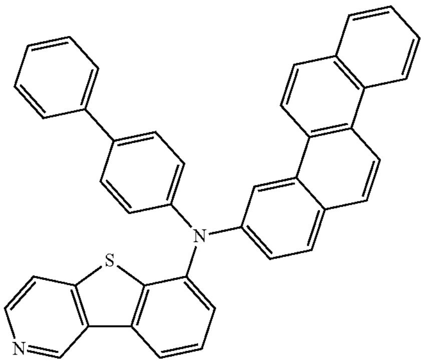
-continued
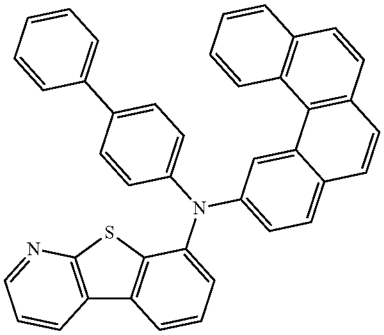
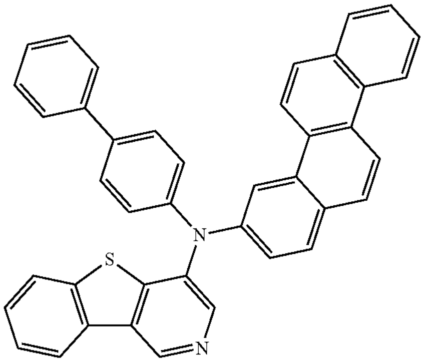
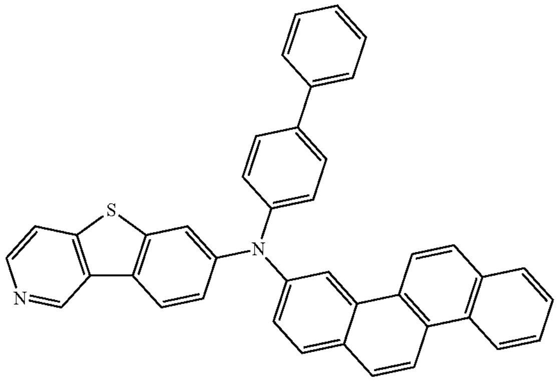
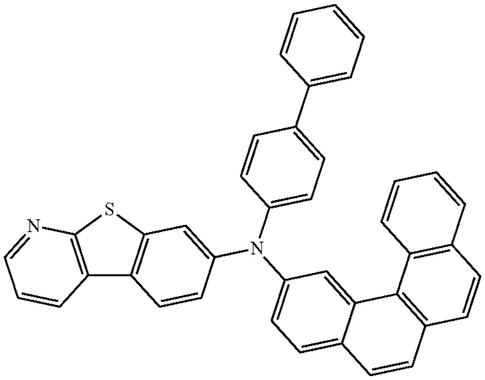

-continued
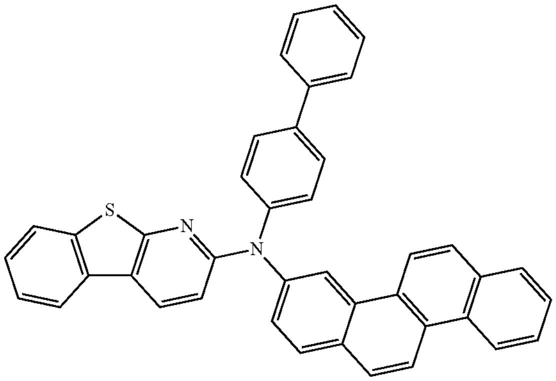
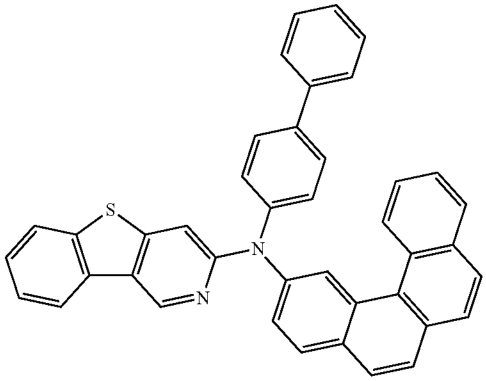
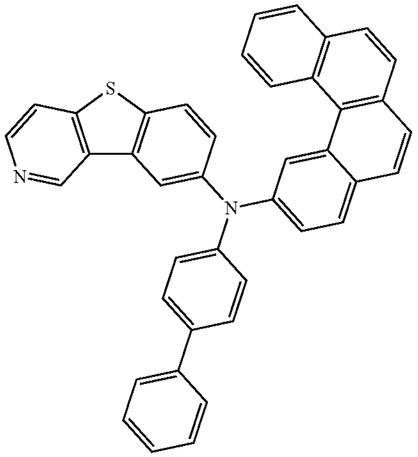
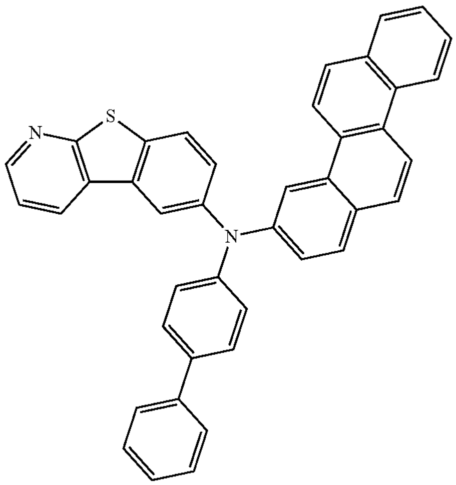
-continued
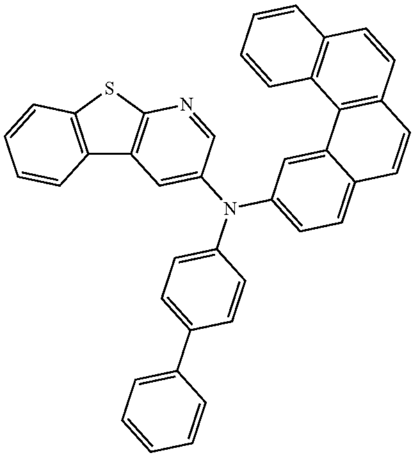
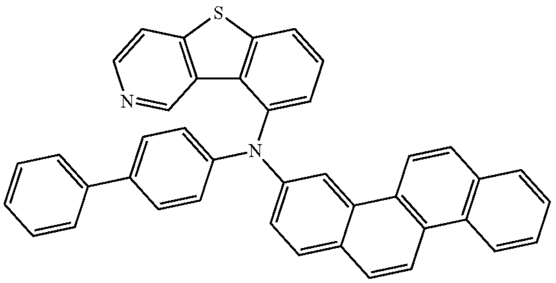
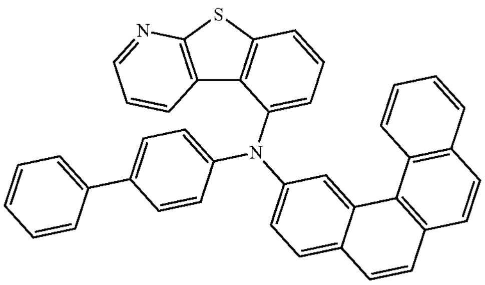
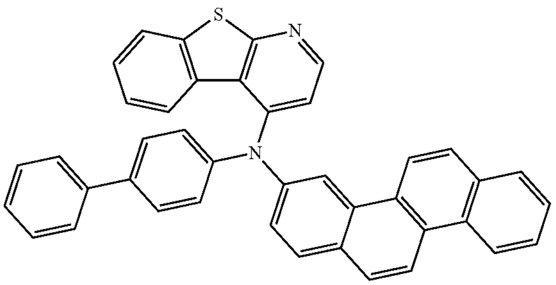
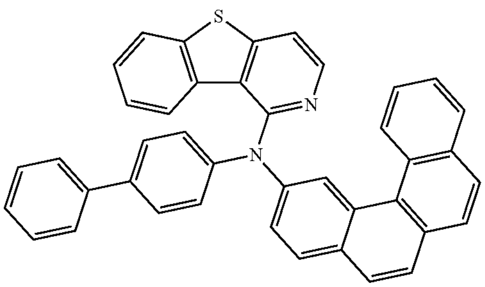

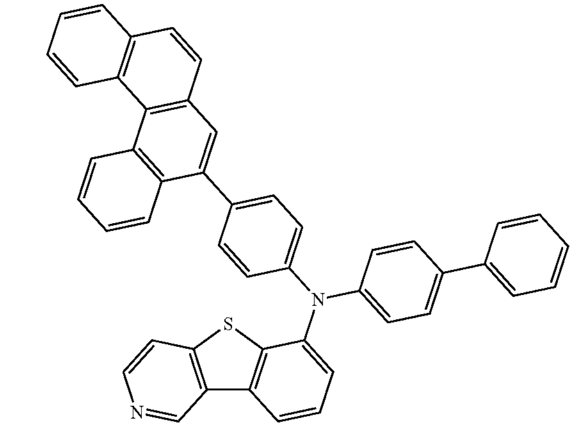
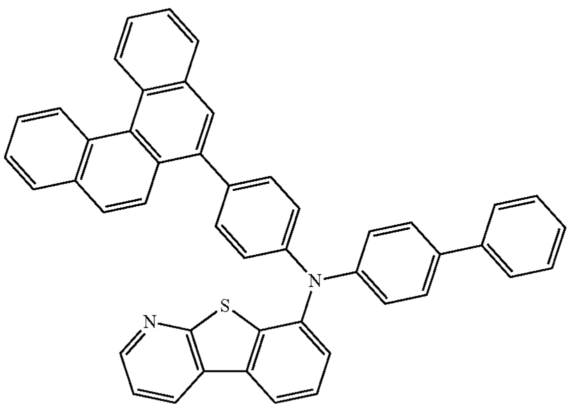
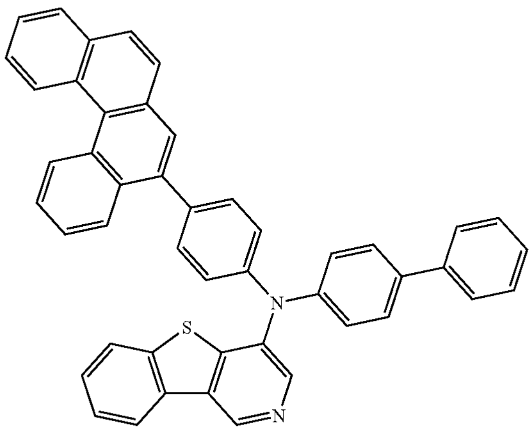
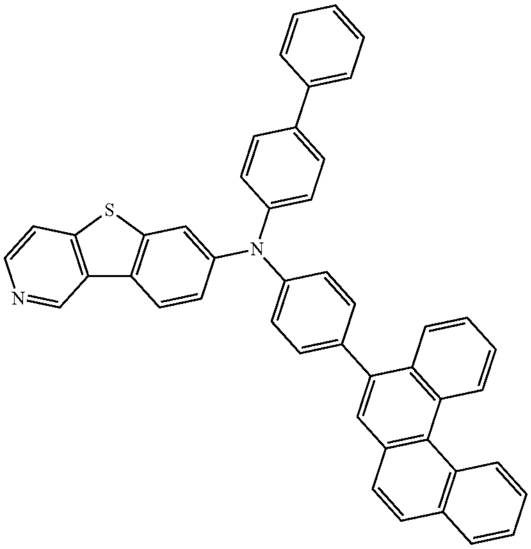
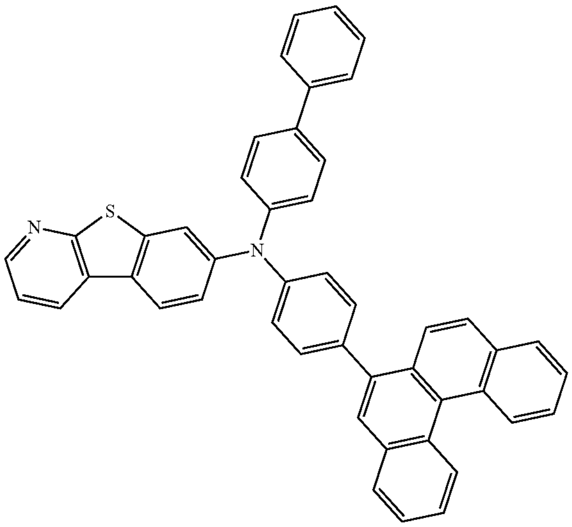
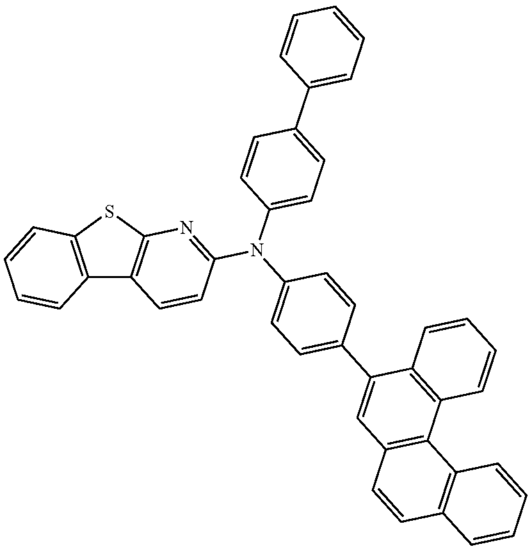

-continued
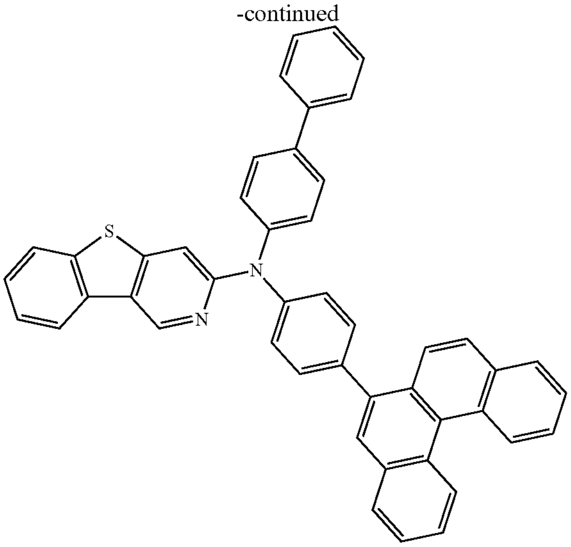
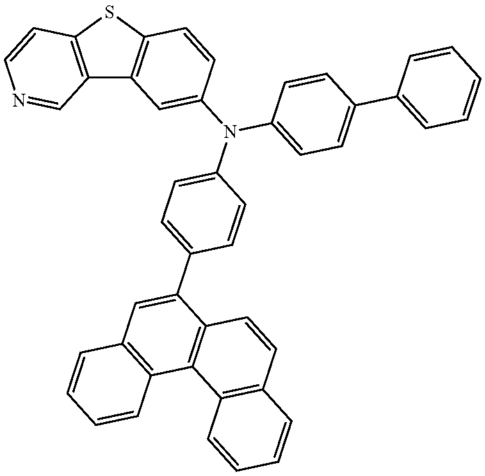
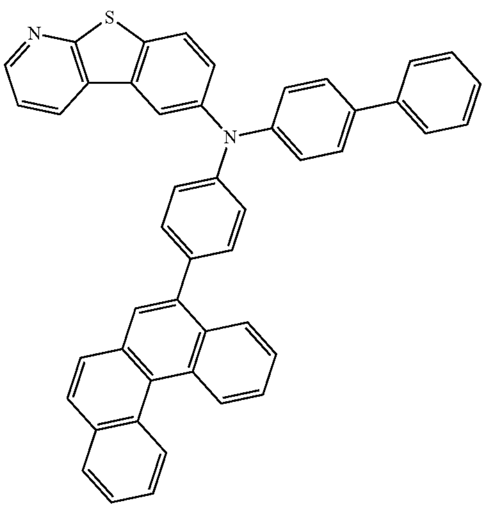
-continued
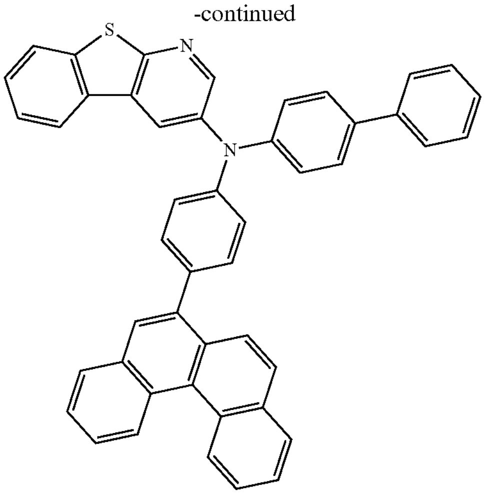
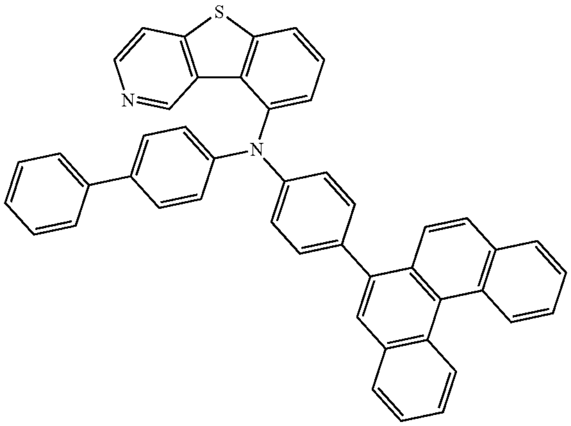
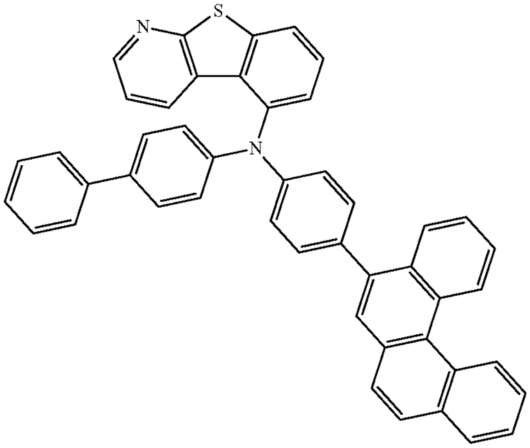

-continued
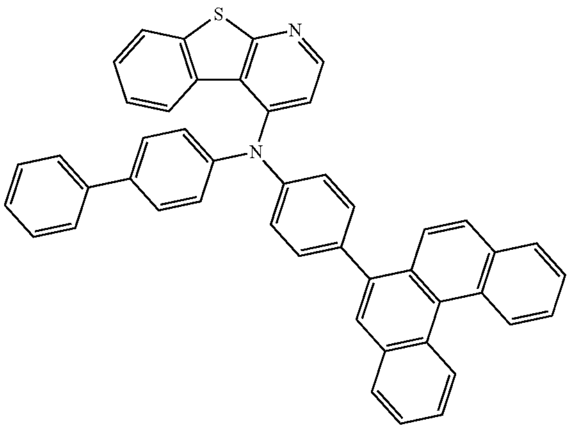
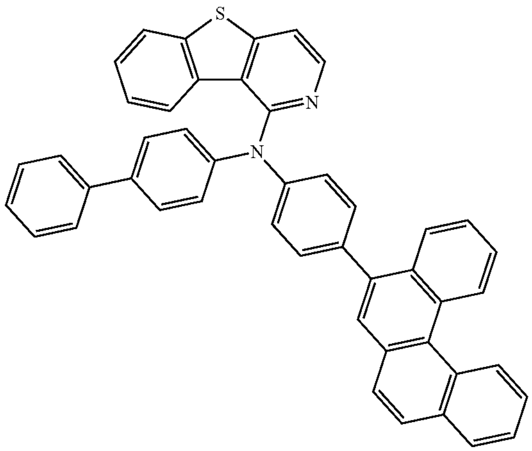
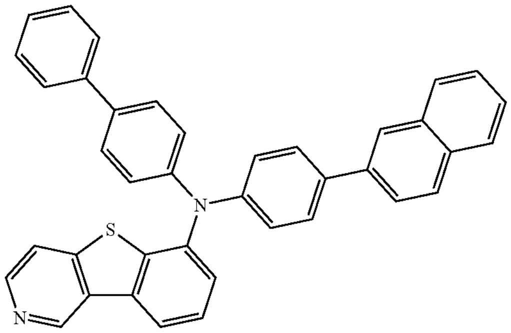
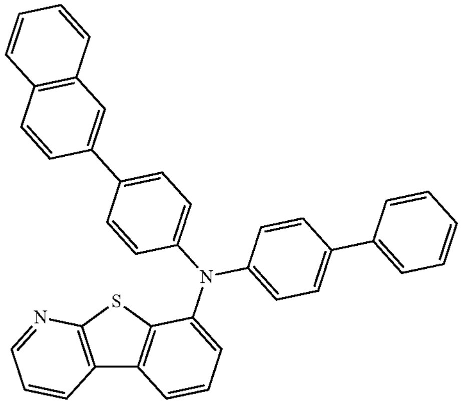
-continued
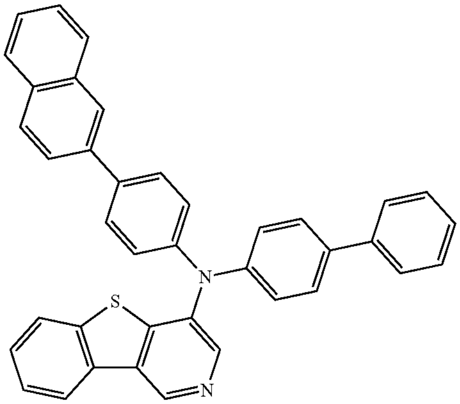
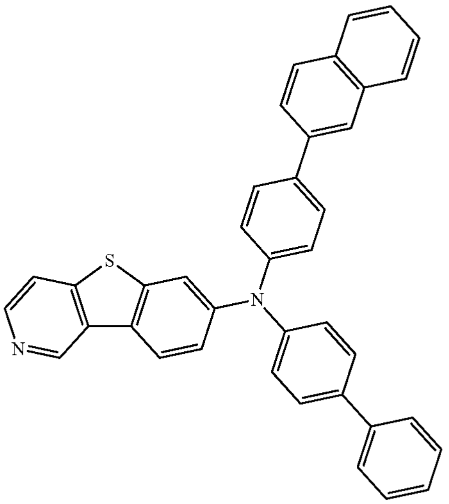
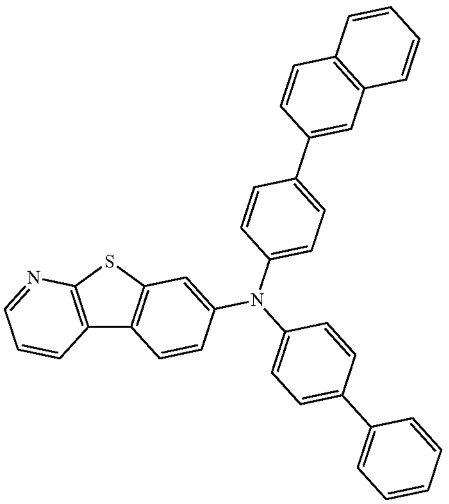

-continued
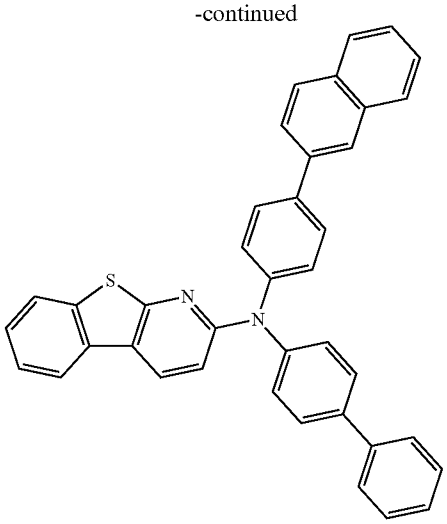
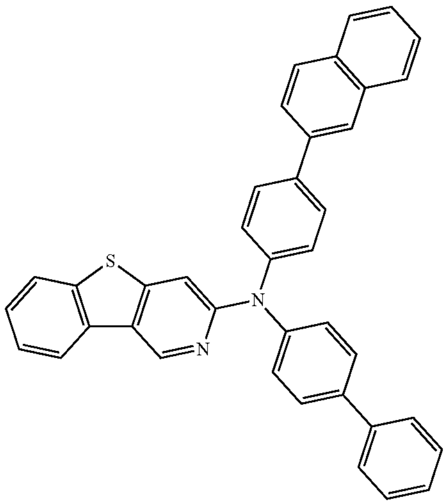
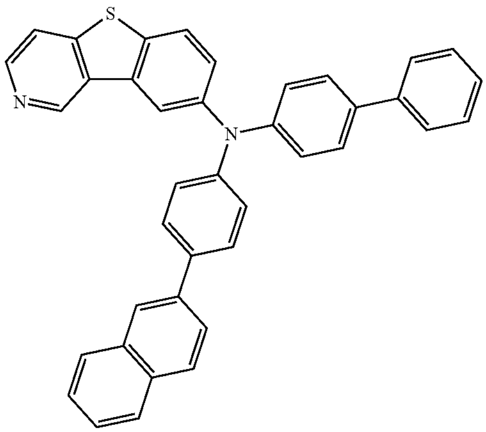
-continued
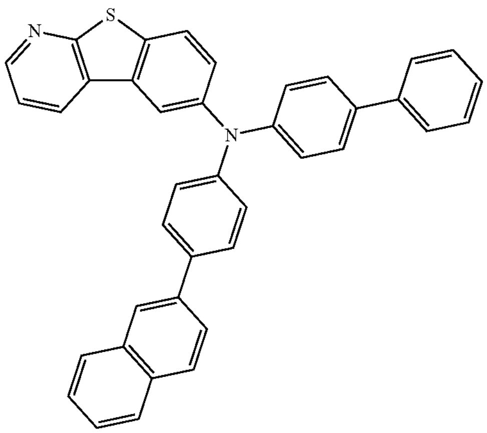
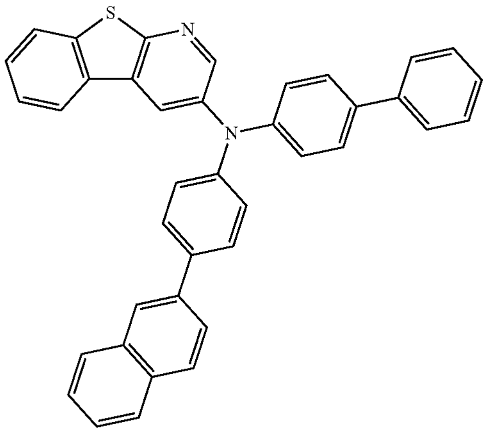
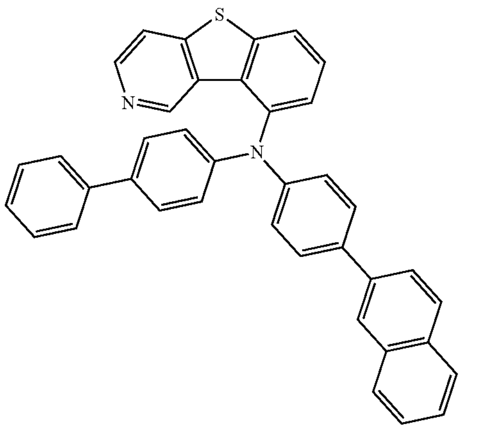
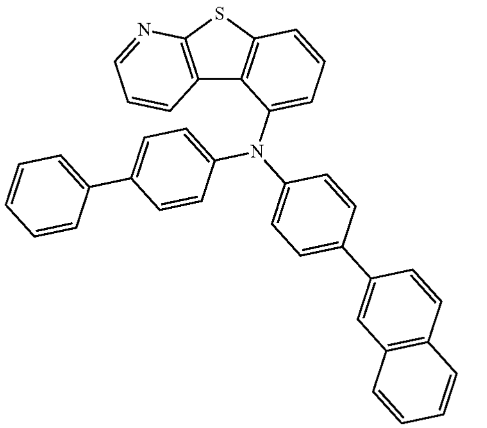

-continued
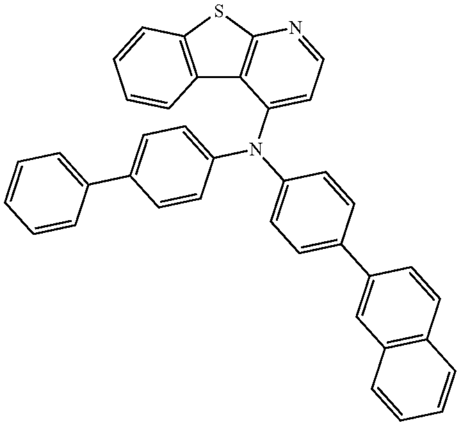
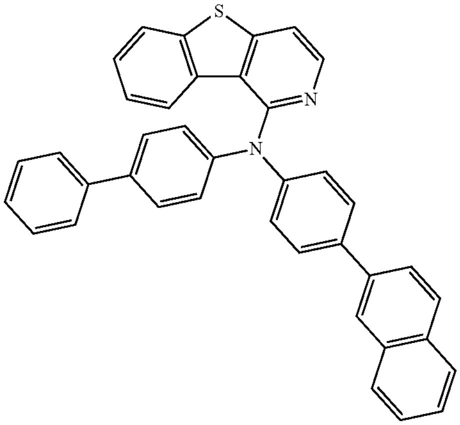
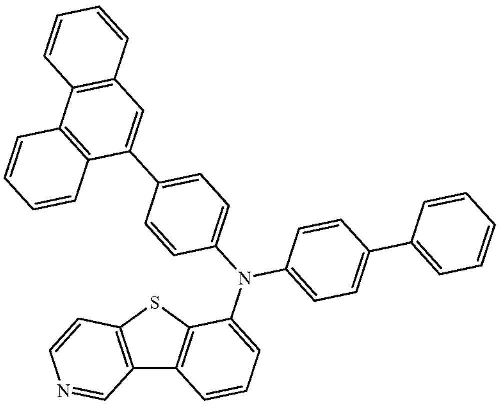
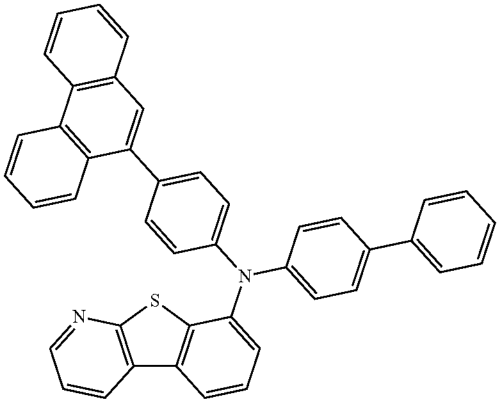
-continued
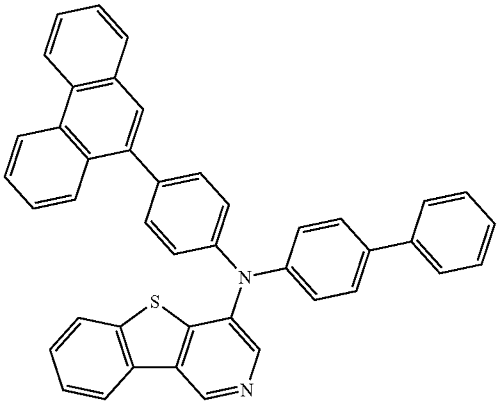
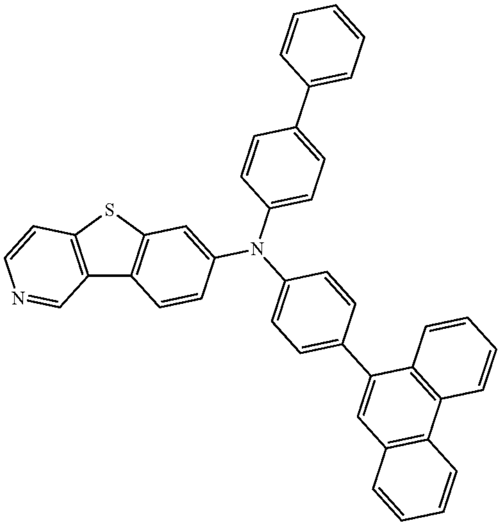
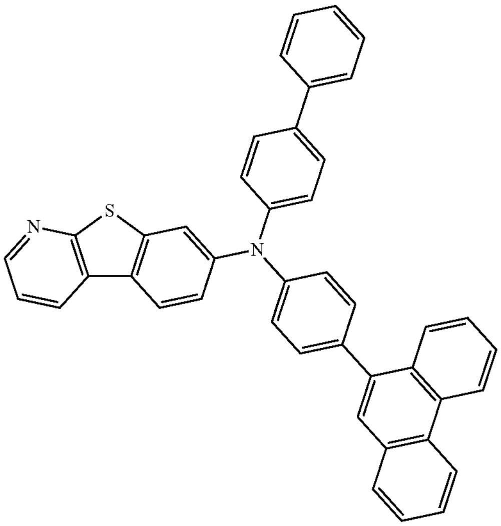

-continued
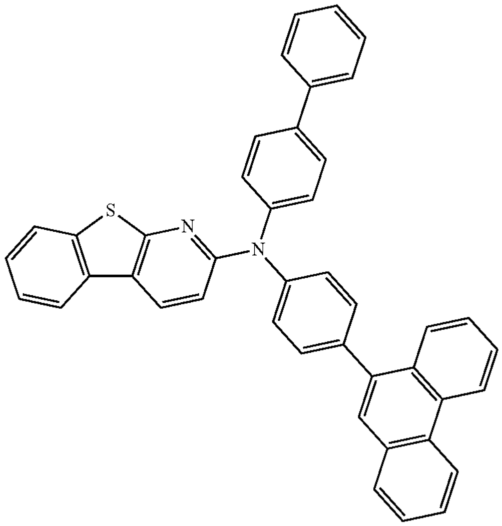
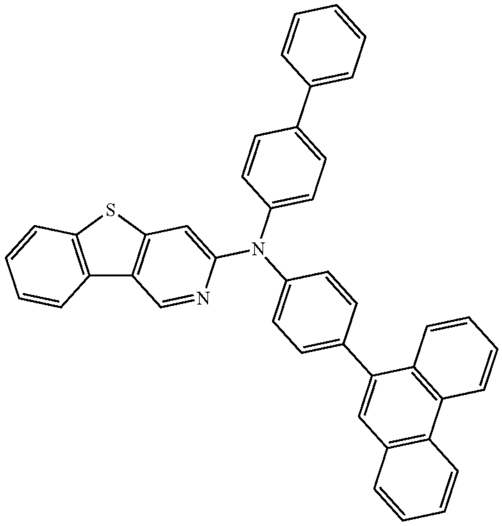
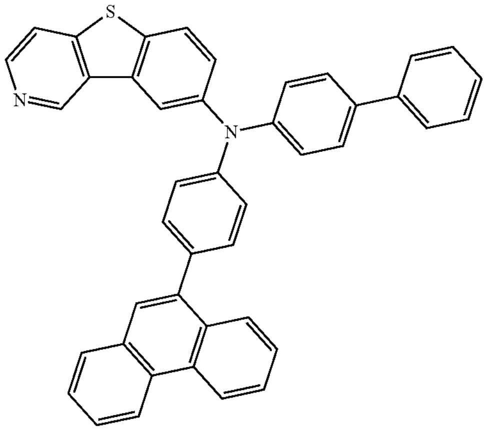
-continued
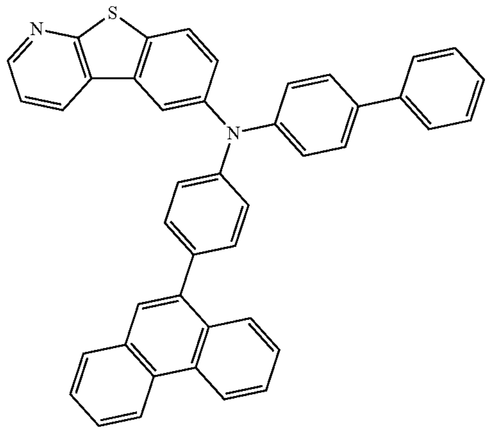
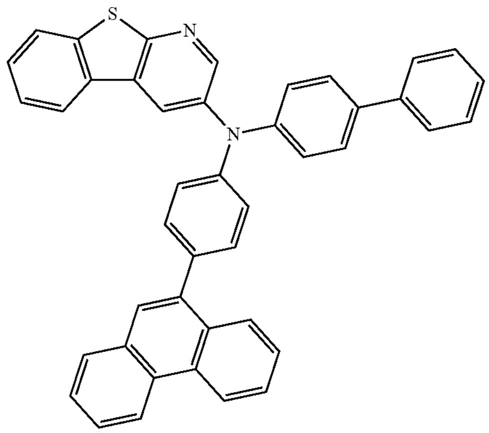
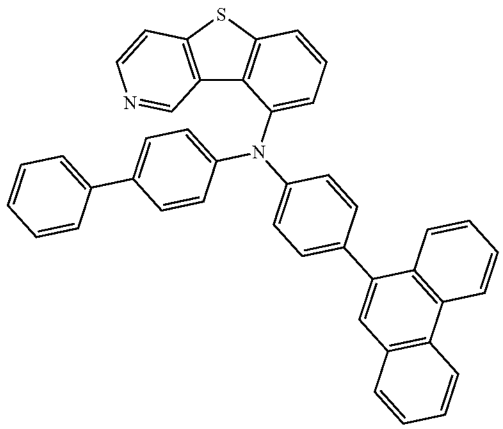
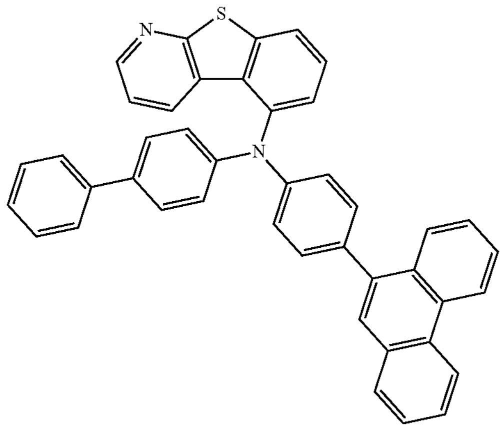

-continued
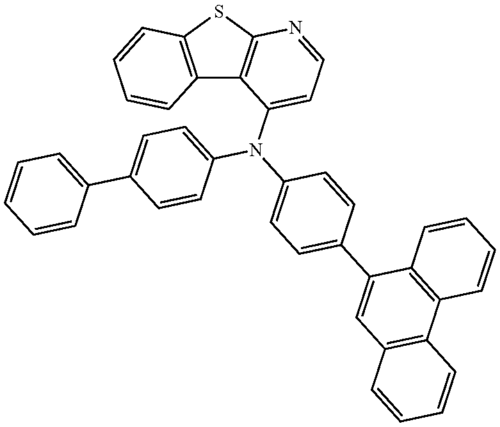
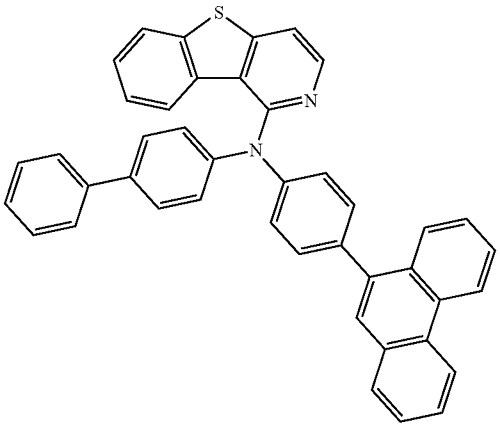
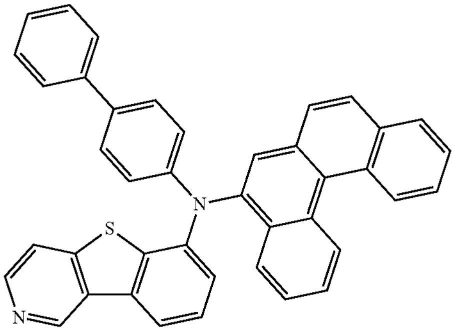
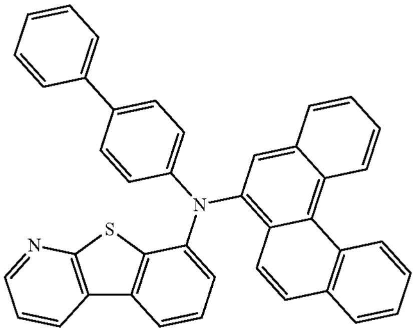
-continued
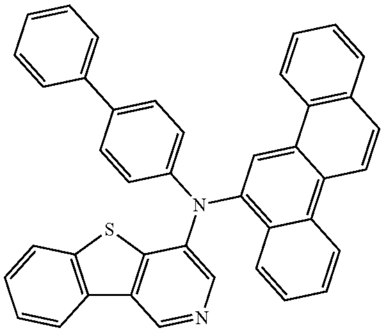
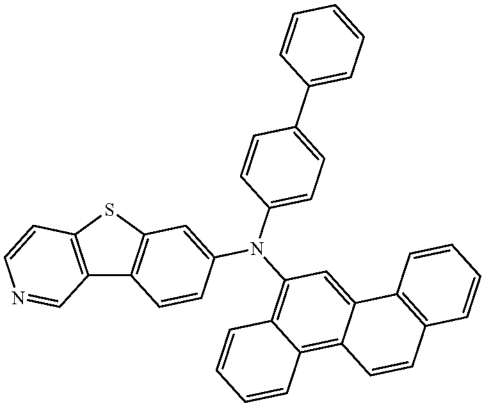
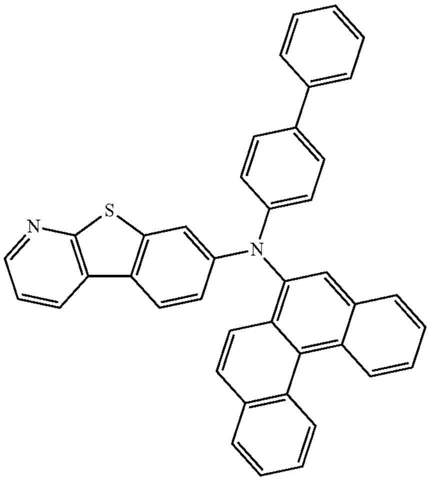
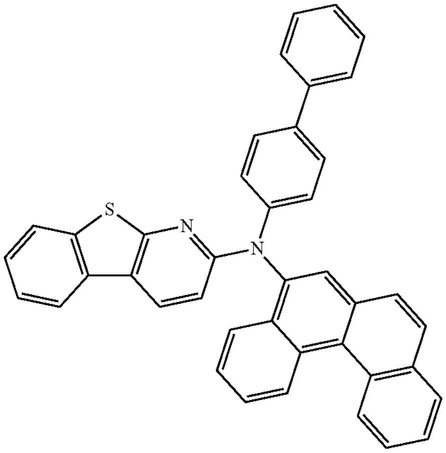

-continued
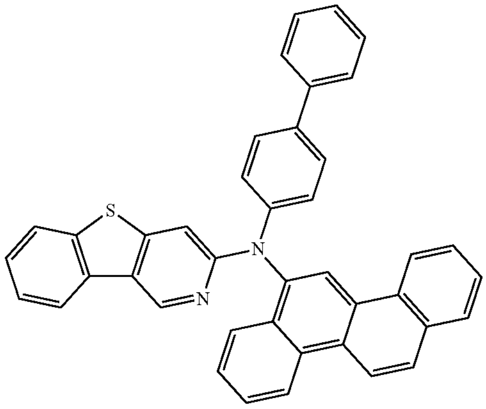
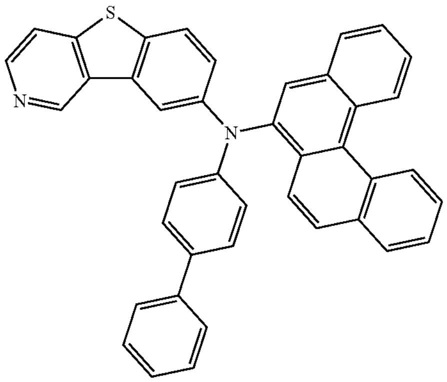
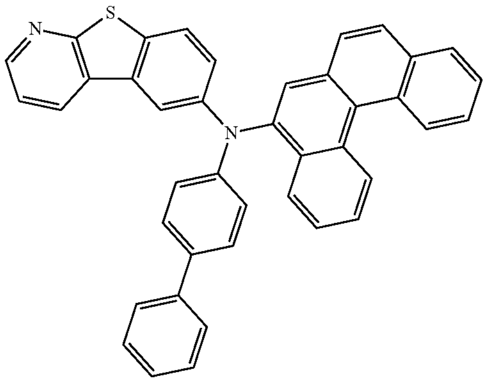
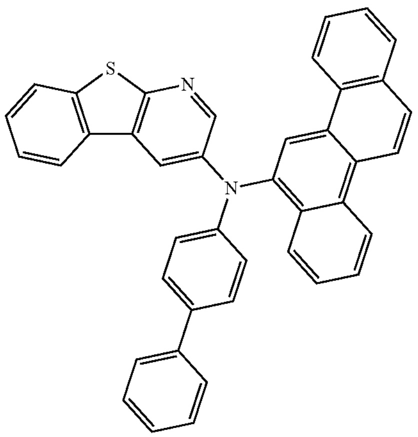
-continued
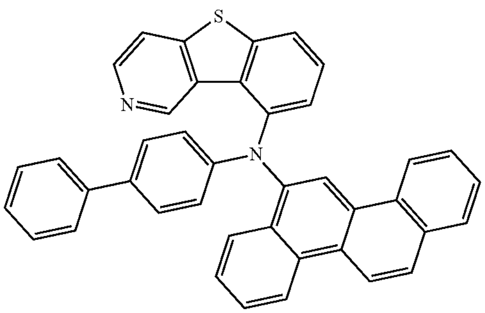
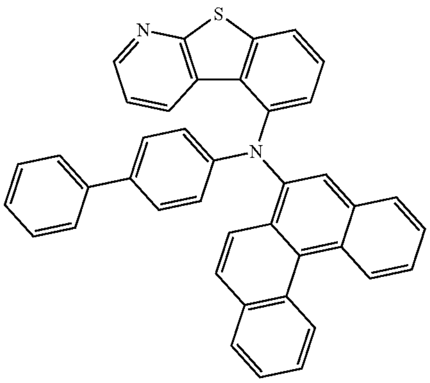
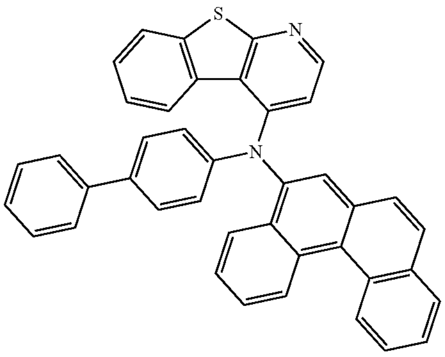
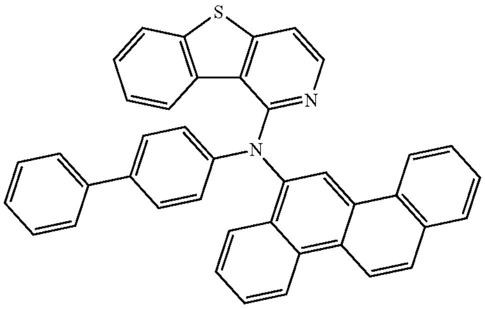
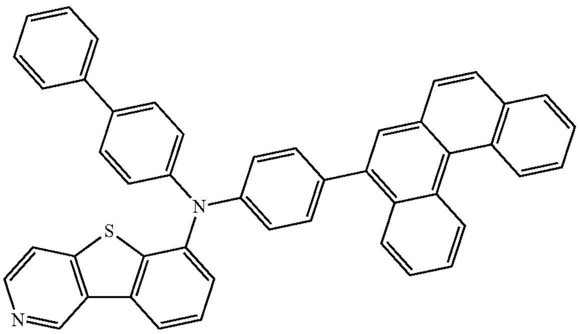

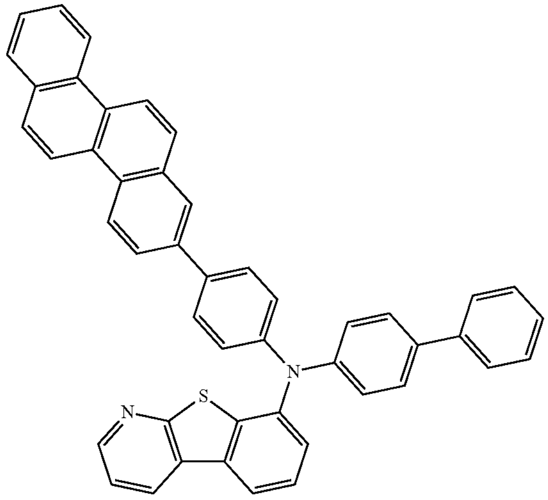
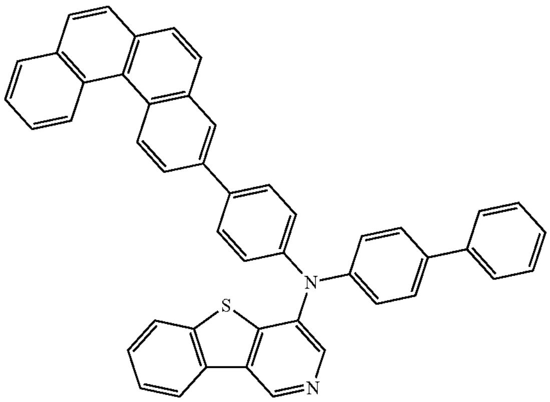
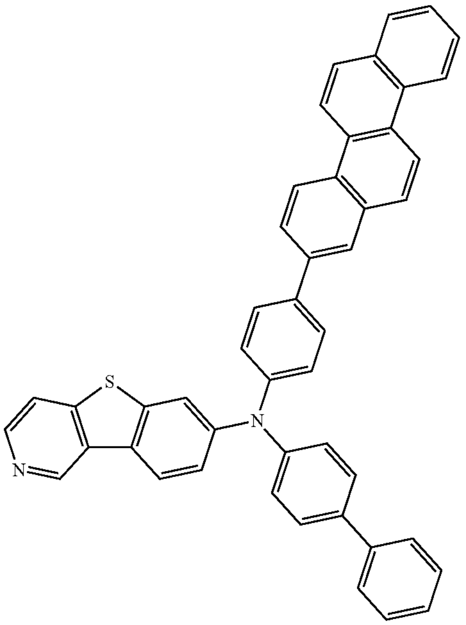
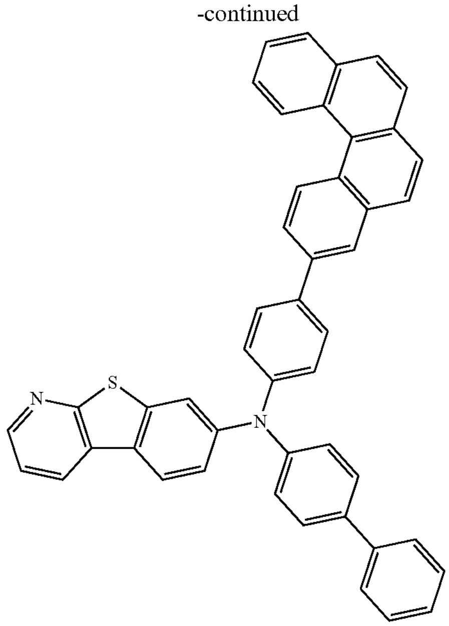
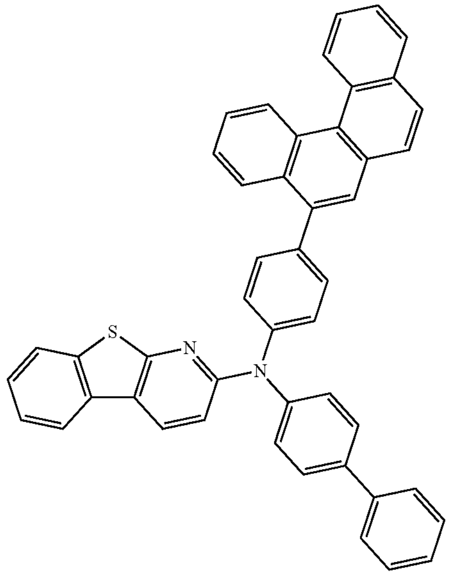

-continued
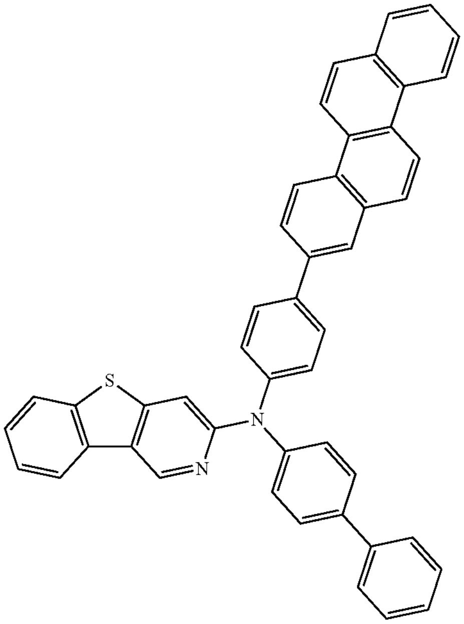
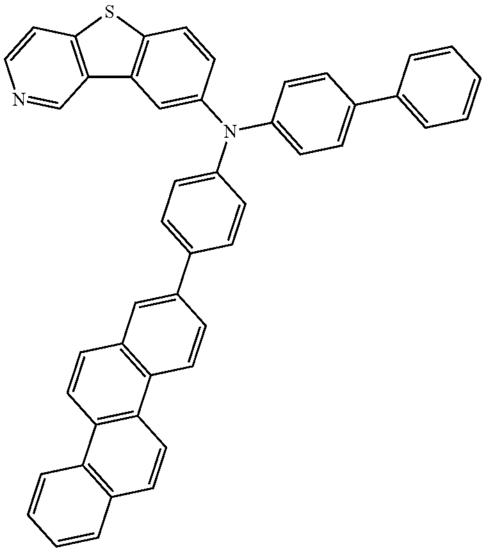
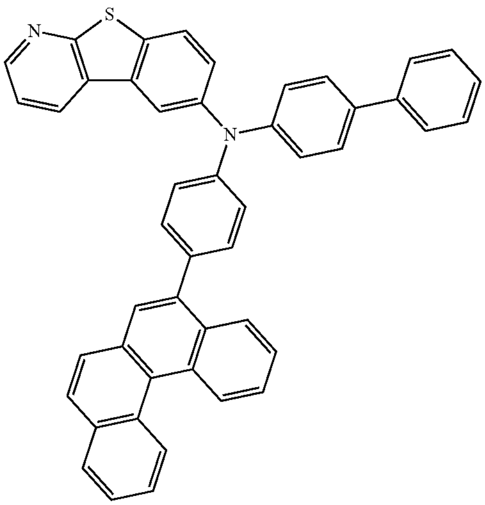
-continued
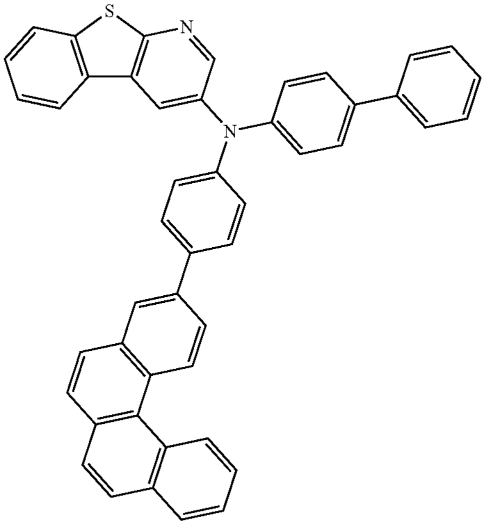
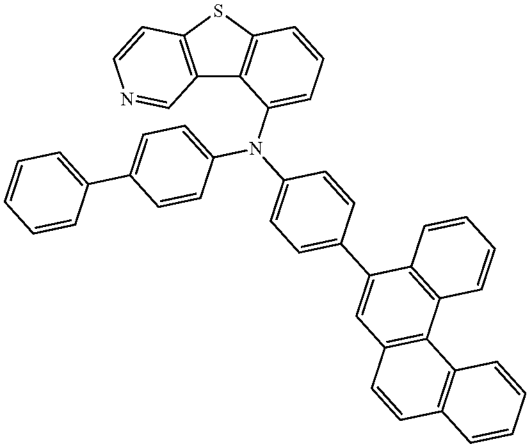
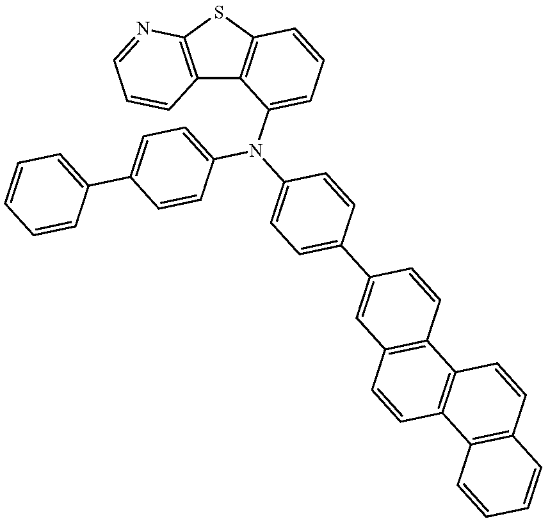

-continued
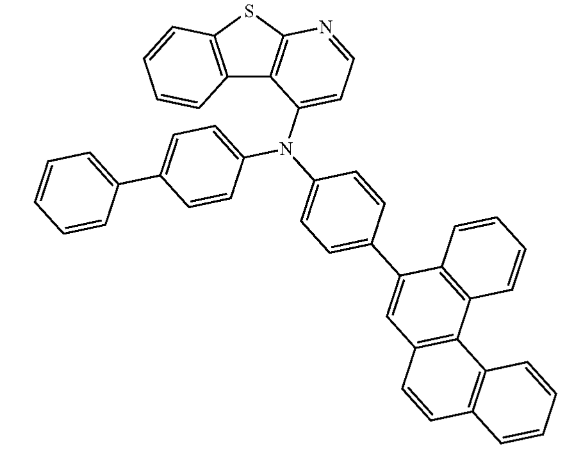
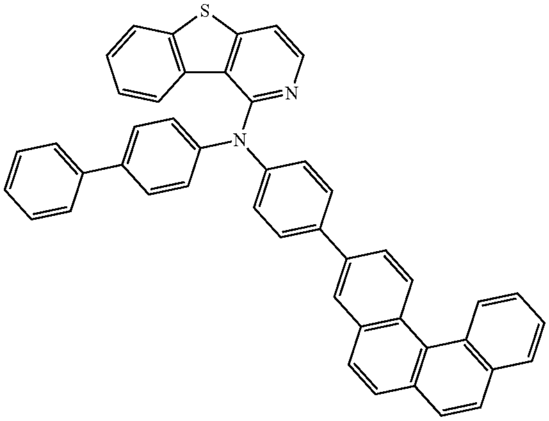
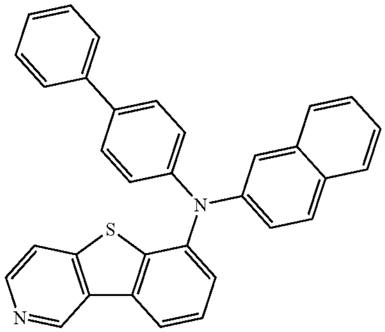
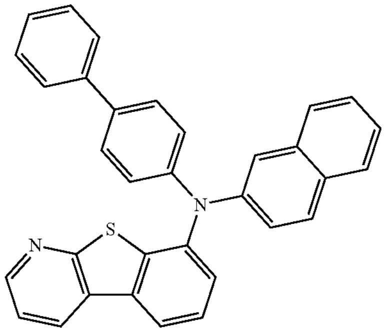
-continued
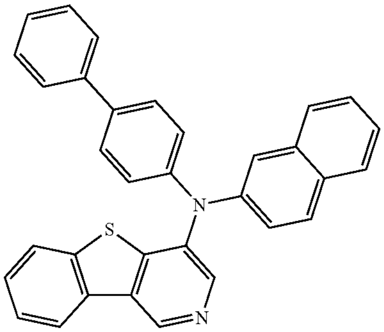
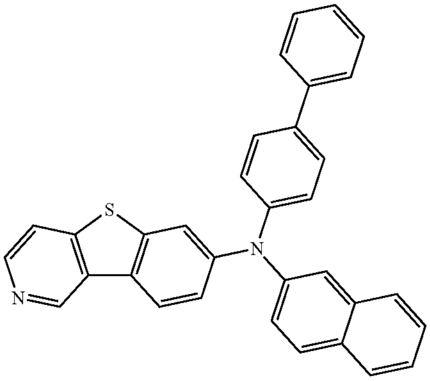
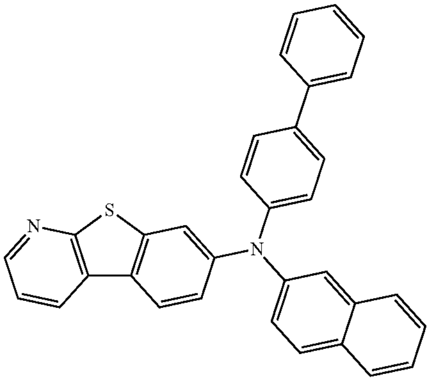
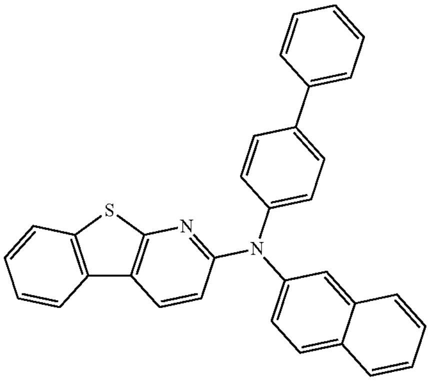

-continued
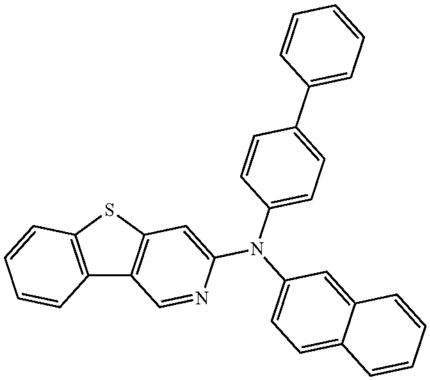
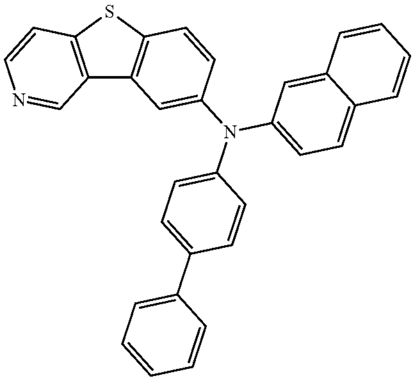
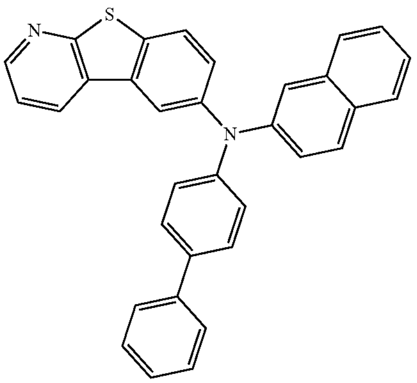
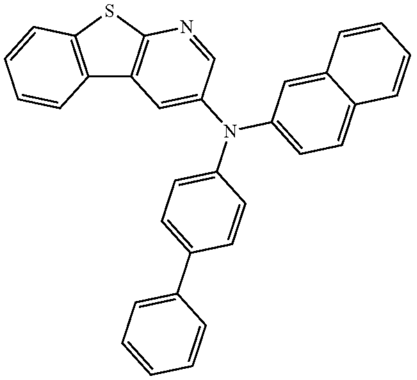
-continued
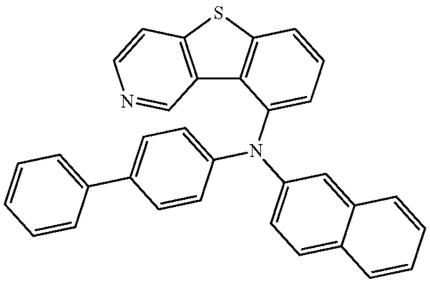
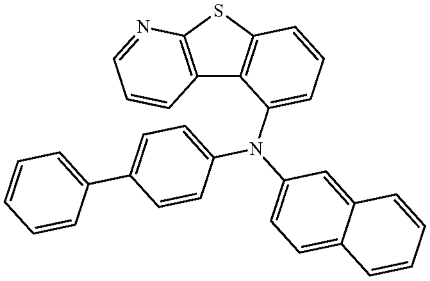
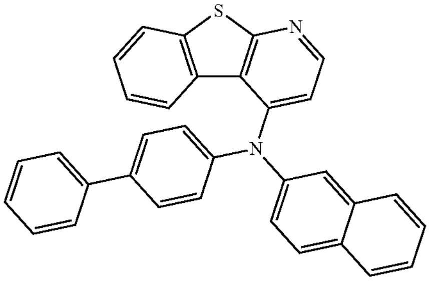
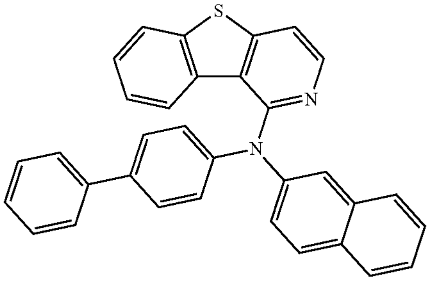
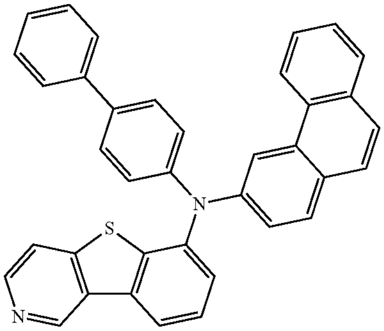

-continued
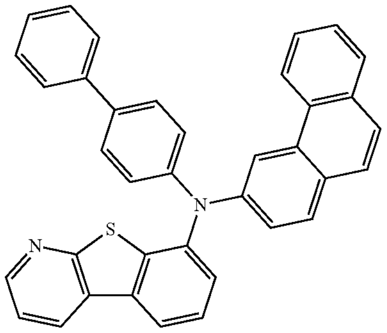
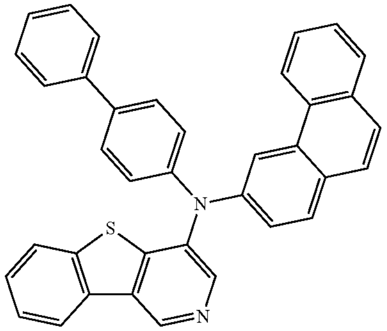
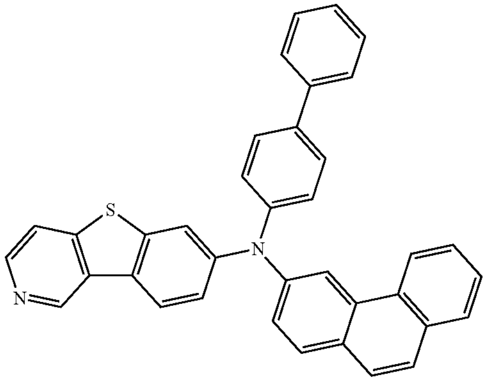
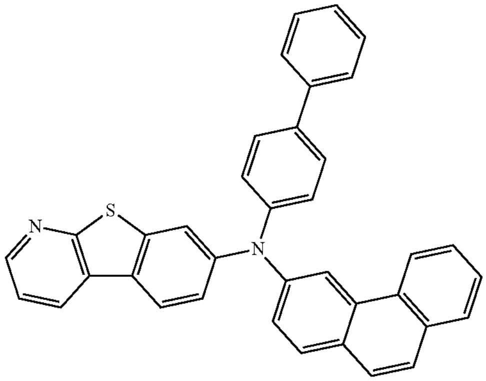
-continued
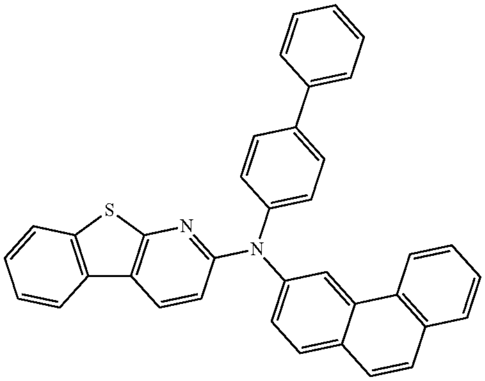
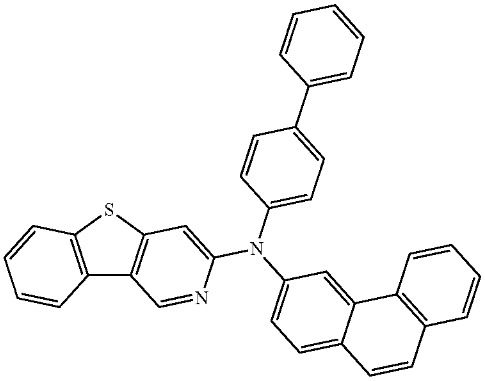
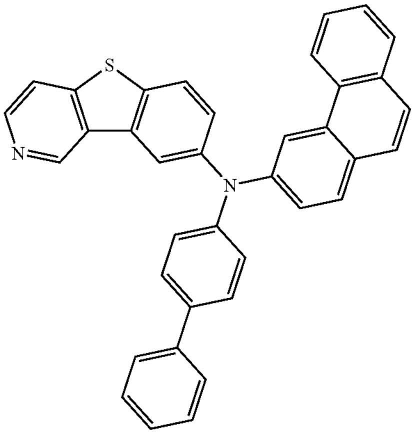
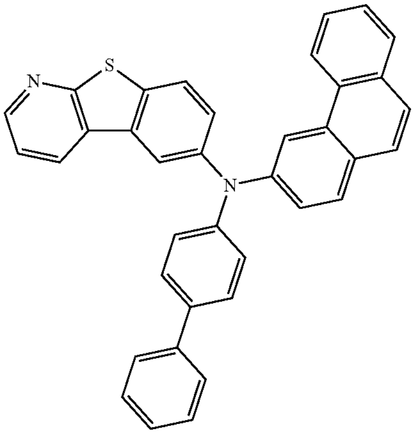

-continued
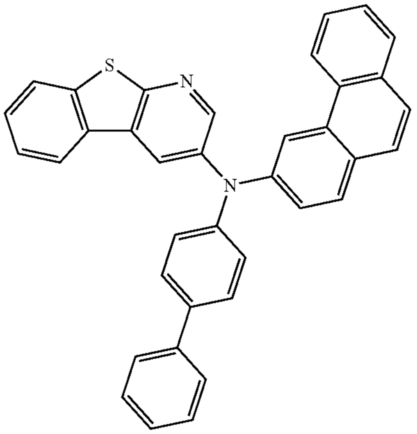
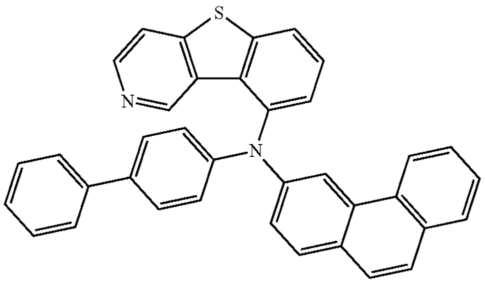
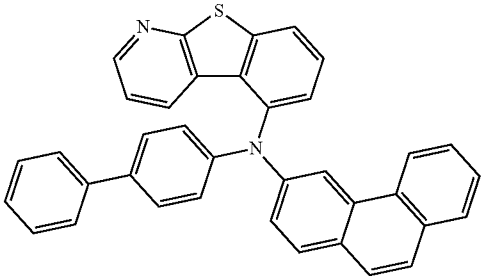
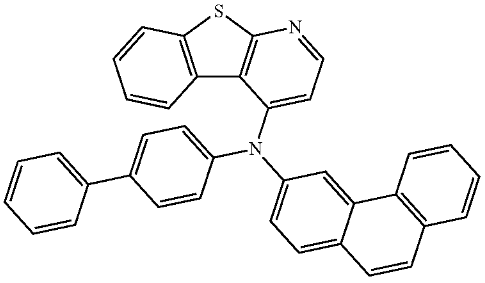
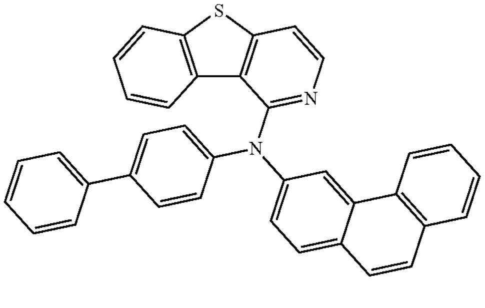
-continued
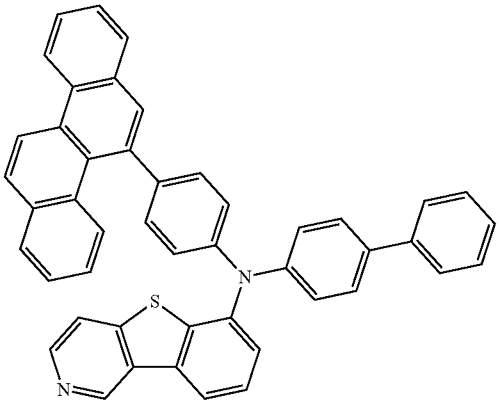
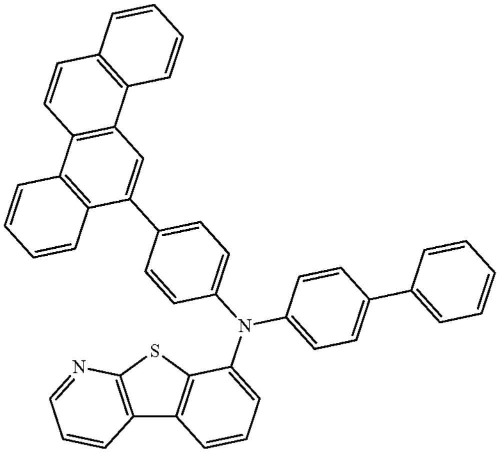
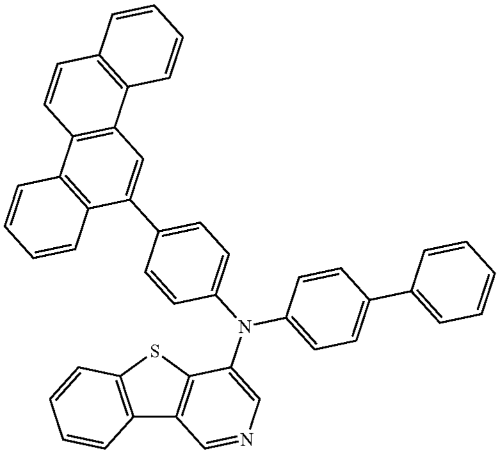

-continued
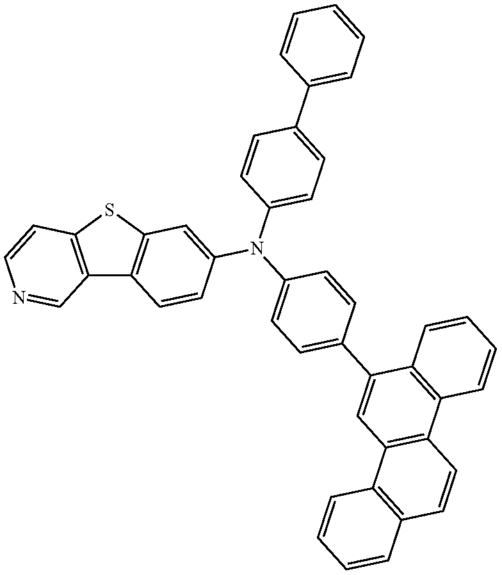
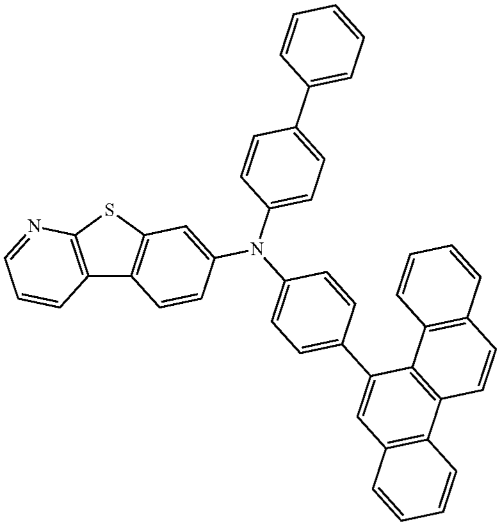
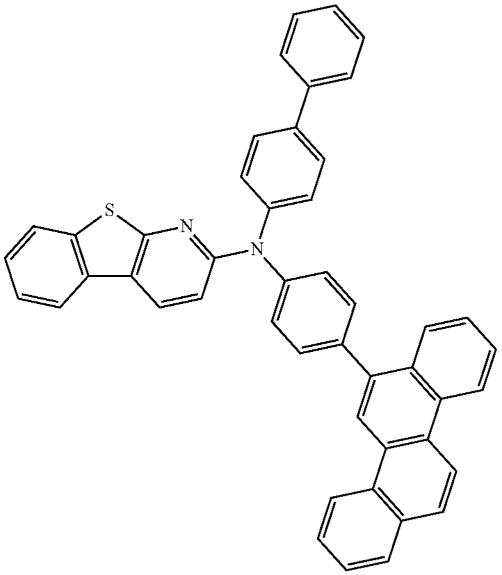
-continued
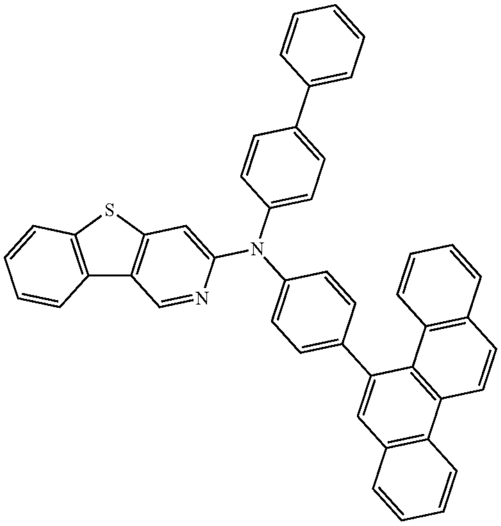
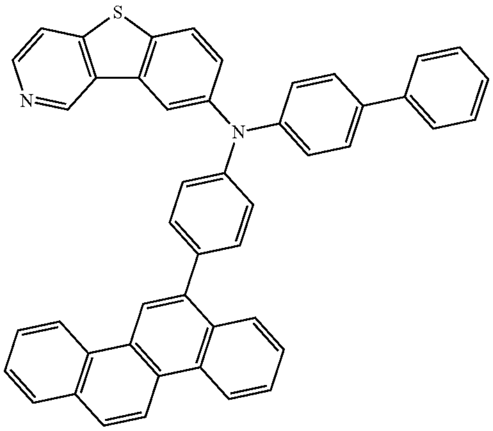
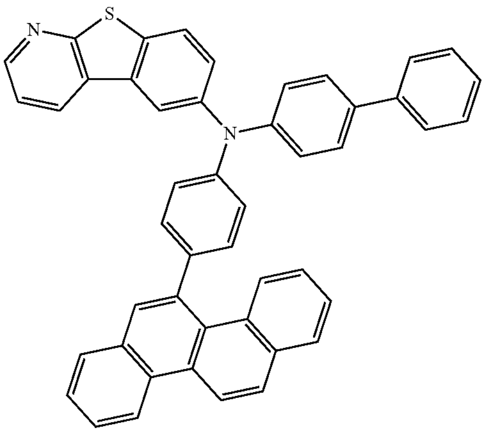

-continued
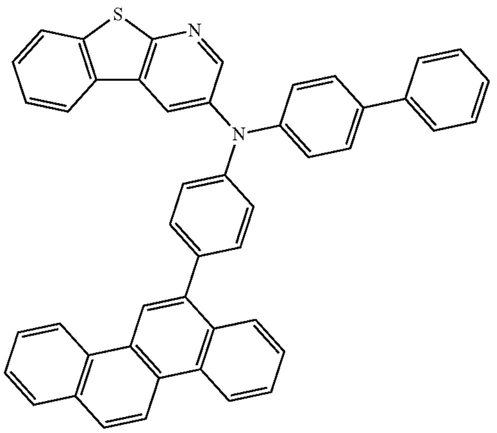
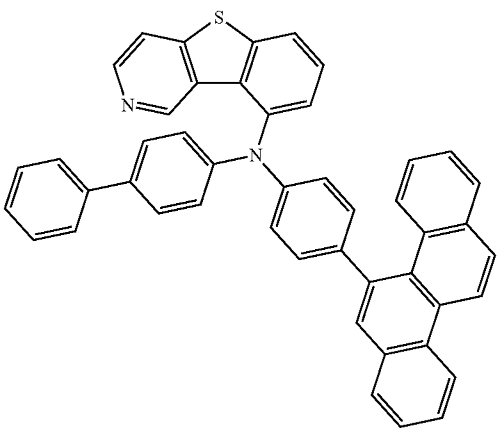
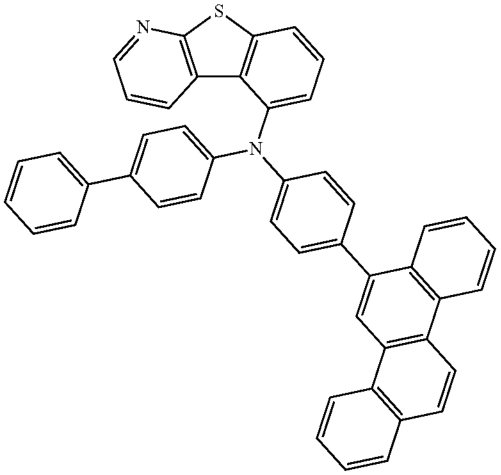
-continued
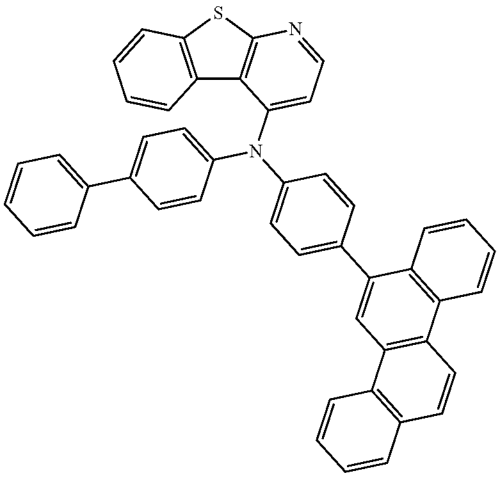
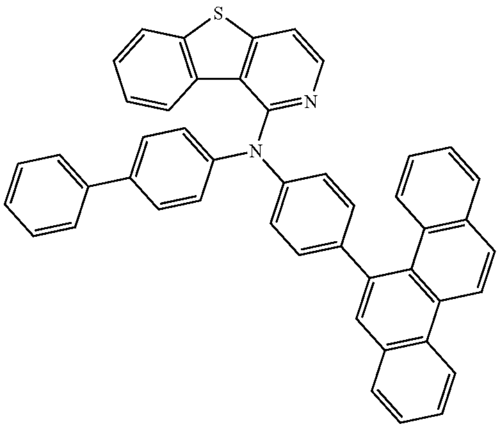
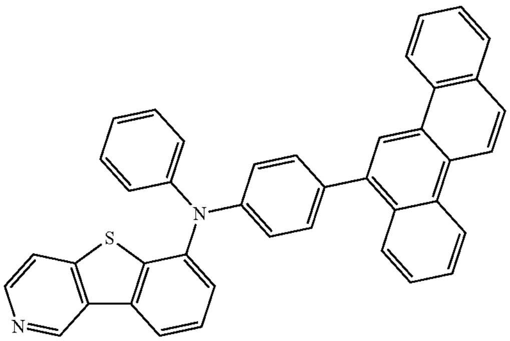

-continued
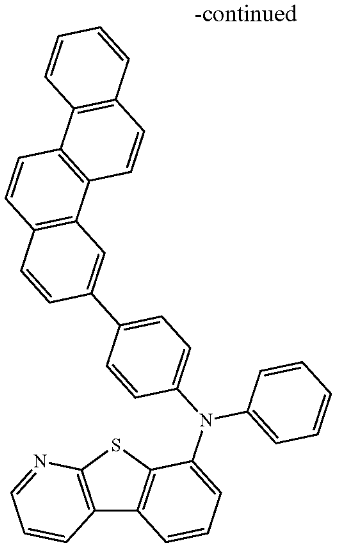
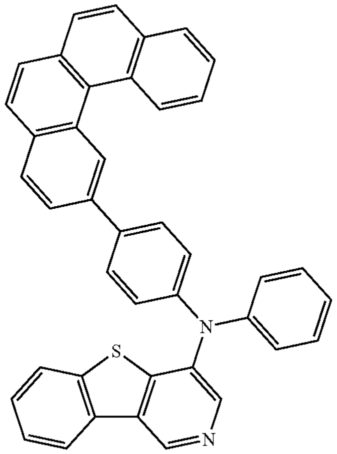
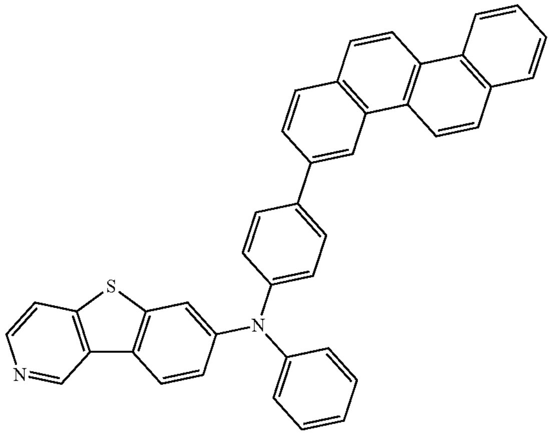
-continued
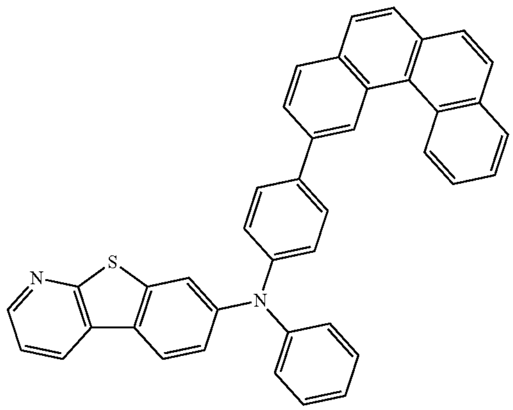
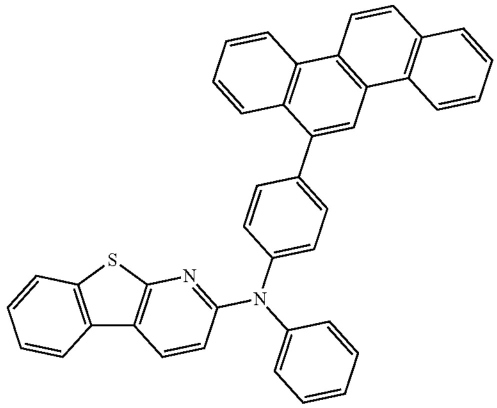
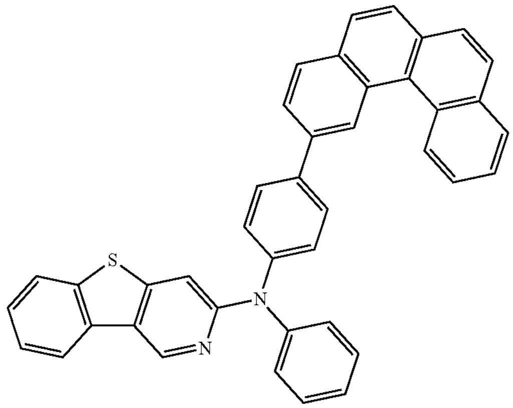
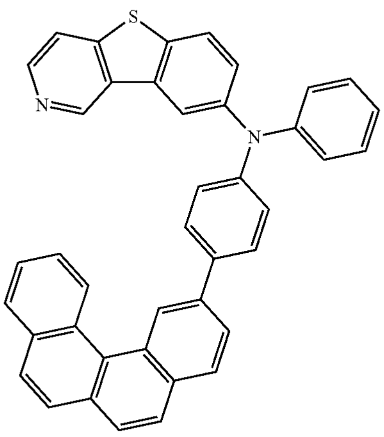

-continued
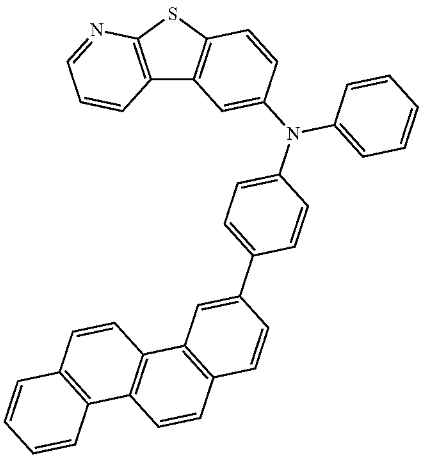
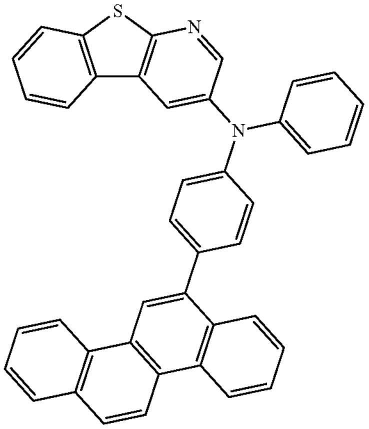
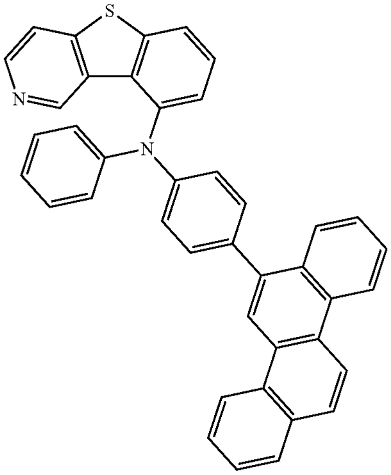
-continued
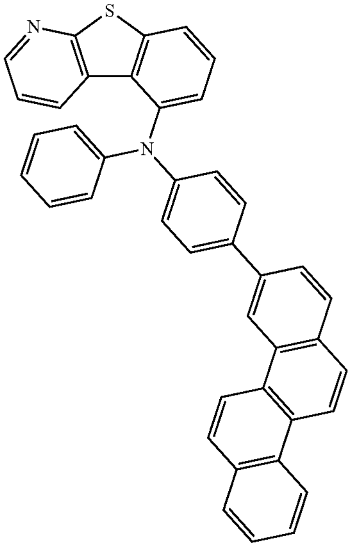
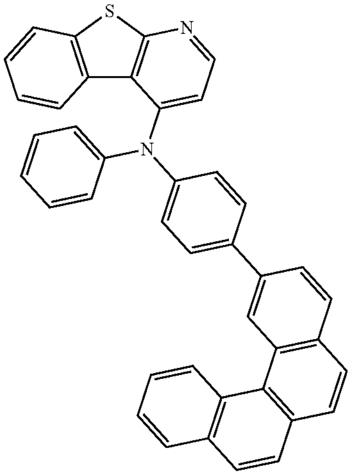
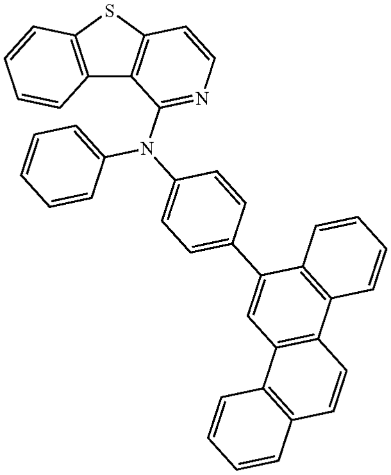

-continued
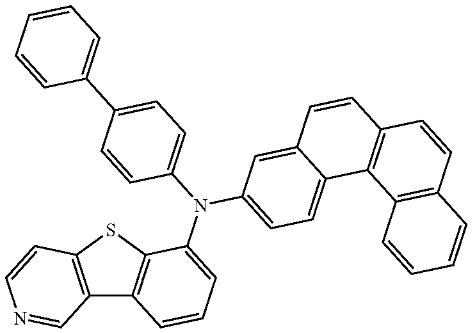
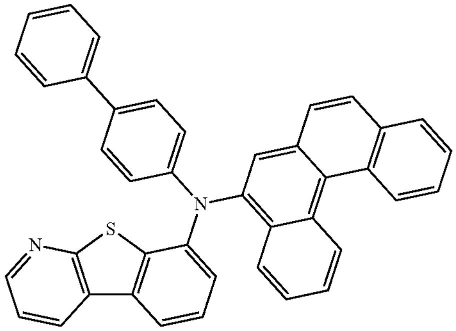
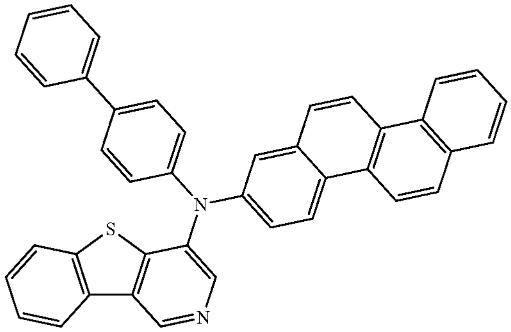
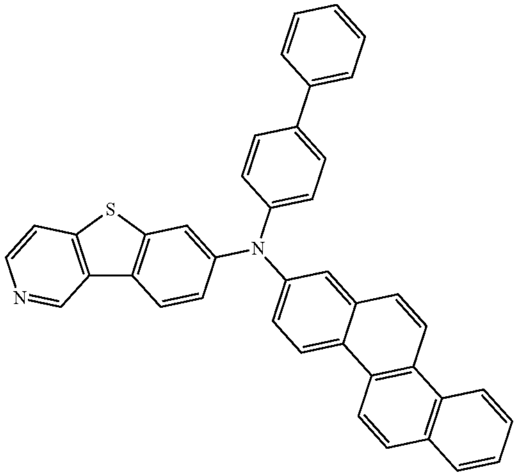
-continued
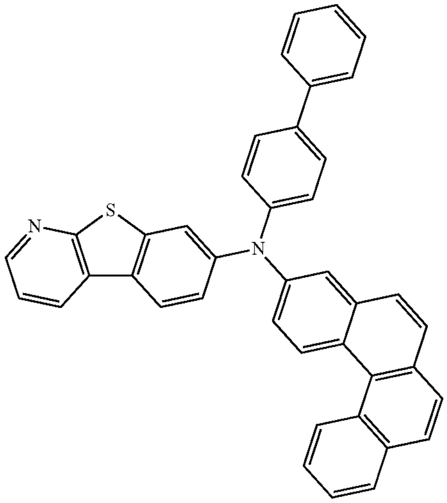
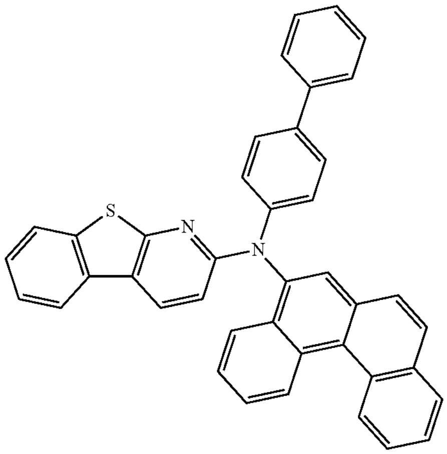
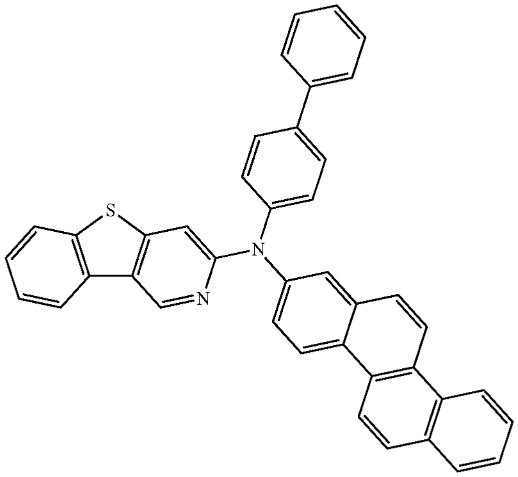

-continued
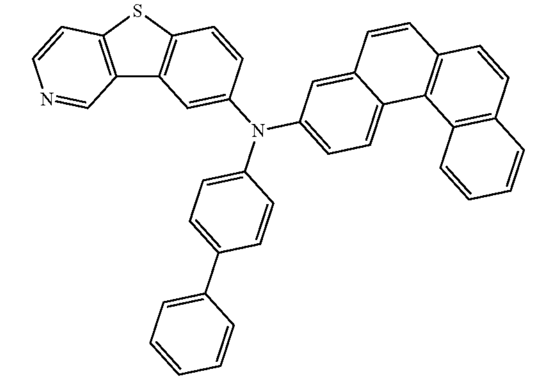
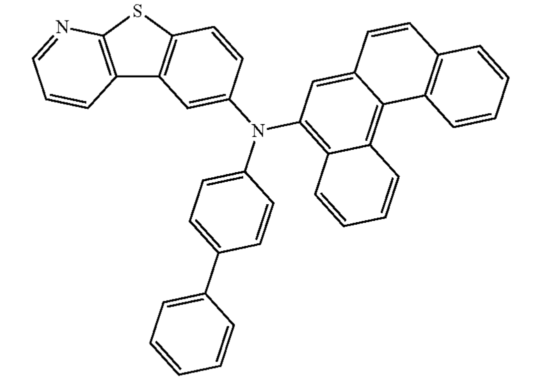
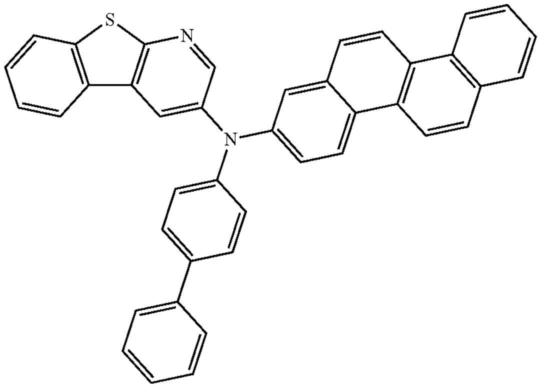
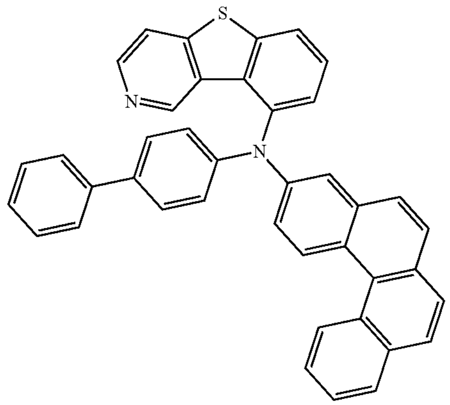
-continued
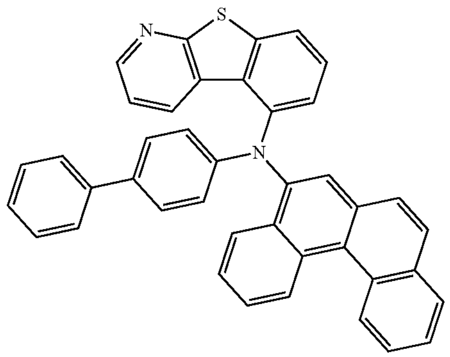
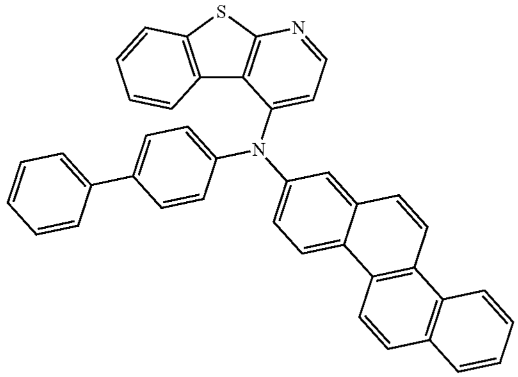
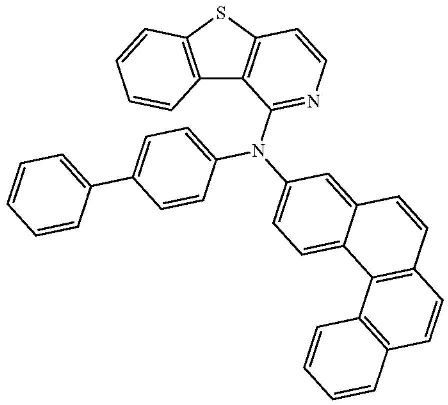
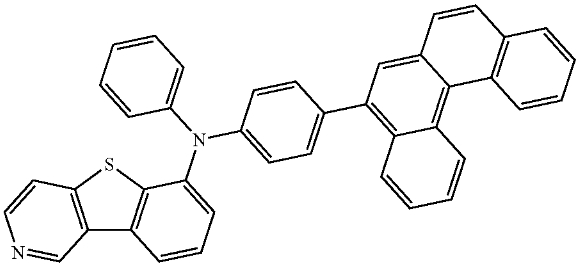

-continued
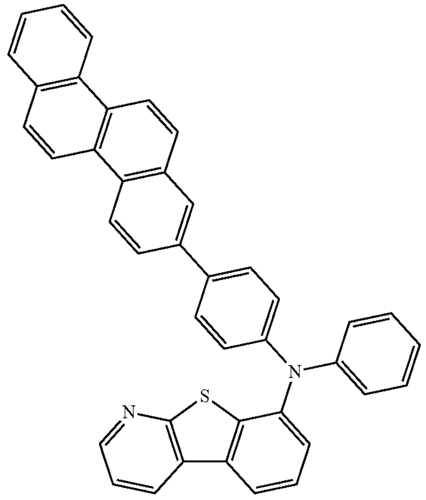
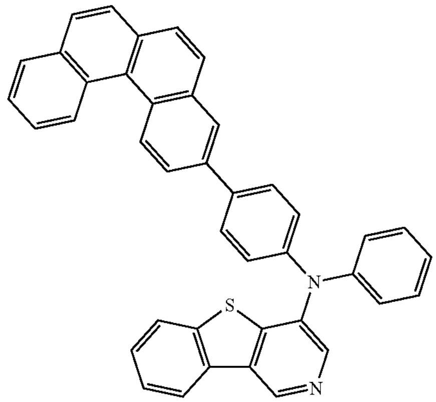
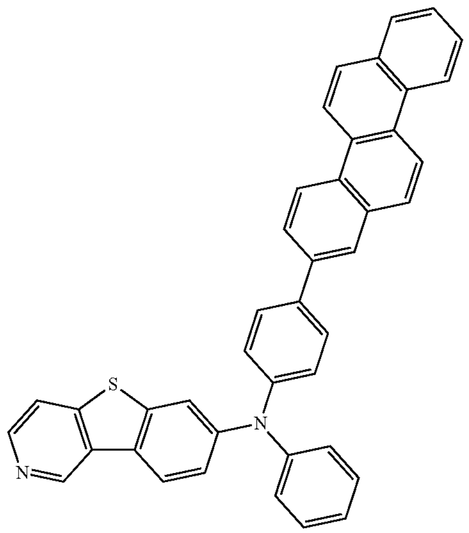
-continued
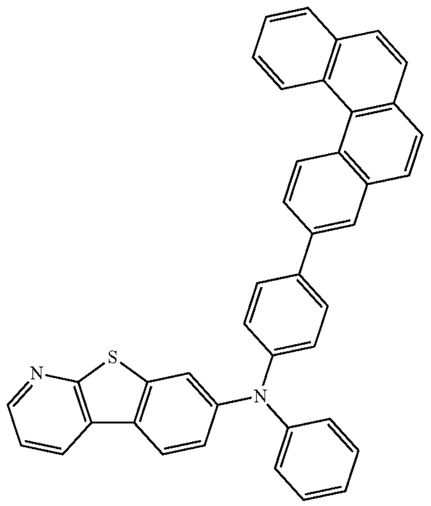
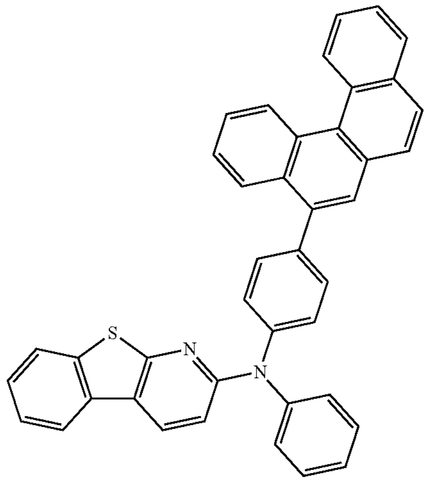
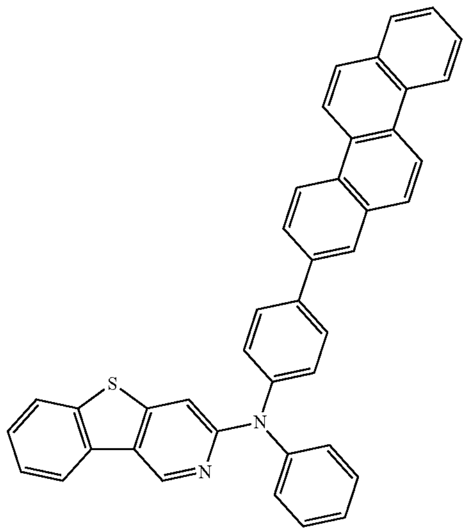

-continued
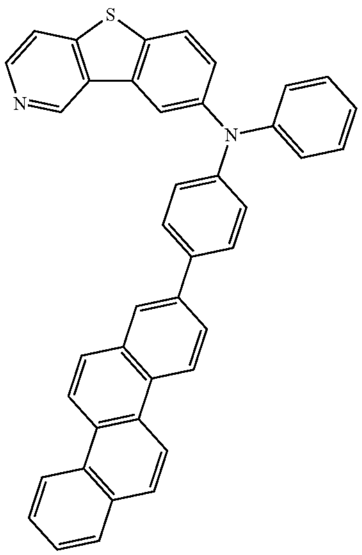
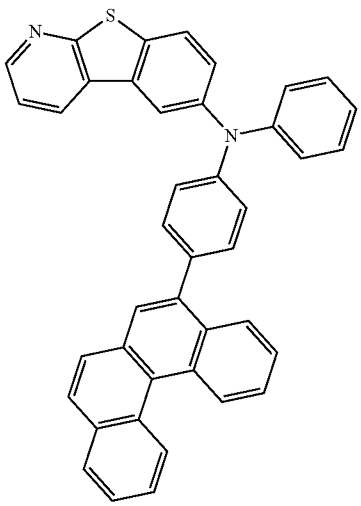
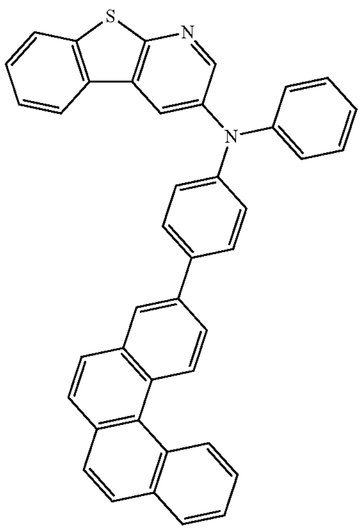
-continued
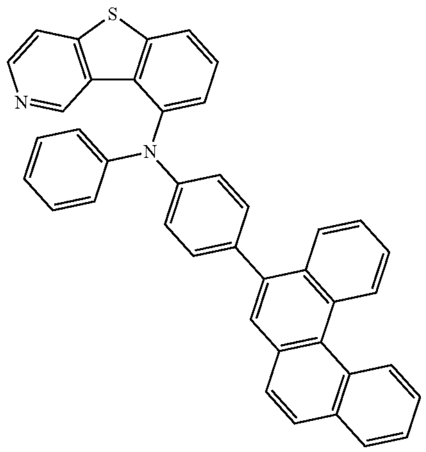
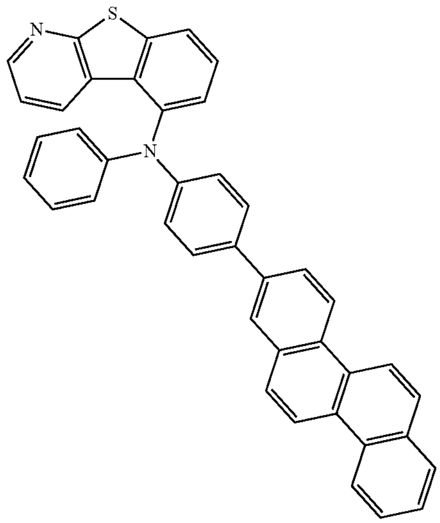
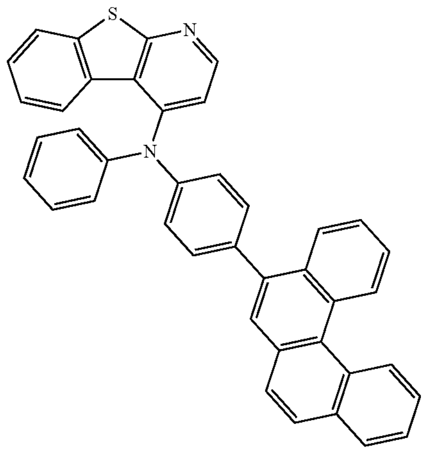

-continued
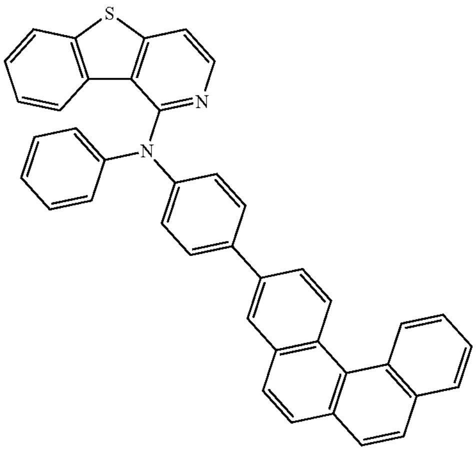
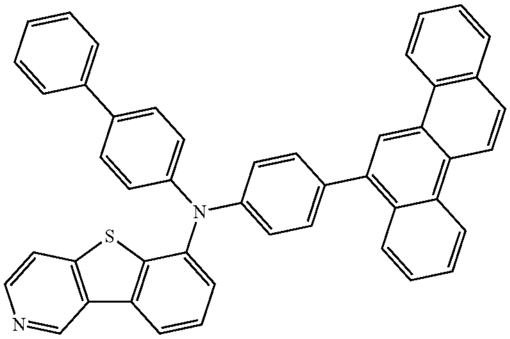
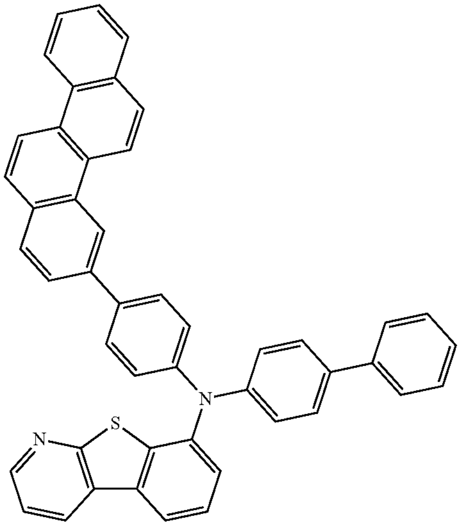
-continued
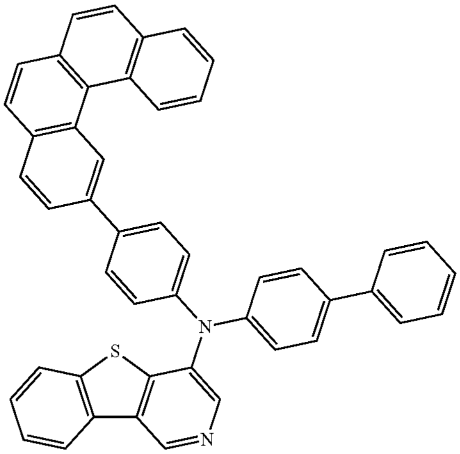
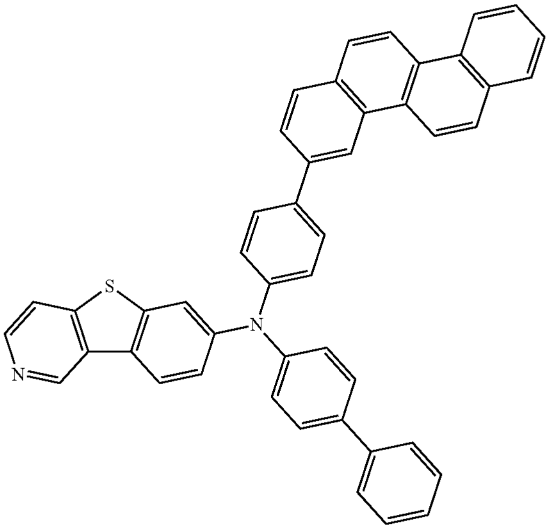
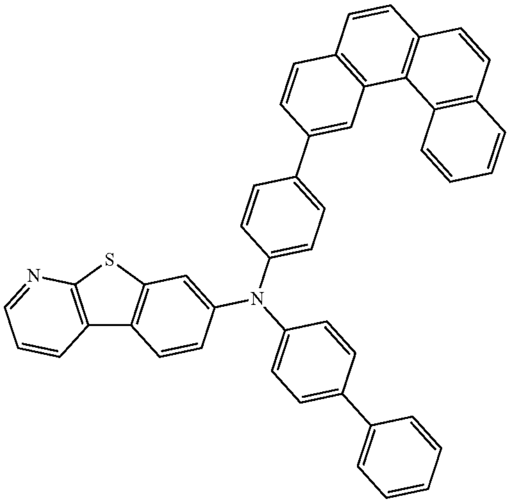

-continued
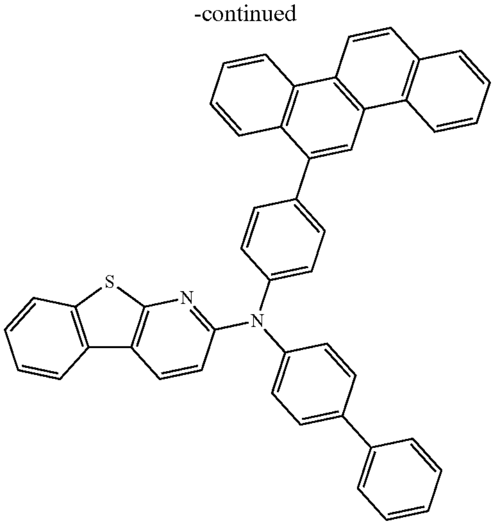
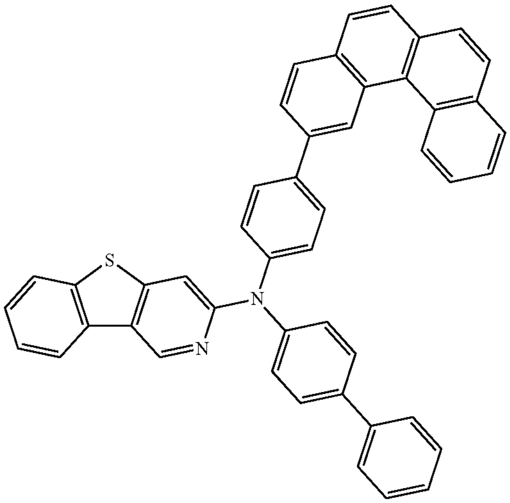
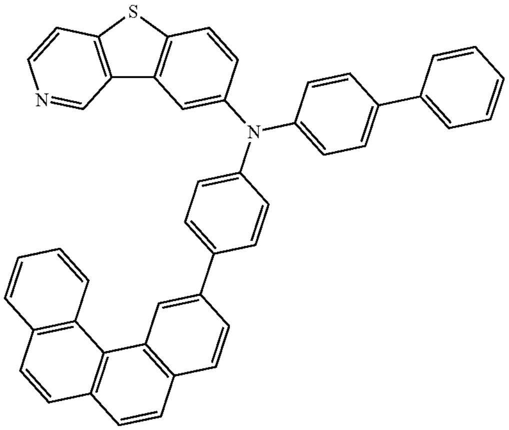
-continued
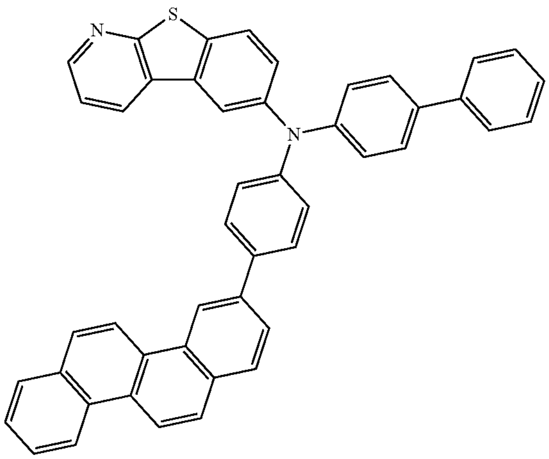
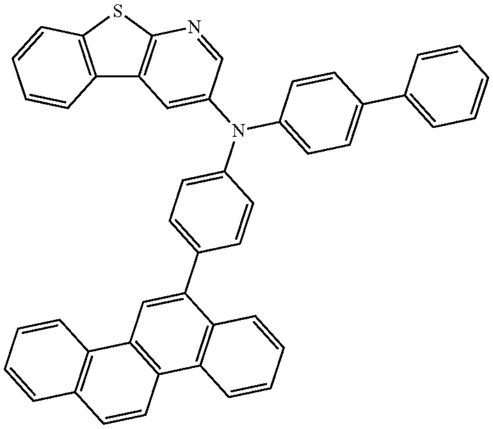
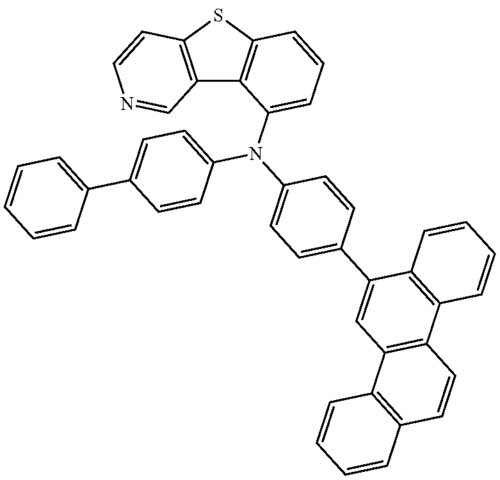

-continued
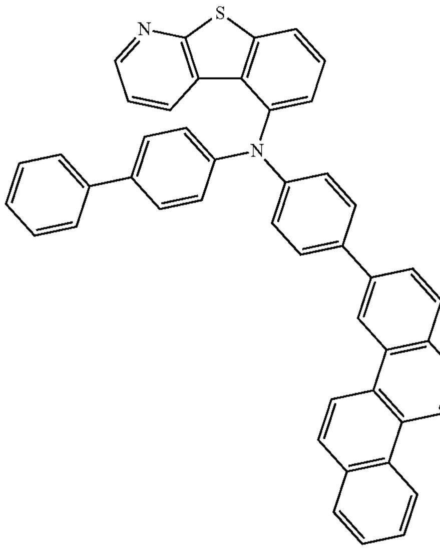
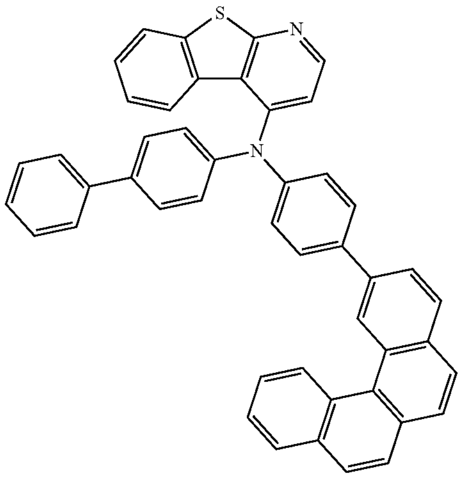
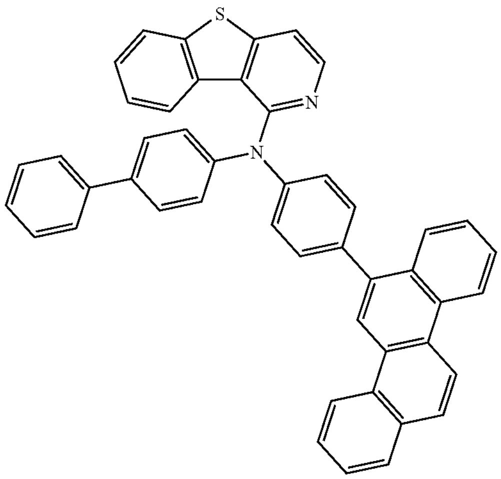
-continued
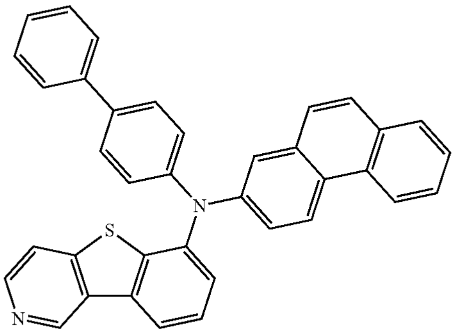
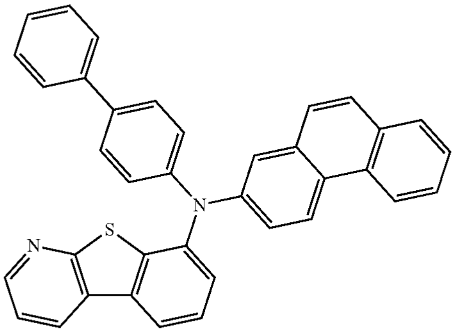
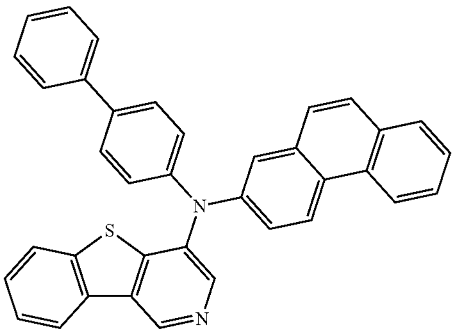
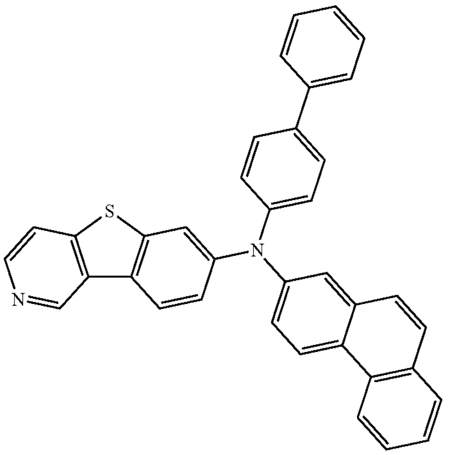

-continued
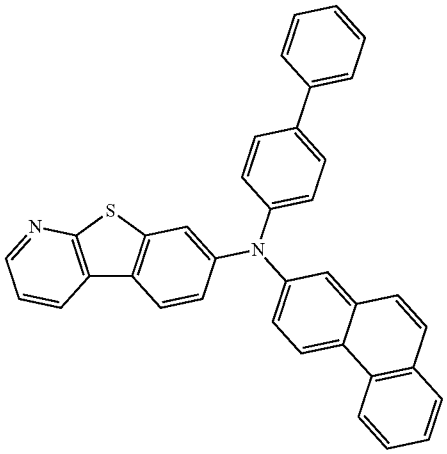
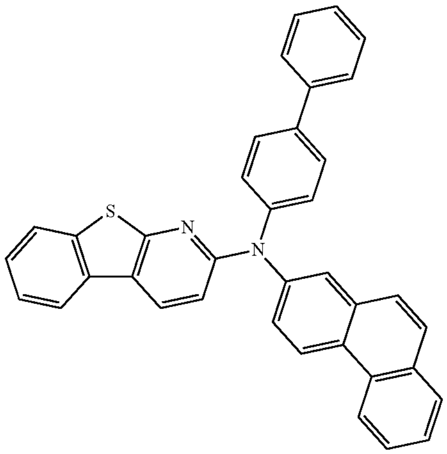
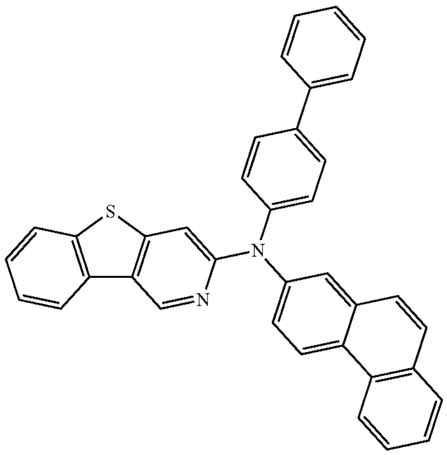
-continued
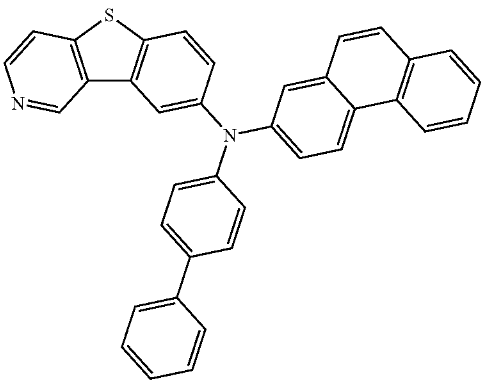
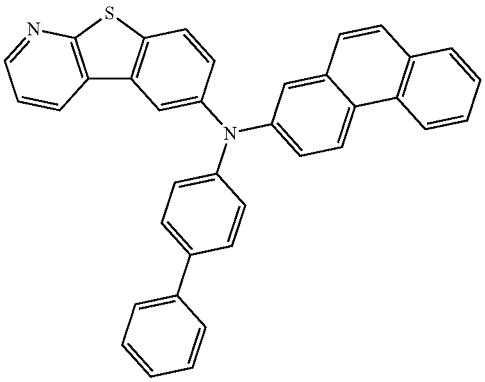
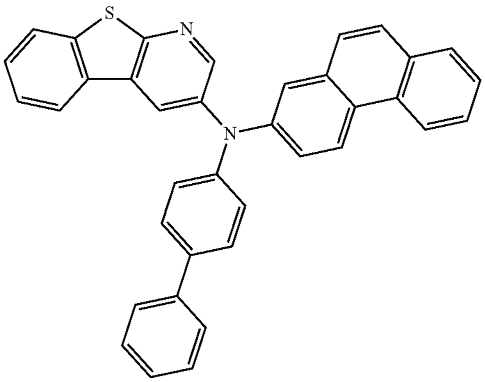
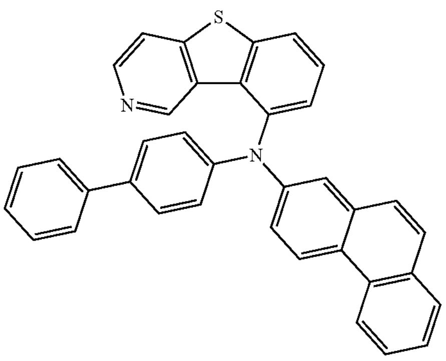

-continued
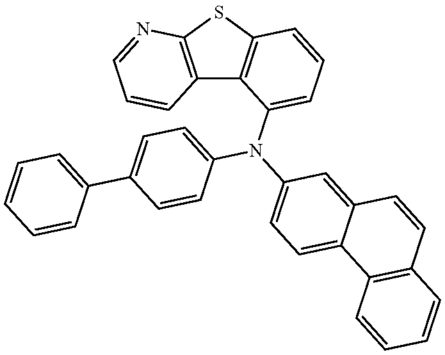
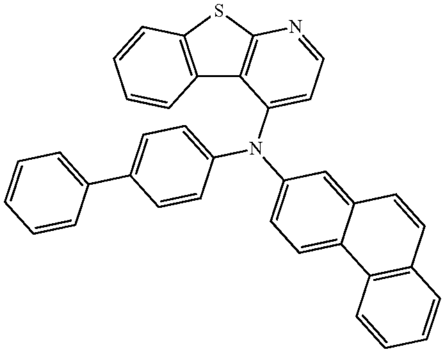
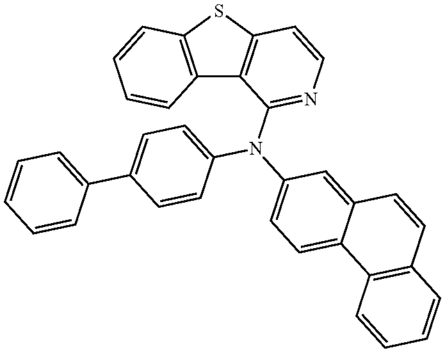
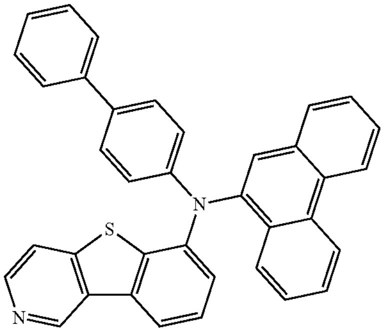
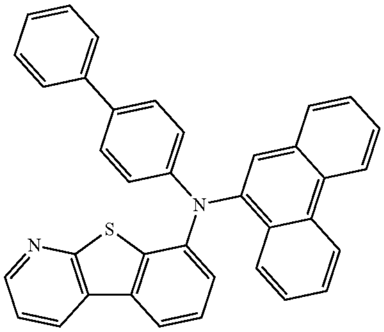
-continued
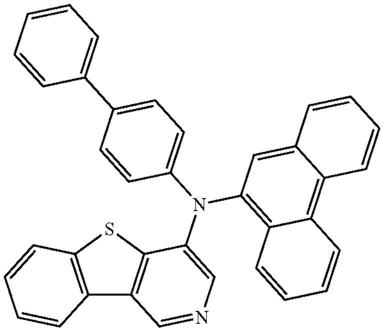
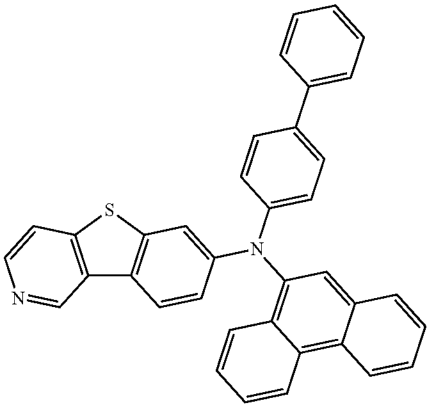
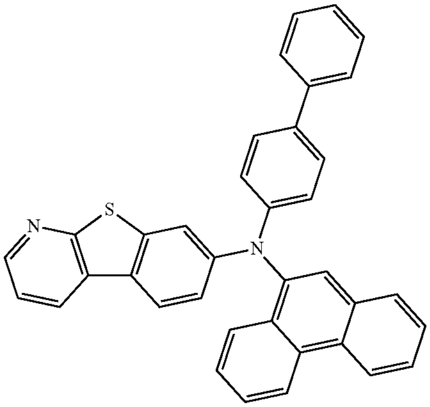
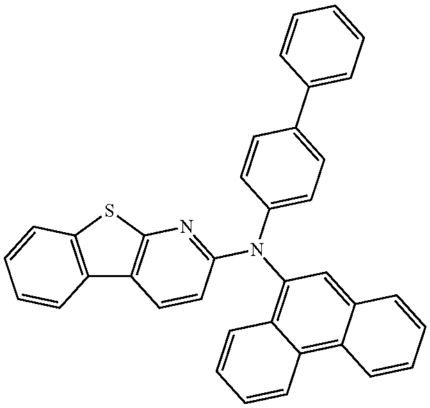

-continued
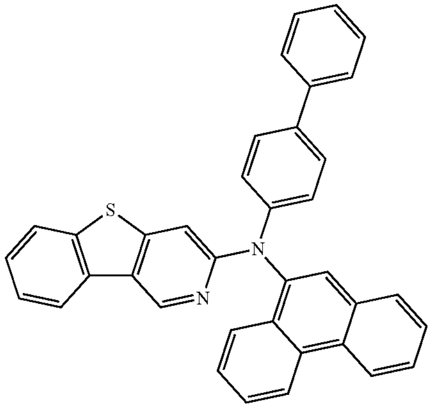
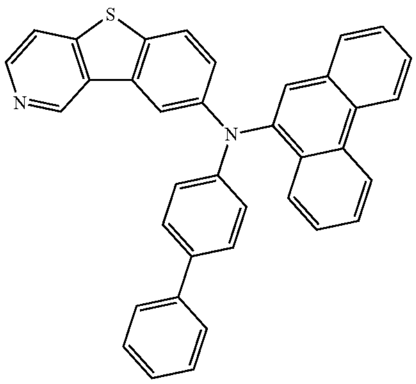
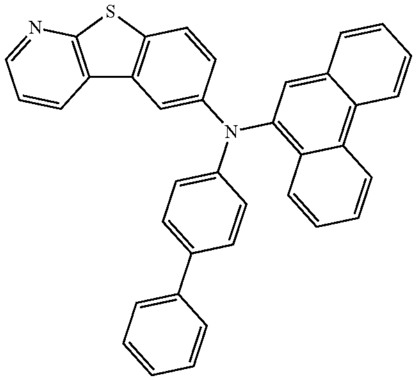
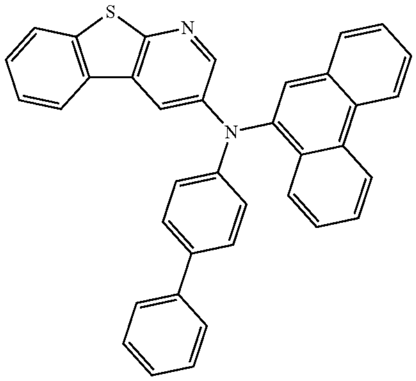
-continued
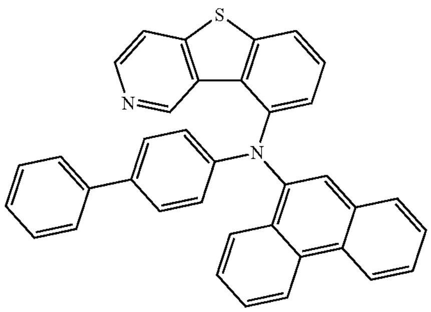
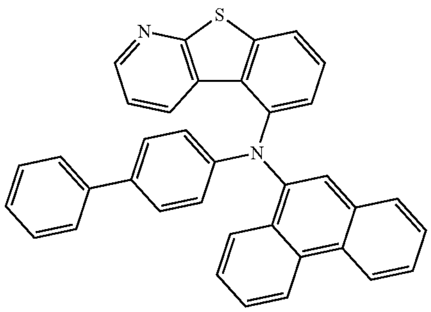
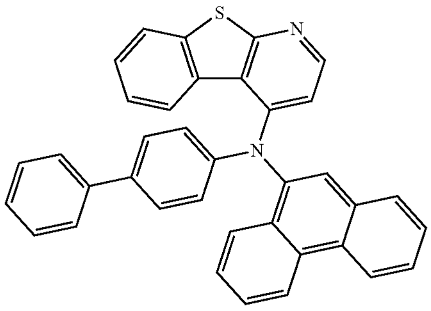
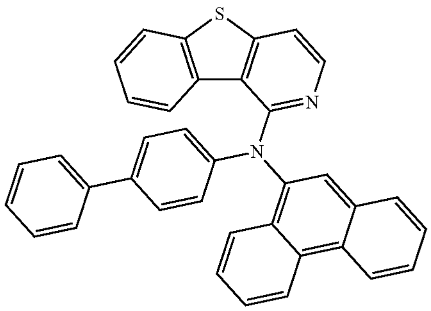
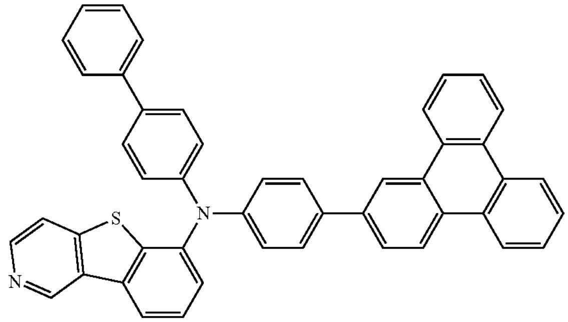

-continued
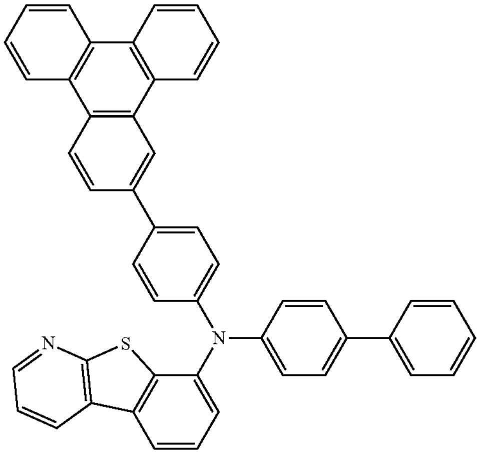
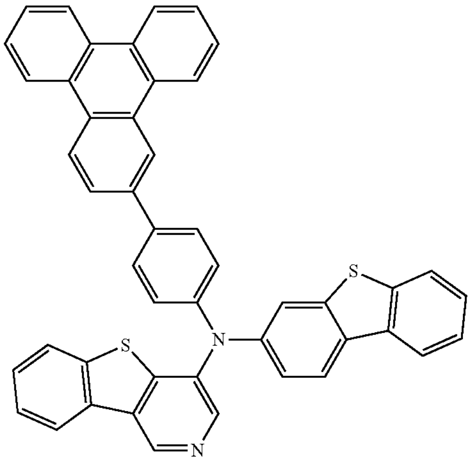
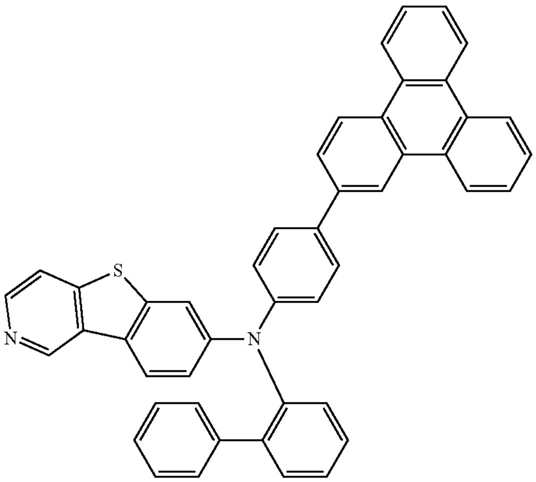
-continued
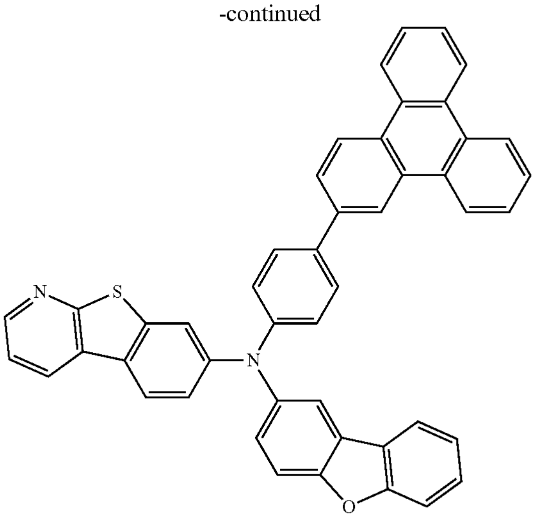
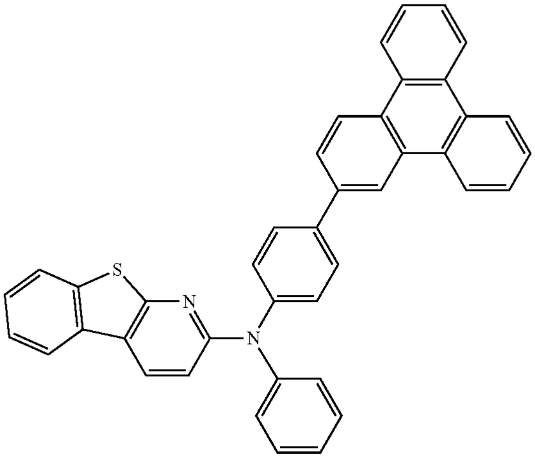
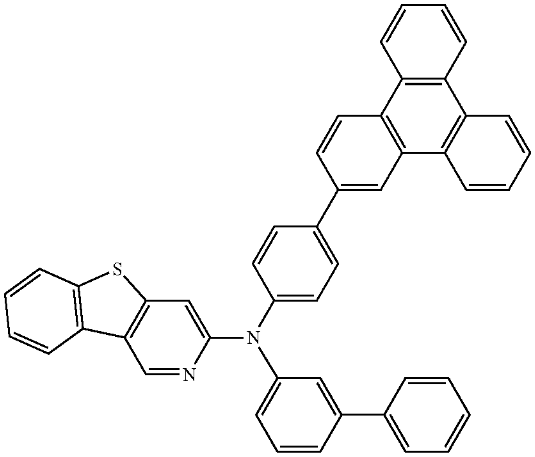

-continued
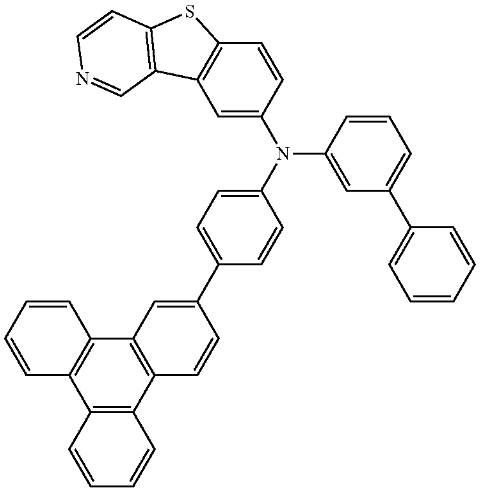
-continued
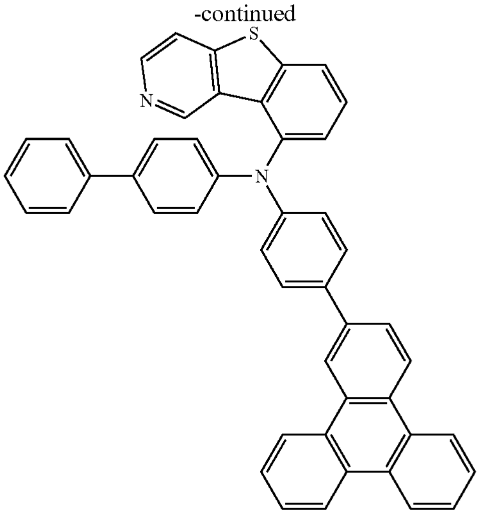
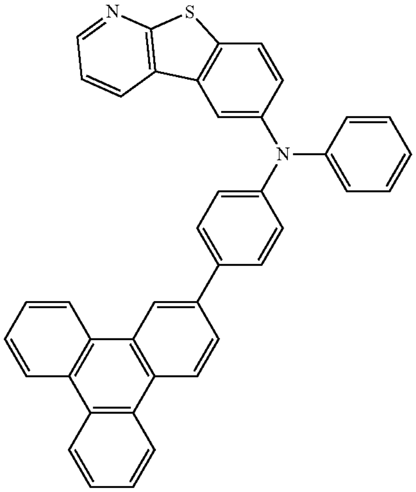
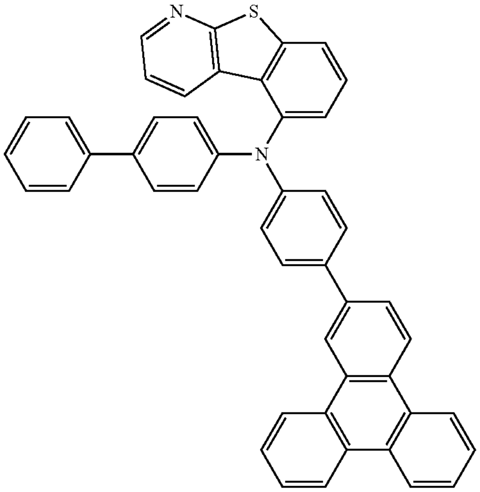
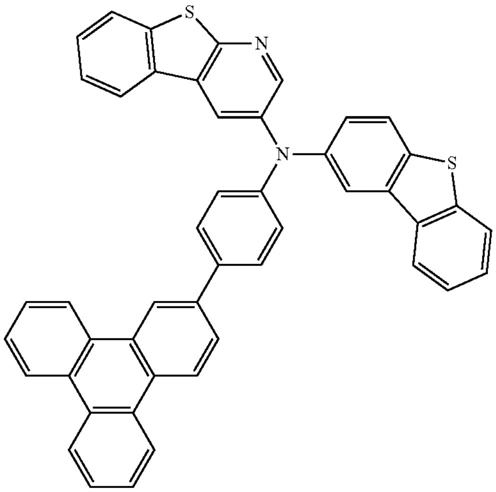
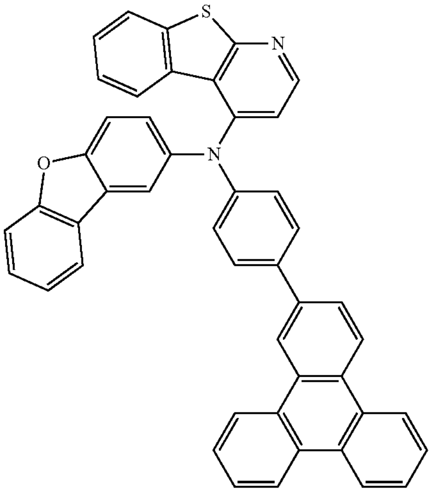

-continued
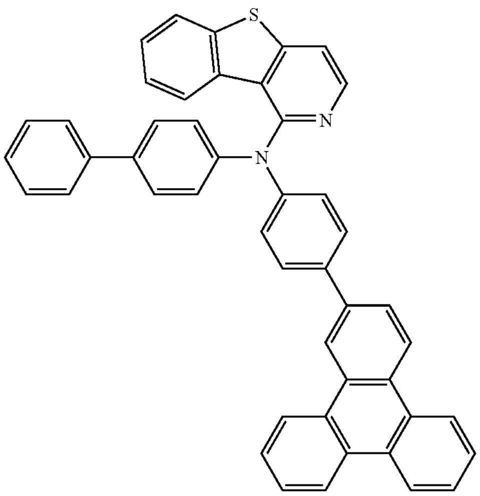 [SMILES: c1ccc(-c2ccc(N(c3ccc(-c4ccc5c6ccccc6c6ccccc6c5c4)cc3)c3nccc4sc5ccccc5c34)cc2)cc1]
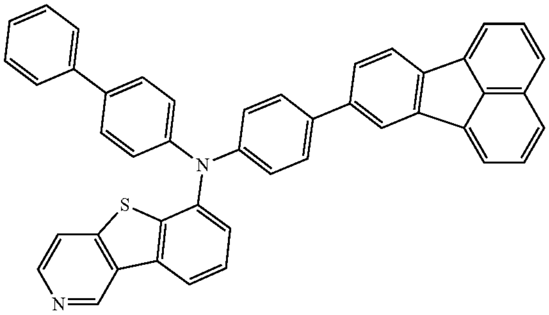
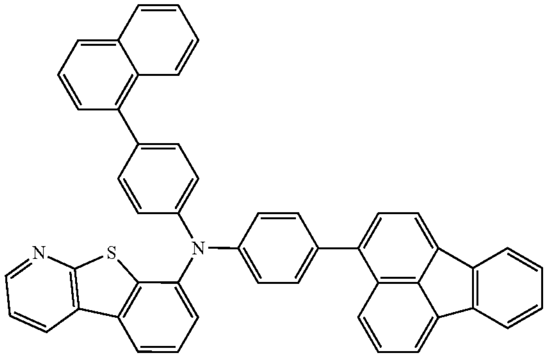
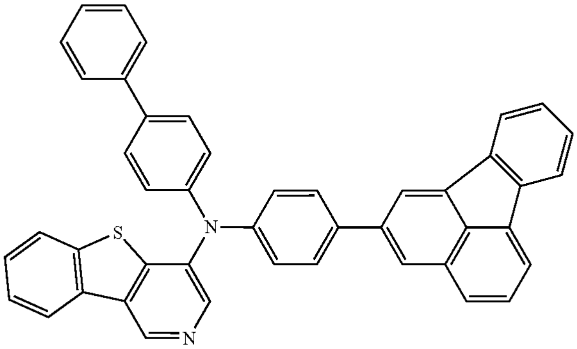
-continued
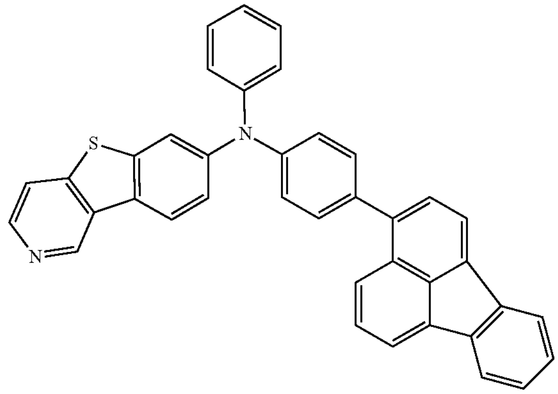
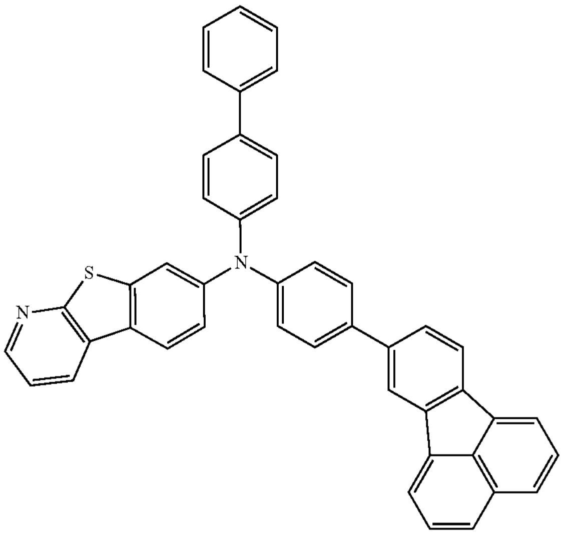
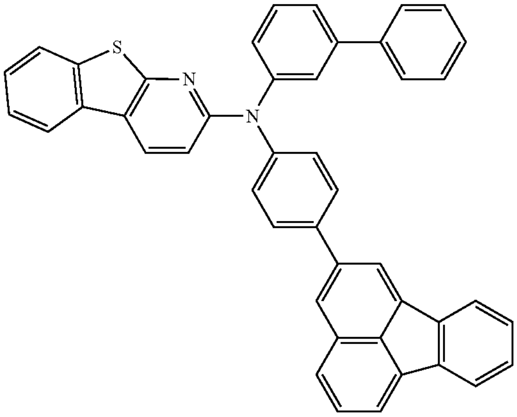

-continued
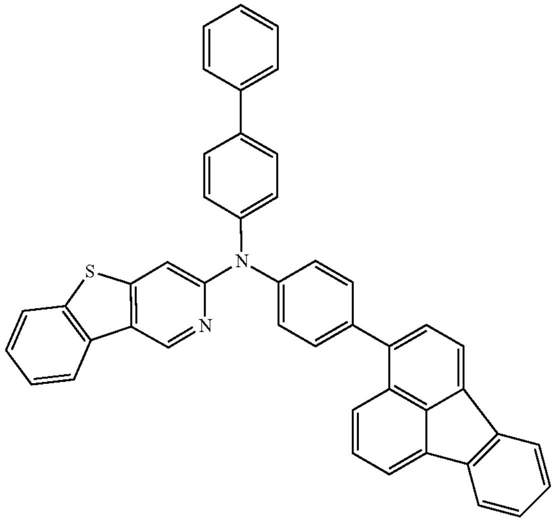
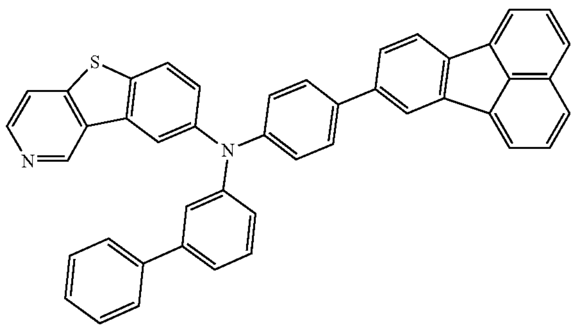
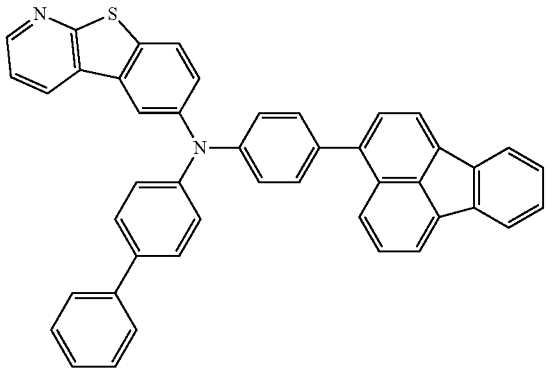
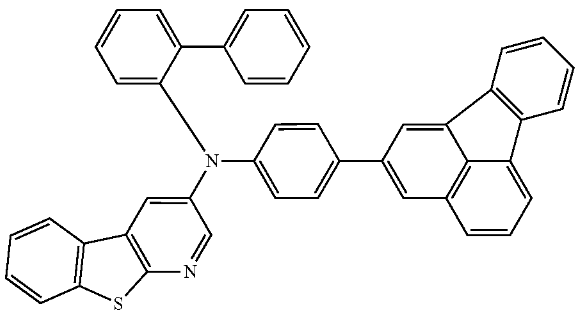
-continued
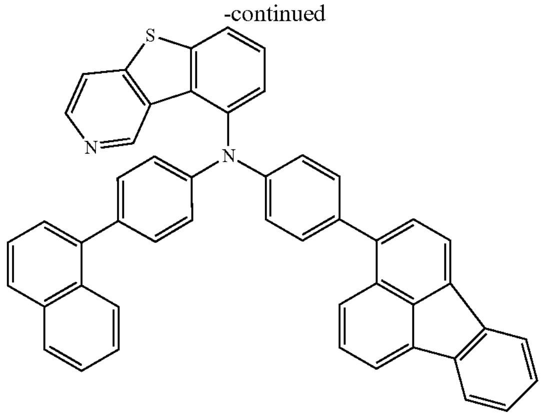
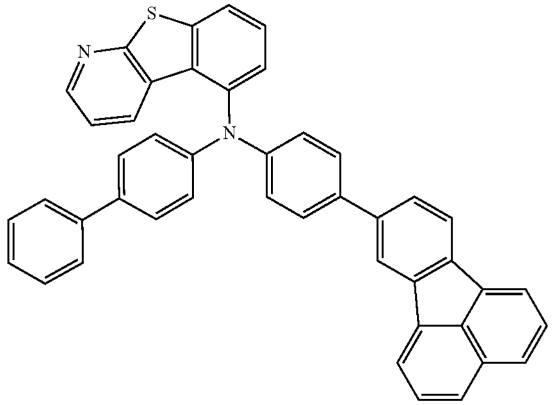
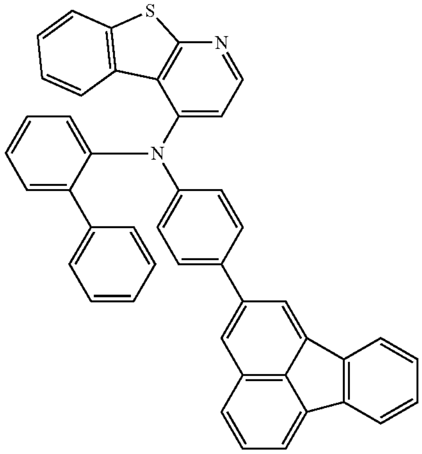
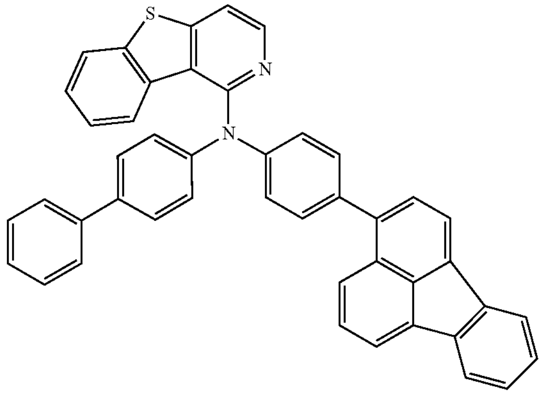

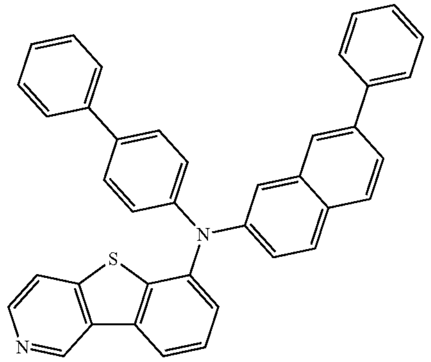
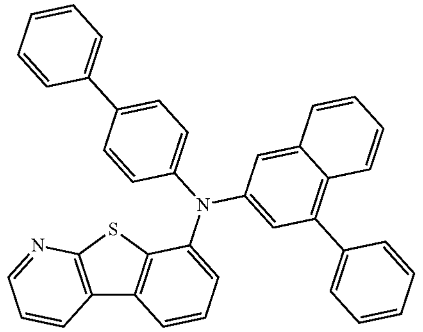
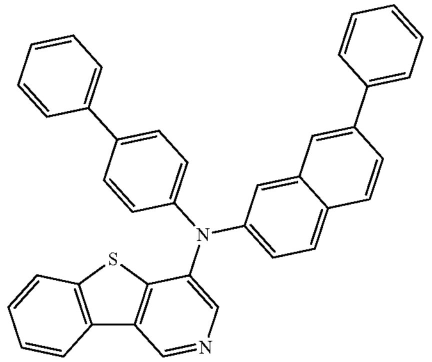
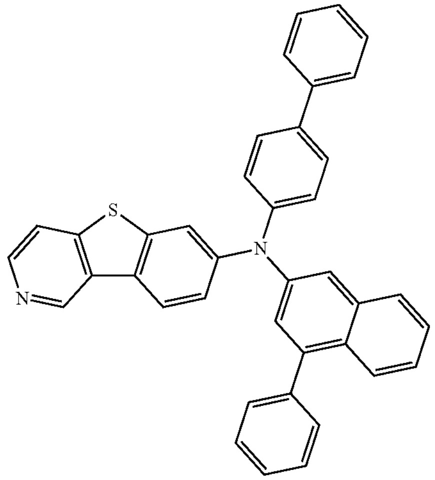
-continued
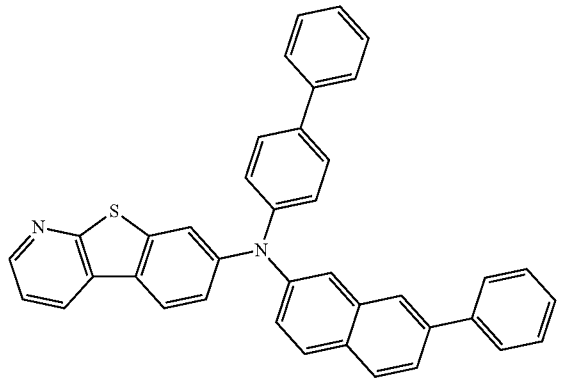
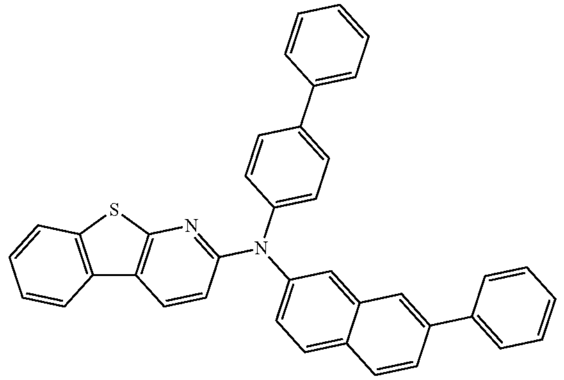
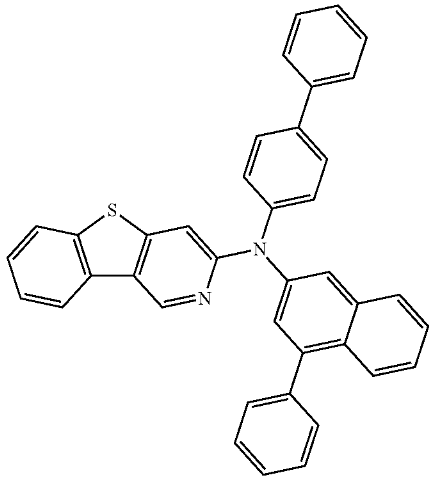
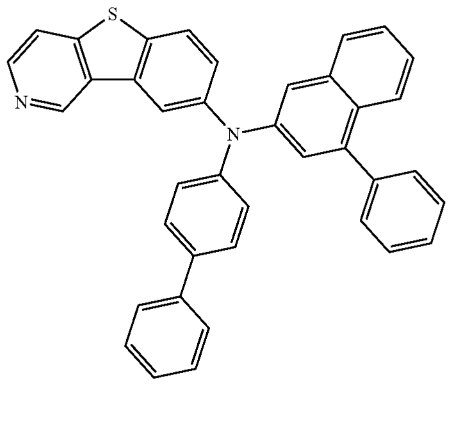

-continued
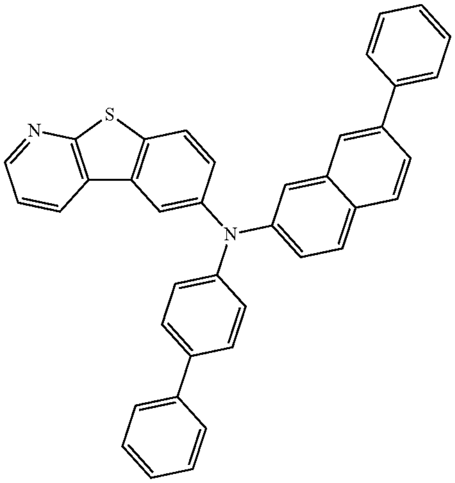
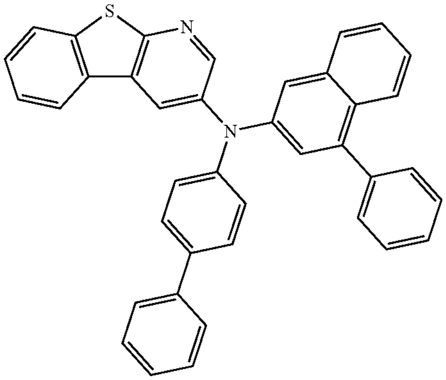
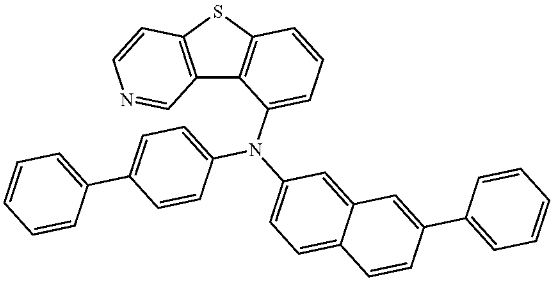
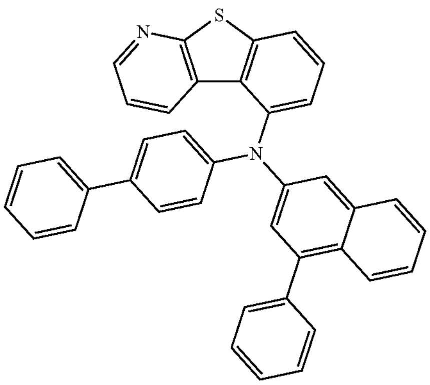
-continued
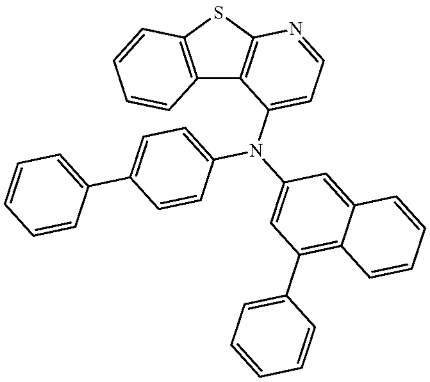
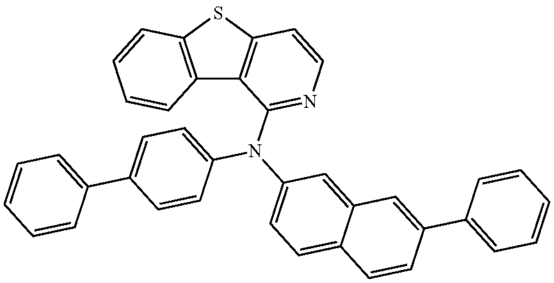
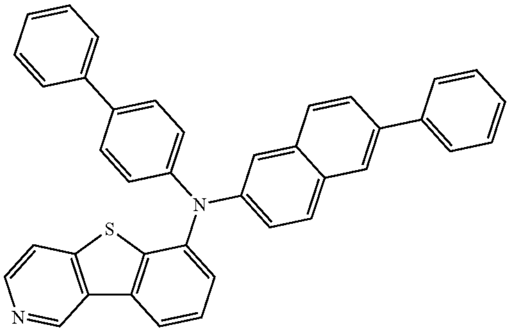
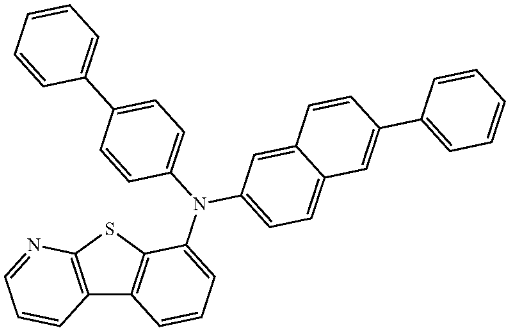
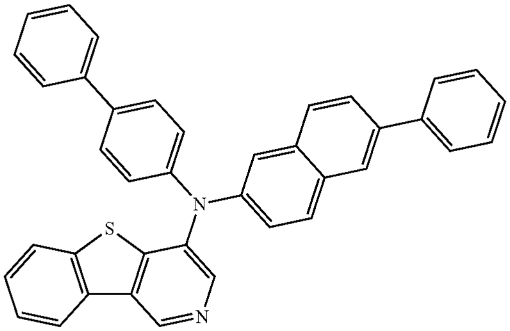

-continued
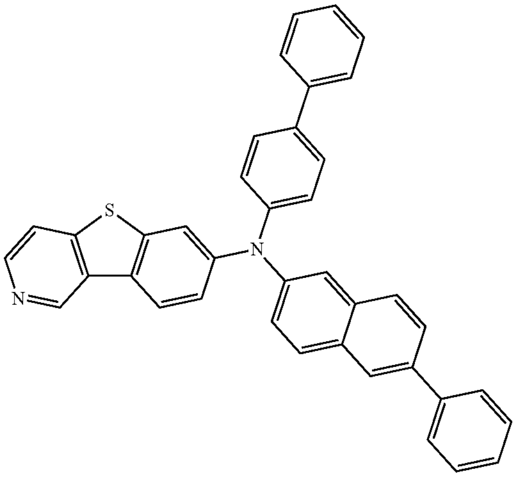
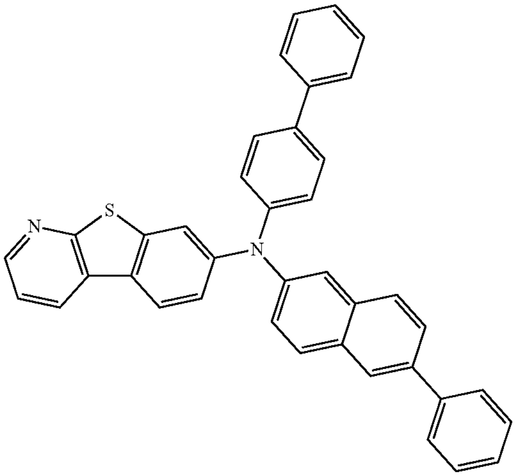
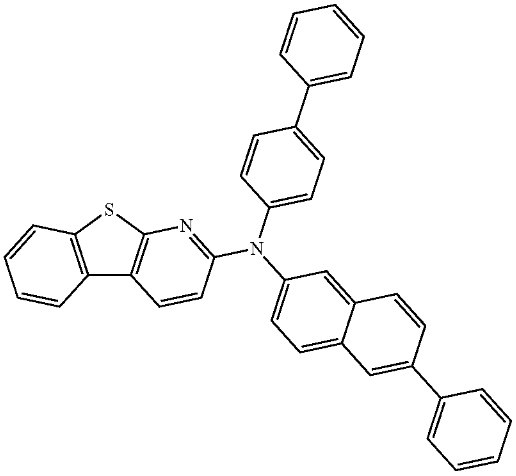
-continued
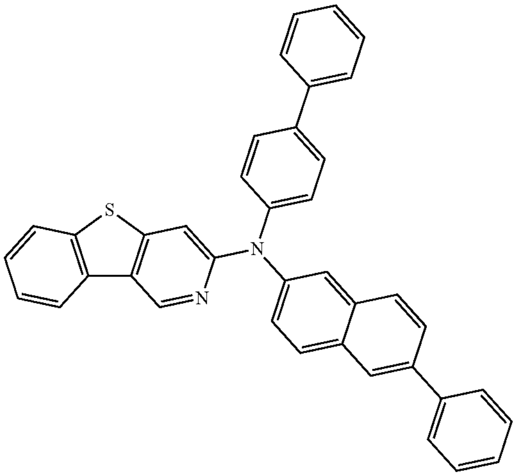
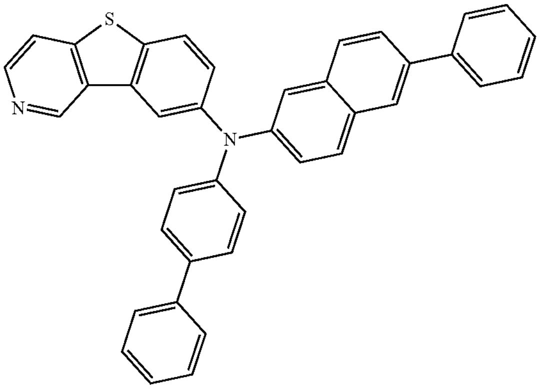
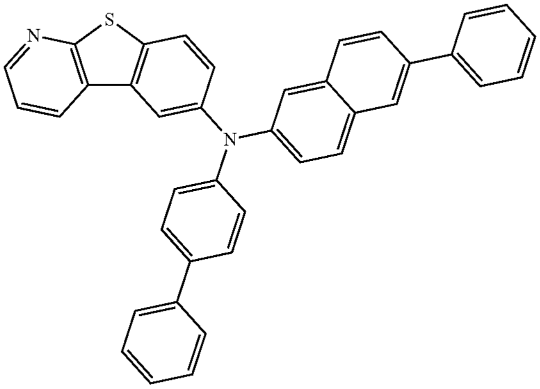
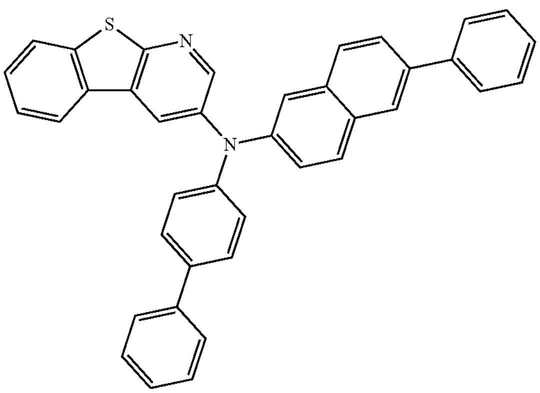

-continued
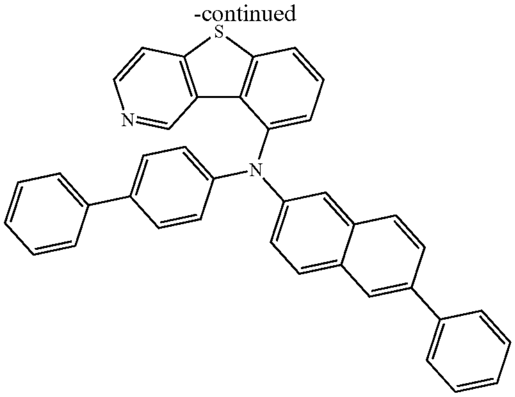
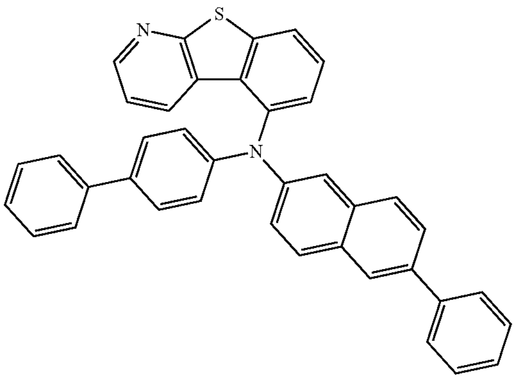
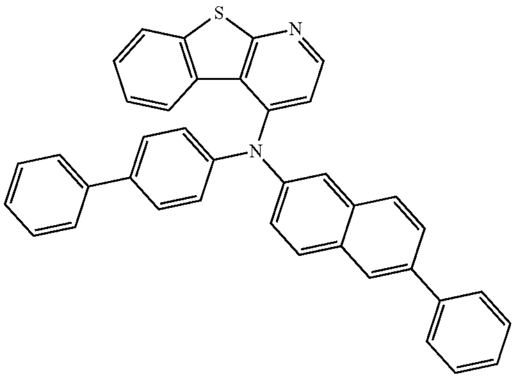
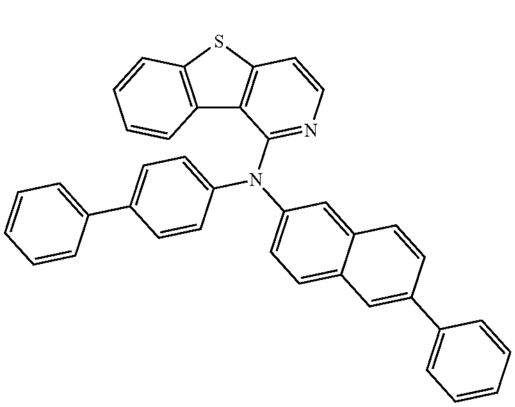
-continued
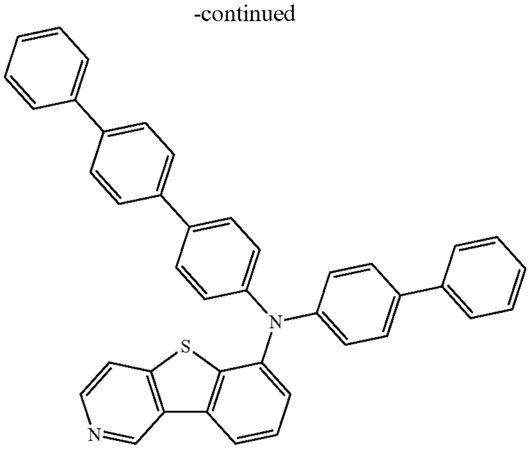
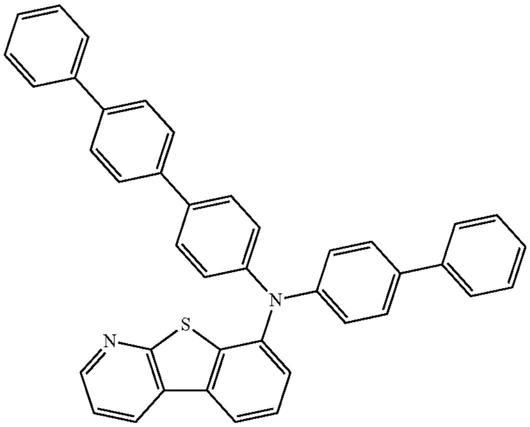
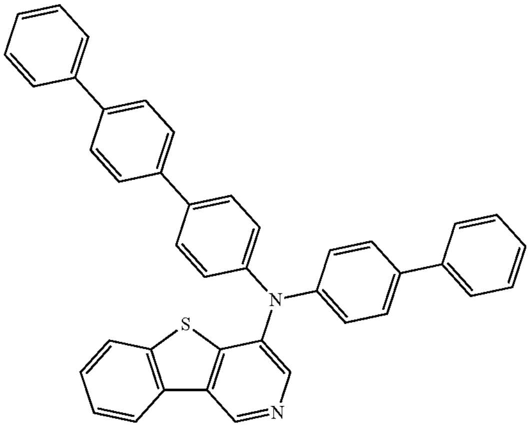

-continued
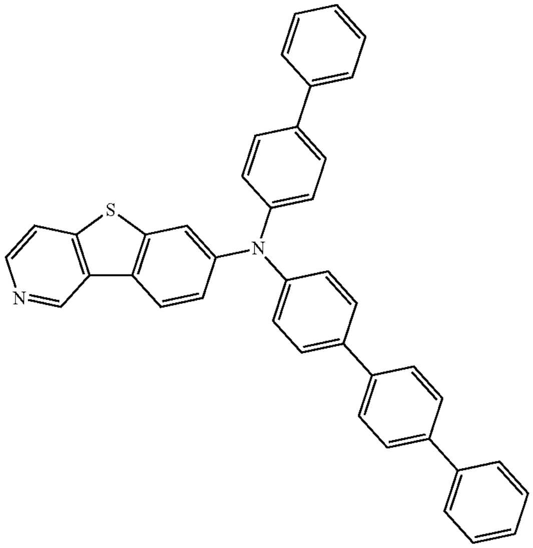
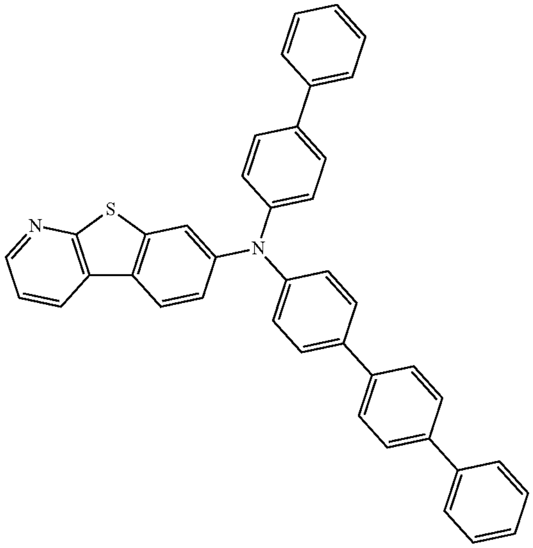
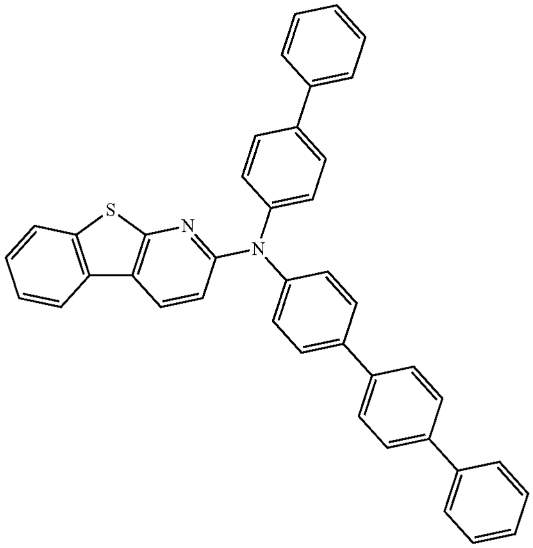
-continued
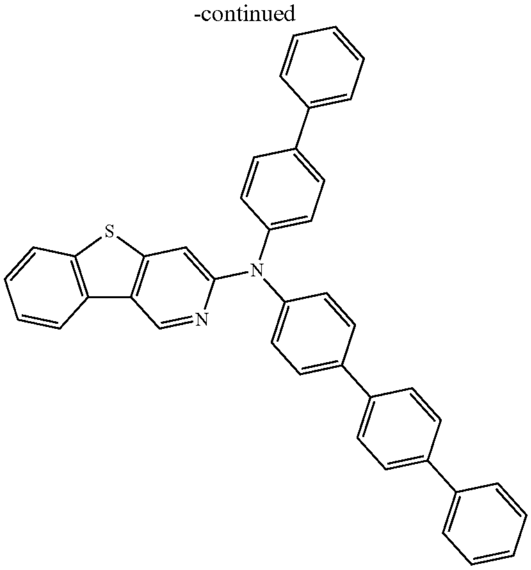
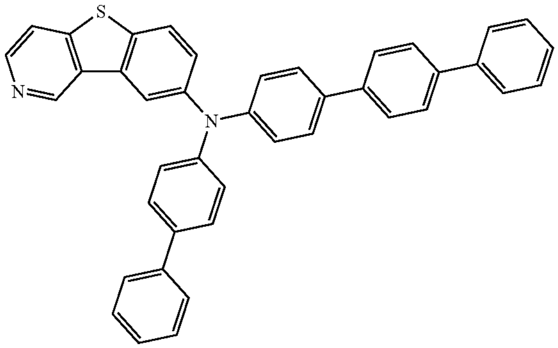
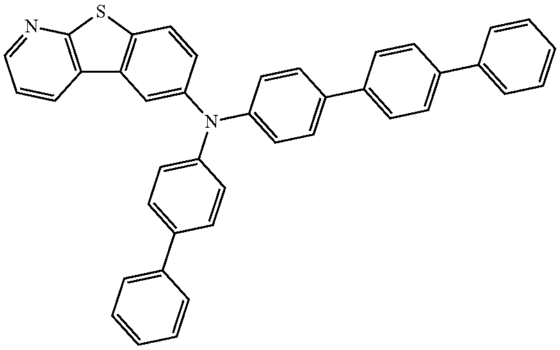
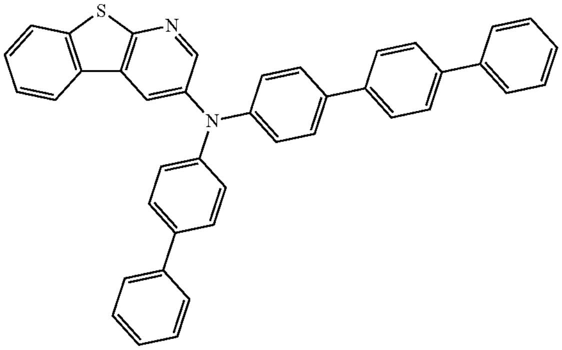

-continued
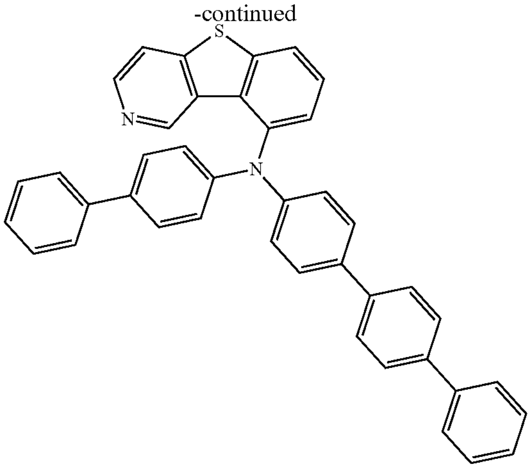
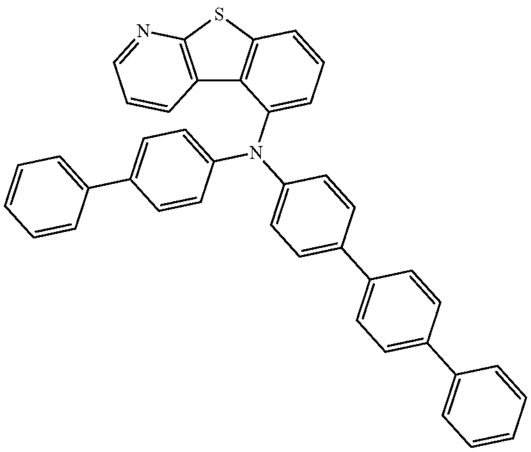
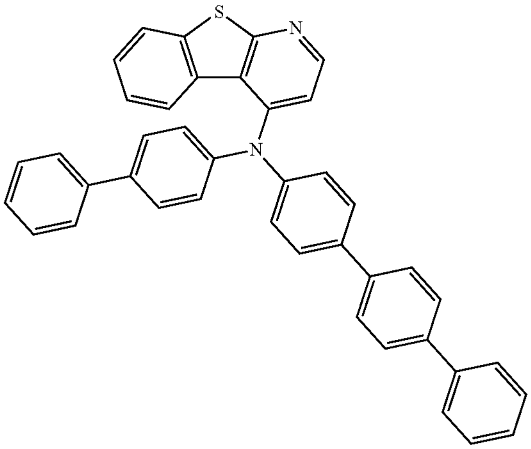
-continued
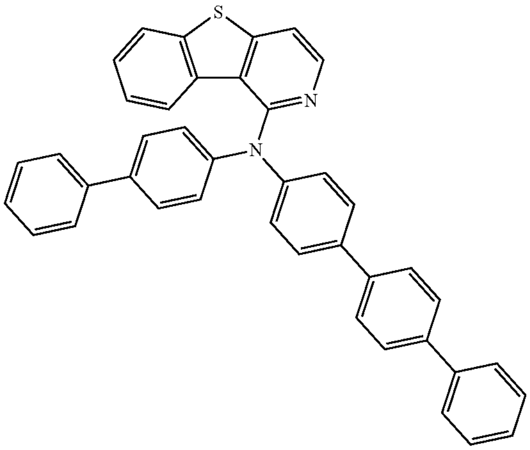
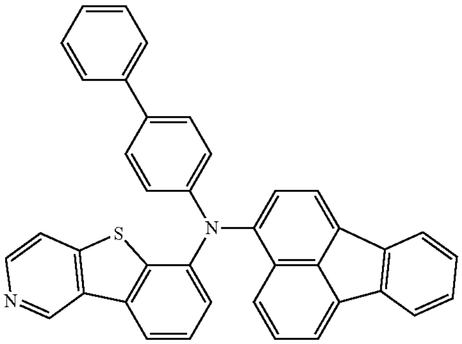
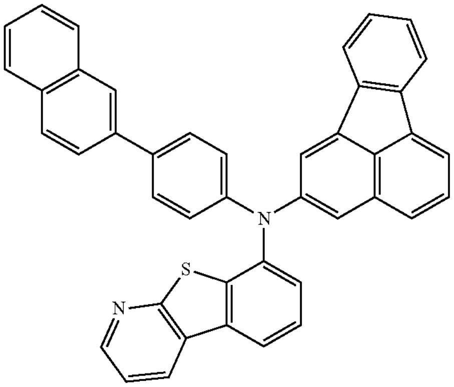
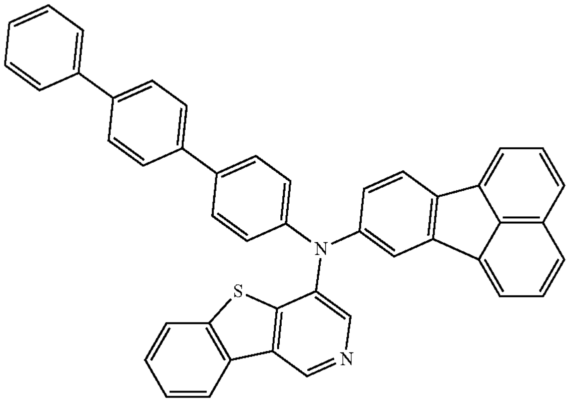

-continued
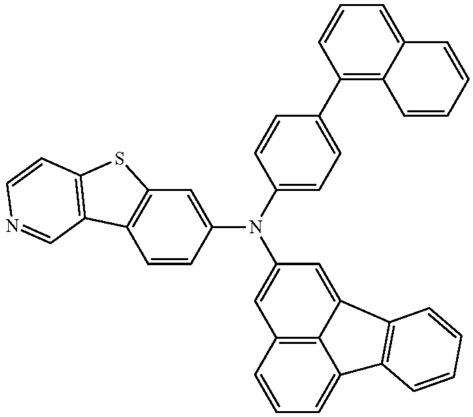
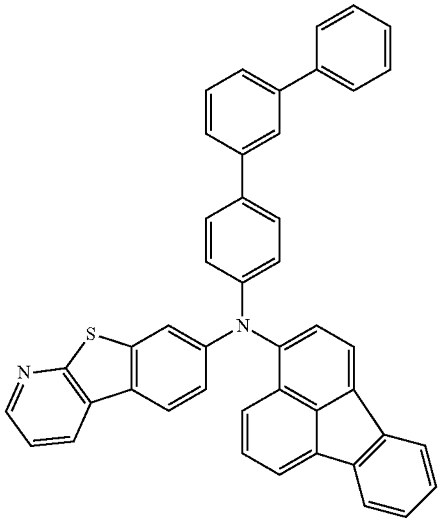
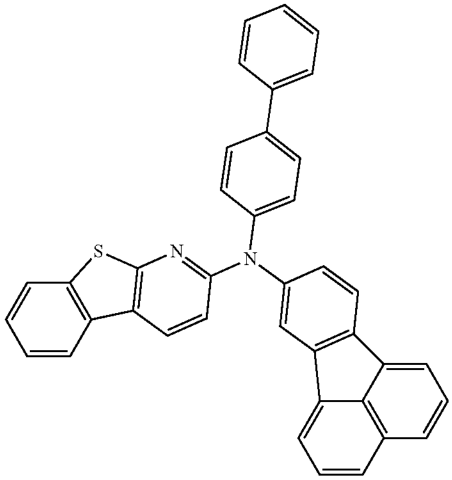
-continued
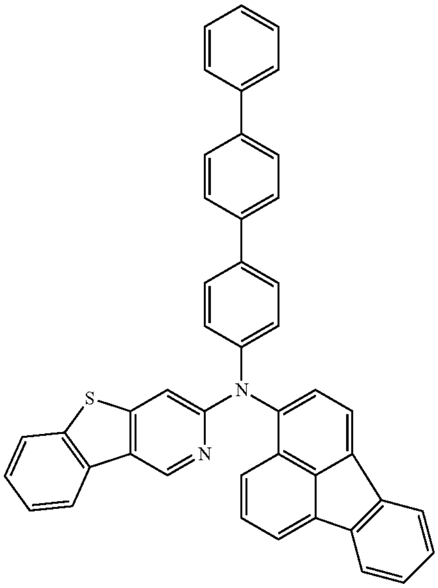
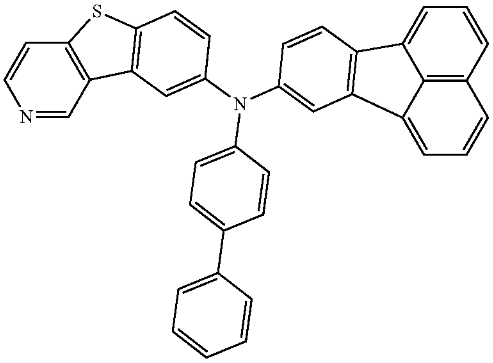
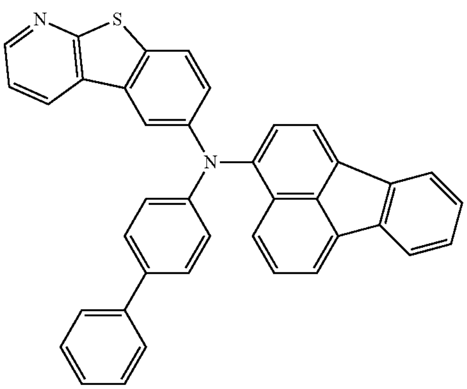

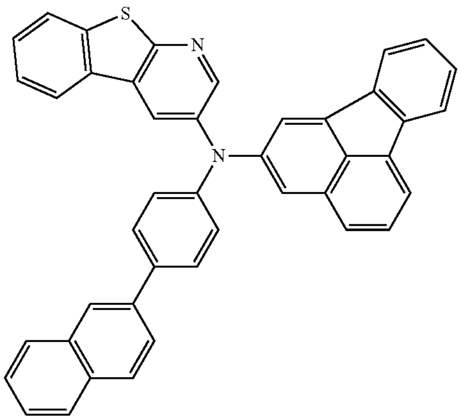
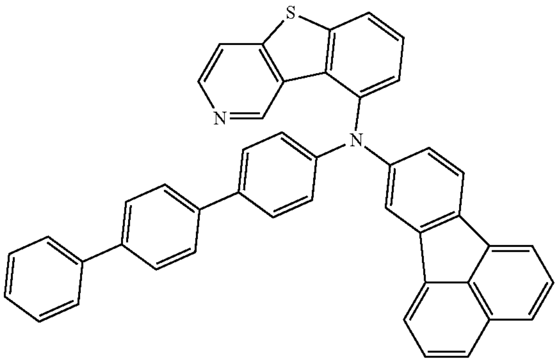
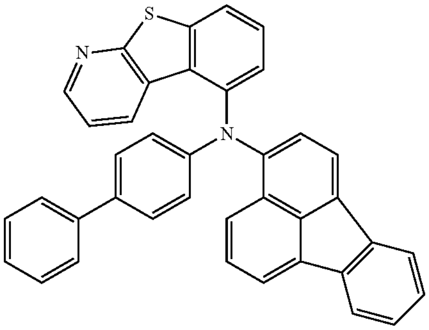
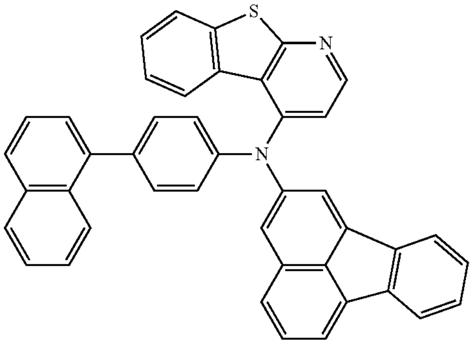
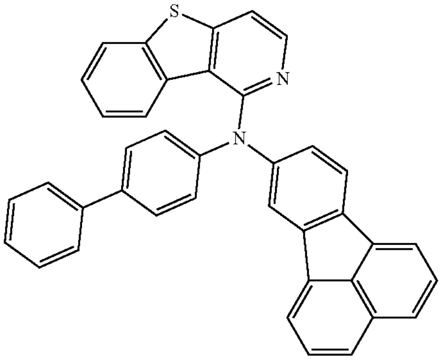
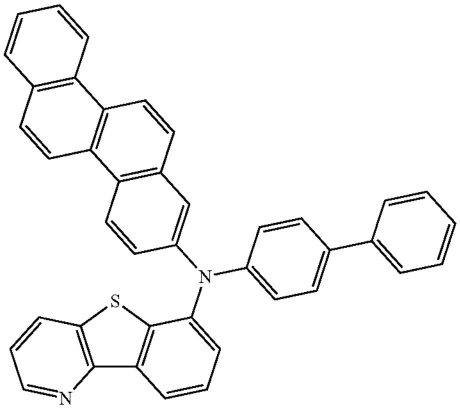
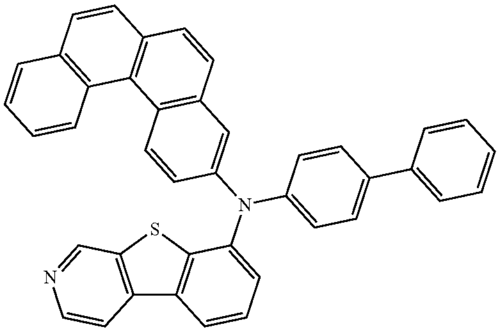
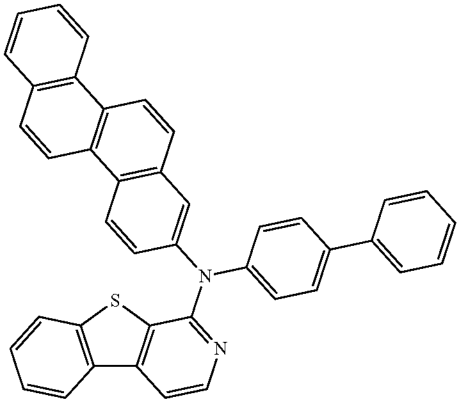

-continued
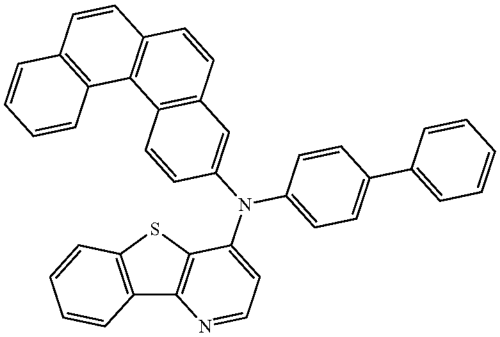
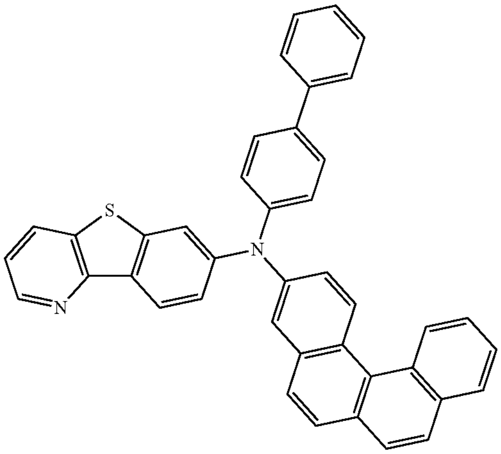
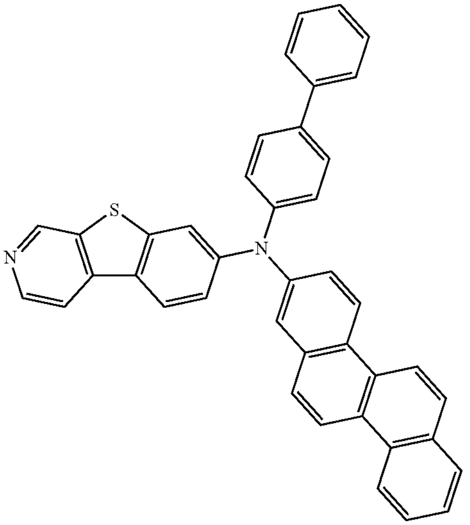
-continued
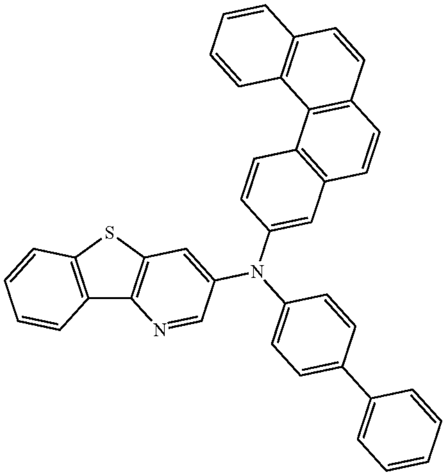
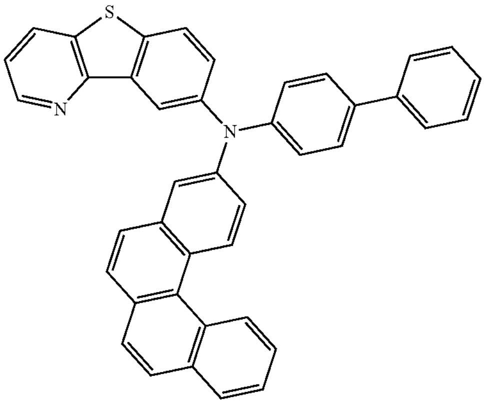
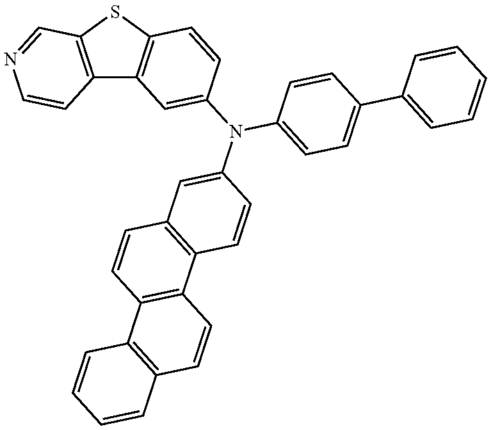
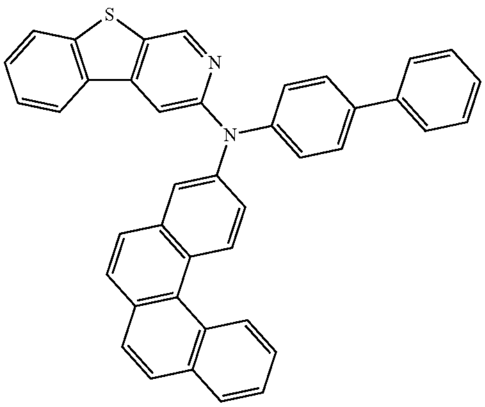

-continued
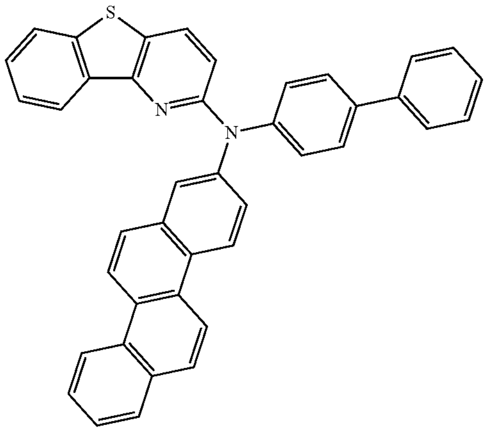
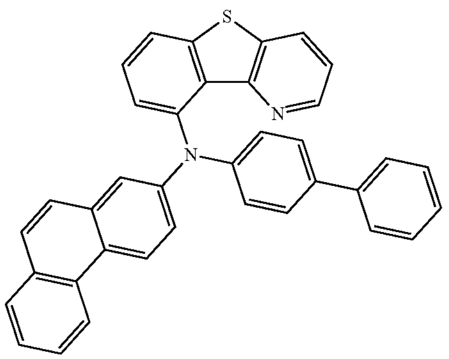
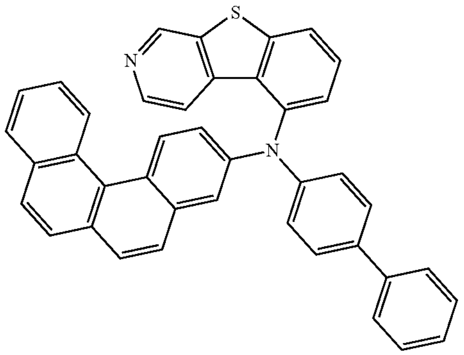
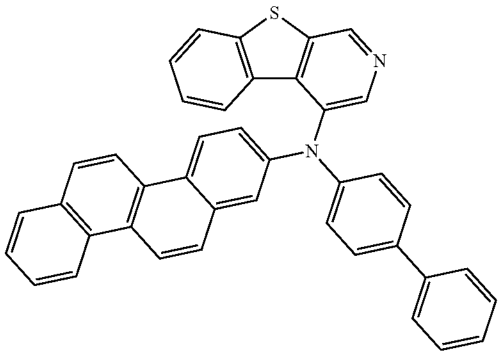
-continued
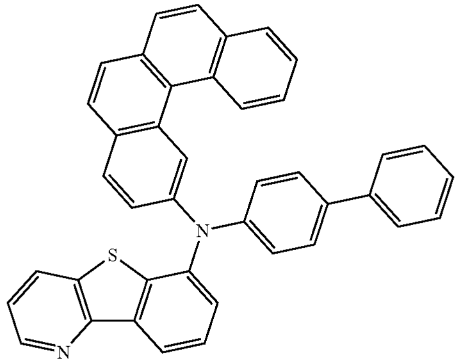
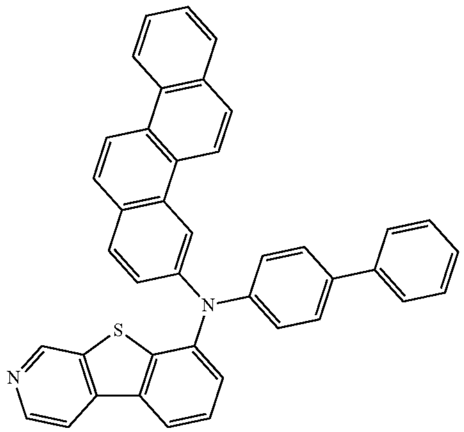
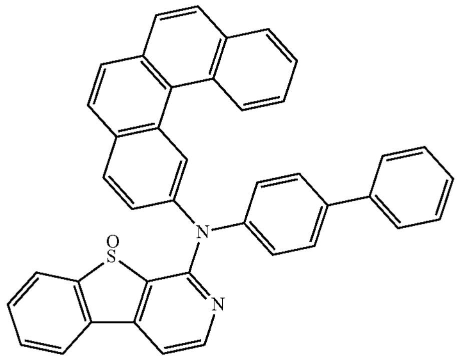
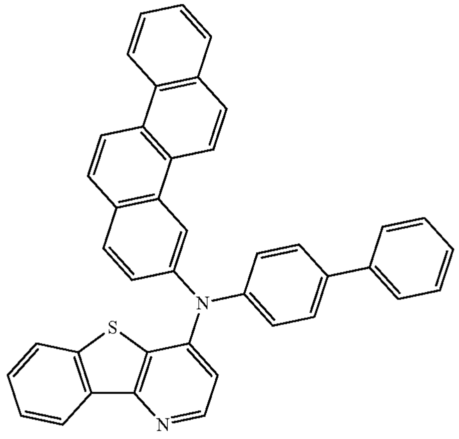

-continued
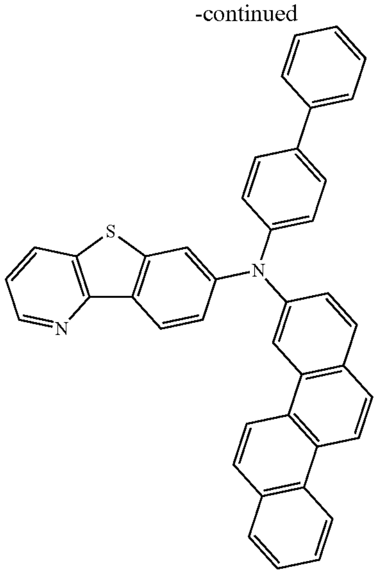
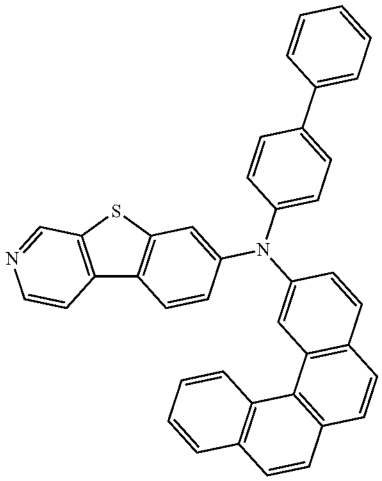
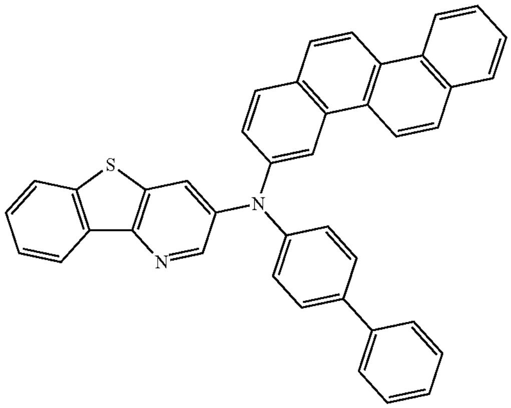
-continued
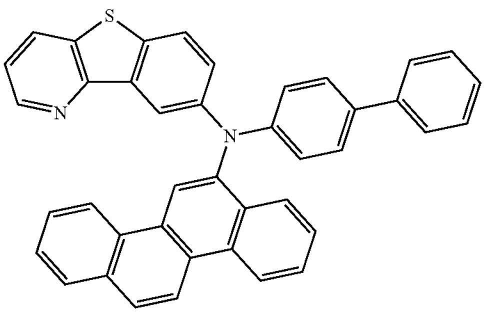
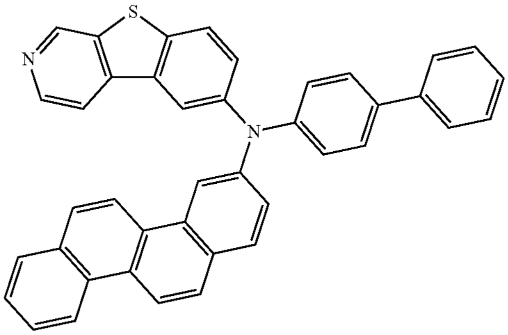
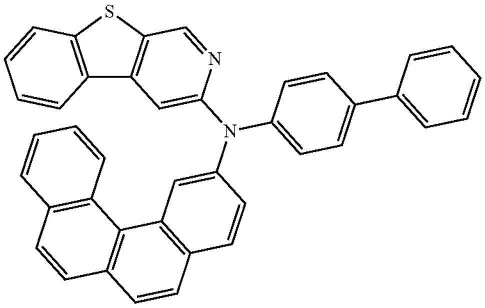
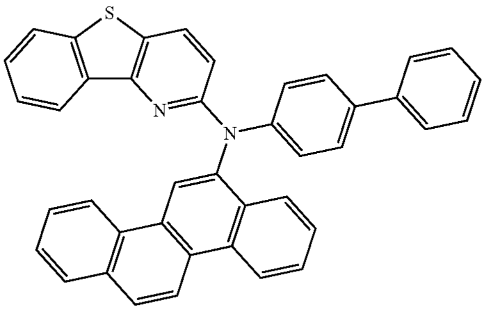
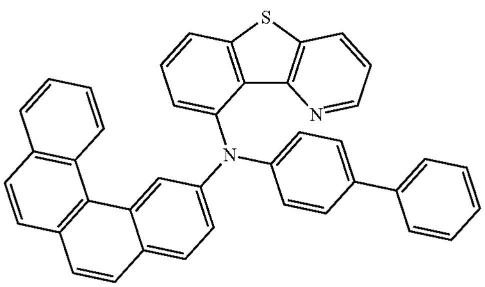

-continued
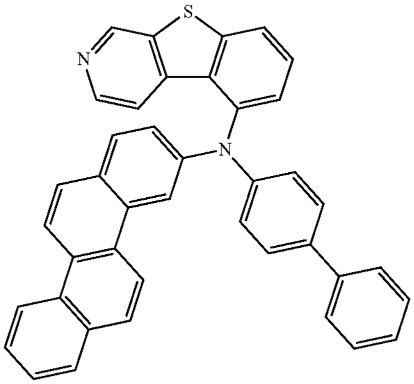
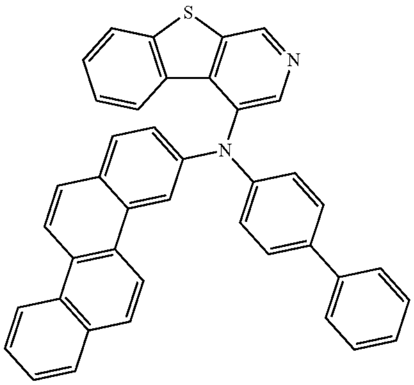
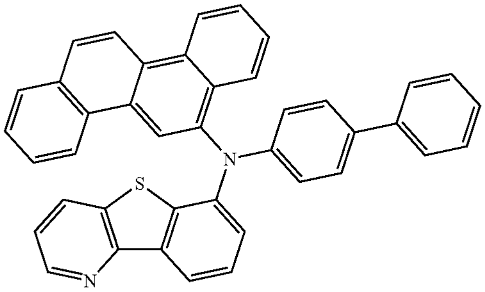
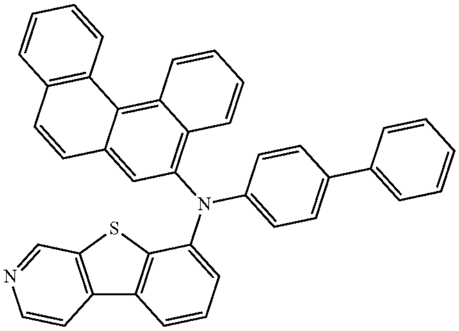
-continued
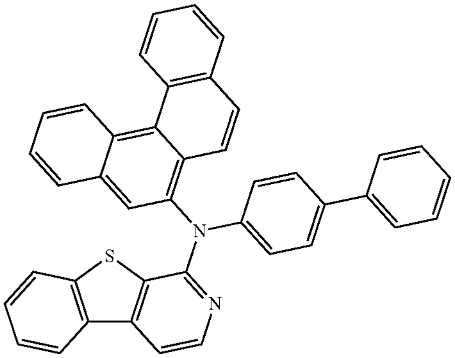
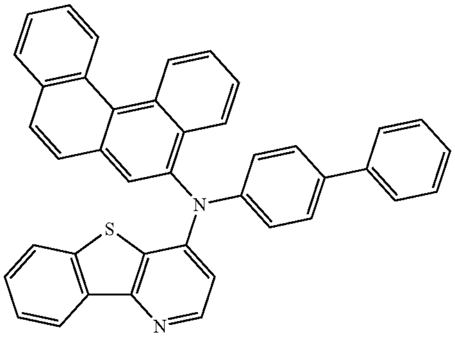
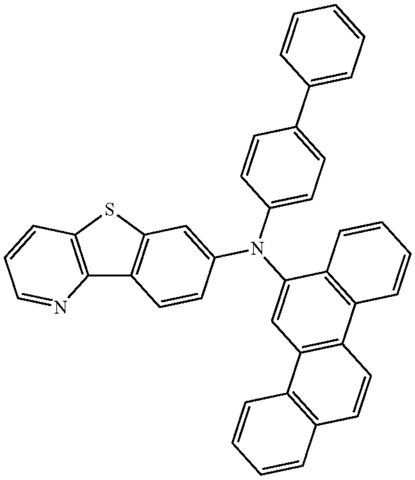
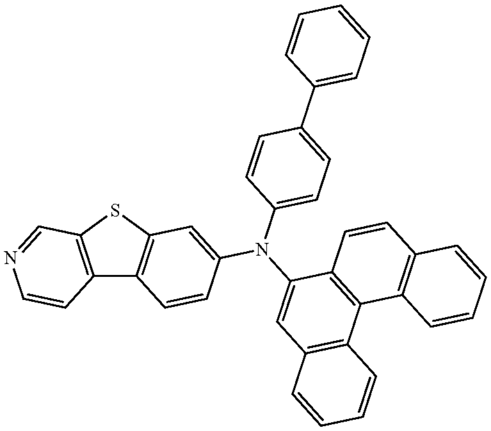

-continued
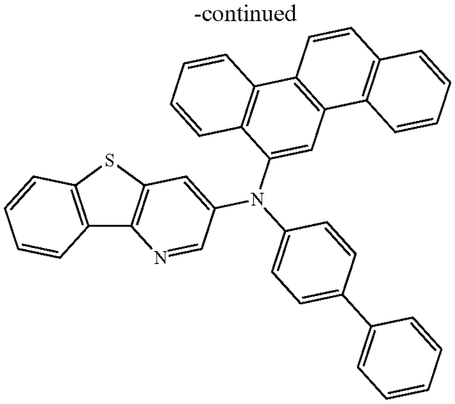
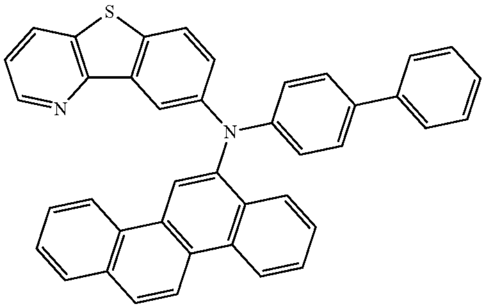
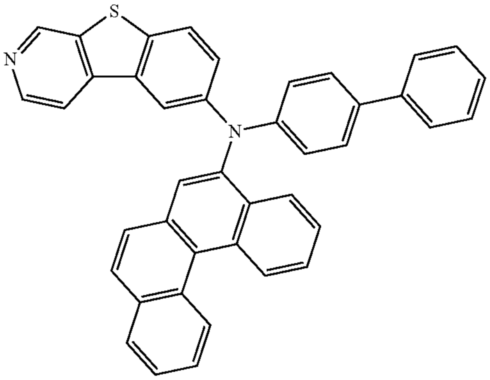
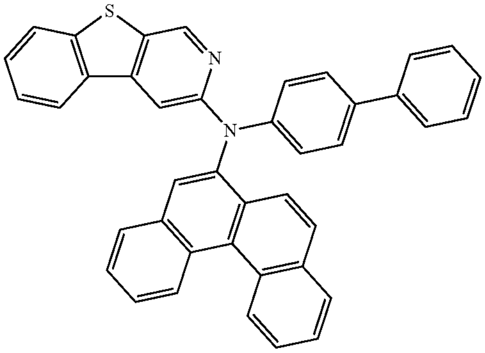
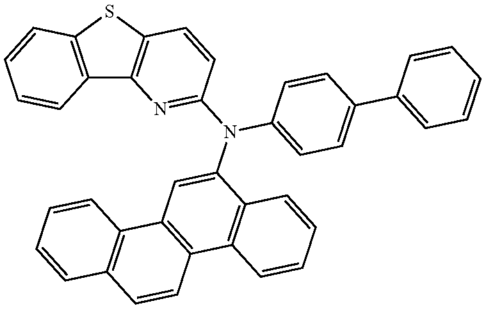
-continued
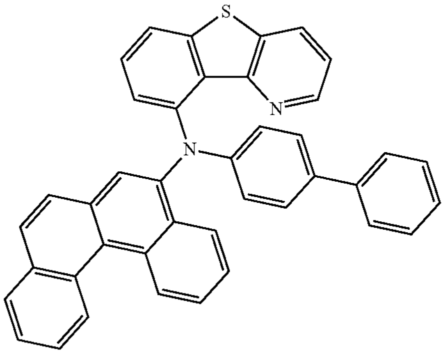
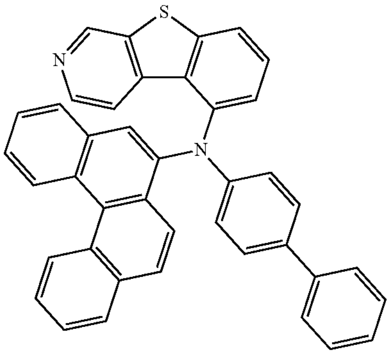
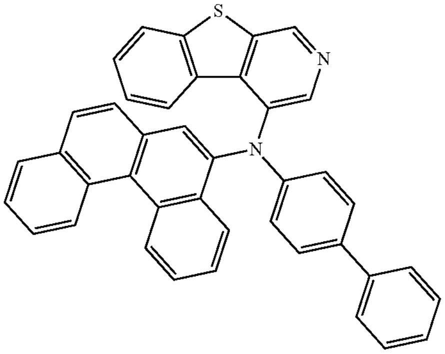
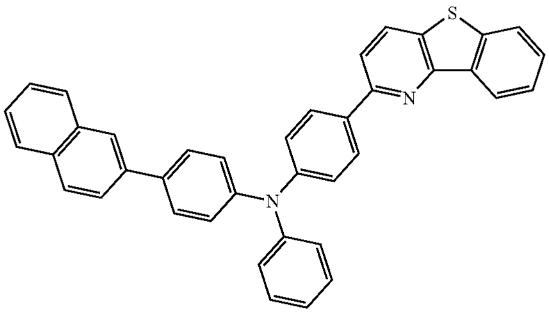
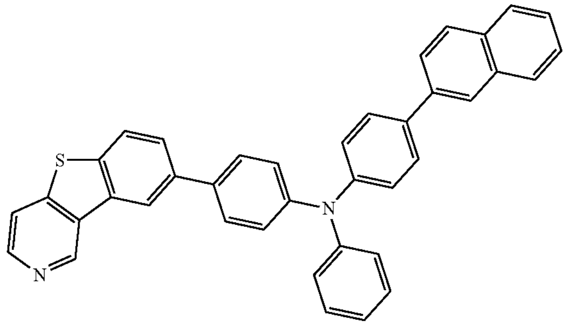

-continued
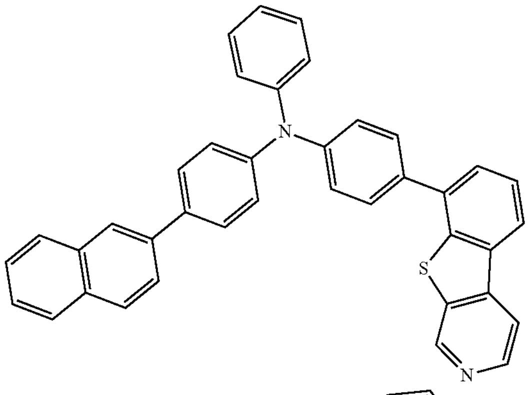
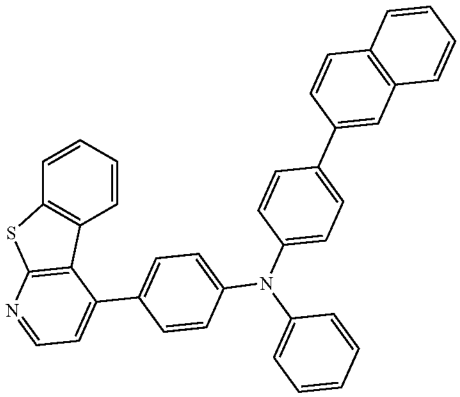
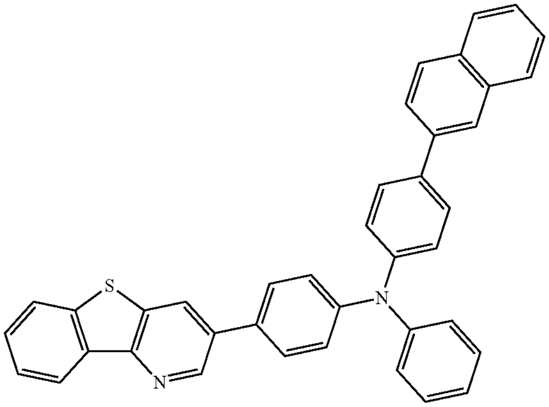
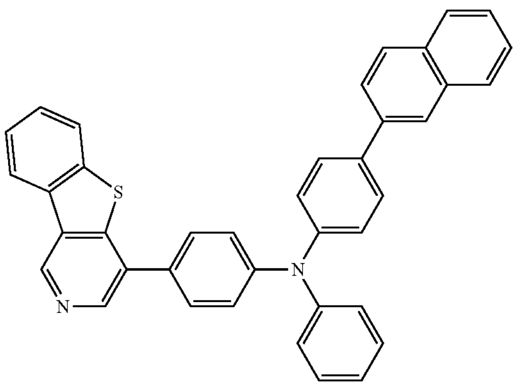
-continued
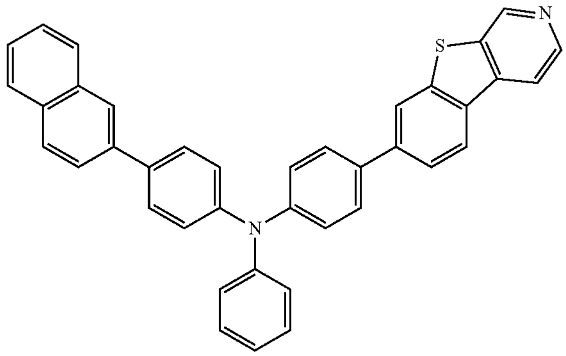
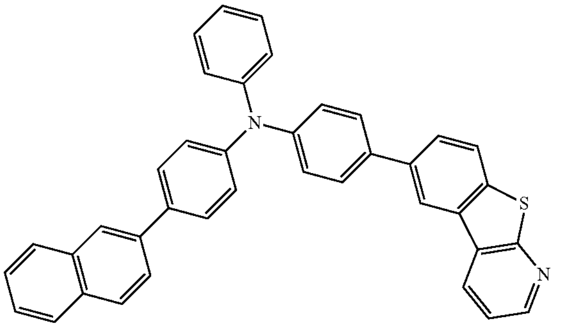
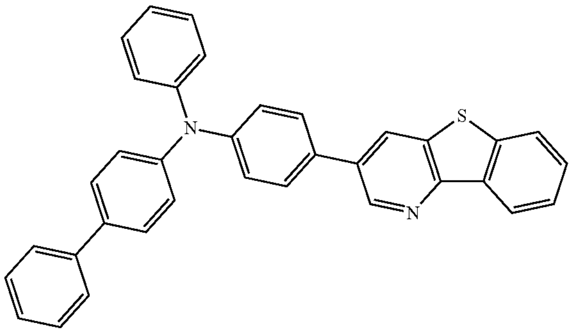
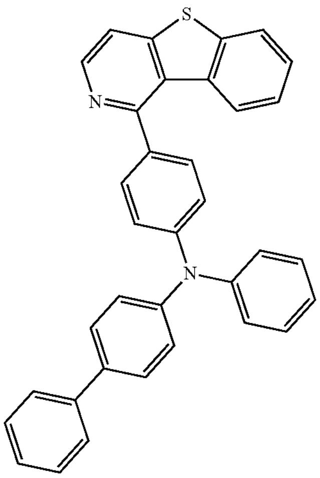

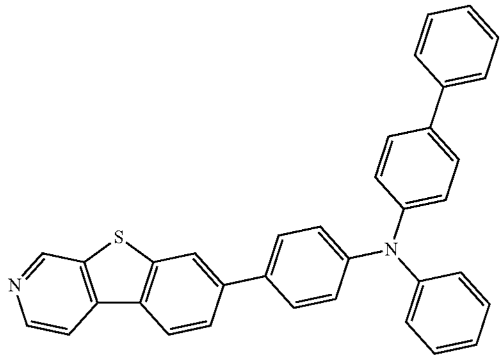
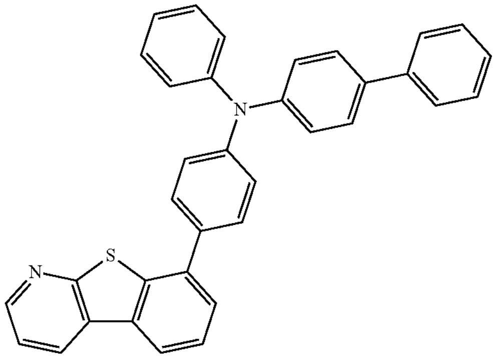
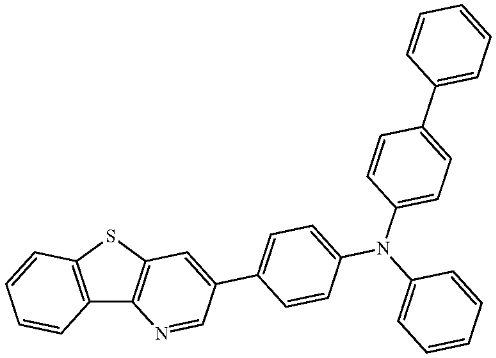
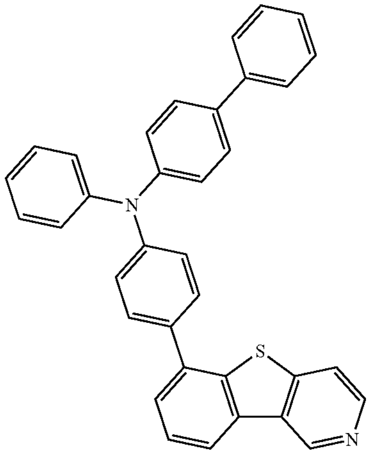
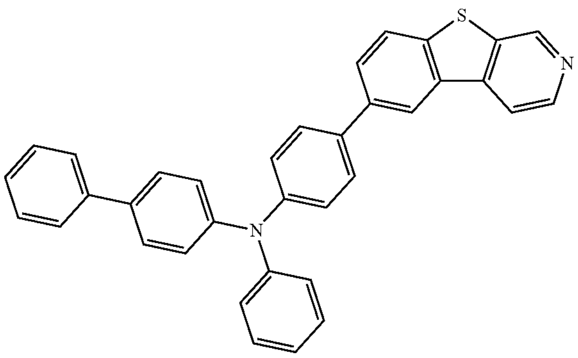
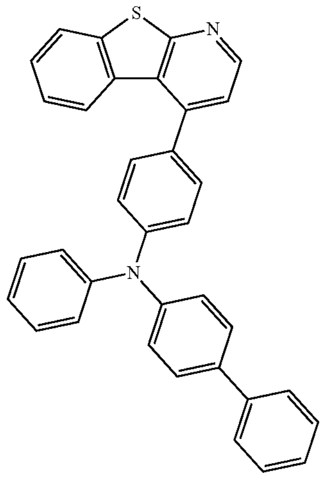
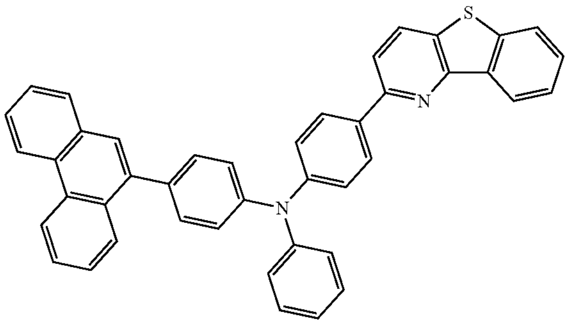
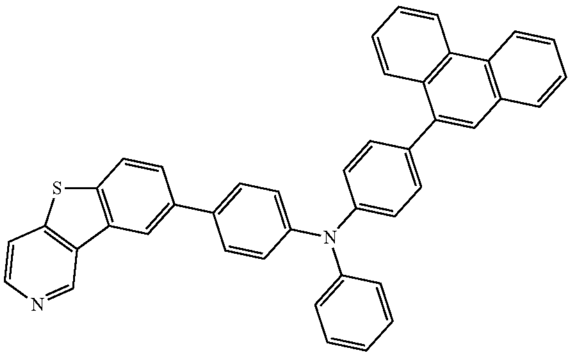

-continued
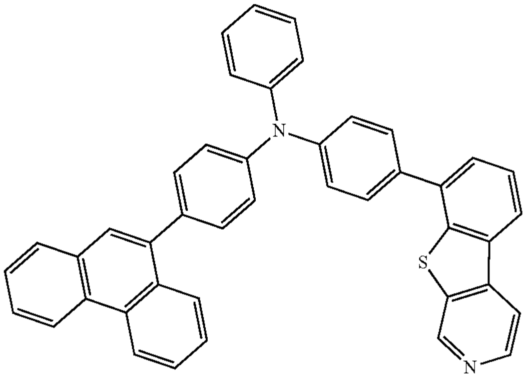
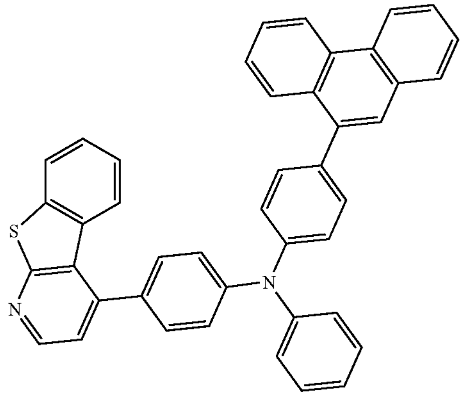
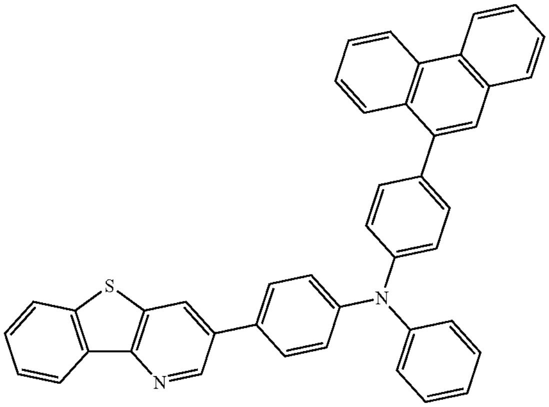
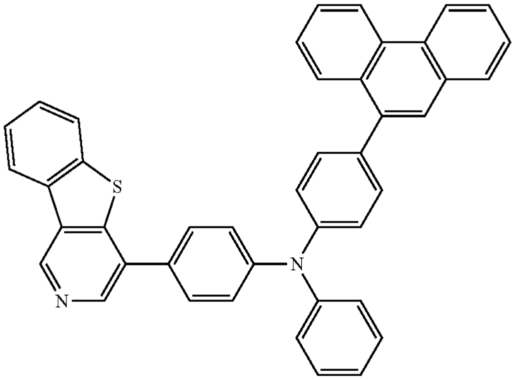
-continued
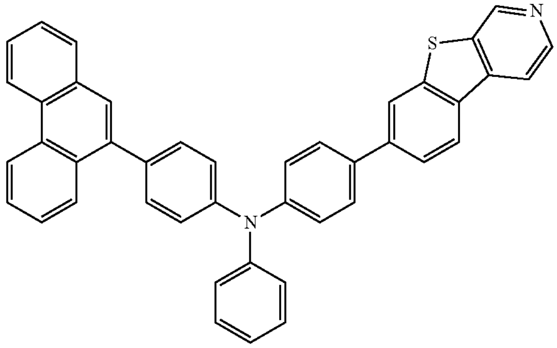
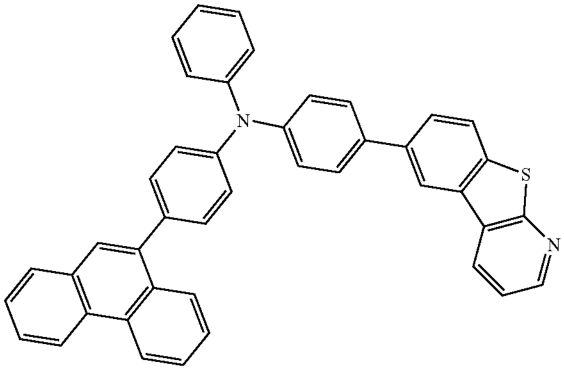
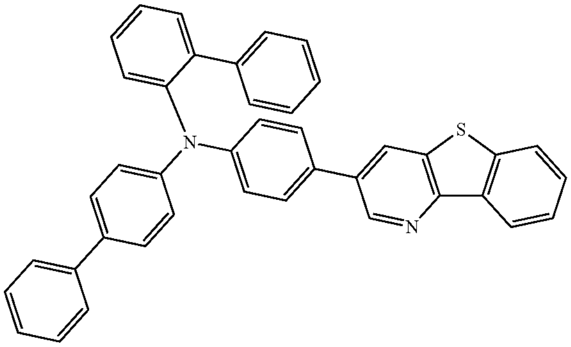
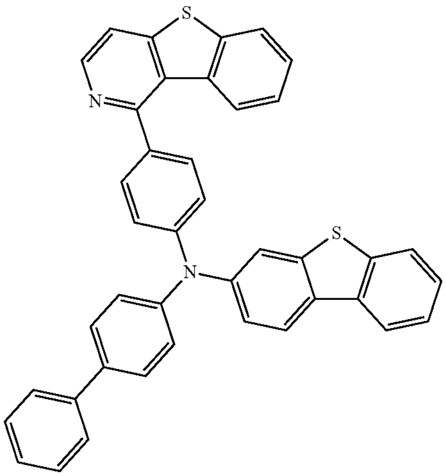

-continued
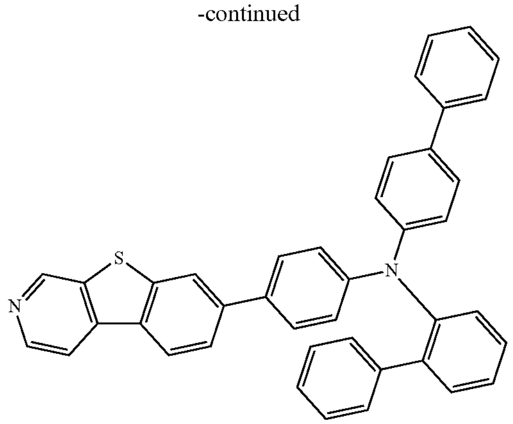
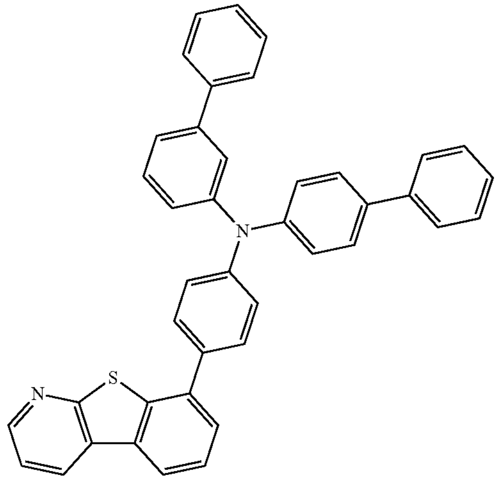
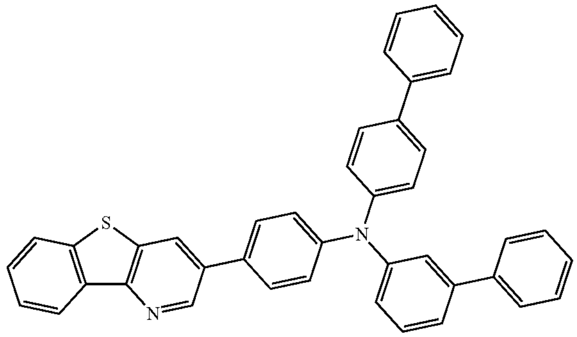
-continued
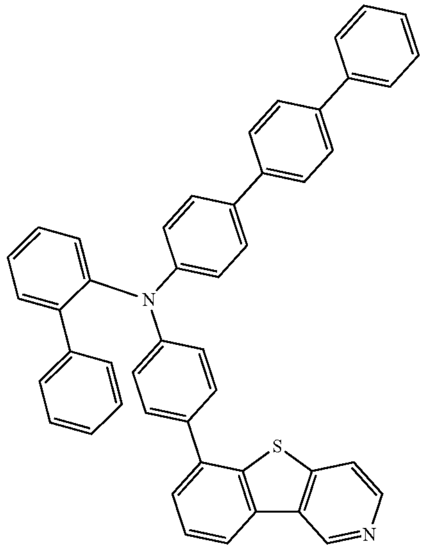
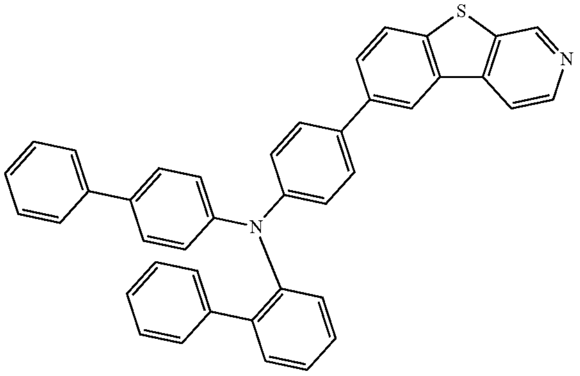
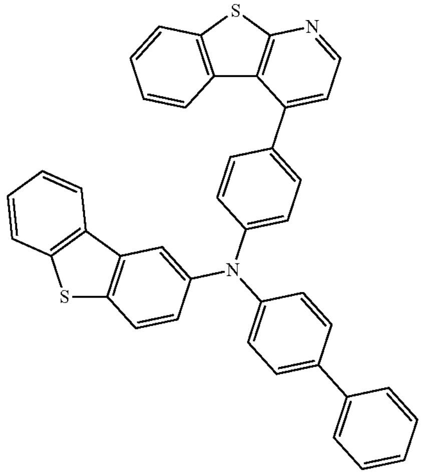

-continued
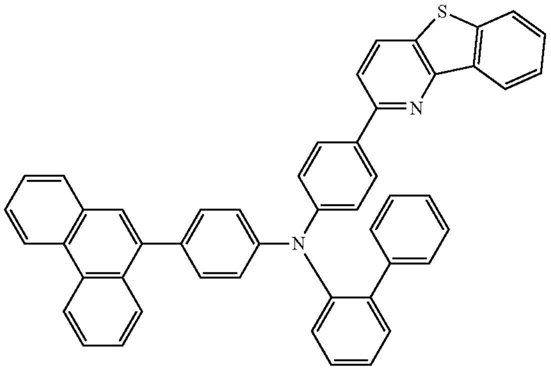
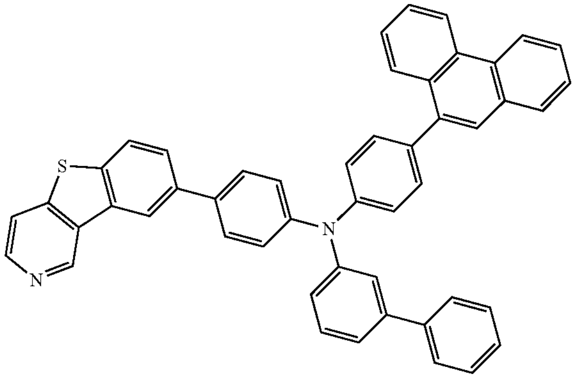
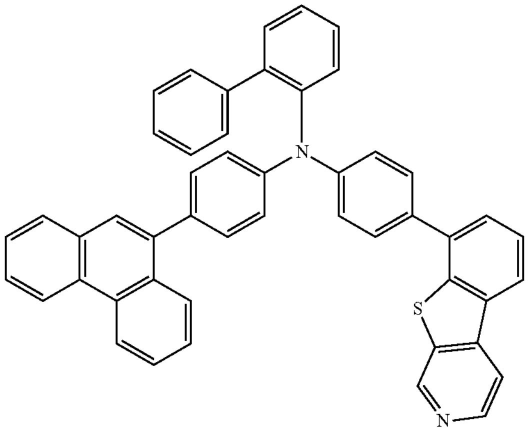
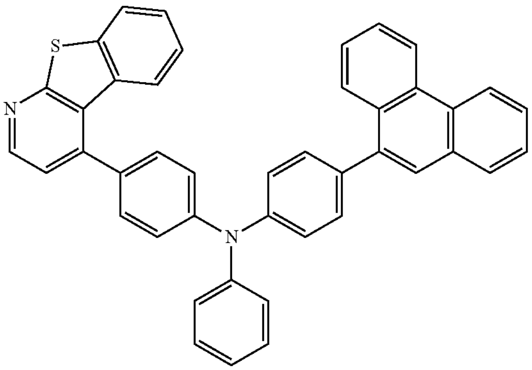
-continued
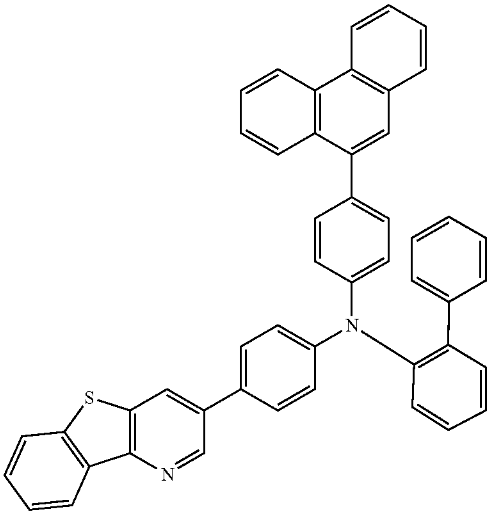
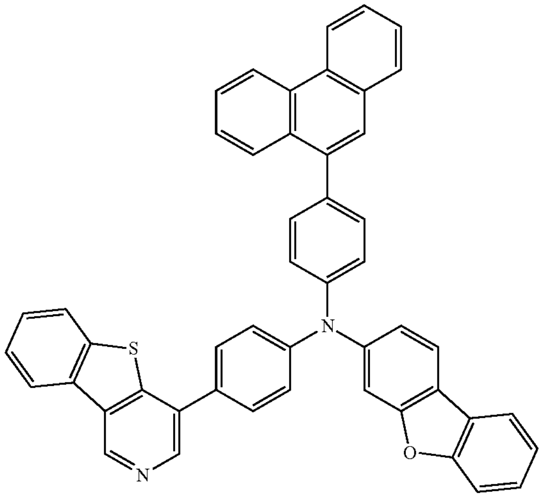
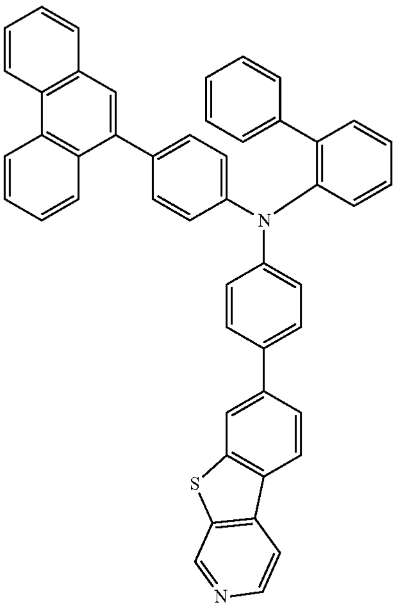

-continued
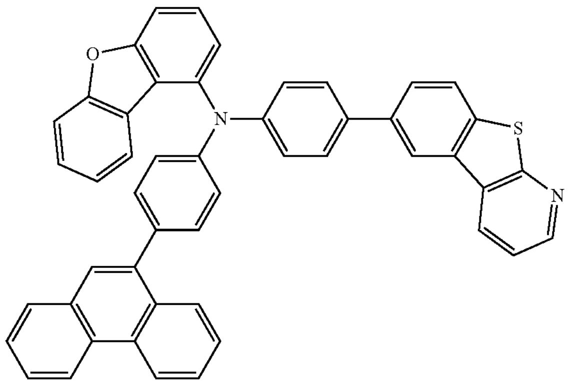
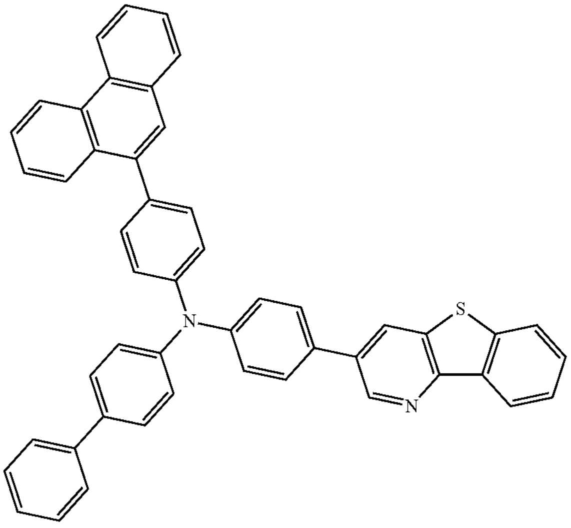
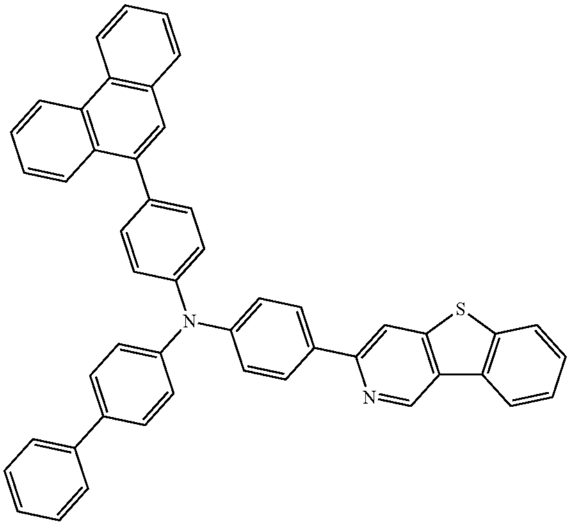
-continued
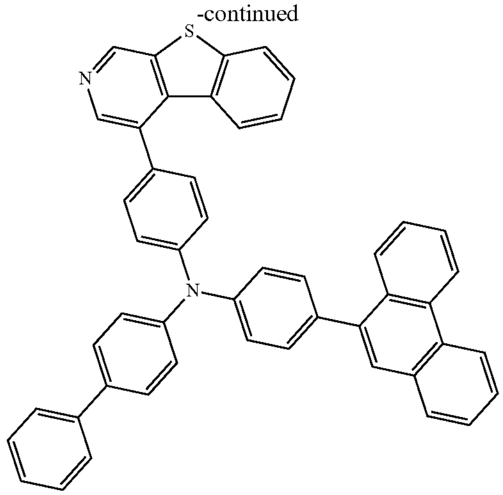
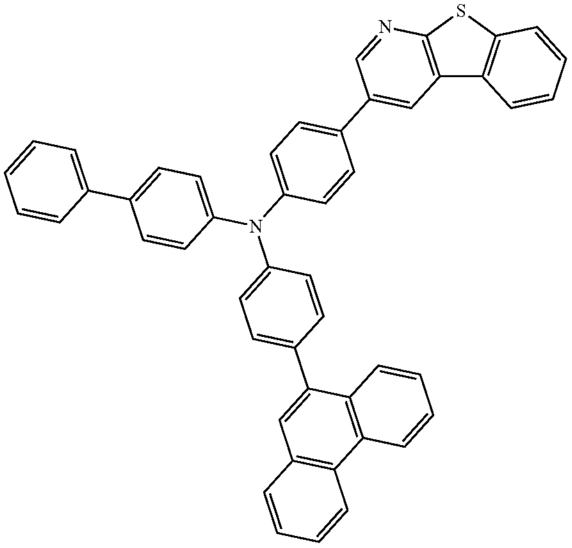
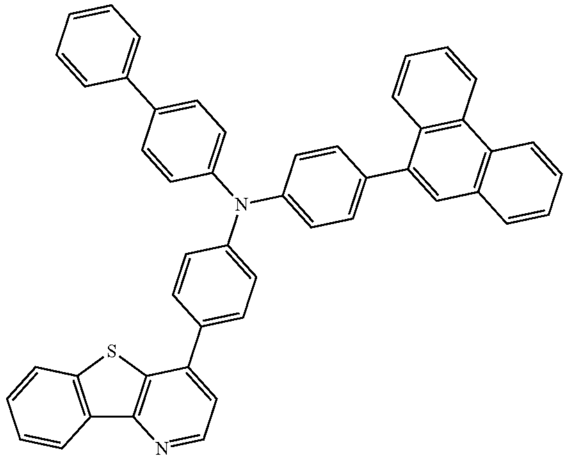

-continued
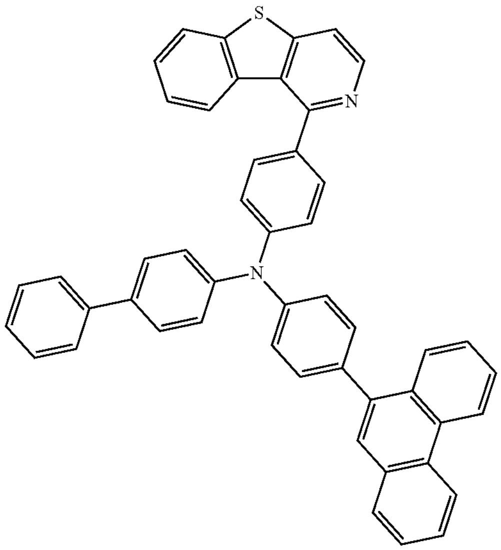
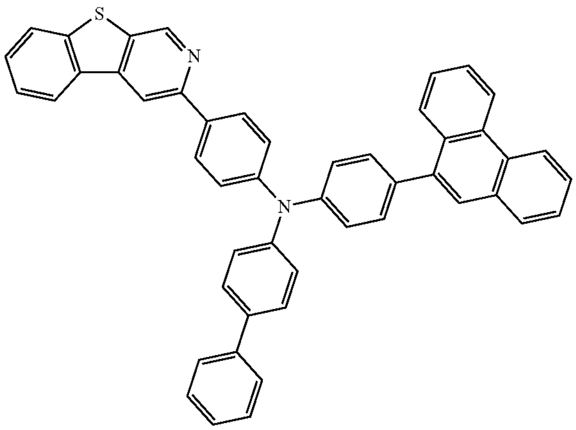
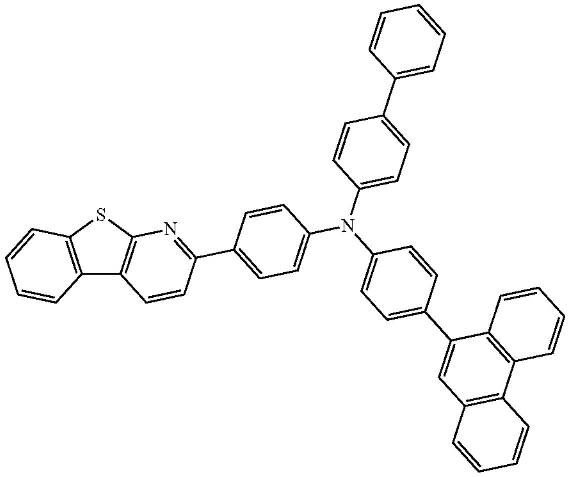
-continued
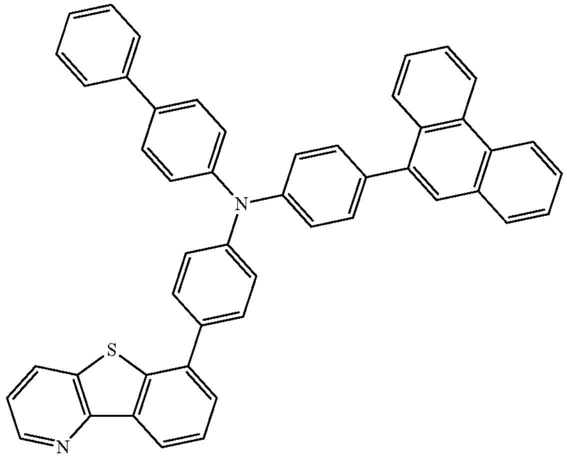
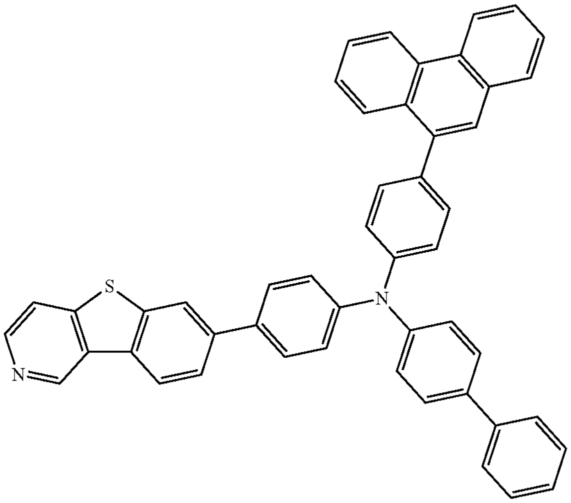
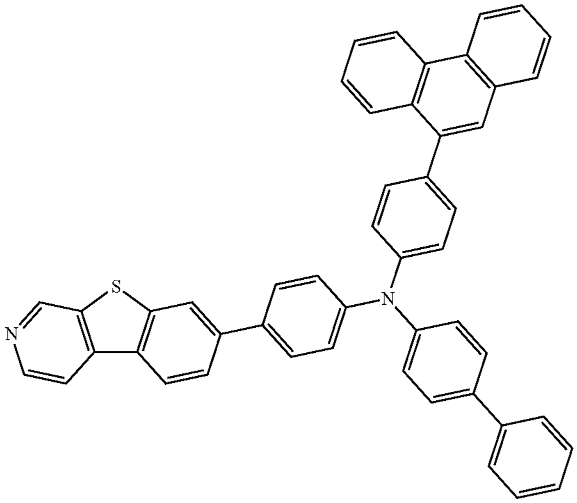

-continued
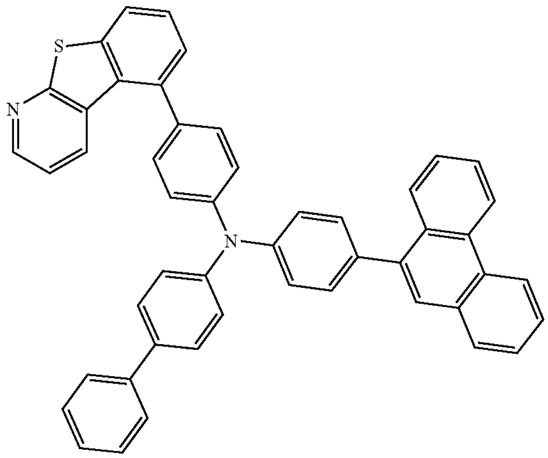
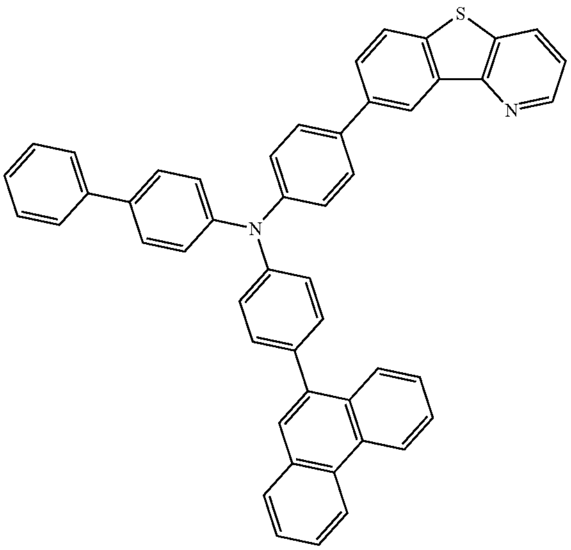
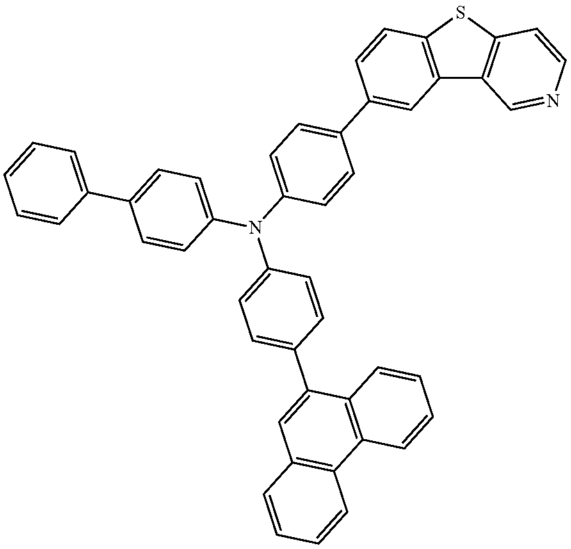
-continued
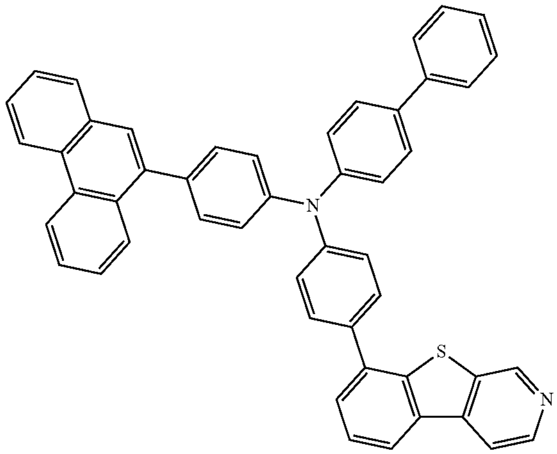
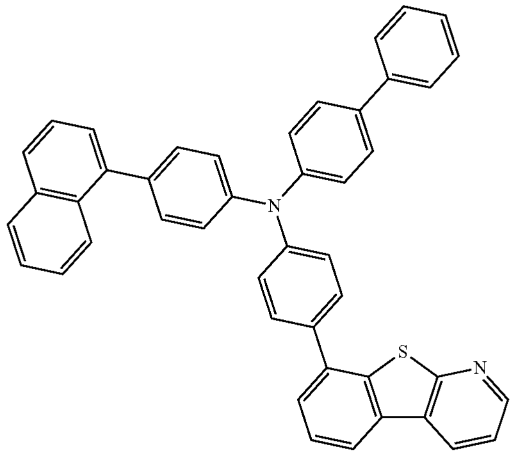
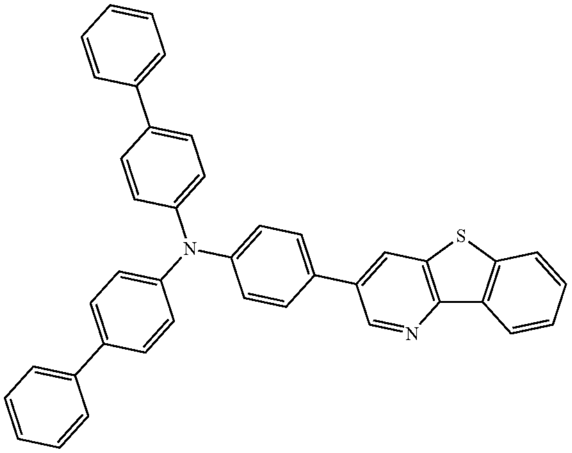

-continued
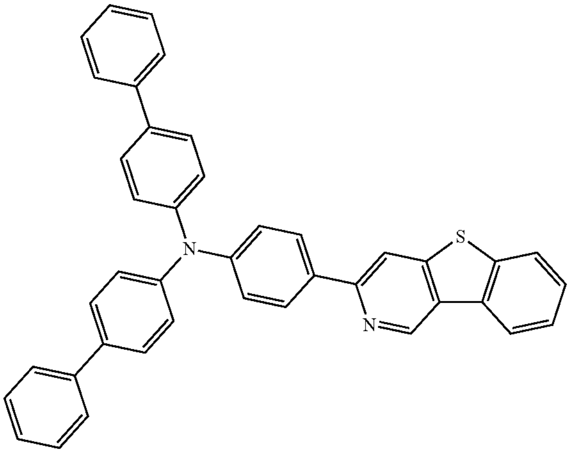
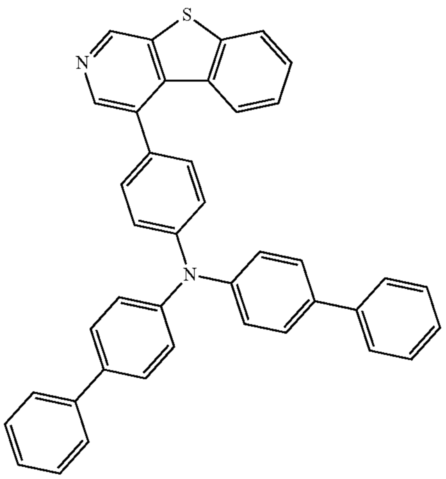
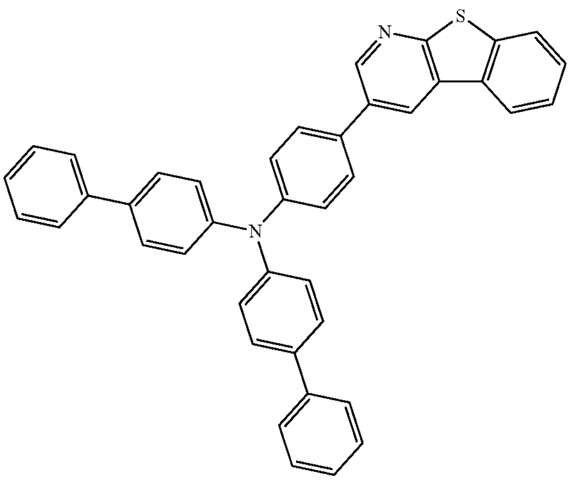
-continued
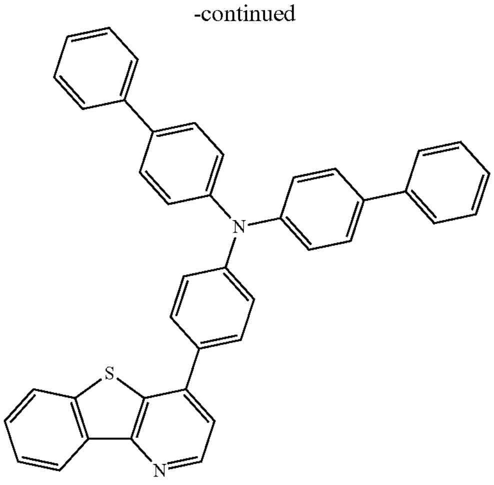
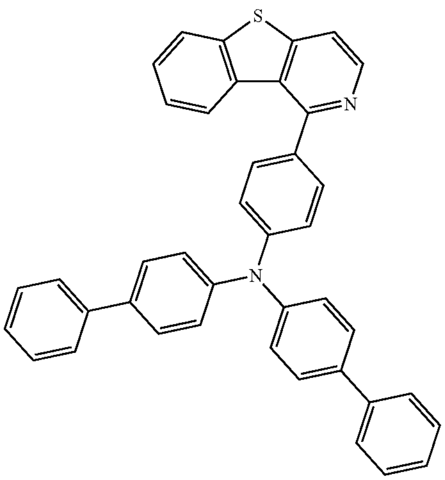
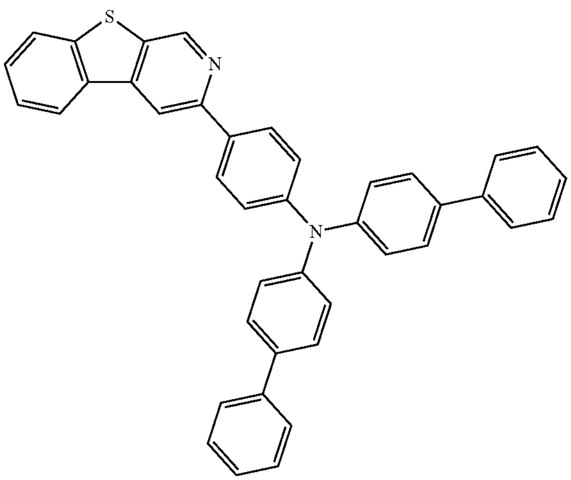

-continued
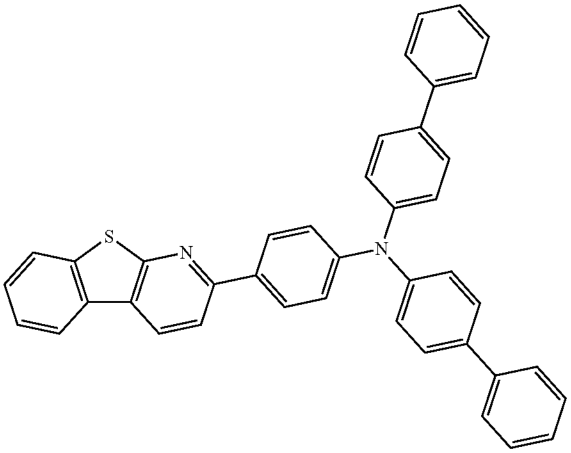
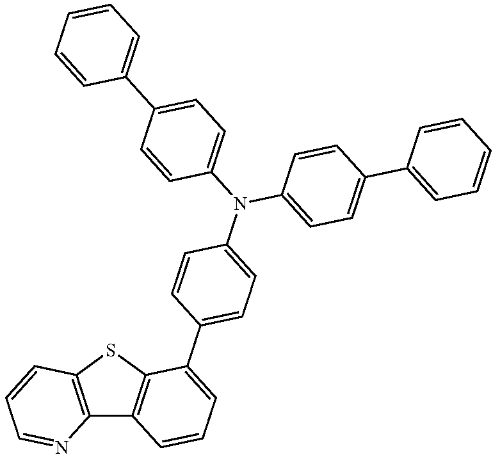
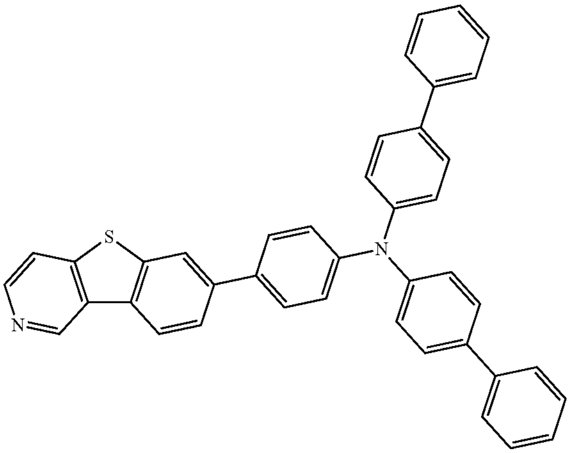
-continued
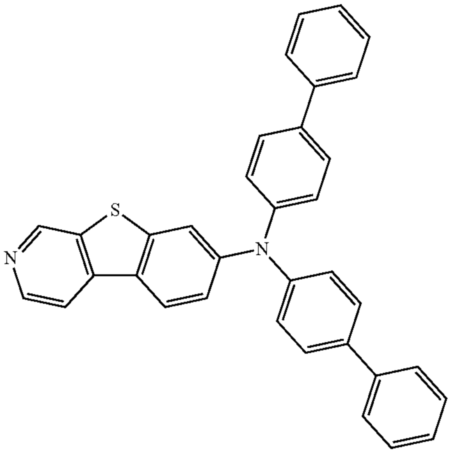
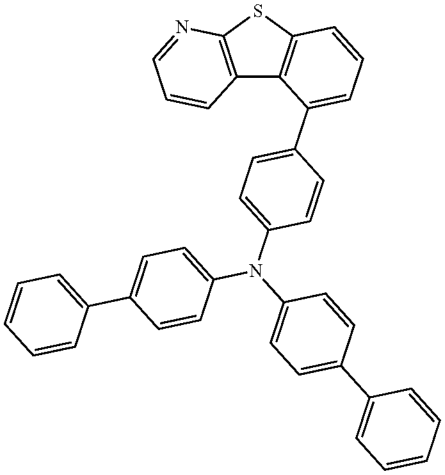
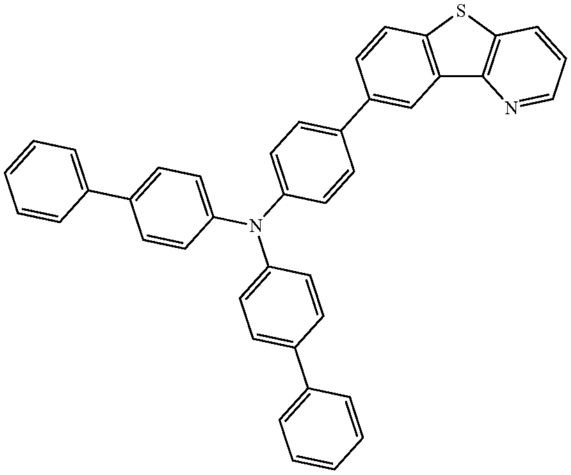

-continued
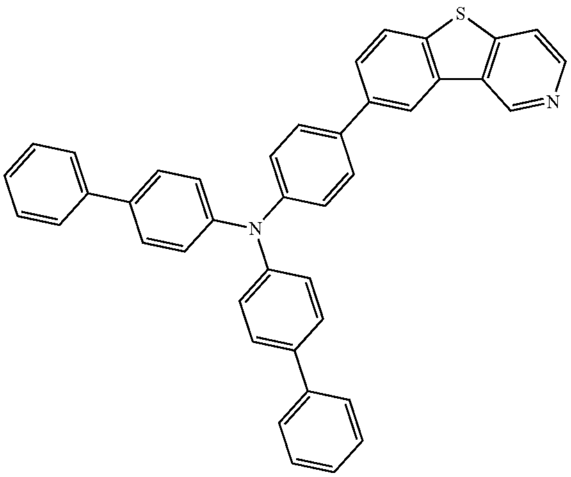
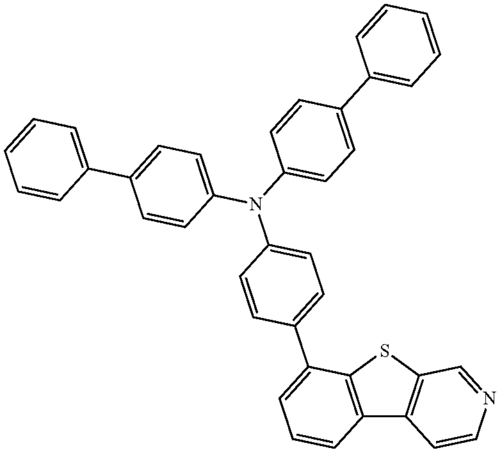
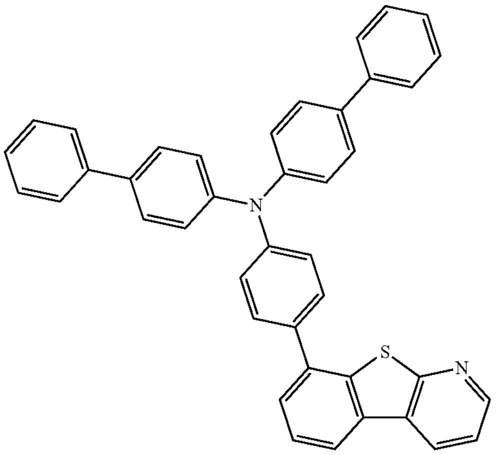
-continued
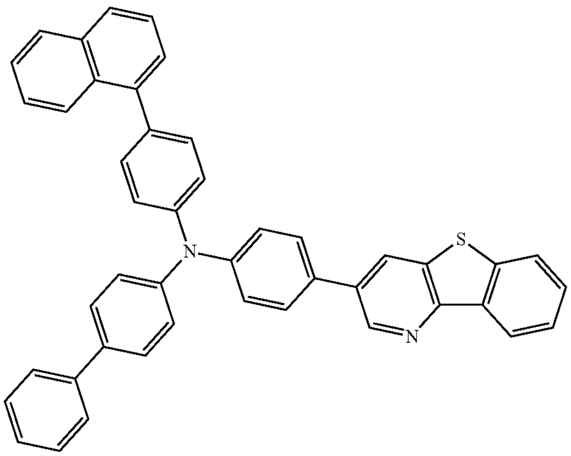
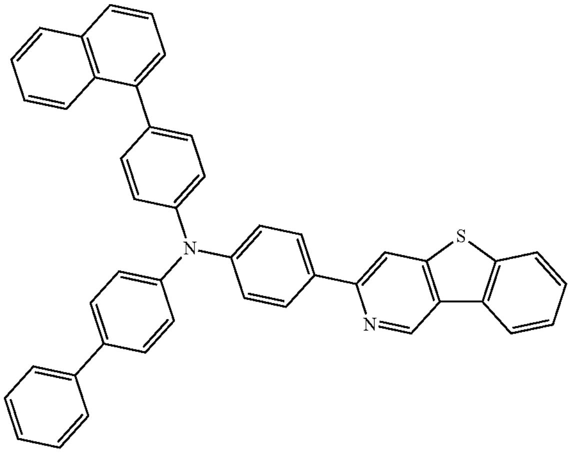
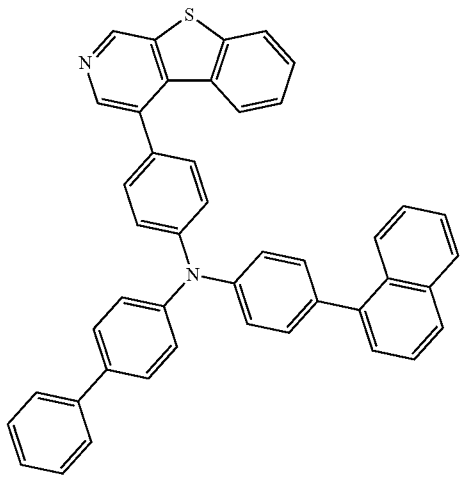

-continued
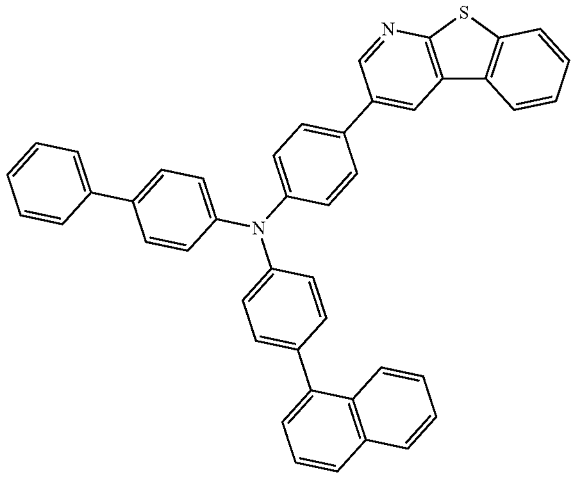
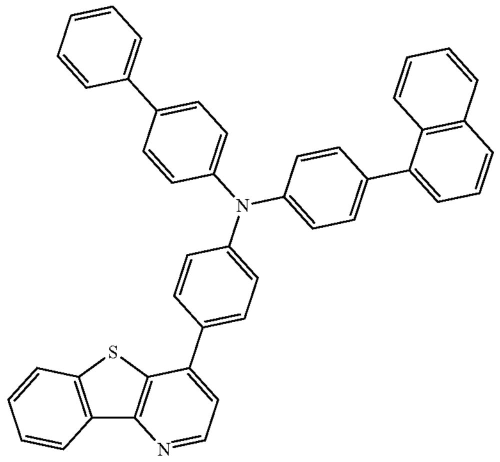
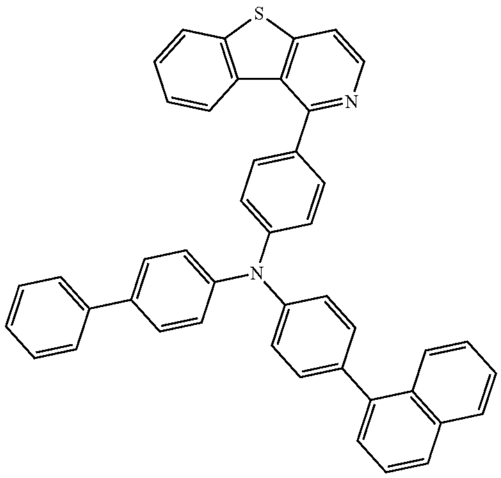
-continued
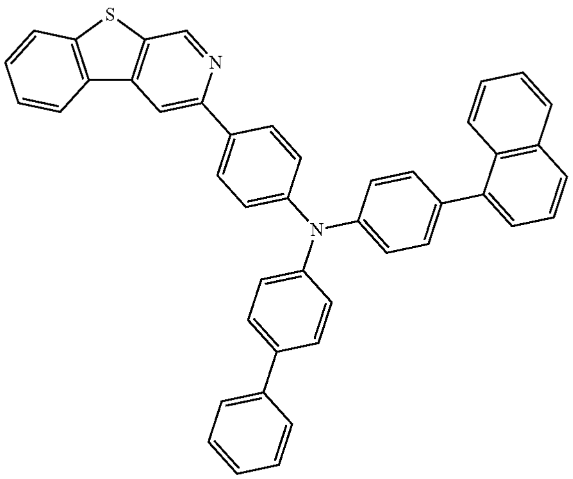
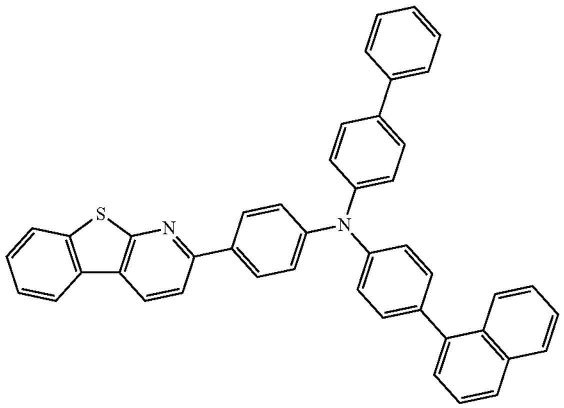
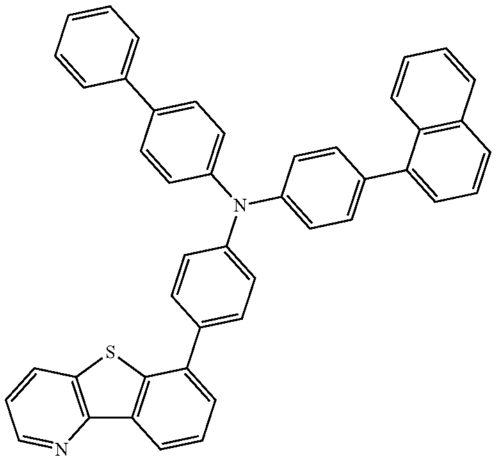

-continued
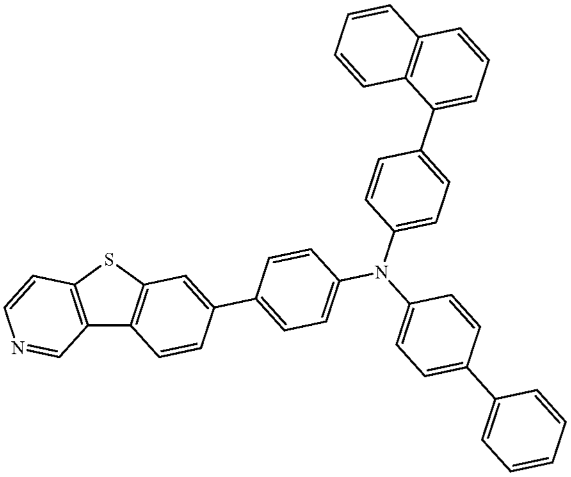
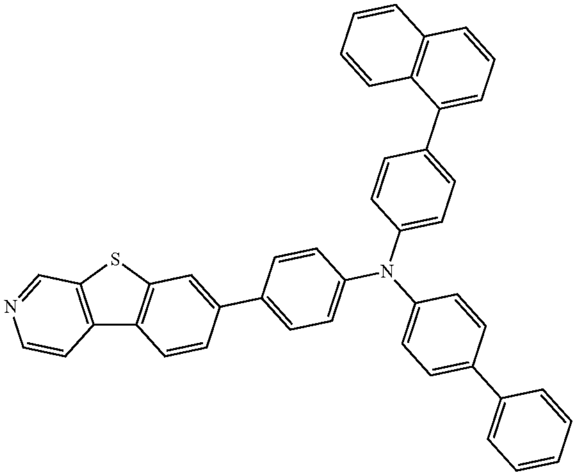
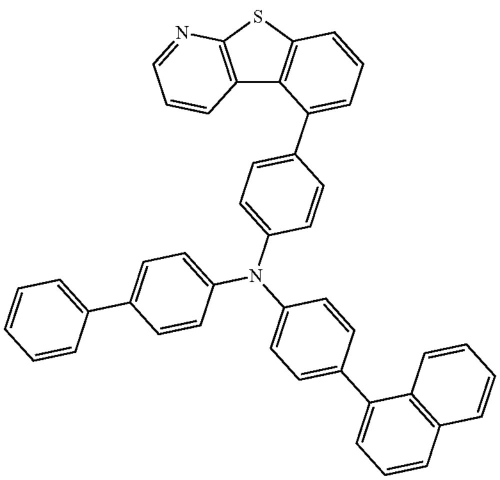
-continued
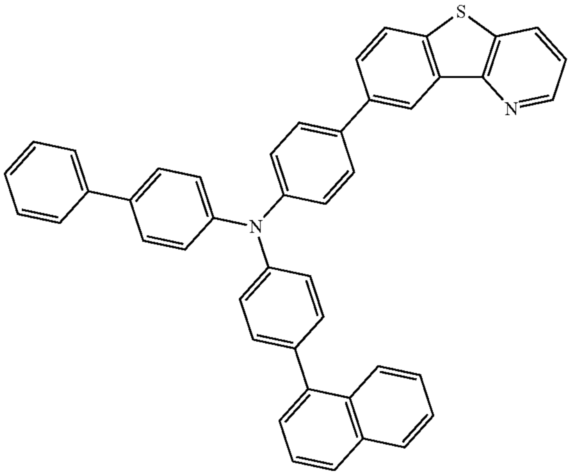
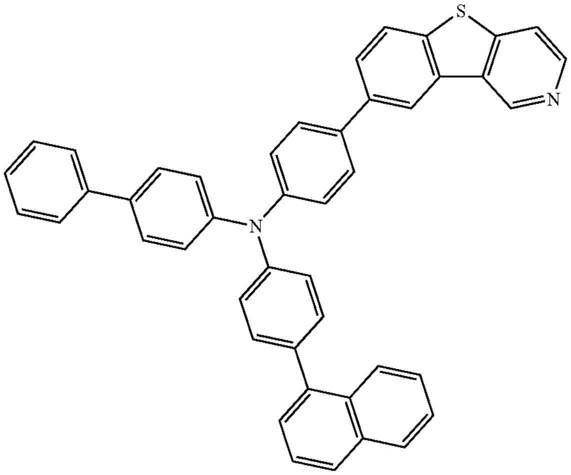
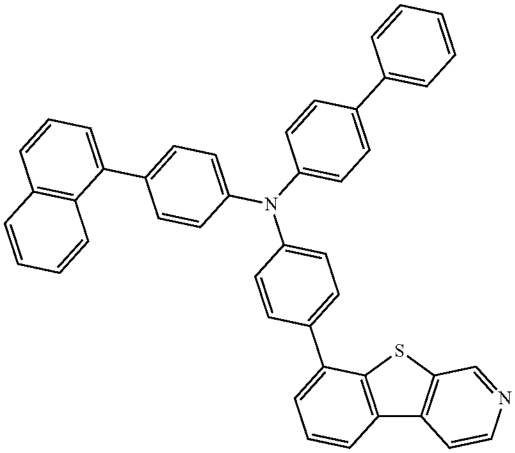

-continued
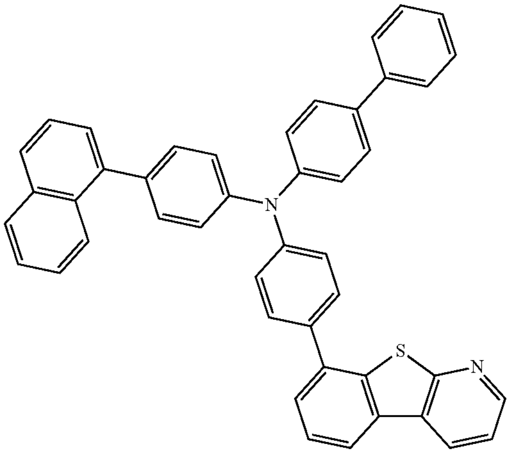
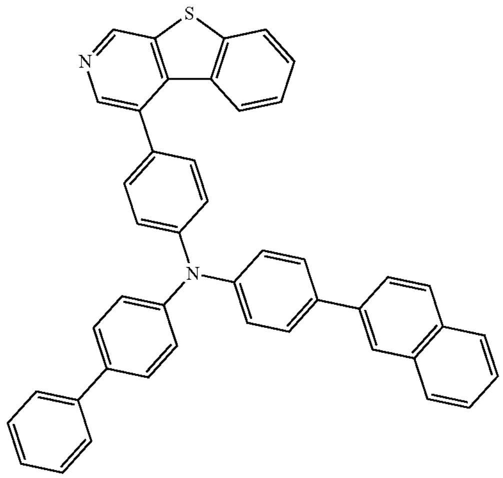
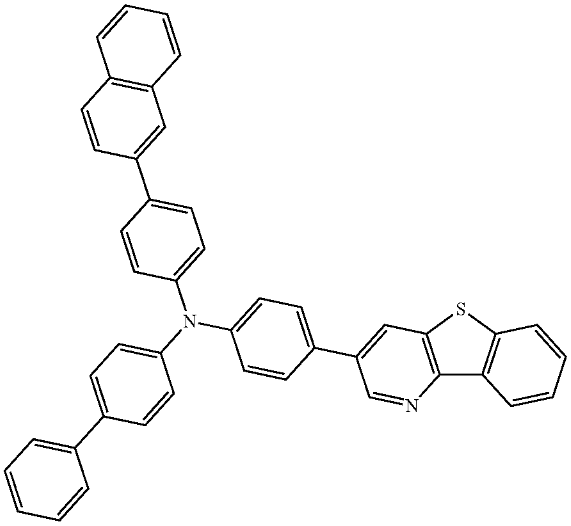
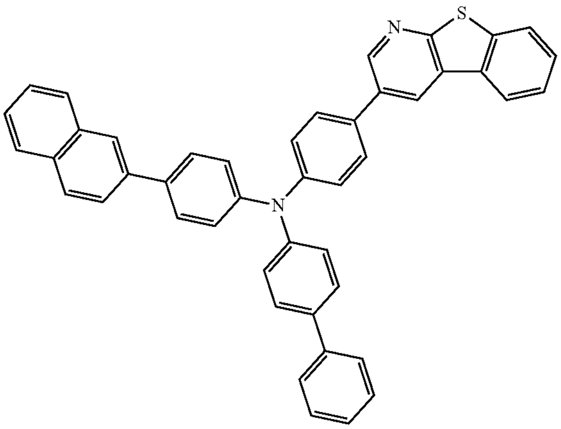
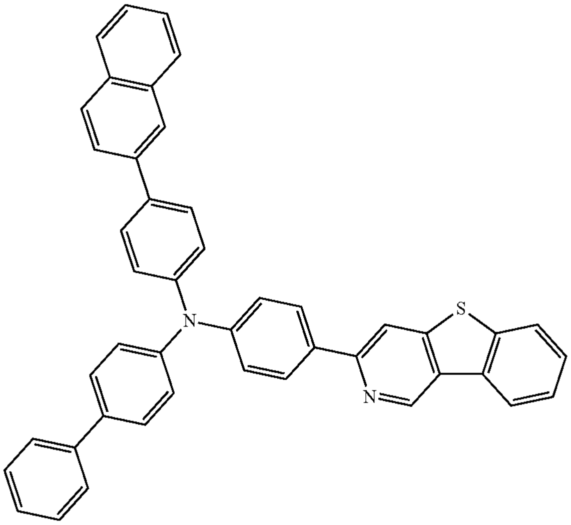
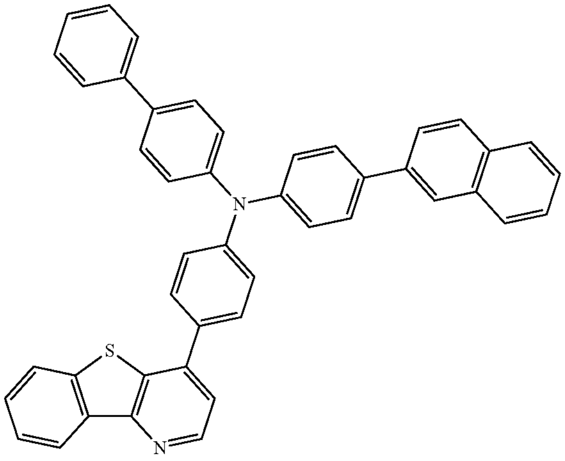
-continued -continued
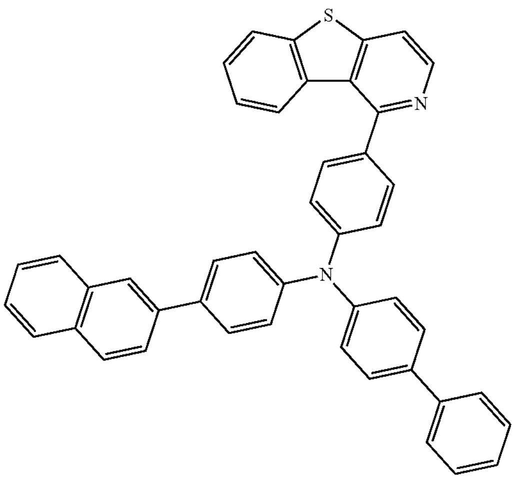
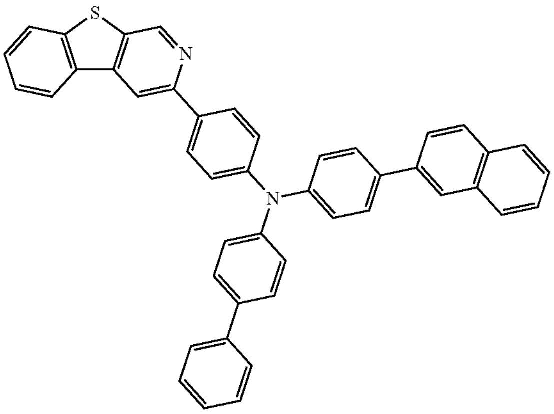
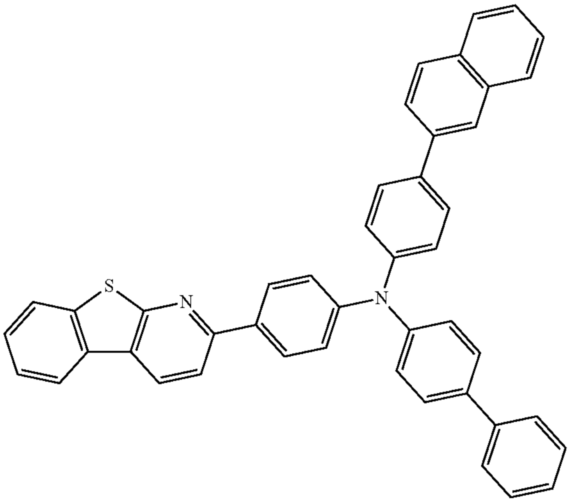
-continued
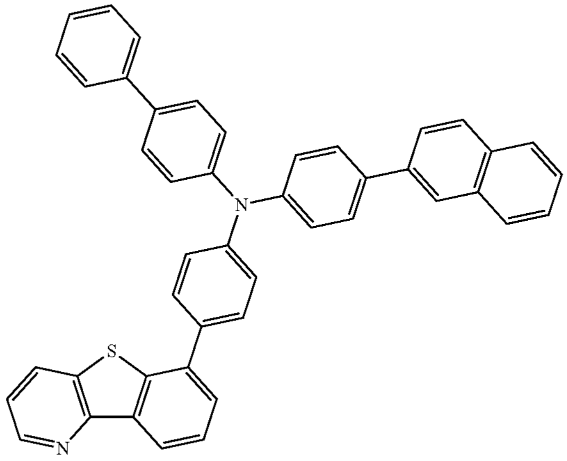
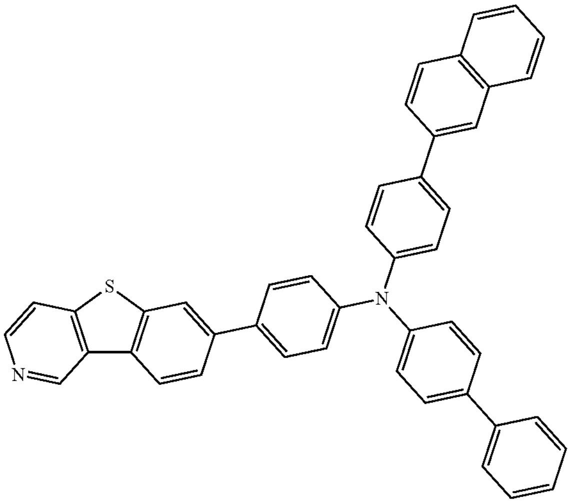
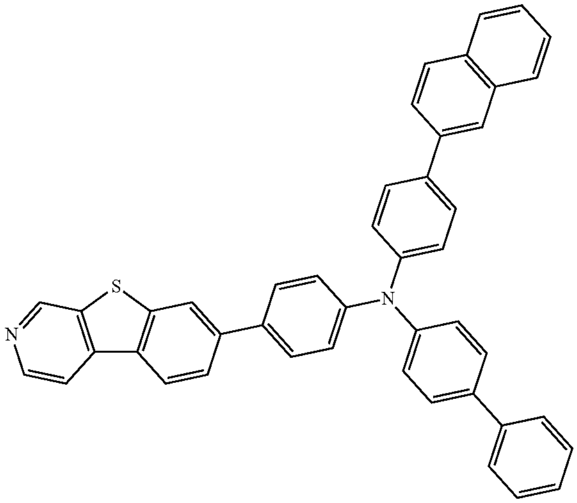

-continued
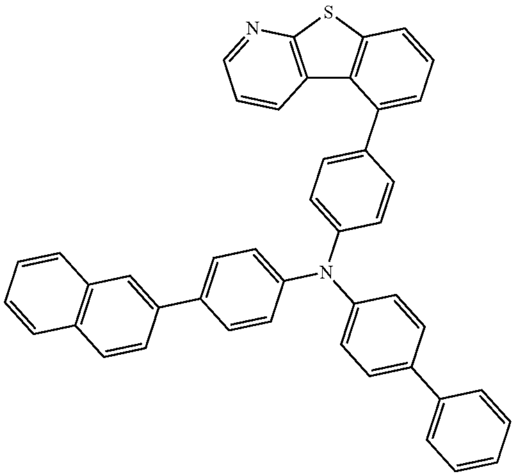
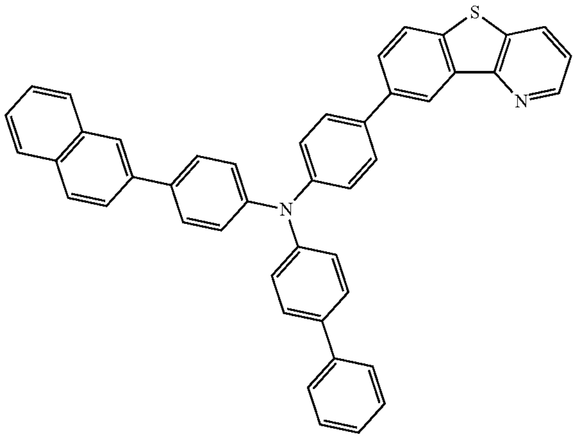
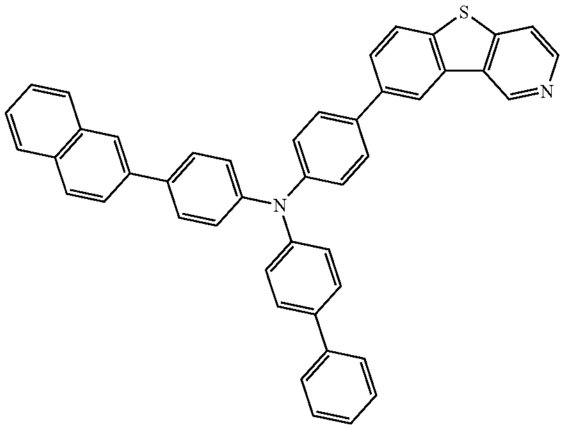
-continued
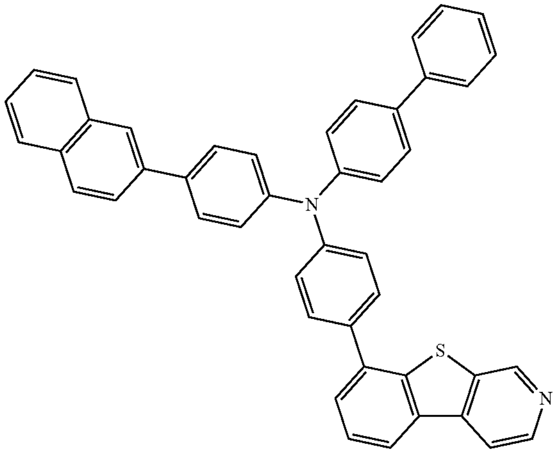
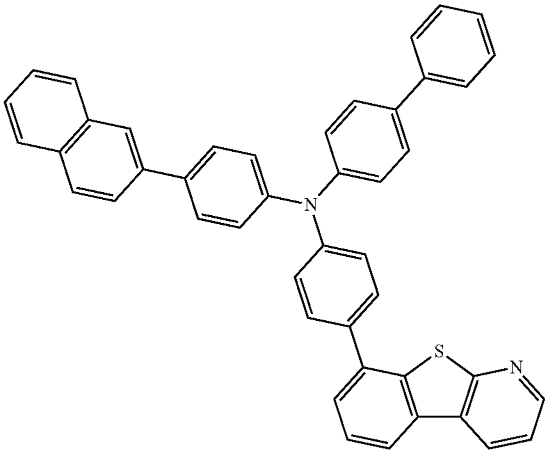
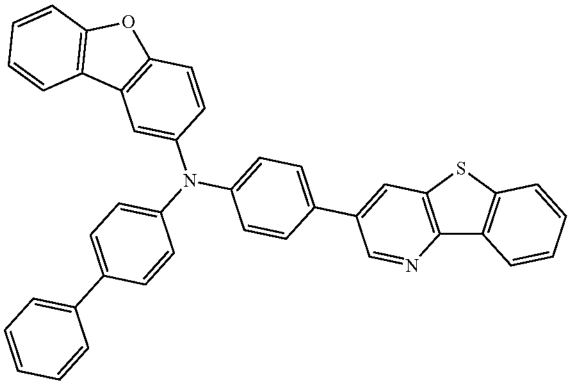
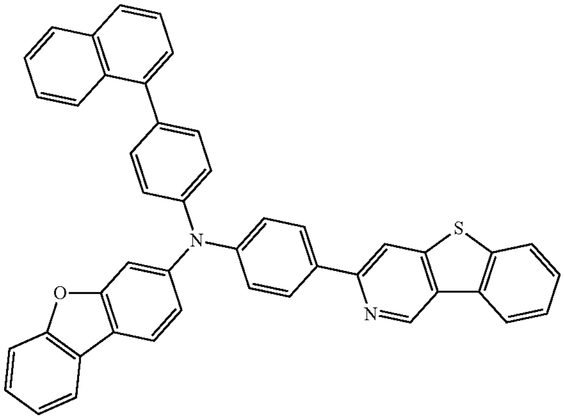

-continued
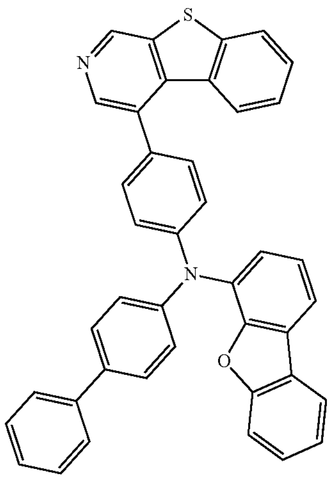
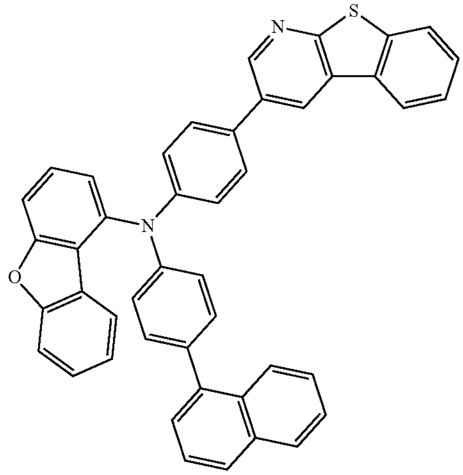
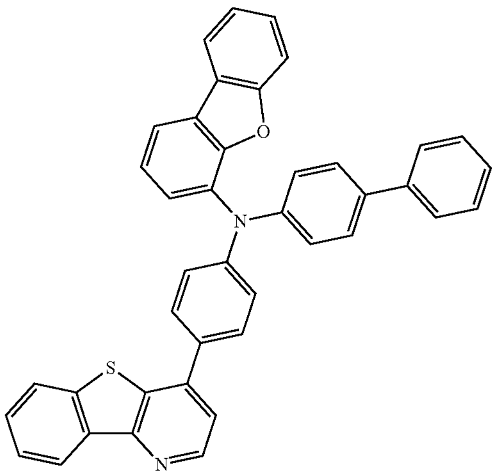
-continued
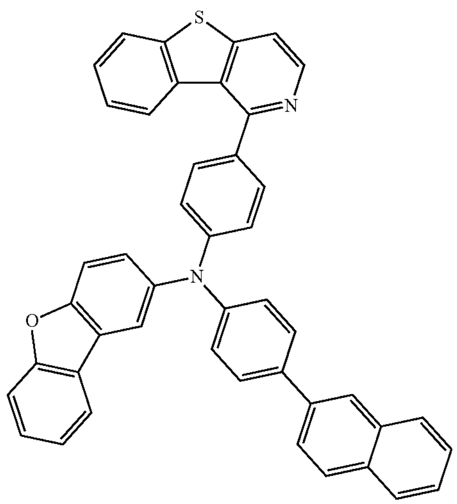
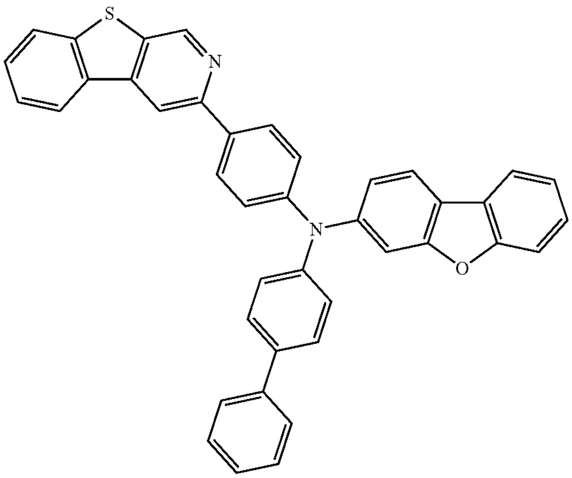
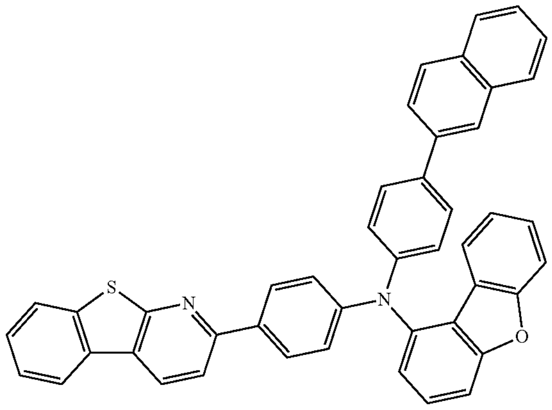

-continued
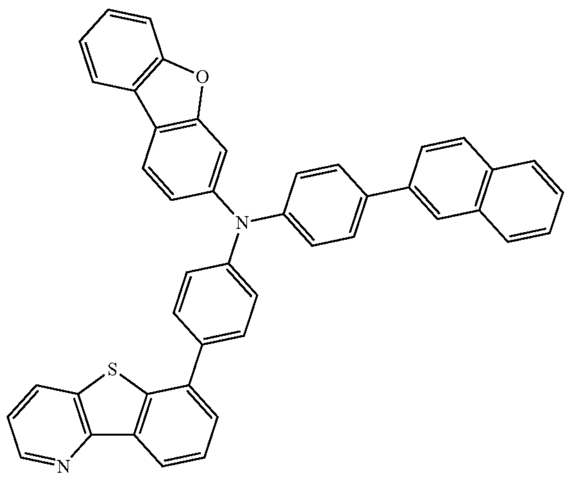
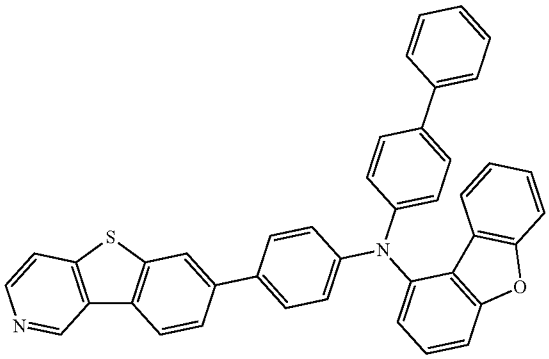
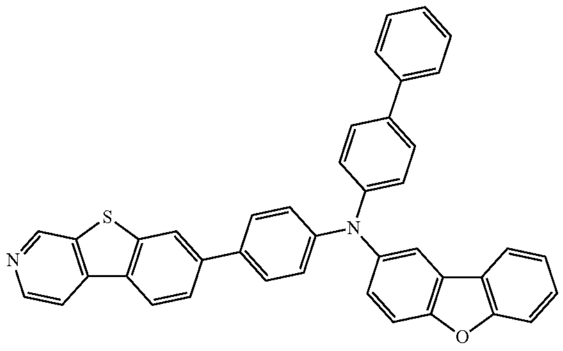
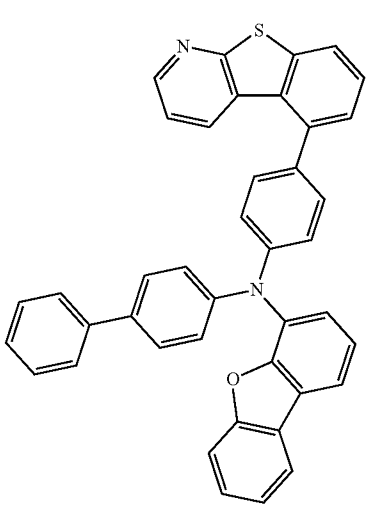
-continued
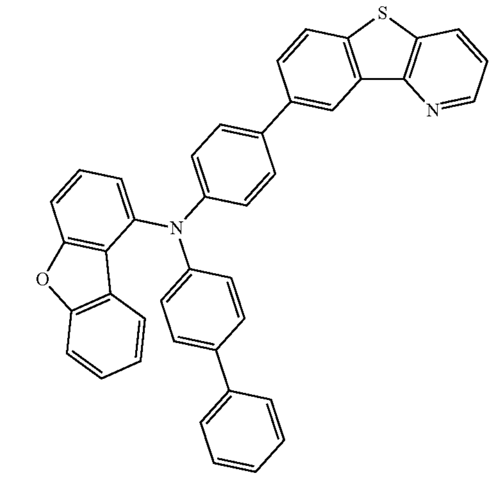
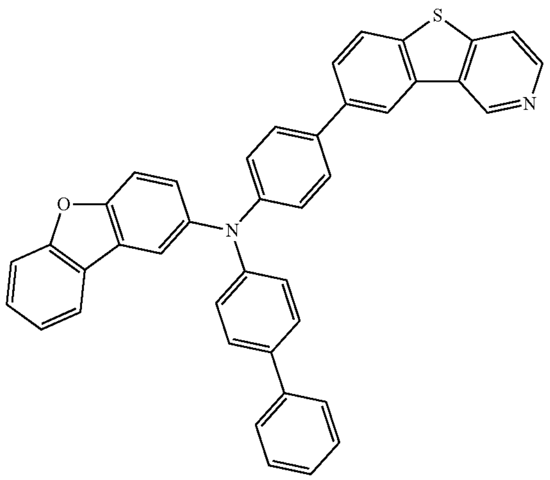
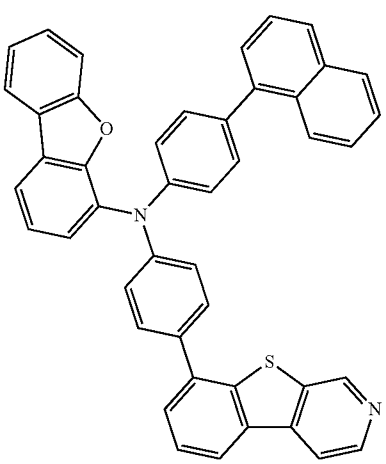

-continued
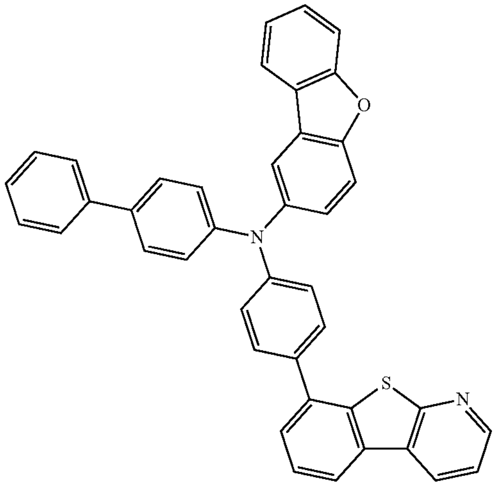
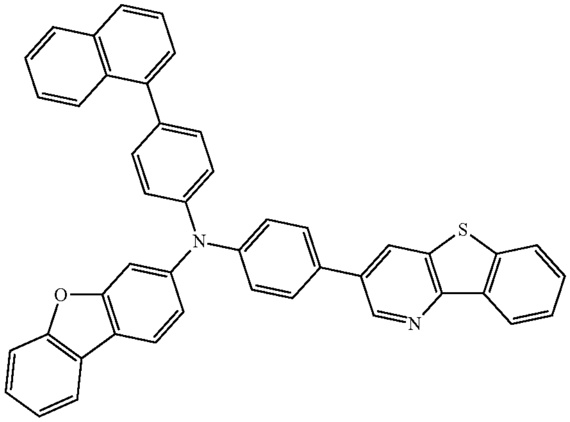
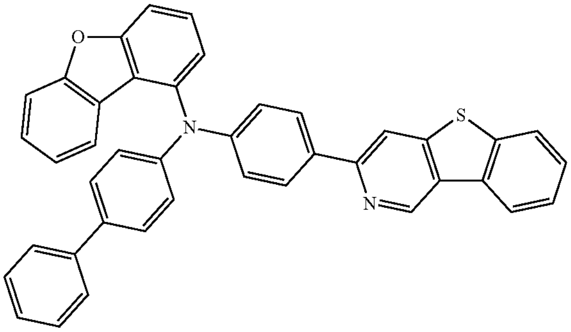
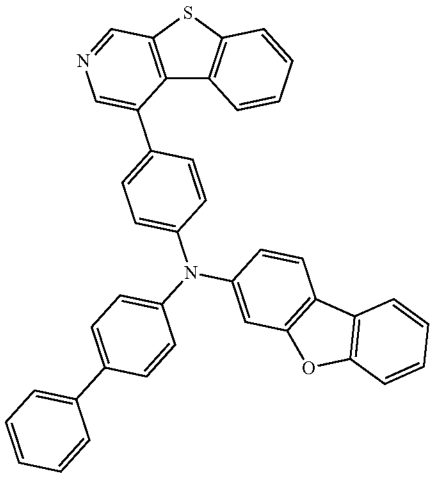
-continued
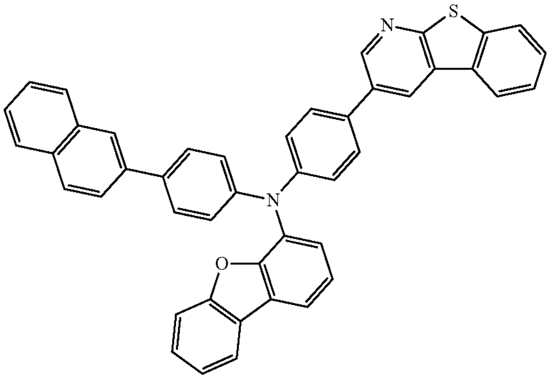
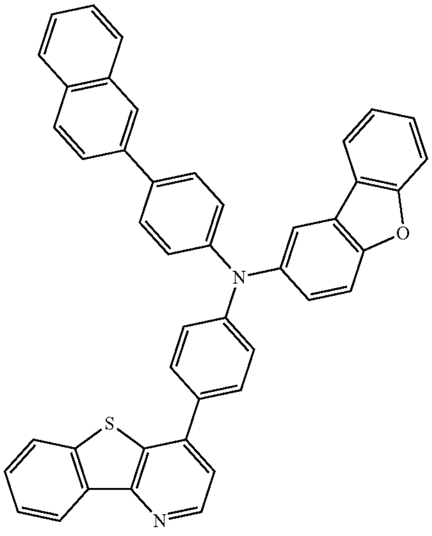
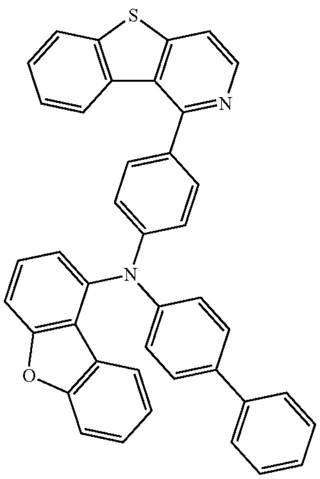

-continued
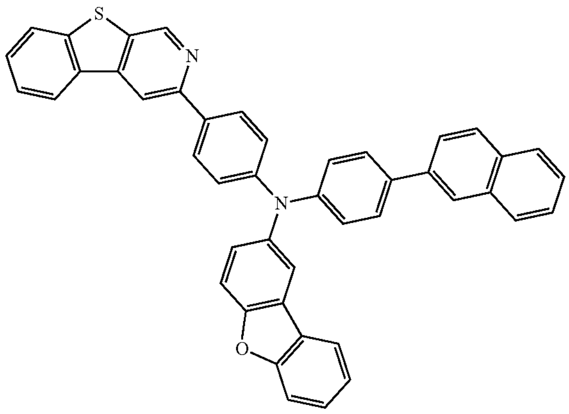
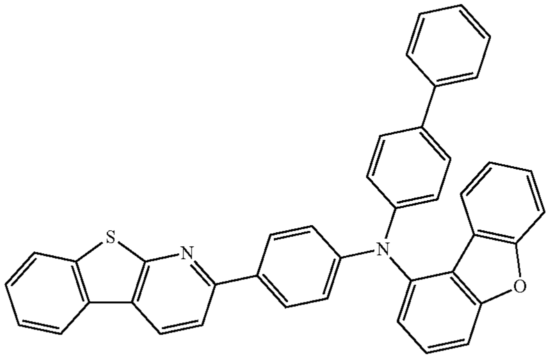
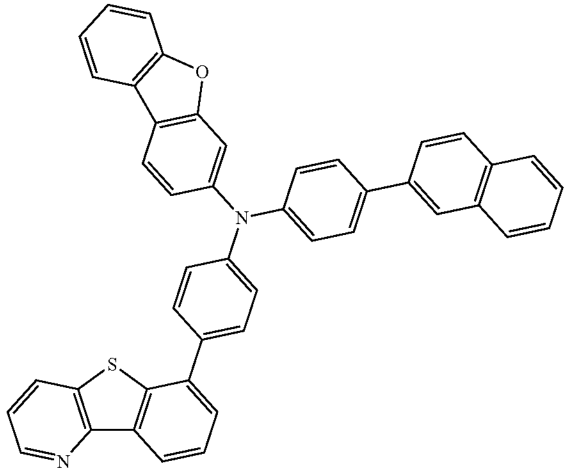
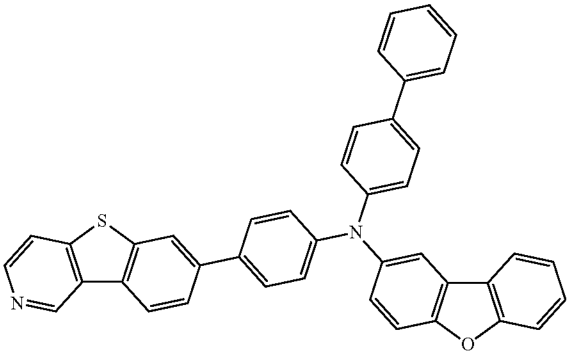
-continued
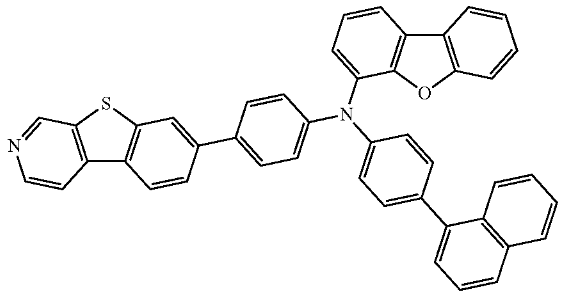
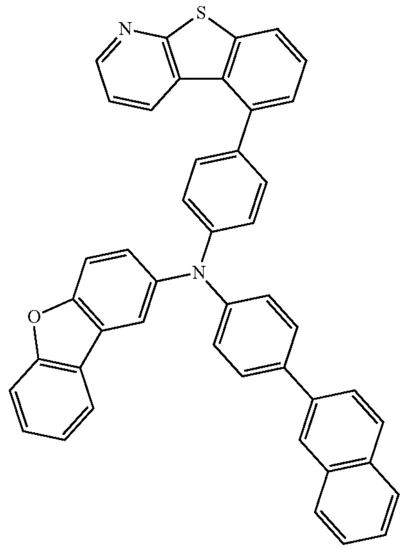
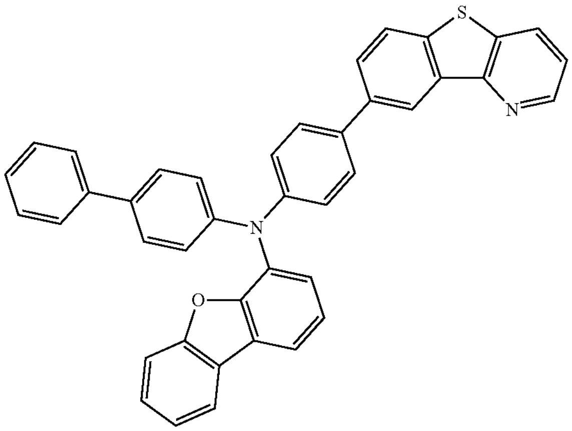

-continued
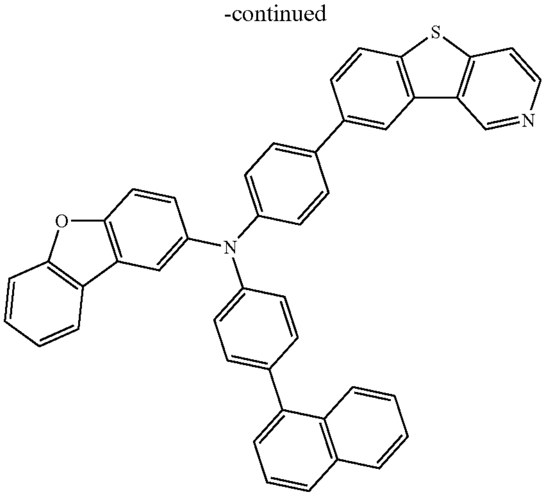
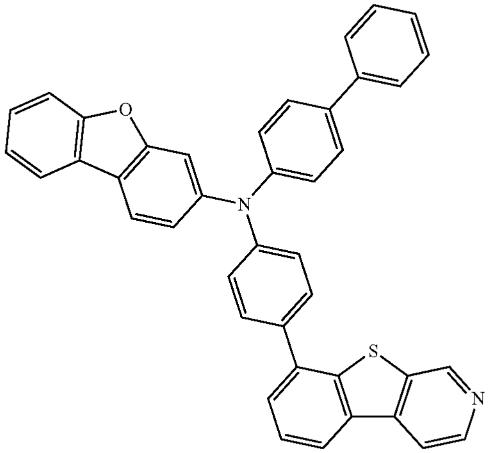
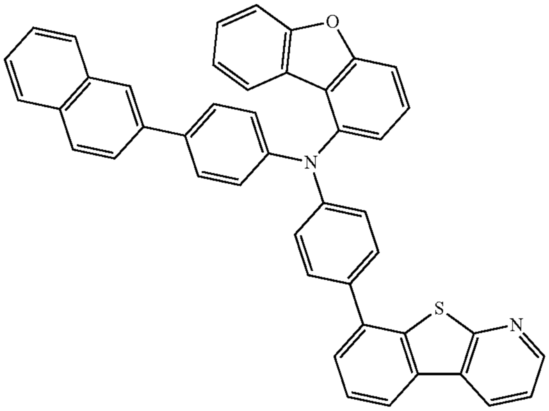
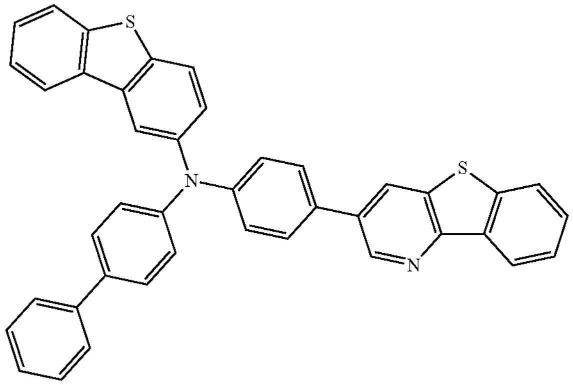
-continued
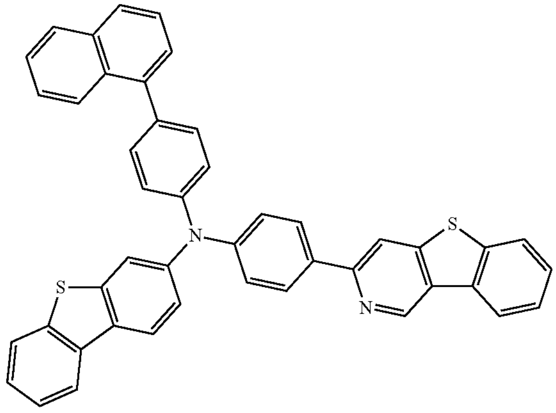
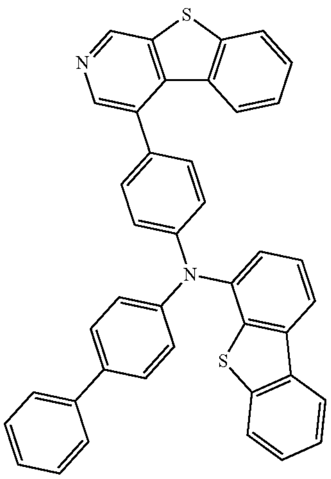
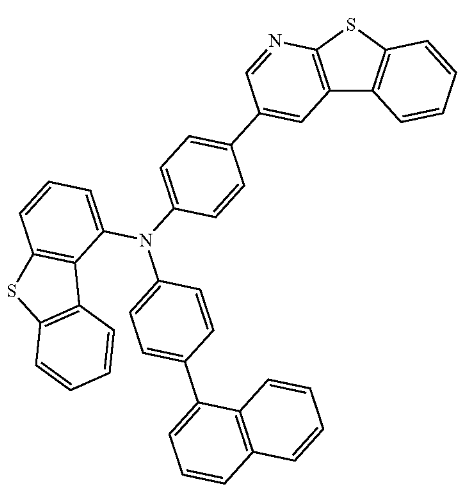

-continued
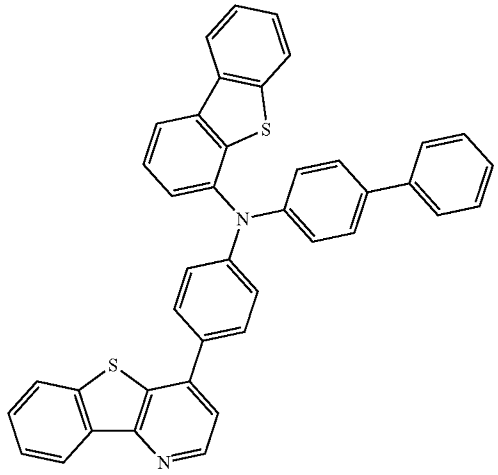
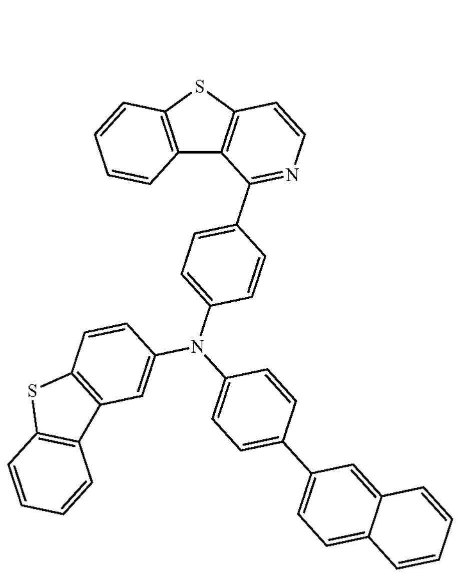
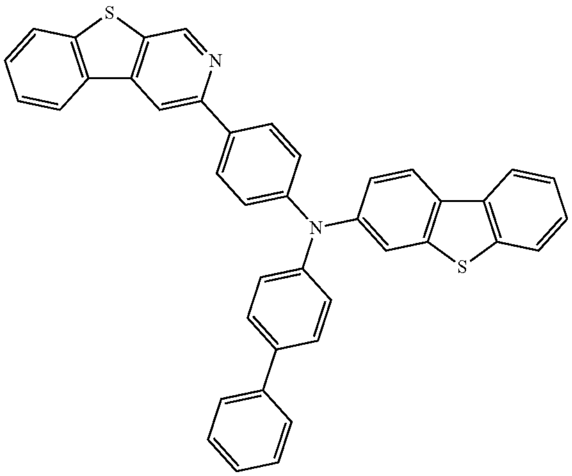
-continued
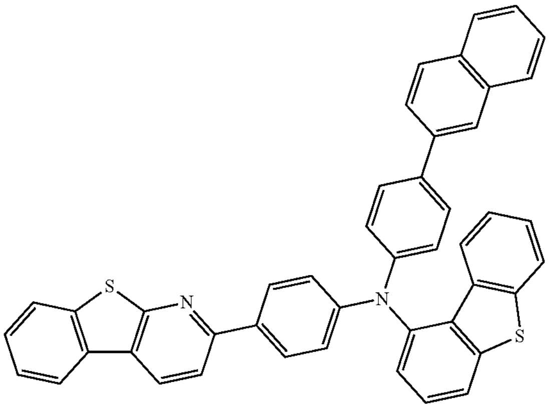
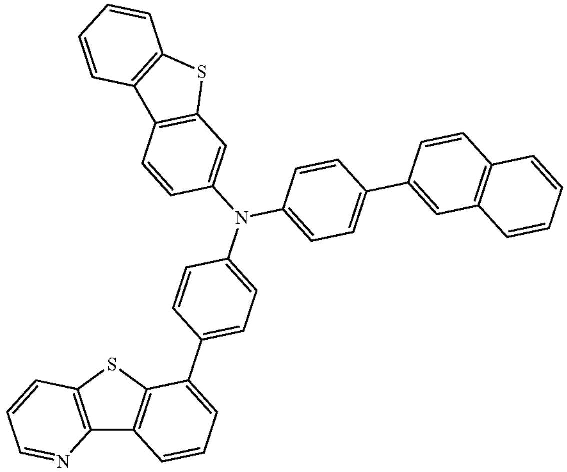
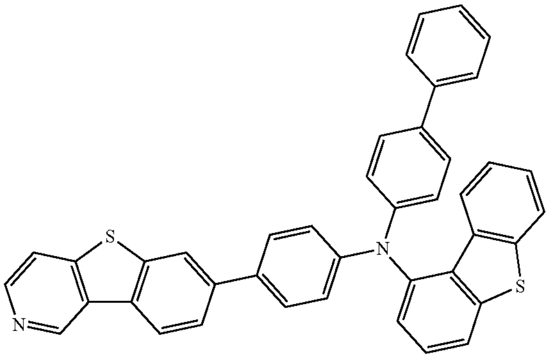
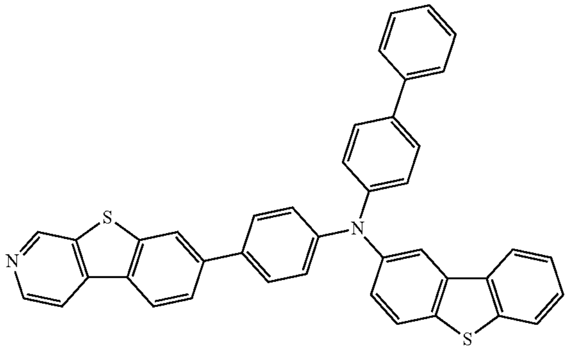

-continued
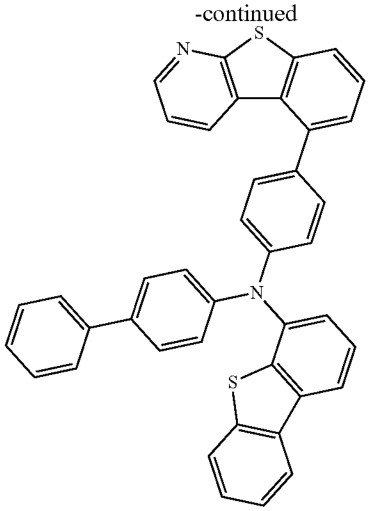
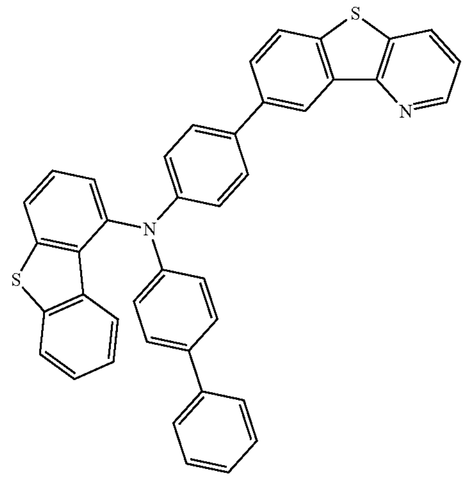
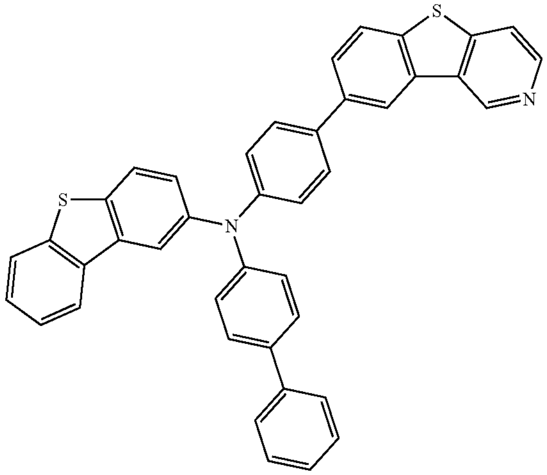
-continued
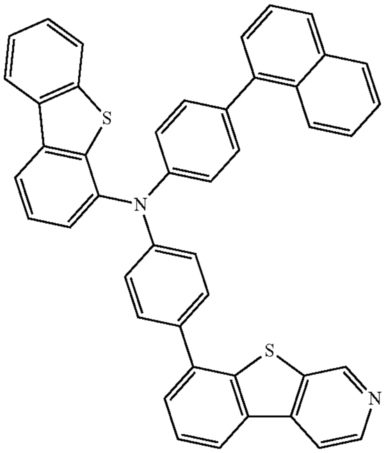
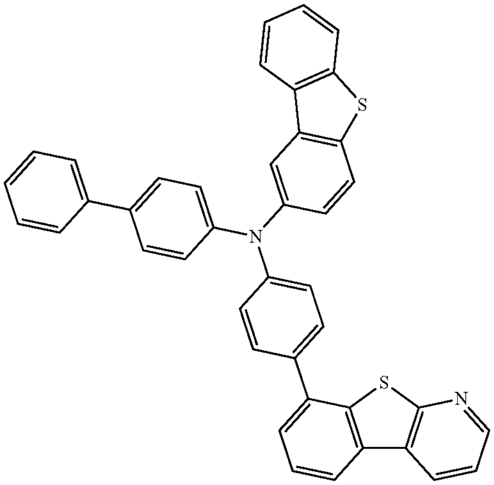
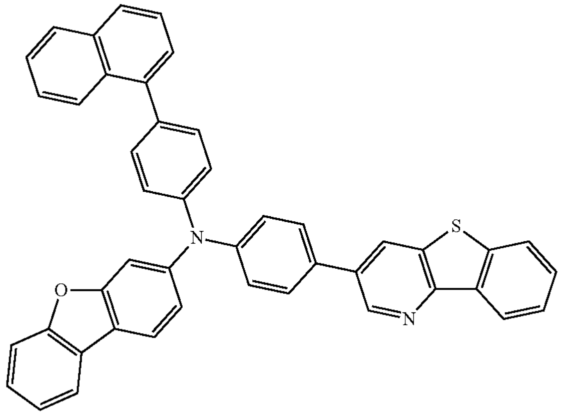
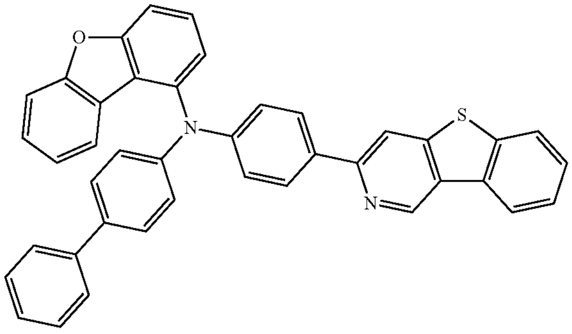

-continued
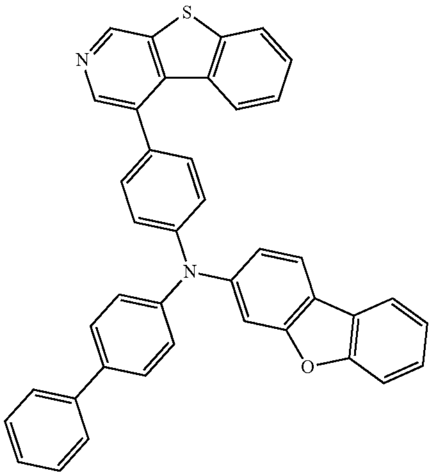
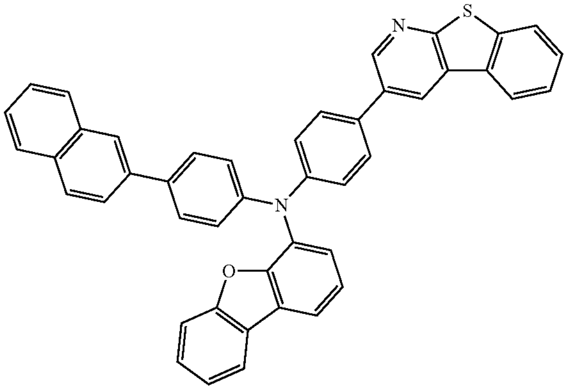
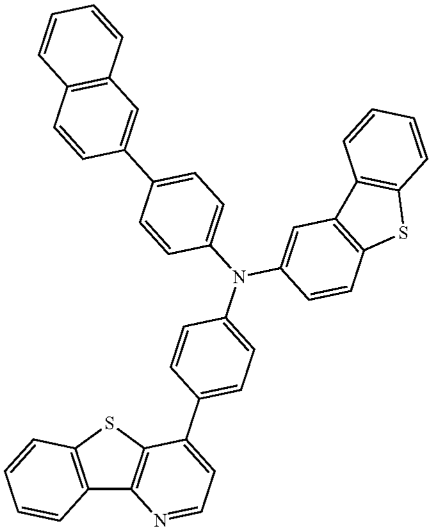
-continued
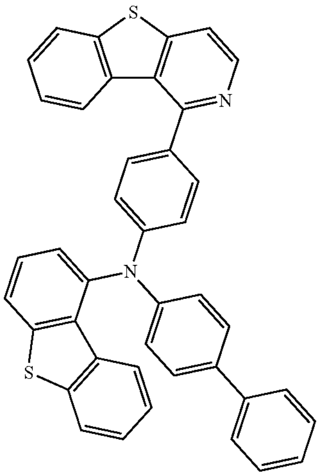
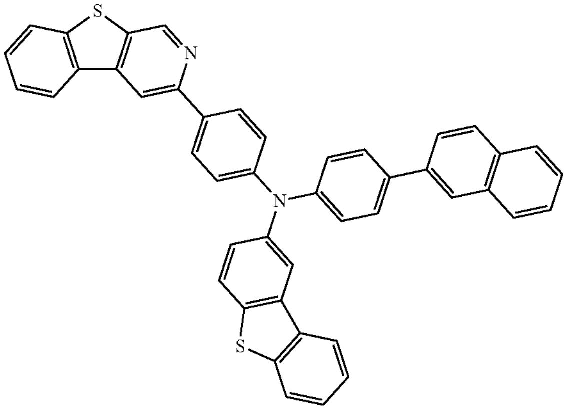
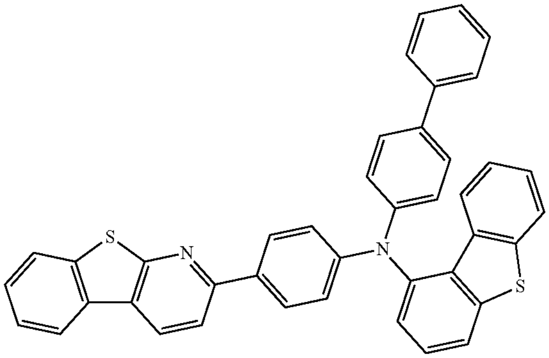
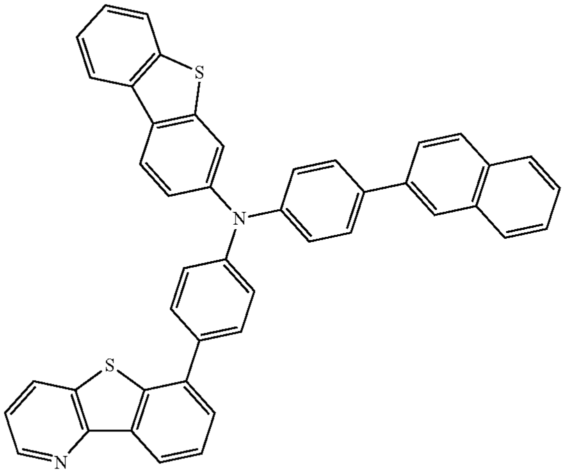

-continued
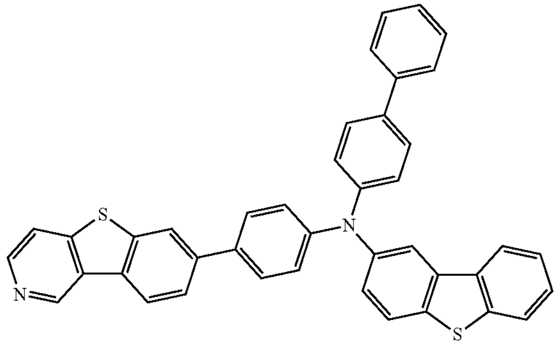
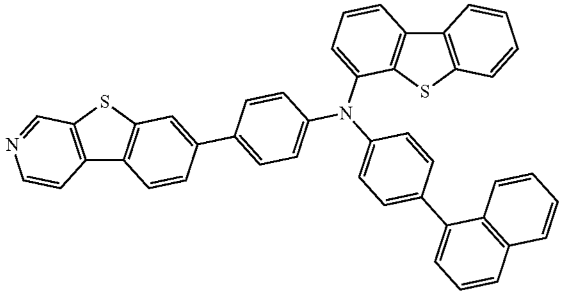
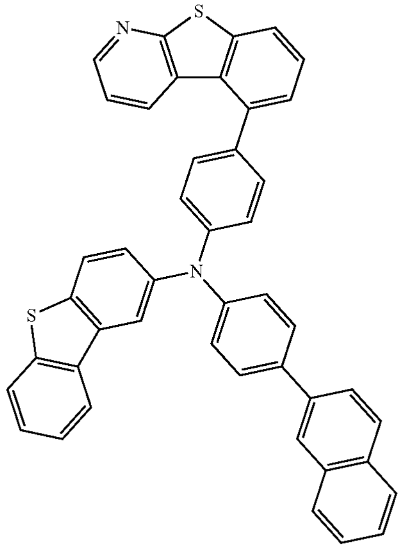
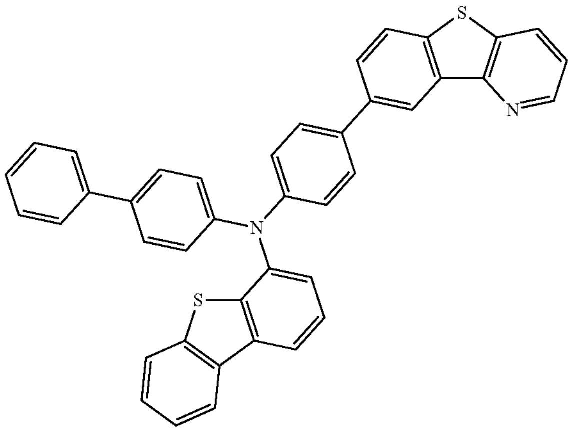
-continued
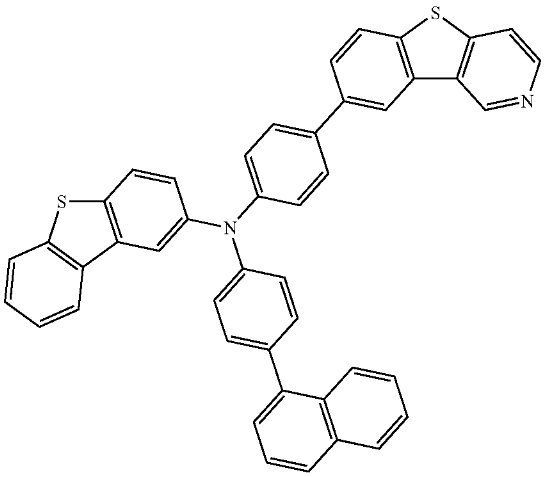
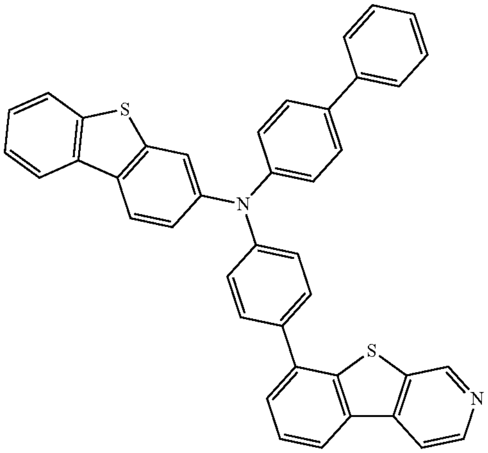
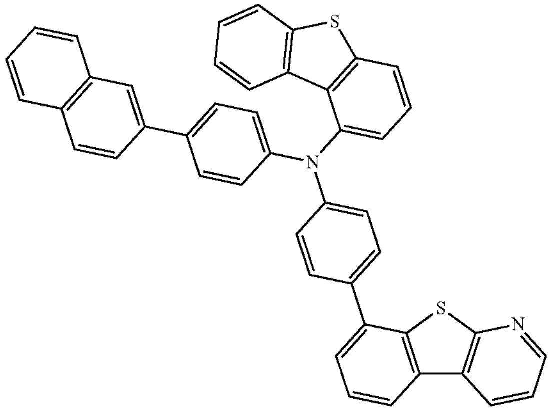
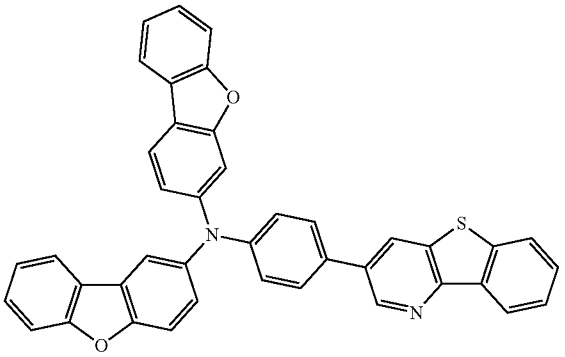

-continued
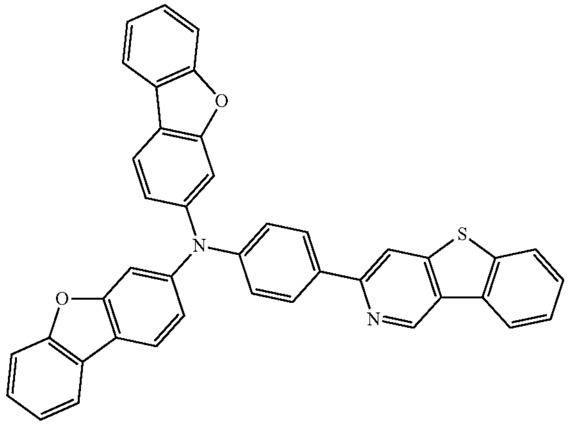
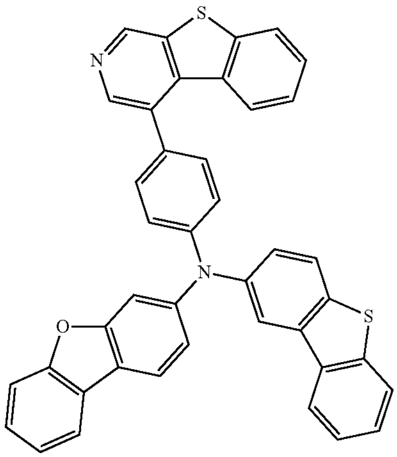
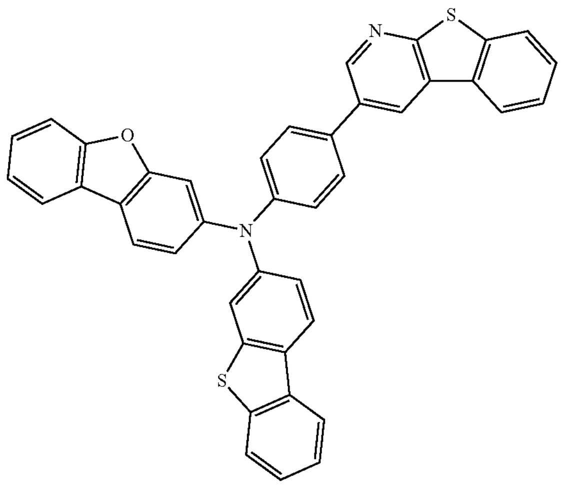
-continued
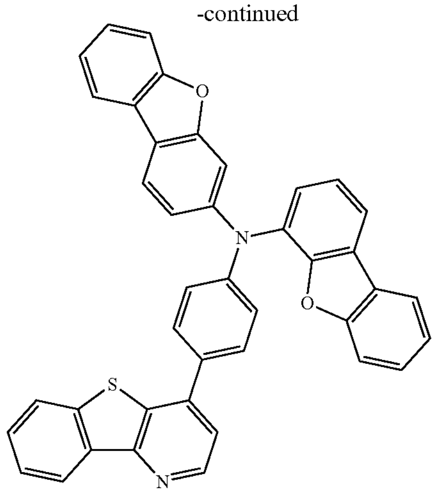
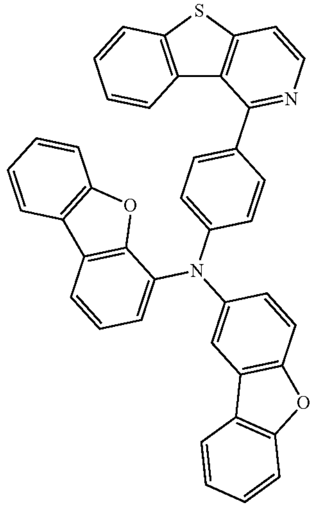
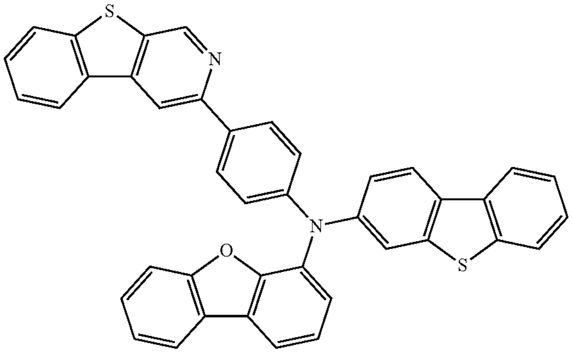
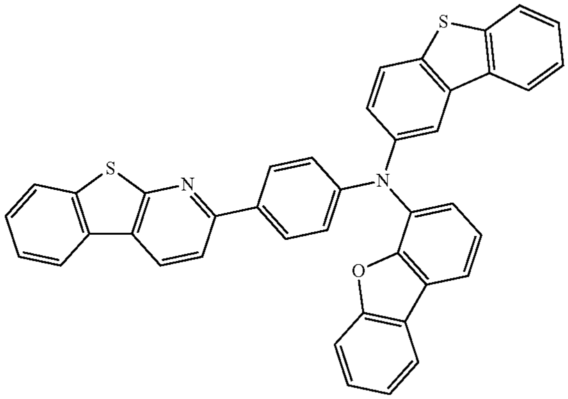

-continued
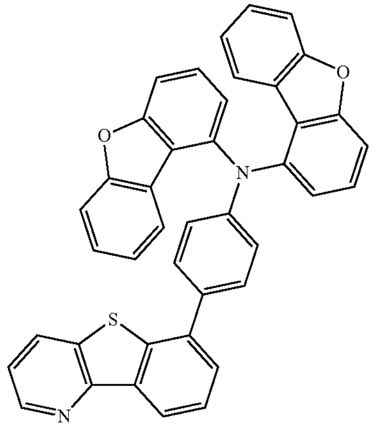
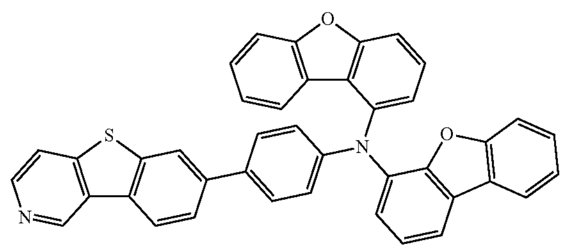
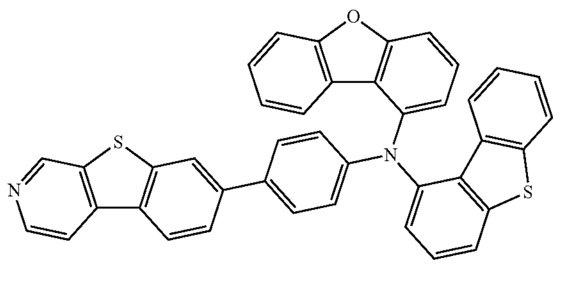
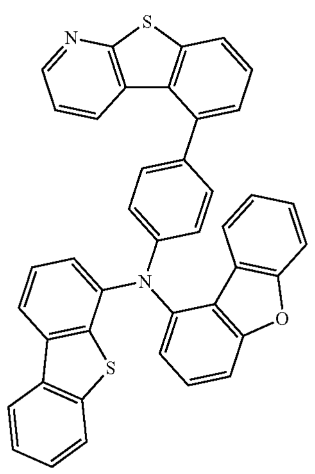
-continued
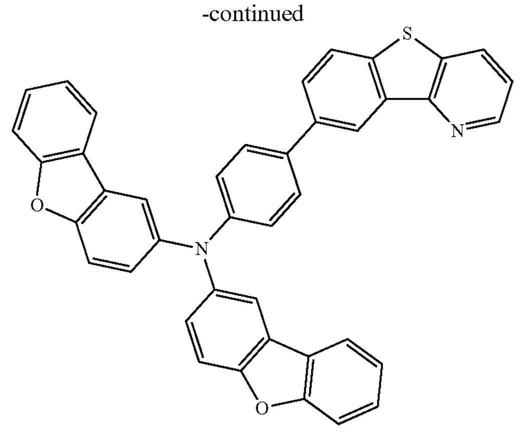
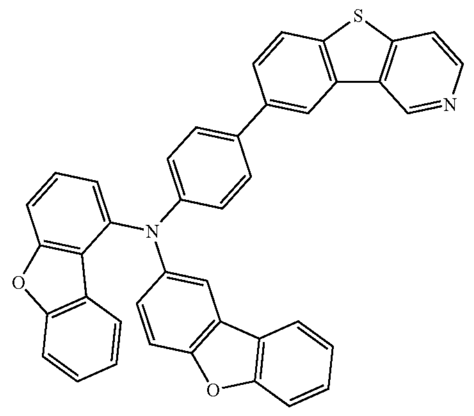
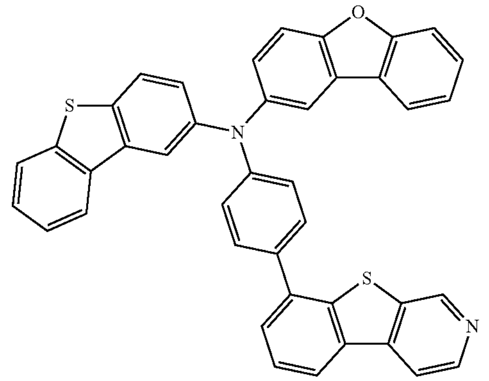
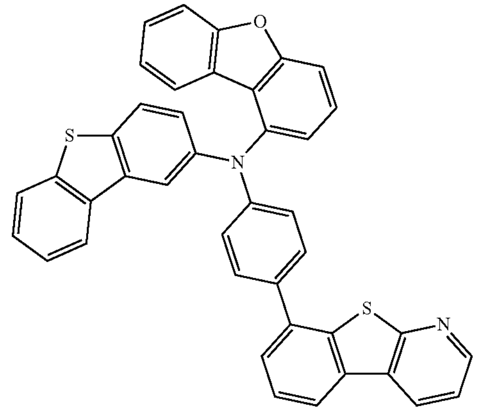

-continued
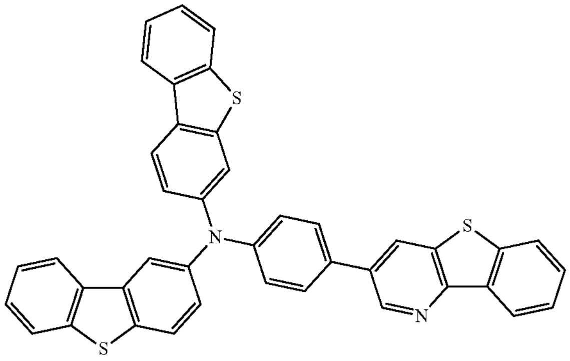
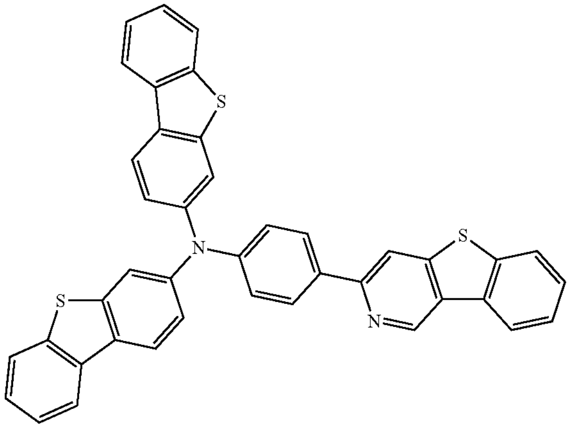
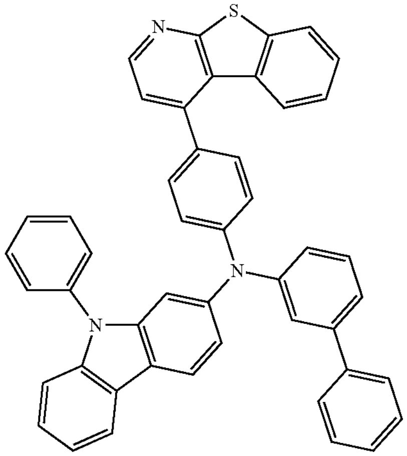
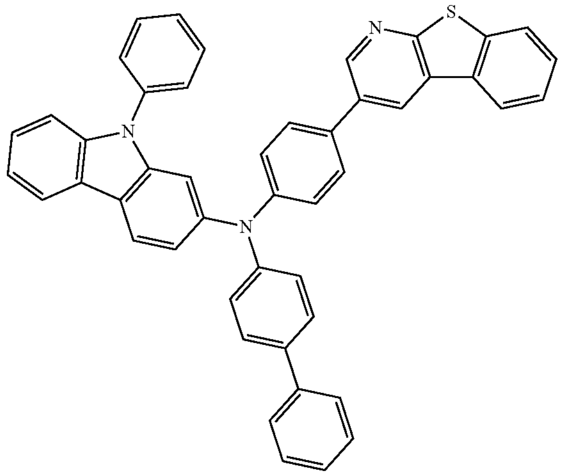
-continued
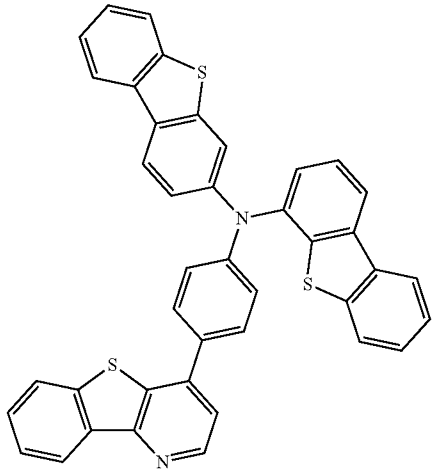
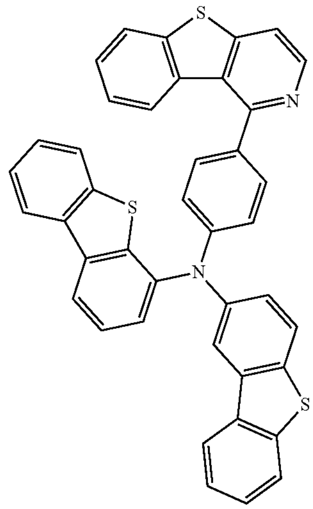
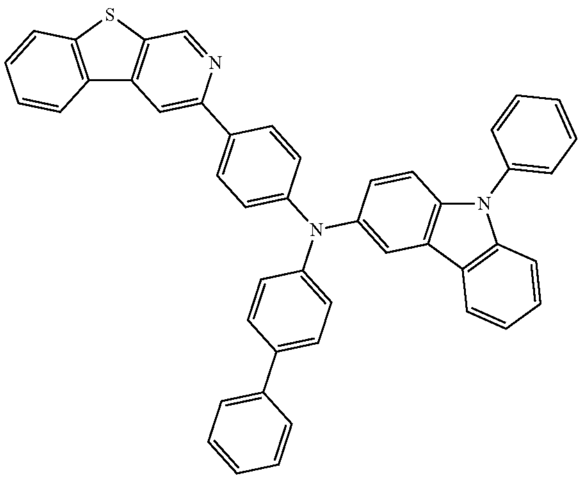

-continued
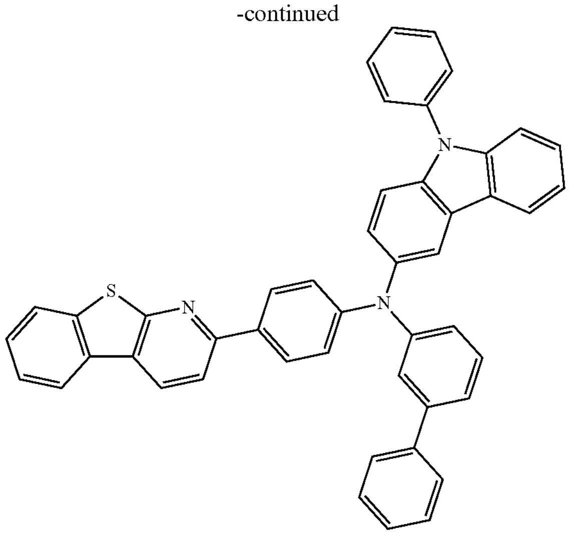
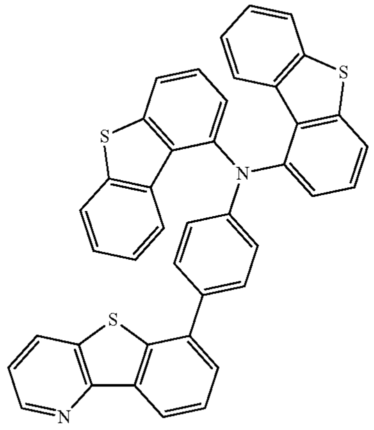
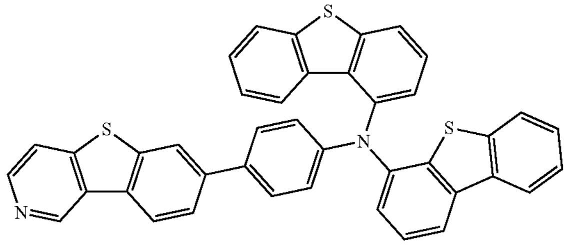
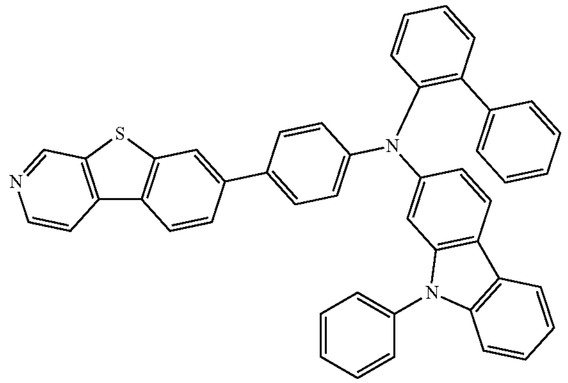
-continued
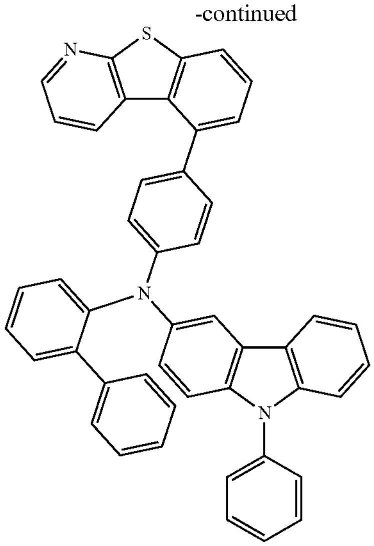
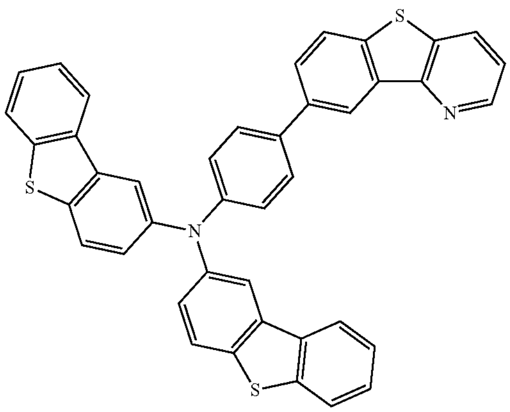
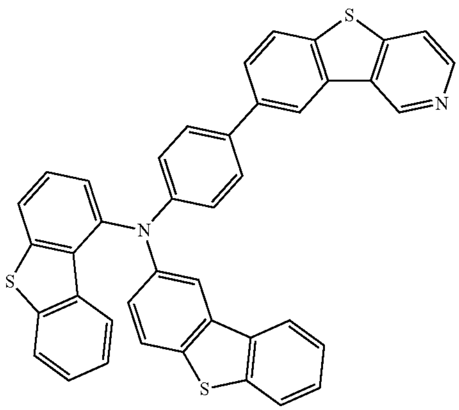

-continued
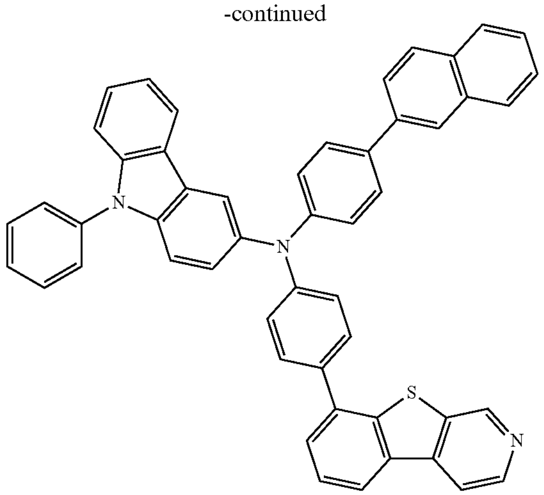
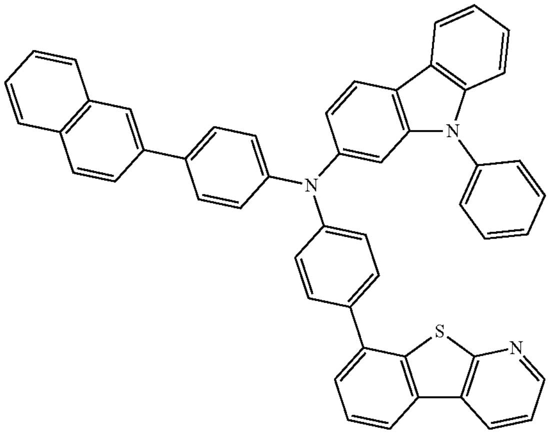
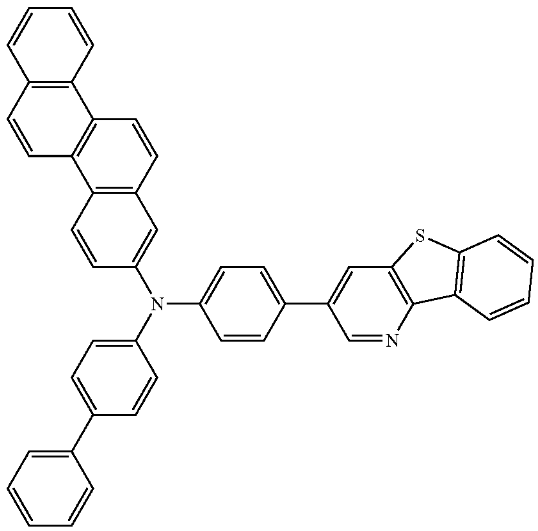
-continued
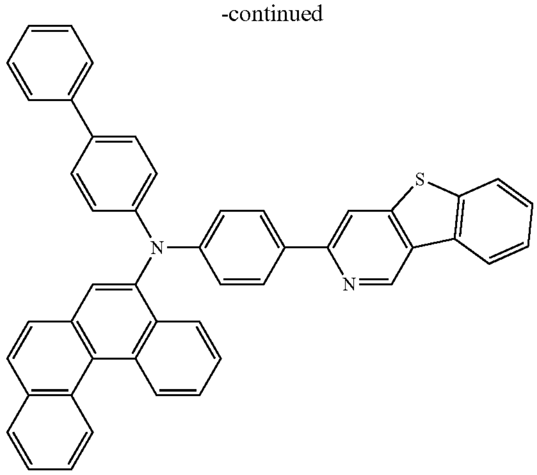
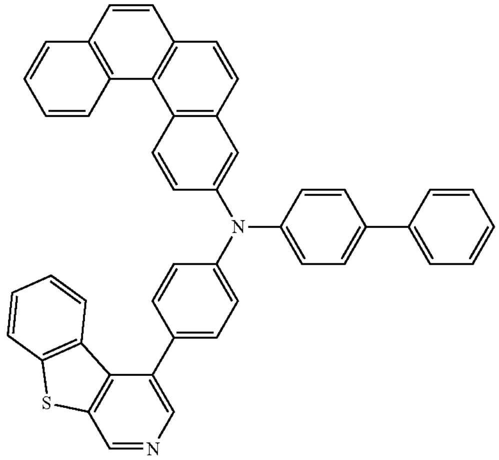
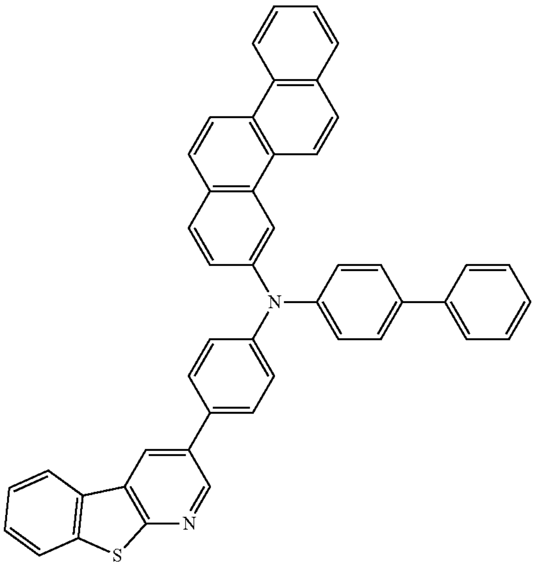

-continued
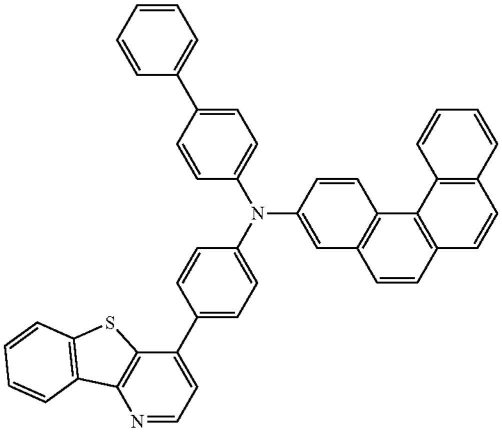
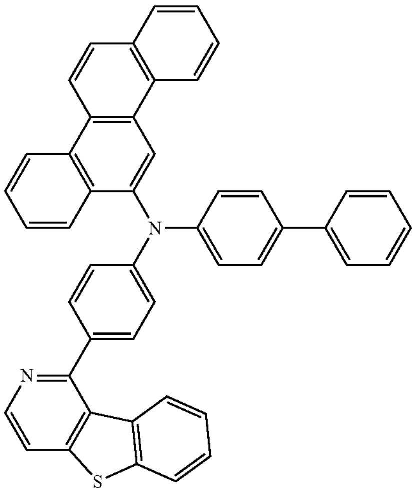
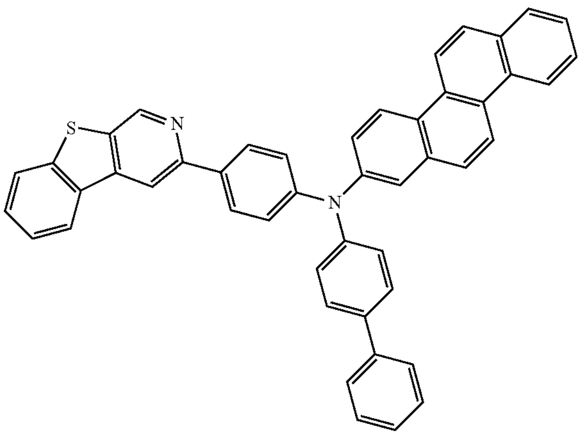
-continued
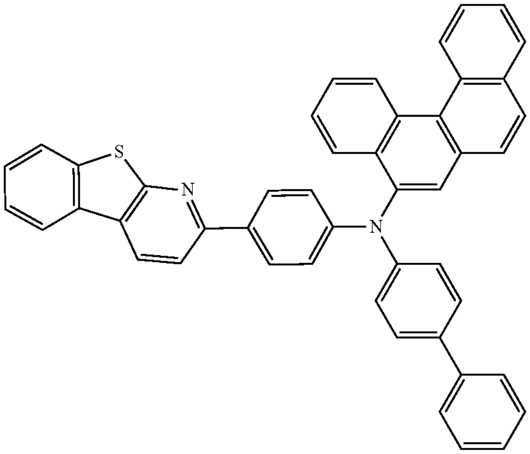
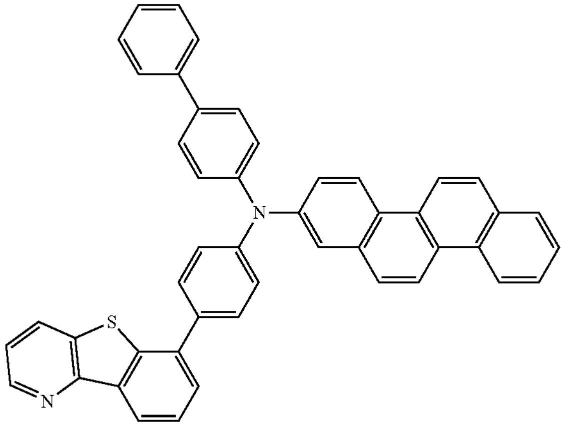
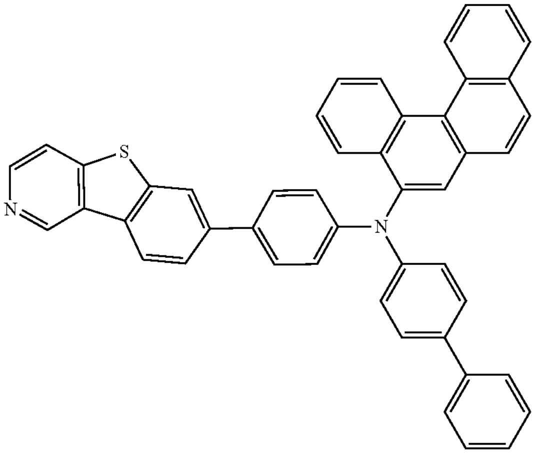

-continued
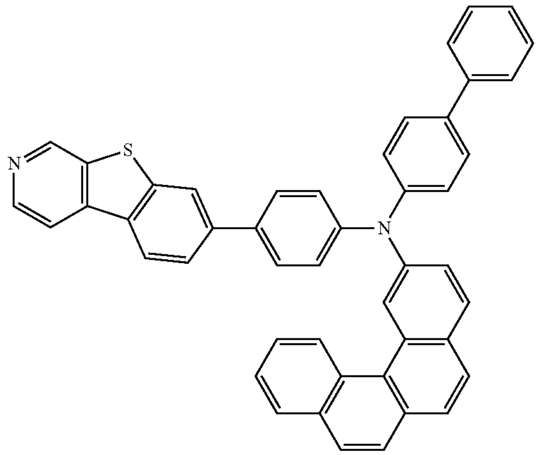
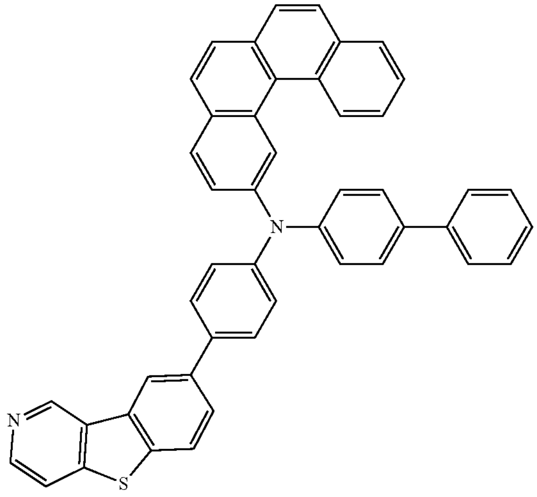
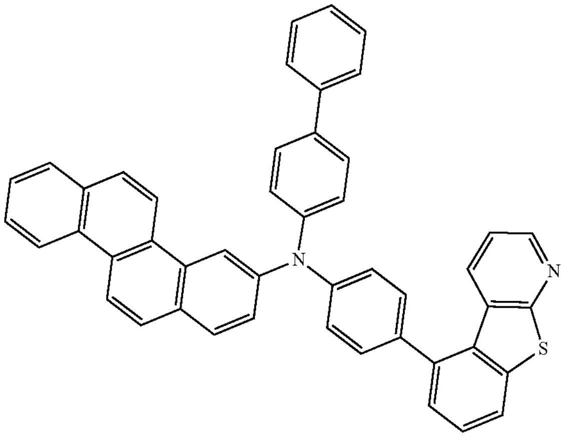
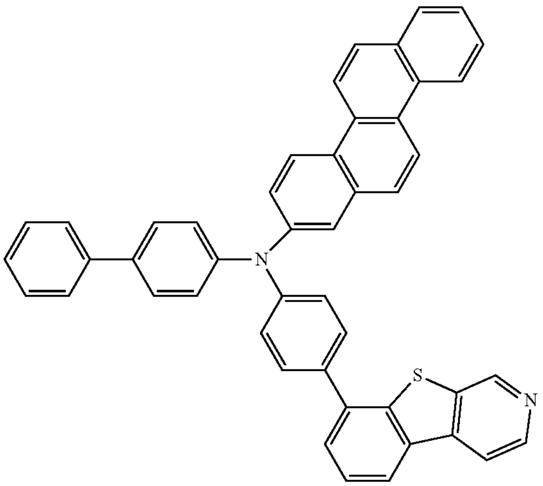
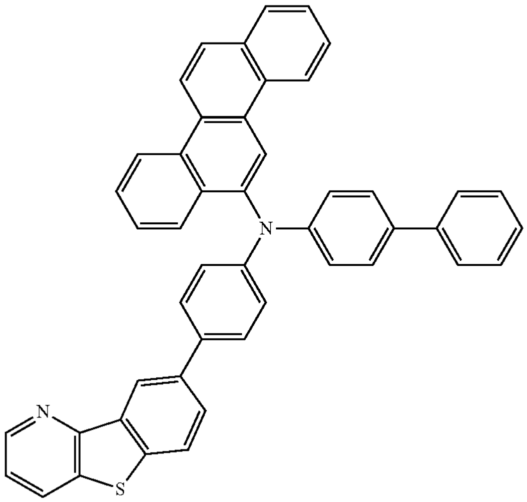
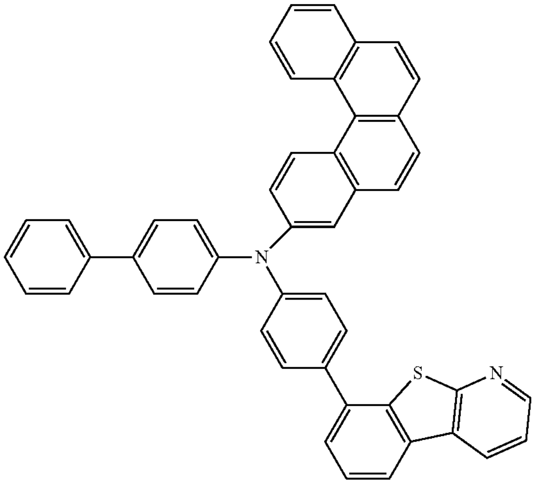 [SMILES: c1ccc(-c2ccc(N(c3ccc(-c4cccc5c4sc4ncccc45)cc3)c3ccc4c(ccc5ccc6ccccc6c54)c3)cc2)cc1]

-continued
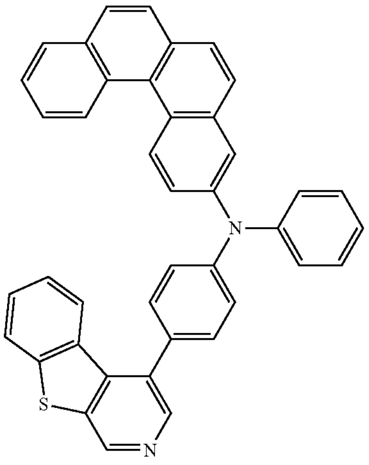
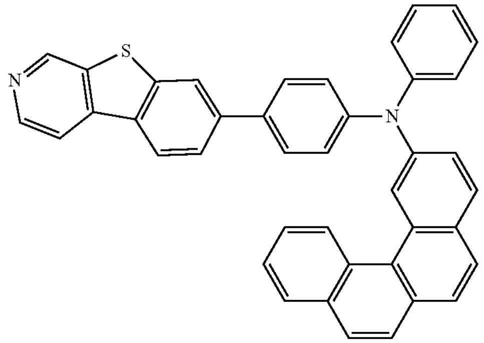
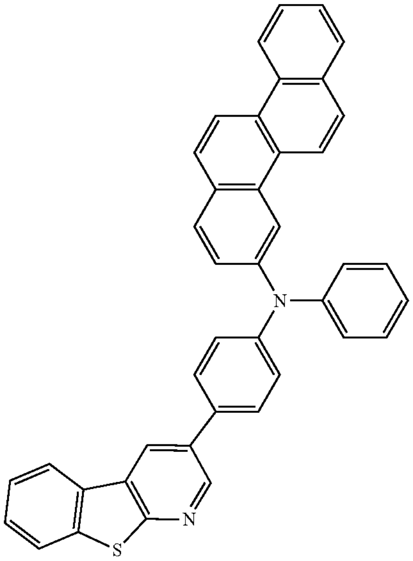
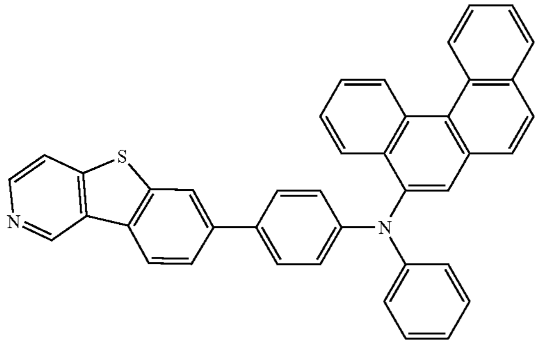
-continued
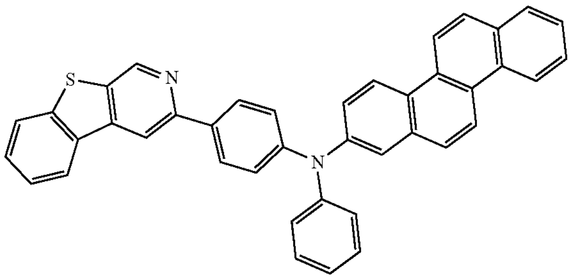
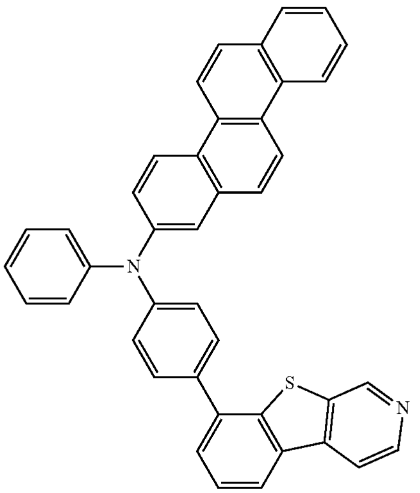
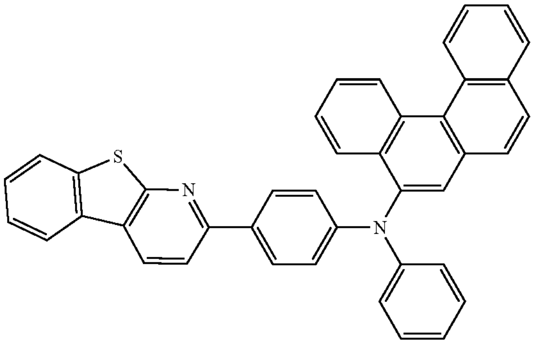
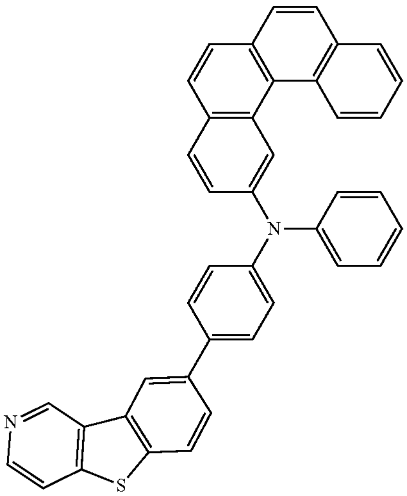

-continued
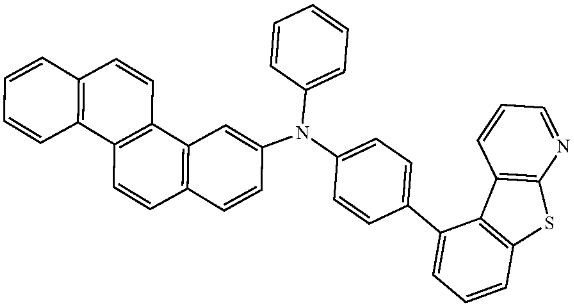
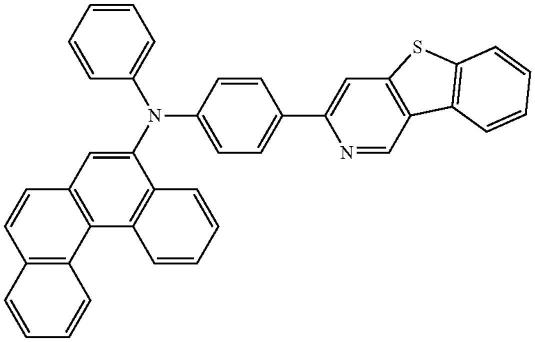
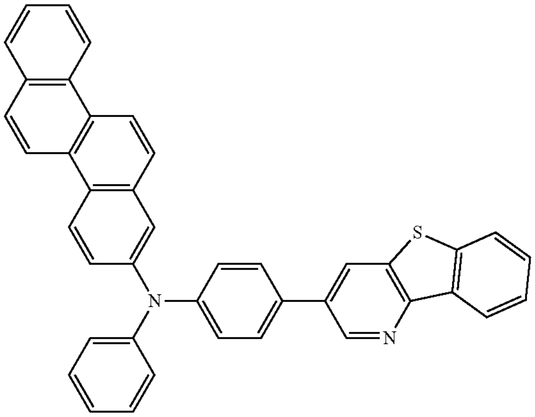
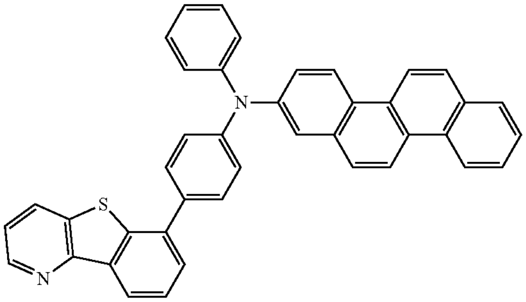
-continued
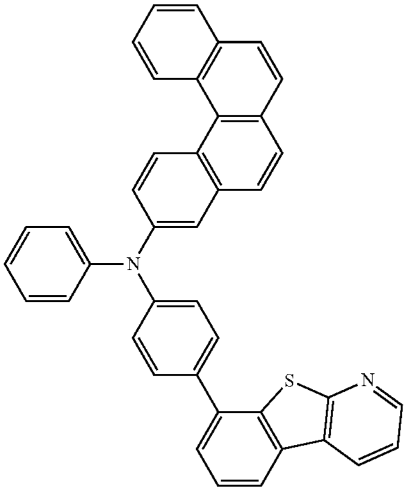
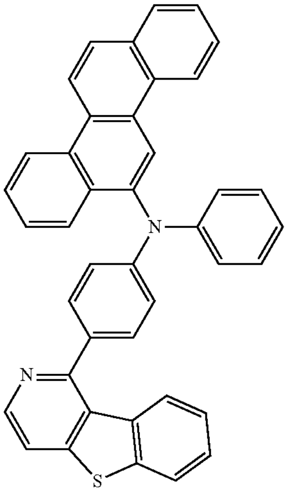
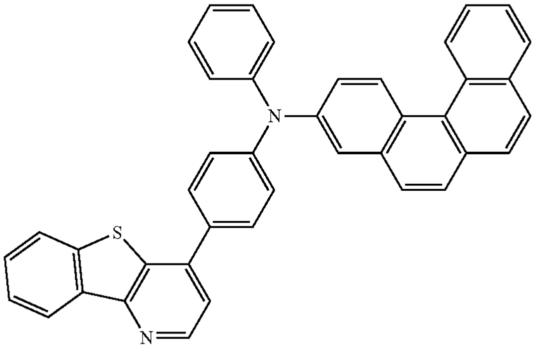

-continued
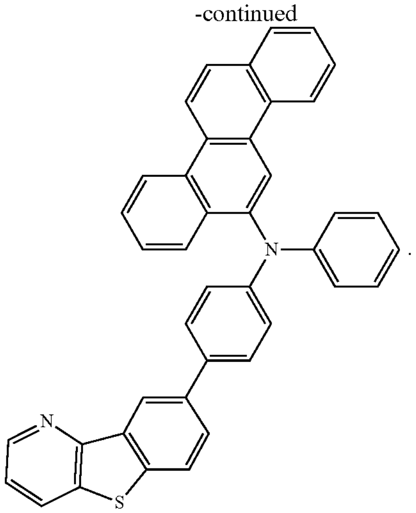
7. An organic light emitting device comprising:
a first electrode;
a second electrode opposite to the first electrode; and
one or more organic material layers between the first electrode and the second electrode, wherein one or more layers of the organic material layers comprises the compound of claim 1.
* * * * *